US008163756B2

(12) United States Patent
Flynn et al.

(10) Patent No.: US 8,163,756 B2
(45) Date of Patent: Apr. 24, 2012

(54) ENZYME MODULATORS AND TREATMENTS

(75) Inventors: Daniel L. Flynn, Lawrence, KS (US); Peter A. Petillo, Lawrence, KS (US)

(73) Assignee: Deciphera Pharmaceuticals, LLC, Lawrence, KS (US)

( * ) Notice: Subject to any disclaimer, the term of this patent is extended or adjusted under 35 U.S.C. 154(b) by 1029 days.

(21) Appl. No.: 11/963,740

(22) Filed: Dec. 21, 2007

(65) Prior Publication Data

US 2008/0113967 A1    May 15, 2008

Related U.S. Application Data

(63) Continuation of application No. 11/318,399, filed on Dec. 23, 2005, now abandoned.

(60) Provisional application No. 60/639,087, filed on Dec. 23, 2004, provisional application No. 60/638,986, filed on Dec. 23, 2004, provisional application No. 60/638,987, filed on Dec. 23, 2004, provisional application No. 60/638,968, filed on Dec. 23, 2004.

(51) Int. Cl.
C07D 401/02 (2006.01)
A61K 31/44 (2006.01)

(52) U.S. Cl. ............ 514/253.04; 514/309; 514/312; 514/341; 544/331; 546/141; 546/153; 546/275.4

(58) Field of Classification Search .................. None
See application file for complete search history.

(56) References Cited

U.S. PATENT DOCUMENTS

| | | | |
|---|---|---|---|
| 3,528,980 A | 9/1970 | Islip | |
| 3,818,024 A | 6/1974 | Krenzer | |
| 3,939,122 A | 2/1976 | Merten et al. | |
| 3,949,002 A | 4/1976 | Feasey et al. | |
| 4,093,624 A | 6/1978 | Revankar et al. | |
| 4,296,237 A | 10/1981 | Cragoe, Jr. et al. | |
| 4,366,189 A | 12/1982 | Burdeska et al. | |
| 4,432,992 A | 2/1984 | Cragoe, Jr. et al. | |
| 4,525,450 A | 6/1985 | Itoh et al. | |
| 4,816,454 A | 3/1989 | Zoller et al. | |
| 4,853,397 A * | 8/1989 | Sirrenberg et al. | 514/364 |
| 5,103,014 A | 4/1992 | Musser et al. | |
| 5,162,360 A | 11/1992 | Creswell et al. | |
| 5,319,099 A | 6/1994 | Kamata et al. | |
| 5,494,925 A | 2/1996 | Court et al. | |
| 5,621,010 A | 4/1997 | Sueda et al. | |
| 5,721,231 A | 2/1998 | Moriwaki et al. | |
| 5,811,456 A | 9/1998 | Seman et al. | |
| 6,020,357 A | 2/2000 | Pinto et al. | |
| 6,080,763 A | 6/2000 | Regan et al. | |
| 6,197,599 B1 | 3/2001 | Chin et al. | |
| 6,235,786 B1 | 5/2001 | Dai et al. | |
| 6,294,573 B1 | 9/2001 | Curtin et al. | |
| 6,297,261 B1 | 10/2001 | Christophersen et al. | |
| 6,319,921 B1 | 11/2001 | Cirillo et al. | |
| 6,410,254 B1 | 6/2002 | Finer et al. | |
| 6,500,628 B1 | 12/2002 | Robison | |
| 6,525,046 B1 | 2/2003 | Cirillo et al. | |
| 6,645,990 B2 | 11/2003 | Askew et al. |
| 6,916,924 B2 | 7/2005 | Tan et al. |
| 7,030,128 B2 | 4/2006 | Blackaby et al. |
| 7,135,550 B2 | 11/2006 | Come et al. |
| 7,144,911 B2 | 12/2006 | Flynn et al. |
| 7,202,257 B2 | 4/2007 | Flynn et al. |
| 7,211,575 B2 | 5/2007 | Moss et al |
| 7,342,037 B2 | 3/2008 | Flynn et al. |
| 7,531,566 B2 | 5/2009 | Flynn et al. |
| 2002/0058678 A1 | 5/2002 | Cirillo et al. |
| 2003/0060455 A1 | 3/2003 | Moss et al. |
| 2003/0207870 A1 | 11/2003 | Dumas et al. |
| 2003/0232865 A1 | 12/2003 | Cirillo et al. |
| 2004/0043388 A1 | 3/2004 | Come et al. |
| 2004/0157827 A1 | 8/2004 | Pevarello et al. |
| 2004/0171075 A1 | 9/2004 | Flynn et al. |
| 2004/0180906 A1 | 9/2004 | Flynn et al. |
| 2004/0229937 A1 | 11/2004 | Dumas et al. |
| 2005/0014753 A1 | 1/2005 | Ding et al. |
| 2005/0165024 A1 | 7/2005 | Milanov et al. |
| 2005/0165031 A1 | 7/2005 | Grotzfeld et al. |
| 2005/0192314 A1 | 9/2005 | Mehta et al. |
| 2005/0197371 A1 | 9/2005 | Milanov et al. |
| 2005/0267182 A1 | 12/2005 | Milanov et al. |
| 2005/0288286 A1 | 12/2005 | Flynn et al. |
| 2007/0037794 A1 | 2/2007 | Ungashe et al. |
| 2007/0078121 A1 | 4/2007 | Flynn et al. |
| 2007/0155764 A1 | 7/2007 | Lang et al. |
| 2007/0191336 A1 | 8/2007 | Flynn et al. |

(Continued)

FOREIGN PATENT DOCUMENTS

DE      4343831      6/1995

(Continued)

OTHER PUBLICATIONS

Wu et al., Toxicology, 236, pp. 1-6, 2007.*
El-Feky et al, Pharmazie (1996), 51(8), 540-543.*
Puglisi et al, European Journal of Medicinal Chemistry (1989), 24(3), 277-85.*
U.S. Appl. No. 11/721,026, filed Nov. 2, 2008, Flynn et al.
U.S. Appl. No. 12/268,997, filed Nov. 11, 2008, Flynn et al.
"Additions and Corrections," Journal of Medicinal Chemistry, 32(12):2583 (1989).
"NHLBI LBC Computational Biophysics Section," CHARMM Documentation Index, http://www.lobos.nih.gov/Charmm/chmdoc.html, printed Mar. 4, 2005 (1 page).
"Trilateral Project WM4—Comparative Studies in New Technologies: Report on Comparative Study on Protein 3-Dimensional (3-D) Structure Related Claims—ANNEX 3: Comments of the USPTO." Vienna, Austria, Nov. 4-8, pp. 58-79 (2002).
Aklilu, F., et al., "Increased PTHRP Production by a Tyrosine Kinase Oncogene, Tpr-Met: Rose of the Ras Signaling Pathway," The American Physiological Society, pp. E277-E283 (1996).

(Continued)

Primary Examiner — Zinna Northington Davis
(74) Attorney, Agent, or Firm — Cooley LLP

(57) ABSTRACT

Novel compounds and methods of using those compounds for the treatment of inflammatory conditions, hyperproliferative diseases, cancer, and diseases characterized by hyper-vascularization are provided. In a preferred embodiment, modulation of the activation state of p38 kinase protein, abl kinase protein, bcr-abl kinase protein, braf kinase protein, VEGFR kinase protein, or PDGFR kinase protein comprises the step of contacting said kinase protein with the novel compounds.

8 Claims, 1 Drawing Sheet

U.S. PATENT DOCUMENTS

| | | |
|---|---|---|
| 2008/0045531 A1 | 2/2008 | Flynn et al. |
| 2008/0045706 A1 | 2/2008 | Flynn et al. |
| 2008/0090856 A1 | 4/2008 | Flynn et al. |
| 2008/0113967 A1 | 5/2008 | Flynn et al. |
| 2008/0132506 A1 | 6/2008 | Flynn et al. |
| 2008/0187978 A1 | 8/2008 | Flynn et al. |
| 2008/0220497 A1 | 9/2008 | Flynn et al. |
| 2008/0248487 A1 | 10/2008 | Flynn et al. |
| 2008/0248548 A1 | 10/2008 | Flynn et al. |
| 2009/0069310 A1 | 3/2009 | Flynn et al. |
| 2009/0075986 A1 | 3/2009 | Flynn et al. |
| 2009/0105230 A1 | 4/2009 | Flynn et al. |
| 2009/0137021 A1 | 5/2009 | Flynn et al. |
| 2009/0312349 A1 | 12/2009 | Flynn et al. |

FOREIGN PATENT DOCUMENTS

| | | |
|---|---|---|
| EP | 0021228 | 1/1981 |
| EP | 0025232 | 3/1981 |
| EP | 0661276 | 7/1995 |
| EP | 0692483 | 1/1996 |
| EP | 0739884 | 10/1996 |
| EP | 0816329 | 1/1998 |
| EP | 0867435 | 9/1998 |
| EP | 0927555 | 7/1999 |
| EP | 928790 | 7/1999 |
| EP | 0956855 | 11/1999 |
| EP | 1281399 | 2/2003 |
| FR | 2337554 | 8/1977 |
| FR | 2396549 | 2/1979 |
| GB | 971307 | 9/1964 |
| GB | 1127875 | 9/1968 |
| GB | 1410279 | 10/1975 |
| GB | 2220206 | 1/1990 |
| JP | 59015247 | 1/1984 |
| JP | 59177557 | 10/1984 |
| JP | 01007804 | 1/1989 |
| JP | 9221476 | 8/1997 |
| JP | 11209350 | 8/1999 |
| JP | 2000275886 | 10/2000 |
| JP | 20012687 | 7/2002 |
| WO | WO 91/19708 | 12/1991 |
| WO | WO 92/08693 | 5/1992 |
| WO | WO 94/18176 | 8/1994 |
| WO | WO 94/21617 | 9/1994 |
| WO | WO 94/24095 | 10/1994 |
| WO | WO 95/15954 | 6/1995 |
| WO | WO 95/29902 | 11/1995 |
| WO | WO 95/34540 | 12/1995 |
| WO | WO 96/16046 | 5/1996 |
| WO | WO 96/19477 | 6/1996 |
| WO | WO 97/34900 | 9/1997 |
| WO | WO 97/40028 | 10/1997 |
| WO | WO 98/22103 | 5/1998 |
| WO | WO 98/37079 | 8/1998 |
| WO | WO 98/52558 | 11/1998 |
| WO | WO 99/15164 | 4/1999 |
| WO | WO 99/23091 | 5/1999 |
| WO | WO 99/23093 | 5/1999 |
| WO | WO 99/32106 | 7/1999 |
| WO | WO 99/32110 | 7/1999 |
| WO | WO 99/32111 | 7/1999 |
| WO | WO 99/32455 | 7/1999 |
| WO | WO 99/37622 | 7/1999 |
| WO | WO 99/59959 | 11/1999 |
| WO | WO 00/06550 | 2/2000 |
| WO | WO 00/07980 | 2/2000 |
| WO | WO 00/18738 | 4/2000 |
| WO | WO 00/21927 | 4/2000 |
| WO | WO 00/41698 | 7/2000 |
| WO | WO 00/42012 | 7/2000 |
| WO | WO 00/43384 | 7/2000 |
| WO | WO 00/55139 | 9/2000 |
| WO | WO 00/59506 | 10/2000 |
| WO | WO 01/12621 | 2/2001 |
| WO | WO 01/14372 | 3/2001 |
| WO | WO 01/74771 | 10/2001 |
| WO | WO 01/96298 | 12/2001 |
| WO | WO 02/14291 | 2/2002 |
| WO | WO 02/14311 | 2/2002 |
| WO | WO 02/28835 | 4/2002 |
| WO | WO 02/32872 | 4/2002 |
| WO | WO 02/34727 | 5/2002 |
| WO | WO 02/060869 | 8/2002 |
| WO | WO 02/060876 | 8/2002 |
| WO | WO 02/062763 | 8/2002 |
| WO | WO 02/070662 | 9/2002 |
| WO | WO 03/005999 | 1/2003 |
| WO | WO 03/037891 | 5/2003 |
| WO | WO 03/053368 | 7/2003 |
| WO | WO 03/059373 | 7/2003 |
| WO | WO 03/068223 | 8/2003 |
| WO | WO 03/068229 | 8/2003 |
| WO | WO 03/072577 | 9/2003 |
| WO | WO 03/084539 | 10/2003 |
| WO | WO 03/099771 | 12/2003 |
| WO | WO 2004/004720 | 1/2004 |
| WO | WO 2004/056783 | 7/2004 |
| WO | WO 2004/060306 | 7/2004 |
| WO | WO 2004/061084 | 7/2004 |
| WO | WO 2004/078128 | 9/2004 |
| WO | WO 2004/089286 | 10/2004 |
| WO | WO 2004/113352 | 12/2004 |
| WO | WO 2005/002673 | 1/2005 |
| WO | WO 2005/048948 | 6/2005 |
| WO | WO 2005/051366 | 6/2005 |
| WO | WO 2005/110994 | 11/2005 |
| WO | WO 2006/014290 | 2/2006 |
| WO | WO 2006/028958 | 3/2006 |
| WO | WO 2006/071940 | 7/2006 |
| WO | WO 2006/081034 | 8/2006 |
| WO | WO 2007/008917 | 1/2007 |
| WO | WO 2007/076473 | 7/2007 |
| WO | WO 2008/046003 | 4/2008 |
| WO | WO 2008/131276 | 10/2008 |

OTHER PUBLICATIONS

Albericio, F., et al., "Synthesis of a Sulfahydantoin Library," J. Comb. Chem., 3:290-300 (2001).

Almerico, A. M., et al., "On the Preparation of 1-aryl-2-heteroaryl- and 2-aryl-1-heteroaryl-pyrroles as Useful Building Blocks for Biologically Interesting Heterocycles," ARKIVOC, Rudy Abramovitch Issue, pp. 129-142 (2001).

Anzai, K., et al., "Alkyl- and Arylthiation of Uracil and Indole," J. Heterocyclic Chem., 16:567-569 (1979).

Askew, B., et al., "Molecular Recognition with Convergent Functional Groups. 6. Synthetic and Structural Studies with a Model Receptor for Nucleic Acid Components," J. Am. Chem., 111:1082-1090 (1989).

Bais, R., et al., "Inhibition of Endogenous Oxalate Production: Biochemical Considerations of the Roles of Glycollate Oxidase and Lactate Dehydrogenase," Clinical Science, 76:303-309 (1989).

Baker, B. R., et al., "Irreversible Enzyme Inhibitors. 188. Inhibition of Mammalian Thymidine Phosphorylase," Journal of Medicinal Chemistry, 14:612-616 (1971).

Barker, S. C., et al., "Characterization of pp60$^{c\text{-}src}$ Tyrosine Kinase Activities Using a Continuous Assay: Autoactivation of the Enzyme is an Intermolecular Autophosphorylation Process," Biochemistry, 35:14843-14851 (1995).

Bausch, M. J., et al., "Proton-Transfer Chemistry of Urazoles and Related Imides, Amides, and Diacyl Hydrazides," J. Org. Chem., 56:5643-5651 (1991).

Benvenuti, M., et al., "Crystallization of Soluble Proteins in Vapor Diffusion for X-Ray Crystallography," Nature Protocols, 2(7):1633-1651 (2007).

Bosca, L., et al., "Circular Dichroism Analysis of Ligand-Induced Conformational Changes in Protein Kinase C," Biochem J., 290:827-832 (1993).

Boschelli, D., et al., "4-Anilino-3-quinolinecarbonitriles: An Emerging Class of Kinase Inhibitors," Current Topics in Medicinal Chemistry 2:1051-1063 (2002).

Le Bourdonnec, B., et al., "Synthesis and Pharmacological Evaluation of New Pyrazolidine-3,5-diones as AT$_1$ Angiotensin II Receptor Antagonists," J. Med. Chem., 43:2685-2697 (2000).

Boyer, S. "Small Molecule Inhibitors of KDR (VEGFR-2) Kinase: An Overview of Structure Activity Relationships," Current Topics in Medicinal Chemistry, 2:973-1000 (2002).

Brady, G. P., et al., "Fast Prediction and Visualization of Protein Binding Pockets with PASS." Journal of Computer-Aided Molecular Design, 14:383-401 (2000).

Brasher, B., et al., "c-Abul has High Intrinsic Tyrosine Kinase Activity that is Stimulated by Mutation of the Src Homology 3 Domain and by Autophosphorylation at Two Distinct Regulatory Tyrosines," Journal of Biological Chemistry, 275:35631-35637 (2000).

Bullock, W., et al., "Prospects for Kinase Activity Modulators in the Treatment of Diabetes and Diabetic Complications," Current Topics in Medicinal Chemistry, 2:915-938 (2002).

Byron, D. J., et al., "The Synthesis of some Substituted Biphenyl-4-carboxylic Acids, 4-Biphenylylacetic Acids, and 4-Aminobiphenyls," J. Chem. Soc. (C), Organic, pp. 840-845 (1966).

Cardillo, G. et al., "Sulle 1,2-difenil-3,5-dichetopirazolidine," Gazz. Chim., Ital., 9:973-985 (1966)—Italian Language—English Summary.

Chen, F. et al., "Biochemical Evidence for the Autophosphorylation and Transphosphorylation of Transforming Growth Factor β Receptor Kinases," Proc. Natl. Acad. Sci. USA, 92:1565-1569 (1995).

Cheng, S., et al., "Novel Solution Phase Strategy for the Synthesis of Chemical Libraries Containing Small Organic Molecules," J. Am. Chem. Soc., 118:2567-2573 (1996).

Cheng, H., et al., "Synthesis and SAR of Heteroaryl-phenyl-substituted Pyrazole Derivatives as Highly Selective and Potent Canine COX-2 Inhibitors," Bioorganic & Medicinal Chemistry Letters, 16:2076-2080 (2006).

Chu, Y-H, et al., "Using Affinity Capillary Electrophoresis to Determine Binding Stoichiometries of Protein-Ligand Interactions," Biochemistry, 33:10616-10621 (1994).

Cirillo, P., et al. "The Non-Diaryl Heterocycle Classes of p38 MAP Kinase Inhibitors," Current Topics in Medicinal Chemistry, 2:1021-1035 (2002).

Closier, M. D., et al., "Nitrofuryl Heterocyclics. 1", Journal of Medicinal Chemistry, 13(4):638-640 (1970).

Cockerill, G. S., et al., "Small Molecule Inhibitors of the Class 1 Receptor Tyrosine Kinase Family," Current Topics in Medicinal Chemistry, 2:1001-1010 (2002).

Colton, I., et al., "Affinity Capillary Electrophoresis: A Physical-Organic Tool for Studying Interactions in Biomolecular Recognition," Electrophoresis, 19:367-382 (1998).

Cortes, J., et al., "Results of Imatinib Mesylate Therapy in Patients with Refractory or Recurrent Acute Myeloid Leukemia, High-Risk Myelodysplastic Syndrome, and Myeloproliferative Disorders," Cancer, 97(11):2760-2766 (2003).

Cross, D., et al., "Inhibition of Glycogen Synthase Kinase-3 by Insulin Mediated by Protein Kinase B," Nature, 378:785-789 (1995).

Dajani, R., et al., "Crystal Structure of Glycogen Synthase Kinas 3β: Structural Basis for Phosphate-Primed Substrate Specificity and Autoinhibition," Cell, 105:721-732 (2001).

Dajani, R., et al., "Structural Basis for Recruitment of Glycogen Synthase Kinase 3β to the Axin-APC Scaffold Complex," The EMBO Journal, 22(3):494-501 (2003).

Daley, G., et al., "Induction of Chronic Myelogenous Leukemia in Mice by the P210$^{bcr/abl}$ Gene of the Philadelphia Chromosome," Science, 247:824-830 (1990) (8 pgs).

Davis, R., et al., "Iterative Size-Exclusion Chromatography Coupled with Liquid Chromatographic Mass Spectrometry to Enrich and Identify Tight-Binding Ligands from Complex Mixtures," Tetrahedron, 55:11653-11667 (1999).

de Boer, B., et al., "Synthesis and Characterization of Conjugated Mono- and Dithiol Oligomers and Characterization of Their Self-Assembled Monolayers," Langmuir, 19:4272-4284 (2003).

de Silva, MV, et al., "Gastrointestinal Stromal Tumors (GIST): C-kit Mutations, CD117 Expression, Differential Diagnosis and Targeted Cancer Therapy with Imatinib," Pathology Oncology Research, 9(1):13-19 (2003).

Deng, Z., et al., "Expression, Characterization, and Crystallization of the Pyrophosphate-Dependent Phosphofructo-1-Kinase of *Borrelia burgdorferi*," Archives of Biochemistry and Biophysics, 371(2):326-331 (1999).

Dess, D., et al., "A Useful 12-I-5 Triacetoxyperiodiane (the Dess-Martin Periodiane) for Selective Oxidation of Primary or Secondary Alcohols and a Variety of Related 12-I-5 Species," J. Am. Chem., Soc., 113:7277-7287 (1991).

Dumas, J., "Preface," Current Topics in Medicinal Chemistry (2002) (1 Page).

Dumas, J., "Protein Kinase Inhibitors: Emerging Pharmacophores," Exp. Opin. Ther. Patents, 11:405-429 (2001).

Dumas, J., et al., "Discovery of a New Class of p38 Kinase Inhibitors," Bioorganic & Medicinal Chemistry Letters, 10:2047-2050 (2000).

Dumas, J., et al., "Recent Developments in the Discovery of Protein Kinase Inhibitors from the Urea Class," Current Opinion in Drug Discovery & Development, 7(5):600-616 (2004).

Dumas, J. et al., "1-Phenyl-5-PyrazolylUreas: Potent and Selective p38 Kinase Inhibitors," Bioorganic & Medicinal Chemistry Letters, 10: 2051-2054 (2000).

Ettmayer, P., et al., "Lessons Learned from Marketed and Investigational Prodrugs," Journal of Medicinal Chemistry, 47(10):2393-2404 (2004).

Ewing, T., "Critical Evaluation of Search Algorithms for Automated Molecular Docking and Database Screening," Journal of Computational Chemistry, 18(9):1175-1189 (1997).

Farooqui, A., et al., "Interactions Between Neural Membrane Glycerophospholipid and Sphingolipid Mediators: A Recipe for Neural Cell Survival or Suicide," Journal of Neuroscience Research, 85:1834-1850 (2007).

Fathalla, O. A., "Synthesis of New Pyrazolo[1,5-a]pyrimidine Derivative Using 5-Aminouracil and Ketene Dithiacetal," Arch Pharm Res, 22(6):571-574 (1999).

Fathalla, O. A., et al., "Synthesis of New Uracil-5-Sulfonamide Derivatives and Immuno-Stimulatory Effect of a Chemically Modified Hemolymph of *Biomphalaria alexandrina* on Schistosoma Manosi Infected Mice," Arch Pharm Res., 26(5):358-366, 2003.

Fathalla, O. A., et al., "Synthesis of New Uracil-5-Sulphonamide-*p*-Phenyl Derivatives and Their Effect on *Biomphalaria alexandrina* Snail's Nucleoproteins," Arch. Pharm. Res., 23(2):128-138 (2000).

Flatt, A., et al., "Synthesis of Thiol Substituted Oligoanilines for Molecular Device Candidates," Tetrahedron Letters, 44:6699-6702 (2003).

Fletcher, C., et al., "Diagnosis of Gastrointestinal Stromal Tumors: A Consensus Approach," Human Pathology 33(5):459-465 (2002).

Frame, S., et al., "A Common Phosphate Binding Site Explains the Unique Substrate Specificity of GSK3 and Its Inactivation by Phosphorylation," Molecular Cell, 7:1321-1327 (2001).

Furyua, S., et al., "Addition of 4-Ethoxyimidazoles to Dimethyl Acetylenedicarboxylate and Transformation of the Adducts to Pyrimidian-5-yl Acetates," Chem. Pharm. Bull., 36(5):1669-1675 (1988).

Garcia-Tellado, F., et al., "Molecular Recognition in the Solid Waste State: Controlled Assembly of Hydrogen-Bonded Molecular Sheets," J. Am. Chem. Soc., 113:9265-9269 (1991).

Gishizky, M., et al., "Efficient Transplantation of BCR-ABL-Induced Chronic Myelogenous Leukemia-Like Syndrome in Mice," Proceedings of the National Academy of Sciences of the United States of America, 90(8):3755-3759 (1993) (6 pages).

Greene, T., et al., "Chapter 7: Protection for the Amino Group," in Protective Groups in Organic Synthesis, Third Edition, pp. 494-653 (1999).

Griffith, W., et al., "TPAP: Tetra-n-propylammonium Perruthenate, A Mild and Convenient Oxidant for Alcohols," Aldrichimica Acta, 23(1):13-19 (1990).

Guzel, Y., "Investigation of the Relationship Between the Inhibitory Activity of Glycolic Acid Oxidase (GAO) and its Chemical Structure: Electron-Topological Approach," Journal of Molecular Structure, 366:131-137 (1996).

Haar, E., et al., "Structure of GSK3β Reveals a Primed Phosphorylation Mechanism," Nature Structural Biology, 8(7):593-596 (2001).

Haesslein, J., et al., "Recent Advances in Cyclin-Dependent Kinase Inhibition. Purine-Based Derivatives as Anti-Cancer Agents. Roles and Perspectives for the Future," Current Topics in Medicinal Chemistry, 2:1037-1050 (2002).

Heegaard, N., et al., "Affinity Capillary Electrophoresis: Important Application Areas and Some Recent Developments," Journal of Chromatography B, 715:29-54 (1998).

Honda, S., et al., "Determination of the Association Constant of Monovalent Mode Protein-Sugar Interaction by Capillary Zone Electrophoresis," Journal of Chromatography, 597:377-382 (1992).

Hu, S., et al., "Capillary Electrophoresis for the Analysis of Biopolymers," Anal., Chem., 74:2833-2850 (2002).

Huang, M., et al., "Inhibition of Nucleoside Transport by Protein Kinase Inhibitors," The Journal of Pharmacology and Experimental Therapeutics, 304(2):753-760 (2003).

Hubbard, S., "Crystal Structure of the Activated Insulin Receptor Tyrosine Kinase in Complex with Peptide Substrate and ATP Analog," The EMBO Journal, 16(18):5573-5581 (1997).

Hubbard, S., et al., "Crystal Structure of the Tyrosine Kinase Domain of the Human Insulin Receptor," Nature, 374:746-754 (1994).

Hughes, K., et al., "Modulation of the Glycogen Synthase Kinase-3 Family by Tyrosine Phosphorylation," The EMBO Journal, 12(2):803-808 (1993).

Huse, M., et al., "Crystal Structure of the Cytoplasmic Domain of the Type I TGFβ Receptor in Complex with FKBP12," Cell, 96:425-436 (1999).

Huse, M., et al., "The Conformational Plasticity of Protein Kinases," Cell, 109:275-282 (2002).

Huse, M., et al., "The TGFβ Receptor Activation Process: An Inhibitor- to Substrate-Binding Switch," Molecular Cell, 8:671-682 (2001).

Igarashi, Y., et al., "Antimicrobial Activities of 2-arylthio-*N*-alkylmaleimides," Journal of Industrial Microbiology, 9:91-96 (1992).

International Human Genome Sequencing Consortium, "Initial Sequencing and Analysis of the Human Genome," Nature, 409:860-921 (2001).

Ishida, T., et al., "Molecular Arrangement and Electrical Conduction of Self-Assembled Monolayers Made from Terphenyl Thiols," Surface Sciences, 514:187-193 (2002).

Islip, P., et al., "Nitrofuryl Heterocyclics. 3," Journal of Medicinal Chemistry, 16(11):1309-1310 (1973).

Jackson, P., et al., "N-Terminal Mutations Activate the Leukemogenic Potential of the Myristoylated form of *c-abl*," The EMBO Journal, 8(2):449-456 (1989).

Jackson, P., et al., "Pyridinylimidazole Based p38 MAP Kinase Inhibitors," Current Topics in Medicinal Chemistry, 2:1011-1020 (2002).

Jiang, F., et al., ""Soft Docking:" Matching of Molecular Surface Cubes," J. Mol. Biol., 219:79-102 (1991).

Jiang, Y., et al., "Synthesis and SAR Investigations for Novel Melanin-Concentrating Hormone 1 Receptor ($MCH_1$) Antagonists Part 1. The Discovery of Arylacetamides as Viable Replacements for the Dihydropyrimidione Moiety of an HTS Hit," J. Med. Chem., 50:3870-3882 (2007).

Johnson, W. C., "Circular Dichroism Spectroscopy and the Vacuum Ultraviolet Region," Ann. Rev. Phys. Chem., 29:93-114 (1978).

Johnson, W. C., "Protein Secondary Structure and Circular Dichroism: A Practical Guide," Proteins: Structure, Function, and Genetics, 7:205-214 (1990).

Johnson, B. W., et al., "An Evaluation of the Effect of Light Stabilisers on the Exterior Durability of Polyester Powder Coatings for the Architectural Market," Surface Coatings International, 3:134-141 (1999).

Johnson, C.R., et al., "The Stereochemistry of Oxidation at Sulfur Oxidation of 2-Thiabicyclo[2.2.1]Heptane," Tetrahedron, 25:5649-5653 (1969).

Kallander L., et al., "4-Aryl-1,2,3-triazole: A Novel Template for a Reversible Methionine Aminopeptidase 2 Inhibitor, Optimized to Inhibit Angiogenesis in Vivo," J. Med. Chem, 2005, 48, 5644-5647; American Chemical Society (2005); Published on web.

Katritzky, A., et al., "Novel Chromophoric Heterocycles Based on Maleimide and Naphthoquinone," J. Heterocyclic Chem., 26:885-892 (1989).

Kern, V., et al., "Synthese von Makromolekeln einheitlicher Größe.. II Mitt: Syntheses neuer Diol-oligo-urethane nach dem Duplikationsverfahren," Makromolekulara Chemie, 16:89-107 (1955)—English Summary (20 pages).

Kim, S., et al., "Solid Phase Synthesis of Benzamidine and Butylamine-Derived Hydantoin Libraries," Molecular Diversity, 3:129-132 (1998).

Klayman, D., et al., "The Reaction of S-Methiodide Derivatives of Activated Thioureas with Hydroxylic Compounds. A Novel Synthesis of Mercaptans," J. Org. Chem., 37(10):1532-1537 (1972).

Kleywegt, G., et al., "Detection, Delineation, Measurement and Display of Cavities in Macromolecular Structures," Acta Cryst, D50:178-185 (1994).

Koch, A., et al., "QSAR and Molecular Modelling for a Series of Isomeric X-Sulfanilamido-1-phenylpyrazoles," Quant. Struct. Act. Relat., 12:373-382 (1993).

Krasovitskii, B.M., et al., "Synthesis and Spectral-Luminescence Properties of Hetarylethylene Derivatives of 2,5-Diphenyloxazole and 2,5-Diphenyl-1,3,4-Oxadiazole", Khimiya Geterotsiklicheskikh Soedinenii, 5:617-621 (1982)—English Translation (10 pages).

Kuhn, P., et al., "The Genesis of High-Throughput Structure-Based Drug Discovery using Protein Crystallography," Analytical Techniques, Current Opinion in Chemical Biology, 6:704-710 (2002).

Kumar, S., et al., "P38 Map Kinases: Key Signaling Molecules as Therapeutic Targets for Inflammatory Diseases," Nature Reviews Drug Discovery, 2:717-726 (2003).

Kundrot, C. E., "Which Strategy for a Protein Crystallization Project," CMLS, Cell. Mol. Life Sci., 61:525-536 (2004).

Kundu, N., et al., "Depropargylation Under Palladium-Copper Catalysis: Synthesis of Diaryl Sulfides," Tetrahedron, 57:5885-5895 (2001).

Kurogi, Y., et al., "Discovery of Novel Mesangial Cell Proliferation Inhibitors Using a Three-Dimensional Database Searching Method," J. Med. Chem., 44:2304-2307 (2001).

Kwong, F., et al., "A General, Efficient, and Inexpensive Catalyst System for the Coupling Aryl Iodides and Thiols," Organic Letters, 4(20):3517-3520 (2002).

Laskowski, R., "SURFNET: A Program for Visualizing Molecular Surfaces, Cavities, and Intermolecular Interactions," Journal of Molecular Graphics, 13:323-330 (1995).

Leca, D., et al., "A New Practical One-Pot Access to Sulfonimidates," Organic Letters, 4(23):4093-4095 (2002).

Lefevre, G., et al., "Roles of Stem Cell Factor/c-Kit and Effects of Glivecâ® /STI571 in Human Uveal Melanoma Cell Tumorigenesis," Journal of Biological Chemistry, 279(30):31769-31779 (2004).

Lesort, M., et al., "Insulin Transiently Increases Tau Phosphorylation: Involvement of Glycogen Synthase Kinase-3β and Fyn Tyrosine Kinase," Journal of Neurochemistry, 72(2):576-584 (1999).

Leung, C., et al., "The Difluoromethylensulfonic Acid Groups as a Monoanionic Phosphate Surrogate for Obtaining PTP1 B Inhibitors," Bioorganic & Medicinal Chemistry, 10:2309-2323 (2002).

Li, Q., et al., "Targeting Serine/Threonine Protein Kinase B/Akt and Cell-cycle Checkpoint Kinases for Treating Cancer," Current Topics in Medicinal Chemistry, 2:939-971 (2002).

Li, S., et al., "The P190, P210, and P230 Forms of the *BCR/ABL* Oncogene Induce a Similar Chronic Myeloid Leukemia-like Syndrome in Mice but Have Different Lymphoid Leukemogenic Activity," J. Exp. Med., 189(9):1399-1412 (1999).

Link, P.A., et al., "Synthesis of 8-Substituted 5-Deazaflavins," J. Heterocyclic Chem, 22:841-848 (1985).

Lipinski, C., et al., "Experimental and Computational Approaches to Estimate Solubility and Permeability in Drug Discovery and Development Settings," Advanced Drug Delivery Reviews, 23:3-25 (1997).

Lohse O., et al., "The Palladium Catalysed Suzuki Coupling of 2- and 4-Chloropyridines," Synlett 1999, No. 1, 45-48, Thieme Stuttgart, New York (1999).

Loren, J., et al., "*N*H-1,2,3-Triazoles from Azidomethyl Pivalate and Carbamates: Base-Labile N-Protecting Groups," SYNLETT, 18:2847-2850 (2005).

Lorenzi, P., et al., "Amino Acid Ester Prodrugs of 2-Bromo-5,6-dichloro-1-(β-D-ribofuranosyl)benzimidazole Enhance Metabolic Stability in Vitro and in Vivo," Journal of Pharmacology and Experimental Therapeutics, 314(2):883-890 (2005).

Lowinger, T., et al., "Design and Discovery of Small Molecules Targeting Raf-1 Kinase," Current Pharmaceutical Design, 8:2269-2278 (2002) (11 pages).

Ma, P., et al., "*c-MET* Mutational Analysis in Small Cell Lung Cancer: Novel Juxtamembrane Domain Mutations Regulating Cytoskeletal Functions," Cancer Research, 63:6272-6281 (2003).

Ma, P., et al., "c-Met: Structure, Functions and Potential for Therapeutic Inhibition," Cancer and Metastasis Reviews, 22:309-325 (2003).

Mallakpour, S., et al., "Uncatalyzed Polymerization of Bistriazolinediones with Electron-Rich Aromatic Compounds via Electrophilic Aromatic Substitution," Journal of Polymer Science: Part A: Polymer Chemistry, 27:217-235 (1989).

Mamaev, V. P., et al., "Synthesis of 2,5'-Bipyrimidines from Substituted 5-Cyanopyrimidines," Khimiya Geterotsiklicheskikh Soedinenni, 24(3):371-375- (1988)—English Translation.

Smith, M., et al., March's Advanced Organic Chemistry: Reactions, Mechanisms, and Structure, Fifth Edition, Wiley-Interscience Publication (2001) (4 pages).

March, J., et al., "Tautomerism," from March's Advanced Organic Chemistry, 4th Edition, Wiley-Interscience, pp. 69-74, Jun. 2001.

Martinez, A., et al., "First Non-ATP Competitive Glycogen Synthase Kinase 3β (GSK-3β) Inhibitors: Thiadizolidinones (TDZD) as Potential Drugs for the Treatment of Alzheimers Disease," J. Med. Chem., 45(2002)1292-1299 (2002).

Mattsson, P., et al., "Six X-Linked Agammaglobulinemia-Causing Missense Mutations in the Src Homology 2 Domain of Bruton's Tyrosine Kinase: Phosphotyrosine-Binding and Circular Dichroism Analysis," Journal of Immunology, pp. 4170-4177 (2000).

McPherson, A., "Current Approaches to Macromolecular Crystallization," Eur. J. Biochem, 189:1-23 (1990).

Medebielle, M., et al., "A Convenient Synthesis of Perfluoroalkylated and Fluorinated-Aryl Nitrogen Bases by Electrochemically Induced $S_{RN}1$ Substitution," J. Org. Chem., 61:1331-1340 (1996).

Medebielle, M., et al., "A New Convenient Synthesis of 5-Aryl Uracils Using $S_{RN}1$ Aromatic Nucleophilic Substitution," Tetrahedron Letters, 34(21):3409-3412 (1993).

Mikhaleva, M. A., et al., "Relative Reactivities of the Chlorine Atoms of 2,2',4-Trichloro4',5-Dipyrimidinyl in its Reaction with Piperidine," Khimiya Geterotsiklicheskikh Soedinenii, 6:821-826 (1979)—English Translation (12 pages).

Morris, G., et al., "Automated Docking of Flexible Ligands to Macromolecules," AutoDock Website, www.scripps.edu/mb/olson/doc/autodock/, printed Mar. 3, 2005 (3 pages).

Morris, G., et al., "Automated Docking Using a Lamarckian Genetic Algorithm and an Empirical Binding Free Energy Function," Journal of Computational Chemistry, 19(14):1639-1662 (1998).

Morstyn, G., et al., "Stem Cell Factor is a Potent Synergistic Factor in Hematopoiesis," Oncology, 51:205-214 (1994).

Moss, G. P., et al., Basic Terminology of Stereochemistry, Pure & Appl. Chem., (6812):2193-2222 (1996).

Muller, P., "Glossary of Terms Used in Physical Organic Chemistry," Pure & Appl. Chem., 66(5):1077-1184 (1994).

Muller, G., et al., "A General Synthesis of 4-Substituted 1,1-Dioxo-1,2,5-thiadiazolidin-3-ones Derived from a-Amino Acids," J. Org. Chem., 54:4471-473 (1989).

Murayama, T., et al., "JNK (c-Jun $NH_2$ Terminal Kinase) and p38 During Ischemia Reperfusion Injury in the Small Intestine," Transplantation, 81(9):1325-1330 (2006).

Mutlib, A., et al., "Disposition of 1-[3-(Aminomethyl)phenyl]-*N*-[3-fluoro-2'-(methylsulfonyl)-[1,1'-biphenyl]-4-yl]-3(trifluoromethyl)-1*H*-pyrazole-5-carboxamide (DPC 423) by Novel Metabolic Pathways. Characterization of Unusual Metabolites by Liquid Chromatography/Mass Spectrometry and NMR," Chem. Res. Toxicol., 15:48-62 (2002).

Mutlib, A., et al., "P450-Mediated Metabolism of 1-[3-(Aminomethyl)phenyl]-*N*-[3-fluoro-2'-(methylsulfonyl)-[1,1'-biphenyl]-4-yl]-3(trifluoromethyl)-1*H*-pyrazole-5-carboxamide (DCP 423) and its Analogues to Aldoximes. Characterization of Glutathione Conjugates of Postulated Intermediates Derived from Aloximes," Chem. Res. Toxicol., 15:63-75 (2002).

Nagano, M. et al. "Studies on Organic Sulfur Compounds. XIV. The Reaction of N-alkoxy-carbonyl-N'-(2-thiazolyl)thioureas with some oxidants." Chemical and Pharmaceutical Bulletin. vol. 21, No. 11, pp. 2408-2416. Nov. 1973.

Nagar, B., et al., "Crystal Structures of the Kinase Domain of c-Abl in Complex with the Small Molecule Inhibitors PD173955 and Imatinib (STI-571)," Cancer Research, 62:4236-4243 (2002).

Nagar, B., et al., "Structural Basis for the Autoinhibition of c-Abl Tyrosine Kinase," Cell, 112:859-871 (2003).

Nakopoulou, L., et al., "c-Met Tyrosine Kinase Receptor Expression is Associated with Abnormal β-catenin Expression and Favourable Prognostic Factors in Invasive Breast Carcinoma," Histopathology, 36:313-325 (2000).

Nantaka-Namirski, et al., "Condensation Reaction of Ethyl (4-Uracil)-Acetate with Ethyl Orthoformate," ACTA Polon. Pharm XXVII, 28(5):455-463 (1971).

National Academy of Sciences, "Abstracts of Papers Presented at the Autumn Meeting, Nov. 14-16, 1960," Science, 132:1488-1501 (1960) (15 pages).

Nicolaou, K. C., et al.,"Molecular Design and Chemical Synthesis of a Highly Potent Epothilone," ChemMedChem, 1:41-44 (2006).

Nikolaev, A. V., et al., "Solubility Polytherm in the System $HNO_3$-$H_2O$-$(C_4H_9O)PO(C_4H_9)_2$," Doklady Akademii Nauk SSSR, 160(4):841-844 (1965)—English Translation.

Nofal, Z. M., et al., "Synthesis of Novel Uracil-5-Sulphonamide Derivatives of Possible Biological Activity," Egypt J. Chem., 33(4):375-380 (1990).

O'Dell, J., et al., "Treatment of Rheumatoid Arthritis with Methotrexate Alone, Sulfasalazine and Hydroxychloroquine, or a Combination of All Three Medications," New England J. Med., 334(20):1287-1291(1996).

O'Neill, L., "Targeting Signal Transduction as a Strategy to Treat Inflammatory Diseases," Nature Review Drug Discovery, Published Online Jun. 9, 2006, www.nature.com/reviews/drugdisc (15 pages).

Okano, M., et al., "*o*-Bromophenylzinc Compound: A Readily Available and Efficient Synthetic Equivalent of *o*-Phenylene 1-Anion 2-Cation," Tetrahedron Letters 39:3001-3004 (1998).

Okishio, N., et al., "Differential Ligand Recognition by the Src and Phosphatidylinositol 3-Kinase Src Homology 3 Domains: Circular Dichroism and Ultraviolet Resonance Raman Studies," Biochemistry, 42:208-216 (2003).

Okishio, N., et al., "Identification of Tyrosine Residues Involved in Ligand Recognition by the Phosphatidylinositol 3-Kinase Src Homology 3 Domain: Circular Dichroism and UV Resonance Raman Studies," Biochemistry, 40:15797-15804 (2001).

Okishio, N., et al., "Role of the Conserved Acidic Residue Asp21 in the Structure of Phosphatidylinositol 3-Kinase Src Homolgy 3 Domain: Circular Dichroism and Nuclear Magnetic Resonance Studies," Biochemistry 40:119-129 (2001).

Parang, K., et al., "Mechanism-based Design of a Protein Kinase Inhibitor," Nature Structural Biology, 8(1):37-41 (2001).

Pargellis, C., et al., "Inhibition of p38 MAP Kinase by Utilizing a Novel Allosteric Binding Site," Nature Structural Biology, 9(4):268-272 (2002).

Park, M., et al., "Mechanism of *met* Oncogene Activation," Cell, 45:895-904 (1986).

Pearlman, D. A., et al., "Assisted Model Building with Energy Refinement," Amber Home Page, amber.scripts.edu (9 pages), 2005.

Pedersen, C., "The Preparation of Some N-Methyl-1,2,3-Triazoles," Acta Chimica Scandinavica, 13(5):888-892 (1959).

Peng, H., et al., "Identification of Novel Inhibitors of BCR-ABL Tyrosine Kinase via Virtual Screening," Bioorganic & Medicinal Chemistry Letters, 13:3693-3699 (2003).

Pereira, P., et al., "The Role of c-kit and Imatinib Mesylate in Uveal Melonoma," Journal of Carcinogenesis, 4:19 (2005) (8 pages).

Picard, J., et al., "Inhibitors of Acyl-CoA: Cholesterol *O*-Acyltrasferase. 17. Structure-Activity Relationships of Several Series of Compounds Derived from *N*-Chlorosulfonyl Isocyanate," J. Med. Chem., 39:1243-1252 (1996).

Pluk, H., et al., "Autoinhibition of c-Abl," Cell, 108:247-259 (2002).

Ponzetto, C., et al., "A Novel Recognition Motif for Phosphatidylinositol 3-Kinase Binding Mediates Its Association with the Hepatocyte Growth Factor/Scatter Factor Receptor," Molecular and Cellular Biology, 13(8):4600-4608 (1993).

Raimbault, C., et al., "Effects of pH and KCl on the Conformations of Creatine Kinase from Rabbit Muscle," Eur. J. Biochem., 234:570-578 (1995).

Rebek, J., et al. "Convergent Functional Groups: Synthetic and Structural Studies," J. Am. Chem. Soc., 107:7476-7481 (1985).

Rebek, J., et al., "Convergent Functional Groups. 2. Structure and Selectivity in Olefin Epoxidation with Peracids," J. Org. Chem., 51:1649-1653 (1986).

Reed, J., et al., "Circular Dichroic Evidence for an Ordered Sequence Ligand/Binding Site Interactions in the Catalytic Reaction of the cAMP-Dependent Protein Kinase," Biochemistry, 24:2967-2973 (1985).

Regan, J., et al., "Pyrazole Urea-Based Inhibitors of p38 MAP Kinase: From Lead Compound to Clinical Candidate," J. Med. Chem., 45:2994-3008 (2002).

Regan, J., et al., "Structure-Activity Relationships of the p38α MAP Kinase Inhibitor 1-(5-tert-Butyl-2-p-tolyl-2H-pyrazol-3-yl)-3-[4-(2-morpholin-4-yl-ethoxy)naph-thalen-1-yl]urea (BIRB 796)," J. Med. Chem., 46:4676-4686 (2003).

Rooney, C. S., et al., "Inhibitors of Gylcolic Acid Oxidase. 4-Substituted 3-Hydroxy-1H-pyrrole-2,5-dione Derivatives," J. Med. Chem., 26(5):700-714 (1983).

Roux, P., et al., "ERK and p38 MAPK-Activated Protein Kinases: a Family of Protein Kinases with Diverse Biological Functions," Microbiology and Molecular Biology Reviews, 68(2):320-344 (2004).

Rowley, J., "A New Consistent Chromosomal Abnormality in Chronic Myelogenous Leukemia Identified by Quinacrine Fluorescence and Giemsa Staining," Nature, 243:290-293 (1973).

Russell, M., et al., "3-[3-(Piperdin-1-yl)propyl]indoles as Highly Selective h5-HT$_{1D}$ Receptor," J. Med. Chem., 42:4981-5001 (1999).

Saiga, A., et al., "Consecutive Cross-Coupling of o-Phenylenedizinc Compound with Acyl and/or Aryl Halides in the Presence of Pd(0)-tris(2,4,6-trimethoxyphenyl)phosphine," Tetrahedron Letters, 41:4629-4632 (2000).

Sakamoto, T., et al., "Condensed Heteroaromatic Ring Systems. XIX. Synthesis and Reactions of 5-(Tributylstannyl)Isoxazoles," Tetrahedron, 47(28):5111-5118 (1991).

Sakuma, Y., et al., "c-kit Gene Mutations in Intracranial Germinomas," Cancer Sci, 95(9):716-720 (2004).

Satsangi, R.K., et al., "1-(4-Substituted-thiazol-2-yl)hydatoins as Anti-inflammatory and CNS-Active Agents," Pharmazie, 38:341-342 (1983).

Schiering, N., et al., "Crystal structure of the tyrosine kinase domanin of the hepatocyte growth factor receptor c-Met and its complex with the microbial alkaloid K-252a,", 2003.

Schindler, T., et al., "Structural Mechanism for STI-571 Inhibition of Abelson Tyrosine Kinase," Science, 289:1938-1942 (2000).

Schmidt, L., et al., "Germline and Somatic Mutations in the Tyrosine Kinase Domain of the MET proto-oncogene in Papillary Renal Carcinomas," Nature Genetics, 16:68-73 (1997).

Schmidt, L., et al., "Novel Mutations of the MET Proto-oncogene in Papillary Renal Carcinomas," Oncogene, 18:2343-2350 (1999).

Seimiya, H., et al., "Telomere Shortening and Growth Inhibition of Human Cancer Cells by Novel Synthetic Telomerase Inhibitors MST-312, MST-295, and MST-199," Molecular Cancer Therapeutics, 1:657-665 (2002).

Seminario, J., et al., "Theoretical Study of a Molecular Resonant Tunneling Diode," J. Am. Chem. Soc., 122:3015-3020 (2000).

Shah, J, et al., "Circular Dichroic Studies of Protein Kinase C and its Interactions with Calcium and Lipid Vesicles," Biochimica et Biophysica Acta, 1119:19-26 (1992).

Shi, X., et al., "Abnormal Diels-Alder Reaction of 5-Alkoxythiazoles with Highly Reactive Dienophiles; 4-Phenyl-3H-1,2,4-triazole-3,5(4H)-dione, Diethyl Azodicarboxylate, and Diethyl Oxomalonate," Bull. Chem. Soc. Jpn., 65:3315-3321 (1992).

Shinkai, S., et al., "Coenzyme Models, Part 45. Synthesis of Atropisomeric Flavins and their Novel Redox-induced Racemisation," J. Chem. Soc. Perkin Trans., pp. 313-319 (1988).

Shiozaki, S., et al., "Impaired Differentiation of Endocrine and Exocrine Cells of the Pancreas in Transgenic Mouse Expressing the Truncated Type II Activin Receptor," Biochimica et Biophysica Acta, 1450:1-11 (1999).

Stout, T. J., et al., "High-Throughput Structural Biology in Drug Discovery: Protein Kinases," Current Pharmaceutical Design, 10:1069-1082 (2004).

Sugden, P., et al., ""Stress-Responsive" Mitogen-Activated Protein Kinases (c-Jun N-Terminal Kinases and p38 Mitogen-Activated Protein Kinases) in the Myocardium," Circulation Research—Journal of the American Heart Association, 83:345-352 (1998).

Tanis, Q., et al., "Two Distinct Phosphorylation Pathways Have Additive Effects on Abl Family Kinase Activation," Molecular and Cellular Biology, 23(11):3884-3896 (2003).

Teague, S., "Implications of Protein Flexibility for Drug Discovery," Nature Reviews, 2:527-541 (2003).

Tominaga, Y., et al., "General Model for Estimation of the Inhibition of Protein Kinases Using Monte Carlo Simulations," J. Med. Chem., 47:2534-2549 (2004).

Tremblay, M., et al., "Efficient Solid-Phase Synthesis of Sulfahydantoins," J. Comb. Chem., 4:429-435 (2002).

Tsuzuki, Y., et al., "Synthesis and Structure-Activity Relationships of Novel 7-Substituted 1,4-Dihydro-4-oxo-1-(2-thiazolyl)-1,8-napthyridine-3-carboxylic Acids as Antitumor Agents. Part 2," J. Med. Chem., 47:2097-2109 (2004).

Van Etten, R., "Cycling, Stressed-Out and Nervous: Cellular Functions of c-Abl," Trends in Cell Biology, 9:179-186 (1999).

Venter, J. C., et al., "The Sequence of the Human Genome," Science, 291:1304-1351, Feb. 16, 2001; Erratum, Jun. 8, 2001 (49 pages).

Waetzig, G. H., et al., "Review Article: Mitogen-Activated Protein Kinases in Chronic Intestinal Inflammation—Targeting Ancient Pathways to Treat Modern Diseases," Aliment Pharmacol Ther, 18:17-32 (2003).

Wan, P., et al., "Mechanism of Activation of the RAF-ERK Signaling Pathway by Oncogenic Mutations of B-RAF," Cell, 116:855-867 (2004).

Welker, P., et al., "Glucocorticoid-Induced Modulation of Cytokine Secretion from Normal and Leukemic Human Myelomonocytic Cells," Int. Arch. Allergy Immunol, 109:110-115 (1996).

Wentland, M., et al., "3-Quinolinecarboxamides. A Series of Novel Orally-Active Antiherpetic Agents," J. Med. Chem., 36:1580-1596 (1993).

Wilson, K., et al., "The Structural Basis for the Specificity of Pyridinylimidazole Inhibitors of p38 MAP Kinase," Chemistry & Biology, 4(6):423-431 (1997).

Wilson, R. M., et el., "Laser-Jet Delayed Trapping: Electron-Transfer Trapping of the Photoenol from 2-Methylbenzophenone," J. Am. Chem. Soc., 109:4743-4745 (1987).

Wolter, M., et al., "Copper-Catalyzed Coupling of Aryl Iodides with Aliphatic Alcohols," Organic Letters, 4(6):973-976 (2002).

Wrana, J., et al., "Mechanism of Activation of the TGF-β Receptor," Nature, 370:341-347 (1994).

Wu, S., et al., "Discovery of a Novel Family of CDK Inhibitors with the Program LIDAEUS: Structual Basis for Ligand-Induced Disordering of the Activation Loop," Structure, 11:399-410 (2003).

Yang, J., et al., "Molecular Mechanism for the Regulation of Protein Kinase B/Akt by Hydrophobic Motif Phosphorylation," Molecular Cell, 9:1227-1240 (2002).

Yang, B., et al., "Palladium-Catalyzed Amination of Arly Halides and Sulfonates," Journal of Organometallic Chemistry, 576:125-146 (1999).

Yarden, Y., et al., "Human Proto-oncogene c-kit: a New Cell Surface Receptor Tyrosine Kinase for an Unidentified Ligand," The EMBO Journal, 6(11):3341-3351 (1987).

Yoneda, F., et al., "A New Synthesis of Purines," J.C.S. Chem. Comm., p. 551 (1974).

Yonezawa, N., et al., "Synthesis of Sequentially Controlled Isomeric, Wholly aromatic Polyketones Composed of 2-trifluoromethylbiphenylene and 2,2'-dimethoxybiphenylene Units," Reactive & Functional Polymers, 52:19-30 (2002).

Yoshimoto, M., et al., "Correlation Analysis of Baker's Studies on Enzyme Inhibition. 2. Chymotrypsin, Trypsin, Thymidine Phosphorylase, Uridine Phosphorylase, Thimidylate Synthetase, Cytosine Nucleoside Deaminase, Dihodrofolate Reductase, Malate Dehydrogenase, Glutamate Dehydrogenase, Lactate Dehydrogenase, and Glyceraldehyde-phosphate Dehydrogenase," Journal of Medicinal Chemistry, 19(1):71-98, (1976).

Yoshino, K., et al., "Organic Phosphorous Compounds. 2. Synthesis and Coronary Vasodilator Activity of (Benzothiazolybenzyl) Phosphonate Derivatives," J. Med. Chem., 32:1528-1532 (1989).

Yu, J., et al., "Frequency of TPR-MET Rearrangement in Patients with Gastric Carcinoma and in First-Degree Relatives," Cancer, 88(8):1801-1806 (2000).

Zaidi, S. M. M., et al., "New Anti-Mycobacterial Hydantoins," Pharmazie, 35:755-756 (1980).

Zhen, Z., et al., "Structural and Functional Domains Critical for Constitutive Activation of the HGF-Receptor (Met)," Oncogene, 9(6):1691-1697 (1994).

Zinner, G., et al., "Zur Weiteren Kenntnis Bicyclischer 3.5-Dioxopyrazolidine," Die Pharmazie, 25(5):309-312 (1970).

Zvilichovsky, G., et al., "Aminolysis and Polymerization of 3-(p-Toluenesulfonoxy) Hydantoin," Israel Journal of Chemistry, 7:547-554 (1969).

International Search Report for PCT/US2005/047270, mailed Jul. 29, 2008 (5 pages).

Extended European Search Report for EP 05 85 8777, dated Jun. 10, 2010 (9 pages).

\* cited by examiner

○ kinase ATP binding domain
◌ kinase ATP binding domain hinge region
☐ "DFG-in conformation" kinase pocket
▓ kinase "switch" pocket ○ kinase ATP binding domain
◌ kinase ATP binding domain hinge region
☐ "DFG-in conformation" kinase pocket
▓ kinase "switch" pocket

SEQUENCE LISTING

<160> NUMBER OF SEQ ID NOS: 6

<210> SEQ ID NO 1
<211> LENGTH: 284
<212> TYPE: PRT
<213> ORGANISM: Homo sapiens
<220> FEATURE:
<221> NAME/KEY: MISC_FEATURE
<223> OTHER INFORMATION: Ab1

<400> SEQUENCE: 1

Ser Pro Asn Tyr Asp Lys Trp Glu Met Glu Arg Thr Asp Ile Thr Met
1               5                   10                  15

Lys His Lys Leu Gly Gly Gly Gln Tyr Gly Glu Val Tyr Glu Gly Val
            20                  25                  30

Trp Lys Lys Tyr Ser Leu Thr Val Ala Val Lys Thr Leu Lys Glu Asp
        35                  40                  45

Thr Met Glu Val Glu Glu Phe Leu Lys Glu Ala Ala Val Met Lys Glu
    50                  55                  60

Ile Lys His Pro Asn Leu Val Gln Leu Leu Gly Val Cys Thr Arg Glu
65                  70                  75                  80

Pro Pro Phe Tyr Ile Ile Thr Glu Phe Met Thr Tyr Gly Asn Leu Leu

```
                        85                  90                  95
Asp Tyr Leu Arg Glu Cys Asn Arg Gln Glu Val Asn Ala Val Val Leu
                100                 105                 110

Leu Tyr Met Ala Thr Gln Ile Ser Ser Ala Met Glu Tyr Leu Glu Lys
            115                 120                 125

Lys Asn Phe Ile His Arg Asp Leu Ala Ala Arg Asn Cys Leu Val Gly
        130                 135                 140

Glu Asn His Leu Val Lys Val Ala Asp Phe Gly Leu Ser Arg Leu Met
145                 150                 155                 160

Thr Gly Asp Thr Tyr Thr Ala His Ala Gly Ala Lys Phe Pro Ile Lys
                165                 170                 175

Trp Thr Ala Pro Glu Ser Leu Ala Tyr Asn Lys Phe Ser Ile Lys Ser
            180                 185                 190

Asp Val Trp Ala Phe Gly Val Leu Leu Trp Glu Ile Ala Thr Tyr Gly
        195                 200                 205

Met Ser Pro Tyr Pro Gly Ile Asp Leu Ser Gln Val Tyr Glu Leu Leu
    210                 215                 220

Glu Lys Asp Tyr Arg Met Glu Arg Pro Glu Gly Cys Pro Glu Lys Val
225                 230                 235                 240

Tyr Glu Leu Met Arg Ala Cys Trp Gln Trp Asn Pro Ser Asp Arg Pro
                245                 250                 255

Ser Phe Ala Glu Ile His Gln Ala Phe Glu Thr Met Phe Gln Glu Ser
            260                 265                 270

Ser Ile Ser Asp Glu Val Glu Lys Glu Leu Gly Lys
        275                 280

<210> SEQ ID NO 2
<211> LENGTH: 315
<212> TYPE: PRT
<213> ORGANISM: Homo sapiens
<220> FEATURE:
<221> NAME/KEY: MISC_FEATURE
<223> OTHER INFORMATION: KDR

<400> SEQUENCE: 2

Asp Pro Asp Glu Leu Pro Leu Asp Glu His Cys Glu Arg Leu Pro Tyr
1               5                   10                  15

Asp Ala Ser Lys Trp Glu Phe Pro Arg Asp Arg Leu Lys Leu Gly Lys
            20                  25                  30

Pro Leu Gly Arg Gly Ala Phe Gly Gln Val Ile Glu Ala Asp Ala Phe
        35                  40                  45

Gly Ile Asp Lys Thr Ala Thr Cys Arg Thr Val Ala Val Lys Met Leu
    50                  55                  60

Lys Glu Gly Ala Thr His Ser Glu His Arg Ala Leu Met Ser Glu Leu
65                  70                  75                  80

Lys Ile Leu Ile His Ile Gly His His Leu Asn Val Val Asn Leu Leu
                85                  90                  95

Gly Ala Cys Thr Lys Pro Gly Gly Pro Leu Met Val Ile Val Glu Phe
                100                 105                 110

Cys Lys Phe Gly Asn Leu Ser Thr Tyr Leu Arg Ser Lys Arg Asn Glu
            115                 120                 125

Phe Val Pro Tyr Lys Val Ala Pro Glu Asp Leu Tyr Lys Asp Phe Leu
        130                 135                 140

Thr Leu Glu His Leu Ile Cys Tyr Ser Phe Gln Val Ala Lys Gly Met
145                 150                 155                 160

Glu Phe Leu Ala Ser Arg Lys Cys Ile His Arg Asp Leu Ala Ala Arg
```

-continued

```
                 165                 170                 175

Asn Ile Leu Leu Ser Glu Lys Asn Val Val Lys Ile Cys Asp Phe Gly
            180                 185                 190

Leu Ala Arg Asp Ile Tyr Lys Asp Pro Asp Tyr Val Arg Lys Gly Asp
            195                 200                 205

Ala Arg Leu Pro Leu Lys Trp Met Ala Pro Glu Thr Ile Phe Asp Arg
            210                 215                 220

Val Tyr Thr Ile Gln Ser Asp Val Trp Ser Phe Gly Val Leu Leu Trp
225                 230                 235                 240

Glu Ile Phe Ser Leu Gly Ala Ser Pro Tyr Pro Gly Val Lys Ile Asp
                245                 250                 255

Glu Glu Phe Cys Arg Arg Leu Lys Glu Gly Thr Arg Met Arg Ala Pro
                260                 265                 270

Asp Tyr Thr Thr Pro Glu Met Tyr Gln Thr Met Leu Asp Cys Trp His
                275                 280                 285

Gly Glu Pro Ser Gln Arg Pro Thr Phe Ser Glu Leu Val Glu His Leu
            290                 295                 300

Gly Asn Leu Leu Gln Ala Asn Ala Gln Gln Asp
305                 310                 315

<210> SEQ ID NO 3
<211> LENGTH: 348
<212> TYPE: PRT
<213> ORGANISM: Homo sapiens
<220> FEATURE:
<221> NAME/KEY: MISC_FEATURE
<223> OTHER INFORMATION: B-Raf(V599E) construct 1

<400> SEQUENCE: 3

Lys Ser Pro Gly Gln Arg Glu Arg Lys Ser Ser Ser Ser Ser Glu Asp
1               5                   10                  15

Arg Asn Arg Met Lys Thr Leu Gly Arg Arg Asp Ser Ser Asp Asp Trp
            20                  25                  30

Glu Ile Pro Asp Gly Gln Ile Thr Val Gly Gln Arg Ile Gly Ser Gly
            35                  40                  45

Ser Phe Gly Thr Val Tyr Lys Gly Lys Trp His Gly Asp Val Ala Val
        50                  55                  60

Lys Met Leu Asn Val Thr Ala Pro Thr Pro Gln Gln Leu Gln Ala Phe
65                  70                  75                  80

Lys Asn Glu Val Gly Val Leu Arg Lys Thr Arg His Val Asn Ile Leu
                85                  90                  95

Leu Phe Met Gly Tyr Ser Thr Lys Pro Gln Leu Ala Ile Val Thr Gln
            100                 105                 110

Trp Cys Glu Gly Ser Ser Leu Tyr His His Leu His Ile Ile Glu Thr
        115                 120                 125

Lys Phe Glu Met Ile Lys Leu Ile Asp Ile Ala Arg Gln Thr Ala Gln
    130                 135                 140

Gly Met Asp Tyr Leu His Ala Lys Ser Ile Ile His Arg Asp Leu Lys
145                 150                 155                 160

Ser Asn Asn Ile Phe Leu His Glu Asp Leu Thr Val Lys Ile Gly Asp
                165                 170                 175

Phe Gly Leu Ala Thr Val Lys Ser Arg Trp Ser Gly Ser His Gln Phe
            180                 185                 190

Glu Gln Leu Ser Gly Ser Ile Leu Trp Met Ala Pro Glu Val Ile Arg
            195                 200                 205

Met Gln Asp Lys Asn Pro Tyr Ser Phe Gln Ser Asp Val Tyr Ala Phe
```

-continued

```
             210                 215                 220
Gly Ile Val Leu Tyr Glu Leu Met Thr Gly Gln Leu Pro Tyr Ser Asn
225                 230                 235                 240

Ile Asn Asn Arg Asp Gln Ile Ile Phe Met Val Gly Arg Gly Tyr Leu
                245                 250                 255

Ser Pro Asp Leu Ser Lys Val Arg Ser Asn Cys Pro Lys Ala Met Lys
                260                 265                 270

Arg Leu Met Ala Glu Cys Leu Lys Lys Arg Asp Glu Arg Pro Leu
            275                 280                 285

Phe Pro Gln Ile Leu Ala Ser Ile Glu Leu Leu Ala Arg Ser Leu Pro
290                 295                 300

Lys Ile His Arg Ser Ala Ser Glu Pro Ser Leu Asn Arg Ala Gly Phe
305                 310                 315                 320

Gln Thr Glu Asp Phe Ser Leu Tyr Ala Cys Ala Ser Pro Lys Thr Pro
                325                 330                 335

Ile Gln Ala Gly Gly Tyr Gly Ala Phe Pro Val His
                340                 345

<210> SEQ ID NO 4
<211> LENGTH: 294
<212> TYPE: PRT
<213> ORGANISM: Homo sapiens
<220> FEATURE:
<221> NAME/KEY: MISC_FEATURE
<223> OTHER INFORMATION: B-Raf(V599E) construct 2

<400> SEQUENCE: 4

Glu Asp Arg Asn Arg Met Lys Thr Leu Gly Arg Arg Asp Ser Ser Asp
1               5                   10                  15

Asp Trp Glu Ile Pro Asp Gly Gln Ile Thr Val Gly Gln Arg Ile Gly
                20                  25                  30

Ser Gly Ser Phe Gly Thr Val Tyr Lys Gly Lys Trp His Gly Asp Val
            35                  40                  45

Ala Val Lys Met Leu Asn Val Thr Ala Pro Thr Pro Gln Gln Leu Gln
        50                  55                  60

Ala Phe Lys Asn Glu Val Gly Val Leu Arg Lys Thr Arg His Val Asn
65                  70                  75                  80

Ile Leu Leu Phe Met Gly Tyr Ser Thr Lys Pro Gln Leu Ala Ile Val
                85                  90                  95

Thr Gln Trp Cys Glu Gly Ser Ser Leu Tyr His His Leu His Ile Ile
            100                 105                 110

Glu Thr Lys Phe Glu Met Ile Lys Leu Ile Asp Ile Ala Arg Gln Thr
        115                 120                 125

Ala Gln Gly Met Asp Tyr Leu His Ala Lys Ser Ile Ile His Arg Asp
    130                 135                 140

Leu Lys Ser Asn Asn Ile Phe Leu His Glu Asp Leu Thr Val Lys Ile
145                 150                 155                 160

Gly Asp Phe Gly Leu Ala Thr Glu Lys Ser Arg Trp Ser Gly Ser His
                165                 170                 175

Gln Phe Glu Gln Leu Ser Gly Ser Ile Leu Trp Met Ala Pro Glu Val
            180                 185                 190

Ile Arg Met Gln Asp Lys Asn Pro Tyr Ser Phe Gln Ser Asp Val Tyr
        195                 200                 205

Ala Phe Gly Ile Val Leu Tyr Glu Leu Met Thr Gly Gln Leu Pro Tyr
    210                 215                 220

Ser Asn Ile Asn Asn Arg Asp Gln Ile Ile Phe Met Val Gly Arg Gly
```

|  |  |  |  |  |  |  |  |  |  |  |  |  |  |  |
|---|---|---|---|---|---|---|---|---|---|---|---|---|---|---|
| 225 |  |  |  |  | 230 |  |  |  |  | 235 |  |  |  | 240 |

Tyr Leu Ser Pro Asp Leu Ser Lys Val Arg Ser Asn Cys Pro Lys Ala
                        245                        250                        255

Met Lys Arg Leu Met Ala Glu Cys Leu Lys Lys Arg Asp Glu Arg
                        260                        265                        270

Pro Leu Phe Pro Gln Ile Leu Ala Ser Ile Glu Leu Leu Ala Arg Ser
                        275                        280                        285

Leu Pro Lys Ile His Arg
      290

<210> SEQ ID NO 5
<211> LENGTH: 333
<212> TYPE: PRT
<213> ORGANISM: Homo sapiens
<220> FEATURE:
<221> NAME/KEY: MISC_FEATURE
<223> OTHER INFORMATION: MEK1

<400> SEQUENCE: 5

Met Glu Leu Lys Asp Asp Asp Phe Glu Lys Ile Ser Glu Leu Gly Ala
1                 5                     10                  15

Gly Asn Gly Gly Val Val Phe Lys Val Ser His Lys Pro Ser Gly Leu
                 20                     25                    30

Val Met Ala Arg Lys Leu Ile His Leu Glu Ile Lys Pro Ala Ile Arg
             35                     40                    45

Asn Gln Ile Ile Arg Glu Leu Gln Val Leu His Glu Cys Asn Ser Pro
  50                    55                     60

Tyr Ile Val Gly Phe Tyr Gly Ala Phe Tyr Ser Asp Gly Glu Ile Ser
65                70                     75                    80

Ile Cys Met Glu His Met Asp Gly Gly Ser Leu Asp Gln Val Leu Lys
             85                     90                    95

Lys Ala Gly Arg Ile Pro Glu Gln Ile Leu Gly Lys Val Ser Ile Ala
                100                   105                110

Val Ile Lys Gly Leu Thr Tyr Leu Arg Glu Lys His Lys Ile Met His
             115                    120                  125

Arg Asp Val Lys Pro Ser Asn Ile Leu Val Asn Ser Arg Gly Glu Ile
130               135                    140

Lys Leu Cys Asp Phe Gly Val Ser Gly Gln Leu Ile Asp Ser Met Ala
145               150                    155                  160

Asn Ser Phe Val Gly Thr Arg Ser Tyr Met Ser Pro Glu Arg Leu Gln
             165                    170                  175

Gly Thr His Tyr Ser Val Gln Ser Asp Ile Trp Ser Met Gly Leu Ser
                180                   185                190

Leu Val Glu Met Ala Val Gly Arg Tyr Pro Ile Pro Pro Pro Asp Ala
             195                    200                  205

Lys Glu Leu Glu Leu Met Phe Gly Cys Gln Val Glu Gly Asp Ala Ala
        210                    215                    220

Glu Thr Pro Pro Arg Pro Arg Thr Pro Gly Arg Pro Leu Ser Ser Tyr
225               230                    235                  240

Gly Met Asp Ser Arg Pro Pro Met Ala Ile Phe Glu Leu Leu Asp Tyr
             245                    250                  255

Ile Val Asn Glu Pro Pro Pro Lys Leu Pro Ser Gly Val Phe Ser Leu
             260                    265                270

Glu Phe Gln Asp Phe Val Asn Lys Cys Leu Ile Lys Asn Pro Ala Glu
            275                    280                  285

Arg Ala Asp Leu Lys Gln Leu Met Val His Ala Phe Ile Lys Arg Ser

```
                290                 295                 300
Asp Ala Glu Glu Val Asp Phe Ala Gly Trp Leu Cys Ser Thr Ile Gly
305                 310                 315                 320

Leu Asn Gln Pro Ser Thr Pro Thr His Ala Ala Gly Val
                325                 330

<210> SEQ ID NO 6
<211> LENGTH: 360
<212> TYPE: PRT
<213> ORGANISM: Homo sapiens
<220> FEATURE:
<221> NAME/KEY: MISC_FEATURE
<223> OTHER INFORMATION: P38-alpha

<400> SEQUENCE: 6

Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45

Arg Val Ala Val Lys Lys Leu Ser Arg Pro Phe Gln Ser Ile Ile His
50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
210                 215                 220

Gly Thr Asp His Ile Asn Gln Leu Gln Gln Ile Met Arg Leu Thr Gly
225                 230                 235                 240

Thr Pro Pro Ala Tyr Leu Ile Asn Arg Met Pro Ser His Glu Ala Arg
                245                 250                 255

Asn Tyr Ile Gln Ser Leu Thr Gln Met Pro Lys Met Asn Phe Ala Asn
            260                 265                 270

Val Phe Ile Gly Ala Asn Pro Leu Ala Val Asp Leu Leu Glu Lys Met
        275                 280                 285

Leu Val Leu Asp Ser Asp Lys Arg Ile Thr Ala Ala Gln Ala Leu Ala
290                 295                 300

His Ala Tyr Phe Ala Gln Tyr His Asp Pro Asp Asp Glu Pro Val Ala
305                 310                 315                 320

Asp Pro Tyr Asp Gln Ser Phe Glu Ser Arg Asp Leu Leu Ile Asp Glu
```

| | | | 325 | | | | 330 | | | | 335 | | |
|---|---|---|---|---|---|---|---|---|---|---|---|---|---|
| Trp | Lys | Ser | Leu | Thr | Tyr | Asp | Glu | Val | Ile | Ser | Phe | Val | Pro Pro Pro |
| | | | 340 | | | | | 345 | | | | 350 | |
| Leu | Asp | Gln | Glu | Glu | Met | Glu | Ser | | | | | | |
| | | | 355 | | | | | 360 | | | | | |

ENZYME MODULATORS AND TREATMENTS

CROSS-REFERENCE TO RELATED APPLICATIONS

The present application is a continuation application of Ser. No. 11/318,399, filed Dec. 23, 2005, entitled ENZYME MODULATORS AND TREATMENTS, and is hereby incorporated by reference in its entirety. This application claims the benefit of (1) Provisional Application Ser. No. 60/639,087 filed Dec. 23, 2004; (2) Provisional Application Ser. No. 60/638,986, filed Dec. 23, 2004; (3) Provisonal Application Ser. No. 60/638,987, filed Dec. 23, 2004; and (4) Provisional Application Ser. No. 60/638,968, filed Dec. 23, 2004. These four provisional applications are incorporated by reference herein in their entirety.

FIELD OF THE INVENTION

The present invention relates to novel kinase inhibitors and modulator compounds useful for the treatment of various diseases. More particularly, the invention is concerned with such compounds, kinase/compound adducts, methods of treating diseases, and methods of synthesis of the compounds. Preferably, the compounds are useful for the modulation of kinase activity of C-Abl, c-Kit, VEGFR, PDGFR, Raf and P38 kinases and disease polymorphs thereof.

SEQUENCE LISTING

The following application contains 6 sequence listings in paper form and in computer readable format (CRF). The content of the enclosed CRF is hereby incorporated by reference.

BACKGROUND OF THE INVENTION

Several members of the protein kinase family have been clearly implicated in the pathogenesis of various proliferative diseases and thus represent important targets for treatment of these diseases. Some of the proliferative diseases relevant to this invention include cancer, rheumatoid arthritis, atherosclerosis, and retinopathies. Important examples of kinases which have been shown to cause or contribute to the pathogensis of these diseases include C-Abl kinase and the oncogenic fusion protein BCR-Abl kinase; PDGF receptor kinase; VEGF receptor kinases; MAP kinase p38α; and the RAF kinase family.

C-Abl kinase is an important non-receptor tyrosine kinase involved in cell signal transduction. This ubiquitously expressed kinase—upon activation by upstream signaling factors including growth factors, oxidative stress, integrin stimulation, and ionizing radiation—localizes to the cell plasma membrane, the cell nucleus, and other cellular compartments including the actin cytoskeleton (Van Etten, *Trends Cell Biol.* (1999) 9: 179). There are two normal isoforms of Abl kinase: Abl-1A and Abl-1B. The N-terminal half of c-Abl kinase is important for autoinhibition of the kinase domain catalytic activity (Pluk et al, *Cell* (2002) 108: 247). Details of the mechanistic aspects of this autoinhibition have recently been disclosed (Nagar et al, *Cell* (2003) 112: 859). The N-terminal myristolyl amino acid residue of Abl-1B has been shown to intramolecularly occupy a hydrophobic pocket formed from alpha-helices in the C-lobe of the kinase domain. Such intramolecular binding induces a novel binding area for intramolecular docking of the SH2 domain and the SH3 domain onto the kinase domain, thereby distorting and inhibiting the catalytic activity of the kinase. Thus, an intricate intramolecular negative regulation of the kinase activity is brought about by these N-terminal regions of c-Abl kinase. An aberrant dysregulated form of c-Abl is formed from a chromosomal translocation event, referred to as the Philadelphia chromosome (P. C. Nowell et al, *Science* (1960) 132: 1497; J. D. Rowley, *Nature* (1973) 243: 290). This abnormal chromosomal translocation leads aberrant gene fusion between the Abl kinase gene and the breakpoint cluster region (BCR) gene, thus encoding an aberrant protein called Bcr-Abl (G. Q. Daley et al, *Science* (1990) 247: 824; M. L. Gishizky et al, *Proc. Natl. Acad. Sci. USA* (1993) 90: 3755; S. Li et al, *J. Exp. Med.* (1999) 189: 1399). the Bcr-Abl fusion protein does not include the regulatory myristolylation site (B. Nagar et al, *Cell* (2003) 112: 859) and as a result functions as an oncoprotein which causes chronic myeloid leukemia (CML). CML is a malignancy of pluripotent hematopoietic stem cells. The p210 form of Bcr-Abl is seen in 95% of patients with CML, and in 20% of patients with acute lymphocytic leukemia. A p185 form has also been disclosed and has been linked to being causative of up to 10% of patients with acute lymphocytic leukemia.

Growth factor receptor kinases contribute to the growth and metastasis of tumors by stimulating the proliferation of endothelial cells, fibroblasts, smooth muscle cells, and matrix proteins. Conditions such as hypoxia can induce tumor cells to secrete growth factors which subsequently result in the growth of new blood vessels to support the tumor. These growth factors include platelet derived growth factor (PDGF) and transforming growth factor-beta (TGF-beta), which subsequently stimulate secretion of other growth factors including vascular endothelial growth factor (VEGF), fibroblast growth factor, and epidermal growth factor (EGF). The formation of new blood vessels, which is known as angiogenesis, also provides the tumor with a route to metastasize to remote secondary sites. Inhibiting angiogenic factors that support stromal growth has been proposed as a useful therapy for treating cancers (R. M. Shaheen et al, *Cancer Research* (1999) 59: 5412; R. M. Shaheen et al, *Cancer Research* (2001) 61: 1464). Mutations of the PGDF receptor have also been identified which constitutively active in absence of growth factor. VEGF can also stimulate the formation of new lymphatic vessels through direct action on the so-called VEGF-3 receptor, providing yet another pathway for tumor metastasis. Among the three known VEGF receptors, in particular the so-called VEGFR2 (otherwise known as the kinase insert domain-containing receptor tyrosine kinase or KDR) has been demonstrated to be responsible for the role of VEGF in tumor angiogenesis.

A major signaling pathway downstream of cell surface growth factor receptor activation is the Ras-RAF-MEK-ERK-MAP kinase pathway (Peyssonnaux, C. et al, *Biol. Cell* (2001) 93: 53-62, Cancers arise when mutations occur in one or more of the proteins involved in this signaling cascade. Cell proliferation and differentiation become dysregulated and cell survival mechanisms are activated which allow unregulated cancer cells to override protective programmed cell death surveillance. Mutations in the p21-Ras protein have been shown to be a major cause of dysregulation of this signaling pathway, leading to the development of human cancers. P21-Ras mutations have been identified in approximately 30% of human cancers (Bolton et al, *Ann. Rep. Med. Chem.* (1994) 29: 165-174). Cancer-causing mutations in the P21-Ras protein lead to a constitutively active signaling cascade, causing unregulated activation of the downstream components of the RAF-MEK-ERK-MAP kinase pathway (Magnuson et al., *Semin. Cancer Biol.* (1994) 5: 247-253). The three RAF kinases which participate in this signaling cascade are known as ARAF, BRAF, and CRAF (Peyssonnaux, C. et al, *Biol. Cell* (2001) 93: 53-62; Avruch, J., *Recent Prog. Horm. Res.* (2001) 56: 127-155; Kolch, W., *Biochem. J.* (2000) 351: 289-305). These RAF kinase isoforms are all activated by Ras, and thus are activated in cancers that result from mutated and upregulated p21-Ras protein activity. In addition to activation of this signaling cascade at the initial p21-Ras protein level, mutations have also been found in BRAF kinase which results in activation of the cascade downstream from p21-Ras (Davies, H., et al, *Nature* (2002) 417: 949-954). A dominant single site mutation at position 599 in the BRAF kinase was shown to be particularly aggressive and linked to approximately 80% of the observed human malignant melanomas. This mutation substitutes the negatively charged amino acid glutamic acid for the normally occurring neutral amino acid valine. This single site mutation is sufficient to render the mutated BRAF kinase constitutively active, resulting in signaling pathway dysregulation and human cancer. Hence small molecule inhibitors of BRAF kinase are a rational approach to the treatment of human malignancy, whether the signaling mutation is at the level of the upstream p21-Ras protein or at the level of BRAF kinase.

The MAP kinase p38α has recently been identified as an important mechanistic target for the treatment of inflammatory diseases. Inhibition of the MAP kinase p38-alpha has been demonstrated to result in the suppression the production and release the proinflammatory mediators TNF-alpha, IL-1 beta, IL-6, IL-8 and other proinflammatory cytokines (Chen, Z. et al, *Chem. Rev.* (2001) 101: 2449). Recently, p38-alpha kinase has been implicated in the regulation of tissue factor expression in monocytes, suggesting a role for inhibition of p38-alpha kinase in the treatment of thrombotic disorders and atherosclerosis (Chu, A. J., et al, *J. Surg. Res.* (2001) 101: 85-90; Eto, M., et al, *Circulation* (2002) 105: 1756-1759). The p38-alpha kinase has also been shown to be involved in thrombin-induced proinflammatory conditions (V. Marin, et al, *Blood*, Aug. 1, 2001, 98: 667-673). Validation of this approach has been achieved by the successful application of various protein therapeutic agents for the treatment of severe chronic inflammatory disease. Monoclonal antibodies to TNF have shown effectiveness in the treatment of rheumatoid arthritis, ulcerative colitis, and Crohn's disease (Rankin, E. C. C., et al, *British J. Rheum.* (1997) 35: 334-342; Stack, W. A., et al, *Lancet* (1997) 349: 521-524). Enbrel (etanercept), a soluble TNF receptor, has been developed by Immunex, Inc., and marketed currently by Amgen for the treatment of rheumatoid arthritis (Brower et al, *Nature Biotechnology* (1997) 15: 1240; Pugsley, M. K., *Curr. Opin. Invest. Drugs* (2001) 2: 1725). Ro 45-2081, a recombinant soluble TNF-alpha receptor chimeric protein, has also shown effectiveness in the treatment of the acute phase of lung injury and in animal models of allergic lung disease (Renzetti, et al, *Inflamm Res.* (1997) 46: S143). Remicade (infliximab) is a monoclonal TNF-alpha antibody that has shown effectiveness in the treatment of rheumatoid arthritis and Crohn's disease (Bondeson, J. et al, *Int. J. Clin. Pract.* (2001) 55: 211).

Importantly, small molecule inhibitors of kinase activity have been shown to produce therapeutic benefit as anticipated. The most important example thus far is Gleevec (Imatinib), which is an inhibitor of BCR-Abl kinase (J. Zimmermann et al, WO 99/03854; N. von Bubnoff et al, *Cancer Research* (2003) 63: 6395; B. J. Druker et al, *Nature Medicine* (1996) 2: 561; J. Zimmermann et al, *Bioorganic and Medicinal Chemistry Letters* (1997) 7: 187). Gleevec has been shown to produce clinical remissions in CML patients. However, resistance to the effects of Gleevec have often been encountered (M. E. Gorre et al, *Science* (2001) 293: 876). Over 17 mutations of Bcr-Abl kinase have been associated with Gleevec resistance (N. von Bubnoff et al, *Lancet* (2002) 359: 487; S. Branford et al, *Blood* (2002) 99: 3472; C. Roche-Lestienne et al, *Blood* (2002) 100: 1014; N. P. Shah et al, *Cancer Cell* (2002) 2: 117; A. Hochhaus et al, *Leukemia* (2002) 16: 2190; H. K. Al-Ali et al, *Hematology* (2004) 5: 55). These mutations are primarily found in the kinase active site domain of Bcr-Abl, and frequently occur in regions proximal to the ATP binding pocket.

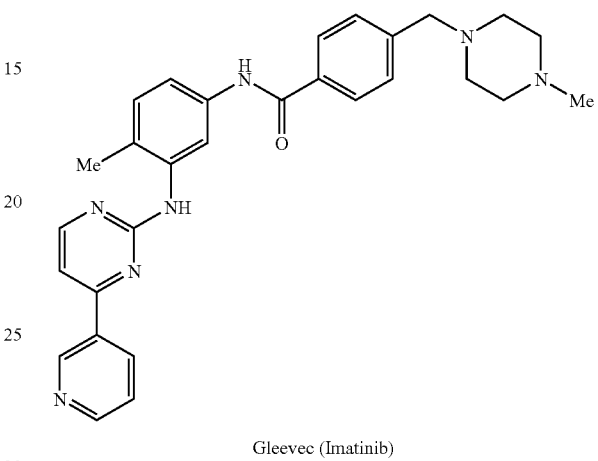

Gleevec (Imatinib)

The majority of small molecule kinase inhibitors that have been reported have been shown to bind in one of three ways. Most of the reported inhibitors interact with the ATP binding domain of the active site and exert their effects by competing with ATP for occupancy. Other inhibitors have been shown to bind to a separate hydrophobic region of the protein known as the "DFG-in-conformation" pocket, and still others have been shown to bind to both the ATP domain and the "DFG-in-conformation" pocket. Examples specific to inhibitors of RAF kinases can be found in Lowinger et al, *Current Pharmaceutical Design* (2002) 8: 2269-2278; Dumas, J. et al., *Current Opinion in Drug Discovery & Development* (2004) 7: 600-616; Dumas, J. et al, WO 2003068223 A1 (2003); Dumas, J., et al, WO 9932455 A1 (1999), and Wan, P. T. C., et al, *Cell* (2004) 116: 855-867

Physiologically, kinases are regulated by a common activation/deactivation mechanism wherein a specific activation loop sequence of the kinase protein binds into a specific pocket on the same protein which is referred to as the switch control pocket. Such binding occurs when specific amino acid residues of the activation loop are modified for example by phosphorylation, oxidation, or nitrosylation. The binding of the activation loop into the switch pocket results in a conformational change of the protein into its active form (Huse, M. and Kuriyan, J. *Cell* (109) 275-282.)

SUMMARY OF THE INVENTION

The present invention describes novel potent and selective inhibitors of CAbl kinase, VEGFR2/KDR kinase, and BRAF kinase. The compounds of this invention inhibit kinase activity in a novel way by binding into the "switch pocket" remote from the ATP-cofactor pocket with or without concomitant binding into the "DFG-in-conformation" pocket. X-ray structures determined from small molecule/BRAF co-crystals have confirmed this novel mode of binding to the kinase by the compounds of this present invention, and illustrate the novel features of this binding mode when compared to inhibitors which anchor or bind into the ATP pocket of BRAF kinase. The novel inhibitors of the present invention in some cases also exhibit a preference for inhibiting the oncogenic mutant form of a kinase (V599E-BRAF) and a sparing of normal wild-type kinase that lack the cancer-causing mutation, wherein the oncogenic mutation is a modification of a critical binding amino acid residue of the switch control pocket. An example of this profile has been identified for BRAF, wherein mutation of the valine 599 residue to a glutamic acid residue results in an oncogenic form of BRAF and for which it has been found that compounds of this invention inhibit the oncogenic mutant form of BRAF but not the wild type BRAF. This desirable feature of inhibitor selectivity enables the use of a BRAF inhibitor to treat mammalian cancer caused by mutant V559E BRAF kinase, while sparing the normal wildtype BRAF kinase present in non-cancerous cells. Enhanced safety and selectivity realized from this "wild-type kinase-sparing" provides safer inhibitors that target the cancer-causing forms of BRAF kinase.

FIGS. 1 and 2 further illustrates the novel binding interaction for the compounds of this invention with kinases. In FIG. 1, the known interactions of kinase inhibitors reported previously are defined as directed to a combination of the ATP binding domain, an adjacent binding area known as the ATP binding domain hinge region, and in some cases a third domain known as the "DFG-in conformation" kinase pocket.

The binding modality of the compounds of this invention is illustrated in FIG. 2. The unique feature is the necessary engagement of another binding domain within the kinase referred to as the switch pocket. Compounds of this invention uniquely and necessarily bind within the switch pocket, and optionally the "DFG-in conformation" domain, and optionally to the ATP binding domain hinge region. This unique binding modality confers upon compounds of this invention a novel mechanism to modulate kinase activity as well as significant advantages over previously described kinase inhibitors in achieving a therapeutically important degree of selectivity for the preferred target over inhibitors which occupy the ATP binding domain. The novel binding modality of the compounds of this invention also avoids mutations within the ATP binding domain which commonly confer resistance to inhibition by compounds which require interaction with the ATP binding domain.

Compounds of the present invention find utility in the treatment of mammalian cancers and especially human cancers including but not limited to malignant melanoma, colorectal cancer, ovarian cancer, papillary thyroid carcinoma, non small cell lung cancer, and mesothelioma. Compounds of the present invention also find utility in the treatment of rheumatoid arthritis and retinopathies including diabetic retinal neuropathy and macular degeneration.

DESCRIPTION OF THE PREFERRED EMBODIMENTS

Figure 1:
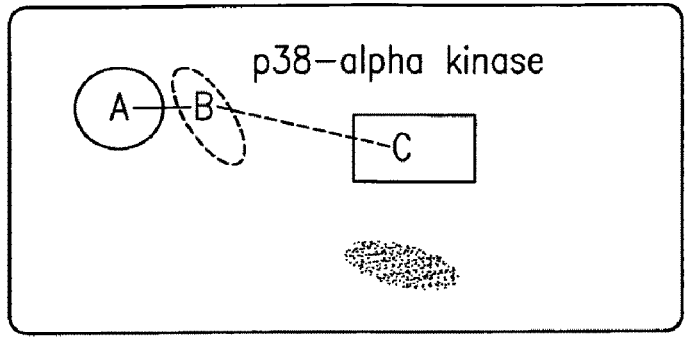
FIG. 1 is an illustration of the kinase binding domains of known kinase inhibitors.
Figure 2:
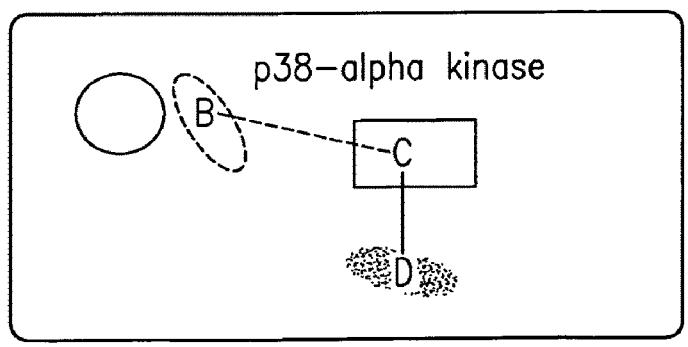
FIG. 2 is an illustration of the binding modality of compounds of the present invention to kinases.

The following descriptions refer to various compounds and moieties thereof. Generally, the following definitions apply to these descriptions, with the understanding that in some instances the descriptions are further limited. However, as broadly defined, the following definitions apply.

Carbocyclyl refers to monocyclic saturated carbon rings taken from cyclopropyl, cyclobutyl, cyclopentyl, cyclohexyl, and cycloheptanyl;

Aryl refers to monocyclic or fused bicyclic ring systems characterized by delocalized π electrons (aromaticity) shared among the ring carbon atoms of at least one carbocyclic ring; preferred aryl rings are taken from phenyl, naphthyl, tetrahydronaphthyl, indenyl, and indanyl;

Heteroaryl refers to monocyclic or fused bicyclic ring systems characterized by delocalized π electrons (aromaticity) shared among the ring carbon or heteroatoms including nitrogen, oxygen, or sulfur of at least one carbocyclic or heterocyclic ring; heteroaryl rings are taken from, but not limited to, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyridinyl, pyrimidinyl, pyrazinyl, pyridazinyl, triazinyl, indolyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, dihydropurinonyl, pyrrolopyrimidinyl, purinyl, pyrazolopyridinyl, pyrazolopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalazinyl, benzodioxyl, indolinyl, benzisotbiazoline-1,1, 3-trionyl, dihydroquinolinyl, tetrahydroquinolinyl, dihydroisoquinolyl, tetrahydroisoquinolinyl, benzoazepinyl, benzodiazepinyl, benzoxapinyl, or benzoxazepinyl;

Heterocyclyl refers to monocyclic rings containing carbon and heteroatoms taken from oxygen, nitrogen, or sulfur and wherein there is not delocalized π electrons (aromaticity) shared among the ring carbon or heteroatoms; heterocyclyl rings include, but are not limited to, oxetanyl, azetadinyl, tetrahydrofuranyl, pyrrolidinyl, oxazolinyl, oxazolidinyl, pyranyl, thiopyranyl, tetrahydropyranyl, dioxalinyl, piperidinyl, morpholinyl, thiomorpholinyl, piperazinyl, azepinyl, oxepinyl, diazepinyl, tropanyl, homotropanyl;

Poly-aryl refers to two or more monocyclic or fused bicyclic ring systems characterized by delocalized π electrons (aromaticity) shared among the ring carbon atoms of at least one carbocyclic ring wherein the rings contained therein are optionally linked together.

Poly-heteroaryl refers to two or more monocyclic or fused bicyclic systems characterized by delocalized π electrons (aromaticity) shared among the ring carbon or heteroatoms including nitrogen, oxygen, or sulfur of at least one carbocyclic or heterocyclic ring wherein the rings contained therein are optionally linked together, wherein at least one of the monocyclic or fused bicyclic rings of the poly-heteroaryl system is taken from heteroaryl as defined broadly above and the other rings are taken from either aryl, heteroaryl, or heterocyclyl as defined broadly above;

Poly-heterocyclyl refers to two or more monocyclic or fused bicyclic ring systems containing carbon and heteroatoms taken from oxygen, nitrogen, or sulfur and wherein there is not delocalized π electrons (aromaticity) shared among the ring carbon or heteroatoms wherein the rings contained therein are optionally linked, wherein at least one of the monocyclic or fused bicyclic rings of the poly-heteroaryl system is taken from heterocyclyl as defined broadly above and the other rings are taken from either aryl, heteroaryl, or heterocyclyl as defined broadly above;

Lower alkyl refers to straight or branched chain C1-C6alkyls;

Substituted in connection with a moiety refers to the fact that a further substituent may be attached to the moiety to any acceptable location on the moiety.

The term salts embraces pharmaceutically acceptable salts commonly used to form alkali metal salts and to form addition salts of free acids or free bases. The nature of the salt is not critical, provided that it is pharmaceutically-acceptable. Suitable pharmaceutically-acceptable acid addition salts may be prepared. from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclyl, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, (3-hydroxybutyric, galactaric and galacturonic acid. Suitable pharmaceutically-acceptable base addition salts of compounds of Formula I include metallic salts and organic salts. More preferred metallic salts include, but are not limited to appropriate alkali metal (group Ia) salts, alkaline earth metal (group IIa) salts and other physiological acceptable metals. Such salts can be made from aluminum, calcium, lithium, magnesium, potassium, sodium and zinc. Preferred organic salts can be made from tertiary amines and quaternary ammonium salts, including in part, tromethamine, diethylamine, N,N'-dibenzylethylenediamine, chloroprocaine, choline, diethanolamine, ethylenediamine, meglumine (N-methylglucamine) and procaine.

The term prodrug refers to derivatives of active compounds which revert in vivo into the active form. For example, a carboxylic acid form of an active drug may be esterified to create a prodrug, and the ester is subsequently converted in vivo to revert to the carboxylic acid form. See Ettmayer et. al, *J. Med. Chem.*, 2004, 47(10), 2393-2404 and Lorenzi et. al, *J. Pharm. Exp. Therpeutics*, 2005, 883-8900 for reviews.

Protein Definitions

PGDF refers to platelet-derived growth factor; PGDFR refers to platelet-derived growth factor receptor; VEGF refers to vascular endothelial growth factor; VEGFR refers to vascular endothelial growth factor receptor; MAP kinase refers to mitogen-activated protein kinase; BCR refers to breakpoint cluster region; CML refers to chronic myeloid leukemia; TGF-beta refers to transforming growth factor beta; EGF refers to epidermal growth factor; KDR refers to kinase insert domain-containing receptor; TNF refers to tumor necrosis factor; ATP refers to adenosine triphosphate; DFG-in-conformation refers to the tripeptide sequence aspartylphenylalanylglycyl in the kinase protein sequence; V599E refers to the mutational replacement of valine 599 of BRAF kinase by glutamic acid; FGFR refers to fibroblast growth factor receptor; TrkA refers to tyrosine receptor kinase type A and neurotrophic tyrosine kinase type 1 (NTRK1); TrkB refers to tyrosine receptor kinase type B and neurotrophic tyrosine kinase type 2 (NTRK2); EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, EPHB7, and EPHB8 refers to members of the ephrin receptor subfamily of the receptor tyrosine kinases.

1. First Aspect of the Invention—C-Abl Kinase Modulator Compounds, Methods, Preparations and Adducts
1.1 Generally—A2 Bicyclic Compounds The invention includes compounds of the formula

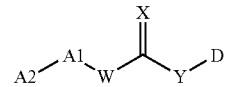

I wherein A2 is selected from the group consisting of bicyclic fused aryl, bicyclic fused heteroaryl, and bicyclic fused heterocyclyl rings, each A2 moiety presenting a proximal ring bonded with A1 and a distal ring attached to the proximal ring, and either the distal ring has a heteroatom in the ring structure thereof and/or the distal ring has Z2 or Z3 substituents;

A1 is selected from the group consisting of R2' and R7-substituted phenyl, pyridyl, or pyrimidinyl, R2-substituted monocyclic 5-membered ring heteroaryl, and R2'-substituted monocyclic heterocyclyl moieties;

W and Y are CHR4, NR3, or O and wherein W and Y are not simultaneously O;

X is O, S, or NR3;

D comprises a member of the group consisting of Z5- or Z6-substituted mono- and poly-aryl, of Z5- or Z6-substituted mono- and poly-heteroaryl, of Z5- or Z6-substituted mono- and poly-heterocyclyl, of Z5- or Z6-substituted mono- and poly-arylalkyl, of Z5- or Z6-substituted mono- and poly-aryl branched alkyl, of Z5- or Z6-substituted mono- and poly-heteroarylalkyl, of Z5- or Z6-substituted mono- and poly-heteroaryl branched alkyl, of Z5- or Z6-substituted mono- and poly-heterocyclylalkyl, of Z5- or Z6-substituted mono- and poly-heterocyclyl branched alkyl, alkyl, and carbocyclyl moieties;

each Z2 is independently and individually selected from the group consisting of hydroxyl, hydroxyC1-C6alkyl, cyano, (R3)$_2$N—, (R4)$_2$N—, (R4)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—C(=O)—, (R4)$_2$N—C(=O)—, (R4)$_2$N—CO—C1-C6alkyl, carboxyl, carboxyC1-C6alkyl, C1-C6alkoxycarbonyl, C1-C6alkoxycarbonylC1-C6alkyl, (R3)$_2$NSO$_2$, (R4)$_2$NSO$_2$, —SO$_2$R5-, —(CH$_2$)$_n$N(R4)C(O)R8, =O, =NOH, =N(OR6), heteroarylC1-C6alkyl, heterocyclylC1-C6alkyl, heteroaryloxyC1-C6alkyl, heterocyclyloxyC1-C6alkyl, arylaminoC1-C6alkyl, heteroarylaminoC1-C6alkyl, heterocyclylaminoC1-C6alkyl, or moieties of the formulae

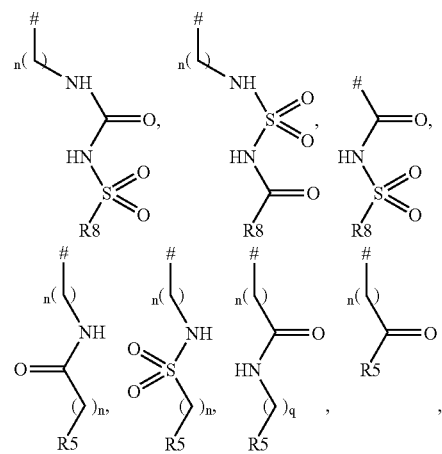

-continued

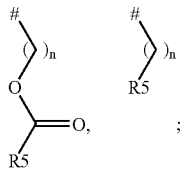

wherein the symbol (#) indicates the point of attachment of the Z2 moiety to the A2 ring of formula I;

in the event that Z2 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z2 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z2 may cyclize to form a C3-C7 heterocyclyl ring;

each Z3 is independently and individually selected from the group consisting of H, C1-C6alkyl, hydroxyl, hydroxyC1-C6alkyl, cyano, C1-C6alkoxy, C1-C6alkoxyC1-C6alkyl, halogen, CF$_3$, (R3)$_2$N—, (R4)$_2$N—, (R4)$_2$NC1-C6alkyl, (R4)$_2$NC2-C6alkylN(R4)-(CH$_2$)$_n$, (R4)$_2$NC2-C6alkylO-(CH$_2$)$_n$, —R8C(=O)—, (R4)$_2$N—CO—C1-C6alkyl, carboxyl, carboxyC1-C6alkyl, C1-C6alkoxycarbonyl, C1-C6alkoxycarbonylC1-C6alkyl, (R3)$_2$NSO$_2$, —SO$_2$R3, SOR3, (R4)$_2$NSO$_2$, —SO$_2$R4, —SOR4, —(CH$_2$)$_n$N(R4)C(O)R8, —C=(NOH)R6, —C=(NOR3)R6, heteroaryl, heterocyclyl, heteroarylC1-C6alkyl, heterocyclylC1-C6alkyl, heteroaryloxy, heterocyclyloxy, heteroaryloxyC1-C6alkyl, heterocyclyloxyC1-C6alkyl, arylamino, heteroarylamino, heterocyclylamino, arylaminoC1-C6alkyl, heteroarylaminoC1-C6alkyl, heterocyclylaminoC1-C6alkyl, or moieties of the formulae

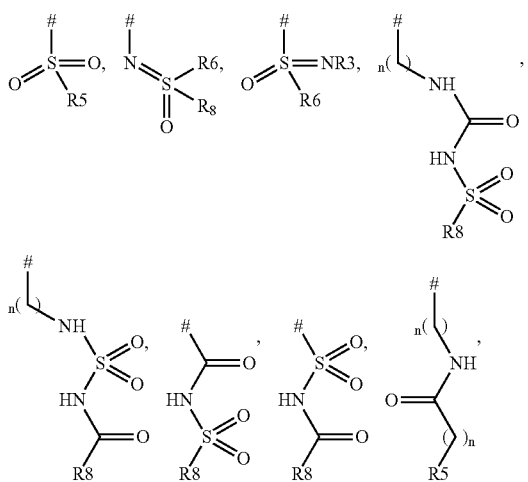

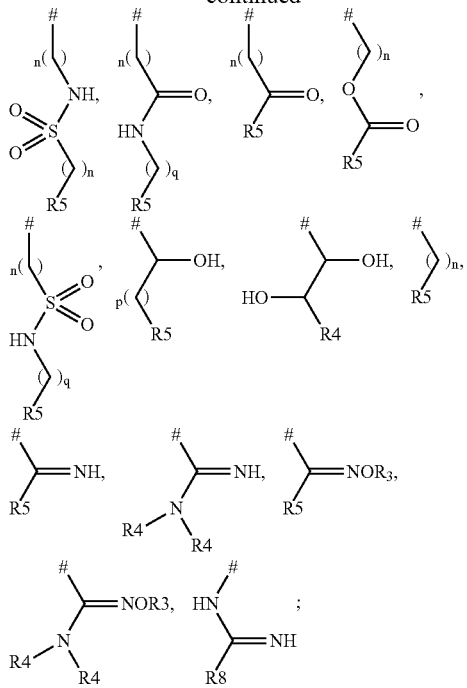

wherein the symbol (#) indicates the point of attachment of the Z3 moiety to the A2 ring of formula I;

in the event that Z3 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z3 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z3 may cyclize to form a C3-C7 heterocyclyl ring;

each Z5 is independently and individually selected from the group consisting of H, C1-C6alkyl, branched C3-C7alkyl, halogen, fluoroalkyl, cyano, hydroxyl, alkoxy, oxo, aminocarbonyl, carbonylamino, aminosulfonyl, sulfonylamino, —N(R3)$_2$, —O—(CH$_2$)$_q$—N(R4)$_2$, —N(R3)-(CH$_2$)$_q$—N(R4)$_2$, —R5, —O—(CH$_2$)$_q$—O-Alkyl, —O—(CH$_2$)$_q$—N(R4)$_2$, —N(R3)-(CH$_2$)$_q$—O-Alkyl, —N(R3)-(CH$_2$)$_q$—N(R4)$_2$, —O—(CH$_2$)$_q$—R5, and —N(R3)-(CH$_2$)$_q$—R5;

wherein two R3 moieties are independently and individually taken from the group consisting of C1-C6alkyl and branched C3-C6alkyl and are attached to the same nitrogen heteroatom of Z5 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z5 may cyclize to form a C3-C7 heterocyclyl ring;

each Z6 is independently and individually selected from the group consisting of H, C1-C6alkyl, branched C3-C7alkyl, hydroxyl, C1-C6alkoxy, (R3)$_2$N—, —N(R3)COR8, (R4)$_2$N—, —R5, —N(R4)COR8, —N(R3)SO$_2$R6-, —CON(R3)$_2$, —CON(R4)$_2$, —COR5, —SO$_2$NHR4, heteroaryl, heterocyclyl, heteroaryloxy, heterocyclyloxy, arylamino, heteroarylamino, and heterocyclylamino;

wherein two R3 moieties are independently and individually taken from the group consisting of C1-C6alkyl and branched C3-C6alkyl and are attached to the same nitrogen heteroatom of Z6 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z6 may cyclize to form a C3-C7 heterocyclyl ring;

each R2 is selected from the group consisting of alkyl, branched alkyl, fluoroalkyl, wherein the alkyl group is partially or fully fluorinated, and R19 substituted C3-C8-carbocyclyl wherein R19 is H, and C1-C6alkyl;

each R2' is selected from the group consisting of halogen and R2;

each R3 is independently and individually selected from the group consisting of H, C1-C6alkyl, branched C3-C7alkyl, C3-C7carbocyclyl, or phenyl;

each R4 is selected from the group consisting of H, C1-C6alkyl, hydroxyC1-C6 alkyl, dihydroxyC1-C6alkyl, C1-C6alkoxyC1-C6alkyl, branched C3-C7alkyl, branched hydroxyC1-C6 alkyl, branched C1-C6alkoxyC1-C6alkyl, branched dihydroxyC1-C6alkyl, carbocyclyl, hydroxyl substituted carbocyclyl, alkoxy substituted carbocyclyl, dihydroxy substituted carbocyclyl, phenyl, heteroaryl, heterocyclyl, phenylC1-C6alkyl, heteroarylC1-C6alkyl, and heterocyclylC1-C6alkyl;

each R5 is independently and individually selected from the group consisting of

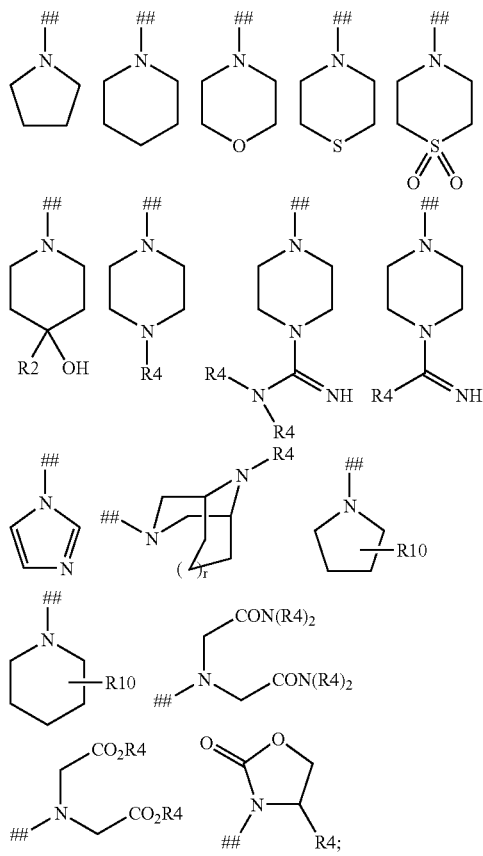

and wherein the symbol (##) is the point of attachment to respective R8, R10, Z2, or Z3, moieties containing a R5 moiety;

wherein two R4 moieties independently and individually taken from the group consisting of C1-C6alkyl, branched C3-C6alkyl, hydroxyalkyl, and alkoxyalkyl and are attached to the same nitrogen heteroatom of R5 may cyclize to form a C3-C7 heterocyclyl ring;

each R6 is independently and individually selected from the group consisting of C1-C6alkyl, branched C3-C7alkyl, carbocyclyl, phenyl, heteroaryl, and heterocyclyl;

each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

each R8 is independently and individually selected from the group consisting of C1-C6alkyl, branched C3-C7alkyl, fluoroalkyl wherein the alkyl moiety is partially or fully fluorinated, carbocyclyl, phenyl, C1-C6phenylalkyl, heteroaryl or heteroarylC1-C6alkyl, heterocyclyl, heterocyclylC1-C6alkyl, OH, C1-C6alkoxy, $N(R3)_2$, $N(R4)_2$, or R5;

wherein two R3 moieties are independently and individually taken from the group consisting of C1-C6alkyl and branched C3-C6alkyl and are attached to the same nitrogen heteroatom of R8 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of R8 may cyclize to form a C3-C7 heterocyclyl ring;

each R10 is independently and individually selected from the group consisting of $CO_2H$, $CO_2C1$-C6alkyl, $CO-N(R4)_2$, OH, C1-C6alkoxy, $-N(R4)_2$;

wherein two R4 moieties independently and individually taken from the group consisting of C1-C6alkyl, branched C3-C6alkyl, hydroxyalkyl, and alkoxyalkyl and are attached to the same nitrogen heteroatom of R10 may cyclize to form a C3-C7 heterocyclyl ring;

and n is 0-4; p is 1-4; q is 2-6; r is 0 or 1;

and tautomers, diastereomers, geometric isomers, enantiomers, hydrates, prodrugs and salts of any of the foregoing.

1.1.1 Preferred D Moieties 1.1.1a

Preferably, the compounds of formula I above contain D moieties of the formula

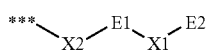

II wherein E1 is selected from the group consisting cyclopropyl, cyclobutyl, cyclopentyl, cyclohexyl, pyrrolidinyl piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl and naphthyl;

wherein the symbol (***) is the point of attachment to the Y group of formula I;

X1 is selected from the group consisting of O, S, NR3, $-C(=O)-$, $-O-(CH_2)n-$, $-S-(CH_2)n-$, $-NR3-(CH_2)n-$, $-O-(CH_2)q-O-$, $-O-(CH_2)q-NR3-$, $-N(R3)-(CH_2)q-N(R3)-$, $-(CH_2)n-N(R4)-C(=O)-$, $-(CH_2)n-N(R4)-C(=O)(CH_2)n-$, $-(CH_2)n-CO-N(R4)-$, $-(CH_2)p-$, C2-C5alkenyl, C2-C5alkynyl, C3-C6cycloalkyl, and a direct bond wherein the E1 ring and the E2 ring are directly linked by a covalent bond;

and wherein the carbon atoms of $-(CH2)n-$, $-(CH2)q-$, $(CH2)p$, C2-C5alkenyl, and C2-C5alkynyl moieties of X1 may be further substituted by one or more C1-C6alkyl;

X2 is selected from the group consisting of C1-C6 alkyl, C3-C6 branched alkyl, or a direct bond wherein E1 is directly linked to the Y group of formula I;

and wherein the carbon atoms of —(CH$_2$)n-, —(CH$_2$)q-, —(CH$_2$)p-, C2-C5alkenyl, and C2-C5 alkynyl of X2 can be further substituted by one or more C1-C6alkyl;

and E2 is selected from the group comprising cyclopentyl, cyclohexyl, phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyridinyl, pyrimidinyl, pyrazinyl, pyridazinyl, triazinyl, fused bicyclic rings selected from the group comprising indolyl, isoindolyl, isoindolinyl, isoindolonyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, imidazopyrimidinyl, imidazolonopyrimidinyl, dihydropurinonyl, pyrrolopyrimidinyl, purinyl, pyrazolopyridinyl, pyrazolopyrimidinyl, isoxazolopyrimidinyl, isothiazolopyrimidinyl, furylopyrimidinyl, thienopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalazinyl, benzodioxyl, indolinyl, benzisothiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, benzoxazepinyl, non-fused bicyclic rings comprising pyridylpyridiminyl pyrimidinylpyrimidinyl, oxazolylpyrimidinyl, thiazolylpyrimidinyl, imidazolylpyrimidinyl, isoxazolylpyrimidinyl, isothiazolylpyrimidinyl, pyrazolylpyrimidinyl, triazolylpyrimidinyl, oxadiazoylpyrimidinyl, thiadiazoylpyrimidinyl, morpholinylpyrimidinyl, dioxothiomorpholinylpyrimidinyl, thiomorpholinylpyrimidinyl, and heterocyclyls selected from the group comprising oxetanyl, azetadinyl, tetrahydrofuranyl, pyrrolidinyl, oxazolinyl, oxazolidinyl, imidazolonyl, pyranyl, thiopyranyl, tetrahydropyranyl, dioxalinyl, piperidinyl, morpholinyl, thiomorpholinyl, dioxothiomorpholinyl, piperazinyl, azepinyl, oxepinyl, diazepinyl, tropanyl, and homotropanyl;

and n is 0-4; p is 1-4; q is 2-6.

1.1.1b

Additional preferred D moieties comprise carbocyclyls and a moiety of the formula

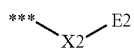

X2 is selected from the group consisting of C1-C6 alkyl, C3-C6 branched alkyl, or a direct bond wherein E2 is directly linked to the Y group of formula I.

1.1.1c

More preferred D moieties from 1.1.1b comprise the compounds of Formula III wherein the E2 ring is selected from the group comprising cyclopentyl, cyclohexyl, phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyridinyl, pyrimidinyl, pyrazinyl, pyridazinyl, triazinyl, fused bicyclic rings selected from the group comprising indolyl, isoindolyl, isoindolinyl, isoindolonyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, imidazopyrimidinyl, imidazolonopyrimidinyl, dihydropurinonyl, pyrrolopyrimidinyl, purinyl, pyrazolopyridinyl, pyrazolopyrimidinyl, isoxazolopyrimidinyl, isothiazolopyrimidinyl, furylopyrimidinyl, thienopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalazinyl, benzodioxyl, indolinyl, benzisothiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, benzoxazepinyl, non-fused bicyclic rings comprising pyridylpyridiminyl pyrimidinylpyrimidinyl, oxazolylpyrimidinyl, thiazolylpyrimidinyl, imidazolylpyrimidinyl, isoxazolylpyrimidinyl, isothiazolylpyrimidinyl, pyrazolylpyrimidinyl, triazolylpyrimidinyl, oxadiazoylpyrimidinyl, thiadiazoylpyrimidinyl, morpholinylpyrimidinyl, dioxothiomorpholinylpyrimidinyl, thiomorpholinylpyrimidinyl, and heterocyclyls selected from the group comprising oxetanyl, azetadinyl, tetrahydrofuranyl, pyrrolidinyl, oxazolinyl, oxazolidinyl, imidazolonyl, pyranyl, thiopyranyl, tetrahydropyranyl, dioxalinyl, piperidinyl, morpholinyl, thiomorpholinyl, dioxothiomorpholinyl, piperazinyl, azepinyl, oxepinyl, diazepinyl, tropanyl, and homotropanyl.

1.1.2 Preferred A2 Moieties 1.1.2a

Preferred A2 moieties of Formula I are selected from the group consisting of

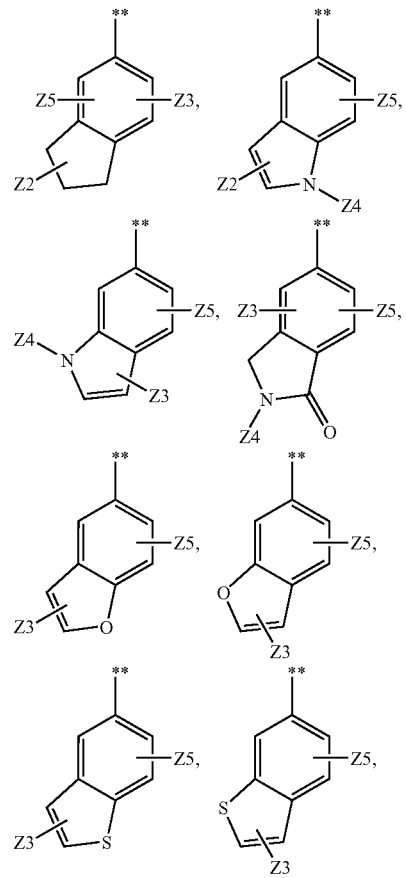

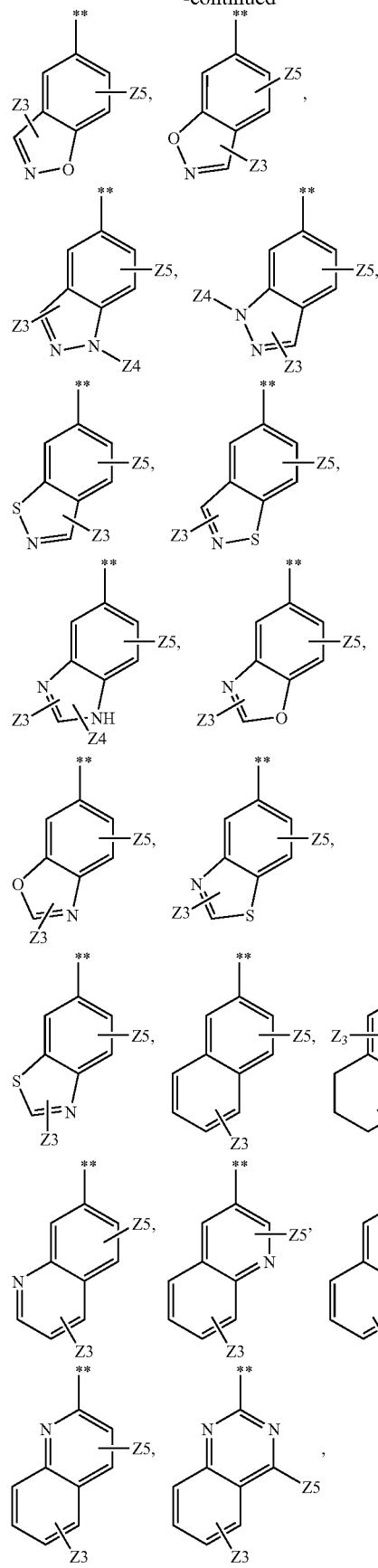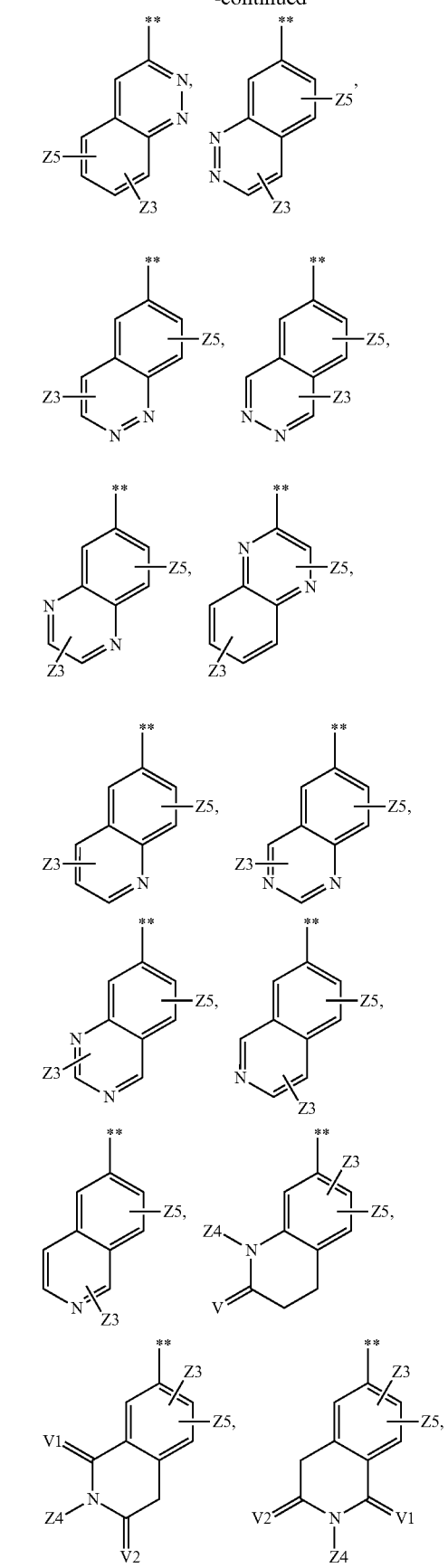

-continued
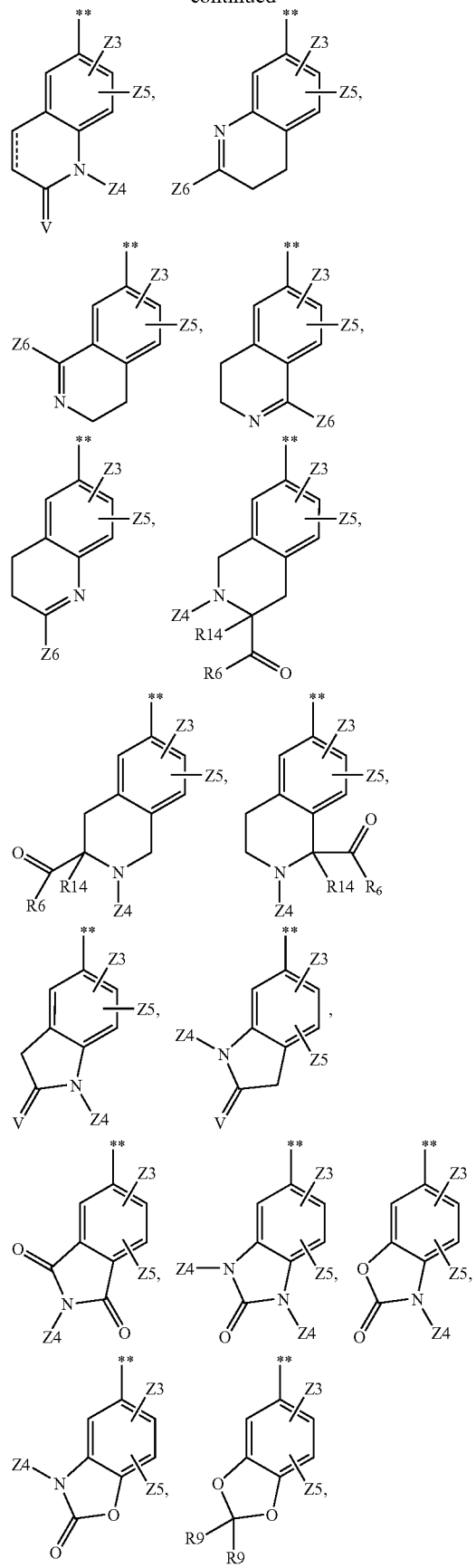
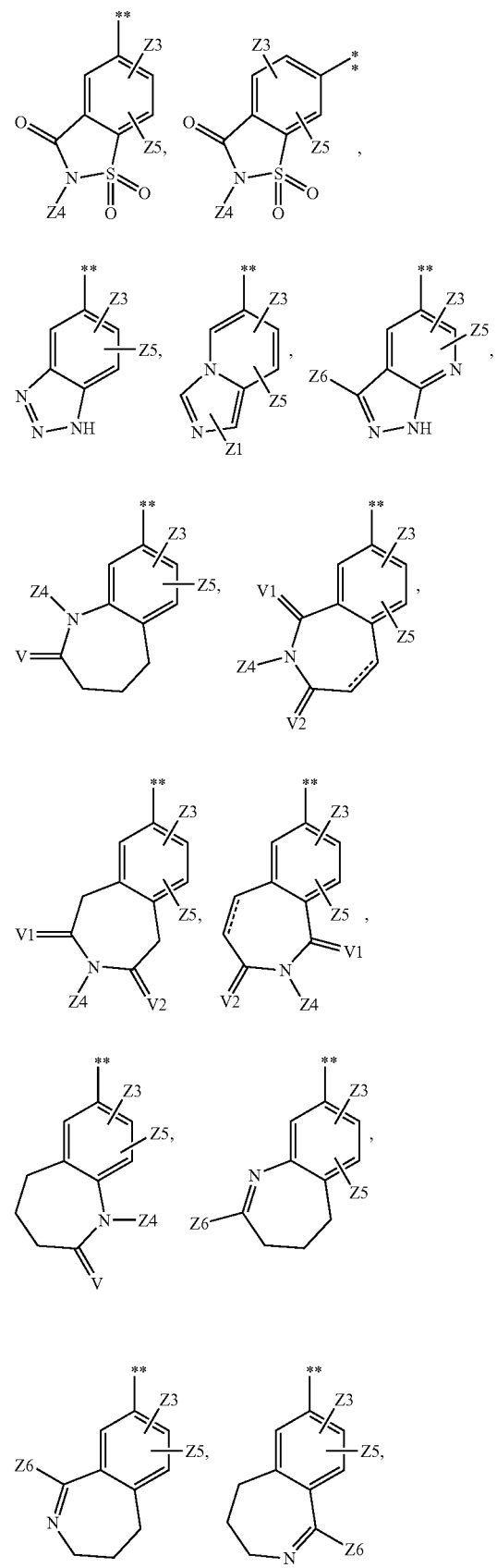

-continued

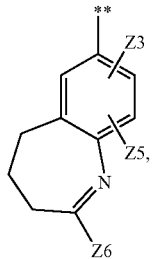

and wherein the symbol (**) is the point of attachment to the A1 ring of formula I;

and wherein ═ indicates either a saturated or an unsaturated bond;

wherein each Z3 and Z5 may be independently attached to either of the rings making up the foregoing bicyclic structures;

each R9 is independently and individually selected from the group consisting of H, F, C1-C6alkyl, branched C4-C7alkyl, carbocyclyl, phenyl, phenyl C1-C6alkyl, heterocyclyl and heterocyclylC1-C6alkyl;

each R13 is independently and individually selected from the group consisting of H, C1-C6alkyl, branched C3-C7alkyl, carbocyclyl, hydroxyC2-C7alkyl, C1-C6alkoxyC2-C7alkyl, $(R4)_2N$—CO, $(R4)_2N$—CO—C1-C6alkyl, carboxyC1-C6alkyl, C1-C6alkoxycarbonyl, C1-C6alkoxycarbonylC1-C6alkyl, $(R4)_2N$—C2-C6alkyl, $(R4)_2N$—C2-C6alkylN(R4)-$(CH_2)_q$, R5-C2-C6alkylN(R4)-$(CH_2)_q$, $(R4)_2N$—C2-C6alkylO-$(CH_2)_q$, R5-C2-C6alkyl-O—$(CH_2)_q$, —$(CH_2)_qN$(R4)C(O)R8, aryl, arylC1-C6alkyl, heteroaryl, heteroarylC1-C6alkyl, heterocyclyl, heterocyclylC1-C6alkyl, aryloxyC2-C6alkyl, heteroaryloxyC2-C6alkyl, heterocyclyloxyC2-C6alkyl, arylaminoC2-C6alkyl, heteroarylaminoC2-C6alkyl, and heterocyclylaminoC2-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom of R13 may cyclize to form a C3-C7 heterocyclyl ring;

each R14 is independently and respectively selected from the group consisting of H and C1-C6alkyl;

V, V1, and V2 are each independently and respectively selected from the group consisting of O and $H_2$;

each Z4 is a substituent attached to a ring nitrogen and is independently and individually selected from the group consisting of H, C1-C6alkyl, hydroxyC2-C6alkyl, C1-C6alkoxyC2-C6alkyl, $(R4)_2N$—C2-C6alkyl, $(R4)_2N$—C2-C6alkylN(R4)-C2-C6alkyl, $(R4)_2N$—C2-C6alkyl-O—C2-C6alkyl, $(R4)_2N$—CO—C2-C6alkyl, carboxyC2-C6alkyl, C1-C6alkoxycarbonylC2-C6alkyl, —C2-C6alkylN(R4)C(O)R8, R8-C(═NR3)-, —$SO_2R8$, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

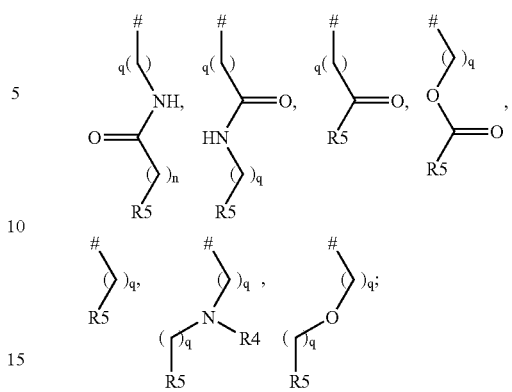

wherein the symbol (#) indicates the point of attachment of the Z4 moiety to the A2 ring for formula I;

in the event that Z4 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z4 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z4 may cyclize to form a C3-C7 heterocyclyl ring;

and n is 0-4; p is 1-4; q is 2-6; r is 0 or 1; v is 1 or 2.

1.1.2b

More preferred A2 moieties are selected from the group consisting of

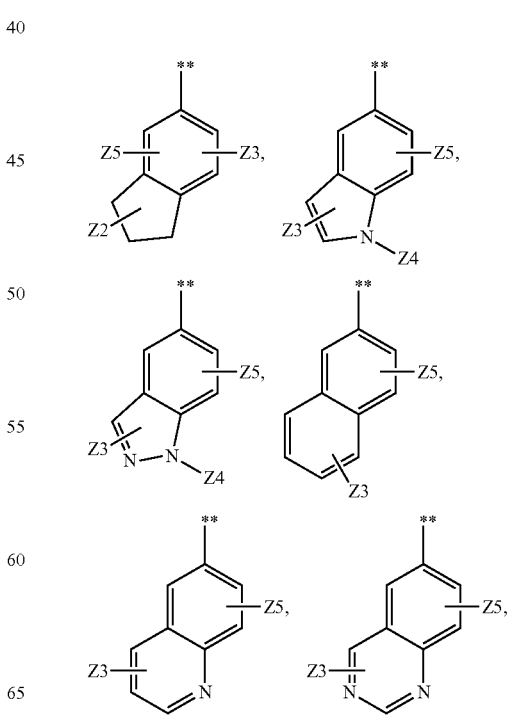

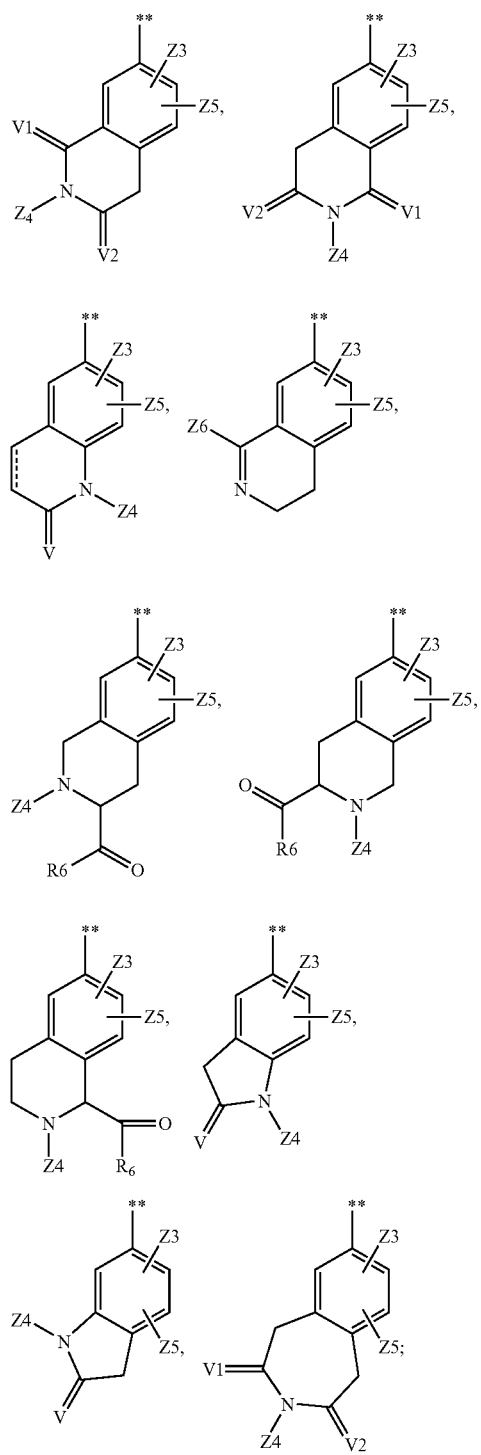
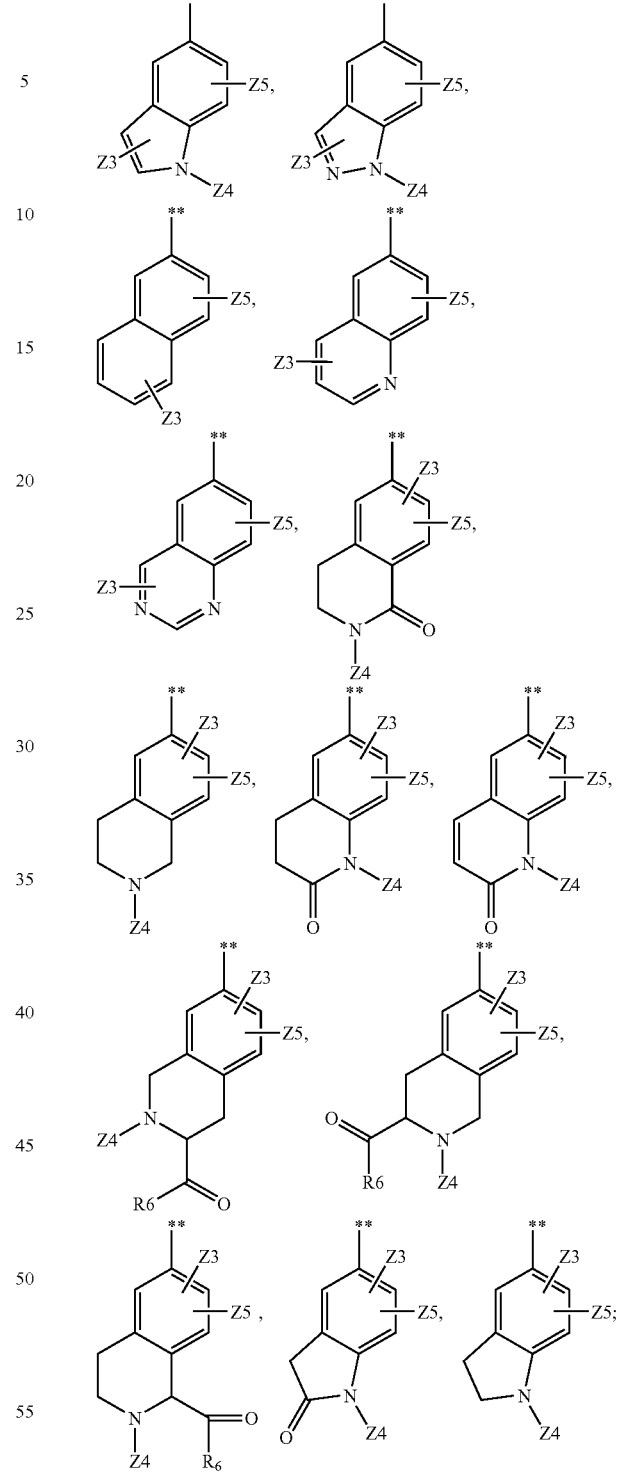

and wherein the symbol (**) is the point of attachment to the A1 ring for formula I;
wherein each Z3 and Z5 is independently attached to either aryl or heteroaryl ring of the A2 bicyclic ring.

1.1.2c

Still more preferred A2 moieties are selected from the group consisting of and wherein the symbol (**) is the point of attachment to the A1 ring of formula I;
wherein each Z3 and Z5 is independently attached to either aryl or heteroaryl ring of the A2 bicyclic ring.

1.1.3 Preferred Classes of Compounds 1.1.3a

Compounds as defined in 1.1.1a wherein the A2 group is defined in 1.1.2a.

1.1.3b
Compounds as defined in 1.1.3a wherein the A2 group is defined in 1.1.2b.
1.1.3c
Compounds as defined in 1.1.3a wherein the A2 group is defined in 1.1.2c.
1.1.3d
Compounds as defined in 1.1.1b wherein the A2 group is defined in 1.1.2a.
1.1.3e
Compounds as defined in 1.1.3c wherein the A2 group is defined in 1.1.2b.
1.1.3f
Compounds as defined in 1.1.3c wherein the A2 group is defined in 1.1.2c.

1.1.4 Preferred A1 Moieties 1.1.4a

A1 moieties are selected from the group consisting of

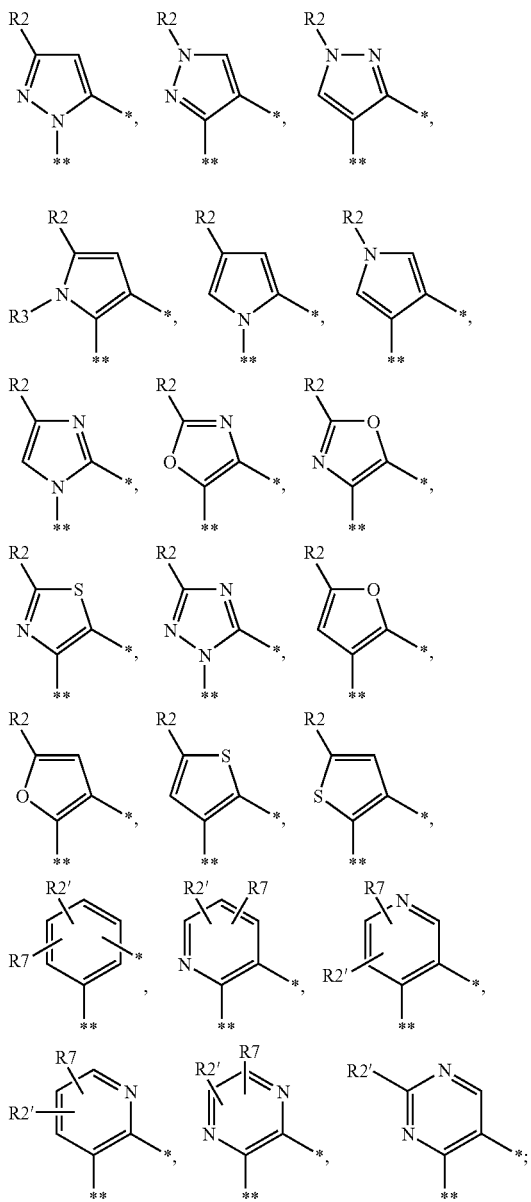

wherein the symbol (*) denotes the attachment to the W moiety of formula I and the symbol (**) denotes the attachment to the A2 moiety of formula I;

each R7 is selected from the group consisting of halogen, C1-C3fluoroalkyl wherein the alkyl moiety is partially or fully fluorinated, C1-C3alkyl, cyclopropyl, cyano, or C1-C3alkoxy.

1.1.4b

Preferred A1 moieties are selected from the group consisting of

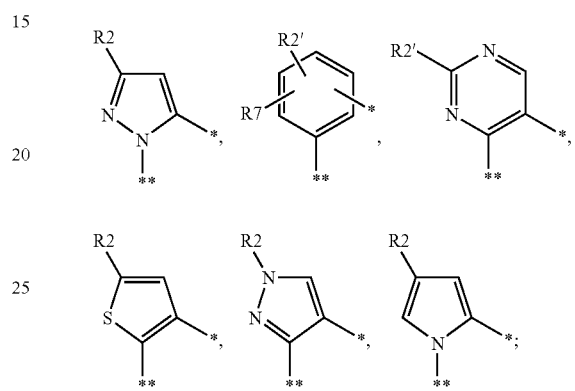

wherein the symbol (*) denotes the attachment to the W moiety of formula I and the symbol (**) denotes the attachment to the A2 moiety of formula I.

1.1.4c

Still more preferred A1 moieties are selected from the group consisting of

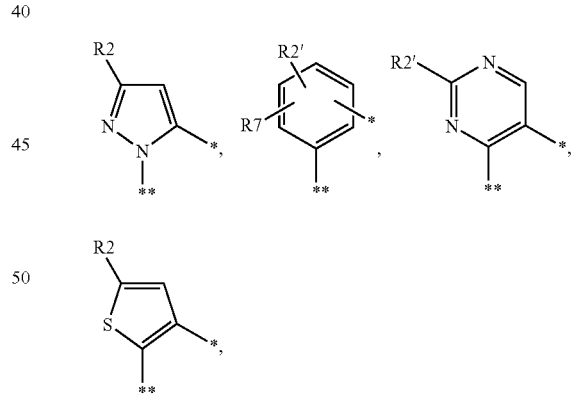

wherein the symbol (*) denotes the attachment to the W moiety of formula I and the symbol (**) denotes the attachment to the A2 moiety of formula I.

1.1.5 Preferred W and Y Moieties 1.1.5a (1) W and Y are each NH, and X=O; (2) W=NH, Y=CHR4 and X=O; or (3) W=CHR4, Y=NH, and X=O.

1.1.5b

W and Y are each NH and X=O.

1.1.6 Further Preferred Compounds

1.1.6a

Further preferred compounds are of the formula

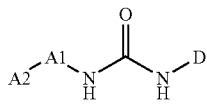

wherein A2 is selected from the group consisting of

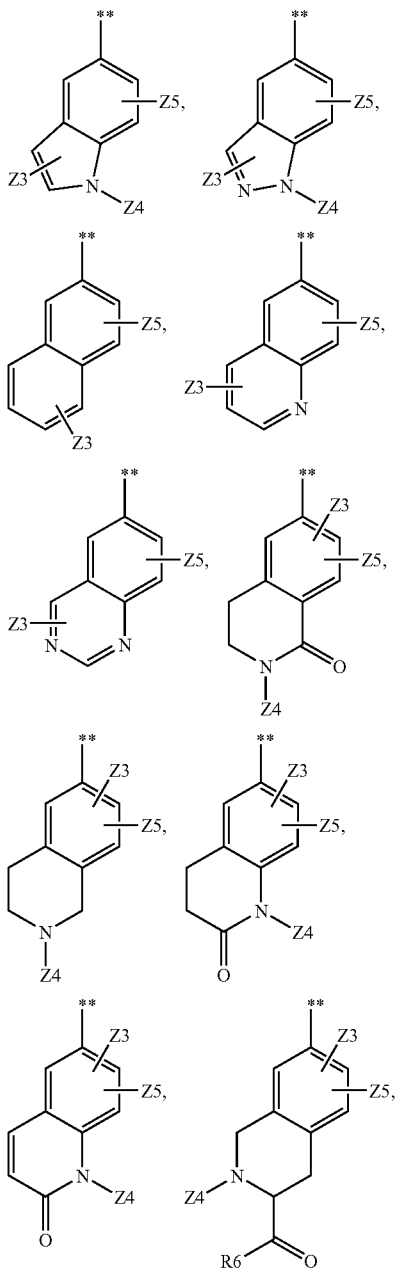

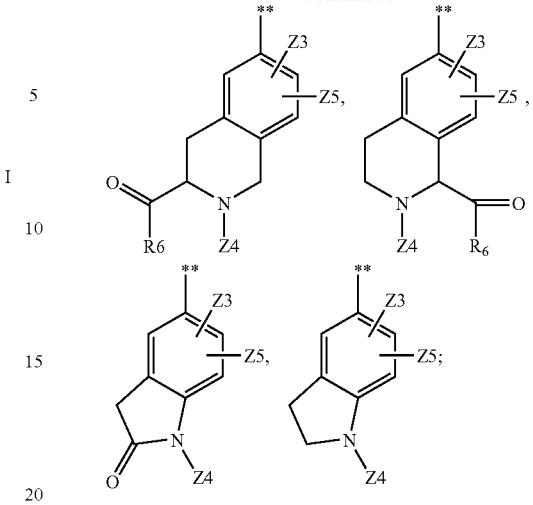

wherein each Z3 and Z5 is independently attached to either aryl or heteroaryl ring of the A2 bicyclic ring;

wherein the symbol (**) denotes the attachment to the A1 moiety of formula I;

A1 is selected from the group consisting of

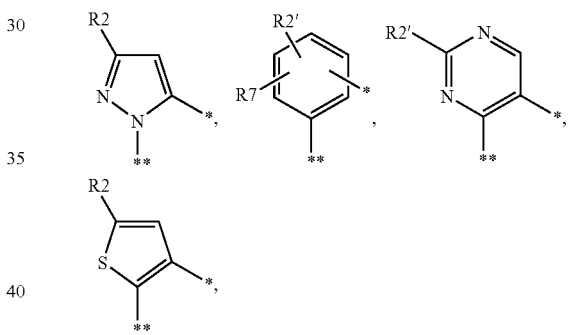

wherein the symbol (*) denotes the attachment to the W moiety of formula I and the symbol (**) denotes the attachment to the A2 moiety of formula I;

X is O, S, or NR3;

D is selected from the group consisting of 2,3-dichlorophenyl, 2-fluorophenyl, 3-fluorophenyl, 4-fluorophenyl, 3-cyanophenyl, 2,3-difluorophenyl, 2,4-difluorophenyl, 3,4-difluorophenyl, 2,5-difluorophenyl, 3,5-difluorophenyl, 2,3,5-trifluorophenyl, 2,4,5-trifluorophenyl, 2,3,4-trifluorophenyl, 3,4,5-trifluorophenyl, 4-cyanophenyl, 3-fluoro-5-cyanophenyl, 3-(R8SO$_2$)-phenyl, 3-(hydroxyC1-C3alkyl)-phenyl, 3-(R3O—N═C(R6))-phenyl, 3-phenoxyphenyl, 4 phenoxyphenyl,

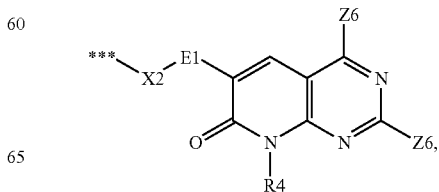

-continued
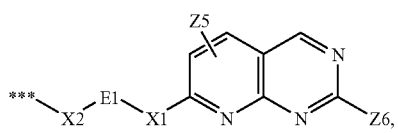
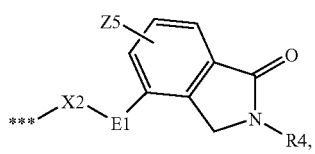
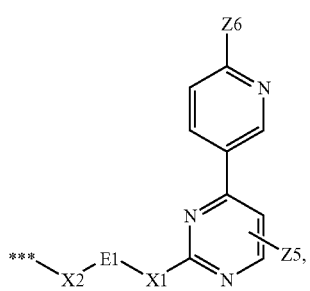
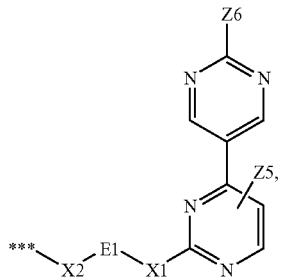
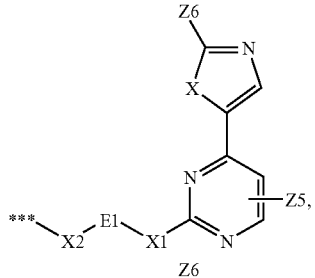
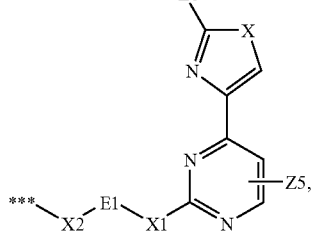
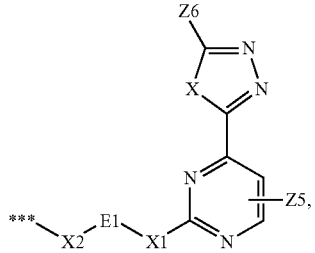
-continued
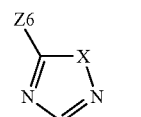
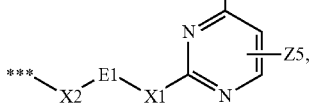
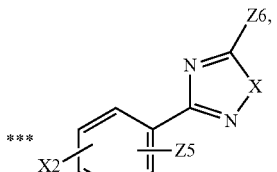
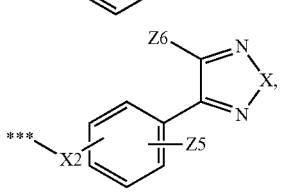
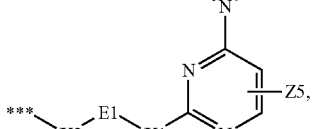
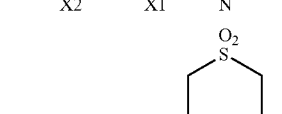
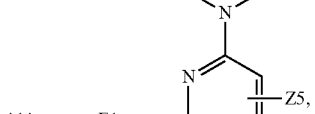
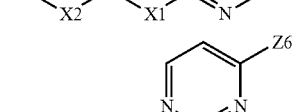
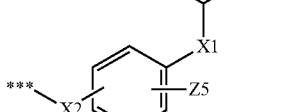
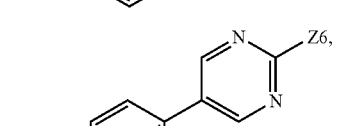
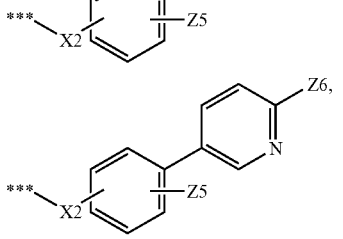

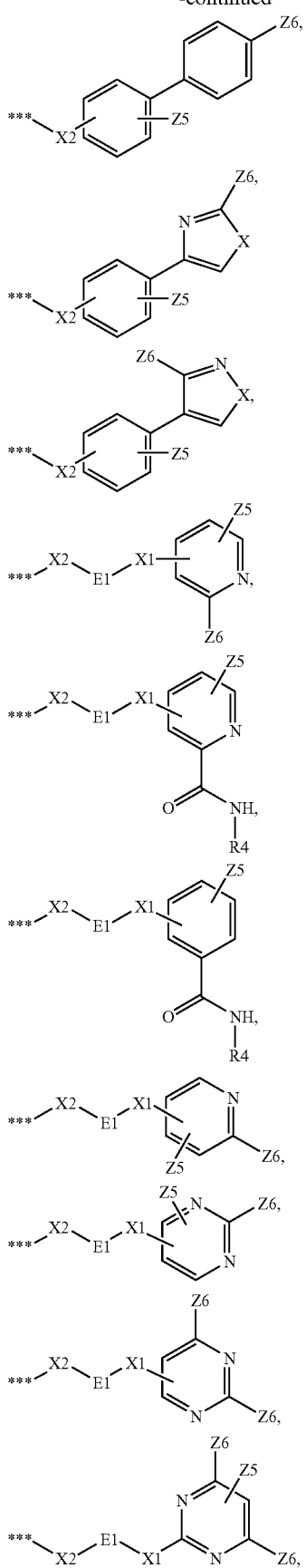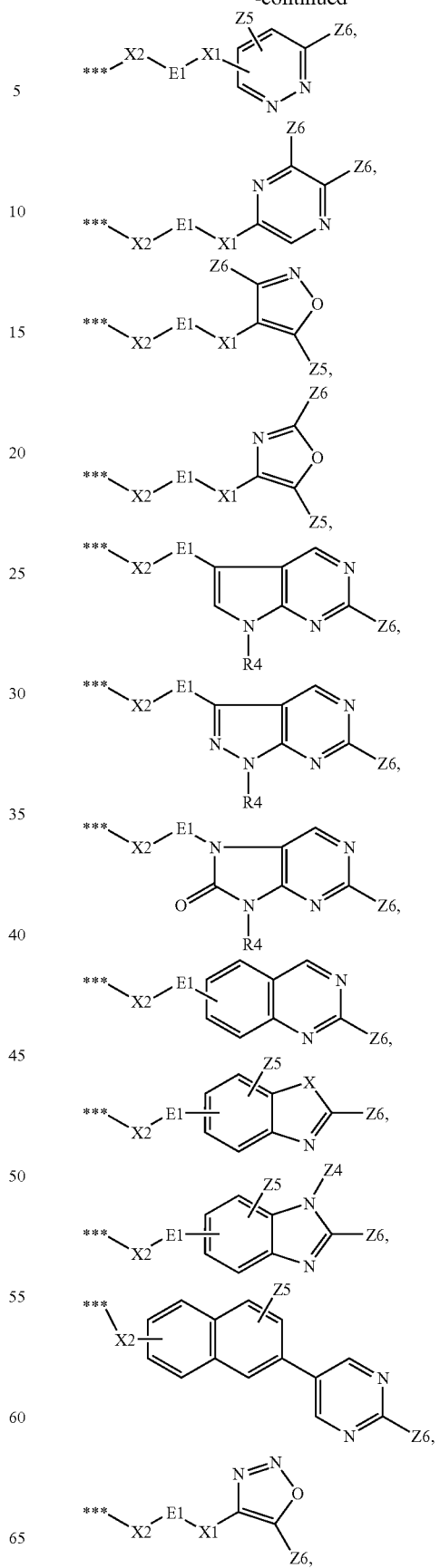

-continued

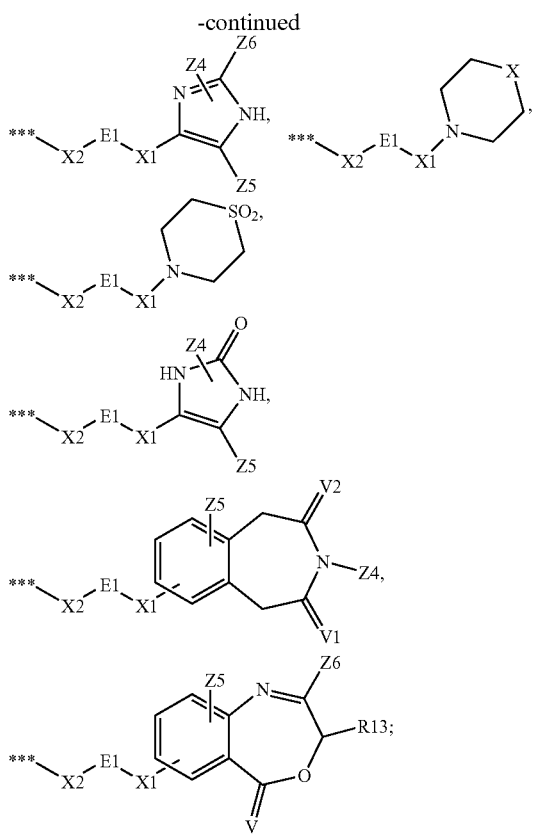

wherein E1 is selected from the group consisting cyclopropyl, cyclobutyl, cyclopentyl, cyclohexyl, pyrrolidinyl piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl and naphthyl;

X1 is selected from the group consisting of O, S, NR3, —C(=O)—, —O—(CH$_2$)n-, —S—(CH$_2$)n-, —NR3-(CH$_2$)n-, —O—(CH$_2$)q-O—, —O—(CH$_2$)q-NR3-, —N(R3)-(CH$_2$)q-N(R3)-, —(CH$_2$)n-N(R4)-C(=O)—, —(CH$_2$)n-N(R4)-C(=O)(CH$_2$)n-, —(CH$_2$)n-CO—N(R4)-, —(CH$_2$)p-, C2-C5alkenyl, C2-C5alkynyl, C3-C6cycloalkyl, and a direct bond wherein the E1 ring and the E2 ring are directly linked by a covalent bond;

and wherein the carbon atoms of —(CH2)n-, —(CH2)q-, (CH2)p, C2-C5alkenyl, and C2-C5alkynyl moieties of X1 may be further substituted by one or more C1-C6alkyl;

X2 is selected from the group consisting of C1-C6 alkyl, C3-C6 branched alkyl, or a direct bond wherein E1 is directly linked to the Y group of formula I;

and wherein the carbon atoms of —(CH$_2$)n-, —(CH$_2$)q-, —(CH$_2$)p-, C2-C5alkenyl, and C2-C5alkynyl of X2 can be further substituted by one or more C1-C6alkyl;

each R2 is selected from the group consisting of alkyl, branched alkyl, fluoroalkyl, wherein the alkyl group is partially or fully fluorinated, and R19 substituted C3-C8carbocyclyl wherein R19 is H, and C1-C6alkyl;

each R2' is selected from the group consisting of halogen and R2;

each R3 is independently and individually selected from the group consisting of H, C1-C6alkyl, branched C3-C7alkyl, C3-C7carbocyclyl, or phenyl;

wherein two R3 moieties independently and individually taken from the group consisting of C1-C6alkyl and branched C3-C7alkyl are attached to the same nitrogen heteroatom, the two R3 moieties may cyclize to form a C3-C7 heterocyclyl ring;

each R4 is selected from the group consisting of H, C1-C6alkyl, hydroxyC1-C6 alkyl, dihydroxyC1-C6alkyl, C1-C6alkoxyC1-C6alkyl, branched C3-C7alkyl, branched hydroxyC1-C6 alkyl, branched C1-C6alkoxyC1-C6alkyl, branched dihydroxyC1-C6alkyl, carbocyclyl, hydroxyl substituted carbocyclyl, alkoxy substituted carbocyclyl, dihydroxy substituted carbocyclyl, phenyl, heteroaryl, heterocyclyl, phenylC1-C6alkyl, heteroarylC1-C6alkyl, and heterocyclylC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom may cyclize to form a C3-C7 heterocyclyl ring;

each R5 is independently and individually selected from the group consisting of

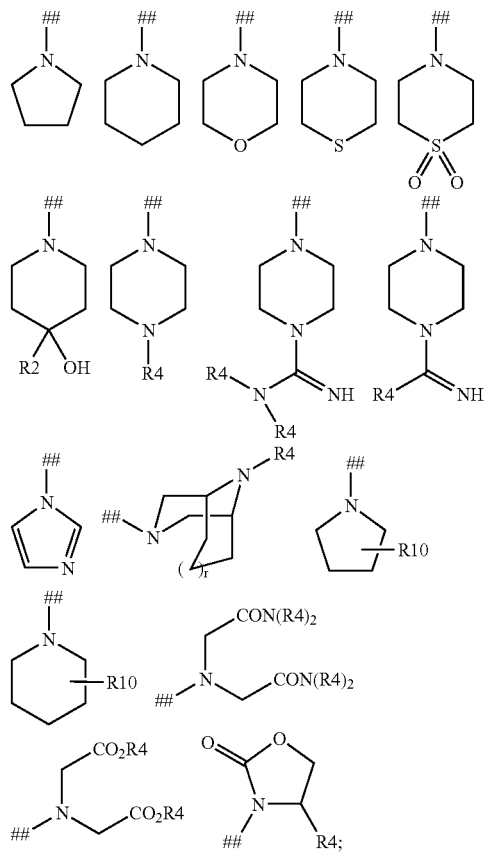

and wherein the symbol (##) is the point of attachment to respective R8, R10, R13, Z2, Z3, Z4, Z5, or A2 ring moieties containing a R5 moiety;

wherein two R4 moieties independently and individually taken from the group consisting of C1-C6alkyl, branched C3-C6alkyl, hydroxyalkyl, and alkoxyalkyl and are attached to the same nitrogen heteroatom of R5 may cyclize to form a C3-C7 heterocyclyl ring;

wherein each R6 is independently and individually selected from the group consisting of C1-C6alkyl, branched C3-C7alkyl, carbocyclyl, phenyl, heteroaryl, and heterocyclyl;

each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

each R8 is independently and individually selected from the group consisting of C1-C6alkyl, branched C3-C7alkyl, fluoroalkyl wherein the alkyl moiety is partially or fully fluorinated, carbocyclyl, phenyl, C1-C6phenylalkyl, heteroaryl or heteroarylC1-C6alkyl, heterocyclyl, heterocyclylC1-C6alkyl, OH, C1-C6alkoxy, N(R3)$_2$, N(R4)$_2$, or R5;

wherein two R3 moieties are independently and individually taken from the group consisting of C1-C6alkyl and branched C3-C6alkyl and are attached to the same nitrogen heteroatom of R8 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of R8 may cyclize to form a C3-C7 heterocyclyl ring;

each R10 is independently and individually selected from the group consisting of CO$_2$H, CO$_2$C1-C6alkyl, CO—N(R4)$_2$, OH, C1-C6alkoxy, —N(R4)$_2$;

wherein two R4 moieties independently and individually taken from the group consisting of C1-C6alkyl, branched C3-C6alkyl, hydroxyalkyl, and alkoxyalkyl and are attached to the same nitrogen heteroatom of R10 may cyclize to form a C3-C7 heterocyclyl ring;

each R13 is independently and individually selected from the group consisting of H, C1-C6alkyl, branched C3-C7alkyl, carbocyclyl, hydroxyC2-C7alkyl, C1-C6alkoxyC2-C7alkyl, (R4)$_2$N—CO, (R4)$_2$N—CO—C1-C6alkyl, carboxyC1-C6alkyl, C1-C6alkoxycarbonyl, C1-C6alkoxycarbonylC1-C6alkyl, (R4)$_2$N—C2-C6alkyl, (R4)$_2$N—C2-C6alkylN(R4)-(CH$_2$)$_q$, R5-C2-C6alkylN(R4)-(CH$_2$)$_q$, (R4)$_2$N—C2-C6alkylO-(CH$_2$)$_q$, R5-C2-C6alkyl-O—(CH$_2$)$_q$, —(CH$_2$)$_q$N(R4)C(O)R8, aryl, arylC1-C6alkyl, heteroaryl, heteroarylC1-C6alkyl, heterocyclyl, heterocyclylC1-C6alkyl, aryloxyC2-C6alkyl, heteroaryloxyC2-C6alkyl, heterocyclyloxyC2-C6alkyl, arylaminoC2-C6alkyl, heteroarylaminoC2-C6alkyl, and heterocyclylaminoC2-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom of R13 may cyclize to form a C3-C7 heterocyclyl ring;

each R14 is independently and respectively selected from the group consisting of H and C1-C6alkyl;

V, V1, and V2 are each independently and respectively selected from the group consisting of O and H$_2$;

each Z3 is independently and individually selected from the group consisting of H, C1-C6alkyl, hydroxyl, hydroxyC1-C6alkyl, cyano, C1-C6alkoxy, C1-C6alkoxyC1-C6alkyl, halogen, CF$_3$, (R3)$_2$N—, (R4)$_2$N—, (R4)$_2$NC1-C6alkyl, (R4)$_2$NC2-C6alkylN(R4)-(CH$_2$)$_n$, (R4)$_2$NC2-C6alkylO-(CH$_2$)$_n$, R8CO—, (R4)$_2$N—CO—C1-C6alkyl, carboxyl, carboxyC1-C6alkyl, C1-C6alkoxycarbonyl, C1-C6alkoxycarbonylC1-C6alkyl, (R3)$_2$NSO$_2$, —SO$_2$R3, SOR3, (R4)$_2$NSO$_2$, —SO$_2$R4, —SOR4, —(CH$_2$)$_n$N(R4)C(O)R8, —C=(NOH)R6, —C=(NOR3)R6, heteroaryl, heterocyclyl, heteroarylC1-C6alkyl, heterocyclylC1-C6alkyl, heteroaryloxy, heterocyclyloxy, heteroaryloxyC1-C6alkyl, heterocyclyloxyC1-C6alkyl, arylamino, heteroarylamino, heterocyclylamino, arylaminoC1-C6alkyl, heteroarylaminoC1-C6alkyl, heterocyclylaminoC1-C6alkyl, or moieties of the formulae

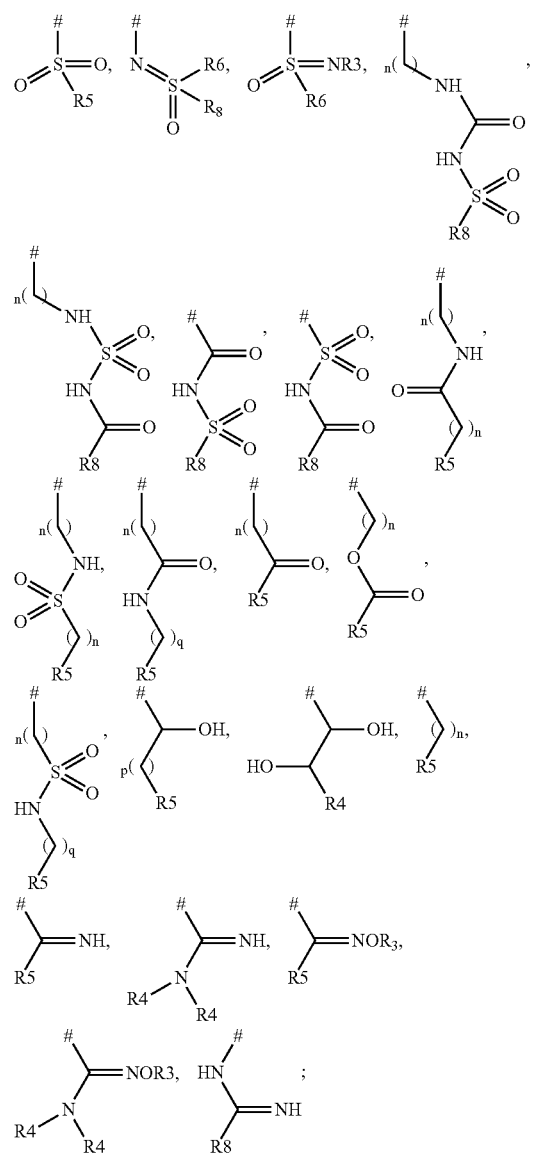

wherein the symbol (#) indicates the point of attachment of the Z3 moiety to the A2 ring of formula I;

in the event that Z3 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z3 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z3 may cyclize to form a C3-C7 heterocyclyl ring;

each Z4 is a substituent attached to a ring nitrogen and is independently and individually selected from the group consisting of H, C1-C6alkyl, hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C2-C6alkyl, carboxyC2-C6alkyl, C1-C6alkoxycarbonylC2-C6alkyl, —C2-C6alkylN (R4)C(O)R8, R8-C(=NR3)-, —SO$_2$R8, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

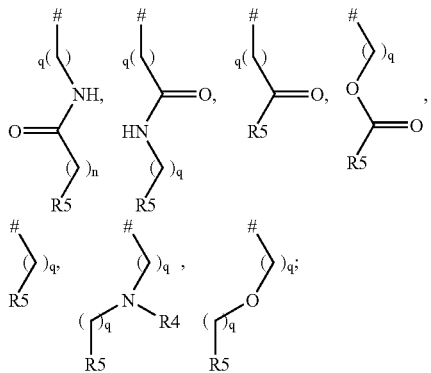

wherein the symbol (#) indicates the point of attachment of the Z4 moiety to the A2 ring for formula I;

in the event that Z4 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z4 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z4 may cyclize to form a C3-C7 heterocyclyl ring;

Z5 is independently and individually selected from the group consisting of H, C1-C6alkyl, branched C3-C7alkyl, halogen, fluoroalkyl, cyano, hydroxyl, alkoxy, oxo, aminocarbonyl, carbonylamino, aminosulfonyl, sulfonylamino, —N(R3)$_2$, —O—(CH$_2$)q-N(R4)$_2$, —N(R3)-(CH$_2$)q-N(R4)$_2$, —R5, —O—(CH$_2$)q-O-Alkyl, —O—(CH$_2$)q-N(R4)$_2$, —N(R3)-(CH$_2$)q-O-Alkyl, —N(R3)-(CH$_2$)q-N(R4)$_2$, —O—(CH$_2$)q-R5, and —N(R3)-(CH$_2$)q-R5;

wherein two R3 moieties are independently and individually taken from the group consisting of C1-C6alkyl and branched C3-C6alkyl and are attached to the same nitrogen heteroatom of Z5 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z5 may cyclize to form a C3-C7 heterocyclyl ring;

Each Z6 is independently and individually selected from the group consisting of H, C1-C6alkyl, branched C3-C7alkyl, hydroxyl, C1-C6alkoxy, (R3)$_2$N—, —N(R3)COR8, (R4)$_2$N—, —R5, —N(R4)COR8, —N(R3)SO$_2$R6-, —CON(R3)$_2$, —CON(R4)$_2$, —COR5, —SO$_2$NHR4, heteroaryl, heterocyclyl, heteroaryloxy, heterocyclyloxy, arylamino, heteroarylamino, and heterocyclylamino;

wherein two R3 moieties are independently and individually taken from the group consisting of C1-C6alkyl and branched C3-C6alkyl and are attached to the same nitrogen heteroatom of Z6 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z6 may cyclize to form a C3-C7 heterocyclyl ring;

and n is 0-4; p is 1-4; q is 2-6; r is 0 or 1; v is 1 or 2;

and tautomers, diastereomers, geometric isomers, enantiomers, hydrates, prodrugs and salts of any of the foregoing.
1.1.6b The following specific compounds are most preferred:
1-(3-t-butyl-1-(1-(methanesulfonylureidoamidomethyl)naphthalen-3-yl)-1H-pyrazol-5-yl)3-(2,3-dichlorophenyl)urea, 1-(1-(4-(2-amino-2-oxoethyl)naphthalen-2-yl)-3-t-butyl-1H-pyrazol-5-yl)-3-(2,3-dichlorophenyl)urea, 1-(3-t-butyl-1-(4-(hydroxymethyl)naphthalen-2-yl)-1H-pyrazol-5-yl)-3-(2,3-dichlorophenyl)urea, 1-(1-(4-(2-aminoethyl)naphthalen-2-yl)-3-t-butyl-1H-pyrazol-5-yl)-3-(2,3-dichlorophenyl)urea, 1-(3-t-butyl-1-(1,2,3,4-tetrahydroisoquinolin-6-yl)-1H-pyrazol-5-yl)-3-(2,3-dichlorophenyl)urea, (3S)-6-(3-t-butyl-5-(3-(2,3-dichlorophenyl)ureido)-1H-pyrazol-1-yl)-1,2,3,4-tetrahydroisoquinoline-3-carboxylic acid, 6-(3-t-butyl-5-(3-(2,3-dichlorophenyl)ureido)-1H-pyrazol-1-yl)-1,2,3,4-tetrahydroisoquinoline-3-carboxylic acid, 1-(1-(4-(2-amino-2-oxoethyl)naphthalen-2-yl)-3-t-butyl-1 H-pyrazol-5-yl)-3-(2,3,4-trifluorophenyl)urea, 1-(3-t-butyl-1-(4-(hydroxymethyl)naphthalen-2-yl)-1H-pyrazol-5-yl)-3-(2,4,5-trifluorophenyl)urea, 1-(1-(4-(2-amino-2-oxoethyl)naphthalen-2-yl)-3-t-butyl-1H-pyrazol-5-yl)-3-(2,4,5-trifluorophenyl)urea, 1-(3-t-butyl-1-(4-(2-(2,3-dihydroxypropylamino)-2-oxoethyl)naphthalen-2-yl)-1H-pyrazol-5-yl)-3-(2,4,5-trifluorophenyl)urea, 1-(3-t-butyl-1-(4-((1-amino-1-oxo-methylamino)methyl)naphthalen-2-yl)-1H-pyrazol-5-yl)-3-(2,4,5-trifluorophenyl)urea, 1-(3-t-butyl-1-(1,2,3,4-tetrahydroisoquinolin-6-yl)-1H-pyrazol-5-yl)-3-(2,4,5-trifluorophenyl)urea, 1-(1-(4-(2-amino-2-oxoethyl)naphthalen-2-yl)-3-t-butyl-1H-pyrazol-5-yl)-3-(2,3,5-trifluorophenyl)urea, 1-(3-t-butyl-1-(4-(2-(2,3-dihydroxypropylamino)-2-oxoethyl)naphthalen-2-yl)-1H-pyrazol-5-yl)-3-(2,3,5-trifluorophenyl)urea, 1-(3-t-butyl-1-(4-(hydroxymethyl)naphthalen-2-yl)-1H-pyrazol-5-yl)-3-(2,3,5-trifluorophenyl)urea, 1-(1-(4-(aminomethyl)naphthalen-2-yl)-3-t-butyl-1H-pyrazol-5-yl)-3-(2,3,5-trifluorophenyl)urea, 1-(3-t-butyl-1-(4-((1-amino-1-oxo-methylamino)methyl)naphthalen-2-yl)-1H-pyrazol-5-yl)-3-(2,3,5-trifluorophenyl)urea, 1-(3-t-butyl-1-(4-(hydroxymethyl)naphthalen-2-yl)-1H-pyrazol-5-yl)-3-(3,4,5-trifluorophenyl)urea, 1-(3-t-butyl-1-(4-(2-(2,3-dihydroxypropylamino)-2-oxoethyl)naphthalen-2-yl)-1H-pyrazol-5-yl)-3-(3,4,5-trifluorophenyl)urea, 1-(3-t-butyl-1-(4-(hydroxymethyl)naphthalen-2-yl)-1H-pyrazol-5-yl)-3-(3,5-difluorophenyl)urea, 1-(1-(4-(2-amino-2-oxoethyl)naphthalen-2-yl)-3-t-butyl-1H-pyrazol-5-yl)-3-(3,5-difluorophenyl)urea, 1-(1-(4-(2-amino-2-oxoethyl)naphthalen-2-yl)-3-t-butyl-1H-pyrazol-5-yl)-3-(2,5-difluorophenyl)urea, 1-(3-t-butyl-1-(4-(2-(1,3-dihydroxypropan-2-ylamino)-2-oxoethyl)naphthalen-2-yl)-1H-pyrazol-5-yl)-3-(2,5-difluorophenyl)urea, 1-(1-(4-(aminomethyl)naphthalen-2-yl)-3-t-butyl-1H-pyrazol-5-yl)-3-(3-cyanophenyl)urea, 1-(3-t-butyl-1-(1,2,3,4-tetrahydroisoquinolin-6-yl)-1H-pyrazol-5-yl)-3-(3-cyanophenyl)urea, 1-(3-t-butyl-1-(1H-indol-5-yl)-1H-pyrazol-5-yl)-3-(3-(pyridin-3-yloxy)phenyl)urea, 1-(3-t-butyl-1-(indolin-5-yl)-1H-pyrazol-5-yl)-3-(3-(pyridin-3-yloxy)phenyl)urea, 1-(1-(4-(2-amino-2-oxoethyl)naphthalen-2-yl)-3-t-butyl-1H-pyrazol-5-yl)-3-(3-(pyridin-3-yloxy)phenyl)urea, 1-(3-t-butyl-1-(4-(2-(2,3- dihydroxypropylamino)-2-oxoethyl)naphthalen-2-yl)-1H-pyrazol-5-yl)-3-(3-(pyridin-3-yloxy)phenyl)urea, 1-(3-t-butyl-1-(4-(hydroxymethyl)naphthalen-2-yl)-1 H-pyrazol-5-yl)-3-(3-(pyridin-3-yloxy)phenyl)urea, 1-(1-(4-(aminomethyl)naphthalen-2-yl)-3-t-butyl-1H-pyrazol-5-yl)-3-(3-(pyridin-3-yloxy)phenyl)urea, 1-(3-t-butyl-1-(1,2,3,4-tetrahydroisoquinolin-6-yl)-1H-pyrazol-5-yl)-3-(3-(pyridin-3-yloxy)phenyl)urea, 1-(3-t-butyl-1-(1,2,3,4-tetrahydroisoquinolin-6-yl)-1H-pyrazol-5-yl)-3-(3-(5-chloropyridin-3-yloxy)phenyl)urea, 6-(3-t-butyl-5-(3-(3-(pyridin-3-yloxy)phenyl)ureido)-1H-pyrazol-1-yl)-1,2,3,4-tetrahydroisoquinoline-3-carboxylic acid, 1-(3-t-butyl-1-(3-carbamoyl-1,2,3,4-tetrahydroisoquinolin-6-yl)-1H-pyrazol-5-yl)-3-(3-(pyridin-3-yloxy)phenyl)urea, 1-(3-t-butyl-1-(3-(methylcarbamoyl)-1,2,3,4-tetrahydroisoquinolin-6-yl)-1H-pyrazol-5-yl)-3-(3-(pyridin-3-yloxy)phenyl)urea, 1-(3-t-butyl-1-(1-(methylcarbamoyl)-1,2,3,4-tetrahydroisoquinolin-6-yl)-1H-pyrazol-5-yl)-3-(3-(pyridin-3-yloxy)phenyl)urea, 1-(3-t-butyl-1-(2-oxo-1,2-dihydroquinolin-6-yl)-1H-pyrazol-5-yl)-3-(3-(pyridin-3-yloxy)phenyl)urea, 1-(3-t-butyl-1-(quinolin-6-yl)-1H-pyrazol-5-yl)-3-(3-(pyridin-3-yloxy)phenyl)urea, 1-(3-cyclopentyl-1-(2-oxo-1,2-dihydroquinolin-6-yl)-1H-pyrazol-5-yl)-3-(3-(pyridin-3-yloxy)phenyl)urea, 1-(3-t-butyl-1-(1,2,3,4-tetrahydroisoquinolin-6-yl)-1H-pyrazol-5-yl)-3-(4-(2-(methylcarbamoyl)pyridin-4-yloxy)phenyl)urea, 1-(3-t-butyl-1-(2-oxo-1,2-dihydroquinolin-6-yl)-1H-pyrazol-5-yl)-3-(4-(2-(methylcarbamoyl)pyridin-4-yloxy)phenyl)urea, 1-(3-t-butyl-1-(2-(piperazin-1-yl)quinolin-6-yl)-1H-pyrazol-5-yl)-3-(4-(2-(methylcarbamoyl)pyridin-4-yloxy)phenyl)urea, 1-(1-(2-(2-aminoethylamino)quinolin-6-yl)-3-t-butyl-1H-pyrazol-5-yl)-3-(4-(2-(methylcarbamoyl)pyridin-4-yloxy)phenyl)urea, 1-(3-cyclopentyl-1-(2-oxo-1, 2-dihydroquinolin-6-yl)-1H-pyrazol-5-yl)-3-(4-(2-(methylcarbamoyl)pyridin-4-yloxy)phenyl)urea, 1-(3-t-butyl-1-(2-(dimethylamino)quinolin-6-yl)-1H-pyrazol-5-yl)-3-(4-(2-(methylcarbamoyl)pyridin-4-yloxy)phenyl)urea, 1-(3-t-butyl-1-(2-((R)-3-(dimethylamino)pyrrolidin-1-yl)quinolin-6-yl)-1H-pyrazol-5-yl)-3-(4-(2-(methylcarbamoyl)pyridin-4-yloxy)phenyl)urea, 1-(1-(2-aminoquinolin-6-yl)-3-t-butyl-1H-pyrazol-5-yl)-3-(4-(2-(methylcarbamoyl)pyridin-4-yloxy)phenyl)urea, 1-(3-t-butyl-1-(2-(methylamino)quinolin-6-yl)-1H-pyrazol-5-yl)-3-(4-(2-(methylcarbamoyl)pyridin-4-yloxy)phenyl)urea, 1-(3-t-butyl-1-(2-oxo-1,2-dihydroquinolin-6-yl)-1H-pyrazol-5-yl)-3-(3-(2-(methylcarbamoyl)pyridin-4-yloxy)phenyl)urea, 1-(3-t-butyl-1-(1,2,3,4-tetrahydroisoquinolin-6-yl)-1H-pyrazol-5-yl)-3-(4-(1-oxoisoindolin-4-yl)phenyl)urea, 1-(3-t-butyl-1-(indolin-5-yl)-1H-pyrazol-5-yl)-3-(4-(1-oxoisoindolin-4-yl)phenyl)urea, 1-(3-t-butyl-1-(1-(methylsulfonyl)indolin-5-yl)-1H-pyrazol-5-yl)-3-(4-(1-oxoisoindolin-4-yl)phenyl)urea, 6-(3-t-butyl-5-(3-(4-(1-oxoisoindolin-4-yl)phenyl)ureido)-1H-pyrazol-1-yl)-1,2,3,4-tetrahydroisoquinoline-3-carboxylic acid, 1-(3-t-butyl-1-(1, 2,3,4-tetrahydroisoquinolin-6-yl)-1H-pyrazol-5-yl)-3-(3-(8-methyl-7-oxo-7,8-dihydropyrido[2,3-d]pyrimidin-6-yl)phenyl)urea, 1-(3-t-butyl-1-(2-oxo-1,2,3,4-tetrahydroquinolin-6-yl)-1H-pyrazol-5-yl)-3-(3-(8-methyl-7-oxo-7,8-dihydropyrido[2,3-d]pyrimidin-6-yl)phenyl)urea, 1-(3-t-butyl-1-(2-oxo-1,2-dihydroquinolin-6-yl)-1H-pyrazol-5-yl)-3-(3-(8-methyl-7-oxo-7,8-dihydropyrido[2,3-d]pyrimidin-6-yl)phenyl)urea, 1-(3-t-butyl-1-(3-carbamoyl-1,2,3,4-tetrahydroisoquinolin-6-yl)-1H-pyrazol-5-yl)-3-(3-(8-methyl-7-oxo-7,8-dihydropyrido[2,3-d]pyrimidin-6-yl)phenyl)urea, 1-(3-t-butyl-1-(1-(methylsulfonyl)indolin-5-yl)-1H-pyrazol-5-yl)-3-(3-(8-methyl-7-oxo-7,8-dihydropyrido[2,3-d]pyrimidin-6-yl)phenyl)urea, 1-(3-t-butyl-1-(1H-indol-5-yl)-1H-pyrazol-5-yl)-3-(3-(8-methyl-7-oxo-7,8-dihydropyrido[2,3-d]pyrimidin-6-yl)phenyl)urea, 1-(3-t-butyl-1-(2-(piperazin-1-yl)quinolin-6-yl)-1H-pyrazol-5-yl)-3-(3-(8-methyl-7-oxo-7,8-dihydropyrido[2,3-d] pyrimidin-6-yl)phenyl)urea, 1-(3-t-butyl-1-(1,2,3,4-tetrahydroisoquinolin-6-yl)-1H-pyrazol-5-yl)-3-(4-methyl-3-(4-(pyridin-3-yl)pyrimidin-2-ylamino)phenyl)urea, 1-(3-t-butyl-1-(2-(piperazin-1-yl)quinolin-6-yl)-1H-pyrazol-5-yl)-3-(4-methyl-3-(4-(pyridin-3-yl)pyrimidin-2-ylamino) phenyl)urea 1.1.7 Methods
1.1.7a Methods of Protein Modulation The invention includes methods of modulating kinase activity of a variety of kinases, e.g. C-Abl kinase, BCR-Abl kinase. The kinases may be wildtype kinases, oncogenic forms thereof, aberrant fusion proteins thereof or polymorphs of any of the foregoing. The method comprises the step of contacting the kinase species with compounds of the invention and especially those set forth in sections 1.1 and 1.1.6a. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, kinase cellular localization, and recruitment of other proteins into signaling complexes through modulation of kinase conformation.

The methods of the invention may also involve the step of inducing, synergizing, or promoting the binding of a second modulator compound of said kinase, especially C-Abl kinase or BCR-Abl kinase, to form a ternary adduct, such co-incident binding resulting in enhanced biological modulation of the kinase when compared to the biological modulation of the protein affected by either of said compounds alone. The second compound may interact at a substrate, co-factor or regulatory site on the kinase, with the second site being distinct from the site of interaction of the first compound. For example, the second site may be an ATP co-factor site. The second compounds may be taken from the group consisting of N-(4-methyl-3-(4-(pyridin-3-yl)pyrimidin-2-ylamino)phenyl)-4-((4-methylpiperazin-1-yl)methyl)benzamide (Gleevec); N-(2-chloro-6-methylphenyl)-2-(6-(4-(2-hydroxyethyl)piperazin-1-yl)-2-methylpyrimidin-4-ylamino) thiazole-5-carboxamide (BMS-354825); 6-(2,6-dichlorophenyl)-2-(3-(hydroxymethyl)phenylamino)-8-methylpyrido[2,3-d]pyrimidin-7(8H)-one (PD 166326); 6-(2,6-dichlorophenyl)-8-methyl-2-(3-(methylthio)phenylamino)pyrido[2,3-d]pyrimidin-7(8H)-one (PD 173955); 6-(2,6-dichlorophenyl)-2-(4-fluoro-3-methylphenylamino)-8-methylpyrido[2,3-d]pyrimidin-7(8H)-one (PD180970); 6-(2,6-dichlorophenyl)-2-(4-ethoxyphenylamino)-8-methylpyrido[2,3-d]pyrimidin-7(8H)-one (PD 173958); 6-(2,6-dichlorophenyl)-2-(4-fluorophenylamino)-8-methylpyrido[2,3-d]pyrimidin-7(8H)-one (PD 173956); 6-(2,6-dichlorophenyl)-2-(4-(2-(diethylamino)ethoxy)phenylamino)-8-methylpyrido[2,3-d]pyrimidin-7(8H)-one (PD 166285); 2-(4-(2-aminoethoxy)phenylamino)-6-(2,6-dichlorophenyl)-8-methylpyrido[2,3-d]pyrimidin-7(8H)-one; N-(3-(6-(2,6-dichlorophenyl)-8-methyl-7-oxo-7,8-dihydropyrido[2,3-d]pyrimidin-2-ylamino)phenyl)acetamide (SKI DV-MO16); 2-(4-aminophenylamino)-6-(2,6-dichlorophenyl)-8-methylpyrido[2,3-d]pyrimidin-7(8H)-one (SKI DV 1-10); 6-(2,6-dichlorophenyl)-2-(3-hydroxyphenylamino)-8-methylpyrido[2,3-d]pyrimidin-7(8H)-one (SKI DV2-89); 2-(3-aminophenylamino)-6-(2,6-dichlorophenyl)-8-methylpyrido[2,3-d]pyrimidin-7(8H)-one (SKI DV 2-43);

N-(4-(6-(2,6-dichlorophenyl)-8-methyl-7-oxo-7,8-dihydropyrido[2,3-d]pyrimidin-2-ylamino)phenyl)acetamide (SKI DV-M017); 6-(2,6-dichlorophenyl)-2-(4-hydroxyphenylamino)-8-methylpyrido[2,3-d]pyrimidin-7(8H)-one (SKI DV-MO17); 6-(2,6-dichlorophenyl)-2-(3-ethylphenylamino)-8-methylpyrido[2,3-d]pyrimidin-7(8H)-one (SKI DV 2 87).

1.1.7b Treatment Methods

The methods of the invention also include treating individuals suffering from a condition selected from the group consisting of cancer and hyperproliferative diseases. These methods comprise administering to such individuals compounds of the invention, and especially those of section 1.1 and 1.1.6a. Exemplary conditions include chronic myelogenous leukemia, acute lymphocytic leukemia, gastrointestinal stromal tumors, and hypereosinophillic syndrome. The administration method is not critical, and may be from the group consisting of oral, parenteral, inhalation, and subcutaneous.

1.1.8 Pharmaceutical Preparations

The compounds of the invention, especially those of 1.1 and 1.1.6a may form a part of a pharmaceutical composition by combining one or more such compounds with a pharmaceutically acceptable carrier. Additionally, the compositions may include an additive selected from the group consisting of adjuvants, excipients, diluents, and stabilizers.

1.1.9 Kinase/Compound Adducts

The invention also provides adducts in the form of compounds of the invention bound with a species of kinase such as a wild-type kinase, oncogenic forms thereof, aberrant fusion proteins thereof and polymorphs of any of the foregoing. The compounds are advantageously selected from the groups defined in sections 1.1 and 1.1.6a.

1.2 Generally—Monocyclic A2 Compounds with Polycyclic E2 Rings

The invention includes compounds of the formula

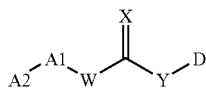

I wherein A2 is selected from the group consisting of a Z1-substituted phenyl, Z1-substituted pyridyl, Z1-substituted pyrimidinyl, Z1-substituted thienyl, Z1 or Z4'-substituted monocyclic heterocyclyl rings, and other monocyclic heteroaryls, excluding tetrazolyl, 1,2,4-oxadiazolonyl, 1,2,4-triazolonyl, and alkyl-substituted pyrrolyl wherein the pyrrolyl nitrogen is the site of attachment to the A1 ring;

A1 is selected from the group consisting of R2' and R7-substituted phenyl, pyridyl, or pyrimidinyl, R2-substituted monocyclic 5-membered ring heteroaryl, and R2'-substituted monocyclic heterocyclyl moieties;

W and Y are CHR4, NR3, or O and wherein W and Y are not simultaneously O;

X is O, S, or NR3;

each Z1 is a substituent attached to a ring carbon and is independently and individually selected from the group consisting of hydroxyC1-C6alkyl, C2-C6alkoxy, C1-C6alkoxyC1-C6alkyl, (R4)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—C(=O)—, (R4)$_2$N—C(=O)—, (R4)$_2$N—CO—C1-C6alkyl, C1-C6alkoxycarbonyl, carboxyC1-C6alkyl, C1-C6alkoxycarbonylC1-C6alkyl, (R3)$_2$NSO$_2$, SOR3, (R4)$_2$NSO$_2$, —SO$_2$R3', —SOR4, —C(=O)R6, —C(=NOH)R6, —C(=NOR3)R6, —(CH$_2$)$_n$N(R4)C(O)R8, monocyclic heteroaryl, monocyclic heterocyclyl, monocyclic heteroarylC1-C6alkyl, monocyclic heterocyclylC1-C6alkyl, monocyclic heteroaryloxy, monocyclic heterocylyloxy, monocyclic heteroaryloxyC1-C6alkyl, monocyclic heterocyclyloxyC1-C6alkyl, arylamino, monocyclic heteroarylamino, monocyclic heterocyclylamino, arylaminoC1-C6alkyl, monocyclic heteroarylaminoC1-C6alkyl, monocyclic heterocyclylaminoC1-C6alkyl, or moieties of the formulae

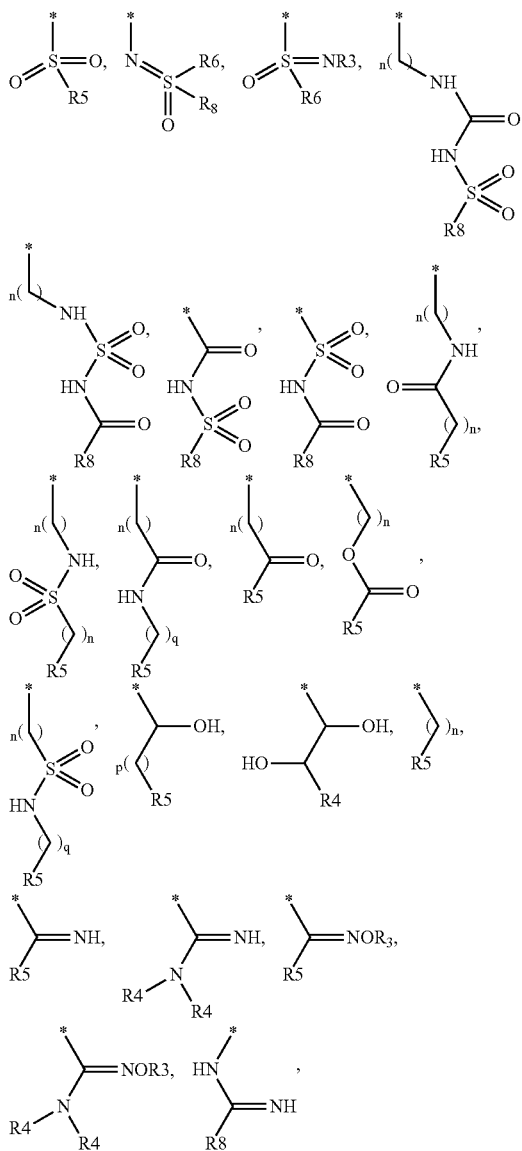

cyano wherein the site of attachment to the A2 ring is meta to the point of attachment to the A1 ring and wherein A2 is phenyl, and cyano wherein the site of attachment is to a substitutable position when A2 is pyridyl, pyrimidinyl or a five-membered ring;

wherein the asterisk (*) indicates the point of attachment of the Z1 moiety to the A2 ring;

in the event that Z1 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z1 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z1 may cyclize to form a C3-C7 heterocyclyl ring;

each Z4' is a substituent attached to a ring nitrogen and is independently and individually selected from the group consisting of hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C2-C6alkyl, carboxyC2-C6alkyl, C1-C6alkoxycarbonylC2-C6alkyl, —C2-C6alkylN(R4)C(O)R8, R8-C(=NR3)-, —SO$_2$R8, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

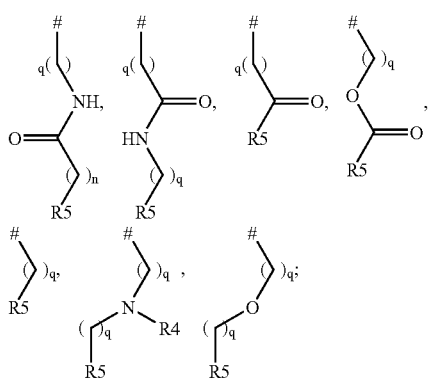

wherein the symbol (#) indicates the point of attachment of the Z4' moiety to the A1 ring of formula I;

in the event that Z4' contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z4' may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z4' may cyclize to form a C3-C7 heterocyclyl ring;

each R2 is selected from the group consisting of alkyl, branched alkyl, fluoroalkyl, wherein the alkyl group is partially or fully fluorinated, and R19 substituted C3-C8carbocyclyl wherein R19 is H, and C1-C6alkyl;

each R2' is selected from the group consisting of halogen and R2;

each R3 is independently and individually selected from the group consisting of H, C1-C6alkyl, branched C3-C7alkyl, C3-C7cycloalkyl, or phenyl;

each R3' is independently and individually selected from the group consisting of C2-C6alkyl, branched C3-C7alkyl, C3-C7cycloalkyl, aryl, arylalkyl, heteroaryl, and heteroarylalkyl;

each R4 is selected from the group consisting of H, C1-C6alkyl, hydroxyC1-C6 alkyl, dihydroxyC1-C6alkyl, C1-C6alkoxyC1-C6alkyl, branched C3-C7alkyl, branched hydroxyC1-C6 alkyl, branched C1-C6alkoxyC1-C6alkyl, branched dihydroxyC1-C6alkyl, carbocyclyl, hydroxyl substituted carbocyclyl, alkoxy substituted carbocyclyl, dihydroxy substituted carbocyclyl, phenyl, heteroaryl, heterocyclyl, phenylC1-C6alkyl, heteroarylC1-C6alkyl, and heterocyclylC1-C6alkyl;

each R5 is independently and individually selected from the group consisting of

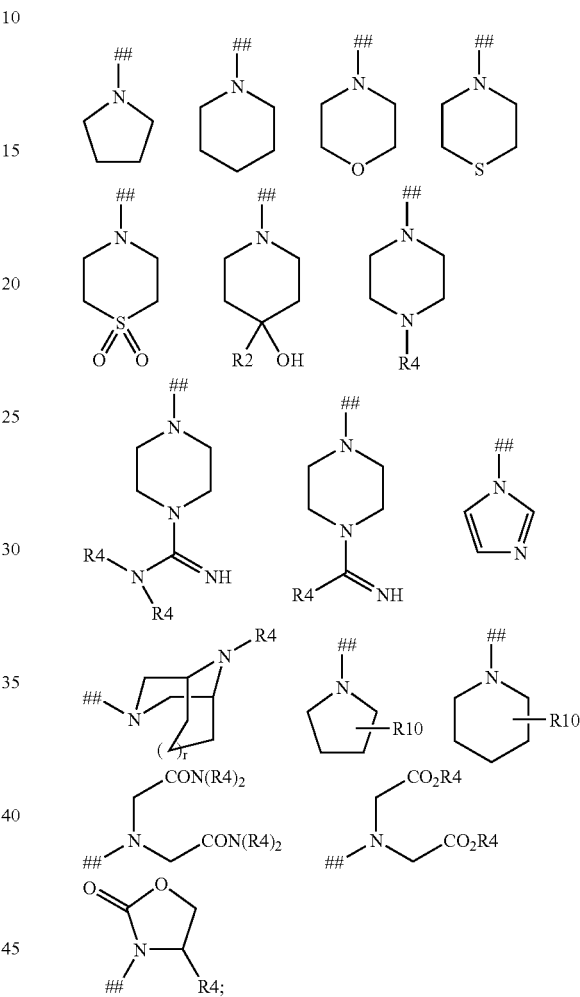

and wherein the symbol (##) is the point of attachment to respective R8, R10, Z1, Z4', Z5, Z6 or A2 ring moieties containing a R5 moiety;

wherein two R4 moieties independently and individually taken from the group consisting of C1-C6alkyl, branched C3-C6alkyl, hydroxyalkyl, and alkoxyalkyl and are attached to the same nitrogen heteroatom of R5 may cyclize to form a C3-C7 heterocyclyl ring;

wherein each R6 is independently and individually selected from the group consisting of C1-C6alkyl, branched C3-C7alkyl, carbocyclyl, phenyl, heteroaryl, and heterocyclyl;

each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

each R8 is independently and individually selected from the group consisting of C1-C6alkyl, C1-C6 fluoroalkyl wherein the alkyl moiety is partially or fully fluorinated, branchedC4-

C7alkyl, carbocyclyl, phenyl, C1-C6phenylalkyl, heteroaryl or heteroarylC1-C6alkyl, heterocyclyl, heterocyclylC1-C6alkyl, OH, C1-C6alkoxy, N(R3)$_2$, N(R4)$_2$, or R5;

wherein two R3 moieties are independently and individually taken from the group consisting of C1-C6alkyl and branched C3-C6alkyl and are attached to the same nitrogen heteroatom of R8 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of R8 may cyclize to form a C3-C7 heterocyclyl ring;

each R10 is independently and individually selected from the group consisting of CO$_2$H, CO$_2$C1-C6alkyl, CO—N(R4)$_2$, OH, C1-C6alkoxy, —N(R4)$_2$;

wherein two R4 moieties independently and individually taken from the group consisting of C1-C6alkyl, branched C3-C6alkyl, hydroxyalkyl, and alkoxyalkyl and are attached to the same nitrogen heteroatom of R10 may cyclize to form a C3-C7 heterocyclyl ring;

D comprises a moiety taken from group consisting of moieties of the formula

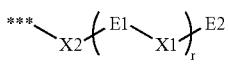

wherein the symbol (***) is the point of attachment to the Y group of formula I;
wherein E2 is taken from the group consisting of poly-aryl, poly-heteroaryl, mono- and poly heterocyclyl, and carbocyclyl;
wherein E1 is taken from the group consisting of mono- and poly-aryl, mono- and poly-heteroaryl, mono- and poly heterocyclyl and carbocyclyl;
X1 is selected from the group consisting of O, S, NR3, —C(=O)—, —O—(CH$_2$)n-, —S—(CH$_2$)n-, —NR3-(CH$_2$)n-, —O—(CH$_2$)q-O—, —O—(CH$_2$)q-NR3-, —N(R3)-(CH$_2$)q-N(R3)-, —(CH$_2$)n-N(R4)-C(=O)—, —(CH$_2$)n-N(R4)-C(=O)(CH$_2$)n-, —(CH$_2$)n-CO—N(R4)-, —(CH$_2$)p-, C2-C5alkenyl, C2-C5alkynyl, C3-C6cycloalkyl, and a direct bond wherein the E1 ring and the E2 ring are directly linked by a covalent bond;
and wherein the carbon atoms of —(CH2)n-, —(CH2)q-, —(CH2)p, C2-C5alkenyl, and C2-C5alkynyl moieties of X1 may be further substituted by one or more C1-C6alkyl;
X2 is selected from the group consisting of C1-C6 alkyl, C3-C6 branched alkyl, or a direct bond wherein either E1 or E2 is directly linked to the Y group of formula I;
and n is 0-4; p is 1-4; q is 2-6, r is 0 or 1;
and tautomers, diastereomers, geometric isomers, enantiomers, hydrates, prodrugs, and salts of any of the foregoing.

1.2.1 Preferred D Moieties 1.2.1a

Preferably, the compounds of formula I in 1.2 contain D moieties wherein E1 is selected from the group consisting cyclopropyl, cyclobutyl, cyclopentyl, cyclohexyl, pyrrolidinyl piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl and naphthyl;
wherein E2 is comprises the group consisting of cyclopentyl, cyclohexyl, non-fused bicyclic rings comprising pyridylpyridiminyl pyrimidinylpyrimidinyl, oxazolylpyrimidinyl, thiazolylpyrimidinyl, imidazolylpyrimidinyl, isoxazolylpyrimidinyl, isothiazolylpyrimidinyl, pyrazolylpyrimidinyl, triazolylpyrimidinyl, oxadiazoylpyrimidinyl, thiadiazoylpyrimidinyl, morpholinylpyrimidinyl, dioxothiomorpholinylpyrimidinyl, thiomorpholinylpyrimidinyl, and heterocyclyls selected from the group comprising oxetanyl, azetadinyl, tetrahydrofuranyl, pyrrolidinyl, oxazolinyl, oxazolidinyl, imidazolonyl, pyranyl, thiopyranyl, tetrahydropyranyl, dioxalinyl, piperidinyl, morpholinyl, thiomorpholinyl, dioxothiomorpholinyl, piperazinyl, azepinyl, oxepinyl, diazepinyl, tropanyl, and homotropanyl.

1.2.1b

Additionally preferred D moieties of formula I in 1.2 comprise a formula

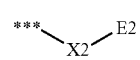

IV wherein X2 is selected from the group consisting of C1-C6 alkyl, C3-C6 branched alkyl, or a direct bond wherein E2 is directly linked to the Y group of formula I.

1.2.1c

More preferred D moieties of 1.2.1b are wherein E2 is cyclopentyl, cyclohexyl, non-fused bicyclic rings comprising pyridylpyridiminyl pyrimidinylpyrimidinyl, oxazolylpyrimidinyl, thiazolylpyrimidinyl, imidazolylpyrimidinyl, isoxazolylpyrimidinyl, isothiazolylpyrimidinyl, pyrazolylpyrimidinyl, triazolylpyrimidinyl, oxadiazoylpyrimidinyl, thiadiazoylpyrimidinyl, morpholinylpyrimidinyl, dioxothiomorpholinylpyrimidinyl, thiomorpholinylpyrimidinyl, and heterocyclyls selected from the group comprising oxetanyl, azetadinyl, tetrahydrofuranyl, pyrrolidinyl, oxazolinyl, oxazolidinyl, imidazolonyl, pyranyl, thiopyranyl, tetrahydropyranyl, dioxalinyl, piperidinyl, morpholinyl, thiomorpholinyl, dioxothiomorpholinyl, piperazinyl, azepinyl, oxepinyl, diazepinyl, tropanyl, and homotropanyl.

1.2.2 Preferred A2 Moieties 1.2.2a

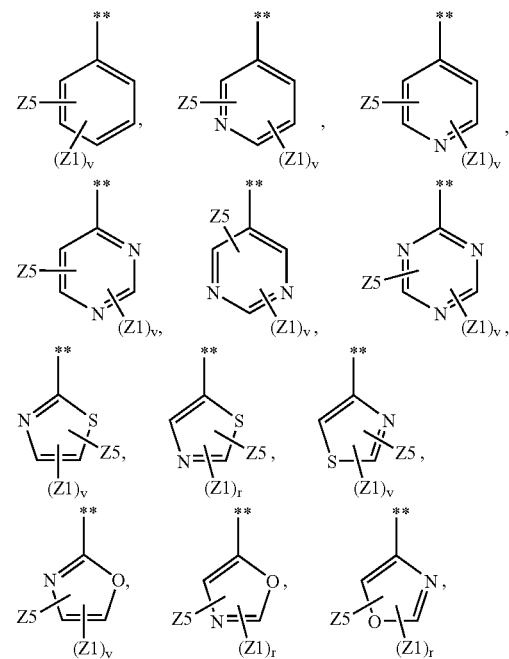

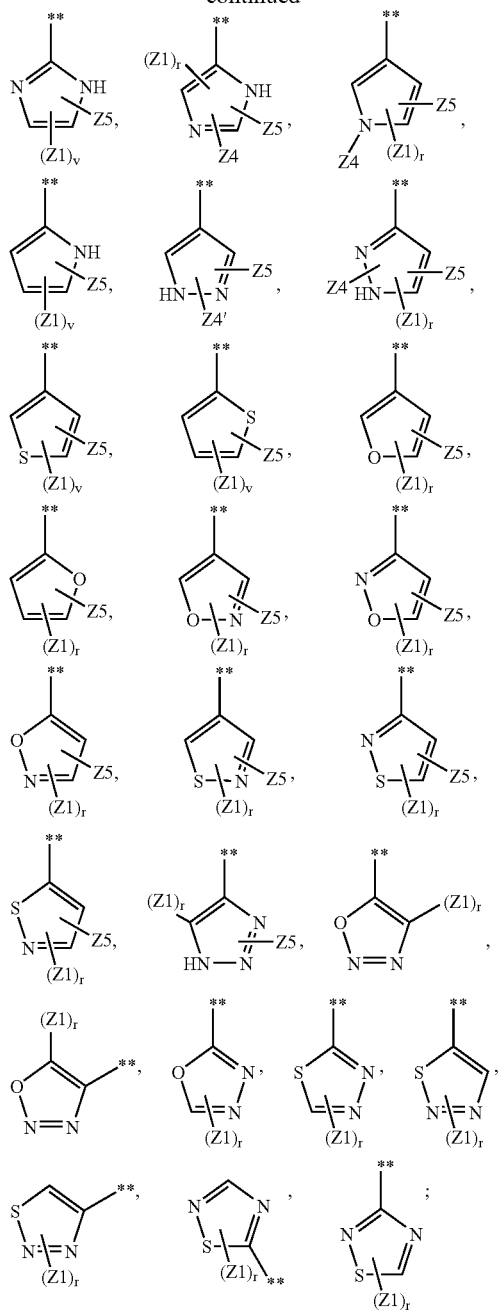

and wherein the symbol (**) is the point of attachment to the A1 ring of formula I;

each Z4 is independently and individually selected from the group consisting of H, C1-C6alkyl, hydroxyC2-C6alkyl, C1-C6alkoxyC2-C6alkyl, (R4)₂N—C2-C6alkyl, (R4)₂N—C2-C6alkylN(R4)-C2-C6alkyl, (R4)₂N—C2-C6alkyl-O—C2-C6alkyl, (R4)₂N—CO—C2-C6alkyl, carboxyC2-C6alkyl, C1-C6alkoxycarbonylC2-C6alkyl, —C2-C6alkylN(R4)C(O)R8, R8-C(=NR3)-, —SO₂R8, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

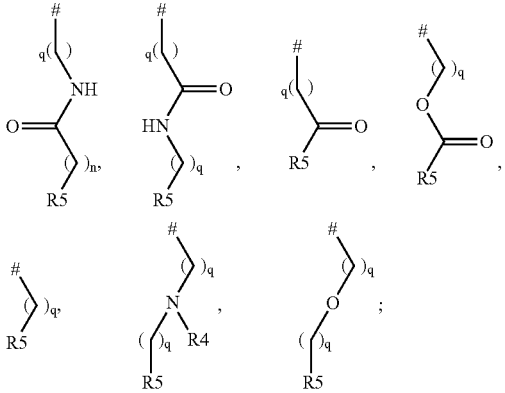

wherein the symbol (#) indicates the point of attachment of the Z4 moiety to the A2 ring for formula I;

in the event that Z4 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z4 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z4 may cyclize to form a C3-C7 heterocyclyl ring;

Z5 is independently and individually selected from the group consisting of H, C1-C6alkyl, branched C3-C7alkyl, halogen, fluoroalkyl, cyano, hydroxyl, alkoxy, oxo, aminocarbonyl, carbonylamino, aminosulfonyl, sulfonylamino, —N(R3)₂, —O—(CH₂)q-N(R4)₂, —N(R3)-(CH₂)q-N(R4)₂, —R5, —O—(CH₂)q-O-Alkyl, —O—(CH₂)q-N(R4)₂, —N(R3)-(CH₂)q-O-Alkyl, —N(R3)-(CH₂)q-N(R4)₂, —O—(CH₂)q-R5, and —N(R3)-(CH₂)q-R5;

wherein two R3 moieties are independently and individually taken from the group consisting of C1-C6alkyl and branched C3-C6alkyl and are attached to the same nitrogen heteroatom of Z5 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z5 may cyclize to form a C3-C7 heterocyclyl ring;

and n is 0-4; p is 1-4; q is 2-6; r is 0 or 1; v is 1 or 2.

1.2.2b

More preferred A2 moieties are selected from the group consisting of

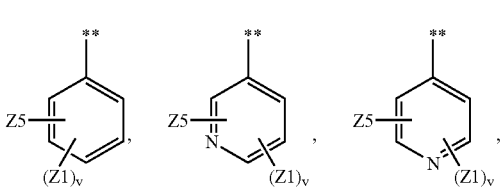

-continued

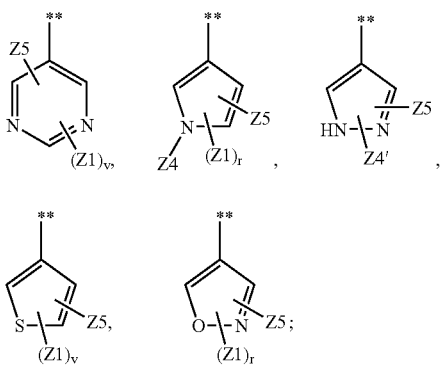

and wherein the symbol (**) is the point of attachment to the A1 ring for formula I.

1.2.2c

Even more preferred A2 moieties are selected from the group consisting of

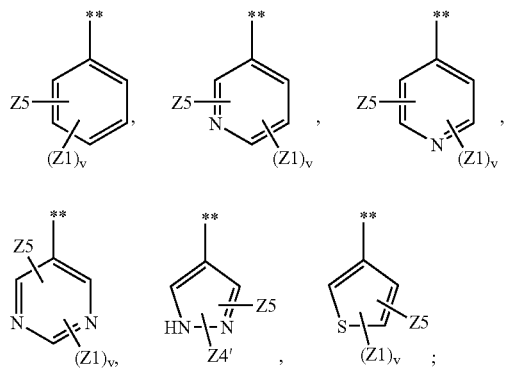

and wherein the symbol (**) is the point of attachment to the A1 ring of formula I.

1.2.3 Preferred Classes of Compounds 1.2.3a
Compounds as defined in 1.2.1a wherein the A2 group is defined in 1.2.2a.

1.2.3b
Compounds as defined in 1.2.3a wherein the A2 group is defined in 1.2.2b.

1.2.3c
Compounds as defined in 1.2.3a wherein the A2 group is defined in 1.2.2c.

1.2.3d
Compounds as defined in 1.2.1b wherein the A2 group is defined in 1.2.2a.

1.2.3e
Compounds as defined in 1.2.3c wherein the A2 group is defined in 1.2.2b.

1.2.3f
Compounds as defined in 1.2.3c wherein the A2 group is defined in 1.2.2c.

1.2.4 Preferred A1 Moieties 1.2.4a
These preferred A1 moieties are defined in 1.1.4a.

1.2.4b
These more preferred A1 moieties are defined in 1.1.4b.

1.2.4c
These even more preferred A1 moieties are defined in 1.1.4c.

1.2.5 Preferred W and Y Moieties 1.2.5a
(1) W and Y are each NH, and X=O; (2) W=NH, Y=CHR4 and X=O; or (3) W=CHR4, Y=NH, and X=O.

1.2.5b
W and Y are each NH and X=O.

1.2.6 Further Preferred Compounds 1.2.6a
The invention includes compounds of the formula

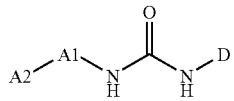

I wherein A2 is selected from the group consisting of

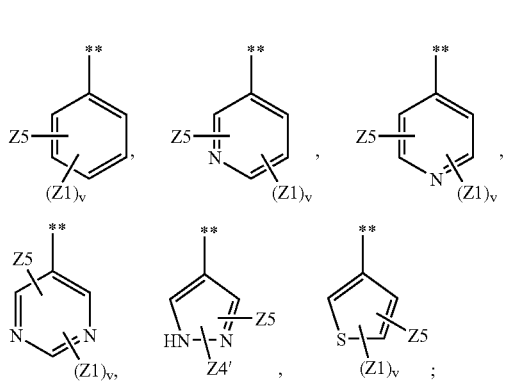

and wherein the symbol (**) is the point of attachment to the A1 ring of formula I.

A1 is selected from the group consisting of wherein the symbol (*) denotes the attachment to the W moiety of formula I and the symbol (**) denotes the attachment to the A2 moiety of formula I;

X is O, S, or NR3;

D comprises a member of

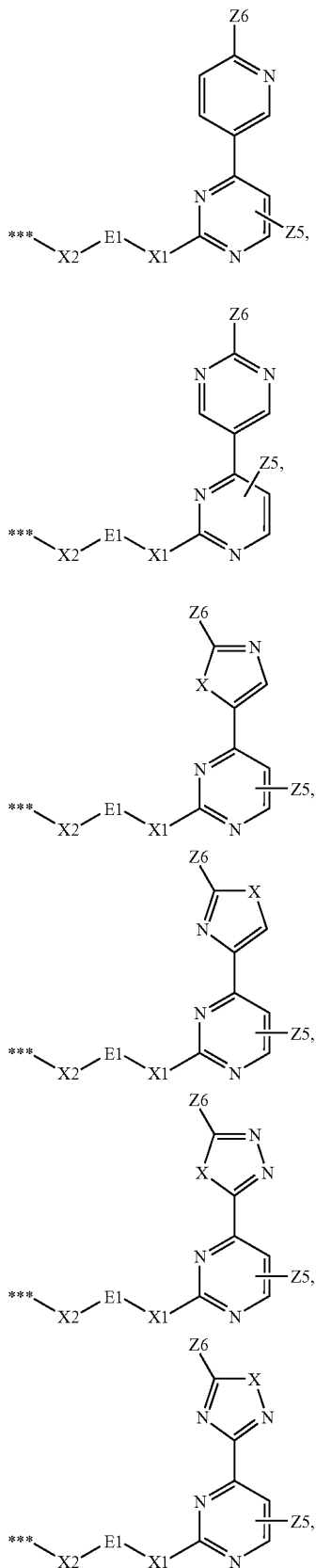

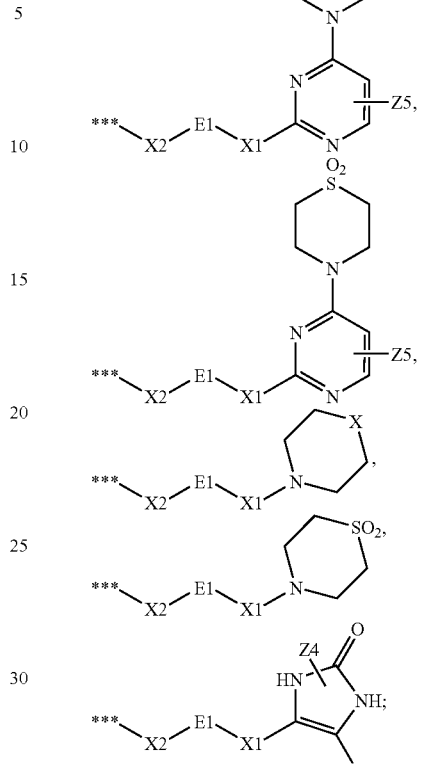

wherein E1 is selected from the group consisting cyclopropyl, cyclobutyl, cyclopentyl, cyclohexyl, pyrrolidinyl piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl and naphthyl;

wherein the symbol (***) denotes the attachment to the Y moiety of formula I;

X1 is selected from the group consisting of O, S, NR3, —C(=O)—, —O—(CH$_2$)n-, —S—(CH$_2$)n-, —NR3-(CH$_2$)n-, —O—(CH$_2$)q-O—, —O—(CH$_2$)q-NR3-, —N(R3)-(CH$_2$)q-N(R3)—, —(CH$_2$)n-N(R4)-C(=O)—, —(CH$_2$)n-N(R4)-C(=O)(CH$_2$)n-, —(CH$_2$)n-CO—N(R4)-, —(CH$_2$)p-, C2-C5alkenyl, C2-C5alkynyl, C3-C6cycloalkyl, and a direct bond wherein the E1 ring and the E2 ring are directly linked by a covalent bond;

and wherein the carbon atoms of —(CH2)n-, —(CH2)q-, (CH2)p, C2-C5alkenyl, and C2-C5alkynyl moieties of X1 may be further substituted by one or more C1-C6alkyl;

X2 is selected from the group consisting of C1-C6 alkyl, C3-C6 branched alkyl, or a direct bond wherein E1 is directly linked to the Y group of formula I;

each Z1 is a substituent attached to a ring carbon and is independently and individually selected from the group consisting of hydroxyC1-C6alkyl, C2-C6alkoxy, C1-C6alkoxyC1-C6alkyl, (R4)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—C(=O)—, (R4)$_2$N—C(=O)—, (R4)$_2$N—CO—C1-C6alkyl, C1-C6alkoxycarbonyl, carboxyC1-C6alkyl, C1-C6alkoxycarbonylC1-C6alkyl, (R3)$_2$NSO$_2$, SOR3, (R4)$_2$NSO$_2$, —SO$_2$R3', —SOR4, —C(=O)R6, —C(=NOH)R6, —C(=NOR3)R6, —(CH$_2$)$_n$N(R4)C(O)R8, monocyclic heteroaryl, monocyclic heterocyclyl, monocyclic heteroarylC1-

C6alkyl, monocyclic heterocyclylC1-C6alkyl, monocyclic heteroaryloxy, monocyclic heterocyclyloxy, monocyclic heteroaryloxyC1-C6alkyl, monocyclic heterocyclyloxyC1-C6alkyl, arylamino, monocyclic heteroarylamino, monocyclic heterocyclylamino, arylaminoC1-C6alkyl, monocyclic heteroarylaminoC1-C6alkyl, monocyclic heterocyclylaminoC1-C6alkyl, or moieties of the formulae

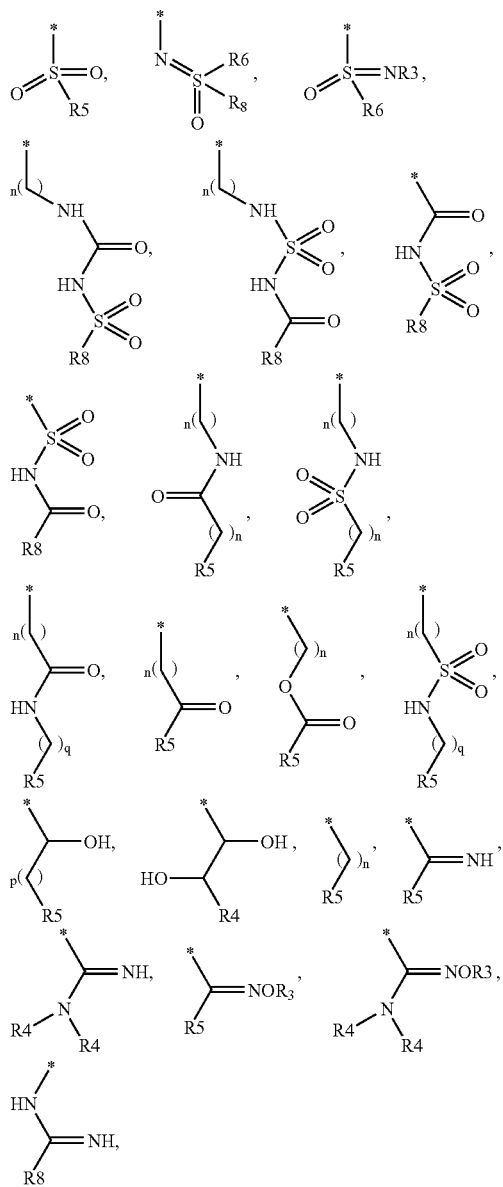

cyano wherein the site of attachment to the A2 ring is meta to the point of attachment to the A1 ring and wherein A2 is phenyl, and cyano wherein the site of attachment is to a substitutable position when A2 is pyridyl, pyrimidinyl or a five-membered ring;

In the foregoing definition of Z1, alkyl moieties may optionally be substituted by one or more C1-C6alkyl;

Wherein the asterisk (*) indicates the point of attachment of the Z1 moiety to the A2 ring;

in the event that Z1 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z1 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z1 may cyclize to form a C3-C7 heterocyclyl ring;

each Z4 is a substituent attached to a ring nitrogen and is independently and individually selected from the group consisting of H, C1-C6alkyl, hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C2-C6alkyl, carboxyC2-C6alkyl, C1-C6alkoxycarbonylC2-C6alkyl, —C2-C6alkylN(R4)C(O)R8, R8-C(=NR3)-, —SO$_2$R8, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

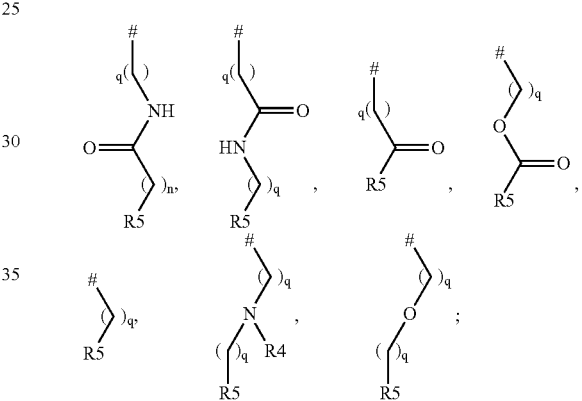

wherein the symbol (#) indicates the point of attachment of the Z4 moiety to the A2 ring for formula I;

in the event that Z4 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z4 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z4 may cyclize to form a C3-C7 heterocyclyl ring;

each Z4' is a substituent attached to a ring nitrogen and is independently and individually selected from the group consisting of hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C2-C6alkyl, carboxyC2-C6alkyl, C1-C6alkoxycarbonylC2-C6alkyl, —C2-C6alkylN(R4)C(O)R8, R8-C(=NR3)-, —SO$_2$R8, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

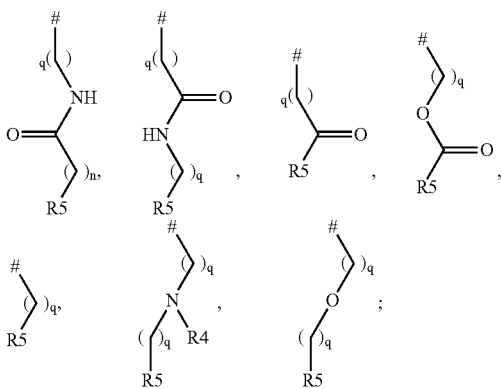

wherein the symbol (#) indicates the point of attachment of the Z4' moiety to the A1 ring of formula I;
in the event that Z4' contains an alkyl or alkylene moiety, such moieties may be further substituted with one or more C1-C6alkyls;
wherein two R3 moieties are independently and individually taken from the group consisting of C1-C6alkyl and branched C3-C6alkyl and are attached to the same nitrogen heteroatom of Z4' may cyclize to form a C3-C7 heterocyclyl ring;
wherein two R4 moieties independently and individually taken from the group consisting of C1-C6alkyl, branched C3-C6alkyl, hydroxyalkyl, and alkoxyalkyl and are attached to the same nitrogen heteroatom of Z4' may cyclize to form a C3-C7 heterocyclyl ring;
Z5 is independently and individually selected from the group consisting of H, C1-C6alkyl, branched C3-C7alkyl, halogen, fluoroalkyl, cyano, hydroxyl, alkoxy, oxo, aminocarbonyl, carbonylamino, aminosulfonyl, sulfonylamino, —N(R3)$_2$, —O—(CH$_2$)q-N(R4)$_2$, —N(R3)-(CH$_2$)q—N(R4)$_2$, —R5, —O—(CH$_2$)q-O-Alkyl, —O—(CH$_2$)q-N(R4)$_2$, —N(R3)-(CH$_2$)q-O-Alkyl, —N(R3)-(CH$_2$)q-N(R4)$_2$, —O—(CH$_2$)q-R5, and —N(R3)-(CH$_2$)q-R5;
wherein two R3 moieties are independently and individually taken from the group consisting of C1-C6alkyl and branched C3-C6alkyl and are attached to the same nitrogen heteroatom of Z5 may cyclize to form a C3-C7 heterocyclyl ring;
wherein two R4 moieties independently and individually taken from the group consisting of C1-C6alkyl, branched C3-C6alkyl, hydroxyalkyl, and alkoxyalkyl and are attached to the same nitrogen heteroatom of Z5 may cyclize to form a C3-C7 heterocyclyl ring;
Each Z6 is independently and individually selected from the group consisting of H, C1-C6alkyl, branched C3-C7alkyl, hydroxyl, C1-C6alkoxy, (R3)$_2$N—, —N(R3)COR8, (R4)$_2$N—, —R5, —N(R4)COR8, —N(R3)SO$_2$R6-, —CON(R3)$_2$, —CON(R4)$_2$, —COR5, —SO$_2$NHR4, heteroaryl, heterocyclyl, heteroaryloxy, heterocyclyloxy, arylamino, heteroarylamino, and heterocyclylamino;
wherein two R3 moieties are independently and individually taken from the group consisting of C1-C6alkyl and branched C3-C6alkyl and are attached to the same nitrogen heteroatom of Z6 may cyclize to form a C3-C7 heterocyclyl ring;
wherein two R4 moieties independently and individually taken from the group consisting of C1-C6alkyl, branched C3-C6alkyl, hydroxyalkyl, and alkoxyalkyl and are attached to the same nitrogen heteroatom of Z6 may cyclize to form a C3-C7 heterocyclyl ring;
each R2 is selected from the group consisting of alkyl, branched alkyl, fluoroalkyl, wherein the alkyl group is partially or fully fluorinated, and R19 substituted C3-C8carbocyclyl wherein R19 is H, and C1-C6alkyl;
each R2' is selected from the group consisting of halogen and R2;
each R3 is independently and individually selected from the group consisting of H, C1-C6alkyl, branched C3-C7alkyl, C3-C7cycloalkyl, or phenyl;
each R3' is independently and individually selected from the group consisting of C2-C6alkyl, branched C3-C7alkyl, C3-C7cycloalkyl, aryl, arylalkyl, heteroaryl, and heteroarylalkyl;
each R4 is selected from the group consisting of H, C1-C6alkyl, hydroxyC1-C6 alkyl, dihydroxyC1-C6alkyl, C1-C6alkoxyC1-C6alkyl, branched C3-C7alkyl, branched hydroxyC1-C6 alkyl, branched C1-C6alkoxyC1-C6alkyl, branched dihydroxyC1-C6alkyl, carbocyclyl, hydroxyl substituted carbocyclyl, alkoxy substituted carbocyclyl, dihydroxy substituted carbocyclyl, phenyl, heteroaryl, heterocyclyl, phenylC1-C6alkyl, heteroarylC1-C6alkyl, and heterocyclylC1-C6alkyl;
each R5 is independently and individually selected from the group consisting of

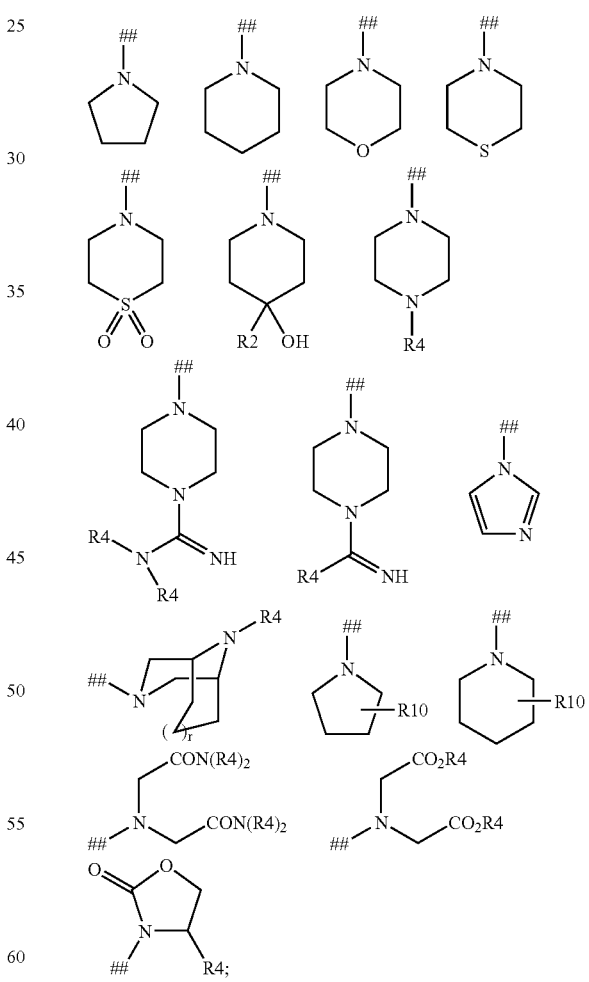

and wherein the symbol (##) is the point of attachment to respective R8, R10, Z1, Z4', Z5, Z6 or A2 ring moieties containing a R5 moiety;
wherein two R4 moieties independently and individually taken from the group consisting of C1-C6alkyl, branched C3-C6alkyl, hydroxyalkyl, and alkoxyalkyl and are attached to the same nitrogen heteroatom of R5 may cyclize to form a C3-C7 heterocyclyl ring;

wherein each R6 is independently and individually selected from the group consisting of C1-C6alkyl, branched C3-C7alkyl, carbocyclyl, phenyl, heteroaryl, and heterocyclyl;

each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

each R8 is independently and individually selected from the group consisting of C1-C6alkyl, C1-C6 fluoroalkyl wherein the alkyl moiety is partially or fully fluorinated, branchedC4-C7alkyl, carbocyclyl, phenyl, C1-C6phenylalkyl, heteroaryl or heteroarylC1-C6alkyl, heterocyclyl, heterocyclylC1-C6alkyl, OH, C1-C6alkoxy, $N(R3)_2$, $N(R4)_2$, or R5;

wherein two R3 moieties are independently and individually taken from the group consisting of C1-C6alkyl and branched C3-C6alkyl and are attached to the same nitrogen heteroatom of R8 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of R8 may cyclize to form a C3-C7 heterocyclyl ring;

each R10 is independently and individually selected from the group consisting of $CO_2H$, $CO_2$C1-C6alkyl, CO—$N(R4)_2$, OH, C1-C6alkoxy, —$N(R4)_2$;

wherein two R4 moieties independently and individually taken from the group consisting of C1-C6alkyl, branched C3-C6alkyl, hydroxyalkyl, and alkoxyalkyl and are attached to the same nitrogen heteroatom of R10 may cyclize to form a C3-C7 heterocyclyl ring;

and n is 0-4; p is 1-4; q is 2-6; r is 0 or 1; v is 1 or 2;

and tautomers, diastereomers, geometric isomers, enantiomers, hydrates, prodrugs and salts of any of the foregoing.

1.2.6b

The following specific compounds are most preferred: 1-(3-t-butyl-1-(3-(2-(2,3-dihydroxypropylamino)-2-oxoethyl)phenyl)-1H-pyrazol-5-yl)-3-(4-methyl-3-(4-(pyridin-3-yl)pyrimidin-2-ylamino)phenyl)urea, 1-(1-(3-(2-amino-2-oxoethyl)phenyl)-3-t-butyl-1H-pyrazol-5-yl)-3-(4-methyl-3-(4-(pyridin-3-yl)pyrimidin-2-ylamino)phenyl)urea, 1-(2-(3-(2-amino-2-oxoethyl)phenyl)-5-t-butylthiophen-3-yl)-3-(4-methyl-3-(4-(pyridin-3-yl)pyrimidin-2-ylamino)phenyl)urea, 1-(1-(3-(1H-pyrazol-4-yl)phenyl)-3-cyclopentyl-1H-pyrazol-5-yl)-3-(4-(6-(thiazol-4-yl)pyrimidin-4-yloxy)phenyl)urea, 1-(1-(3-(2-amino-2-oxoethyl)phenyl)-3-cyclopentyl-1H-pyrazol-5-yl)-3-(3-(4-(pyridin-3-yl)pyrimidin-2-yloxy)phenyl)urea, 1-(1-(3-(2-amino-2-oxoethyl)phenyl)-3-cyclopentyl-1H-pyrazol-5-yl)-3-(3-(4-(isoxazol-4-yl)pyrimidin-2-ylamino)phenyl)urea, 1-(1-(3-(1H-pyrazol-4-yl)phenyl)-3-t-butyl-1H-pyrazol-5-yl)-3-(4-methyl-3-(4-(pyridin-3-yl)pyrimidin-2-ylamino)phenyl) urea 1.2.7 Methods 1.2.7a Methods of Protein Modulation The invention includes methods of modulating kinase activity of a variety of kinases, e.g. C-Abl kinase, BCR-Abl kinase. The kinases may be wildtype kinases, oncogenic forms thereof, aberrant fusion proteins thereof or polymorphs of any of the foregoing. The method comprises the step of contacting the kinase species with compounds of the invention and especially those set forth in sections 1.2 and 1.2.6a. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, kinase cellular localization, and recruitment of other proteins into signaling complexes through modulation of kinase conformation.

The methods of the invention may also involve the step of inducing, synergizing, or promoting the binding of a second modulator compound of said kinase, especially C-Abl kinase or BCR-Abl kinase, to form a ternary adduct, such co-incident binding resulting in enhanced biological modulation of the kinase when compared to the biological modulation of the protein affected by either of said compounds alone. The second compound may interact at a substrate, co-factor or regulatory site on the kinase, with the second site being distinct from the site of interaction of the first compound. For example, the second site may be an ATP co-factor site. The second compounds may be taken from the group consisting of N-(4-methyl-3-(4-(pyridin-3-yl)pyrimidin-2-ylamino)phenyl)-4-((4-methylpiperazin-1-yl)methyl)benzamide (Gleevec); N-(2-chloro-6-methylphenyl)-2-(6-(4-(2-hydroxyethyl)piperazin-1-yl)-2-methylpyrimidin-4-ylamino) thiazole-5-carboxamide (BMS-354825); 6-(2,6-dichlorophenyl)-2-(3-(hydroxymethyl)phenylamino)-8-methylpyrido[2,3-d]pyrimidin-7(8H)-one (PD 166326); 6-(2,6-dichlorophenyl)-8-methyl-2-(3-(methylthio)phenylamino)pyrido[2,3-d]pyrimidin-7(8H)-one (PD 173955); 6-(2,6-dichlorophenyl)-2-(4-fluoro-3-methylphenylamino)-8-methylpyrido[2,3-d]pyrimidin-7(8H)-one (PD180970); 6-(2,6-dichlorophenyl)-2-(4-ethoxyphenylamino)-8-methylpyrido[2,3-d]pyrimidin-7(8H)-one (PD 173958); 6-(2,6-dichlorophenyl)-2-(4-fluorophenylamino)-8-methylpyrido[2,3-d]pyrimidin-7(8H)-one (PD 173956); 6-(2,6-dichlorophenyl)-2-(4-(2-(diethylamino)ethoxy)phenylamino)-8-methylpyrido[2,3-d]pyrimidin-7(8H)-one (PD 166285); 2-(4-(2-aminoethoxy)phenylamino)-6-(2,6-dichlorophenyl)-8-methylpyrido[2,3-d]pyrimidin-7(8H)-one; N-(3-(6-(2,6-dichlorophenyl)-8-methyl-7-oxo-7,8-dihydropyrido[2,3-d]pyrimidin-2-ylamino)phenyl)acetamide (SKI DV-MO16); 2-(4-aminophenylamino)-6-(2,6-dichlorophenyl)-8-methylpyrido[2,3-d]pyrimidin-7(8H)-one (SKI DV 1-10); 6-(2,6-dichlorophenyl)-2-(3-hydroxyphenylamino)-8-methylpyrido[2,3-d]pyrimidin-7(8H)-one (SKI DV2-89); 2-(3-aminophenylamino)-6-(2,6-dichlorophenyl)-8-methylpyrido[2,3-d]pyrimidin-7(8H)-one (SKI DV 2-43); N-(4-(6-(2,6-dichlorophenyl)-8-methyl-7-oxo-7,8-dihydropyrido[2,3-d]pyrimidin-2-ylamino)phenyl)acetamide (SKI DV-M017); 6-(2,6-dichlorophenyl)-2-(4-hydroxyphenylamino)-8-methylpyrido[2,3-d]pyrimidin-7(8H)-one (SKI DV-MO17); 6-(2,6-dichlorophenyl)-2-(3-ethylphenylamino)-8-methylpyrido[2,3-d]pyrimidin-7(8H)-one (SKI DV 2 87).

1.2.7b Treatment Methods

The methods of the invention also include treating individuals suffering from a condition selected from the group consisting of cancer and hyperproliferative diseases. These methods comprise administering to such individuals compounds of the invention, and especially those of section 1.2 and 1.2.6a. Exemplary conditions include chronic myelogenous leukemia, acute lymphocytic leukemia, gastrointestinal stromal tumors, and hypereosinophillic syndrome. The administration method is not critical, and may be from the group consisting of oral, parenteral, inhalation, and subcutaneous.

1.2.8 Pharmaceutical Preparations

The compounds of the invention, especially those of 1.2 and 1.2.6a may form a part of a pharmaceutical composition by combining one or more such compounds with a pharmaceutically acceptable carrier. Additionally, the compositions may include an additive selected from the group consisting of adjuvants, excipients, diluents, and stablilizers.

1.2.9 Kinase/Compound Adducts

The invention also provides adducts in the form of compounds of the invention bound with a species of kinase such as a wild-type kinase, oncogenic forms thereof, aberrant fusion proteins thereof and polymorphs of any of the foregoing. The compounds are advantageously selected from the groups defined in sections 1.2 and 1.2.6a.

1.3 Generally—Monocyclic A2 Compounds with Monocyclic E2 Rings

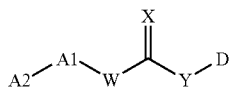

I wherein A2 is selected from the group consisting of a Z7-substituted phenyl, Z7-substituted pyridyl, Z7-substituted pyrimidinyl, Z1-substituted thienyl, Z1 or Z4'-substituted monocyclic heterocyclyl rings and other monocyclic heteroaryls, excluding tetrazolyl, 1,2,4-oxadiazolonyl, 1,2,4-triazolonyl, and alkyl-substituted pyrrolyl wherein the pyrrolyl nitrogen is the site of attachment to the A1 ring;

A1 is selected from the group consisting of R2' and R7-substituted phenyl, pyridyl, or pyrimidinyl, R2-substituted monocyclic 5-membered ring heteroaryl, and R2'-substituted monocyclic heterocyclyl moieties;

W and Y are CHR4, NR3, or O and wherein W and Y are not simultaneously O;

X is O, S, or NR3;

each R2 is selected from the group consisting of alkyl, branched alkyl, fluoroalkyl, wherein the alkyl group is partially or fully fluorinated, and R19 substituted C3-C8carbocyclyl wherein R19 is H, and C1-C6alkyl;

each R2' is selected from the group consisting of halogen and R2;

each R3 is independently and individually selected from the group consisting of H, C1-C6alkyl, branched C3-C7alkyl, C3-C7cycloalkyl, or phenyl;

each R3' is independently and individually selected from the group consisting of C2-C6alkyl, branched C3-C7alkyl, C3-C7cycloalkyl, aryl, arylalkyl, heteroaryl, and heteroarylalkyl;

each R4 is selected from the group consisting of H, C1-C6alkyl, hydroxyC1-C6 alkyl, dihydroxyC1-C6alkyl, C1-C6alkoxyC1-C6alkyl, branched C3-C7alkyl, branched hydroxyC1-C6 alkyl, branched C1-C6alkoxyC1-C6alkyl, branched dihydroxyC1-C6alkyl, carbocyclyl, hydroxyl substituted carbocyclyl, alkoxy substituted carbocyclyl, dihydroxy substituted carbocyclyl, phenyl, heteroaryl, heterocyclyl, phenylC1-C6alkyl, heteroarylC1-C6alkyl, and heterocyclylC1-C6alkyl;

each R5 is independently and individually selected from the group consisting of

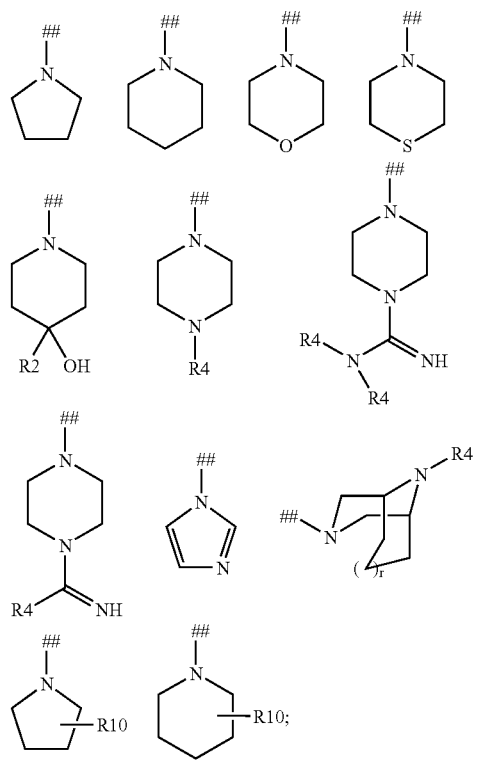

and wherein the symbol (##) is the point of attachment to respective R8, R10, Z1, Z4', Z5, Z6 and Z7 moieties containing a R5 moiety;

wherein two R4 moieties independently and individually taken from the group consisting of C1-C6alkyl, branched C3-C6alkyl, hydroxyalkyl, and alkoxyalkyl and are attached to the same nitrogen heteroatom of R5 may cyclize to form a C3-C7 heterocyclyl ring;

wherein each R6 is independently and individually selected from the group consisting of C1-C6alkyl, branched C3-C7alkyl, carbocyclyl, phenyl, heteroaryl, and heterocyclyl;

each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

each R8 is independently and individually selected from the group consisting of C1-C6alkyl, C1-C6 fluoroalkyl wherein the alkyl moiety is partially or fully fluorinated, branchedC4-C7alkyl, carbocyclyl, phenyl, C1-C6phenylalkyl, heteroaryl or heteroarylC1-C6alkyl, heterocyclyl, heterocyclylC1-C6alkyl, OH, C1-C6alkoxy, N(R3)$_2$, N(R4)$_2$, or R5;

wherein two R3 moieties are independently and individually taken from the group consisting of C1-C6alkyl and branched C3-C6alkyl and are attached to the same nitrogen heteroatom of R8 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of R8 may cyclize to form a C3-C7 heterocyclyl ring;

each R10 is independently and individually selected from the group consisting of CO$_2$H, CO$_2$C1-C6alkyl, CO—N(R4)$_2$, OH, C1-C6alkoxy, —N(R4)$_2$;

wherein two R4 moieties independently and individually taken from the group consisting of C1-C6alkyl, branched C3-C6alkyl, hydroxyalkyl, and alkoxyalkyl and are attached to the same nitrogen heteroatom of R10 may cyclize to form a C3-C7 heterocyclyl ring;

D comprises a moiety taken from group consisting of

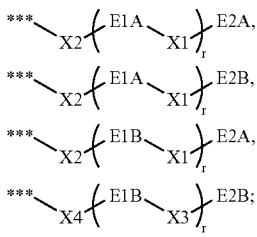

wherein the symbol (***) is the point of attachment to the Y group of formula I;

wherein E1A is taken from the groups consisting of carbocyclyl, mono- and poly-heterocyclyl and mono- and poly-heteroaryl;

wherein E1B is taken from the groups consisting of phenyl and naphthyl;

wherein E2A is taken from the group consisting of naphthyl, a 5-membered ring heteroaryl, or a fused bicyclic heteroaryl;

wherein E2B is taken from the group consisting of phenyl, pyridyl, and pyrimidyl;

X1 is selected from the group consisting of O, S, NR3, —C(=O)—, —O—(CH$_2$)n-, —S—(CH$_2$)n-, —NR3-(CH$_2$)n-, —O—(CH$_2$)q-O—, —O—(CH$_2$)q-NR3-, —N(R3)-(CH$_2$)q-N(R3)-, —(CH$_2$)n-N(R4)-C(=O)—, —(CH$_2$)n-N(R4)-C(=O)(CH$_2$)n-, —(CH$_2$)n-CO—N(R4)-, —(CH$_2$)p-, C2-C5alkenyl, C2-C5alkynyl, C3-C6cycloalkyl, and a direct bond wherein the E1A or E1B ring and the E2A or E2B ring are directly linked by a covalent bond;

and wherein the carbon atoms of —(CH2)n-, —(CH2)q-, (CH2)p, C2-C5alkenyl, and C2-C5alkynyl moieties of X1 may be further substituted by one or more C1-C6alkyl;

X2 is selected from the group consisting of C1-C6 alkyl, C3-C6 branched alkyl, or a direct bond wherein E1A or E1B or E2A or E2B are directly linked to the Y group of formula I;

X3 is selected from the group consisting of NR3, —C(=O)—, —O—(CH$_2$)n-, —S—(CH$_2$)n-, —NR3-(CH$_2$)n-, —O—(CH$_2$)q-O—, —O—(CH$_2$)q-NR3-, —N(R3)-(CH$_2$)q-N(R3)-, —(CH$_2$)n-N(R4)-C(=O)—, —(CH$_2$)n-N(R4)-C(=O)(CH$_2$)n-, —(CH$_2$)n-CO—N(R4)-, —(CH$_2$)q-, C2-C5alkenyl, C2-C5alkynyl, C3-C6cycloalkyl, and a direct bond wherein the either the E1B ring or E2B ring are directly linked by a covalent bond;

and wherein the carbon atoms of —(CH2)q-, C2-C5alkenyl, and C2-C5alkynyl moieties of X3 may be further substituted by one or more C1-C6alkyl;

X4 is selected from the group consisting of C1-C6 alkyl, C3-C6 branched alkyl;

each Z1 is a substituent attached to a ring carbon and is independently and individually selected from the group consisting of hydroxyC1-C6alkyl, C2-C6alkoxy, C1-C6alkoxyC1-C6alkyl, (R4)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—C(=O)—, (R4)$_2$N—C(=O)—, (R4)$_2$N—CO—C1-C6alkyl, C1-C6alkoxycarbonyl, carboxyC1-C6alkyl, C1-C6alkoxycarbonylC1-C6alkyl, (R3)$_2$NSO$_2$, SOR3, (R4)$_2$NSO$_2$, —SO$_2$R3', —SOR4, —C(=O)R6, —C(=NOH)R6, —C(=NOR3)R6, —(CH$_2$)$_n$N(R4)C(O)R8, monocyclic heteroaryl, monocyclic heterocyclyl, monocyclic heteroarylC1-C6alkyl, monocyclic heterocyclylC1-C6alkyl, monocyclic heteroaryloxy, monocyclic heterocyclyloxy, monocyclic heteroaryloxyC1-C6alkyl, monocyclic heterocyclyloxyC1-C6alkyl, arylamino, monocyclic heteroarylamino, monocyclic heterocyclylamino, arylaminoC1-C6alkyl, monocyclic heteroarylaminoC1-C6alkyl, monocyclic heterocyclylaminoC1-C6alkyl, or moieties of the formulae

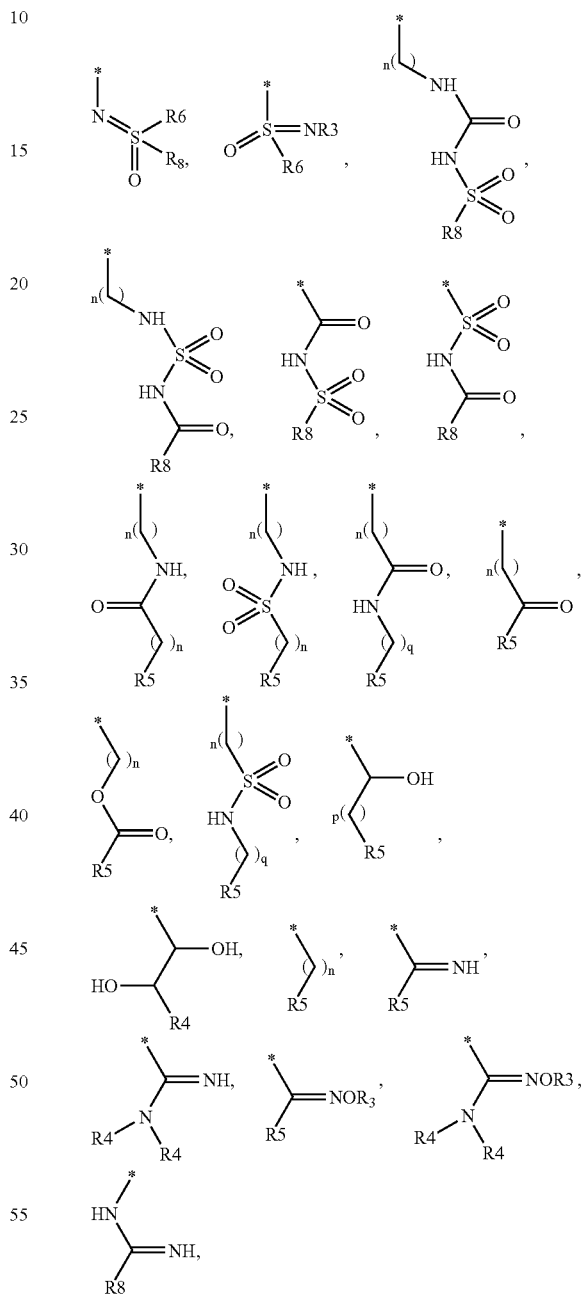

and cyano wherein the site of attachment to the A2 ring is meta to the point of attachment to the A1 ring and wherein A2 is phenyl, cyano wherein the site of attachment is to a substitutable position when A2 is pyridyl, pyrimidinyl or a five-membered ring;

Wherein the asterisk (*) indicates the point of attachment of the Z1 moiety to the A2 ring;

in the event that Z1 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z1 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z1 may cyclize to form a C3-C7 heterocyclyl ring;

each Z4' is a substituent attached to a ring nitrogen and is independently and individually selected from the group consisting of hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C2-C6alkyl, carboxyC2-C6alkyl, C1-C6alkoxycarbonylC2-C6alkyl, —C2-C6alkylN(R4)C(O)R8, R8-C(=NR3)-, —SO$_2$R8, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

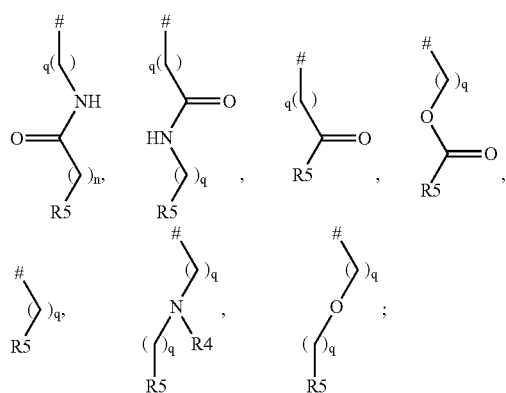

wherein the symbol (#) indicates the point of attachment of the Z4' moiety to the A1 ring of formula I;

in the event that Z4' contains an alkyl or alkylene moiety, such moieties may be further substituted with one or more C1-C6alkyls;

each Z7 is a substituent attached to a ring carbon and is independently and individually selected from the group consisting of hydroxyC2-C6alkyl, C1-C6alkoxyC1-C6alkyl, (R6)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—CO, (R4)$_2$N—CO, —SO$_2$R3', SOR3, —SOR4, —C(=O)R6, —C(=NOH)R6, —C(=NOR3)R6, (CH$_2$)$_n$N(R4)C(O)N(R4)$_2$, (CH$_2$)$_n$N(R4)C(O)R5, monocyclic heteroaryl, monocyclic heterocyclyl, monocyclic heteroarylC1-C6alkyl, monocyclic heterocyclylC1-C6alkyl, monocyclic heteroaryloxy, monocyclic heterocyclyloxy, monocyclic heteroaryloxyC1-C6alkyl, monocyclic heterocyclyloxyC1-C6alkyl, arylamino, monocyclic heteroarylamino, monocyclic heterocyclylamino, arylaminoC1-C6alkyl, monocyclic heteroarylaminoC1-C6alkyl, monocyclic heterocyclylaminoC1-C6alkyl, or moieties of the formulae

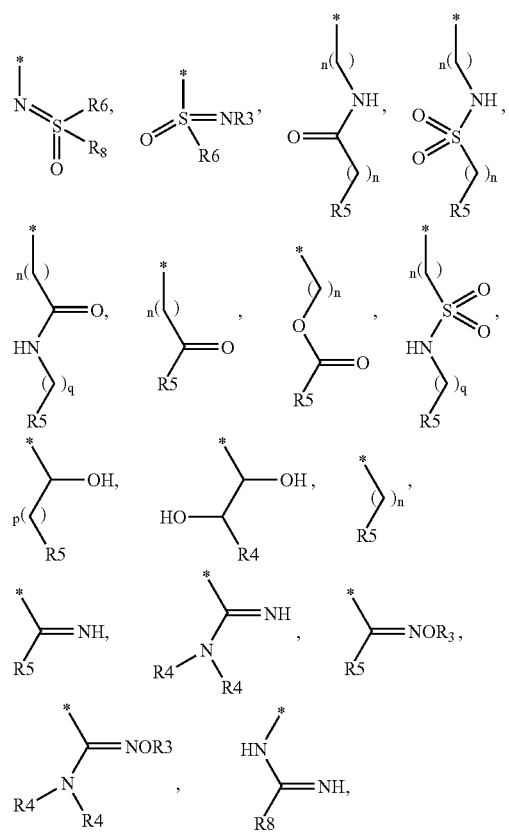

cyano wherein the site of attachment to the A2 ring is meta to the point of attachment to the A1 ring and wherein A2 is phenyl, and cyano wherein the site of attachment is to a substitutable position when A2 is pyridyl, pyrimidinyl or a five-membered ring;

In the foregoing definition of Z7, alkyl moieties may optionally be substituted by one or more C1-C6alkyl;

Wherein the asterisk (*) indicates the point of attachment of the Z1 moiety to the A2 ring;

in the event that Z7 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z7 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z7 may cyclize to form a C3-C7 heterocyclyl ring;

and n is 0-4; p is 1-4; q is 2-6, r is 0 or 1;

and tautomers, diastereomers, geometric isomers, enantiomers, hydrates, prodrugs, and salts of any of the foregoing.

1.3.1 Preferred D Moieties 1.3.1a

Preferably, the compounds of formula I in 1.3 contain D moieties wherein E1A is selected from the group consisting cyclopropyl, cyclobutyl, cyclopentyl, cyclohexyl, pyrrolidinyl piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl and naphthyl;

wherein E2A is comprises the group consisting of cyclopentyl, cyclohexyl, non-fused bicyclic rings comprising pyridylpyridiminyl pyrimidinylpyrimidinyl, oxazolylpyrimidinyl, thiazolylpyrimidinyl, imidazolylpyrimidinyl, isoxazolylpyrimidinyl, isothiazolylpyrimidinyl, pyrazolylpyrimidinyl, triazolylpyrimidinyl, oxadiazoylpyrimidinyl, thiadiazoylpyrimidinyl, morpholinylpyrimidinyl, dioxothiomorpholinylpyrimidinyl, thiomorpholinylpyrimidinyl, and heterocyclyls selected from the group comprising oxetanyl, azetadinyl, tetrahydrofuranyl, pyrrolidinyl, oxazolinyl, oxazolidinyl, imidazolonyl, pyranyl, thiopyranyl, tetrahydropyranyl, dioxalinyl, piperidinyl, morpholinyl, thiomorpholinyl, dioxothiomorpholinyl, piperazinyl, azepinyl, oxepinyl, diazepinyl, tropanyl, and homotropanyl.

1.3.1b

Additionally preferred D moieties of formula I in 1.3 comprise a formula

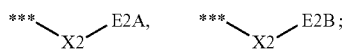

X2 is selected from the group consisting of C1-C6 alkyl, C3-C6 branched alkyl, or a direct bond wherein E2A or E2B is directly linked to the Y group of formula I.

1.3.1c

More preferred D moieties of 1.3.1b are wherein the E2A ring is selected from the group comprising naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl and fused bicyclic rings selected from the group comprising indolyl, isoindolyl, isoindolinyl, isoindolonyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, imidazopyrimidinyl, imidazolonopyrimidinyl, dihydropurinonyl, pyrrolopyrimidinyl, purinyl, pyrazolopyridinyl, pyrazolopyrimidinyl, isoxazolopyrimidinyl, isothiazolopyrimidinyl, furylopyrimidinyl, thienopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalazinyl, benzodioxyl, indolinyl, benzisothiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, benzoxazepinyl.

1.3.2 Preferred A2 Moieties 1.3.2a

Preferably, the compounds of formula I in section 1.3 contain A2 moieties as defined in section 1.2.2a.

1.3.2b

More preferred A2 moieties are selected from the group consisting of

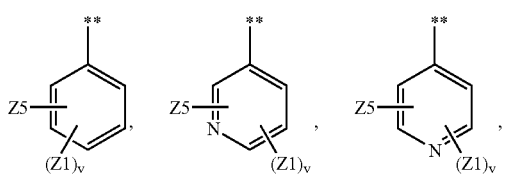

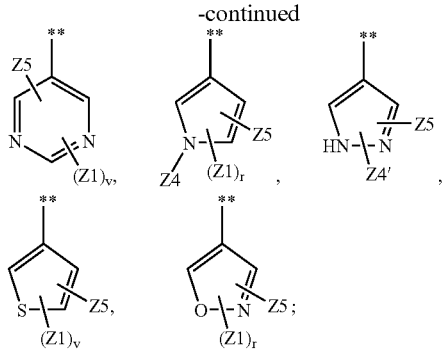

wherein the symbol (**) is the point of attachment to the A1 ring for formula I.

1.3.2c

Even more preferred A2 moieties are selected from the group consisting of

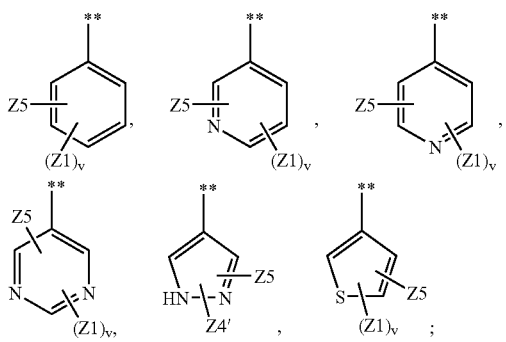

and wherein the symbol (**) is the point of attachment to the A1 ring of formula I.

1.3.3 Preferred Classes of Compounds 1.3.3a

Compounds as defined in 1.3.1a wherein the A2 group is defined in 1.3.2a.

1.3.3b

Compounds as defined in 1.3.3a wherein the A2 group is defined in 1.3.2b.

1.3.3c

Compounds as defined in 1.3.3a wherein the A2 group is defined in 1.3.2c.

1.3.3d

Compounds as defined in 1.3.1b wherein the A2 group is defined in 1.3.2a.

1.3.3e

Compounds as defined in 1.3.3c wherein the A2 group is defined in 1.3.2b.

1.3.3f

Compounds as defined in 1.3.3c wherein the A2 group is defined in 1.3.2c.

1.3.4 Preferred A1 Moieties 1.3.4a

These preferred A1 moieties are defined in 1.1.4a.

1.3.4b

These more preferred A1 moieties are defined in 1.1.4b.

1.3.4c

These even more preferred A1 moieties are defined in 1.1.4c.

1.3.5 Preferred W and Y Moieties
1.3.5a
(1) W and Y are each NH, and X=O; (2) W=NH, Y=CHR4 and X=O; or (3) W=CHR4, Y=NH, and X=O.
1.3.5b
W and Y are each NH and X=O.
1.3.6 Further Preferred Compounds
1.3.6a
The invention includes compounds of the formula

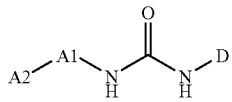  I wherein A2 is selected from the group consisting of

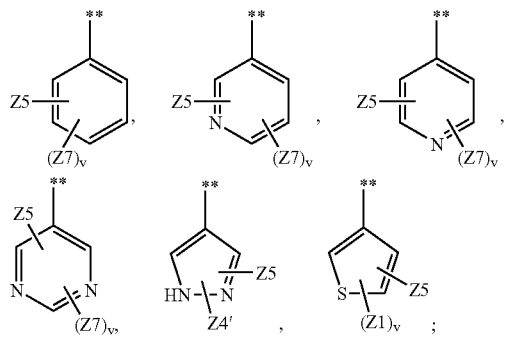

wherein the symbol (**) denotes the attachment to the A1 moiety of formula I;
A1 is selected from the group consisting of

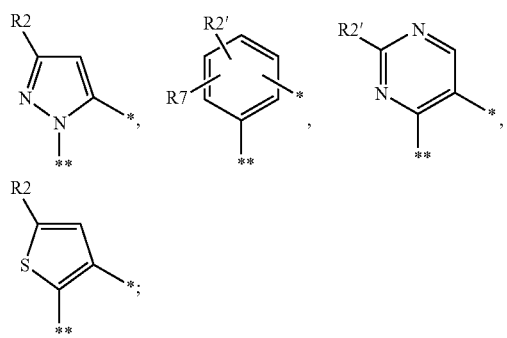

wherein the symbol (*) denotes the attachment to the W moiety of formula I and the symbol (**) denotes the attachment to the A2 moiety of formula I;
X is O, S, or NR3;
D comprises a member of 2,3-dichlorophenyl, 2-fluorophenyl, 3-fluorophenyl, 4-fluorophenyl, 3-cyanophenyl, 2,3-difluorophenyl, 2,4-difluorophenyl, 3,4-difluorophenyl, 2,5-difluorophenyl, 3,5-difluorophenyl, 2,3,5-trifluorophenyl, 2,4,5-trifluorophenyl, 2,3,4-trifluorophenyl, 3,4,5-trifluorophenyl, 4-cyanophenyl, 3-fluoro-5-cyanophenyl, 3-($R8SO_2$)-phenyl, 3-(hydroxyC1-C3alkyl)-phenyl, 3-(R3O—N=C(R6))-phenyl, 3-phenoxyphenyl, 4 phenoxyphenyl,

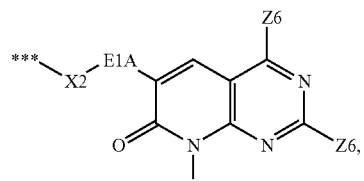
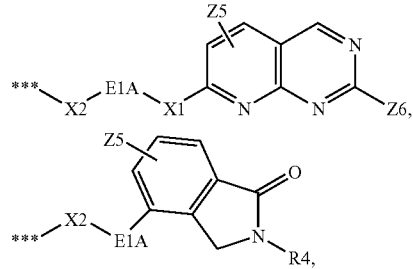
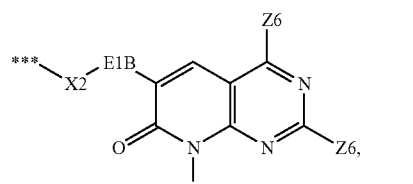
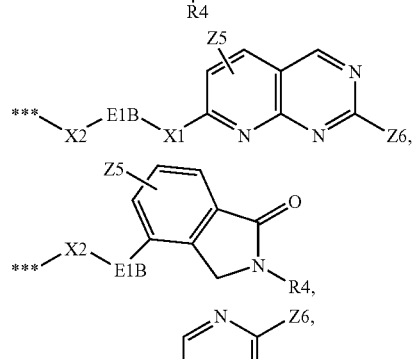
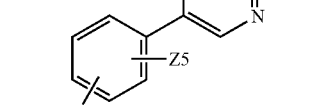
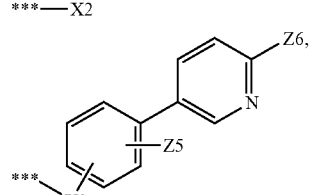
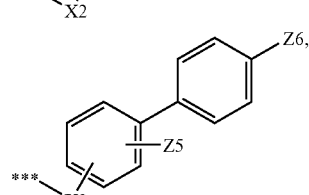
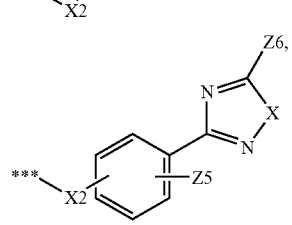

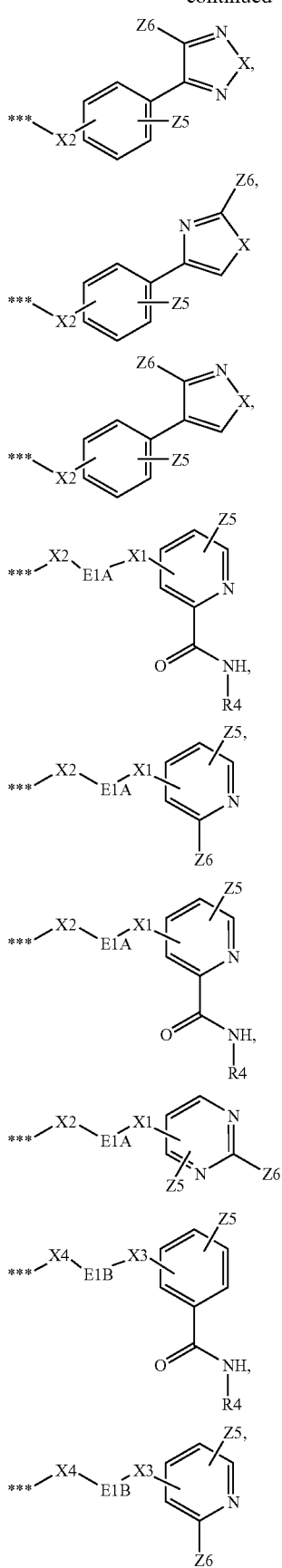
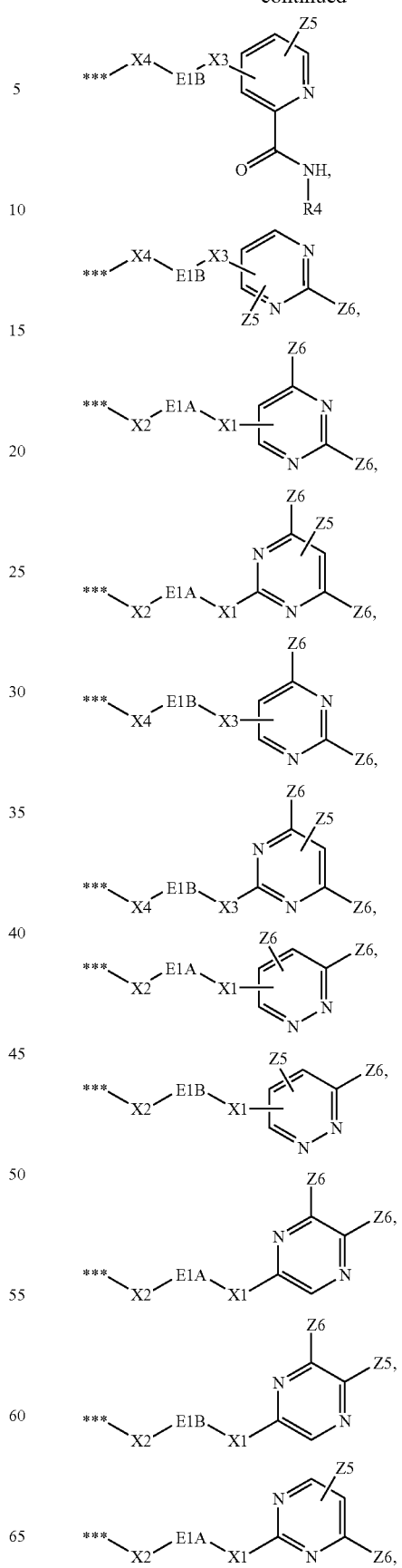

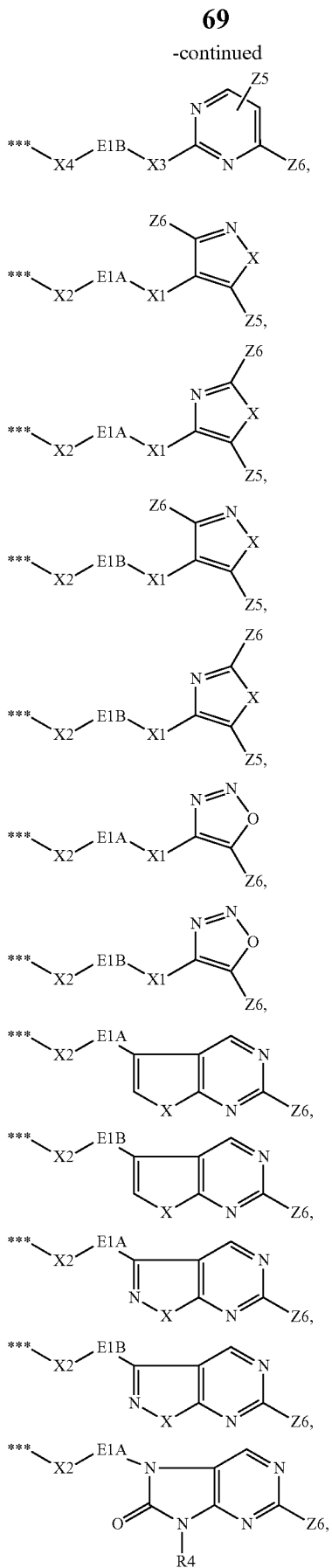
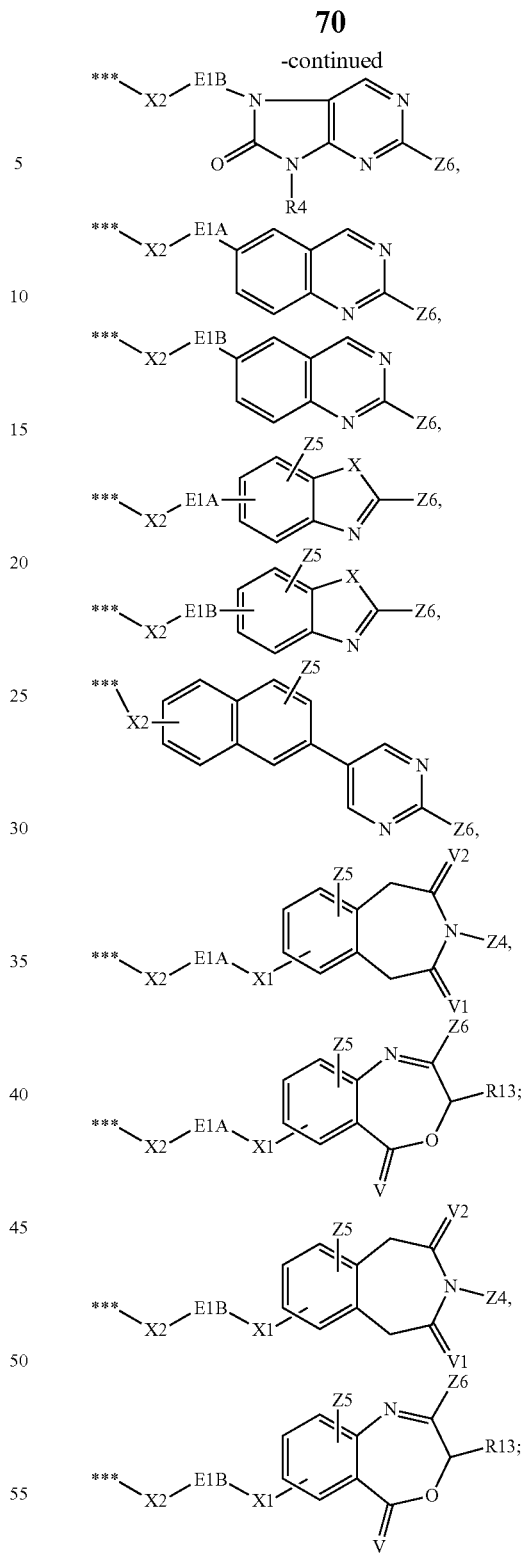

wherein E1A is taken from the groups consisting of cyclopropyl, cyclobutyl, cyclopentyl, cyclohexyl, pyrrolidinyl piperidinyl, thienyl, oxazolyl, thiazolyl, isoxazolyl, isothiazolyl, pyrrolyl, pyrazolyl, oxadiazolyl, thiadiazolyl, furyl, imidazolyl, pyridyl, and pyrimidinyl;

wherein E1B is taken from the groups consisting of phenyl and naphthyl;

wherein E2A is taken from the group comprising naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl and f fused bicyclic rings selected from the group consisting of indolyl, isoindolyl, isoindolinyl, isoindolonyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, imidazopyrimidinyl, imidazolonopyrimidinyl, dihydropurinonyl, pyrrolopyrimidinyl, purinyl, pyrazolopyridinyl, pyrazolopyrimidinyl, isoxazolopyrimidinyl, isothiazolopyrimidinyl, furylopyrimidinyl, thienopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalazinyl, benzodioxyl, indolinyl, benzisothiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, benzoxazepinyl;

wherein E2B is taken from the group consisting of phenyl, pyridyl, and pyrimidyl;

wherein the symbol (***) denotes the attachment to the Y moiety of formula I;

X1 is selected from the group consisting of O, S, NR3, —C(=O)—, —O—(CH$_2$)n-, —S—(CH$_2$)n-, —NR3-(CH$_2$)n-, —O—(CH$_2$)q-O—, —O—(CH$_2$)q-NR3-, —N(R3)-(CH$_2$)q-N(R3)-, —(CH$_2$)n-N(R4)-C(=O)—, —(CH$_2$)n-N(R4)-C(=O)(CH$_2$)n-, —(CH$_2$)n-CO—N(R4)-, —(CH$_2$)p-, C2-C5alkenyl, C2-C5alkynyl, C3-C6cycloalkyl, and a direct bond wherein the E1 ring and the E2 ring are directly linked by a covalent bond;

and wherein the carbon atoms of —(CH2)n-, —(CH2)q-, (CH2)p, C2-C5alkenyl, and C2-C5alkynyl moieties of X1 may be further substituted by one or more C1-C6alkyl;

X2 is selected from the group consisting of C1-C6 alkyl, C3-C6 branched alkyl, or a direct bond wherein E1 is directly linked to the Y group of formula I;

each R2 is selected from the group consisting of alkyl, branched alkyl, fluoroalkyl, wherein the alkyl group is partially or fully fluorinated, and R19 substituted C3-C8carbocyclyl wherein R19 is H, and C1-C6alkyl;

X3 is selected from the group consisting of NR3, —C(=O)—, —O—(CH$_2$)n-, —S—(CH$_2$)n-, —NR3-(CH$_2$)n-, —O—(CH$_2$)q-O—, —O—(CH$_2$)q-NR3-, —N(R3)-(CH$_2$)q-N(R3)-, —(CH$_2$)n-N(R4)-C(=O)—, —(CH$_2$)n-N(R4)-C(=O)(CH$_2$)n-, —(CH$_2$)n-CO—N(R4)-, —(CH$_2$)q-, C2-C5alkenyl, C2-C5alkynyl, C3-C6cycloalkyl, and a direct bond wherein the either the E1B ring or E2B ring are directly linked by a covalent bond;

and wherein the carbon atoms of —(CH2)q-, C2-C5alkenyl, and C2-C5alkynyl moieties of X3 may be further substituted by one or more C1-C6alkyl;

X4 is selected from the group consisting of C1-C6 alkyl, C3-C6 branched alkyl;

each R2' is selected from the group consisting of halogen and R2;

each R3 is independently and individually selected from the group consisting of H, C1-C6alkyl, branched C3-C7alkyl, C3-C7carbocyclyl, or phenyl;

wherein two R3 moieties independently and individually taken from the group consisting of C1-C6alkyl and branched C3-C7alkyl are attached to the same nitrogen heteroatom, the two R3 moieties may cyclize to form a C3-C7 heterocyclyl ring;

each R4 is selected from the group consisting of H, C1-C6alkyl, hydroxyC1-C6 alkyl, dihydroxyC1-C6alkyl, C1-C6alkoxyC1-C6alkyl, branched C3-C7alkyl, branched hydroxyC1-C6 alkyl, branched C1-C6alkoxyC1-C6alkyl, branched dihydroxyC1-C6alkyl, carbocyclyl, hydroxyl substituted carbocyclyl, alkoxy substituted carbocyclyl, dihydroxy substituted carbocyclyl, phenyl, heteroaryl, heterocyclyl, phenylC1-C6alkyl, heteroarylC1-C6alkyl, and heterocyclylC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom may cyclize to form a C3-C7 heterocyclyl ring;

each R5 is independently and individually selected from the group consisting of

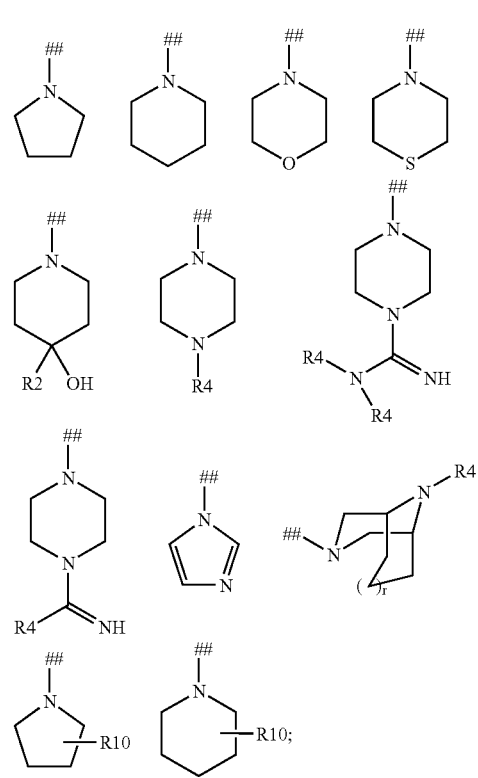

and wherein the symbol (##) is the point of attachment to respective R8, R10, Z4, Z5, Z6 or A2 ring moieties containing a R5 moiety;

wherein two R4 moieties independently and individually taken from the group consisting of C1-C6alkyl, branched C3-C6alkyl, hydroxyalkyl, and alkoxyalkyl and are attached to the same nitrogen heteroatom of R5 may cyclize to form a C3-C7 heterocyclyl ring;

wherein each R6 is independently and individually selected from the group consisting of C1-C6alkyl, branched C3-C7alkyl, carbocyclyl, phenyl, heteroaryl, and heterocyclyl;

each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

each R8 is independently and individually selected from the group consisting of C1-C6alkyl, C1-C6 fluoroalkyl wherein the alkyl moiety is partially or fully fluorinated, branchedC4-C7alkyl, carbocyclyl, phenyl, C1-C6phenylalkyl, heteroaryl or heteroarylC1-C6alkyl, heterocyclyl, heterocyclylC1-C6alkyl, OH, C1-C6alkoxy, N(R3)$_2$, N(R4)$_2$, or R5;

wherein two R3 moieties are independently and individually taken from the group consisting of C1-C6alkyl and branched C3-C6alkyl and are attached to the same nitrogen heteroatom of R8 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of R8 may cyclize to form a C3-C7 heterocyclyl ring;

each R10 is independently and individually selected from the group consisting of $CO_2H$, $CO_2C1$-C6alkyl, CO—N(R4)$_2$, OH, C1-C6alkoxy, —N(R4)$_2$;

wherein two R4 moieties independently and individually taken from the group consisting of C1-C6alkyl, branched C3-C6alkyl, hydroxyalkyl, and alkoxyalkyl and are attached to the same nitrogen heteroatom of R10 may cyclize to form a C3-C7 heterocyclyl ring;

each Z1 is a substituent attached to a ring carbon and is independently and individually selected from the group consisting of hydroxyC1-C6alkyl, C2-C6alkoxy, C1-C6alkoxyC1-C6alkyl, (R4)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—C(═O)—, (R4)$_2$N—C(═O)—, (R4)$_2$N—CO—C1-C6alkyl, C1-C6alkoxycarbonyl, carboxyC1-C6alkyl, C1-C6alkoxycarbonylC1-C6alkyl, (R3)$_2$NSO$_2$, SOR3, (R4)$_2$NSO$_2$, —SO$_2$R3', —SOR4, —C(═O)R6, —C(═NOH)R6, —C(═NOR3)R6, —(CH$_2$)$_n$N(R4)C(O)R8, monocyclic heteroaryl, monocyclic heterocyclyl, monocyclic heteroarylC1-C6alkyl, monocyclic heterocyclylC1-C6alkyl, monocyclic heteroaryloxy, monocyclic heterocyclyloxy, monocyclic heteroaryloxyC1-C6alkyl, monocyclic heterocyclyloxyC1-C6alkyl, arylamino, monocyclic heteroarylamino, monocyclic heterocyclylamino, arylaminoC1-C6alkyl, monocyclic heteroarylaminoC1-C6alkyl, monocyclic heterocyclylaminoC1-C6alkyl, or moieties of the formulae

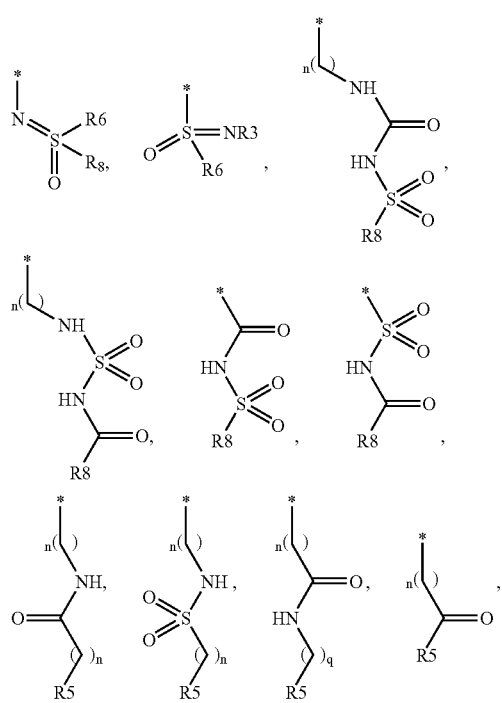

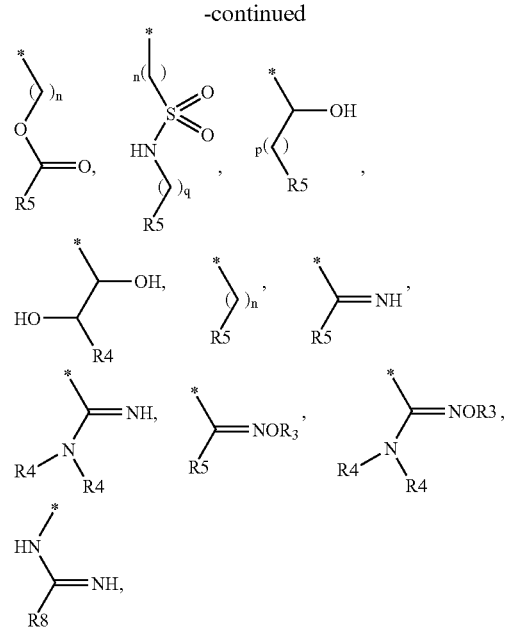

In the foregoing definition of Z1, alkyl moieties may optionally be substituted by one or more C1-C6alkyl;

Wherein the asterisk (*) indicates the point of attachment of the Z1 moiety to the A2 ring;

in the event that Z1 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z1 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z1 may cyclize to form a C3-C7 heterocyclyl ring;

each Z4 is a substituent attached to a ring nitrogen and is independently and individually selected from the group consisting of H, C1-C6alkyl, hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C2-C6alkyl, carboxyC2-C6alkyl, C1-C6alkoxycarbonylC2-C6alkyl, —C2-C6alkylN(R4)C(O)R8, R8-C(═NR3)-, —SO$_2$R8, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

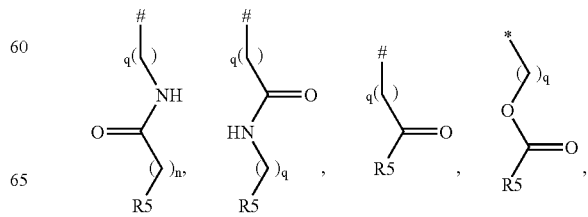

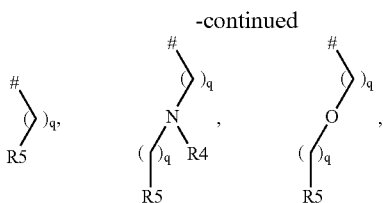

wherein the symbol (#) indicates the point of attachment of the Z4 moiety to the A2 ring for formula I;

in the event that Z4 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z4 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z4 may cyclize to form a C3-C7 heterocyclyl ring;

Z5 is independently and individually selected from the group consisting of H, C1-C6alkyl, branched C3-C7alkyl, halogen, fluoroalkyl, cyano, hydroxyl, alkoxy, oxo, aminocarbonyl, carbonylamino, aminosulfonyl, sulfonylamino, —N(R3)$_2$, —O—(CH$_2$)q-N(R4)$_2$, —N(R3)-(CH$_2$)q-N(R4)$_2$, —R5, —O—(CH$_2$)q-O-Alkyl, —O—(CH$_2$)q-N(R4)$_2$, —N(R3)-(CH$_2$)q-O-Alkyl, —N(R3)-(CH$_2$)q-N(R4)$_2$, —O—(CH$_2$)q-R5, and —N(R3)-(CH$_2$)q-R5;

wherein two R3 moieties are independently and individually taken from the group consisting of C1-C6alkyl and branched C3-C6alkyl and are attached to the same nitrogen heteroatom of Z5 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z5 may cyclize to form a C3-C7 heterocyclyl ring;

Each Z6 is independently and individually selected from the group consisting of H, C1-C6alkyl, branched C3-C7alkyl, hydroxyl, C1-C6alkoxy, (R3)$_2$N—, —N(R3)COR8, (R4)$_2$N—, —R5, —N(R4)COR8, —N(R3)SO$_2$R6-, —CON(R3)$_2$, —CON(R4)$_2$, —COR5, —SO$_2$NHR4, heteroaryl, heterocyclyl, heteroaryloxy, heterocyclyloxy, arylamino, heteroarylamino, and heterocyclylamino;

wherein two R3 moieties are independently and individually taken from the group consisting of C1-C6alkyl and branched C3-C6alkyl and are attached to the same nitrogen heteroatom of Z6 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z6 may cyclize to form a C3-C7 heterocyclyl ring;

each Z7 is a substituent attached to a ring carbon and is independently and individually selected from the group consisting of hydroxyC2-C6alkyl, C1-C6alkoxyC1-C6alkyl, (R6)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—CO, (R4)$_2$N—CO, —SO$_2$R3', SOR3, —SOR4, —C(=O)R6, —C(=NOH)R6, —C(=NOR3)R6, (CH$_2$)$_n$N(R4)C(O)N(R4)$_2$, (CH$_2$)$_n$N(R4)C(O)R5, monocyclic heteroaryl, monocyclic heterocyclyl, monocyclic heteroarylC1-C6alkyl, monocyclic heterocyclylC1-C6alkyl, monocyclic heteroaryloxy, monocyclic heterocyclyloxy, monocyclic heteroaryloxyC1-C6alkyl, monocyclic heterocyclyloxyC1-C6alkyl, arylamino, monocyclic heteroarylamino, monocyclic heterocyclylamino, arylaminoC1-C6alkyl, monocyclic heteroarylaminoC1-C6alkyl, monocyclic heterocyclylaminoC1-C6alkyl, or moieties of the formulae

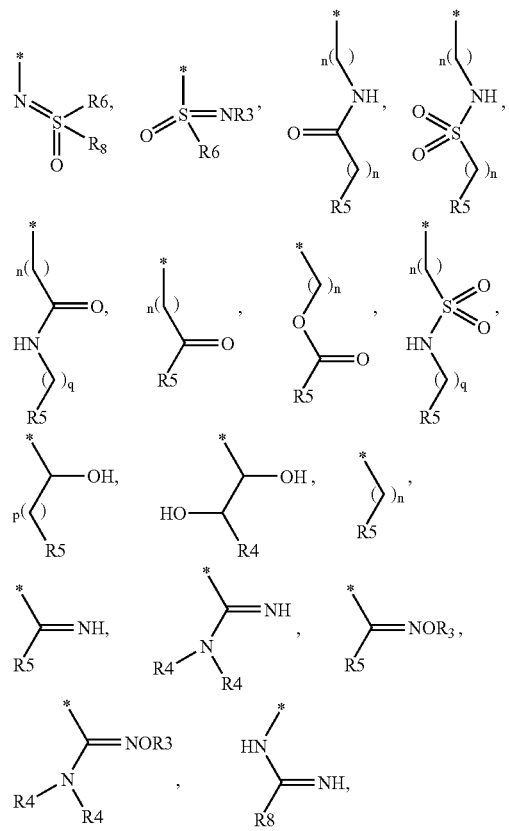

cyano wherein the site of attachment to the A2 ring is meta to the point of attachment to the A1 ring and wherein A2 is phenyl, and cyano wherein the site of attachment is to a substitutable position when A2 is pyridyl, pyrimidinyl or a five-membered ring;

In the foregoing definition of Z7, alkyl moieties may optionally be substituted by one or more C1-C6alkyl;

Wherein the asterisk (*) indicates the point of attachment of the Z1 moiety to the A2 ring;

in the event that Z7 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z7 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z7 may cyclize to form a C3-C7 heterocyclyl ring;

and n is 0-4; p is 1-4; q is 2-6; r is 0 or 1; v is 1 or 2;

and tautomers, diastereomers, geometric isomers, enantiomers, hydrates, prodrugs and salts of any of the foregoing.

1.3.6b

The following specific compounds are most preferred: 1-(3-t-butyl-1-(3-(pyridin-3-yl)phenyl)-1H-pyrazol-5-yl)-3-(3-(pyridin-3-yloxy)phenyl)urea, 1-(1-(3-(1H-pyrazol-4-yl)phenyl)-3-t-butyl-1H-pyrazol-5-yl)-3-(4-(1-oxoisoindolin-4-yl)phenyl)urea 1.3.7 Methods 1.3.7a Methods of Protein Modulation The invention includes methods of modulating kinase activity of a variety of kinases, e.g. C-Abl kinase, BCR-Abl kinase. The kinases may be wildtype kinases, oncogenic forms thereof, aberrant fusion proteins thereof or polymorphs of any of the foregoing. The method comprises the step of contacting the kinase species with compounds of the invention and especially those set forth in sections 1.3 and 1.3.6a. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, kinase cellular localization, and recruitment of other proteins into signaling complexes through modulation of kinase conformation.

The methods of the invention may also involve the step of inducing, synergizing, or promoting the binding of a second modulator compound of said kinase, especially C-Abl kinase or BCR-Abl kinase, to form a ternary adduct, such co-incident binding resulting in enhanced biological modulation of the kinase when compared to the biological modulation of the protein affected by either of said compounds alone. The second compound may interact at a substrate, co-factor or regulatory site on the kinase, with the second site being distinct from the site of interaction of the first compound. For example, the second site may be an ATP co-factor site. The second compounds may be taken from the group consisting of N-(4-methyl-3-(4-(pyridin-3-yl)pyrimidin-2-ylamino)phenyl)-4-((4-methylpiperazin-1-yl)methyl)benzamide (Gleevec); N-(2-chloro-6-methylphenyl)-2-(6-(4-(2-hydroxyethyl)piperazin-1-yl)-2-methylpyrimidin-4-ylamino)thiazole-5-carboxamide (BMS-354825); 6-(2,6-dichlorophenyl)-2-(3-(hydroxymethyl)phenylamino)-8-methylpyrido[2,3-d]pyrimidin-7(8H)-one (PD 166326); 6-(2,6-dichlorophenyl)-8-methyl-2-(3-(methylthio)phenylamino)pyrido[2,3-d]pyrimidin-7(8H)-one (PD 173955); 6-(2,6-dichlorophenyl)-2-(4-fluoro-3-methylphenylamino)-8-methylpyrido[2,3-d]pyrimidin-7(8H)-one (PD180970); 6-(2,6-dichlorophenyl)-2-(4-ethoxyphenylamino)-8-methylpyrido[2,3-d]pyrimidin-7(8H)-one (PD 173958); 6-(2,6-dichlorophenyl)-2-(4-fluorophenylamino)-8-methylpyrido[2,3-d]pyrimidin-7(8H)-one (PD 173956); 6-(2,6-dichlorophenyl)-2-(4-(2-(diethylamino)ethoxy)phenylamino)-8-methylpyrido[2,3-d]pyrimidin-7(8H)-one (PD 166285); 2-(4-(2-aminoethoxy)phenylamino)-6-(2,6-dichlorophenyl)-8-methylpyrido[2,3-d]pyrimidin-7(8H)-one; N-(3-(6-(2,6-dichlorophenyl)-8-methyl-7-oxo-7,8-dihydropyrido[2,3-d]pyrimidin-2-ylamino)phenyl)acetamide (SKI DV-MO16); 2-(4-aminophenylamino)-6-(2,6-dichlorophenyl)-8-methylpyrido[2,3-d]pyrimidin-7(8H)-one (SKI DV 1-10); 6-(2,6-dichlorophenyl)-2-(3-hydroxyphenylamino)-8-methylpyrido[2,3-d]pyrimidin-7(8H)-one (SKI DV2-89); 2-(3-aminophenylamino)-6-(2,6-dichlorophenyl)-8-methylpyrido[2,3-d]pyrimidin-7(8H)-one (SKI DV 2-43); N-(4-(6-(2,6-dichlorophenyl)-8-methyl-7-oxo-7,8-dihydropyrido[2,3-d]pyrimidin-2-ylamino)phenyl)acetamide (SKI DV-M017); 6-(2,6-dichlorophenyl)-2-(4-hydroxyphenylamino)-8-methylpyrido[2,3-d]pyrimidin-7(8H)-one (SKI DV-MO17); 6-(2,6-dichlorophenyl)-2-(3-ethylphenylamino)-8-methylpyrido[2,3-d]pyrimidin-7(8H)-one (SKI DV 2 87).

1.3.7b Treatment Methods

The methods of the invention also include treating individuals suffering from a condition selected from the group consisting of cancer and hyperproliferative diseases. These methods comprise administering to such individuals compounds of the invention, and especially those of section 1.3 and 1.3.6a. Exemplary conditions include chronic myelogenous leukemia, acute lymphocytic leukemia, gastrointestinal stromal tumors, and hypereosinophillic syndrome. The administration method is not critical, and may be from the group consisting of oral, parenteral, inhalation, and subcutaneous.

1.3.8 Pharmaceutical Preparations

The compounds of the invention, especially those of 1.3 and 1.3.6a may form a part of a pharmaceutical composition by combining one or more such compounds with a pharmaceutically acceptable carrier. Additionally, the compositions may include an additive selected from the group consisting of adjuvants, excipients, diluents, and stabilizers.

1.3.9 Kinase/Compound Adducts

The invention also provides adducts in the form of compounds of the invention bound with a species of kinase such as a wild-type kinase, oncogenic forms thereof, aberrant fusion proteins thereof and polymorphs of any of the foregoing. The compounds are advantageously selected from the groups defined in sections 1.3 and 1.3.6a.

2. Second Aspect of the Invention—VEGFR and PDGFR Kinase Modulator Compounds, Methods, Preparations and Adducts 2.1 Generally—A2 Bicyclic Compounds The invention includes compounds of formula I as defined in section 1.1, wherein each R2 is selected from the group consisting of monocyclic heteroaryl, C1-C6alkyl, branched C3-C7alkyl, and R19 substituted C3-C8carbocyclyl wherein R19 is H, or C1-C6alkyl, C1-C6fluoroalkyl wherein the alkyl group is partially or fully fluorinated, phenyl wherein the phenyl group is optionally substituted by one or more fluorine substituents, wherein Z1' is independently and individually selected from the group consisting of H, C1-C6alkyl, C3-C7cycloalkyl, hydroxyC1-C6alkyl, C1-C6alkoxyC1-C6alkyl, (R4)$_2$N—C1-C6alkyl, (R4)$_2$N—C2-C6alkylN(R4)-(CH$_2$)$_p$, (R4)$_2$N—C2-C6alkylO-(CH$_2$)$_p$, (R4)$_2$N—CO—C1-C6alkyl, carboxyC1-C6alkyl, C1-C6alkoxycarbonylC1-C6alkyl, —(CH$_2$)$_p$N(R4)C(O)R8, aryl, arylC1-C6alkyl, heteroaryl, heteroarylC1-C6alkyl, heterocyclyl, heterocyclylC1-C6alkyl, aryloxyC1-C6alkyl, heteroaryloxyC1-C6alkyl, heterocyclyloxyC1-C6alkyl, arylaminoC1-C6alkyl, heteroarylaminoC1-C6alkyl, or heterocyclylaminoC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom of Z1' may cyclize to form a C3-C7 heterocyclyl ring;

each Z2 is independently and individually selected from the group consisting of hydroxyl, hydroxyC1-C6alkyl, cyano, (R3)$_2$N—, (R4)$_2$N—, (R4)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—C(═O)—, (R4)$_2$N—C(═O)—, (R4)$_2$N—CO—C1-C6alkyl, carboxyl, carboxyC1-C6alkyl, C1-C6alkoxycarbonyl, C1-C6alkoxycarbonylC1-C6alkyl, (R3)$_2$NSO$_2$, (R4)$_2$NSO$_2$, —SO$_2$R5-, —(CH$_2$)$_n$N(R4)C(O)R8, ═O, ═NOH, ═N(OR6), heteroarylC1-C6alkyl, heterocyclylC1-C6alkyl, heteroaryloxyC1-C6alkyl, heterocyclyloxyC1-C6alkyl, arylaminoC1-C6alkyl, heteroarylaminoC1-C6alkyl, heterocyclylaminoC1-C6alkyl, or moieties of the formulae

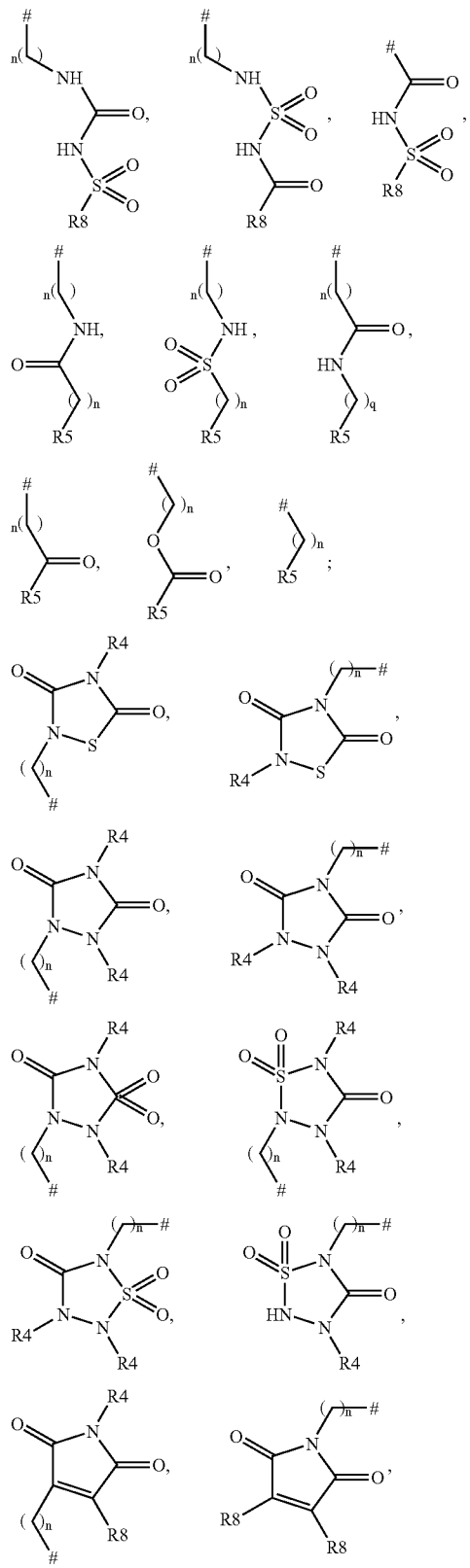

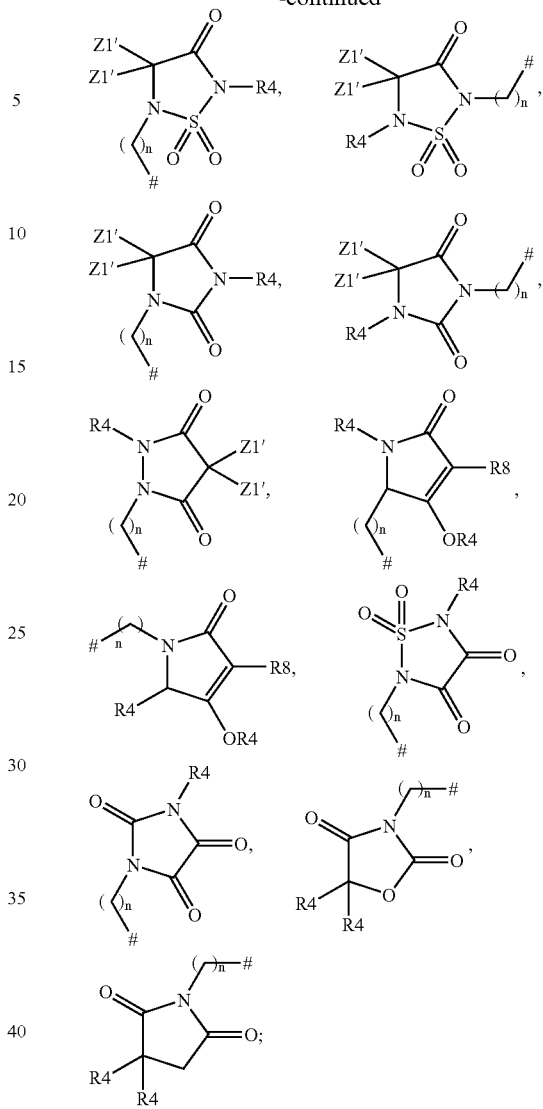

wherein the symbol (#) indicates the point of attachment of the Z2 moiety to the A2 ring of formula I;

in the event that Z2 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z2 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z2 may cyclize to form a C3-C7 heterocyclyl ring;

each Z3 is independently and individually selected from the group consisting of H, C1-C6alkyl, hydroxyl, hydroxyC1-C6alkyl, cyano, C1-C6alkoxy, C1-C6alkoxyC1-C6alkyl, halogen, $CF_3$, $(R3)_2N-$, $(R4)_2N-$, $(R4)_2NC1$-C6alkyl, $(R4)_2NC2$-C6alkylN(R4)-$(CH2)_n$, $(R4)_2NC2$-C6alkylO-$(CH_2)_n$, R8CO—, $(R4)_2N-CO-C1$-C6alkyl, carboxyl, carboxyC1-C6alkyl, C1-C6alkoxycarbonyl, C1-C6alkoxycarbonylC1-C6alkyl, $(R3)_2NSO_2$, $-SO_2R3$, SOR3, $(R4)_2NSO_2$, $-SO_2R4$, $-SOR4$, $-(CH_2)_nN(R4)C$ (O)R8, —C═(NOH)R6, —C═(NOR3)R6, heteroaryl, heterocyclyl, heteroarylC1-C6alkyl, heterocyclylC1-C6alkyl, heteroaryloxy, heterocyclyloxy, heteroaryloxyC1-C6alkyl, heterocyclyloxyC1-C6alkyl, arylamino, heteroarylamino, heterocyclylamino, arylaminoC1-C6alkyl, heteroarylaminoC1-C6alkyl, heterocyclylaminoC1-C6alkyl, or moieties of the formulae

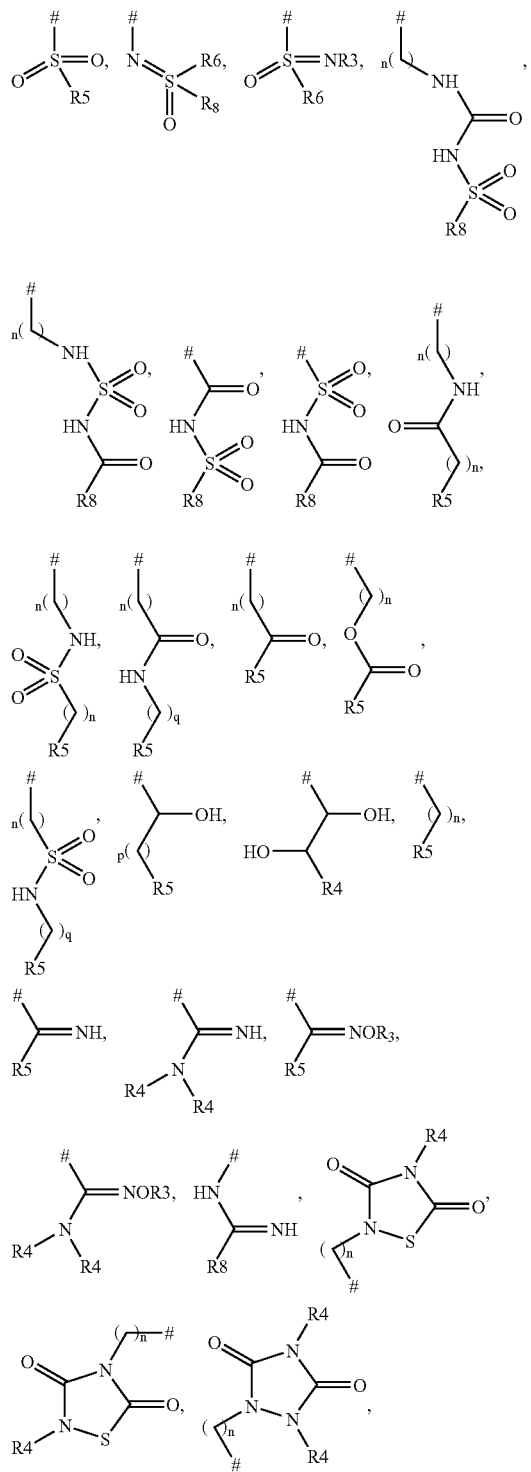

-continued

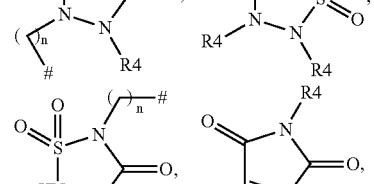

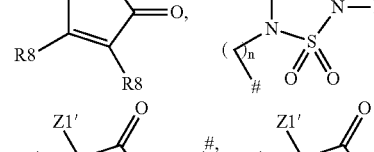
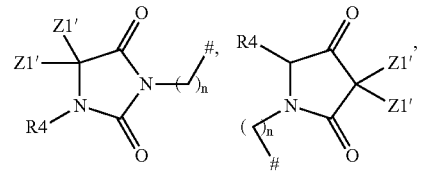
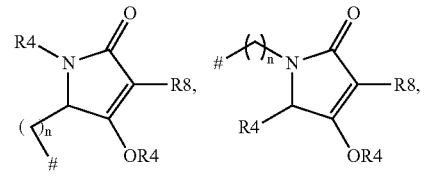
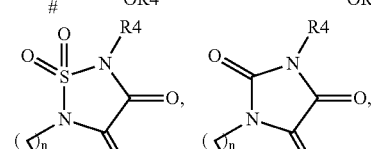
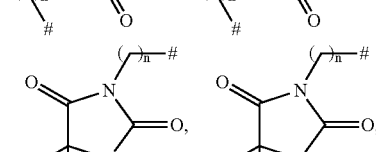
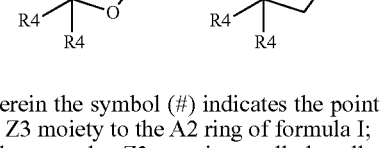

wherein the symbol (#) indicates the point of attachment of the Z3 moiety to the A2 ring of formula I;
in the event that Z3 contains an alkyl or alkylene moiety, such moieties may be further substituted with one or more C1-C6alkyls;
wherein two R3 moieties are independently and individually taken from the group consisting of C1-C6alkyl and branched C3-C6alkyl and are attached to the same nitrogen heteroatom of Z3 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z3 may cyclize to form a C3-C7 heterocyclyl ring;

2.1.1 Preferred D Moieties 2.1.1a

Preferred compounds of Formula I as defined above in section 2.1 contain D moieties as defined in section 1.1.1a.

2.1.1b

Additionally preferred compounds of Formula I as defined above in section 2.1 contain D moieties as defined in section 1.1.1b.

2.1.1c

More preferred compounds of Formula I as defined above in section 2.1.1b contain D moieties as defined in section 1.1.1c.

2.1.2 Preferred A2 Moieties 2.1.2a

Compounds of Formula I as defined above in section 2.1 have preferred A2 moieties as defined in section 1.1.2a;

2.1.2b More Preferred A2 Moieties

Compounds of Formula I as defined above in section 2.1 have more preferred A2 moieties selected from group consisting of

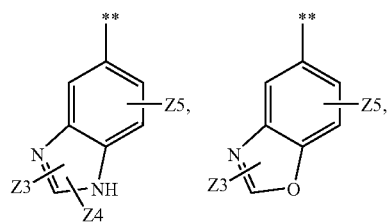

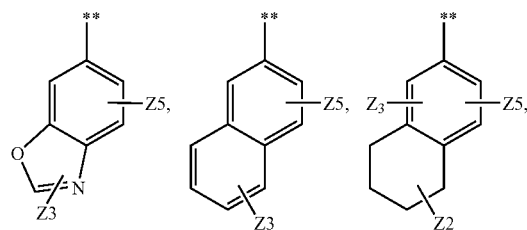

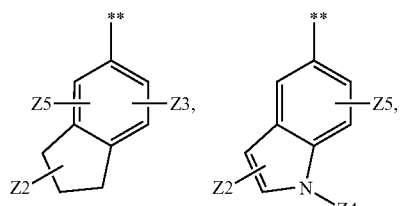

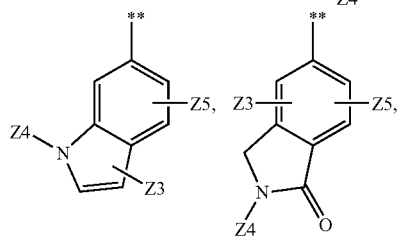

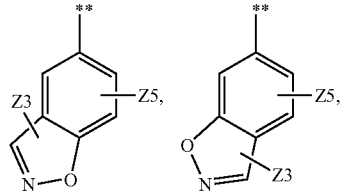

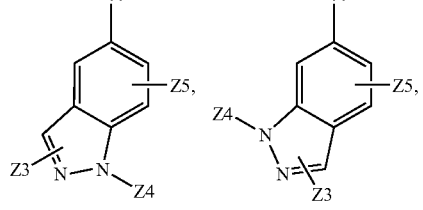

-continued

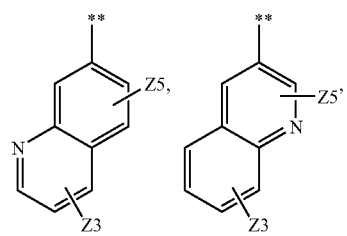

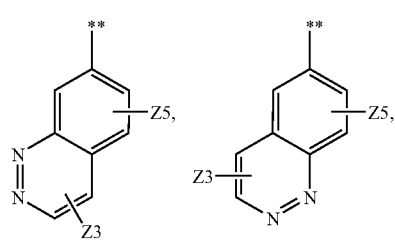

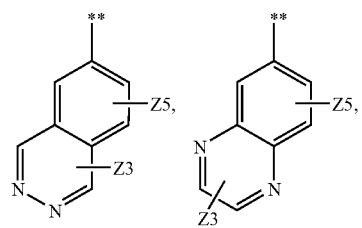

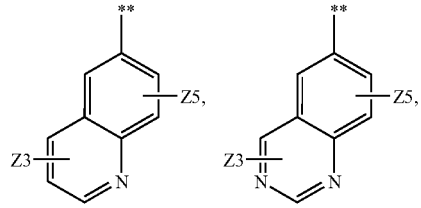

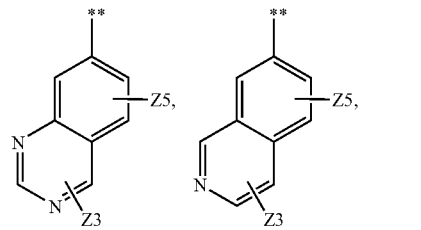

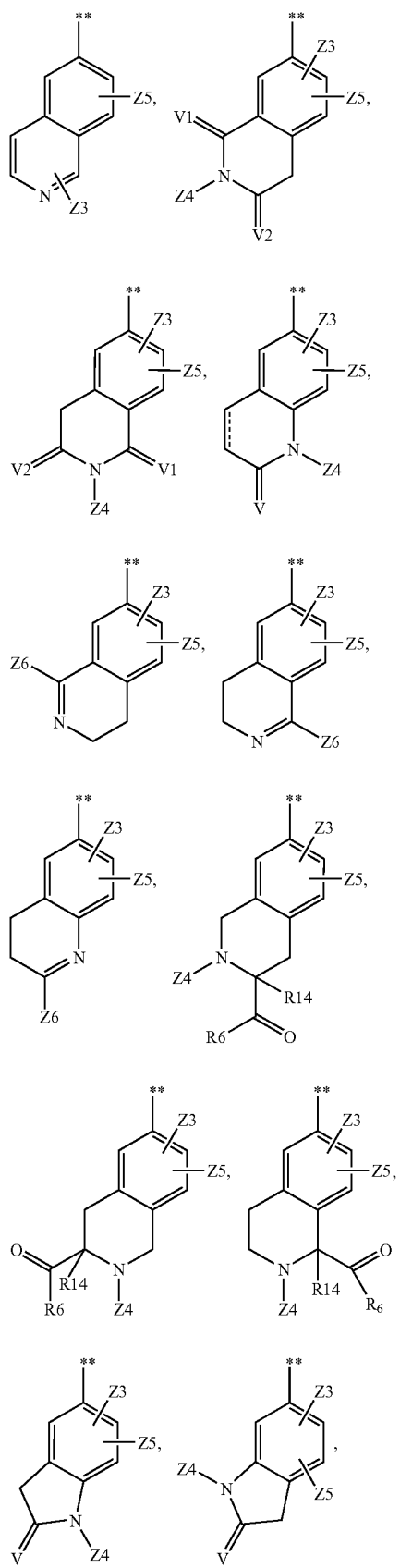
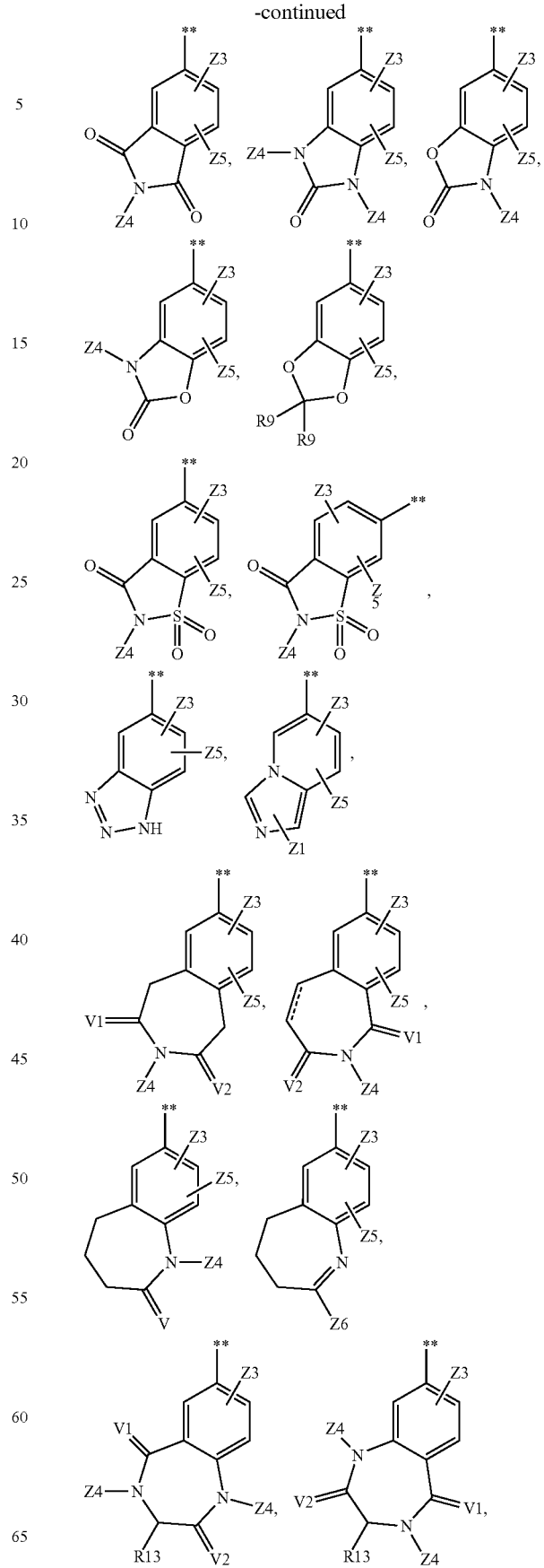

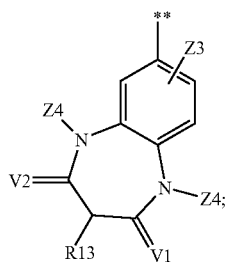
and wherein the symbol (**) is the point of attachment to the A1 ring for formula I;
wherein each Z3 and Z5 is independently attached to either aryl or heteroaryl ring of the A2 bicyclic ring.
2.1.2c
Still more preferred compounds of Formula I as defined above in section 2.1 have A2 moieties selected from group consisting of
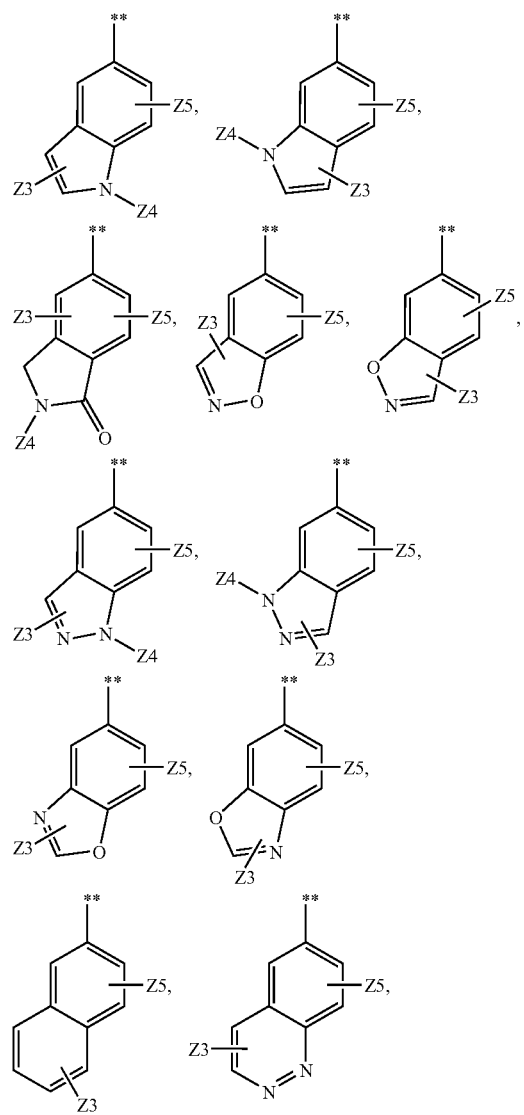
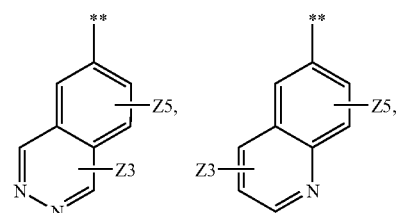
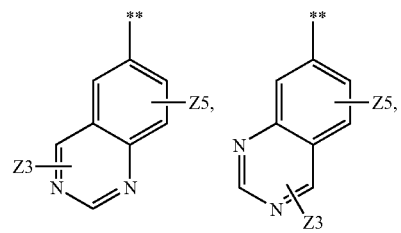
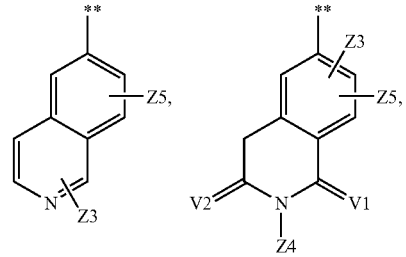
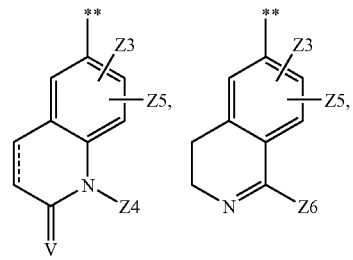
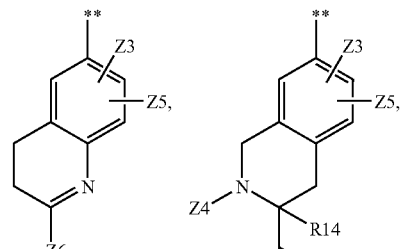
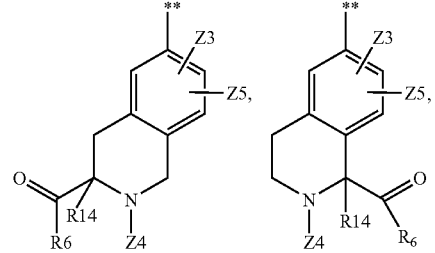

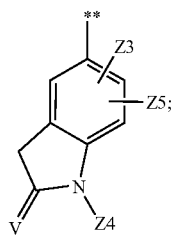

and wherein the symbol (**) is the point of attachment to the A1 ring of formula I;

wherein each Z3 and Z5 is independently attached to either aryl or heteroaryl ring of the A2 bicyclic ring.

2.1.3 Preferred Classes of Compounds 2.1.3a
Compounds as defined in 2.1.1a wherein the A2 group is defined in 2.1.2a.

2.1.3b
Compounds as defined in 2.1.3a wherein the A2 group is defined in 2.1.2b.

2.1.3c
Compounds as defined in 2.1.3a wherein the A2 group is defined in 2.1.2c.

2.1.3d
Compounds as defined in 2.1.1b wherein the A2 group is defined in 2.1.2a.

2.1.3e
Compounds as defined in 2.1.3c wherein the A2 group is defined in 2.1.2b.

2.1.3f
Compounds as defined in 2.1.3c wherein the A2 group is defined in 2.1.2c.

2.1.4 Preferred A1 Moieties 2.1.4a
Compounds of Formula I as defined above in section 2.1 have preferred A1 moieties selected from group defined in section 1.1.4a;

each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

2.1.4b
Compounds of Formula I as defined above in section 2.1 have more preferred A1 moieties selected from group consisting of

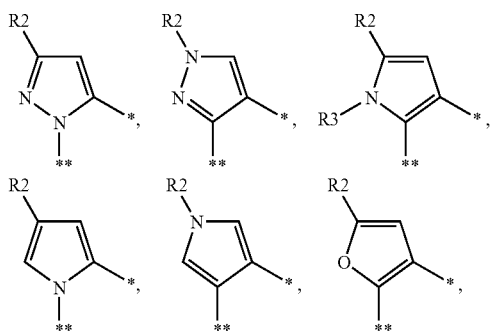

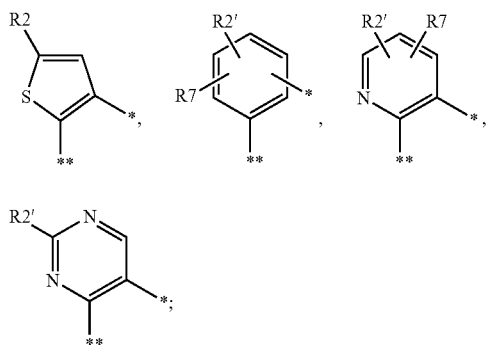

wherein the symbol (*) denotes the attachment to the W moiety of formula I and the symbol (**) denotes the attachment to the A2 moiety of formula I.

2.1.4c
Compounds of Formula I as defined above in section 2.1 have even more preferred A1 moieties selected from group consisting of

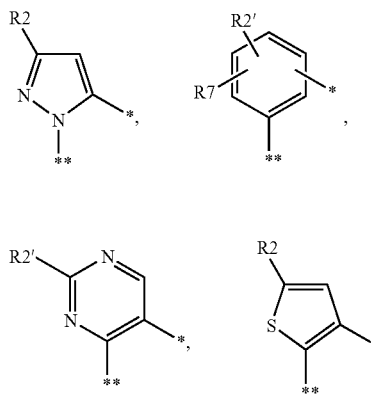

wherein the symbol (*) denotes the attachment to the W moiety of formula I and the symbol (**) denotes the attachment to the A2 moiety of formula I.

2.1.5 Preferred W and Y Moieties 2.1.5a
(1) W and Y are each NH, and X=O; (2) W=NH, Y=CHR4 and X=O; or (3) W=CHR4, Y=NH, and X=O.

2.1.5b
W and Y are each NH and X=O.

2.1.6 Further Preferred Compounds 2.1.6a
Further preferred compounds are of the formula

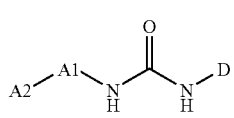

I wherein A2 is selected from the group consisting of
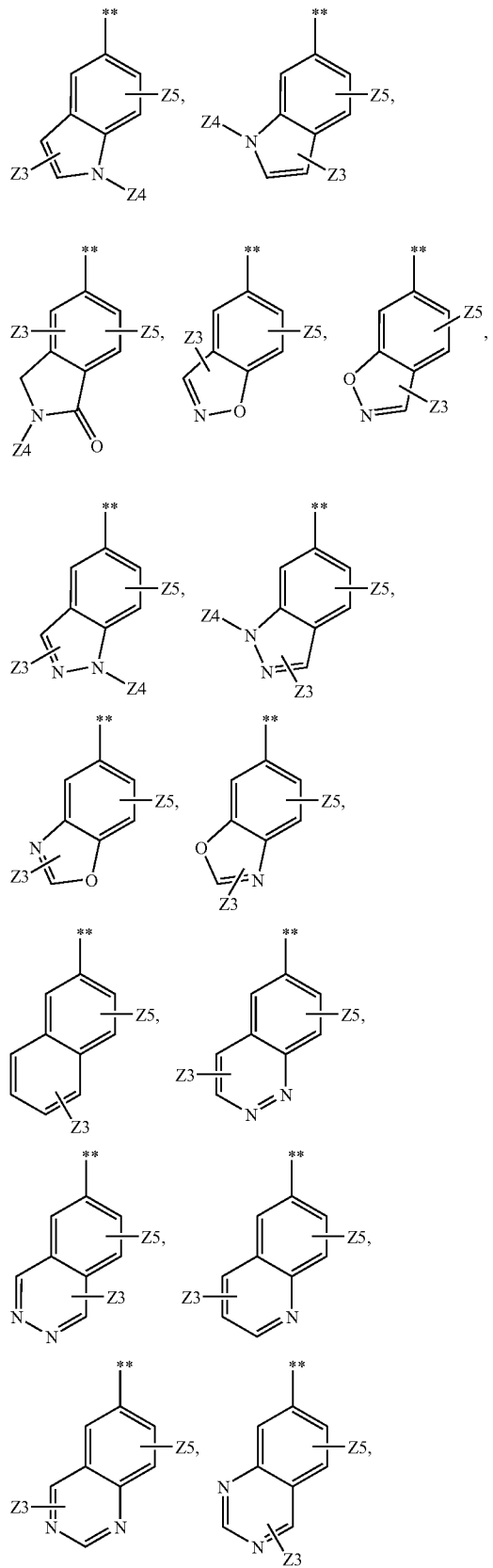
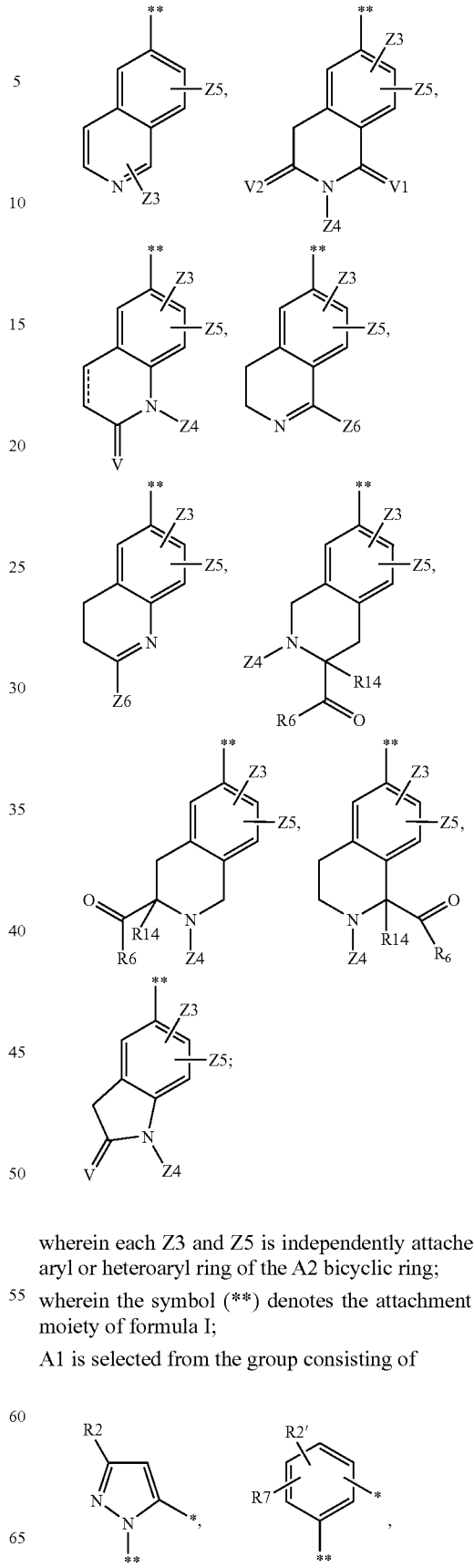
wherein each Z3 and Z5 is independently attached to either aryl or heteroaryl ring of the A2 bicyclic ring;
wherein the symbol (**) denotes the attachment to the A1 moiety of formula I;
A1 is selected from the group consisting of
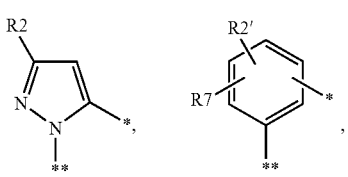

-continued

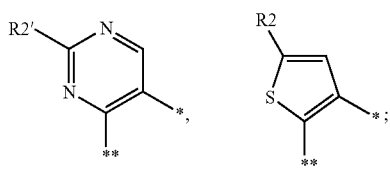

wherein the symbol (*) denotes the attachment to the W moiety of formula I and the symbol (**) denotes the attachment to the A2 moiety of formula I;

X is O, S, or NR3;

D comprises a member of 2,3-dichlorophenyl, 3,4-dichlorophenyl, 3,5-dichlorophenyl, 4-chlorophenyl, 3-chlorophenyl, 3-bromophenyl, 2,3-difluorophenyl, 2,4-difluorophenyl, 3,4-difluorophenyl, 2,5-difluorophenyl, 3,5-difluorophenyl, 2,3,5-trifluorophenyl, 2,4,5-trifluorophenyl, 2,3,4-trifluorophenyl, 3,4,5-trifluorophenyl, 4-cyanophenyl, 3-(R8SO$_2$)-phenyl, 3-phenoxyphenyl, 4 phenoxyphenyl,

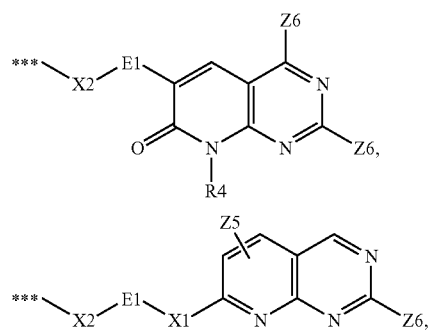

-continued

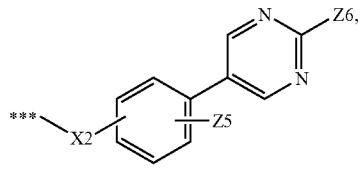

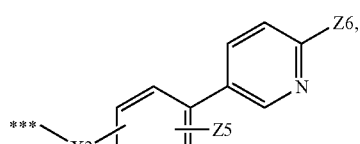

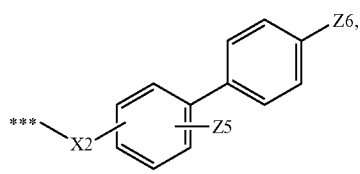

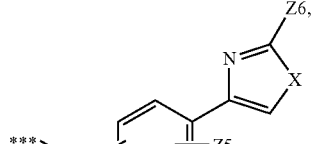

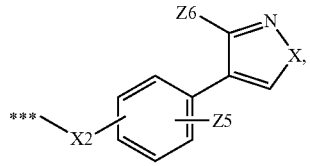

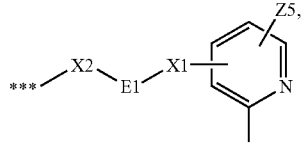


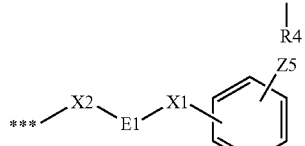

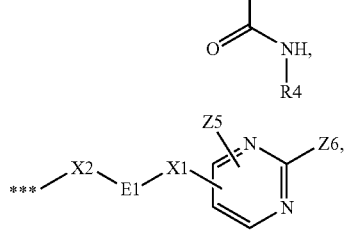

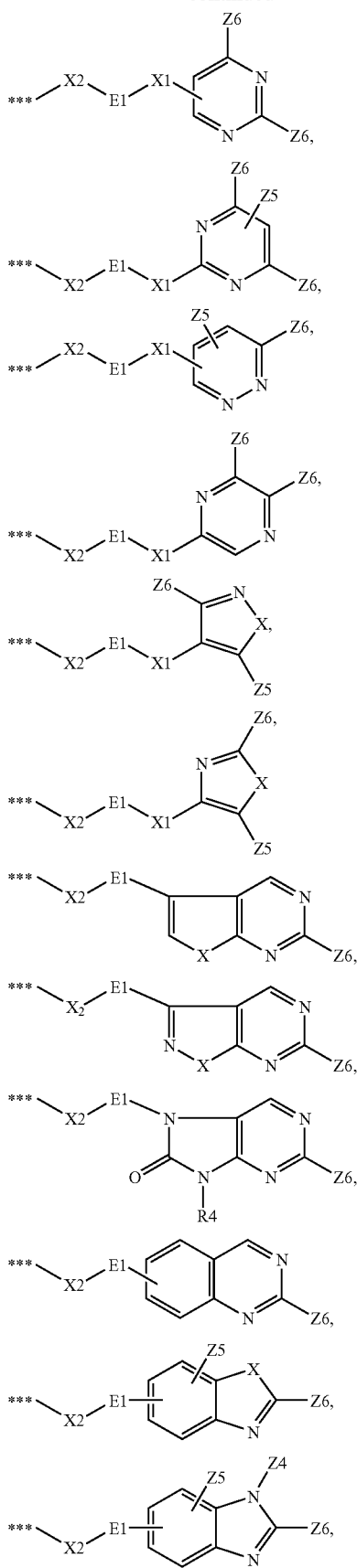
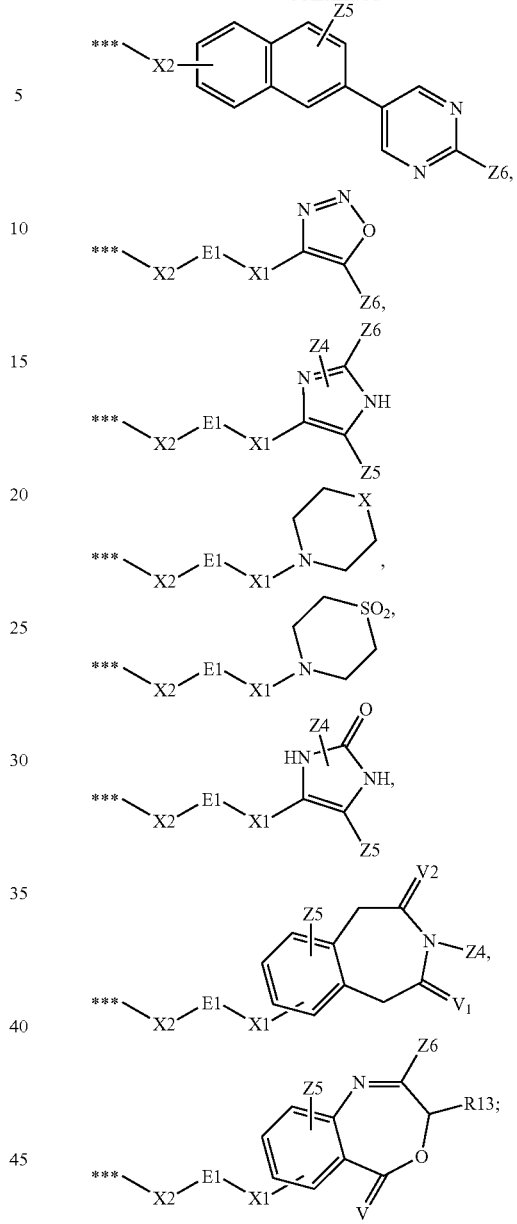

wherein E1 is selected from the group consisting cyclopropyl, cyclobutyl, cyclopentyl, cyclohexyl, pyrrolidinyl piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl and naphthyl;

wherein the symbol (***) denotes the attachment to the Y moiety of formula I;

X1 is selected from the group consisting of O, S, NR3, —C(=O)—, —O—(CH$_2$)n-, —S—(CH$_2$)n-, —NR3-(CH$_2$)n-, —O—(CH$_2$)q-O—, —O—(CH$_2$)q-NR3-, —N(R3)-(CH$_2$)q-N(R3)-, —(CH$_2$)n-N(R4)-C(=O)—, —(CH$_2$)n-N(R4)-C(=O)(CH$_2$)n-, —(CH$_2$)n-CO—N(R4)-, —(CH$_2$)p-, C2-C5alkenyl, C2-C5alkynyl, C3-C6cycloalkyl, and a direct bond wherein the E1 ring and the E2 ring are directly linked by a covalent bond;

and wherein the carbon atoms of —(CH2)n-, —(CH2)q-, (CH2)p, C2-C5alkenyl, and C2-C5alkynyl moieties of X1 may be further substituted by one or more C1-C6alkyl;

X2 is selected from the group consisting of C1-C6 alkyl, C3-C6 branched alkyl, or a direct bond wherein E1 is directly linked to the Y group of formula I;

each R2 is selected from the group consisting of C1-C6alkyl, branched C3-C7alkyl, and R19 substituted C3-C8carbocyclyl wherein R19 is H, or C1-C6alkyl, C1-C6fluoroalkyl wherein the alkyl group is partially or fully fluorinated, phenyl wherein the phenyl group is optionally substituted by one or more fluorine substituents, or monocyclic heteroaryl;

each R2' is selected from the group consisting of halogen and R2;

each R3 is independently and individually selected from the group consisting of H, C1-C6alkyl, branched C3-C7alkyl, C3-C7carbocyclyl, or phenyl;

wherein two R3 moieties independently and individually taken from the group consisting of C1-C6alkyl and branched C3-C7alkyl are attached to the same nitrogen heteroatom, the two R3 moieties may cyclize to form a C3-C7 heterocyclyl ring;

each R4 is selected from the group consisting of H, C1-C6alkyl, hydroxyC1-C6 alkyl, dihydroxyC1-C6alkyl, C1-C6alkoxyC1-C6alkyl, branched C3-C7alkyl, branched hydroxyC1-C6 alkyl, branched C1-C6alkoxyC1-C6alkyl, branched dihydroxyC1-C6alkyl, carbocyclyl, hydroxyl substituted carbocyclyl, alkoxy substituted carbocyclyl, dihydroxy substituted carbocyclyl, phenyl, heteroaryl, heterocyclyl, phenylC1-C6alkyl, heteroarylC1-C6alkyl, and heterocyclylC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom may cyclize to form a C3-C7 heterocyclyl ring;

each R5 is independently and individually selected from the group consisting of

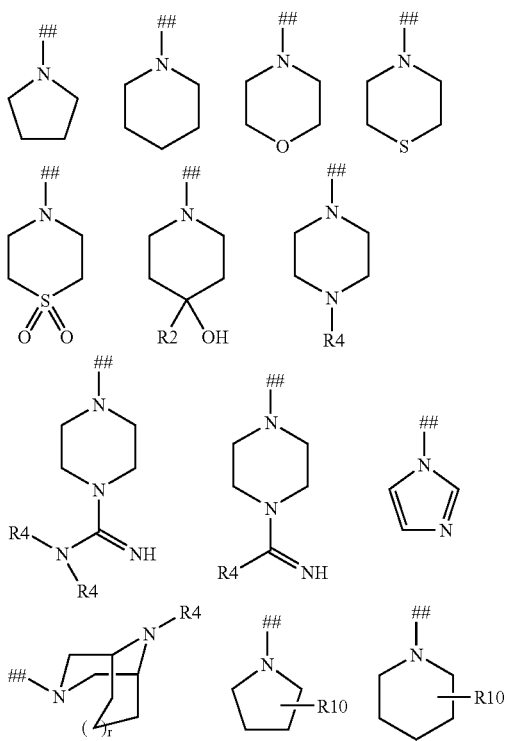

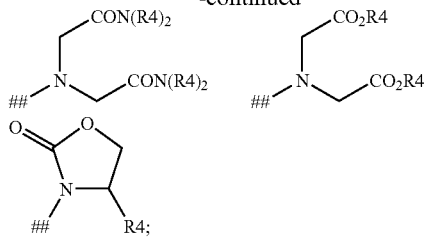

and wherein the symbol (##) is the point of attachment to respective R8, R10, R13, Z2, Z3, Z4, Z5, or A2 ring moieties containing a R5 moiety;

wherein two R4 moieties independently and individually taken from the group consisting of C1-C6alkyl, branched C3-C6alkyl, hydroxyalkyl, and alkoxyalkyl and are attached to the same nitrogen heteroatom of R5 may cyclize to form a C3-C7 heterocyclyl ring;

wherein each R6 is independently and individually selected from the group consisting of C1-C6alkyl, branched C3-C7alkyl, carbocyclyl, phenyl, heteroaryl, and heterocyclyl;

each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

each R8 is independently and individually selected from the group consisting of C1-C6alkyl, C1-C6 fluoroalkyl wherein the alkyl moiety is partially or fully fluorinated, branchedC4-C7alkyl, carbocyclyl, phenyl, C1-C6phenylalkyl, heteroaryl or heteroarylC1-C6alkyl, heterocyclyl, heterocyclylC1-C6alkyl, OH, C1-C6alkoxy, N(R3)$_2$, N(R4)$_2$, or R5;

wherein two R3 moieties are independently and individually taken from the group consisting of C1-C6alkyl and branched C3-C6alkyl and are attached to the same nitrogen heteroatom of R8 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of R8 may cyclize to form a C3-C7 heterocyclyl ring;

each R10 is independently and individually selected from the group consisting of CO$_2$H, CO$_2$C1-C6alkyl, CO—N(R4)$_2$, OH, C1-C6alkoxy, —N(R4)$_2$;

wherein two R4 moieties independently and individually taken from the group consisting of C1-C6alkyl, branched C3-C6alkyl, hydroxyalkyl, and alkoxyalkyl and are attached to the same nitrogen heteroatom of R10 may cyclize to form a C3-C7 heterocyclyl ring;

each R13 is independently and individually selected from the group consisting of H, C1-C6alkyl, branched C3-C7alkyl, carbocyclyl, hydroxyC2-C7alkyl, C1-C6alkoxyC2-C7alkyl, (R4)$_2$N—CO, (R4)$_2$N—CO—C1-C6alkyl, carboxyC1-C6alkyl, C1-C6alkoxycarbonyl, C1-C6alkoxycarbonylC1-C6alkyl, (R4)$_2$N—C2-C6alkyl, (R4)$_2$N—C2-C6alkylN(R4)-(CH$_2$)$_q$, R5-C2-C6alkylN(R4)-(CH$_2$)$_q$, (R4)$_2$N—C2-C6alkylO-(CH$_2$)$_q$, R5-C2-C6alkyl-O—(CH$_2$)$_q$, —(CH$_2$)$_q$N(R4)C(O)R8, aryl, arylC1-C6alkyl, heteroaryl, heteroarylC1-C6alkyl, heterocyclyl, heterocyclylC1-C6alkyl, aryloxyC2-C6alkyl, heteroaryloxyC2-C6alkyl, heterocyclyloxyC2-C6alkyl, arylaminoC2-C6alkyl, heteroarylaminoC2-C6alkyl, and heterocyclylaminoC2-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom of R13 may cyclize to form a C3-C7 heterocyclyl ring;

each R14 is independently and respectively selected from the group consisting of H and C1-C6alkyl;

wherein Z1' is independently and individually selected from the group consisting of H, C1-C6alkyl, C3-C7cycloalkyl, hydroxyC1-C6alkyl, C1-C6alkoxyC1-C6alkyl, (R4)$_2$N—C1-C6alkyl, (R4)$_2$N—C2-C6alkylN(R4)-(CH$_2$)$_p$, (R4)$_2$N—C2-C6alkylO-(CH$_2$)$_p$, (R4)$_2$N—CO—C1-C6alkyl, carboxyC1-C6alkyl, C1-C6alkoxycarbonylC1-C6alkyl, —(CH$_2$)$_p$N(R4)C(O)R8, aryl, arylC1-C6alkyl, heteroaryl, heteroarylC1-C6alkyl, heterocyclyl, heterocyclylC1-C6alkyl, aryloxyC1-C6alkyl, heteroaryloxyC1-C6alkyl, heterocyclyloxyC1-C6alkyl, arylaminoC1-C6alkyl, heteroarylaminoC1-C6alkyl, or heterocyclylaminoC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom of Z1' may cyclize to form a C3-C7 heterocyclyl ring;

each Z3 is independently and individually selected from the group consisting of H, C1-C6alkyl, hydroxyl, hydroxyC1-C6alkyl, cyano, C1-C6alkoxy, C1-C6alkoxyC1-C6alkyl, halogen, CF$_3$, (R3)$_2$N—, (R4)$_2$N—, (R4)$_2$NC1-C6alkyl, (R4)$_2$NC2-C6alkylN(R4)-(CH$_2$)$_n$, (R4)$_2$NC2-C6alkylO-(CH$_2$)$_n$, R8CO—, (R4)$_2$N—CO—C1-C6alkyl, carboxyl, carboxyC1-C6alkyl, C1-C6alkoxycarbonyl, C1-C6alkoxycarbonylC1-C6alkyl, (R3)$_2$NSO$_2$, —SO$_2$R3, SOR3, (R4)$_2$NSO$_2$, —SO$_2$R4, —SOR4, —(CH$_2$)$_n$N(R4)C(O)R8, —C=(NOH)R6, —C=(NOR3)R6, heteroaryl, heterocyclyl, heteroarylC1-C6alkyl, heterocyclylC1-C6alkyl, heteroaryloxy, heterocyclyloxy, heteroaryloxyC1-C6alkyl, heterocyclyloxyC1-C6alkyl, arylamino, heteroarylamino, heterocyclylamino, arylaminoC1-C6alkyl, heteroarylaminoC1-C6alkyl, heterocyclylaminoC1-C6alkyl, or moieties of the formulae

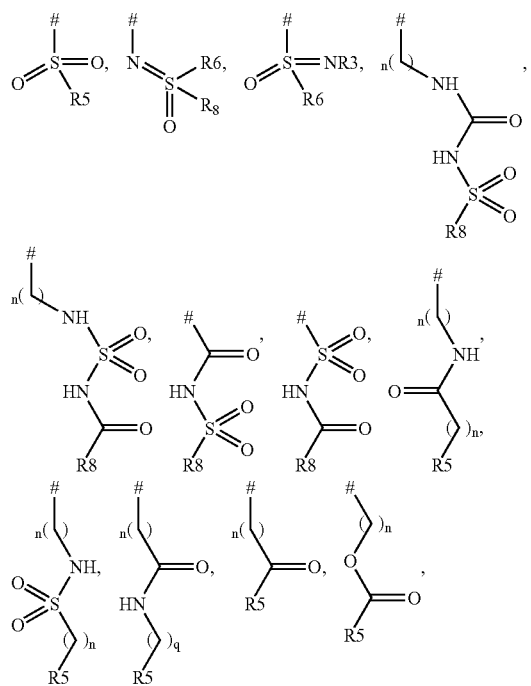

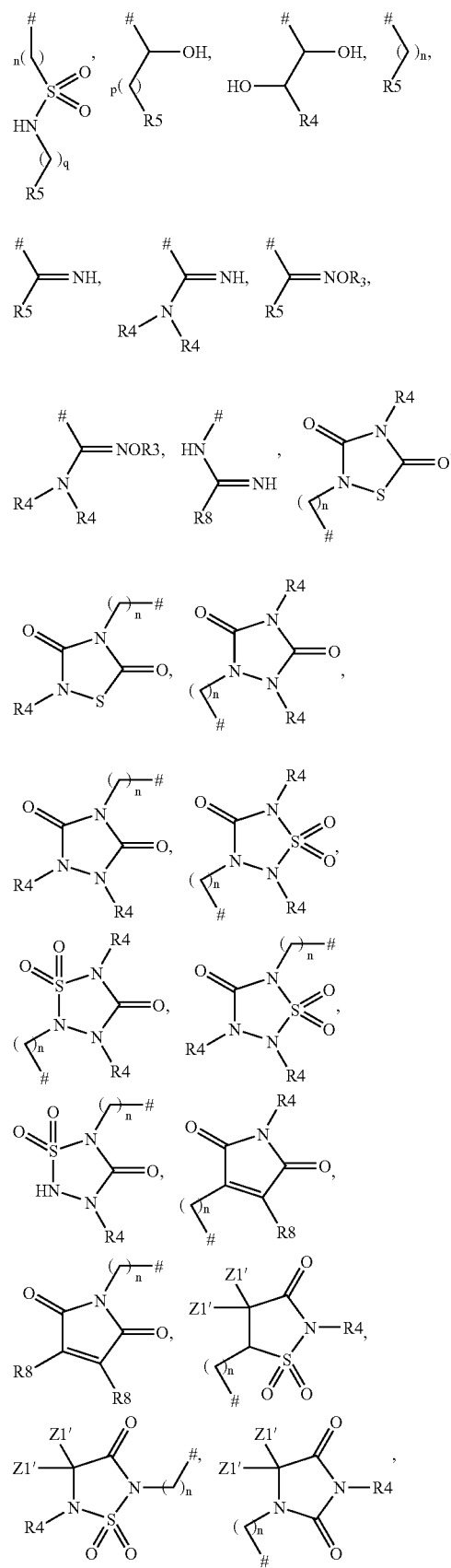

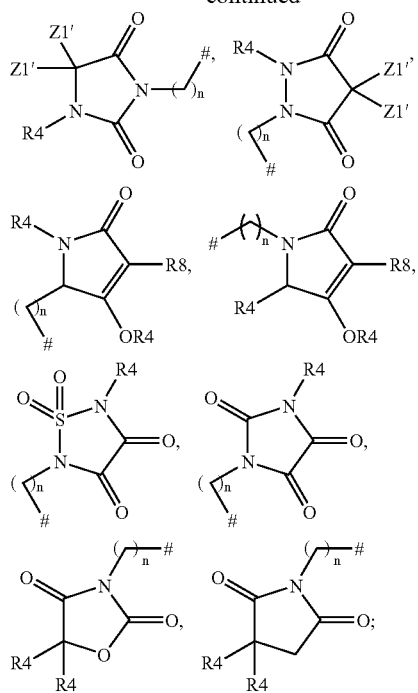
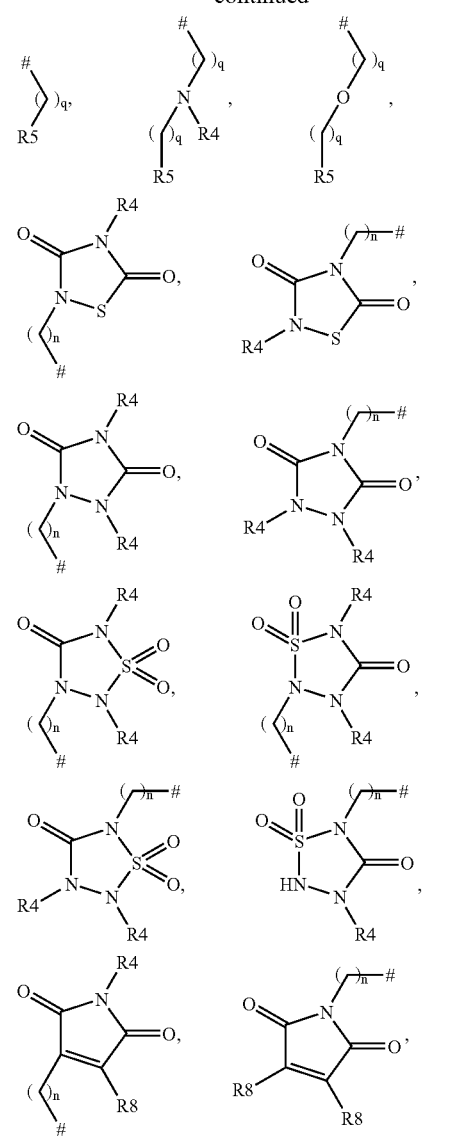

wherein the symbol (#) indicates the point of attachment of the Z3 moiety to the A2 ring of in the event that Z3 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z3 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z3 may cyclize to form a C3-C7 heterocyclyl ring;

each Z4 is independently and individually selected from the group consisting of H, C1-C6alkyl, hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C2-C6alkyl, carboxyC2-C6alkyl, C1-C6alkoxycarbonylC2-C6alkyl, —C2-C6alkylN(R4)C(O)R8, R8-C(=NR3)-, —SO$_2$R8, —COR8, heteroaryl, heteroarylC1-C6alkyl, heterocyclyl, heterocyclylC1-C6alkyl, heteroaryloxyC2-C6alkyl, heterocycly-loxyC2-C6alkyl, arylaminoC2-C6alkyl, heteroarylaminoC2-C6alkyl, heterocyclylaminoC2-C6alkyl, and moieties of the formulae

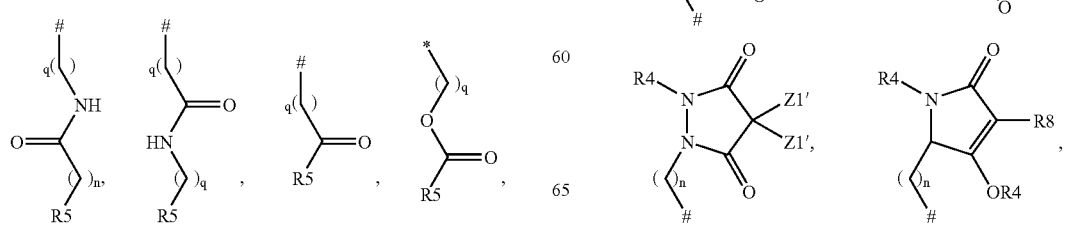

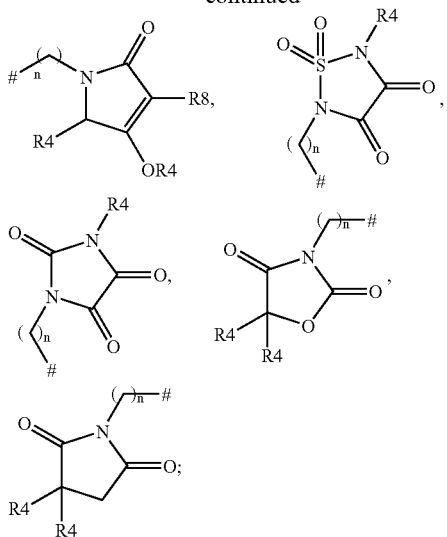

wherein the symbol (#) indicates the point of attachment of the Z4 moiety to the A2 ring for formula I;

in the event that Z4 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z4 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z4 may cyclize to form a C3-C7 heterocyclyl ring;

Z5 is independently and individually selected from the group consisting of H, C1-C6alkyl, branched C3-C7alkyl, halogen, fluoroalkyl, cyano, hydroxyl, alkoxy, oxo, aminocarbonyl, carbonylamino, aminosulfonyl, sulfonylamino, —N(R3)$_2$, —O—(CH$_2$)q-N(R4)$_2$, —N(R3)-(CH$_2$)q-N(R4)$_2$, —R5, —O—(CH$_2$)q-O-Alkyl, —O—(CH$_2$)q-N(R4)$_2$, —N(R3)-(CH$_2$)q-O-Alkyl, —N(R3)-(CH$_2$)q-N(R4)$_2$, —O—(CH$_2$)q-R5, and —N(R3)-(CH$_2$)q-R5;

wherein two R3 moieties are independently and individually taken from the group consisting of C1-C6alkyl and branched C3-C6alkyl and are attached to the same nitrogen heteroatom of Z5 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z5 may cyclize to form a C3-C7 heterocyclyl ring;

Each Z6 is independently and individually selected from the group consisting of H, C1-C6alkyl, branched C3-C7alkyl, hydroxyl, C1-C6alkoxy, (R3)$_2$N—, —N(R3)COR8, (R4)$_2$N—, —R5, —N(R4)COR8, —N(R3)SO$_2$R6-, —CON(R3)$_2$, —CON(R4)$_2$, —COR5, —SO$_2$NHR4, heteroaryl, heterocyclyl, heteroaryloxy, heterocyclyloxy, arylamino, heteroarylamino, and heterocyclylamino;

wherein two R3 moieties are independently and individually taken from the group consisting of C1-C6alkyl and branched C3-C6alkyl and are attached to the same nitrogen heteroatom of Z6 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z6 may cyclize to form a C3-C7 heterocyclyl ring;

and n is 0-4; p is 1-4; q is 2-6; r is 0 or 1; v is 1 or 2;

V, V1, and V2 are each independently and respectively selected from the group consisting of O and H$_2$;

and tautomers, diastereomers, geometric isomers, enantiomers, hydrates, prodrugs, and salts of any of the foregoing.

2.1.6b

The following specific compounds of Formula I are more preferred:

1-(3-t-butyl-1-(1-methyl-1H-indol-5-yl)-1H-pyrazol-5-yl)-3-(2,3-dichlorophenyl)urea, 1-(3-t-butyl-1-(1H-indazol-5-yl)-1H-pyrazol-5-yl)-3-(2,3-dichlorophenyl)urea, 1-(3-t-butyl-1-(1-(methylsulfonyl)indolin-5-yl)-1H-pyrazol-5-yl)-3-(2,3-dichlorophenyl)urea, 2-(3-(3-t-butyl-5-(3-(2,3-dichlorophenyl)ureido)-1H-pyrazol-1-yl)naphthalen-1-yl) acetic acid, 1-(1-(4-(2-amino-2-oxoethyl)naphthalen-2-yl)-3-t-butyl-1H-pyrazol-5-yl)-3-(2,3-dichlorophenyl)urea, 1-(3-t-butyl-1-(4-(hydroxymethyl)naphthalen-2-yl)-1H-pyrazol-5-yl)-3-(2,3-dichlorophenyl)urea, 1-(3-t-butyl-1-(1-(methylcarbamoyl)-1,2,3,4-tetrahydroisoquinolin-6-yl)-1H-pyrazol-5-yl)-3-(2,3-dichlorophenyl)urea, 1-(3-t-butyl-1-(2-oxo-1,2,3,4-tetrahydroquinolin-6-yl)-1H-pyrazol-5-yl)-3-(2,3-dichlorophenyl)urea, 1-(3-t-butyl-1-(2-oxo-1,2-dihydroquinolin-6-yl)-1H-pyrazol-5-yl)-3-(2,3-dichlorophenyl)urea, 1-(3-t-butyl-1-(1-carbamimidoyl-1,2,3,4-tetrahydroquinolin-6-yl)-1H-pyrazol-5-yl)-3-(2,3-dichlorophenyl)urea, 1-(3-t-butyl-1-(1-(methylsulfonyl)indolin-5-yl)-1H-pyrazol-5-yl)-3-(2,4,5-trifluorophenyl)urea, 1-(3-t-butyl-1-(1-(methylsulfonyl)indolin-5-yl)-1H-pyrazol-5-yl)-3-(2,3,5-trifluorophenyl)urea, 1-(1-(4-(2-amino-2-oxoethyl)naphthalen-2-yl)-3-t-butyl-1H-pyrazol-5-yl)-3-(2,3,5-trifluorophenyl)urea, 1-(3-t-butyl-1-(4-(2-(2,3-dihydroxypropylamino)-2-oxoethyl)naphthalen-2-yl)-1H-pyrazol-5-yl)-3-(2,3,5-trifluorophenyl)urea, 1-(3-t-butyl-1-(1-(methylsulfonyl)indolin-5-yl)-1H-pyrazol-5-yl)-3-(2,3-difluorophenyl)urea, 1-(1-(4-(2-amino-2-oxoethyl)naphthalen-2-yl)-3-t-butyl-1H-pyrazol-5-yl)-3-(2,5-difluorophenyl)urea, 1-(3-t-butyl-1-(1H-indol-5-yl)-1H-pyrazol-5-yl)-3-(3-(pyridin-3-yloxy)phenyl)urea, 1-(3-t-butyl-1-(indolin-5-yl)-1H-pyrazol-5-yl)-3-(3-(pyridin-3-yloxy)phenyl)urea, 1-(1-(4-(2-amino-2-oxoethyl)naphthalen-2-yl)-3-t-butyl-1H-pyrazol-5-yl)-3-(3-(pyridin-3-yloxy)phenyl)urea, 1-(3-t-butyl-1-(4-(2-(2,3-dihydroxypropylamino)-2-oxoethyl)naphthalen-2-yl)-1H-pyrazol-5-yl)-3-(3-(pyridin-3-yloxy)phenyl)urea, 1-(3-t-butyl-1-(4-(hydroxymethyl)naphthalen-2-yl)-1H-pyrazol-5-yl)-3-(3-(pyridin-3-yloxy)phenyl)urea, 1-(1-(4-(aminomethyl)naphthalen-2-yl)-3-t-butyl-1H-pyrazol-5-yl)-3-(3-(pyridin-3-yloxy)phenyl)urea, 1-(3-t-butyl-1-(1,2,3,4-tetrahydroisoquinolin-6-yl)-1H-pyrazol-5-yl)-3-(3-(pyridin-3-yloxy)phenyl)urea, 1-(3-t-butyl-1-(1,2,3,4-tetrahydroisoquinolin-6-yl)-1H-pyrazol-5-yl)-3-(3-(5-chloropyridin-3-yloxy)phenyl)urea, 6-(3-t-butyl-5-(3-(3-(pyridin-3-yloxy)phenyl)ureido)-1H-pyrazol-1-yl)-1,2,3,4-tetrahydroisoquinoline-3-carboxylic acid, 1-(3-t-butyl-1-(3-carbamoyl-1,2,3,4-tetrahydroisoquinolin-6-yl)-1H-pyrazol-5-yl)-3-(3-(pyridin-3-yloxy)phenyl)urea, 1-(3-t-butyl-1-(3-(methylcarbamoyl)-1,2,3,4-tetrahydroisoquinolin-6-yl)-1H-pyrazol-5-yl)-3-(3-(pyridin-3-yloxy)phenyl)urea, 1-(3-t-butyl-1-(1-(methylcarbamoyl)-1,2,3,4-tetrahydroisoquinolin-6-yl)-1H-pyrazol-5-yl)-3-(3-(pyridin-3-yloxy)phenyl)urea, 1-(3-t-butyl-1-(2-oxo-1,2-dihydroquinolin-6-yl)-1H-pyrazol-5-yl)-3-(3-(pyridin-3-yloxy)phenyl)urea, 1-(3-t-butyl-1-(quinolin-6-yl)-1H-pyrazol-5-yl)-3-(3-(pyridin-3-yloxy)phenyl)urea, 1-(1-(1-

((2,3-dihydroxypropyl)carbamoyl)-1,2,3,4-tetrahydroisoquinolin-6-yl)-3-t-butyl-1H-pyrazol-5-yl)-3-(3-(pyridin-3-yloxy)phenyl)urea, 1-(3-cyclopentyl-1-(2-oxo-1,2-dihydroquinolin-6-yl)-1H-pyrazol-5-yl)-3-(3-(pyridin-3-yloxy) phenyl)urea, 1-(3-t-butyl-1-(1,2,3,4-tetrahydroisoquinolin-6-yl)-1H-pyrazol-5-yl)-3-(4-(2-(methylcarbamoyl)pyridin-4-yloxy)phenyl)urea, 1-(3-t-butyl-1-(2-oxo-1,2-dihydroquinolin-6-yl)-1H-pyrazol-5-yl)-3-(4-(2-(methylcarbamoyl)pyridin-4-yloxy)phenyl)urea, 1-(3-t-butyl-1-(2-(piperazin-1-yl)quinolin-6-yl)-1H-pyrazol-5-yl)-3-(4-(2-(methylcarbamoyl)pyridin-4-yloxy)phenyl)urea, 1-(1-(2-(2-aminoethylamino)quinolin-6-yl)-3-t-butyl-1H-pyrazol-5-yl)-3-(4-(2-(methylcarbamoyl)pyridin-4-yloxy) phenyl)urea, 1-(3-cyclopentyl-1-(2-oxo-1,2-dihydroquinolin-6-yl)-1H-pyrazol-5-yl)-3-(4-(2-(methylcarbamoyl) pyridin-4-yloxy)phenyl)urea, 1-(3-t-butyl-1-(2-(dimethylamino)quinolin-6-yl)-1H-pyrazol-5-yl)-3-(4-(2-(methylcarbamoyl)pyridin-4-yloxy)phenyl)urea, 1-(3-t-butyl-1-(2-((R)-3-(dimethylamino)pyrrolidin-1-yl)quinolin-6-yl)-1H-pyrazol-5-yl)-3-(4-(2-(methylcarbamoyl)pyridin-4-yloxy)phenyl)urea, 1-(1-(2-aminoquinolin-6-yl)-3-t-butyl-1H-pyrazol-5-yl)-3-(4-(2-(methylcarbamoyl)pyridin-4-yloxy)phenyl)urea, 1-(3-t-butyl-1-(2-(methylamino) quinolin-6-yl)-1H-pyrazol-5-yl)-3-(4-(2-(methylcarbamoyl) pyridin-4-yloxy)phenyl)urea, 1-(3-t-butyl-1-(2-oxo-1,2-dihydroquinolin-6-yl)-1H-pyrazol-5-yl)-3-(3-(2-(methylcarbamoyl)pyridin-4-yloxy)phenyl)urea, 1-(3-t-butyl-1-(1,2,3,4-tetrahydroisoquinolin-6-yl)-1H-pyrazol-5-yl)-3-(4-(1-oxoisoindolin-4-yl)phenyl)urea, 1-(3-t-butyl-1-(indolin-5-yl)-1H-pyrazol-5-yl)-3-(4-(1-oxoisoindolin-4-yl) phenyl)urea, 1-(3-t-butyl-1-(1-(methylsulfonyl)indolin-5-yl)-1H-pyrazol-5-yl)-3-(4-(1-oxoisoindolin-4-yl)phenyl) urea, 6-(3-t-butyl-5-(3-(4-(1-oxoisoindolin-4-yl)phenyl) ureido)-1H-pyrazol-1-yl)-1,2,3,4-tetrahydroisoquinoline-3-carboxylic acid, 6-(3-t-butyl-5-(3-(4-(1-oxoisoindolin-4-yl) phenyl)ureido)-1H-pyrazol-1-yl)-1,2,3,4-tetrahydroisoquinoline-3-carboxylic acid, 2.1.7 Methods 2.1.7a Methods of Protein Modulation The invention includes methods of modulating kinase activity of a variety of kinases, e.g. receptor tyrosine kinases including VEGFR1, VEGFR2, FLT-1, FLT-3, PDGFRa, PDGFRb, FGFR1, FGFR2, FGFR3, FGFR4, TrkA, TrkB, EGFR, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, EPHB7, EPHB8. The kinases may be wildtype kinases, oncogenic forms thereof, aberrant fusion proteins thereof or polymorphs of any of the foregoing. The method comprises the step of contacting the kinase species with compounds of the invention and especially those set forth in sections 2.1 and 2.1.6a. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, kinase cellular localization, and recruitment of other proteins into signaling complexes through modulation of kinase conformation.

2.1.7b Treatment Methods

The methods of the invention also include treating individuals suffering from a condition selected from the group consisting of cancer, secondary cancer growth arising from metastasis, hyperproliferative diseases, and diseases characterized by hyper-vascularization. These methods comprise administering to such individuals compounds of the invention, and especially those of section 2.1 and 2.1.6a. Exemplary conditions include glioblastomas, ovarian cancer, pancreatic cancer, prostate cancer, lung cancers, breast cancers, kidney cancers, cervical carcinomas, metastasis of primary solid tumor secondary sites, ocular diseases characterized by hyperproliferation leading to blindness including various retinopathies including diabetic retinopathy and age-related macular degeneration, or rheumatoid arthritis characterized by the in-growth of a vascularized pannus. The administration method is not critical, and may be from the group consisting of oral, parenteral, inhalation, and subcutaneous.

2.1.8 Pharmaceutical Preparations

The compounds of the invention, especially those of 2.1 and 2.1.6a may form a part of a pharmaceutical composition by combining one or more such compounds with a pharmaceutically acceptable carrier. Additionally, the compositions may include an additive selected from the group consisting of adjuvants, excipients, diluents, and stablilizers.

2.1.9 Kinase/Compound Adducts

The invention also provides adducts in the form of compounds of the invention bound with a species of kinase such as a wild-type kinase, oncogenic forms thereof, aberrant fusion proteins thereof and polymorphs of any of the foregoing. The compounds are advantageously selected from the groups defined in sections 2.1 and 2.1.6a.

2.2 Generally—Monocyclic A2 Compounds with Polycyclic E2 Rings

The invention includes compounds of the formula I as defined in section 1.2 wherein each R2 is selected from the group consisting of monocyclic heteroaryl, C1-C6alkyl, branched C3-C7alkyl, and R19 substituted C3-C8carbocyclyl wherein R19 is H, or C1-C6alkyl, C1-C6fluoroalkyl wherein the alkyl group is partially or fully fluorinated, phenyl wherein the phenyl group is optionally substituted by one or more fluorine substituents;

each Z1 is a substituent attached to a ring carbon and is independently and individually selected from the group consisting of hydroxyC1-C6alkyl, C2-C6alkoxy, C1-C6alkoxyC1-C6alkyl, (R4)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—C(=O)—, (R4)$_2$N—C(—O)—, (R4)$_2$N—CO—C1-C6alkyl, C1-C6alkoxycarbonyl, carboxyC1-C6alkyl, C1-C6alkoxycarbonylC1-C6alkyl, (R3)$_2$NSO$_2$, SOR3, (R4)$_2$NSO$_2$, —SO$_2$R3', —SOR4, —C(=O)R6, —C(=NOH)R6, —C(=NOR3)R6, —(CH$_2$)$_n$N(R4)C(O)R8, monocyclic heteroaryl, monocyclic heterocyclyl, monocyclic heteroarylC1-C6alkyl, monocyclic heterocyclylC1-C6alkyl, monocyclic heteroaryloxy, monocyclic heterocyclyloxy, monocyclic heteroaryloxyC1-C6alkyl, monocyclic heterocyclyloxyC1-C6alkyl, arylamino, monocyclic heteroarylamino, monocyclic heterocyclylamino, arylaminoC1-C6alkyl, monocyclic heteroarylaminoC1-C6alkyl, monocyclic heterocyclylaminoC1-C6alkyl, or moieties of the formulae

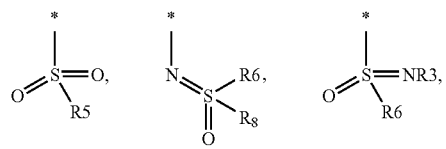

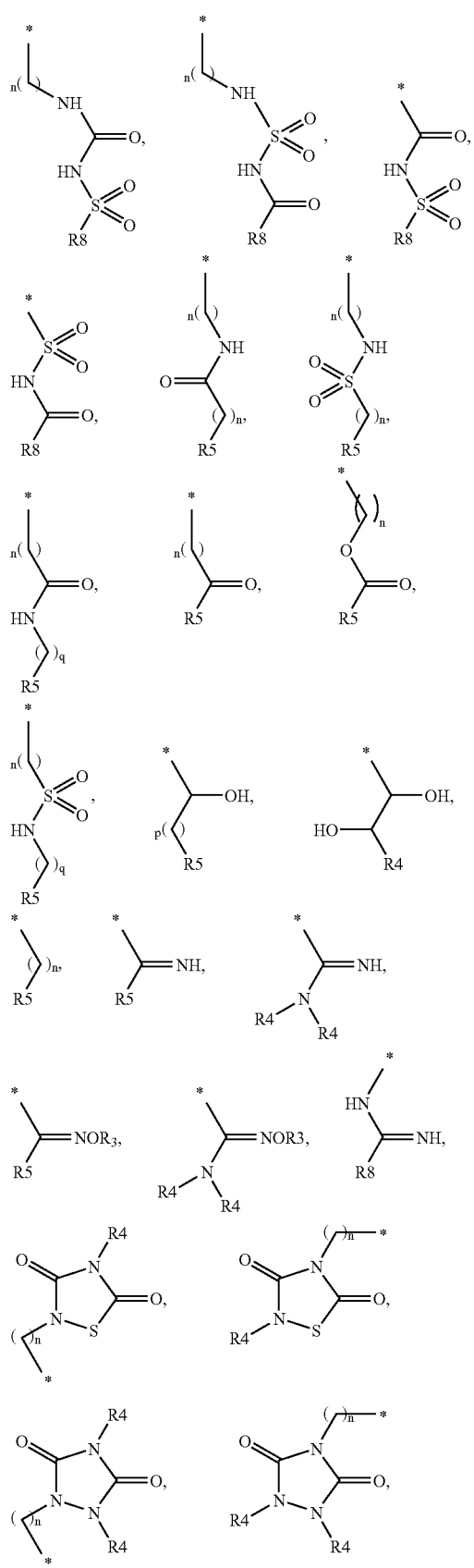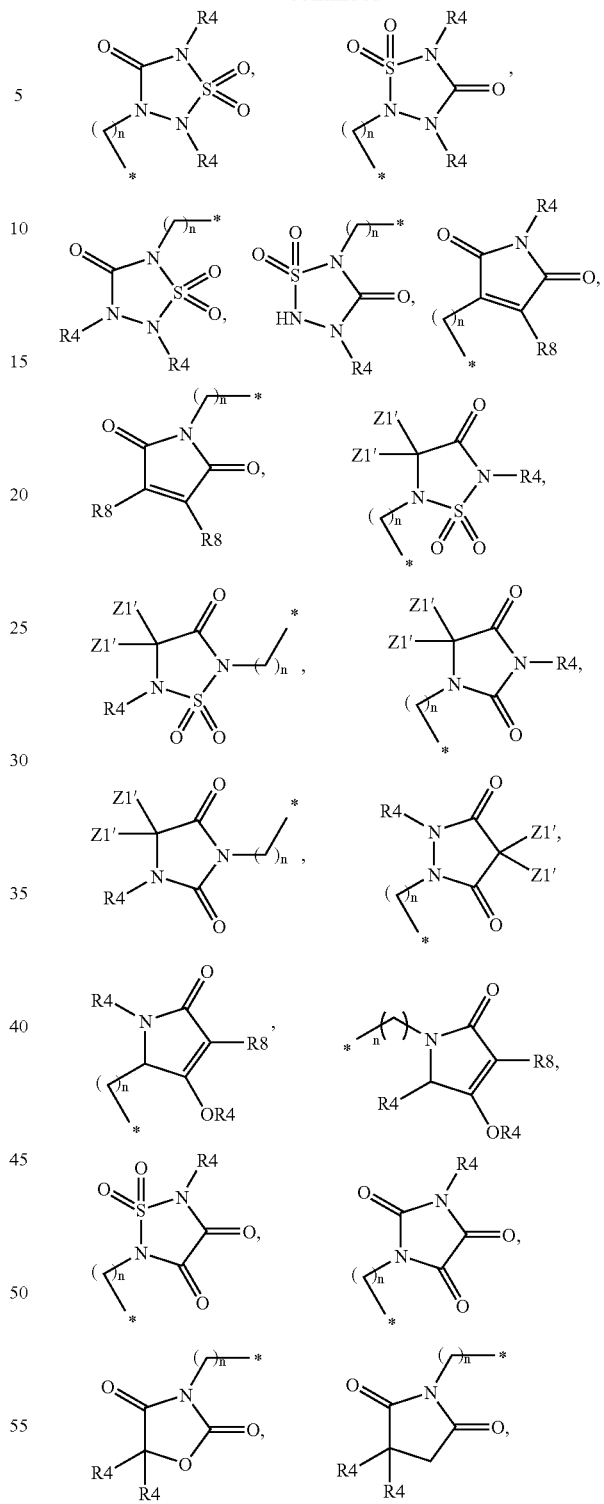
cyano wherein the site of attachment to the A2 ring is meta to the point of attachment to the A1 ring and wherein A2 is phenyl, and cyano wherein the site of attachment is to a substitutable position when A2 is pyridyl, pyrimidinyl or a five-membered ring;
wherein the asterisk (*) indicates the point of attachment of the Z1 moiety to the A2 ring;

in the event that Z1 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z1 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z1 may cyclize to form a C3-C7 heterocyclyl ring;

wherein Z1' is independently and individually selected from the group consisting of H, C1-C6alkyl, C3-C7cycloalkyl, hydroxyC1-C6alkyl, C1-C6alkoxyC1-C6alkyl, (R4)$_2$N—C1-C6alkyl, (R4)$_2$N—C2-C6alkylN(R4)-(CH$_2$)$_p$, (R4)$_2$N—C2-C6alkylO-(CH$_2$)$_p$, (R4)$_2$N—CO—C1-C6alkyl, carboxyC1-C6alkyl, C1-C6alkoxycarbonylC1-C6alkyl, —(CH$_2$)$_p$N(R4)C(O)R8, aryl, arylC1-C6alkyl, heteroaryl, heteroarylC1-C6alkyl, heterocyclyl, heterocyclylC1-C6alkyl, aryloxyC1-C6alkyl, heteroaryloxyC1-C6alkyl, heterocyclyloxyC1-C6alkyl, arylaminoC1-C6alkyl, heteroarylaminoC1-C6alkyl, or heterocyclylaminoC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom of Z1' may cyclize to form a C3-C7 heterocyclyl ring;

each Z4' is a substituent attached to a ring nitrogen and is independently and individually selected from the group consisting of hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C2-C6alkyl, carboxyC2-C6alkyl, C1-C6alkoxycarbonylC2-C6alkyl, —C2-C6alkylN(R4)C(O)R8, R8-C(=NR3)-, —SO$_2$R8, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

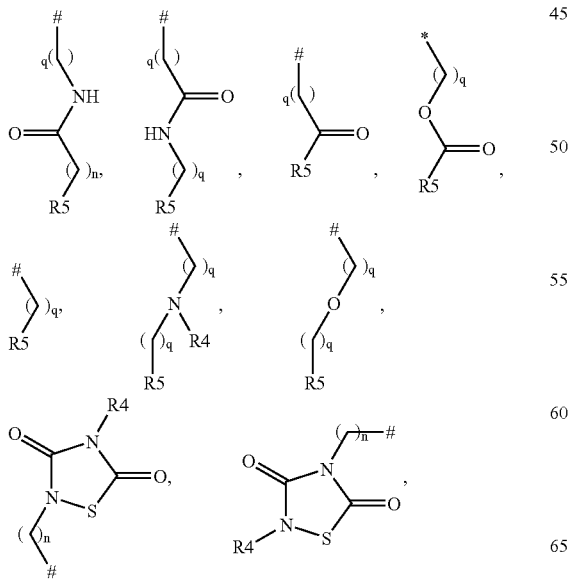

-continued

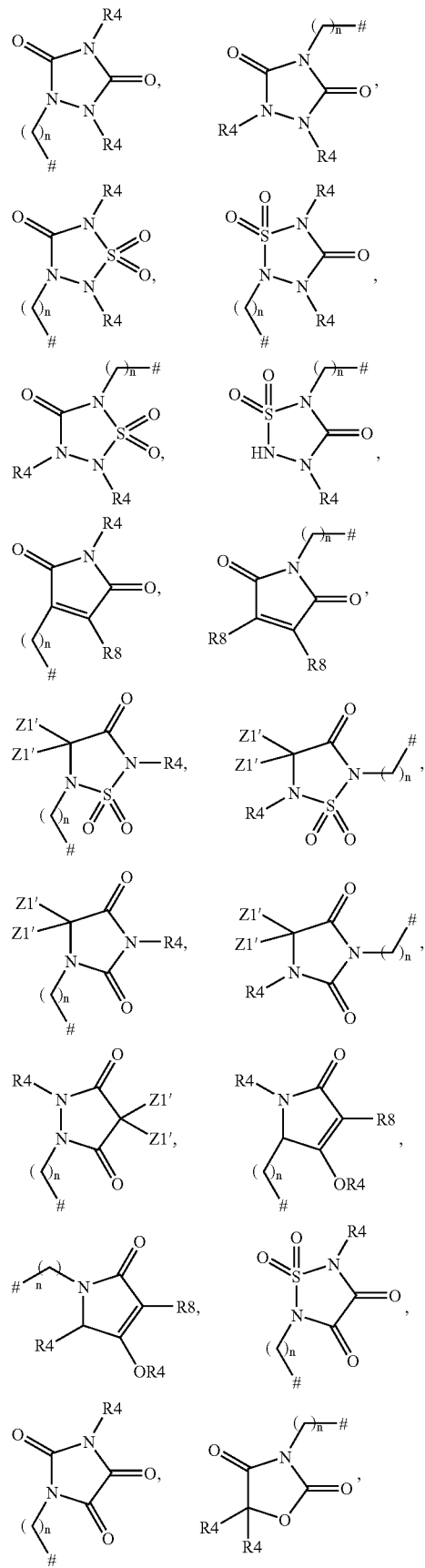

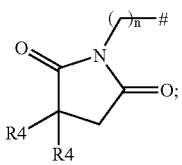

wherein the symbol (4) indicates the point of attachment of the Z4' moiety to the A1 ring of formula I;
in the event that Z4' contains an alkyl or alkylene moiety, such moieties may be further substituted with one or more C1-C6alkyls;
wherein two R3 moieties are independently and individually taken from the group consisting of C1-C6alkyl and branched C3-C6alkyl and are attached to the same nitrogen heteroatom of Z4' may cyclize to form a C3-C7 heterocyclyl ring;
wherein two R4 moieties independently and individually taken from the group consisting of C1-C6alkyl, branched C3-C6alkyl, hydroxyalkyl, and alkoxyalkyl and are attached to the same nitrogen heteroatom of Z4' may cyclize to form a C3-C7 heterocyclyl ring;

2.2.1 Preferred D Moieties 2.2.1a
Preferably, the compounds of formula I in 2.2 contain D moieties wherein E1 and E2 are as defined in section 1.2.1

2.2.1b
Additionally preferred D moieties of formula I in 2.2 are as defined in section 1.2.1b 2.2.1c
More preferred D moieties of 2.2.1b are wherein E2 is defined as in section 1.2.1c 2.2.2 Preferred A2 Moieties 2.2.2a
Compounds of Formula I as defined above in section 2.2 have preferred A2 moieties as defined in section 1.2.2a;
wherein two R4 moieties independently and individually taken from the group consisting of C1-C6alkyl, branched C3-C6alkyl, hydroxyalkyl, and alkoxyalkyl and are attached to the same nitrogen heteroatom of Z1' may cyclize to form a C3-C7 heterocyclyl ring;
each Z4 is a substituent attached to a ring nitrogen and is independently and individually selected from the group consisting of H, C1-C6alkyl, hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C2-C6alkyl, carboxyC2-C6alkyl, C1-C6alkoxycarbonylC2-C6alkyl, —C2-C6alkylN(R4)C(O)R8, R8-C(=NR3)-, —SO$_2$R8, —COR8, heteroaryl, heteroarylC1-C6alkyl, heterocyclyl, heterocyclylC1-C6alkyl, heteroaryloxyC2-C6alkyl, heterocycly-loxyC2-C6alkyl, arylaminoC2-C6alkyl, heteroarylaminoC2-C6alkyl, heterocyclylaminoC2-C6alkyl, and moieties of the formulae

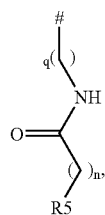 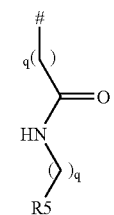 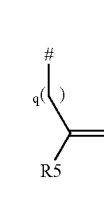 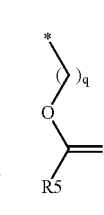

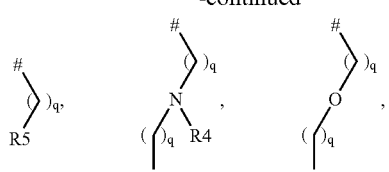

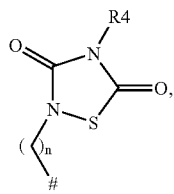 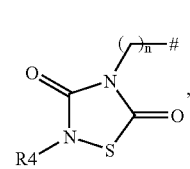

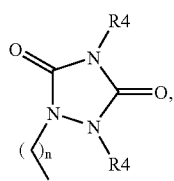 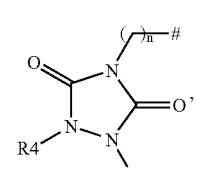

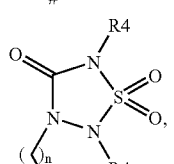 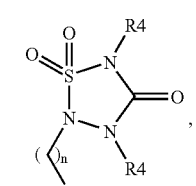

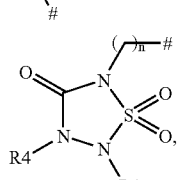 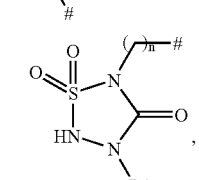

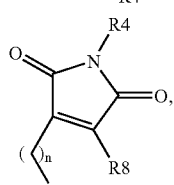 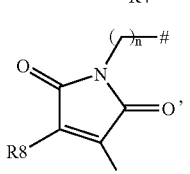

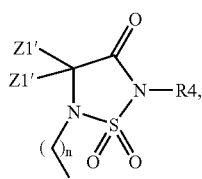 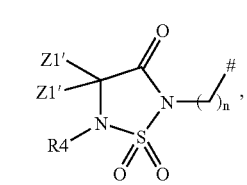

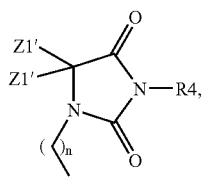 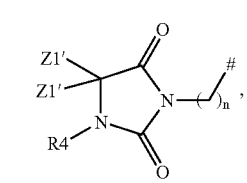

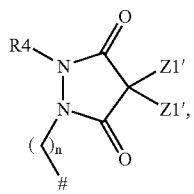 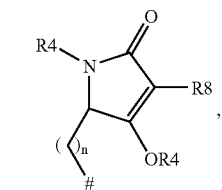

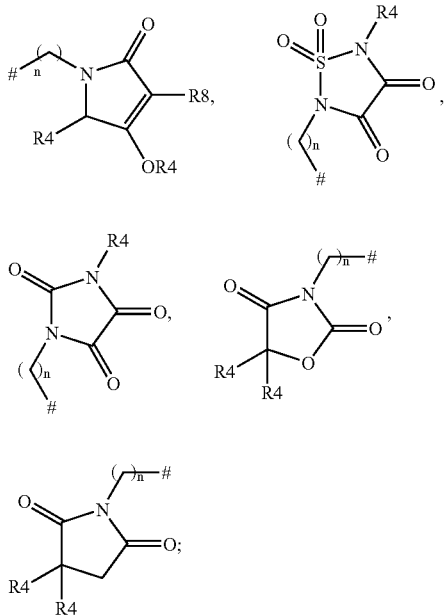

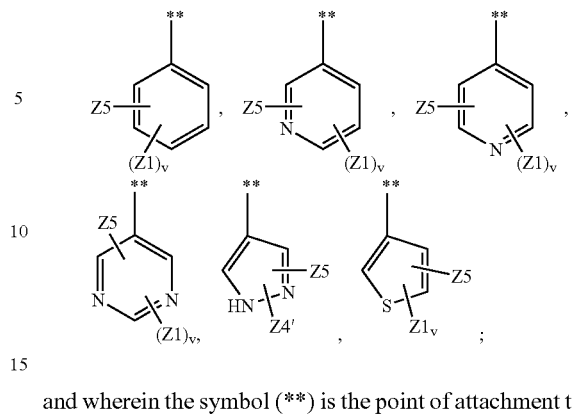

and wherein the symbol (**) is the point of attachment to the A1 ring for formula I.

2.2.2c

Even more preferred A2 moieties are selected from the group consisting of

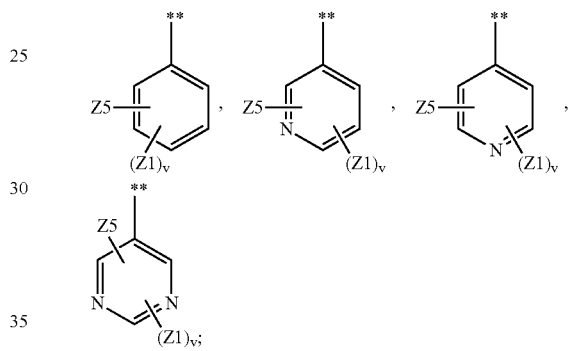

and wherein the symbol (**) is the point of attachment to the A1 ring of formula I.

2.2.3 Preferred Classes of Compounds 2.2.3a

Compounds as defined in 2.2.1a wherein the A2 group is defined in 2.2.2a.

2.2.3b

Compounds as defined in 2.2.3a wherein the A2 group is defined in 2.2.2b.

2.2.3c

Compounds as defined in 2.2.3a wherein the A2 group is defined in 2.2.2c.

2.2.3d

Compounds as defined in 2.2.1b wherein the A2 group is defined in 2.2.2a.

2.2.3e

Compounds as defined in 2.2.3c wherein the A2 group is defined in 2.2.2b.

2.2.3f

Compounds as defined in 2.2.3c wherein the A2 group is defined in 2.2.2c.

2.2.4 Preferred A1 Moieties 2.2.4a

These preferred A1 moieties are defined in 2.1.4a.

2.2.4b

These more preferred A1 moieties are defined in 2.1.4b.

2.2.4c

These even more preferred A1 moieties are defined in 2.1.4c.

wherein the symbol (#) indicates the point of attachment of the Z4 moiety to the A2 ring for formula I;

in the event that Z4 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z4 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z4 may cyclize to form a C3-C7 heterocyclyl ring;

Z5 is independently and individually selected from the group consisting of H, C1-C6alkyl, branched C3-C7alkyl, halogen, fluoroalkyl, cyano, hydroxyl, alkoxy, oxo, aminocarbonyl, carbonylamino, aminosulfonyl, sulfonylamino, —N(R3)$_2$, —O—(CH$_2$)q-N(R4)$_2$, —N(R3)-(CH$_2$)q-N(R4)$_2$, —R5, —O—(CH$_2$)q-O-Alkyl, —O—(CH$_2$)q-N(R4)$_2$, —N(R3)-(CH$_2$)q-O-Alkyl, —N(R3)-(CH$_2$)q-N(R4)$_2$, —O—(CH$_2$)q-R5, and —N(R3)-(CH$_2$)q-R5;

wherein two R3 moieties are independently and individually taken from the group consisting of C1-C6alkyl and branched C3-C6alkyl and are attached to the same nitrogen heteroatom of Z5 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z5 may cyclize to form a C3-C7 heterocyclyl ring;

and n is 0-4; p is 1-4; q is 2-6; r is 0 or 1; v is 1 or 2.

2.2.2b

More preferred A2 moieties are selected from the group consisting of

2.2.5 Preferred W and Y Moieties

2.2.5a
(1) W and Y are each NH, and X=O; (2) W=NH, Y=CHR4 and X=O; or (3) W=CHR4, Y=NH, and X=O.

2.2.5b
W and Y are each NH and X=O.

2.2.6 Further Preferred Compounds

2.2.6a
Further preferred compounds are of the formula

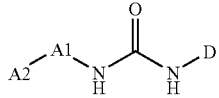
I wherein A2 is selected from the group consisting of

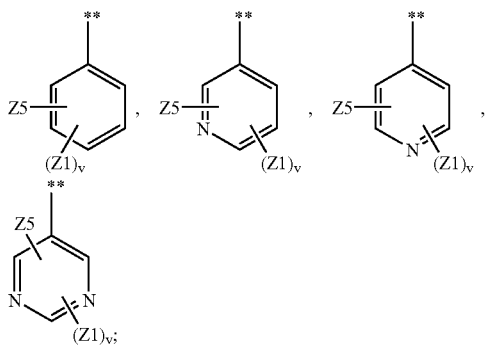

wherein the symbol (**) denotes the attachment to the A1 moiety of formula I;
A1 is selected from the group consisting of

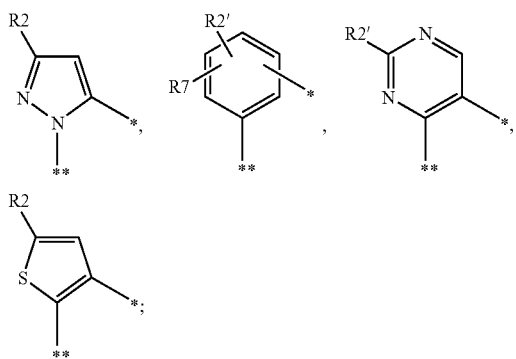

wherein the symbol (*) denotes the attachment to the W moiety of formula I and the symbol (**) denotes the attachment to the A2 moiety of formula I;
X is O, S, or NR3;
D comprises a member of

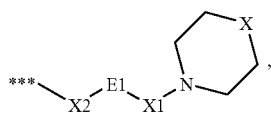

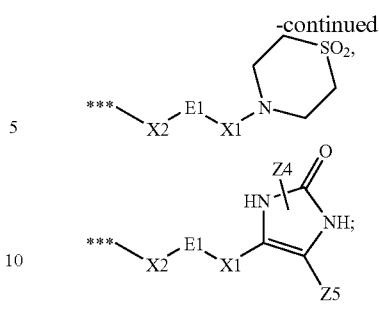

wherein E1 is selected from the group consisting cyclopropyl, cyclobutyl, cyclopentyl, cyclohexyl, pyrrolidinyl piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl and naphthyl;
wherein the symbol (***) denotes the attachment to the Y moiety of formula I;
X1 is selected from the group consisting of O, S, NR3, —C(=O)—, —O—(CH$_2$)n-, —S—(CH$_2$)n-, —NR3-(CH$_2$)n-, —O—(CH$_2$)q-O—, —O—(CH$_2$)q-NR3-, —N(R3)-(CH$_2$)q-N(R3)-, —(CH$_2$)n-N(R4)-C(=O)—, —(CH$_2$)n-N(R4)-C(=O)(CH$_2$)n-, —(CH$_2$)n-N(R4)-, —(CH$_2$)p-, —(CH$_2$)n-CO—N(R4)-, —(CH$_2$)p-, C2-C5alkenyl, C2-C5alkynyl, C3-C6cycloalkyl, and a direct bond wherein the E1 ring and the E2 ring are directly linked by a covalent bond;
and wherein the carbon atoms of —(CH2)n-, —(CH2)q-, (CH2)p, C2-C5alkenyl, and C2-C5alkynyl moieties of X1 may be further substituted by one or more C1-C6alkyl;
X2 is selected from the group consisting of C1-C6 alkyl, C3-C6 branched alkyl, or a direct bond wherein E1 is directly linked to the Y group of formula I;
each R2 is selected from the group consisting of C1-C6alkyl, branched C3-C7alkyl, and R19 substituted C3-C8carbocyclyl wherein R19 is H, or C1-C6alkyl, C1-C6fluoroalkyl wherein the alkyl group is partially or fully fluorinated, phenyl wherein the phenyl group is optionally substituted by one or more fluorine substituents, or monocyclic heteroaryl;
each R2' is selected from the group consisting of halogen and R2;
each R3 is independently and individually selected from the group consisting of H, C1-C6alkyl, branched C3-C7alkyl, C3-C7carbocyclyl, or phenyl;
wherein two R3 moieties independently and individually taken from the group consisting of C1-C6alkyl and branched C3-C7alkyl are attached to the same nitrogen heteroatom, the two R3 moieties may cyclize to form a C3-C7 heterocyclyl ring;
each R4 is selected from the group consisting of H, C1-C6alkyl, hydroxyC1-C6 alkyl, dihydroxyC1-C6alkyl, C1-C6alkoxyC1-C6alkyl, branched C3-C7alkyl, branched hydroxyC1-C6 alkyl, branched C1-C6alkoxyC1-C6alkyl, branched dihydroxyC1-C6alkyl, carbocyclyl, hydroxyl substituted carbocyclyl, alkoxy substituted carbocyclyl, dihydroxy substituted carbocyclyl, phenyl, heteroaryl, heterocyclyl, phenylC1-C6alkyl, heteroarylC1-C6alkyl, and heterocyclylC1-C6alkyl;
wherein two R4 moieties independently and individually taken from the group consisting of C1-C6alkyl, branched C3-C6alkyl, hydroxyalkyl, and alkoxyalkyl and are attached to the same nitrogen heteroatom may cyclize to form a C3-C7 heterocyclyl ring;
each R5 is independently and individually selected from the group consisting of

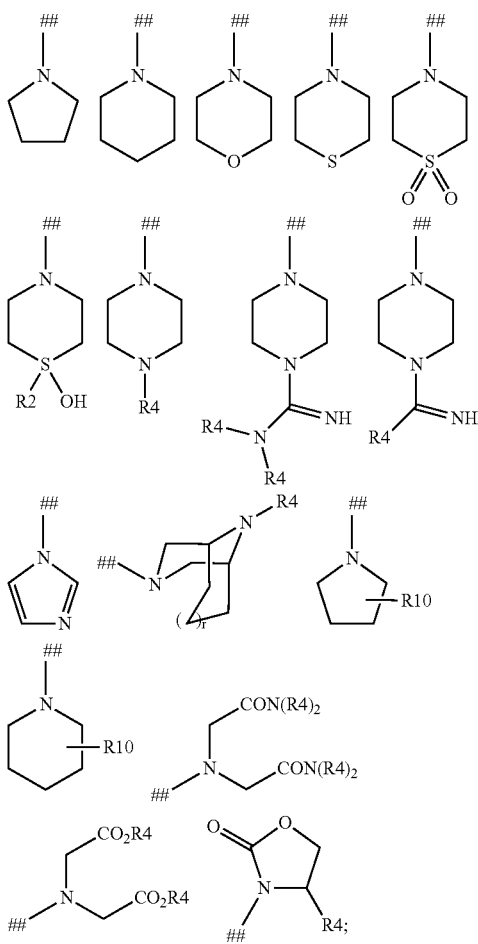

and wherein the symbol (##) is the point of attachment to respective R8, R10, Z1, Z4, Z5, Z6 or A2 ring moieties containing a R5 moiety;

wherein two R4 moieties independently and individually taken from the group consisting of C1-C6alkyl, branched C3-C6alkyl, hydroxyalkyl, and alkoxyalkyl and are attached to the same nitrogen heteroatom of R5 may cyclize to form a C3-C7 heterocyclyl ring;

wherein each R6 is independently and individually selected from the group consisting of C1-C6alkyl, branched C3-C7alkyl, carbocyclyl, phenyl, heteroaryl, and heterocyclyl;

each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

each R8 is independently and individually selected from the group consisting of C1-C6alkyl, C1-C6 fluoroalkyl wherein the alkyl moiety is partially or fully fluorinated, branchedC4-C7alkyl, carbocyclyl, phenyl, C1-C6phenylalkyl, heteroaryl or heteroarylC1-C6alkyl, heterocyclyl, heterocyclylC1-C6alkyl, OH, C1-C6alkoxy, N(R3)$_2$, N(R4)$_2$, or R5;

wherein two R3 moieties are independently and individually taken from the group consisting of C1-C6alkyl and branched C3-C6alkyl and are attached to the same nitrogen heteroatom of R8 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of R8 may cyclize to form a C3-C7 heterocyclyl ring;

each R10 is independently and individually selected from the group consisting of CO$_2$H, CO$_2$C1-C6alkyl, CO—N(R4)$_2$, OH, C1-C6alkoxy, —N(R4)$_2$;

wherein two R4 moieties independently and individually taken from the group consisting of C1-C6alkyl, branched C3-C6alkyl, hydroxyalkyl, and alkoxyalkyl and are attached to the same nitrogen heteroatom of R10 may cyclize to form a C3-C7 heterocyclyl ring;

each Z1 is a substituent attached to a ring carbon and is independently and individually selected from the group consisting of hydroxyC1-C6alkyl, C2-C6alkoxy, C1-C6alkoxyC1-C6alkyl, (R4)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—C(=O)—, (R4)$_2$N—C(=O)—, (R4)$_2$N—CO—C1-C6alkyl, C1-C6alkoxycarbonyl, carboxyC1-C6alkyl, C1-C6alkoxycarbonylC1-C6alkyl, (R3)$_2$NSO$_2$, SOR3, (R4)$_2$NSO$_2$, —SO$_2$R3', —SOR4, —C(=O)R6, —C(=NOH)R6, —C(=NOR3)R6, —(CH$_2$)$_n$N(R4)C(O)R8, monocyclic heteroaryl, monocyclic heterocyclyl, monocyclic heteroarylC1-C6alkyl, monocyclic heterocyclylC1-C6alkyl, monocyclic heteroaryloxy, monocyclic heterocyclyloxy, monocyclic heteroaryloxyC1-C6alkyl, monocyclic heterocyclyloxyC1-C6alkyl, arylamino, monocyclic heteroarylamino, monocyclic heterocyclylamino, arylaminoC1-C6alkyl, monocyclic heteroarylaminoC1-C6alkyl, monocyclic heterocyclylaminoC1-C6alkyl, or moieties of the formulae

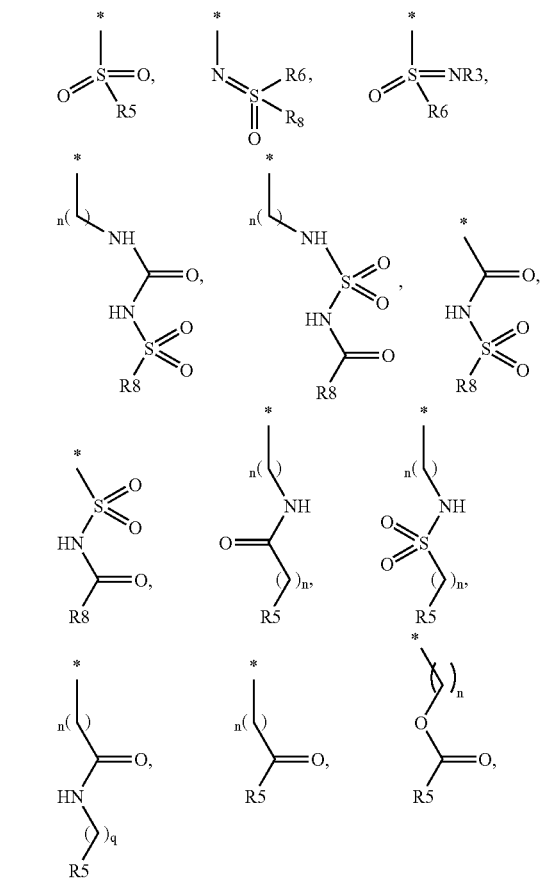

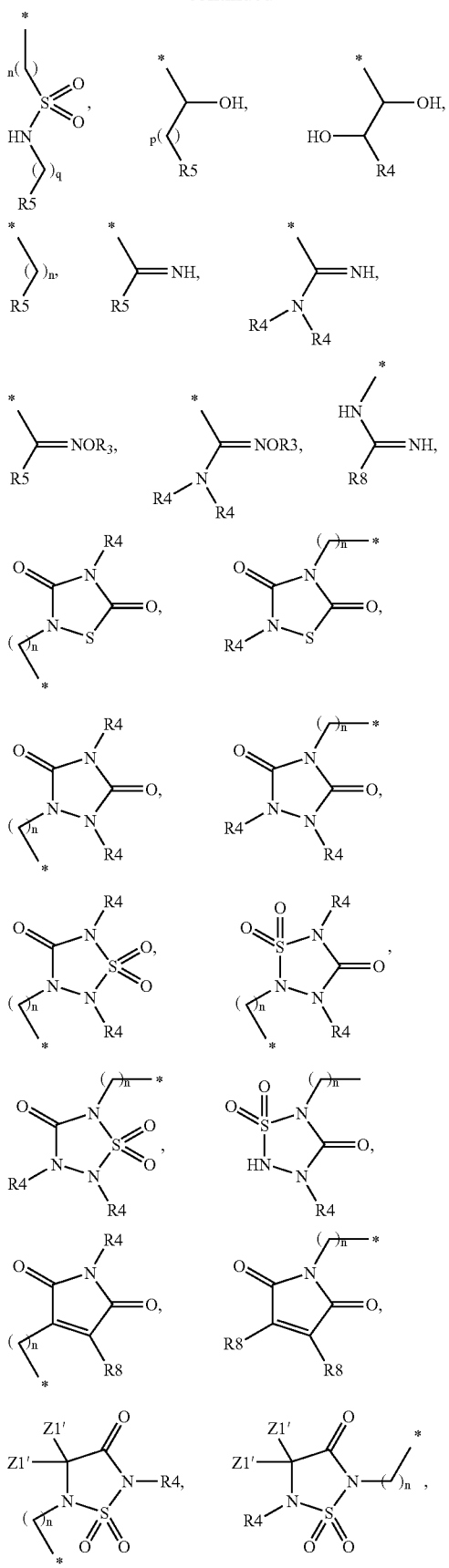
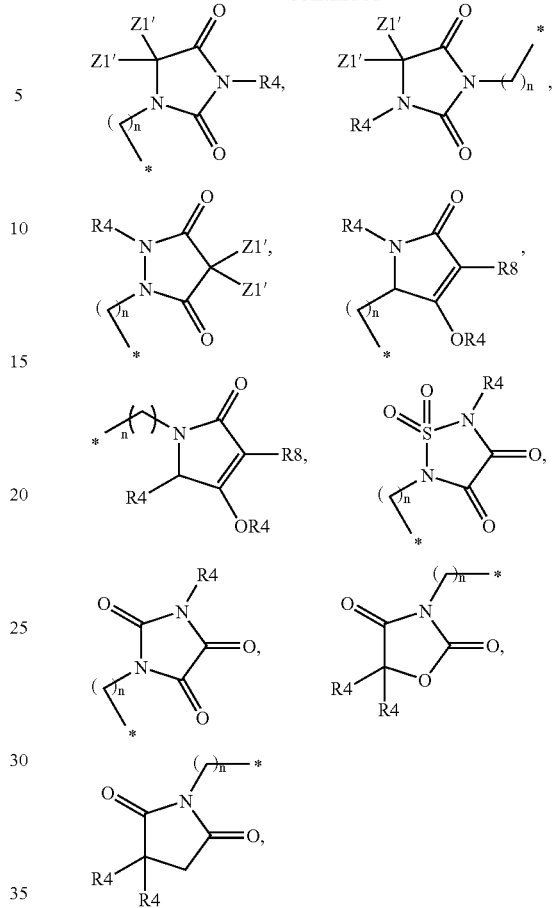

cyano wherein the site of attachment to the A2 ring is meta to the point of attachment to the A1 ring and wherein A2 is phenyl, and cyano wherein the site of attachment is to a substitutable position when A2 is pyridyl, pyrimidinyl or a five-membered ring;

In the foregoing definition of Z1, alkyl moieties may optionally be substituted by one or more C1-C6alkyl;

Wherein the asterisk (*) indicates the point of attachment of the Z1 moiety to the A2 ring;

in the event that Z1 contains an alkyl or alkylene moiety, such moieties may be further substituted with one or more C1-C6alkyls;

In the foregoing definition of Z1, alkyl moieties may optionally be substituted by one or more C1-C6alkyl;

Wherein the asterisk (*) indicates the point of attachment of the Z1 moiety to the A2 ring;

in the event that Z1 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z1 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z1 may cyclize to form a C3-C7 heterocyclyl ring;

wherein Z1' is independently and individually selected from the group consisting of H, C1-C6alkyl, C3-C7cycloalkyl, hydroxyC1-C6alkyl, C1-C6alkoxyC1-C6alkyl, (R4)$_2$N—C1-C6alkyl, (R4)$_2$N—C2-C6alkylN(R4)-(CH$_2$)$_p$, (R4)$_2$N—C2-C6alkylO-(CH$_2$)$_p$, (R4)$_2$N—CO—C1-C6alkyl, carboxyC1-C6alkyl, C1-C6alkoxycarbonylC1-C6alkyl, —(CH$_2$)$_p$N(R4)C(O)R8, aryl, arylC1-C6alkyl, heteroaryl, heteroarylC1-C6alkyl, heterocyclyl, heterocyclylC1-C6alkyl, aryloxyC1-C6alkyl, heteroaryloxyC1-C6alkyl, heterocyclyloxyC1-C6alkyl, arylaminoC1-C6alkyl, heteroarylaminoC1-C6alkyl, or heterocyclylaminoC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom of Z1' may cyclize to form a C3-C7 heterocyclyl ring;

each Z4 is a substituent attached to a ring nitrogen and is independently and individually selected from the group consisting of H, C1-C6alkyl, hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O-C2-C6alkyl, (R4)$_2$N—CO—C2-C6alkyl, carboxyC2-C6alkyl, C1-C6alkoxycarbonylC2-C6alkyl, —C2-C6alkylN(R4)C(O)R8, R8-C(=NR3)-, —SO$_2$R8, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

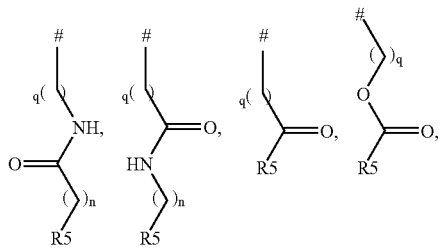
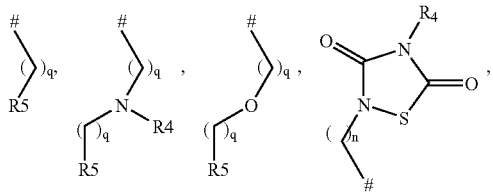
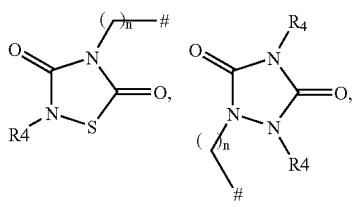
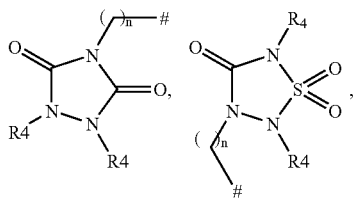

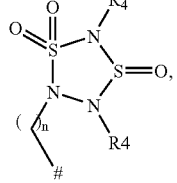
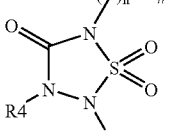
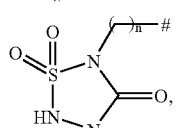
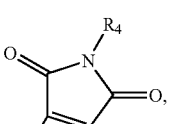
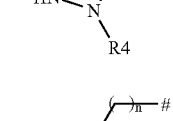
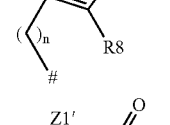
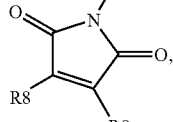
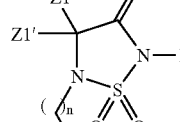
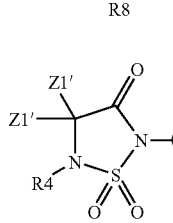
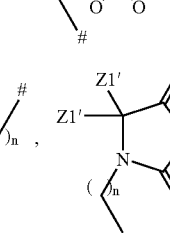
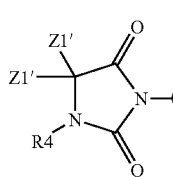
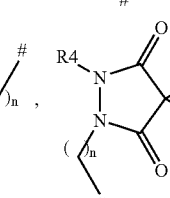
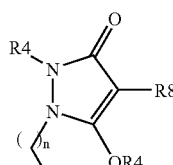
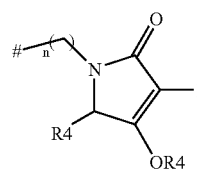
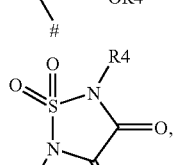
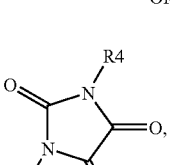
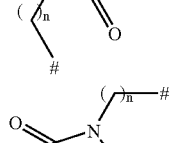
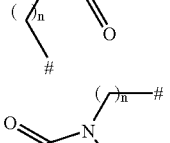

wherein the symbol (#) indicates the point of attachment of the Z4 moiety to the A2 ring for formula I;

in the event that Z4 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z4 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z4 may cyclize to form a C3-C7 heterocyclyl ring;

Z5 is independently and individually selected from the group consisting of H, C1-C6alkyl, branched C3-C7alkyl, halogen, fluoroalkyl, cyano, hydroxyl, alkoxy, oxo, aminocarbonyl, carbonylamino, aminosulfonyl, sulfonylamino, —N(R3)$_2$, —O—(CH$_2$)q-N(R4)$_2$, —N(R3)-(CH$_2$)q-N(R4)$_2$, —R5, —O—(CH$_2$)q-O-Alkyl, —O—(CH$_2$)q-N(R4)$_2$, —N(R3)-(CH$_2$)q-O-Alkyl, —N(R3)-(CH$_2$)q-N(R4)$_2$, —O—(CH$_2$)q-R5, and —N(R3)-(CH$_2$)q-R5;

wherein two R3 moieties are independently and individually taken from the group consisting of C1-C6alkyl and branched C3-C6alkyl and are attached to the same nitrogen heteroatom of Z5 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z5 may cyclize to form a C3-C7 heterocyclyl ring;

Each Z6 is independently and individually selected from the group consisting of H, C1-C6alkyl, branched C3-C7alkyl, hydroxyl, C1-C6alkoxy, (R3)$_2$N—, —N(R3)COR8, (R4)$_2$N—, —R5, —N(R4)COR8, —N(R3)SO$_2$R6-, —CON (R3)$_2$, —CON(R4)$_2$, —COR5, —SO$_2$NHR4, heteroaryl, heterocyclyl, heteroaryloxy, heterocyclyloxy, arylamino, heteroarylamino, and heterocyclylamino;

wherein two R3 moieties are independently and individually taken from the group consisting of C1-C6alkyl and branched C3-C6alkyl and are attached to the same nitrogen heteroatom of Z6 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z6 may cyclize to form a C3-C7 heterocyclyl ring;

and n is 0-4; p is 1-4; q is 2-6; r is 0 or 1; v is 1 or 2;

and tautomers, diastereomers, geometric isomers, enantiomers, hydrates, prodrugs and salts of any of the foregoing.

2.2.6b

The following specific compounds of Formula I are more preferred: 1-(1-(3-(1H-pyrazol-4-yl)phenyl)-3-t-butyl-1H-pyrazol-5-yl)-3-(4-(6-(thiazol-4-yl)pyrimidin-4-yloxy)phenyl)urea, 1-(2-(3-(2-amino-2-oxoethyl)phenyl)-5-t-butylthiophen-3-yl)-3-(4-(4-(pyridin-3-yl)pyrimidin-2-yloxy)phenyl)urea, 1-(1-(3-(2-amino-2-oxoethyl)phenyl)-3-t-butyl-1H-pyrazol-5-yl)-3-(4-(4-(isoxazol-4-yl)pyrimidin-2-yl)phenyl)urea, 1-(1-(3-(2-amino-2-oxoethyl)phenyl)-3-t-butyl-1H-pyrazol-5-yl)-3-(3-(4-(pyridin-3-yl)pyrimidin-2-yloxy)phenyl)urea, 1-(1-(3-(1H-pyrazol-4-yl)phenyl)-3-t-butyl-1H-pyrazol-5-yl)-3-(4-(4-(pyridin-3-yl)pyrimidin-2-yloxy)phenyl)urea 2.2.7 Methods 2.2.7a Methods of Protein Modulation The invention includes methods of modulating kinase activity of a variety of kinases, e.g. receptor tyrosine kinases including VEGFR1, VEGFR2, FLT-1, FLT-3, PDGFRa, PDGFRb, FGFR1, FGFR2, FGFR3, FGFR4, TrkA, TrkB, EGFR, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, EPHB7, EPHB8. The kinases may be wildtype kinases, oncogenic forms thereof, aberrant fusion proteins thereof or polymorphs of any of the foregoing. The method comprises the step of contacting the kinase species with compounds of the invention and especially those set forth in sections 2.2 and 2.2.6a. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, kinase cellular localization, and recruitment of other proteins into signaling complexes through modulation of kinase conformation.

2.2.7b Treatment Methods

The methods of the invention also include treating individuals suffering from a condition selected from the group consisting of cancer, secondary cancer growth arising from metastasis, hyperproliferative diseases, and diseases characterized by hyper-vascularization. These methods comprise administering to such individuals compounds of the invention, and especially those of section 2.2 and 2.2.6a. Exemplary conditions include glioblastomas, ovarian cancer, pancreatic cancer, prostate cancer, lung cancers, breast cancers, kidney cancers, cervical carcinomas, metastasis of primary solid tumor secondary sites, ocular diseases characterized by hyperproliferation leading to blindness including various retinopathies including diabetic retinopathy and age-related macular degeneration, or rheumatoid arthritis characterized by the in-growth of a vascularized pannus. The administration method is not critical, and may be from the group consisting of oral, parenteral, inhalation, and subcutaneous.

2.2.8 Pharmaceutical Preparations

The compounds of the invention, especially those of 2.2 and 2.2.6a may form a part of a pharmaceutical composition by combining one or more such compounds with a pharmaceutically acceptable carrier. Additionally, the compositions may include an additive selected from the group consisting of adjuvants, excipients, diluents, and stablilizers.

2.2.9 Kinase/Compound Adducts

The invention also provides adducts in the form of compounds of the invention bound with a species of kinase such as a wild-type kinase, oncogenic forms thereof, aberrant fusion proteins thereof and polymorphs of any of the foregoing. The compounds are advantageously selected from the groups defined in sections 2.2 and 2.2.6a.

2.3 Generally—Monocyclic A2 Compounds with Monocyclic E2 Rings

The invention includes compounds of the formula I as defined in section 1.3 wherein each R2 is selected from the group consisting of C1-C6alkyl, branched C3-C7alkyl, and R19 substituted C3-C8carbocyclyl wherein R19 is H, or C1-C6alkyl, C1-C6fluoroalkyl wherein the alkyl group is partially or fully fluorinated, phenyl wherein the phenyl group is optionally substituted by one or more fluorine substituents, or monocyclic heteroaryl;

wherein each Z1 is a substituent attached to a ring carbon and is independently and individually selected from the group consisting of hydroxyC1-C6alkyl, C2-C6alkoxy, C1-C6alkoxyC1-C6alkyl, (R4)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—C(=O)—, (R4)$_2$N—C(=O)—, (R4)$_2$N—CO—C1-C6alkyl, C1-C6alkoxycarbonyl, carboxyC1-C6alkyl, C1-C6alkoxycarbonylC1-C6alkyl, (R3)$_2$NSO$_2$, SOR3, (R4)$_2$NSO$_2$, —SO$_2$R3', —SOR4, —C(=O)R6, —C(=NOH)R6, —C(=NOR3)R6, —(CH$_2$)$_n$N(R4)C(O)R8, monocyclic heteroaryl, monocyclic heterocyclyl, monocyclic heteroarylC1-

C6alkyl, monocyclic heterocyclylC1-C6alkyl, monocyclic heteroaryloxy, monocyclic heterocyclyloxy, monocyclic heteroaryloxyC1-C6alkyl, monocyclic heterocyclyloxyC1-C6alkyl, arylamino, monocyclic heteroarylamino, monocyclic heterocyclylamino, arylaminoC1-C6alkyl, monocyclic heteroarylaminoC1-C6alkyl, monocyclic heterocyclylaminoC1-C6alkyl, or moieties of the formulae

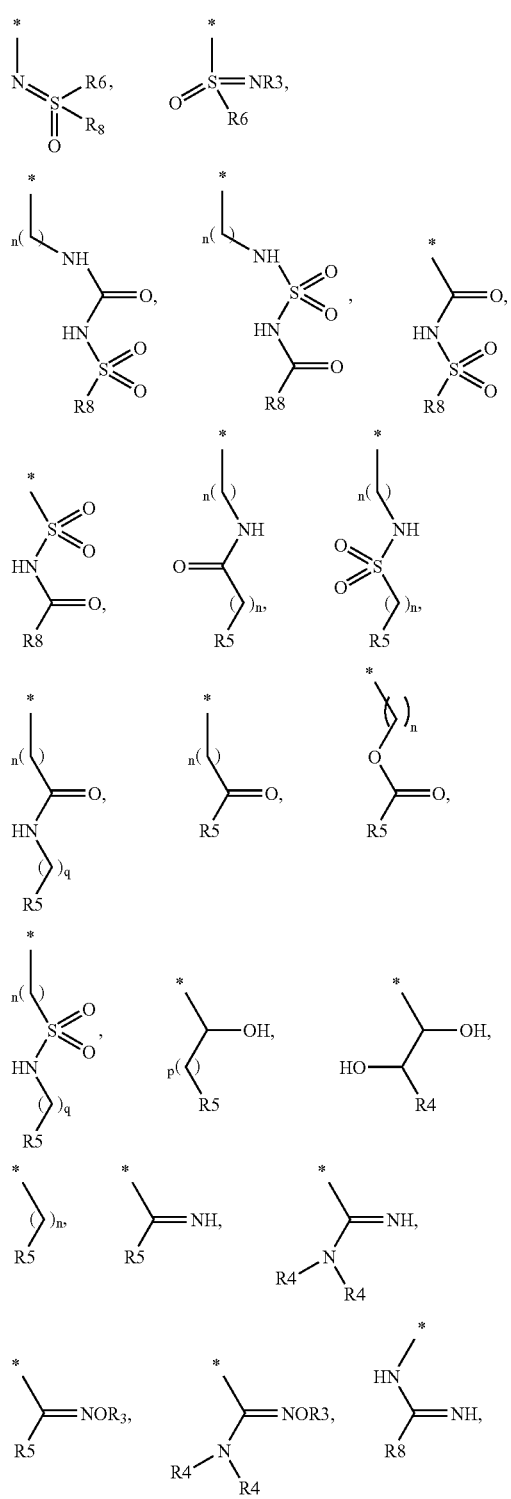

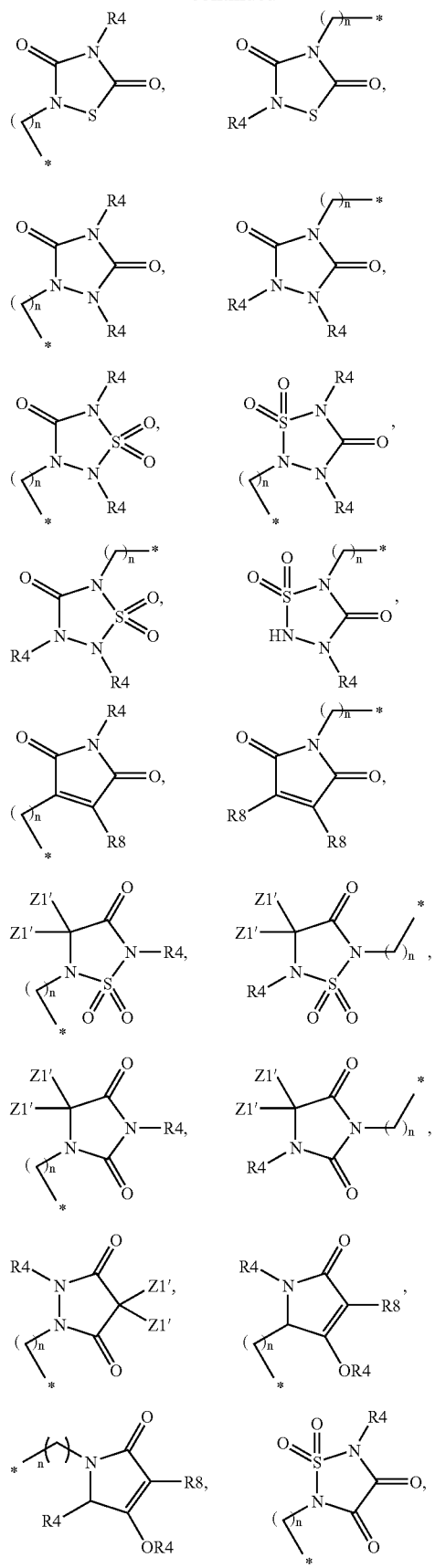

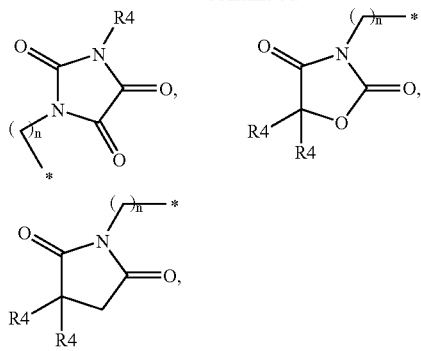

wherein the site of attachment to the A2 ring is meta to the point of attachment to the A1 ring and wherein A2 is phenyl, and cyano wherein the site of attachment is to a substitutable position when A2 is pyridyl, pyrimidinyl or a five-membered ring;

Wherein the asterisk (*) indicates the point of attachment of the Z1 moiety to the A2 ring;

in the event that Z1 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z1 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z1 may cyclize to form a C3-C7 heterocyclyl ring;

wherein Z1' is independently and individually selected from the group consisting of H, C1-C6alkyl, C3-C7cycloalkyl, hydroxyC1-C6alkyl, C1-C6alkoxyC1-C6alkyl, (R4)$_2$N—C1-C6alkyl, (R4)$_2$N—C2-C6alkylN(R4)-(CH$_2$)$_p$, (R4)$_2$N—C2-C6alkylO-(CH$_2$)$_p$, (R4)$_2$N—CO—C1-C6alkyl, carboxyC1-C6alkyl, C1-C6alkoxycarbonylC1-C6alkyl, —(CH$_2$)$_p$N(R4)C(O)R8, aryl, arylC1-C6alkyl, heteroaryl, heteroarylC1-C6alkyl, heterocyclyl, heterocyclylC1-C6alkyl, aryloxyC1-C6alkyl, heteroaryloxyC1-C6alkyl, heterocyclyloxyC1-C6alkyl, arylaminoC1-C6alkyl, heteroarylaminoC1-C6alkyl, or heterocyclylaminoC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom of Z1' may cyclize to form a C3-C7 heterocyclyl ring;

each Z4' is a substituent attached to a ring nitrogen and is independently and individually selected from the group consisting of hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C2-C6alkyl, carboxyC2-C6alkyl, C1-C6alkoxycarbonylC2-C6alkyl, —C2-C6alkylN(R4)C(O)R8, R8-C(=NR3)-, —SO$_2$R8, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

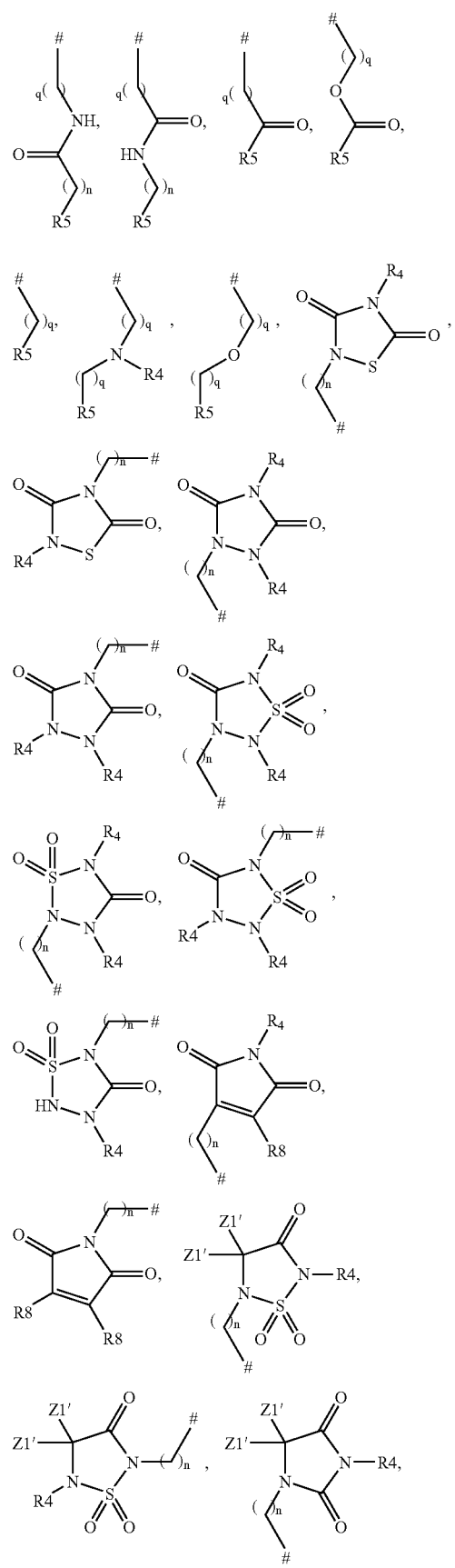

-continued

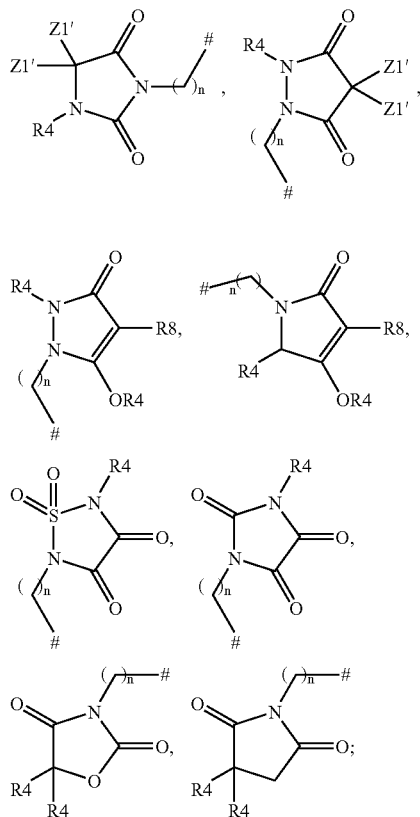

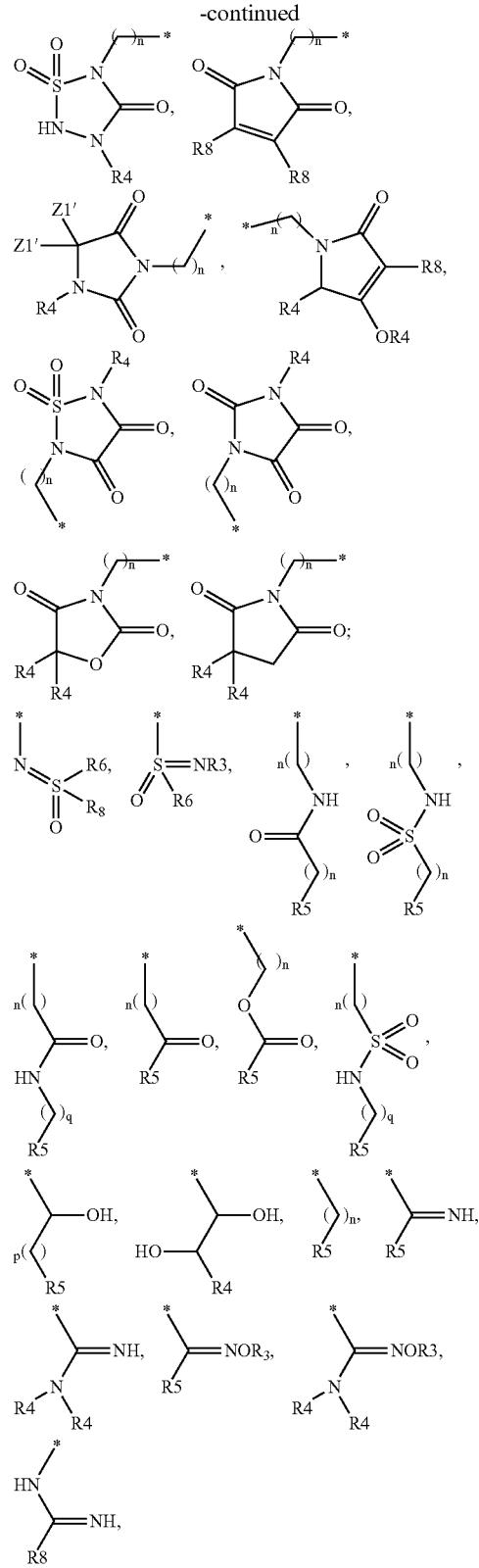

wherein the symbol (#) indicates the point of attachment of the Z4' moiety to the A1 ring of formula I;

in the event that Z4' contains an alkyl or alkylene moiety, such moieties may be further substituted with one or more C1-C6alkyls;

each Z7 is a substituent attached to a ring carbon and is independently and individually selected from the group consisting of hydroxyC2-C6alkyl, C1-C6alkoxyC1-C6alkyl, (R6)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—CO, (R4)$_2$N—CO, —SO$_2$R3', SOR3, —SOR4, —C(=O)R6, —C(=NOH)R6, —C(=NOR3)R6, (CH$_2$)$_n$N(R4)C(O)N(R4)$_2$, (CH$_2$)$_n$N(R4)C(O)R5, monocyclic heteroaryl, monocyclic heterocyclyl, monocyclic heteroarylC1-C6alkyl, monocyclic heterocyclylC1-C6alkyl, monocyclic heteroaryloxy, monocyclic heterocyclyloxy, monocyclic heteroaryloxyC1-C6alkyl, monocyclic heterocyclyloxyC1-C6alkyl, arylamino, monocyclic heteroarylamino, monocyclic heterocyclylamino, arylaminoC1-C6alkyl, monocyclic heteroarylaminoC1-C6alkyl, monocyclic heterocyclylaminoC1-C6alkyl, or moieties of the formulae

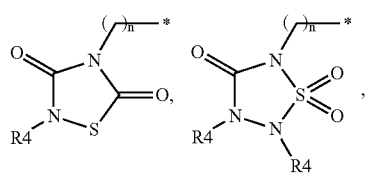

cyano wherein the site of attachment to the A2 ring is meta to the point of attachment to the A1 ring and wherein A2 is phenyl, and cyano wherein the site of attachment is to a substitutable position when A2 is pyridyl, pyrimidinyl or a five-membered ring;

In the foregoing definition of Z7, alkyl moieties may optionally be substituted by one or more C1-C6alkyl;
Wherein the asterisk (*) indicates the point of attachment of the Z1 moiety to the A2 ring;
in the event that Z7 contains an alkyl or alkylene moiety, such moieties may be further substituted with one or more C1-C6alkyls;
wherein two R3 moieties are independently and individually taken from the group consisting of C1-C6alkyl and branched C3-C6alkyl and are attached to the same nitrogen heteroatom of Z7 may cyclize to form a C3-C7 heterocyclyl ring;
wherein two R4 moieties independently and individually taken from the group consisting of C1-C6alkyl, branched C3-C6alkyl, hydroxyalkyl, and alkoxyalkyl and are attached to the same nitrogen heteroatom of Z7 may cyclize to form a C3-C7 heterocyclyl ring;
and n is 0-4; p is 1-4; q is 2-6, r is 0 or 1;
and tautomers, diastereomers, geometric isomers, enantiomers, hydrates, prodrugs, and salts of any of the foregoing.

2.3.1 Preferred D Moieties
2.3.1a
Preferably, the compounds of formula I in 2.3 contain D moieties wherein E1 and E2 are as defined in section 1.3.1a.
2.3.1b
Additionally preferred D moieties of formula I in 2.3 are as defined in section 1.3.1b.
2.3.1c
More preferred D moieties of 2.2.1b are wherein E2 is defined as in section 1.3.1c.
2.3.2 Preferred A2 Moieties
2.3.2a
Compounds of Formula I as defined above in section 2.3 have preferred A2 moieties as defined in section 2.2.2a.
2.3.2b
More preferred A2 moieties are selected from the group consisting of

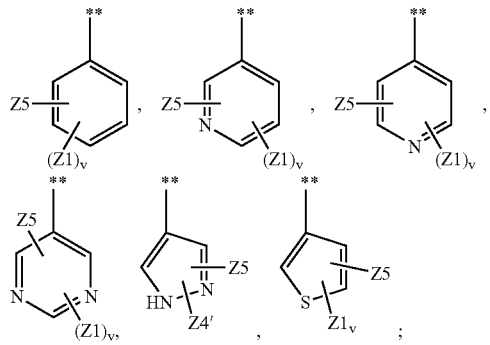

and wherein the symbol (**) is the point of attachment to the A1 ring for formula I.
2.3.2c
Even more preferred A2 moieties are selected from the group consisting of

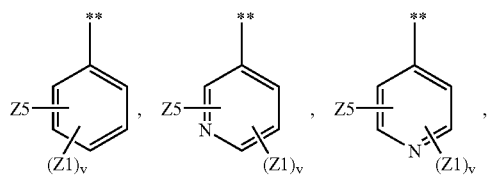

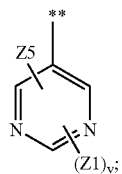

and wherein the symbol (**) is the point of attachment to the A1 ring of formula I.
2.3.3 Preferred Classes of Compounds
2.3.3a
Compounds as defined in 2.3.1a wherein the A2 group is defined in 2.3.2a.
2.3.3b
Compounds as defined in 2.3.3a wherein the A2 group is defined in 2.3.2b.
2.3.3c
Compounds as defined in 2.3.3a wherein the A2 group is defined in 2.3.2c.
2.3.3d
Compounds as defined in 2.3.1b wherein the A2 group is defined in 2.3.2a.
2.3.3e
Compounds as defined in 2.3.3c wherein the A2 group is defined in 2.3.2b.
2.3.3f
Compounds as defined in 2.3.3c wherein the A2 group is defined in 2.3.2c.
2.3.4 Preferred A1 Moieties
2.3.4a
These preferred A1 moieties are defined in 2.1.4a.
2.3.4b
These more preferred A1 moieties are defined in 2.1.4b.
2.3.4c
These even more preferred A1 moieties are defined in 2.1.4c.
2.3.5 Preferred W and Y Moieties
2.3.5a
(1) W and Y are each NH, and X=O; (2) W=NH, Y=CHR4 and X=O; or (3) W=CHR4, Y=NH, and X=O.
2.3.5b
W and Y are each NH and X=O.
2.3.6 Further Preferred Compounds
2.3.6a
Further preferred compounds are of the formula

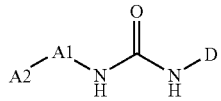

I wherein A2 is selected from the group consisting of

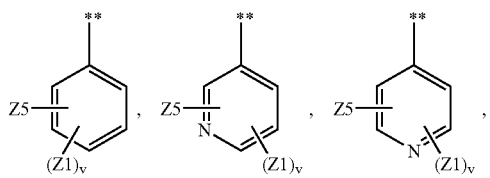

-continued

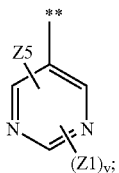

wherein the symbol (**) denotes the attachment to the A1 moiety of formula I;

A1 is selected from the group consisting of

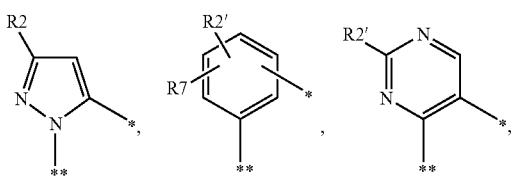

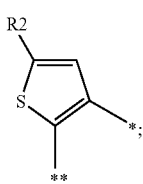

wherein the symbol (*) denotes the attachment to the W moiety of formula I and the symbol (**) denotes the attachment to the A2 moiety of formula I;

X is O, S, or NR3;

D comprises a member of 2,3-dichlorophenyl, 3,4-dichlorophenyl, 3,5-dichlorophenyl, 4-chlorophenyl, 3-chlorophenyl, 3-bromophenyl, 2,3-difluorophenyl, 2,4-difluorophenyl, 3,4-difluorophenyl, 2,5-difluorophenyl, 3,5-difluorophenyl, 2,3,5-trifluorophenyl, 2,4,5-trifluorophenyl, 2,3,4-trifluorophenyl, 3,4,5-trifluorophenyl, 4-cyanophenyl, 3-($R8SO_2$)-phenyl, 3-phenoxyphenyl, 4 phenoxyphenyl,

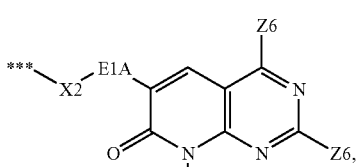

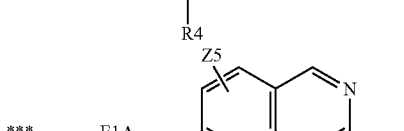

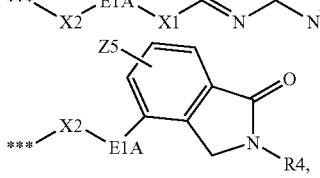

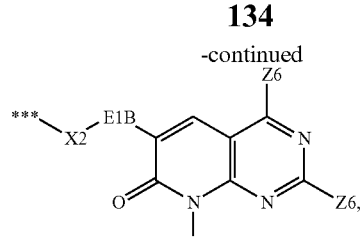

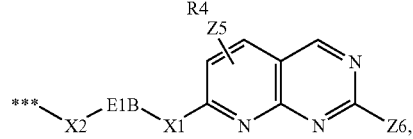

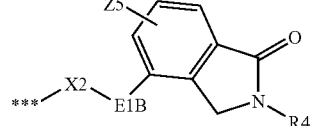

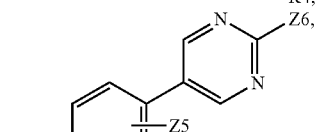

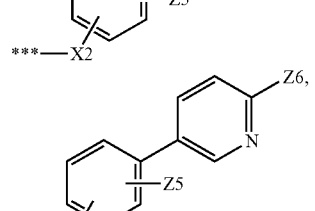

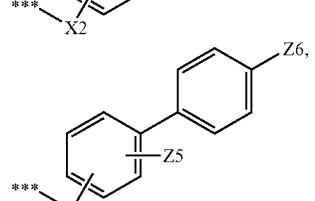

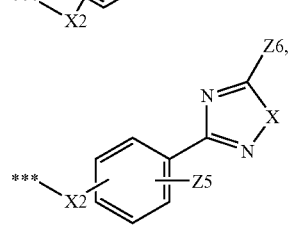

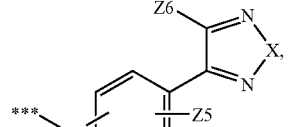

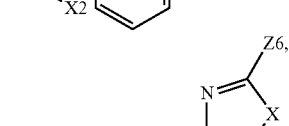

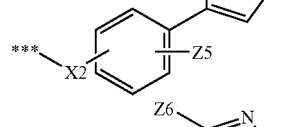

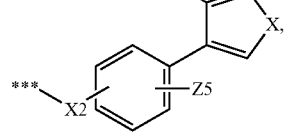

-continued
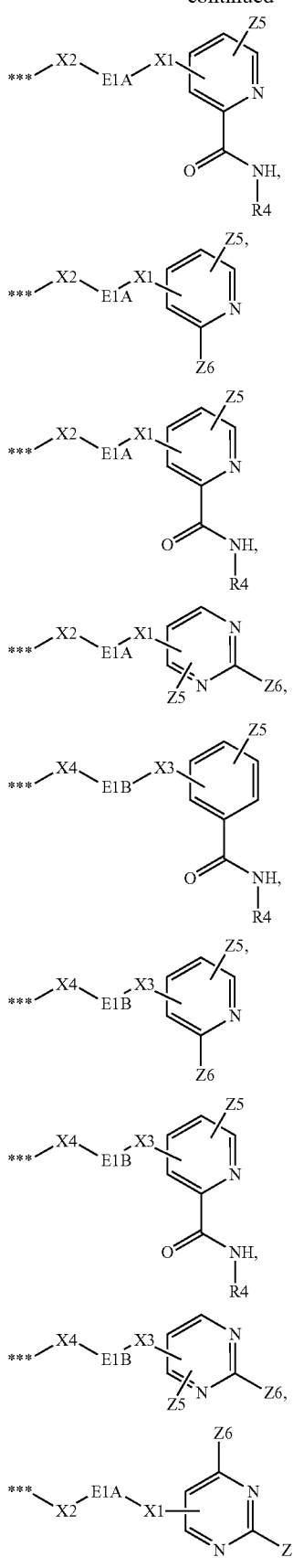
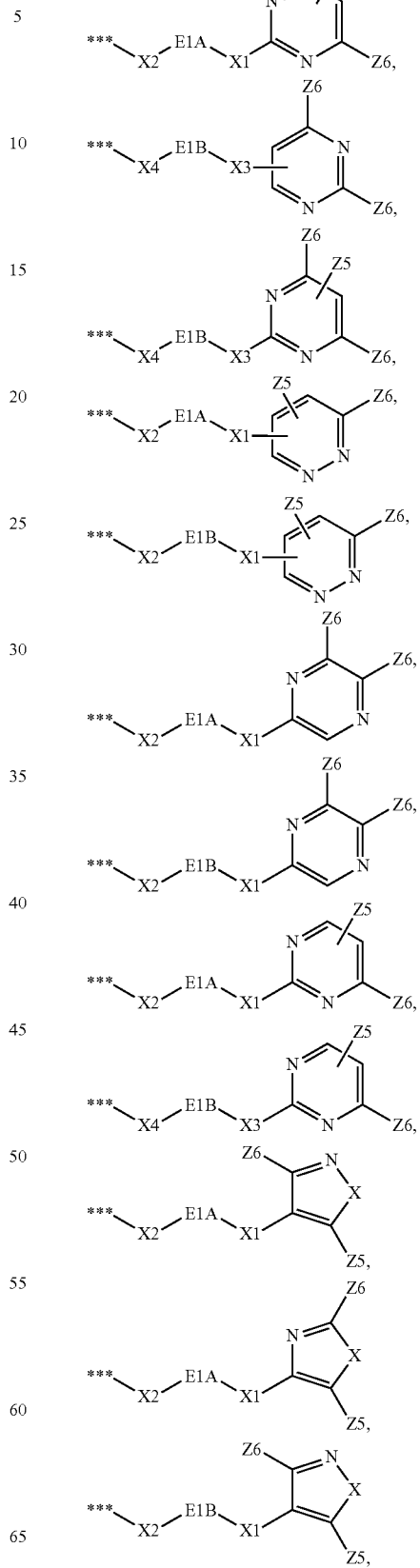

-continued

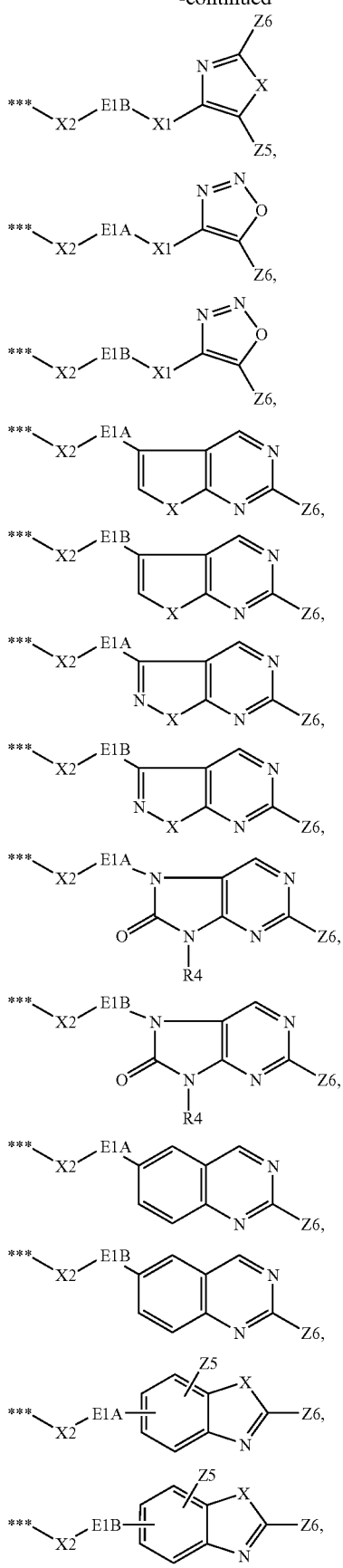

-continued

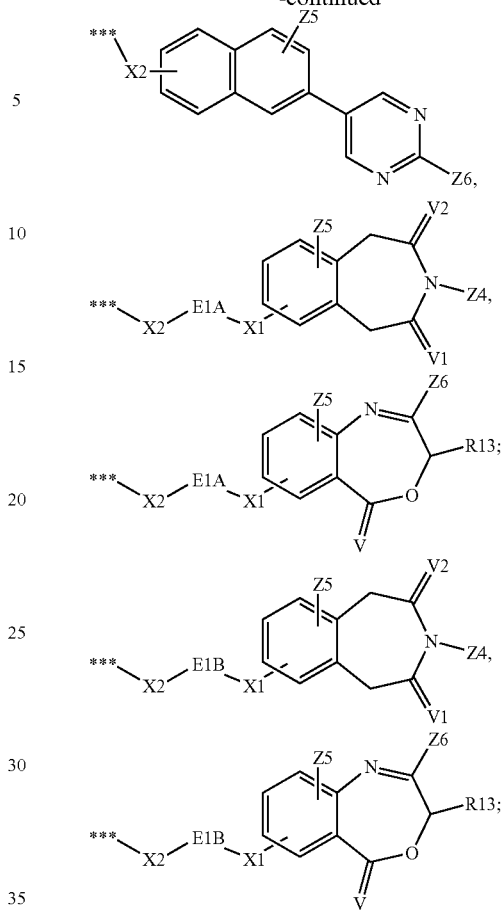

wherein E1A is taken from the groups consisting of cyclopropyl, cyclobutyl, cyclopentyl, cyclohexyl, pyrrolidinyl piperidinyl, thienyl, oxazolyl, thiazolyl, isoxazolyl, isothiazolyl, pyrrolyl, pyrazolyl, oxadiazolyl, thiadiazolyl, furyl, imidazolyl, pyridyl, and pyrimidinyl;

wherein E1B is taken from the groups consisting of phenyl and naphthyl;

wherein E2A is taken from the group comprising naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl and fused bicyclic rings selected from the group comprising indolyl, isoindolyl, isoindolinyl, isoindolonyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, imidazopyrimidinyl, imidazolonopyrimidinyl, dihydropurinonyl, pyrrolopyrimidinyl, purinyl, pyrazolopyridinyl, pyrazolopyrimidinyl, isoxazolopyrimidinyl, isothiazolopyrimidinyl, furylopyrimidinyl, thienopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalazinyl, benzodioxyl, indolinyl, benzisothiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, benzoxazepinyl;

wherein E2B is taken from the group consisting of phenyl, pyridyl, and pyrimidyl;

wherein the symbol (***) denotes the attachment to the Y moiety of formula I;

X1 is selected from the group consisting of O, S, NR3, —C(=O)—, —O—(CH$_2$)n-, —S—(CH$_2$)n-, —NR3-(CH$_2$)n-, —O—(CH$_2$)q-O—, —O—(CH$_2$)q-NR3-, —N(R3)-(CH$_2$)q-N(R3)-, —(CH$_2$)n-N(R4)-C(=O)—, —(CH$_2$)n-N(R4)-C(=O)(CH$_2$)n-, —(CH$_2$)n-CO—N(R4)-, —(CH$_2$)p-, C2-C5alkenyl, C2-C5alkynyl, C3-C6cycloalkyl, and a direct bond wherein the E1 ring and the E2 ring are directly linked by a covalent bond;

and wherein the carbon atoms of —(CH2)n-, —(CH2)q-, (CH2)p, C2-C5alkenyl, and C2-C5alkynyl moieties of X1 may be further substituted by one or more C1-C6alkyl;

X2 is selected from the group consisting of C1-C6 alkyl, C3-C6 branched alkyl, or a direct bond wherein E1 is directly linked to the Y group of formula I;

each R2 is selected from the group consisting of C1-C6alkyl, branched C3-C7alkyl, and R19 substituted C3-C8carbocyclyl wherein R19 is H, or C1-C6alkyl, C1-C6fluoroalkyl wherein the alkyl group is partially or fully fluorinated, phenyl wherein the phenyl group is optionally substituted by one or more fluorine substituents, or monocyclic heteroaryl;

X3 is selected from the group consisting of NR3, —C(=O)—, —O—(CH$_2$)n-, —S—(CH$_2$)n-, —NR3-(CH$_2$)n-, —O—(CH2)q-O—, —O—(CH$_2$)q-NR3-, —N(R3)-(CH$_2$)q-N(R3)-, —(CH$_2$)n-N(R4)-C(=O)—, —(CH$_2$)n-N(R4)-C(=O)(CH$_2$)n-, —(CH$_2$)n-CO—N(R4)-, —(CH$_2$)q-, C2-C5 alkenyl, C2-C5alkynyl, C3-C6cycloalkyl, and a direct bond wherein the either the E1B ring or E2B ring are directly linked by a covalent bond;

and wherein the carbon atoms of —(CH2)q-, C2-C5alkenyl, and C2-C5alkynyl moieties of X3 may be further substituted by one or more C1-C6alkyl;

X4 is selected from the group consisting of C1-C6 alkyl, C3-C6 branched alkyl;

each R2' is selected from the group consisting of halogen and R2;

each R3 is independently and individually selected from the group consisting of H, C1-C6alkyl, branched C3-C7alkyl, C3-C7carbocyclyl, or phenyl;

wherein two R3 moieties independently and individually taken from the group consisting of C1-C6alkyl and branched C3-C7alkyl are attached to the same nitrogen heteroatom, the two R3 moieties may cyclize to form a C3-C7 heterocyclyl ring;

each R4 is selected from the group consisting of H, C1-C6alkyl, hydroxyC1-C6 alkyl, dihydroxyC1-C6alkyl, C1-C6alkoxyC1-C6alkyl, branched C3-C7alkyl, branched hydroxyC1-C6 alkyl, branched C1-C6alkoxyC1-C6alkyl, branched dihydroxyC1-C6alkyl, carbocyclyl, hydroxyl substituted carbocyclyl, alkoxy substituted carbocyclyl, dihydroxy substituted carbocyclyl, phenyl, heteroaryl, heterocyclyl, phenylC1-C6alkyl, heteroarylC1-C6alkyl, and heterocyclylC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom may cyclize to form a C3-C7 heterocyclyl ring;

each R5 is independently and individually selected from the group consisting of

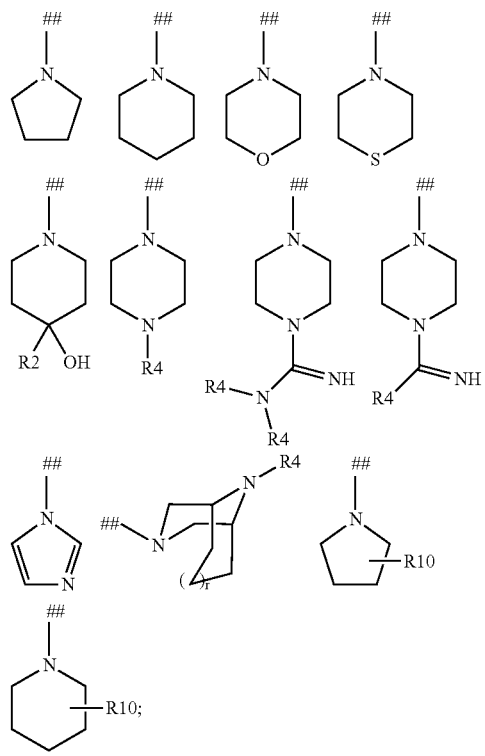

and wherein the symbol (##) is the point of attachment to respective R8, R10, Z4, Z5, Z6 or A2 ring moieties containing a R5 moiety;

wherein two R4 moieties independently and individually taken from the group consisting of C1-C6alkyl, branched C3-C6alkyl, hydroxyalkyl, and alkoxyalkyl and are attached to the same nitrogen heteroatom of R5 may cyclize to form a C3-C7 heterocyclyl ring;

wherein each R6 is independently and individually selected from the group consisting of C1-C6alkyl, branched C3-C7alkyl, carbocyclyl, phenyl, heteroaryl, and heterocyclyl;

each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

each R8 is independently and individually selected from the group consisting of C1-C6alkyl, C1-C6 fluoroalkyl wherein the alkyl moiety is partially or fully fluorinated, branchedC4-C7alkyl, carbocyclyl, phenyl, C1-C6phenylalkyl, heteroaryl or heteroarylC1-C6alkyl, heterocyclyl, heterocyclylC1-C6alkyl, OH, C1-C6alkoxy, N(R3)$_2$, N(R4)$_2$, or R5;

wherein two R3 moieties are independently and individually taken from the group consisting of C1-C6alkyl and branched C3-C6alkyl and are attached to the same nitrogen heteroatom of R8 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of R8 may cyclize to form a C3-C7 heterocyclyl ring;

each R10 is independently and individually selected from the group consisting of CO$_2$H, CO$_2$C1-C6alkyl, CO—N(R4)$_2$, OH, C1-C6alkoxy, —N(R4)$_2$;

wherein two R4 moieties independently and individually taken from the group consisting of C1-C6alkyl, branched C3-C6alkyl, hydroxyalkyl, and alkoxyalkyl and are attached to the same nitrogen heteroatom of R10 may cyclize to form a C3-C7 heterocyclyl ring;

wherein Z1' is independently and individually selected from the group consisting of H, C1-C6alkyl, C3-C7cycloalkyl, hydroxyC1-C6alkyl, C1-C6alkoxyC1-C6alkyl, (R4)$_2$N—C1-C6alkyl, (R4)$_2$N—C2-C6alkylN(R4)-(CH$_2$)$_p$, (R4)$_2$N—C2-C6alkylO-(CH$_2$)$_p$, (R4)$_2$N—CO—C1-C6alkyl, carboxyC1-C6alkyl, C1-C6alkoxycarbonylC1-C6alkyl, —(CH$_2$)$_p$N(R4)C(O)R8, aryl, arylC1-C6alkyl, heteroaryl, heteroarylC1-C6alkyl, heterocyclyl, heterocyclylC1-C6alkyl, aryloxyC1-C6alkyl, heteroaryloxyC1-C6alkyl, heterocyclyloxyC1-C6alkyl, arylaminoC1-C6alkyl, heteroarylaminoC1-C6alkyl, or heterocyclylaminoC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom of Z1' may cyclize to form a C3-C7 heterocyclyl ring;

each Z4 is a substituent attached to a ring nitrogen and is independently and individually selected from the group consisting of H, C1-C6alkyl, hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C2-C6alkyl, carboxyC2-C6alkyl, C1-C6alkoxycarbonylC2-C6alkyl, —C2-C6alkylN(R4)C(O)R8, R8-C(=NR3)-, —SO$_2$R8, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

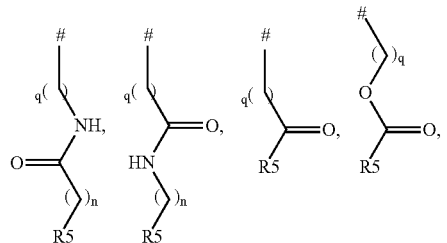

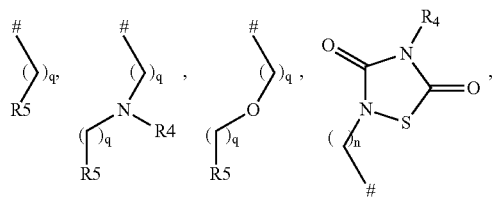

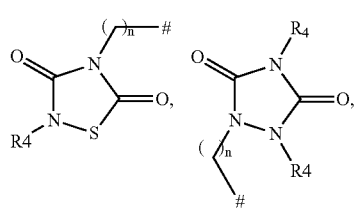

-continued

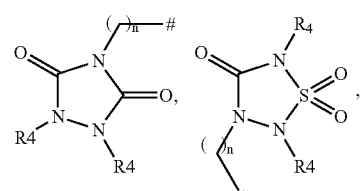

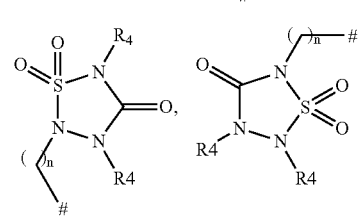

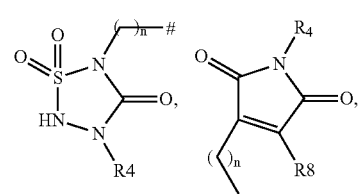

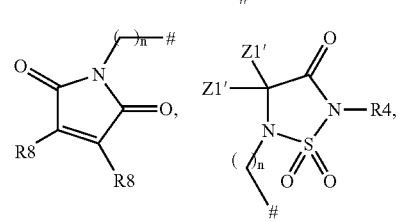

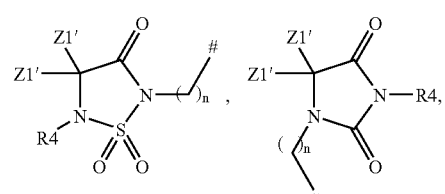

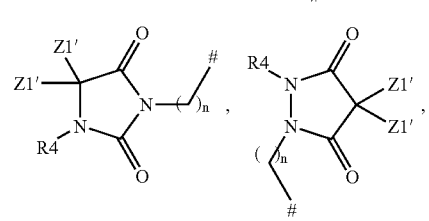

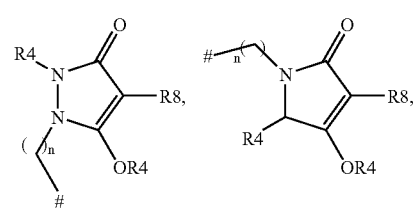

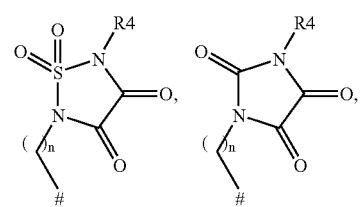

143

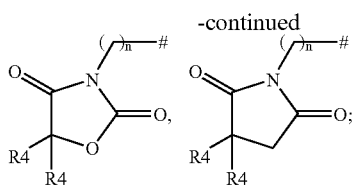
-continued

144 cyclic heterocyclyloxyC1-C6alkyl, arylamino, monocyclic heteroarylamino, monocyclic heterocyclylamino, arylaminoC1-C6alkyl, monocyclic heteroarylaminoC1-C6alkyl, monocyclic heterocyclylaminoC1-C6alkyl, or moieties of the formulae

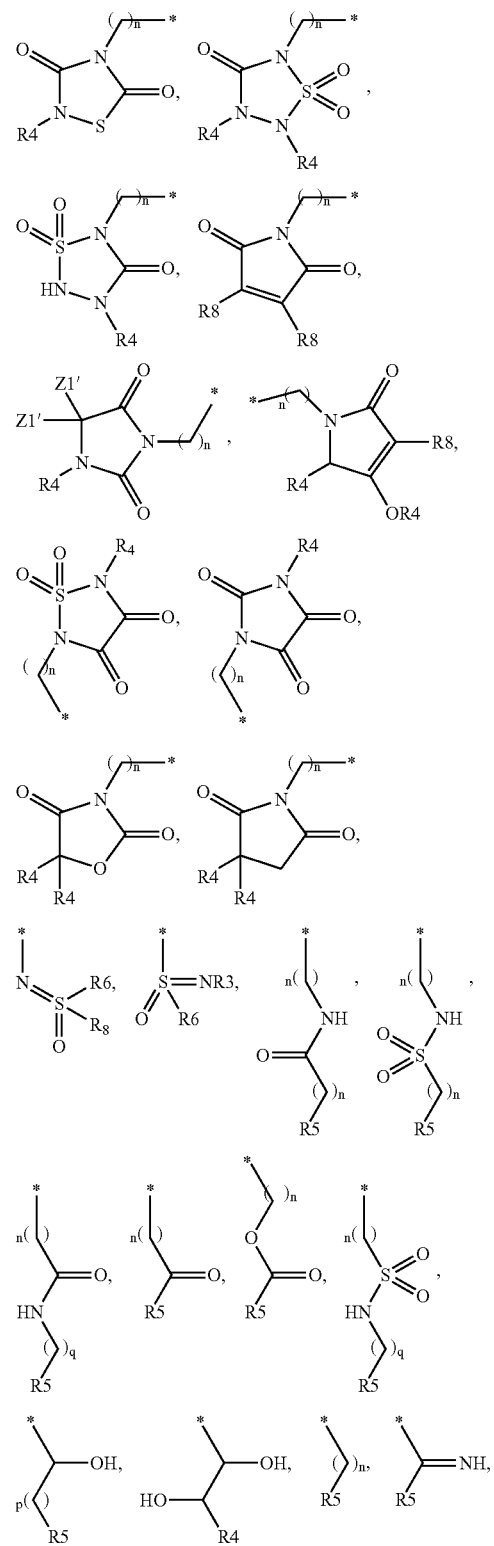

wherein the symbol (#) indicates the point of attachment of the Z4 moiety to the A2 ring for formula I;
in the event that Z4 contains an alkyl or alkylene moiety, such moieties may be further substituted with one or more C1-C6alkyls;
wherein two R3 moieties are independently and individually taken from the group consisting of C1-C6alkyl and branched C3-C6alkyl and are attached to the same nitrogen heteroatom of Z4 may cyclize to form a C3-C7 heterocyclyl ring;
wherein two R4 moieties independently and individually taken from the group consisting of C1-C6alkyl, branched C3-C6alkyl, hydroxyalkyl, and alkoxyalkyl and are attached to the same nitrogen heteroatom of Z4 may cyclize to form a C3-C7 heterocyclyl ring;
Z5 is independently and individually selected from the group consisting of H, C1-C6alkyl, branched C3-C7alkyl, halogen, fluoroalkyl, cyano, hydroxyl, alkoxy, oxo, aminocarbonyl, carbonylamino, aminosulfonyl, sulfonylamino, —N(R3)$_2$, —O—(CH$_2$)q-N(R4)$_2$, —N(R3)-(CH$_2$)q-N(R4)$_2$, —R5, —O—(CH$_2$)q-O-Alkyl, —O—(CH$_2$)q-N(R4)$_2$, —N(R3)-(CH$_2$)q-O-Alkyl, —N(R3)-(CH$_2$)q-N(R4)$_2$, —O—(CH$_2$)q-R5, and —N(R3)-(CH$_2$)q-R5;
wherein two R3 moieties are independently and individually taken from the group consisting of C1-C6alkyl and branched C3-C6alkyl and are attached to the same nitrogen heteroatom of Z5 may cyclize to form a C3-C7 heterocyclyl ring;
wherein two R4 moieties independently and individually taken from the group consisting of C1-C6alkyl, branched C3-C6alkyl, hydroxyalkyl, and alkoxyalkyl and are attached to the same nitrogen heteroatom of Z5 may cyclize to form a C3-C7 heterocyclyl ring;
Each Z6 is independently and individually selected from the group consisting of H, C1-C6alkyl, branched C3-C7alkyl, hydroxyl, C1-C6alkoxy, (R3)$_2$N—, —N(R3)COR8, (R4)$_2$N—, —R5, —N(R4)COR8, —N(R3)SO$_2$R6-, —CON(R3)$_2$, —CON(R4)$_2$, —COR5, —SO$_2$NHR4, heteroaryl, heterocyclyl, heteroaryloxy, heterocyclyloxy, arylamino, heteroarylamino, and heterocyclylamino;
wherein two R3 moieties are independently and individually taken from the group consisting of C1-C6alkyl and branched C3-C6alkyl and are attached to the same nitrogen heteroatom of Z6 may cyclize to form a C3-C7 heterocyclyl ring;
wherein two R4 moieties independently and individually taken from the group consisting of C1-C6alkyl, branched C3-C6alkyl, hydroxyalkyl, and alkoxyalkyl and are attached to the same nitrogen heteroatom of Z6 may cyclize to form a C3-C7 heterocyclyl ring;
each Z7 is a substituent attached to a ring carbon and is independently and individually selected from the group consisting of hydroxyC2-C6alkyl, C1-C6alkoxyC1-C6alkyl, (R6)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—CO, (R4)$_2$N—CO, —SO$_2$R3', SOR3, —SOR4, —C(=O)R6, —C(=NOH)R6, —C(=NOR3)R6, (CH$_2$)$_n$N(R4)C(O)N(R4)$_2$, (CH$_2$)$_n$N(R4)C(O)R5, monocyclic heteroaryl, monocyclic heterocyclyl, monocyclic heteroarylC1-C6alkyl, monocyclic heterocyclylC1-C6alkyl, monocyclic heteroaryloxy, monocyclic heterocyclyloxy, monocyclic heteroaryloxyC1-C6alkyl, mono-

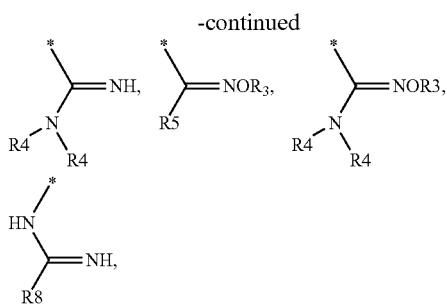

cyano wherein the site of attachment to the A2 ring is meta to the point of attachment to the A1 ring and wherein A2 is phenyl, and cyano wherein the site of attachment is to a substitutable position when A2 is pyridyl, pyrimidinyl or a five-membered ring;

In the foregoing definition of Z7, alkyl moieties may optionally be substituted by one or more C1-C6alkyl;

Wherein the asterisk (*) indicates the point of attachment of the Z1 moiety to the A2 ring;

in the event that Z7 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z7 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z7 may cyclize to form a C3-C7 heterocyclyl ring;

and n is 0-4; p is 1-4; q is 2-6; r is 0 or 1; v is 1 or 2;

and tautomers, diastereomers, geometric isomers, enantiomers, hydrates, prodrugs and salts of any of the foregoing.

2.3.6b

The following specific compounds of Formula I are more preferred: 1-(1-(3-(1H-pyrazol-4-yl)phenyl)-3-t-butyl-1H-pyrazol-5-yl)-3-(2,3-dichlorophenyl)urea, 1-(1-(3-(2-amino-2-oxoethyl)phenyl)-3-t-butyl-1H-pyrazol-5-yl)-3-(3-(pyridin-3-yloxy)phenyl)urea, 1-(1-(3-(2-amino-2-oxoethyl)phenyl)-3-(trifluoromethyl)-1H-pyrazol-5-yl)-3-(3-(pyridin-3-yloxy)phenyl)urea, 1-(3-t-butyl-1-(3-(pyridin-3-yl)phenyl)-1H-pyrazol-5-yl)-3-(3-(pyridin-3-yloxy)phenyl)urea, 1-(1-(3-(2-amino-2-oxoethyl)phenyl)-3-t-butyl-1H-pyrazol-5-yl)-3-(3-(pyrazin-2-yloxy)phenyl)urea, 1-(1-(3-(2-amino-2-oxoethyl)phenyl)-3-t-butyl-1H-pyrazol-5-yl)-3-(4-(2-(methylcarbamoyl)pyridin-4-yloxy)phenyl)urea, 1-(1-(3-(2-amino-2-oxoethyl)phenyl)-3-t-butyl-1H-pyrazol-5-yl)-3-(4-(1-oxoisoindolin-4-yl)phenyl)urea, 1-(1-(3-(2-amino-2-oxoethyl)phenyl)-3-cyclopentyl-1H-pyrazol-5-yl)-3-(4-(1-oxoisoindolin-4-yl)phenyl)urea, 1-(1-(3-(1H-pyrazol-4-yl)phenyl)-3-t-butyl-1H-pyrazol-5-yl)-3-(4-(1-oxoisoindolin-4-yl)phenyl)urea 2.3.7 Methods 2.3.7a Methods of Protein Modulation The invention includes methods of modulating kinase activity of a variety of kinases, e.g. receptor tyrosine kinases including VEGFR1, VEGFR2, FLT-1, FLT-3, PDGFRa, PDGFRb, FGFR1, FGFR2, FGFR3, FGFR4, TrkA, TrkB, EGFR, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, EPHB7, EPHB8. The kinases may be wildtype kinases, oncogenic forms thereof, aberrant fusion proteins thereof or polymorphs of any of the foregoing. The method comprises the step of contacting the kinase species with compounds of the invention and especially those set forth in sections 2.3 and 2.3.6a. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, kinase cellular localization, and recruitment of other proteins into signaling complexes through modulation of kinase conformation.

2.3.7b Treatment Methods

The methods of the invention also include treating individuals suffering from a condition selected from the group consisting of cancer, secondary cancer growth arising from metastasis, hyperproliferative diseases, and diseases characterized by hyper-vascularization. These methods comprise administering to such individuals compounds of the invention, and especially those of section 2.3 and 2.3.6a. Exemplary conditions include glioblastomas, ovarian cancer, pancreatic cancer, prostate cancer, lung cancers, breast cancers, kidney cancers, cervical carcinomas, metastasis of primary solid tumor secondary sites, ocular diseases characterized by hyperproliferation leading to blindness including various retinopathies including diabetic retinopathy and age-related macular degeneration, or rheumatoid arthritis characterized by the in-growth of a vascularized pannus. The administration method is not critical, and may be from the group consisting of oral, parenteral, inhalation, and subcutaneous.

2.3.8 Pharmaceutical Preparations

The compounds of the invention, especially those of 2.3 and 2.3.6a may form a part of a pharmaceutical composition by combining one or more such compounds with a pharmaceutically acceptable carrier. Additionally, the compositions may include an additive selected from the group consisting of adjuvants, excipients, diluents, and stablilizers.

2.3.9 Kinase/Compound Adducts

The invention also provides adducts in the form of compounds of the invention bound with a species of kinase such as a wild-type kinase, oncogenic forms thereof, aberrant fusion proteins thereof and polymorphs of any of the foregoing. The compounds are advantageously selected from the groups defined in sections 2.3 and 2.3.6a.

3. First Aspect of the Invention—Raf Kinase Modulator Compounds, Methods, Preparations and Adducts 3.1 Generally—A2 Bicyclic Compounds The invention includes compounds of formula I as defined in section 2.1, wherein each R2 is independently and individually selected from the group consisting of C1-C6alkyl, branched C3-C7alkyl, C1-C6fluoroalkyl, wherein the alkyl group is partially or fully fluorinated, monocyclic heteroaryl, and R19 substituted C3-C8carbocyclyl wherein R19 is H, and C1-C6alkyl.

3.1.1 Preferred D Moieties 3.1.1a

Preferred compounds of Formula I as defined above in section 3.1 contain D moieties as defined in section 1.1.1a.

3.1.1b

Additionally preferred compounds of Formula I as defined above in section 3.1 contain D moieties as defined in section 1.1.1b.

3.1.1c

More preferred compounds of Formula I as defined above in section 3.1.1b contain D moieties as defined in section 1.1.1c.

3.1.2 Preferred A2 Moieties

3.1.2a

Compounds of Formula I as defined above in section 3.1 have preferred A2 moieties as defined in section 1.1.2a.

3.1.2b More preferred A2 Moieties

Compounds of Formula I as defined above in section 3.1 have more preferred A2 moieties selected from group consisting of

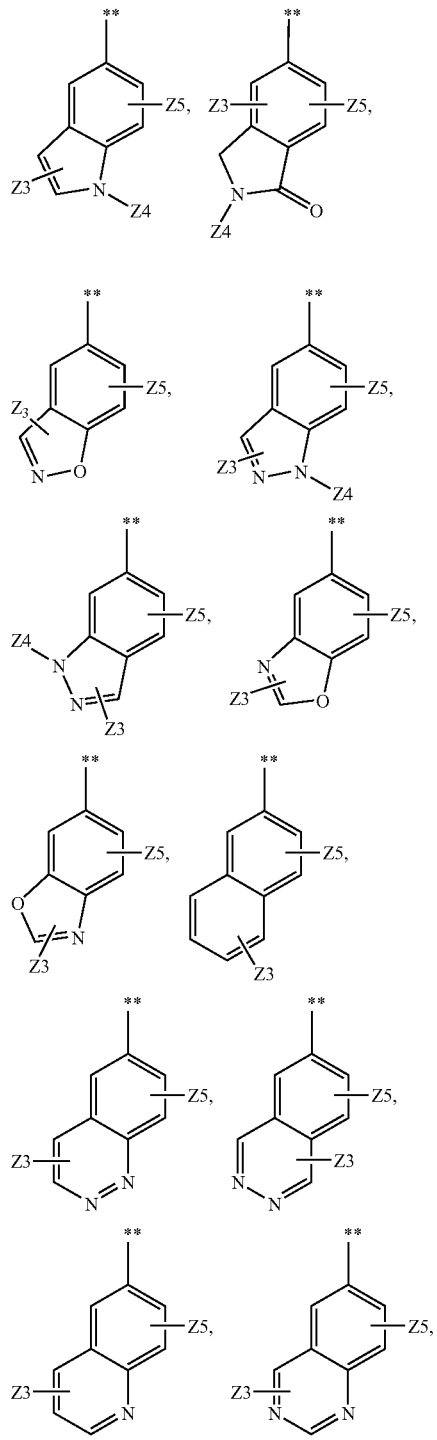

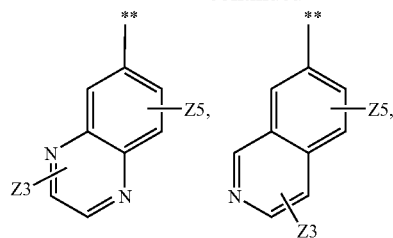

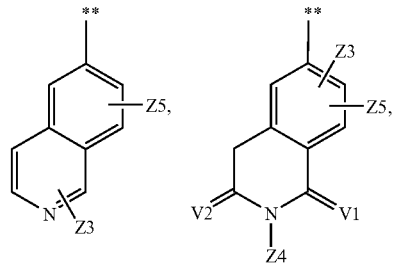

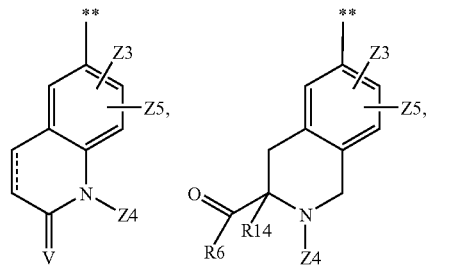

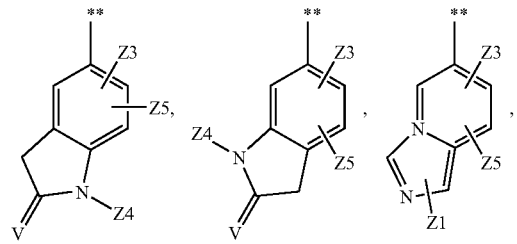

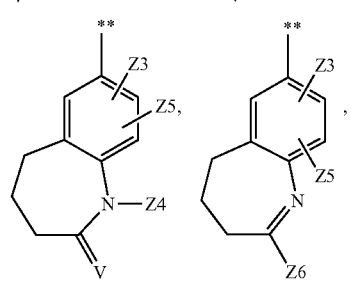

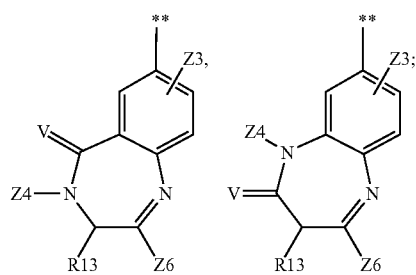

and wherein the symbol (*) is the point of attachment to the A1 ring for formula I;

wherein each Z3 and Z5 is independently attached to either aryl or heteroaryl ring of the A2 bicyclic ring.

3.1.2c
Still more preferred compounds of Formula I as defined above in section 3.1 have A2 moieties selected from group consisting of

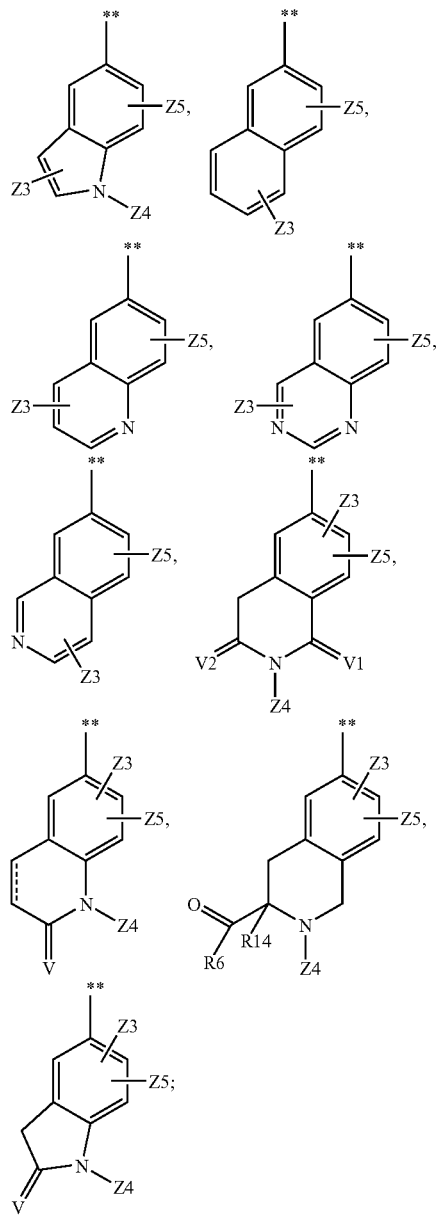

and wherein the symbol (**) is the point of attachment to the A1 ring of formula I;
wherein each Z3 and Z5 is independently attached to either aryl or heteroaryl ring of the A2 bicyclic ring.

3.1.3 Preferred Classes of Compounds
3.1.3a
Compounds as defined in 3.1.1a wherein the A2 group is defined in 3.1.2a.
3.1.3b
Compounds as defined in 3.1.3a wherein the A2 group is defined in 3.1.2b.
3.1.3c
Compounds as defined in 3.1.3a wherein the A2 group is defined in 3.1.2c.

3.1.3d
Compounds as defined in 3.1.1b wherein the A2 group is defined in 3.1.2a.
3.1.3e
Compounds as defined in 3.1.3c wherein the A2 group is defined in 3.1.2b.
3.1.3f
Compounds as defined in 3.1.3c wherein the A2 group is defined in 3.1.2c.

3.1.4 Preferred A1 Moieties
3.1.4a
Compounds of Formula I as defined above in section 3.1 have preferred A1 moieties selected from group defined in section 1.1.4a;
wherein each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

3.1.4b
Compounds of Formula I as defined above in section 3.1 have more preferred A1 moieties selected from group consisting of

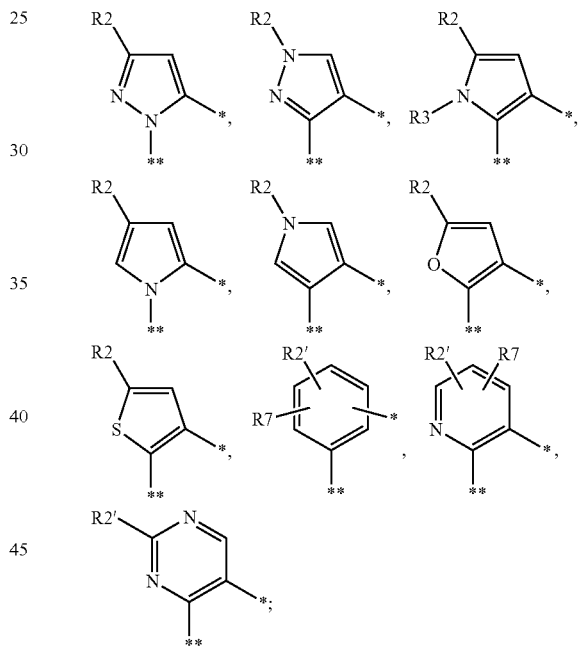

wherein the symbol (*) denotes the attachment to the W moiety of formula I and the symbol (**) denotes the attachment to the A2 moiety of formula I.

3.1.4c
Compounds of Formula I as defined above in section 3.1 have even more preferred A1 moieties selected from group consisting of

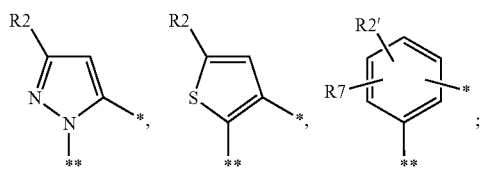

wherein the symbol (*) denotes the attachment to the W moiety of formula I and the symbol (**) denotes the attachment to the A2 moiety of formula I.

3.1.5 Preferred W and Y Moieties 3.1.5a (1) W and Y are each NH, and X=O; (2) W=NH, Y=CHR4 and X=O; or (3) W=CHR4, Y=NH, and X=O.

3.1.5b

W and Y are each NH and X=O.

3.1.6 Further Preferred Compounds 3.1.6a

Further preferred compounds are of the formula

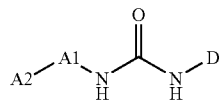

I wherein A2 is selected from the group consisting of

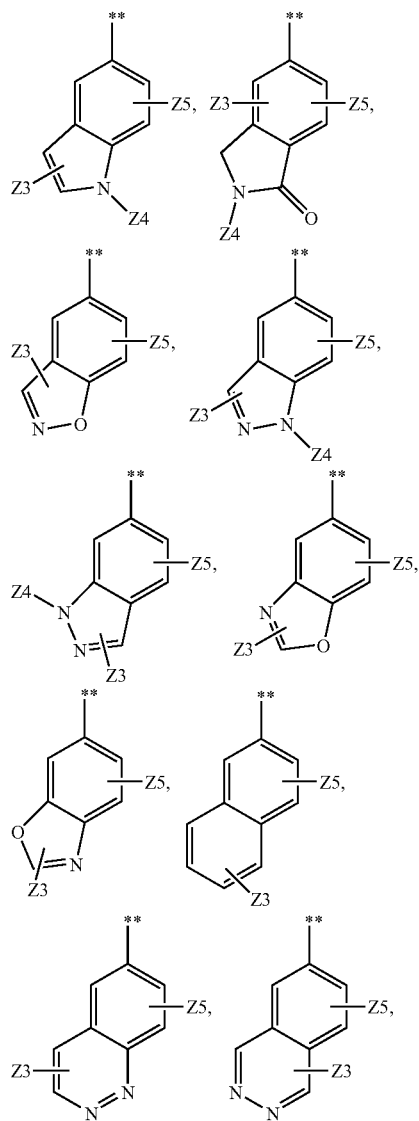

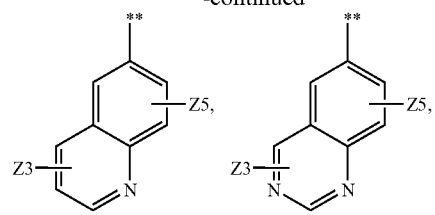

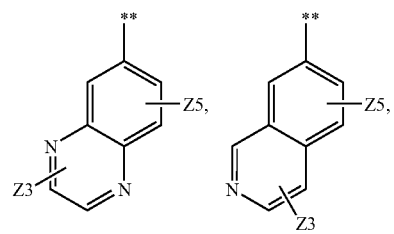

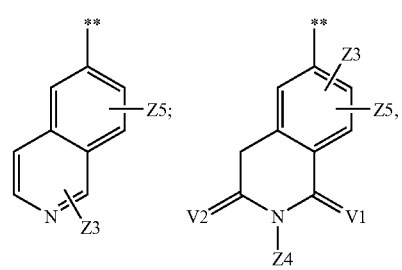

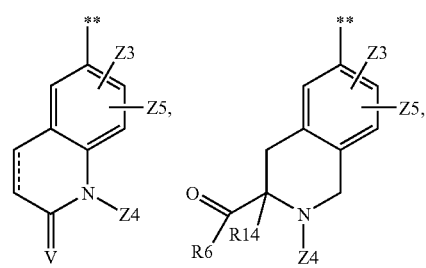

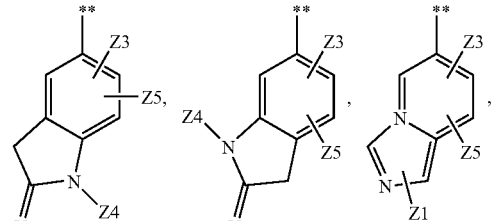

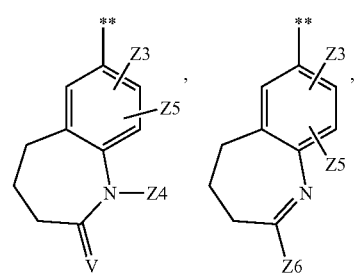

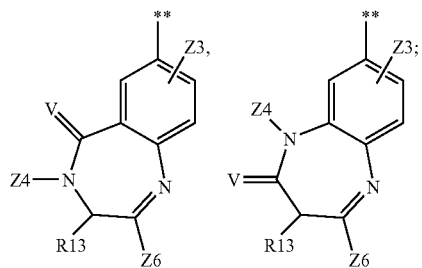

wherein each Z3 and Z5 is independently attached to either aryl or heteroaryl ring of the A2 bicyclic ring;

wherein the symbol (**) denotes the attachment to the A1 moiety of formula I;

A1 is selected from the group consisting of

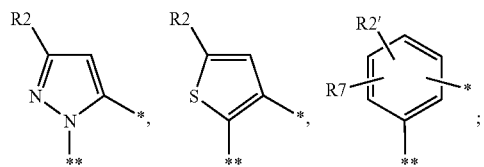

wherein the symbol (*) denotes the attachment to the W moiety of formula I and the symbol (**) denotes the attachment to the A2 moiety of formula I;

X is O, S, or NR3;

D comprises a member of 2,3-dichlorophenyl, 2,3-difluorophenyl, 2,4-difluorophenyl, 3,4-difluorophenyl, 2,5-difluorophenyl, 3,5-difluorophenyl, 2,3,5-trifluorophenyl, 2,4,5-trifluorophenyl, 2,3,4-trifluorophenyl, 3,4,5-trifluorophenyl, 3-phenoxyphenyl, 4-phenoxyphenyl, cyclohexyl,

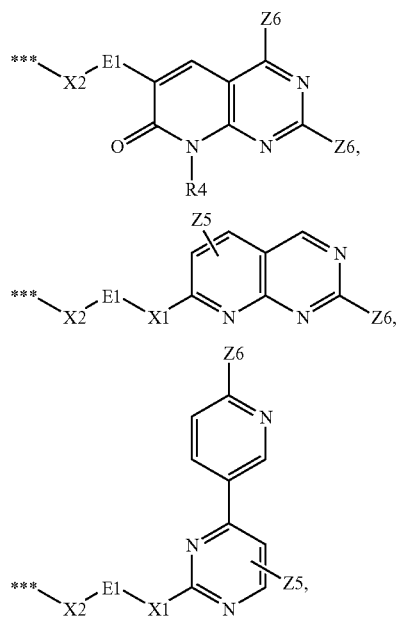

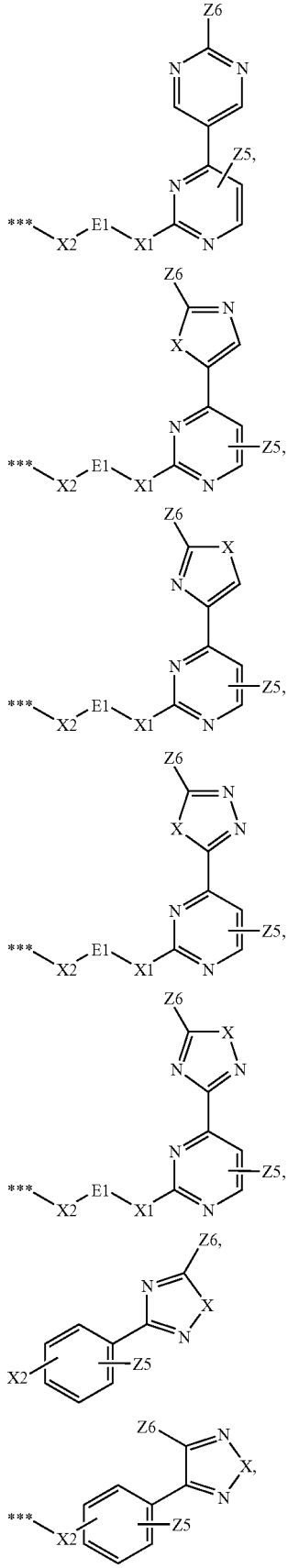

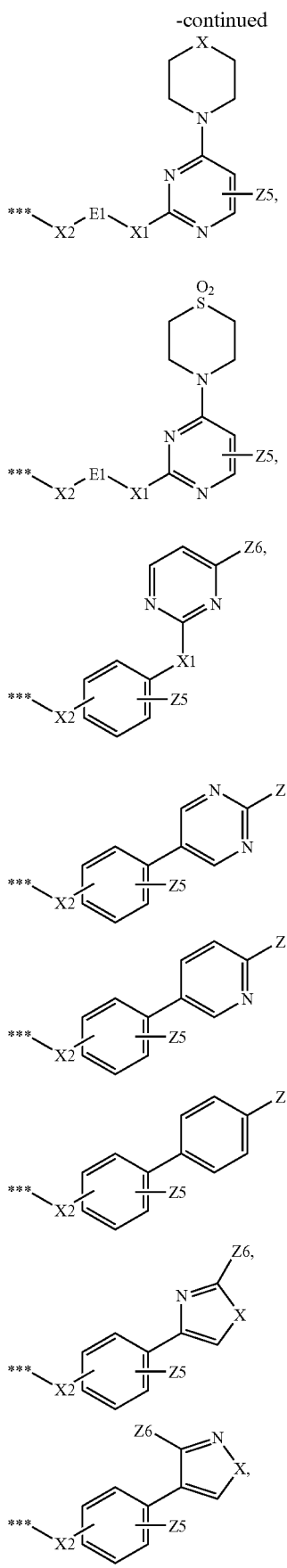
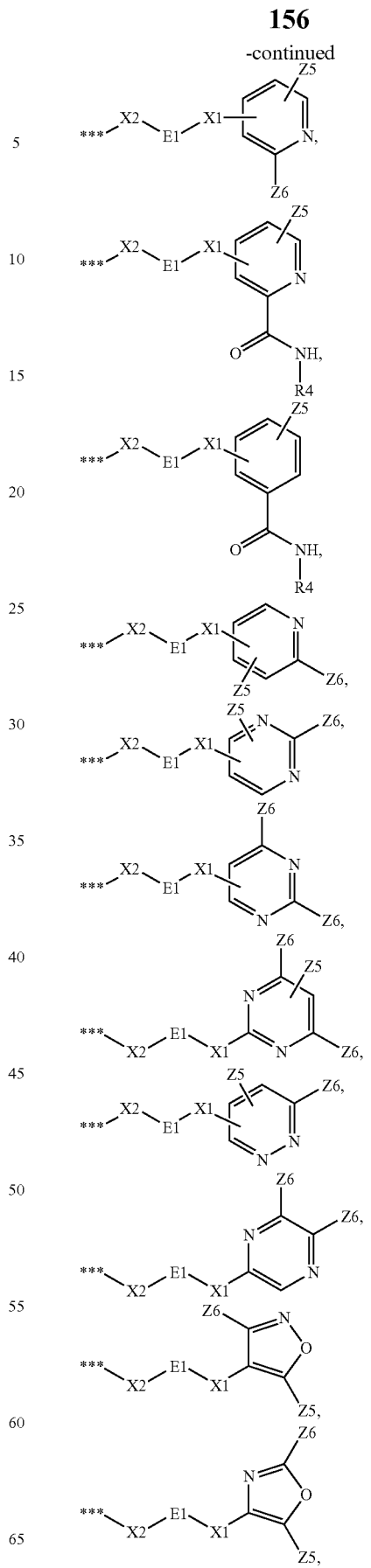

-continued

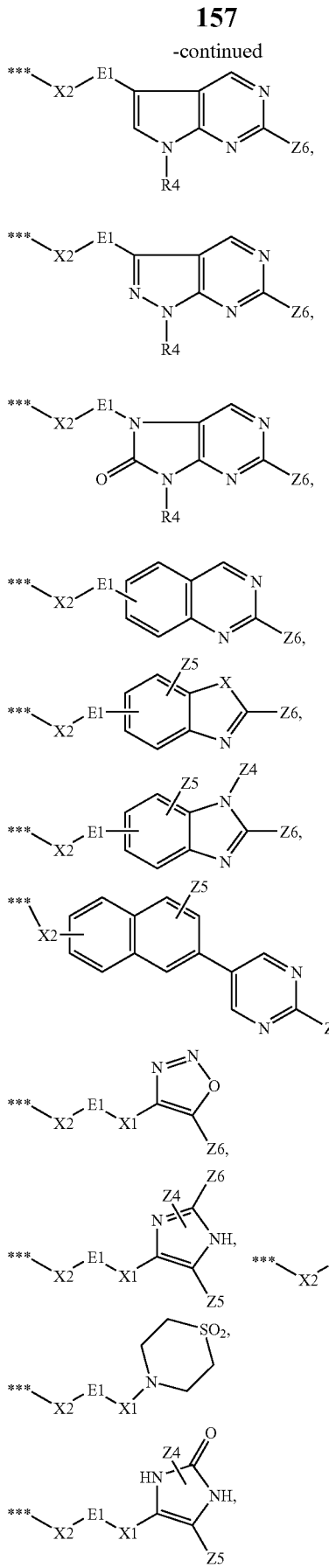

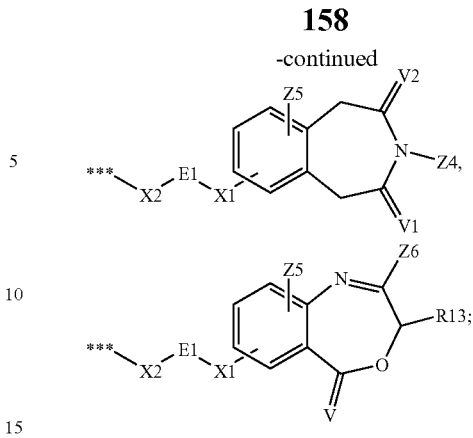

wherein E1 is selected from the group consisting cyclopropyl, cyclobutyl, cyclopentyl, cyclohexyl, pyrrolidinyl piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl and naphthyl;

wherein the symbol (***) denotes the attachment to the Y moiety of formula I;

X1 is selected from the group consisting of O, S, NR3, —C(=O)—, —O—(CH₂)n-, —S—(CH₂)n-, —NR3-(CHR2)n-, —O—(CH₂)q-O—, —O—(CH₂)q-NR3-, —N(R3)-(CH₂)q-N(R3)-, —(CH₂)n-N(R4)-C(=O)—, —(CH₂)n-N(R4)-C(=O)(CH₂)n-, —(CH₂)n-CO—N(R4)-, —(CH₂)p-, C2-C5alkenyl, C2-C5alkynyl, C3-C6cycloalkyl, and a direct bond wherein the E1 ring and the E2 ring are directly linked by a covalent bond;

and wherein the carbon atoms of —(CH2)n-, —(CH2)q-, (CH2)p, C2-C5alkenyl, and C2-C5alkynyl moieties of X1 may be further substituted by one or more C1-C6alkyl;

X2 is selected from the group consisting of C1-C6 alkyl, C3-C6 branched alkyl, or a direct bond wherein E1 is directly linked to the Y group of formula I;

Each R2 is independently and individually selected from the group consisting of C1-C6alkyl, branched C3-C7alkyl, C1-C6fluoroalkyl, wherein the alkyl group is partially or fully fluorinated, monocyclic heteroaryl, and R19 substituted C3-C8carbocyclyl wherein R19 is H, and C1-C6alkyl;

each R2' is selected from the group consisting of halogen and R2;

each R3 is independently and individually selected from the group consisting of H, C1-C6alkyl, branched C3-C7alkyl, C3-C7carbocyclyl, or phenyl;

wherein two R3 moieties independently and individually taken from the group consisting of C1-C6alkyl and branched C3-C7alkyl are attached to the same nitrogen heteroatom, the two R3 moieties may cyclize to form a C3-C7 heterocyclyl ring;

each R4 is selected from the group consisting of H, C1-C6alkyl, hydroxyC1-C6 alkyl, dihydroxyC1-C6alkyl, C1-C6alkoxyC1-C6alkyl, branched C3-C7alkyl, branched hydroxyC1-C6 alkyl, branched C1-C6alkoxyC1-C6alkyl, branched dihydroxyC1-C6alkyl, carbocyclyl, hydroxyl substituted carbocyclyl, alkoxy substituted carbocyclyl, dihydroxy substituted carbocyclyl, phenyl, heteroaryl, heterocyclyl, phenylC1-C6alkyl, heteroarylC1-C6alkyl, and heterocyclylC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom may cyclize to form a C3-C7 heterocyclyl ring;

each R5 is independently and individually selected from the group consisting of

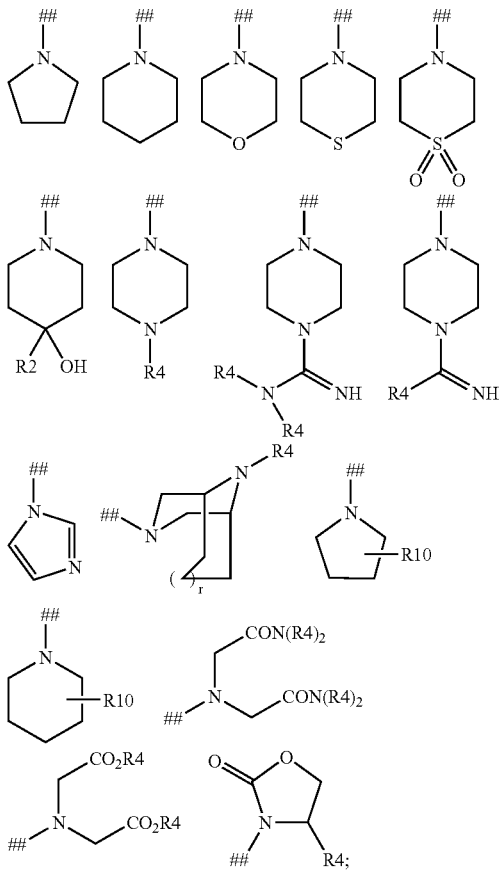

and wherein the symbol (##) is the point of attachment to respective R8, R10, R13, Z2, Z3, Z4, Z5, or A2 ring moieties containing a R5 moiety;

wherein two R4 moieties independently and individually taken from the group consisting of C1-C6alkyl, branched C3-C6alkyl, hydroxyalkyl, and alkoxyalkyl and are attached to the same nitrogen heteroatom of R5 may cyclize to form a C3-C7 heterocyclyl ring;

wherein each R6 is independently and individually selected from the group consisting of C1-C6alkyl, branched C3-C7alkyl, carbocyclyl, phenyl, heteroaryl, and heterocyclyl;

each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

each R8 is independently and individually selected from the group consisting of C1-C6alkyl, C1-C6 fluoroalkyl wherein the alkyl moiety is partially or fully fluorinated, branchedC4-C7alkyl, carbocyclyl, phenyl, C1-C6phenylalkyl, heteroaryl or heteroarylC1-C6alkyl, heterocyclyl, heterocyclylC1-C6alkyl, OH, C1-C6alkoxy, N(R3)$_2$, N(R4)$_2$, or R5;

wherein two R3 moieties are independently and individually taken from the group consisting of C1-C6alkyl and branched C3-C6alkyl and are attached to the same nitrogen heteroatom of R8 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of R8 may cyclize to form a C3-C7 heterocyclyl ring;

each R10 is independently and individually selected from the group consisting of CO$_2$H, CO$_2$C1-C6alkyl, CO—N(R4)$_2$, OH, C1-C6alkoxy, —N(R4)$_2$;

wherein two R4 moieties independently and individually taken from the group consisting of C1-C6alkyl, branched C3-C6alkyl, hydroxyalkyl, and alkoxyalkyl and are attached to the same nitrogen heteroatom of R10 may cyclize to form a C3-C7 heterocyclyl ring;

each R13 is independently and individually selected from the group consisting of H, C1-C6alkyl, branched C3-C7alkyl, carbocyclyl, hydroxyC2-C7alkyl, C1-C6alkoxyC2-C7alkyl, (R4)$_2$N—CO, (R4)$_2$N—CO—C1-C6alkyl, carboxyC1-C6alkyl, C1-C6alkoxycarbonyl, C1-C6alkoxycarbonylC1-C6alkyl, (R4)$_2$N—C2-C6alkyl, (R4)$_2$N—C2-C6alkylN(R4)-(CH$_2$)$_q$, R5-C2-C6alkylN(R4)-(CH$_2$)$_q$, (R4)$_2$N—C2-C6alkylO-(CH$_2$)$_q$, R5-C2-C6alkyl-O—(CH$_2$)$_q$, —(CH$_2$)$_q$N(R4)C(O)R8, aryl, arylC1-C6alkyl, heteroaryl, heteroarylC1-C6alkyl, heterocyclyl, heterocyclylC1-C6alkyl, aryloxyC2-C6alkyl, heteroaryloxyC2-C6alkyl, heterocyclyloxyC2-C6alkyl, arylaminoC2-C6alkyl, heteroarylaminoC2-C6alkyl, and heterocyclylaminoC2-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom of R13 may cyclize to form a C3-C7 heterocyclyl ring;

each R14 is independently and respectively selected from the group consisting of H and C1-C6alkyl;

wherein Z1' is independently and individually selected from the group consisting of H, C1-C6alkyl, C3-C7cycloalkyl, hydroxyC1-C6alkyl, C1-C6alkoxyC1-C6alkyl, (R4)$_2$N—C1-C6alkyl, (R4)$_2$N—C2-C6alkylN(R4)-(CH$_2$)$_p$, (R4)$_2$N—C2-C6alkylO-(CH$_2$)$_p$, (R4)$_2$N—CO—C1-C6alkyl, carboxyC1-C6alkyl, C1-C6alkoxycarbonylC1-C6alkyl, —(CH$_2$)$_p$N(R4)C(O)R8, aryl, arylC1-C6alkyl, heteroaryl, heteroarylC1-C6alkyl, heterocyclyl, heterocyclylC1-C6alkyl, aryloxyC1-C6alkyl, heteroaryloxyC1-C6alkyl, heterocyclyloxyC1-C6alkyl, arylaminoC1-C6alkyl, heteroarylaminoC1-C6alkyl, or heterocyclylaminoC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom of Z1' may cyclize to form a C3-C7 heterocyclyl ring;

each Z3 is independently and individually selected from the group consisting of H, C1-C6alkyl, hydroxyl, hydroxyC1-C6alkyl, cyano, C1-C6alkoxy, C1-C6alkoxyC1-C6alkyl, halogen, CF$_3$, (R3)$_2$N—, (R4)$_2$N—, (R4)$_2$NC1-C6alkyl, (R4)$_2$NC2-C6alkylN(R4)-(CH$_2$)$_n$, (R4)$_2$NC2-C6alkylO-(CH$_2$)$_n$, R8CO—, (R4)$_2$N—CO—C1-C6alkyl, carboxyl, carboxyC1-C6alkyl, C1-C6alkoxycarbonyl, C1-C6alkoxycarbonylC1-C6alkyl, (R3)$_2$NSO$_2$, —SO$_2$R3, SOR3, (R4)$_2$NSO$_2$, —SO$_2$R4, —SOR4, —(CH$_2$)$_n$N(R4)C(O)R8, —C=(NOH)R6, —C=(NOR3)R6, heteroaryl, heterocyclyl, heteroarylC1-C6alkyl, heterocyclylC1-C6alkyl, heteroaryloxy, heterocyclyloxy, heteroaryloxyC1-C6alkyl, heterocyclyloxyC1-C6alkyl, arylamino, heteroarylamino, heterocyclylamino, arylaminoC1-C6alkyl, heteroarylaminoC1-C6alkyl, heterocyclylaminoC1-C6alkyl, or moieties of the formulae

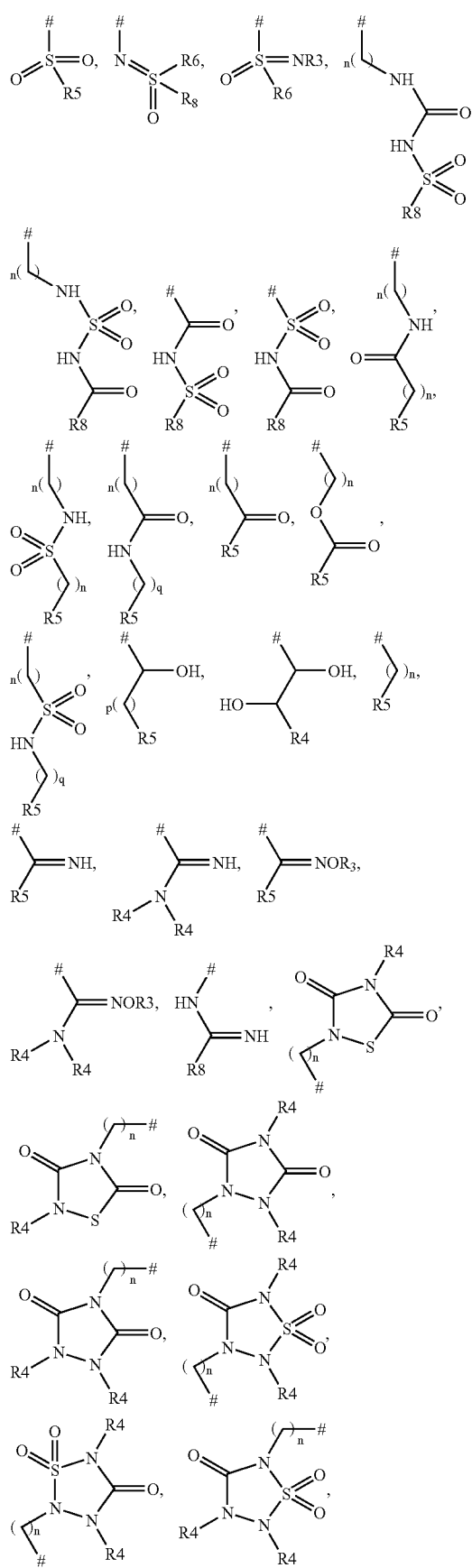
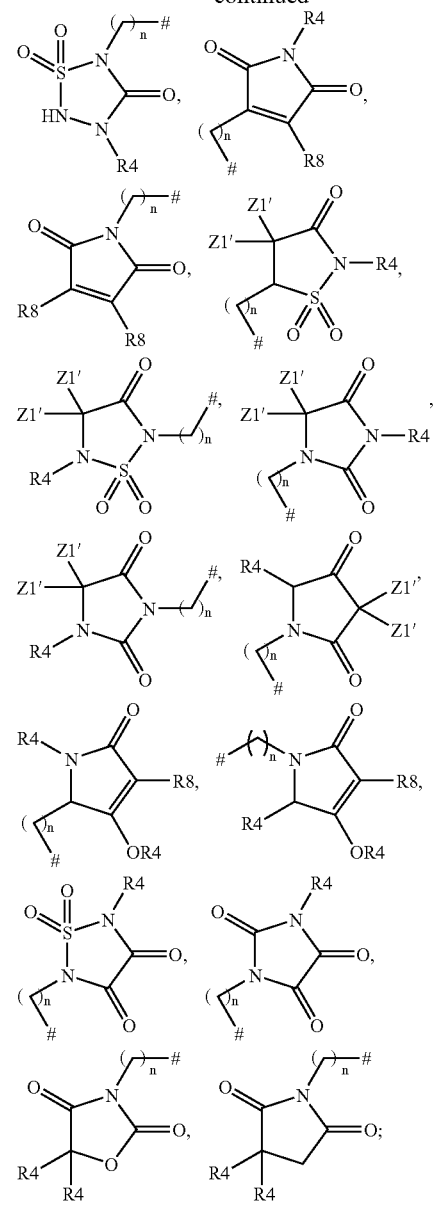

wherein the symbol (#) indicates the point of attachment of the Z3 moiety to the A2 ring of formula I;

in the event that Z3 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z3 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z3 may cyclize to form a C3-C7 heterocyclyl ring;

each Z4 is independently and individually selected from the group consisting of H, C1-C6alkyl, hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C2-C6alkyl, carboxyC2-

C6alkyl, C1-C6alkoxycarbonylC2-C6alkyl, —C2-C6alkylN(R4)C(O)R8, R8-C(=NR3)-, —SO₂R8, —COR8, heteroaryl, heteroarylC1-C6alkyl, heterocyclyl, heterocyclylC1-C6alkyl, heteroaryloxyC2-C6alkyl, heterocycyloxyC2-C6alkyl, arylaminoC2-C6alkyl, heteroarylaminoC2-C6alkyl, heterocyclylaminoC2-C6alkyl, and moieties of the formulae

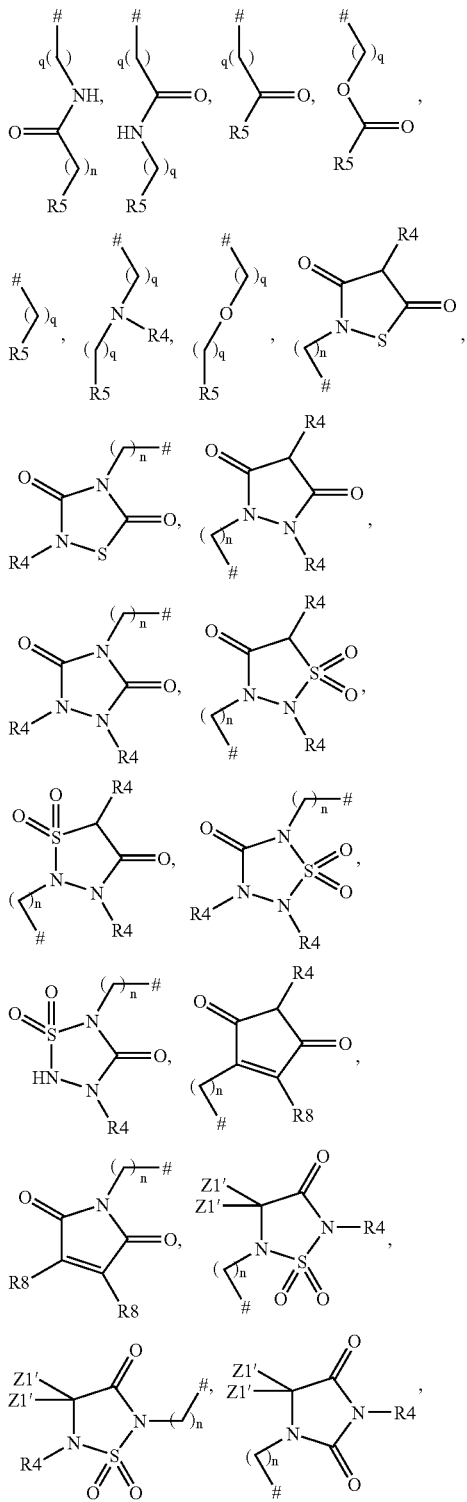

wherein the symbol (#) indicates the point of attachment of the Z4 moiety to the A2 ring for formula I;

in the event that Z4 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z4 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z4 may cyclize to form a C3-C7 heterocyclyl ring;

Z5 is independently and individually selected from the group consisting of H, C1-C6alkyl, branched C3-C7alkyl, halogen, fluoroalkyl, cyano, hydroxyl, alkoxy, oxo, aminocarbonyl, carbonylamino, aminosulfonyl, sulfonylamino, —N(R3)₂, —O—(CH₂)q-N(R4)₂, —N(R3)-(CH₂)q-N(R4)₂, —R5, —O—(CH₂)q-O-Alkyl, —O—(CH₂)q-N(R4)₂, —N(R3)-(CH₂)q-O-Alkyl, —N(R3)-(CH₂)q-N(R4)₂, —O—(CH₂)q-R5, and —N(R3)-(CH₂)q-R5;

wherein two R3 moieties are independently and individually taken from the group consisting of C1-C6alkyl and branched C3-C6alkyl and are attached to the same nitrogen heteroatom of Z5 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z5 may cyclize to form a C3-C7 heterocyclyl ring;

Each Z6 is independently and individually selected from the group consisting of H, C1-C6alkyl, branched C3-C7alkyl, hydroxyl, C1-C6alkoxy, (R3)₂N—, —N(R3)COR8, (R4)₂N—, —R5, —N(R4)COR8, —N(R3)SO₂R6-, —CON(R3)₂, —CON(R4)₂, —COR5, —SO₂NHR4, heteroaryl, heterocyclyl, heteroaryloxy, heterocyclyloxy, arylamino, heteroarylamino, and heterocyclylamino;

wherein two R3 moieties are independently and individually taken from the group consisting of C1-C6alkyl and branched C3-C6alkyl and are attached to the same nitrogen heteroatom of Z6 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z6 may cyclize to form a C3-C7 heterocyclyl ring;

and n is 0-4; p is 1-4; q is 2-6; r is 0 or 1; v is 1 or 2;

V, V1, and V2 are each independently and respectively selected from the group consisting of O and $H_2$;

and tautomers, diastereomers, geometric isomers, enantiomers, hydrates, prodrugs, and salts of any of the foregoing.

3.1.6b

The following specific compounds are most preferred: 1-(3-t-butyl-1-(3-hydroxy-2,3-dihydro-1H-inden-5-yl)-1H-pyrazol-5-yl)-3-(2,3-dichlorophenyl)urea, 1-(3-t-butyl-1-(3-(hydroxyimino)-2,3-dihydro-1H-inden-5-yl)-1H-pyrazol-5-yl)-3-(2,3-dichlorophenyl)urea, 1-(3-t-butyl-1-(1-methyl-1H-indol-5-yl)-1H-pyrazol-5-yl)-3-(2,3-dichlorophenyl)urea, 1-(3-t-butyl-1-(1H-indazol-5-yl)-1H-pyrazol-5-yl)-3-(2,3-dichlorophenyl)urea, 1-(3-t-butyl-1-(indolin-6-yl)-1H-pyrazol-5-yl)-3-(2,3-dichlorophenyl)urea, 1-(1-(1-acetylindolin-6-yl)-3-t-butyl 1 H-pyrazol-5-yl)-3-(2,3-dichlorophenyl)urea, 1-(3-t-butyl-1-(1-(methylsulfonyl)indolin-6-yl)-1H-pyrazol-5-yl)-3-(2,3-dichlorophenyl)urea, 1-(3-t-butyl-1-(indolin-5-yl)-1H-pyrazol-5-yl)-3-(2,3-dichlorophenyl)urea, 1-(3-t-butyl-1-(1-(methylsulfonyl)indolin-5-yl)-1H-pyrazol-5-yl)-3-(2,3-dichlorophenyl)urea, 1-(1-(4-(aminomethyl)naphthalen-2-yl)-3-t-butyl-1H-pyrazol-5-yl)-3-(2,3-dichlorophenyl)urea, 1-(3-t-butyl-1-(4-((1-methylsulfonylamino-1-oxo-methylamino)methyl)naphthalen-2-yl)-1H-pyrazol-5-yl)-3-(2,3-dichlorophenyl)urea, 2-(3-(3-t-butyl-5-(3-(2,3-dichlorophenyl)ureido)-1H-pyrazol-1-yl)naphthalen-1-yl)acetic acid, 1-(1-(4-(2-amino-2-oxoethyl)naphthalen-2-yl)-3-t-butyl-1H-pyrazol-5-yl)-3-(2,3-dichlorophenyl)urea, 1-(3-t-butyl-1-(4-(hydroxymethyl)naphthalen-2-yl)-1H-pyrazol-5-yl)-3-(2,3-dichlorophenyl)urea, 1-(3-t-butyl-1-(quinolin-6-yl)-1H-pyrazol-5-yl)-3-(2,3-dichlorophenyl)urea, 1-(3-t-butyl-1-(1,2,3,4-tetrahydroisoquinolin-6-yl)-1H-pyrazol-5-yl)-3-(2,3-dichlorophenyl)urea, 1-(3-t-butyl-1-(1-oxo-1,2,3,4-tetrahydroisoquinolin-6-yl)-1H-pyrazol-5-yl)-3-(2,3-dichlorophenyl)urea, 1-(3-t-butyl-1-(2-(methylsulfonyl)-1,2,3,4-tetrahydroisoquinolin-6-yl)-1H-pyrazol-5-yl)-3-(2,3-dichlorophenyl)urea, (3S)-6-(3-t-butyl-5-(3-(2,3-dichlorophenyl)ureido)-1H-pyrazol-1-yl)-1,2,3,4-tetrahydroisoquinoline-3-carboxylic acid, 1-(3-t-butyl-1-(3-carbamoyl-1,2,3,4-tetrahydroisoquinolin-6-yl)-1H-pyrazol-5-yl)-3-(2,3-dichlorophenyl)urea, 1-(3-t-butyl-1-(2-oxo-1,2,3,4-tetrahydroquinolin-6-yl)-1H-pyrazol-5-yl)-3-(2,3-dichlorophenyl)urea, 1-(3-t-butyl-1-(2-oxo-1,2-dihydroquinolin-6-yl)-1H-pyrazol-5-yl)-3-(2,3-dichlorophenyl)urea, 1-(3-t-butyl-1-(1-carbamimidoyl-1,2,3,4-tetrahydroquinolin-6-yl)-1H-pyrazol-5-yl)-3-(2,3-dichlorophenyl)urea, 1-(3-t-butyl-1-(2-oxo-2,3,4,5-tetrahydro-1H-benzo[d]azepin-7-yl)-1H-pyrazol-5-yl)-3-(2,3-dichlorophenyl)urea, 1-(3-t-butyl-1-(3-(methylsulfonyl)-2,3,4,5-tetrahydro-1H-benzo[d]azepin-7-yl)-1H-pyrazol-5-yl)-3-(2,3-dichlorophenyl)urea, 1-(3-t-butyl-1-(4-oxo-3,4-dihydroquinazolin-7-yl)-1H-pyrazol-5-yl)-3-(2,3-dichlorophenyl)urea, 1-(1-(4-(2-amino-2-oxoethyl)naphthalen-2-yl)-3-t-butyl-1H-pyrazol-5-yl)-3-(2,3,4-trifluorophenyl)urea, 1-(3-t-butyl-1-(quinolin-6-yl)-1H-pyrazol-5-yl)-3-(2,3,4-trifluorophenyl)urea, 1-(3-t-butyl-1-(2-oxo-1,2,3,4-tetrahydroquinolin-6-yl)-1H-pyrazol-5-yl)-3-(2,3,4-trifluorophenyl)urea, 1-(3-t-butyl-1-(2-oxo-1,2-dihydroquinolin-6-yl)-1H-pyrazol-5-yl)-3-(2,3,4-trifluorophenyl)urea, 1-(3-t-butyl-1-(1-(methylsulfonyl)indolin-5-yl)-1H-pyrazol-5-yl)-3-(2,4,5-trifluorophenyl)urea, 1-(3-t-butyl-1-(4-(hydroxymethyl)naphthalen-2-yl)-1H-pyrazol-5-yl)-3-(2,4,5-trifluorophenyl)urea, 1-(1-(4-(2-amino-2-oxoethyl)naphthalen-2-yl)-3-t-butyl-1H-pyrazol-5-yl)-3-(2,4,5-trifluorophenyl)urea, 1-(3-t-butyl-1-(4-(2-(2,3-dihydroxypropylamino)-2-oxoethyl)naphthalen-2-yl)-1H-pyrazol-5-yl)-3-(2,4,5-trifluorophenyl)urea, 1-(1-(4-(aminomethyl)naphthalen-2-yl)-3-t-butyl-1H-pyrazol-5-yl)-3-(2,4,5-trifluorophenyl)urea, 1-(3-t-butyl-1-(4-((1-amino-1-oxo-methylamino)methyl)naphthalen-2-yl)-1H-pyrazol-5-yl)-3-(2,4,5-trifluorophenyl)urea, 1-(3-t-butyl-1-(quinolin-6-yl)-1H-pyrazol-5-yl)-3-(2,4,5-trifluorophenyl)urea, 1-(3-t-butyl-1-((3S)-3-carbamoyl-1,2,3,4-tetrahydroisoquinolin-7-yl)-1H-pyrazol-5-yl)-3-(2,4,5-trifluorophenyl)urea, 1-(3-t-butyl-1-(1,2,3,4-tetrahydroisoquinolin-6-yl)-1H-pyrazol-5-yl)-3-(2,4,5-trifluorophenyl)urea, 1-(3-t-butyl-1-(2-oxo-1,2,3,4-tetrahydroquinolin-6-yl)-1H-pyrazol-5-yl)-3-(2,4,5-trifluorophenyl)urea, 1-(3-t-butyl-1-(1-(methylsulfonyl)indolin-5-yl)-1H-pyrazol-5-yl)-3-(2,3,5-trifluorophenyl)urea, 1-(3-t-butyl-1-(4-(2-(2,3-dihydroxypropylamino)-2-oxoethyl)naphthalen-2-yl)-1H-pyrazol-5-yl)-3-(2,3,5-trifluorophenyl)urea, 1-(3-t-butyl-1-(4-(hydroxymethyl)naphthalen-2-yl)-1H-pyrazol-5-yl)-3-(2,3,5-trifluorophenyl)urea, 1-(3-t-butyl-1-(quinolin-6-yl)-1H-pyrazol-5-yl)-3-(2,3,5-trifluorophenyl)urea, 1-(3-t-butyl-1-(2-oxo-1,2-dihydroquinolin-6-yl)-1H-pyrazol-5-yl)-3-(2,3,5-trifluorophenyl)urea, 1-(1-(4-(2-amino-2-oxoethyl)naphthalen-2-yl)-3-t-butyl 1 H-pyrazol-5-yl)-3-(3,4,5-trifluorophenyl)urea, 1-(3-t-butyl-1-(4-(hydroxymethyl)naphthalen-2-yl)-1H-pyrazol-5-yl)-3-(3,5-difluorophenyl)urea, 1-(3-t-butyl-1-(1-(methylsulfonyl)indolin-5-yl)-1H-pyrazol-5-yl)-3-(2,3-difluorophenyl)urea, 1-(3-t-butyl-1-(4-(hydroxymethyl)naphthalen-2-yl)-1H-pyrazol-5-yl)-3-(2,3-difluorophenyl)urea, 1-(1-(4-(2-amino-2-oxoethyl)naphthalen-2-yl)-3-t-butyl-1H-pyrazol-5-yl)-3-(2,3-difluorophenyl)urea, 1-(3-t-butyl-1-(2-oxo-1,2,3,4-tetrahydroquinolin-6-yl)-1H-pyrazol-5-yl)-3-(2,3-difluorophenyl)urea, 1-(3-t-butyl-1-(4-(hydroxymethyl)naphthalen-2-yl)-1H-pyrazol-5-yl)-3-(2,4-difluorophenyl)urea, 1-(1-(4-(2-amino-2-oxoethyl)naphthalen-2-yl)-3-t-butyl-1H-pyrazol-5-yl)-3-(2,4-difluorophenyl)urea, 1-(3-t-butyl-1-(2-oxo-1,2-dihydroquinolin-6-yl)-1H-pyrazol-5-yl)-3-(2,4-difluorophenyl)urea, 1-(1-(4-(2-amino-2-oxoethyl)naphthalen-2-yl)-3-t-butyl-1H-pyrazol-5-yl)-3-(4-fluorophenyl)urea, 1-(3-t-butyl-1-(1,2,3,4-tetrahydroisoquinolin-6-yl)-1H-pyrazol-5-yl)-3-(3-phenoxyphenyl)urea, 1-(3-t-butyl-1-(2-oxo-1,2,3,4-tetrahydroquinolin-6-yl)-1H-pyrazol-5-yl)-3-(3-phenoxyphenyl)urea, 1-(3-t-butyl-1-(1H-indol-5-yl)-1H-pyrazol-5-yl)-3-(3-(pyridin-3-yloxy)phenyl)urea, 1-(1-(4-(2-amino-2-oxoethyl)naphthalen-2-yl)-3-t-butyl-1H-pyrazol-5-yl)-3-(3-(pyridin-3-yloxy)phenyl)urea, 1-(3-t-butyl-1-(4-(hydroxymethyl)naphthalen-2-yl)-1H-pyrazol-5-yl)-3-(3-(pyridin-3-yloxy)phenyl)urea, 1-(1-(4-(aminomethyl)naphthalen-2-yl)-3-t-butyl-1H-pyrazol-5-yl)-3-(3-(pyridin-3-yloxy)phenyl)urea, 1-(3-t-butyl-1-(1,2,3,4-tetrahydroisoquinolin-6-yl)-1H-pyrazol-5-yl)-3-(3-(5-chloropyridin-3-yloxy)phenyl)urea, 1-(3-t-butyl-1-(2-oxo-1,2-dihydroquinolin-6-yl)-1H-pyrazol-5-yl)-3-(3-(pyridin-3-yloxy)phenyl)urea, 1-(3-t-butyl-1-(1,2,3,4-tetrahydroisoquinolin-6-yl)-1H-pyrazol-5-yl)-3-(4-(2-(methylcarbamoyl)pyridin-4-yloxy)phenyl)urea, 1-(3-t-butyl-1-(2-oxo-1,2-dihydroquinolin-6-yl)-1H-pyrazol-5-yl)-

3-(4-(2-(methylcarbamoyl)pyridin-4-yloxy)phenyl)urea, 1-(1-(2-(2-aminoethylamino)quinolin-6-yl)-3-t-butyl-1H-pyrazol-5-yl)-3-(4-(2-(methylcarbamoyl)pyridin-4-yloxy)phenyl)urea, 1-(3-cyclopentyl-1-(2-oxo-1,2-dihydroquinolin-6-yl)-1H-pyrazol-5-yl)-3-(4-(2-(methylcarbamoyl)pyridin-4-yloxy)phenyl)urea, 1-(3-t-butyl-1-(2-(dimethylamino)quinolin-6-yl)-1H-pyrazol-5-yl)-3-(4-(2-(methylcarbamoyl)pyridin-4-yloxy)phenyl)urea, 1-(1-(2-aminoquinolin-6-yl)-3-t-butyl-1 H-pyrazol-5-yl)-3-(4-(2-(methylcarbamoyl)pyridin-4-yloxy)phenyl)urea, 1-(3-t-butyl-1-(2-(methylamino)quinolin-6-yl)-1H-pyrazol-5-yl)-3-(4-(2-(methylcarbamoyl)pyridin-4-yloxy)phenyl)urea, 1-(3-t-butyl-1-(2-oxo-1,2-dihydroquinolin-6-yl)-1H-pyrazol-5-yl)-3-(3-(2-(methylcarbamoyl)pyridin-4-yloxy)phenyl)urea, 1-(3-t-butyl-1-(1,2,3,4-tetrahydroisoquinolin-6-yl)-1H-pyrazol-5-yl)-3-(3-(8-methyl-7-oxo-7,8-dihydropyrido[2,3-d]pyrimidin-6-yl)phenyl)urea, 1-(3-t-butyl-1-(2-oxo-1,2,3,4-tetrahydroquinolin-6-yl)-1H-pyrazol-5-yl)-3-(3-(8-methyl-7-oxo-7,8-dihydropyrido[2,3-d]pyrimidin-6-yl)phenyl)urea, 1-(3-cyclopentyl-1-(2-oxo-1,2-dihydroquinolin-6-yl)-1H-pyrazol-5-yl)-3-(3-(8-methyl-7-oxo-7,8-dihydropyrido[2,3-d]pyrimidin-6-yl)phenyl)urea, 1-(3-t-butyl-1-(2-oxo-1,2-dihydroquinolin-6-yl)-1H-pyrazol-5-yl)-3-(3-(8-methyl-7-oxo-7,8-dihydropyrido[2,3-d]pyrimidin-6-yl)phenyl)urea, 1-(3-t-butyl-1-(3-carbamoyl-1,2,3,4-tetrahydroisoquinolin-6-yl)-1H-pyrazol-5-yl)-3-(3-(8-methyl-7-oxo-7,8-dihydropyrido[2,3-d]pyrimidin-6-yl)phenyl)urea, 1-(3-t-butyl-1-(indolin-5-yl)-1H-pyrazol-5-yl)-3-(3-(8-methyl-7-oxo-7,8-dihydropyrido[2,3-d]pyrimidin-6-yl)phenyl)urea, 1-(3-t-butyl-1-(1-(methylsulfonyl)indolin-5-yl)-1H-pyrazol-5-yl)-3-(3-(8-methyl-7-oxo-7,8-dihydropyrido[2,3-d]pyrimidin-6-yl)phenyl)urea, 1-(3-t-butyl-1-(1H-indol-5-yl)-1H-pyrazol-5-yl)-3-(3-(8-methyl-7-oxo-7,8-dihydropyrido[2,3-d]pyrimidin-6-yl)phenyl)urea, 1-(3-cyclopentyl-1-(2-oxo-1,2,3,4-tetrahydroquinolin-6-yl)-1H-pyrazol-5-yl)-3-(3-(8-methyl-7-oxo-7,8-dihydropyrido[2,3-d]pyrimidin-6-yl)phenyl)urea, 1-(3-t-butyl-1-(1,2,3,4-tetrahydroisoquinolin-6-yl)-1H-pyrazol-5-yl)-3-(4-methyl-3-(4-(pyridin-3-yl)pyrimidin-2-ylamino)phenyl)urea.

3.1.7 Methods
3.1.7a Methods of Protein Modulation

The invention includes methods of modulating kinase activity of RAF kinases and other kinases in the RAS-RAF-MEK-ERK-MAP kinase pathway including, but not limited to, A-Raf, B-Raf, and C-Raf. The kinases may be wildtype kinases, oncogenic forms thereof, aberrant fusion proteins thereof or polymorphs of any of the foregoing. The method comprises the step of contacting the kinase species with compounds of the invention and especially those set forth in sections 3.1 and 3.1.6a. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, kinase cellular localization, and recruitment of other proteins into signaling complexes through modulation of kinase conformation.

3.1.7b Treatment Methods

The methods of the invention also include treating individuals suffering from a condition selected from the group consisting of cancer and hyperproliferative diseases. These methods comprise administering to such individuals compounds of the invention, and especially those of section 3.1 and 3.1.6a. condition being melanomas, glioblastomas, ovarian cancer, pancreatic cancer, prostate cancer, lung cancers, breast cancers, kidney cancers, cervical carcinomas, metastisis of primary solid tumor secondary sites, ocular diseases characterized by hyperproliferation leading to blindness including various retinopathies including diabetic retinopathy and age-related macular degeneration, rheumatoid arthritis characterized by the in-growth of a vascularized pannus, or a disease caused by a mutation in the RAS-RAF-MEK-ERK-MAP kinase pathway. The administration method is not critical, and may be from the group consisting of oral, parenteral, inhalation, and subcutaneous.

3.1.8 Pharmaceutical Preparations

The compounds of the invention, especially those of 3.1 and 3.1.6a may form a part of a pharmaceutical composition by combining one or more such compounds with a pharmaceutically acceptable carrier. Additionally, the compositions may include an additive selected from the group consisting of adjuvants, excipients, diluents, and stablilizers.

3.1.9 Kinase/Compound Adducts

The invention also provides adducts in the form of compounds of the invention bound with a species of kinase such as a wild-type kinase, oncogenic forms thereof, aberrant fusion proteins thereof and polymorphs of any of the foregoing. The compounds are advantageously selected from the groups defined in sections 3.1 and 3.1.6a.

3.2 Generally—Monocyclic A2 Compounds with Polycyclic E2 Rings

The invention includes compounds of the formula I as defined in section 2.2, wherein each R2 is independently and individually selected from the group consisting of C1-C6alkyl, branched C3-C7alkyl, C1-C6fluoroalkyl, wherein the alkyl group is partially or fully fluorinated, monocyclic heteroaryl, and R19 substituted C3-C8carbocyclyl wherein R19 is H, and C1-C6alkyl;

3.2.1 Preferred D Moieties
3.2.1a

Preferably, the compounds of formula I in 3.2 contain D moieties wherein E1 and E2 are as defined in section 1.2.1
3.2.1b Additionally preferred D moieties of formula I in 3.2 are as defined in section 1.2.1b
3.2.1c More preferred D moieties of 3.2.1b are where E2 is defined as in section 1.2.1c 3.2.2 Preferred A2 Moieties
3.2.2a Compounds of Formula I as defined above in section 3.2 have preferred A2 moieties as defined in section 2.2.2a;
3.2.2b More preferred A2 moieties are selected from the group consisting of

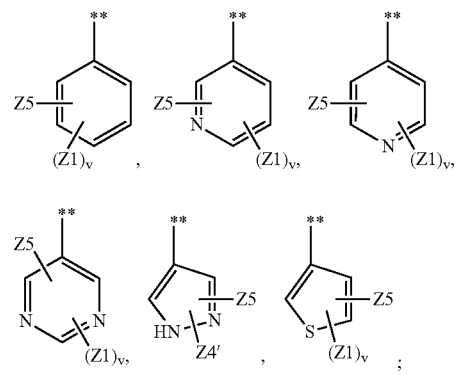

and wherein the symbol (**) is the point of attachment to the A1 ring for formula I.

3.2.2c

Even more preferred A2 moieties are selected from the group consisting of

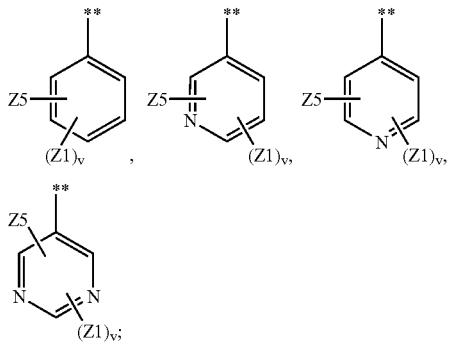

and wherein the symbol (**) is the point of attachment to the A1 ring of formula I.

3.2.3 Preferred Classes of Compounds 3.2.3a

Compounds as defined in 3.2.1a wherein the A2 group is defined in 3.2.2a.

3.2.3b

Compounds as defined in 3.2.3a wherein the A2 group is defined in 3.2.2b.

3.2.3c

Compounds as defined in 3.2.3a wherein the A2 group is defined in 3.2.2c.

3.2.3d

Compounds as defined in 3.2.1b wherein the A2 group is defined in 3.2.2a.

3.2.3e

Compounds as defined in 3.2.3c wherein the A2 group is defined in 3.2.2b.

3.2.3f

Compounds as defined in 3.2.3c wherein the A2 group is defined in 3.2.2c.

3.2.4 Preferred A1 Moieties 3.2.4a

These preferred A1 moieties are defined in 3.1.4a.

3.2.4b

These more preferred A1 moieties are defined in 3.1.4b.

3.2.4c

These even more preferred A1 moieties are defined in 3.1.4c.

3.2.5 Preferred W and Y Moieties 3.2.5a (1) W and Y are each NH, and X=O; (2) W=NH, Y=CHR4 and X=O; or (3) W=CHR4, Y=NH, and X=O.

3.2.5b

W and Y are each NH and X=O.

3.2.6 Further Preferred Compounds 3.2.6a

Further preferred compounds are of the formula

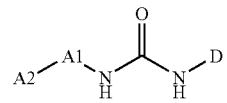

I wherein A2 is selected from the group consisting of

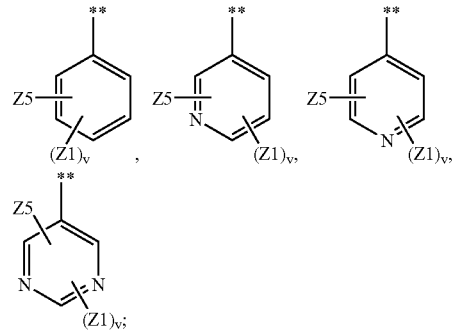

wherein the symbol (**) denotes the attachment to the A1 moiety of formula I;

A1 is selected from the group consisting of

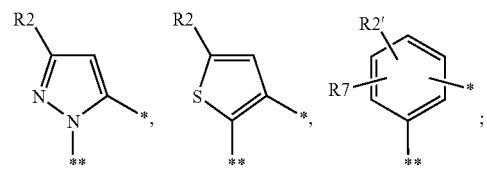

wherein the symbol (*) denotes the attachment to the W moiety of formula I and the symbol (**) denotes the attachment to the A2 moiety of formula I;

X is O, S, or NR3;

D comprises a member of

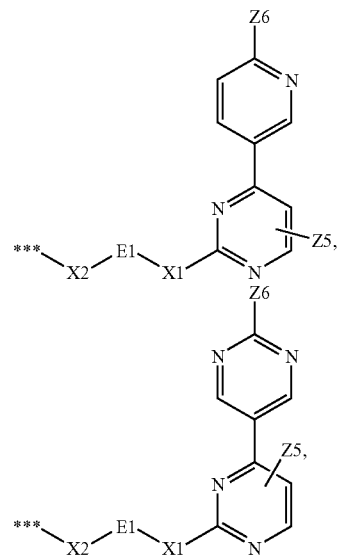

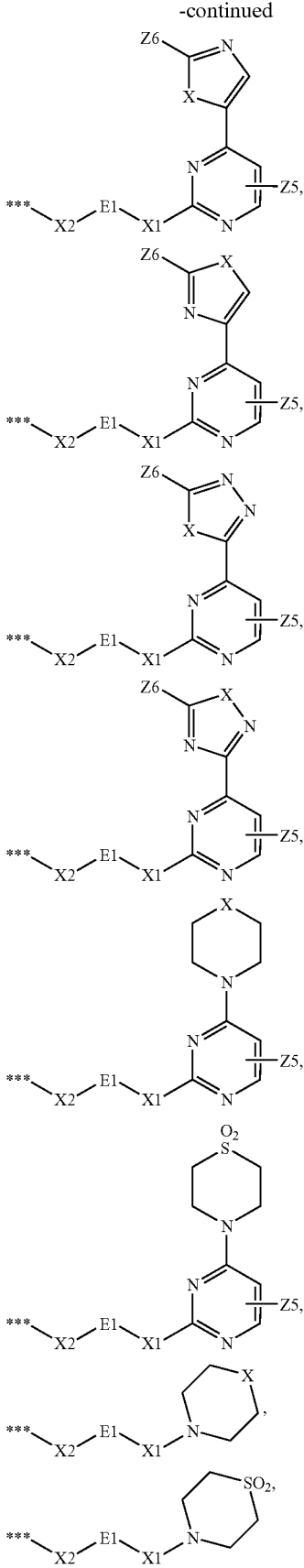

-continued

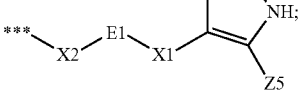

wherein E1 is selected from the group consisting cyclopropyl, cyclobutyl, cyclopentyl, cyclohexyl, pyrrolidinyl piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl and naphthyl;

wherein the symbol (***) denotes the attachment to the Y moiety of formula I;

X1 is selected from the group consisting of O, S, NR3, —C(=O)—, —O—(CH₂)n-, —S—(CH₂)n-, —NR3-(CH₂)n-, —O—(CH₂)q-O—, —O—(CH₂)q-NR3-, —N(R3)-(CH₂)q-N(R3)-, —(CH₂)n-N(R4)-C(=O)—, —(CH₂)n-N(R4)-C(=O)(CH₂)n-, —(CH₂)n-CO—N(R4)-, —(CH₂)p-, C2-C5alkenyl, C2-C5alkynyl, C3-C6cycloalkyl, and a direct bond wherein the E1 ring and the E2 ring are directly linked by a covalent bond;

and wherein the carbon atoms of —(CH2)n-, —(CH2)q-, (CH2)p, C2-C5alkenyl, and C2-C5alkynyl moieties of X1 may be further substituted by one or more C1-C6alkyl;

X2 is selected from the group consisting of C1-C6 alkyl, C3-C6 branched alkyl, or a direct bond wherein E1 is directly linked to the Y group of formula I;

Each R2 is independently and individually selected from the group consisting of C1-C6alkyl, branched C3-C7alkyl, C1-C6fluoroalkyl, wherein the alkyl group is partially or fully fluorinated, monocyclic heteroaryl, and R19 substituted C3-C8carbocyclyl wherein R19 is H, and C1-C6alkyl;

each R2' is selected from the group consisting of halogen and R2;

each R3 is independently and individually selected from the group consisting of H, C1-C6alkyl, branched C3-C7alkyl, C3-C7carbocyclyl, or phenyl;

wherein two R3 moieties independently and individually taken from the group consisting of C1-C6alkyl and branched C3-C7alkyl are attached to the same nitrogen heteroatom, the two R3 moieties may cyclize to form a C3-C7 heterocyclyl ring;

each R4 is selected from the group consisting of H, C1-C6alkyl, hydroxyC1-C6 alkyl, dihydroxyC1-C6alkyl, C1-C6alkoxyC1-C6alkyl, branched C3-C7alkyl, branched hydroxyC1-C6 alkyl, branched C1-C6alkoxyC1-C6alkyl, branched dihydroxyC1-C6alkyl, carbocyclyl, hydroxyl substituted carbocyclyl, alkoxy substituted carbocyclyl, dihydroxy substituted carbocyclyl, phenyl, heteroaryl, heterocyclyl, phenylC1-C6alkyl, heteroarylC1-C6alkyl, and heterocyclylC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom may cyclize to form a C3-C7 heterocyclyl ring;

each R5 is independently and individually selected from the group consisting of

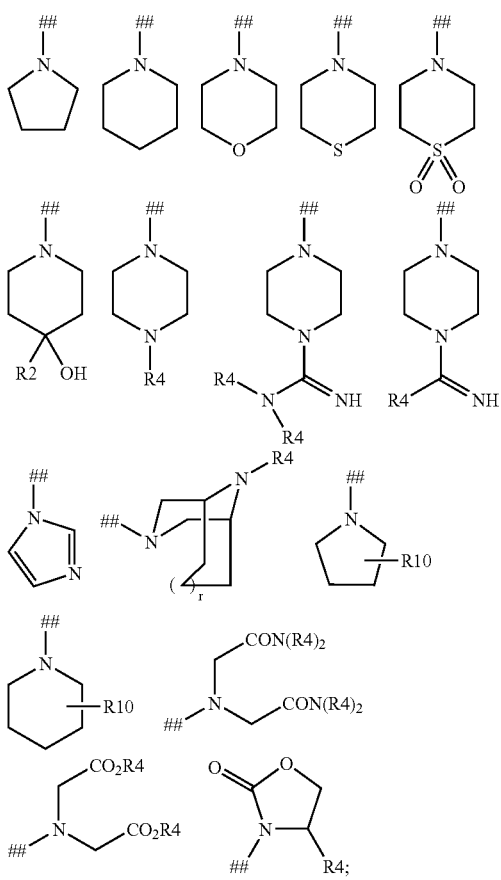

each R10 is independently and individually selected from the group consisting of $CO_2H$, $CO_2C1$-C6alkyl, $CO$—$N(R4)_2$, OH, C1-C6alkoxy, —$N(R4)_2$;

wherein two R4 moieties independently and individually taken from the group consisting of C1-C6alkyl, branched C3-C6alkyl, hydroxyalkyl, and alkoxyalkyl and are attached to the same nitrogen heteroatom of R10 may cyclize to form a C3-C7 heterocyclyl ring;

each Z1 is a substituent attached to a ring carbon and is independently and individually selected from the group consisting of hydroxyC1-C6alkyl, C2-C6alkoxy, C1-C6alkoxyC1-C6alkyl, $(R4)_2NC1$-C6alkyl, $(R4)_2NC2$-C6alkylN(R4)-$(CH_2)_n$, $(R4)_2NC2$-C6alkylO-$(CH_2)_n$, $(R3)_2N$—$C(=O)$—, $(R4)_2N$—$C(=O)$—, $(R4)_2N$—CO—C1-C6alkyl, C1-C6alkoxycarbonyl, carboxyC1-C6alkyl, C1-C6alkoxycarbonylC1-C6alkyl, $(R3)_2NSO_2$, SOR3, $(R4)_2NSO_2$, —$SO_2R3'$, —SOR4, —$C(=O)R6$, —$C(=NOH)R6$, —$C(=NOR3)R6$, —$(CH_2)_nN(R4)C(O)R8$, monocyclic heteroaryl, monocyclic heterocyclyl, monocyclic heteroarylC1-C6alkyl, monocyclic heterocyclylC1-C6alkyl, monocyclic heteroaryloxy, monocyclic heterocyclyloxy, monocyclic heteroaryloxyC1-C6alkyl, monocyclic heterocyclyloxyC1-C6alkyl, arylamino, monocyclic heteroarylamino, monocyclic heterocyclylamino, arylaminoC1-C6alkyl, monocyclic heteroarylaminoC1-C6alkyl, monocyclic heterocyclylaminoC1-C6alkyl, or moieties of the formulae

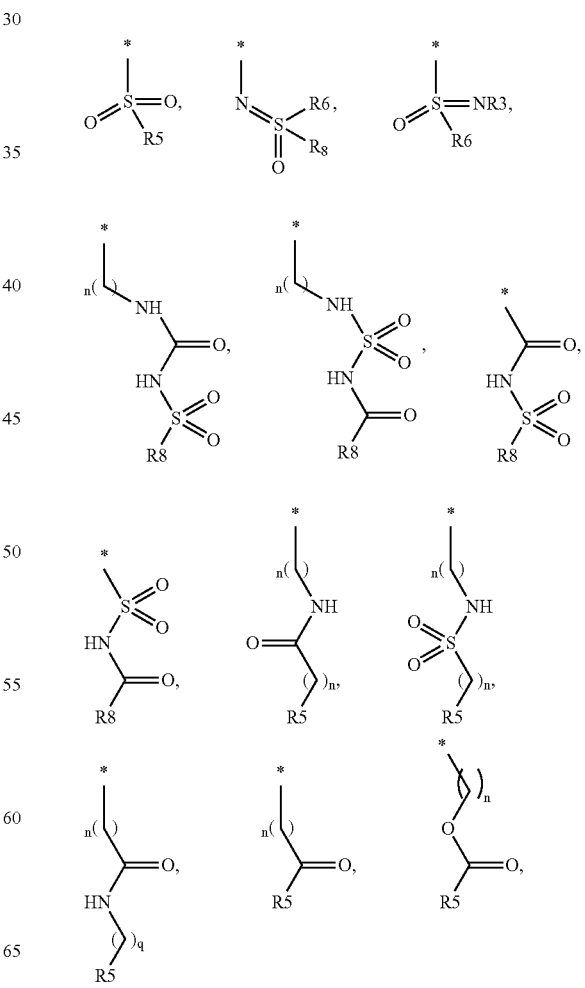

and wherein the symbol (##) is the point of attachment to respective R8, R10, Z1, Z4, Z5, Z6 or A2 ring moieties containing a R5 moiety;

wherein two R4 moieties independently and individually taken from the group consisting of C1-C6alkyl, branched C3-C6alkyl, hydroxyalkyl, and alkoxyalkyl and are attached to the same nitrogen heteroatom of R5 may cyclize to form a C3-C7 heterocyclyl ring;

wherein each R6 is independently and individually selected from the group consisting of C1-C6alkyl, branched C3-C7alkyl, carbocyclyl, phenyl, heteroaryl, and heterocyclyl;

each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

each R8 is independently and individually selected from the group consisting of C1-C6alkyl, C1-C6 fluoroalkyl wherein the alkyl moiety is partially or fully fluorinated, branchedC4-C7alkyl, carbocyclyl, phenyl, C1-C6phenylalkyl, heteroaryl or heteroarylC1-C6alkyl, heterocyclyl, heterocyclylC1-C6alkyl, OH, C1-C6alkoxy, $N(R3)_2$, $N(R4)_2$, or R5;

wherein two R3 moieties are independently and individually taken from the group consisting of C1-C6alkyl and branched C3-C6alkyl and are attached to the same nitrogen heteroatom of R8 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of R8 may cyclize to form a C3-C7 heterocyclyl ring;

-continued

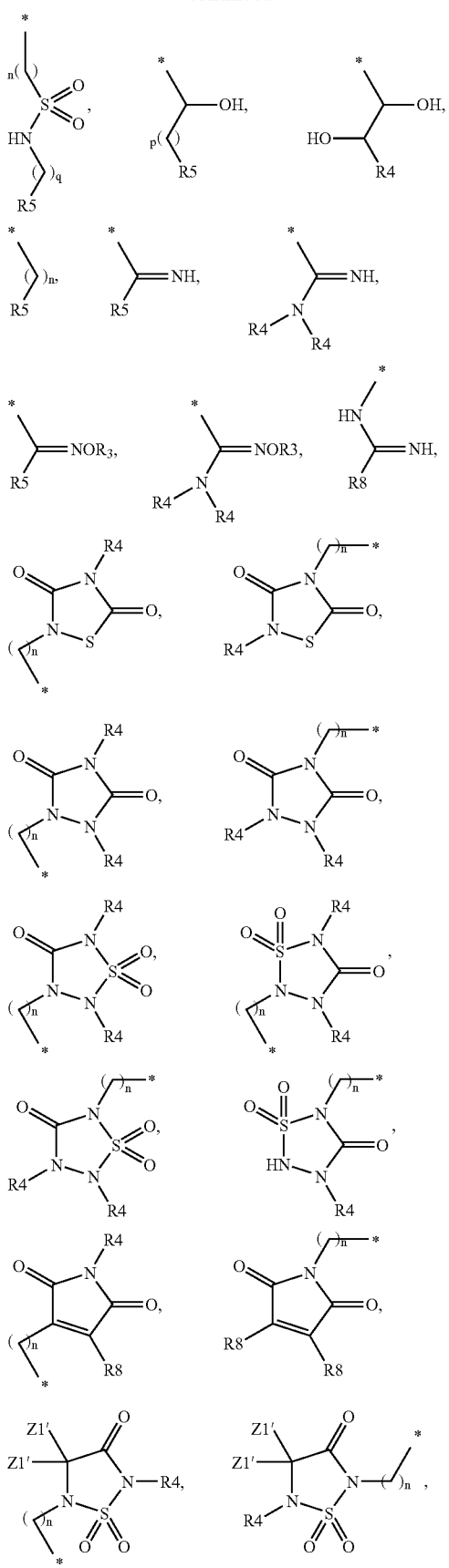
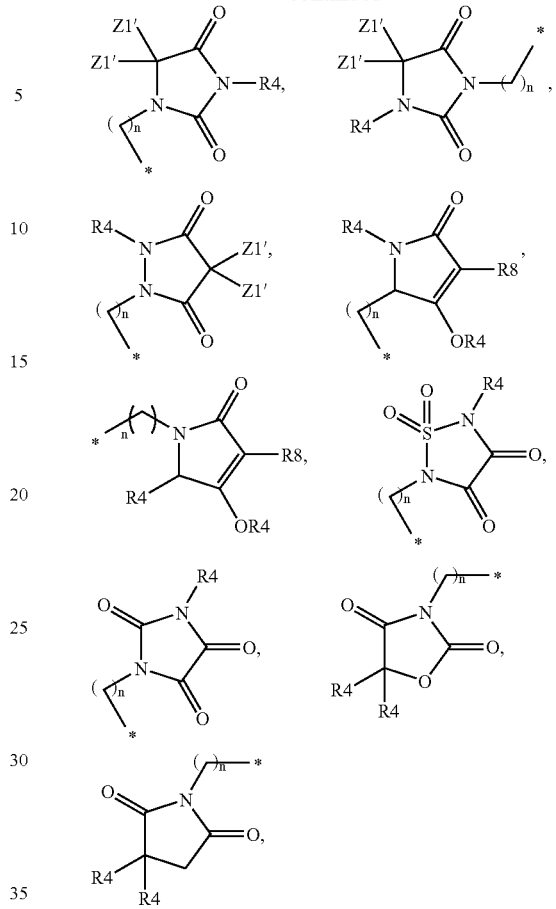

cyano wherein the site of attachment to the A2 ring is meta to the point of attachment to the A1 ring and wherein A2 is phenyl, and cyano wherein the site of the attachment is to a substitutable position when A2 is pyridyl, pyrimidinyl or a five-membered ring;

In the foregoing definition of Z1, alkyl moieties may optionally be substituted by one or more C1-C6alkyl;

Wherein the asterisk (*) indicates the point of attachment of the Z1 moiety to the A2 ring;

in the event that Z1 contains an alkyl or alkylene moiety, such moieties may be further substituted with one or more C1-C6alkyls;

In the foregoing definition of Z1, alkyl moieties may optionally be substituted by one or more C1-C6alkyl;

Wherein the asterisk (*) indicates the point of attachment of the Z1 moiety to the A2 ring;

in the event that Z1 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z1 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z1 may cyclize to form a C3-C7 heterocyclyl ring;

wherein Z1' is independently and individually selected from the group consisting of H, C1-C6alkyl, C3-C7cycloalkyl, hydroxyC1-C6alkyl, C1-C6alkoxyC1-C6alkyl, (R4)$_2$N—C1-C6alkyl, (R4)$_2$N—C2-C6alkylN(R4)-(CH$_2$)$_p$, (R4)$_2$N—C2-C6alkylO-(CH$_2$)$_p$, (R4)$_2$N—CO—C1-C6alkyl, carboxyC1-C6alkyl, C1-C6alkoxycarbonylC1-C6alkyl, —(CH$_2$)$_p$N(R4)C(O)R8, aryl, arylC1-C6alkyl, heteroaryl, heteroarylC1-C6alkyl, heterocyclyl, heterocyclylC1-C6alkyl, aryloxyC1-C6alkyl, heteroaryloxyC1-C6alkyl, heterocyclyloxyC1-C6alkyl, arylaminoC1-C6alkyl, heteroarylaminoC1-C6alkyl, or heterocyclylaminoC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom of Z1' may cyclize to form a C3-C7 heterocyclyl ring;

each Z4 is a substituent attached to a ring nitrogen and is independently and individually selected from the group consisting of H, C1-C6alkyl, hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C2-C6alkyl, carboxyC2-C6alkyl, C1-C6alkoxycarbonylC2-C6alkyl, —C2-C6alkylN(R4)C(O)R8, R8-C(=NR3)-, —SO$_2$R8, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

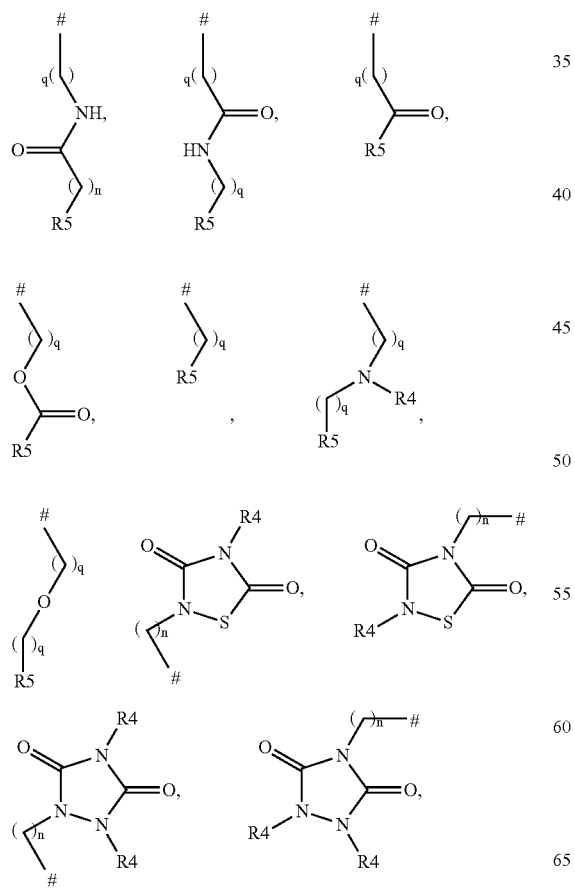
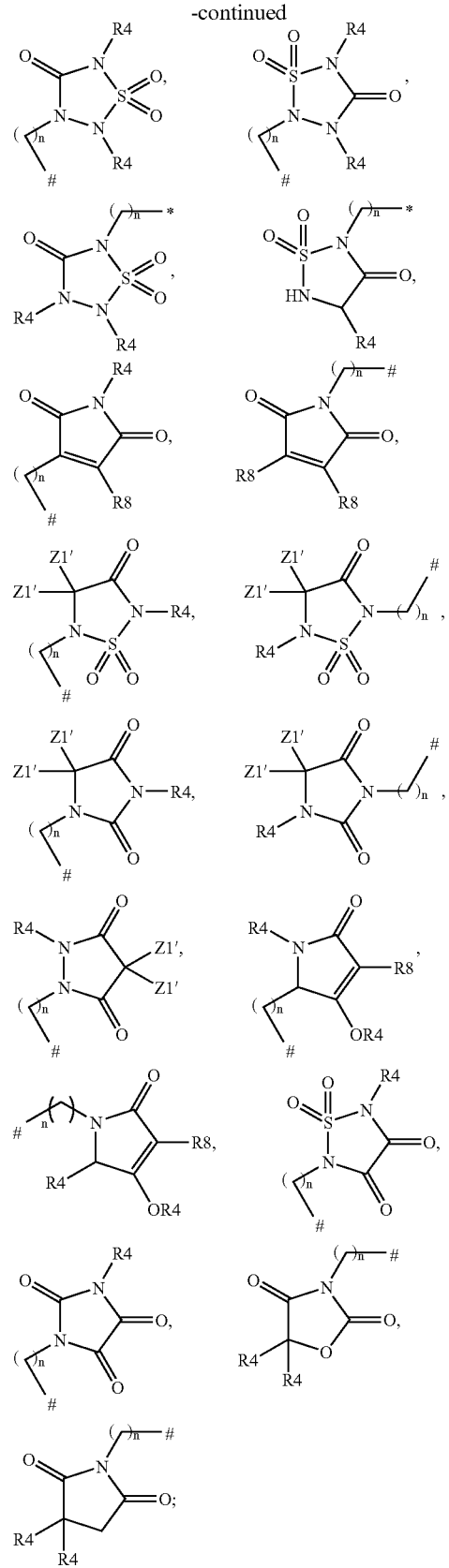

wherein the symbol (#) indicates the point of attachment of the Z4 moiety to the A2 ring for formula I;

in the event that Z4 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z4 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z4 may cyclize to form a C3-C7 heterocyclyl ring;

Z5 is independently and individually selected from the group consisting of H, C1-C6alkyl, branched C3-C7alkyl, halogen, fluoroalkyl, cyano, hydroxyl, alkoxy, oxo, aminocarbonyl, carbonylamino, aminosulfonyl, sulfonylamino, —N(R3)$_2$, —O—(CH$_2$)q-N(R4)$_2$, —N(R3)-(CH$_2$)q-N(R4)$_2$, —R5, —O—(CH$_2$)q-O-Alkyl, —O—(CH$_2$)q-N(R4)$_2$, —N(R3)-(CH$_2$)q-O-Alkyl, —N(R3)-(CH$_2$)q-N(R4)$_2$, —O—(CH$_2$)q-R5, and —N(R3)-(CH$_2$)q-R5;

wherein two R3 moieties are independently and individually taken from the group consisting of C1-C6alkyl and branched C3-C6alkyl and are attached to the same nitrogen heteroatom of Z5 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z5 may cyclize to form a C3-C7 heterocyclyl ring;

Each Z6 is independently and individually selected from the group consisting of H, C1-C6alkyl, branched C3-C7alkyl, hydroxyl, C1-C6alkoxy, (R3)$_2$N—, —N(R3)COR8, (R4)$_2$N—, —R5, —N(R4)COR8, —N(R3)SO$_2$R6-, —CON(R3)$_2$, —CON(R4)$_2$, —COR5, —SO$_2$NHR4, heteroaryl, heterocyclyl, heteroaryloxy, heterocyclyloxy, arylamino, heteroarylamino, and heterocyclylamino;

wherein two R3 moieties are independently and individually taken from the group consisting of C1-C6alkyl and branched C3-C6alkyl and are attached to the same nitrogen heteroatom of Z6 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z6 may cyclize to form a C3-C7 heterocyclyl ring;

and n is 0-4; p is 1-4; q is 2-6; r is 0 or 1; v is 1 or 2;

and tautomers, diastereomers, geometric isomers, enantiomers, hydrates, prodrugs and salts of any of the foregoing.

3.2.6b

The following specific compounds of Formula I are more preferred: 1-(1-(3-(2-amino-2-oxoethyl)phenyl)-3-t-butyl-1H-pyrazol-5-yl)-3-(4-methyl-3-(4-(pyridin-3-yl)pyrimidin-2-ylamino)phenyl)urea, 1-(3-t-butyl-1-(3-(2-(2,3-dihydroxypropylamino)-2-oxoethyl)phenyl)-1H-pyrazol-5-yl)-3-(4-methyl-3-(4-(pyridin-3-yl)pyrimidin-2-ylamino) phenyl)urea, 1-(2-(3-(2-amino-2-oxoethyl)phenyl)-5-t-butylthiophen-3-yl)-3-(4-(4-(pyridin-3-yl)pyrimidin-2-yloxy)phenyl)urea, 1-(3-t-butyl-1-(3-(2-(2,3-dihydroxypropylamino)-2-oxoethyl)phenyl)-1H-pyrazol-5-yl)-3-(4-(6-(thiazol-4-yl)pyrimidin-4-yloxy)phenyl)urea, 1-(1-(3-(2-amino-2-oxoethyl)phenyl)-3-t-butyl-1H-pyrazol-5-yl)-3-(3-(4-(pyridin-3-yl)pyrimidin-2-yloxy)phenyl)urea, 1-(1-(3-(2-amino-2-oxoethyl)phenyl)-3-t-butyl-1H-pyrazol-5-yl)-3-(3-(4-(isoxazol-4-yl)pyrimidin-2-ylamino)phenyl) urea 3.2.7 Methods 3.2.7a Methods of Protein Modulation The invention includes methods of modulating kinase activity of RAF kinases and other kinases in the RAS-RAF-MEK-ERK-MAP kinase pathway including, but not limited to, A-Raf, B-Raf, and C-Raf. The kinases may be wildtype kinases, oncogenic forms thereof, aberrant fusion proteins thereof or polymorphs of any of the foregoing. The method comprises the step of contacting the kinase species with compounds of the invention and especially those set forth in sections 3.2 and 3.2.6a. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, kinase cellular localization, and recruitment of other proteins into signaling complexes through modulation of kinase conformation.

3.2.7b Treatment Methods

The methods of the invention also include treating individuals suffering from a condition selected from the group consisting of cancer and hyperproliferative diseases. These methods comprise administering to such individuals compounds of the invention, and especially those of section 3.2 and 3.2.6a. condition being melanomas, glioblastomas, ovarian cancer, pancreatic cancer, prostate cancer, lung cancers, breast cancers, kidney cancers, cervical carcinomas, metastisis of primary solid tumor secondary sites, ocular diseases characterized by hyperproliferation leading to blindness including various retinopathies including diabetic retinopathy and age-related macular degeneration, rheumatoid arthritis characterized by the in-growth of a vascularized pannus, or a disease caused by a mutation in the RAS-RAF-MEK-ERK-MAP kinase pathway. The administration method is not critical, and may be from the group consisting of oral, parenteral, inhalation, and subcutaneous.

3.2.8 Pharmaceutical Preparations

The compounds of the invention, especially those of 3.2 and 3.2.6a may form a part of a pharmaceutical composition by combining one or more such compounds with a pharmaceutically acceptable carrier. Additionally, the compositions may include an additive selected from the group consisting of adjuvants, excipients, diluents, and stablilizers.

3.2.9 Kinase/Compound Adducts

The invention also provides adducts in the form of compounds of the invention bound with a species of kinase such as a wild-type kinase, oncogenic forms thereof, aberrant fusion proteins thereof and polymorphs of any of the foregoing. The compounds are advantageously selected from the groups defined in sections 3.2 and 3.2.6a.

3.3 Generally—Monocyclic A2 Compounds with Monocyclic E2 Rings

The invention includes compounds of the formula I as defined in section 2.3 wherein each R2 is independently and individually selected from the group consisting of C1-C6alkyl, branched C3-C7alkyl, C1-C6fluoroalkyl, wherein the alkyl group is partially or fully fluorinated, monocyclic heteroaryl, and R19 substituted C3-C8carbocyclyl wherein R19 is H, and C1-C6alkyl.

3.3.1 Preferred D Moieties 3.3.1a

Preferably, the compounds of formula I in 3.3 contain D moieties wherein E1 and E2 are as defined in section 1.3.1a.

3.3.1b
Additionally preferred D moieties of formula I in 3.3 are as defined in section 1.3.1b.

3.3.1c
More preferred D moieties of 3.2.1b are wherein E2 is defined as in section 1.3.1c.

3.3.2 Preferred A2 Moieties 3.3.2a
Compounds of Formula I as defined above in section 3.3 have preferred A2 moieties as defined in section 2.2.2a.

3.3.2b
More preferred A2 moieties are selected from the group consisting of

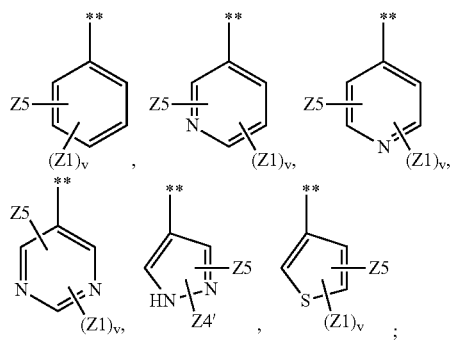

and wherein the symbol (**) is the point of attachment to the A1 ring for formula I.

3.3.2c
Even more preferred A2 moieties are selected from the group consisting of

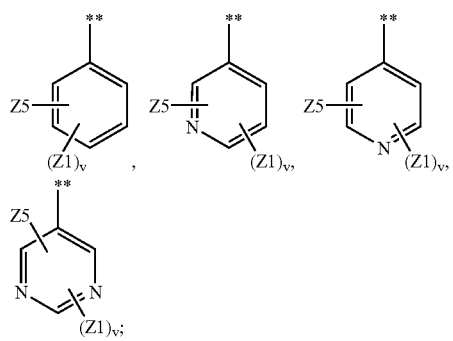

and wherein the symbol (**) is the point of attachment to the A1 ring of formula I.

3.3.3 Preferred Classes of Compounds 3.3.3a
Compounds as defined in 3.3.1a wherein the A2 group is defined in 3.3.2a.

3.3.3b
Compounds as defined in 3.3.3a wherein the A2 group is defined in 3.3.2b.

3.3.3c
Compounds as defined in 3.3.3a wherein the A2 group is defined in 3.3.2c.

3.3.3d
Compounds as defined in 3.3.1b wherein the A2 group is defined in 3.3.2a.

3.3.3e
Compounds as defined in 3.3.3c wherein the A2 group is defined in 3.3.2b.

3.3.3f
Compounds as defined in 3.3.3c wherein the A2 group is defined in 3.3.2c.

3.3.4 Preferred A1 Moieties 3.3.4a
These preferred A1 moieties are defined in 3.1.4a.

3.3.4b
These more preferred A1 moieties are defined in 3.1.4b.

3.3.4c
These even more preferred A1 moieties are defined in 3.1.4c.

3.3.5 Preferred W and Y Moieties 3.3.5a
(1) W and Y are each NH, and X=O; (2) W=NH, Y=CHR4 and X=O; or (3) W=CHR4, Y=NH, and X=O.

3.3.5b
W and Y are each NH and X=O.

3.3.6 Further Preferred Compounds 3.3.6a
Further preferred compounds are of the formula

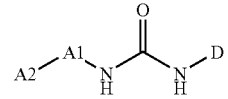

I wherein A2 is selected from the group consisting of

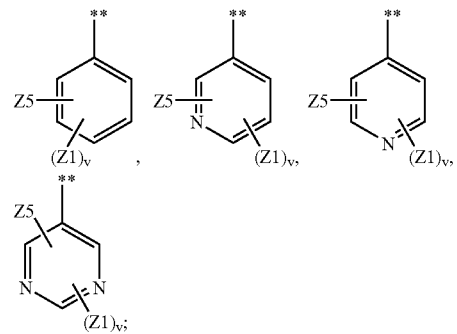

wherein the symbol (**) denotes the attachment to the A1 moiety of formula I;

A1 is selected from the group consisting of

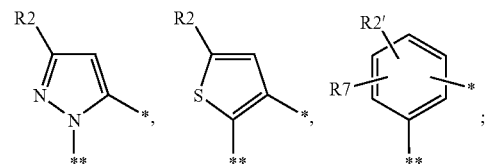

wherein the symbol (*) denotes the attachment to the W moiety of formula I and the symbol (**) denotes the attachment to the A2 moiety of formula I;

X is O, S, or NR3;

D comprises a member of 2,3-dichlorophenyl, 2,3-difluorophenyl, 2,4-difluorophenyl, 3,4-difluorophenyl, 2,5-difluorophenyl, 3,5-difluorophenyl, 2,3,5-trifluorophenyl, 2,4,5- trifluorophenyl, 2,3,4-trifluorophenyl, 3,4,5-trifluorophenyl, 3-phenoxyphenyl, 4-phenoxyphenyl, cyclohexyl,
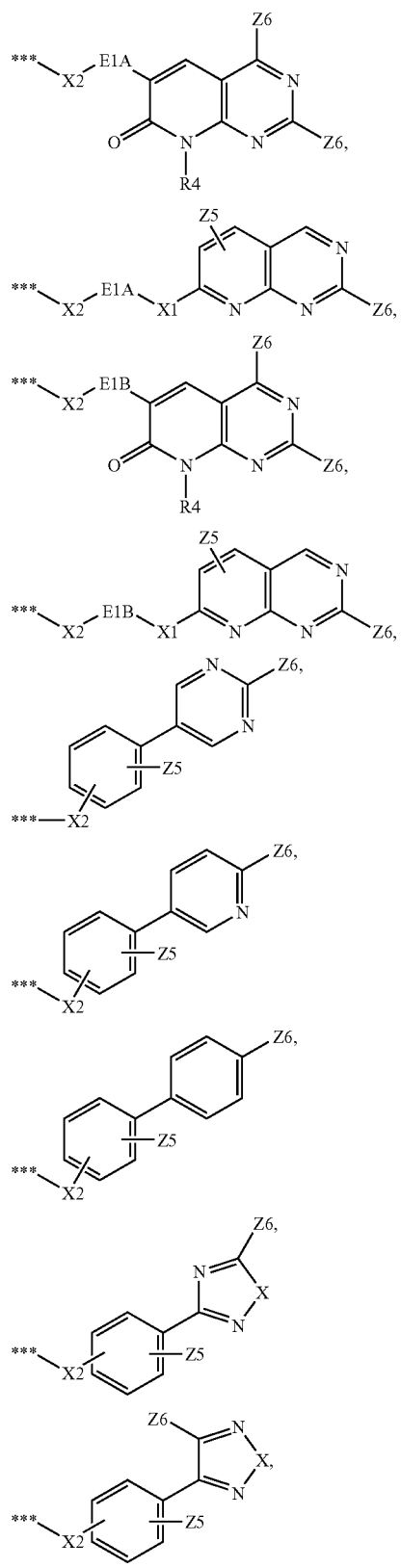
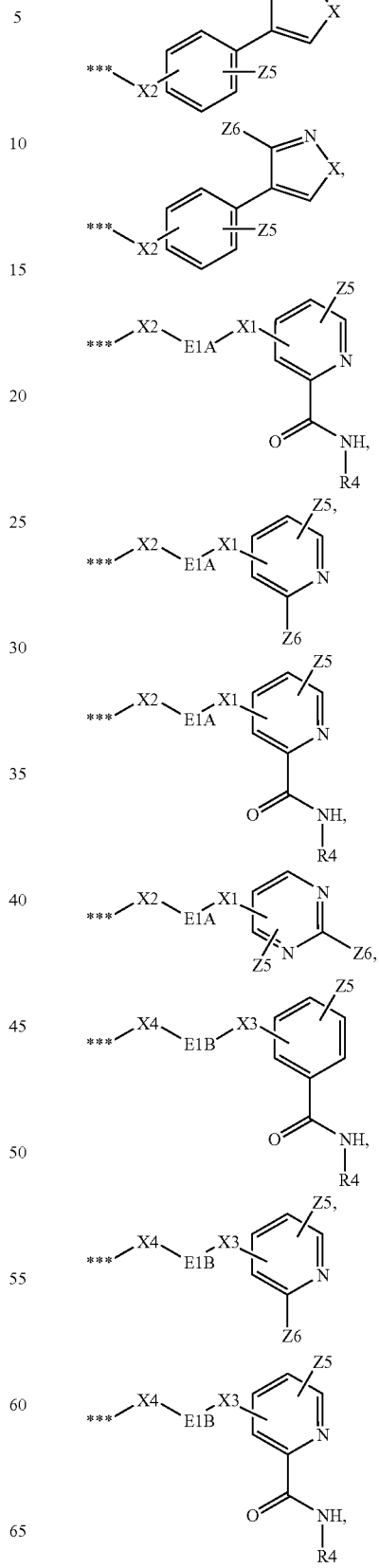

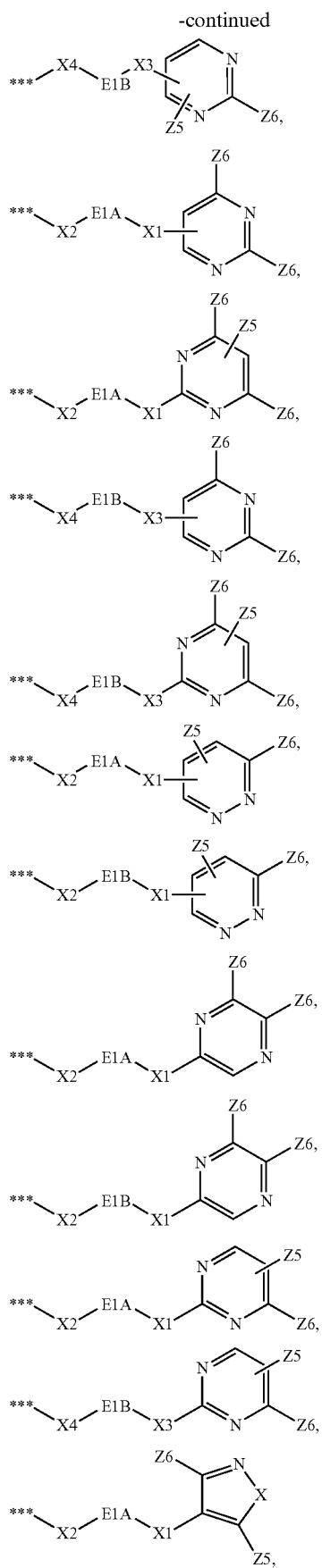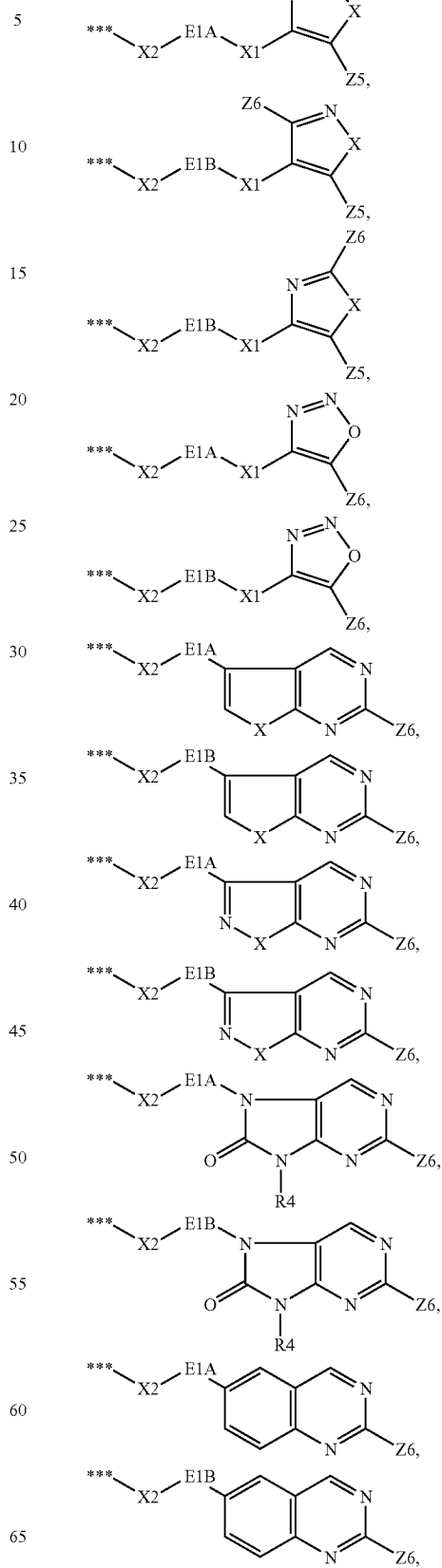

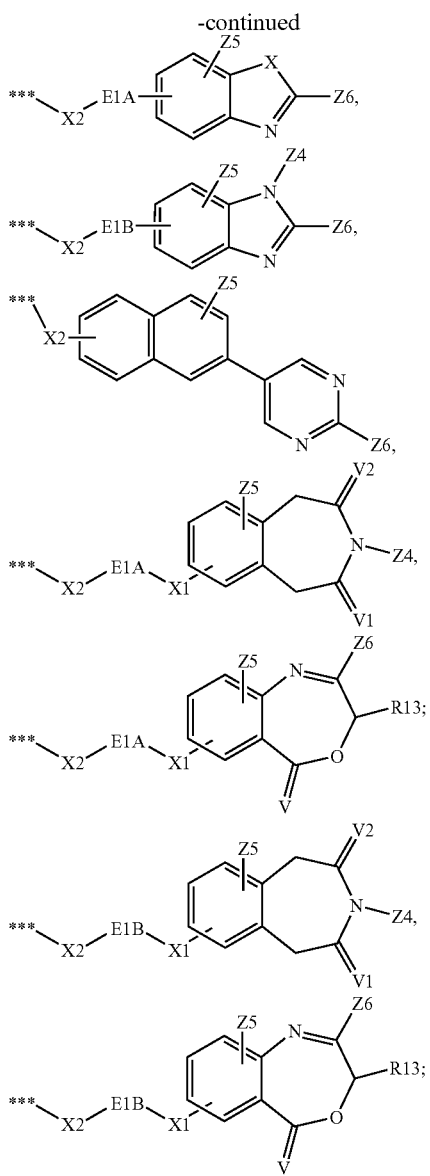

wherein E1A is taken from the groups consisting of cyclopropyl, cyclobutyl, cyclopentyl, cyclohexyl, pyrrolidinyl piperidinyl, thienyl, oxazolyl, thiazolyl, isoxazolyl, isothiazolyl, pyrrolyl, pyrazolyl, oxadiazolyl, thiadiazolyl, furyl, imidazolyl, pyridyl, and pyrimidinyl;

wherein E1B is taken from the groups consisting of phenyl and naphthyl;

wherein E2A is taken from the group comprising naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl and fused bicyclic rings selected from the group comprising indolyl, isoindolyl, isoindolinyl, isoindolonyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, imidazopyrimidinyl, imidazolonopyrimidinyl, dihydropurinonyl, pyrrolopyrimidinyl, purinyl, pyrazolopyridinyl, pyrazolopyrimidinyl, isoxazolopyrimidinyl, isothiazolopyrimidinyl, furylopyrimidinyl, thienopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalazinyl, benzodioxyl, indolinyl, benzisothiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, benzoxazepinyl;

wherein E2B is taken from the group consisting of phenyl, pyridyl, and pyrimidyl;

wherein the symbol (***) denotes the attachment to the Y moiety of formula I;

X1 is selected from the group consisting of O, S, NR3, —C(=O)—, —O—(CH₂)n-, —S—(CH₂)n-, —NR3-(CH₂)n-, —O—(CH₂)q-O—, —O—(CH₂)q-NR3-, —N(R3)-(CH₂)q-N(R3)-, —(CH₂)n-N(R4)-C(=O)—, —(CH₂)n-N(R4)-C(=O)(CH₂)n-, —(CH₂)n-CO—N(R4)-, —(CH₂)p-, C2-C5alkenyl, C2-C5alkynyl, C3-C6cycloalkyl, and a direct bond wherein the E1 ring and the E2 ring are directly linked by a covalent bond;

and wherein the carbon atoms of —(CH2)n-, —(CH2)q-, (CH2)p, C2-C5alkenyl, and C2-C5alkynyl moieties of X1 may be further substituted by one or more C1-C6alkyl;

X2 is selected from the group consisting of C1-C6 alkyl, C3-C6 branched alkyl, or a direct bond wherein E1 is directly linked to the Y group of formula I;

X3 is selected from the group consisting of NR3, —C(=O)—, —O—(CH₂)n-, —S—(CH₂)n-, —NR3-(CH₂)n-, —O—(CH₂)q-O—, —O—(CH₂)q-NR3-, —N(R3)-(CH₂)q-N(R3)-, —(CH₂)n-N(R4)-C(=O)—, —(CH₂)n-N(R4)-C(=O)(CH₂)n-, —(CH₂)n-CO—N(R4)-, —(CH₂)q-, C2-C5alkenyl, C2-C5alkynyl, C3-C6cycloalkyl, and a direct bond wherein the either the E1B ring or E2B ring are directly linked by a covalent bond;

and wherein the carbon atoms of —(CH2)q-, C2-C5alkenyl, and C2-C5alkynyl moieties of X3 may be further substituted by one or more C1-C6alkyl;

X4 is selected from the group consisting of C1-C6 alkyl, C3-C6 branched alkyl;

Each R2 is independently and individually selected from the group consisting of C1-C6alkyl, branched C3-C7alkyl, C1-C6fluoroalkyl, wherein the alkyl group is partially or fully fluorinated, monocyclic heteroaryl, and R19 substituted C3-C8carbocyclyl wherein R19 is H, and C1-C6alkyl;

each R2' is selected from the group consisting of halogen and R2;

each R3 is independently and individually selected from the group consisting of H, C1-C6alkyl, branched C3-C7alkyl, C3-C7carbocyclyl, or phenyl;

wherein two R3 moieties independently and individually taken from the group consisting of C1-C6alkyl and branched C3-C7alkyl are attached to the same nitrogen heteroatom, the two R3 moieties may cyclize to form a C3-C7 heterocyclyl ring;

each R4 is selected from the group consisting of H, C1-C6alkyl, hydroxyC1-C6 alkyl, dihydroxyC1-C6alkyl, C1-C6alkoxyC1-C6alkyl, branched C3-C7alkyl, branched hydroxyC1-C6 alkyl, branched C1-C6alkoxyC1-C6alkyl, branched dihydroxyC1-C6alkyl, carbocyclyl, hydroxyl substituted carbocyclyl, alkoxy substituted carbocyclyl, dihydroxy substituted carbocyclyl, phenyl, heteroaryl, heterocyclyl, phenylC1-C6alkyl, heteroarylC1-C6alkyl, and heterocyclylC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom may cyclize to form a C3-C7 heterocyclyl ring;

each R5 is independently and individually selected from the group consisting of

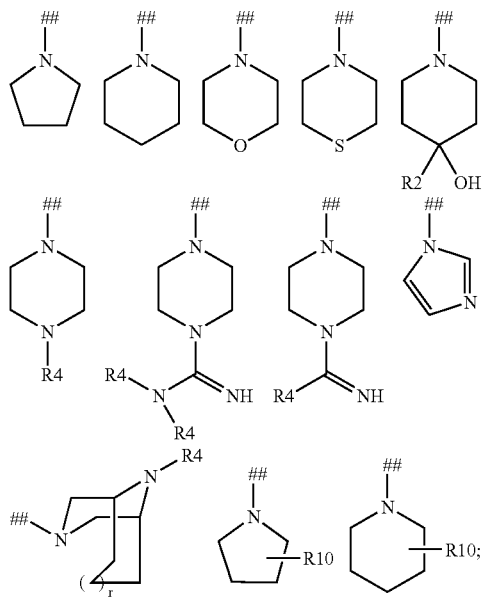

and wherein the symbol (##) is the point of attachment to respective R8, R10, Z4, Z5, Z6 or A2 ring moieties containing a R5 moiety;

wherein two R4 moieties independently and individually taken from the group consisting of C1-C6alkyl, branched C3-C6alkyl, hydroxyalkyl, and alkoxyalkyl and are attached to the same nitrogen heteroatom of R5 may cyclize to form a C3-C7 heterocyclyl ring;

wherein each R6 is independently and individually selected from the group consisting of C1-C6alkyl, branched C3-C7alkyl, carbocyclyl, phenyl, heteroaryl, and heterocyclyl;

each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

each R8 is independently and individually selected from the group consisting of C1-C6alkyl, C1-C6 fluoroalkyl wherein the alkyl moiety is partially or fully fluorinated, branchedC4-C7alkyl, carbocyclyl, phenyl, C1-C6phenylalkyl, heteroaryl or heteroarylC1-C6alkyl, heterocyclyl, heterocyclylC1-C6alkyl, OH, C1-C6alkoxy, N(R3)$_2$, N(R4)$_2$, or R5;

wherein two R3 moieties are independently and individually taken from the group consisting of C1-C6alkyl and branched C3-C6alkyl and are attached to the same nitrogen heteroatom of R8 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of R8 may cyclize to form a C3-C7 heterocyclyl ring;

each R10 is independently and individually selected from the group consisting of CO$_2$H, CO$_2$C1-C6alkyl, CO—N(R4)$_2$, OH, C1-C6alkoxy, —N(R4)$_2$;

wherein two R4 moieties independently and individually taken from the group consisting of C1-C6alkyl, branched C3-C6alkyl, hydroxyalkyl, and alkoxyalkyl and are attached to the same nitrogen heteroatom of R10 may cyclize to form a C3-C7 heterocyclyl ring;

wherein Z1' is independently and individually selected from the group consisting of H, C1-C6alkyl, C3-C7cycloalkyl, hydroxyC1-C6alkyl, C1-C6alkoxyC1-C6alkyl, (R4)$_2$N—C1-C6alkyl, (R4)$_2$N—C2-C6alkylN(R4)-(CH$_2$)$_p$, (R4)$_2$N—C2-C6alkylO-(CH$_2$)$_p$, (R4)$_2$N—CO—C1-C6alkyl, carboxyC1-C6alkyl, C1-C6alkoxycarbonylC1-C6alkyl, —(CH$_2$)$_p$N(R4)C(O)R8, aryl, arylC1-C6alkyl, heteroaryl, heteroarylC1-C6alkyl, heterocyclyl, heterocyclylC1-C6alkyl, aryloxyC1-C6alkyl, heteroaryloxyC1-C6alkyl, heterocyclyloxyC1-C6alkyl, arylaminoC1-C6alkyl, heteroarylaminoC1-C6alkyl, or heterocyclylaminoC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom of Z1' may cyclize to form a C3-C7 heterocyclyl ring;

each Z4 is a substituent attached to a ring nitrogen and is independently and individually selected from the group consisting of H, C1-C6alkyl, hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C2-C6alkyl, carboxyC2-C6alkyl, C1-C6alkoxycarbonylC2-C6alkyl, —C2-C6alkylN(R4)C(O)R8, R8-C(=NR3)-, —SO$_2$R8, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

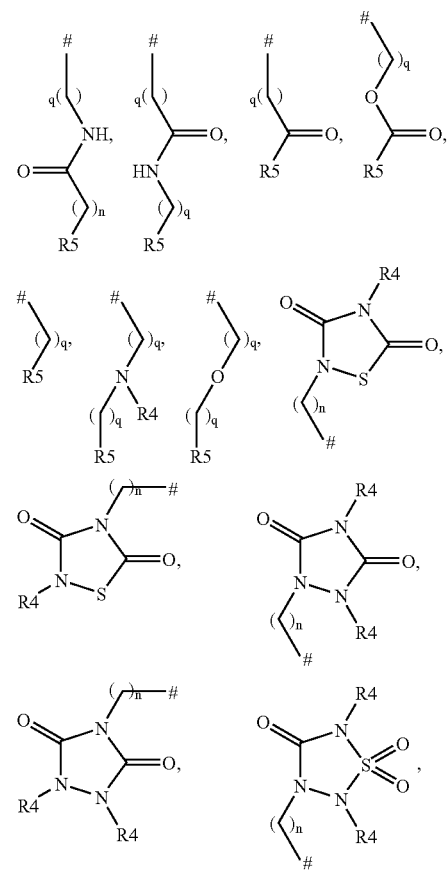

-continued

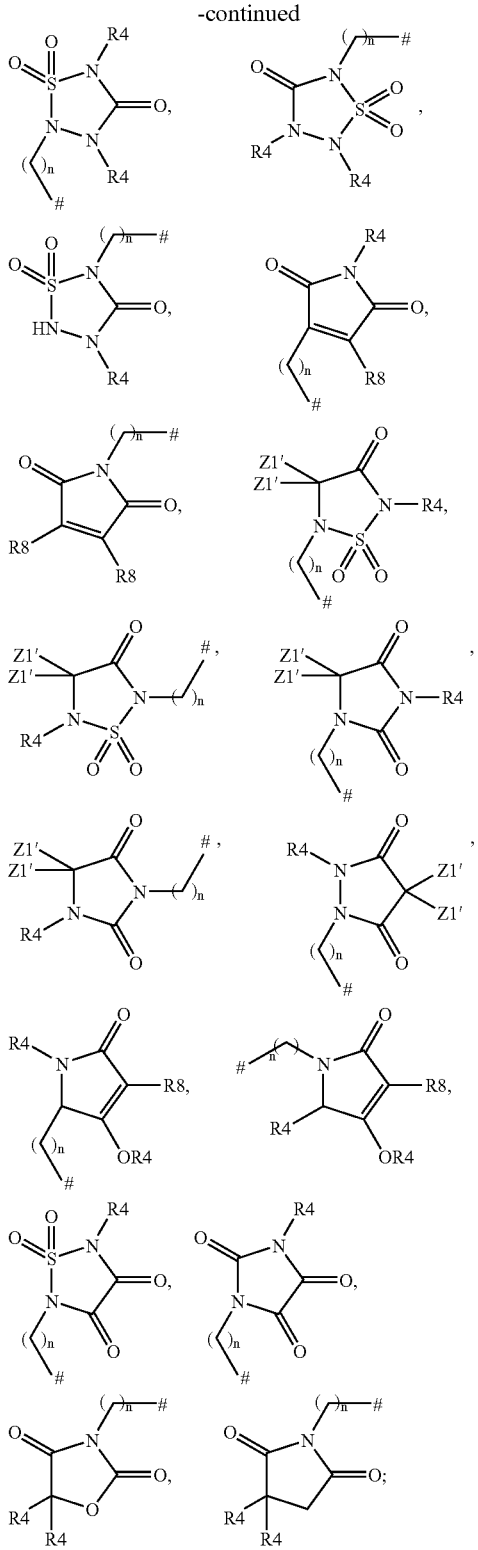

wherein the symbol (4) indicates the point of attachment of the Z4 moiety to the A2 ring for formula I;
in the event that Z4 contains an alkyl or alkylene moiety, such moieties may be further substituted with one or more C1-C6alkyls;
wherein two R3 moieties are independently and individually taken from the group consisting of C1-C6alkyl and branched C3-C6alkyl and are attached to the same nitrogen heteroatom of Z4 may cyclize to form a C3-C7 heterocyclyl ring;
wherein two R4 moieties independently and individually taken from the group consisting of C1-C6alkyl, branched C3-C6alkyl, hydroxyalkyl, and alkoxyalkyl and are attached to the same nitrogen heteroatom of Z4 may cyclize to form a C3-C7 heterocyclyl ring;
Z5 is independently and individually selected from the group consisting of H, C1-C6alkyl, branched C3-C7alkyl, halogen, fluoroalkyl, cyano, hydroxyl, alkoxy, oxo, aminocarbonyl, carbonylamino, aminosulfonyl, sulfonylamino, —N(R3)$_2$, —O—(CH$_2$)q-N(R4)$_2$, —N(R3)-(CH$_2$)q-N(R4)$_2$, —R5, —O—(CH$_2$)q-O-Alkyl, —O—(CH$_2$)q-N(R4)$_2$, —N(R3)-(CH$_2$)q-O-Alkyl, —N(R3)-(CH$_2$)q-N(R4)$_2$, —O—(CH$_2$)q-R5, and —N(R3)-(CH$_2$)q-R5;
wherein two R3 moieties are independently and individually taken from the group consisting of C1-C6alkyl and branched C3-C6alkyl and are attached to the same nitrogen heteroatom of Z5 may cyclize to form a C3-C7 heterocyclyl ring;
wherein two R4 moieties independently and individually taken from the group consisting of C1-C6alkyl, branched C3-C6alkyl, hydroxyalkyl, and alkoxyalkyl and are attached to the same nitrogen heteroatom of Z5 may cyclize to form a C3-C7 heterocyclyl ring;
Each Z6 is independently and individually selected from the group consisting of H, C1-C6alkyl, branched C3-C7alkyl, hydroxyl, C1-C6alkoxy, (R3)$_2$N—, —N(R3)COR8, (R4)$_2$N—, —R5, —N(R4)COR8, —N(R3)SO$_2$R6-, —CON(R3)$_2$, —CON(R4)$_2$, —COR5, —SO$_2$NHR4, heteroaryl, heterocyclyl, heteroaryloxy, heterocyclyloxy, arylamino, heteroarylamino, and heterocyclylamino;
wherein two R3 moieties are independently and individually taken from the group consisting of C1-C6alkyl and branched C3-C6alkyl and are attached to the same nitrogen heteroatom of Z6 may cyclize to form a C3-C7 heterocyclyl ring;
wherein two R4 moieties independently and individually taken from the group consisting of C1-C6alkyl, branched C3-C6alkyl, hydroxyalkyl, and alkoxyalkyl and are attached to the same nitrogen heteroatom of Z6 may cyclize to form a C3-C7 heterocyclyl ring;
each Z7 is a substituent attached to a ring carbon and is independently and individually selected from the group consisting of hydroxyC2-C6alkyl, C1-C6alkoxyC1-C6alkyl, (R6)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—CO, (R4)$_2$N—CO, —SO$_2$R3', SOR3, —SOR4, —C(=O)R6, —C(=NOH)R6, —C(=NOR3)R6, (CH$_2$)$_n$N(R4)C(O)N(R4)$_2$, (CH$_2$)$_n$N(R4)C(O)R5, monocyclic heteroaryl, monocyclic heterocyclyl, monocyclic heteroarylC1-C6alkyl, monocyclic heterocyclylC1-C6alkyl, monocyclic heteroaryloxy, monocyclic heterocyclyloxy, monocyclic heteroaryloxyC1-C6alkyl, monocyclic heterocyclyloxyC1-C6alkyl, arylamino, monocyclic heteroarylamino, monocyclic heterocyclylamino, arylaminoC1-C6alkyl, monocyclic heteroarylaminoC1-C6alkyl, monocyclic heterocyclylaminoC1-C6alkyl, or moieties of the formulae

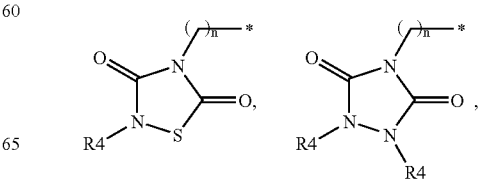

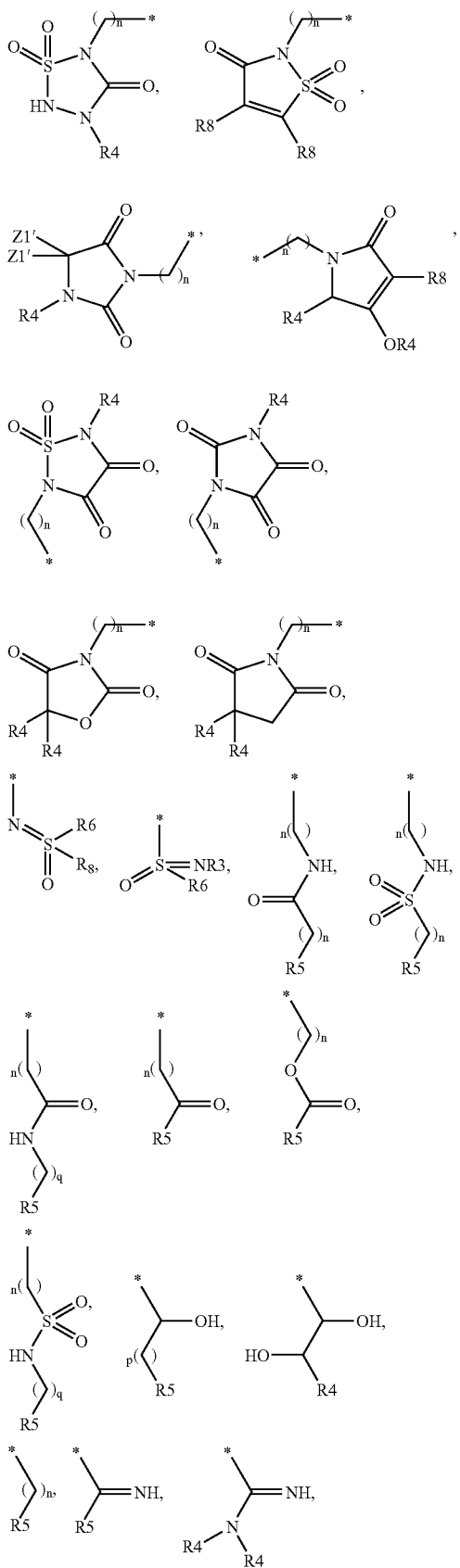
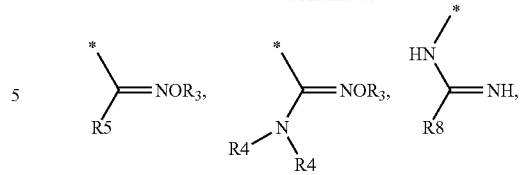

cyano wherein the site of attachment to the A2 ring is meta to the point of attachment to the A1 ring and wherein A2 is phenyl, and cyano wherein the site of attachment is to a substitutable position when A2 is pyridyl, pyrimidinyl or a five-membered ring;

In the foregoing definition of Z7, alkyl moieties may optionally be substituted by one or more C1-C6alkyl;

Wherein the asterisk (*) indicates the point of attachment of the Z1 moiety to the A2 ring;

in the event that Z7 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z7 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z7 may cyclize to form a C3-C7 heterocyclyl ring;

and n is 0-4; p is 1-4; q is 2-6; r is 0 or 1; v is 1 or 2;

and tautomers, diastereomers, geometric isomers, enantiomers, hydrates, prodrugs and salts of any of the foregoing.

3.3.6b

The following specific compounds of Formula I are more preferred: 1-(3-t-butyl-1-(3-(pyridin-3-yl)phenyl)-1H-pyrazol-5-yl)-3-(2,3-dichlorophenyl)urea, 1-(1-(3-(1H-pyrazol-4-yl)phenyl)-3-t-butyl-1H-pyrazol-5-yl)-3-(2,3-dichlorophenyl)urea, 1-(1-(3-(2-amino-2-oxoethyl)phenyl)-3-cyclopentyl-1H-pyrazol-5-yl)-3-(2,3-dichlorophenyl)urea, 1-(1-(3-(1-amino-1-oxopropan-2-yl)phenyl)-3-t-butyl-1H-pyrazol-5-yl)-3-(2,3-dichlorophenyl)urea, 1-(3-t-butyl-1-(3-(2-(2-hydroxyethylamino)-2-oxoethyl)phenyl)-1H-pyrazol-5-yl)-3-(2,3-dichlorophenyl)urea, 1-(3-t-butyl-1-(3-(2-(2,3-dihydroxypropylamino)-2-oxoethyl)phenyl)-1 H-pyrazol-5-yl)-3-(2,3-dichlorophenyl)urea, 1-(3-t-butyl-1-(3-(2-((S)-3-(dimethylamino)pyrrolidin-1-yl)-2-oxoethyl)phenyl)-1H-pyrazol-5-yl)-3-(2,3-dichlorophenyl)urea, 1-(3-t-butyl-1-(3-((2,4,5-trioxoimidazolidin-1-yl)methyl)phenyl)-1H-pyrazol-5-yl)-3-(2,3-dichlorophenyl)urea, 1-(3-t-butyl-1-(3-((4,5-dioxo-2,2-dioxo-2,1,3-thiadiaol-yl)methyl)phenyl)-1H-pyrazol-5-yl)-3-(2,3-dichlorophenyl)urea, 1-(3-t-butyl-1-(3-carbamimidoylphenyl)-1H-pyrazol-5-yl)-3-(2,3-dichlorophenyl)urea, 1-(1-(3-(N-hydroxycarbamimidoyl)phenyl)-3-t-butyl-1H-pyrazol-5-yl)-3-(2,3-dichlorophenyl)urea, 1-(1-(4-(N-hydroxycarbamimidoyl)phenyl)-3-t-butyl-1H-pyrazol-5-yl)-3-(2,3-dichlorophenyl)urea, 1-(3-t-butyl-1-(3-(2-hydroxyethyl)phenyl)-1H-pyrazol-5-yl)-3-(2,3-dichlorophenyl)urea, 1-(3-t-butyl-1-(3-(5-oxo-4,5-dihydro-1,3,4-oxadiazol-2-yl)phenyl)-1H-pyrazol-5-yl)-3-(2,3-dichlorophenyl)urea, 1-(3-t-butyl-1-(3-cyanophenyl)-1H-pyrazol-5-yl)-3-(2,3,4-trifluorophenyl)urea, 1-(1-(3-(2-amino-2-oxoethyl)phenyl)-3-t-butyl-1H-pyrazol-5-yl)-3-(2,4,5-trifluorophenyl)urea, 2-(3-(3-t-butyl-5-(3-(2,3-difluorophenyl)ureido)-1H-pyrazol-1-yl)phenyl)acetic acid, 1-(1-(3-(2-amino-2-oxoethyl)phenyl)-3-t-butyl-1H-pyrazol-5-yl)-3-(3-(pyridin-3-yloxy)phenyl)urea, 1-(1-(3-(2-amino- 2-oxoethyl)phenyl)-3-t-butyl-1H-pyrazol-5-yl)-3-(4-(2-(methylcarbamoyl)pyridin-4-yloxy)phenyl)urea, 1-(1-(3-(2-amino-2-oxoethyl)phenyl)-3-t-butyl-1H-pyrazol-5-yl)-3-(3-(8-methyl-7-oxo-7,8-dihydropyrido[2,3-d]pyrimidin-6-yl) phenyl)urea, 1-(1-(3-(2-amino-2-oxoethyl)phenyl)-3-cyclopentyl-1H-pyrazol-5-yl)-3-(3-(8-methyl-7-oxo-7,8-dihydropyrido[2,3-d]pyrimidin-6-yl)phenyl)urea.

3.3.7 Methods 3.3.7a Methods of Protein Modulation

The invention includes methods of modulating kinase activity of RAF kinases and other kinases in the RAS-RAF-MEK-ERK-MAP kinase pathway including, but not limited to, A-Rat, B-Rat, and C-Raf. The kinases may be wildtype kinases, oncogenic forms thereof, aberrant fusion proteins thereof or polymorphs of any of the foregoing. The method comprises the step of contacting the kinase species with compounds of the invention and especially those set forth in sections 3.3 and 3.3.6a. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, kinase cellular localization, and recruitment of other proteins into signaling complexes through modulation of kinase conformation.

3.3.7b Treatment Methods

The methods of the invention also include treating individuals suffering from a condition selected from the group consisting of cancer and hyperproliferative diseases. These methods comprise administering to such individuals compounds of the invention, and especially those of section 3.3 and 3.3.6a. condition being melanomas, glioblastomas, ovarian cancer, pancreatic cancer, prostate cancer, lung cancers, breast cancers, kidney cancers, cervical carcinomas, metastisis of primary solid tumor secondary sites, ocular diseases characterized by hyperproliferation leading to blindness including various retinopathies including diabetic retinopathy and age-related macular degeneration, rheumatoid arthritis characterized by the in-growth of a vascularized pannus, or a disease caused by a mutation in the RAS-RAF-MEK-ERK-MAP kinase pathway. The administration method is not critical, and may be from the group consisting of oral, parenteral, inhalation, and subcutaneous.

3.3.8 Pharmaceutical Preparations

The compounds of the invention, especially those of 3.3 and 3.3.6a may form a part of a pharmaceutical composition by combining one or more such compounds with a pharmaceutically acceptable carrier. Additionally, the compositions may include an additive selected from the group consisting of adjuvants, excipients, diluents, and stablilizers.

3.3.9 Kinase/Compound Adducts

The invention also provides adducts in the form of compounds of the invention bound with a species of kinase such as a wild-type kinase, oncogenic forms thereof, aberrant fusion proteins thereof and polymorphs of any of the foregoing. The compounds are advantageously selected from the groups defined in sections 3.3 and 3.3.6a.

4. First Aspect of the Invention—P38 Kinase Modulator Compounds, Methods, Preparations and Adducts 4.1 Generally—A2 Bicyclic Compounds The invention includes compounds of formula I as defined in section 2.1, wherein R2 is selected from the group consisting of monocyclic heteroaryl, C1-C6alkyl, branched C3-C7alkyl, a R19-substituted C3-C8carbocyclyl wherein R19 is H, or C1-C6alkyl, C1-C6fluoroalkyl wherein the alkyl group is partially or fully fluorinated, and phenyl wherein the phenyl group is optionally substituted by one or more fluorine substituents or chlorine;

4.1.1 Preferred D Moieties 4.1.1a

Preferred compounds of Formula I as defined above in section 4.1 contain D moieties as defined in section 1.1.1a.

4.1.1b

Additionally preferred compounds of Formula I as defined above in section 4.1 contain D moieties as defined in section 1.1.1b.

4.1.1c

More preferred compounds of Formula I as defined above in section 4.1.1b contain D moieties as defined in section 1.1.1c.

4.1.2 Preferred A2 Moieties 4.1.2a

Compounds of Formula I as defined above in section 4.1 have preferred A2 moieties as defined in section 1.1.2a.

4.1.2b More Preferred A2 Moieties

Compounds of Formula I as defined above in section 4.1 have more preferred A2 moieties selected from group consisting of

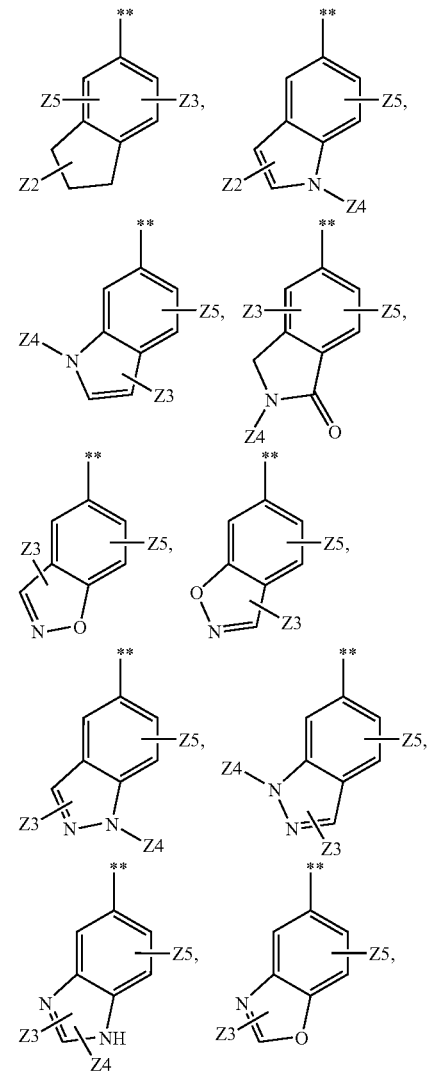

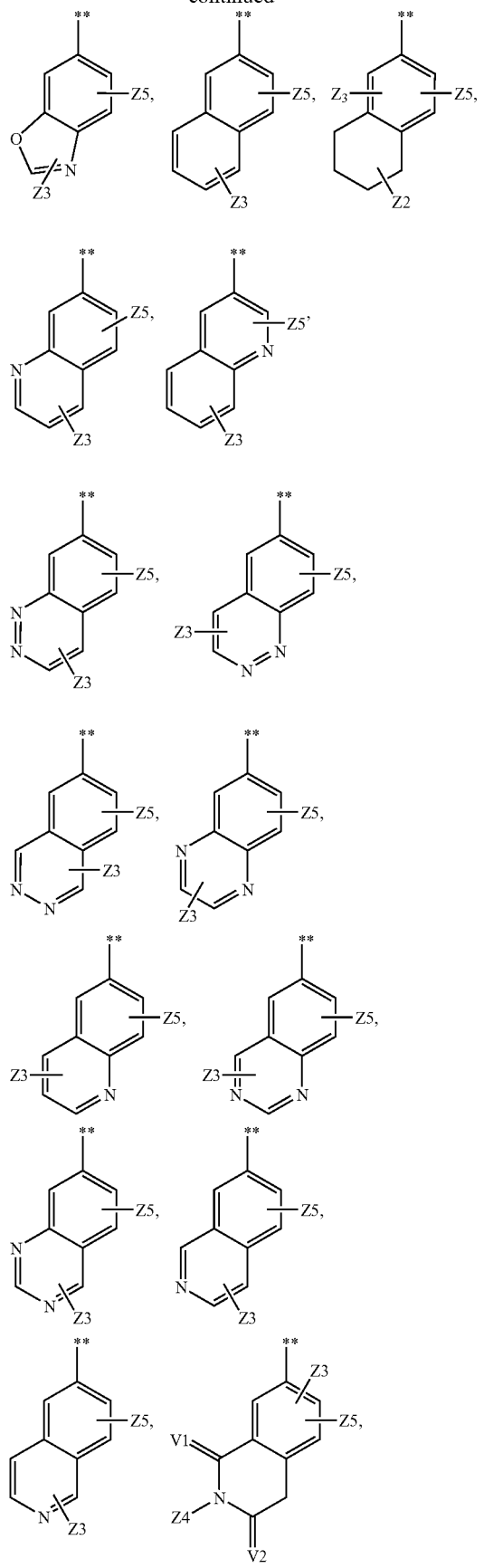
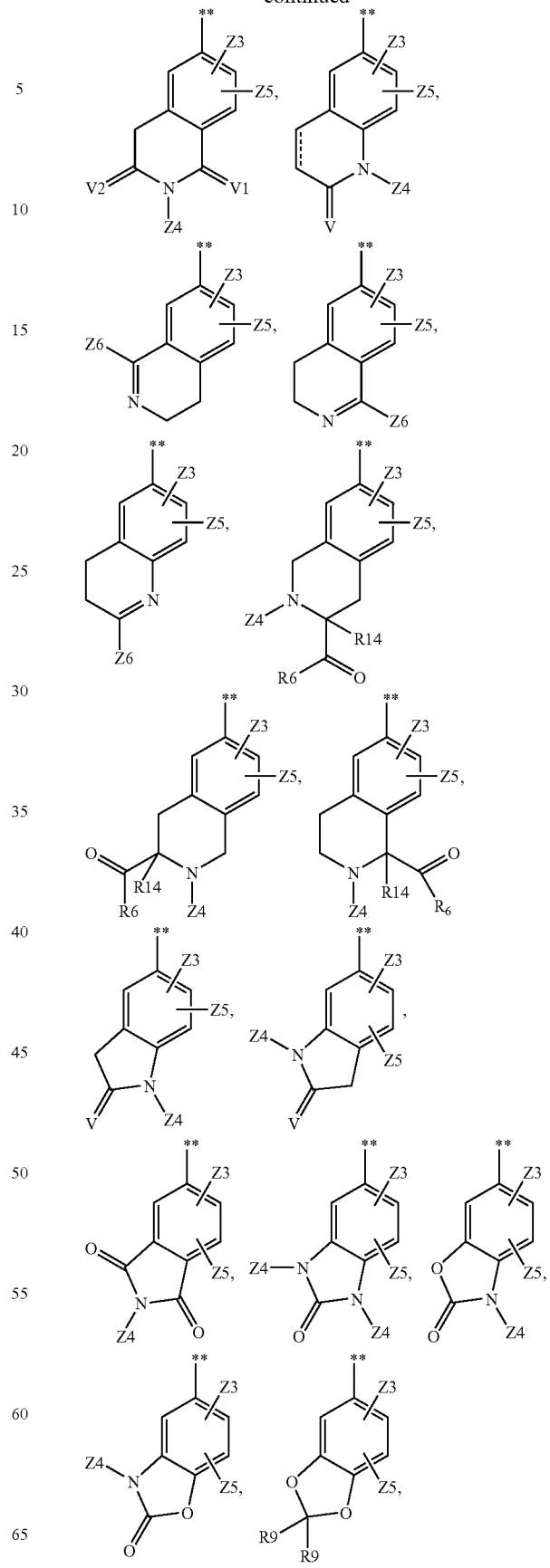

-continued
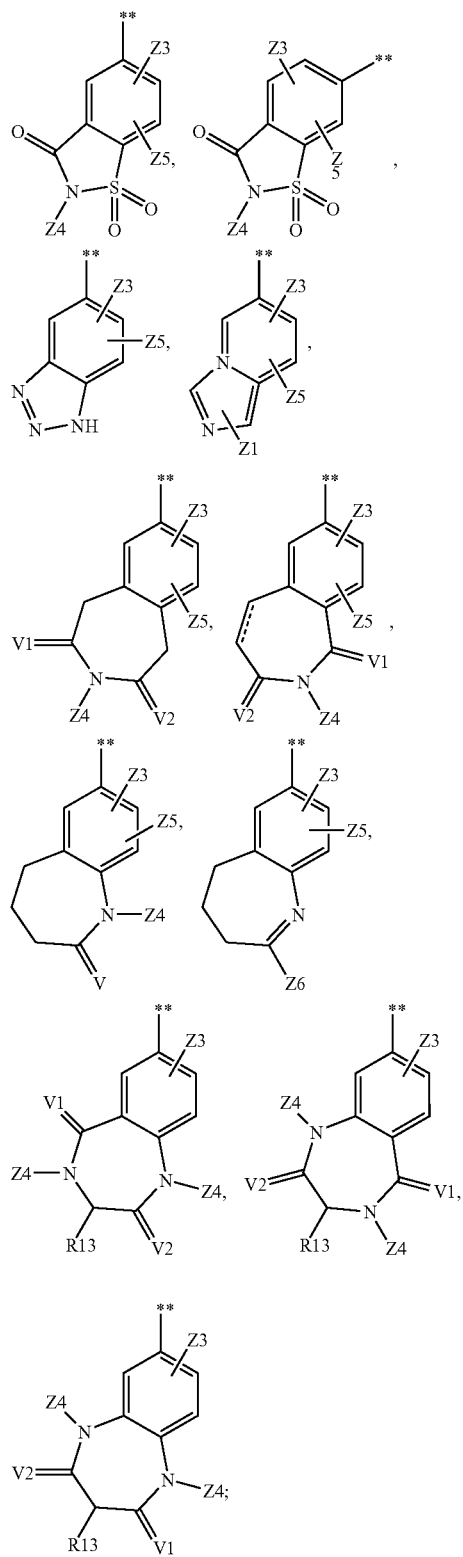
and wherein the symbol (**) is the point of attachment to the A1 ring for formula I;
wherein each Z3 and Z5 is independently attached to either aryl or heteroaryl ring of the A2 bicyclic ring.
4.1.2c
Still more preferred compounds of Formula I as defined above in section 4.1 have A2 moieties selected from group consisting of
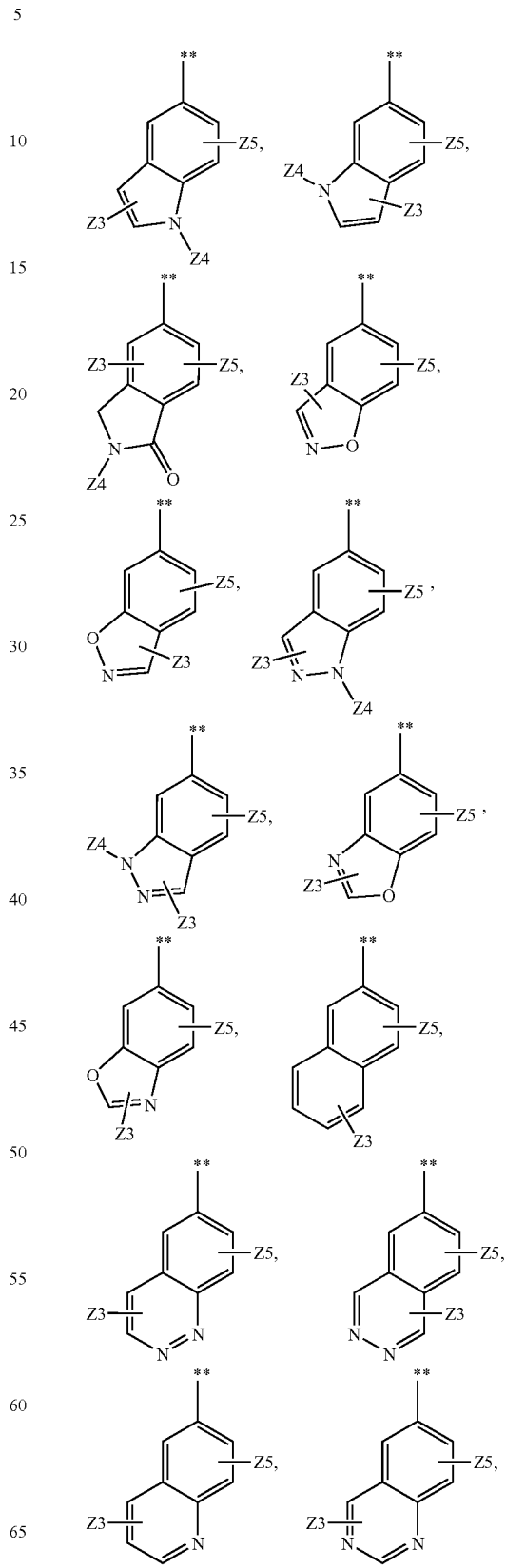

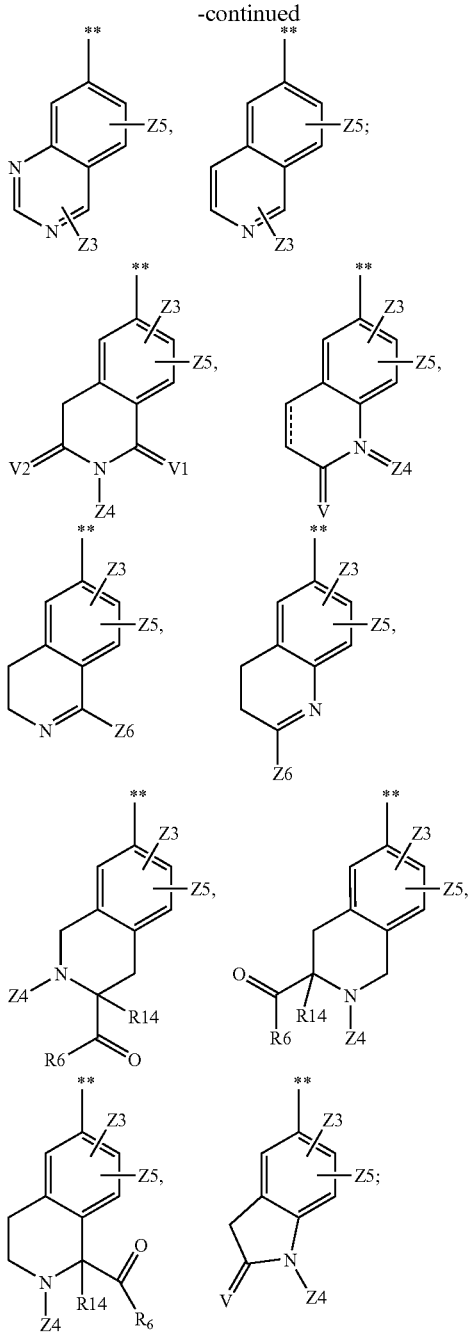

and wherein the symbol (**) is the point of attachment to the A1 ring of formula I,
wherein each Z3 and Z5 is independently attached to either aryl or heteroaryl ring of the A2 bicyclic ring.

4.1.3 Preferred Classes of Compounds 4.1.3a
Compounds as defined in 4.1.1a wherein the A2 group is defined in 4.1.2a.

4.1.3b
Compounds as defined in 4.1.3a wherein the A2 group is defined in 4.1.2b.

4.1.3c
Compounds as defined in 4.1.3a wherein the A2 group is defined in 4.1.2c.

4.1.3d
Compounds as defined in 4.1.1b wherein the A2 group is defined in 4.1.2a.

4.1.3e
Compounds as defined in 4.1.3c wherein the A2 group is defined in 4.1.2b.

4.1.3f
Compounds as defined in 4.1.3c wherein the A2 group is defined in 4.1.2c.

4.1.4 Preferred A1 Moieties 4.1.4a
Compounds of Formula I as defined above in section 4.1 have preferred A1 moieties selected from group defined in section 4.1.4a;
wherein each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

4.1.4b
Compounds of Formula I as defined above in section 4.1 have more preferred A1 moieties selected from group consisting of

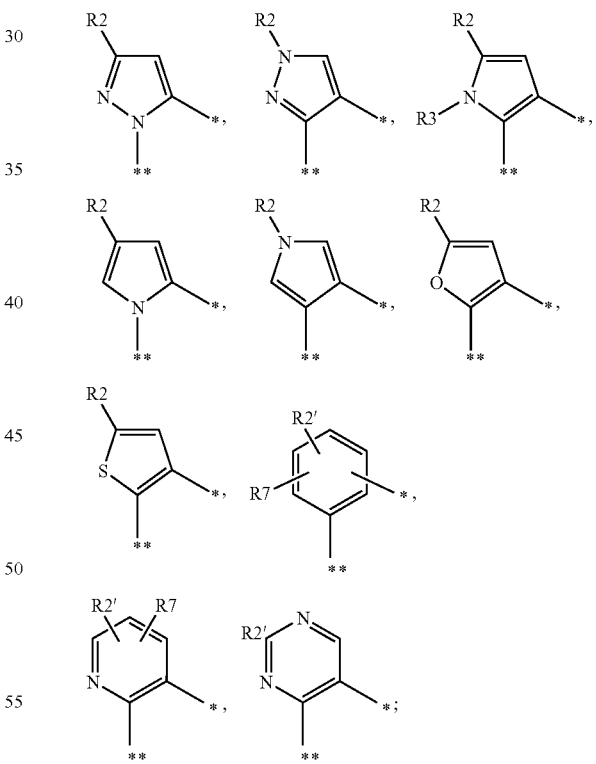

wherein the symbol (*) denotes the attachment to the W moiety of formula I and the symbol (**) denotes the attachment to the A2 moiety of formula I.

4.1.4c
Compounds of Formula I as defined above in section 4.1 have even more preferred A1 moieties selected from group consisting of

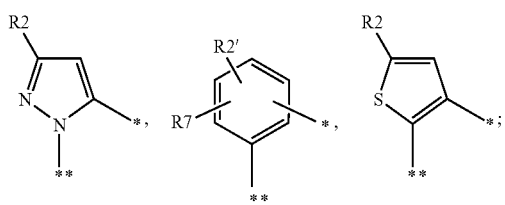

wherein the symbol (*) denotes the attachment to the W moiety of formula I and the symbol (**) denotes the attachment to the A2 moiety of formula I.

4.1.5 Preferred W and Y Moieties 4.1.5a (1) W and Y are each NH, and X=O; (2) W=NH, Y=CHR4 and X=O; or (3) W=CHR4, Y=NH, and X=O.

4.1.5b

W and Y are each NH and X=O.

4.1.6 Further Preferred Compounds 4.1.6a

Further preferred compounds are of the formula

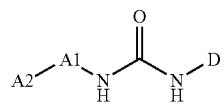

I

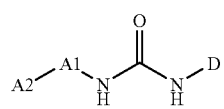

I wherein A2 is selected from the group consisting of

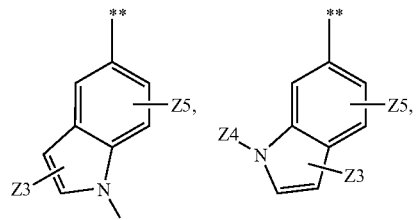

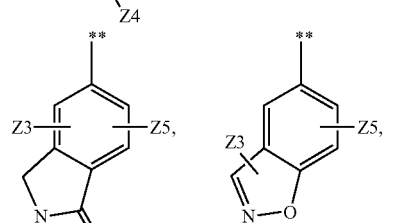

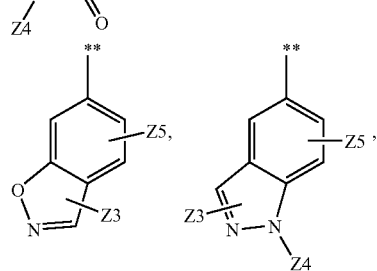

-continued

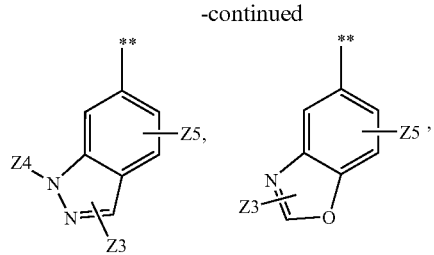

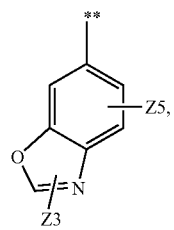

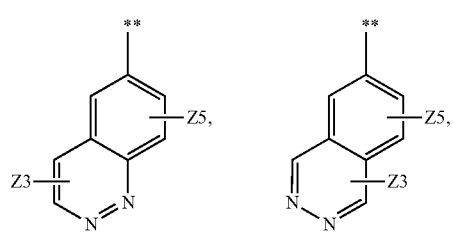

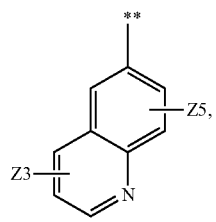

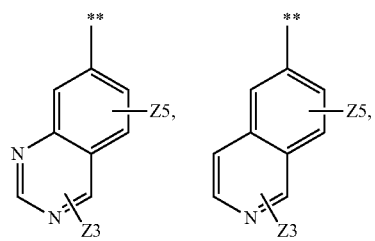

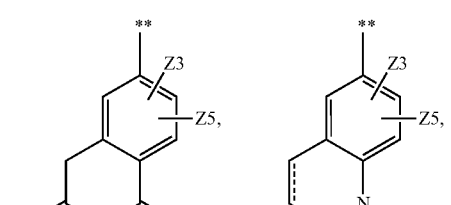

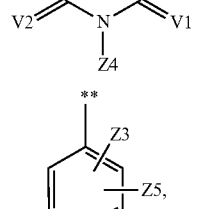

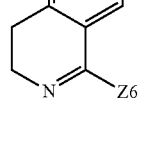

-continued

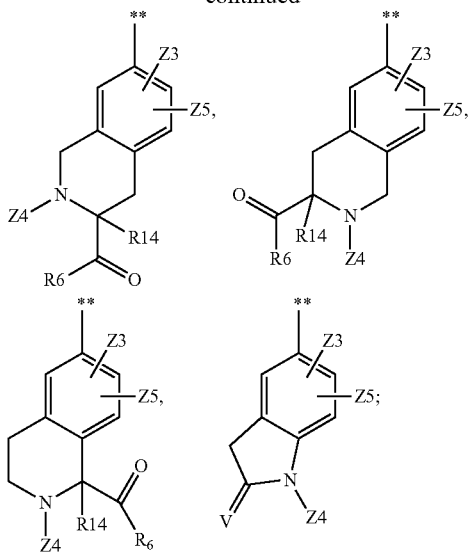

wherein each Z3 and ZS is independently attached to either aryl or heteroaryl ring of the A2 bicyclic ring;
wherein the symbol (**) denotes the attachment to the A1 moiety of formula I;
A1 is selected from the group consisting of

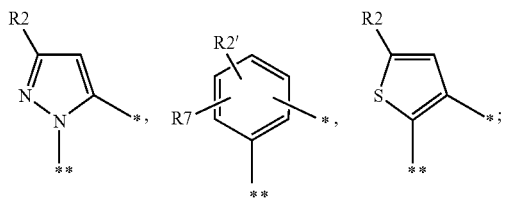

wherein the symbol (*) denotes the attachment to the W moiety of formula I and the symbol (**) denotes the attachment to the A2 moiety of formula I;
X is O, S, or NR3;
D comprises a member of 2,3-dichlorophenyl, 2,4-dichlorophenyl, 3,4-dichlorophenyl, 3,5-dichlorophenyl, 3-chlorophenyl, 4-chlorophenyl, 3-bromophenyl, 4-bromophenyl, 3-trifluoromethylphenyl, 3-trifluoromethyl-4-chlorophenyl, 2,3,4-trifluorophenyl, 2,3,4-trifluorophenyl, 2,4,5-trifluorophenyl, 2,3,5-trifluorophenyl, 3,4,5-trifluorophenyl, 2,3-difluorophenyl, 2,4-difluorophenyl, 2,5-difluorophenyl, 3,4-difluorophenyl, 2-fluorophenyl, 3-fluorophenyl, 4-fluorophenyl, 3-cyanophenyl, 3-phenoxyphenyl, 4 phenoxyphenyl, 1-naphthyl-2,3-dihydro-1H-inden-1-yl, 1,2,3,4-tetrahydronaphthalen1-yl, benzo[d][1,3]dioxol-5-yl or benzo[d][1,3]dioxol-4-yl,

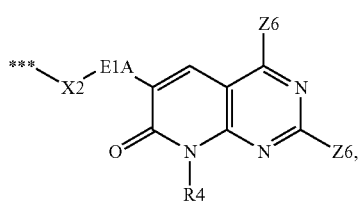

-continued

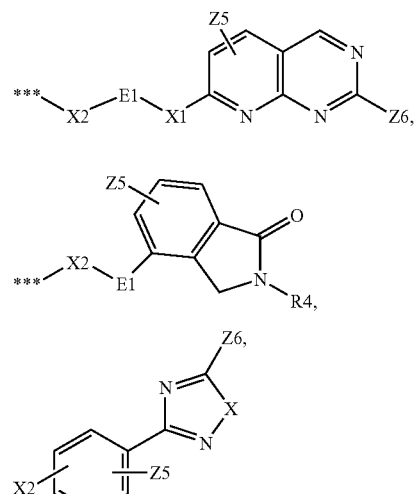

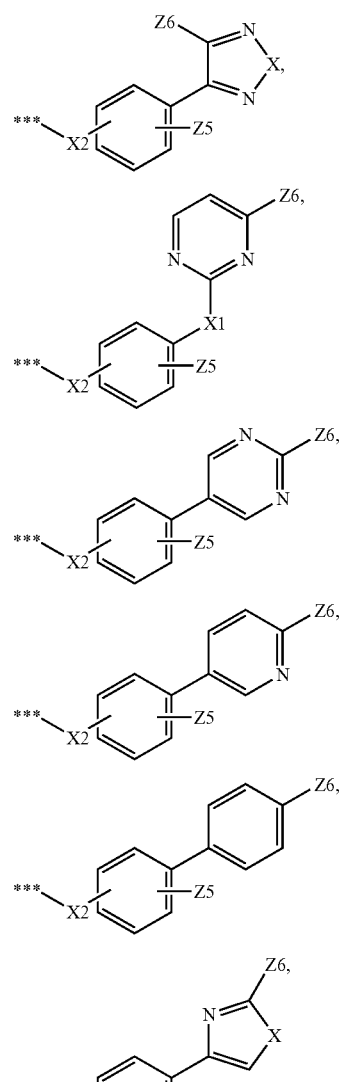

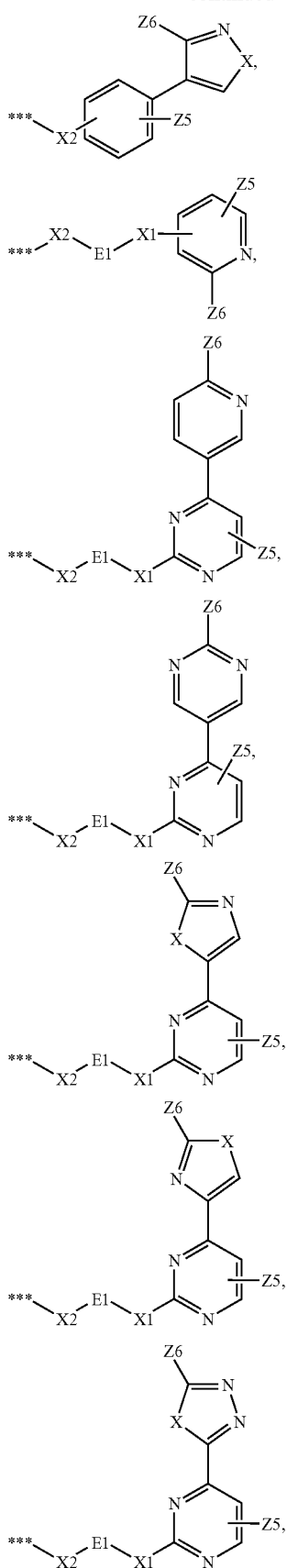
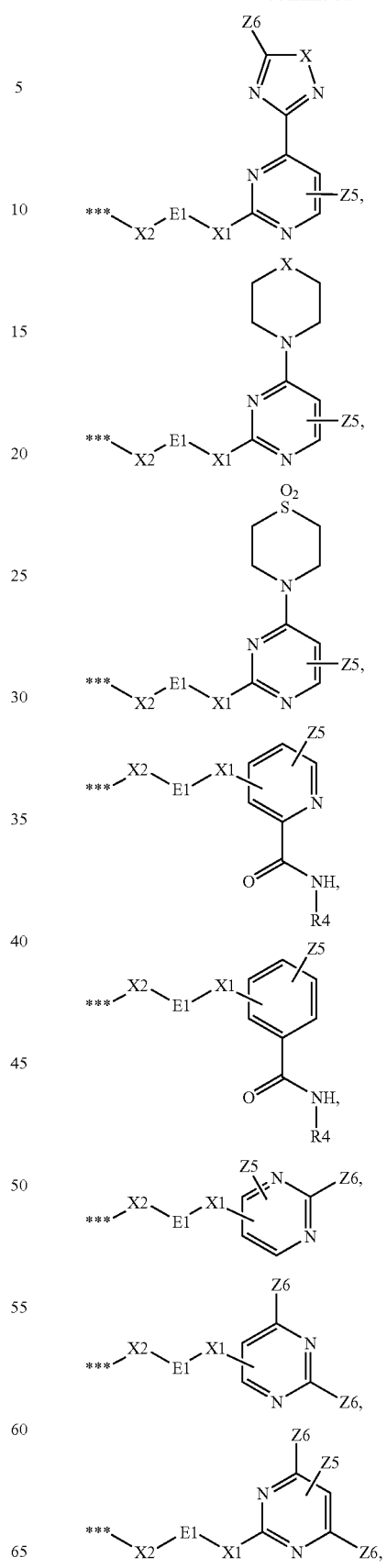

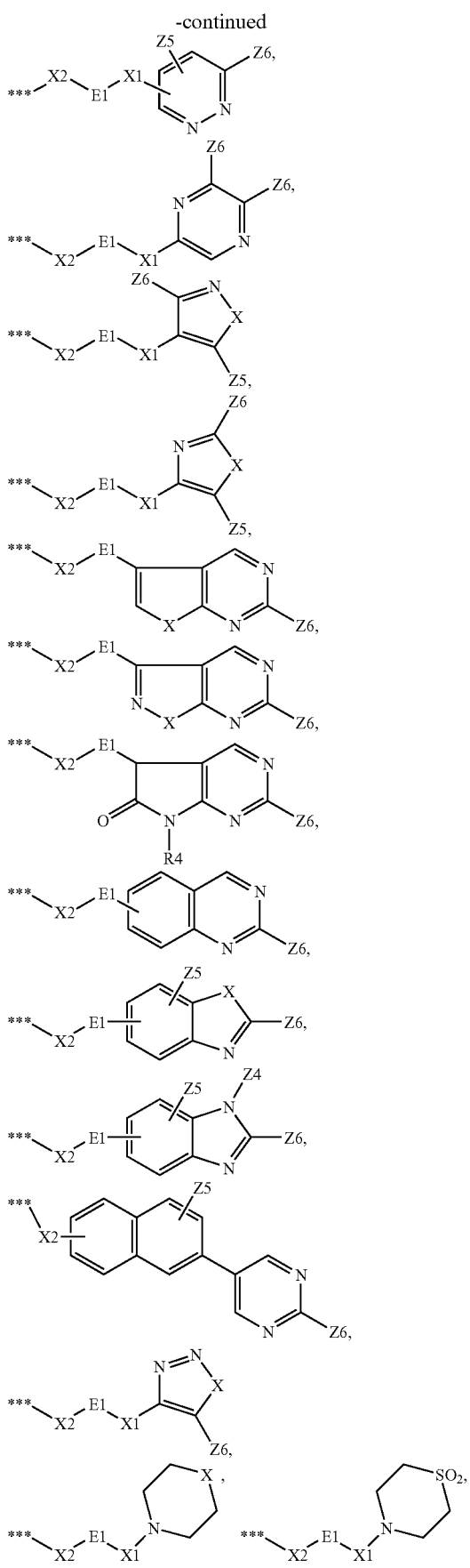

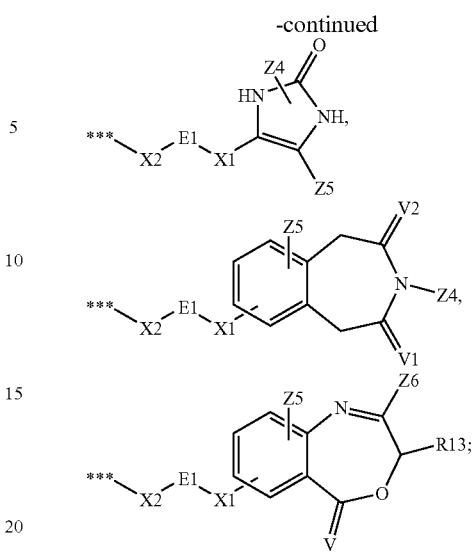

wherein E1 is selected from the group consisting cyclopropyl, cyclobutyl, cyclopentyl, cyclohexyl, pyrrolidinyl piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl and naphthyl;

wherein the symbol (***) denotes the attachment to the Y moiety of formula I;

X1 is selected from the group consisting of O, S, NR3, —C(=O)—, —O—(CH$_2$)n-, —S—(CH$_2$)n-, —NR3-(CH$_2$)n-, —O—(CH$_2$)q-O—, —O—(CH$_2$)q-NR3-, —N(R3)-(CH$_2$)q-N(R3)-, —(CH$_2$)n-N(R4)-C(=O)—, —(CH$_2$)n-N(R4)-C(=O)(CH$_2$)n-, —(CH$_2$)n-CO—N(R4)-, —(CH$_2$)p-, C2-C5alkenyl, C2-C5alkynyl, C3-C6cycloalkyl, and a direct bond wherein the E1 ring and the E2 ring are directly linked by a covalent bond;

and wherein the carbon atoms of —(CH2)n-, —(CH2)q-, (CH2)p, C2-C5alkenyl, and C2-C5alkynyl moieties of X1 may be further substituted by one or more C1-C6alkyl;

X2 is selected from the group consisting of C1-C6 alkyl, C3-C6 branched alkyl, or a direct bond wherein E1 is directly linked to the Y group of formula I;

each R2 is selected from the group consisting of monocyclic heteroaryl, C1-C6alkyl, branched C3-C7alkyl, a R19-substituted C3-C8carbocyclyl wherein R19 is H, or C1-C6alkyl, C1-C6fluoroalkyl wherein the alkyl group is partially or fully fluorinated, and phenyl wherein the phenyl group is optionally substituted by one or more fluorine substituents or chlorine;

each R2' is selected from the group consisting of halogen and R2;

each R3 is independently and individually selected from the group consisting of H, C1-C6alkyl, branched C3-C7alkyl, C3-C7carbocyclyl, or phenyl;

wherein two R3 moieties independently and individually taken from the group consisting of C1-C6alkyl and branched C3-C7alkyl are attached to the same nitrogen heteroatom, the two R3 moieties may cyclize to form a C3-C7 heterocyclyl ring;

each R4 is selected from the group consisting of H, C1-C6alkyl, hydroxyC1-C6 alkyl, dihydroxyC1-C6alkyl, C1-C6alkoxyC1-C6alkyl, branched C3-C7alkyl, hydroxyC1-C6 alkyl, branched C1-C6alkoxyC1-C6alkyl, branched dihydroxyC1-C6alkyl, carbocyclyl, hydroxyl substituted carbocyclyl, alkoxy substituted carbocyclyl, dihydroxy substituted carbocyclyl, phenyl, heteroaryl, heterocyclyl, phenylC1-C6alkyl, heteroarylC1-C6alkyl, and heterocyclylC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom may cyclize to form a C3-C7 heterocyclyl ring;

each R5 is independently and individually selected from the group consisting of

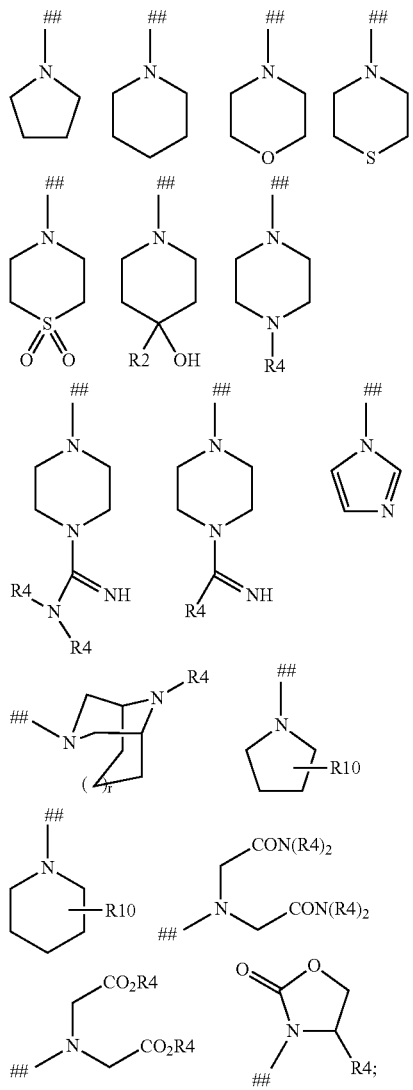

and wherein the symbol (##) is the point of attachment to respective R8, R10, R13, Z2, Z3, Z4, Z5, or A2 ring moieties containing a R5 moiety;

wherein two R4 moieties independently and individually taken from the group consisting of C1-C6alkyl, branched C3-C6alkyl, hydroxyalkyl, and alkoxyalkyl and are attached to the same nitrogen heteroatom of R5 may cyclize to form a C3-C7 heterocyclyl ring;

wherein each R6 is independently and individually selected from the group consisting of C1-C6alkyl, branched C3-C7alkyl, carbocyclyl, phenyl, heteroaryl, and heterocyclyl;

each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

each R8 is independently and individually selected from the group consisting of C1-C6alkyl, C1-C6 fluoroalkyl wherein the alkyl moiety is partially or fully fluorinated, branchedC4-C7alkyl, carbocyclyl, phenyl, C1-C6phenylalkyl, heteroaryl or heteroarylC1-C6alkyl, heterocyclyl, heterocyclylC1-C6alkyl, OH, C1-C6alkoxy, $N(R3)_2$, $N(R4)_2$, or R5;

wherein two R3 moieties are independently and individually taken from the group consisting of C1-C6alkyl and branched C3-C6alkyl and are attached to the same nitrogen heteroatom of R8 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of R8 may cyclize to form a C3-C7 heterocyclyl ring;

each R10 is independently and individually selected from the group consisting of $CO_2H$, $CO_2C1$-C6alkyl, CO—$N(R4)_2$, OH, C1-C6alkoxy, —$N(R4)_2$;

wherein two R4 moieties independently and individually taken from the group consisting of C1-C6alkyl, branched C3-C6alkyl, hydroxyalkyl, and alkoxyalkyl and are attached to the same nitrogen heteroatom of R10 may cyclize to form a C3-C7 heterocyclyl ring;

each R13 is independently and individually selected from the group consisting of H, C1-C6alkyl, branched C3-C7alkyl, carbocyclyl, hydroxyC2-C7alkyl, C1-C6alkoxyC2-C7alkyl, $(R4)_2N$—CO, $(R4)_2N$—CO—C1-C6alkyl, carboxyC1-C6alkyl, C1-C6alkoxycarbonyl, C1-C6alkoxycarbonylC1-C6alkyl, $(R4)_2N$—C2-C6alkyl, $(R4)_2N$—C2-C6alkylN(R4)-$(CH_2)_q$, R5-C2-C6alkylN(R4)-$(CH_2)_q$, $(R4)_2N$—C2-C6alkylO-$(CH_2)_q$, R5-C2-C6alkyl-O—$(CH_2)_q$, —$(CH_2)_qN(R4)C(O)R8$, aryl, arylC1-C6alkyl, heteroaryl, heteroarylC1-C6alkyl, heterocyclyl, heterocyclylC1-C6alkyl, aryloxyC2-C6alkyl, heteroaryloxyC2-C6alkyl, heterocyclyloxyC2-C6alkyl, arylaminoC2-C6alkyl, heteroarylaminoC2-C6alkyl, and heterocyclylaminoC2-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom of R13 may cyclize to form a C3-C7 heterocyclyl ring;

each R14 is independently and respectively selected from the group consisting of H and C1-C6alkyl;

wherein Z1' is independently and individually selected from the group consisting of H, C1-C6alkyl, C3-C7cycloalkyl, hydroxyC1-C6alkyl, C1-C6alkoxyC1-C6alkyl, $(R4)_2N$—C1-C6alkyl, $(R4)_2N$—C2-C6alkylN(R4)-$(CH_2)_p$, $(R4)_2N$—C2-C6alkylO-$(CH_2)_p$, $(R4)_2N$—CO—C1-C6alkyl, carboxyC1-C6alkyl, C1-C6alkoxycarbonylC1-C6alkyl, —$(CH_2)_pN(R4)C(O)R8$, aryl, arylC1-C6alkyl, heteroaryl, heteroarylC1-C6alkyl, heterocyclyl, heterocyclylC1-C6alkyl, aryloxyC1-C6alkyl, heteroaryloxyC1-C6alkyl, heterocyclyloxyC1-C6alkyl, arylaminoC1-C6alkyl, heteroarylaminoC1-C6alkyl, or heterocyclylaminoC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom of Z1' may cyclize to form a C3-C7 heterocyclyl ring;

each Z3 is independently and individually selected from the group consisting of H, C1-C6alkyl, hydroxyl, hydroxyC1-C6alkyl, cyano, C1-C6alkoxy, C1-C6alkoxyC1-C6alkyl, halogen, $CF_3$, $(R3)_2N$—, $(R4)_2N$—, $(R4)_2NC1$-C6alkyl, (R4)₂NC2-C6alkylN(R4)-(CH₂)$_n$, (R4)₂NC2-C6alkylO-(CH₂)$_n$, R8CO—, (R4)₂N—CO—C1-C6alkyl, carboxyl, carboxyC1-C6alkyl, C1-C6alkoxycarbonyl, C1-C6alkoxycarbonylC1-C6alkyl, (R3)₂NSO₂, —SO₂R3, SOR3, (R4)₂NSO₂, —SO₂R4, —SOR4, —(CH₂)$_n$N(R4)C(O)R8, —C=(NOH)R6, —C=(NOR3)R6, heteroaryl, heterocyclyl, heteroarylC1-C6alkyl, heterocyclylC1-C6alkyl, heteroaryloxy, heterocyclyloxy, heteroaryloxyC1-C6alkyl, heterocyclyloxyC1-C6alkyl, arylamino, heteroarylamino, heterocyclylamino, arylaminoC1-C6alkyl, heteroarylaminoC1-C6alkyl, heterocyclylaminoC1-C6alkyl, or moieties of the formulae

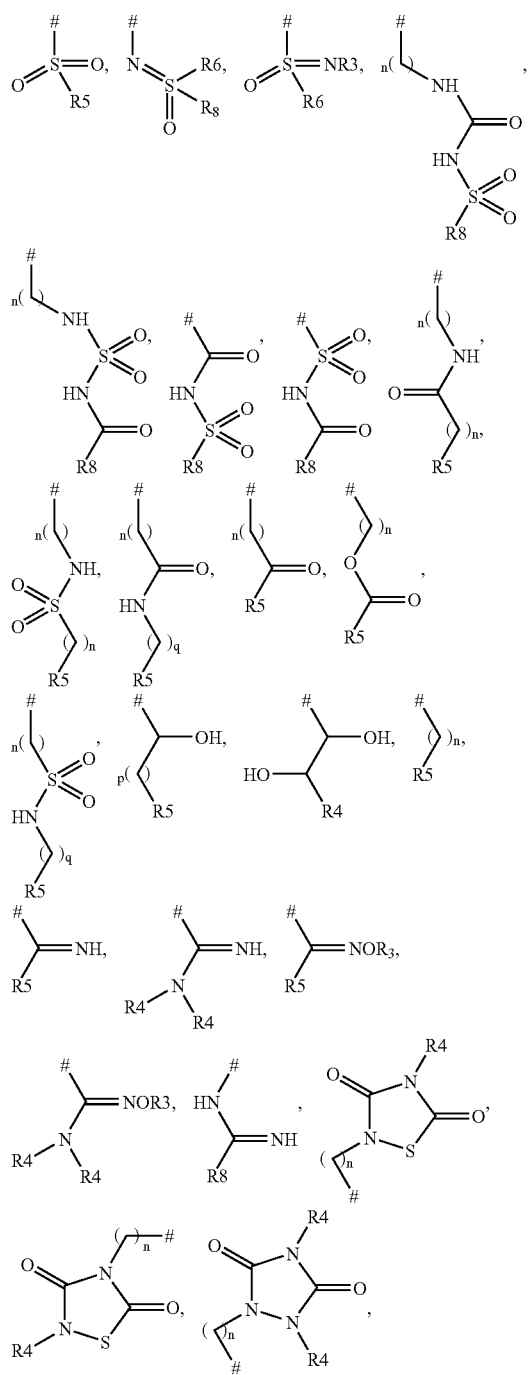

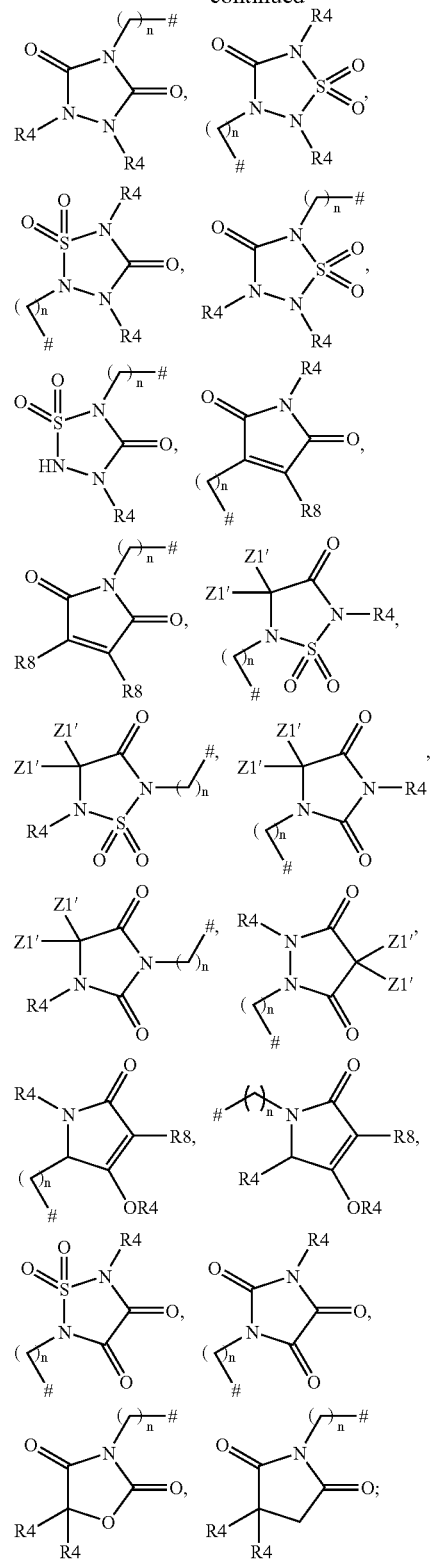

wherein the symbol (#) indicates the point of attachment of the Z3 moiety to the A2 ring of formula I;

in the event that Z3 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z3 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z3 may cyclize to form a C3-C7 heterocyclyl ring;

each Z4 is independently and individually selected from the group consisting of H, C1-C6alkyl, hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C2-C6alkyl, carboxyC2-C6alkyl, C1-C6alkoxycarbonylC2-C6alkyl, —C2-C6alkylN(R4)C(O)R8, R8-C(=NR3)-, —SO$_2$R8, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

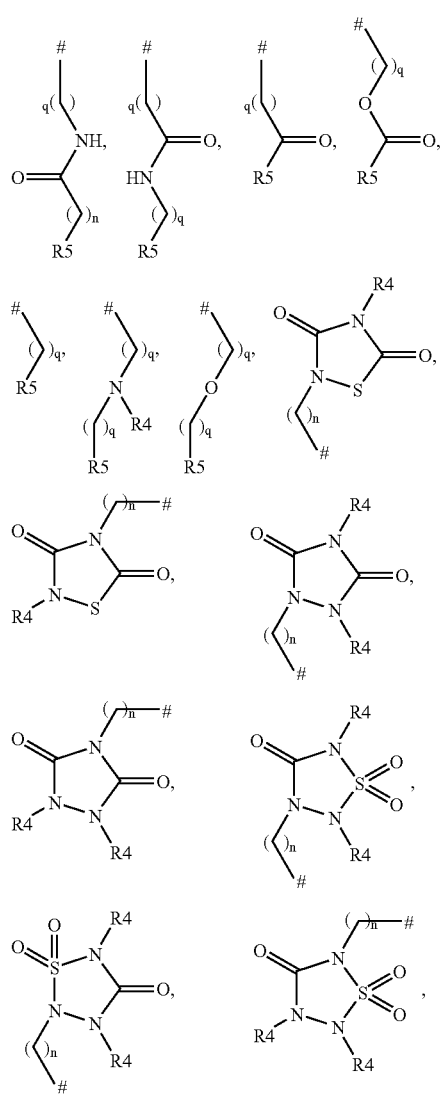
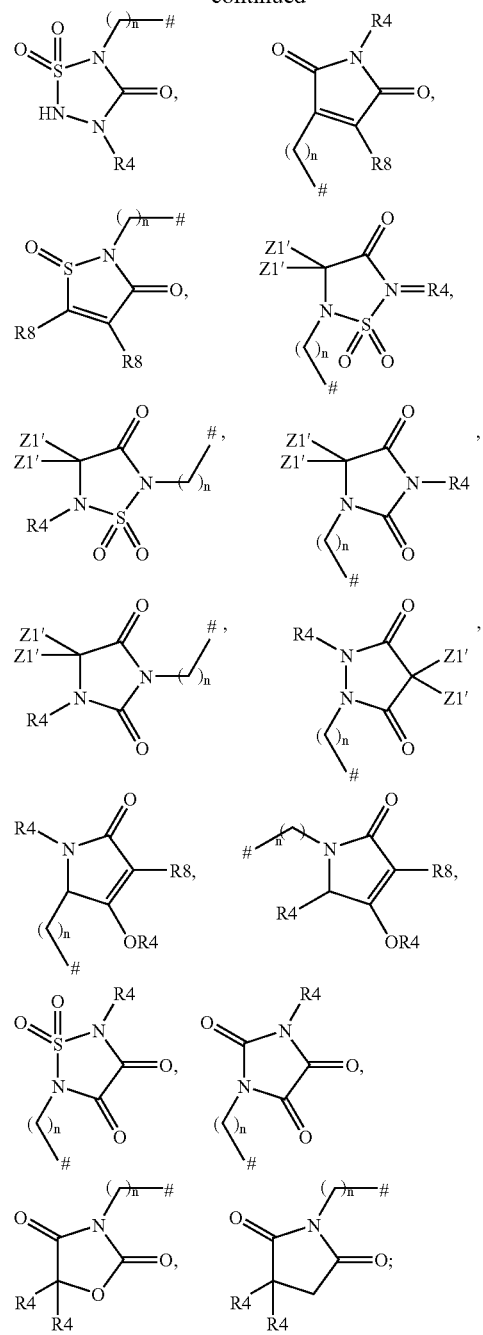

wherein the symbol (#) indicates the point of attachment of the Z4 moiety to the A2 ring for formula I;

in the event that Z4 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z4 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z4 may cyclize to form a C3-C7 heterocyclyl ring;

Z5 is independently and individually selected from the group consisting of H, C1-C6alkyl, branched C3-C7alkyl, halogen, fluoroalkyl, cyano, hydroxyl, alkoxy, oxo, aminocarbonyl, carbonylamino, aminosulfonyl, sulfonylamino, —N(R3)$_2$, —O—(CH$_2$)q-N(R4)$_2$, —N(R3)-(CH$_2$)q-N(R4)$_2$, —R5, —O—(CH$_2$)q-O-Alkyl, —O—(CH$_2$)q-N(R4)$_2$, —N(R3)-(CH$_2$)q-O-Alkyl, —N(R3)-(CH$_2$)q-N(R4)$_2$, —O—(CH$_2$)q-R5, and —N(R3)-(CH$_2$)q-R5;

wherein two R3 moieties are independently and individually taken from the group consisting of C1-C6alkyl and branched C3-C6alkyl and are attached to the same nitrogen heteroatom of Z5 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z5 may cyclize to form a C3-C7 heterocyclyl ring;

Each Z6 is independently and individually selected from the group consisting of H, C1-C6alkyl, branched C3-C7alkyl, hydroxyl, C1-C6alkoxy, (R3)$_2$N—, —N(R3)COR8, (R4)$_2$N—, —R5, —N(R4)COR8, —N(R3)SO$_2$R6-, —CON(R3)$_2$, —CON(R4)$_2$, —COR5, —SO$_2$NHR4, heteroaryl, heterocyclyl, heteroaryloxy, heterocyclyloxy, arylamino, heteroarylamino, and heterocyclylamino;

wherein two R3 moieties are independently and individually taken from the group consisting of C1-C6alkyl and branched C3-C6alkyl and are attached to the same nitrogen heteroatom of Z6 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z6 may cyclize to form a C3-C7 heterocyclyl ring;

and n is 0-4; p is 1-4; q is 2-6; r is 0 or 1; v is 1 or 2;

V, V1, and V2 are each independently and respectively selected from the group consisting of O and H$_2$;

and tautomers, diastereomers, geometric isomers, enantiomers, hydrates, prodrugs, and salts of any of the foregoing.

4.1.6b

The following specific compounds are most preferred: 1-(3-t-butyl-1-(3-hydroxy-2,3-dihydro-1H-inden-5-yl)-1H-pyrazol-5-yl)-3-(2,3-dichlorophenyl)urea, 1-(3-t-butyl-1-(3-oxo-2,3-dihydro-1H-inden-5-yl)-1H-pyrazol-5-yl)-3-(2,3-dichlorophenyl)urea, 1-(3-t-butyl-1-(3-(hydroxyimino)-2,3-dihydro-1H-inden-5-yl)-1H-pyrazol-5-yl)-3-(2,3-dichlorophenyl)urea, 1-(3-t-butyl-1-(indolin-6-yl)-1H-pyrazol-5-yl)-3-(2,3-dichlorophenyl)urea, 1-(3-t-butyl-1-(indolin-5-yl)-1H-pyrazol-5-yl)-3-(2,3-dichlorophenyl)urea, 1-(3-t-butyl-1-(1-(methylsulfonyl)indolin-5-yl)-1H-pyrazol-5-yl)-3-(2,3-dichlorophenyl)urea, 2-(3-(3-t-butyl-5-(3-(2,3-dichlorophenyl)ureido)-1H-pyrazol-1-yl)naphthalen-1-yl)acetic acid, 1-(1-(4-(2-amino-2-oxoethyl)naphthalen-2-yl)-3-t-butyl-1H-pyrazol-5-yl)-3-(2,3-dichlorophenyl)urea, 1-(3-t-butyl-1-(4-(hydroxymethyl)naphthalen-2-yl)-1H-pyrazol-5-yl)-3-(2,3-dichlorophenyl)urea, 1-(3-t-butyl-1-(2-(methylsulfonyl)-1,2,3,4-tetrahydroisoquinolin-7-yl)-1H-pyrazol-5-yl)-3-(2,3-dichlorophenyl)urea, 1-(3-t-butyl-1-(2-(methylsulfonyl)-1,2,3,4-tetrahydroisoquinolin-6-yl)-1H-pyrazol-5-yl)-3-(2,3-dichlorophenyl)urea, 1-(3-t-butyl-1-(1-(methylcarbamoyl)-1,2,3,4-tetrahydroisoquinolin-6-yl)-1H-pyrazol-5-yl)-3-(2,3-dichlorophenyl)urea, 1-(3-t-butyl-1-(2-oxo-2,3,4,5-tetrahydro-1H-benzo[d]azepin-7-yl)-1H-pyrazol-5-yl)-3-(2,3-dichlorophenyl)urea, 1-(3-t-butyl-1-(3-(methylsulfonyl)-2,3,4,5-tetrahydro-1H-benzo[d]azepin-7-yl)-1H-pyrazol-5-yl)-3-(2,3-dichlorophenyl)urea, 1-(1-(3-carbamoyl-2,3-dihydro-1H-inden-5-yl)-3-cyclopentyl-1H-pyrazol-5-yl)-3-(2,3-dichlorophenyl)urea, 1-(3-t-butyl-1-(indolin-6-yl)-1H-pyrazol-5-yl)-3-(naphthalen-1-yl)urea, 1-(3-t-butyl-1-(indolin-5-yl)-1H-pyrazol-5-yl)-3-(naphthalen-1-yl)urea, 1-(1-(4-(2-amino-2-oxoethyl)naphthalen-2-yl)-3-t-butyl-1H-pyrazol-5-yl)-3-(3-(pyridin-3-yloxy)phenyl)urea, 1-(3-t-butyl-1-(3-carbamoyl-1,2,3,4-tetrahydroisoquinolin-6-yl)-1H-pyrazol-5-yl)-3-(3-(8-methyl-7-oxo-7,8-dihydropyrido[2,3-d]pyrimidin-6-yl)phenyl)urea, 1-(3-t-butyl-1-(indolin-5-yl)-1H-pyrazol-5-yl)-3-(3-(8-methyl-7-oxo-7,8-dihydropyrido[2,3-d]pyrimidin-6-yl)phenyl)urea, 4.1.7 Methods 4.1.7a Methods of Protein Modulation The invention includes methods of modulating kinase activity of the p38 family of kinases including, but not limited to p38-alpha and other MAP kinases. The kinases may be wildtype kinases, oncogenic forms thereof, aberrant fusion proteins thereof or polymorphs of any of the foregoing. The method comprises the step of contacting the kinase species with compounds of the invention and especially those set forth in sections 4.1 and 4.1.6a. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, kinase cellular localization, and recruitment of other proteins into signaling complexes through modulation of kinase conformation.

4.1.7b Treatment Methods

The methods of the invention also include treating individuals suffering from a condition selected from the group consisting of inflammation, osteoarthritis, respiratory diseases, stroke, systemic shock, immunological diseases, and cardiovascular disease. These methods comprise administering to such individuals compounds of the invention, and especially those of section 4.1 and 4.1.6a, said condition being human inflammation, rheumatoid arthritis, rheumatoid spondylitis, ostero-arthritis, asthma, gouty arthritis, sepsis, septic shock, endotoxic shock, Gram-negative sepsis, toxic shock syndrome, adult respiratory distress syndrome, stroke, reperfusion injury, neural trauma, neural ischemia, psoriasis, restenosis, chronic pulmonary inflammatory disease, bone resorptive diseases, graft-versus-host reaction, Chron's disease, ulcerative colitis, inflammatory bowel disease, pyresis, and combinations thereof. The administration method is not critical, and may be from the group consisting of oral, parenteral, inhalation, and subcutaneous.

4.1.8 Pharmaceutical Preparations

The compounds of the invention, especially those of 4.1 and 4.1.6a may form a part of a pharmaceutical composition by combining one or more such compounds with a pharmaceutically acceptable carrier. Additionally, the compositions may include an additive selected from the group consisting of adjuvants, excipients, diluents, and stablilizers.

4.1.9 Kinase/Compound Adducts

The invention also provides adducts in the form of compounds of the invention bound with a species of kinase such as a wild-type kinase, oncogenic forms thereof, aberrant fusion proteins thereof and polymorphs of any of the foregoing. The compounds are advantageously selected from the groups defined in sections 4.1 and 4.1.6a.

4.2 Generally—Monocyclic A2 Compounds with Polycyclic E2 Rings

The invention includes compounds of the formula I as defined in section 2.2, wherein R2 is selected from the group consisting of monocyclic heteroaryl, C1-C6alkyl, branched C3-C7alkyl, a R19-substituted C3-C8carbocyclyl wherein R19 is H, or C1-C6alkyl, C1-C6fluoroalkyl wherein the alkyl group is partially or fully fluorinated, and phenyl wherein the phenyl group is optionally substituted by one or more fluorine substituents or chlorine;

4.2.1 Preferred D Moieties 4.2.1a

Preferably, the compounds of formula I in 4.2 contain D moieties wherein E1 and E2 are as defined in section 1.2.1

4.2.1b

Additionally preferred D moieties of formula I in 4.2 are as defined in section 1.2.1b 4.2.1c More preferred D moieties of 4.2.1b are where E2 is defined as in section 1.2.1c 4.2.2 Preferred A2 Moieties 4.2.2a Compounds of Formula I as defined above in section 4.2 have preferred A2 moieties as defined in section 2.2.2a;

4.2.2b

More preferred A2 moieties are selected from the group consisting of

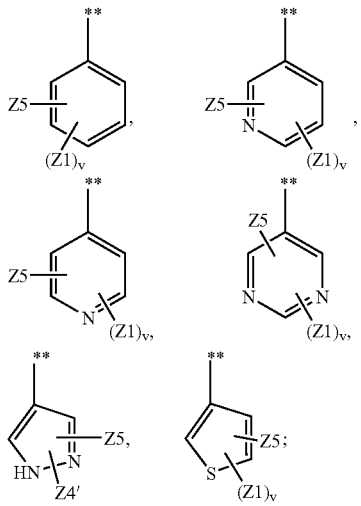

and wherein the symbol (**) is the point of attachment to the A1 ring for formula I.

4.2.2c

Even more preferred A2 moieties are selected from the group consisting of

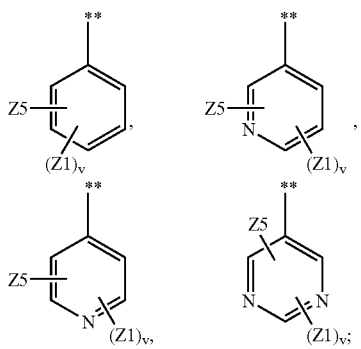

and wherein the symbol (**) is the point of attachment to the A1 ring of formula I.

4.2.3 Preferred Classes of Compounds 4.2.3a

Compounds as defined in 4.2.1a wherein the A2 group is defined in 4.2.2a.

4.2.3b

Compounds as defined in 4.2.3a wherein the A2 group is defined in 4.2.2b.

4.2.3c

Compounds as defined in 4.2.3a wherein the A2 group is defined in 4.2.2c.

4.2.3d

Compounds as defined in 4.2.1b wherein the A2 group is defined in 4.2.2a.

4.2.3e

Compounds as defined in 4.2.3c wherein the A2 group is defined in 4.2.2b.

4.2.3f

Compounds as defined in 4.2.3c wherein the A2 group is defined in 4.2.2c.

4.2.4 Preferred A1 Moieties 4.2.4a

These preferred A1 moieties are defined in 4.1.4a.

4.2.4b

These more preferred A1 moieties are defined in 4.1.4b.

4.2.4c

These even more preferred A1 moieties are defined in 4.1.4c.

4.2.5 Preferred W and Y Moieties 4.2.5a (1) W and Y are each NH, and X=O; (2) W=NH, Y=CHR4 and X=O; or (3) W=CHR4, Y=NH, and X=O.

4.2.5b

W and Y are each NH and X=O.

4.2.6 Further Preferred Compounds 4.2.6a

Further preferred compounds are of the formula

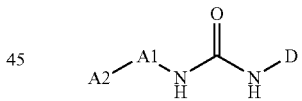

I wherein A2 is selected from the group consisting of

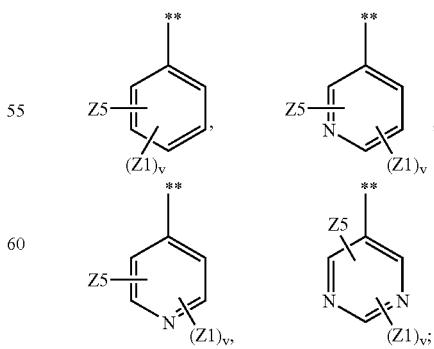

wherein the symbol (**) denotes the attachment to the A1 moiety of formula I;

A1 is selected from the group consisting of

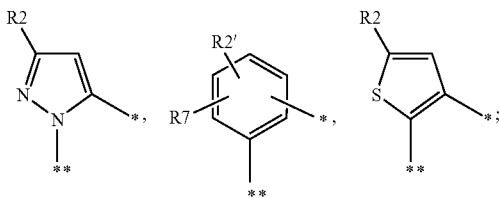

wherein the symbol (*) denotes the attachment to the W moiety of formula I and the symbol (**) denotes the attachment to the A2 moiety of formula I;

X is O, S, or NR3;

D comprises a member of

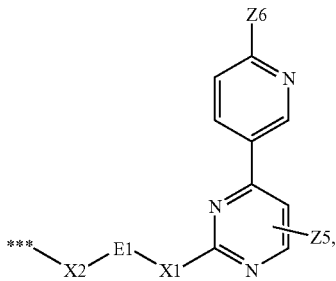

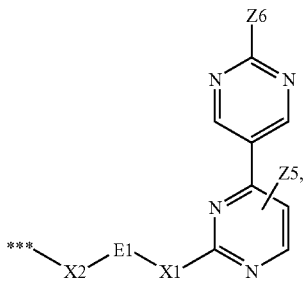

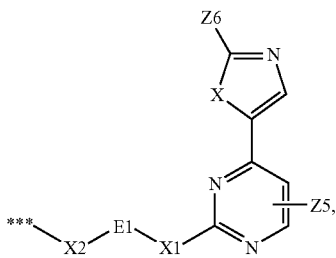

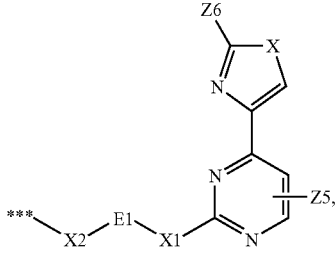

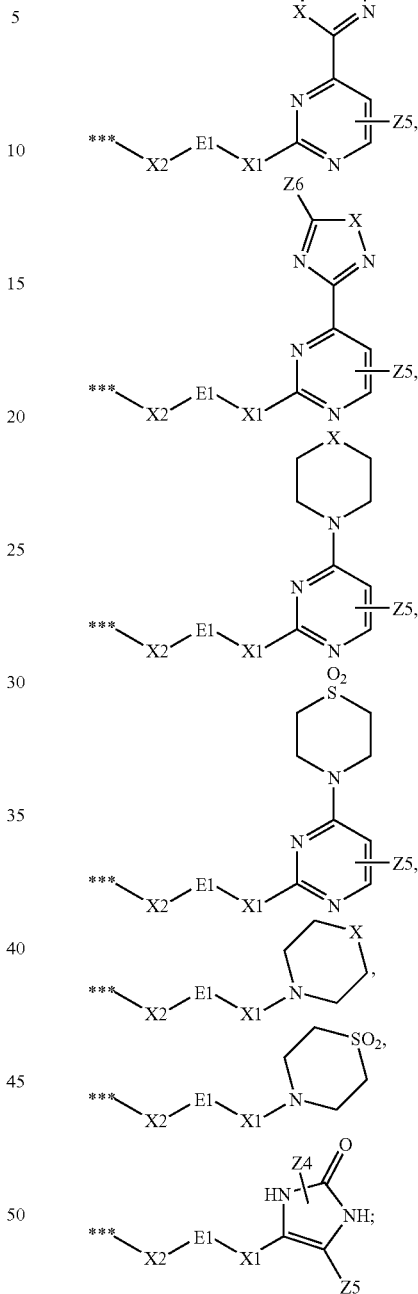

wherein E1 is selected from the group consisting cyclopropyl, cyclobutyl, cyclopentyl, cyclohexyl, pyrrolidinyl piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl and naphthyl;

wherein the symbol (***) denotes the attachment to the Y moiety of formula I;

X1 is selected from the group consisting of O, S, NR3, —C(═O)—, —O—(CH₂)n-, —S—(CH₂)n-, —NR3-(CH₂)n-, —O—(CH₂)q-O—, —O—(CH₂)q-NR3-, —N(R3)(CH₂)q-N(R3)-, —(CH₂)n-N(R4)-C(═O)—, —(CH₂)n-N(R4)-C(═O)(CH₂)n-, —(CH₂)n-CO—N(R4)-, —(CH₂)p-, C2-C5alkenyl, C2-C5alkynyl, C3-C6cycloalkyl, and a direct bond wherein the E1 ring and the E2 ring are directly linked by a covalent bond;

and wherein the carbon atoms of —(CH2)n-, —(CH2)q-, (CH2)p, C2-C5alkenyl, and C2-C5alkynyl moieties of X1 may be further substituted by one or more C1-C6alkyl;

X2 is selected from the group consisting of C1-C6 alkyl, C3-C6 branched alkyl, or a direct bond wherein E1 is directly linked to the Y group of formula I;

each R2 is selected from the group consisting of monocyclic heteroaryl, C1-C6alkyl, branched C3-C7alkyl, a R19-substituted C3-C8carbocyclyl wherein R19 is H, or C1-C6alkyl, C1-C6fluoroalkyl wherein the alkyl group is partially or fully fluorinated, and phenyl wherein the phenyl group is optionally substituted by one or more fluorine substituents or chlorine;

each R2' is selected from the group consisting of halogen and R2;

each R3 is independently and individually selected from the group consisting of H, C1-C6alkyl, branched C3-C7alkyl, C3-C7carbocyclyl, or phenyl;

wherein two R3 moieties independently and individually taken from the group consisting of C1-C6alkyl and branched C3-C7alkyl are attached to the same nitrogen heteroatom, the two R3 moieties may cyclize to form a C3-C7 heterocyclyl ring;

each R4 is selected from the group consisting of H, C1-C6alkyl, hydroxyC1-C6 alkyl, dihydroxyC1-C6alkyl, C1-C6alkoxyC1-C6alkyl, branched C3-C7alkyl, branched hydroxyC1-C6 alkyl, branched C1-C6alkoxyC1-C6alkyl, branched dihydroxyC1-C6alkyl, carbocyclyl, hydroxyl substituted carbocyclyl, alkoxy substituted carbocyclyl, dihydroxy substituted carbocyclyl, phenyl, heteroaryl, heterocyclyl, phenylC1-C6alkyl, heteroarylC1-C6alkyl, and heterocyclylC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom may cyclize to form a C3-C7 heterocyclyl ring;

each R5 is independently and individually selected from the group consisting of

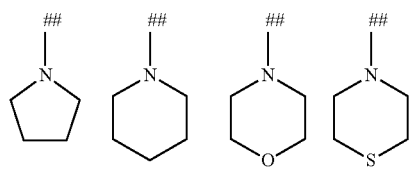

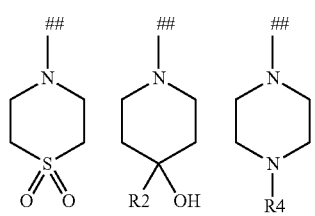

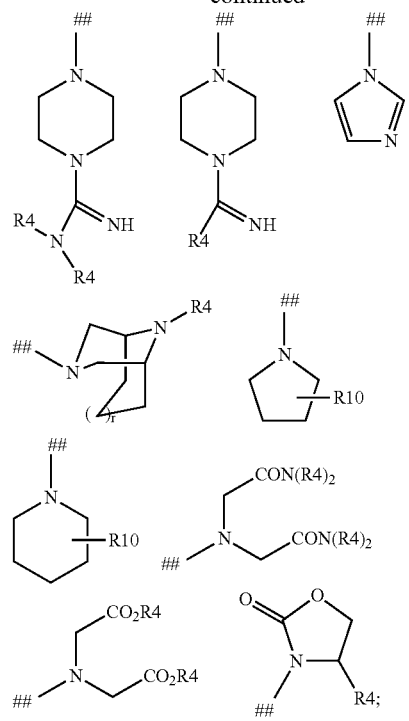

and wherein the symbol (##) is the point of attachment to respective R8, R10, Z1, Z4, Z5, Z6 or A2 ring moieties containing a R5 moiety;

wherein two R4 moieties independently and individually taken from the group consisting of C1-C6alkyl, branched C3-C6alkyl, hydroxyalkyl, and alkoxyalkyl and are attached to the same nitrogen heteroatom of R5 may cyclize to form a C3-C7 heterocyclyl ring;

wherein each R6 is independently and individually selected from the group consisting of C1-C6alkyl, branched C3-C7alkyl, carbocyclyl, phenyl, heteroaryl, and heterocyclyl;

each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

each R8 is independently and individually selected from the group consisting of C1-C6alkyl, C1-C6 fluoroalkyl wherein the alkyl moiety is partially or fully fluorinated, branchedC4-C7alkyl, carbocyclyl, phenyl, C1-C6phenylalkyl, heteroaryl or heteroarylC1-C6alkyl, heterocyclyl, heterocyclylC1-C6alkyl, OH, C1-C6alkoxy, N(R3)$_2$, N(R4)$_2$, or R5;

wherein two R3 moieties are independently and individually taken from the group consisting of C1-C6alkyl and branched C3-C6alkyl and are attached to the same nitrogen heteroatom of R8 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of R8 may cyclize to form a C3-C7 heterocyclyl ring;

each R10 is independently and individually selected from the group consisting of CO$_2$H, CO$_2$C1-C6alkyl, CO—N(R4)$_2$, OH, C1-C6alkoxy, —N(R4)$_2$;

wherein two R4 moieties independently and individually taken from the group consisting of C1-C6alkyl, branched C3-C6alkyl, hydroxyalkyl, and alkoxyalkyl and are attached to the same nitrogen heteroatom of R10 may cyclize to form a C3-C7 heterocyclyl ring;

each Z1 is a substituent attached to a ring carbon and is independently and individually selected from the group consisting of hydroxyC1-C6alkyl, C2-C6alkoxy, C1-C6alkoxyC1-C6alkyl, (R4)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—C(=O)—, (R4)$_2$N—C(=O)—, (R4)$_2$N—CO—C1-C6alkyl, C1-C6alkoxycarbonyl, carboxyC1-C6alkyl, C1-C6alkoxycarbonylC1-C6alkyl, (R3)$_2$NSO$_2$, SOR3, (R4)$_2$NSO$_2$, —SO$_2$R3', —SOR4, —C(=O)R6, —C(=NOH)R6, —C(=NOR3)R6, —(CH$_2$)$_n$N(R4)C(O)R8, monocyclic heteroaryl, monocyclic heterocyclyl, monocyclic heteroarylC1-C6alkyl, monocyclic heterocyclylC1-C6alkyl, monocyclic heteroaryloxy, monocyclic heterocyclyloxy, monocyclic heteroaryloxyC1-C6alkyl, monocyclic heterocyclyloxyC1-C6alkyl, arylamino, monocyclic heteroarylamino, monocyclic heterocyclylamino, arylaminoC1-C6alkyl, monocyclic heteroarylaminoC1-C6alkyl, monocyclic heterocyclylaminoC1-C6alkyl, or moieties of the formulae

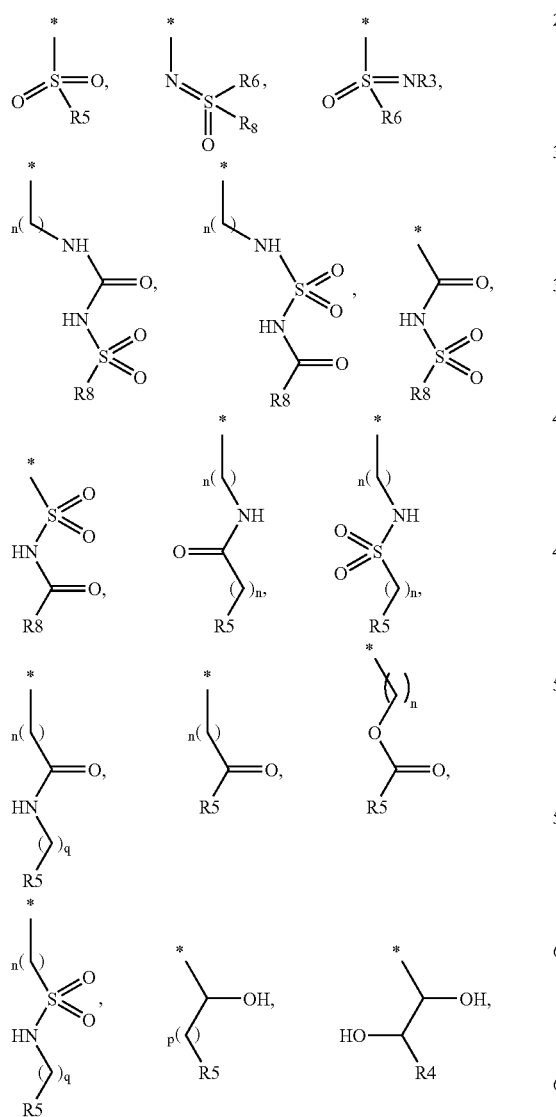

-continued

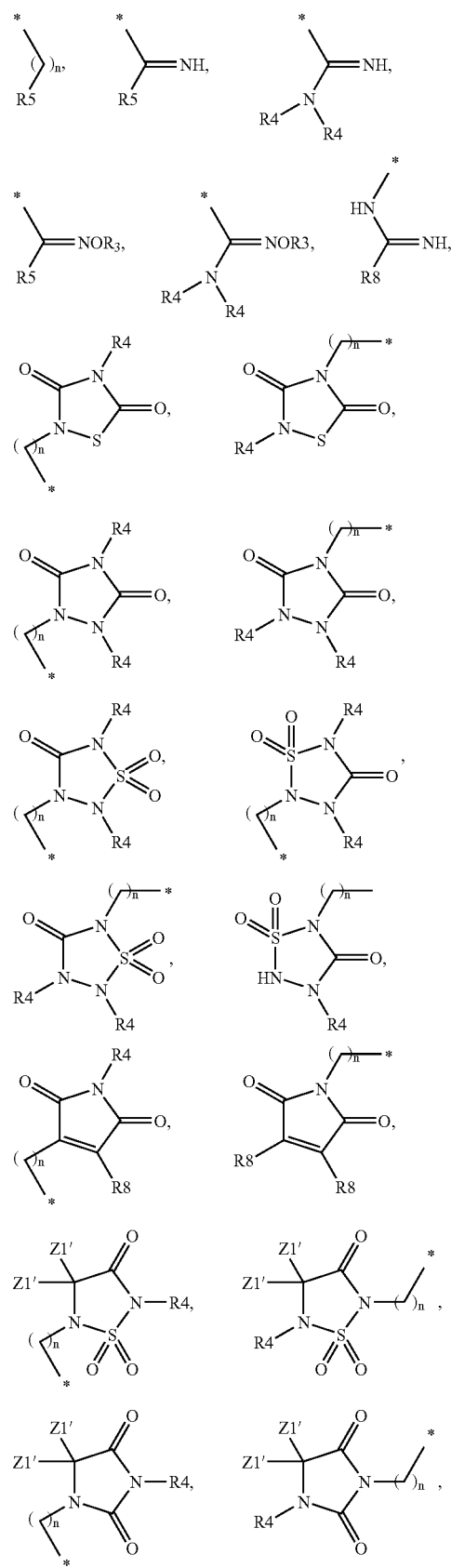

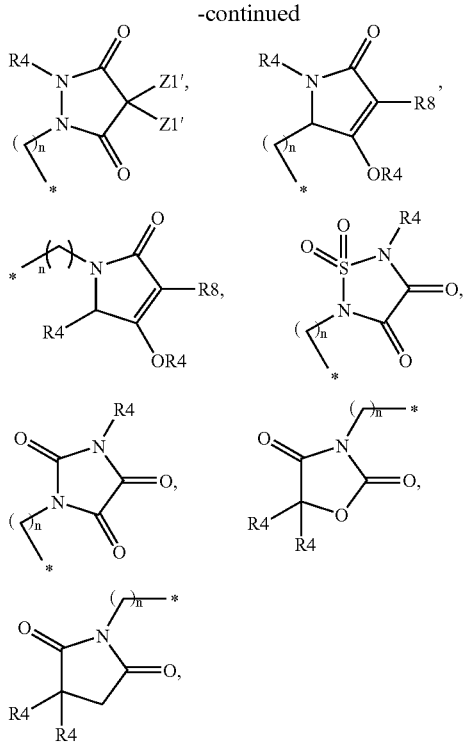

cyano wherein the site of attachment to the A2 ring is meta to the point of attachment to the A1 ring and wherein A2 is phenyl, and cyano wherein the site of attachment is to a substitutable position when A2 is pyridyl, pyrimidinyl or a five-membered ring;

In the foregoing definition of Z1, alkyl moieties may optionally be substituted by one or more C1-C6alkyl;
Wherein the asterisk (*) indicates the point of attachment of the Z1 moiety to the A2 ring;
in the event that Z1 contains an alkyl or alkylene moiety, such moieties may be further substituted with one or more C1-C6alkyls;
In the foregoing definition of Z1, alkyl moieties may optionally be substituted by one or more C1-C6alkyl;
Wherein the asterisk (*) indicates the point of attachment of the Z1 moiety to the A2 ring;
in the event that Z1 contains an alkyl or alkylene moiety, such moieties may be further substituted with one or more C1-C6alkyls;
wherein two R3 moieties are independently and individually taken from the group consisting of C1-C6alkyl and branched C3-C6alkyl and are attached to the same nitrogen heteroatom of Z1 may cyclize to form a C3-C7 heterocyclyl ring;
wherein two R4 moieties independently and individually taken from the group consisting of C1-C6alkyl, branched C3-C6alkyl, hydroxyalkyl, and alkoxyalkyl and are attached to the same nitrogen heteroatom of Z1 may cyclize to form a C3-C7 heterocyclyl ring;
wherein Z1' is independently and individually selected from the group consisting of H, C1-C6alkyl, C3-C7cycloalkyl, hydroxyC1-C6alkyl, C1-C6alkoxyC1-C6alkyl, $(R4)_2N$—C1-C6alkyl, $(R4)_2N$—C2-C6alkylN(R4)-$(CH_2)_p$, $(R4)_2N$—C2-C6alkylO-$(CH_2)_p$, $(R4)_2N$—CO—C1-C6alkyl, carboxyC1-C6alkyl, C1-C6alkoxycarbonylC1-C6alkyl, —$(CH_2)_pN(R4)C(O)R8$ aryl, arylC1-C6alkyl, heteroaryl, heteroarylC1-C6alkyl, heterocyclyl, heterocyclylC1-C6alkyl, aryloxyC1-C6alkyl, heteroaryloxyC1-C6alkyl, heterocyclyloxyC1-C6alkyl, arylaminoC1-C6alkyl, heteroarylaminoC1-C6alkyl, or heterocyclylaminoC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom of Z1' may cyclize to form a C3-C7 heterocyclyl ring;

each Z4 is a substituent attached to a ring nitrogen and is independently and individually selected from the group consisting of H, C1-C6alkyl, hydroxyC2-C6alkyl, C1-C6alkoxyC2-C6alkyl, $(R4)_2N$—C2-C6alkyl, $(R4)_2N$—C2-C6alkylN(R4)-C2-C6alkyl, $(R4)_2N$—C2-C6alkyl-O—C2-C6alkyl, $(R4)_2N$—CO—C2-C6alkyl, carboxyC2-C6alkyl, C1-C6alkoxycarbonylC2-C6alkyl, —C2-C6alkylN(R4)C(O)R8, R8-C(=NR3)-, —$SO_2R8$, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

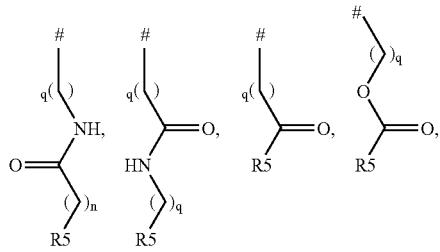

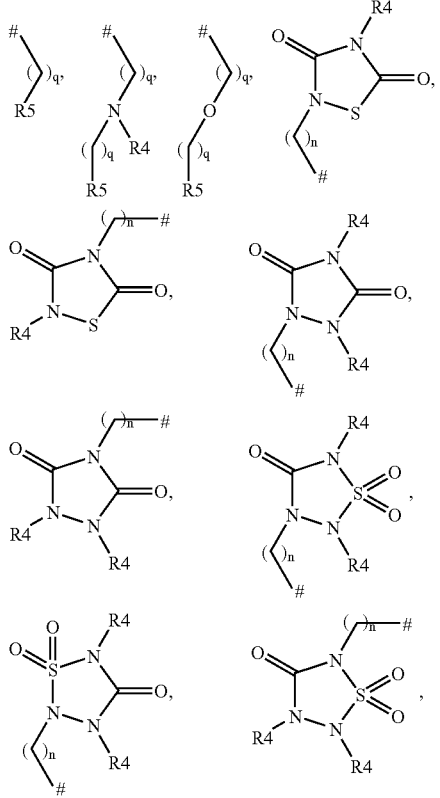

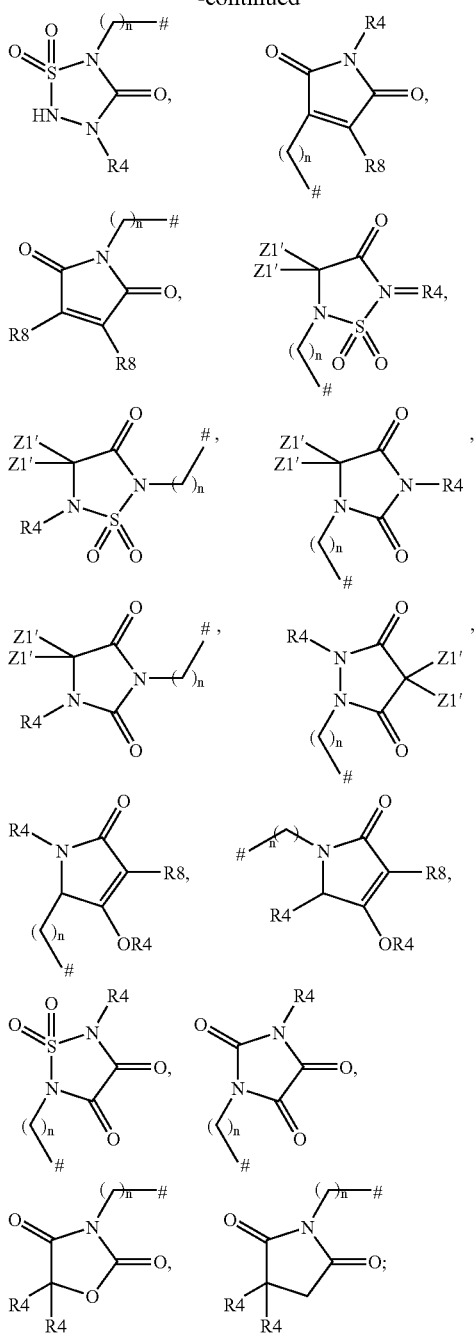

wherein the symbol (#) indicates the point of attachment of the Z4 moiety to the A2 ring for formula I;

in the event that Z4 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z4 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z4 may cyclize to form a C3-C7 heterocyclyl ring;

Z5 is independently and individually selected from the group consisting of H, C1-C6alkyl, branched C3-C7alkyl, halogen, fluoroalkyl, cyano, hydroxyl, alkoxy, oxo, aminocarbonyl, carbonylamino, aminosulfonyl, sulfonylamino, —N(R3)$_2$, —O—(CH$_2$)q-N(R4)$_2$, —N(R3)-(CH$_2$)q-N(R4)$_2$, —R5, —O—(CH$_2$)q-O-Alkyl, —O—(CH$_2$)q-N(R4)$_2$, —N(R3)-(CH$_2$)q-O-Alkyl, —N(R3)-(CH$_2$)q-N(R4)$_2$, —O—(CH$_2$)q-R5, and —N(R3)-(CH$_2$)q-R5;

wherein two R3 moieties are independently and individually taken from the group consisting of C1-C6alkyl and branched C3-C6alkyl and are attached to the same nitrogen heteroatom of Z5 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z5 may cyclize to form a C3-C7 heterocyclyl ring;

Each Z6 is independently and individually selected from the group consisting of H, C1-C6alkyl, branched C3-C7alkyl, hydroxyl, C1-C6alkoxy, (R3)$_2$N—, —N(R3)COR8, (R4)$_2$N—, —R5, —N(R4)COR8, —N(R3)SO$_2$R6-, —CON(R3)$_2$, —CON(R4)$_2$, —COR5, —SO$_2$NHR4, heteroaryl, heterocyclyl, heteroaryloxy, heterocyclyloxy, arylamino, heteroarylamino, and heterocyclylamino;

wherein two R3 moieties are independently and individually taken from the group consisting of C1-C6alkyl and branched C3-C6alkyl and are attached to the same nitrogen heteroatom of Z6 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z6 may cyclize to form a C3-C7 heterocyclyl ring;

and n is 0-4; p is 1-4; q is 2-6; r is 0 or 1; v is 1 or 2;

and tautomers, diastereomers, geometric isomers, enantiomers, hydrates, prodrugs and salts of any of the foregoing.

4.2.6b

The following specific compounds of Formula I are more preferred: 1-(1-(3-(2-amino-2-oxoethyl)phenyl)-3-t-butyl-1H-pyrazol-5-yl)-3-(4-methyl-3-(4-(pyridin-3-yl)pyrimidin-2-ylamino)phenyl)urea, 1-(3-t-butyl-1-(3-(2-(2,3-dihydroxypropylamino)-2-oxoethyl)phenyl)-1H-pyrazol-5-yl)-3-(4-methyl-3-(4-(pyridin-3-yl)pyrimidin-2-ylamino)phenyl)urea 4.2.7 Methods 4.2.7a Methods of Protein Modulation The invention includes methods of modulating kinase activity of the p38 family of kinases including, but not limited to p38-alpha and other MAP kinases. The kinases may be wildtype kinases, oncogenic forms thereof, aberrant fusion proteins thereof or polymorphs of any of the foregoing. The method comprises the step of contacting the kinase species with compounds of the invention and especially those set forth in sections 4.2 and 4.2.6a. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, kinase cellular localization, and recruitment of other proteins into signaling complexes through modulation of kinase conformation.

4.2.7b Treatment Methods

The methods of the invention also include treating individuals suffering from a condition selected from the group consisting of inflammation, osteoarthritis, respiratory diseases, stroke, systemic shock, immunological diseases, and cardiovascular disease. These methods comprise administering to such individuals compounds of the invention, and especially those of section 4.2 and 4.2.6a, said condition being human inflammation, rheumatoid arthritis, rheumatoid spondylitis, ostero-arthritis, asthma, gouty arthritis, sepsis, septic shock, endotoxic shock, Gram-negative sepsis, toxic shock syndrome, adult respiratory distress syndrome, stroke, reperfusion injury, neural trauma, neural ischemia, psoriasis, restenosis, chronic pulmonary inflammatory disease, bone resorptive diseases, graft-versus-host reaction, Chron's disease, ulcerative colitis, inflammatory bowel disease, pyresis, and combinations thereof. The administration method is not critical, and may be from the group consisting of oral, parenteral, inhalation, and subcutaneous.

4.2.8 Pharmaceutical Preparations

The compounds of the invention, especially those of 4.2 and 4.2.6a may form a part of a pharmaceutical composition by combining one or more such compounds with a pharmaceutically acceptable carrier. Additionally, the compositions may include an additive selected from the group consisting of adjuvants, excipients, diluents, and stablilizers.

4.2.9 Kinase/Compound Adducts

The invention also provides adducts in the form of compounds of the invention bound with a species of kinase such as a wild-type kinase, oncogenic forms thereof, aberrant fusion proteins thereof and polymorphs of any of the foregoing. The compounds are advantageously selected from the groups defined in sections 4.2 and 4.2.6a.

4.3 Generally—Monocyclic A2 Compounds with Monocyclic E2 Rings

The invention includes compounds of the formula I as defined in section 2.3 wherein R2 is selected from the group consisting of monocyclic heteroaryl, C1-C6alkyl, branched C3-C7alkyl, a R19-substituted C3-C8carbocyclyl wherein R19 is H, or C1-C6alkyl, C1-C6fluoroalkyl wherein the alkyl group is partially or fully fluorinated, and phenyl wherein the phenyl group is optionally substituted by one or more fluorine substituents or chlorine;

4.3.1 Preferred D Moieties 4.3.1a

Preferably, the compounds of formula I in 4.3 contain D moieties wherein E1 and E2 are as defined in section 1.3.1a.

4.3.1b

Additionally preferred D moieties of formula I in 4.3 are as defined in section 1.3.1b.

4.3.1c

More preferred D moieties of 3.2.1b are wherein E2 is defined as in section 1.3.1c.

4.3.2 Preferred A2 Moieties 4.3.2a

Compounds of Formula I as defined above in section 4.3 have preferred A2 moieties as defined in section 2.2.2a.

4.3.2b

More preferred A2 moieties are selected from the group consisting of

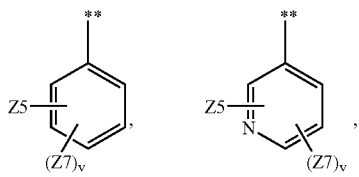

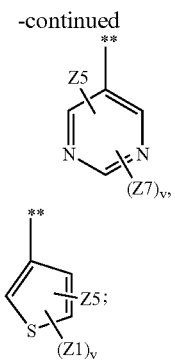

and wherein the symbol (**) is the point of attachment to the A1 ring for formula I.

4.3.2c

Even more preferred A2 moieties are selected from the group consisting of

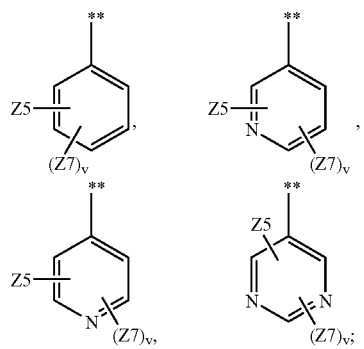

and wherein the symbol (**) is the point of attachment to the A1 ring of formula I.

4.3.3 Preferred Classes of Compounds 4.3.3a

Compounds as defined in 4.3.1a wherein the A2 group is defined in 4.3.2a.

4.3.3b

Compounds as defined in 4.3.3a wherein the A2 group is defined in 4.3.2b.

4.3.3c

Compounds as defined in 4.3.3a wherein the A2 group is defined in 4.3.2c.

4.3.3d

Compounds as defined in 4.3.1b wherein the A2 group is defined in 4.3.2a.

4.3.3e

Compounds as defined in 4.3.3c wherein the A2 group is defined in 4.3.2b.

4.3.3f

Compounds as defined in 4.3.3c wherein the A2 group is defined in 4.3.2c.

4.3.4 Preferred A1 Moieties 4.3.4a

These preferred A1 moieties are defined in 4.1.4a.

4.3.4b

These more preferred A1 moieties are defined in 4.1.4b.

4.3.4c

These even more preferred A1 moieties are defined in 4.1.4c.

4.3.5 Preferred W and Y Moieties 4.3.5a (1) W and Y are each NH, and X=O; (2) W=NH, Y=CHR4 and X=O; or (3) W=CHR4, Y=NH, and X=O.

4.3.5b

W and Y are each NH and X=O.

4.3.6 Further Preferred Compounds 4.3.6a

Further preferred compounds are of the formula

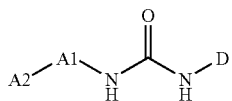
I wherein A2 is selected from the group consisting of

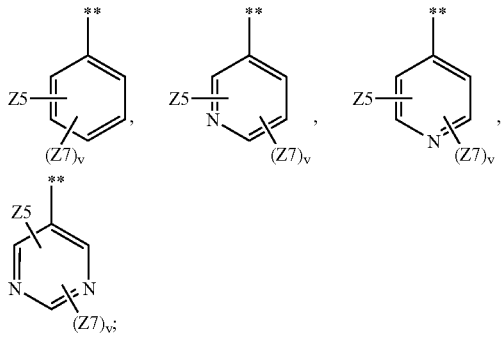

wherein the symbol (**) denotes the attachment to the A1 moiety of formula I;

A1 is selected from the group consisting of

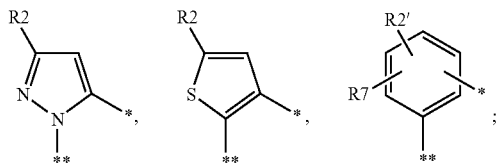

wherein the symbol (*) denotes the attachment to the W moiety of formula I and the symbol (**) denotes the attachment to the A2 moiety of formula I;

X is O, S, or NR3;

D comprises a member of 2,3-dichlorophenyl, 2,4-dichlorophenyl, 3,4-dichlorophenyl, 3,5-dichlorophenyl, 3-chlorophenyl, 4-chlorophenyl, 3-bromophenyl, 4-bromophenyl, 3-trifluoromethylphenyl, 3-trifluoromethyl-4-chlorophenyl, 2,3,4-trifluorophenyl, 2,3,4-trifluorophenyl, 2,4,5-trifluorophenyl, 2,3,5-trifluorophenyl, 3,4,5-trifluorophenyl, 2,3-difluorophenyl, 2,4-difluorophenyl, 2,5-difluorophenyl, 3,4-difluorophenyl, 2-fluorophenyl, 3-fluorophenyl, 4-fluorophenyl, 3-cyanophenyl, 3-phenoxyphenyl, 4 phenoxyphenyl, 1-naphthyl-2,3-dihydro-1H-inden-1-yl, 1,2,3,4-tetrahydronaphthalen1-yl, benzo[d][1,3]dioxol-5-yl or benzo[d][1,3]dioxol-4-yl,

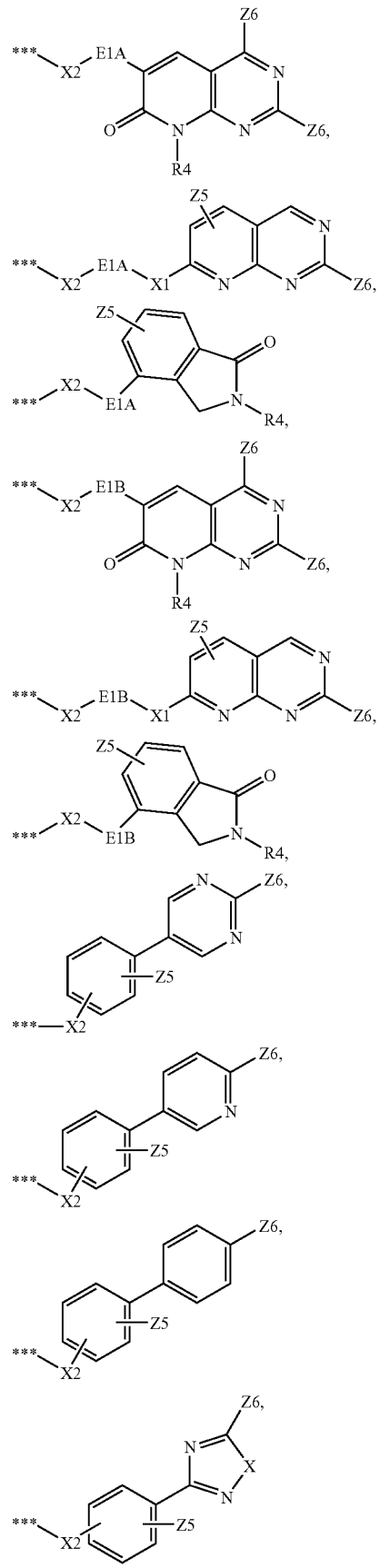

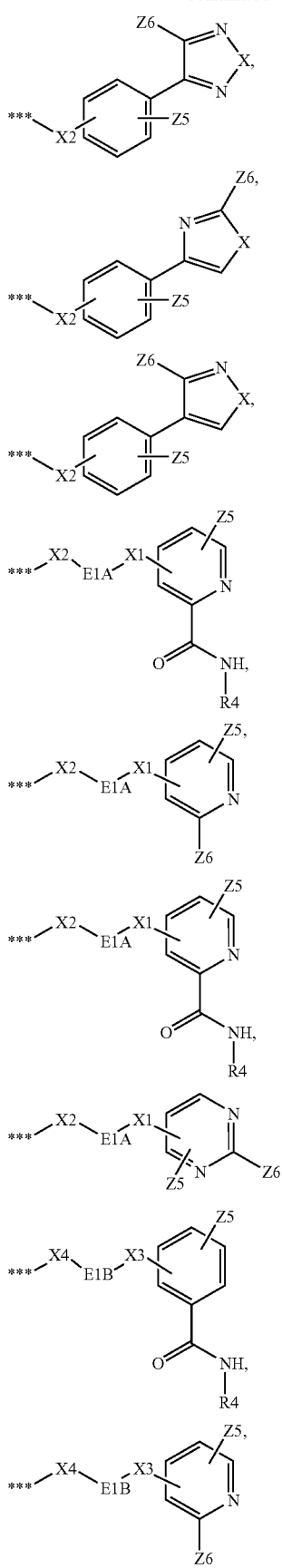
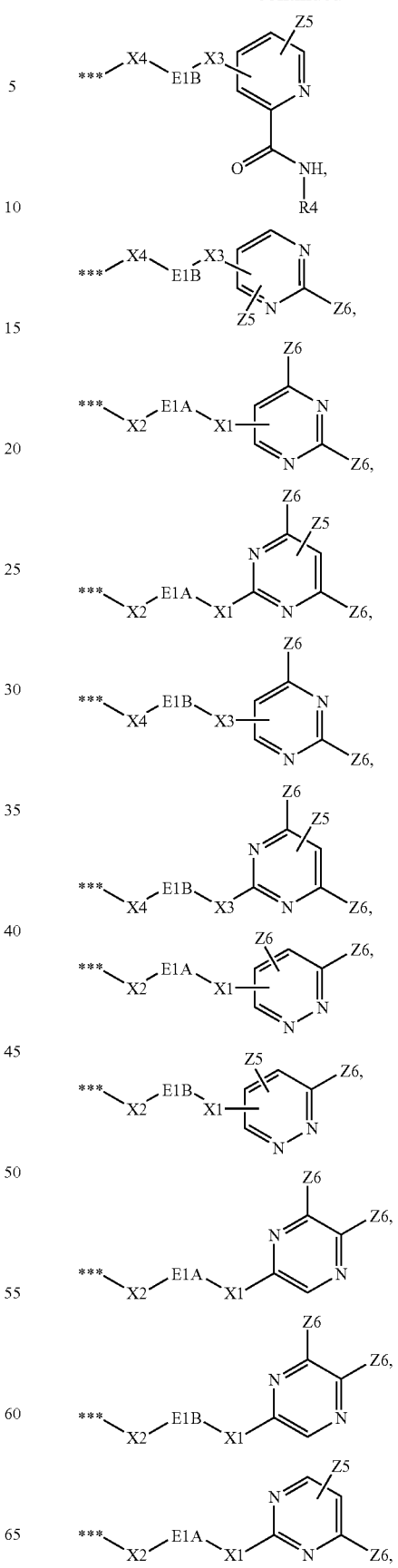

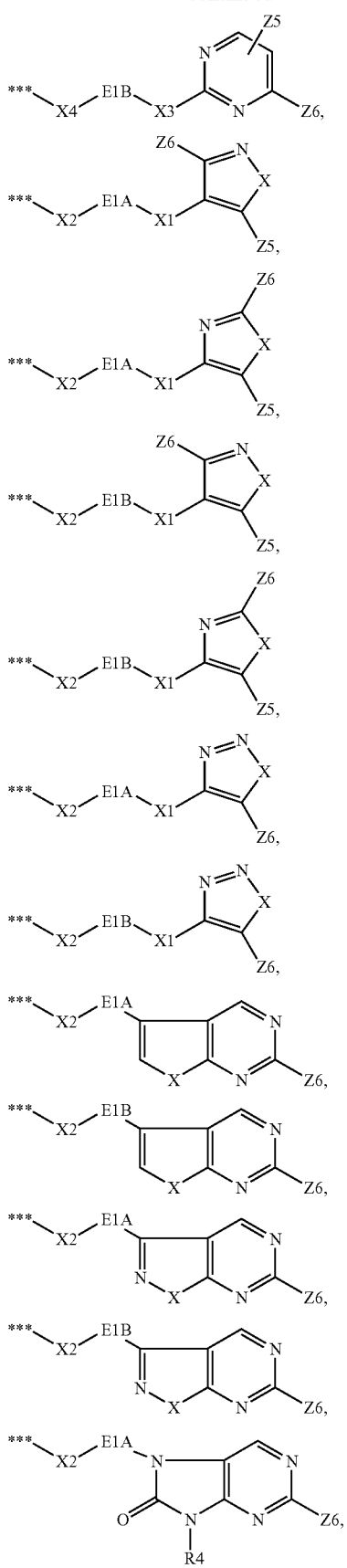
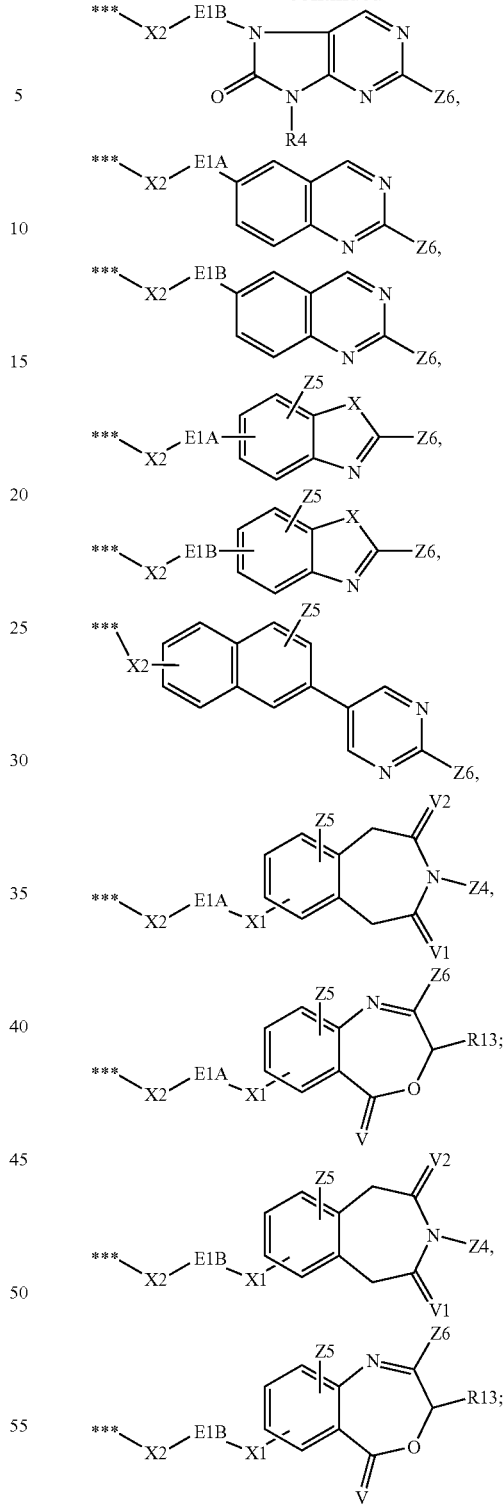
wherein E1A is taken from the groups consisting of cyclopropyl, cyclobutyl, cyclopentyl, cyclohexyl, pyrrolidinyl piperidinyl, thienyl, oxazolyl, thiazolyl, isoxazolyl, isothiazolyl, pyrrolyl, pyrazolyl, oxadiazolyl, thiadiazolyl, furyl, imidazolyl, pyridyl, and pyrimidinyl;
wherein E1B is taken from the groups consisting of phenyl and naphthyl;

wherein E2A is taken from the group comprising naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl and fused bicyclic rings selected from the group comprising indolyl, isoindolyl, isoindolinyl, isoindolonyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, imidazopyrimidinyl, imidazolonopyrimidinyl, dihydropurinonyl, pyrrolopyrimidinyl, purinyl, pyrazolopyridinyl, pyrazolopyrimidinyl, isoxazolopyrimidinyl, isothiazolopyrimidinyl, furylopyrimidinyl, thienopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalazinyl, benzodioxyl, indolinyl, benzisothiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, benzoxazepinyl;

wherein E2B is taken from the group consisting of phenyl, pyridyl, and pyrimidyl;

wherein the symbol (***) denotes the attachment to the Y moiety of formula I;

X1 is selected from the group consisting of O, S, NR3, —C(=O)—, —O—(CH₂)n-, —S—(CH₂)n-, —NR3-(CH₂)n-, —O—(CH₂)q-O—, —O—(CH₂)q-NR3-, —N(R3)-(CH₂)q-N(R3)-, —(CH₂)n-N(R4)-C(=O)—, —(CH₂)n-N(R4)-C(=O)(CH₂)n-, —(CH₂)n-CO—N(R4)-, —(CH₂)p-, C2-C5alkenyl, C2-C5alkynyl, C3-C6cycloalkyl, and a direct bond wherein the E1 ring and the E2 ring are directly linked by a covalent bond;

and wherein the carbon atoms of —(CH2)n-, —(CH2)q-, (CH2)p, C2-C5alkenyl, and C2-C5alkynyl moieties of X1 may be further substituted by one or more C1-C6alkyl;

X2 is selected from the group consisting of C1-C6 alkyl, C3-C6 branched alkyl, or a direct bond wherein E1 is directly linked to the Y group of formula I;

X3 is selected from the group consisting of NR3, —C(=O)—, —O—(CH₂)n-, —S—(CH₂)n-, —NR3-(CH₂)n-, —O—(CH₂)q-O—, —O—(CH₂)q-NR3-, —N(R3)-(CH₂)q-N(R3)-, —(CH₂)n-N(R4)-C(=O)—, —(CH₂)n-N(R4)-C(=O)(CH₂)n-, —(CH₂)n-CO—N(R4)-, —(CH₂)q-, C2-C5alkenyl, C2-C5alkynyl, C3-C6cycloalkyl, and a direct bond wherein the either the E1B ring or E2B ring are directly linked by a covalent bond;

and wherein the carbon atoms of —(CH2)q-, C2-C5alkenyl, and C2-C5alkynyl moieties of X3 may be further substituted by one or more C1-C6alkyl;

X4 is selected from the group consisting of C1-C6 alkyl, C3-C6 branched alkyl;

each R2 is selected from the group consisting of monocyclic heteroaryl, C1-C6alkyl, branched C3-C7alkyl, a R19-substituted C3-C8carbocyclyl wherein R19 is H, or C1-C6alkyl, C1-C6fluoroalkyl wherein the alkyl group is partially or fully fluorinated, and phenyl wherein the phenyl group is optionally substituted by one or more fluorine substituents or chlorine;

each R2' is selected from the group consisting of halogen and R2;

each R3 is independently and individually selected from the group consisting of H, C1-C6alkyl, branched C3-C7alkyl, C3-C7carbocyclyl, or phenyl;

wherein two R3 moieties independently and individually taken from the group consisting of C1-C6alkyl and branched C3-C7alkyl are attached to the same nitrogen heteroatom, the two R3 moieties may cyclize to form a C3-C7 heterocyclyl ring;

each R4 is selected from the group consisting of H, C1-C6alkyl, hydroxyC1-C6 alkyl, dihydroxyC1-C6alkyl, C1-C6alkoxyC1-C6alkyl, branched C3-C7alkyl, branched hydroxyC1-C6 alkyl, branched C1-C6alkoxyC1-C6alkyl, branched dihydroxyC1-C6alkyl, carbocyclyl, hydroxyl substituted carbocyclyl, alkoxy substituted carbocyclyl, dihydroxy substituted carbocyclyl, phenyl, heteroaryl, heterocyclyl, phenylC1-C6alkyl, heteroarylC1-C6alkyl, and heterocyclylC1-C6alkyl;

wherein two R4 moieties independently and individually taken from the group consisting of C1-C6alkyl, branched C3-C6alkyl, hydroxyalkyl, and alkoxyalkyl and are attached to the same nitrogen heteroatom may cyclize to form a C3-C7 heterocyclyl ring;

each R5 is independently and individually selected from the group consisting of

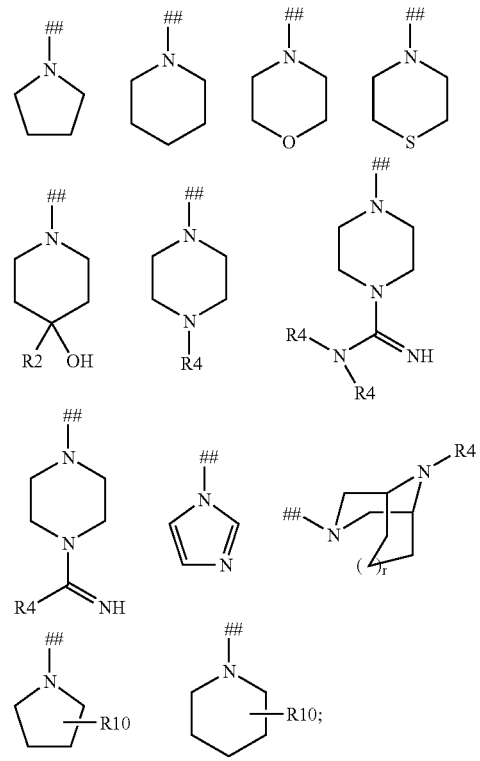

and wherein the symbol (##) is the point of attachment to respective R8, R10, Z4, Z5, Z6 or A2 ring moieties containing a R5 moiety;

wherein two R4 moieties independently and individually taken from the group consisting of C1-C6alkyl, branched C3-C6alkyl, hydroxyalkyl, and alkoxyalkyl and are attached to the same nitrogen heteroatom of R5 may cyclize to form a C3-C7 heterocyclyl ring;

wherein each R6 is independently and individually selected from the group consisting of C1-C6alkyl, branched C3-C7alkyl, carbocyclyl, phenyl, heteroaryl, and heterocyclyl;

each R7 is selected from the group consisting of H, halogen, C1-C3fluoroalkyl wherein the alkyl moiety is partially or fully fluorinated, C1-C3alkyl, cyclopropyl, cyano, or C1-C3alkoxy;

each R8 is independently and individually selected from the group consisting of C1-C6alkyl, C1-C6 fluoroalkyl wherein the alkyl moiety is partially or fully fluorinated, branchedC4-C7alkyl, carbocyclyl, phenyl, C1-C6phenylalkyl, heteroaryl or heteroarylC1-C6alkyl, heterocyclyl, heterocyclylC1-C6alkyl, OH, C1-C6alkoxy, N(R3)$_2$, N(R4)$_2$, or R5;
wherein two R3 moieties are independently and individually taken from the group consisting of C1-C6alkyl and branched C3-C6alkyl and are attached to the same nitrogen heteroatom of R8 may cyclize to form a C3-C7 heterocyclyl ring;
wherein two R4 moieties independently and individually taken from the group consisting of C1-C6alkyl, branched C3-C6alkyl, hydroxyalkyl, and alkoxyalkyl and are attached to the same nitrogen heteroatom of R8 may cyclize to form a C3-C7 heterocyclyl ring;
each R10 is independently and individually selected from the group consisting of CO$_2$H, CO$_2$C1-C6alkyl, CO—N(R4)$_2$, OH, C1-C6alkoxy, —N(R4)$_2$;
wherein two R4 moieties independently and individually taken from the group consisting of C1-C6alkyl, branched C3-C6alkyl, hydroxyalkyl, and alkoxyalkyl and are attached to the same nitrogen heteroatom of R10 may cyclize to form a C3-C7 heterocyclyl ring;
each R13 is independently and individually selected from the group consisting of H, C1-C6alkyl, branched C3-C7alkyl, carbocyclyl, hydroxyC2-C7alkyl, C1-C6alkoxyC2-C7alkyl, (R4)$_2$N—CO, (R4)$_2$N—CO—C1-C6alkyl, carboxyC1-C6alkyl, C1-C6alkoxycarbonyl, C1-C6alkoxycarbonylC1-C6alkyl, (R4)$_2$N—C2-C6alkyl, (R4)$_2$N—C2-C6alkylN(R4)-(CH$_2$)$_q$, R5-C2-C6alkylN(R4)-(CH$_2$)$_q$, (R4)$_2$N—C2-C6alkylO-(CH$_2$)$_q$, R5-C2-C6alkyl-O—(CH$_2$)$_q$, —(CH$_2$)$_q$N(R4)C(O)R8, aryl, arylC1-C6alkyl, heteroaryl, heteroarylC1-C6alkyl, heterocyclyl, heterocyclylC1-C6alkyl, aryloxyC2-C6alkyl, heteroaryloxyC2-C6alkyl, heterocyclyloxyC2-C6alkyl, arylaminoC2-C6alkyl, heteroarylaminoC2-C6alkyl, and heterocyclylaminoC2-C6alkyl;
wherein two R4 moieties independently and individually taken from the group consisting of C1-C6alkyl, branched C3-C6alkyl, hydroxyalkyl, and alkoxyalkyl and are attached to the same nitrogen heteroatom of R13 may cyclize to form a C3-C7 heterocyclyl ring;
wherein Z1' is independently and individually selected from the group consisting of H, C1-C6alkyl, C3-C7cycloalkyl, hydroxyC1-C6alkyl, C1-C6alkoxyC1-C6alkyl, (R4)$_2$N—C1-C6alkyl, (R4)$_2$N—C2-C6alkylN(R4)-(CH$_2$)$_p$, (R4)$_2$N—C2-C6alkylO-(CH$_2$)$_p$, (R4)$_2$N—CO—C1-C6alkyl, carboxyC1-C6alkyl, C1-C6alkoxycarbonylC1-C6alkyl, —(CH$_2$)$_p$N(R4)C(O)R8, aryl, arylC1-C6alkyl, heteroaryl, heteroarylC1-C6alkyl, heterocyclyl, heterocyclylC1-C6alkyl, aryloxyC1-C6alkyl, heteroaryloxyC1-C6alkyl, heterocyclyloxyC1-C6alkyl, arylaminoC1-C6alkyl, heteroarylaminoC1-C6alkyl, or heterocyclylaminoC1-C6alkyl;
wherein two R4 moieties independently and individually taken from the group consisting of C1-C6alkyl, branched C3-C6alkyl, hydroxyalkyl, and alkoxyalkyl and are attached to the same nitrogen heteroatom of Z1' may cyclize to form a C3-C7 heterocyclyl ring;
each Z4 is a substituent attached to a ring nitrogen and is independently and individually selected from the group consisting of H, C1-C6alkyl, hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C2-C6alkyl, carboxyC2-C6alkyl, C1-C6alkoxycarbonylC2-C6alkyl, —C2-C6alkylN(R4)C(O)R8, R8-C(=NR3)-, —SO$_2$R8, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

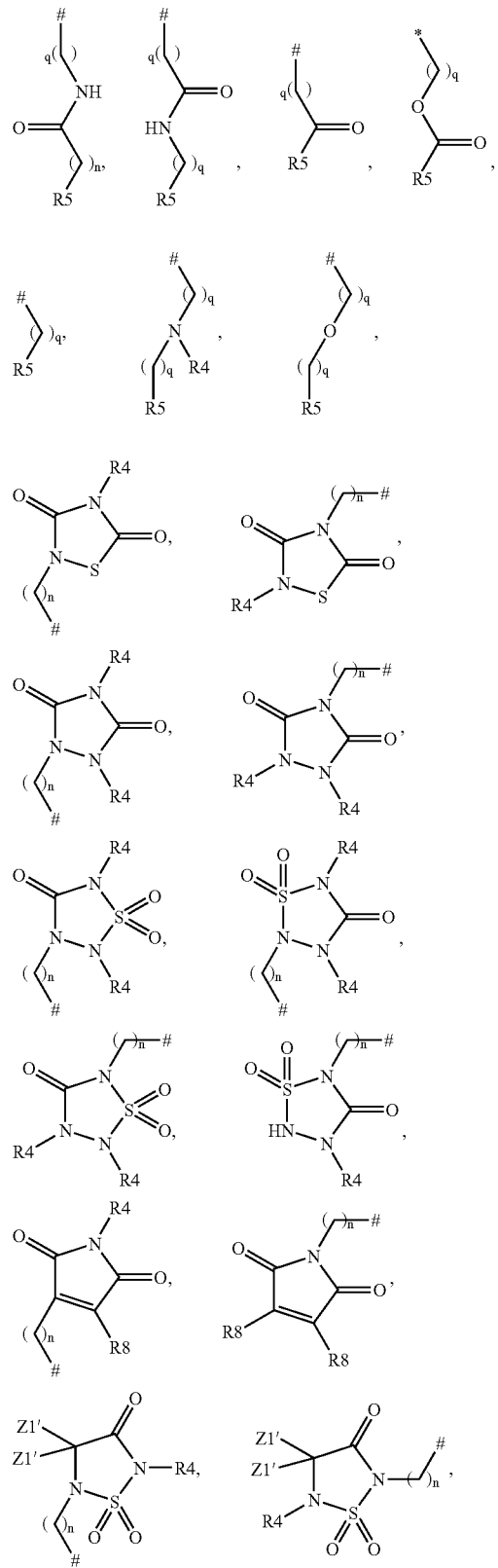

-continued

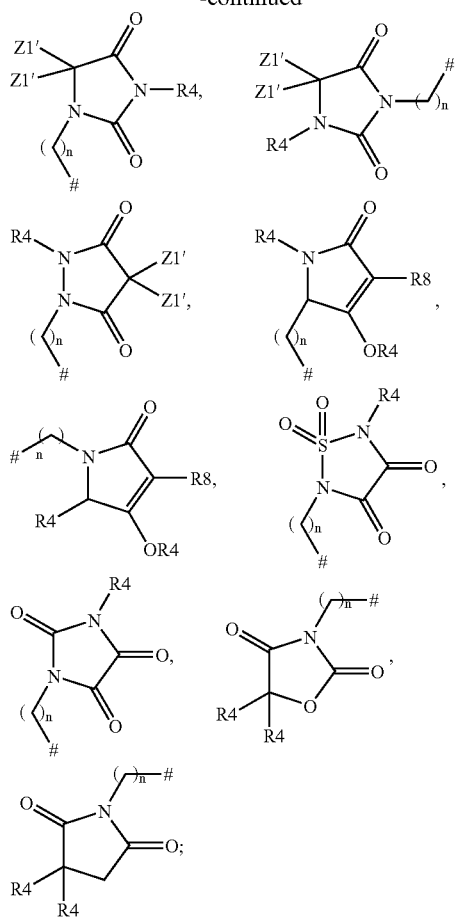

wherein the symbol (#) indicates the point of attachment of the Z4 moiety to the A2 ring for formula I;
in the event that Z4 contains an alkyl or alkylene moiety, such moieties may be further substituted with one or more C1-C6alkyls;
wherein two R3 moieties are independently and individually taken from the group consisting of C1-C6alkyl and branched C3-C6alkyl and are attached to the same nitrogen heteroatom of Z4 may cyclize to form a C3-C7 heterocyclyl ring;
wherein two R4 moieties independently and individually taken from the group consisting of C1-C6alkyl, branched C3-C6alkyl, hydroxyalkyl, and alkoxyalkyl and are attached to the same nitrogen heteroatom of Z4 may cyclize to form a C3-C7 heterocyclyl ring;
Z5 is independently and individually selected from the group consisting of H, C1-C6alkyl, branched C3-C7alkyl, halogen, fluoroalkyl, cyano, hydroxyl, alkoxy, oxo, aminocarbonyl, carbonylamino, aminosulfonyl, sulfonylamino, —N(R3)$_2$, —O—(CH$_2$)q-N(R4)$_2$, —N(R3)-(CH$_2$)q-N(R4)$_2$, —R5, —O—(CH$_2$)q-O-Alkyl, —O—(CH$_2$)q-N(R4)$_2$, —N(R3)-(CH$_2$)q-O-Alkyl, —N(R3)-(CH$_2$)q-N(R4)$_2$, —O—(CH$_2$)q-R5, and —N(R3)-(CH$_2$)q-R5;
wherein two R3 moieties are independently and individually taken from the group consisting of C1-C6alkyl and branched C3-C6alkyl and are attached to the same nitrogen heteroatom of Z5 may cyclize to form a C3-C7 heterocyclyl ring;
wherein two R4 moieties independently and individually taken from the group consisting of C1-C6alkyl, branched C3-C6alkyl, hydroxyalkyl, and alkoxyalkyl and are attached to the same nitrogen heteroatom of Z5 may cyclize to form a C3-C7 heterocyclyl ring;

Each Z6 is independently and individually selected from the group consisting of H, C1-C6alkyl, branched C3-C7alkyl, hydroxyl, C1-C6alkoxy, (R3)$_2$N—, —N(R3)COR8, (R4)$_2$N—, —R5, —N(R4)COR8, —N(R3)SO$_2$R6-, —CON(R3)$_2$, —CON(R4)$_2$, —COR5, —SO$_2$NHR4, heteroaryl, heterocyclyl, heteroaryloxy, heterocyclyloxy, arylamino, heteroarylamino, and heterocyclylamino;
wherein two R3 moieties are independently and individually taken from the group consisting of C1-C6alkyl and branched C3-C6alkyl and are attached to the same nitrogen heteroatom of Z6 may cyclize to form a C3-C7 heterocyclyl ring;
wherein two R4 moieties independently and individually taken from the group consisting of C1-C6alkyl, branched C3-C6alkyl, hydroxyalkyl, and alkoxyalkyl and are attached to the same nitrogen heteroatom of Z6 may cyclize to form a C3-C7 heterocyclyl ring;
each Z7 is a substituent attached to a ring carbon and is independently and individually selected from the group consisting of hydroxyC2-C6alkyl, C1-C6alkoxyC1-C6alkyl, (R6)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—CO, (R4)$_2$N—CO, —SO$_2$R3', SOR3, —SOR4, —C(═O)R6, —C(═NOH)R6, —C(═NOR3)R6, (CH$_2$)$_n$N(R4)C(O)N(R4)$_2$, (CH$_2$)$_n$N(R4)C(O)R5, monocyclic heteroaryl, monocyclic heterocyclyl, monocyclic heteroarylC1-C6alkyl, monocyclic heterocyclylC1-C6alkyl, monocyclic heteroaryloxy, monocyclic heterocyclyloxy, monocyclic heteroaryloxyC1-C6alkyl, monocyclic heterocyclyloxyC1-C6alkyl, arylamino, monocyclic heteroarylamino, monocyclic heterocyclylamino, arylaminoC1-C6alkyl, monocyclic heteroarylaminoC1-C6alkyl, monocyclic heterocyclylaminoC1-C6alkyl, or moieties of the formulae

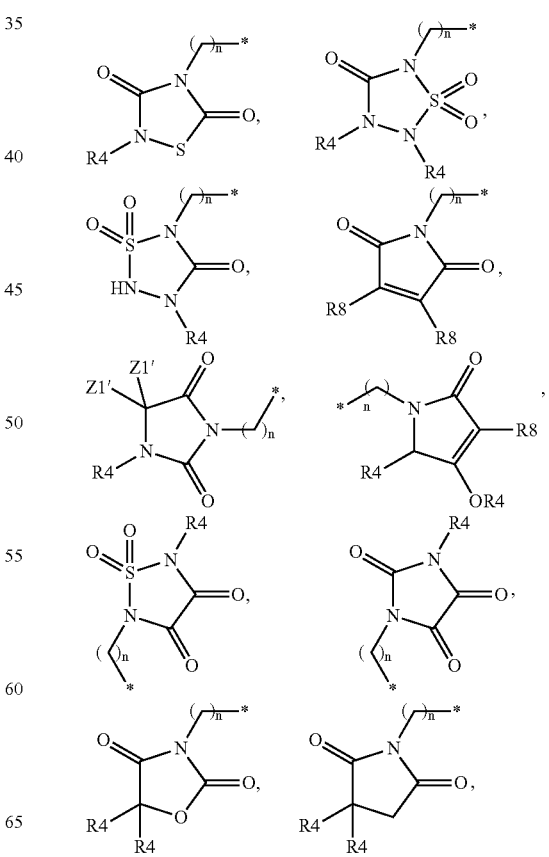

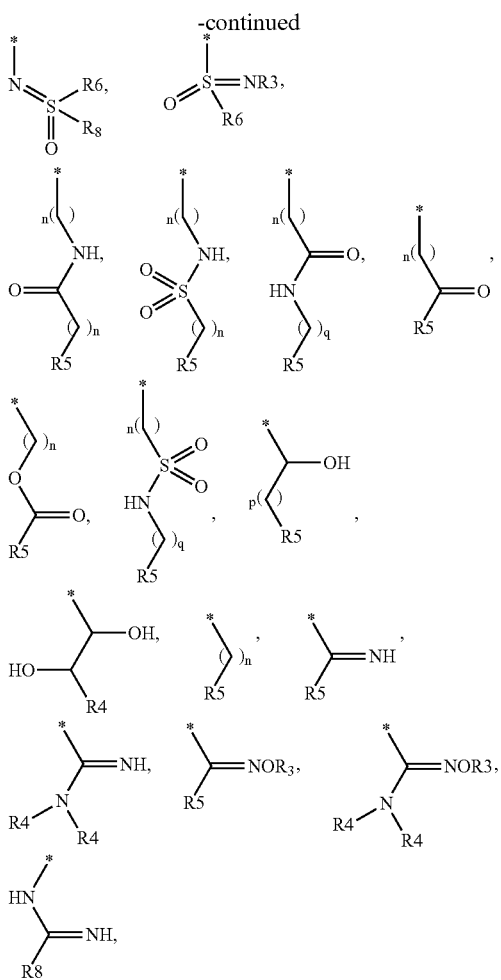

cyano wherein the site of attachment to the A2 ring is meta to the point of attachment to the A1 ring and wherein A2 is phenyl, and cyano wherein the site of attachment is to a substitutable position when A2 is pyridyl, pyrimidinyl or a five-membered ring;

In the foregoing definition of Z7, alkyl moieties may optionally be substituted by one or more C1-C6alkyl;

Wherein the asterisk (*) indicates the point of attachment of the Z1 moiety to the A2 ring;

in the event that Z7 contains an alkyl or alkylene moiety, such moieties may be further substituted with one or more C1-C6alkyls;

wherein two R3 moieties are independently and individually taken from the group consisting of C1-C6alkyl and branched C3-C6alkyl and are attached to the same nitrogen heteroatom of Z7 may cyclize to form a C3-C7 heterocyclyl ring;

wherein two R4 moieties independently and individually taken from the group consisting of C1-C6alkyl, branched C3-C6alkyl, hydroxyalkyl, and alkoxyalkyl and are attached to the same nitrogen heteroatom of Z7 may cyclize to form a C3-C7 heterocyclyl ring;

and n is 0-4; p is 1-4; q is 2-6; r is 0 or 1; v is 1 or 2;

and tautomers, diastereomers, geometric isomers, enantiomers, hydrates, prodrugs and salts of any of the foregoing.

4.3.6b

The following specific compounds of Formula I are more preferred: 1-(1-(3-(2-amino-2-oxoethyl)phenyl)-3-t-butyl-1H-pyrazol-5-yl)-3-(3-(pyridin-3-yloxy)phenyl)urea, 1-(1-(3-(2-amino-2-oxoethyl)phenyl)-3-t-butyl-1H-pyrazol-5-yl)-3-(4-(2-(methylcarbamoyl)pyridin-4-yloxy)phenyl)urea, 1-(1-(3-(2-amino-2-oxoethyl)phenyl)-3-t-butyl-1H-pyrazol-5-yl)-3-(8-methyl-7-oxo-7,8-dihydropyrido[2,3-d]pyrimidin-6-yl)phenyl)urea, 1-(1-(3-(2-amino-2-oxoethyl)phenyl)-3-cyclopentyl-1H-pyrazol-5-yl)-3-(3-(8-methyl-7-oxo-7,8-dihydropyrido[2,3-d]pyrimidin-6-yl)phenyl)urea, 1-(1-(3-(H-pyrazol-4-yl)phenyl)-3-t-butyl-1H-pyrazol-5-yl)-3-(2,3-dichlorophenyl)urea, 2-(3-(5-(3-(2,3-dichlorophenyl)ureido)-3-(3-fluorophenyl)-1H-pyrazol-1-yl)phenyl)acetic acid, 2-(3-(5-(3-(2,3-dichlorophenyl)ureido)-3-(2-fluorophenyl)-1H-pyrazol-1-yl)phenyl)acetic acid, 2-(4-(5-(3-(2,3-dichlorophenyl)ureido)-3-(3-fluorophenyl)-1H-pyrazol-1-yl)phenyl)acetic acid, 2-(4-(5-(3-(2,3-dichlorophenyl)ureido)-3-(2-fluorophenyl)-1H-pyrazol-1-yl)phenyl)acetic acid, 2-(4-(3-cyclopentyl-5-(3-(2,3-dichlorophenyl)ureido)-1H-pyrazol-1-yl)phenyl)acetic acid, 1-(1-(3-(2-amino-2-oxoethyl)phenyl)-3-cyclopentyl-1H-pyrazol-5-yl)-3-(2,3-dichlorophenyl)urea, 1-(1-(3-(2-amino-2-oxoethyl)phenyl)-3-(3-fluorophenyl)-1H-pyrazol-5-yl)-3-(2,3-dichlorophenyl)urea, 1-(1-(3-(2-amino-2-oxoethyl)phenyl)-3-(2-fluorophenyl)-1H-pyrazol-5-yl)-3-(2,3-dichlorophenyl)urea, 1-(2,3-dichlorophenyl)-3-(3-(2-fluorophenyl)-1-(3-(2-(2-hydroxyethylamino)-2-oxoethyl)phenyl)-1H-pyrazol-5-yl)urea, 1-(2,3-dichlorophenyl)-3-(1-(3-(2-(2,3-dihydroxypropylamino)-2-oxoethyl)phenyl)-3-(2-fluorophenyl)-1H-pyrazol-5-yl)urea, 1-(3-t-butyl-1-(3-(2-((S)-3-hydroxypyrrolidin-1-yl)-2-oxoethyl)phenyl)-1H-pyrazol-5-yl)-3-(2,3-dichlorophenyl)urea, 1-(3-t-butyl-1-(3-(2-((R)-3-(dimethylamino)pyrrolidin-1-yl)-2-oxoethyl)phenyl)-1H-pyrazol-5-yl)-3-(2,3-dichlorophenyl)urea, 1-(1-(4-(2-amino-2-oxoethyl)phenyl)-3-cyclopentyl-1H-pyrazol-5-yl)-3-(2,3-dichlorophenyl)urea, 1-(2,3-dichlorophenyl)-3-(1-(4-(2-(2,3-dihydroxypropylamino)-2-oxoethyl)phenyl)-3-(2-fluorophenyl)-1H-pyrazol-5-yl)urea, (R)-1-(3-t-butyl-1-(4-(2-(3-hydroxypyrrolidin-1-yl)-2-oxoethyl)phenyl)-1H-pyrazol-5-yl)-3-(2,3-dichlorophenyl)urea, (R)-1-(3-t-butyl-1-(4-(2-(3-methoxypyrrolidin-1-yl)-2-oxoethyl)phenyl)-1H-pyrazol-5-yl)-3-(2,3-dichlorophenyl)urea, (R)-1-(3-t-butyl-1-(4-(2-(3-(dimethylamino)pyrrolidin-1-yl)-2-oxoethyl)phenyl)-1H-pyrazol-5-yl)-3-(2,3-dichlorophenyl)urea, 1-(2,3-dichlorophenyl)-3-(3-(2-fluorophenyl)-1-(3-(hydroxymethyl)phenyl)-1H-pyrazol-5-yl)urea, 1-(3-cyclopentyl-1-(3-(2-(2,3-dihydroxypropylamino)-2-oxoethyl)phenyl)-1H-pyrazol-5-yl)-3-(2,3-dichlorophenyl)urea, 1-(3-cyclopentyl-1-(3-(2-(2-hydroxyethylamino)-2-oxoethyl)phenyl)-1H-pyrazol-5-yl)-3-(2,3-dichlorophenyl)urea, 1-(3-t-butyl-1-(3-(5-oxo-4,5-dihydro-1,3,4-oxadiazol-2-yl)phenyl)-1H-pyrazol-5-yl)-3-(2,3-dichlorophenyl)urea. 1-(1-(3-(2-(2,3-dihydroxypropylamino)-2-oxoethyl)phenyl)-3-(2-fluorophenyl)-1H-pyrazol-5-yl)-3-(naphthalen-1-yl)urea, 1-(1-(3-(2-amino-2-oxoethyl)phenyl)-3-(2-fluorophenyl)-1H-pyrazol-5-yl)-3-(naphthalen-1-yl)urea, 2-(3-(3-(2-fluorophenyl)-5-(3-(naphthalen-1-yl)ureido)-1H-pyrazol-1-yl)phenyl)acetic acid, 4.3.7 Methods 4.3.7a Methods of Protein Modulation The invention includes methods of modulating kinase activity of the p38 family of kinases including, but not limited to p38-alpha and other MAP kinases. The kinases may be wildtype kinases, oncogenic forms thereof, aberrant fusion proteins thereof or polymorphs of any of the foregoing. The method comprises the step of contacting the kinase species with compounds of the invention and especially those set forth in sections 4.3 and 4.3.6a. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, kinase cellular localization, and recruitment of other proteins into signaling complexes through modulation of kinase conformation.

4.3.7b Treatment Methods

The methods of the invention also include treating individuals suffering from a condition selected from the group consisting of inflammation, osteoarthritis, respiratory diseases, stroke, systemic shock, immunological diseases, and cardiovascular disease. These methods comprise administering to such individuals compounds of the invention, and especially those of section 4.3 and 4.3.6a, said condition being human inflammation, rheumatoid arthritis, rheumatoid spondylitis, ostero-arthritis, asthma, gouty arthritis, sepsis, septic shock, endotoxic shock, Gram-negative sepsis, toxic shock syndrome, adult respiratory distress syndrome, stroke, reperfusion injury, neural trauma, neural ischemia, psoriasis, restenosis, chronic pulmonary inflammatory disease, bone resorptive diseases, graft-versus-host reaction, Chron's disease, ulcerative colitis, inflammatory bowel disease, pyresis, and combinations thereof. The administration method is not critical, and may be from the group consisting of oral, parenteral, inhalation, and subcutaneous.

4.3.8 Pharmaceutical Preparations

The compounds of the invention, especially those of 4.3 and 4.3.6a may form a part of a pharmaceutical composition by combining one or more such compounds with a pharmaceutically acceptable carrier. Additionally, the compositions may include an additive selected from the group consisting of adjuvants, excipients, diluents, and stablilizers.

4.3.9 Kinase/Compound Adducts

The invention also provides adducts in the form of compounds of the invention bound with a species of kinase such as a wild-type kinase, oncogenic forms thereof, aberrant fusion proteins thereof and polymorphs of any of the foregoing. The compounds are advantageously selected from the groups defined in sections 4.3 and 4.3.6a.

5. Fifth Aspect of the Invention—Compound Synthesis

Recently, Cu(II)-catalyzed cross coupling reactions have been described for Cu(II) catalyzed cross coupling reactions of aryl or heteroaryl metal reactants with NH-containing heterocycles. These methods have been described by P. Y. S. Lam et al, *Tetrahedron Letters* (1998) 39: 2941), P. Y. S. Lam et al, *Journal of the American Chemical Society* (2000) 122: 7600; D. M. T. Chan et al, *Tetrahedron Letters* (2003) 44: 3863; D. M. T. Chan et al, *Tetrahedron Letters* (1998) 39: 2933; D. A. Evans et al, *Tetrahedron Letters* (1998) 39: 2937.

5.1 Novel Syntheses

The present invention further provides novel methods for synthesizing the useful compounds. Broadly speaking, the synthesis method comprises the steps:
providing a ring compound of the formula

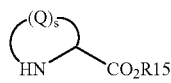

wherein s is 3 or 4,
the ring compound has two double bonds and one reactable ring NH moiety,
Q is independently and individually selected from the group consisting of N and CR2, and R15 is selected from the group consisting of lower alkyl, branched lower alkyl, benzyl, substituted benzyl, or other suitable carboxylic acid protecting group;
each R2 is selected from the group consisting of C1-C6alkyl, branched C3-C7alkyl, carbocyclyl, C1-C6fluoroalkyl wherein the alkyl group is partially or fully fluorinated;
reacting said ring compound with a compound of the formula

A3P-M

In the presence of a transition metal catalyst;
wherein A3P is a protected form of A3;
wherein A3 comprises a member of the group consisting of mono- and poly-aryl, mono- and poly-heteroaryl, mono- and poly-heterocyclyl moieties, P is a protective group wherein A3 is chemically protected so as not to interfere with the reaction of A3P-M with

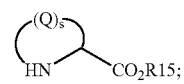

wherein A3P-M is taken from the group consisting of A3P—B(OH)$_2$, -A3P—B(OR16)$_2$, -A3P—B(R17)$_3$M2, -A3P—Si(R18)$_3$, or A3P—Sn(R16)$_3$ wherein R16 is taken from lower alkyl or branched lower alkyl, R17 is halogen, R18 is lower alkoxy, and M2 is Li, K, or Na, and from the formulae

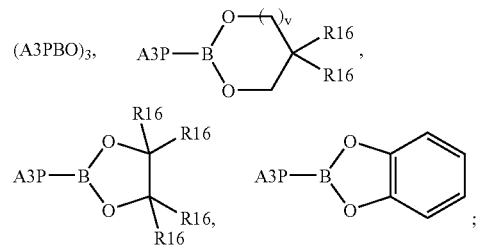

wherein v is 1 or 2;
said reaction generating an intermediate compound of the formula

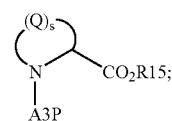

converting said intermediate compound to the carboxylic acid form thereof

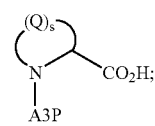

subjecting said carboxylic acid to a Curtiuss rearrangement in the presence of a compound of formula D1-NH$_2$, to yield a compound of the formula

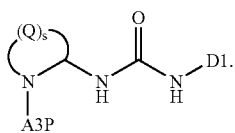

where D1 is selected from the group consisting of mono- and poly-aryl, mono- and poly-heteroaryl, mono- and poly-heterocyclyl.

Preferably, first step of the method involves using a ring compound taken from the group consisting of

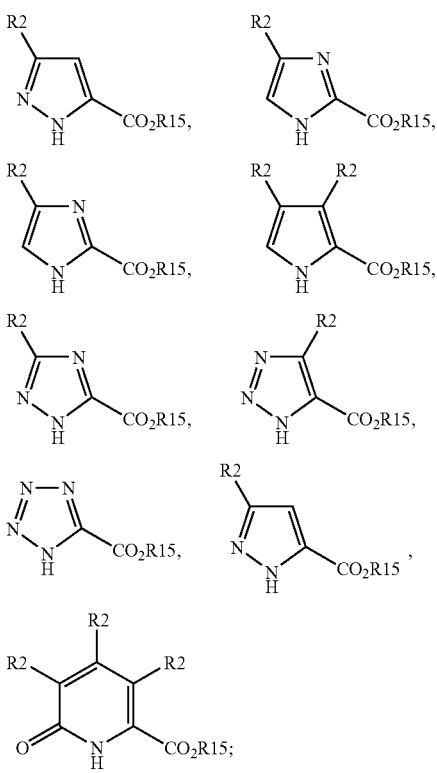

A3P-M is taken from A3P—B(OH)$_2$, A3P—B(OR16)$_2$, or boroxines (A3PBO)$_3$;

said reaction generating an intermediate compound of the formula

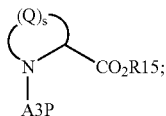

and being catalyzed by a copper(II) catalyst, in an inert solvent taken from the group consisting of dichloromethane, dichloroethane, and N-methylpyrrolidinone, in the presence of a base taken from the group consisting of triethylamine and pyridine, at temperatures ranging from ambient to about 130° C., wherein the reaction is exposed to an atmosphere containing oxygen;

Converting said intermediate compound to the carboxylic acid form thereof

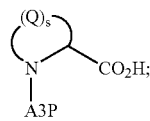

and subjecting said acid form compound to a Curtiuss rearrangement in the presence of a compound of formula D1-NH$_2$, such rearrangement mediated by the use of diphenylphosphoryl azidate in an inert solvent taken from the group consisting of toluene, tetrahydrofuran, and dimethoxyethane, and in the presence of a base taken from the group consisting of triethylamine, pyridine, and di-iso-propylethylamine, at temperatures ranging from 80° C. to 110° C. to yield a desired compound of the formula

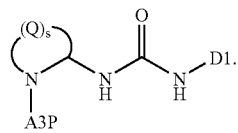

Still more preferably, the starting ring compound is selected from the group consisting of

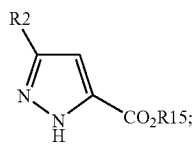

A3P-M is taken from A3P—B(OH)$_2$, A3P—B(OR15)$_2$, or boroxines (A3PBO)$_3$;

said reaction generating an intermediate compound of the formula

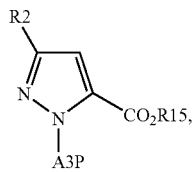

said catalyst comprising copper(II) acetate, said reaction being carried in an inert solvent, selected from the group consisting of dichloromethane, dichloroethane, and N-methylpyrrolidinone, in the presence of a base from the group consisting of triethylamine and pyridine, and in the presence of 4 angstrom sieves at ambient temperature, wherein the reaction is exposed to air, to generate an intermediate compound of the formula

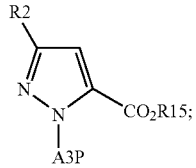

converting said intermediate compound to the carboxylic acid form thereof

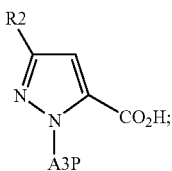

subjecting said carboxylic acid form intermediate to a Curtiuss rearrangement in the presence of a compound of formula D1-NH$_2$, such rearrangement mediated by the use of diphenylphosphoryl azidate in an inert solvent taken from the group consisting of toluene, and in the presence of triethylamine at temperatures ranging from 80° C. to 110° C. to yield a desired compound of the formula.

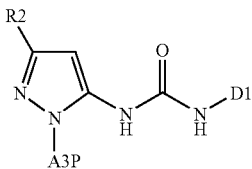

5.2 Other Syntheses

The preparation of intermediates containing A1 rings and their subsequent conversion into compounds of Formula I is illustrated in the following schemes. Throughout this specification, A2P refers to a protected form of A2, as defined above, wherein the Z1, Z2, Z3, or Z4 moieties or heteroatoms attached to A2 are suitably protected to allow their use in multi-step chemistry.

The preparation of intermediates wherein A1 is taken from pyrazolyl A1-1 is illustrated in Schemes 1 through 4. Scheme 1 illustrates the preparation of hydrazines 2. If the amine precursors 1 are readily available, they are converted to the hydrazines 2 by a diazotization/reduction sequence. Preferred conditions react 1 with NaNO$_2$ in aqueous HCl to form the diazonium salt at about 0 C in aqueous solvent or an aqueous/organic cosolvent. The diazonium salt is not isolated, but directly reduced by reaction with SnCl$_2$.2H$_2$0 under acidic conditions, preferably aqueous HCl at between about 0 C and room temperature. The hydrazines 2 are isolated as the HCl addition salts. If the amine precursors 1 are not directly available, they can be formed from the nitro-substituted A2P precursors 3 by reduction, preferably with iron/HCl, SnCl$_2$.2H$_2$0, or catalytic hydrogenation, to give the requisite amines 1. Conversion to the hydrazines 2 is accomplished as described above. Alternatively, reaction of the aryl or heteroaryl bromides 4 with benzophenone hydrazone and a palladium catalyst, preferably with Pd(OAc) 2 and DPPF as ligand, can afford the protected hydrazines 5, which are deprotected under acidic conditions, preferably p-toluenesulfonic acid or ethanolic HCl, to give rise to the desired hydrazines 2 (Hartwig, J. F., et al, *Angew. Chem. Int. Ed.* (1998) 37: 2090; Haddad, N., et al, *Tetrahedron Letters* (2002) 43: 2171-2173). Alternatively, reaction of the aryl or heteroaryl iodides 6 with t-butylcarbazate and a copper (I) catalyst, preferably CuI in DMF at about 80 C with Cs$_2$CO$_3$ base and a ligand such as 1,10-phenanthroline, can afford the BOC-protected hydrazines 7, which are converted to the desired hydrazines 2 by treatment with acid (M. Woltor et al, *Organic Letters* (2001) 3: 3803-3805).

Scheme 1

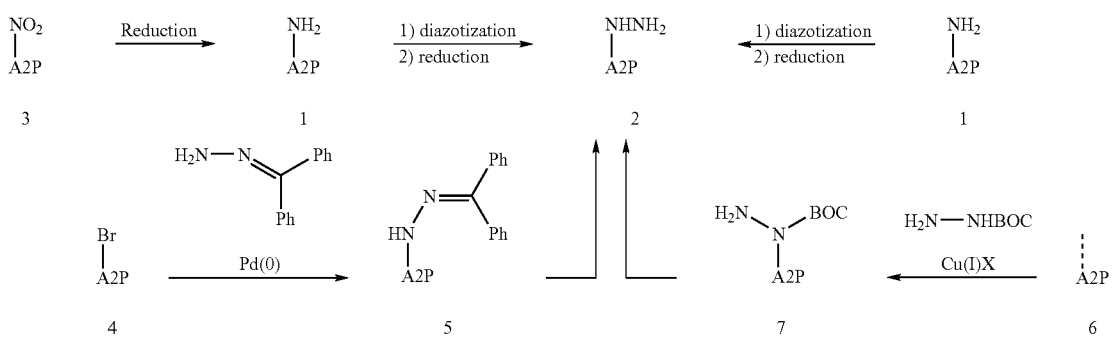

Preparation of pyrazoles 9 and 11 are illustrated in Scheme 2. Reaction of hydrazines 8 with beta-ketonitriles in an alcoholic solvent, preferably EtOH, and an acid catalyst, preferably HCl or p-toluenesulfonic acid, at about 80 C gives aminopyrazoles 9. Analogous treatment of hydrazines 8 with the ethyl 2-(methoxyimino)-4-oxobutanoates 10 affords the pyrazole ethyl esters 11 (Lam, P. Y. S., et al, *Journal of Medicinal Chemistry* (2003) 46: 4405-4418).

Scheme 2

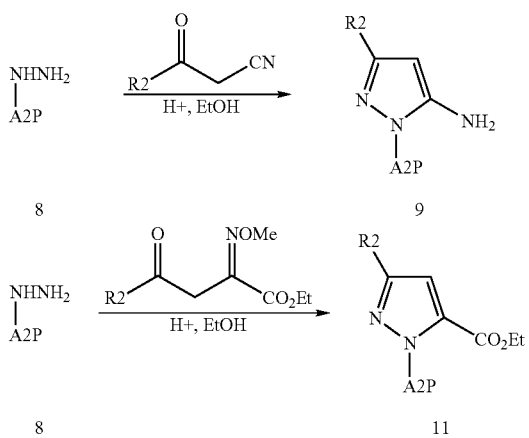

The aminopyrazoles 9 are converted into the desired pyrazole ureas 12 of Formula I (see Scheme 3) by methods described in Scheme 30 for the conversion of the aminothiophene into ureas of Formula I.

Scheme 3

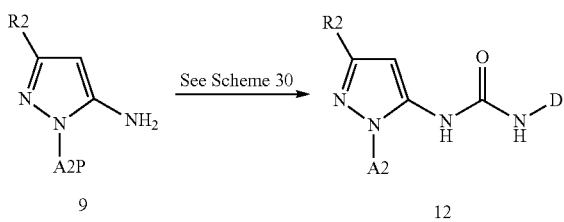

Alternatively, pyrazole ureas of Formula I can be formed from the pyrazole ethyl esters 11 by a sequence illustrated in Scheme 4. Conversion of esters 11 to the carboxylic acids 13 is accomplished by saponification or by treatment with aqueous acid. Curtius-type rearrangement of 13, preferably by treatment with ethyl chloroformate and base, preferably triethylamine, in an organic solvent, preferably THF at about 0 C, and then forming the acyl azide by reaction with sodium azide, and quenching of the in situ rearranged isocyanate with D-NH$_2$ gives rise to the desired pyrazole ureas 14 of Formula I (E1 Haddad, M. et al, *Journal of Heterocyclic Chemistry* (2000) 37: 1247-1252).

Scheme 4

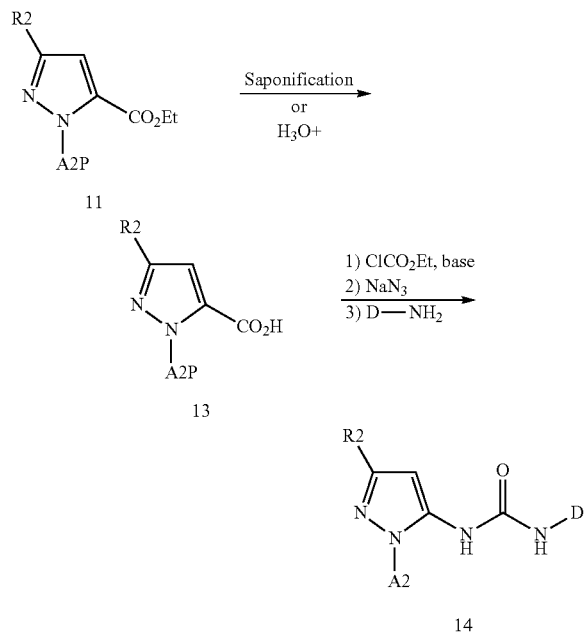

The synthesis of pyrazoles of formula I wherein A1 is A1-2 is exemplified in Scheme 5. Aryl halide 15 (bromo or iodo (preferred)) is reacted with acetylene 16 [CAS 22537-06-0] under standard palladium cross-coupling conditions to yield 17. As described by Coispeau et. al (Bull. Chem. Soc. France, 1970, 689-696), 17 reacts monosubstituted hydrazines in the presence of catalytic mineral acid to yield pyrazole 18, which is readily nitrated under standard conditions at the 4-position to yield 19. Catalytic hydrogenation or reduction utilizing iron/HCl or tin (II) chloride of 19 yields 20, which can be coupled and deprotected as shown in Scheme 6 to yield urea 21.

Scheme 5

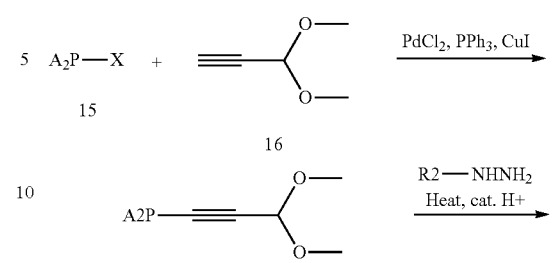

The aminopyrazoles 20 are converted into the desired pyrazole ureas 21 of Formula I by methods described in Scheme 30.

Scheme 6

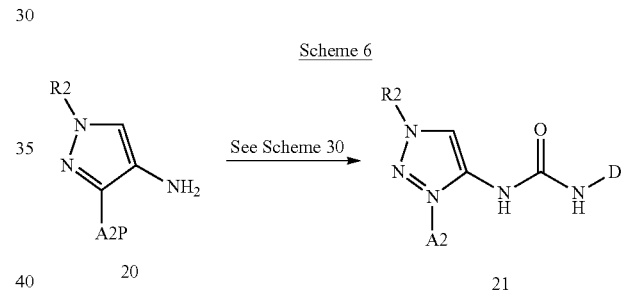

The synthesis of pyrazoles of formula I wherein A1 is A1-3 is exemplified in Scheme 7. Substituted pyrazole 22 is preferentially halogenated (brominated or iodinated) at the 4-position to yield 23 (see: *Bull. Chem. Soc. France,* 1967, 328 and *J. Gen. Chem.* USSR, 1963, 33, 503). Coupling of 23 with boronic acid 24 under standard conditions yields 25 which is nitrated at the 3-position under standard conditions to yield 26. Catalytic hydrogenation or reduction of 26 utilizing iron/HCl or tin (II) chloride yields amine 27 that can be elaborated to deprotected urea 28 of Formula I using the same strategies as outlined in Scheme 30.

Scheme 7

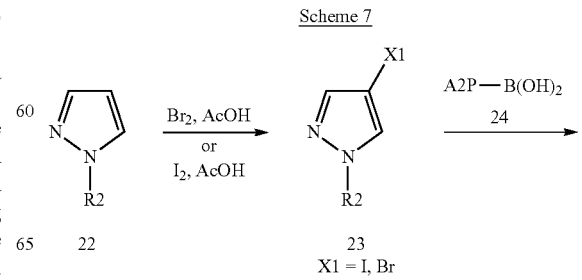

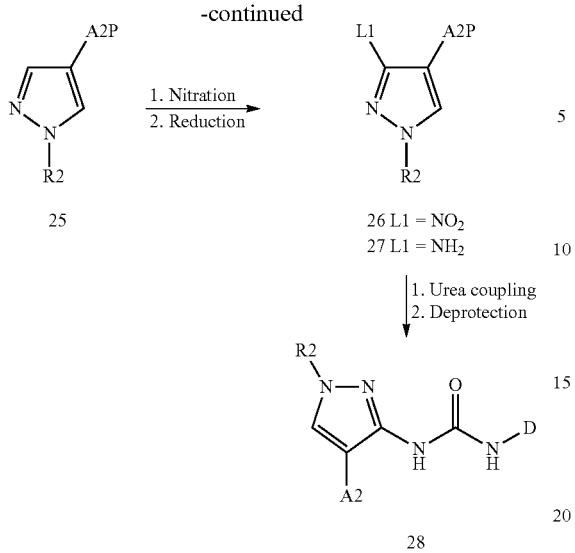

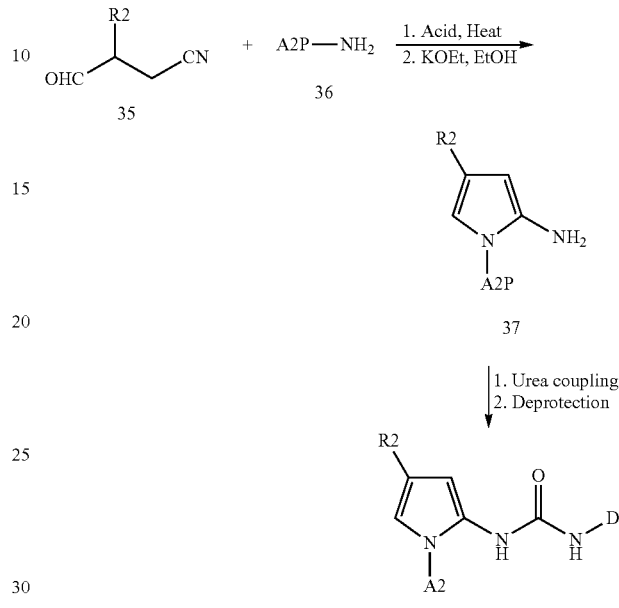

action of potassium ethoxide in ethanol at room temperature to yield pyrrole 37. Elaboration of amine 37 employing the same strategy as shown in Scheme 30 affords deprotected ureas 38 of Formula I.

The synthesis of pyrroles of formula I wherein A1 is A1-4 is exemplified in Scheme 8. Substituted 1,4-dicarbonyl compound 29 (see Scheme 8) is reacted with amine 30 in THF or toluene to yield intermediate pyrrole 31, which, after nitration, reduction (see Scheme 1), urea coupling and deprotection (see Scheme 30) yields pyrazole compounds 34 of Formula I.

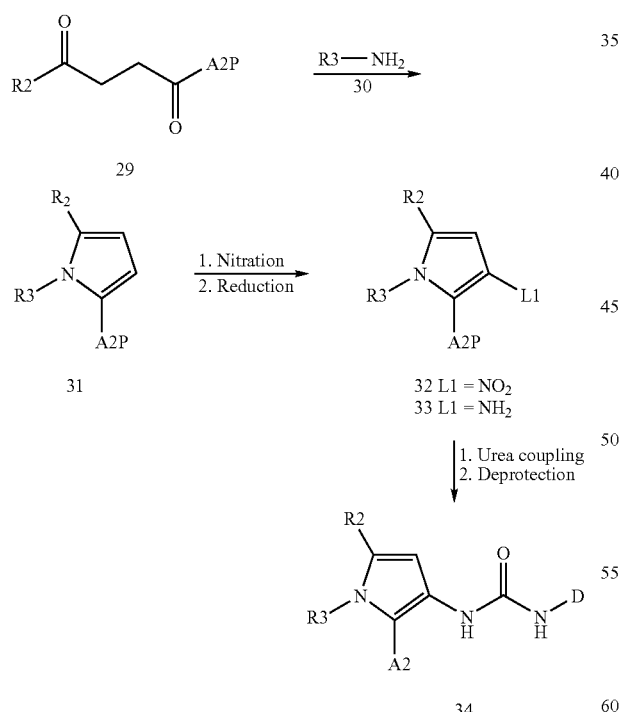

The synthesis of pyrroles of formula I wherein A1 is A1-5 is exemplified in Scheme 9. Substituted aldehydes 35 cyclocondense with amines 36 when reacted with hot acetic acid (See: *J. Chem. Soc. Perkin Trans. I*, 1975, 1910). After workup, the resulting solid is immediately subjected to the The synthesis of pyrroles of formula I wherein A1 is A1-6 is exemplified in Scheme 10. Diethylmaleate 39 is reacted with halide 40 in the presence of NaBr, NiBr$_2$ and ethanol (*Tetrahedron Letters*, 1999, 40(33), 5993) to yield product 41. Reduction of the diacid with LAH in ether to the diol followed by oxidation under Swern or MnO$_2$ conditions to yield dialdehyde 42. In situ cyclization with amine 43 yields pyrrole 44. Nitration of 44 and reduction yields amine 46 which is elaborated to deprotected ureas 47 of Formula I according to the methods described in Scheme 30.

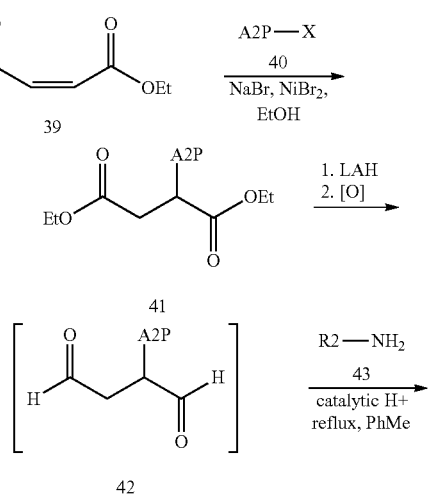

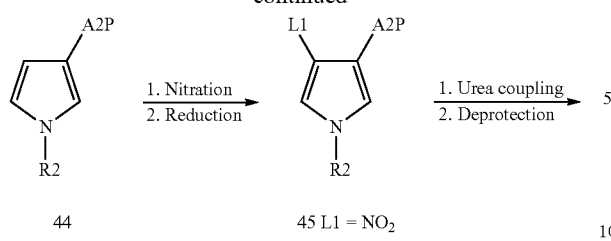

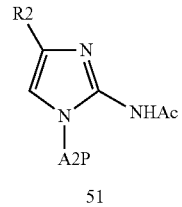

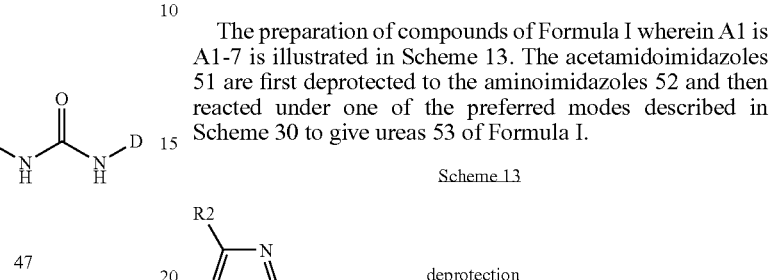

The preparation of compounds of Formula I wherein A1 is A1-7 is illustrated in Scheme 13. The acetamidoimidazoles 51 are first deprotected to the aminoimidazoles 52 and then reacted under one of the preferred modes described in Scheme 30 to give ureas 53 of Formula I.

Scheme 13

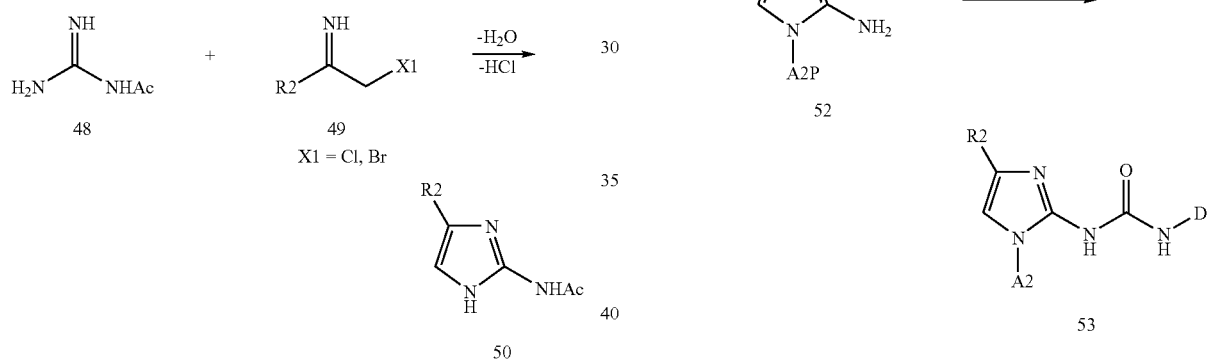

The preparation of intermediates containing ring A1-7 is illustrated in Schemes 11 through 13. Scheme 11 illustrates the preparation of imidazole intermediate 50. Reaction of 48 with 49, affords 50 (cf. Little, T. L. et al. *J. Org. Chem.* 1994, 59 (24), 7299-7305).

Scheme 11

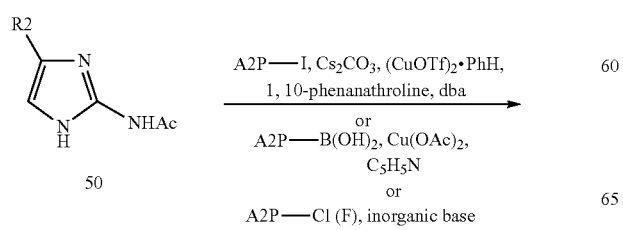

Cross-coupling reaction of 50 is accomplished by two different methods. Scheme 12 illustrates the method of Kiyomori, A. et al. (*Tetrahedron Lett.* 1999, 40 (14), 2657) wherein 50 is reacted with a suitable A2P—I in the presence of $Cs_2CO_3$ as base and $Cu(OTf)_2$ as catalyst. In another preferred mode 50 is cross-coupled with an A2P—$B(OH)_3$ under $Cu(OAc)_2$ catalysis in the presence of pyridine (Chan, D. M. T. et al. *Tetrahedron Lett.* 2003, 44 (19), 3863). In yet another mode, nucleophilic aromatic substitution between 50 and A2P—F (or Cl) in the presence of an inorganic base also provides 51.

Scheme 12

Scheme 14 illustrates the preparation of oxazole intermediates 56. Readily available acid chlorides 54 are converted to the corresponding acyl nitrites 55 by the action of cyanide anion, according to the method of Tanaka, M. et al. (*Synthesis* 1981, 12, 973-4). Employing the conditions of Lakhan, R. et al. (*J. Heterocycl. Chem.* 1988, 25 (5), 1413-1417) reaction of 55 with R2-CHO and $NH_4OAc$ gives oxazoles 56.

Scheme 14

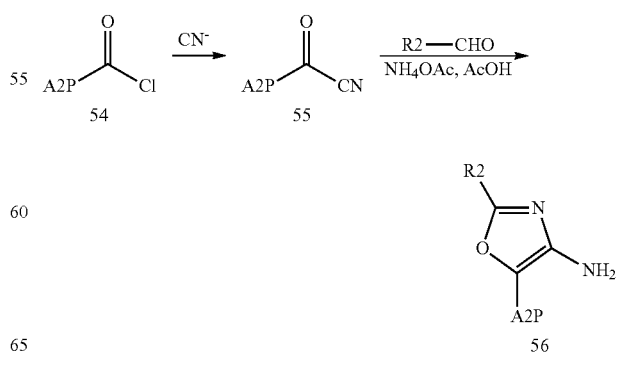

The elaboration of 56 to compounds of Formula I wherein A1 is A1-8, is illustrated in Scheme 15. Conversion of amines 56 to ureas 57 is accomplished by methods analogous to that shown previously in Scheme 30.

Scheme 15

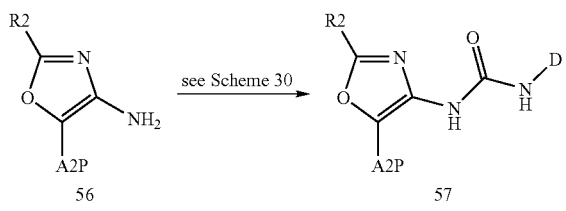

Preparation of compounds of Formula I wherein A1 is A1-9 is illustrated in schemes 16 and 17. Scheme 16 illustrates the preparation of oxazole intermediates 61. Beginning with 58 the aldehyde function is elaborated through a Strecker synthesis (Kendall, E. C. et al. *Org. Synth.* CV 1, 21) to provide amino-nitriles 59. Acylation with R2COCl in the presence of a base generates intermediate 60. Alternatively, 59 can be coupled with R2COOH in the presence of a peptide-coupling or dehydrating agent and a base to also give 60. Finally, treatment of 60 with a strong organic acid (cf. EP 816347) or mineral acid (Kille, G. et al. *Bull. Soc. Chim. France* 1967, 11, 4619) afford the desired aminooxazoles 61.

Scheme 16

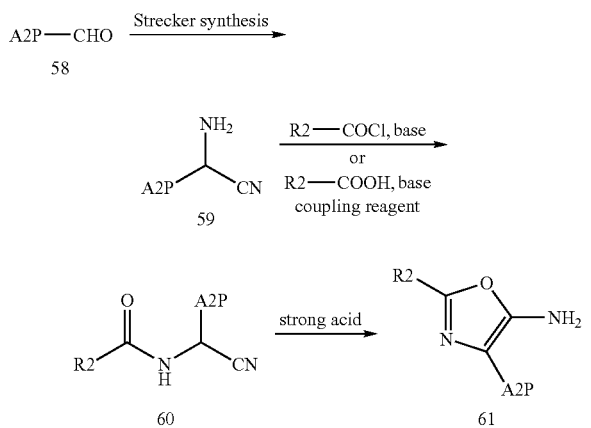

The elaboration of 61 to 6 as shown in Scheme 17, is completely analogous to that shown previously in Scheme 30.

Scheme 17

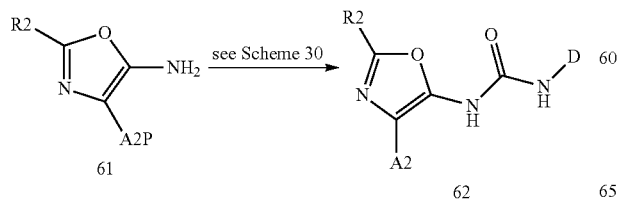

Compounds of Formula I wherein A1 is A1-10 are prepared as shown in schemes 18 through 20. The preparation of thiazole intermediates of formula 67 is illustrated in Schemes 18 through 20. In one preferred mode, acylated intermediate 60, from Scheme 16 (see above), is treated with a thionating reagent such as $P_4S_{10}$ or Lawesson's Reagent to make 63. This, in turn, when treated with strong acid affords the desired 64, by analogy to Scheme 16.

Scheme 18

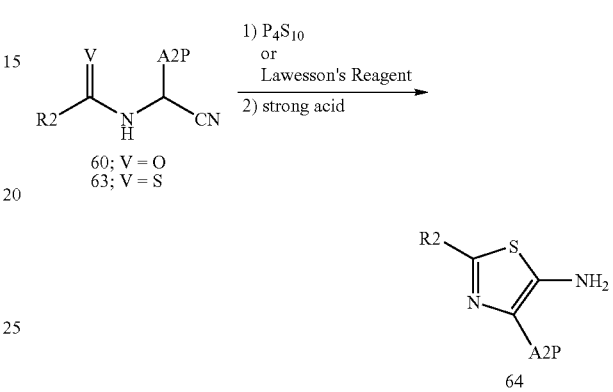

In an alternate preferred mode (Scheme 19), 59, from Scheme 16 (see above) is treated with R2-CHO in the presence of elemental sulfur and a base, according to the method of Gerwald, et al. (*J Prakt. Chem.* 1973, 513, 539) to generate 66. Deprotection under aqueous acidic conditions generates 64.

Scheme 19

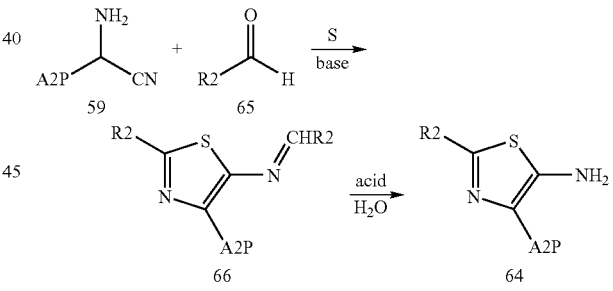

The elaboration of 64 to 6 as shown in Scheme 20, is completely analogous to that shown in Scheme 30.

Scheme 20

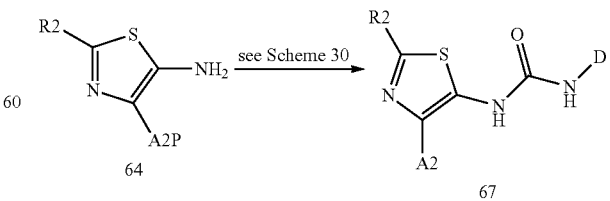

The preparation of compounds of Formula I wherein A1 is A1-11 is illustrated in Schemes 21 and 22. A2P-containing hydrazines, 68, are acylated with R2COCl in the presence of a base to generate intermediates 69. Alternatively, 68 can be coupled with R2COOH in the presence of a peptide-coupling or dehydrating agent and a base to also give 69. Halogenation under the conditions of Joseph, B. et al. (*J. Carbohydrate Chem.* 1993, 12, 1127-38) or Sakamoto, T. et al. (*Chem. Pharm. Bull.* 1988, 36, 800-802) afford hydrazinoyl halides 70. Treatment with base generates the reactive 1,3-dipoles 71 which are trapped with cyanamide to give aminotriazoles 72, in accordance with precedent (EP 285893).

The elaboration of 72 to 73 as shown in Scheme 22, is accomplished according the methods illustrated in Scheme 30.

Scheme 22

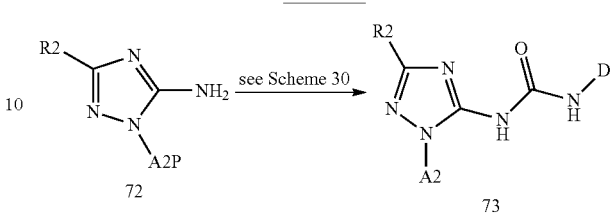

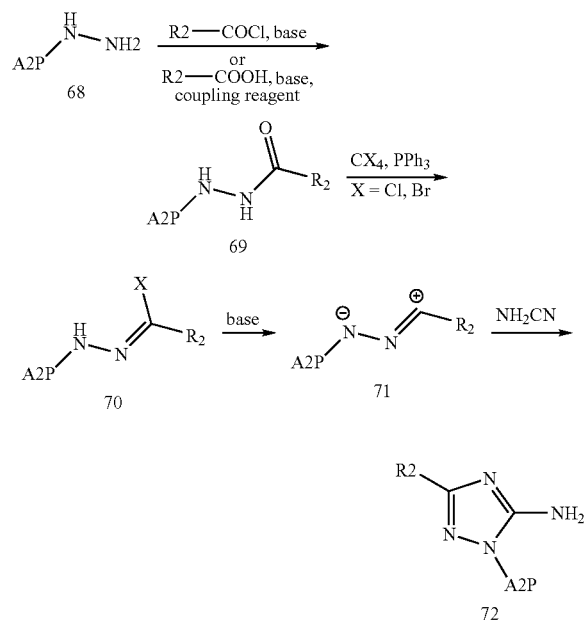

Preparation of compounds of Formula I wherein A1 is A1-12 is illustrated in scheme 23. The preparation of the furan intermediate of formula 81 follows the reported procedure of Toro, A. et al. (*J. Org. Chem.* 2003, 68 (18), 6847). 74 is acylated as described previously, treated with the dilithio species of 76 and finally cyclized with HBr to give 77. Introduction of the A2P moiety is accomplished by several different methods. In one preferred mode, using the method of Pridgen, L. et al. (*J. Org. Chem.* 1982, 47, 1590-1592), 77 is cross-coupled with an A2P—MgBr in the presence of a nickel catalyst to generate 79. In a second preferred mode, reported by Hervet, M. et al. (*Helvetica Chim. Acta.* 2003, 86 (10), 3461), 79 may be obtained by cross-coupling with a stannane in the presence of a palladium catalyst. In a third preferred mode reported by Burke, M. et al. (*Science* 2003, 302 (5645), 613-618), the cross-coupling may be accomplished under Suzuki conditions with an appropriate boronic acid.

Finally, in a fourth preferred mode, 77 is converted to a boronate species, 78, which is then subjected to Suzuki coupling conditions with the requisite A2P—X. Deprotonation of 79 and quenching of the anion with $CO_2$ delivers acid 80. Subjecting 80 to Curtius rearrangement conditions in the presence of $D-NH_2$ to trap the intermediate isocyanate provides 81 using methods analogous to that illustrated in Scheme 4.

Scheme 23

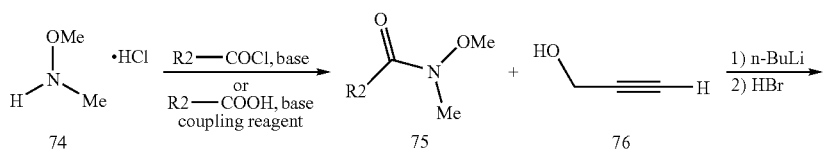

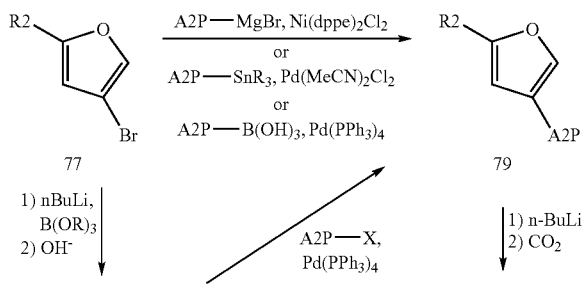

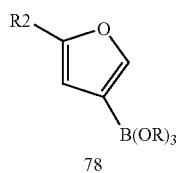

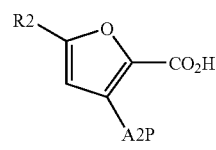

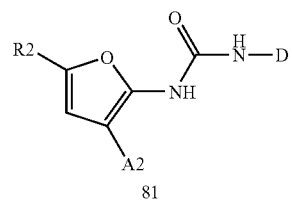

Preparation of compounds of Formula I wherein A1 is A1-13 is illustrated in schemes 24 and 25. Scheme 24 illustrates the preparation of furan intermediates 85. The 1,4-dicarbonyl starting materials 82 are reacted with para-methylbenzenesulphonic acid (TsOH) in a suitable solvent such as toluene to afford furan 83. Nitration of 83 affords 84, which is reduced with iron/HCl, tin (II) chloride, or catalytic hydrogenation conditions to give the 3-aminofuran intermediates 85.

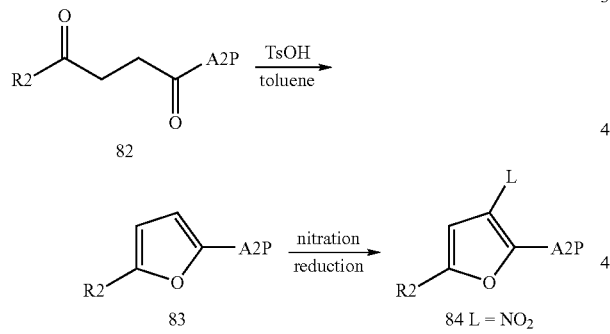

The aminofurans 85 are converted into the desired furanyl ureas 86 of Formula I by methods described in Scheme 30.

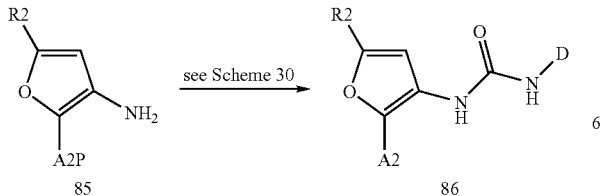

The preparation of compounds of Formula I wherein A1 is A1-14 is illustrated in schemes 26 and 27. Scheme 26 illustrates the preparation of 4,5-disubstituted 2-aminothiophenes 92 according to methods reported by Knoll et al (Knoll, A. et al, *Synthesis* (1984) 51-53; Knoll, A. et al, *J. Prakt. Chem.* (1985), 327: 463-470). The compound 87 is reacted with an excess of formamide derivatives 88 in methanol to afford N-(3-aminothioacryloyl)-formamidines 89. A mixture of substituted N-(3-aminothioacryloyl)-formamidines, 89 and substituted bromides, 90 in a protic solvent, such as methanol or ethanol, is heated, preferably at a reflux temperature. The product thiophene-imines, 91 are treated with aqueous acid to obtain the thiophene-amines 92.

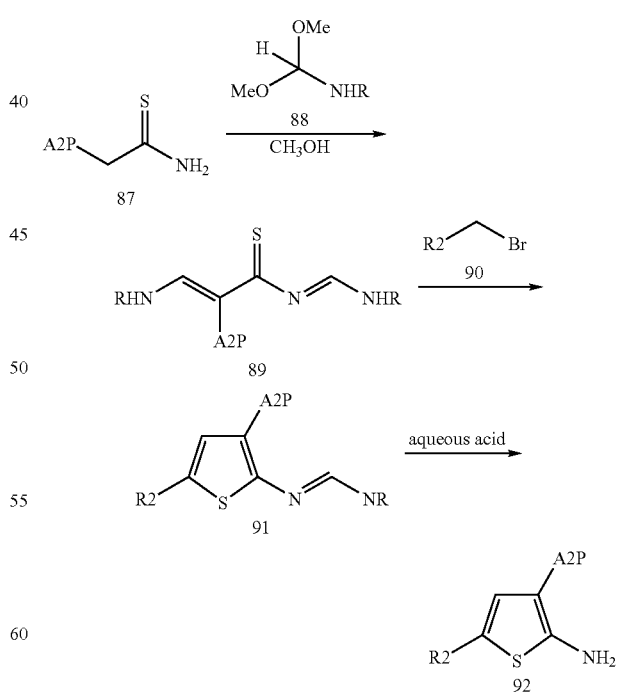

The aminothiophenes 92 are converted into the desired thiophenyl ureas of Formula I by methods described in Scheme 30.

Scheme 27

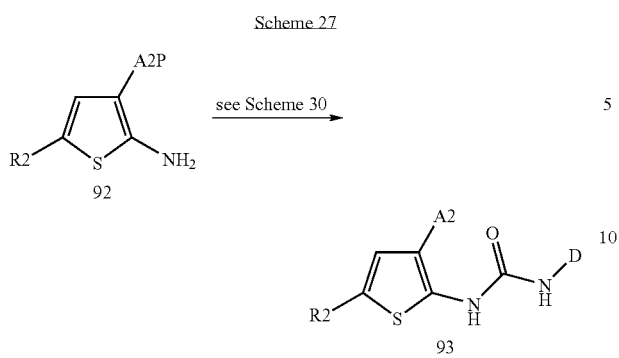

Scheme 28 illustrates the preparation of 1,4-dicarbonyl starting materials 96 for the preparation of compounds of Formula I, wherein A1 is A1-13. One preferred method utilizes a 1,4-conjugate addition procedure, Scheme 28 (a), to transform 94 to 96 by reaction with the unsaturated ketone 95 in the presence of a suitable base such as a lithium, sodium, or potassium amide or hydride base. Another preferred method, Scheme 28 (b), makes use of a transmetallation reaction, converting 97, wherein X1 is halogen, to an organometallic species 98 wherein the metal is magnesium, nickel, or cadmium. In situ reaction of 98 with acid chloride 99 gives rise to the 1,4-dicarbonyl species 96 after acid-catalyzed removal of the ketal protecting group. Alternative reaction of 98 wherein the metal is lithium with the Weinreb amide 100 also affords 96 after acid-catalyzed removal of the ketal protecting group. A third preferred method, illustrated in Scheme 28 (c), makes use of a palladium-catalyzed reaction between the readily available boronic acid 101 and a suitable 2-pyridyl ester 102 as reported by Chatani et al (*Organic Letters* (2004) 6: 3597-3599).

Scheme 28

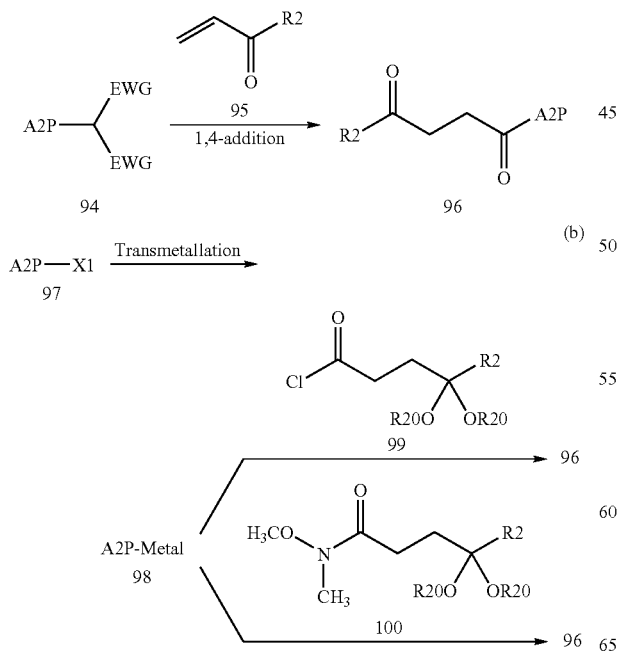

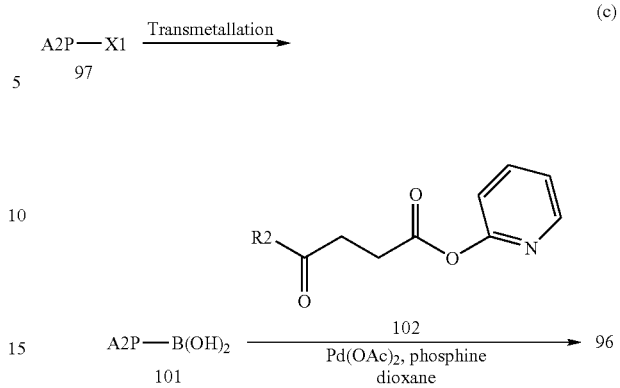

The 1,4-dicarbonyl starting materials 96 are reacted with Lawesson's reagent in a suitable solvent such as THF or toluene to afford thiophene 103. Nitration of 103 affords 104, which is reduced with iron/HCl, tin (II) chloride, or catalytic hydrogenation conditions to give the 3-aminothiophene intermediates 105 (Scheme 29).

Scheme 29

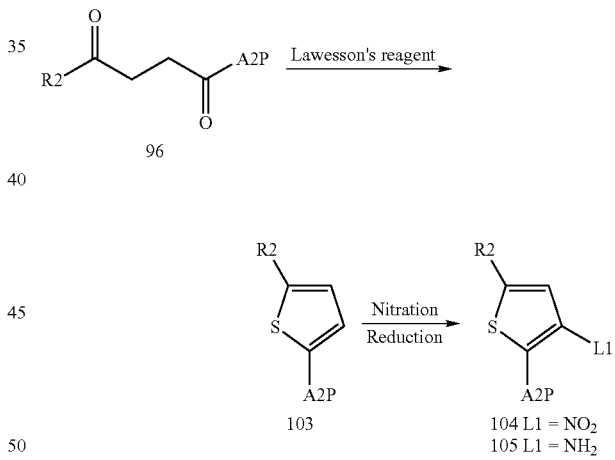

The preparation of compounds of Formula I are illustrated in Scheme 30. The aminothiophenes 106 are reacted with carbonyl diimidazole (CDI) or phosgene CO(Cl)$_2$ to give isocyanates 107. Alternatively, 106 can be reacted with p-nitrophenyl chloroformate to give the p-nitrophenylcarbamates 108 as synthetic equivalents to isocyanates 107. Reaction of isocyanates 107, or the corresponding p-nitrophenylcarbamates 108, with readily available amines D-NH$_2$ affords ureas 109. Alternatively, 106 is reacted with isocyanates 110 or the p-nitrophenylcarbamates 111 to give ureas 109. Removal of the A2P protecting groups from 109 affords the desired compounds of Formula 112.

Scheme 30

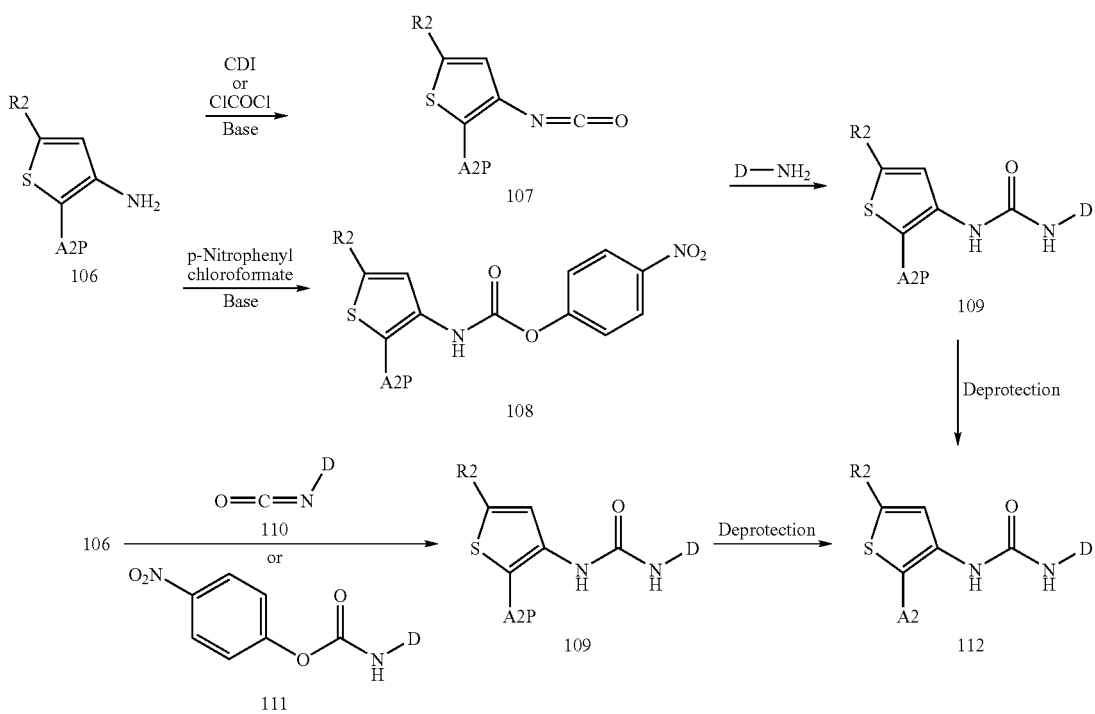

The preparation of compounds of Formula I wherein A1 is A1-16 is illustrated in Schemes 31 and 32. Scheme 31 illustrates the preparation of 2,4-disubstituted N-protected-anilines 117. The commercially available starting materials 113 are converted to 4-substituted anilines 114 by nitration, followed by reduction with iron/HCl, tin (II) chloride, or catalytic hydrogenation conditions. The reaction of 4-substituted anilines 114 with bromine in acetic acid gives 2-brominated anilines 115. The amino groups of 115 are protected to allow their use in Suzuki coupling reactions to obtain 117.

Scheme 31

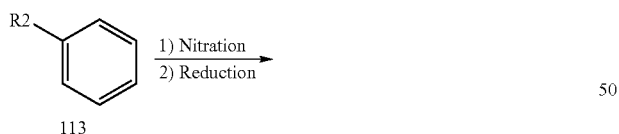

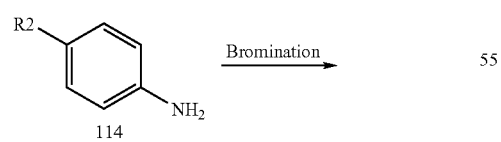

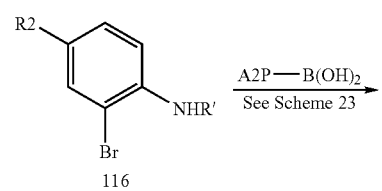

The Suzuki coupled intermediates 117 are converted into the desired phenyl ureas 118 of Formula I by methods described in Scheme 30.

Scheme 32

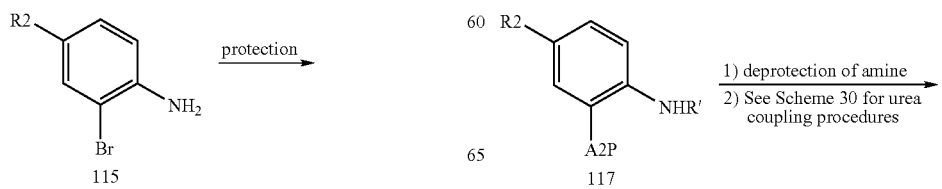

-continued

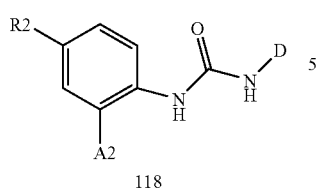
118

The preparation of compounds of Formula I is illustrated in Schemes 33 and 34. Scheme 33 illustrates the preparation of 2,5-disubstituted 2-aminopyridines 125. The commercially available starting material 119 is reacted with sodium nitrate to afford 1-methyl-3,5-dinitro-2-pyridone 120. The reaction of 120 with ketones 121 in the presence of $NH_3$ gives alkyl and/or aryl-substituted 3-nitropyridine derives 122 (Tohda, Y. et al, *Bull. Chem. Soc. of Jpn* (1990), 63: 2820-2827). Reduction followed by selective bromination of 122 affords 123 (Canibano, V. et al, *Synthesis* (2001) 14: 2175-2179). The amino group of 123 is protected to give 124. 124 is reacted with a variety of Suzuki coupling reagents to obtain 125.

Scheme 33

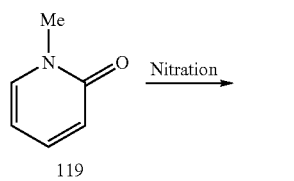
119

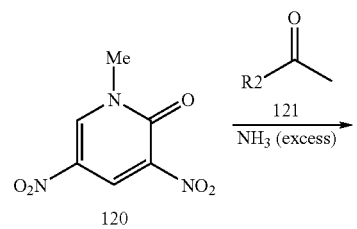
120

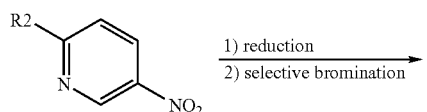
122

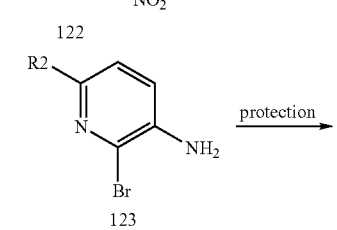
123

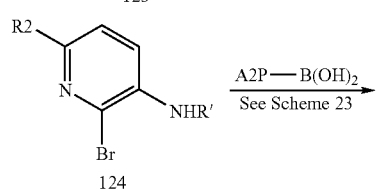
124

-continued

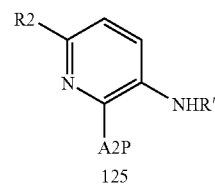
125

The aminopyridines 125 are converted into the desired pyridyl ureas 126 of Formula I by methods described in Scheme 30.

Scheme 34

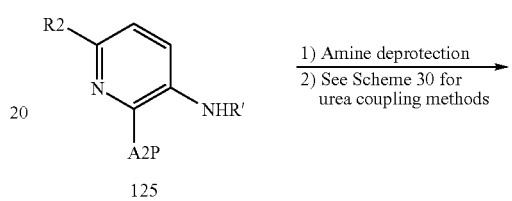
125

126

The preparation of compounds of Formula I wherein A1 is A1-18 is illustrated in Schemes 35 and 35a. Scheme 35 illustrates the preparation of 2,4-disubstituted 5-aminopyridines 132. The commercially available starting materials 127 are converted to 2-substituted-4-nitropyridines 128 under standard nitration conditions. Reduction followed by a second nitration of 128 gives 4-amino-2-substituted-5-nitropyridines 129 which can purified by silica column chromatography from the other isomers. The 4-amino-2-substituted-5-nitropyridines 129 are reacted with HBr and $NaNO_2$ to afford 4-bromopyridines 130. The bromopyridine 130 is reacted with a variety of Suzuki coupling reagents to produce 131. The reduction of the nitro group of 131 with iron/HCl, tin (II) chloride, or catalytic hydrogenation conditions gives 2,4-disubstituted-5-aminopyridines 132.

Scheme 35

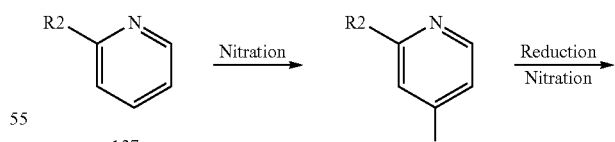
127    128

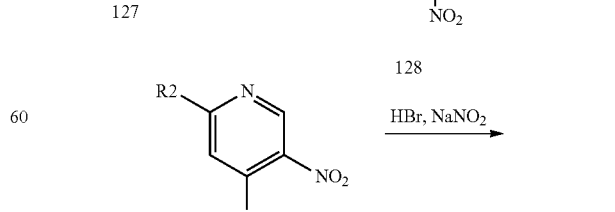
129

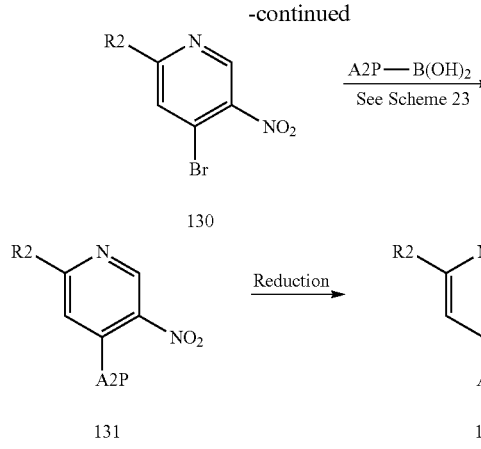

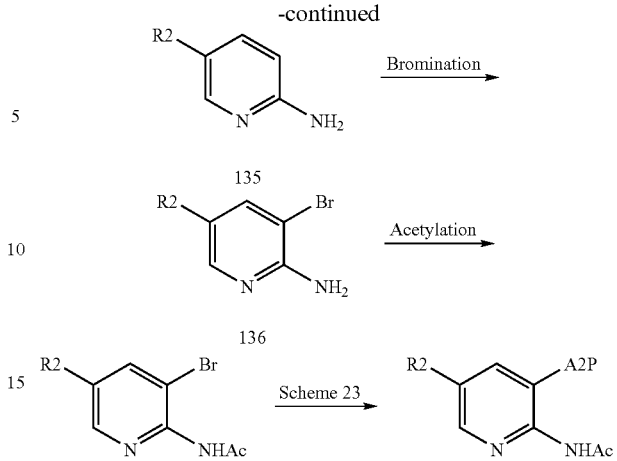

The aminopyridines 132 are converted into the desired pyridyl ureas 133 of Formula I by methods described in Scheme 30.

The preparation of compounds 139 of Formula I are described in Scheme 37. The aminopyridines 138 are first deprotected and then reacted under one of the preferred routes described in Scheme 30.

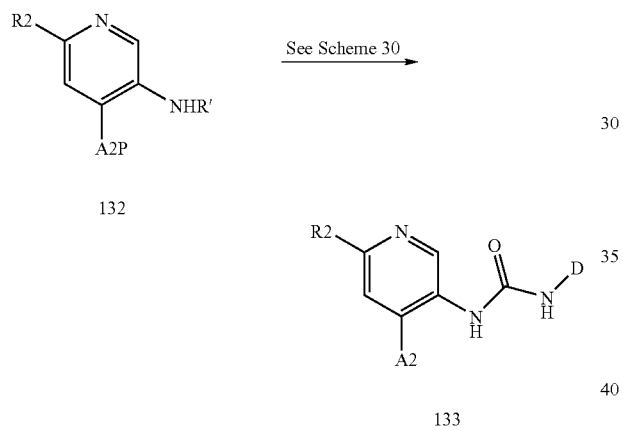

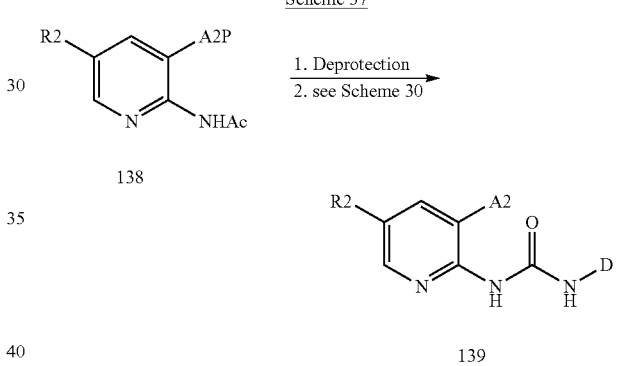

The preparation of compounds of Formula I wherein A1 is A1-19 is illustrated in Schemes 36 and 37. Scheme 36 demonstrates the preparation of substituted pyridines 138. Amination of 134 and subsequent bromination affords 135 as previously reported (*J. Am. Chem. Soc.*, 1990, 112, 8024 and *Heterocycles*, 1986, 24, 1815). Thus 3-alkyl pyridines 134 upon reaction with sodamide gives pyridines 135, which are brominated with bromine to give pyridines 136. The amine functionalities of 136 are acetylated using acetyl chloride or acetic anhydride to give 137. The brominated intermediates 137 are utilized in Suzuki cross coupling reactions to give cross-coupled intermediates 138 utilizing procedures describe above in Scheme 23.

Preparation of compounds of Formula I wherein A1 is A 1-20 is described in scheme 38 and scheme 39 according to reported procedures in *Tetrahedron Lett.*, 2002, 43, 9287 and *J. Heterocycl. Chem.*, 1978, 15, 665. The oximes 140 are reacted with aminoacetonitrile to afford the cyclodehydrated intermediates which are hydrogenated to give 141. Bromination of 141 affords 142. The amine functionalities of 142 are converted to the N-acetate derivatives 143, which are subjected to Suzuki cross-coupling reactions as described in scheme 23 to afford cross-coupled intermediates 144.

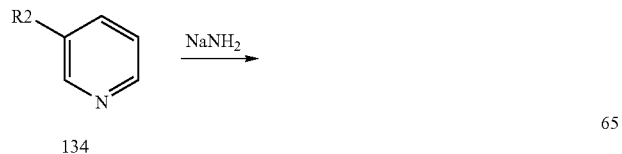

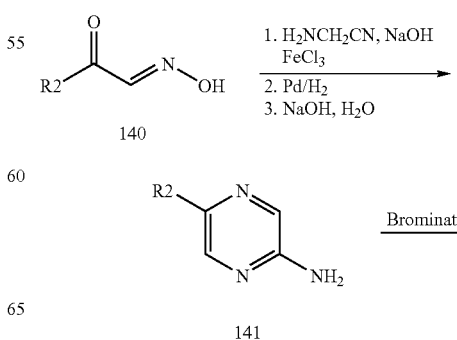

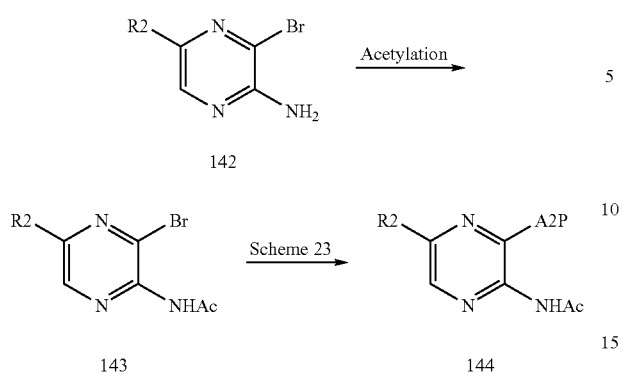

The preparation of compounds of Formula I is illustrated in Scheme 39. The N-Acetyl functionalities of 144 are removed and the resulting amines are converted to ureas 145 of Formula I-B as previously illustrated in scheme 30.

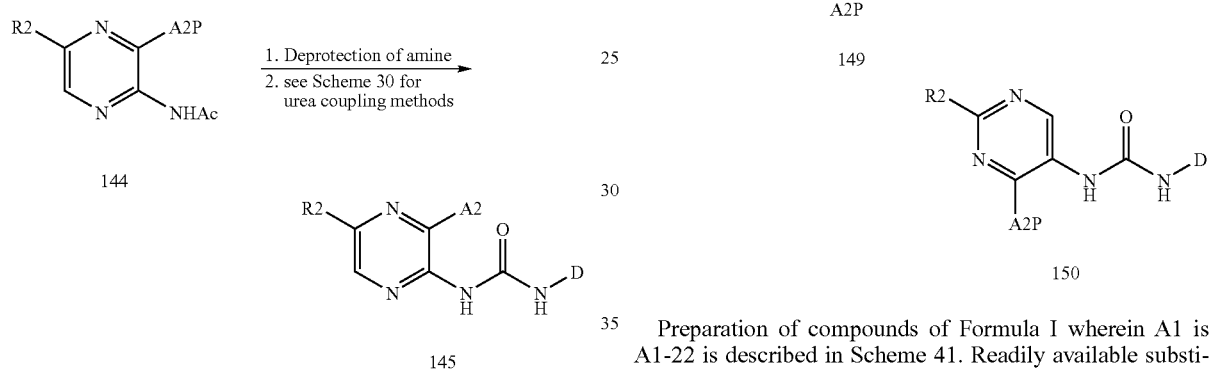

Synthesis of compounds of Formula I wherein A1 is A1-21 is described in Scheme 40. As reported by Palanki et al (*J. Med. Chem.* 2000, 43, 3995-4004) diethyl ethoxymethylenemalonate and trialkylacetamidine are heated with sodium ethoxide to provide pyrimidines 146. The hydroxyl groups of 146 are converted to the bromides by reaction with $PBr_3$ to afford bromopyrimidines 147. Intermediates 147 are converted to 148 using Suzuki cross-coupling methods illustrated above in Scheme 23. The ester functionalities of 148 are hydrolyzed to acids 149, which are utilized in a Curtius rearrangement reaction sequence in the presence of amines D-$NH_2$ using methods reported above in Scheme 4, to give the desired ureas 150 of Formula I.

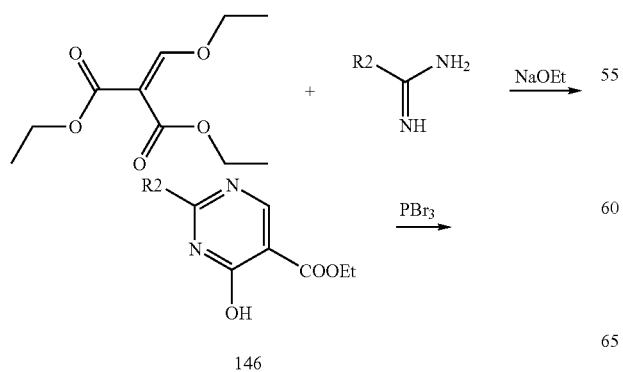

Preparation of compounds of Formula I wherein A1 is A1-22 is described in Scheme 41. Readily available substituted acetic acids 151 are converted into the requisite acid chlorides 152 by reaction with thionyl chloride in the presence of base, preferably triethylamine or pyridine. The acid chlorides are converted to amides 153 by reaction with R2$NH_2$ in the presence of base, preferably triethylamine or pyridine. Reaction of 153 with dimethyloxalate in the presence of base, preferably potassium t-butoxide in DMF, affords hydroxymaleimides 154. Conversion of 154 to the chloro-substituted maleimides 155 is effected by reaction with thionyl chloride. Displacement of chloride by ammonia converts 155 into the amino-substituted maleimides 156. Reaction of 156 with isocyanates D-N=C=O affords the desired compounds 157 of Formula I.

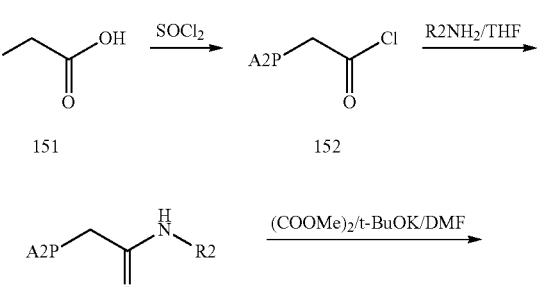

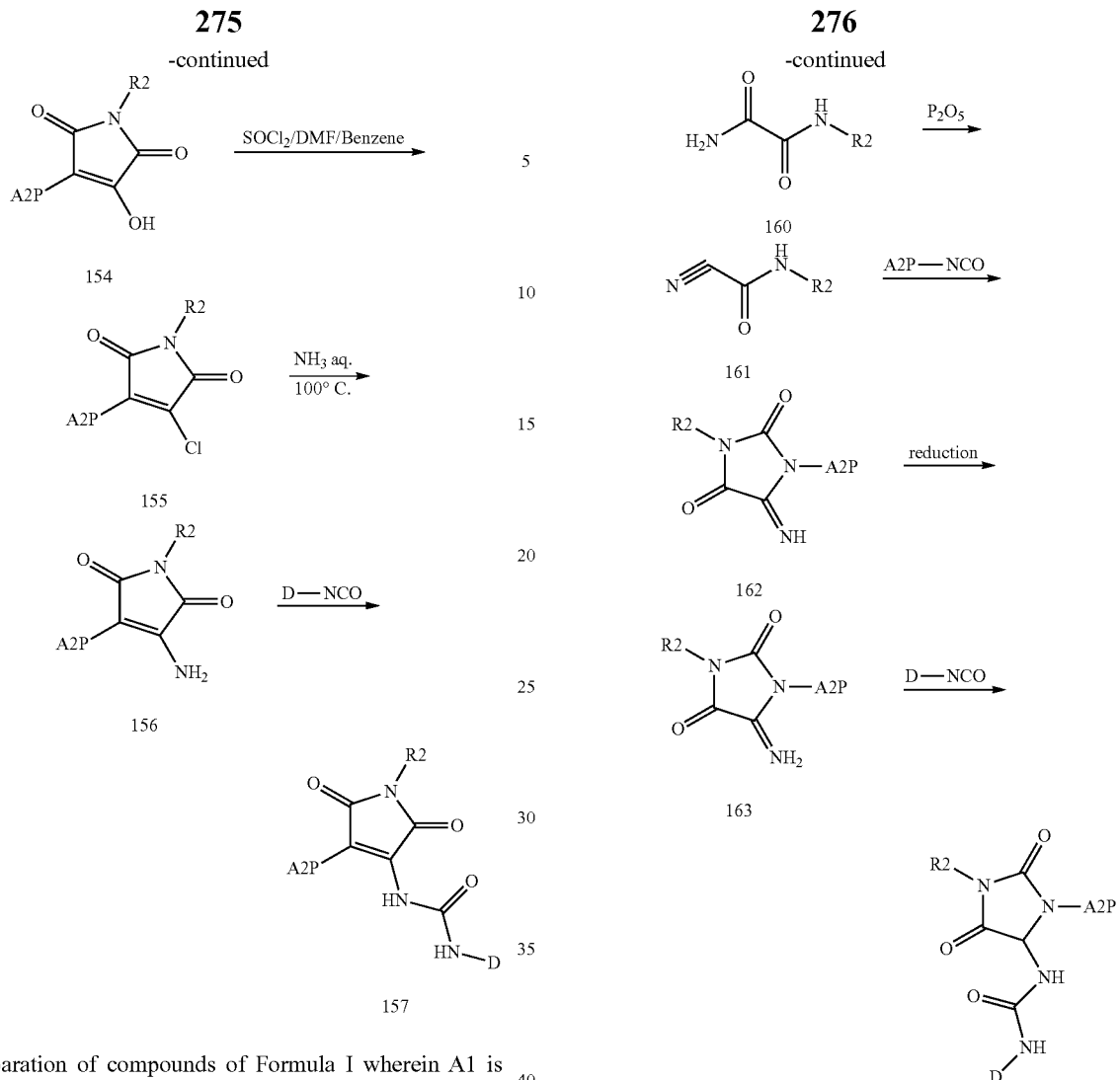

Preparation of compounds of Formula I wherein A1 is A1-23 is described in Scheme 42 according to methods disclosed by W. Buck et al, DE 2107146 (1972). Diethyl oxalate 158 is reacted with one equivalent of R2NH$_2$ to afford the mono amides 159. Subsequent reaction with ammonia gives the diamide 160, which is converted to the acylnitriles 161 by reaction with P$_2$O$_5$. Intermediates 161 are reacted with isocyanates A2P—N═C═O to give the imine-substituted hydantoins 162. Reduction of the imine functionality in 162 gives rise to compounds 163, which are reacted with isocyanates D-N═C═O to give the desired compounds 164 of Formula I.

Scheme 42

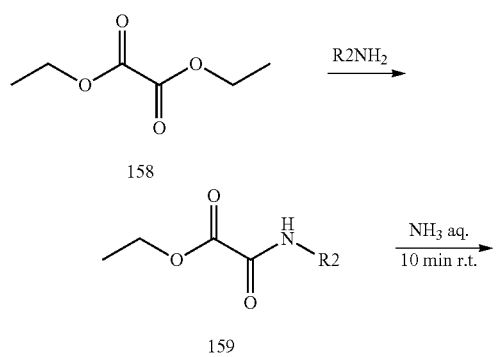

Preparation of compounds of Formula I wherein A1 is A1-23 is described in Scheme 43 according to methods disclosed by A. Sasaki et al, JP 2000198771 A2. Readily available amines 165 are reacted with diethyl bromomalonate 166 to afford amino-substituted diethyl malonates 167. Reaction of 167 with an appropriate alpha-substituted ethyl acrylate 168 followed by NaCl-induced decarboxylation, gives the substituted pyrrolidineones 169. Hydrolysis of the ester functionality of 169 gives rise to 170. Acids 170 are converted to the desired compounds 171 of Formula I by two alternative methods. In the first method, 170 is subjected to a Curtius-type rearrangement in the presence of amines D-NH$_2$, to give 171. In the second approach, 170 is first converted to the primary amides 172, which are then subjected to a modified Hoffman-type rearrangement utilizing bis-trifluoroacetoxy-iodobenzene to afford rearranged amines that are trapped with an isocyanate D-N═C═O.

Scheme 43

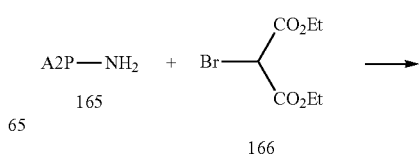

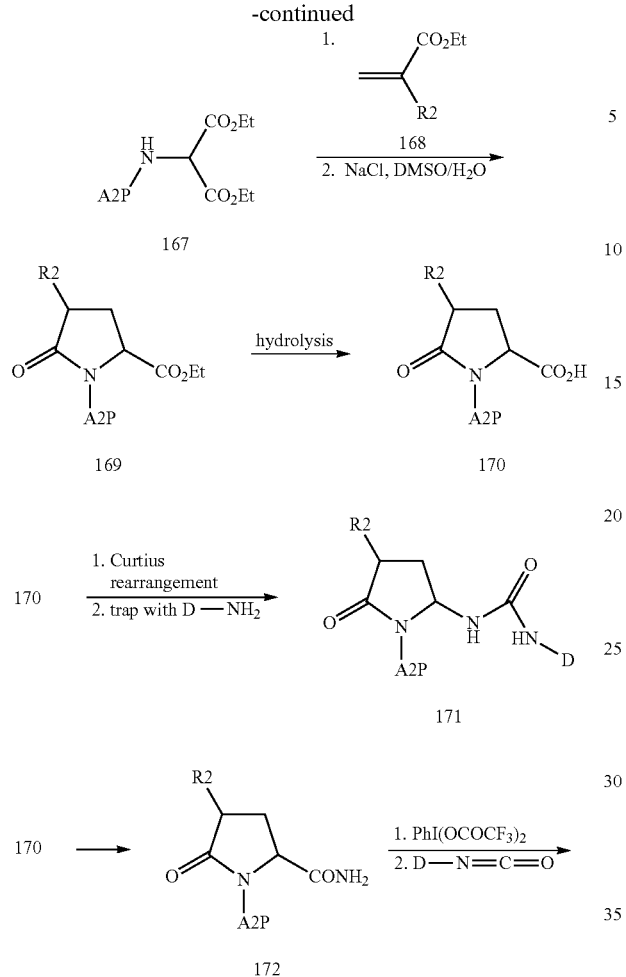

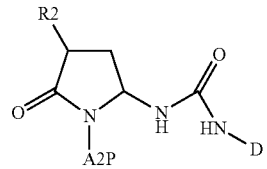

171

II. Synthesis of A2-Containing Intermediates.

The synthesis of intermediates containing A2 rings taken from A2-15 through A2-76 and A2-87 through A2-94, required for the elaboration of compounds in the aforementioned schemes, is accomplished using readily available precursors and transformations readily understood in the art. Such A2-containing intermediates are provided which contain amino, hydrazinyl, carboxyl, or halogen functionalities useful for coupling to the aforementioned intermediates containing A1 rings.

The synthesis of intermediates containing A2 rings taken from A2-1 through A2-14 and A2-77 through A2-117 are detailed below in schemes 44 through 93.

Scheme 44 illustrates the preparation of intermediates A2P corresponding to A2-1 through A2-6. Readily available halogenated substituted benzenes, pyridines, pyrimidines, or triazines 172 through 177 are obtained commercially or are available through diazotization/H-Q2 quench (Sandmeyer reaction) of the corresponding substituted aryl- or heteroaryl-amines 178 through 183. In cases where A2 moieties need to be supplied as the substituted hydrazines, these are either derived from readily available hydrazines or are derived from the substituted aryl- or heteroaryl-amines 178 through 183 by diazotization of the amino groups followed by reduction of the diazonium salts to the corresponding hydrazines 184 through 189.

Scheme 44

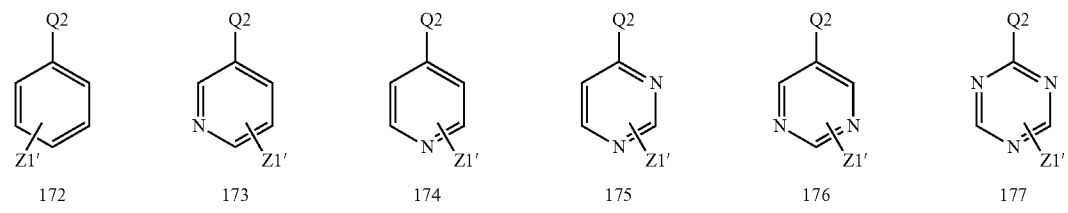

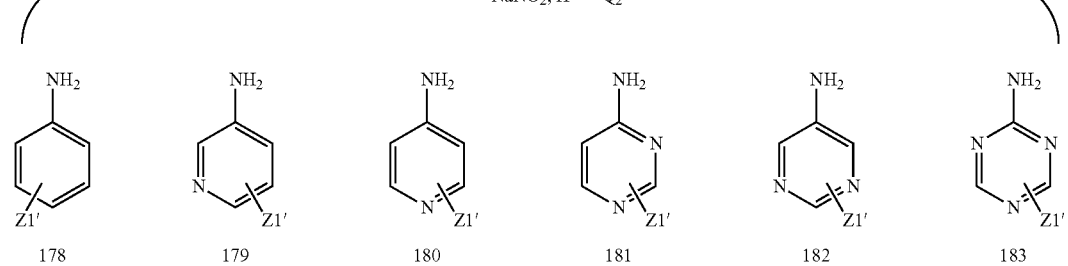

1) NaNO₂; 2) Reduction

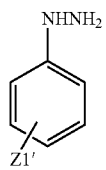
184

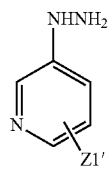
185

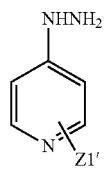
186

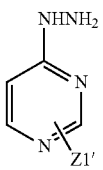
187

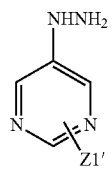
188

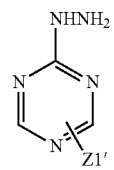
189

Scheme 45 illustrates the preparation of intermediates A2P corresponding to A2-7. Thiourea is reacted with readily available alpha-halocarbonyl compounds 190, wherein Q2 is chloro or bromo, to afford aminothiazoles 191. Aminothiazoles 191 are converted to thiazolylhydrazines 192 by a standard diazotization/reduction sequence. Alternatively, aminothiazoles 191 are converted to thiazolyl halides 193, wherein Q2 is chloro or bromo, by a standard Sandmeyer reaction sequence involving H-Q2 trapping of an in situ formed diazonium salt.

base, affording intermediate aminothiazoles 196 after an acid work-up. Aminothiazoles 196 are converted to the thiazolylhydrazines 197 by a standard diazotization/reduction sequence. Alternatively, aminothiazoles 196 are converted to thiazolyl halides 198, wherein Q2 is chloro or bromo, by a standard Sandmeyer reaction sequence involving H-Q2 trapping of an in situ formed diazonium salt. Alternatively, beta-keto esters 199, wherein Q3 is a halogen leaving group, are reacted with substituted thioamides to afford thiazolyl esters 200. Esters 200 are hydrolyzed to their corresponding acids 201, which are then converted into thiazolyl amines 202 by a Curtius-type rearrangement, or are converted into thiazolyl halides 203 by a Hunsdiecker reaction.

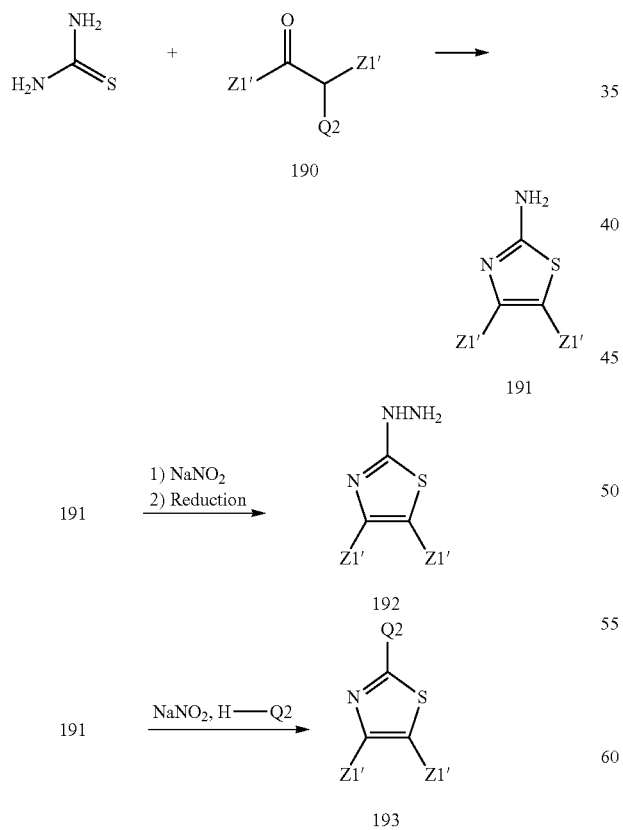

Scheme 45

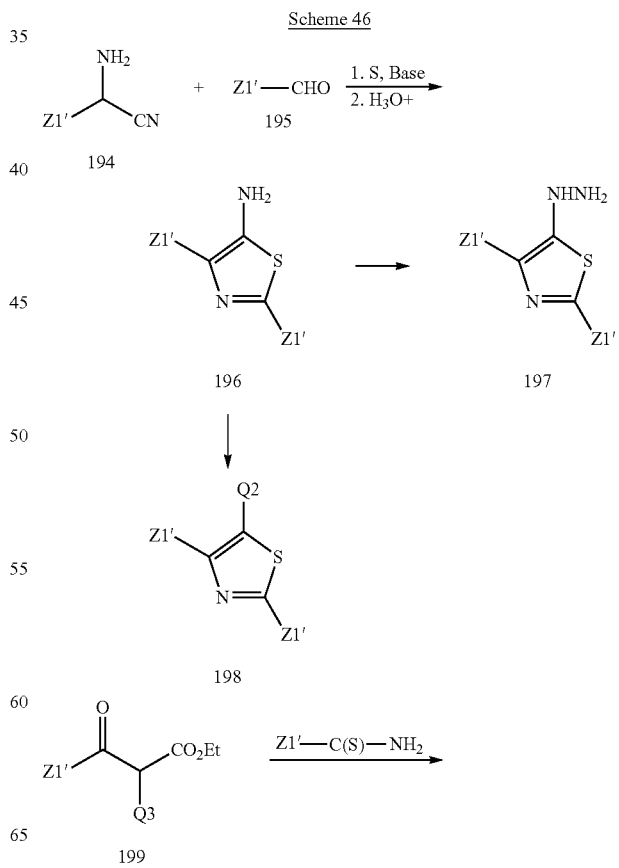

Scheme 46

Scheme 46 illustrates the preparation of intermediates A2P corresponding to A2-8. Readily available aminonitriles 194 are reacted with aldehydes 195 in the presence of sulfur and

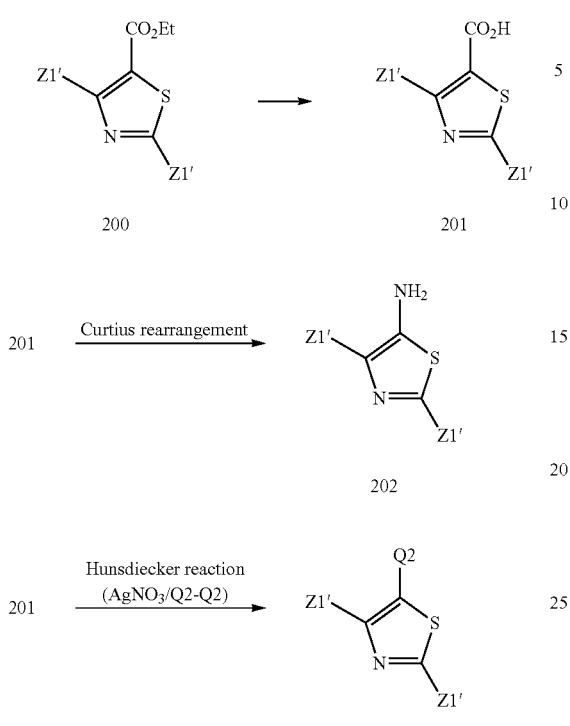

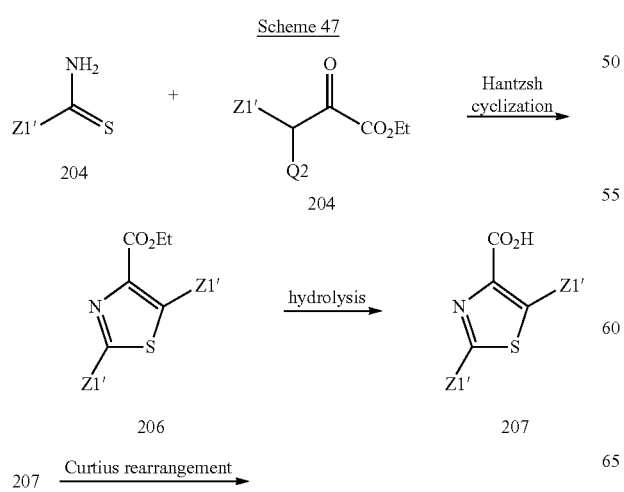

Scheme 47 illustrates the preparation of intermediates A2P corresponding to A2-9. Readily available thioamides 204 and beta-halo-alpha-keto esters 205 undergo a Hantzch cyclization to afford thiazolyl esters 206. Esters 206 are hydrolyzed to their corresponding acids 207, which undergo a Curtius-type rearrangement to afford the requisite aminothiazoles 208, which then undergo a standard diazotization/reduction sequence to give thiazolyl hydrazines 209. Alternatively, acids 207 undergo a Hunsdiecker reaction to afford the corresponding thiazolyl halides 210, wherein Q2 is chloro or bromo.

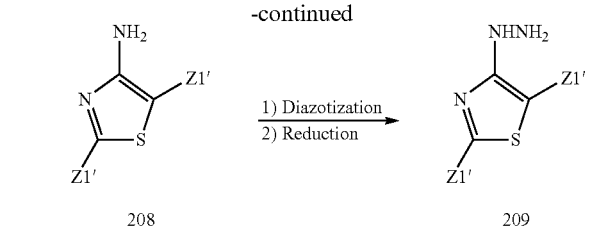

Scheme 48 illustrates the preparation of intermediates A2P corresponding to A2-10. Ketal-protected amino ketones 211 are converted to the oxazolyl esters 212 by reaction with ethyl oxalyl chloride. Hydrolysis of the esters 212 affords acids 213. Acids 213 are converted to the hydrazines 215 and halides 216 by reaction sequences described above in Scheme 47.

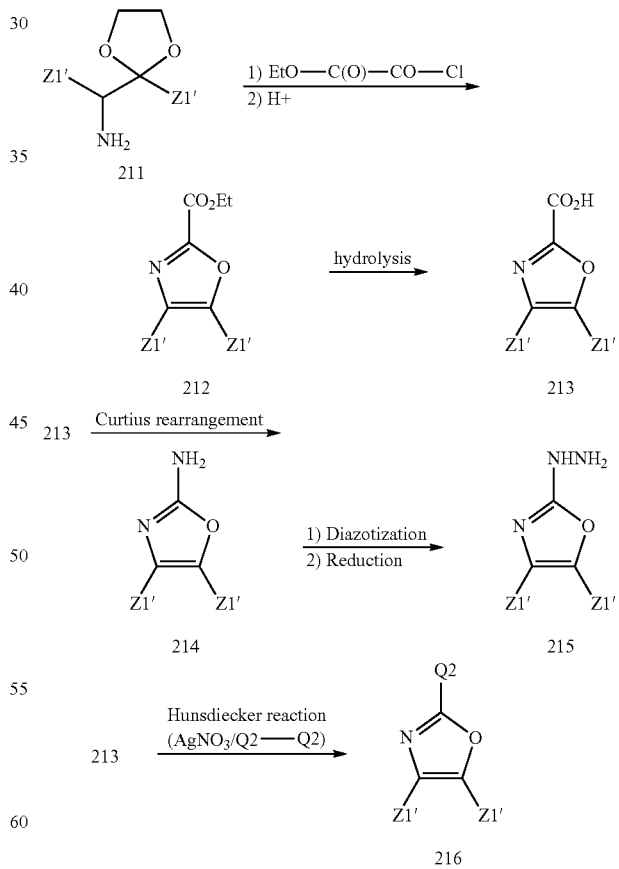

Scheme 49 illustrates the preparation of intermediates A2P corresponding to A2-11. Readily available aminonitriles 217 are reacted with substituted acid chlorides 218 in the presence of base, affording intermediate N-acyl aminonitriles 219.

Cyclization of 219 affords the aminooxazoles 220. Conversion of 220 to the oxazolyl hydrazines 221 or the oxazolyl halides 222 is effected as described above in Scheme 45.

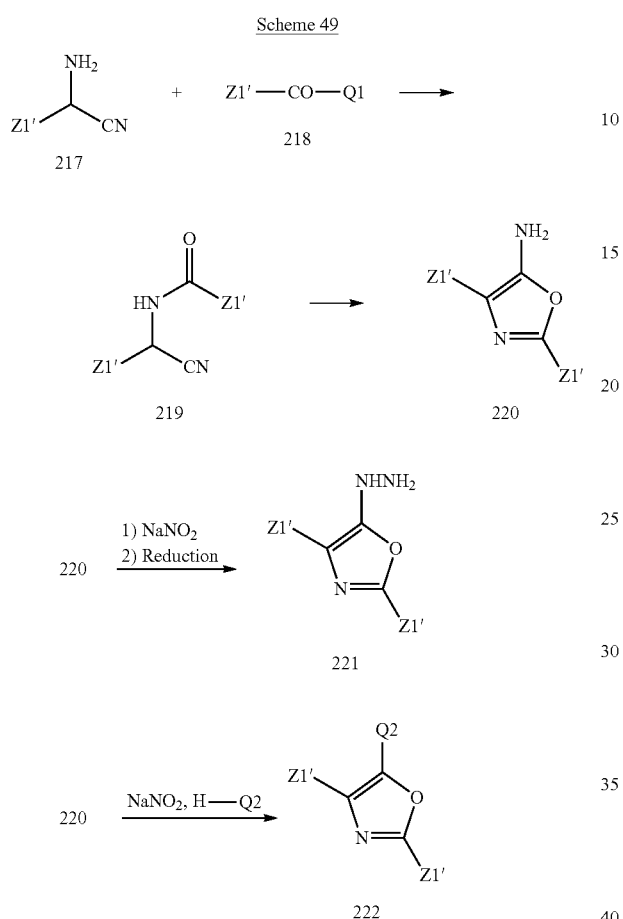

Scheme 50 illustrates the preparation of intermediates A2P corresponding to A2-12. Acyl nitriles 223 are reacted with aldehydes 195 in the presence of ammonium acetate/acetic acid to give the aminooxazoles 224 using conditions reported above in Scheme 46. The aminooxazoles 224 are converted to the hydrazines 225 under standard diazotization/reduction conditions. Alternatively, alpha-amino-beta-ketoesters 226 are acylated to give intermediates 227, which are cyclized to the oxazolyl esters 228 in the presence of a cyclodehydrating reagent such as thionyl chloride, triphenyl phosphine/carbon tetra-chloride, or Burgess reagent. Hydrolysis of esters 228 gives rise to acids 229, which are converted to oxazolyl hydrazines 231 and oxazolyl halides 232 by employing reaction conditions described above in Scheme 47.

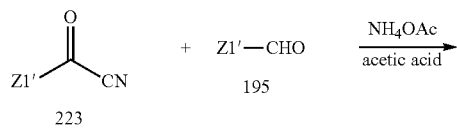

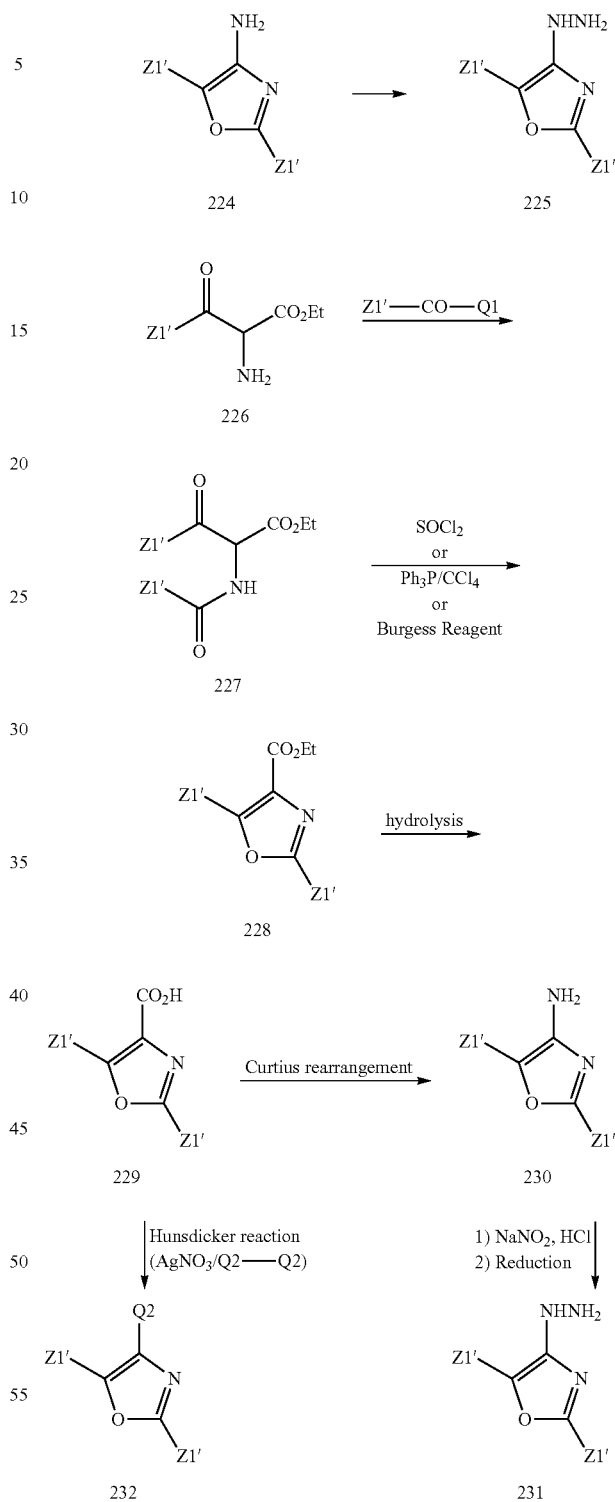

Scheme 51 illustrates the preparation of intermediates A2P corresponding to A2-13. Aminoketones 232 are reacted with cyanamide to afford the aminoimidazoles 233. Conversion of 233 to the corresponding hydrazines 234 and the halides 235 is accomplished by employing reaction conditions described above in Scheme 45.

Scheme 51

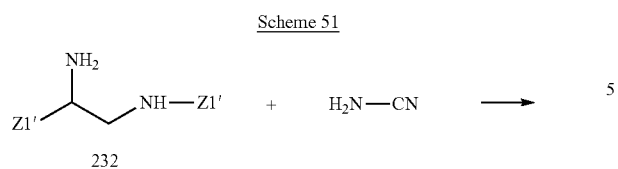

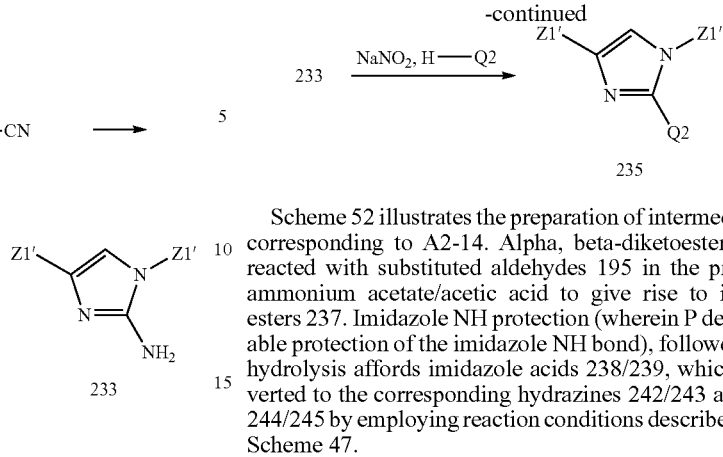

Scheme 52 illustrates the preparation of intermediates A2P corresponding to A2-14. Alpha, beta-diketoesters 236 are reacted with substituted aldehydes 195 in the presence of ammonium acetate/acetic acid to give rise to imidazolyl esters 237. Imidazole NH protection (wherein P denotes suitable protection of the imidazole NH bond), followed by ester hydrolysis affords imidazole acids 238/239, which are converted to the corresponding hydrazines 242/243 and halides 244/245 by employing reaction conditions described above in Scheme 47.

Scheme 52

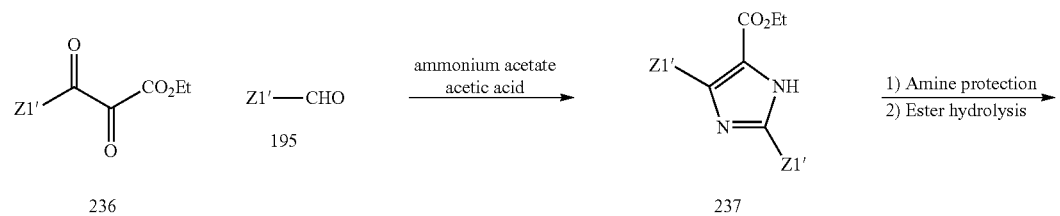

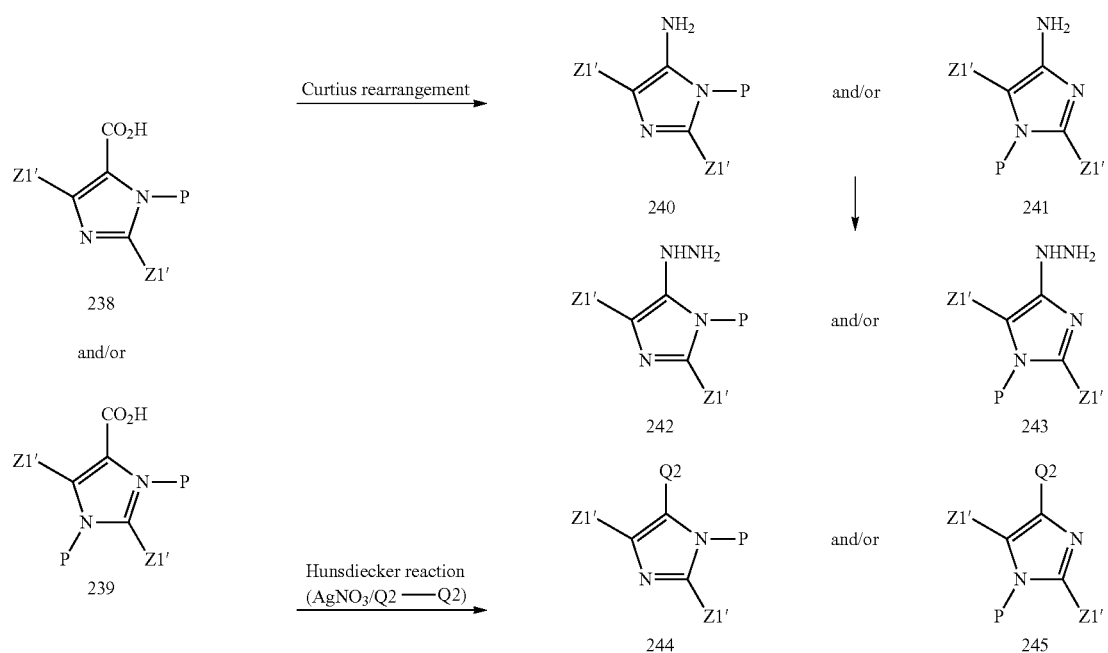

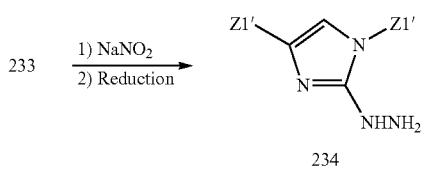

A2-77 V=$H_2$

The synthesis of compounds of Formula I wherein A2 is A2-77 is shown in Scheme 53. Nitration of commercially available tetrahydroisoquinoline (246) by the action of $H_2SO_4$ and $HNO_3$ affords 7-nitrotetrahydroisoquinoline 247 (see WO 03/0999284). Protection of 247 as its trifluoroacetamide yields 248, and conversion of the nitro group to the corresponding hydrazine by (a) reduction of the nitro group, (b) oxidation of the resulting amino group to the diazonium with NaNO$_2$, and (c) reduction of the diazonium with SnCl$_2$ or FeCl$_3$ yields 249, which corresponds to the protected form of intermediate A2-77 containing hydrazines (V=H$_2$). In the case where the corresponding halide is required, conversion of the amine 248 to the diazonium salt, and Sandmeyer displacement with CuI and KI$_3$ iodine (see Harrington and Hegedus, J. Org. Chem. 1984, 49(15), 2657-2662) results in iodide 250.

A2-78 V1=O, V2=H.

The synthesis of intermediates containing A2-78 (V1=O, V2=H$_2$) is shown in Scheme 55. Commercially available phenethylamine 256 is converted to the carbamate 257, and then cyclized utilizing polyphosphoric acid (PPA) to give the tetrahydroisoquinolone 258. 258 is nitrated under standard conditions to give 259, which is either converted to hydrazine 260 or iodide 261 using methodology outlined in Scheme 53.

Scheme 53

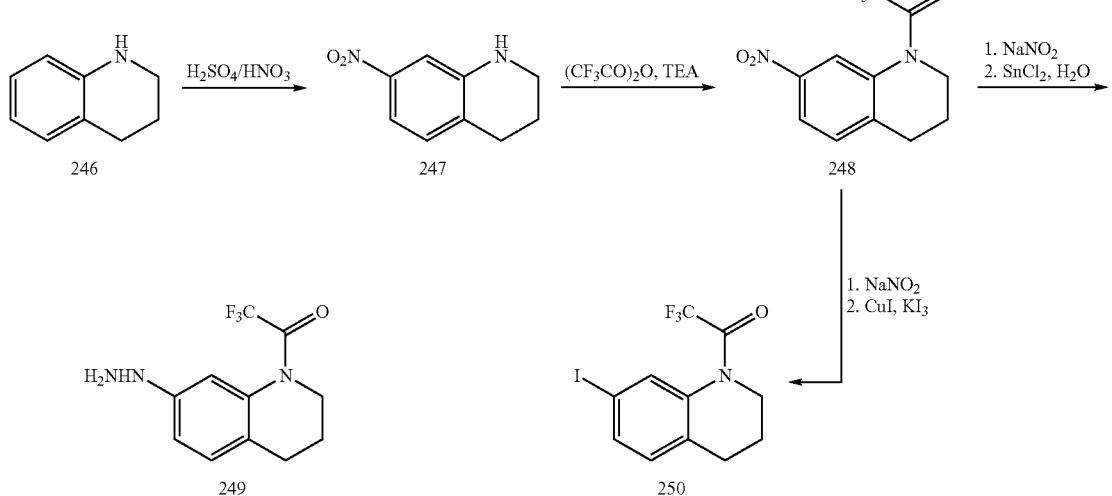

A2-77 V=O

Synthesis of intermediates containing A2-77 (V=O) is shown in Scheme 54. Utilizing the procedure published by Doherty et. al (see WO 03/0999284), Wittig homologation of commercially available 2,4-dinitrobenzaldehyde (251) with ethyl (triphenylphosphoranylidene)-acetate results in propenoate 252. Catalytic hydrogenation in the presence of glacial acetic acid and ethanol results in the target 1H-quinolin-2-one 253 which, utilizing the same oxidation/reduction sequence as shown in Scheme 53 results in hydrazine 254 (R15, V=O) and iodide (255). At the conclusion of the synthesis that utilizes 254 or 255, reduction of the amide with LAH under standard conditions provides an optional synthesis of intermediates containing A2-77 (V=H$_2$).

Scheme 54

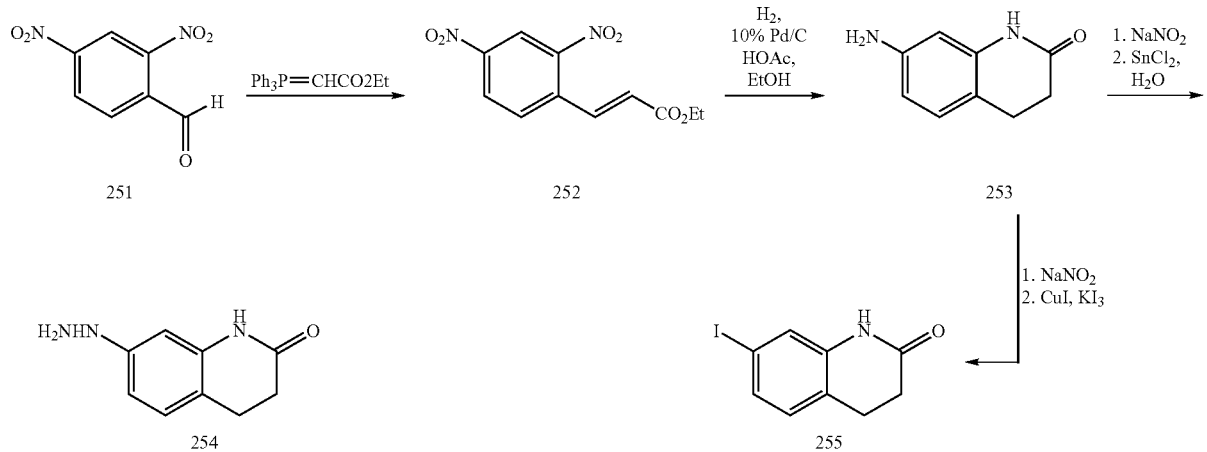

Scheme 55

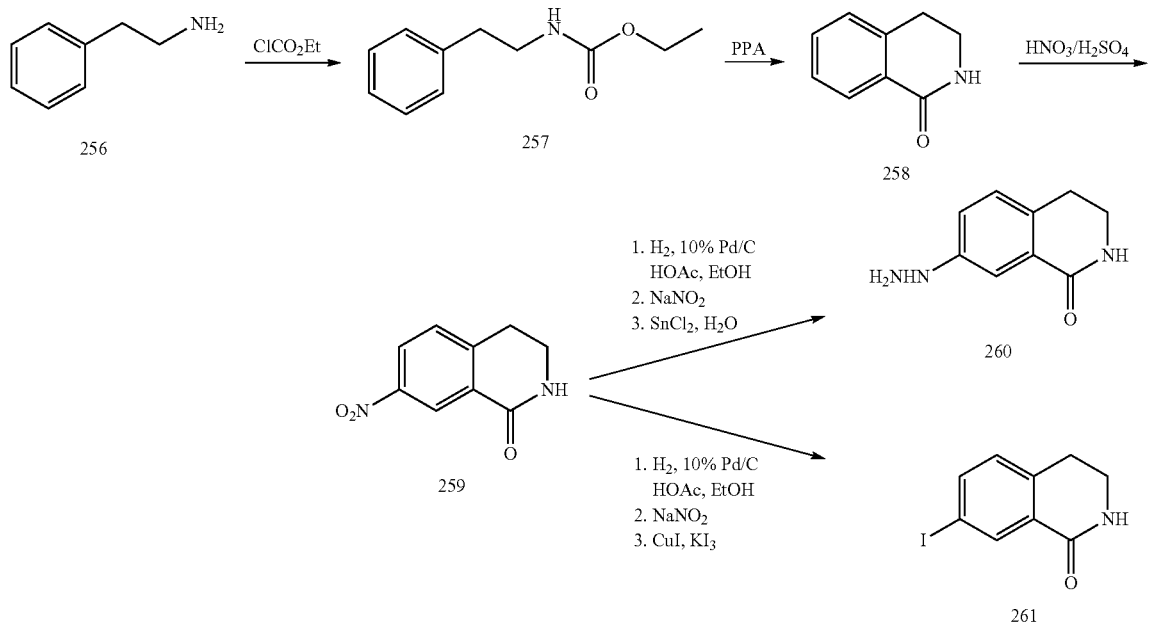

A2-78 V1 and V2=H₂

The synthesis of intermediates containing A2-78, wherein V1 and V2 are H₂, is shown in Scheme 56. Reduction of 259 with LAH affords the amino-substituted tetra-hydroisoquinoline which is selectively protected at the ring nitrogen by reaction with trifluoroacetic anhydride and base, preferably triethylamine. Aniline 262 is then converted into the hydrazine 263 or the iodide 264 using methodology outlined in Scheme 54.

Scheme 56

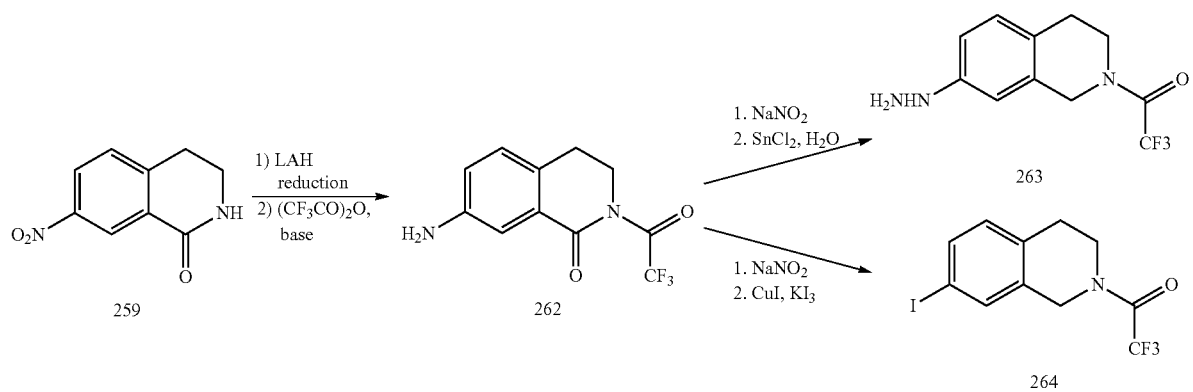

A2-77 and A2-98 V=H₂

The preparation of intermediates containing A2-77 and A2-98 wherein V is H₂ is illustrated in Scheme 57. In these schemes, R7 is a suitable moiety that conforms to the generic definition of Z4 or a protected form of such moiety. Compounds 267 and 268 are prepared by reductive alkylation of 265 or 266 with an appropriate aldehyde and sodium triacetoxyborohydride as the reducing agent. 269 and 270 are synthesized from 265 or 266 by simple amide formation using an acid chloride and base, preferably triethylamine or pyridine. 271 and 272 are synthesized by amidine or guanidine formation utilizing a thioamide or a thiourea, respectively. Intermediates 273, 274, 279, 280, 285 and 286 are prepared by palladium-catalyzed bromide substitution with benzophenone hydrazone as described by Haddad et al. (*Tetrahedron Lett.* 2002, 43, 2171-2173). 273, 274, 279, 280, 285 and 286 are either directly implemented by reaction with a suitable A1-containing intermediate, or, if required, first hydrolyzed to hydrazines 275, 276, 281, 282, 287 and 288 respectively, under acidic conditions. The bromide functionalities in 267 to 272 are substituted by boronic acid affording 277, 278, 283, 284, 289 and 290, respectively. After suitably protecting the amidine or guanidine substructure, the bromide is transformed into an organometallic species such as a grignard compound, and subsequently reacted with trimethyl borate to afford 277, 278, 283, 284, 289 and 290 after acid hydrolysis. In cases where R7 functionalities prohibit the use of organometallic reagents, the boronic acids are mildly formed from the bromides by utilizing a procedure employing bis(pinacolato)diboron and Pd(dppf).
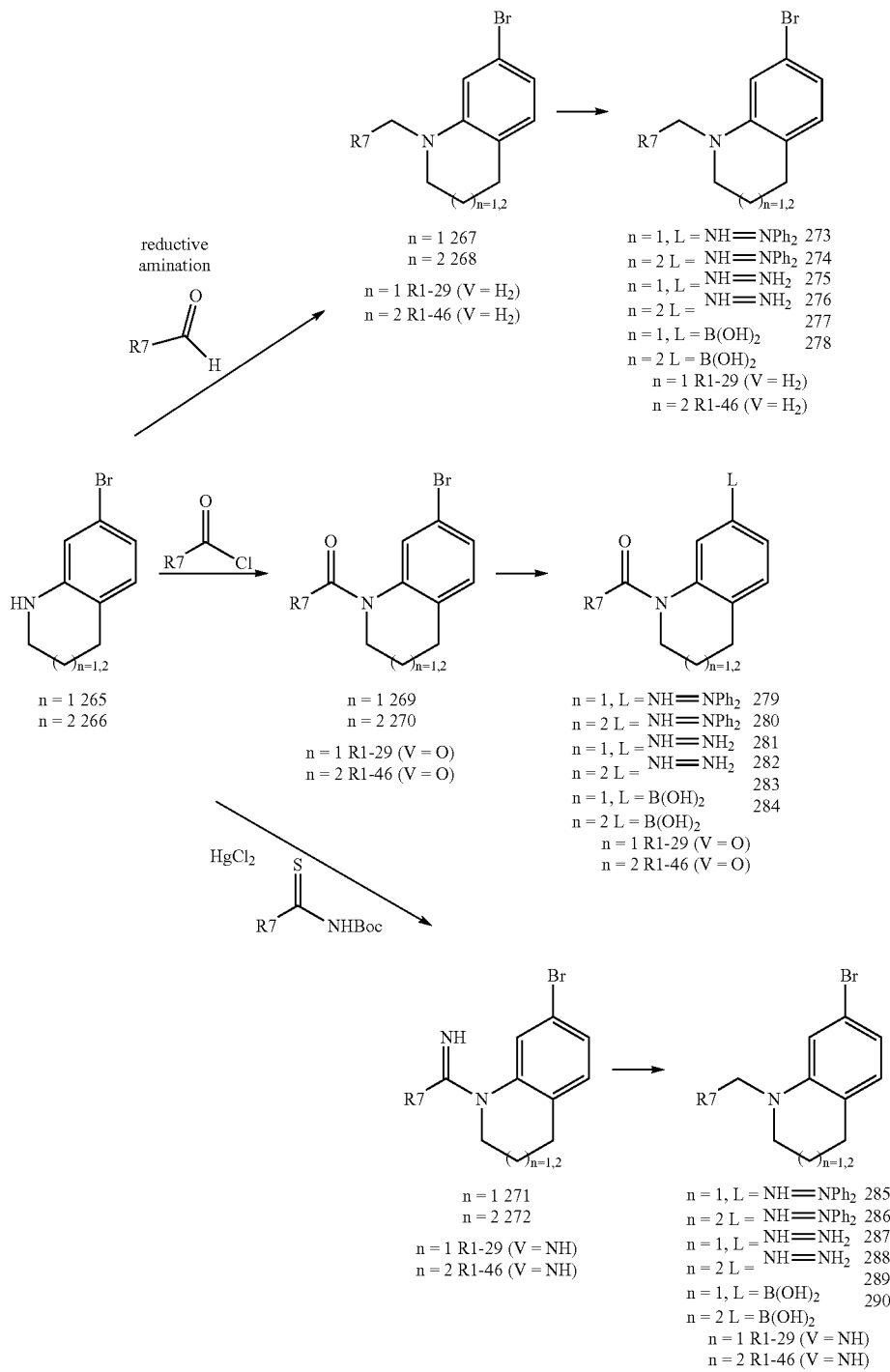
Scheme 57
A2-78 and A2-99, V1 and V2=H.
The preparation of intermediates containing A2-78 or A2-99 wherein V1 and V2 are $H_2$ is illustrated in Scheme 58. 291 and 292 are converted to intermediates 293 to 316 using methods described above in Scheme 57.

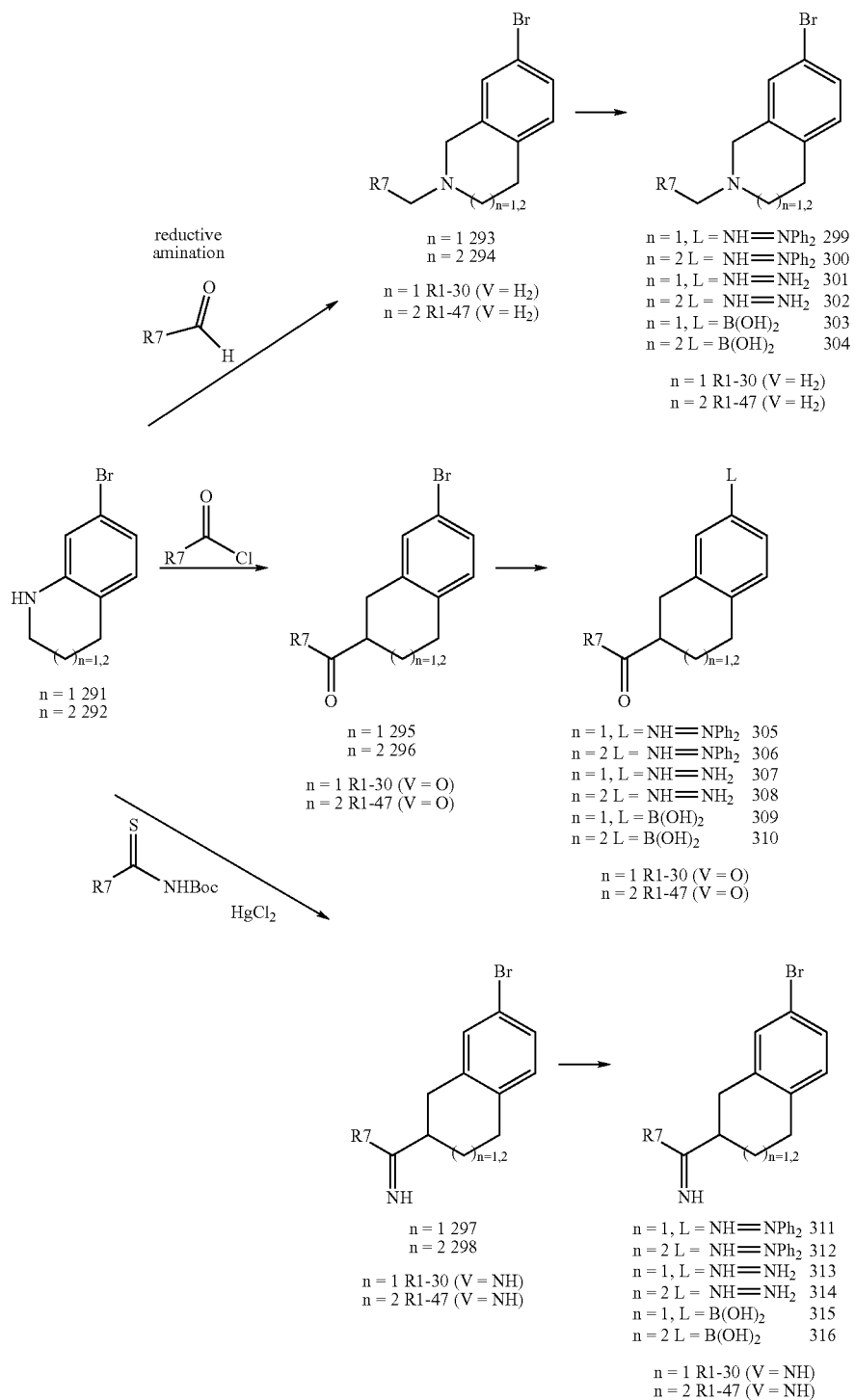

A2-79, V1 and V2=O

The synthesis of intermediates containing A2-79 wherein V1 and V2 are O is shown in Scheme 59. The commercially available starting material 2-chloro-4-nitrobenzoic acid 317 is reacted with dimethyl malonate 318, NaOMe, and catalytic amount of Cu(I) Br to give 319 using conditions described by Quallich, G. J. et al (Quallich, G. J. et al, *J. Org. Chem.* (1998), 63: 4116-4119). The diester 319 is converted into diacid 320 under basic hydrolytic conditions. The diacid 320 is reacted with a primary amine containing a standard amine protecting group (such as benzyl) at about 115° C. to afford the ring closure product 321. Reduction of 321 under catalytic hydrogenation conditions gives 322. The dione 322 is converted into the hydrazine (323), bromide (324) or boronic acid (325) using standard conditions or those conditions described above in Scheme 47.

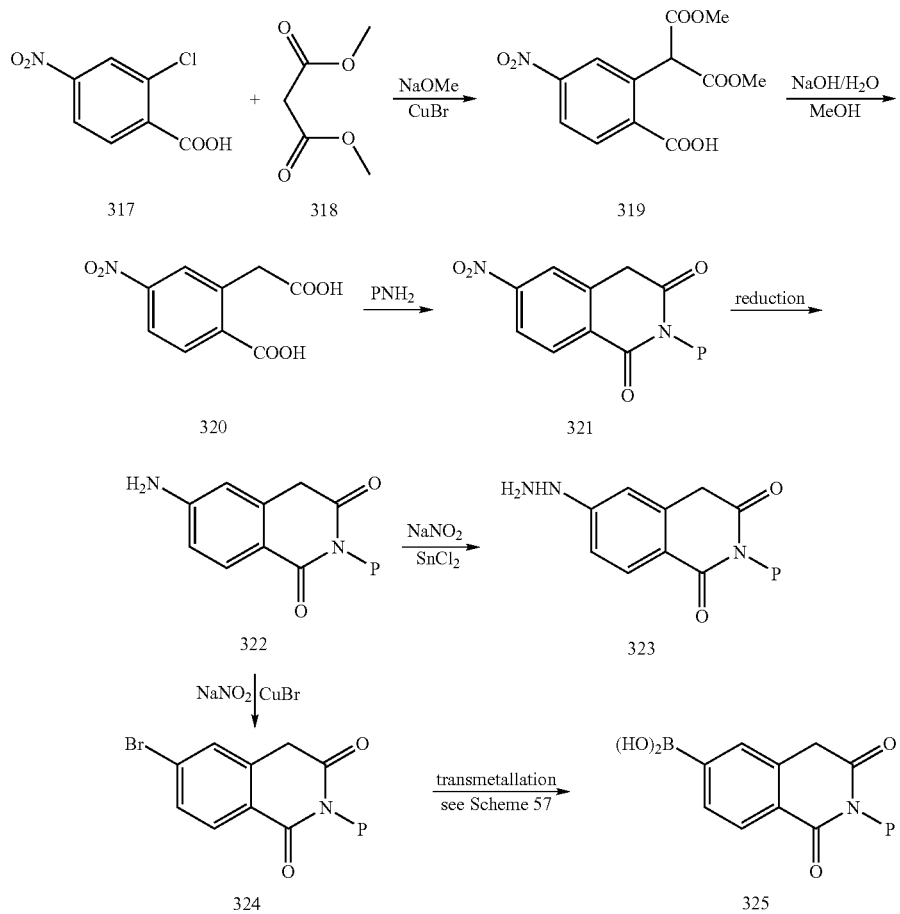

A2-79, V1 and V2=H2

The synthesis of intermediates containing A2-79 wherein V1 and V2 are $H_2$ is shown in Scheme 60. Reduction of 321 (from Scheme 59) with $NaBH_4$ in the presence of $BF_3OEt_2$ yields the tetrahydroisoquinoline 326. Subsequent reduction of the nitro functionality of 326 under catalytic hydrogenation conditions gives 327. Intermediate 327 is converted to the hydrazine 328, bromide 329 or boronic acid 330 using the methodology described in Scheme 59.

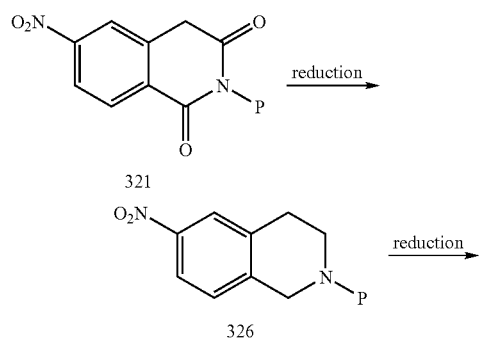

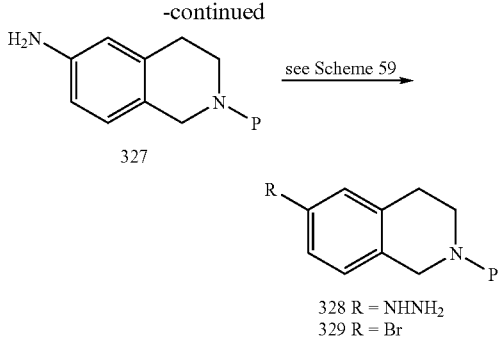

A2-79 V1=O, V2=H

The synthesis of intermediates containing A2-79 wherein V1 is O and V2 is $H_2$ is shown in Scheme 61. The selective reduction of 321 wherein P is a standard amine protecting group (from Scheme 59) with $NaBH_4$ in the presence of TFA gives the lactam 331 (Snow, R. J. et al, *J. Org. Chem.*, (2002), 45:3394-3405). Reduction of the nitro functionality of 331 under catalytic hydrogenation conditions yields amine 332. Intermediate 332 is converted into the hydrazine 333, bromide 334 or boronic acid 335 using the methodology outlined in Scheme 59.

Scheme 61

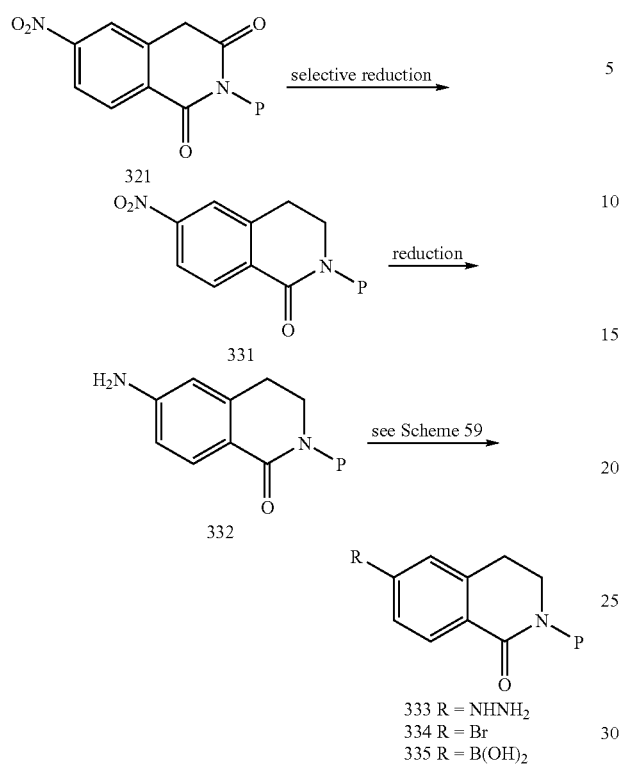

A2-79 V1=O, V2=H

The synthesis of intermediates containing A2-79 wherein V1 is H₂ and V2 is O is shown in Scheme 62, utilizing methods reported by Tamura, Y. et al (*Synthesis* 1981, 534-537). The commercially available starting material 4-nitrobenzylamine 336 is protected with acetyl chloride to yield 337. Intermediate 337 is treated with □-(methylthio)acetyl chloride to give 338. Oxidation of 338 with 3-chloroperbenzoic acid gives the sulfoxide 339. Treatment of sulfoxide 339 with p-TsOH yields the lactam 340. Lactam 340 reacts with Raney Ni to afford the dihydroisoquinolinone 341. Reduction of the nitro functionality of 341 under catalytic hydrogenation conditions yields amine 342. Intermediate 342 is converted into the hydrazine 343, bromide 344 or boronic acid 345 using the methodology outlined in Scheme 59.

Scheme 62

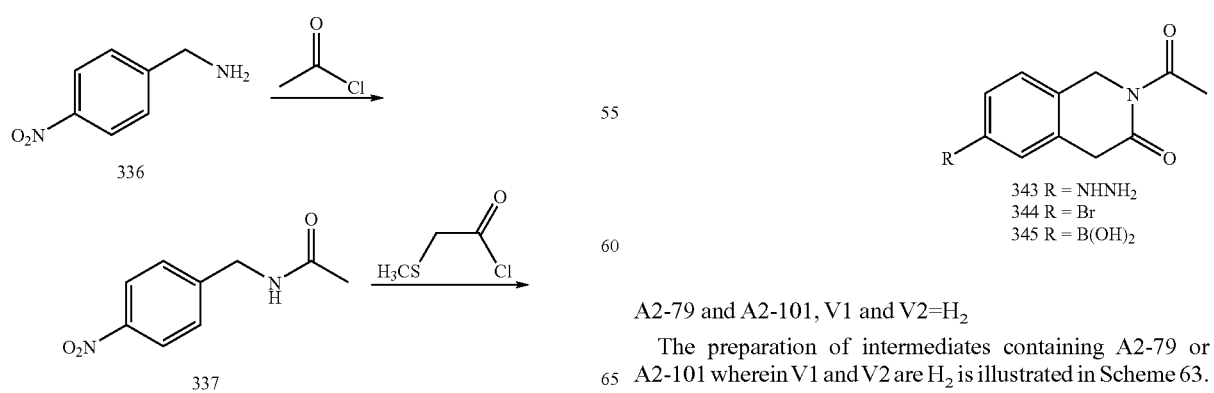

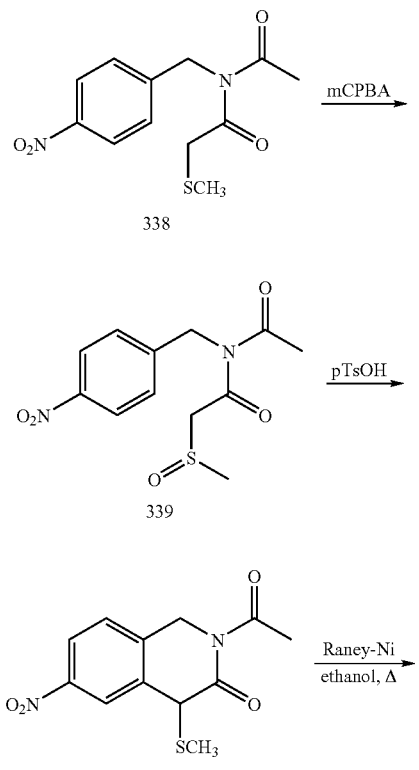

A2-79 and A2-101, V1 and V2=H₂

The preparation of intermediates containing A2-79 or A2-101 wherein V1 and V2 are H₂ is illustrated in Scheme 63. 346 and 347 are converted to intermediates 348 to 371 using methods described above in Scheme 57.

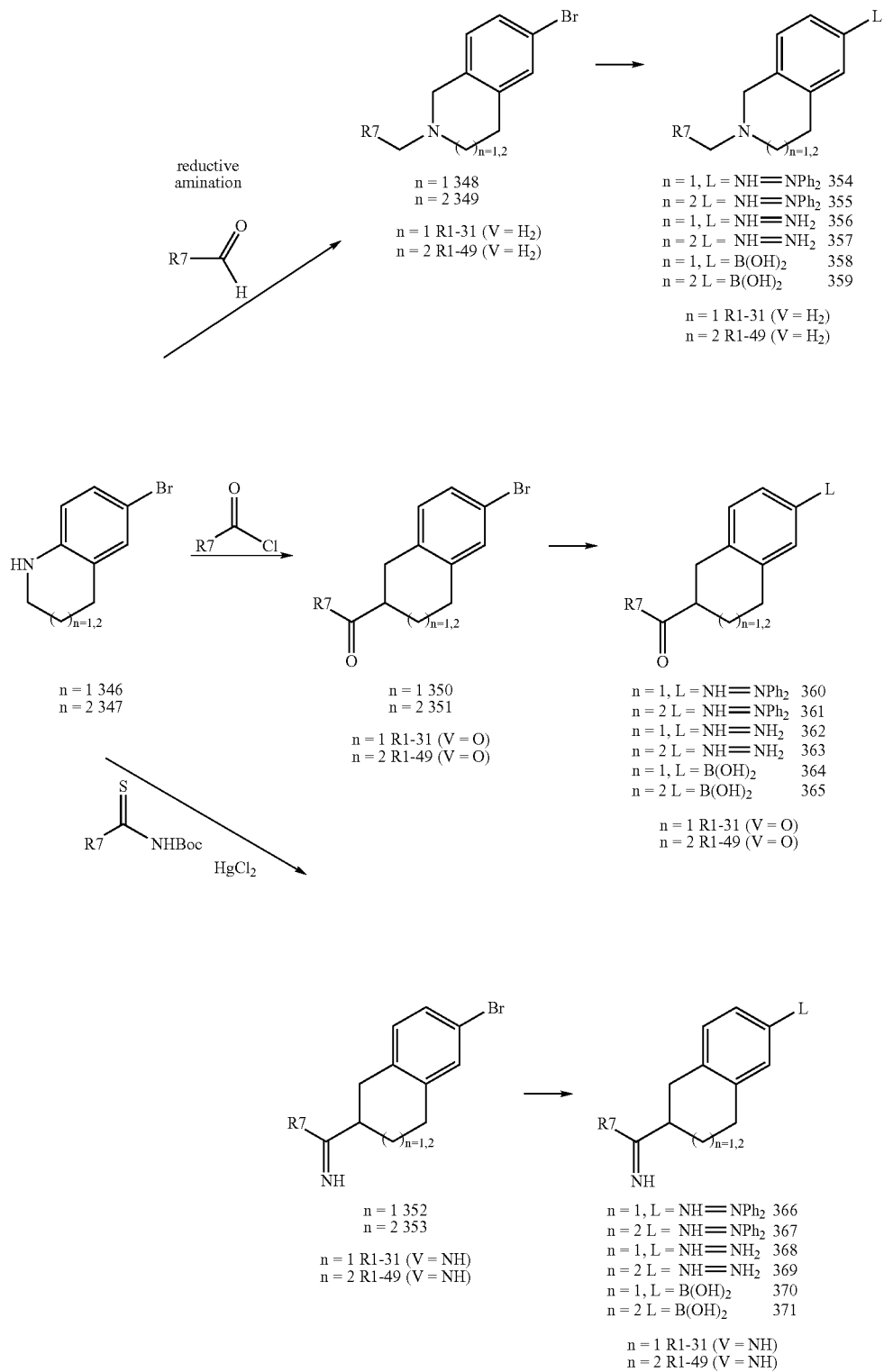
Scheme 63
A2-80 and A2-102 V=$H_2$
The preparation of intermediates containing A2-80 or A2-102 wherein V is $H_2$ is illustrated in Scheme 64. 372 and 373 are converted to intermediates 374 to 397 using methods described above in Scheme 57.

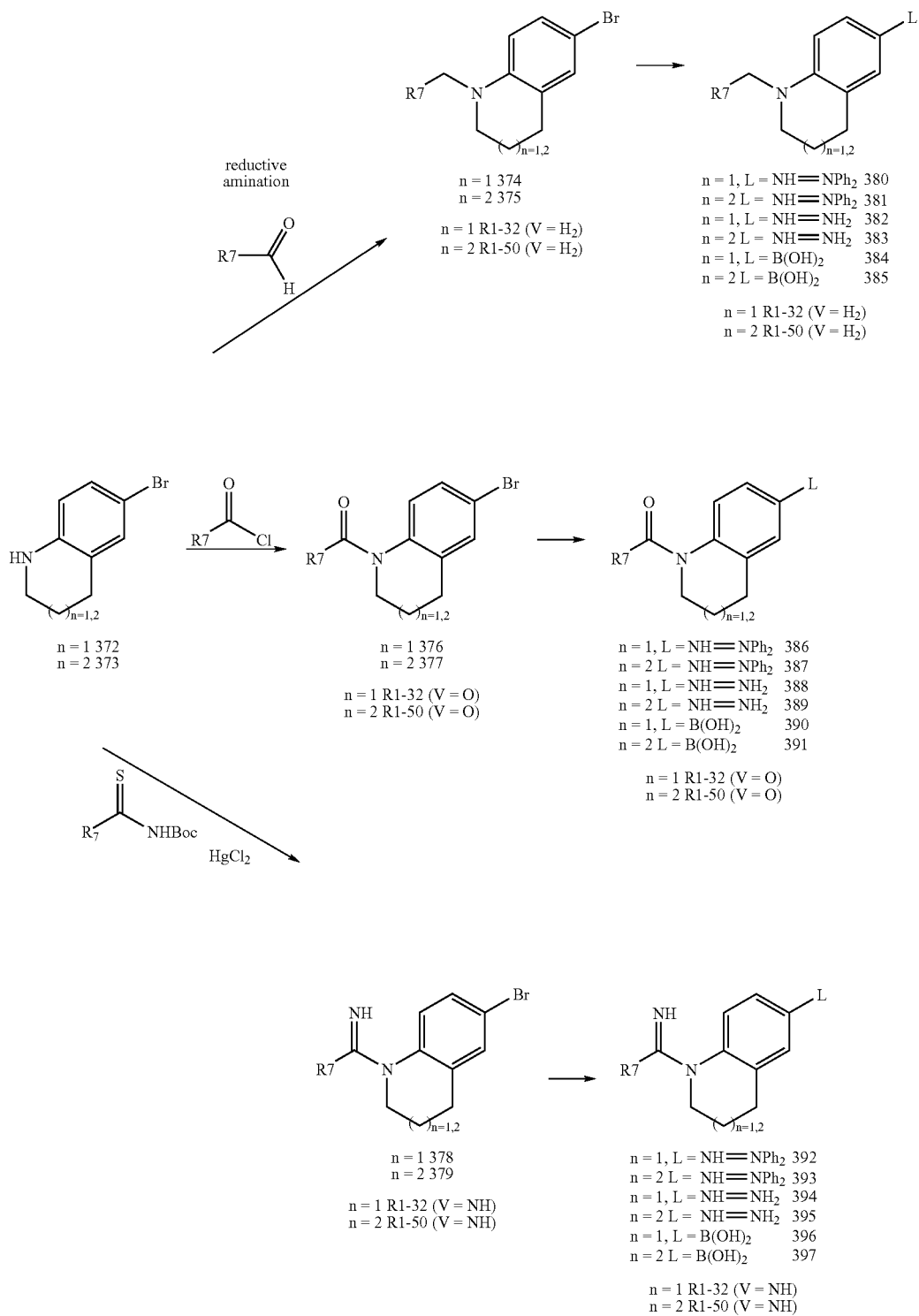

Scheme 64

A2-80 V=O

The synthesis of intermediates containing A2-80 (V=O) is shown in Scheme 65. Acylation of 4-nitroaniline 398, and Friedel-Crafts alkylation by the action of AlCl$_3$ results in 400 (see Zhang et. al Huaxue Yanjiu Yu Yingyong, 2002, 14(5), 618-619; Zhang et. al Huaxue Yanjiu Yu Yingyong, 2003, 17(5), 534-529). Elaboration of the nitro group in 400 to the hydrazine 401 (R18, V=O) and the iodide 402 (R18, V=O) proceeds under the same conditions outlined in Schemes 53 and 54. At the conclusion of the synthesis that utilizes 401 or 402, reduction of the amide with LAH under standard conditions yields intermediates A2-80 (V=H$_2$).

Scheme 65

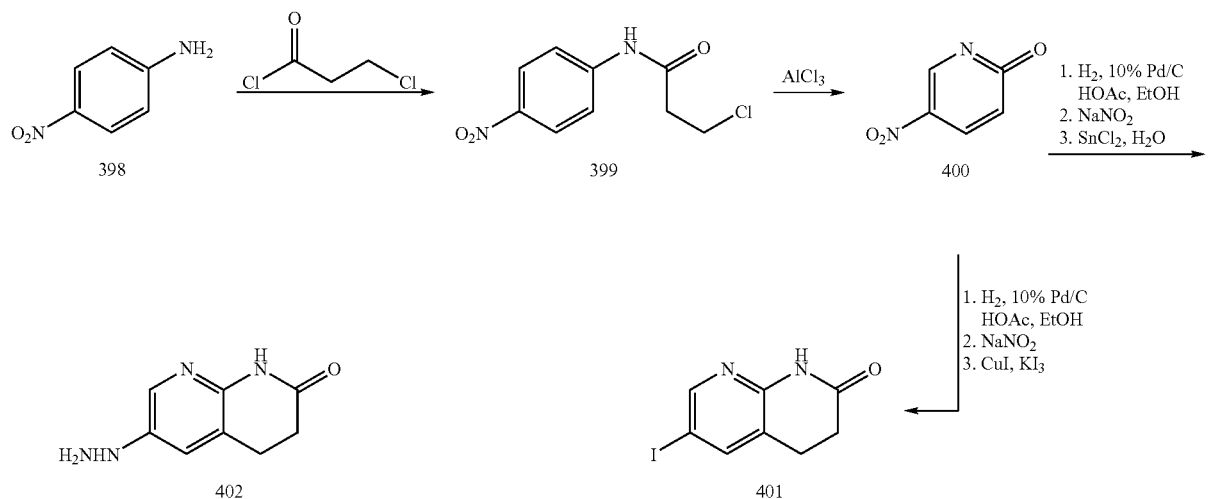

Alternatively, 400 can be reduced with LAH to yield 403 and subsequently protected as the trifluoroacetamide (404, which is converted to the hydrazine (405, R18, V=H2) or iodide (46, R18, V=H2) (Scheme 66) using the same methodology outlined in Scheme 53.

Structures 415 and 416 can be obtained when the bromide is reacted with benzophenone hydrazone under palladium catalysis as described by Haddad et al. (*Tetrahedron Lett.* 2002, 43, 2171-2173). 415 and 416 can either be directly implemented for reaction with a suitable A1 intermediate or,

Scheme 66

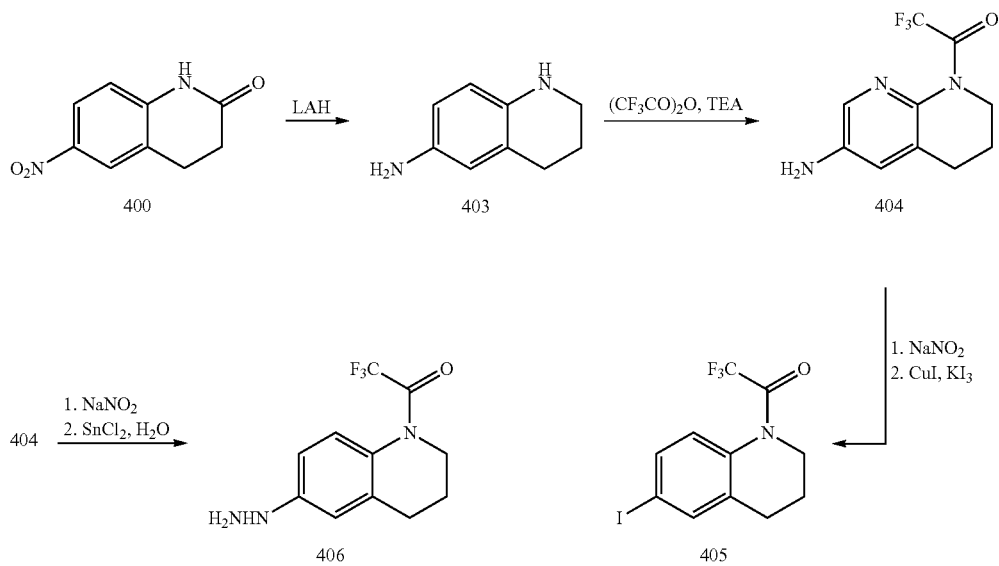

A2-81 and A2-103

The preparation of intermediates containing A2-81 and A2-103 is illustrated in Scheme 67. 407 and 408 (see Scheme 54) are activated either by transformation into the corresponding thiolactams 409 and 410 using Lawesson's reagent in dioxane or by transformation into imino ester 411 and 412 using trimethyloxonium tetrafluorborate. The displacement reaction with a primary amine (if one R4 is H) or a secondary amine affords amidines 413 and 414 when heated in a suitable solvent such as methanol or dioxane. From the thiolactam, displacement is supported by addition of mercury chloride.

if required, first hydrolyzed to hydrazines 417 and 418 under acidic conditions. The bromide in 413 and 414 can be substituted by a boronic acid affording 419 and 420. After suitably protecting the amidine substructure, the bromide is transformed into an organometallic species such as a grignard compound and subsequently reacted with trimethyl borate to afford 419 and 420 after acid hydrolysis. In cases where R4 or R5 prohibits the use of organometallic reagents, the boronic acid can be mildly introduced with bis(pinacolato)diboron and Pd(dppf).

Scheme 67
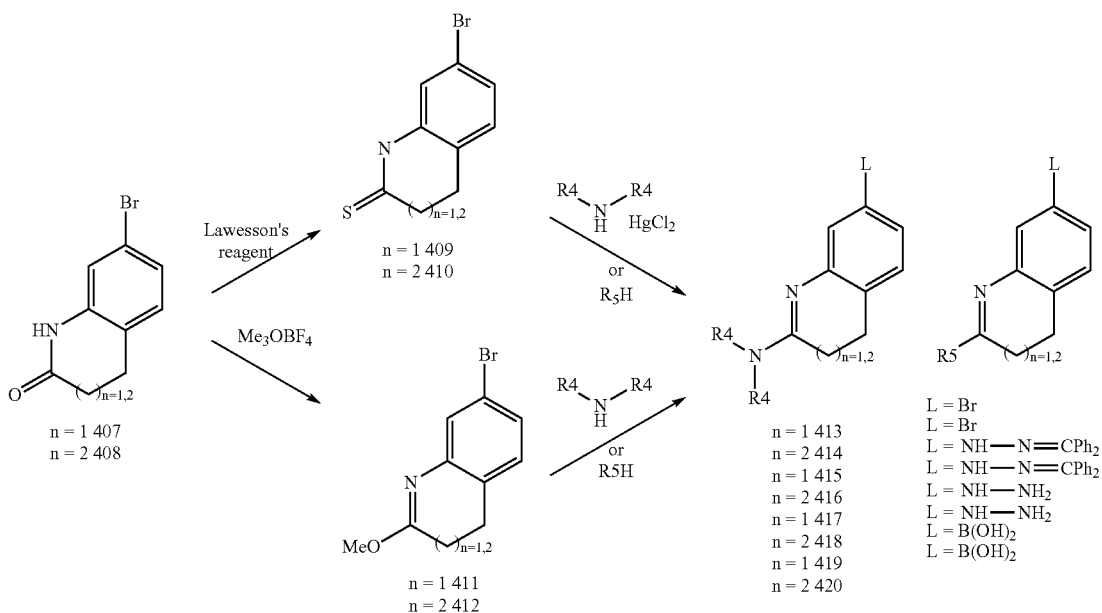
A2-82 and A2-104
The preparation of intermediates containing A2-82 or A2-104 is illustrated in Scheme 68. 421 and 422 (Scheme 55) are converted to intermediates 423 to 434 utilizing the methods described above in Scheme 67.
Scheme 68
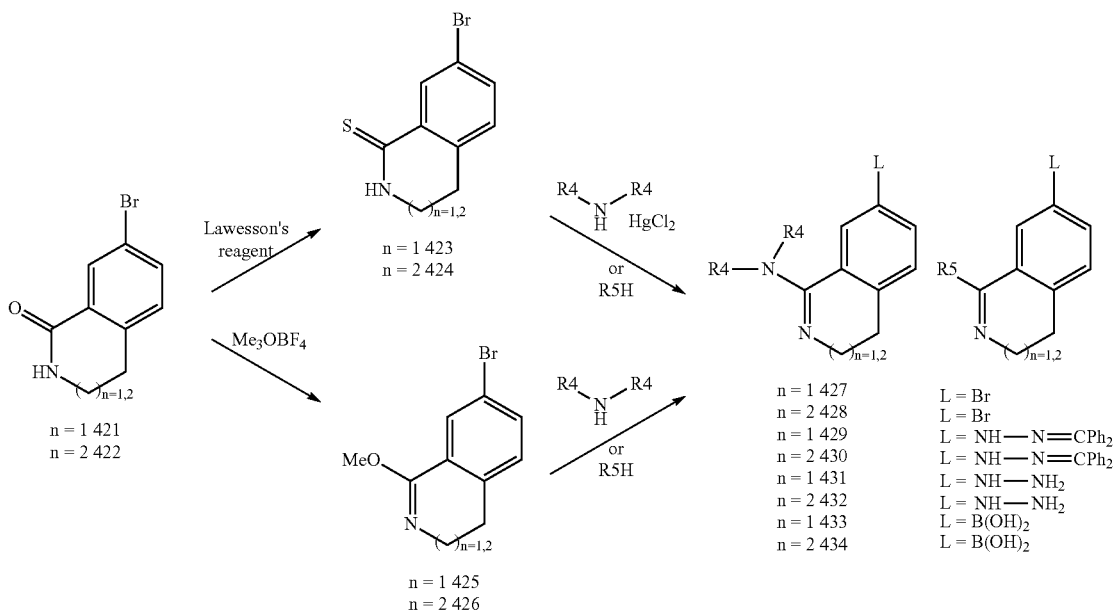
A2-83 and A2-105
The preparation of intermediates containing A2-83 or A2-105 is illustrated in Scheme 69. 435 and 436 are converted into intermediates 437 to 448 using methods described above in Scheme 67.

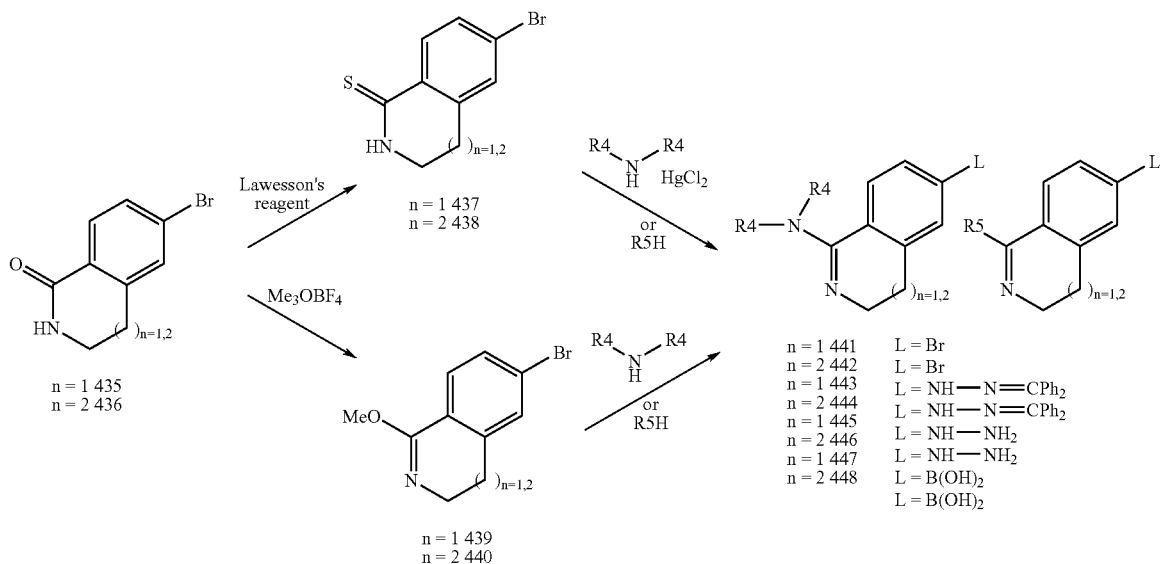

Scheme 69

A2-84 and A2-106

The preparation of intermediates containing A2-84 or A2-106 is illustrated in Scheme 70. 449 and 450 are converted into intermediates 451 to 462 using methods described above in Scheme 67.

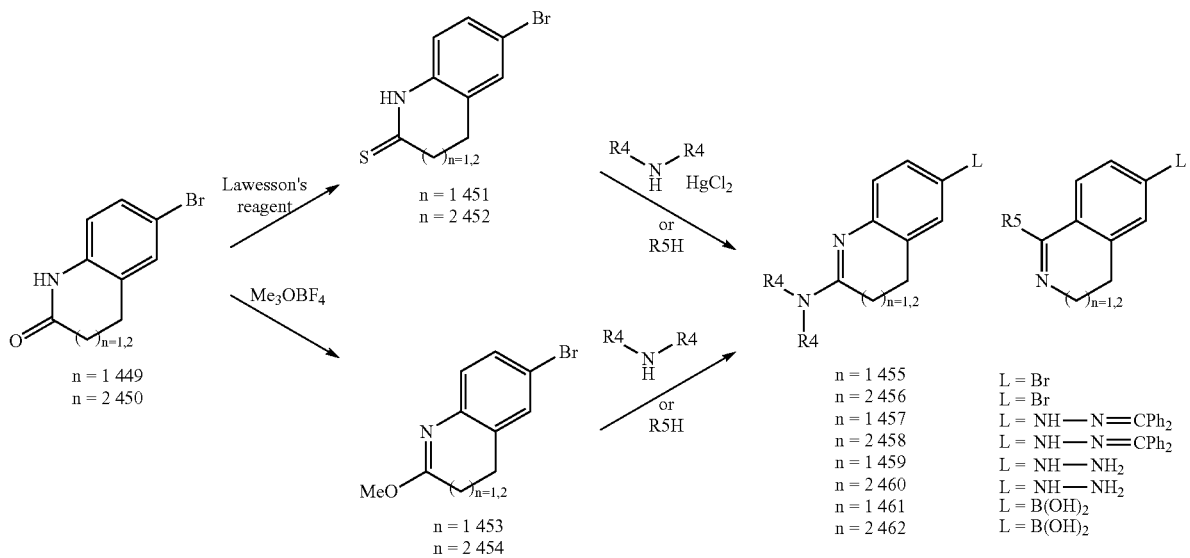

Scheme 70

A2-85 and A2-86

The preparation of intermediates containing A2-85 or Ar-86 is illustrated in Scheme 71. 463 (1,2,3,4-tetrahydroisoquinoline-3-carboxylic acid) is commercially available in each enantiomeric form and as a racemic mixture. Nitration of 463 with sulfuric acid and potassium nitrate gives a mixture of 6- and 7-nitrated compounds 464 and 465. According to the literature (*Bioorg. Med. Chem. Lett.* 2002, 10, 3529-3544), these compounds are separated from each other by derivative crystallization. N-protection with a standard amine protecting group gives 466 and 467, respectively. Amide formation by reacting 466 or 467 with amines HN(R4)$_2$ or HR5 (fix scheme 71) by employing an acid-activating reagent, preferably EDCI/HOBt in the presence of base, preferably triethylamine, afford amides 468. 469, 480 and 481. Deprotection of the amine protecting group gives rise to nitro compounds 470, 471, 482 and 483. The bromides 472, 473, 484 and 485 are obtained by hydrogenation of the nitro group and subsequent Sandmeyer reaction via a diazotization/CuBr reaction sequence. 474, 475, 486 and 487 are prepared by palladium-catalyzed bromide substitution with benzophenone hydrazone as described by Haddad et al. (*Tetrahedron Lett.* 2002, 43, 2171-2173). 474, 475, 486 and 487 are either directly implemented by reaction with a suitable A1-containing intermediate, or, if required, first hydrolyzed to hydrazines 476, 477, 488 and 489, respectively, under acidic conditions. The bromide functionalities in 470, 471, 482 and 483 are substituted by a boronic acid affording 478, 479, 490 and 491. The bromide is transformed into an organometallic species such as a grignard compound and subsequently reacted with trimethyl borate to afford 478, 479, 490 and 491 after acid hydrolysis. In cases where R4 or R5 functionalities prohibit the use of organometallic reagents, the boronic acids are mildly formed from the bromides by utilizing a procedure employing bis(pinacolato)diboron and Pd(dppf).

Scheme 71

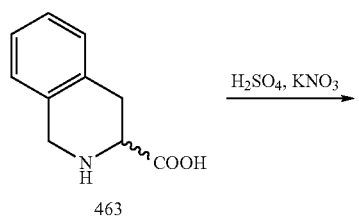

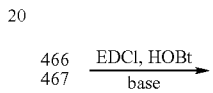

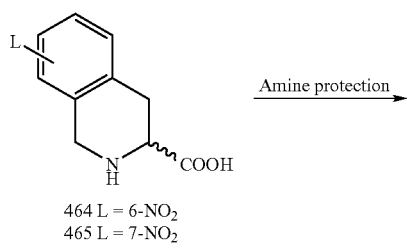

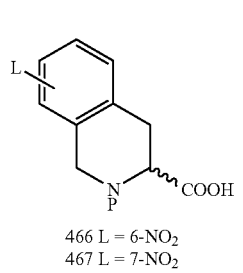

466 L = 6-NO₂
467 L = 7-NO₂

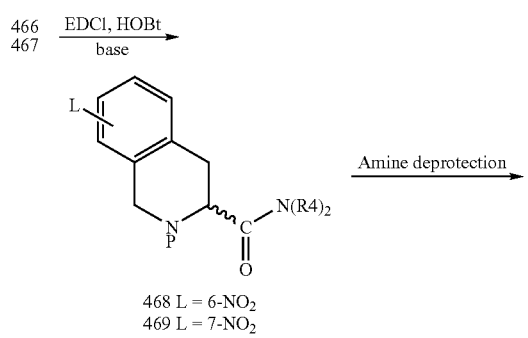

468 L = 6-NO₂
469 L = 7-NO₂

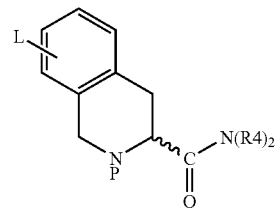

470 L = 6-NO₂
471 L = 7-NO₂
472 L = 6-Br
473 L = 7-Br
474 L = 6-NH=NPh₂
475 L = 7-NH=NPh₂
476 L = 6-NH=NH₂
477 L = 7-NH=NH₂
478 L = B(OH)₂
479 L = B(OH)₂

466  EDCl, HOBt
467  —————→
       base

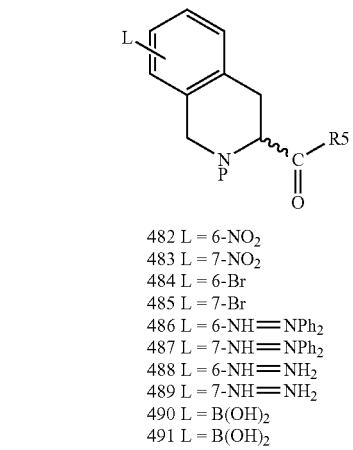

480 L = 6-NO₂
481 L = 7-NO₂

482 L = 6-NO₂
483 L = 7-NO₂
484 L = 6-Br
485 L = 7-Br
486 L = 6-NH=NPh₂
487 L = 7-NH=NPh₂
488 L = 6-NH=NH₂
489 L = 7-NH=NH₂
490 L = B(OH)₂
491 L = B(OH)₂

A2-95

The synthesis of intermediates containing A2-95 is illustrated in Scheme 72. Commercially available substituted benzoic acid 492 is optionally subjected to a reductive amination reaction employing readily available aldehydes R30-CHO and sodium triacetoxyborohydride to give 493. Reduction of the nitro functionalities of 492 or 493 afford the amines 494 and 499. Conversion of 494 or 499 to the benzotriazoles 495 or 500, respectively, is effected by treatment with NO₃ anion as described in WO 04/041274. Conversion of 495 or 500 to substituted amines 496 or 501, hydrazines 497 or 502, or halides 498 or 503 is accomplished using conditions described in Scheme 47.

Scheme 72

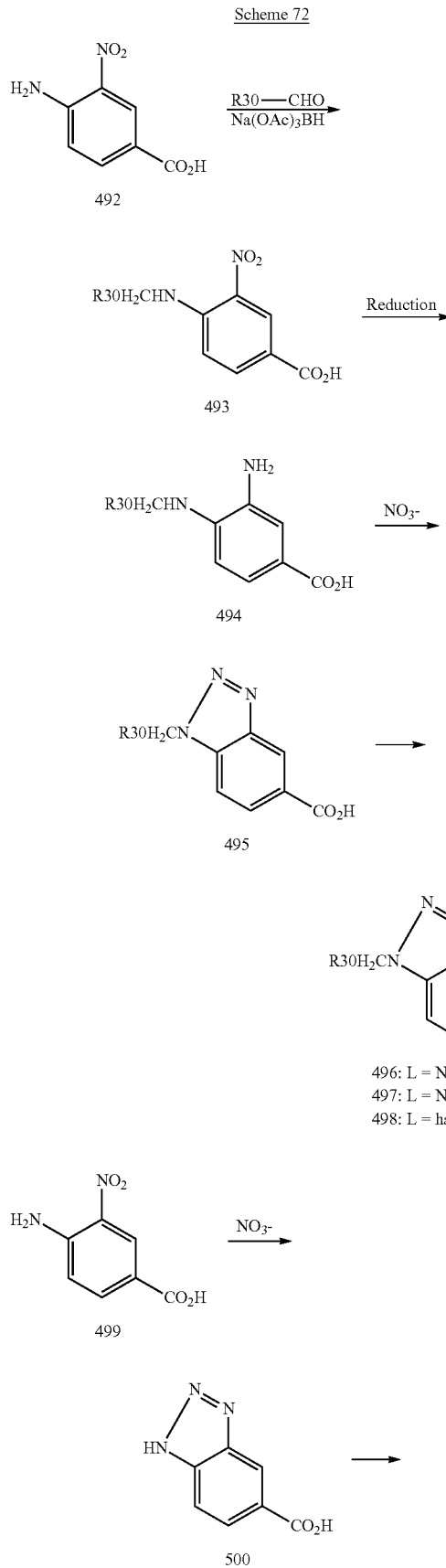

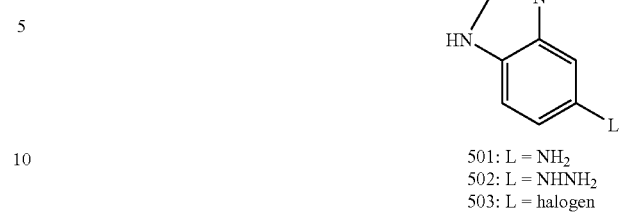

A2-96

The synthesis of intermediates containing A2-96 is illustrated in Scheme 73. Commercially available pyridine diester 504 is reacted with sodium borohydride/calcium chloride to give the selective reduction product 505 (P. Potier et al. *Tetrahedron* 1975, 31, 419-422). Oxidation of the alcohol functionality of 505, preferably with $MnO_2$, gives aldehyde 506. Oxime formation, followed by reduction with zinc/acetic acid, gives pyridinemethanamine 507 (M. Ohta et al. *Chem. Pharm. Bull.* 1996, 44 (5), 991-999). Intermediate 507 is converted to its formamide 508, which is subjected to cyclodehydration with $POCl_3$ to give the imidazopyridine ester 509 (Q. Li et al. *Bioorg. Med. Chem. Lett.* (2002) 12, 465-469). Hydrolysis of the ester 509 affords acid 510. Acid 510 is converted to the amine 511, hydrazine 512, or halide 513 using conditions described in Scheme 47.

Scheme 73

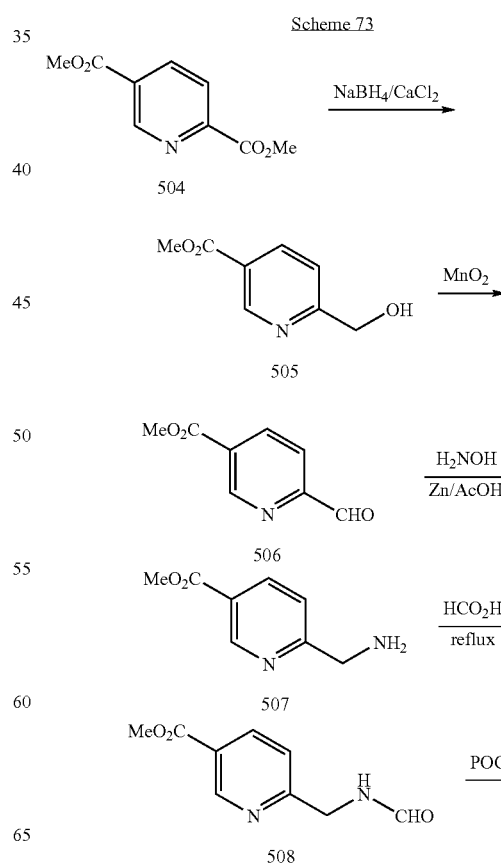

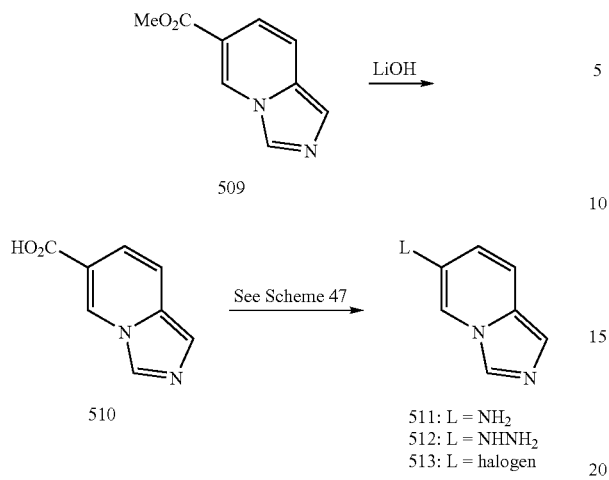

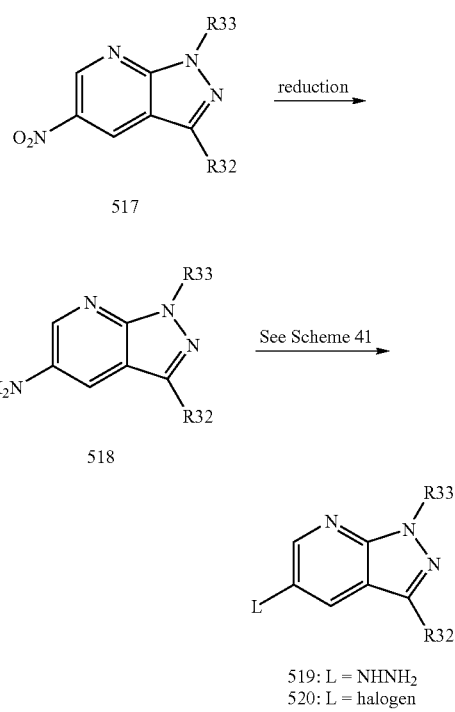

A2-97

The synthesis of intermediates containing A2-97 is illustrated in Scheme 74. Readily available 3-acylpyridines 514, wherein R32 is a substituent which conforms to the definition of a protected or unprotected Z1 moiety, are converted to the 2-chloropyridines 515 as reported in *Can. J. Chem.* (1988) 66: 420-428. Displacement of the chloro substituent in 515 with various hydrazines, wherein R33 conforms to the definition of a protected or unprotected Z4 moiety, followed by in situ cyclization, gives pyrazolylpyridines 516. Nitration of 516 under standard conditions gives 517, which are subjected to reduction to afford the amino-substituted pyrazolylpyridines 518. Conversion of 518 to hydrazines 519 or halides 520 is effected as described in Scheme 41.

A2-98, V=O

Scheme 75 illustrates the preparation of intermediates containing A2-98 wherein V is O. The commercially available starting material 7-nitro-3,4-dihydronaphthalen-1(2H)-one 521 is reacted with hydroxylamine, followed by PCl5, to give lactam 522. The nitro functionality of 522 is reduced under catalytic hydrogenation conditions to afford amine 523. The aminobenzoazepinone 523 is converted into the hydrazine 524, bromide 525 or boronic acid 526 as described in Scheme 59.

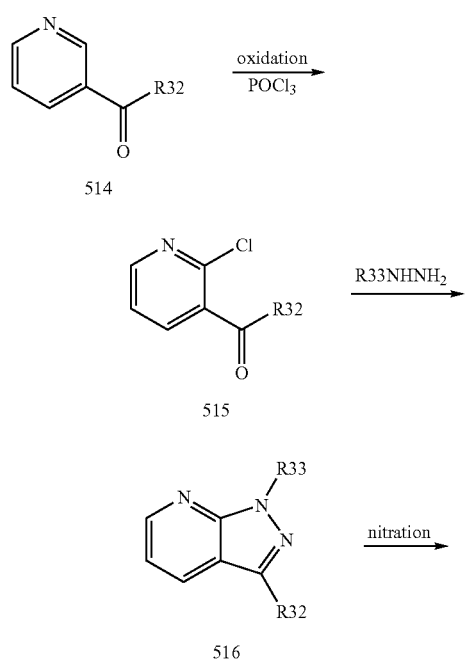

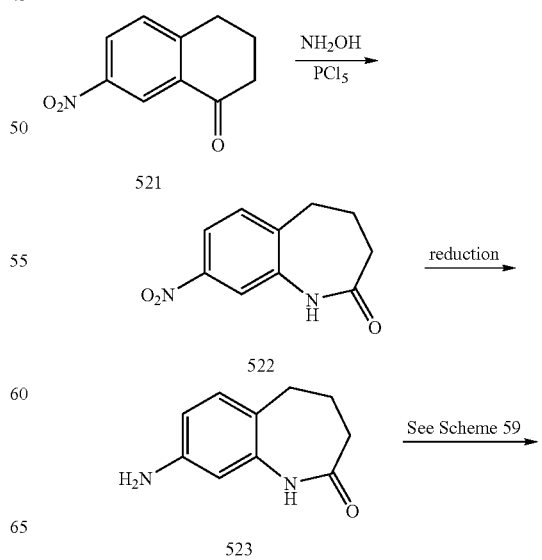

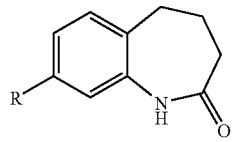

524 R = NHNH$_2$
525 R = Br
526 R = B(OH)$_2$

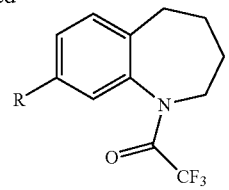

530 R = NHNH$_2$
531 R = Br
532 R = B(OH)$_2$

A2-98, V=H$_2$

The synthesis of intermediates containing A2-98 wherein V is H$_2$ is shown in Scheme 76. 522 (from Scheme 75) is reduced, preferably with diborane, borane.THF, or borane.Me$_2$S, to yield 527, which is subsequently protected as the trifluoroacetamide (528) by reaction with trifluoroacetic anhydride in the presence of base, preferably triethylamine (TEA). Reduction of the nitro functionality of 528 under catalytic hydrogenation conditions affords amine 529, which is converted into the hydrazine 530, bromide 531 and/or boronic acid 532 using the methodology described in Scheme 59.

A2-99, V1 and V2=O

Scheme 77 illustrates the preparation of intermediates containing A2-99 wherein V1 and V2 are O. The commercially available starting material 2-(2-carboxyethyl)benzoic acid 533 is reacted with fuming nitric acid to give the nitrobenzoic acid 534. The nitrobenzoic acid 534 is treated with trifluoroacetamide in the presence of HOBt and EDCI to give the cyclic imide 535 (Nazar, F. et al, *Tetrahedron Lett.*, (1999), 40: 3697-3698). The by-products and excess of reagents can be removed by using a mixed bed sulfonic acid-substituted resin and a tertiary amine-substituted resin (Flynn, D. L. et al, *J. Am. Chem. Soc.*, (1997), 119: 4874-4881). Reduction of the nitro functionality of 535 under catalytic hydrogenation conditions affords the amine-substituted benzazepinedione 536 (Snow, R. J. et al, *J. Org. Chem.*, (2002), 45: 3394-3405). The benzazepinedione 536 is converted into the hydrazine 537, bromide 538, or boronic acid 539 using the methodology described in Scheme 59.

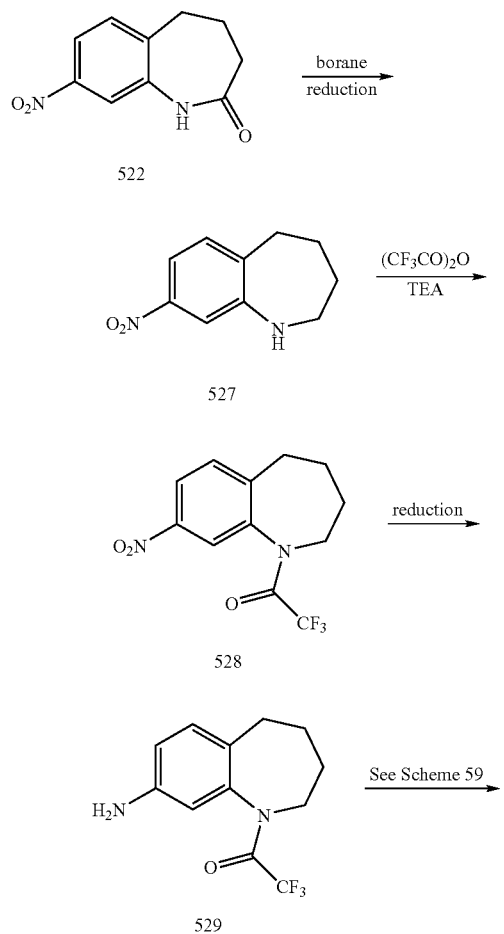

Scheme 76

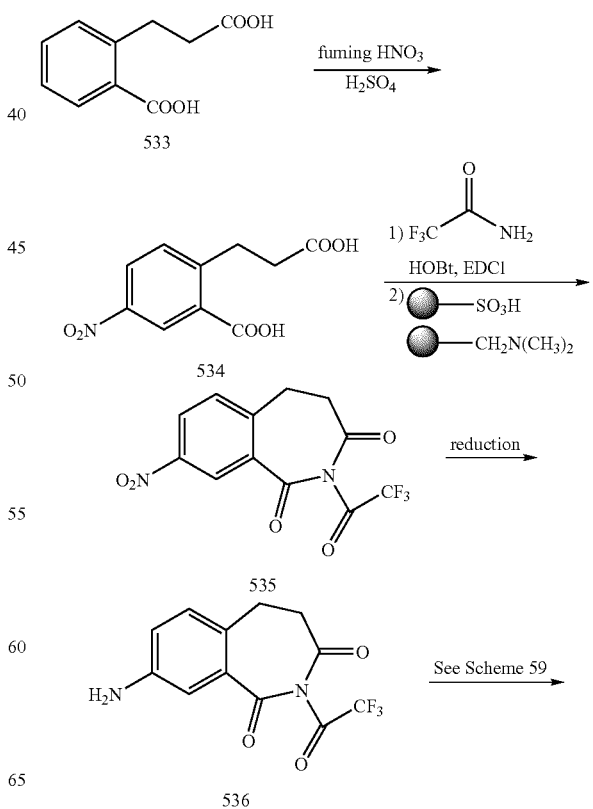

Scheme 77

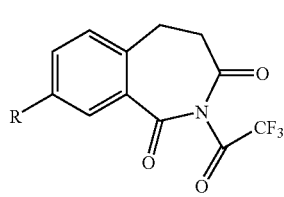

537 R = NHNH$_2$
538 R = Br
539 R = B(OH)$_2$

An alternative synthesis of intermediates containing A2-99 wherein V1 and V2 are O is shown in Scheme 78. The commercially available starting material 2-chloro-5-nitrobenzoic acid 540 yields 541 by reaction with vinyl tri-n-butyltin under Stille cross-coupling conditions (Littke, A. F. et al, *Angew. Chem., Int. Ed. Engl.*, (1999), 38: 2411-2413). Intermediate 541 is reacted with thionyl chloride, followed by a primary amine containing a standard amine protecting group (such as benzylamine) to obtain the amide 542. Reaction of 542 with acrylic acid in the presence of an acid-activating reagent, such as EDCI/HOBt in the presence of base, preferably triethylamine (TEA), affords the diene 543. A Ring Closing Metathesis (RCM) reaction of 543 utilizing Grubbs' catalyst gives the benzazepinedione 544. Reduction of 544 under catalytic hydrogenation conditions produces 545 (Knobloch, K. et al, *European J. of Org. Chem.*, (2001), 17: 3313-3332). Intermediate 545 is converted into the hydrazine 546, bromide 547 or boronic acid 548 as described in Scheme 77. Alternatively, intermediate 544 is selectively reduced at the nitro functionality, preferably with stannous chloride, to afford amine-substituted benzazepinedione 549, wherein the ring C—C bond is unsaturated. Intermediate 549 is converted into the hydrazine 550, bromide 551 or boronic acid 552 as described in Scheme 77.

Scheme 78

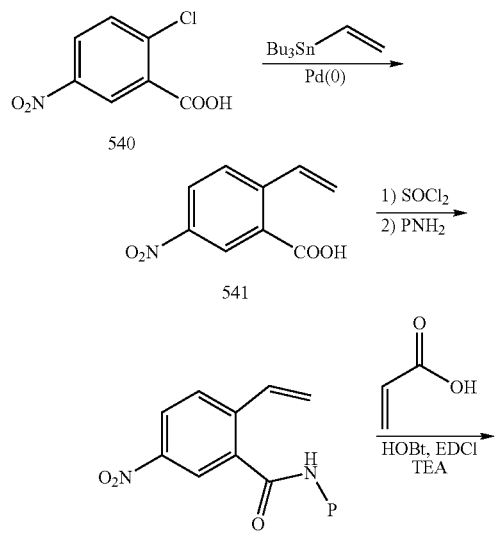

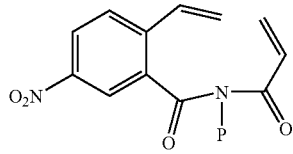

543

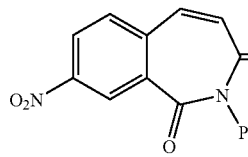

544

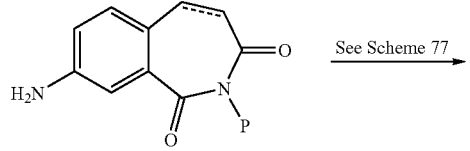

545: ring C—C bond is saturated
549: ring C—C bond is unsaturated

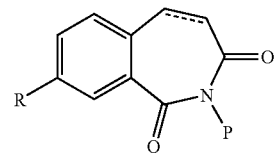

546 R = NHNH$_2$
547 R = Br
548 R = B(OH)$_2$
(ring C—C bond is saturated)

550 R = NHNH$_2$
551 R = Br
552 R = B(OH)$_2$
(ring C—C bond is unsaturated)

A2-99, V1 and V2=H$_2$

The synthesis of intermediates containing A2-99 wherein V1 and V2 are H$_2$ is shown in Scheme 70. Reduction of 545 with LAH yields the benzoazepine 553. 553 is converted into the hydrazine 554, bromide 525 or boronic acid 556 using the methodology described in Scheme 59.

Scheme 79

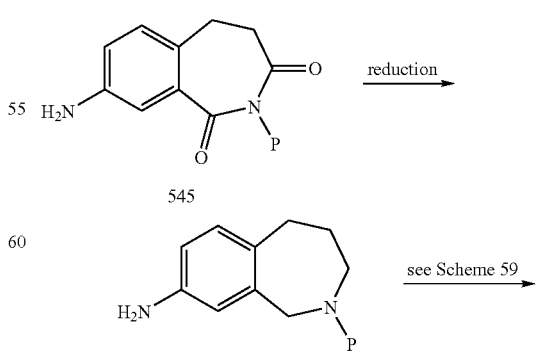

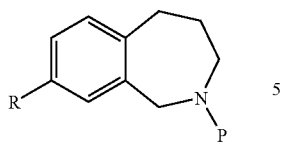

554 R = NHNH₂
555 R = Br
556 R = B(OH)₂

A2-99, A1=O, V2=H₂

The synthesis of intermediates containing A2-99 wherein V1 is O and V2 is H₂ is shown in Scheme 80. Allylation of 542, wherein P is a para-methoxybenzyl (PMB) or BOC protecting group, with allyl chloride affords the RCM precursor 557. RCM reaction of 557 with Grubb' catalyst affords the tetrahydrobenzazepinenone 558. Reduction of 558 under catalytic hydrogenation conditions gives 559 which is reduced at the ring C—C bond and the nitro functionality (Knobloch, K. et al, *European J. of Org. Chem.*, (2001), 17: 3313-3332). 559 is converted into the hydrazine 560, bromide 561, or boronic acid 562 as described in Scheme 77. Alternatively, intermediate 558 is selectively reduced at the nitro functionality, preferably with stannous chloride, to afford amine-substituted benzazepinedione 563 wherein the ring C—C bond is unsaturated. Intermediate 562 is converted into the hydrazine 564, bromide 565 or boronic acid 566 as described in Scheme 78.

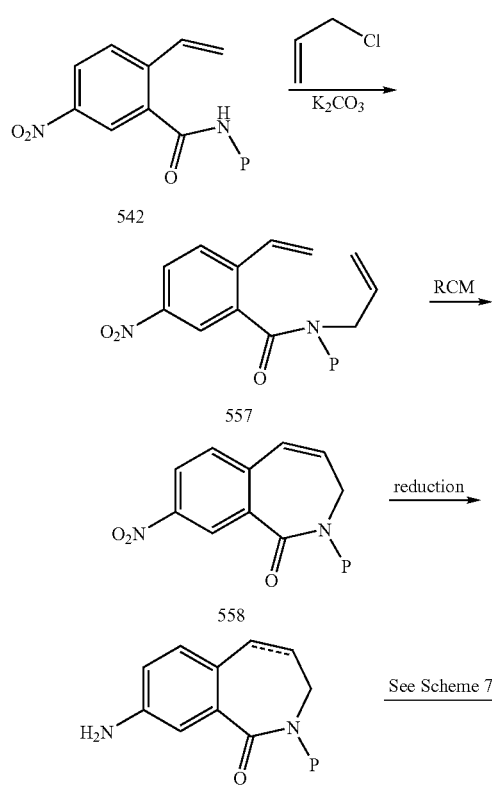

559: ring C—C bond is saturated
563: ring C—C bond is unsaturated

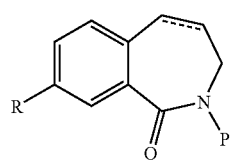

560 R = NHNH₂
561 R = Br
562 R = B(OH)₂
ring C—C bond is saturated
564 R = NHNH₂
565 R = Br
566 R = B(OH)₂
ring C—C bond is unsaturated

A2-99, V1=H₂, V2=O

The synthesis of intermediates containing A2-99 wherein V1 is H₂ and V2 is O is shown in Scheme 81. The readily available starting material N-PMB protected 2-bromo-5-nitrobenzylamine 567 is reacted with vinyl boronic acid under Suzuki palladium(0)-catalyzed conditions to yield 568. 568 is coupled with acrylic acid in the presence of an acid-activating reagent, preferably EDCI/HOBt, in the presence of base, preferably triethylamine (TEA), to give 569. RCM reaction of 569 with Grubbs' catalyst affords the dihydrobenzazepineone 570. Reduction of 570 under catalytic hydrogenation conditions yields the tetrahydrobenzoazepineone 571 which is reduced at the ring C—C bond and nitro group, with concomitant removal of the PMB protecting group (Knobloch, K. et al, *European J. of Org. Chem.*, (2001), 17: 3313-3332). 571 is converted into the hydrazine 572, bromide 573 or boronic acid 574 as described in Scheme 78. Alternatively, intermediate 570 is selectively reduced at the nitro functionality, preferably with stannous chloride, to afford amine-substituted benzazepinedione 575, wherein the ring C—C bond is unsaturated. Intermediate 575 is converted into the hydrazine 576, bromide 577 or boronic acid 578 as described in Scheme 78.

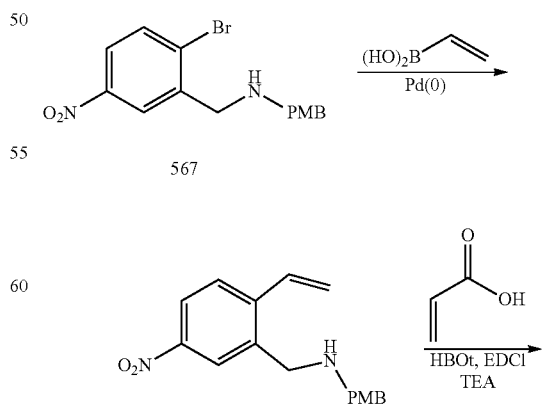

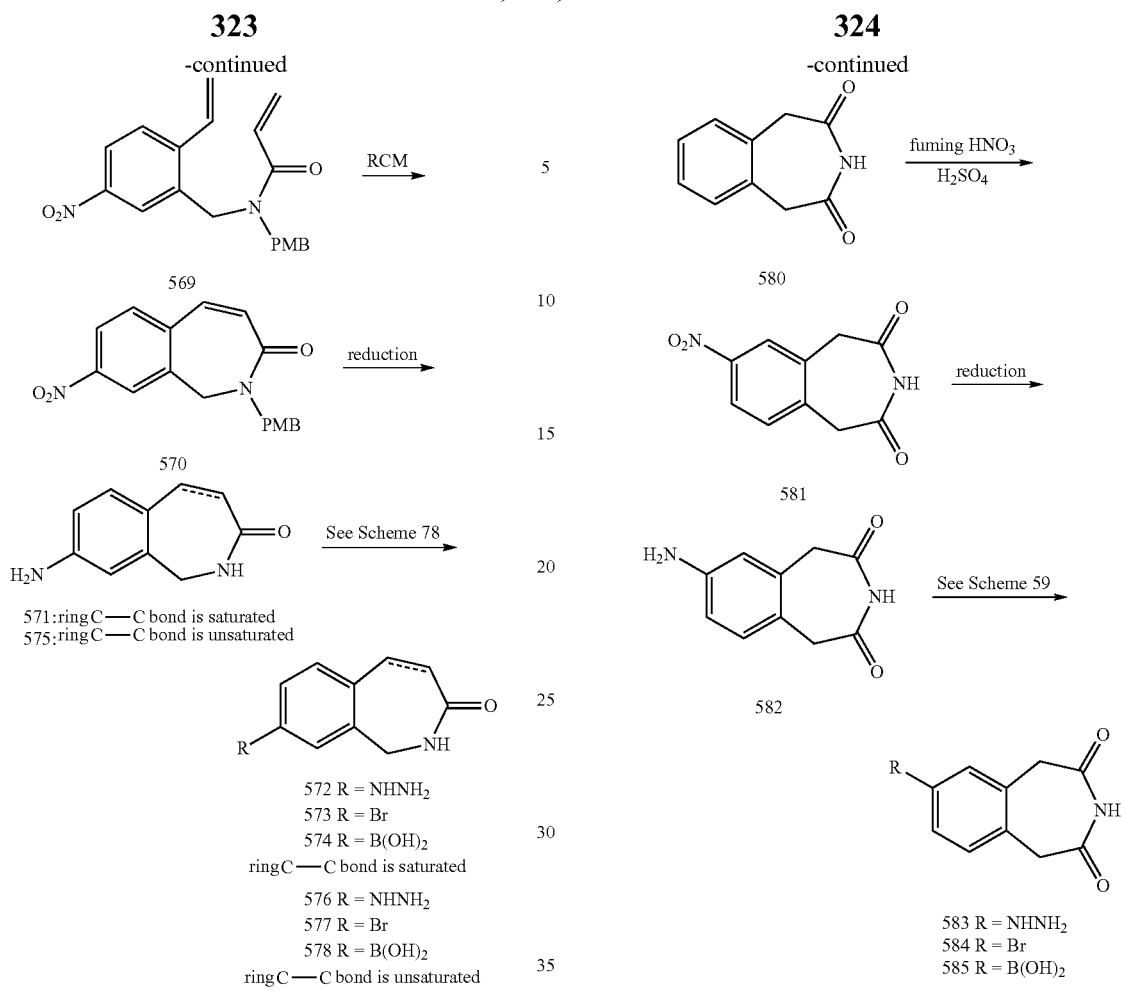

A2-100, V1 and V2=O

Scheme 82 illustrates the preparation of intermediates containing A2-100 wherein V1 and V2 are O. The commercially available starting material 1,2-phenylendiacetic acid 579 is coupled with trifluoroacetamide under HOBt and EDCI conditions to give the cyclic imide 580 (Nazar, F. et al, *Tetrahedron Lett.*, (1999), 40: 3697-3698). The by-products and excess of reagents can be removed by using a mixed resin containing sulfonic acid-substituted resin and a tertiary amine-substituted resin (Flynn, D. L. et al, *J. Am. Chem. Soc.*, (1997), 119: 4874-4881). Nitration of 580 produces 581. Reduction of the nitro functionality of 581 under catalytic hydrogenation conditions affords the amine-substituted benzazepinedione 582. The amine-substituted benzazepindione 582 is converted into the hydrazine 583, bromide 584, or boronic acid 585 using the methodology described in Scheme 59.

A2-100, V1 and V2=H2

The synthesis of intermediates containing A2-100 wherein V1 and V2 are H$_2$ is shown in Scheme 83. Reduction of 586 with NaBH$_4$ in the presence of BF$_3$.OEt$_2$ yields the nitroazepine 587. Protection of 587 with trifluoroacetic anhydride in the presence of base, preferably triethylamine (TEA), gives 588. Reduction of the nitro functionality of 588 under catalytic hydrogenation conditions yields amine 589. Amine 589 is converted into the hydrazine 590, bromide 591, or boronic acid 592 using the methodology described in Scheme 59.

Scheme 82

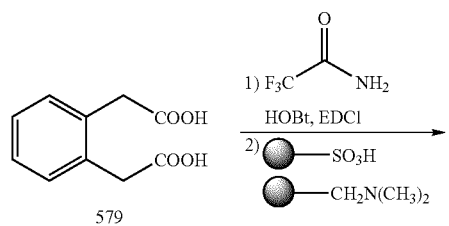

Scheme 83

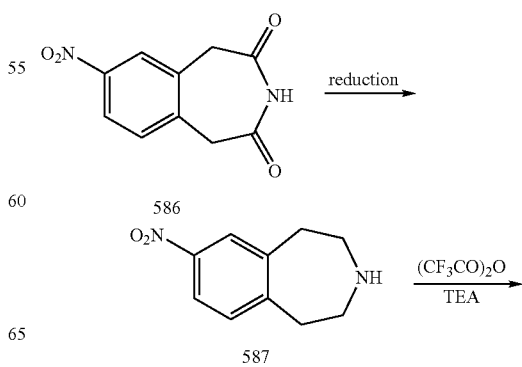

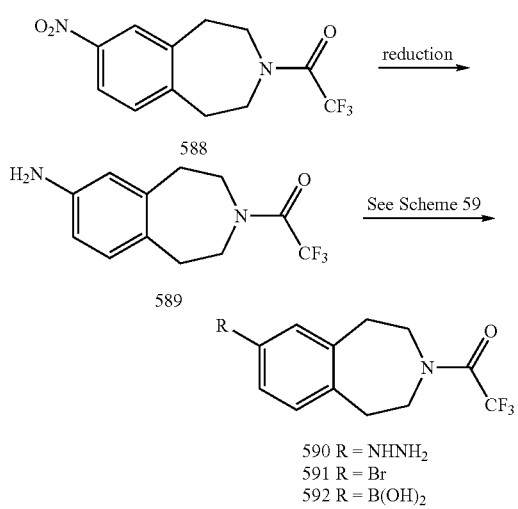

A2-100, V1=O, V2=H₂

The synthesis of intermediates containing A2-100 wherein V1 is O and V2 is H₂ is shown in Scheme 84. The commercially available starting material 4-nitrophenethylamine 593 is converted into the hydrazine 594, bromide 595, or boronic acid 596 using the methodology outlined in Scheme 62.

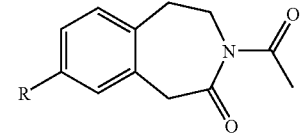

A2-100, V1 and V2=H2

The preparation of intermediates containing A2-100 wherein V1 and V2 are H₂ is illustrated in Scheme 85. 597 is converted to intermediates 598 to 609 using methods described above in Scheme 57.

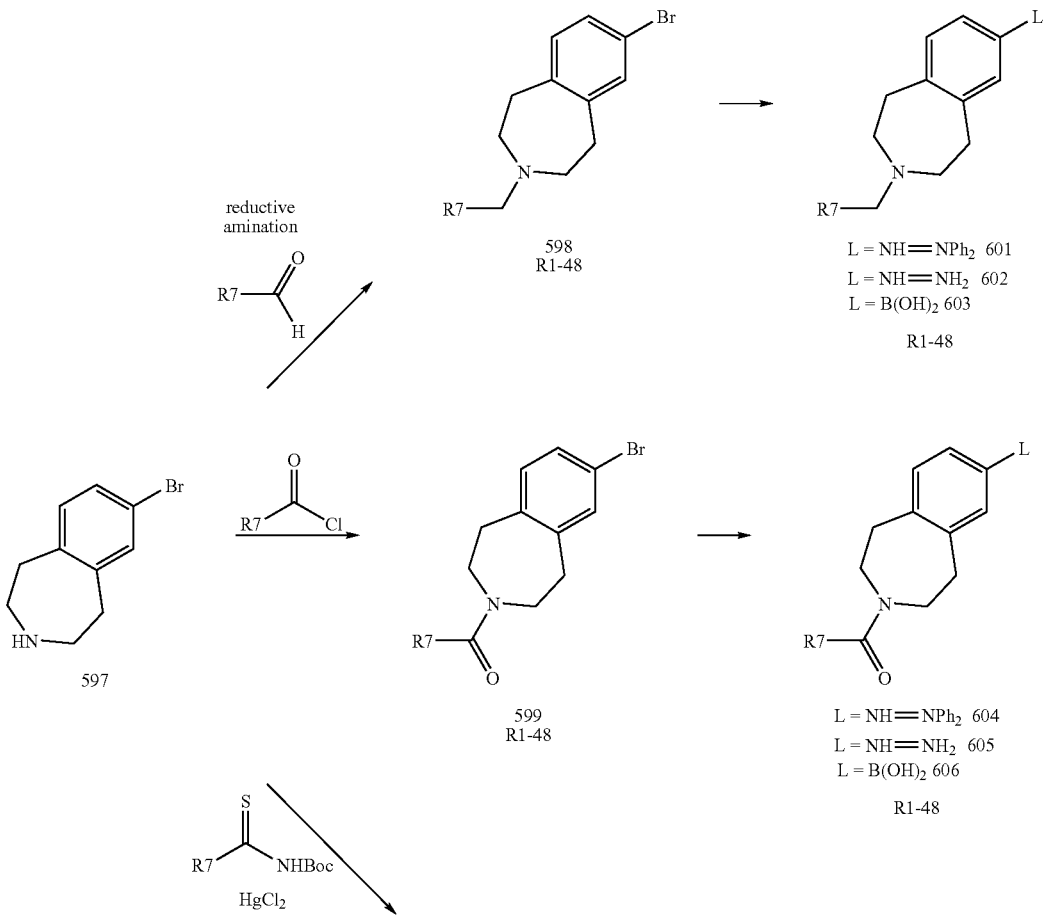

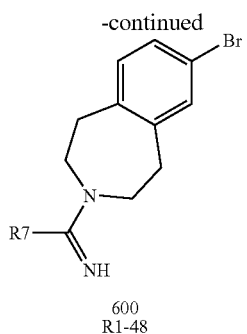

600
R1-48

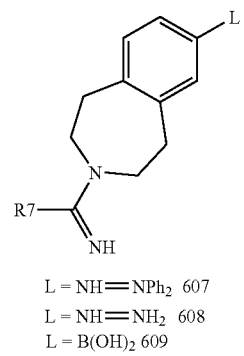

L = NH═NPh$_2$ 607
L = NH═NH$_2$ 608
L = B(OH)$_2$ 609

R1-48

A2-101, V1 and V2═O

Scheme 86 illustrates the preparation of intermediates containing A2-101 wherein V1 and V2 are O. The commercially available starting material 2-amino-4-nitrobenzoic acid 610 is converted into 2-iodo-4-nitrobenzoic acid 611 by a Sandmeyer reaction sequence. The iodobenzoic acid 611 is reacted with acrylonitrile under Heck conditions to give the unsaturated nitrile 612 (Bumagin, N. A. et al, *J. Organometallic Chem.* (1989), 371: 397-401). Intermediate 612 is converted into the acid chloride 613 and then subjected to acid-catalyzed cyclization, giving the ring closure product 614 (Puar, M. S. et al, *Tetrahedron* (1978), 34: 2887-90). Reduction of the nitro functionality of 614 under catalytic hydrogenation conditions affords the amine-substituted benzazepinedione 615 (Knobloch, K. et al, *European J. of Org. Chem.*, (2001), 17: 3313-3332). Intermediate 615 is converted into the hydrazine 616, bromide 617, or boronic acid 618 using the methodology described in Scheme 59. Alternatively, intermediate 614 is selectively reduced at the nitro functionality, preferably with stannous chloride, to afford amine-substituted benzazepinedione 619, wherein the ring C—C bond is unsaturated. Intermediate 619 is converted into the hydrazine 620, bromide 621 or boronic acid 622 as described in Scheme 78.

Scheme 86

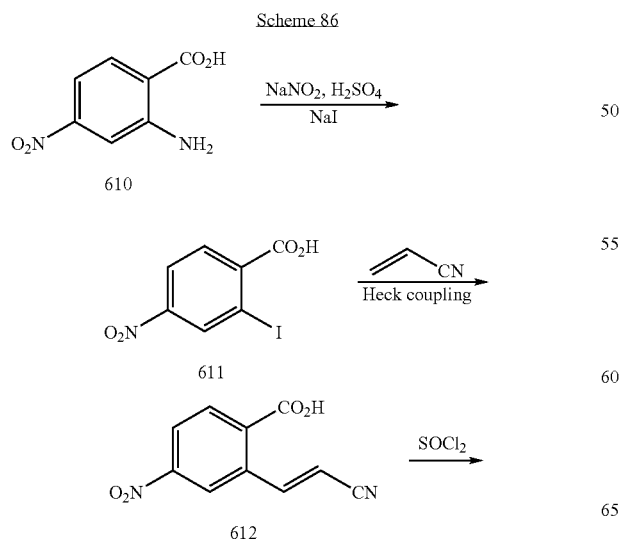

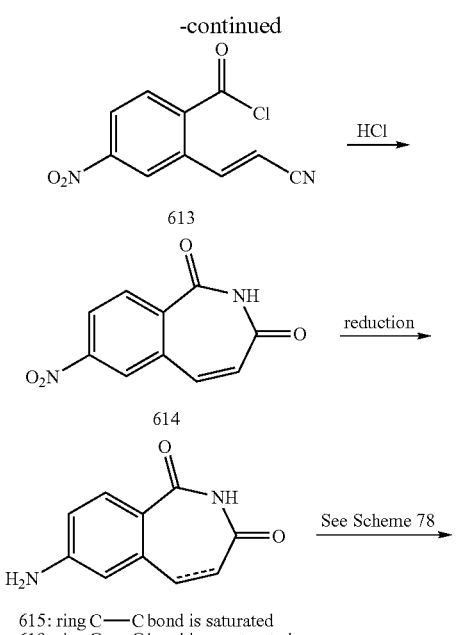

615: ring C—C bond is saturated
619: ring C—C bond is unsaturated

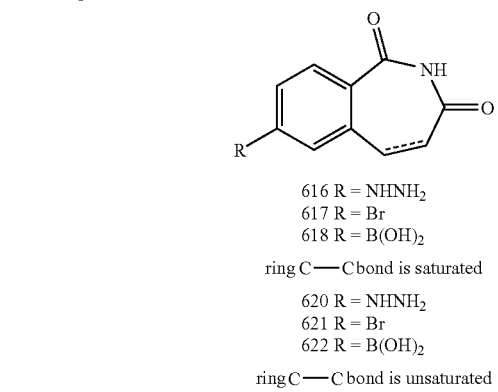

616 R = NHNH$_2$
617 R = Br
618 R = B(OH)$_2$ ring C—C bond is saturated

620 R = NHNH$_2$
621 R = Br
622 R = B(OH)$_2$ ring C—C bond is unsaturated

An alternative synthesis of intermediates containing A2-101 wherein V1 and V2 are O is shown in Scheme 87. The commercially available starting material 2-chloro-4-nitrobenzoic acid 623, wherein P is an amine protecting group, preferably a para-methoxybenzyl (PMB) group, is converted to the hydrazines 629 or 633, bromides 630 or 634, or boronic acids 631, 635 using the methodology described in scheme 78.

329

Scheme 87

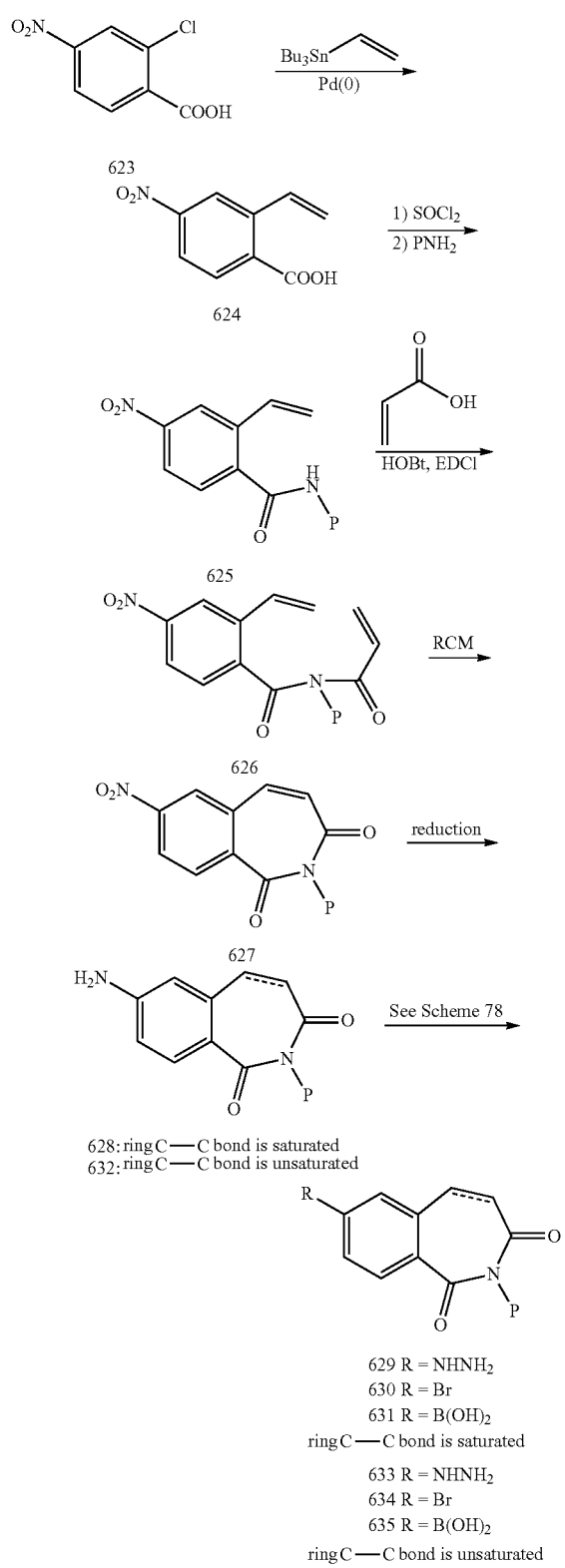

628: ring C—C bond is saturated
632: ring C—C bond is unsaturated

629 R = NHNH₂
630 R = Br
631 R = B(OH)₂
ring C—C bond is saturated

633 R = NHNH₂
634 R = Br
635 R = B(OH)₂
ring C—C bond is unsaturated

A2-101, V1 and V2=H₂

The synthesis of intermediates containing A2-101 wherein V1 and V2 are H₂ is shown in Scheme 88. Reduction of 628 with NaBH₄ in the presence of BF₃OEt₂ (U.S. Pat. No. 6,121,

330

283) yields the tetrahydroazepine 636. 636 is converted into hydrazine 637, bromide 638 or boronic acid 639 using the methodology described in Scheme 59.

Scheme 88

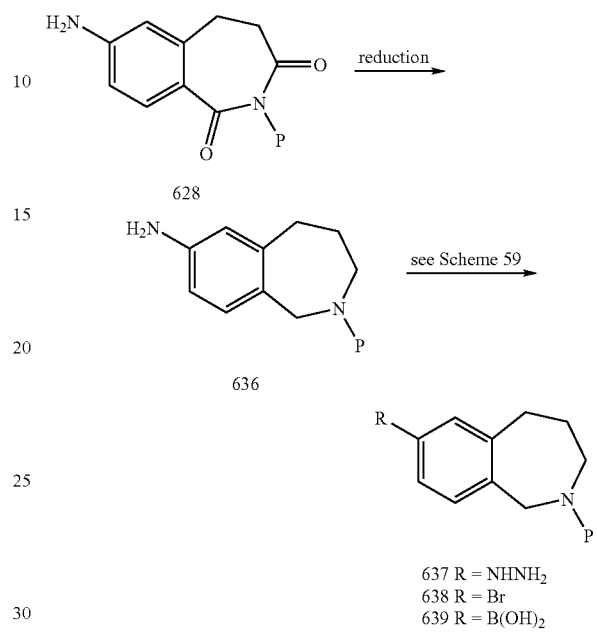

637 R = NHNH₂
638 R = Br
639 R = B(OH)₂

A2-101, V1=O, V2=H₂

The synthesis of intermediates containing A2-101 wherein V1 and V2 is H₂ is shown in Scheme 89. Intermediates 625 (see Scheme 87) is converted to the hydrazines 643 or 647, bromides 644 or 648, or boronic acids 645 or 649 as shown in Scheme 89.

Scheme 89

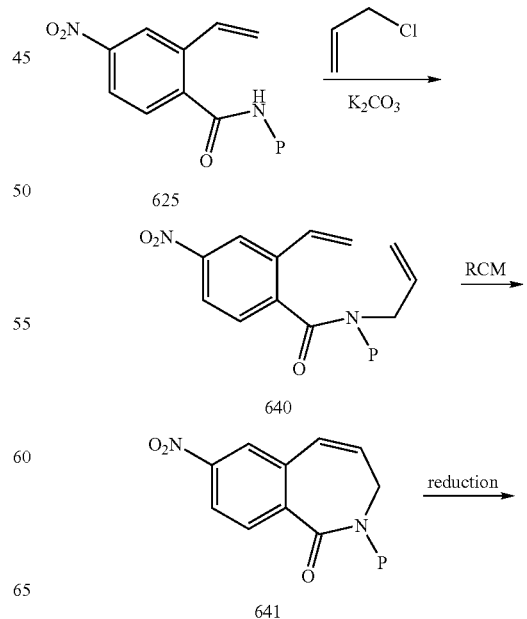

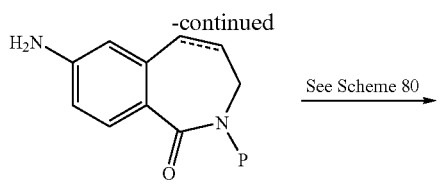

642: ring C—C bond is saturated
646: ring C—C bond is unsaturated

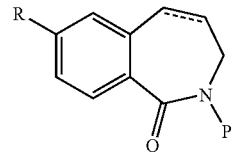

643 R = NHNH₂
644 R = Br
645 R = B(OH)₂ ring C—C bond is saturated

647 R = NHNH₂
648 R = Br
649 R = B(OH)₂ ring C—C bond is unsaturated

A2-101, V1=O, V2=H₂

The synthesis of intermediates containing A2-101 wherein V1 and V2 is H₂ is shown in Scheme 90. The readily available starting material 2-chloro-4-nitrobenzylamine 650 is converted to the hydrazines 651 or 654, bromides 652 or 655, or boronic acids 653 or 656 using the methodology described in Scheme 81.

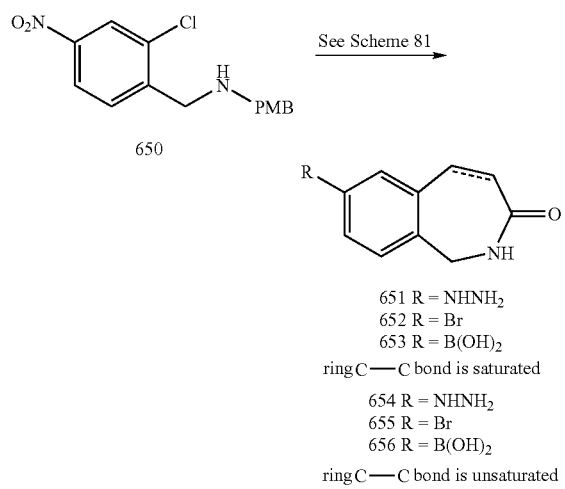

Scheme 90

650

651 R = NHNH₂
652 R = Br
653 R = B(OH)₂ ring C—C bond is saturated

654 R = NHNH₂
655 R = Br
656 R = B(OH)₂ ring C—C bond is unsaturated

A2-102, V=O

Scheme 91 illustrates the preparation of intermediates containing A2-102 wherein V is O, using methodology reported by Schultz, C. et al (*J. Med. Chem.* (1999), 42: 2909-2919). The commercially available starting material 2-amino-5-nitrobenzoic acid 657 is converted into the ester 658. The ester 658 is treated with ethyl 4-chloro-oxobutanoate in the presence of pyridine to yield 659. Dieckman cyclization of 659 using potassium hydride as base in mixture of toluene and DMF affords the dihydrobenzazepineone 660. Heating 660 in wet DMSO yields the tetrahydrobenzoazepinedione 661. Reduction of the nitro functionally of 661 under catalytic hydrogenation condition, followed by selective reduction with Et₃SiH (Blecker, C. et al, *Pharmazie*, (1999), 54: 645-650) gives the lactam 662. The lactam 662 is converted into the hydrazine 663, bromide 664 or boronic acid 665 using the methodology described in Scheme 59.

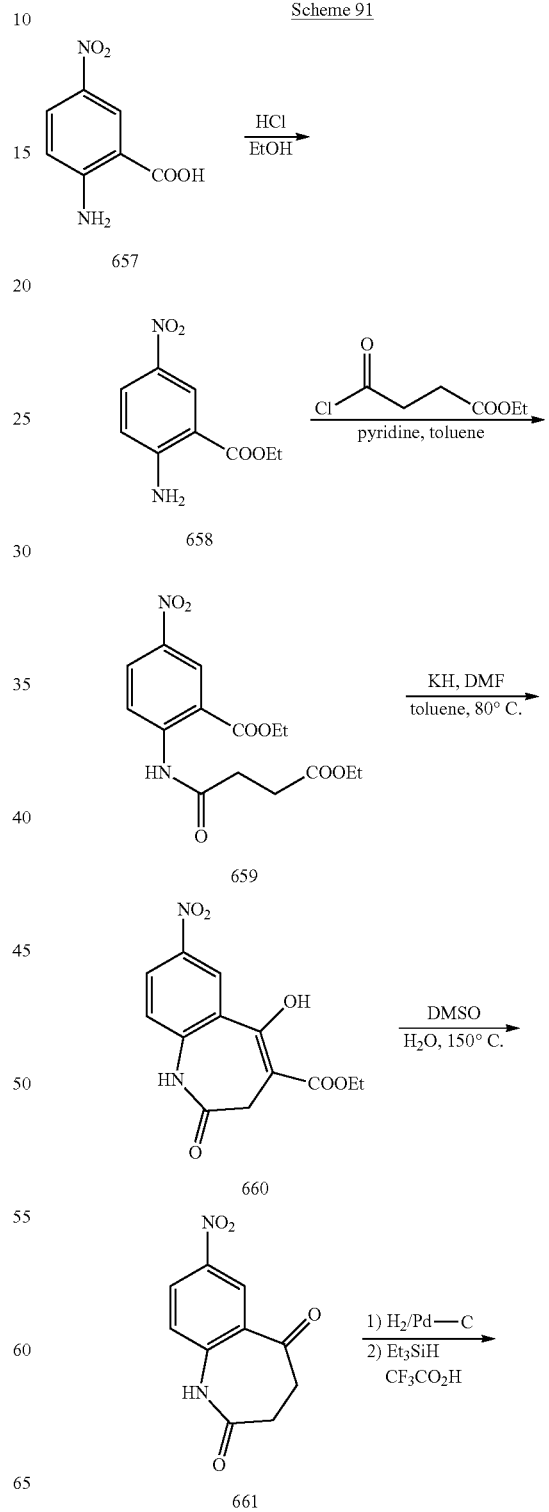

Scheme 91

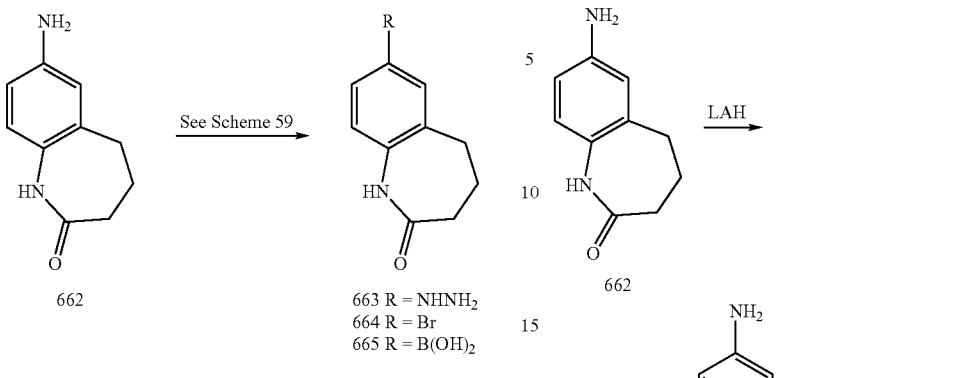

An alternative synthesis of intermediates containing A2-102 wherein V is O is shown in Scheme 92. Nitration of tetralin 666 gives 5- and 6-nitrotetralin as a mixture of regioisomers, which is fractionated to yield 6-nitrotetralin 667. Oxidation of 667 with $CrO_3$ affords 6-nitro-1-tetralone 668. The nitrotetralone 668 can be converted into the hydrazine 663, bromide 664 or boronic acid 665 using the methodology described in Scheme 75.

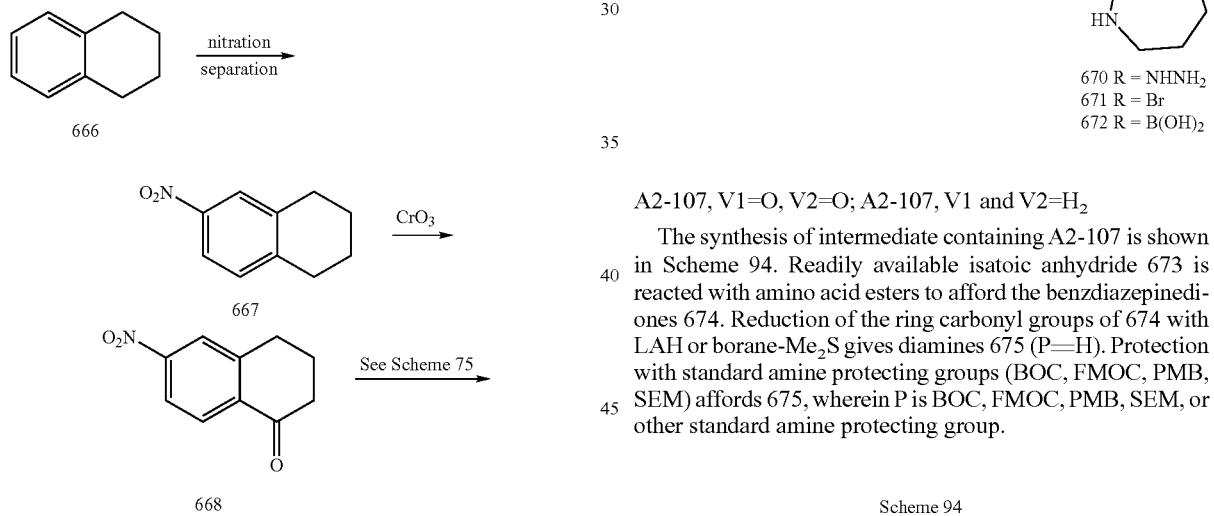

A2-102, V=$H_2$

The synthesis of intermediates containing A2-102 wherein V is $H_2$ is shown in Scheme 93. Intermediate 662 (see Scheme 91) is treated with LAH to afford the tetrahydrobenzazepine 669. The tetrahydrobenzazepine 669 is converted into the hydrazine 670, bromide 671 or boronic acid 672 using the methodology described in Scheme 59.

A2-107, V1=O, V2=O; A2-107, V1 and V2=$H_2$

The synthesis of intermediate containing A2-107 is shown in Scheme 94. Readily available isatoic anhydride 673 is reacted with amino acid esters to afford the benzdiazepinediones 674. Reduction of the ring carbonyl groups of 674 with LAH or borane-$Me_2S$ gives diamines 675 (P=H). Protection with standard amine protecting groups (BOC, FMOC, PMB, SEM) affords 675, wherein P is BOC, FMOC, PMB, SEM, or other standard amine protecting group.

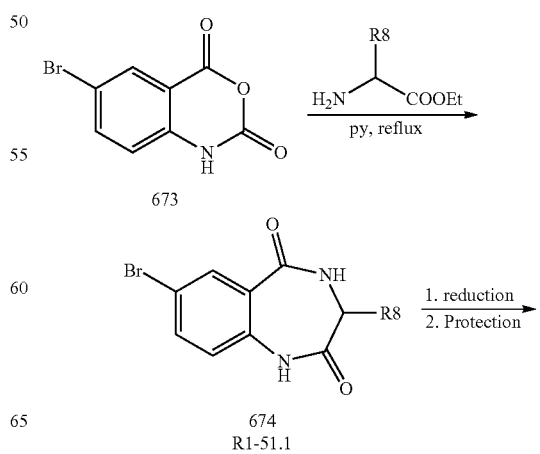

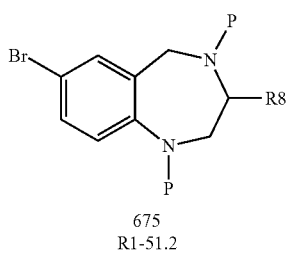

675
R1-51.2

J. Med. Chem., 1999, 42, 5241

A2-107, V1=H$_2$, V2=O

The synthesis of intermediates containing A2-107 wherein V1 is H$_2$ and V2 is O is shown in Scheme 95. Iodination of ortho-amino benzyl alcohol 676 with ICl affords 677. N-acylation of 677 with protected amino acid esters gives amides 678. Oxidation of the alcohol functions of 678 to the aldehydes 679 takes place under standard oxidation conditions, preferably MnO$_2$, TPAP, or periodinane oxidation. Removal of the amine protecting groups, preferably Fmoc, with base, preferably piperidine, with in situ reduction of the formed imines, preferably with sodium triacetoxyborohydride, gives benzdiazepinones 680. Amino group protection, preferably with trifluoroacetic anhydride and base, preferably triethylamine, gives the desired intermediates 681.

Scheme 95

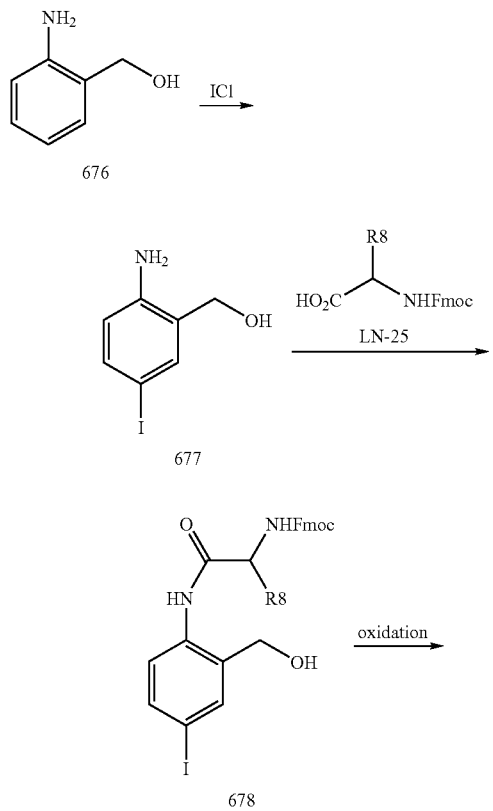

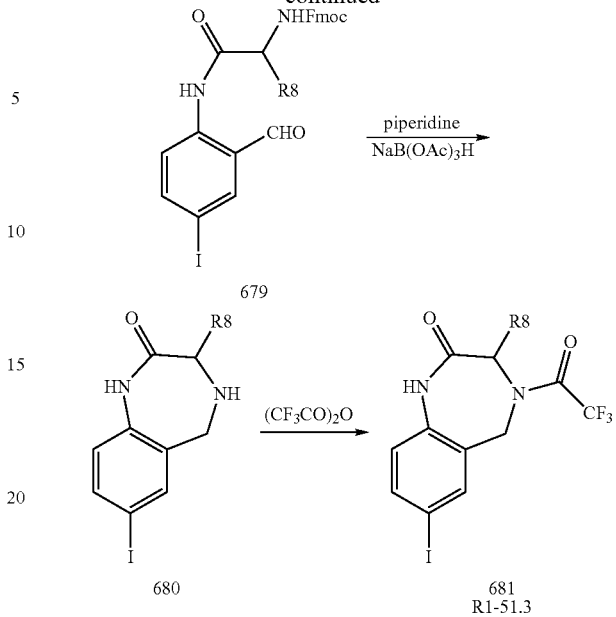

A2-107, V1=O, V2=H

The synthesis of intermediates containing A2-107 wherein V1 is O and V2 is H$_2$ is shown in Scheme 96. Nucleophilic aromatic substitution reactions between 682 and various substituted ethanediamines 683, wherein P is a standard amine protecting group, affords 684. Amine deprotection, followed by amide formation using standard acid-activating reagents, including EDCI and base, affords benzdiazepinones 685. Utilization of diamines 683 wherein R8 is H affords benzdiazepinones 685 corresponding to the structures A2-107, wherein V2 is H$_2$. Utilization of diamines wherein R8 is substituted results in structures A2-107 wherein V2 is H, R8.

Scheme 96

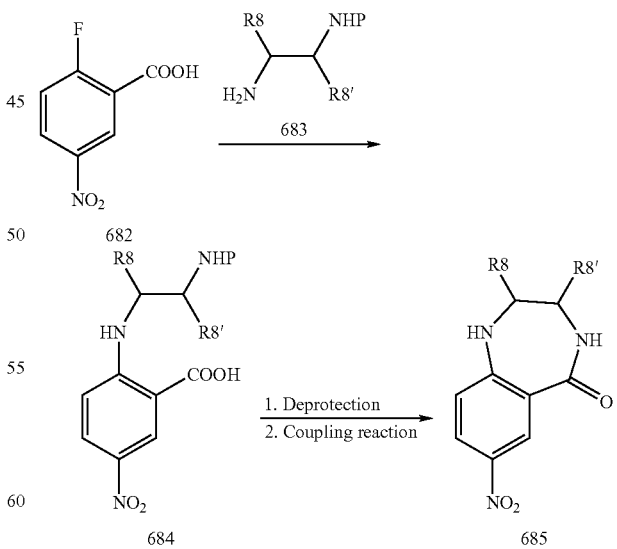

A2-108 and A2-110, V1 and V2=O

The preparation of the intermediates containing A2-108 and A2-110 wherein V1 and V2=O is illustrated in schemes 97 and 98. In one preferred mode, shown in 97, following the procedure of Uskokovic, M. et al. (U.S. Pat. No. 3,291,824), a readily available and suitably substituted anthranilic acid, 686 or 687, is acylated with an R8-containing alpha-halo acid halide, 688 to give intermediate 689 or 690. This, in turn, is cyclized by refluxing in DMF, affording 691 or 692. R' is then converted, if needed, to a group R (693 or 694) suitable for attachment to any of the A1 moieties disclosed in this invention. For example, when R' is Br or I, 691 or 692 may be used directly in a metal-mediated cross-coupling, such as a Heck, Suzuki or Stille protocol (see Scheme 23). Alternatively, when R' is Br or I, it may be subjected to Pd-mediated alkoxycarbonylation using a published procedure (Stille, J. K. et al, *J. Org. Chem.* 1975, 40 (4), 532; Heck, R. F., et al., *J. Org. Chem.* 1974, 39 (23), 3318) to give an ester. This functionality is saponified or reduced to afford the carboxylic acid or aldehyde, respectively. Also, when R' is Br or I, it may be converted to a boronic ester as shown previously in Scheme 23. When R' is $NO_2$, hydrogenation provides the amine. Diazotization, followed by reduction (see Scheme 30), provides the hydrazine.

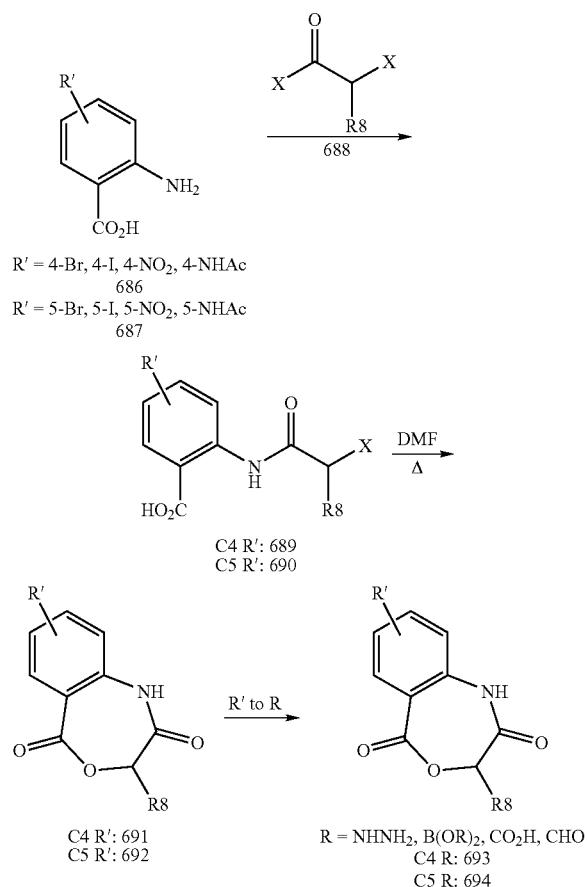

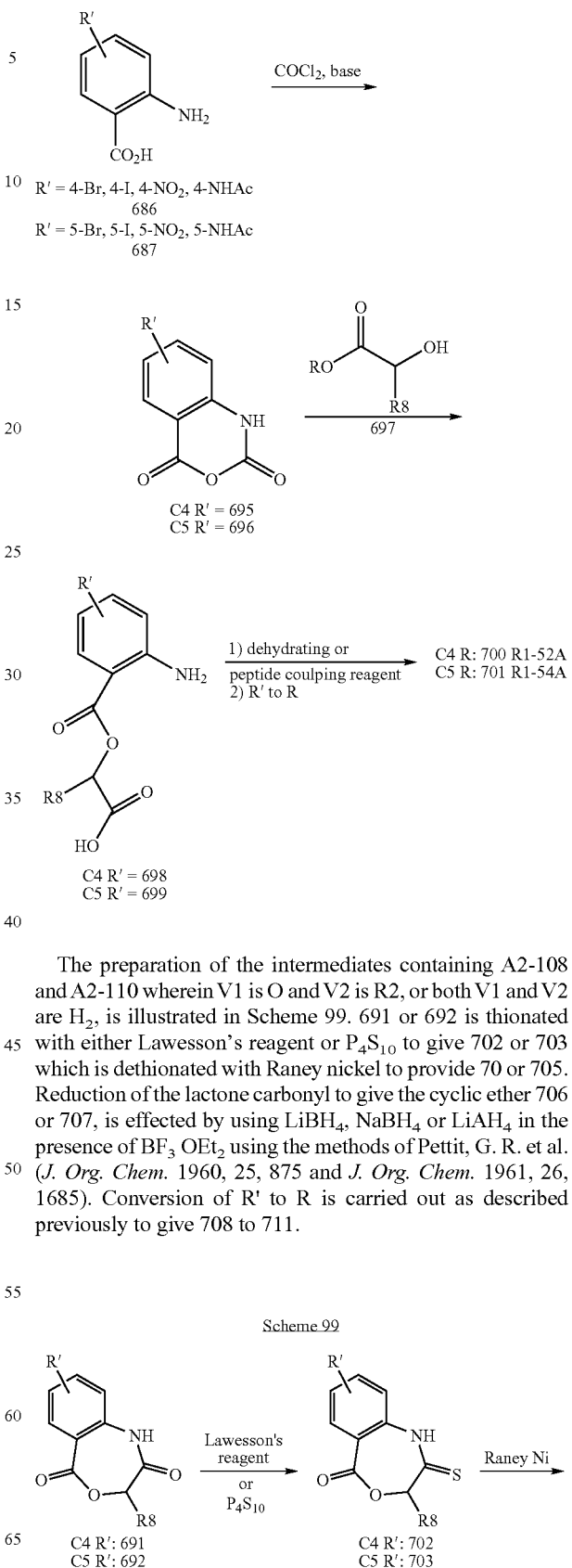

In another preferred mode, shown in Scheme 98, 686 or 687 is converted to its anhydride, 695 or 696 with phosgene or an equivalent. Reacting this with an alpha-hydroxy ester 697 in the presence of a base gives the ester, 698 or 699. Subsequently, the ring is closed using a peptide-coupling or dehydrating reagent. Finally, R' is modified to R to give 700 or 701 as detailed above.

The preparation of the intermediates containing A2-108 and A2-110 wherein V1 is O and V2 is R2, or both V1 and V2 are $H_2$, is illustrated in Scheme 99. 691 or 692 is thionated with either Lawesson's reagent or $P_4S_{10}$ to give 702 or 703 which is dethionated with Raney nickel to provide 70 or 705. Reduction of the lactone carbonyl to give the cyclic ether 706 or 707, is effected by using $LiBH_4$, $NaBH_4$ or $LiAH_4$ in the presence of $BF_3$ $OEt_2$ using the methods of Pettit, G. R. et al. (*J. Org. Chem.* 1960, 25, 875 and *J. Org. Chem.* 1961, 26, 1685). Conversion of R' to R is carried out as described previously to give 708 to 711.

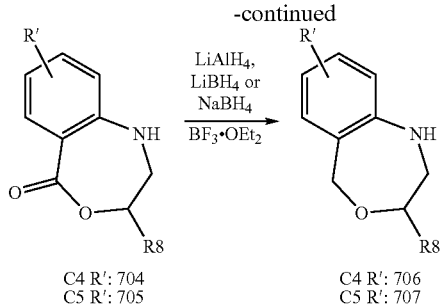

C4 R': 704
C5 R': 705

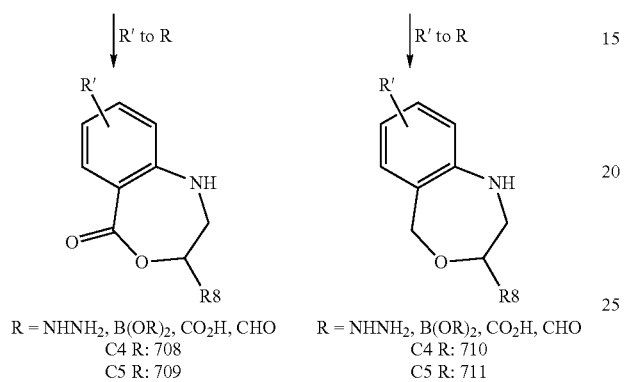

R = NHNH$_2$, B(OR)$_2$, CO$_2$H, CHO
C4 R: 708
C5 R: 709

R = NHNH$_2$, B(OR)$_2$, CO$_2$H, CHO
C4 R: 710
C5 R: 711

The preparation of the intermediates containing A2-108 and A2-110 wherein V1 is H$_2$ and V2 is O is illustrated in Scheme 100. 712 or 713 is esterified and selectively reduced with LiBH$_4$, using the method of H. C. Brown et al. (*J. Org. Chem.* 1982, 47, 4702) to give the primary alcohol. Halogenation gives 714 or 715 wherein X is Cl or Br. Depending on the identity of R'', reduction or deprotection affords 716 or 717 which is acylated with 718 to provide the alpha-hydroxy amide 719 or 720. Treatment of 719 or 720 with a strong non-nucleophilic base, such as NaH or KH affords 721 or 722. Conversion of R' to R is carried out as described previously to give 723 and 724.

Scheme 100

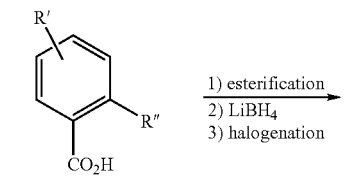

R' = Br, I, NO$_2$, NHAc
R'' = NO$_2$ or NHAc
R' ≠ R''
C4 R': 712
C5 R': 713

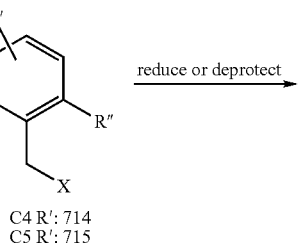

C4 R': 714
C5 R': 715

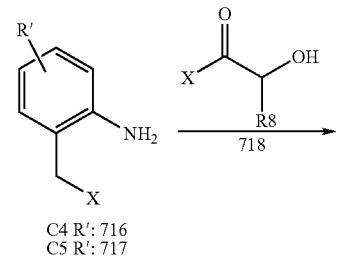

C4 R': 716
C5 R': 717

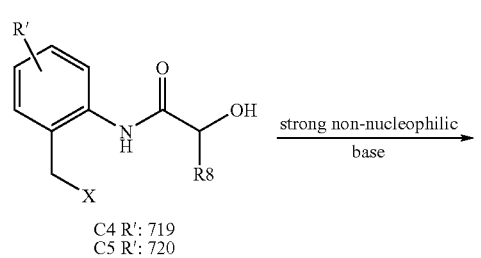

C4 R': 719
C5 R': 720

C4 R': 721
C5 R': 722

C4 R': 723
C5 R': 724

The preparation of the intermediates containing A2-108 and A2-110 wherein V1 is O or H$_2$ and V2 is H$_2$, is illustrated in Scheme 101. 704 or 705 (V=O) or 706 or 707 (V=H, H) can be converted to 725 or 726 (V=O) or 727 or 728 (V=H, H) using the method outlined in Scheme 57. Conversion of R' to R is carried out as described previously to give 729 to 732.

Scheme 101

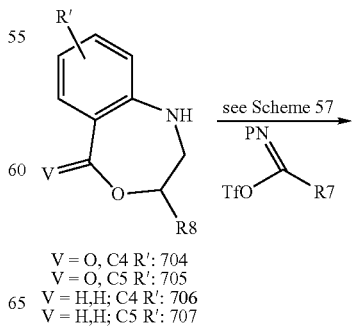

V = O, C4 R': 704
V = O, C5 R': 705
V = H,H; C4 R': 706
V = H,H; C5 R': 707

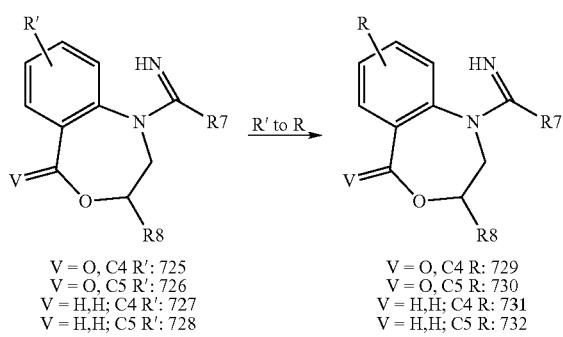

V = O, C4 R': 725
V = O, C5 R': 726
V = H,H; C4 R': 727
V = H,H; C5 R': 728

V = O, C4 R: 729
V = O, C5 R: 730
V = H,H; C4 R: 731
V = H,H; C5 R: 732

A2-109, V1 and V2=O, A2-109, V1 and V2=H$_2$

The synthesis of intermediates containing A2-109 wherein V1 and V2 are both O or both H$_2$ is illustrated in Scheme 102. The readily available bromo-substituted isatoic anhydride 733 is reacted with amino acid esters 734 to afford amides 735. Hydrolysis of the ester functionality of 735 gives the carboxylic acids which are cyclized to afford benzdiazepinediones 736 by employment of a standard acid-activating reagent, typified by EDC and base, preferably triethylamine. Reduction of the amide carbonyl functions of 736 utilizing LAH, diborane, or BH$_3$.Me$_2$S gives benzdiazepines 737.

Scheme 102

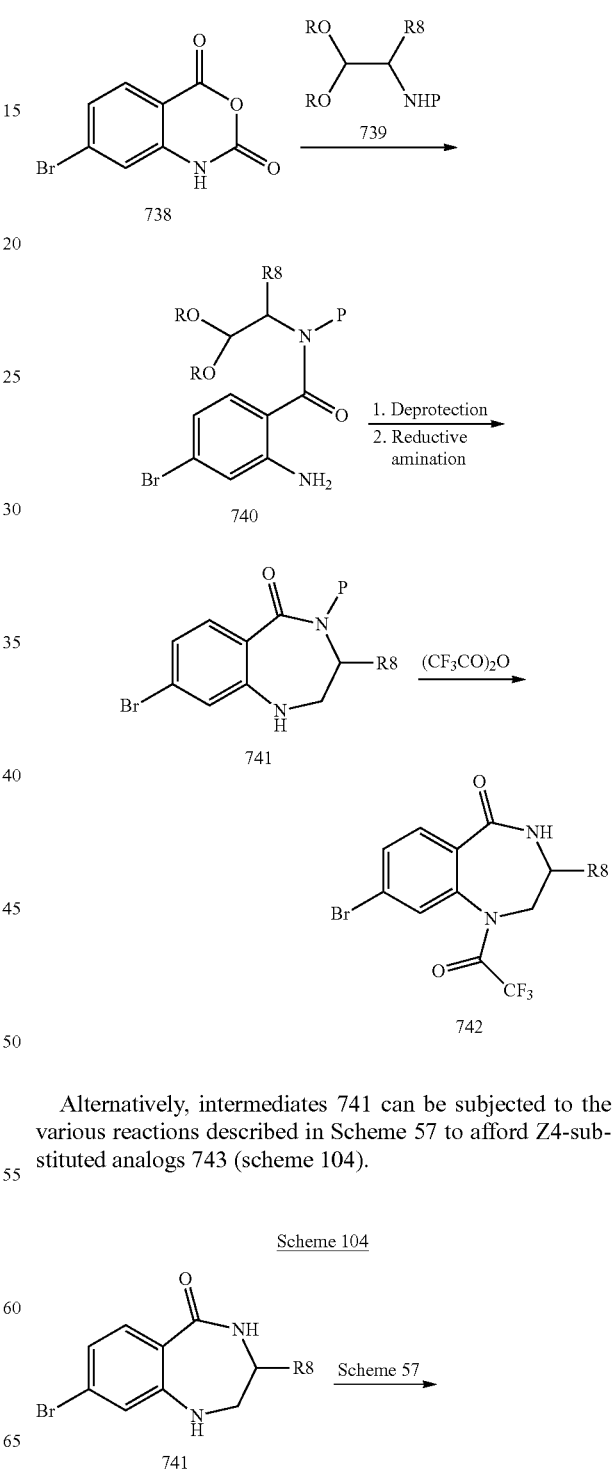

A2-109, V1=O, V2=H$_2$

The synthesis of intermediates containing A2-109 wherein V1 is O and V2 is H$_2$ is illustrated in Scheme 103. Isatoic anhydride 738 is reacted with acetal-protected amino ketones 739 to give amides 740. Deprotection of the acetal protection with acid, preferably p-toluenesulfonic acid or HCl, affords the aldehydes which are subjected to reductive amination conditions, preferably sodium triacetoxyborohydride, to give benzdiazepineones 741. Protection of the ring nitrogen atom with trifluoroacetic anhydride and base, preferably triethylamine, affords intermediates 742.

Scheme 103

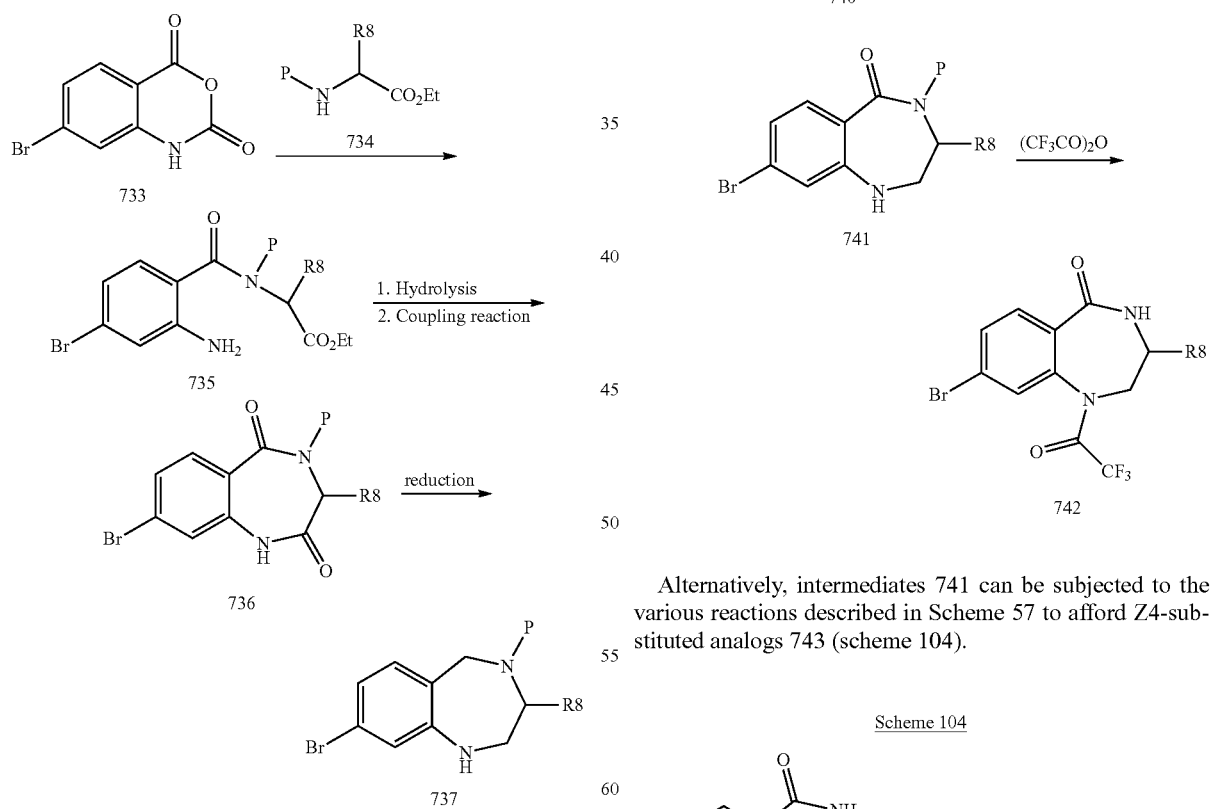

Alternatively, intermediates 741 can be subjected to the various reactions described in Scheme 57 to afford Z4-substituted analogs 743 (scheme 104).

Scheme 104

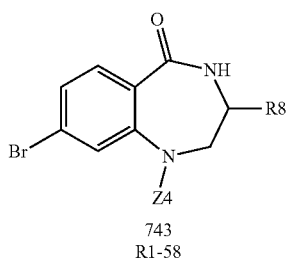

743
R1-58

X = O, NH

A2-109, V1=H$_2$, V2=O

The synthesis of intermediates containing A2-109 wherein V1 is H$_2$ and V2 is O is illustrated in Scheme 105. Readily available 744 is oxidized to the aldehyde 745 using standard oxidizing reagents, preferably MnO$_2$, TPAP, or a periodinane. Reductive amination of 745 with amino acid esters 746, wherein P is an substituted alkyl protecting group or H, affords intermediates 747. Hydrolysis of the ester function of 747 and cyclization employing standard acid-activating reagents, including EDC and base, triethylamine, affords the desired benzdiazepineone intermediates 748. Concomitant reduction of the lactam carbonyl and nitro functional groups with LAH gives rise to intermediate benzdiazepines 749. Selective protection of the ring nitrogen atom with trifluoroacetic anhydride and base, preferably triethylamine, gives 750. Alternatively, 748 is converted into Z4-substituted benzdiazepineones 751 by a sequence involving amine deprotection and derivatization with Z4 moieties as described in Scheme 57. Alternatively, 749 is converted into regioisomeric Z4-substituted benzdiazepineones 752 using methods described in Scheme 57.

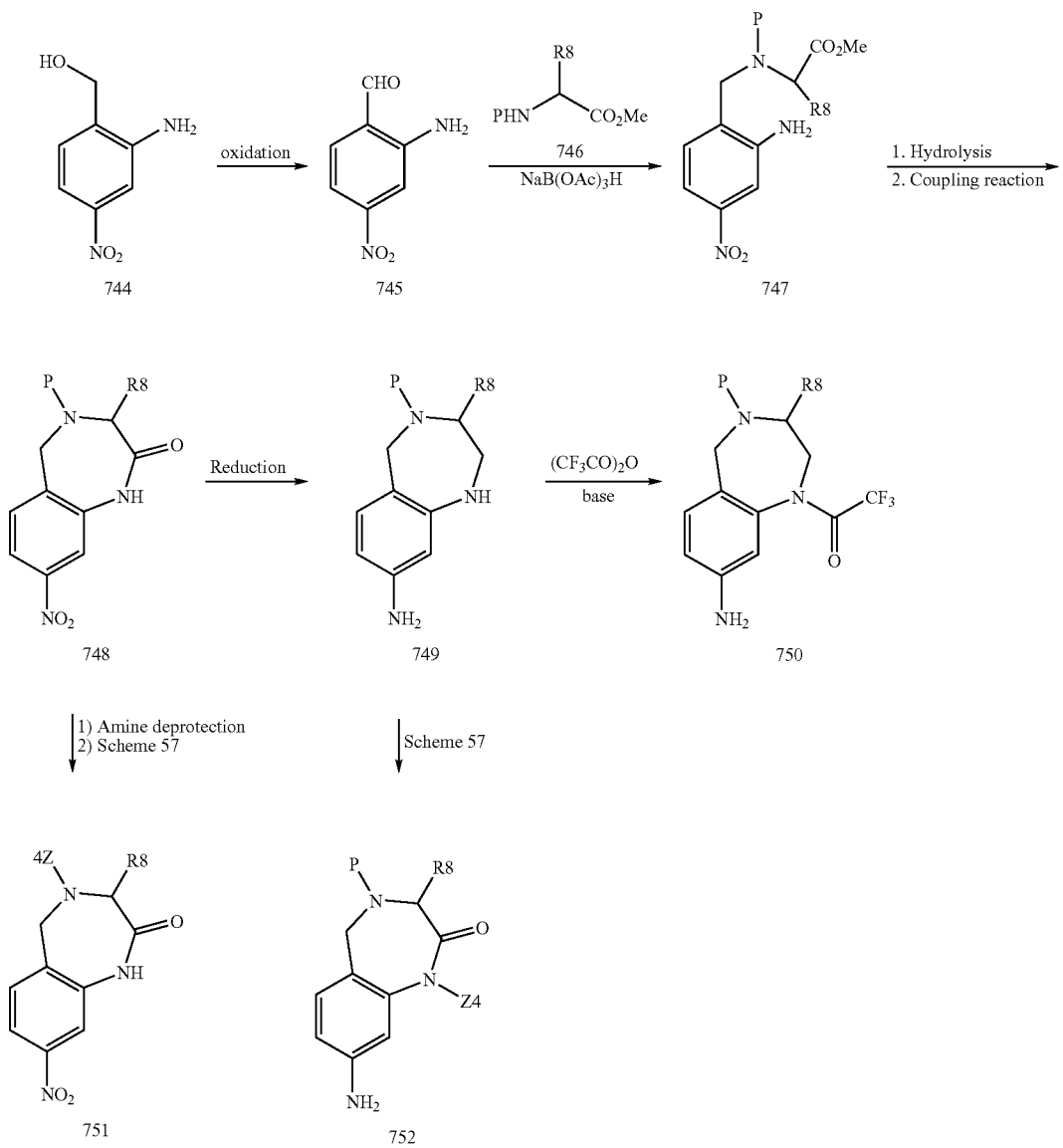

A2-111, V1 and V2=O, A2-111, V1 and V2=H$_2$

The synthesis of intermediates containing A2-111 wherein V1 and V2 are O or V1 and V2 are H$_2$ is illustrated in Scheme 106. Nitroaniline 753, wherein P is a substituted alkyl amine protecting, is coupled with the malonyl half esters 754 employing standard acid-activating reagents, including EDCI/HOBT or ethyl chloroformate in the presence of base, preferably triethylamine, to give amides 755. Reduction of the nitro group under standard conditions, followed by hydrolysis of the ester functionality affords acids 756. Cyclization of 756 to benzdiazepinediones 757 is effected by EDCI/HOBT in the presence of base, preferably triethylamine. Amide nitrogen deprotection, followed by reduction of the ring carbonyl functionalities by LAH or borane affords the requisite benzdiazepines 758.

ing group, is coupled with substituted hydroxy acids 759, wherein P' is a standard alcohol protecting group, in the presence of an acid-activating reagent, including but not limited to EDCI/HOBT or ethyl chloroformate in the presence of a base, preferably triethylamine, to give amides 760. Reduction of the nitro group using standard conditions, followed by removal of the alcohol protecting group P', affords 761. Mild alcohol oxidation, preferably with MNO2, TPAP, or a periodinane, gives the aldehyde which is subjected to reductive amination cyclization conditions, preferably sodium triacetoxyborohydride, to afford benzdiazepinones 762. Optional amide deprotection and amine protection using trifluoroacetic anhydride in the presence of base, preferably triethylamine, gives trifluoroacetyl protected benzdiazepineones 763.

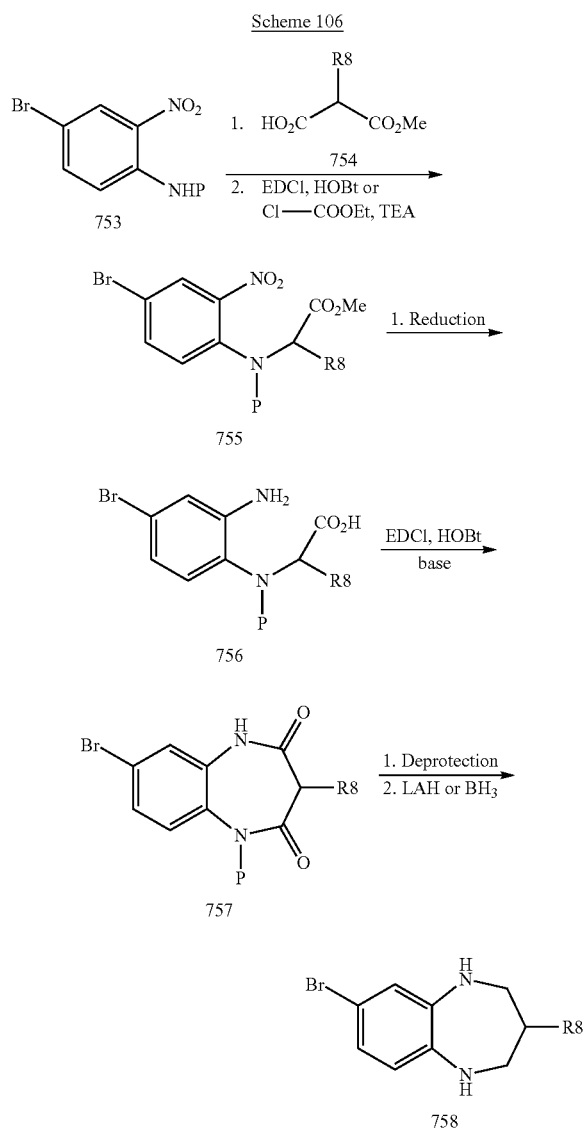

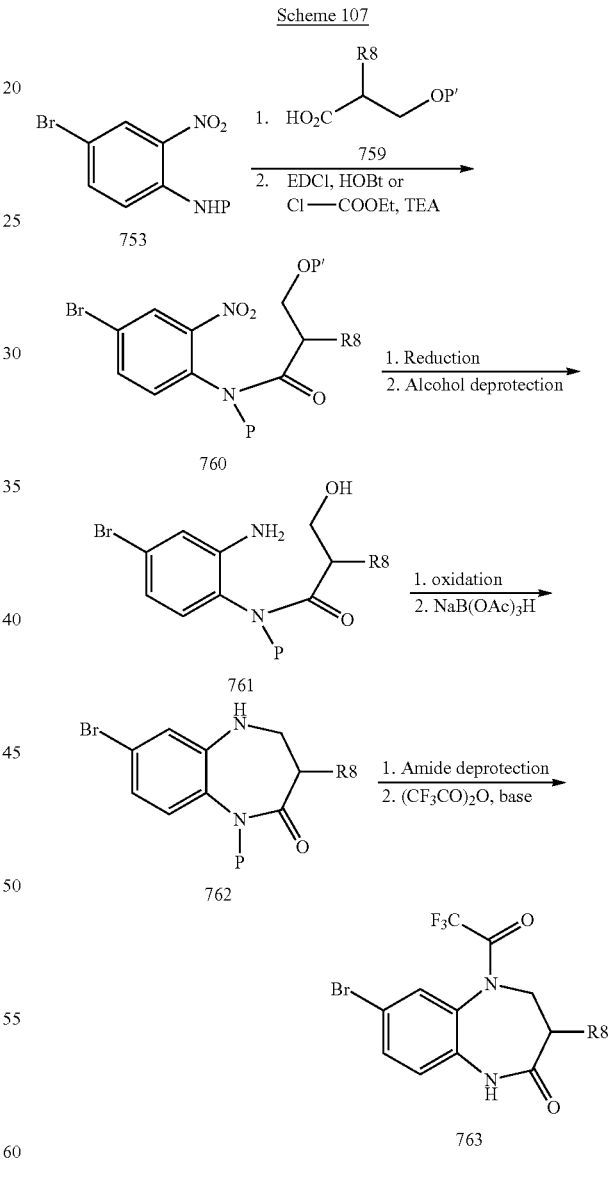

A2-111, V1=O, V2=H$_2$

The synthesis of intermediates containing A2-111 wherein V1 is O and V2 is H$_2$ is illustrated in Scheme 107. Readily available 753, wherein P is a substituted alkyl amine protect-

A2-111, V1=O V2=H$_2$

The synthesis of intermediates containing A2-111 wherein V1 is O and V2 is H$_2$ and the ring amino nitrogen is substituted with a Z4 moeity, is illustrated in Scheme 108. 762 is converted into Z4-substituted analogs 764 using conditions described in Scheme 57.

Scheme 108

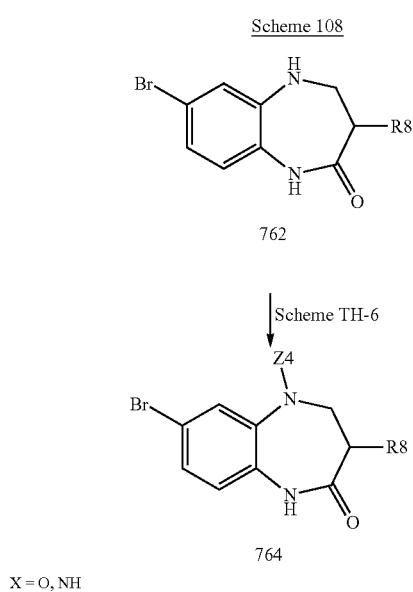

X = O, NH

A2-111, V1=H$_2$, V2=O;

The synthesis of intermediates containing A2-111 wherein V1 is H$_2$ and V2 is O is illustrated in Scheme 109. Starting amine 753 is reacted with substituted malonaldehydes 754 under standard reductive amination conditions, preferably sodium triacetoxyborohydride, to afford nitro esters 765. Reduction of the nitro functionality under standard conditions and ester hydrolysis gives acids 766, which are cyclized to benzdiazepineones 767 in the presence of an acid-activating reagent, preferably EDCI/HOBt or ethyl chloroformate in the presence of a base, preferably triethylamine, to afford benzdiazepineones 767. Protection of the ring amino nitrogen is effected by reaction of 767 with t-butoxycarbonyl anhydride, (BOC)$_2$O, in the presence of base, preferably triethylamine, to give the requisite protected benzdiazepineones 768.

Scheme 109

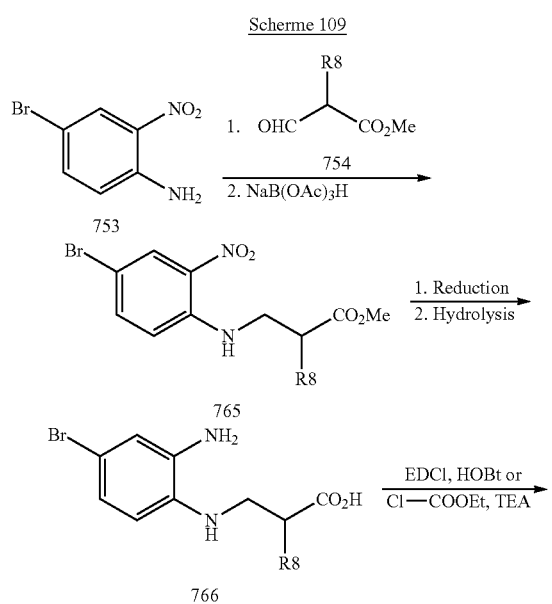

-continued

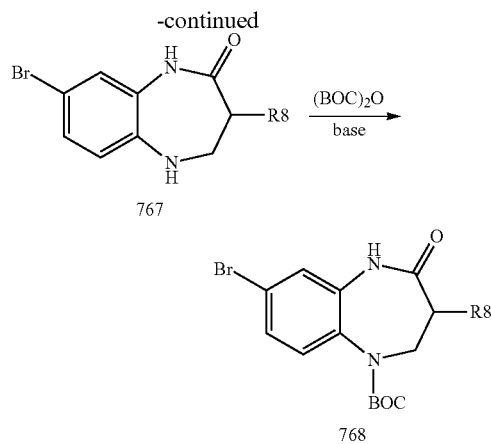

A2-112, V=O;

The synthesis of intermediates containing A2-112 wherein V is O is illustrated in Scheme 110. Using methods described in Scheme 69, 674 is converted to amidines 769 or 770.

Scheme 110

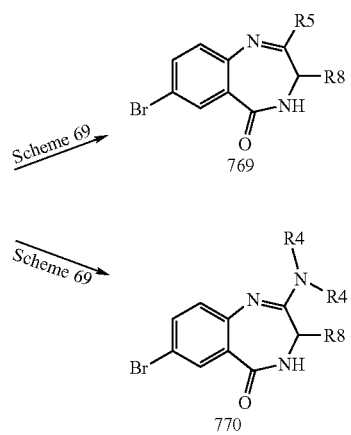

A2-113 and A2-115

The preparation of the intermediates containing A2-113 and A2-115 is illustrated in Scheme 111. By analogy to the sequence shown in Scheme 70, the lactams 771 or 772 are converted to 773 through 776 bearing an exocyclic amine function. Conversion of R' to R is carried out as described previously to give 777 to 780.

Scheme 111

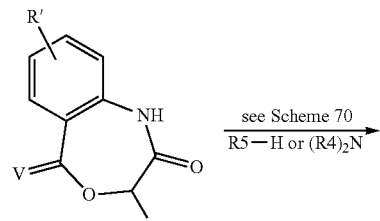

V = H,H; C4 R': 771
V = H,H; C5 R': 772

349
-continued

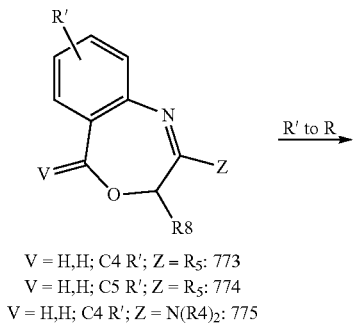

V = H,H; C4 R'; Z = R$_5$: 773
V = H,H; C5 R'; Z = R$_5$: 774
V = H,H; C4 R'; Z = N(R4)$_2$: 775
V = H,H; C5 R'; Z = N(R4)$_2$: 776

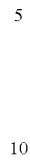 R' to R

350
-continued

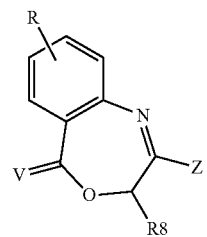

V = H,H; C4 R; Z = R$_5$: 777
V = H,H; C5 R; Z = R$_5$: 778
V = H,H; C4 R; Z = N(R4)$_2$: 779
V = H,H; C5 R; Z = N(R4)$_2$: 780

A2-114, V=O
The synthesis of intermediates containing A2-114 wherein V is O is illustrated in Scheme 112. Using methods described in Scheme 69, 738 is converted to amidines 781 or 782.

Scheme 112

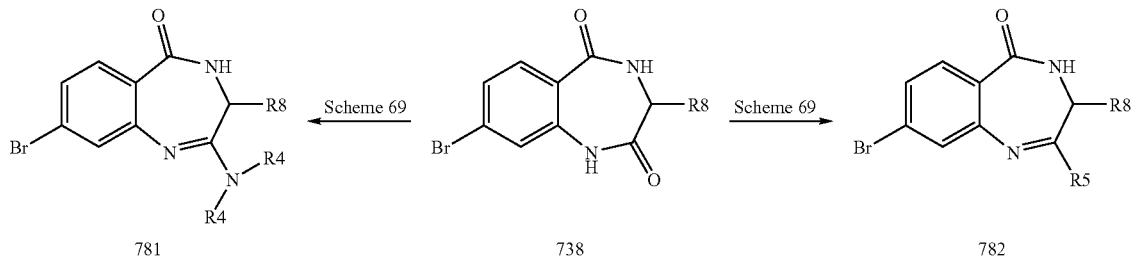

A2-117, V=O
The synthesis of intermediates containing A2-117 wherein V is O is illustrated in Scheme 113. Using methods described in Scheme 69, 757 is converted to amidines 783 or 784.

Scheme 113

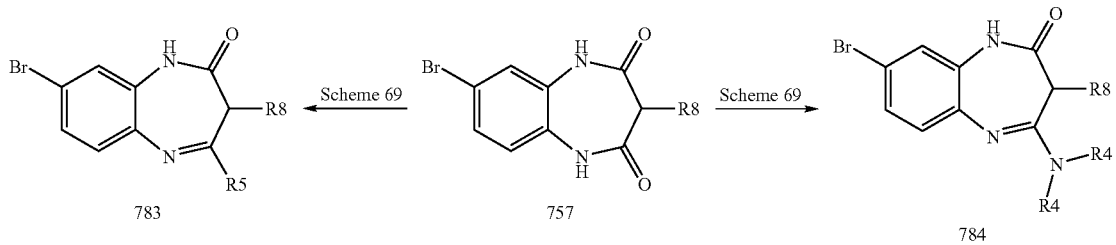

A2-117, V=H2;
The synthesis of intermediates containing A2-117 wherein V is O is illustrated in Scheme 114. Using methods described in Scheme 69, 763 is converted to amidines 785 or 786.

Scheme 114

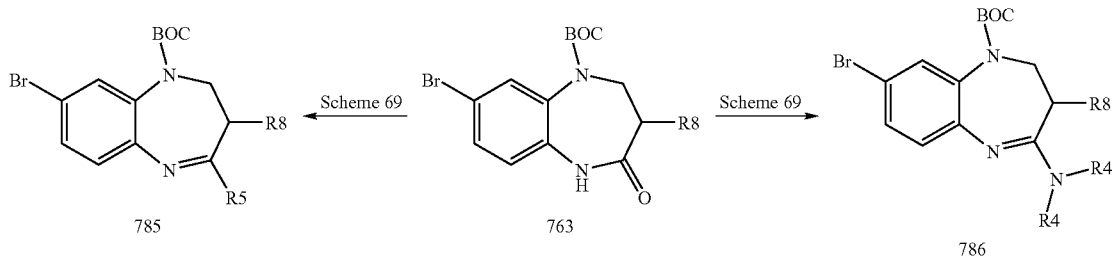

III. Synthesis of Other Intermediates

Synthesis of R5 Intermediates When R5 is pyrrolidine (R5-1) [CAS 123-75-1], piperidine (R5-2) [CAS 110-98-4], azepine [CAS 11-49-9], morpholine (R5-3) [CAS 110-91-8] or thiomorpholine (R5-4) [CAS 123-90-0], these materials are purchased from a number of commercial sources. When R5 is 2-substituted pyrrolidine (R5-12), 2-substituted piperidine (R5-13), HN(CH$_2$CON(R4))$_2$ (R5-14), HN(CH$_2$CO$_2$R4)$_2$ (R5-15), or 4-substituted oxazolidinone (R5-16), these are prepared from commercially available precursors using standard methods and performed by one of ordinary skill in the art.

When R5 is thiomorpholinsulphone (R5-5) [790, CAS 39093-93-1], the synthesis is shown in Scheme 114. Benzylamine 787 and divinylsulphone 788 are reacted together in refluxing methylenechloride to yield benzyl-protected thiomorpholinesulphone 789, which upon hydrogenation yields 790.

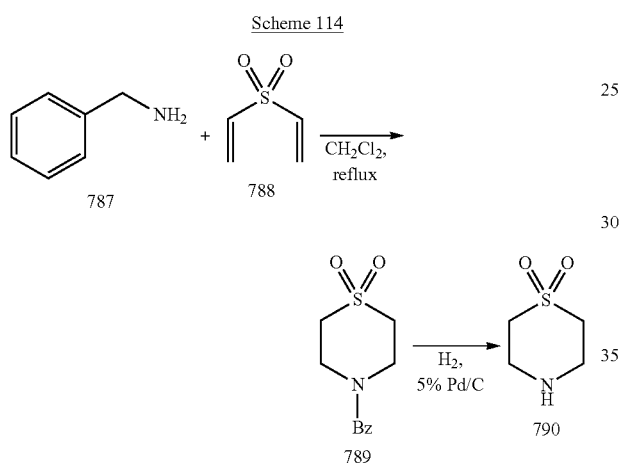

When R5 is 4-alkyl-4-piperidinol (R5-6), the synthesis proceeds as shown in Scheme 115. Commercially available N-Boc-4-piperidone is reacted with the requisite Grignard or alkyllithium reagent to yield N-Boc-4-alkyl-4-piperidinol 791, which is readily deprotected to yield species of type 792.

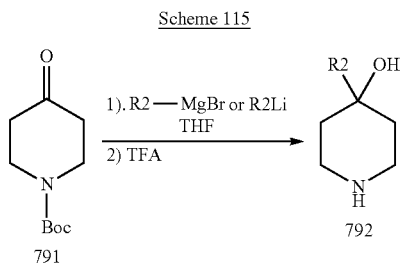

When R5 is 4-N-alkylpiperazine (R5-7), the synthesis proceeds as shown in Scheme 116. Commercially available N-Boc-piperazine is reacted with a suitable aldehyde under reductive amination conditions followed by deprotection to yield species of type 794. When R4=phenyl [CAS 92-54-6], the synthesis proceeds as published by Bloomer et al (see BioOrg. Med. Chem. Lett., 2001, 11(14), 1925).

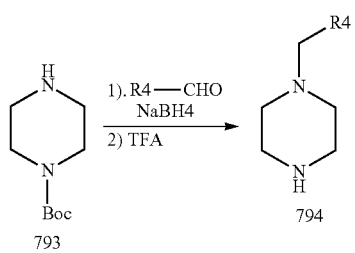

Synthesis of Z1, Z2, and Z4 Intermediates

The syntheses of five-membered heterocycle intermediates Z1, Z2, and Z4 corresponding to Z1-1 through Z1-21, Z2-1 through Z2-21, and Z4-1 through Z4-21 are performed as described in U.S. Continuation-In-Part Application: ANTI-INFLAMMATORY MEDICAMENTS; U.S. patent application Ser. No. 10/886,329, now U.S. Pat. No. 7,202,257, attached by reference herein.

Synthesis of Sulfoximes

The Syntheses of sulfoxime moieties

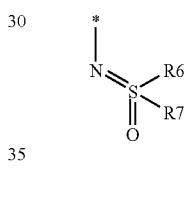

is accomplished using the method reported by Cho, G. Y., et al, *Organic Letters* (2004) 6: 3293-3296.

General Methods

General method A: To a stirring suspension of the starting pyrazole amine (0.5 mmol, 1.0 eq) in dry THF (2.0 ml) was added pyridine (5.0 mmol, 10.0 eq). The resulting slurry was stirred at RT for 1 h, treated with the appropriate isocyanate (1.0 mmol, 2.0 eq) and stirred overnight at RT. The reaction was diluted with EtOAc and 1M HCl (10 ml) and the layers separated. The aqueous was extracted with EtOAc (2×), and the combined organic extracts were washed with H$_2$O (1×), satd. NaHCO$_3$ (1×) and brine (2×), dried (MgSO$_4$), filtered, concentrated, and purified via column chromatography to yield the target compound.

General method B: A solution of the starting pyrazole amine (0.5 mmol, 1.0 eq), triethylamine (2.0 eq) and CDI (2.0 eq) in DMF (5.0 mL) was stirred at RT for 6 h. The appropriate amine (1.0 mmol, 2 eq) was added and the solution was stirred at RT for 5 h, then poured into H$_2$O (50 mL). The mixture was extracted with CH$_2$Cl$_2$ (3×50 mL) and the combined organic extracts were washed with 1N HCl, brine, dried (Na$_2$SO$_4$), filtered, concentrated and purified by preparative TLC to afford the target compound.

General method C: To a stirred solution of the starting ester (0.23 mmol, 1.0 eq) in THF (5 mL) was added LiAlH$_4$ powder (18 mg, 0.5 mmol) portionwise at 0° C. under N$_2$. The mixture was stirred at RT for 2 h, quenched with H$_2$O, and extracted with EtOAc. The combined organic layers were washed with brine, dried (Na$_2$SO$_4$), filtered and concentrated to yield the crude product, which was purified either by preparative TLC or column chromatography to afford the target compound.

General method D: To a solution of the starting pyrazole amine (1 eq) in EtOAc were added 2,2,2-trichloroethylchloroformate (1.1 eq) and saturated NaHCO$_3$ (2-3 eq) at 0° C. After stirring for 3 h at RT, the layers were separated and the aqueous layer extracted with EtOAc. The combined organic extracts were washed with brine, dried (Na$_2$SO$_4$) and concentrated under vacuum to yield the crude TROC carbamate of the pyrazole amine. To the carbamate (1 eq) in DMSO were added diisopropylethylamine (2 eq), the appropriate amine (2 eq) and the mixture was stirred at 60° C. for 16 h or until all the starting carbamate was consumed. Water was added to the mixture and the product was extracted with EtOAc (2×25 mL). The combined organic extracts were washed with brine solution, dried (Na$_2$SO$_4$) and concentrated to yield crude product, which was purified by column chromatography to yield the target compound.

General method E: A mixture of the starting ester (1 eq) in an aqueous solution of LiOH (2N, 5 mL) and THF (10 mL) was stirred overnight at RT. After removal of the organic solvent, the mixture was extracted with Et$_2$O. The aqueous layer was then acidified with 2N HCl to pH 4 and extracted with EtOAc. The combined organic layers were washed with brine, dried (Na$_2$SO$_4$), filtered and concentrated to give the crude product, which was purified by reverse phase chromatography to afford the target acid.

General method F: To the starting Boc-protected amine dissolved in EtOAc (5 mL) was added 3N HCl/EtOAc (6 mL). The solution was stirred at RT for 3 h. The solid was filtered and dried under vacuum to obtain the target amine as the HCl salt.

General method G: To the starting trifluoroacetamide protected amine dissolved in MeOH (2 mL) was added 2N sodium hydroxide solution (2 mL) and the resulting mixture was stirred at RT for 5 h. The solution was further basified with 2N NaOH (20 mL) and the mixture was extracted with ether (3×20 mL) and subsequently with 1-butanol (3×20 mL). The combined butanol extracts were concentrated and dried to yield the deprotected amine.

General method H: To a suspension of the amine (150 mg, 0.67 mmol) in EtOAc (2 mL) was added aqueous 1N NaOH. The reaction mixture was cooled to 0° C. and treated with isopropenyl chloroformate (0.1 mL, 0.94 mmol) over 30 sec. The reaction mixture was stirred 15 min at 0° C. and 1 h at RT. The reaction was poured into THF-EtOAc (1:1; 40 mL) and washed with H$_2$O (2×10 mL) and brine (2×10 mL). The organics were dried (Na$_2$SO$_4$), concentrated and the residue purified via column chromatography to provide the target (prop-1-en-2-yl)carbamate.

General method I: PyBop (0.11 g, 0.22 mmol) was added to a solution of a starting acid (typically 0.2 mmol) in DMF (1 mL) and was stirred for 5 min at RT. To this mixture was added the appropriate amine (either neat or 1 mL of 0.5 M dioxane solution) and the resulting solution stirred for 5 h and was followed by the addition of 3M HCl (2 mL), water (15 mL) and the aqueous extracted with EtOAc (2×20 mL). The combined organic extracts were washed with brine, dried (Na$_2$SO$_4$), filtered, concentrated and purified via column chromatography to yield the amide.

General method J: To a solution of a starting acid (typically 0.21 mmol) in DMF (2 mL) was added NH$_4$Cl (56 mg, 1 mmol) or the appropriate amine, i-Pr$_2$NEt (110 mg, 0.84 mmol), EDC (60 mg, 0.31 mmol) and HOBT (48 mg, 0.31 mmol). The mixture was stirred at RT for 6 h, then diluted with EtOAc (30 mL). The organic extracts were washed with water (2×25 mL) and brine, dried (Na$_2$SO$_4$) and concentrated to afford the target amide.

General method K: To a stirring suspension of a starting acid (typically 0.11 mmol), and the appropriate amine (1.5 eq, either neat or in a 0.5 M dioxane solution) and TBTU (1.5 eq) in DMF (1.1 ml) was added i-Pr$_2$NEt (5.0 eq). The resulting solution was stirred at RT overnight and was then diluted with H$_2$O (11 ml) and extracted with EtOAc (3×). The combined organics were washed with 1M HCl (1×), satd Na$_2$CO$_3$ (2×), dried (MgSO$_4$), filtered and evaporation to provided the target amide.

General method L: NaH (2.3 g of a 60% dispersion, 57 mmol) was activated by washing with hexanes (3×15 mL). THF (20 mL) was added and heated to 80° C. At this point a solution of the appropriate ester (19 mmol) and MeCN (0.91 g, 21 mmol) in THF (40 mL) was added slowly via syringe. After stirring about 30 min a vigorous reaction was observed and soon the color of the reaction turned to dark blue and it was stirred for 10 more min. The reaction mixture was then poured into a biphasic mixture of ice cold 5% HCl (100 mL) and EtOAc (100 mL). The organic layer was separated and aqueous layer was extracted with EtOAc (1×50 mL). The combined organic extracts were washed with brine, dried (MgSO$_4$) and concentrated to afford the desired 3-oxo-3-substituted-propanenitrile which was used as is in the next reaction.

General method M: To a suspension of the appropriate aniline (1.05 g, 6.95 mmol) in conc. HCl (3 mL) was added a solution of NaNO$_2$ (0.57 g, 8.34 mmol) in H$_2$O (3 mL) at 0° C. slowly. After stirring for 1 h, to the mixture was added SnCl$_2$.2H$_2$O (2.98 g, 14 mmol) dissolved in conc. HCl (3 mL) at such a rate that the temperature of the mixture was not allowed to cross 5° C. After stirring for 2 h, a solution of the appropriate 3-oxo-3-substituted-propanenitrile (8 mmol; general method L or commercially available) in EtOH (10 mL) was added and the mixture was heated at 60° C. for 16 h. The mixture was cooled to RT and the solvent was removed under vacuum. The residue was basified with solid NaHCO$_3$ and the product was extracted with ethyl acetate (2×50 ml). The combined organic extracts were washed with brine, dried (Na$_2$SO$_4$) and concentrated under vacuum to yield the desired pyrazole amine.

Example A1

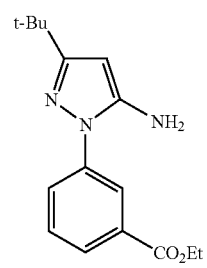

To a solution of m-aminobenzoic acid (200 g, 1.46 mmol) in conc. HCl (200 mL) was added an aqueous solution (250 mL) of NaNO$_2$ (102 g, 1.46 mmol) at 0° C. and the reaction mixture was stirred for 1 h. A solution of SnCl$_2$.2H$_2$O (662 g, 2.92 mmol) in conc. HCl (2 L) was then added at 0° C. The reaction solution was stirred for an additional 2 h at RT. The precipitate was filtered and washed with EtOH and ether to give 3-hydrazinobenzoic acid hydrochloride as a white solid, which was used for the next reaction without further purification. ¹H NMR (400 MHz, DMSO-d₆): δ 10.8 (s, 3H), 8.46 (s, 1H), 7.53 (s, 1H), 7.48 (d, J=7.6 Hz, 1H), 7.37 (m, 1H), 7.21 (d, J=7.6 Hz, 1H).

A mixture of 3-hydrazinobenzoic acid hydrochloride (200 g, 1.06 mol) and 4,4-dimethyl-3-oxopentanenitrile (146 g, 1.167 mol) in EtOH (2 L) was heated at reflux overnight. The reaction solution was evaporated under reduced pressure. The residue was purified by column chromatography to give 3-(5-amino-3-t-butyl-pyrazol-1-yl)-benzoic acid ethyl ester (116 g, 40%) as a white solid together with 3-(5-amino-3-t-butyl-pyrazol-1-yl)benzoic acid (93 g, 36%). 3-(5-amino-3-t-butyl-pyrazol-1-yl)benzoic acid and ethyl ester. ¹H NMR (400 MHz, DMSO-d₆): δ 8.09 (s, 1H), 8.05 (brd, J=8.0 Hz, 1H), 7.87 (brd, J=8.0 Hz, 1H), 7.71 (t, J=8.0 Hz, 1H), 5.64 (s, 1H), 4.35 (q, J=7.2 Hz, 2H), 1.34 (t, J=7.2 Hz, 3H), 1.28 (s, 9H).

Example A2

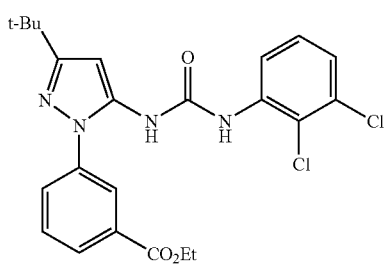

Using general method A, Example A1 (1 g, 3.09 mmol) and 1,2-dichloro-3-isocyanatobenzene (0.7 g, 3.71 mmol) were combined to afford ethyl 3-{3-t-butyl-5-[3-(2,3-dichlorophenyl)ureido]-1H-pyrazol-1-yl}benzoate (0.6 g, 41% yield). ¹H NMR (300 MHz, DMSO-d₆): δ 9.24 (brs, 1H), 8.70 (brs, 1H), 8.05 (t, J=1.8 Hz, 1H), 8.00 (t, J=5.1 Hz, 1H), 7.97-7.93 (m, 1H), 7.84-7.80 (m, 1H), 7.67 (t, J=8.1 Hz, 1H), 7.39 (d, J=4.8 Hz, 2H), 6.39 (s, 1H), 4.31 (q, J=7.2 Hz, 2H), 1.27 (s, 9H), 1.26 (t, J=7.2 Hz, 3H).

Example 1

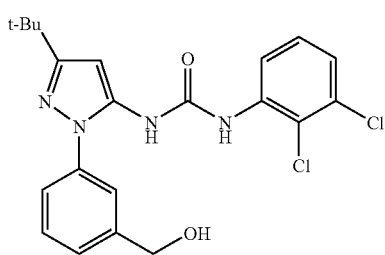

Using general method C, Example A2 (80 mg, 0.17 mmol) was reduced to afford 1-[3-t-butyl-1-(3-hydroxymethyl-phenyl)-1H-pyrazol-5-yl]-3-(2,3-dichlorophenyl)urea (50 mg, 68% yield). ¹H NMR (300 MHz, DMSO-d₆): δ 9.20 (brs, 1H), 8.75 (brs, 1H), 8.04 (dd, J=3.6 and 6 Hz 1H) 7.49-7.44 (m 2H), 7.37-7.32 (m, 2H), 7.30-7.28 (m, 2H), 6.37 (s, 1H), 4.56 (s, 2H), 1.24 (s, 9H).

Example 2

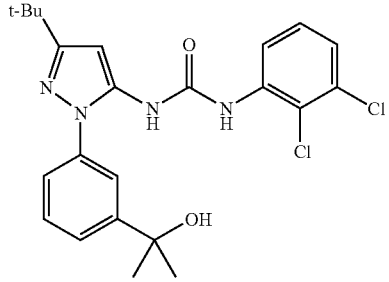

To a solution of Example A2 (100 mg, 0.21 mmol) in fresh THF (10 mL) was added dropwise a solution of MeMgBr (1.5 mL, 1.4 M in toluene/THF) at 0° C. under N₂. After stirring for 1 h, the resulting mixture was allowed to rise to RT and stirred for 1 h. The reaction mixture was quenched by addition of aqueous 1N HCl (5 mL) and the mixture was extracted with EtOAc (3×). The combined organic layers were washed with brine, dried (Na₂SO₄), filtered, concentrated and purified via column chromatography to afford 1-{3-t-butyl-1-[3-(2-hydroxypropan-2-yl)phenyl]-1H-pyrazol-5-yl}-3-(2,3-dichlorophenyl)urea (50 mg, 52% yield). ¹H NMR (300 MHz, DMSO-d₆): δ 9.19 (brs, 1H), 8.72 (brs, 1H), 8.06 (dd, J=3.0, and 6.6 Hz, 1H), 7.58 (m, 1H), 7.46-7.43 (m, 2H), 7.32-7.27 (m, 3H), 6.36 (s, 1H), 1.42 (s, 6H), 1.26 (s, 9H).

Example A3

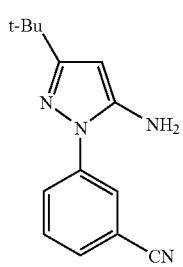

To a solution of Example A1 (14.4 g, 50 mmol) and formamide (4.5 g, 0.1 mol) in DMF (50 mL) was added NaOMe (5.4 g 0.1 mol) at RT. The mixture was stirred at 100° C. for 2 h, concentrated and the residue dissolved in EtOAc (150 mL). The organic layer was washed with H₂O and brine, dried (Na₂SO₄), filtered and purified by column chromatography to afford 3-(5-amino-3-t-butyl-1H-pyrazol-1-yl)benzamide (6 g, 48% yield).

A solution of 3-(5-amino-3-t-butyl-1H-pyrazol-1-yl)benzamide (5.2 g, 20 mmol) in SOCl₂ (50 mL) was heated at reflux for 6 h. After removal of the solvent, the residue was dissolved in EtOAc (100 mL). The organic layer was washed with saturated NaHCO₃ and brine, dried (Na₂SO₄), filtered, and purified by column chromatography to afford 3-(5-amino-3-t-butyl-1H-pyrazol-1-yl)benzonitrile (3.5 g, 73% yield).

General Experimental for Examples 3-12

A solution of Example A3 and the appropriate isocyanate (general method A) or the appropriate aniline (general method B) were converted to the target compound.

| Example | | Name | MS (EI) (M + H⁺) | ¹H NMR (300 MHz, DMSO-d₆) |
|---|---|---|---|---|
| Example 3 | 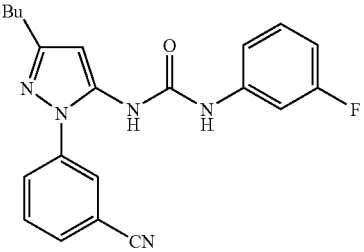 | 1-[3-t-butyl-1-(3-cyanophenyl)-1H-pyrazol-5-yl]-3-(2-fluorophenyl)urea 55 mg, 29% yield General method A | 378 | δ 8.90 (brs, 2H), 8.04-7.99 (m, 2H), 7.85 (t, J = 8.1 Hz, 2H), 7.70 (t, J = 8.1 Hz, 2H), 7.20 (m, 1H), 7.09 (m, 1H), 6.99 (m, 1H), 6.40 (s, 1H), 1.25 (s, 9H) |
| Example 4 | 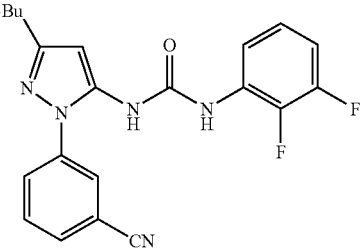 | 1-[3-t-butyl-1-(3-cyan-phenyl)-1H-pyrazol-5-yl]-3-(2,3-difluorophenyl)urea 55 mg, 28% yield General method B | 396 | δ 9.07 (brs, 1H), 8.92 (s, 1H), 8.00 (s, 1H), 7.88-7.81 (m, 3H), 7.73 (t, J = 7.8 Hz, 1H), 7.12-6.97 (m, 2H), 6.40 (s, 1H), 1.25 (s, 9H) |
| Example 5 | 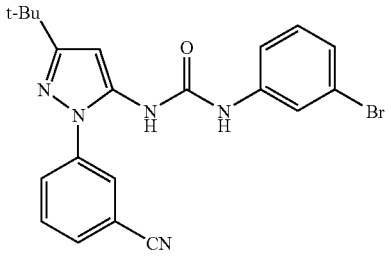 | 1-(3-t-butyl-1-(3-cyanophenyl)-1H-pyrazol-5-yl)-3-(3-bromophenyl)urea 38.4 mg, 42% yield General method A | 440 | δ 7.77-7.70 (m, 3H), 7.52 (s, 1H), 7.46-7.44 (m, 2H), 7.35 (s, 1H), 7.16-7.13 (m, 1H), 7.06-7.04 (m, 2H), 6.35 (s, 1H), 1.29 (s, 9H) |
| Example 6 | 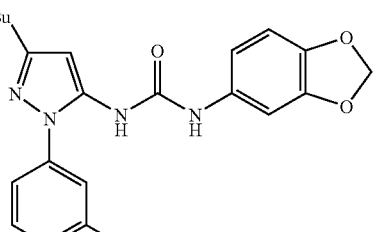 | 1-(benzo[d][1,3]dioxol-5-yl)-3-(3-t-butyl-1-(3-cyanophenyl)-1H-pyrazol-5-yl)urea 107.4 mg, 15% yield General method A | 404.2 | Δ 8.92 (s, 1H), 8.47 (s, 1H), 8.02-8.01 (m, 1H), 7.91-7.89 (m, 1H), 7.86-7.84 (m, 1H), 7.75-7.71 (m, 1H), 7.12-7.11 (m, 1H), 6.82-6.79 (m, 1H), 6.73-6.70 (m, 1H), 6.39 (s, 1H), 5.96 (s, 2H), 1.28 (s, 9H) |
| Example 7 | 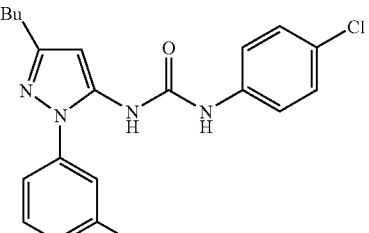 | 1-(3-t-butyl-1-(3-cyanophenyl)-1H-pyrazol-5-yl)-3-(4-chlorophenyl)urea 264 mg, 37% yield General method A | 394.2 | δ 7.87 (s, 1H), 7.81-7.79 (m, 1H), 7.58-7.53 (m, 3H), 7.26 (brs, 3H), 6.48 (brs, 1H), 1.37 (s, 9H) |

-continued

| Example | Name | MS (EI) (M + H+) | 1H NMR (300 MHz, DMSO-d6) |
|---|---|---|---|
| 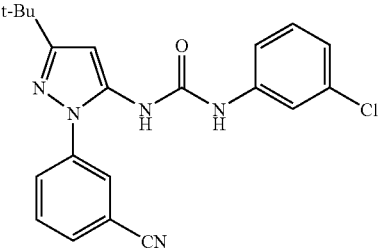<br>Example 8 | 1-(3-t-butyl-1-(3-cyanophenyl)-1H-pyrazol-5-yl)-3-(3-chlorophenyl)urea<br>32.8 mg, 40% yield<br>General method A | 394.2 | δ 7.79-7.76 (m, 2H), 7.60 (s, 1H), 7.48-7.44 (3H), 7.26-7.25 (m, 1H), 7.16-7.12 (m, 1H), 7.05-7.01 (m, 2H), 6.37 (s, 1H), 1.31 (s, 9H) |
| 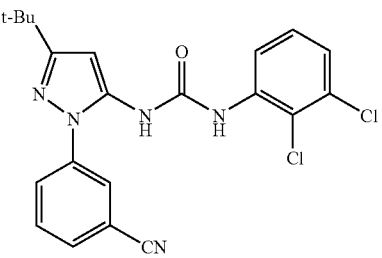<br>Example 9 | 1-(3-t-butyl)-1-(3-cyanophenyl)-1H-pyrazol-5-yl)-3-(2,3-dichlorophenyl)urea<br>16.9 mg, 19% yield<br>General method A | 428.0 | δ 8.12-8.09 (m, 1H), 7.95 (s, 1H), 7.85-7.83 (m, 1H), 7.64-7.54 (m, 3H), 7.25-7.19 (m, 2H), 6.52 (s, 1H), 1.40 (s, 9H) |
| 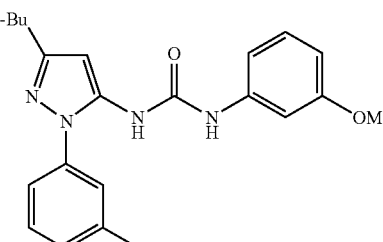<br>Example 10 | 1-(3-t-butyl)-1-(3-cyanophenyl)-1H-pyrazol-5-yl)-3-(3-methoxyphenyl)urea<br>15 mg, 19% yield<br>General method A | 390.2 | δ 7.78-7.75 (m, 2H), 7.51-7.44 (m, 2H), 7.33 (s, 1H), 7.24 (s, 1H), 7.18-7.14 (m, 1H), 6.93-6.91 (m, 1H), 6.72-6.70 (m, 1H), 6.65-6.62 (m, 1H), 6.38 (s, 1H), 3.74 (s, 3H), 1.32 (s, 9H) |
| 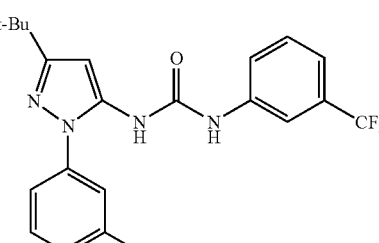<br>Example 11 | 1-(3-t-butyl)-1-(3-cyanophenyl)-1H-pyrazol-5-yl)-3-(3-trifluoromethyl)-phenyl)urea<br>36.7 mg, 41% yield<br>General method A | 428.3 | δ 9.40 (s, 1H), 8.64 (s, 1H), 8.05-8.04 (m, 1H), 7.97 (s, 1H), 7.94-7.91 (m, 1H), 7.86-7.84 (m, 1H), 7.75-7.71 (m, 1H), 7.55-7.48 (m, 2H), 7.32-7.31 (m, 1H), 6.44 (s, 1H), 1.30 (s, 9H) |
| 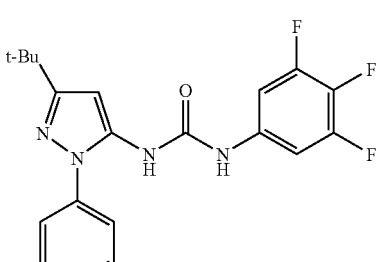<br>Example 12 | 1-(3-t-butyl)-1-(3-cyanophenyl)-1H-pyrazol-5-yl)-3-(3,4,5-trifluorophenyl)urea<br>68 mg, 55% yield<br>General method D | 414.0 | (acetone-d6): δ 8.76 (brs, 1H), 8.09 (brs, 1H), 8.02 (t, J = 1.6 Hz, 1H,), 7.97 (dt, J = 8.0, and 2.0 Hz, 1H,), 7.76 (dt, J = 8.0, and 1.4 Hz, 1H,), 7.71 (t, J = 8.0 Hz, 1H,), 7.35-7.29 (m, 2H), 6.44 (s, 1H), 1.32 (s, 9H). |

Example 13

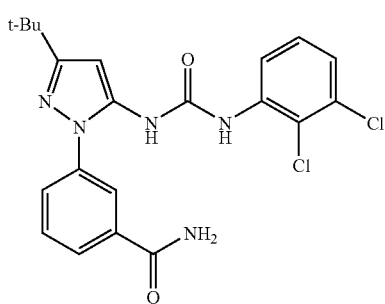

Example 9 (80 mg, 0.19 mmol) was suspended in conc. HCl (0.93 mL) and briskly stirred. More conc. HCl (1 mL) was added several times to maintain good stirring and keep the solids wetted. The reaction was stirred at RT for 5 h and 24 h at 40° C. The reaction was cooled to RT, diluted with $H_2O$ and EtOAc and the layers separated. The aqueous was extracted with EtOAc (2×). Solids in the aqueous layer were collected by filtration, rinsed sparingly with $H_2O$ and dried. These solids were suspended in MeOH, then collected by filtration, rinsed with MeOH and washed with EtOAc to afford 1-[3-t-butyl-1-(3-carbamoylphenyl)-1H-pyrazol-5-yl]-3-(2,3-dichlorophenyl)urea (47.3 mg, 57% yield) as a white solid. $^1$H NMR (400 MHz, DMSO-$d_6$): δ 9.81 (brs, 1H), 8.99 (brs, 1H), 8.25 (brs, 1H), 8.08 (s, 1H), 7.99-7.97 (m, 1H), 7.90-7.87 (m, 1H), 7.75-7.71 (m, 1H), 7.60-7.57 (m, 1H), 7.49 (brs, 1H), 7.32-7.28 (m, 2H), 6.38 (brs, 1H), 1.29 (s, 9H); MS (ESI) m/z: 446.3 (M+H$^+$), 448.3 (M+2H$^+$).

Example A4

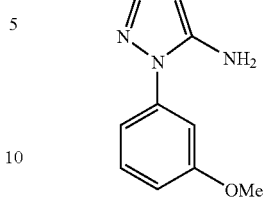

To a solution of commercially available 3-methoxyphenylhydrazine hydrochloride (1.0 g, 5.7 mmol) in toluene (5 mL) was added commercially available pivaloylacetonitrile (0.70 g, 5.5 mmol). The reaction mixture was heated at reflux for 5 h, filtered and washed with hexane to obtain 3-t-butyl-1-(3-methoxyphenyl)-1H-pyrazol-5-amine (1.22 g, 89% yield) as its hydrochloride salt as a pale yellow solid which was used without further purification. $^1$H NMR (300 MHz, CDCl$_3$): δ 7.35 (t, J=8.4 Hz, 1H), 7.04 (t, J=2.1 Hz, 1H), 7.00 (dd, J=1.5 and 7.5 Hz, 1H), 6.95 (dd, J=2.1 and 8.4 Hz, 1H), 5.90 (brs, 2H), 5.83 (s, 1H), 3.81 (s, 3H), 1.89 (s, 9H); MS (EI) m/z: 246 (M+H$^+$).

General Experimental for Examples 14-17

Using general method A, a solution of Example A4 (70 mg, 0.29 mmol) and the appropriate isocyanate (0.29 mmol) were converted to the target compound.

| Example | Name | MS (EI) (M + H$^+$) | $^1$H NMR (300 MHz/ 400 MHz, CDCl$_3$) |
|---|---|---|---|
| 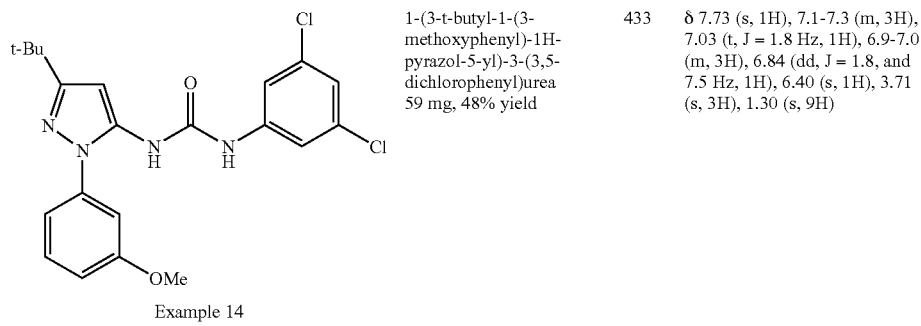<br>Example 14 | 1-(3-t-butyl-1-(3-methoxyphenyl)-1H-pyrazol-5-yl)-3-(3,5-dichlorophenyl)urea<br>59 mg, 48% yield | 433 | δ 7.73 (s, 1H), 7.1-7.3 (m, 3H), 7.03 (t, J = 1.8 Hz, 1H), 6.9-7.0 (m, 3H), 6.84 (dd, J = 1.8, and 7.5 Hz, 1H), 6.40 (s, 1H), 3.71 (s, 3H), 1.30 (s, 9H) |
| 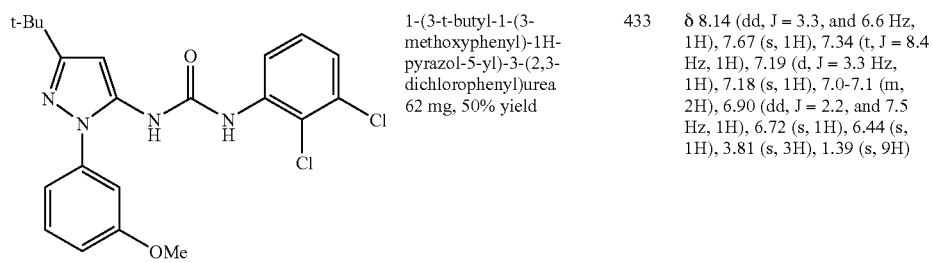<br>Example 15 | 1-(3-t-butyl-1-(3-methoxyphenyl)-1H-pyrazol-5-yl)-3-(2,3-dichlorophenyl)urea<br>62 mg, 50% yield | 433 | δ 8.14 (dd, J = 3.3, and 6.6 Hz, 1H), 7.67 (s, 1H), 7.34 (t, J = 8.4 Hz, 1H), 7.19 (d, J = 3.3 Hz, 1H), 7.18 (s, 1H), 7.0-7.1 (m, 2H), 6.90 (dd, J = 2.2, and 7.5 Hz, 1H), 6.72 (s, 1H), 6.44 (s, 1H), 3.81 (s, 3H), 1.39 (s, 9H) |

| Example | Name | MS (EI) (M + H⁺) | $^1$H NMR (300 MHz/ 400 MHz, CDCl$_3$) |
|---|---|---|---|
| Example 16 | 1-(3-t-butyl-1-(3-methoxyphenyl)-1H-pyrazol-5-yl)-3-(4-cyanophenyl)urea 79 mg, 71% yield | 390 | δ 8.70 (s, 1H), 7.47 (AB quartet, J = 8.7 Hz, 2H), 7.40 (AB quartet, J = 8.7 Hz, 2H), 7.37 (s, 1H), 7.11 (t, J = 7.8 Hz, 1H), 6.7-6.9 (m, 3H), 6.42 (s, 1H), 3.59 (s, 3H), 1.24 (s, 9H) |
| Example 17 | 1-(3-t-butyl-1-(3-methoxyphenyl)-1H-pyrazol-5-yl)-3-(3-cyanophenyl)urea 35 mg, 50% yield | 390 | δ 8.14 (s, 1H), 7.61 (s, 1H), 7.52 (m, 1H), 7.35 (t, J = 8.0 Hz, 1H), 7.29 (d, J = 6.9 Hz, 1H), 7.21 (d, J = 8.0 Hz, 1H), 7.18 (s, 1H), 6.90 (s, 1H), 6.88 (d, J = 7.6 Hz, 1H), 6.80 (dd, J = 2.4, and 7.6 Hz, 1H), 6.42 (s, 1H), 3.67 (s, 3H), 1.30 (s, 9H) |

Example 18

Example 19

A mixture of commercially available (4-methoxyphenyl)-hydrazine (17.4 g, 0.1 mol) and commercially available pivaloylacetonitrile (13.8 g, 0.11 mol) in EtOH (500 mL) and conc. HCl (50 mL) was heated at reflux overnight. After removal of the solvent, the residue was purified by column chromatography to afford 3-t-butyl-1-(4-methoxyphenyl)-1H-pyrazol-5-amine (20 g, 82% yield). $^1$H NMR (300 MHz, DMSO-d$_6$): δ 7.38 (d, J=9.0 Hz, 2H), 6.97 (d, J=9.0 Hz, 2H), 5.32 (s, 1H), 4.99 (brs, 2H), 3.75 (s, 3H), 1.17 (s, 9H); MS (ESI) m/z: 246 (M+H⁺).

Using general method A, a solution of the previous compound (123 mg, 0.29 mmol) and the 1,2-dichloro-3-isocyanatobenzene (98 mg, 0.5 mmol) were combined to afford 1-[3-t-butyl-1-(4-methoxyphenyl)-1H-pyrazol-5-yl]-3-(2,3-dichlorophenyl)urea (65 mg, 30% yield). $^1$H NMR (300 MHz, DMSO-d$_6$): δ 9.12 (s, 1H), 8.75 (s, 1H), 8.05 (m, 1H), 7.38 (d, J=7.2 Hz, 2H), 7.29-7.27 (m, 2H), 7.05 (d, J=6.9 Hz, 2H), 6.33 (s, 1H), 3.79 (s, 3H), 1.24 (s, 9H); MS (ESI) m/z: 433 (M+H⁺).

Using General method A, ethyl 4-(3-t-butyl-5-amino-1H-pyrazol-1-yl)benzoate (1 g, 3.09 mmol, prepared from ethyl 4-hydrazinobenzoate and pivaloylacetonitrile by the procedure of Regan, et al., *J. Med. Chem.*, 45, 2994 (2002)) and 1,2-dichloro-3-isocyanato-benzene (0.7 g, 3.71 mmol) were combined to afford ethyl 4-{3-t-butyl-5-[3-(2,3-dichlorophenyl)-ureido]-1H-pyrazol-1-yl}benzoate (0.7 g, 48% yield). $^1$H NMR (300 MHz, DMSO-d$_6$): δ 9.20 (brs, 1H), 8.77 (brs, 1H), 8.04 (m, 1H), 7.44 (brs, 4H), 7.29-7.26 (m, 2H), 6.36 (s, 1H), 4.31 (q, J=7.2 Hz, 2H), 1.27 (s, 9H), 1.26 (t, J=7.2 Hz, 3H).

Using General method C, ethyl 4-{3-t-butyl-5-[3-(2,3-dichlorophenyl)-ureido]-1H-pyrazol-1-yl}benzoate (80 mg, 0.17 mmol) was reduced to afford 1-{3-t-butyl-1-[4-(hydroxymethyl)-phenyl]-1H-pyrazol-5-yl}-3-(2,3-dichlorophenyl)urea (50 mg, 68% yield). $^1$H NMR (300 MHz, DMSO-d$_6$): δ 9.20 (brs, 1H), 8.77 (brs, 1H), 8.04 (m, 1H) 7.45 (br s, 4H), 7.30-7.25 (m, 2H), 6.36 (s, 1H), 4.55 (s, 2H), 1.27 (s, 9H).

Example 20

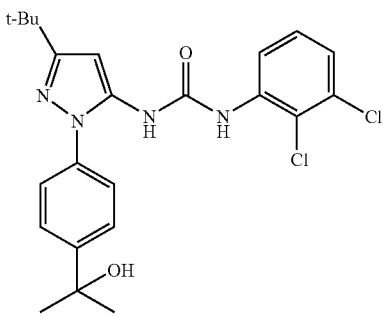

Using the same procedureas for Example 2, Example 19 (100 mg, 0.21 mmol) in fresh THF (10 mL) was transformed to 1-{3-t-butyl-1-[4-(2-hydroxypropan-2-yl)phenyl]-1H-pyrazol-5-yl}-3-(2,3-dichlorophenyl)urea (50 mg, 52% yield). $^1$H NMR (300 MHz, DMSO-d$_6$): δ 9.25 (brs, 1H), 8.79 (brs, 1H), 8.03 (m, 1H), 7.60 (d, J=8.4 Hz, 2H), 7.42 (d, J=8.4 Hz, 2H), 7.30-7.28 (m, 2H), 6.36 (s, 1H), 1.45 (s, 6H), 1.25 (s, 9H).

Example A5

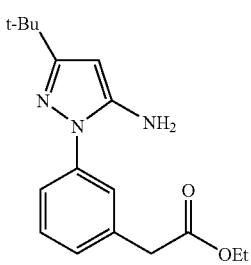

A mixture of 1-(3-nitrophenyl)ethanone (82.5 g, 0.5 mol), p-TsOH (3 g) and sulfur (32 g, 1.0 mol) in morpholine (100 mL) was heated at reflux for 3 h. After removal of the solvent, the residue was dissolved in dioxane (100 mL). The mixture was treated with conc. HCl (100 mL) and then heated at reflux for 5 h. After removal of the solvent, the residue was extracted with EtOAc (3×150 mL). The combined organic extracts were washed with brine, dried (Na$_2$SO$_4$), filtered, and concentrated. The residue was dissolved in EtOH (250 mL) and SOCl$_2$ (50 mL) and heated at reflux for 2 h. After removal of the solvent, the residue was extracted with EtOAc (3×150 mL). The combined organic extracts were washed with brine, dried (Na$_2$SO$_4$), filtered, concentrated and purified via column chromatography to afford ethyl (3-nitrophenyl)acetate (40 g). $^1$H NMR (300 MHz, DMSO-d$_6$): δ 8.17 (s, 1H,), 8.11 (d, J=7.2 Hz, 1H), 7.72 (d, J=7.2 Hz, 1H), 7.61 (t, J=7.8 Hz, 1H), 4.08 (q, J=7.2 Hz, 2H), 3.87 (s, 2H), 1.17 (t, J=7.2 Hz, 3H).

A mixture of ethyl (3-nitrophenyl)acetate (21 g, 0.1 mol) and 10% Pd/C (2 g) in MeOH (300 mL) was stirred at RT under H$_2$ 40 (psi) for 2 h. The reaction mixture was filtered and the filtrate was concentrated to afford ethyl (3-aminophenyl)acetate (17 g). MS (ESI) m/z: 180 (M+H$^+$).

To a suspension of (3-aminophenyl)acetic acid (17 g, 94 mmol) in conc. HCl (50 mL) was added dropwise a solution of NaNO$_2$ (6.8 g, 0.1 mol) in H$_2$O at 0° C. The mixture was stirred for 1 h, after which a solution of SnCl$_2$.2H$_2$O (45 g, 0.2 mol) in conc. HCl was added dropwise at such a rate that the reaction mixture never rose above 5° C. The resulted mixture was stirred for 2 h. The precipitate was collected by suction, and washed with Et$_2$O to afford ethyl (3-hydrazinophenyl)acetate (15 g). MS (ESI) m/z: 195 (M+H$^+$).

A solution of ethyl (3-hydrazinophenyl)acetate (15 g, 65 mmol) and 4,4-dimethyl-3-oxopentanenitrile (12.5 g, 0.1 mol) in EtOH (100 mL) containing conc. HCl (25 mL) was heated at reflux overnight. After removal of the solvent, the residue was washed with Et$_2$O to afford ethyl 2-(3-(5-amino-3-t-butyl-1H-pyrazol-1-yl)phenyl)acetate (18 g). MS (ESI) m/z: 302 (M+H$^+$).

Example A6

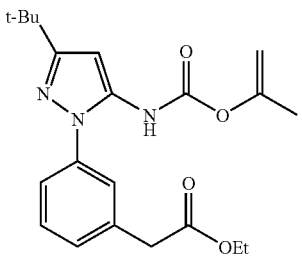

Using general method H, Example A5 (1.08 g, 3.18 mmol) was transformed to ethyl 2-(3-(3-t-butyl-5-((prop-1-en-2-yloxy)carbonyl)-1H-pyrazol-1-yl)phenyl)acetate (1.23 g, 100% yield). $^1$H NMR (400 MHz, CDCl$_3$): δ 7.50-7.32 (m, 4H), 6.80-6.48 (brs, 1H), 4.81 (brs, 1H), 4.75 (s, 1H), 4.17 (q, J=7.1 Hz, 2H), 3.70 (s, 2H), 1.98 (brs, 3H), 1.36 (s, 9H), 1.29 (t, J=7.1 Hz, 3H); MS (ESI) m/z: 386.2 (M+H$^+$).

Example A7

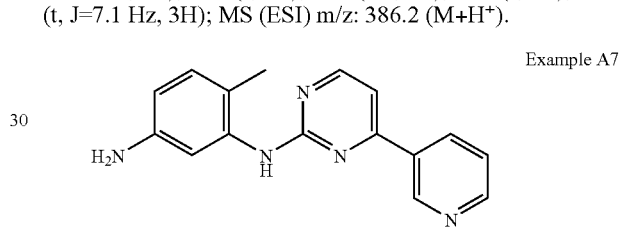

To a solution of N-(3-amino-4-methylphenyl)acetamide (5 g, 25 mmol, commercially available) in DMF (5 mL) was added 2-chloro-4-(pyridin-3-yl)-pyrimidine (4 g, 35 mmol, commercially available) and KI (0.5 g, 3 mmol). After stirring at 100° C. overnight, the reaction mixture was cooled to 10° C., quenched with H$_2$O, (100 mL), extracted with CH$_2$Cl$_2$ (2×100 mL) and the combined organic layers were dried (Na$_2$SO$_4$) and concentrated. The residue was dissolved in conc. HCl (10 mL), stirred at 80° C. for 2 h, and then concentrated to yield 6-methyl-N'-(4-(pyridin-3-yl)pyrimidin-2-yl)benzene-1,3-diamine hydrochloride (4.5 g, 65% yield) as the HCl salt. $^1$H NMR (300 MHz, CDCl$_3$): δ 7.93-7.96 (m, 2H), 7.50-7.47 (m, 1H), 7.47-7.41 (m, 5H), 7.25-7.27 (m, 2H), 2.21 (s, 3H); MS (ESI) m/e: 277 (M+H$^+$).

Example 21

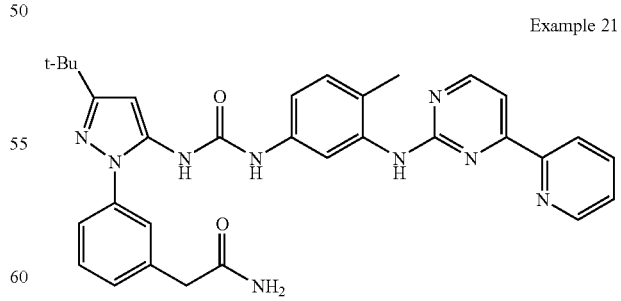

Example A6 (150 mg, 0.39 mmol) and Example A7 (108 mg, 0.39 mmol) and N-methylpyrrolidine (8.9 mg, 0.10 mmol) in THF (0.4 mL) were heated at 55° C. for 24 h. The crude reaction mixture was chromatographed on silica gel to provide ethyl 2-(3-(3-t-butyl-5-(3-(4-methyl-3-(4-(pyridin- 3-yl)pyrimidin-2-ylamino)phenyl)ureido)-1H-pyrazol-1-yl)
phenyl)acetate (236 mg, 100% yield) as a straw-colored solid.
¹H NMR (400 MHz, DMSO-d₆): δ 9.29 (d, J=1.6 Hz, 1H),
8.99 (s, 1H), 8.85 (s, 1H), 8.69 (dd, J=4.7, and 1.6 Hz, 1H),
8.51-8.46 (m, 2H), 8.42 (s, 1H), 7.82 (d, J=1.4 Hz, 1H),
7.54-7.40 (m, 5H), 7.31 (d, J=7.5 Hz, 1H), 7.12 (d, J=7.5 Hz,
1H), 7.06 (dd, J=8.0, and 2.1 Hz, 1H), 6.40 (s, 1H), 4.07 (q,
J=7.0 Hz, 2H), 3.76 (s, 2H), 2.19 (s, 3H), 1.27 (s, 9H), 1.18 (t,
J=7.0 Hz, 3H); MS (ESI) m/z: 605.3 (M+H⁺).

To this material (97 mg, 0.16 mmol) was added 7N NH₃/
MeOH (1.0 mL, 7.0 mmol) and the resultant solution was
heated to 55° C. overnight in a sealed vessel. The reaction
mixture was concentrated in vacuo and the residue dissolved
in boiling EtOAc. Upon cooling, crystallization ensued. The
solid was collected, pulverized, and suspended in THF (10
mL). 1N HCl (0.15 mmol) was added and the solution was
stirred overnight and then concentrated to dryness. Acetonitrile was added and the suspension was concentrated to dryness again. To a suspension of the pumpkin-orange colored
solid in MeCN (10 mL) was added just enough MeOH to
affect dissolution. The resultant solution was then concentrated to about 2 mL by distillation at atmospheric pressure.
The fine orange precipitate that formed was collected by
filtration, washed with MeCN and dried in vacuo to provide
1-(1-(3-(2-amino-2-oxoethyl)phenyl)-3-t-butyl-1H-pyrazol-
5-yl)-3-(4-methyl-3-(4-(pyridin-3-yl)pyrimidin-2-ylamino)
phenyl)urea as the hydrochloride salt (30 mg, 32% yield). ¹H
NMR (400 MHz, DMSO-d₆): δ 9.44 (brs, 1H), 9.30 (brs, 1H),
9.11 (brs, 1H), 9.01 (m, 1H), 8.92 (m, 1H), 8.62 (m, 2H), 7.95
(m, 1H), 7.83 (s, 1H), 7.56 (m, 2H), 7.45-7.37 (m, 4H), 7.29
(d, J=7.8 Hz, 1H), 7.13 (d, J=7.6 Hz, 1H), 7.07 (d, J=7.3 Hz,
1H), 6.37 (s, 1H), 3.47 (s, 2H), 2.19 (s, 3H), 1.27 (s, 9H); MS
(ESI) m/z: 576.2 (M+H⁺).

Example 22

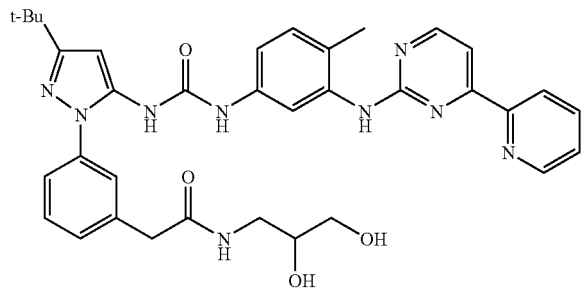

Using the same method as for Example 21, ethyl 2-(3-(3-
t-butyl-5-(3-(4-methyl-3-(4-(pyridin-3-yl)pyrimidin-2-
ylamino)phenyl)ureido)-1H-pyrazol-1-yl)phenyl)acetate
(137 mg, 0.23 mmol) and 1-amino-2,3-dihydroxypropane
(49 mg, 0.54 mmol) were combined to yield 1-(3-t-butyl-1-
(3-(2-(2,3-dihydroxypropylamino)-2-oxoethyl)phenyl)-1H-
pyrazol-5-yl)-3-(4-methyl-3-(4-(pyridin-3-yl)pyrimidin-2-
ylamino)phenyl)urea (81 mg, 69% yield). ¹H NMR (400
MHz, DMSO-d₆): δ 9.29 (dd, J=2.2, and 0.8 Hz, 1H), 8.95 (s,
1H), 8.86 (s, 1H), 8.69 (dd, J=4.8, and 1.6 Hz, 1H), 8.51-8.47
(m, 2H), 8.38 (s, 1H), 8.10 (brt, J=5.8 Hz, 1H), 7.83 (d, J=1.6
Hz, 1H), 7.51 (ddd, J=8.4, 4.7, and 0.8 Hz, 1H), 7.47-7.42 (m,
3H), 7.36 (m, 1H), 7.31 (brd, J=7.6 Hz, 1H), 7.11 (d, J=8.5
Hz, 1H), 7.05 (dd, J=8.5, and 2.1 Hz, 1H), 6.41 (s, 1H), 4.76
(d, J=4.8 Hz, 1H), 4.51 (t, J=5.8 Hz, 1H), 3.53 (s, 2H), 3.48
(m, 1H), 3.30-3.18 (m, 3H), 2.96 (m, 1H), 2.19 (s, 3H), 1.27
(s, 9H); MS (ESI) m/z: 650.3 (M+H⁺).

Example A8

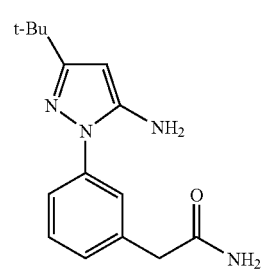

To a solution of Example A5 (6.0 g, 20 mmol) and formamide (1.8 g, 40 mmol) in DMF (20 mL) was added NaOMe
(2.1 g, 40 mmol) at RT. The mixture was heated at reflux for
1 h, concentrated and the residue was purified via column
chromatography to afford 2-[3-(5-amino-3-t-butyl-1H-pyrazol-1-yl)phenyl]acetamide (2.0 g, 40% yield). ¹H NMR (300
MHz, DMSO-d₆): δ 7.44-7.31 (m, 4H), 7.11 (m, 1H), 6.87
(brs, 1H), 5.33 (s, 1H), 5.12 (s, 2H), 3.38 (s, 2H), 1.17 (s, 9H);
MS (ESI) m/z: 273 (M+H⁺).

Example A9

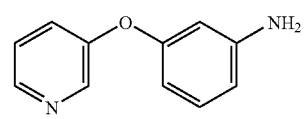

To a solution of 3-hydroxypyridine (5.01 g, 52.7 mmol) in
DMSO (60 mL) was added NaH (1.39 g, 57.9 mmol, 2.31 g of
60% suspended in oil) and stirred for 30 min at RT. To the
slurry was added 1-fluoro-3-nitrobenzene (9.66 g, 68.5
mmol) and mixture was heated to 80° C. for 72 h. The mixture
was poured into satd NH₄Cl solution (200 mL), and extracted
with EtOAc (3×125 mL). The combined organic extracts
were washed with H2O (75 mL), brine, dried (Na₂SO₄) and
concentrated to yield a crude residue which was purified by
column chromatography afford (4.43 g, 39% yield) pure 3-(3-
nitrophenoxy)pyridine as a syrup. ¹H NMR (400 MHz,
Acetone-d₆): δ 8.49-8.47 (m, 2H), 8.07-8.05 (m, 1H), 7.85 (t,
J=2.4 Hz, 1H), 7.74 (t, J=8.4 Hz, 1H), 7.58-7.53 (m, 2H),
7.51-7.47 (m, 1H); MS (ESI) m/z: 217.0 (M+H⁺).

Example A10

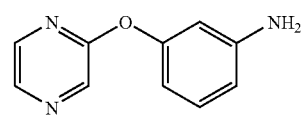

To a solution of 3-(3-nitrophenoxy)pyridine (4.43 g, 20.5
mmol) in EtOAc (50 mL) was added PtO₂ (0.4 g) and the
mixture was stirred at RT overnight under H₂ (1 atm). The
mixture was filtered through Celite®, the Celite® washed
with EtOAc (2×20 mL) and the combined filtrates concentrated to yield (3.77 g, 99% yield) pure 3-(pyridin-3-yloxy)
benzenamine as a syrup. ¹H NMR (400 MHz, DMSO-d₆): δ
8.34-8.32 (m, 2H), 7.40-7.39 (m, 2H), 7.02 (t, J=8.0 Hz, 1H),
6.37-6.35 (m, 1H), 6.02-6.14 (m, 2H), 5.28 (brs, 2H); MS
(ESI) m/z: 187.0 (M+H⁺).

To a solution of 3-nitrophenol (0.151 g, 0.733 mmol) in
DMSO (5 mL) was added NaH (35 mg of a 60% dispersion,
0.88 mmol) at 0° C. under Ar atmosphere. After stirring for 30
min, 2-iodopyrazine (0.133 mg, 0.953 mmol) was added and mixture heated to 85° C. for 4 h. To the mixture was added satd. NH₄Cl solution (25 mL) and the product extracted with EtOAc (2×25 mL). The combined organic extracts were washed with brine, dried (Na₂SO₄) and concentrated to yield a crude residue which was purified by column chromatography to afford (97 mg, 61% yield) 2-(3-nitrophenoxy)pyrazine as a white solid. ¹H NMR (400 MHz, CDCl₃): δ 8.53 (brs, 1H), 8.38 (d, J=2.4 Hz, 1H), 8.16-8.09 (m, 3H), 7.63 (t, J=8.0 Hz, 1H), 7.57-7.54 (m, 1H); MS (ESI) m/z: 218.0 (M+H⁺).

To a solution of 2-(3-nitrophenoxy)pyrazine (97 mg, 0.45 mmol) in EtOAc (10 mL) was added PtO₂ (10 mg) and the mixture was stirred for 4 h under H₂ (1 atm). The mixture was filtered through Celite® and the Celite® was washed with EtOAc (2×5 mL). The combined filtrates were concentrated to yield (78 mg, 93%) 3-(pyrazi-yloxy)benzenamine as a solid. ¹H NMR (400 MHz, DMSO-d₆): δ 8.44 (d, J=1.6 Hz, 1H), 8.35 (d, J=2.4 Hz, 1H), 8.23-8.22 (m, 1H), 7.04 (t, J=8.0 Hz, 1H), 6.43 (dd, J=8.0 Hz, and 2.0 Hz, 1H), 6.31 (t, J=2.0 Hz, 1H), 6.26 (dd, J=8.0 Hz, 2.0 Hz, 1H), 5.27 (brs, 2H); MS (ESI) m/z: 188.1 (M+H⁺).

Example A11

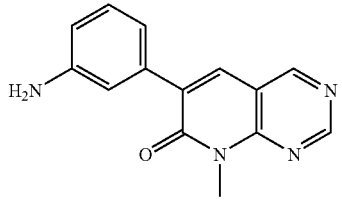

To a solution of 2-ethoxymethylenemalonic acid diethyl ester (59.0 g, 273 mmol) in EtOH (300 mL) was added 2-methyl-isothiourea (41.5 g, 150 mmol) in an ice-H₂O bath. An EtOHic solution of EtONa (2M, 300 mL) was added dropwise maintaining the reaction temperature under 5° C. The mixture was warmed to RT and stirred for 3 h. After standing overnight, the solvent was removed under reduced pressure and the residue was dissolved in H₂O (800 mL) at 0° C. The solution was acidified to pH 3 with conc. HCl and the precipitate collected by filtration and air-dried to yield 4-hydroxy-2-methylsulfanyl-pyrimidine-5-carboxylic acid ethyl ester as a white solid (50.8 g, 87.6% yield). ¹H NMR (400 MHz, DMSO-d₆): δ 8.48 (s, 1H), 4.20 (q, J=9.6 Hz, 2H), 2.51 (s, 3H), 1.23 (t, J=9.6 Hz, 3H).

A mixture of 4-hydroxy-2-(methylsulfanyl)pyrimidine-5-carboxylic acid ethyl ester (50 g, 0.234 mmol), POCl₃ (110 mL, 1.17 mmol) and diethylaniline (70 mL, 0.28 mmol) was refluxed for 5 h. The solvent was removed under vacuum and the residue was dissolved in ice H₂O and cautiously neutralized with aqueous NaHCO₃. After extraction with EtOAc (3×400 mL), the organic extracts were combined, dried and concentrated to give 4-chloro-2-(methylsulfanyl)pyrimidine-5-carboxylic acid ethyl ester as a yellow solid (42 g, 77% yield). ¹H NMR (300 MHz, CDCl₃): δ 8.92 (s, 1H), 4.41 (q, J=7.2 Hz, 2H), 1.40 (t, J=7.2 Hz, 3H).

To a solution of 4-chloro-2-(methylsulfanyl)pyrimidine-5-carboxylic acid ethyl ester (42 g, 0.181 mol) in EtOH (400 mL) was added MeNH₂ (12.3 g, 0.398 mmol) in EtOH (100 mL) at 0° C. and the mixture stirred for 3 h. The mixture was concentrated to remove most of the solvent and then partitioned between H₂O (200 mL) and CH₂Cl₂ (500 mL). The organic layer was washed with brine, dried and concentrated to give 4-(methylamino)-2-(methylsulfanyl)pyrimidine-5-carboxylic acid ethyl ester as a white solid (36.0 g, 88% yield). ¹H NMR (300 MHz, CDCl₃): δ 8.59 (s, 1H), 8.18 (brs, 1H), 4.31 (q, J=7.2 Hz, 2H), 3.05 (d, J=4.8 Hz, 3H), 2.52 (s, 3H), 1.34 (t, J=7.2 Hz, 3H).

To a solution of 4-(methylamino)-2-(methylsulfanyl)pyrimidine-5-carboxylic acid ethyl ester (30 g, 132 mmol) in THF (300 mL) was added LiAlH₄ powder (7.5 g, 198 mmol) at RT. After 1 h, the reaction was carefully quenched with H₂O (10 mL) and 10% NaOH (7 mL). The mixture was stirred for 1 h and then filtered. The filtrate was concentrated to give crude (4-(methylamino)-2-(methylthio)pyrimidin-5-yl)methanol (22.0 g, 90% yield), which was used in the next reaction without further purification. ¹H NMR (300 MHz, DMSO-d₆): δ 7.79 (s, 1H), 6.79 (m, 1H), 5.04 (t, J=5.4 Hz, 1H), 4.27 (d, J=5.4 Hz, 2H), 2.83 (d, J=4.8 Hz, 3H), 2.40 (s, 3H).

A mixture of (4-(methylamino)-2-(methylthio)pyrimidin-5-yl)methanol (22.0 g, 119 mmol) and MnO₂ (44 g, 714 mmol) in CHCl₃ (300 mL) was stirred at RT for 3 h. The reaction was filtered and the filtrate concentrated to give 4-(methylamino)-2-(methylsulfanyl)pyrimidine-5-carbaldehyde as a pale solid (20 g, 92% yield). ¹H NMR (400 MHz, DMSO-d₆): δ 9.71 (s, 1H), 8.60 (brs, 1H), 8.49 (s, 1H), 2.96 (d, J=4.8 Hz, 3H), 2.48 (s, 3H).

To a solution of 4-(methylamino)-2-(methylsulfanyl)pyrimidine-5-carbaldehyde (10.0 g, 55 mmol) and (3-nitrophenyl)acetonitrile (10.5 g, 65 mmol) in DMF (150 mL) was added K₂CO₃ (38 g, 275 mmol) at RT. The mixture was stirred at 100° C. for 18 h. After cooling, the reaction was diluted with DMF (50 mL) and filtered. The filtrate was concentrated to give crude 8-methyl-2-(methylsulfanyl)-6-(3-nitrophenyl)-8H-pyrido[2,3-d]pyrimidin-7-ylideneamine (9.0 g, 50% yield) which was used in the next reaction without further purification.

A solution of 8-methyl-2-(methylsulfanyl)-6-(3-nitrophenyl)-8H-pyrido[2,3-d]pyrimidin-7-ylideneamine (9.0 g, crude product) in Ac₂O (100 mL) was refluxed for 20 min. The mixture was concentrated to give a brown solid. The solid was then dissolved in conc. HCl (50 mL) and heated for 30 min. The reaction mixture was cooled and filtered to give a brown solid, which was purified by reverse phase chromatography to give 8-methyl-(2-methylsulfanyl)-6-(3-nitrophenyl)-8H-pyrido[2,3-d]pyrimidin-7-one as a white solid (1.1 g, 21% yield, two steps). ¹H NMR (300 MHz, DMSO-d₆): δ 8.95 (s, 1H), 8.60 (m, 1H), 8.34 (s, 1H), 8.25 (d, J=5.4 Hz, 1H), 8.16 (d, J=5.1 Hz, 1H), 7.75 (t, J=5.4 Hz, 1H), 3.68 (t, J=5.4 Hz, 3H), 2.62 (s, 3H).

To a solution of 8-methyl-2-(methylsulfanyl)-6-(3-nitrophenyl)-8H-pyrido[2,3-d]pyrimidin-7-one (1.0 g, 3 mmol) in EtOH (10 mL) was added Raney® nickel (5 g) and the mixture refluxed for 3 h. After cooling, the reaction was filtered and the filtrate concentrated to give 8-methyl-6-(3-nitrophenyl)-8H-pyrido[2,3-d]pyrimidin-7-one (0.35 g, 41% yield), which was used in the next reaction without further purification.

To a solution of 8-methyl-6-(3-nitrophenyl)-8H-pyrido[2,3-d]pyrimidin-7-one (0.35 g, 1.2 mmol) in EtOH (10 mL) was added Pd (0.2 g). The mixture was stirred under an atmosphere of H₂ (30 psi) for 1.5 h. After removal of the catalyst by filtration, the solvent was evaporated under vacuum to give 6-(3-aminophenyl)-8-methyl-8H-pyrido[2,3-d]pyrimidin-7-one (150 mg, 50% yield) as a white solid. ¹H NMR (300 MHz, DMSO-d₆): δ 9.08 (d, J=4.2 Hz, 1H), 8.18 (s, 1H), 7.85 (m, 1H), 7.80 (d, J=5.4 Hz, 1H), 7.64 (t, J=7.8 Hz, 1H), 7.43 (d, J=5.4 Hz, 1H), 3.85 (s, 3H).

Example A12

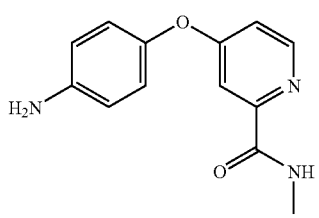

To stirred anhydrous DMF (25 mL) was slowly added SOCl$_2$ (125 mL) at such a rate that the reaction temperature was maintained at 40-50° C. Pyridine-2-carboxylic acid (25 g, 0.2 mol) was added in portions over 30 min and the resulting mixture was heated at reflux for 16 h during which time a yellow solid precipitated. After cooling to RT, the mixture was diluted with toluene (80 mL) and concentrated. This process was repeated three times. The resulting dry residue was washed with toluene and dried under reduced pressure to yield 4-chloro-pyridine-2-carbonyl chloride (27.6 g, 79%), which was used in the next step without purification.

To a solution of 4-chloro-pyridine-2-carbonyl chloride (27.6 g, 0.16 mol) in anhydrous THF (100 mL) at 0° C. was added dropwise a solution of MeNH$_2$ in EtOH. The resulting mixture was stirred at 3° C. for 4 h. The reaction mixture was concentrated under reduced pressure to yield a solid, which was suspended in EtOAc and filtered. The filtrate was washed with brine (2×100 mL), dried and concentrated to yield 4-chloro-N-methylpicolinamide as a yellow solid (16.4 g, 60% yield). $^1$H NMR (300 MHz, DMSO-d$_6$): δ 8.78 (d, J=7.2 Hz, 1H), 8.54 (d, J=7.2 Hz, 1H), 7.95 (s, 1H), 7.67-7.65 (m, 1H), 2.79 (d, J=4.8 Hz, 3H); MS (ESI) m/z: 171 (M+H$^+$).

A solution of 4-aminophenol (9.6 g, 88 mmol) in anhydrous DMF (100 mL) was treated with NaH (5.28 g of a 60% dispersion, 132 mmol), and the reddish-brown mixture was stirred at RT for 2 h. The contents were treated with 4-chloro-N-methylpicolinamide (15 g, 88 mmol) and K$_2$CO$_3$ (6.5 g, 44 mmol) and heated at 80° C. for 8 h. The mixture was cooled to RT and partitioned between EtOAc and brine. The aqueous phase was extracted with EtOAc. The combined organic layers were washed with brine (2×50 mL), dried (Na$_2$SO$_4$) and concentrated to afford 4-(4-amino-phenoxy)pyridine-2-carboxylic acid methylamide (15 g, 71% yield). $^1$H NMR (300 MHz, DMSO-d$_6$): δ 8.71 (d, J=1.8 Hz, 1H), 8.43 (d, J=5.7 Hz, 1H), 7.32 (d, J=2.7 Hz, 1H), 7.06-7.03 (m, 1H), 6.76 (dd, J=8.7 Hz, 4H), 5.15 (s, 2H), 2.76 (d, J=4.8 Hz, 3H); MS (ESI) m/z: 244 (M+H$^+$).

Example A13

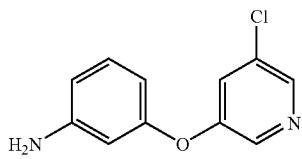

A solution of 5-chloro-3-hydroxypyridine (0.45 g, 3.5 mmol) and NaH (0.15 g of 60% dispersion, 3.83 mmol) in DMSO (10 mL) was stirred at RT for 30 min and then treated with 1-fluoro-3-nitrobenzene (0.69 g, 4.9 mmol). The mixture was heated at 120° C. for 24 h, cooled to RT, quenched with satd. NH$_4$Cl (50 mL), and extracted with EtOAc (3×25 mL). The combined organic extracts were washed with brine, dried (Na$_2$SO$_4$) and concentrated to yield a crude residue which was purified via column chromatography using to yield 3-chloro-5-(3-nitrophenoxy)pyridine (0.2 g, 23% yield) as a yellow solid. $^1$H NMR (400 MHz, CDCl$_3$): □ 8.46 (d, J=-2.0 Hz, 1H), 8.35 (d, J=2.0 Hz, 1H), 8.09 (dd, J=8.4 Hz, 2.0 Hz, 1H), 7.89 (t, J=2.0 Hz, 1H), 7.60 (t, J=8.0 Hz, 1H), 7.41-7.39 (m, 2H); MS (ESI) m/z: 251.0 (M+H$^+$).

To a solution of 3-chloro-5-(3-nitrophenoxy)pyridine (0.2 g, 0.8 mmol) in EtOAc (10 mL) was added PtO$_2$ (0.02 g) and the mixture was stirred for 4 h under H$_2$ (1 atm). It was then filtered through a Celite® pad and washed with EtOAc (2×5 mL). The combined organic extracts were concentrated to afford 3-(5-chloropyridin-3-yloxy)benzenamine (0.165 g, 93% yield) which was used without further purification. $^1$H NMR (400 MHz, DMSO-d$_6$): δ 8.39 (d, J=2.0 Hz, 1H), 8.31 (d, J=2.8 Hz, 1H), 7.54-7.53 (m, 1H), 7.05 (t, J=8.0 Hz, 1H), 6.42-6.39 (m, 1H), 6.25-6.19 (m, 2H), 5.33 (brs, 2H); MS (ESI) m/z: 221.0 (M+H$^+$).

Example 23

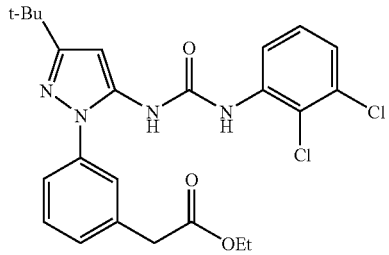

Using general method A, Example A10 (2.0 g, 6.6 mmol) and 1,2-dichloro-3-isocyanato-benzene (1.1 g, 7.5 mmol) were combined to afford ethyl 2-(3-(3-t-butyl-5-(3-(2,3-dichlorophenyl)ureido)-1H-pyrazol-1-yl)phenyl)acetate (2.2 g, 68% yield). $^1$H NMR (300 MHz, DMSO-d$_6$): δ 9.22 (s, 1H), 8.75 (s, 1H), 8.05 (m, 1H), 7.46-7.21 (m, 6H), 6.35 (s, 1H), 4.04 (q, J=7.2 Hz, 2H,), 3.72 (s, 2H), 1.24 (s, 9H), 1.16 (t, J=7.2 Hz, 3H); MS (ESI) m/z: 489 (M+H$^+$).

Example 24

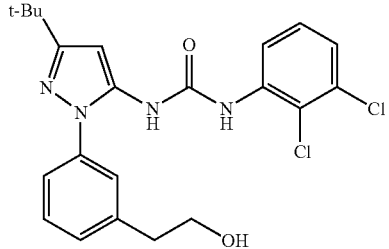

Using general method C, Example 23 (100 mg, 0.21 mmol) was reduced to yield 1-{3-t-butyl-1-[3-(2-hydroxyethyl)phenyl]-1H-pyrazol-5-yl}-3-(2,3-dichlorophenyl)urea (60 mg, 64% yield). $^1$H NMR (300 MHz, DMSO-d$_6$): δ 9.18 (s, 1H), 8.74 (s, 1H), 8.02 (m, 1H), 7.42-7.22 (m, 4H), 6.35 (s, 1H), 3.61 (t, J=7.2 Hz, 2H), 2.76 (t, J=6.9 Hz, 2H), 1.24 (s, 9H); MS (ESI) m/z: 447 (M+H$^+$).

General Experimental for Examples 25-29

A solution of Example A8 and the appropriate amine were converted to the target compound using the general method indicated.

| Example | Name | MS (EI) (M + H⁺) | ¹H NMR (300 MHz/ 400 MHz, DMSO-d₆) |
|---|---|---|---|
| 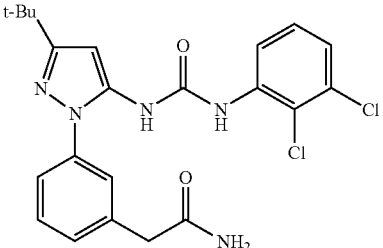 Example 25 | 1-{1-[3-(2-amino-2-oxoethyl)phenyl]-3-t-butyl-1H-pyrazol-5-yl}-3-(2,3-dichlorophenyl)urea 60 mg, 26% yield General method B | 459 | δ 9.23 (s, 1H), 8.75 (s, 1H), 8.04 (m, 1H), 7.50 (brs, 1H), 7.45-7.25 (m, 7H), 6.90 (brs, 1H), 6.36 (s, 1H), 3.42 (s, 2H), 1.24 (s, 9H) |
| 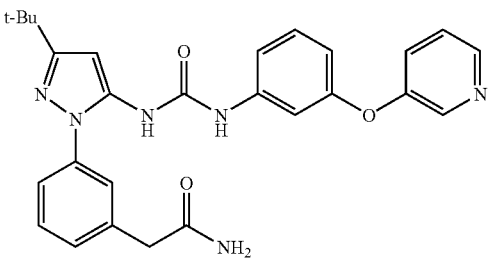 Example 26 | 1-(1-(3-(2-amino-2-oxoethyl)phenyl)-3-t-butyl-1H-pyrazol-5-yl)-3-(3-(pyridin-3-yloxy)phenyl)urea 49 mg, 46% yield General method D | 485.2 | δ 9.14 (s, 1H), 8.40-8.37 (m, 3H), 7.52 (brs, 1H), 7.46-7.40 (m, 4H), 7.36-7.25 (m, 4H), 7.09 (dt, J = 7.2 Hz, 1.2 Hz, 1H), 6.93 (brs, 1H), 6.69-6.66 (m, 1H), 6.34 (s, 1H), 3.45 (s, 2H), 1.27 (s, 9H) |
| 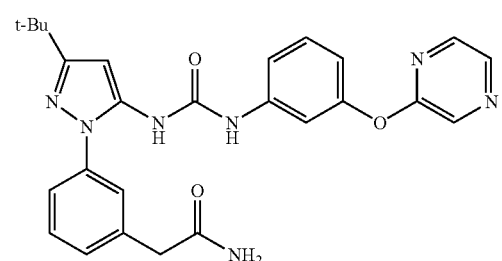 Example 27 | 1-(1-(3-(2-amino-2-oxoethyl)phenyl)-3-t-butyl-1H-pyrazol-5-yl)-3-(3-(pyrazin-2-yloxy)phenyl)urea 58 mg, 46% yield General method D | 486.2 | δ 9.35 (s, 1H), 8.57 (s, 1H), 8.53 (d, J = 1.2 Hz, 1H), 8.38 (d, J = 2.8 Hz, 1H), 8.22 (dd, J = 2.8 Hz, 1.6 Hz, 1H), 7.54 (brs, 1H), 7.46-7.29 (m, 6H), 7.15 (dt, J = 8.4 Hz, 0.8 Hz, 1H), 6.93 (brs, 1H), 6.80 (dd, J = 8.0 Hz, 1.6 Hz, 1H), 6.35 (s, 1H), 3.46 (s, 2H), 1.27 (s, 9H) |
| 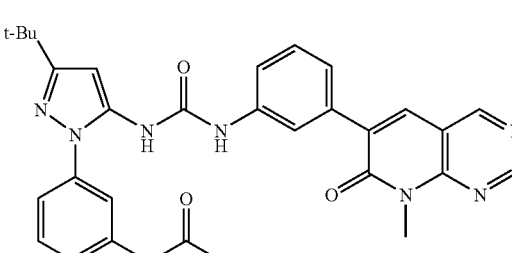 Example 28 | 1-(1-(3-(2-amino-2-oxoethyl)phenyl)-3-t butyl-1H-pyrazol-5-yl)-3-(3-(8-methyl-7-oxo-7,8-dihydropyrido[2,3-d]pyrimidin-6-yl)phenyl)urea 56 mg, 45% yield General method D | 551.2 | δ 9.40 (s, 1H), 9.17 (s, 1H), 9.13 (s, 1H), 8.62 (s, 1H), 8.17 (s, 1H), 7.83 (t, J = 1.6 Hz, 1H), 7.57 (brs, 1H), 7.47-7.28 (m, 7H), 6.94 (s, 1H), 6.39 (s, 1H), 3.71 (s, 3H), 3.48 (s, 2H), 1.28 (s, 9H) |
| 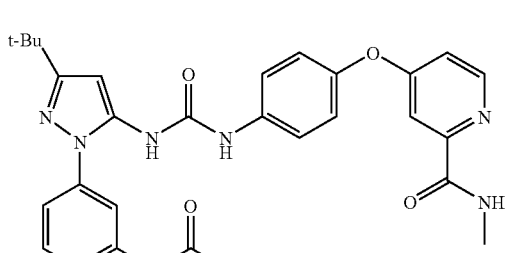 Example 29 | 1-(1-(3-(2-amino-2-oxoethyl)phenyl)-3-t-butyl-1H-pyrazol-5-yl)-3-(4-(2-(methylcarbamoyl)-pyridin-4-yloxy)phenyl)urea 60 mg, 40% yield General method D | 542.3 | δ 9.32 (s, 1H), 8.82 (d, J = 3.6 Hz, 1H), 8.57 (s, 1H), 8.51 (d, J = 5.6 Hz, 1H), 7.56-7.38 (m, 6H), 7.31 (d, J = 7.6 Hz, 1H), 7.16-7.13 (m, 3H), 6.94 (s, 1H), 6.38 (s, 1H), 3.48 (s, 2H), 2.79 (d, J = 4.8 Hz, 3H), 1.29 (s, 9H) |

Example A14

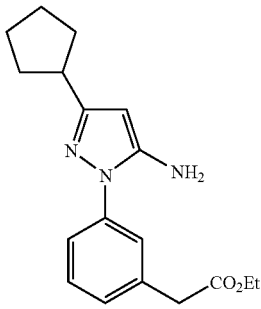

To a mixture of (3-aminophenyl)acetic acid ethyl ester (15 g, 84 mmol) in conc. HCl (20 mL) was added sodium nitrite (6 g, 87 mmol) aqueous solution dropwise under ice-salt bath. The resulting mixture was stirred at 0° C. for 30 min and then added a solution of $SnCl_2.2H_2O$ (38 g, 168 mmol) in conc. HCl dropwise also at such a rate that the reaction mixture never rose above 5° C. After the addition was completed, the mixture was stirred for another 2 h at room temperature. The precipitate was collected by suction and washed with ethyl ether to afford (3-Hydrazinophenyl)acetic acid ethyl ester hydrochloride (17 g, 88%) as a brown solid. MS (ESI) m/z: 195 (M+H+). A solution of (3-hydrazinophenyl)acetic acid ethyl ester hydrochloride (17 g, 74 mmol) and 3-cyclopentyl-3-oxopropionitrile (12.2 g, 88.8 mol) in alcohol (150 mL) containing conc. HCl (10 mL) was heated to reflux overnight. After removed of the solvent, the precipitate was collected by suction and washed with ethyl ether to afford the crude product, which was purified by column chromatography to afford [3-(5-amino-3-cyclopentylpyrazol-1-yl)phenyl]acetic acid ethyl ester hydrochloride (8.8 g, 34% yield) as a yellow solid. $^1$H NMR (300 MHz, DMSO-d$_6$): δ 7.40-7.66 (m, 4H), 5.68 (s, 1H), 4.05 (q, J=7.2 Hz, 2H), 3.75 (s, 2H), 3.00-3.08 (m, 1H), 1.98-2.00 (m, 2H), 1.58-1.70 (m, 6H), 1.17 (t, J=7.2 Hz, 3H); MS (ESI) m/z: 314 (M+H+).

Example A15

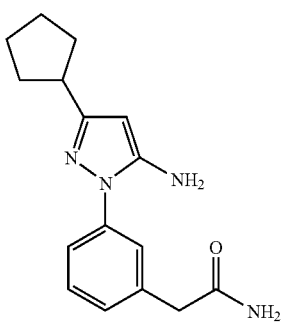

A mixture of Example A14 (0.600 g, 1.7 mmol, 1.0) and 7N NH$_3$ in MeOH (9.8 ml, 69 mmol, 40 eq) was heated in a sealed screw-cap vial at 60° C. for 36 h. More 7N NH$_3$ in MeOH (9.8 ml, 69 mmol, 40 eq) was added and the reaction heated at 60° C. 24 h. The solution was concentrated to a purple residue of 2-(3-(5-amino-3-cyclopentyl-1H-pyrazol-1-yl)phenyl)acetamide. MS (ESI) m/z: 285.2 (M+H+).

Example 30

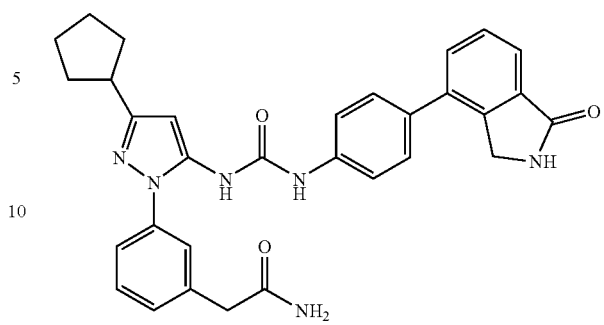

Using general method D, Example A 15 (0.1000 g, 0.218 mmol, 1.00 eq) and 4-(4-aminophenyl)isoindolin-1-one (0.0488 g, 0.218 mmol, made according to literature procedures) were combined to yield 1-(1-(3-(2-amino-2-oxoethyl)phenyl)-3-cyclopentyl-1H-pyrazol-5-yl)-3-(4-(1-oxoisoindolin-4-yl)phenyl)urea (51.7 mg, 44.5% yield). $^1$H NMR (400 MHz, DMSO-d$_6$): δ 9.17 (s, 1H), 8.67 (s, 1H), 8.50 (s, 1H), 7.66-7.62 (m, 2H), 7.59-7.52 (m, 6H), 7.48-7.44 (m, 2H), 7.40-7.37 (m, 1H), 7.32-7.30 (m, 1H), 6.94 (brs, 1H), 6.34 (s, 1H), 5.50 (s, 2H), 3.47 (s, 2H), 3.06-2.98 (m, 1H), 2.03-1.94 (m, 2H), 1.76-1.59 (m, 6H); MS (ESI) m/z: 535.2 (M+H+).

Example 31

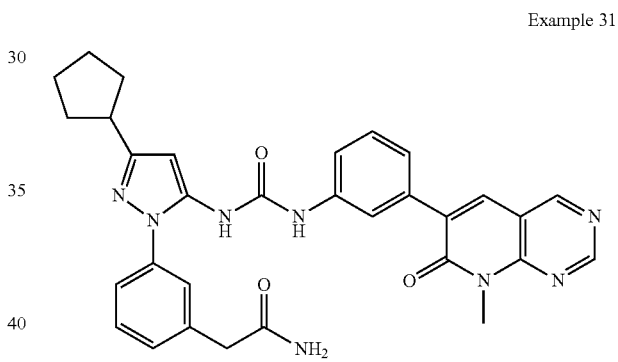

Using general method D, Example A15 (0.0805 g, 0.175 mmol, 1.00 eq) and Example A11 (0.0442 g, 0.175 mmol) were combined to yield 1-(1-(3-(2-amino-2-oxoethyl)phenyl)-3-cyclopentyl-1H-pyrazol-5-yl)-3-(3-(8-methyl-7-oxo-7,8-dihydropyrido[2,3-d]pyrimidin-6-yl)phenyl)urea (18.3 mg, 19% yield). $^1$H NMR (400 MHz, DMSO-d$_6$): δ 9.16 (s, 1H), 9.15 (s, 1H), 9.11 (s, 1H), 8.44 (s, 1H), 8.17 (s, 1H), 7.83-7.82 (m, 1H), 7.53 (brs, 1H), 7.48-7.44 (m, 3H), 7.39-7.35 (m, 2H), 7.32-7.29 (m, 2H), 6.93 (brs, 1H), 6.34 (s, 1H), 3.71 (s, 3H), 3.46 (s, 2H), 3.05-2.97 (m, 1H), 2.02-1.94 (m, 2H), 1.74-1.59 (m, 6H); MS (ESI) m/z: 563.3 (M+H+).

Example 32

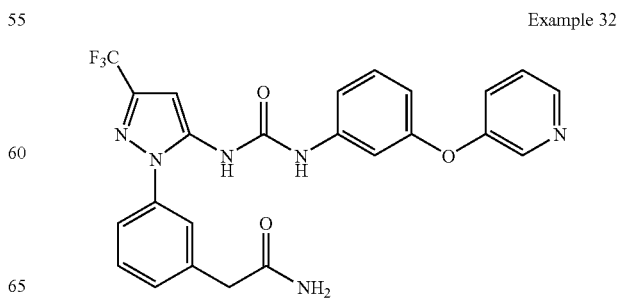

To a suspension of NaH (6.0 g of a 60% dispersion, 0.15 mol) in THF (100 ml) was added dropwise trifluoroacetic acid ethyl ester (14.2 g, 0.1 mol) and anhydrous MeCN (50 g, 0.12 mol) in THF (100 ml). The resulting mixture was refluxed overnight, and then cooled to RT. After removal of the volatiles in vacuo, the residue was diluted in EtOAc and aqueous 10% HCl. The organic layer was washed with H$_2$O and brine, dried (MgSO$_4$), filtered and concentrated to yield 15 g of crude 4,4,4-trifluoro-3-oxo-butyronitrile which was used for the next step reaction without further purification.

A mixture of ethyl (3-hydrazinophenyl)acetate (8.77 g, 0.028 mol, available from Example A5) and 4,4,4-trifluoro-3-oxo-butyronitrile (5.75 g, 0.042 mol) in EtOH (200 mL) was heated at reflux overnight. The mixture was concentrated and the residue purified by column chromatography to yield ethyl 2-(3-(5-amino-3-(trifluoromethyl)-1H-pyrazol-1-yl)phenyl)acetate (5 g, 57% yield) as a yellow oil. $^1$H NMR (300 MHz, DMSO-d$_6$): 7.50-7.43 (m, 3H), 7.30-7.33 (m, 1H), 5.81 (s, 1H), 5.75 (s, 2H), 4.09 (q, J=7.2 Hz, 1H), 3.76 (s, 2H), 3.38 (s, 2H), 1.18 (t, J=7.2 Hz, 3H); MS (ESI) m/z: 314 (M+H$^+$).

A solution of ethyl 2-(3-(5-amino-3-(trifluoromethyl)-1H-pyrazol-1-yl)phenyl)acetate (3 g, 9.58 mmol) in conc. NH$_4$OH (40 mL) was heated at reflux for 2 h. After removal of the solvent, the residue was purified by column chromatography to afford 2-(3-(5-amino-3-(trifluoromethyl)-1H-pyrazol-1-yl)phenyl)acetamide (1.8 mg, 66% yield). $^1$H NMR (300 MHz, DMSO-d$_6$): 7.48-7.42 (m, 4H), 7.30 (s, 1H), 6.91 (s, 1H), 5.77 (s, 1H), 5.73-5.72 (m, 2H), 4.44 (s, 2H). MS (ESI) m/z: 285 (M+H$^+$).

To a solution of phosgene (0.5 mL of 20% w/v solution in toluene) in MeCN (1 mL) was added over a period of 10 min a mixture of Example A9 (0.054 g, 0.29 mmol) and triethylamine (0.076 g, 0.76 mmol) in MeCN (1 mL) at 0° C. under Ar. After stirring for 30 min at RT, a solution of 2-(3-(5-amino-3-(trifluoromethyl)-1H-pyrazol-1-yl)phenyl)acetamide (0.07 g, 0.24 mmol) and Et$_3$N (0.06 g, 0.66 mmol) was added and the resulting mixture stirred at RT for 16 h. The mixture was concentrated, purified via column chromatography, stirred in HCl/EtOAc and the solid collected by filtration to yield 1-(1-(3-(2-amino-2-oxoethyl)phenyl)-3-(trifluoromethyl)-1H-pyrazol-5-yl)-3-(3-(pyridin-3-yloxy)phenyl)urea (0.041 g, 32% yield) as a white solid. $^1$H NMR (400 MHz, DMSO-d$_6$): δ 9.68 (s, 1H), 9.02 (s, 1H), 8.62 (s, 1H), 8.54 (d, J=4.8 Hz, 1H), 7.86-7.84 (m, 1H), 7.76 (dd, J=8.4 Hz, 4.8 Hz, 1H), 7.57-7.34 (m, 7H), 7.16 (dd, J=8.4 Hz, 1.6 Hz, 1H), 6.96 (s, 1H), 6.85 (s, 1H), 6.78 (dd, J=8.4 Hz, 2.0 Hz, 1H), 3.50 (s, 2H); MS (ESI) m/z: 497.0 (M+H$^+$).

Example 33

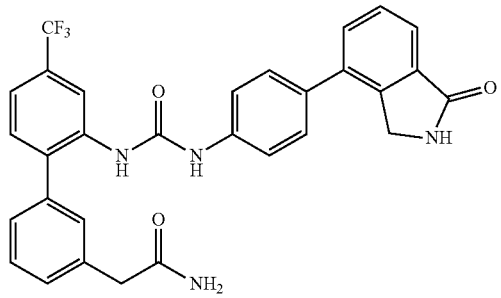

A solution of 2-(3-iodophenyl)acetic acid (1.05 g, 4.0 mmol, commercially available) in EtOH (12 mL) was treated with 2 drops of concentrated sulfuric acid. The resultant solution was heated at reflux for 90 min, cooled to RT and poured into hexanes (50 mL) and EtOAc (50 mL). The organics were with saturated Na$_2$CO$_3$ (2×50 mL), H$_2$O (50 mL), brine (50 mL), dried (MgSO$_4$) and concentrated to yield ethyl 2-(3-iodophenyl)acetate (1.11 g, 95% yield). MS (ESI) m/z: 291.0 (M+H$^+$).

Ethyl 2-(3-iodophenyl)acetate (0.500 g, 1.72 mmol), 4-bromo-3-nitrobenzotrifluoride (1.86 g, 6.89 mmol commercially available), tetrabutylammonium chloride (0.527 g, 1.90 mmol), i-Pr$_2$NEt (0.33 mL, 1.90 mmol) and Pd(OAc)$_2$ (0.039 g, 0.17 mmol) were combined neat in a sealed vial and heated at 130° C. for 65 h. The cooled reaction mixture was applied directly to silica gel and eluted with 25% EtOAc/hexanes to provide 2'-nitro-4'-(trifluoromethyl)-[1,1'-biphenyl]-3-acetic acid ethyl ester (0.107 g, 17% yield). MS (ESI) m/z: 354.0 (M+H$^+$).

2'-Nitro-4'-(trifluoromethyl)-[1,1'-biphenyl]-3-acetic acid ethyl ester (107 mg, 0.30 mmol) in THF (6 mL) was treated with about 150 mg of Raney® nickel (50 wt % in H$_2$O). The reaction was shaken on a Parr apparatus under 50 psi of H$_2$. After 4.5 h, another 200 mg of Raney® nickel was added and the reaction was shaken an additional 2 h under 50 psi H$_2$. The reaction mixture was filtered through Celite®, concentrated in vacuo and purified via column chromatography to afford 2'-amino-4'-(trifluoromethyl)-[1,1'-biphenyl]-3-acetic acid ethyl ester (58 mg, 59% yield). MS (ESI) m/z: 324.2 (M+H$^+$).

2'-Amino-4'-(trifluoromethyl)-[1,1'-biphenyl]-3-acetic acid ethyl ester (45 mg, 0.14 mmol), Example A37 (44 mg, 0.14 mmol) and N-methylpyrrolidine (1 drop) were combined in THF (0.25 mL) in a screw-cap vial. The vial was sealed and the reaction mixture was heated at 55° C. for 65 h. The crude reaction was purified via column chromatography to yield [1,1'-biphenyl]-2'-(3-(4-(1-oxoisoindolin-4-yl)phenyl)-ureido)-4'-(trifluoromethyl)-3-acetic acid ethyl ester (65 mg, 81% yield). MS (ESI) m/z: 574.0 (M+H$^+$).

A solution of [1,1'-biphenyl]-2'-(3-(4-(1-oxoisoindolin-4-yl)phenyl)-ureido)-4'-(trifluoromethyl)-3-acetic acid ethyl ester (63 mg, 0.11 mmol) in THF (2 mL) and H$_2$O (2 mL) was treated with LiOH.H$_2$O (23 mg, 0.55 mmol). After 3 h, 1N HCl (0.6 mL, 0.6 mmol) was added and the reaction mixture was diluted with EtOAc (30 mL). The organic layer was washed with H$_2$O (2×10 mL), brine (10 mL), dried (Na$_2$SO$_4$) and concentrated to yield [1,1'-biphenyl]-2'-(3-(4-(1-oxoisoindolin-4-yl)phenyl)ureido)-4'-(trifluoromethyl)-3-acetic acid (62 mg, 100% yield). MS (ESI) m/z: 546.0 (M+H$^+$).

[1,1'-Biphenyl]-2'-(3-(4-(1-oxoisoindolin-4-yl)phenyl)-ureido)-4'-(trifluoromethyl)-3-acetic acid (62 mg, 0.11 mmol) was combined with HOBT (20 mg, 0.15 mmol) and 0.5M in dioxane NH$_3$ (1.0 mL, 0.5 mmol) in DMF (2 mL). EDC (64 mg, 0.23 mmol) was added and the reaction mixture was stirred at RT for 7 h. The reaction was partitioned between H$_2$O (10 mL) and EtOAc (30 mL). The organic was washed with 1N HCl (2×5 mL), saturated Na$_2$CO$_3$ (10 mL), brine (10 mL), concentrated and purified by reverse phase chromatography to yield [1,1'-biphenyl]-2'-(3-(4-(1-oxoisoindolin-4-yl)phenyl)ureido)-4'-(trifluoromethyl)-3-acetic acid amide (36 mg, 60% yield) as a white powder. $^1$H NMR (400 MHz, DMSO-d$_6$): δ 9.35 (s, 1H), 8.66 (s, 1H), 8.50 (s, 1H), 7.99 (s, 1H), 7.65 (m, 2H), 7.60-7.38 (m, 1H), 7.35 (dt, J=7.5, 1.3 Hz, 1H), 6.96 (brd, J=1.5 Hz, 1H), 4.50 (s, 2H), 3.49 (s, 2H); MS (ESI) m/z: 545.3 (M+H$^+$).

Example 34

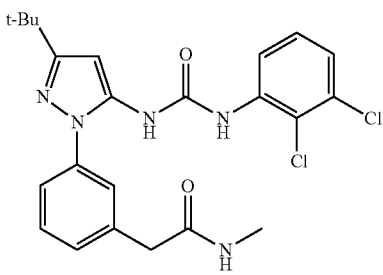

Using General method E, Example 23 (80 mg, 0.17 mmol) was saponified to afford 3-{3-t-butyl-5-[3-(2,3-dichlorophenyl)ureido]-1H-pyrazol-1-yl}benzoic acid (60 mg, 79% yield). $^1$H NMR (300 MHz, DMSO-$d_6$): δ 9.46 (brs, 1H), 8.82 (brs, 1H), 8.05 (brs, 1H), 7.98 (t, J=4.8 Hz, 1H), 7.92 (d, J=7.8 Hz, 1H), 7.80 (d, J=8.7 Hz, 1H), 7.63 (t, J=7.8 Hz, 1H), 7.27 (d, J=4.5 Hz, 2H), 6.37 (s, 1H), 1.26 (s, 9H).

Example 35

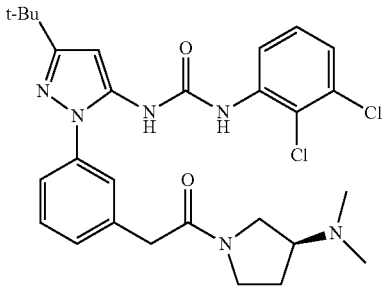

To a stirred solution of Example 34 (0.150 g, 0.325 mmol, 1.0 eq), (3S)-(−)-3-(dimethylamino)pyrrolidine (0.0446 g, 0.390 mmol, 1.2 eq) and TBTU (0.125 g, 0.390 mmol, 1.2 eq) in DMF (3 mL) was added I-PR2NET (0.173 ml, 0.975 mmol, 3.0 eq). The resulting solution was stirred at RT. Upon completion, the reaction was quenched with 3N HCl (pH 1-2) and extracted with EtOAc (1x). This extract was set aside. The aqueous was basified (pH 9-10) with satd. $Na_2CO_3$ and extracted with EtOAc (3x). The combined organics were washed with brine (2x) and dried ($Na_2SO_4$). Filtration and evaporation provided crude product as a glass which was purified by reverse phase chromatography to afford of pure 1-(3-t-butyl-1-(3-(2-((S)-3-(dimethylamino)pyrrolidin-1-yl)-2-oxoethyl)phenyl)-1H-pyrazol-5-yl)-3-(2,3-dichloro-phenyl)urea (0.132 g, 73% yield). $^1$H NMR (400 MHz, DMSO-$d_6$; rotamers): δ 9.41 and 9.39 (s, 1H), 8.88 and 8.87 (s, 1H), 8.08-8.05 (m, 1H), 7.50-7.39 (m, 4H), 7.34-7.27 (m, 4H), 6.38 (s, 1H), 3.02-3.75 (m, 4H), 3.59-3.48 (m, 2H), 2.81-2.75 (m, 6H), 2.33-2.07 (m, 2H), 1.28 (s, 9H); MS (ESI) m/z: 557.3 (M+H$^+$), 559.2 (M+2H$^+$).

Example 36

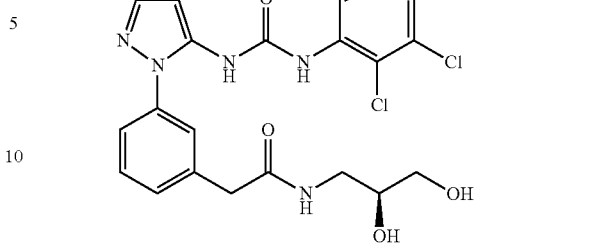

To a stirred solution of Example 34 (130 mg, 0.282 mmol), in DMF (3 mL) was added HOBT (48 mg, 0.310 mmol) and EDC (68 mg, 0.352 mmol). The mixture was stirred for 15 min and then treated with (S)-3-aminopropane-1,2-diol (32 mg, 0.352 mmol), stirred at RT overnight, and then diluted with $H_2O$ (20 mL). The aqueous layer was extracted with EtOAc (20 mL), and the combined organics washed with 5% citric acid (20 mL), saturated $NaHCO_3$ (20 mL), brine (20 mL), dried ($Na_2SO_4$), concentrated, and purified by column chromatography to yield 1-(3-t-butyl-1-(3-(2-((S)-2,3-dihydroxypropylamino)-2-oxoethyl)phenyl)-1H-pyrazol-5-yl)-3-(2,3-dichloro-phenyl)urea (90 mg, 60% yield). $^1$H-NMR (400 MHz, DMSO-$d_6$): δ 1.28 (s, 9H), 2.93-2.96 (m, 1H), 3.19-3.47 (m, 4H), 3.53 (s, 2H), 4.51 (brs, 1H), 4.76 (brs, 1H), 6.39 (s, 1H), 7.29-7.45 (m, 6H), 8.07-8.10 (m, 2H), 8.79 (s, 1H), 9.26 (s, 1H); MS (ESI) m/z: 536.0 (M+H$^+$).

Example 37

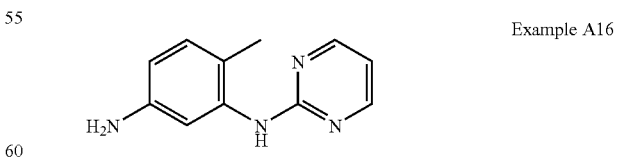

Using the same procedures for Example 36, Example 34 (100 mg, 0.20 mmol) and 2-aminoEtOH (2 mL) were combined to afford 1-(3-t-butyl-{1-[3-(2-hydroxyethylamino)-2-oxo-thyl]-phenyl}-1H-pyrazol-5-yl)-3-(2,3-dichlorophenyl)-urea (70 mg, 69% yield). $^1$H NMR (300 MHz, DMSO-$d_6$): δ 9.22 (s, 1H), 8.74 (s, 1H), 8.08-8.03 (m, 2H), 7.38-7.24 (m, 6H), 6.34 (s, 1H), 3.45 (s, 2H), 3.30 (t, J=6.0 Hz, 2H), 3.04 (t, J=6.0 Hz, 2H), 1.22 (s, 9H); MS (ESI) m/z: 504 (M+H$^+$).

Example A16

To a solution of N-(3-amino-4-methyl-phenyl)acetamide (5 g, 25 mmol) in DMF (5 mL) was added 2-chloropyrimidine (3.8 g, 33 mmol) and KI (0.5 g). The reaction was stirred at 100° C. overnight, cooled to 10° C. (100 mL). The resulting mixture was extracted with $CH_2Cl_2$ (2×100 mL). The combined organic layers were dried ($Na_2SO_4$) and concentrated under vacuum. The residue was dissolved in conc. HCl (10 mL), stirred at 80° C. for 2 h and concentrated under vacuum to yield 6-methyl-N'-(pyrimidin-2-yl)benzene-1,3-diamine hydrochloride (3.75 g, 75% yield). $^1$H NMR (400 MHz, CDCl$_3$): δ 8.36 (dd, J=15.2, 4.8 Hz, 2H), 7.46 (d, J=2.4 Hz, 1H), 6.97 (d, J=8.0 Hz, 1H), 7.26 (s, 1H), 6.67 (t, J=4.8 Hz, 1H), 6.39 (dd, J=8.0, 2.4, Hz, 1H), 2.20 (s, 3H); MS (ESI) m/e: 201 (M+H$^+$).

Example 38

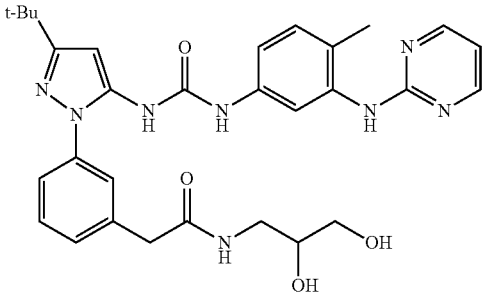

Using the same procedureas for Example 22, Example A6 (145 mg, 0.38 mmol) and Example A16 (80 mg, 0.40 mmol) were combined to yield 1-(3-t-butyl-1-(3-(2-(2,3-dihydroxypropylamino)-2-oxoethyl)phenyl)-1H-pyrazol-5-yl)-3-(4-methyl-3-(pyrimidin-2-ylamino)phenyl)urea (52 mg, 60% yield, 3 steps). $^1$H NMR (400 MHz, DMSO-d$_6$): δ 8.93 (s, 1H), 8.70 (s, 1H), 8.36-8.34 (m, 3H), 8.10 (t, J=5.7 Hz, 1H), 7.54 (d, J=2.2 Hz, 1H), 7.45 (t, J=7.8 Hz, 1H), 7.43 (s, 1H), 7.37-7.30 (m, 2H), 7.16 (dd, J=8.1, and 2.2 Hz, 1H), 7.08 (d, J=8.5 Hz, 1H), 6.74 (t, J=4.8 Hz, 1H), 6.37 (s, 1H), 4.76 (d, J=5.0 Hz, 1H), 4.52 (t, J=6.8 Hz, 1H), 3.54 (s, 2H), 3.49 (m, 1H), 3.31-3.18 (m, 3H), 2.96 (m, 1H), 2.13 (s, 3H), 1.27 (s, 9H); MS (ESI) m/z: 573.3 (M+H$^+$).

Example A17

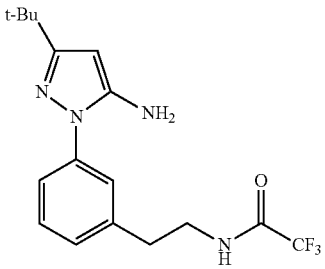

To a stirring solution of 3-nitrophenylacetic acid (10.4 g, 57.3 mmol) in MeOH (250 ml) at RT was added HCl gas until saturation was achieved. The resulting solution was stirred at 70° C. for 1 h. The reaction was cooled and concentrated under reduced pressure. The semisolid residue was dissolved in Et$_2$O, washed with H$_2$O (2×), satd. NaHCO$_3$ (2×), brine (1×) and dried (MgSO$_4$). Filtration and evaporation provided methyl 2-(3-nitrophenyl)acetate as a low-melting solid (10.7 g, 96% yield), which was used without further purification. $^1$H NMR (300 MHz, CDCl$_3$): δ 8.14-8.04 (m, 2H), 7.64-7.58 (m, 1H), 7.47 (brt, J=8.10 Hz, 1H), 3.72 (s, 2H), 3.68 (s, 3H); MS (ESI) m/z: 196.0 (M+H$^+$).

Methyl 2-(3-nitrophenyl)acetate (9.6 g, 49 mmol) was treated with conc. NH$_4$OH (24 ml, 172 mmol). The suspension was stirred briskly at RT until complete, then chilled thoroughly in an ice bath. The solids were collected by filtration, rinsed sparingly with ice H$_2$O and dried to yield pure 2-(3-nitrophenyl)acetamide as an off-white solid (7.47 g, 84% yield). $^1$H NMR (300 MHz, DMSO-d$_6$): δ 8.18-8.02 (m, 2H), 7.75-7.70 (m, 1H), 7.61-7.57 (m, 3H), 7.00 (brs, 1H), 3.58 (s, 3H); MS (ESI) m/z: 181.0 (M+H$^+$).

To a stirring solution of BH$_3$-THF (3.5 ml, 3.5 mmol, 1.0M) was added a solution of 2-(3-nitrophenyl)acetamide (0.25 g, 1.4 mmol) in THF (7.0 mL) at RT. The resulting solution was stirred at RT until the gas evolution had subsided and then heated at 70° C. overnight. The cooled reaction was quenched carefully with 3M HCl (2 ml) and heated again at 70° C. to complete the quench. The reaction was cooled to RT and concentrated to a white solid, which was dissolved in 3M NaOH (pH 14) and extracted with CH$_2$Cl$_2$ (4×). The organics were dried (Na$_2$SO$_4$), filtered, and concentrated to provide 0.20 g (87% yield) of crude product as an oil, which was purified by precipitation from CH$_2$Cl$_2$ and 3M HCl/EtOAc (0.26 ml, 0.78 mmol) to yield 2-(3-nitrophenyl)ethanamine as the HCl salt as an off-white solid (0.164 g). $^1$H NMR (300 Mhz, DMSO-d$_6$): δ 8.18-8.15 (m, 1H), 8.13-8.04 (m, 1H), 8.02 (brs, 3H), 7.76-7.74 (m, 1H), 7.65 (brt, J=7.8 Hz), 3.17-3.08 (m, 2H), 3.06-3.00 (m, 2H); MS (ESI) m/z: 167.0 (M+H$^+$).

To a stirring suspension of 2-(3-nitrophenyl)ethanamine hydrochloride (0.164 g, 0.81 mmol) in dry CH$_2$Cl$_2$ (8 ml) at RT was added i-Pr$_2$NEt (0.42 ml, 2.43 mmol). The reaction was stirred at RT until the solids were dissolved, cooled thoroughly in an ice bath and TFAA (0.14 mL, 1.01 mmol) was added dropwise. The resulting yellow solution was stirred overnight with slow warming to RT. The reaction mixture was washed with ice H$_2$O (2×) and dried (MgSO$_4$). Filtration and evaporation provided N-(3-nitrophenethyl)-2,2,2-trifluoroacetamide (0.215 g, 101% yield) as an oil that solidified on standing. $^1$H NMR (300 MHz, CDCl$_3$): δ 8.17-8.14 (m, 1H), 8.11-8.10 (m, 1H), 7.58-7.52 (m, 2H), 6.4 (brs, 1H), 3.70 (q, J=6.0 Hz, 2H), 3.06 (t, J=6.0 Hz, 2H).

To a solution of N-(3-nitrophenethyl)-2,2,2-trifluoroacetamide (9.05 g, 34.5 mmol) in MeOH (125 ml) at RT was added 10% Pd/C (50% H$_2$O wet) (3.67 g, 1.73 mmol). The resulting suspension was placed under H$_2$ (3 atm) at RT overnight. The reaction was filtered through Celite® and the cake rinsed with MeOH. The filtrate was concentrated to provide N-(3-aminophenethyl)-2,2,2-trifluoroacetamide as an oil (7.83 g, 98% yield). $^1$H NMR (300 MHz, CDCl$_3$): δ 7.16-7.12 (m, 1H), 6.62-6.58 (m, 2H), 6.54-6.53 (m, 1H), 6.34 (brs, 1H), 3.61 (q, J=6.40 Hz, 2H), 2.80 (t, J=6.40 Hz, 2H), 2.68 (brs, 2H); MS (ESI) m/z: 233.3 (M+H$^+$).

To a stirring solution of N-(3-aminophenethyl)-2,2,2-trifluoroacetamide (7.83 g, 33.7 mmol) in EtOAc (80 ml) at RT was added 3N HCl/EtOAc (12.4 ml, 37.1 mmol). Solids precipitated almost immediately. The resulting suspension was cooled in ice 1 h. The solids were collected by filtration, rinsed with EtOAc and dried on the filter. There was obtained pure N-(3-aminophenethyl)-2,2,2-trifluoroacetamide hydrochloride free of less polar impurities as a pale tan solid (7.94 g, 88% yield). $^1$H NMR 300 MHz, (DMSO-d$_6$): δ 10.3 (brs, 3H), 9.61 (t, J=5.32 Hz, 1H), 7.43-7.39 (m, 1H), 7.25-7.23 (m, 2H), 3.42 (q, J=6.6 Hz, 2H), 2.84 (t, J=6.6 Hz, 2H).

N-(3-aminophenethyl)-2,2,2-trifluoroacetamide hydrochloride (0.27 g, 1.0 mmol) was suspended in 6M HCl (2.0 mL) and cooled thoroughly in an ice bath. This was rapidly stirred while a solution of NaNO$_2$ (73 mg) in H$_2$O (1.0 mL) was added slowly. The mixture was stirred at 0-5° C. for 45 min and was then treated with SnCl$_2$.2H$_2$O (1.3 g, 5.8 mmol) in 6N HCl (4.0 mL). The resulting suspension was stirred at 0-5° C. for 3 h and then carefully quenched with 3N NaOH (15 mL) to pH 7-8. The mixture was diluted with Et₂O, filtered through Celite® and the filter cake was washed with H₂O and Et₂O. The layers of the biphasic filtrate were separated and the aqueous extracted with Et₂O (2×). The combined organics extracts were washed with brine (1×), dried (Na₂SO₄), filtered and evaporated to provided N-(3-hydrazinophenethyl)-2,2,2-trifluoroacetamide as a pale yellow oil (0.18 g, 72% yield), which was used without further purification. MS (ESI) m/z: 248.0 (M+H⁺).

To a stirring solution of N-(3-hydrazinophenethyl)-2,2,2-trifluoroacetamide (0.18 g, 0.73 mmol) in absolute EtOH (5 ml) at RT was added pivaloylacetonitrile (0.11 g, 0.87 mmol) and saturated HCl/EtOH (3 drops from a pipet). The resulting solution was stirred at 75-80° C. overnight, then cooled to RT and concentrated. The residue was dissolved in Et₂O and washed with saturated. NaHCO₃. The aqueous was extracted with Et₂O (1×). The combined organics were washed with brine (1×), dried (MgSO₄), filtered, concentrated and purified via flash chromatography to provide N-[3-(5-amino-3-t-butyl-1H-pyrazol-1-yl)phenethyl]-2,2,2-trifluoroacetamide as an orange glass (0.18 g, 70% yield). ¹H NMR (300 MHz, CDCl₃): δ 7.47-7.46 (m, 2H), 7.43-7.39 (m, 1H), 7.14-7.12 (m, 1H), 5.51 (s, 1H), 3.67 (q, J=6.6 Hz, 2H), 2.95 (t, J=6.6 Hz, 2H), 1.33 (s, 9H); MS (ESI) m/z: 355.2 (M+H⁺).

Example 39

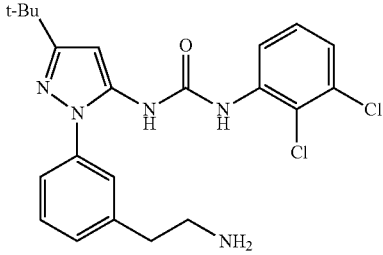

Using general method A, Example A17 (0.180 g, 0.51 mmol) and 2,3-dichlorophenyl isocyanate (82 mg, 0.53 mmol) were combined to yield 1-(3-t-butyl-1-(3-(2-(2,2,2-trifluoro-acetamido)ethyl)phenyl)-1H-pyrazol-5-yl)-3-(2,3-dichloro-phenyl)urea as an orange foam (0.134 g, 52% yield). ¹H NMR (400 MHz, CDCl₃): δ 8.14 (brs, 1H), 7.39-7.20 (m, 8H), 7.03 (brs, 1H), 6.57 (s, 1H), 3.77 (m, 2H), 2.88 (m, 2H), 1.35 (s, 9H); MS (ESI) m/z: 508.3 (M+H⁺).

To a stirring solution of 1-(3-t-butyl-1-(3-(2-(2,2,2-trifluoro-acetamido)ethyl)phenyl)-1 H-pyrazol-5-yl)-3-(2,3-dichloro-phenyl)urea (0.134 g, 0.264 mmol) in MeOH (10 mL) and H₂O (0.6 mL) at RT was added K₂CO₃ (0.182 g, 1.32 mmol). The resulting suspension was stirred at 60-65° C. for 2 h, then cooled to RT and the volatiles evaporated. The residue was carefully dissolved in 1N HCl to pH 1-2 and extracted with Et₂O (2×). The aqueous was then basified (pH 13-14) with 3M NaOH and extracted with CH₂Cl₂ (4×). The combined CH₂Cl₂ extracts were washed with brine (1×), dried (Na₂SO₄), filtered, and concentrated to provided 1-{1-[3-(2-aminoethyl)phenyl]-3-t-butyl-1H-pyrazol-5-yl}-3-(2,3-dichlorophenyl)urea as a foam (25.6 mg, 97% yield). ¹H NMR (400 MHz, CDCl₃): δ 8.17 (dd, J=1.2, and 8.0 Hz, 1H), 7.31-7.28 (m, 4H), 7.14-7.06 (m, 4H), 6.45 (s, 1H), 3.48 (brt, J=4.4 Hz, 2H), 3.46-3.39 (m, 2H), 2.86 (t, J=7.0 Hz, 2H), 1.3 (s, 9H); MS (ESI) m/z: 446.3 (M+H⁺).

Example 40

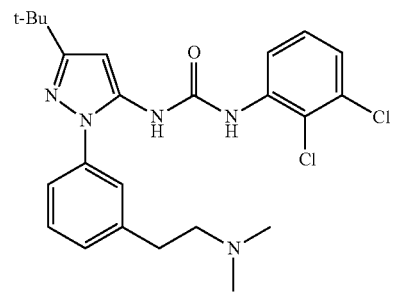

To a stirring solution of Example 39 (54.2 mg, 0.121 mmol) in MeOH (1.2 mL) at RT was added aq. formaldehyde (37 wt %, 0.036 mL, 0.49 mmol) and conc. formic acid (0.037 mL, 0.97 mmol). The reaction was stirred at 60-65° C. overnight, then cooled to RT, diluted with 1N HCl and filtered. The filtrate was made basic (pH 13) with 3N NaOH and extracted with CH₂Cl₂ (2×). The combined organics were washed with brine (1×), dried (Na₂SO₄), filtered, concentrated and purified by column chromatography, to yield 1-(3-t-butyl-1-{3-[2-(dimethylamino)ethyl]phenyl}-1H-pyrazol-5-yl)-3-(2,3-di-chlorophenyl)urea (17.4 mg, 30% yield). ¹H NMR (400 MHz, CDCl₃): δ 8.37-8.34 (m, 1H), 7.51-7.45 (m, 3H), 7.21-7.10 (m, 5H), 6.57 (s, 1H), 3.30-3.27 (m, 2H), 3.23-3.19 (m, 2H), 2.71 (s, 6H), 1.39 (s, 9H); MS (EI) 474.2 (M+H⁺).

Example 41

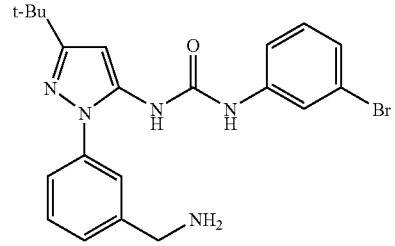

Using general method C, Example 5 (0.17 g, 0.39 mmol) was reduced to yield 1-(1-[3-(aminomethyl)phenyl]-3-t-butyl-1H-pyrazol-5-yl)-3-(3-bromophenyl)urea as the HCl salt (0.131 g, 70% yield). ¹H NMR (300 MHz, DMSO-d₆): δ 9.93 (s, 1H), 8.83 (s, 1H), 8.36 (brs, 3H), 7.82-7.81 (m, 1H), 7.71 (brs, 1H), 7.57-7.55 (m, 2H), 7.48-7.46 (m, 1H), 7.31-7.29 (m, 1H), 7.24-7.20 (m, 1H), 7.15-7.13 (m, 1H), 6.42 (s, 1H), 4.16-4.12 (m, 2H), 1.29 (s, 9H); MS (ESI) m/z: 442.3 (M+H⁺), 444.2 (M+2H⁺).

Example 42

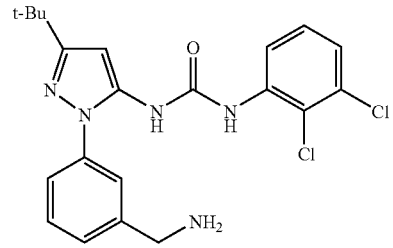

Using general method C, Example 9 (50 mg, 0.12 mmol) was reduced to afford 1-{1-[3-(aminomethyl)phenyl]-3-t-butyl-1H-pyrazol-5-yl}-3-(2,3-dichloro-phenyl)urea as a white solid (20.6 mg, 41% yield). ¹H NMR (300 MHz, DMSO-d₆): δ 9.55 (s, 1H), 8.47 (br s, 3H), 7.97-7.96 (m, 1H), 7.70-7.32 (m, 4H), 7.15-7.11 (m, 3H), 6.81 (s, 1H), 4.10 (br s, 2H), 1.38 (s, 9H); MS (ESI) m/z: 432.2 (M+H⁺), 434.2 (M+2+H⁺).

Example 43

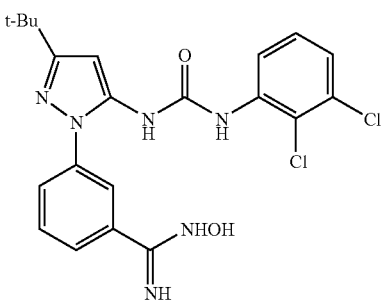

To a stirring solution of Example 9 (80 mg, 0.19 mmol) and hydroxylamine hydrochloride (26 mg, 0.37 mmol,) in absolute EtOH (2.0 mL) was added triethylamine (0.052 mL, 0.37 mmol). The resulting mixture was stirred at 80° C. for 5 h. The reaction was cooled to RT and the volatiles evaporated. The residue was partitioned between EtOAc and H₂O and the aqueous was extracted with EtOAc (3×). The combined organic extracts were washed with saturated NaHCO₃ (2×), brine (1×), dried (Na₂SO₄), filtered and concentrated to provide 1-{1-[3-(N-hydroxycarbamimidoyl)phenyl]-3-t-butyl-1H-pyrazol-5-yl}-3-(2,3-dichlorophenyl)-urea (92 mg), which was used without further purification. MS (ESI) m/z: 461.2 (M+H⁺), 463.3 (M+2H⁺).

Example 44

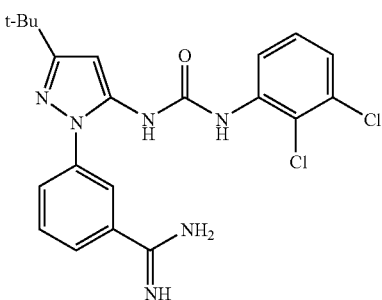

To a stirring suspension of Example 43 (92 mg, 0.20 mmol) and 10% Pd/C (50% H₂O wet, 21 mg, 0.0100 mmol) in absolute EtOH (2 mL) was added Ac₂O (0.019 ml, 0.20 mmol) and 99% formic acid (0.038 mL, 1.00 mmol). The resulting mixture was stirred at 40-45° C. for 18 h. The reaction was cooled to RT, filtered through Celite®, concentrated to dryness and the residue dissolved in EtOAc and H₂O. The layers were separated and the aqueous extracted with EtOAc (2×). The combined organic extracts were washed with saturated NaHCO₃ (1×), brine (1×), then dried (Na₂SO₄), filtered, concentrated and purified via reverse phase chromatography to provide of 1-[3-t-butyl-1-(3-carbamimidoylphenyl)-1H-pyrazol-5-yl]-3-(2,3-dichlorophenyl)urea as the TFA salt (27.2 mg, 24% yield). ¹H NMR (400 MHz, DMSO-d₆): δ9.40 (s, 2H), 9.32 (s, 1H), 9.04 (s, 2H), 8.74 (s, 1H), 8.03-8.00 (m, 2H), 7.94-7.92 (m, 1H), 7.81-7.78 (m, 2H), 7.32-7.31 (m, 2H), 6.45 (br s, 1H), 1.30 (s, 9H); MS (ESI) m/z: 445.2 (M+H⁺), 447.3 (M+2H⁺).

Example A18

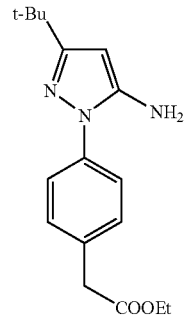

Using general method M, (4-aminophenyl)acetic acid (20 g, 0.13 mol) was converted to ethyl 2-(4-(3-t-butyl-5-amino-1H-pyrazol-1-yl)phenyl)acetate (22.5 g, 57.5% yield). ¹H NMR (300 MHz, DMSO-d₆): δ 7.55-7.45 (m, 4H), 5.61 (s, 1H), 4.08 (q, J=6.9 Hz, 2H), 3.77 (s, 2H), 1.27 (s, 9H), 1.19 (t, J=6.9 Hz, 3H); MS (ESI) m/z: 302 (M+H⁺).

Example 45

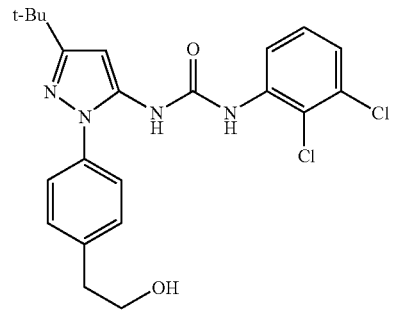

Using general method A, Example A18 (5 g, 14.8 mmol) and 1,2-dichloro-3-isocyanatobenzene (2.8 g, 15.0 mmol) were combined to afford 2-(4-{3-t-butyl-5-[3-(2,3-dichlorophenyl)ureido]-1H-pyrazol-1-yl}phenyl)acetic acid (2.1 g, 29% yield). ¹H NMR (300 MHz, DMSO-d₆): δ 9.24 (s, 1H), 8.77 (s, 1H), 8.05 (m, 1H), 7.47-7.38 (m, 4H), 7.30-7.28 (m, 2H), 6.36 (s, 1H), 4.08 (q, J=7.2 Hz, 2H), 2.72 (s, 2H), 1.25 (s, 9H), 1.18 (t, J=7.2 Hz, 3H); MS (ESI) m/z: 489 (M+H⁺).

Using general method C, 2-(4-{3-t-butyl-5-[3-(2,3-dichlorophenyl)ureido]-1H-pyrazol-1-yl}phenyl)acetic acid (100 mg, 0.21 mmol) was reduced to afford 1-{3-t-butyl-1-[4-(2-hydroxyethyl)-phenyl]-1H-pyrazol-5-yl}-3-(2,3-dichlorophenyl)urea (60 mg, 64% yield). ¹H NMR (300 MHz, DMSO-d₆): δ 9.21 (s, 1H), 8.77 (s, 1H), 8.06 (m, 1H), 7.41-7.34 (m, 4H), 7.30-7.28 (m, 2H), 6.36 (s, 1H), 4.66 (t, J=5.1 Hz, 1H), 3.63 (q, J=7.2 Hz, 2H), 2.77 (t, J=6.9 Hz, 2H), 1.25 (s, 9H); MS (ESI) m/z: 447 (M+H⁺).

Example 46

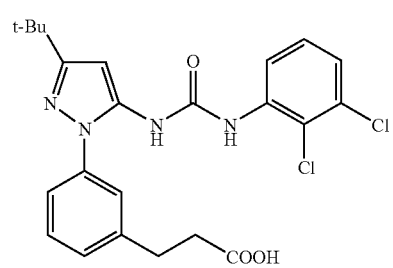

To a solution of 3-nitro-benzaldehyde (15.1 g, 0.1 mol) in CH₂Cl₂ (200 mL) was added dropwise (triphenyl-phosphanylidene)acetic acid ethyl ester (34.8 g, 0.1 mol) in CH₂Cl₂ (100 mL) at 0° C. After the addition was complete, the resulting mixture was stirred for 1 h. After removal the solvent under reduced pressure, the residue was purified by column chromatography to afford 3-(3-nitrophenyl)acrylic acid ethyl ester (16.5 g, 74.6% yield). ¹H NMR (400 MHz, CDCl₃): δ 8.42 (s, 1H), 8.23 (dd, J=0.8, and 8.0 Hz, 1H), 7.82 (d, J=7.6 Hz, 1H), 7.72 (d, J=16.0 Hz, 1H), 7.58 (t, J=8.0 Hz, 1H), 6.56 (d, J=16.0 Hz, 1H), 4.29 (q, J=7.2 Hz, 2H), 1.36 (t, J=6.8 Hz, 3H).

A mixture of 3-(3-nitrophenyl)acrylic acid ethyl ester (16.5 g, 74.6 mmol) and Pd/C (1.65 g) in MeOH (200 mL) was stirred under 40 psi of H₂ at RT for 2 h, then filtered through Celite®. After removal the solvent, 14 g of 3-(3-aminophenyl)propionic acid ethyl ester was obtained. ¹H NMR (400 MHz, CDCl₃): δ 7.11 (t, J=5.6 Hz, 1H), 6.67 (d, J=7.2 Hz, 1H), 6.63-6.61 (m, 2H), 4.13 (q, J=7.2 Hz, 2H), 2.87 (t, J=8.0 Hz, 2H), 2.59 (t, J=7.6 Hz, 2H), 1.34 (t, J=6.8 Hz, 3H); MS (ESI): m/z: 194 (M+H⁺).

To a solution of 3-(3-aminophenyl)propionic acid ethyl ester (14 g, 72.5 mmol) in conc. HCl (200 mL) was added aqueous (10 mL) NaNO₂ (5 g, 72.5 mmol) at 0° C. and the resulting mixture was stirred for 1 h. A solution of SnCl₂.2H₂O (33 g, 145 mmol) in conc. HCl (150 mL) was then added at 0° C. The reaction solution was stirred for an additional 2 h at RT. The precipitate was filtered and washed with EtOH and ether to yield 3-(3-hydrazinophenyl)propionic acid ethyl ester as a white solid, which was used for the next reaction without further purification. MS (ESI): m/z: 209 (M+H⁺).

A mixture of 3-(3-hydrazinophenyl)propionic acid ethyl ester (13 g, 53.3 mmol) and 4,4-dimethyl-3-oxopentanenitrile (6.9 g, 55 mol) in EtOH (150 mL) was heated at reflux overnight. The reaction solution was evaporated under vacuum. The residue was purified by column chromatography to yield ethyl 3-(3-(3-t-butyl-5-amino-1H-pyrazol-1-yl) phenyl)propanoate (14.3 g, 85% yield) as a white solid. ¹H NMR (300 MHz, DMSO-d₆); δ 7.50-7.42 (m, 4H), 5.63 (s, 1H), 5.14 (s, 2H), 4.04 (q, J=6.9 Hz, 2H), 2.92 (t, J=7.5 Hz, 2H), 2.66 (t, J=7.5 Hz, 2H), 1.27 (s, 9H), 1.16 (t, J=7.5 Hz, 3H); MS (ESI) m/z: 316 (M+H⁺).

Using general method A, the previous compound (300 mg, 1.0 mmol) and 1,2-dichloro-3-isocyanato-benzene (187 mg, 1.0 mmol) were combined to afford 3-(3-{3-t-butyl-5-[3-(2,3-dichlorophenyl)ureido]-1H-pyrazol-1-yl}phenyl)propionic acid ethyl ester (210 mg, 42% yield), which was used without further purification. ¹H NMR (300 MHz, DMSO-d₆): δ 9.20 (s, 1H), 8.76 (s, 1H), 8.05 (m, 1H), 7.47-7.26 (m, 6H), 6.38 (s, 1H), 4.04 (q, J=7.2 Hz, 2H), 2.93 (t, J=7.5 Hz, 2H), 2.65 (t, J=7.5 Hz, 2H), 1.28 (s, 9H), 1.15 (t, J=7.2 Hz, 3H); MS (ESI) m/z: 503 (M+H⁺).

Using general method E, the previous compound (100 mg, 0.199 mmol) was saponified to afford 3-(3-{3-t-Butyl-5-[3-(2,3-dichloro-phenyl)ureido]-1H-pyrazol-1-yl}-phenyl)propionic acid (60 mg, 63% yield). ¹H NMR (300 MHz, DMSO-d₆): δ 9.23 (s, 1H), 8.77 (s, 1H), 8.03 (m, 1H), 7.44-7.21 (m, 6H), 6.36 (s, 1H), 2.88 (t, J=7.5 Hz, 2H), 2.58 (t, J=7.5 Hz, 2H), 1.26 (s, 9H); MS (ESI) m/z: 475 (M+H⁺).

Example A19

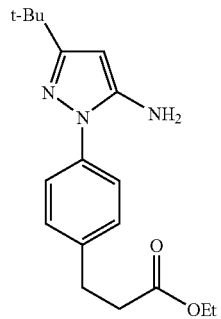

To a solution of 4-nitrobenzaldehyde (15.1 g, 0.1 mol) in CH₂Cl₂ (200 mL) was added dropwise (triphenylphosphanylidene)acetic acid ethyl ester (34.8 g, 0.1 mol) in CH₂Cl₂ (100 mL) at 0° C. After the addition was completed, the resulting mixture was stirred for 2 h. After removal the solvent under reduced pressure, the residue was purified by column chromatography to afford 3-(4-nitrophenyl)acrylic acid ethyl ester (16.5 g, 74.6% yield). ¹H NMR (400 MHz, CDCl₃): δ 8.25 (d, J=8.8 Hz, 2H), 7.71 (d, J=16.0 Hz, 1H), 7.67 (d, J=8.8 Hz, 2H), 6.55 (d, J=16.0 Hz, 2H), 4.29 (q, J=7.2 Hz, 2H), 1.34 (t, J=7.2 Hz, 3H).

A mixture of 3-(4-nitrophenyl)acrylic acid ethyl ester (16.5 g, 74.6 mmol) and Pd/C (1.65 g) in MeOH (200 mL) was stirred under 40 psi of H₂ at RT for 2 h. After filtration over Celite® and removal of the solvent, 14 g of 3-(4-aminophenyl)propionic acid ethyl ester was obtained. ¹H NMR (400 MHz, CDCl₃): δ 6.98 (d, J=8.0 Hz, 2H), 6.61 (d, J=8.4 Hz, 1H), 4.12 (q, J=7.2 Hz, 2H), 2.84 (t, J=8.0 Hz, 2H), 2.55 (t, J=7.6 Hz, 2H), 1.23 (t, J=7.2 Hz, 3H). MS (ESI): m/z: 194 (M+H⁺).

To a solution of 3-(4-aminophenyl)propionic acid ethyl ester (14 g, 72.5 mmol) in conc. HCl (200 mL) was added aqueous (10 mL) NaNO₂ (5 g, 72.5 mmol) at 0° C. and the resulting mixture was stirred for 1 h. A solution of SnCl₂.2H₂O (33 g, 145 mmol) in conc. HCl (150 mL) was then added at 0° C. The reaction solution was stirred for an additional 2 h at RT. The precipitate was filtered and washed with EtOH and Et₂O to yield 3-(4-hydrazinophenyl)propionic acid ethyl ester as a white solid, which was used for the next reaction without further purification. MS (ESI): m/z: 209 (M+H⁺).

A mixture of 3-(4-hydrazinophenyl)propionic acid ethyl ester (13 g, 53.3 mmol) and 4,4-dimethyl-3-oxopentanenitrile (6.9 g, 55 mol) in EtOH (150 mL) was heated at reflux overnight. The reaction solution was evaporated under vacuum. The residue was purified by column chromatography to yield ethyl 3-(4-(3-t-butyl-5-amino-1H-pyrazol-1-yl) phenyl)propanoate (14.3 g, 85% yield) as a white solid. ¹H NMR (300 MHz, DMSO-d₆); δ 7.44 (d, J=8.4 Hz, 2H), 7.27 (d, J=8.7 Hz, 2H), 5.34 (s, 1H), 5.11 (s, 2H), 4.04 (q, J=7.2 Hz, 2H), 2.86 (t, J=7.5 Hz, 2H), 2.61 (t, J=7.5 Hz, 2H), 1.19 (s, 9H), 1.15 (t, J=7.2 Hz, 3H); MS (ESI) m/z: 316 (M+H⁺).

Example 47

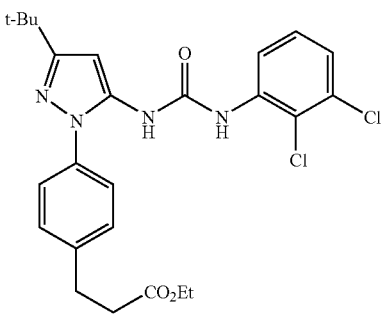

Using general method A, Example A19 (300 mg, 1.0 mmol) and 1,2-dichloro-3-isocyanato-benzene (187 mg, 1.0 mmol) were combined to afford 3-(4-{3-t-butyl-5-[3-(2,3-dichloro-phenyl)ureido]-1H-pyrazol-1-yl}phenyl)propionic acid ethyl ester (250 mg, 50% yield), which was used without further purification. MS (ESI) m/z: 503 (M+H$^+$).

Example 48

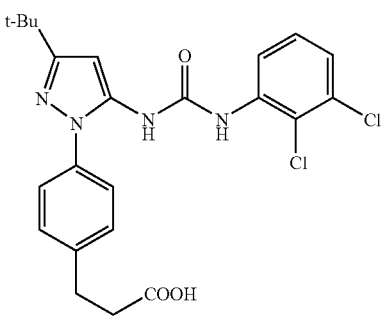

Using general method E, Example 47 (100 mg, 0.199 mmol) was saponified to afford of 3-(3-{3-t-butyl-5-[3-(2,3-dichloro-phenyl)ureido]pyrazol-1-yl}-phenyl)-propionic acid (60 mg, 64% yield). $^1$H NMR (300 MHz, DMSO-d$_6$): δ 9.29 (s, 1H), 8.80 (s, 1H), 8.04 (m, 1H), 7.44-7.33 (m, 4H), 7.29-7.27 (m, 2H), 6.36 (s, 1H), 2.87 (t, J=7.5 Hz, 2H), 2.57 (t, J=7.5 Hz, 2H), 1.25 (s, 9H); MS (ESI) m/z: 475 (M+H$^+$).

Example A20

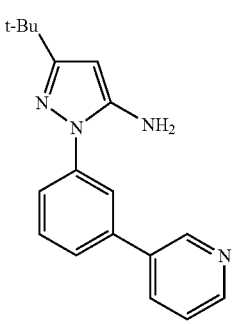

POCl$_3$ (26 g, 0.18 mol) was added over 1 h to anhydrous DMF (66 g) while keeping the temperature at 15-20° C. After the solution had stirred at RT for 1 h, 3-nitrophenyl acetic acid (10 g, 0.06 mol) was added. The solution was heated to 85° C. and stirred for 18 h. The solution was cooled to RT and poured onto 160 g of ice with vigorous stirring. A solution of sodium perchlorate (11 g, 0.09 mol) in H$_2$O was added, and a crystalline precipitate formed over 10 min. The precipitate was filtered, washed with H$_2$O, and dried in vacuo at 50° C. to yield a tan power (E)-N-[3-(dimethylamino)-2-(3-nitrophenyl)-2-propenylidene]-N-methylmethanaminium monoperchlorate (12 g, 58% yield). $^1$H NMR (300 MHz, DMSO-d$_6$): 8.23 (d, J=7.5 Hz, 1H), 8.12 (s, 1H), 7.75-7.64 (m, 4H), 3.22 (s, 3H), 2.39 (s, 6H); MS (ESI) m/z: 349 (M+H$^+$).

A solution of the material from the previous reaction (12 g, 32 mmol) dissolved in DMF (600 mL) were added t-butyl cyanoacetate (5 mL, 35 mmol) and Et$_3$N (4.9 mL, 35 mmol). The solution was stirred at RT for 18 h and then partitioned between H$_2$O and. The aqueous layer was extracted with CH$_2$Cl$_2$ (3×500 mL), the combined organic layers were dried (MgSO$_4$), concentrated and the yellow residue was purified by column to yield 2-cyano-5-dimethylamino-4-(3-nitrophenyl)penta-2,4-dienoic acid t-butyl ester (9 g, 82% yield). $^1$H NMR (300 MHz, DMSO-d$_6$): 8.9-8.23 (m, 1H), 8.05 (s, 1H), 7.72 (s, 1H), 7.50-7.55 (m, 2H), 7.05 (s, 1H), 2.81 (brs, 6H), 1.44 (s, 9H); MS (ESI) m/z: 344 (M+H$^+$).

To a solution of the material from the previous reaction (9 g, 26 mmol) in acetic acid (150 mL) was added gaseous HCl at a moderate rate for 15 min at RT. The solution was stirred at RT for 18 h and then partitioned between H$_2$O and CH$_2$Cl$_2$. The aqueous layer was extracted with CH$_2$Cl$_2$ (3×250 mL), the combined organic layers were dried (MgSO$_4$), concentrated and the yellow residue was purified by column to yield 2-chloro-5-(3-nitrophenyl)pyridine (3.5 g, 55% yield). $^1$H NMR (300 MHz, DMSO-d$_6$): δ 8.65 (s, 1H), 8.42 (s, 1H), 8.29 (d, J=7.8 Hz, 1H), 7.92-7.86 (m, 2H), 7.68 (t, J=-7.8 Hz, 1H), 7.49 (d, J=7.8 Hz, 1H).

To a solution of the material from the previous reaction (5 g, 21 mmol) in MeOH (50 mL) was added Raney-Ni and the mixture stirred at RT under a atmosphere of H$_2$ for 5 h. After the Raney-Ni was filtered, the filtrate was concentrated to yield 3-(6-chloro-pyridin-3-yl)phenylamine (3.8 g, 89% yield). $^1$H NMR (300 MHz, DMSO-d$_6$): □ 8.55 (d, J=2.4 Hz, 1H), 7.97 (dd, J=8.4 Hz, and 2.4 Hz, 1H), 7.52 (d, J=8.4 Hz, 1H), 7.10 (t, J=7.8 Hz, 1H), 6.82-6.76 (m, 2H), 6.60 (d, J=7.8 Hz, 1H), 6.22 (d, 2H); MS (ESI) m/z: 205 (M+H$^+$).

To a solution of the material from the previous reaction (3.5 g, 17 mmol) in conc. HCl (6 mL) was added an aqueous solution (2 mL) of NaNO$_2$ (1.21 g, 17 mmol) at 0° C. and the resulting mixture was stirred for 1 h. A solution of SnCl$_2$.2H$_2$O (8.0 g, 36 mmol) in conc. HCl (7.5 mL) was then added at 0° C. The reaction solution was stirred for an additional 2 h at RT. The precipitate was filtered and washed with EtOH and ether to give [3-(6-chloropyridin-3-yl)phenyl]hydrazine hydrochloride as a white solid, which was used for the next reaction without further purification. MS (ESI) m/z: 220 (M+H$^+$).

A mixture of the material from the previous reaction and 4,4-dimethyl-3-oxo-pentanenitrile (2.18 g, 35 mol) in EtOH (25 mL) was heated at reflux overnight. The reaction solution was concentrated and the residue purified by column chromatography to give 5-t-butyl-2-[3-(6-chloropyridin-3-yl)-phenyl]-2H-pyrazol-3-ylamine (3.7 g, 60% yield, two steps). $^1$H NMR (300 MHz, DMSO-d$_6$): δ8.71 (d, J=1.8 Hz, 1H), 8.17 (d, J=6.3 Hz, 1H), 7.94 (s, 1H), 7.92 (s, 1H), 7.78 (t, J=6.3 Hz, 1H), 7.65 (d, J=6.0 Hz, 1H), 7.57 (d, J=6.3 Hz, 1H), 5.80 (s, 1H), 1.39 (s, 9H); MS (ESI) m/z: 327 (M+H$^+$).

Example 49

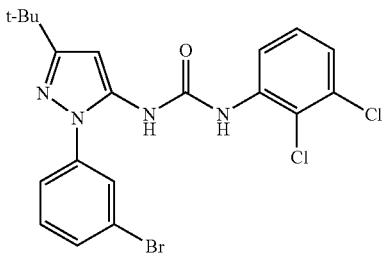

To a solution of 3-bromoaniline (17 g, 0.1 mol) in conc. HCl (200 mL) was added an aqueous solution (20 mL) of NaNO$_2$ (7 g, 0.1 mol) at 0° C. and the resulting mixture was stirred for 1 h. A solution of SnCl$_2$.2H$_2$O (45 g, 0.2 mmol) in conc. HCl (500 mL) was then added at 0° C. The reaction solution was stirred for 2 h at RT. The precipitate was filtered and washed with EtOH and ether to yield (3-bromophenyl) hydrazine hydrochloride as a white solid, which was used for the next reaction without further purification A mixture of (3-bromophenyl)hydrazine hydrochloride (22.2 g, 0.1 mol) and 4,4-dimethyl-3-oxo-pentanenitrile (18.7 g, 0.15 mol) in EtOH (250 mL) was heated at reflux overnight. The reaction was concentrated and the residue purified via column chromatography to yield 2-(3-bromophenyl)-5-t-butyl-2H-pyrazol-3-ylamine as a white solid. $^1$H NMR (400 MHz, DMSO-d$_6$): δ 7.85 (s, 1H), 7.68 (d, J=7.6 Hz, 1H), 7.62 (d, J=7.2 Hz, 1H), 7.50 (t, J=8.0 Hz, 1H), 5.62 (s, 1H), 1.27 (s, 9H).

Using general method D, the material from the previous reaction (0.833 g, 2.51 mmol) and 2,3-dichloroaniline (0.377 g, 2.33 mmol) were combined to yield 1-(1-(3-bromophenyl)-3-t-butyl-1H-pyrazol-5-yl)-3-(2,3-dichlorophenyl)urea (0.389 g, 42% yield). $^1$H NMR (400 MHz, DMSO-d$_6$): δ 9.26 (s, 1H), 8.77 (s, 1H), 8.01 (m, 1H), 7.74 (t, J=2.0 Hz, 1H), 7.62-7.56 (m, 2H), 7.49 (t, J=8.0 Hz, 1H), 7.30 (m, 2H), 6.41 (s, 1H), 1.28 (s, 9H); MS (ESI) m/z: 483.0 (M+H$^+$).

Example 50

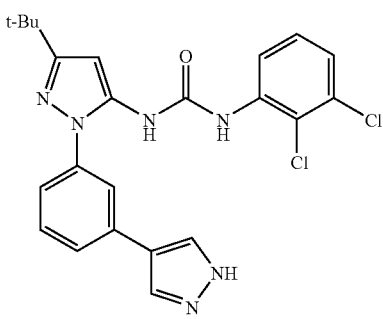

Example 49 (156 mg, 0.32 mmol), t-butyl 4-(4,4,5,5-tetramethyl-1,3,2-dioxaboran-2-yl)-1-pyrazole-carboxylate (146 mg, 0.50 mmol) and Cs$_2$CO$_3$ (316 mg, 0.97 mmol) were combined in DMF (8.0 mL) and H$_2$O (2.5 mL). The reaction mixture was purged of air under vacuum and the head-space was back-filled with N$_2$. Palladium tetrakis(triphenylphosphine) (40 mg, 0.035 mmol) was added and the reaction mixture was heated to 80° C. under N$_2$. After 5.5 h, the reaction mixture was cooled to RT and partitioned between H$_2$O and EtOAc. The organic layer was washed with H$_2$O and brine, dried (Na$_2$SO$_4$), concentrated in vacuo and purified via column chromatography to yield 1-(1-(3-(1H-pyrazol-4-yl) phenyl)-3-t-butyl-1H-pyrazol-5-yl)-3-(2,3-dichlorophenyl) urea (39 mg, 26% yield) as a film. Further purification by reverse phase chromatography provided a white powder. $^1$H NMR (400 MHz, DMSO-d$_6$): δ 9.26 (s, 1H), 8.80 (s, 1H), 8.29 (brs, 1H), 8.06 (m, 1H), 7.99 (brs, 1H), 7.73 (t, J=1.7 Hz, 1H), dt (J=8.4, 1.7 Hz, 1H), 7.51 (t, J=7.9 Hz, 1H), 7.33-7.28 (m, 3H), 6.42 (s, 1H), 1.29 (s, 9H); MS (ESI) m/z: 469.0 (M+H$^+$).

Example 51

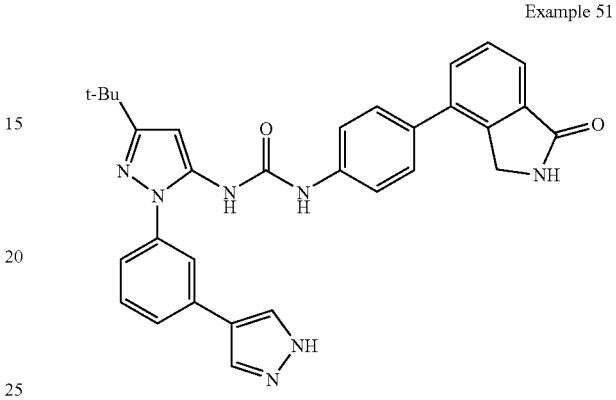

A solution of 1-(3-bromophenyl)-3-t-butyl-1H-pyrazol-5-amine hydrochloride (0.253 g, 0.77 mmol, available from Example 54), t-butyl 4-(4,4,5,5-tetramethyl-1,3,2-dioxaborolan-2-yl)-1H-pyrazole-1-carboxylate (0.28 g, 0.95 mmol, commercially available) and Cs$_2$CO$_3$ (1.0 g, 3.1 mmol) in DMF (5 mL) and H$_2$O (2 mL) was placed under Ar for 15 min. Palladium tetrakis(triphenylphosphine) was added and the reaction mixture was heated at 80° C. overnight. The reaction mixture was poured into H$_2$O (20 mL) and extracted with EtOAc (2×30 mL). The extracts were washed with H$_2$O (10 mL) and brine (10 mL), dried (Na$_2$SO$_4$) concentrated and purified via column chromatography to yield 1-(3-(1H-pyrazol-4-yl)phenyl)-3-t-butyl-1H-pyrazol-5-amine (163 mg, 76% yield). MS (ESI) m/z: 282.3 (M+H$^+$).

1-(3-(1H-pyrazol-4-yl)phenyl)-3-t-butyl-1H-pyrazol-5-amine (160 mg, 0.57 mmol) in EtOAc (3 mL) was cooled to 0° C. and treated with 1M NaOH (0.85 mL, 0.85 mmol) and isopropenyl chloroformate (0.080 mL, 0.74 mmol). The reaction was allowed to warm to RT overnight. The organic layer was washed with saturated NaHCO$_3$, brine, dried (Na$_2$SO$_4$) and was concentrated to a film, which was dissolved in Et$_2$O (5 mL) and the solution was lowed to stand overnight. The resultant crystals were collected, washed with Et$_2$O and dried in vacuo to provide prop-1-en-2-yl 4-(3-(3-t-butyl-5-((prop-1-en-2-yloxy)carbonyl)-1H-pyrazol-1-yl)phenyl)-1H-pyrazole-1-carboxylate (193 mg, 75% yield). $^1$H NMR (400 MHz, DMSO-d$_6$): δ 9.73 (brs, 1H), 8.96 (d, J=–0.7 Hz, 1H), 8.46 (d, J=0.7 Hz, 1H), 7.87 (t, J=1.7 Hz, 1H), 7.81 (dt, J=8.2, 1.3 Hz, 1H), 7.54 (t, J=7.9 Hz, 1H), 7.41 (brd, J=7.9 Hz, 1H), 6.34 (s, 1H), 5.02 (s, 2H), 4.66 (brs, 1H), 4.57 (brs, 1H), 2.06 (s, 3H), 1.76 (brs, 3H), 1.30 (s, 9H). MS (ESI) m/z: 450.2 (M+H$^+$).

Using the procedure for Example 151, prop-1-en-2-yl 4-(3-(3-t-butyl-5-((prop-1-en-2-yloxy)carbonyl)-1H-pyrazol-1-yl)phenyl)-1H-pyrazole-1-carboxylate (63 mg, 0.14 mmol) and 4-(4-aminophenyl)isoindolin-1-one (31 mg, 0.14 mmol) were combined to yield prop-1-en-2-yl 4-(3-(3-t-butyl-5-(3-(4-(1-oxoisoindolin-4-yl)phenyl)ureido)-1H-pyrazol-1-yl)phenyl)-1H-pyrazole-1-carboxylate (75 mg, 87% yield). MS (ESI) m/z: 616.2 (M+H$^+$).

Using general method E, prop-1-en-2-yl 4-(3-(3-t-butyl-5-(3-(4-(1-oxoisoindolin-4-yl)phenyl)ureido)-1H-pyrazol-1- yl)phenyl)-1H-pyrazole-1-carboxylate (75 mg, 0.12 mmol) was saponified to yield 1-(1-(3-(1H-pyrazol-4-yl)phenyl)-3-t-butyl-1H-pyrazol-5-yl)-3-(4-(1-oxoisoindolin-4-yl)phenyl)urea as a white powder (9.5 mg, 15% yield). $^1$H NMR (400 MHz, DMSO-$d_6$): δ 9.24 (s, 1H), 8.66 (s, 1H), 8.50 (s, 1H), 8.30 (brs, 1H), 8.00 (brs, 1H), 7.74 (brs, 1H), 7.69-7.62 (m, 3H), 7.59-7.48 (m, 7H), 7.33 (brd, J=7.9 Hz, 1H), 6.43 (s, 1H), 4.50 (s, 2H), 1.30 (s, 9H). MS (ESI) m/z: 532.3 (M+H$^+$).

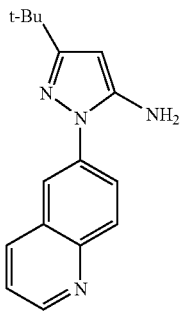

Example A21

To a solution of quinolin-6-ylamine (5 g, 35 mmol) in conc. HCl (12 mL) was added dropwise an aqueous solution (4 mL) of NaNO$_2$ (2.42 g, 35 mmol) at 0° C. The resulting mixture was stirred for 1 h and then treated dropwise with a solution of SnCl$_2$ 2H$_2$O (15.8 g, 70 mmol) in conc. HCl (15 mL) at 0° C. The reaction mixture was stirred for 2 h at RT. The precipitate was collected and washed with EtOH and Et$_2$O to yield 1-(quinolin-6-yl)hydrazine hydrochloride as a yellow powder (4.3 g, 77% yield), which was used for the next reaction without further purification.

A mixture of 1-(quinolin-6-yl)hydrazine hydrochloride (4.0 g, 20.5 mmol) and 4,4-dimethyl-3-oxo-pentanenitrile (3.6 g, 30 mol) in EtOH (50 mL) and conc. HCl (5 mL) was heated at reflux overnight. After removal of the solvent, the residue was purified by column chromatography to yield 3-t-butyl-1-(quinolin-6-yl)-1H-pyrazol-5-amine (2.8 g, 51% yield). $^1$H NMR (300 MHz, DMSO-$d_6$): δ 8.84 (d, J=4.2 Hz, 1H), 8.37 (d, J=7.5 Hz, 1H), 8.09 (s, 1H), 8.04 (s, 2H), 7.52 (m, 1H), 5.46 (s, 1H), 5.40 (brs, 2H), 1.29 (s, 9H).

General Experimental for Examples 52-55

A solution of Example A21 and the appropriate isocyanate or aniline was converted to the target compound using the general method indicated.

| Example | Name | MS (EI) (M + H$^+$) | $^1$H NMR (300 MHz/ 400 MHz, DMSO-$d_6$) |
|---|---|---|---|
| Example 52 | 1-[3-t-butyl-1-(quinolin-6-yl)-1H-pyrazol-5-yl]-3-(2,3-dichlorophenyl)urea 52 mg, 30% yield General method A | 454.2 | δ 9.39 (s, 1H), 8.97 (dd, J = 1.6, and 4.0 Hz, 1H), 8.78 (s, 1H), 8.49 (bd, J = 8.0 Hz, 1H), 8.18 (d, J = 4.8 Hz, 1H), 8.16 (d, J = 2.0 Hz, 1H), 8.06 (dd, J = 4.0, and 6.0 Hz, 1H). 7.96 (dd, J = 2.4, and 9.2 Hz, 1H), 7.63 (dd, J = 4.4, and 8.4 Hz, 1H), 7.31 (d, J = 1.6 Hz, 1H), 7.30 (s, 1H), 6.48 (s, 1H), 1.31 (s, 9H) |
| Example 53 | 1-(3-t-butyl-1-(quinolin-6-yl)-1H-pyrazol-5-yl)-3-(2,4,5-trifluorophenyl)urea 25 mg, 28% yield General method D | 440.2 | δ 9.09 (s, 1H), 9.04 (s, 1H), 8.97 (dd, J = 1.6, and 4.4 Hz, 1H), 8.49 (d, J = 8.4 Hz, 1H), 8.16 (m, 3H), 7.93 (dd, J = 2.0, and 8.8 Hz, 1H). 7.62 (m, 2H), 6.48 (s, 1H), 1.31 (s, 9H) |

| Example | Name | MS (EI) (M + H⁺) | ¹H NMR (300 MHz/ 400 MHz, DMSO-d₆) |
|---|---|---|---|
| Example 54 | 1-(3-t-butyl-1-(quinolin-6-yl)-1H-pyrazol-5-yl)-3-(2,3,5-trifluorophenyl)urea 5 mg, 3% yield General method D | 440.2 | δ 9.33 (s, 1H), 9.13 (s, 1H), 8.97 (m, 1H), 8.49 (d, J = 7.3 Hz, 1H), 8.18 (d, J = 9.2 Hz, 1H), 8.17 (s, 1H), 7.94 (d, J = 8.8 Hz, 1H). 7.87 (m, 1H), 7.63 (m, 1H), 7.12 (m, 1H), 6.50 (s, 1H), 1.25 (s, 9H) |
| Example 55 | 1-(3-t-butyl-1-(quinolin-6-yl)-1H-pyrazol-5-yl)-3-(3-(pyridin-3-yloxy)phenyl)urea HCl salt 62 mg, 55% yield General method D | 551.2 | δ 9.43 (brs, 1H), 9.07 (brs, 1H), 8.81 (brs, 1H), 8.71 (brs, 1H), 8.48 (m, 1H), 8.44 (m, 1H), 8.30 (m, 1H), 8.23 (m, 1H), 8.08 (m, 1H), 7.78 (m, 1H), 7.58 (m, 2H), 7.30 (m, 1H), 7.10 (dd, J = 1.6, and 8.4 Hz, 1H), 6.70 (dd, J = 2.4, and 8.4 Hz, 1H), 6.43 (s, 1H), 1.31 (s, 9H) |

Example A22

To a solution of quinolin-3-ylamine (5 g, 35 mmol) in conc. HCl (12 mL) was added dropwise an aqueous solution (4 mL) of NaNO₂ (2.42 g, 35 mmol) at 0° C. The resulting mixture was stirred for 1 h, and then treated with a solution of SnCl₂.2H₂O (15.8 g, 70 mmol) in conc. HCl (15 mL). The reaction solution was stirred for an additional 2 h at RT. The precipitate was filtered and washed with EtOH and ether to yield 1-(quinolin-3-yl)hydrazine hydrochloride (4.5 g, 81% yield), which was used in the next reaction without further purification.

A mixture of 1-(quinolin-3-yl)hydrazine hydrochloride (4 g, 20.5 mmol) and 4,4-dimethyl-3-oxo-pentanenitrile (3.6 g, 30 mol) in EtOH (50 mL) and conc. HCl (5 mL) was heated at reflux overnight. After removal of the solvent, the residue was purified by column chromatography to yield 3-t-butyl-1-(quinolin-3-yl)-1H-pyrazol-5-amine (3.0 g, 55% yield). ¹H NMR (300 MHz, DMSO-d₆): δ 9.16 (d, J=2.4 Hz, 1H), 8.44 (d, J=2.4 Hz, 1H), 8.03 (s, 1H), 8.00 (s, 1H), 7.72 (t, J=7.2 Hz, 1H), 7.64 (t, J=7.2 Hz, 1H), 5.72 (s, 1H), 5.45 (s, 3H), 1.23 (s, 9H).

Example 56

Using general method A, Example A22 (134 mg, 0.5 mmoL) and 1-chloro-4-isocyanatobenzene (90 mg, 0.6 mmoL) were combined to afford 1-(3-t-butyl-1-(quinolin-3-yl)-1H-pyrazol-5-yl)-3-(4-chlorophenyl)urea (100 mg, 48% yield). ¹H NMR (300 MHz, DMSO-d₆): δ 9.10 (s, 1H), 9.07 (d, J=2.4 Hz, 1H), 8.67 (s, 1H), 8.54 (d, J=2.4 Hz, 1H), 8.10 (s, 1H), 8.07 (s, 1H), 7.81 (t, J=8.4 Hz, 1H), 7.68 (t, J=8.4 Hz, 1H), 7.41 (d, J=8.7 Hz, 2H), 7.27 (t, J=8.7 Hz, 2H), 6.45 (s, 1H), 1.30 (s, 9H).

Example 57

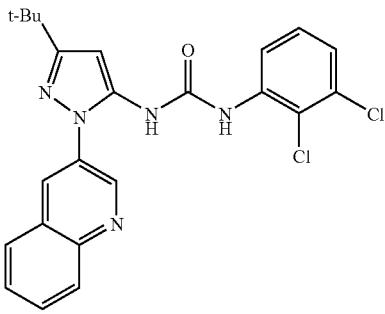

Using general method A, Example A22 (133 mg, 0.5 mmoL) and 2,3-dichlorophenyl isocyanate (0.6 mmol) were combined to afford 1-[3-t-butyl-1-(quinolin-3-yl)-1H-pyrazol-5-yl]-3-(2,3-dichlorophenyl)urea.

Example A23

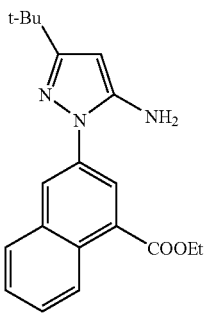

To a solution of 1,8-naphthalic anhydride (25 g, 0.13 mol) in conc. $H_2SO_4$ (100 mL) was added dropwise a solution of conc. $HNO_3$ (7.85 g, 0.13 mol) in conc. $H_2SO_4$ (25 mL) at 0° C. After the addition was complete, the resulting mixture was allowed to warm to RT, stirred for 90 min and then poured into ice-$H_2O$. The solid was filtered by suction, washed with $H_2O$, and re-crystallized from glacial AcOH to yield 3-nitro-1,8-naphthalic anhydride (24.5 g). $^1$H NMR (300 MHz, $CDCl_3$): δ 9.11 (s, 1H), 9.06 (s, 1H), 8.58 (d, J=7.5 Hz, 1H), 8.43 (d, J=7.8 Hz, 1H), 7.82 (t, J=7.8 Hz, 1H).

To a solution of 3-nitro-1,8-naphthalic anhydride (21.8 g, 89.7 mmol) in $H_2O$ (550 mL) containing 14.4 g of NaOH was added a solution of yellow HgO (25.1 g) in a mixture of $H_2O$ (75 mL) and glacial AcOH (25 mL). After reflux for 4 days, the reaction mixture was cooled and filtered to afford the mercurated product, which was then refluxed in 700 mL of 5N HCl for 3 h. The cream-colored precipitate was filtered, washed with cold $H_2O$, dried, and recrystallized from hot glacial AcOH to yield 3-nitronaphthalene-1-carboxylic acid (12 g). $^1$H NMR (300 MHz, DMSO-$d_6$): δ 13.7 (brs, 1H), 9.18 (s, 1H), 8.93 (d, J=8.4 Hz, 1H), 8.70 (s, 1H), 7.88 (t, J=7.8 Hz, 1H), 7.76 (t, J=6.9 Hz, 1H).

To a solution of 3-nitronaphthalene-1-carboxylic acid (4.34 g, 20 mmol) in EtOH (50 mL) was added $SOCl_2$ (3.70 mL, 30 mmol) at 0° C. The mixture was heated at reflux for 2 h and then concentrated. The residue was recrystallized from EtOH to yield ethyl 3-nitronaphthalene-1-carboxylate (4.2 g). $^1$H NMR (300 MHz, DMSO-$d_6$): δ 9.16 (s, 1H), 8.77 (d, J=8.7 Hz, 1H), 8.62 (s, 1H), 8.34 (d, J=8.1 Hz, 1H), 7.87 (t, J=7.2 Hz, 1H), 7.75 (t, J=7.2 Hz, 1H), 4.43 (q, J=7.2 Hz, 2H), 1.38 (t, J=7.2 Hz, 3H).

A mixture of 3-nitronaphthalene-1-carboxylic acid ethyl ester (2.45 g, 10 mmol) and Pd/C (0.3 g) in EtOH (20 mL) was stirred overnight at RT under 35 psi of $H_2$. After filtration, the filtrate was concentrated to yield ethyl 3-aminonaphthalene-1-carboxylate (2.04 g). $^1$H NMR (300 MHz, DMSO-$d_6$): δ 8.63 (m, 1H), 7.93-7.97 (m, 2H), 7.84 (s, 1H), 7.54-7.57 (m, 2H), 4.39 (q, J=7.2 Hz, 2H), 1.35 (t, J=7.2 Hz, 3H).

To a solution of 3-aminonaphthalene-1-carboxylic acid ethyl ester (2 g, 9.3 mmol) in conc. HCl (2 mL) was added dropwise an aqueous solution of $NaNO_2$ (0.63 g, 9.3 mmol) at 0° C. The resulted mixture was stirred for 1 h and then treated dropwise with a solution of $SnCl_2.2H_2O$ (4.2 g, 18.6 mmol) in conc. HCl (10 mL) at 0° C. The reaction mixture was stirred for 2 h at RT. precipitate was collected and washed with EtOH and $Et_2O$ to yield ethyl 3-hydrazinonaphthalene-1-carboxylate hydrochloride as a white solid (1.5 g), which was used for the next reaction without further purification.

A mixture of 3-hydrazinonaphthalene-1-carboxylic acid ethyl ester hydrochloride (1.5 g, 5.6 mmol) and 4,4-dimethyl-3-oxopentanenitrile (875 mg, 7.0 mmol) in EtOH (50 mL) and conc. HCl (5 mL) was heated at reflux overnight. After removal of the solvent, the residue was purified by column chromatography to yield ethyl 3-(5-amino-3-t-butyl-1H-pyrazol-1-yl)-1-naphthoate (1.8 g, 95% yield). $^1$H NMR (300 MHz, DMSO-$d_6$): δ 8.74 (d, J=6.3 Hz, 1H), 8.47 (s, 1H), 8.24 (s, 1H), 8.15 (d, J=6.0 Hz, 1H), 7.76 (t, J=5.7 Hz, 1H), 7.71 (t, J=5.7 Hz, 1H), 5.68 (s, 1H), 4.44 (q, J=5.4 Hz, 2H), 1.37 (t, J=5.4 Hz, 3H), 1.30 (s, 9H).

Example A24

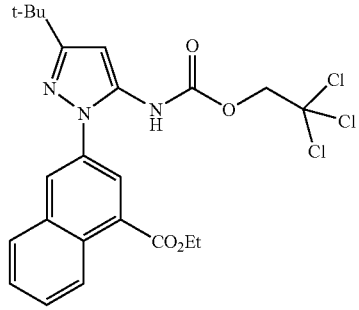

In EtOAc (25 mL) at RT was stirred Example A23 (1.20 g, 3.21 mmol), to this was added saturated $NaHCO_3$ (20 mL). The mixture was stirred for 20 min and then treated dropwise with Troc-Cl (0.66 mL). The mixture was stirred vigorously overnight at RT, then diluted with EtOAc (50 mL) and $H_2O$ (50 mL). The organic phase was separated, washed with 5% citric acid (50 mL), brine (50 mL), dried ($Na_2SO_4$) and concentrated yield an oil. This oil was dissolved in hexane (15 mL), warmed to reflux and then cooled to precipitate. The solids were collected by filtration and dried at 65° C. under reduced pressure to yield 885 mg of ethyl 3-(3-t-butyl-5-((2,2,2-trichloroethoxy)carbonylamino)-1H-pyrazol-1-yl)-1-naphthoate. This material was used without further purification.

Example 58

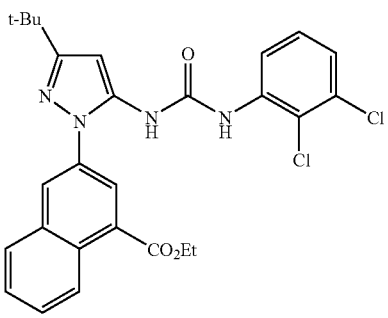

Using general method A, Example A23 (500 mg, 1.3 mmol) and 1,2-dichloro-3-isocyanatobenzene (243 mg, 1.3 mmol) were combined afford 3-{3-t-butyl-5-[3-(2,3-dichlorophenyl)ureido]-pyrazol-1-yl}naphthalene-1-carboxylic acid ethyl ester (265 mg, 39%). $^1$H NMR (300 MHz, DMSO-$d_6$): δ 9.32 (s, 1H), 8.72 (d, J=6.3 Hz, 2H), 8.33 (d, J=2.1 Hz, 1H), 8.22 (d, J=2.1 Hz, 1H), 8.10 (d, J=7.8 Hz, 1H), 7.98 (t, J=5.1 Hz, 1H), 7.71-7.62 (m, 2H), 7.26 (d, J=4.8 Hz, 2H), 6.42 (s, 1H), 4.36 (q, J=7.2 Hz, 2H), 1.29 (t, J=7.2 Hz, 3H), 1.27 (s, 9H); MS (ESI) m/z: 525 (M+H$^+$).

Example 59

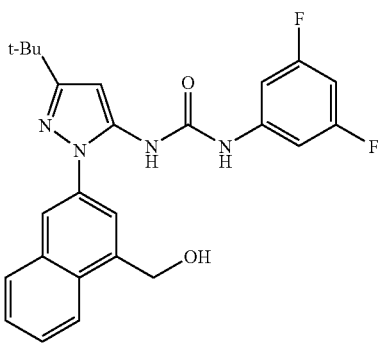

Using general method D, Example A24 (180 mg, 0.351 mmol), and 3,5-difluoroaniline (59 mg, 0.456 mmol) were combined to yield ethyl 3-(3-t-butyl-5-(3-(3,5-difluorophenyl)ureido)-1H-pyrazol-1-yl)-1-naphthoate (100 mg, 57% yield). MS (ESI) m/z: 493.0 (M+H$^+$).

Using general method C, this ester (100 mg, 0.203 mmol) was reduced to yield 1-(3-t-butyl-1-(4-(hydroxymethyl) naphthalen-2-yl)-1H-pyrazol-5-yl)-3-(3,5-difluorophenyl) urea (71 mg, 78% yield). $^1$H NMR (300 MHz, DMSO-$d_6$): δ 1.31 (s, 9H), 5.03 (s, 2H), 5.30-5.60 (brs, 1H), 6.44 (s, 1H), 6.76-6.81 (m, 1H), 7.11-7.12 (d, 2H), 7.59-7.61 (m, 2H), 7.72 (s, 1H), 7.95-8.10 (m, 3H), 8.65 (s, 1H), 9.38 (s, 1H). MS (ESI) m/z: 451.0 (M+H$^+$).

Example 60

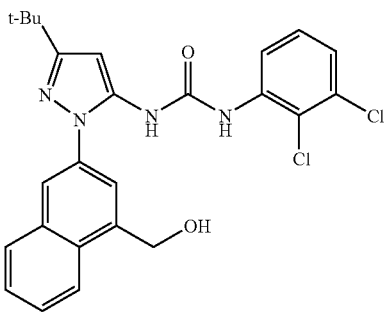

Using general method C, Example 58 (150 mg 0.29 mmol) in anhydrous THF (10 mL) was reduced to afford 1-[5-t-butyl-2-(4-hydroxymethylnaphthalen-2-yl)-2H-pyrazol-3-yl]-3-(2,3-dichloro-phenyl)urea (98 mg, 70% yield). $^1$H NMR (300 MHz, DMSO-$d_6$): δ 9.33 (s, 1H), 8.81 (s, 1H), 8.08 (d, J=8.4 Hz, 3H), 7.98 (s, 1H), 7.75 (s, 1H), 7.65-7.60 (m, 2H), 7.32 (t, J=9.9 Hz, 2H), 6.47 (s, 1H) 5.52 (t, J=6.3 Hz, 1H), 5.05 (d, J=6.3 Hz, 2H), 1.32 (s, 9H). MS (ESI) m/z: 483 (M+H$^+$).

Example 61

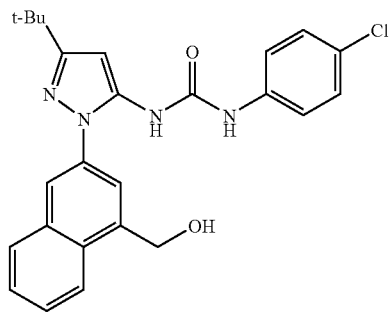

Using general method A, Example A23 (169 mg, 0.5 mmol) and 1-chloro-4-isocyanato-benzene (92 mg) were combined to afford ethyl 3-{3-t-butyl-5-[3-(4-chlorophenyl) ureido]-1H-pyrazol-1-yl}naphthoate (180 mg, 73% yield). $^1$H NMR (300 MHz, DMSO-$d_6$): δ 9.18 (s, 1H), 8.72 (d, J=8.1 Hz, 1H), 8.64 (s, 1H), 8.33 (s, 1H), 8.23 (s, 1H), 8.09 (d, J=7.5 Hz, 1H), 7.62-7.71 (m, 2H), 7.39 (d, J=8.7 Hz, 2H), 7.24-7.27 (d, J=8.7 Hz, 2H), 6.40 (s, 1H), 4.37 (q, J=6.9 Hz, 2H), 1.29 (t, J=6.9 Hz, 3H), 1.28 (s, 9H).

Using general method C, ethyl 3-{3-t-butyl-5-[3-(4-chlorophenyl)ureido]-1H-pyrazol-1-yl}naphthoate (100 mg, 0.20 mmol) was reduced to afford 1-[3-t-butyl-2-(4-(hydroxymethyl)naphthalen-2-yl)-1H-pyrazol-5-yl]-3-(4-chlorophenyl)urea (50 mg, 56% yield). $^1$H NMR (300 MHz, DMSO-$d_6$): δ 9.20 (brs, 1H), 8.58 (brs, 1H), 8.06 (m, 1H), 7.97 (ms, 1H), 7.93 (s, 1H), 7.70 (s, 1H), 7.57 (m, 2H), 7.38 (d, J=9.0 Hz, 2H), 7.25 (d, J=9.0 Hz, 2H), 6.39 (s, 1H), 5.45 (t, J=5.1 Hz, 1H), 5.00 (d, J=5.1 Hz, 2H), 1.28 (s, 9H).

Example 62

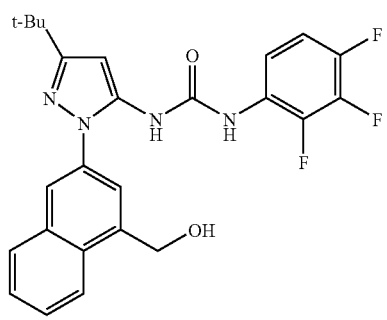

Using general method D, Example A24 (120 mg, 0.234 mmol), and 2,3,4-trifluoroaniline (35 mg, 0.234 mmol) were combined to yield ethyl 3-(3-t-butyl-5-(3-(2,3,4-trifluoro phenyl)ureido)-1H-pyrazol-1-yl)-1-naphthoate as an oil.

Using general method C, ethyl 3-(3-t-butyl-5-(3-(2,3,4-trifluoro phenyl)ureido)-1H-pyrazol-1-yl)-1-naphthoate (120 mg, 0.240 mmol) was reduced to yield 1-(3-t-butyl-1-(4-(hydroxylmethyl)naphthalen-2-yl)-1H-pyrazol-5-yl)-3-(2,3,4-trifluorophenyl)urea (14 mg, 13% yield). $^1$H-NMR (400 MHz, DMSO-$d_6$): δ 1.30 (s, 9H), 5.02-5.05 (m, 2H), 5.49 (m, 1H), 6.45 (s, 1H), 7.20-7.30 (m, 1H), 7.60-8.10 (m, 8H), 8.92 (s, 1H), 9.06 (s, 1H). MS (ESI) m/z: 469.2 (M+H⁺).

Example 63

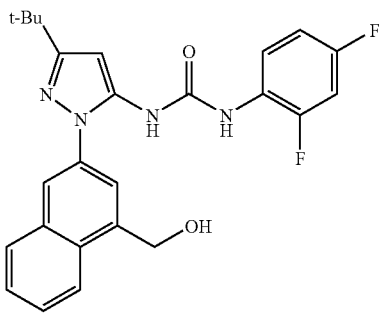

Using general method D, Example A24 (120 mg, 0.234 mmol) and 2,4-difluoroaniline (30 mg, 0.234 mmol) were combined to yield ethyl 3-(3-t-butyl-5-(3-(2,4-difluorophenyl)ureido)-1H-pyrazol-1-yl)-1-naphthoate (89 mg, 21% yield). ¹H-NMR (400 MHz, DMSO-d₆): δ 1.25-1.31 (m, 3H), 1.29 (s, 9H), 4.39-4.47 (m, 2H), 6.45 (s, 1H), 7.02-7.03 (m, 1H), 7.28-7.29 (m, 1H), 7.68-7.73 (m, 2H), 7.99-8.01 (m, 1H), 8.13-8.15 (m, 1H), 8.24 (brs, 1H), 8.36 (s, 1H), 8.76-8.78 (m, 1H), 8.84 (s, 1H), 8.91 (s, 1H); MS (ESI) m/z: 493.2 (M+H⁺).

Using general method C, ethyl 3-(3-t-butyl-5-(3-(2,4-difluorophenyl)ureido)-1H-pyrazol-1-yl)-1-naphthoat (68 mg, 0.14 mmol) was reduced to yield 1-(3-t-butyl-1-(4-(hydroxylmethyl)naphthalen-2-yl)-1H-pyrazol-5-yl)-3-(2,4-difluorophenyl)urea (13 mg, 22% yield). ¹H-NMR (400 MHz, DMSO-d₆): δ 1.30 (s, 9H), 5.04-5.05 (m, 2H), 5.45 (m, 1H), 6.44 (s, 1H), 7.03-7.10 (m, 1H), 7.25-7.30 (m, 1H), 7.59-7.62 (m, 2H), 7.71 (brs, 1H), 7.95 (s, 1H), 8.02-8.10 (m, 3H), 8.88 (s, 2H); MS (ESI) m/z: 451.2 (M+H⁺).

Example 64

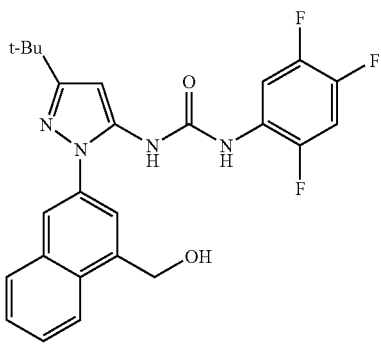

Using general method D, Example A24 (120 mg, 0.234 mmol) and 2,4,5-trifluoroaniline (35 mg, 0.234 mmol) were combined to yield 3-(3-t-butyl-5-(3-(2,4,5-trifluorophenyl)ureido)-1H-pyrazol-1-yl)-1-naphthoate (120 mg, 19% yield). ¹H-NMR (400 MHz, DMSO-d₆): δ 1.25-1.31 (m, 3H), 1.29 (s, 9H), 4.39-4.47 (m, 2H), 6.45 (s, 1H), 7.02-7.03 (m, 1H), 7.28-7.29 (m, 1H), 7.68-7.73 (m, 2H), 7.99-8.01 (m, 1H), 8.13-8.15 (m, 1H), 8.24 (brs, 1H), 8.36 (s, 1H), 8.76-8.78 (m, 1H), 8.84 (s, 1H), 8.91 (s, 1H); MS (ESI) m/z: 493.2 (M+H⁺).

Using general method C, 3-(3-t-butyl-5-(3-(2,4,5-trifluorophenyl)ureido)-1H-pyrazol-1-yl)-1-naphthoate (126 mg, 0.250 mmol) was reduced to yield 1-(3-t-butyl-1-(4-(hydroxymethyl)naphthalen-2-yl)-1H-pyrazol-5-yl)-3-(2,4,5-trifluorophenyl)urea (22 mg). ¹H-NMR (400 MHz, DMSO-d₆): δ 1.30 (s, 9H), 5.04-5.05 (m, 2H), 5.48-5.50 (m, 1H), 6.46 (s, 1H), 7.58-7.71 (m, 4H), 7.95-8.19 (m, 4H), 8.97 (s, 1H), 9.11 (s, 1H). MS (ESI) m/z: 469.2 (M+H⁺).

Example 65

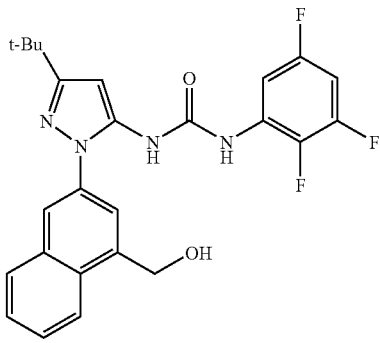

Using general method D, Example A24 (180 mg, 0.351 mmol) and 2,3,5-trifluoroaniline (68 mg, 0.456 mmol) were combined to yield 3-(3-t-butyl-5-(3-(2,3,5-trifluorophenyl)ureido)-1H-pyrazol-1-yl)-1-naphthoate (120 mg, 32% yield).

Using general method C, 3-(3-t-butyl-5-(3-(2,3,5-trifluorophenyl)ureido)-1H-pyrazol-1-yl)-1-naphthoate (52 mg, 0.20 mmol) was reduced to yield 1-(3-t-butyl-1-(4-(hydroxymethyl)naphthalen-2-yl)-1H-pyrazol-5-yl)-3-(2,3,5-trifluorophenyl)urea (24 mg, 50%). ¹H-NMR (400 MHz, DMSO-d₆): δ 1.31 (s, 9H), 5.04-5.05 (d, 2H), 5.49 (t, 1H), 6.48 (s, 1H), 7.10-7.12 (m, 1H), 7.59-7.71 (m, 3H), 7.86-7.90 (m, 1H), 7.96 (s, 1H), 8.03-8.11 (m, 2H), 9.07 (s, 1H), 9.35 (s, 1H); MS (ESI) m/z: 469.0 (M+H⁺).

Example 66

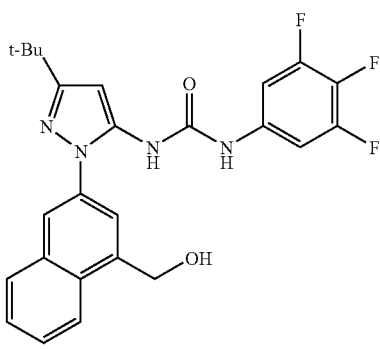

Using general method D, Example A24 (120 mg, 0.234 mmol) and 3,4,5-trifluoroaniline (35 mg, 0.234 mmol) were combined to yield 3-(3-t-butyl-5-(3-(3,4,5-trifluorophenyl)ureido)-1H-pyrazol-1-yl)-1-naphthoate (147 mg, 123% yield). This material was used directly in the next reaction without purification.

Using general method C, 3-(3-t-butyl-5-(3-(3,4,5-trifluorophenyl)ureido)-1H-pyrazol-1-yl)-1-naphthoate (52 mg, 0.203 mmol) was reduced to yield 1-(3-t-butyl-1-(4-(hydroxymethyl)naphthalen-2-yl)-1H-pyrazol-5-yl)-3-(3,4,5-trifluorophenyl)urea (46 mg, 35% yield). ¹H-NMR (400 MHz, DMSO-d₆): δ 1.31 (s, 9H), 5.02-5.04 (m, 2H), 5.48 (t, J=5.5 Hz, 1H), 6.43 (s, 1H), 7.29-7.33 (m, 2H), 7.58-7.62 (m, 2H), 7.72 (s, 1H), 7.94 (s, 1H), 7.99-8.02 (m, 1H), 8.07-8.09 (m, 1H), 8.67 (s, 1H), 9.31 (s, 1H); MS (ESI) m/z: 469.2 (M+H⁺).

Example 67

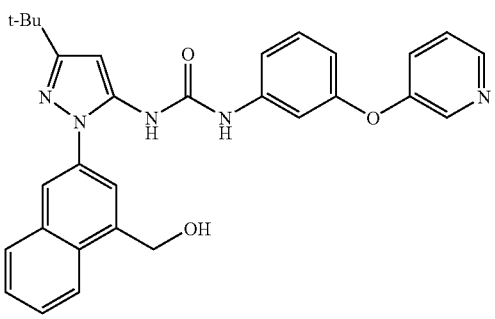

Using general method D, Example A24 (130 mg, 0.24 mmol) and Example A9 (35 mg, 0.234 mmol) were combined to yield 3-(3-t-butyl-5-(3-(3-(pyridin-3-yloxy)phenyl)ureido)-1H-pyrazol-1-yl)-1-naphthoate (122 mg, 91% yield).

Using general method C, 3-(3-t-butyl-5-(3-(3-(pyridin-3-yloxy)phenyl)ureido)-1H-pyrazol-1-yl)-1-naphthoate (52 mg, 0.203 mmol) was reduced to yield 1-(3-t-butyl-1-(4-(hydroxymethyl)naphthalen-2-yl)-1H-pyrazol-5-yl)-3-(3-(pyridin-3-yloxy)phenyl)urea (24 mg, 21% yield). $^1$H-NMR (400 MHz, DMSO-$d_6$): δ 1.30 (s, 9H), 5.03 (s, 2H), 6.41 (s, 1H), 6.67 (d, 1H), 7.07 (d, 1H), 7.24-7.30 (m, 2H), 7.43-7.45 (m, 2H), 7.59-7.61 (m, 2H), 7.71 (s, 1H), 7.95 (s, 1H), 8.00-8.10 (m, 2H), 8.36-8.39 (m, 2H), 8.49 (s, 1H), 9.15 (s, 1H); MS (ESI) m/z: 508.3 (M+H$^+$).

Example A25

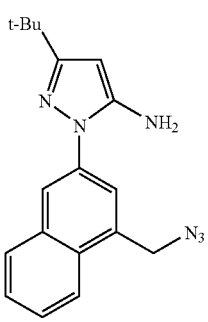

Using general method C, Example A24 (2.0 g, 6.0 mmol) was reduced to yield [3-(5-amino-3-t-butyl-pyrazol-1-yl)naphthalen-1-yl]methanol (1.6 g, 92% yield). $^1$H NMR (300 MHz, DMSO-$d_6$): δ 8.05 (m, 1H), 7.88-7.96 (m, 2H), 7.91 (s, 1H), 7.48-7.52 (m, 2H), 5.40 (s, 1H), 5.38 (t, J=5.4 Hz, 1H), 5.28 (brs, 2H), 4.97 (d, J=5.4 Hz, 2H), 1.24 (s, 9H); MS (ESI) m/z: 296 (M+H$^+$).

To [3-(5-amino-3-t-butyl-pyrazol-1-yl)naphthalen-1-yl]methanol (1.6 g, 5.4 mmol) in THF (20 mL) was added SOCl$_2$ (3.0 g, 25 mmol). The mixture was heated at reflux for 3 h and then concentrated under pressure to yield crude 3-t-butyl-1-[4-(chloromethyl)naphthalen-2-yl]-1H-pyrazol-5-amine (1.5 g), which was used for the next reaction without further purification. MS (ESI) m/z: 314 (M+H$^+$).

To a solution of 3-t-butyl-1-[4-(chloromethyl)naphthalen-2-yl]-1H-pyrazol-5-amine (1.5 g, 4.8 mmol) in DMF (8 mL) was added NaN$_3$ (325 mg, 5.0 mmol). The mixture was stirred at RT overnight, then poured into ice-H$_2$O and extracted with EtOAc (3×100 mL). The combined organic extracts were washed with brine, dried (Na$_2$SO$_4$), filtered, concentrated and purified via column chromatography to afford 1-[4-(azidomethyl)naphthalen-2-yl]-3-t-butyl-1H-pyrazol-5-amine (1.35 g, 88% yield). $^1$H NMR (300 MHz, DMSO-$d_6$): δ 8.06 (m, 2H), 8.04 (m, 1H), 7.85 (s, 1H), 7.54-7.57 (m, 2H), 5.41 (s, 1H), 5.35 (brs, 2H), 4.96 (s, 2H), 1.21 (s, 9H); MS (ESI) m/z: 321 (M+H$^+$).

Example 68

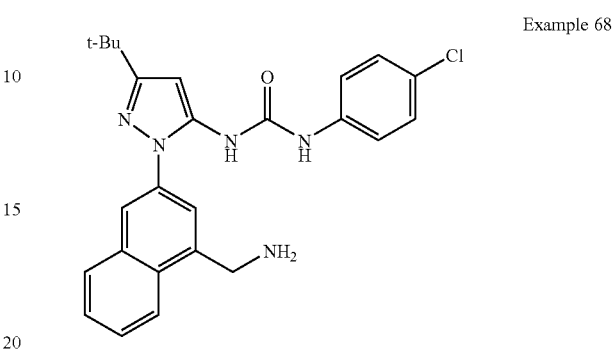

Using general method A, Example A25 (400 mg, 1.25 mmol) and 1-chloro-4-isocyanatobenzene (230 mg, 1.5 mmol) were combined to afford 1-[1-(4-(azidomethyl)naphthalen-2-yl)-3-t-butyl-1 H-pyrazol-5-yl]-3-(4-chlorophenyl)urea (360 mg, 61% yield). MS (ESI) m/z: 474 (M+H$^+$).

A mixture of 1-[1-(4-(azidomethyl)naphthalen-2-yl)-3-t-butyl-1H-pyrazol-5-yl]-3-(4-chlorophenyl)urea (350 mg, 0.74 mmol) and 10% Pd/C (60 mg) in MeOH (20 mL) was stirred at RT under 20 psi of H$_2$ for 3 h and then filtered. The filtrate was concentrated to yield the crude product, which was purified by reverse phase chromatography to afford the product as the TFA salt. A solution of the TFA salt in MeCN/H$_2$O (50 mL) was basified to pH 10 with 1N Na$_2$CO$_3$. After lyophilization, the residue was dissolved in THF and filtered. The filtrate was adjusted to pH 6 with 1N HCl/MeOH (2.0 mL) and then concentrated to afford 1-[1-(4-(aminomethyl)naphthalen-2-yl)-3-t-butyl-1H-pyrazol-5-yl]-3-(4-chlorophenyl)urea (190 mg, 57% yield). $^1$H NMR (300 MHz, DMSO-$d_6$): δ 9.80 (s, 1H), 8.88 (s, 1H), 8.49 (brs, 3H), 8.17-8.18 (m, 2H), 8.08 (d, J=7.2 Hz, 1H), 7.85 (s, 1H), 7.64-7.65 (m, 2H), 7.41 (d, J=6.6 Hz, 2H), 7.21 (d, J=6.6 Hz, 2H), 6.44 (s, 1H), 4.61 (d, J=5.2 Hz, 2H), 1.29 (s, 9H); MS (ESI) m/z: 448 (M+H$^+$).

Example 69

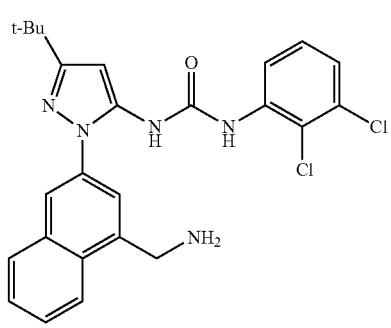

Using the same procedureas for Example 68, Example A25 (400 mg, 1.25 mmol) and 1,2-dichloro-3-isocyanatobenzene (280 mg, 1.5 mmol) were combined to afford 1-[1-(4-(azidomethyl)naphthalen-2-yl)-3-t-butyl-1H-pyrazol-5-yl]-3-(2,3-dichlorophenyl)urea (330 mg, 52% yield). MS (ESI) m/z: 508 (M+H$^+$). This material (320 mg, 0.63 mmol) was reduced to afford 1-[1-(4-(aminomethyl)naphthalen-2-yl)-3-t-butyl- 1H-pyrazol-5-yl]-3-(2,3-dichlorophenyl)urea (185 mg, 61% yield). ¹H NMR (300 MHz, DMSO-d₆): δ 9.71 (s, 1H), 9.04 (s, 1H), 8.53 (brs, 3H), 8.18 (s, 2H), 8.08 (d, J=4.8 Hz, 1H), 7.94 (t, J=6.3 Hz, 1H), 7.89 (s, 1H), 7.62-7.68 (m, 2H), 7.25 (d, J=4.2 Hz, 1H), 6.44 (s, 1H), 4.61 (s, 2H), 1.30 (s, 9H); MS (ESI) m/z: 482 (M+H⁺).

Example A26

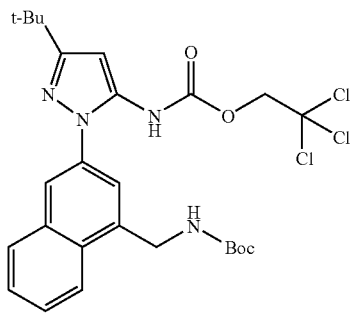

Using general method C, Example A25 (2.0 g, 6.0 mmol) was reduced to yield 1-(4-(aminomethyl)naphthalen-2-yl)-3-t-butyl-1H-pyrazol-5-amine, which was immediately protected as the Boc-amine under standard conditions to yield crude t-butyl (3-(5-amino-3-t-butyl-1H-pyrazol-1-yl)naphthalen-1-yl)methylcarbamate (3.1 g) which was used without further purification. Using general method D, this crude material (3.1 g, 7.9 mmol) was transformed to yield the desired product as a tan-colored foam (5.1 g, 114% yield). ¹H NMR (300 MHz, CDCl₃): δ 8.11 (brd, J=7.6 Hz, 1H), 7.92 (dd, J=2.0, and 7.2 Hz, 1H), 7.85 (d, J=2.0 Hz, 1H), 7.93 (m, 3H), 6.89 (bs, 1H), 6.50 (brs, 1H), 4.94 (brs, 1H), 4.86 (d, J=4.0 Hz, 2H), 4.84 (s, 2H), 1.49 (s, 9H), 1.40 (s, 9H); MS (EI) m/z: 569.0 (M+H⁺).

Example 70

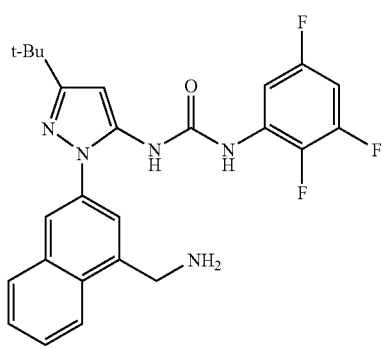

Using general method D, Example A26 (1.0 g, 1.75 mmol), and 2,3,5-trifluoroaniline (0.31 g, 2.11 mmol) were combined to yield t-butyl (3-(3-t-butyl-5-(3-(2,3,5-trifluorophenyl)ureido)-1H-pyrazol-1-yl)naphthalen-1-yl)methylcarbamate.
LC-MS (EI) m/z: 568.2 (M+H⁺). To this material, dissolved in EtOAc (5 mL) was added 3N HCl/EtOAc (5.85 mL). The solution was stirred at room temperature for 3 h. The solid was filtered and dried under vacuum to obtain 1-(1-(4-(aminomethyl)naphthalen-2-yl)-3-t-butyl-1H-pyrazol-5-yl)-3-(2,3,5-trifluorophenyl)urea HCl salt as a white solid (0.31 g, 38% yield). ¹H-NMR (400 MHz, DMSO-d₆): δ 9.49 (brs, 1H), 9.29 (brs, 1H), 8.42 (brs, 2H), 8.22 (d, J=7.2 Hz, 1H), 8.18 (brs, 1H), 8.12 (dd, J=2.4, and 6.8 Hz, 1H), 7.83 (m, 2H), 7.69 (m, 2H), 7.12 (m, 1H), 6.50 (s, 1H), 4.64 (q, J=6.0 Hz, 2H), 1.32 (s, 9H); LC-MS (EI) m/z: 468.2 (M+H⁺).

Example 71

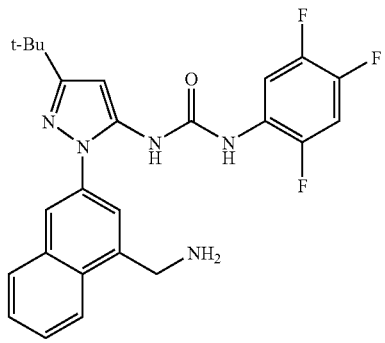

Using the same procedureas for Example 70, Example A26 and 2,4,5-trifluoroaniline were combined to afford 1-(1-(4-(aminomethyl)naphthalen-2-yl)-3-t-butyl-1H-pyrazol-5-yl)-3-(2,4,5-trifluorophenyl)urea as a white solid (0.45 g, 56% yield). ¹H-NMR (400 MHz, DMSO-d₆): δ 9.24 (brs, 1H), 9.19 (brs, 1H), 8.42 (brs, 2H), 8.21 (d, J=7.2 Hz, 1H), 8.18 (brs, 1H), 8.12 (m, 2H), 7.85 (brs, 1H), 7.5-7.7 (m, 3H), 6.49 (s, 1H), 4.64 (q, J=6.0 Hz, 2H), 1.32 (s, 9H); LC-MS (EI) m/z: 468.2 (M+H⁺).

Example 72

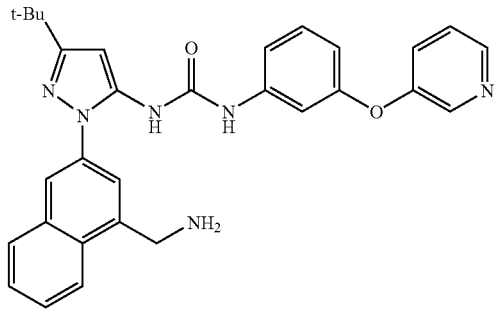

Using the same procedureas for Example 70, Example A26 and Example A9 were combined to yield 1-(1-(4-(aminomethyl)naphthalen-2-yl)-3-t-butyl-1H-pyrazol-5-yl)-3-(3-(pyridin-3-yloxy)phenyl)urea (87 mg, 86% yield). ¹H-NMR (400 MHz, DMSO-d₆): δ 8.45 (m, 4H), 8.19 (m, 2H), 8.11 (m, 1H), 7.88 (m, 1H), 7.68 (m, 1H), 7.0-7.6 (m, 5H), 6.68 (m, 1H), 6.44 (s, 1H), 4.64 (q, J=6.0 Hz, 2H), 1.33 (s, 9H); LC-MS (EI) m/z: 507.2 (M+H⁺).

Example 73

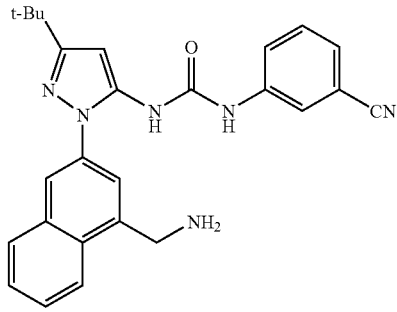

Using the same procedureas for Example 70, Example A26 was combined with 3-aminobenzonitrile to afford 1-(1-(4-(aminomethyl)naphthalen-2-yl)-3-t-butyl-1H-pyrazol-5-yl)-3-(3-cyanophenyl)urea as a white solid. (67 mg, 66% yield). ¹H-NMR (DMSO-d₆): δ 8.45 (m, 4H), 8.19 (m, 2H), 8.11 (m, 1H), 7.88 (m, 1H), 7.68 (m, 1H), 7.0-7.6 (m, 5H), 6.68 (m, 1H), 6.44 (s, 1H), 4.64 (q, J=6.0 Hz, 2H), 1.33 (s, 9H); LC-MS (EI) m/z: 507.2 (M+H⁺).

Example 74

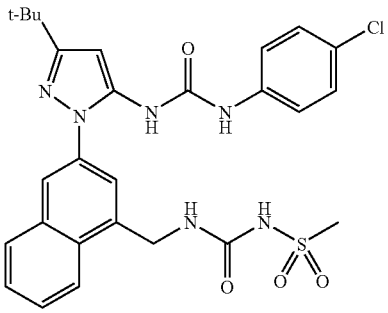

Using the same procedure as Example 122, Example 68 (140 mg, 0.31 mmol) was transformed to yield 1-{3-t-butyl-1-[1-(methanesulfonylureidoamidomethyl)naphthalen-3-yl]-1H-pyrazol-5-yl}-3-(4-chlorophenyl-1-yl)urea (45 mg, 26% yield). $^1$H NMR (300 MHz, DMSO-d$_6$): δ 9.27 (brs, 1H), 8.55 (brs, 1H), 8.11 (m, 1H), 8.00 (m, 1H), 7.92 (s, 1H), 7.55-7.58 (m, 3H), 7.38 (d, J=8.4 Hz, 2H), 7.19 (t, J=9.0 Hz, 2H), 6.39 (s, 1H), 4.69 (s, 2H), 2.95 (s, 3H), 1.28 (s, 9H); MS (ESI) m/z: 569 (M+H⁺).

Example 75

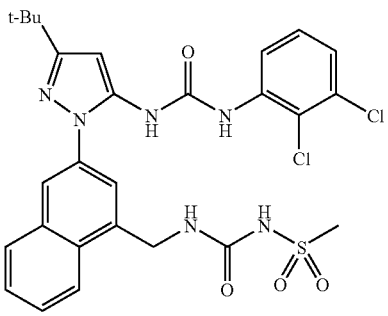

Using the same procedure as Example 122, Example 69 (135 mg, 0.28 mmol) was transformed to yield 1-{3-t-butyl-1-[1-(methanesulfonylureidoamidomethyl)naphthalen-3-yl]-1H-pyrazol-5-yl}-3-(2,3-dichlorophenyl-1-yl)urea (50 mg, 30% yield). $^1$H NMR (300 MHz, DMSO-d$_6$): δ 9.29 (brs, 1H), 8.81 (s, 1H), 8.15 (m, 1H), 7.99-8.00 (m, 2H), 7.92 (s, 1H), 7.55-7.58 (m, 3H), 7.26 (d, J=4.5 Hz, 2H), 6.42 (s, 1H), 4.71 (s, 2H), 2.88 (s, 3H), 1.28 (s, 9H); MS (ESI) m/z: 603 (M+H⁺).

Example A27

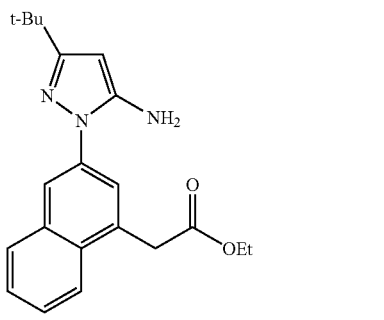

A solution of 3-nitronaphthalene-1-carboxylic acid (10 g, 46 mmol, available from Example A23) in SOCl$_2$ (50 mL) was heated at reflux for 3 h. After removal of the solvent, the resultant 3-nitro-napthalene-1-carbonyl chloride was used without further purification (8.4 g, 78% yield).

A 2-necked round-bottomed flask, equipped with a dropping funnel and distillation apparatus was cooled in acetone-dry ice bath. A mixture of KOH (12 g, 0.2 mmol) in 20 mL of H$_2$O and 60 mL of Carbitol® (2(2-ethoxyethoxy)ethanol) was heated at 70° C. and a solution of N-methyl-N-nitroso-p-toluenesulfonamide (42.5 g, 0.2 mmol) in 300 mL of Et$_2$O was added dropwise. The ethereal diazomethane solution (250 mL, 83%) was collected at −20° C. and then used directly in the next reaction.

To a solution of 3-nitro-napthalene-1-carbonyl chloride (8.4 g, 35.7 mmol) in anhydrous THF (70 mL) was added an ethereal solution of diazomethane (250 mL) dropwise at 0° C. The reaction mixture was stirred for 5 h, and then warmed to RT overnight. Excess diazomethane was decomposed by the dropwise addition of AcOH (50 mL). The mixture was extracted with Et$_2$O (3×150 ml), washed with brine and saturated NaHCO$_3$ aqueous solution, dried and filtered. The filtrate was concentrated to give the crude product, which was purified by column chromatography to yield 2-diazo-1-(3-nitronaphthalen-1-yl)ethanone (7.0 g, 81% yield). $^1$H NMR (300 MHz, DMSO-d$_6$): δ 9.14 (s, 1H), 8.47 (d, J=7.2 Hz, 1H), 8.35 (d, J=7.2 Hz, 1H), 8.35 (s, 1H), 7.84 (t, J=7.2 Hz, 2H), 7.76 (t, J=7.8 Hz, 2H), 6.84 (s, 1H); MS (ESI) m/z: 242 (M+H⁺).

To a mixture of 2-diazo-1-(3-nitronaphthalen-1-yl)ethanone (3 g, 12.4 mmol) in EtOH (40 mL) was heated at 70° C. added AgOAc (300 mg, 1.8 mmol). The resulting mixture was stirred for 2 h. After filtration, the residue was washed with THF (3×30 mL). The combined organic layers were concentrated to the crude product, which was recrystallized from EtOH to give (3-nitronaphthalen-1-yl)acetic acid ethyl ester (2.1 g, 66% yield). $^1$H NMR (300 MHz, DMSO-d$_6$): δ 8.92 (s, 1H), 8.29 (d, J=8.1 Hz, 1H), 8.21 (s, 1H), 8.02 (d, J=8.1 Hz, 1H), 7.79 (t, J=7.2 Hz, 1H), 7.70 (t, J=7.2 Hz, 1H), 4.30 (s, 2H), 4.06 (d, J=7.2 Hz, 2H), 1.14 (t, J=7.2 Hz, 3H); MS (ESI) m/z: 260 (M+H⁺).

A mixture of (3-nitronaphthalen-1-yl)-acetic acid ethyl ester (3 g, 11.58 mmol) and 10% Pd/C (300 mg) in EtOH (100 mL) was stirred under H$_2$ atmosphere (45 psi) at RT overnight. The mixture was filtered over Celite® and washed with EtOH. The filtrate was concentrated to afford (3-aminonaphthalen-1-yl)-acetic acid ethyl ester, which was put to the next reaction without further purification. $^1$H NMR (300 MHz, DMSO-d$_6$), δ 7.65 (d, J=8.1 Hz, 1H), 7.48 (d, J=8.1 Hz, 1H), 7.27 (t, J=8.1 Hz, 1H), 7.08 (t, J=8.1 Hz, 1H), 6.85 (s, 1H), 6.73 (s, 1H), 5.35 (s, 2H), 4.06 (d, J=7.2 Hz, 2H), 3.94 (s, 2H), 1.14 (t, J=7.2 Hz, 3H); MS (ESI) m/z: 260 (M+H⁺).

To a mixture of (3-aminonaphthalen-1-yl)acetic acid ethyl ester (2.7 g, 11.8 mmol) in conc. HCl (20 mL) was added an aqueous solution of NaNO$_2$ (0.9 g, 13 mmol) dropwise at 0-5° C. The resulting mixture was stirred at 0° C. for 30 min and then treated with a solution of SnCl$_2$.2H$_2$O (5.9 g, 26.2 mmol) in conc. HCl at such a rate that the reaction temperature never rose above 5° C. After the addition was completed, the mixture was stirred for another 2 h at RT. The precipitate was collected by filtration and washed with ethyl ether to afford (3-hydrazinonaphthalen-1-yl)-acetic acid ethyl ester hydrochloride as a brown solid (2.3 g, 80% yield).

A solution of [3-(5-amino-3-t-butyl-pyrazol-1-yl)naphthalen-1-yl]acetic acid ethyl ester hydrochloride (3 g, 12.3 mmol) and 4,4-dimethyl-3-oxopentanenitrile (2.3 g, 18.4 mol) in alcohol (30 mL) containing concentrated hydrochloric acid (10 mL) was heated at reflux overnight. After removed of the solvent, the precipitate was collected by suction and washed with ethyl ether to afford [3-(5-amino-3-t-butyl-pyrazol-1-yl)naphthalen-1-yl]acetic acid ethyl ester hydrochloride as a yellow solid (3.5 g, 80% yield). $^1$H NMR (300 MHz, DMSO-$d_6$): δ 8.11 (s, 1H), 8.05 (m, 1H), 8.01 (m, 1H), 7.72 (s, 1H), 7.64 (m, 1H), 5.58 (s, 1H), 4.27 (s, 2H), 4.13 (d, J=7.2 Hz, 2H), 1.31 (s, 3H), 1.22 (t, J=7.2 Hz, 3H); MS (ESI) m/z: 352 (M+H$^+$).

Example 76

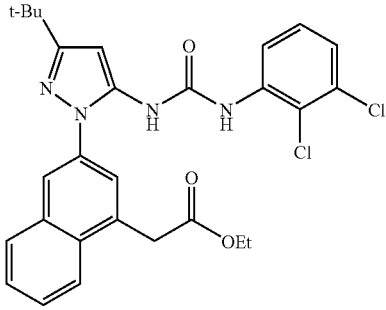

Using general method A, Example A27 (400 mg, 1.1 mmol) and 1,2-dichloro-3-isocyanatobenzene (800 mg, 4.2 mmol) were combined to yield 3-{3-t-butyl-5-[3-(2,3-dichloro-phenyl)ureido]pyrazol-1-yl}naphthalen-1-yl)-acetic acid ethyl ester as a white solid (184 mg, 12.3% yield). $^1$H NMR (300 MHz, DMSO-$d_6$): δ 9.28 (s, 1H), 8.75 (s, 1H), 8.04-7.92 (m, 4H), 7.61-7.54 (m, 3H), 7.28-7.24 (m, 2H), 6.40 (s, 1H), 4.20 (s, 1H), 4.03 (q, J=7.2 Hz, 2H), 1.25 (s, 9H), 1.11 (t, J=7.2 Hz, 3H); MS (ESI) m/z: 539 (M+H$^+$).

Example 77

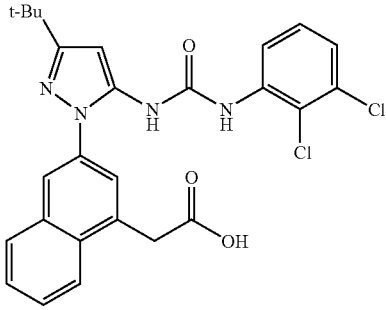

Using general method E, Example 76 (130 mg, 0.24 mmol) was saponified to afford 2-(3-(3-t-butyl-5-(3-(2,3-dichlorophenyl)-ureido)-1H-pyrazol-1-yl)naphthalen-1-yl)acetic acid as a white solid (106 mg, 87% yield). $^1$H NMR (300 MHz, DMSO-$d_6$): δ 9.39 (s, 1H), 8.83 (s, 1H), 8.03-7.97 (m, 4H), 7.63-7.54 (m, 3H), 7.30-7.23 (m, 2H), 6.42 (s, 1H), 4.11 (s, 2H), 1.27 (s, 9H); MS (ESI) m/z: 511 (M+H$^+$).

Example 78

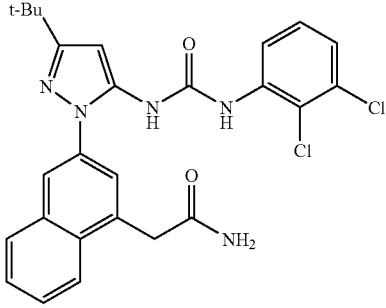

Example 77 (500 mg, 0.98 mmol) was dissolved in a mixed solvent of SOCl$_2$ (5 mL) and DMF (1 mL). The mixture was refluxed for 2 h, after which dry toluene was added and the solvent was removed under vacuum. The process was repeated twice and the crude product of acid chloride was obtained, which was dissolved in dry THF immediately and cooled to −20° C. NH$_3$ was bubbled through the solution for 15 min. The solution was allowed to warm to RT, and the solvent was removed under reduced pressure to yield a residue, which was purified by preparative HPLC to provide 2-(3-{3-t-butyl-5-[3-(2,3-dichlorophenyl)ureido]pyrazol-1-yl}naphthalen-1-yl)acetamide (47 mg, 10% yield). $^1$H NMR (300 MHz, DMSO-$d_6$): 9.41 (s, 1H), 8.81 (s, 1H), 8.09 (m, 1H), 7.99-7.93 (m, 3H), 7.60-7.56 (t, 4H), 7.27-7.24 (m, 2H), 7.00 (s, 1H), 6.40 (s, 1H), 3.84 (s, 2H), 1.26 (s, 1H); MS (ESI) m/z: 510 (M+H$^+$).

Example A28

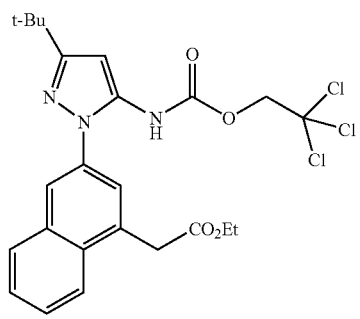

Using general method D, Example A27 (1.50 g, 4.40 mmol) was transformed to ethyl 2-(3-(3-t-butyl-5-((2,2,2-trichloroethoxy)carbonylamino)-1H-pyrazol-1-yl)naphthalen-1-yl)acetate (1.46 g, 63% yield). $^1$H NMR (400 Mhz, DMSO-$d_6$): δ 1.31 (s, 9H), 3.62 (s, 3H), 4.23 (s, 2H), 4.84 (s, 2H), 6.35 (s, 1H), 7.57-7.63 (m, 3H), 7.93-7.98 (m, 3H), 10.09 (s, 1H); MS (ESI) m/z: 514.0 (M+H$^+$).

Example 79

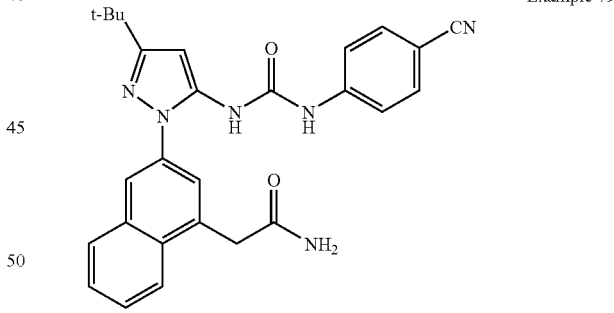

In DMSO (2 mL) was placed Example A28 (120 mg, 0.266 mmol), 4-aminobenzonitrile (31 mg, 0.266 mmol) and i-Pr$_2$NEt base (34 mg, 0.266 mmol). The mixture was stirred overnight at 65° C., cooled to RT and diluted with H$_2$O (20 mL). The mixture was diluted with EtOAc (20 mL) and the organic phase separated, washed with 5% citric acid (20 mL), brine (20 mL), dried (Na$_2$SO$_4$) and concentrated to yield methyl 2-(3-(3-t-butyl-5-(3-(4-cyanophenyl)-ureido)-1H-pyrazol-1-yl)naphthalen-1-yl)acetate as an oil (115 mg, 102% yield). This material was used directly in the next reaction without purification.

Using general method E, the above ester (115 mg, 0.239 mmol) was saponified to yield 2-(3-(3-t-butyl-5-(3-(4-cyanophenyl)ureido)-1H-pyrazol-1-yl)naphthalen-1-yl)-acetic acid as a foam (81 mg, 73% yield). This material was used directly in the next reaction without purification.

In DMF (1 mL) was placed the above acid (81 mg, 0.20 mmol), HOBT (31 mg, 0.2 mmol) and EDC (50 mg, 0.2 mmol). The mixture was stirred for 15 min and treated with a solution of 0.5M $NH_3$ in dioxane (1 mL, 0.5 mmol) and stirred overnight at RT. Additional EDC (30 mg) and 0.5M $NH_3$ in dioxane (1 mL, 0.5 mmol) were added and the reaction stirred until all starting material was consumed. The reaction mixture was diluted with EtOAc (15 mL) and 1N HCl (10 mL). The organic phase was separated, washed with 5% citric acid (10 mL), satd. $NaHCO_3$ (10 mL), brine (10 mL), dried ($Na_2SO_4$), concentrated, and purified to yield 1-(1-(4-(2-amino-2-oxoethyl)naphthalen-2-yl)-3-t-butyl-1H-pyrazol-5-yl)-3-(4-cyanophenyl)urea (17 mg, 21% yield). $^1$H-NMR (400 MHz, DMSO-$d_6$): δ 1.31 (s, 9H), 3.95 (s, 2H), 6.46 (s, 1H), 7.05 (s, 1H), 7.53-7.71 (m, 8H), 7.95-8.02 (m, 2H), 8.13-8.16 (m, 1H), 8.70 (s, 1H), 9.50 (s, 1H); MS (ESI) m/z: 467.3 (M+H$^+$).

General Experimental for Examples 80-99

The following compounds were prepared using the appropriate aniline and the same procedures as for Example 79. For Examples 94-98, 1-amino-2,3-dihydroxypropane was used in place of ammonia. For Example 99, serinol was used in place of ammonia.

| Example | Name | MS (EI) (M + H$^+$) | $^1$H NMR (400 MHz, DMSO-$d_6$) |
|---|---|---|---|
| Example 80 | 1-(1-(4-(2-amino-2-oxoethyl)naphthalen-2-yl)-3-t-butyl-1H-pyrazol-5-yl)-3-(2,3,4-trifluorophenyl)urea 33 mg, 37% yield | 496.3 | δ 1.31 (s, 9H), 3.95 (s, 2H), 6.45 (s, 1H), 7.05 (brs, 1H), 7.25-7.27 (m, 1H), 7.58-7.62 (m, 4H), 7.84-8.16 (m, 4H), 8.94 (brs, 1H), 9.06 (s, 1H) |
| Example 81 | 1-(1-(4-(2-amino-2-oxoethyl)naphthalen-2-yl)-3-t-butyl-1H-pyrazol-5-yl)-3-(2,4,5-trifluorophenyl)urea 36 mg, 32% yield | 496.3 | δ 1.31 (s, 9H), 3.96 (s, 2H), 6.47 (s, 1H), 7.05 (s, 1H), 7.57-7.64 (m, 5H), 7.95 (brs, 1H), 8.02-8.04 (m, 1H), 8.14-8.22 (m, 2H), 8.99 (s, 1H), 9.12 (s, 1H) |
| Example 82 | 1-(1-(4-(2-amino-2-oxoethyl)naphthalen-2-yl)-3-t-butyl-1H-pyrazol-5-yl)-3-(2,4-difluorophenyl)urea 53 mg, 62% yield | 478.3 | δ 1.30 (s, 9H), 3.95 (s, 2H), 6.45 (s, 1H), 7.03-7.05 (m, 2H), 7.26-7.29 (m, 1H), 7.58-7.61 (m, 4H), 7.95-8.16 (m, 4H), 8.90 (brs, 2H) |

-continued

| Example | Name | MS (EI) (M + H⁺) | ¹H NMR (400 MHz, DMSO-d₆) |
|---|---|---|---|
| Example 83 | 1-(1-(4-(2-amino-2-oxoethyl)naphthalen-2-yl)-3-t-butyl-1H-pyrazol-5-yl)-3-(3,5-difluorophenyl)urea 33 mg, 56% yield | 478.3 | δ 1.31 (s, 9H), 3.95 (s, 2H), 6.45 (s, 1H), 6.70-6.80 (m, 1H), 7.04-7.13 (m, 3H), 7.59-7.62 (m, 4H), 7.95 (s, 1H), 7.99-8.02 (m, 1H), 8.14-8.16 (m, 1H), 8.65 (s, 1H), 9.37 (s, 1H) |
| Example 84 | 1-(1-(4-(2-amino-2-oxoethyl)naphthalen-2-yl)-3-t-butyl-1H-pyrazol-5-yl)-3-(4-fluorophenyl)urea 48 mg, 65% yield | 460.2 | δ 1.31 (s, 9H), 3.95 (s, 2H), 6.43 (s, 1H), 7.04-7.11 (m, 3H), 7.38-7.41 (m, 2H), 7.58-7.62 (m, 4H), 7.95 (brs, 1H), 8.00-8.02 (m, 1H), 8.14-8.16 (m, 1H), 8.48 (s, 1H), 9.01 (s, 1H) |
| Example 85 | 1-(1-(4-(2-amino-2-oxoethyl)naphthalen-2-yl)-3-t-butyl-1H-pyrazol-5-yl)-3-(2,3,5-trifluorophenyl)urea 61 mg, 53% yield | 496.3 | 1.31 (s, 9H), 3.96 (s, 2H), 6.48 (s, 1H), 7.04-7.12 (m, 2H), 7.58-7.63 (m, 4H), 7.87-7.90 (m, 1H), 7.96 (s, 1H), 8.02-8.05 (m, 1H), 8.15-8.17 (m, 1H), 9.08 (s, 1H), 9.35 (s, 1H) |
| Example 86 | 1-(1-(4-(2-amino-2-oxoethyl)naphthalen-2-yl)-3-t-butyl-1H-pyrazol-5-yl)-3-(3-(pyridin-3-yloxy)phenyl)urea hydrochloride 69 mg, 46% yield | 535.2 | 1.30 (s, 9H), 3.95 (s, 2H), 6.40 (s, 1H), 6.75 (d, 1H), 7.04 (brs, 1H), 7.10-7.12 (m, 1H), 7.31-7.40 (m, 2H), 7.57-7.64 (m, 4H), 7.76-7.79 (m, 1H), 7.86-7.89 (m, 1H), 7.99-8.02 (m, 2H), 8.12-8.15 (m, 1H), 8.53-8.55 (m, 1H), 8.62 (m, 1H), 8.83 (s, 1H), 9.57 (s, 1H) |

-continued

| Example | | Name | MS (EI) (M + H$^+$) | $^1$H NMR (400 MHz, DMSO-d$_6$) |
|---|---|---|---|---|
| Example 87 | 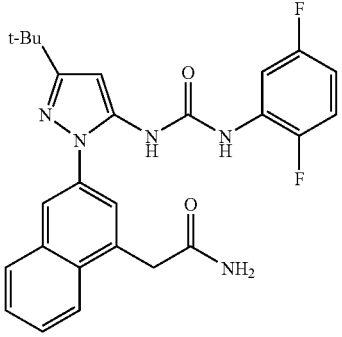 | 1-(1-(4-(2-amino-2-oxoethyl)naphthalen-2-yl)-3-t-butyl-1H-pyrazol-5-yl)-3-(2,5-difluorophenyl)urea, 32 mg, 29% yield | 478.3 | 1.31 (s, 9H), 3.96 (s, 2H), 6.49 (s, 1H), 6.81-6.84 (m, 1H), 7.04 (br.s, 1H), 7.24-7.28 (m, 1H), 7.59-7.64 (m, 4H), 7.96 (brs, 1H), 8.00-8.05 (m, 2H), 8.15-8.17 (m, 1H), 9.05 (s, 1H), 9.15 (s, 1H). |
| Example 88 | 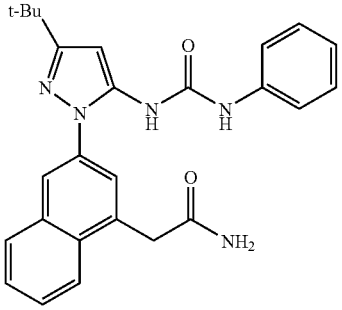 | 1-(1-(4-(2-amino-2-oxoethyl)naphthalen-2-yl)-3-t-butyl-1H-pyrazol-5-yl)-3-phenylurea, 31 mg, 56% yield | 442.3 | 1.31 (s, 9H), 3.95 (s, 2H), 6.45 (s, 1H), 6.96-6.98 (m, 1H), 7.03-7.04 (m, 1H), 7.23-7.27 (m, 2H), 7.37-7.39 (m, 2H), 7.58-7.62 (m, 4H), 7.95 (s, 1H), 8.01-8.14 (m, 2H), 8.50 (s, 1H), 8.98 (s, 1H) |
| Example 89 | 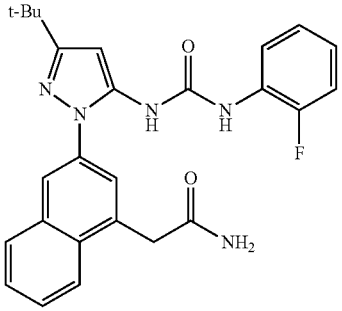 | 1-(1-(4-(2-amino-2-oxoethyl)naphthalen-2-yl)-3-t-butyl-1H-pyrazol-5-yl)-3-(2-fluorophenyl)urea, 42 mg, 54% yield | 460.2 | 1.31 (s, 9H), 3.96 (s, 2H), 6.47 (s, 1H), 6.99-7.22 (m, 4H), 7.60-7.62 (m, 4H), 7.96 (brs, 1H), 8.02-8.04 (m, 1H), 8.11-8.16 (m, 2H), 8.94-8.96 (m, 2H) |
| Example 90 | 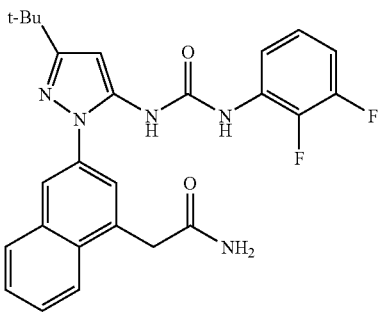 | 1-(1-(4-(2-amino-2-oxoethyl)naphthalen-2-yl)-3-t-butyl-1H-pyrazol-5-yl)-3-(2,3-difluorophenyl)urea, 23 mg, 27% yield | 478.3 | 1.30 (s, 9H), 3.96 (brs, 2H), 6.47 (brs, 1H), 7.03-7.20 (m, 3H), 7.58-7.65 (m, 4H), 7.94-8.16 (m, 4H), 8.99 (brs, 1H), 9.12 (bsr, 1H) |

-continued

| Example | Name | MS (EI) (M + H⁺) | ¹H NMR (400 MHz, DMSO-d₆) |
|---|---|---|---|
| Example 91 | 1-(1-(4-(2-amino-2-oxoethyl)naphthalen-2-yl)-3-t-butyl-1H-pyrazol-5-yl)-3-cyclohexylurea, 41 mg, 73% yield | 448.2 | 1.07-1.31 (m, 5H), 1.31 (s, 9H), 145-1.76 (m, 5H), 3.32 (m, 1H), 3.93 (s, 2H), 6.33 (s, 1H), 6.45-6.46 (d, 1H), 7.03 (brs, 1H), 7.56-7.60 (m, 4H), 7.86 (s, 1H), 7.97 (m, 1H), 8.08 (s, 1H), 8.12 (m, 1H). |
| Example 92 | 1-(1-(4-(2-amino-2-oxoethyl)naphthalen-2-yl)-3-t-butyl-1H-pyrazol-5-yl)-3-(3,4,5-trifluorophenyl)urea, 18 mg, 23% yield | 496.3 | 1.31 (s, 9H), 3.95 (brs, 2H), 6.43 (brs, 1H), 7.04-7.05 (m, 1H), 7.29-7.33 (m, 2H), 7.58-7.63 (m, 4H), 7.94-7.95 (m, 1H), 7.99-8.01 (m, 1H), 8.13-8.16 (m, 1H), 8.67 (s, 1H), 9.32 (s, 1H). |
| Example 93 | 1-(1-(4-(2-amino-2-oxoethyl)naphthalen-2-yl)-3-t-butyl-1H-pyrazol-5-yl)-3-cyclopentylurea, 16 mg, 25% yield | 434.2 | 1.76-1.31 (m, 2H), 1.31 (s, 9H), 1.48-1.56 (m, 4H), 1.77-1.78 (m, 2H), 3.86-3.87 (m, 1H), 3.93 (s, 2H), 6.33 (s, 1H), 6.53-6.54 (m, 1H), 7.03 (m, 1H), 7.56-7.60 (m, 4H), 7.87 (s, 1H), 7.97-7.98 (m, 1H), 8.03 (s, 1H), 8.10-8.20 (m, 1H) |
| Example 94 | 1-(3-t-butyl-1-(4-(2-(2,3-dihydroxypropyl-amino)-2-oxoethyl)naphthalen-2-yl)-1H-pyrazol-5-yl)-3-(2,4,5-trifluorophenyl)urea, 65 mg, 50% yield | 570.2 | 1.31 (s, 9H), 2.95-3.05 (m, 1H), 3.21-3.38 (m, 3H), 3.45-3.55 (m, 1H), 4.02 (s, 2H), 4.48-4.51 (m, 1H), 4.76-4.77 (m, 1H), 6.47 (s, 1H), 7.59-7.62 (m, 4H), 7.95 (s, 1H), 8.01-8.03 (m, 1H), 8.17-8.23 (m, 3H), 9.00 (s, 1H), 9.12 (m, 1H) |

-continued

| Example | Name | MS (EI) (M + H+) | 1H NMR (400 MHz, DMSO-d6) |
|---|---|---|---|
| Example 95 | 1-(3-t-butyl-1-(4-(2-(2,3-dihydroxypropyl-amino)-2-oxoethyl)naphthalen-2-yl)-1H-pyrazol-5-yl)-3-(2,3,5-trifluorophenyl)urea 56 mg, 44% yield | 570.2 | 1.31 (s, 9H), 2.90-3.05 (m, 1H), 3.25-3.32 (m, 3H), 3.45-3.55 (m, 1H), 4.02 (s, 2H), 4.49 (t, 1H), 4.75 (d, 1H), 6.48 (s, 1H), 7.10-7.15 (m, 1H), 7.59-7.63 (m, 3H), 7.80-8.10 (m, 3H), 8.15-8.25 (m, 2H), 9.09 (s, 1H), 9.36 (s, 1H) |
| Example 96 | 1-(3-t-butyl-1-(4-(2-(2,3-dihydroxypropyl-amino)-2-oxoethyl)naphthalen-2-yl)-1H-pyrazol-5-yl)-3-(2,3,4-trifluorophenyl)urea 24 mg, 24% yield | 570.2 | 1.27 (s, 9H), 2.97-3.02 (m, TH), 3.19-3.52 (m, 4H), 4.02 (s, 2H), 4.49 (brs, 2H), 6.45 (s, 1H), 7.24-7.27 (m, 1H), 7.59-7.63 (m, 3H), 7.84-7.94 (m, 2H), 8.00-8.03 (m, 1H), 8.17-8.23 (m, 2H), 8.94 (s, 1H), 9.06 (s, 1H) |
| Example 97 | 1-(3-t-butyl-1-(4-(2-(2,3-dihydroxypropyl-amino)-2-oxoethyl)naphthalen-2-yl)-1H-pyrazol-5-yl)-3-(3-(pyridin-3-yloxy)phenyl)urea 61 mg, 36% yield | 609.2 | 1.30 (s, 9H), 2.97-3.02 (m, 1H), 3.19-3.29 (m, 3H), 3.48-3.50 (m, 1H), 4.02 (s, 2H), 6.40 (s, 1H), 6.72-6.75 (m, 1H), 7.09-7.12 (m, 1H), 7.30-7.38 (m, 2H), 7.57-7.64 (m, 3H), 7.70-7.73 (m, 1H), 7.78-7.80 (m, 1H), 7.97-8.02 (m, 2H), 8.15-8.18 (m, 1H), 8.23-8.26 (m, 1H), 8.51-8.59 (m, 2H), 8.75 (s, 1H), 9.46 (s, 1H) |
| Example 98 | 1-(3-t-butyl-1-(4-(2-(2,3-dihydroxypropyl-amino)-2-oxoethyl)naphthalen-2-yl-1H-pyrazol-5-yl)-3-(3,4,5-trifluorophenyl)urea, 116 mg, 55% yield | 570.2 | 1.30 (s, 9H), 2.95-3.05 (m, 1H), 3.21-3.31 (m, 3H), 3.47-3.50 (m, 1H), 4.01 (s, 2H), 4.51 (t, 1H), 4.77 (d, 1H), 6.44 (s, 1H), 6.29-7.34 (m, 2H), 7.58-7.60 (m, 2H), 7.63 (s, 1H) 7.94 (s, 1H) 7.95-8.01 (m, 1H), 8.16-8.23 (m, 2H), 8.70 (s, 1H), 9.34 (s, 1H) |

-continued

| Example | Name | MS (EI) (M + H⁺) | ¹H NMR (400 MHz, DMSO-d₆) |
|---|---|---|---|
| Example 99 | 1-(3-t-butyl-1-(4-(2-(1,3-dihydroxypropan-2-ylamino)-2-oxoethyl)naphthalen-2-yl)-1H-pyrazol-5-yl)-3-(2,5-difluorophenyl)urea 72 mg, 27% yield | 552.2 | 1.31 (s, 9H), 3.40-3.50 (m, 4H), 3.66-3.74 (m, 1H), 4.02 (s, 2H), 4.4-4.70 (br s, 2H), 6.48 (s, 1H), 6.79-6.84 (m, 1H), 7.22-7.28 (m, 1H), 7.58-7.61 (m, 3H), 7.95 (s, 1H), 7.99-8.05 (m, 3H), 8.17-8.20 (m, 1H), 9.07 (s, 1H), 9.17 (s, 1H). |

Example 100

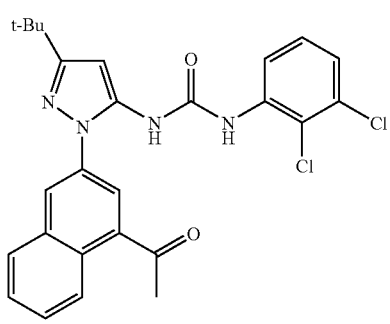

To a solution of Example 58 (240 mg, 0.457 mmol) in THF (10 mL), at 0° C. was added dropwise MeMgCl (0.92 mL, 205 mg, 2.74 mmol). The mixture stirred at 0° C. for 1 h and then warmed to RT for 3 h. The reaction mixture was stirred at RT and treated with two additional batches of MeMgCl (2×0.6 mL, 1.8 mmol), subsequently quenched with H2O (25 mL) and diluted with EtOAc (25 mL) and 5% citric acid (10 mL). The organic phase was separated, washed with brine, dried (Na₂SO₄), concentrated and purified to yield 1-(1-(4-acetyl-naphthalen-2-yl)-3-t-butyl-1 H-pyrazol-5-yl)-3-(2,3-dichlorophenyl)urea (42 mg, 18% yield). ¹H-NMR (300 MHz, DMSO-d₆): δ 1.33 (s, 9H), 2.75 (s, 3H), 6.49 (s, 1H), 7.29-7.33 (m, 2H), 7.64-7.71 (m, 2H), 8.03-8.06 (m, 1H), 8.12-8.14 (m, 1H), 8.26 (s, 1H), 8.31 (s, 1H), 8.58-8.61 (m, 1H), 8.77 (s, 1H), 9.36 (s, 1H); MS (ESI) m/z: 497.0 (M+H⁺).

Example 101

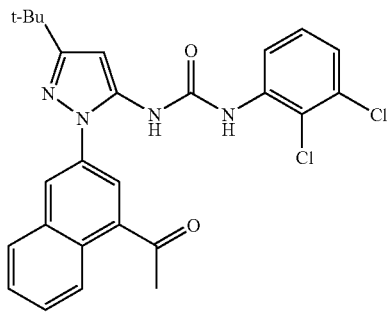

Example 60 (310 mg, 0.641 mmol) and MnO₂ (1.12 g, 12.8 mmol) were refluxed in CH₂Cl₂ (20 mL) for 23 h. The mixture was filtered hot through Celite® and washed with CH₂Cl₂ (2×20 mL). The combined organic solutions were evaporated at reduced pressure to yield 1-(3-t-butyl-1-(4-formylnaphthalen-2-yl)-1H-pyrazol-5-yl)-3-(2,3-dichlorophenyl)urea a pale pink foam which was used without further purification.

To this aldehyde (150 mg, 0.312 mmol) in THF (5 mL) at 0° C. was added dropwise MeMgCl (0.37 mL, 82 mg, 1.09 mmol). The mixture was stirred at 0° C. for 1 h and then warmed to RT and stirred for 7 h. The mixture was treated with an additional batch of MeMgCl (0.2 mL, 0.6 mmol), stirred overnight at RT, treated with additional MeMgCl (0.3 mL, 0.9 mmol) and then quenched with H₂O (25 mL) and diluted with EtOAc (25 mL) and 5% citric acid (10 mL). The organic phase was separated, washed with brine dried (Na₂SO₄), filtered, concentrated and purified to yield 1-(3-t-butyl-1-(4-(1-hydroxyethyl)naphthalen-2-yl)-1H-pyrazol-5-yl)-3-(2,3-dichlorophenyl)urea (65 mg, 42% yield). ¹H-NMR (300 MHz, DMSO-d₆): δ 1.31 (s, 9H), 1.49 (d, J=6.2 Hz, 3H), 5.47-5.48 (m, 1H), 5.53-5.54 (m, 1H), 6.45 (s, 1H), 7.28-7.31 (m, 2H), 7.57-7.60 (m, 2H), 7.83 (s, 1H), 7.94 (s, 1H), 8.02-8.18 (m, 3H), 8.78 (s, 1H), 9.31 (s, 1H); MS (ESI) m/z: 499.0 (M+H⁺).

Example 102

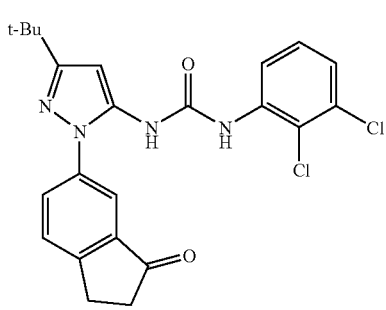

To a solution of 1-indanone (30 g, 0.23 mol) in conc. H₂SO₄ (200 mL) was added a solution of KNO₃ (34 g, 0.34 mol) in conc. H₂SO₄ (100 mL) at 0° C. The resulting mixture was stirred for 2 h, and then poured into ice-H2O (3 L). The mixture was extracted with EtOAc (3×500 mL). The combined organic layers were washed with brine (3×500 mL), dried (Na₂SO₄), filtered, concentrated and purified via column chromatography to afford 6-nitro-indan-1-one (25 g, 61% yield). ¹H-NMR (300 MHz, DMSO-d₆): □ 8.45 (d, J=8.4 Hz, 1H), 8.22 (s, 1H), 7.82 (d, J=8.4 Hz, 1H), 3.20 (t, J=6.0 Hz, 2H), 2.74 (t, J=6.0 Hz, 2H).

A mixture of the 6-nitroindan-1-one (10 g, 56 mmol) and 10% Pd/C (2.0 g) in MeOH (200 mL) was stirred under 30 psi of H₂ at RT for 3 h. After filtration, the filtrate was concentrated to afford 6-aminoindan-1-one (7.2 g, 87% yield). ¹H NMR (300 MHz, DMSO-d₆): δ 7.17 (d, J₁=8.1 Hz, 1H), 6.87 (d, J=8.1 Hz, 1H), 6.71 (s, 1H), 5.24 (s, 2H), 2.85 (t, J=5.4 Hz, 2H), 2.49 (t, J=5.7 Hz, 2H).

To a mixture of 6-aminoindan-1-one (7.2 g, 11.8 mmol) in conc. HCl (20 mL) at 0° C. was added dropwise an aqueous solution of NaNO₂ (0.9 g, 13 mmol). After 30 min, a solution of SnCl₂.2H₂O (5.9 g, 26.2 mmol) in conc. HCl was added dropwise at such a rate that the reaction temperature never rose above 5° C. After the addition was completed, the mixture was stirred at RT for 2 h. The mixture was extracted with Et₂O to afford 6-hydrazinoindan-1-one. MS (ESI) m/z: 199 (M+H⁺).

To a solution of the 6-hydrazinoindan-1-one (2.1 g, 14.3 mmol) and 4,4-dimethyl-3-oxo-pentanenitrile (2.15 g, 1.2 eq) in EtOH (50 mL) was added conc. HCl (5 mL). The resulting mixture was heated at reflux overnight. After removal of the solvent, the residue was washed with ether to afford 6-(5-amino-3-t-butylpyrazol-1-yl)indan-1-one (1.1 g, 38.5% yield), which was put to the next reaction without further purification. MS (ESI) m/z: 270 (M+H⁺).

To a solution of the 6-(5-amino-3-t-butyl-pyrazol-1-yl)indan-1-one (1.5 g, 5.6 mmol) in THF (30 mL) was added a solution of 1,2-dichloro-3-isocyanato-benzene (1.2 g, 6.4 mmol) in THF (5.0 mL) at 0° C. under N₂. The resulting mixture was stirred at RT overnight then poured into H2O. The mixture was extracted with CH₂Cl₂ (3×100 mL). The combined organic layers were washed with brine, dried (Na₂SO₄), filtered, concentrated and purified via column chromatography to afford 1-[5-t-butyl-2-(3-oxo-indan-5-yl)-2H-pyrazol-3-yl]-3-(2,3-dichlorophenyl)urea as a solid (1.1 g, 43% yield). ¹H NMR (300 MHz, DMSO-d₆): δ 9.22 (s, 1H), 8.68 (s, 1H), 7.94 (t, J=5.1 Hz, 1H), 7.78 (d, J=7.8 Hz, 1H), 7.69-7.65 (m, 2H), 7.24 (d, J=4.8 Hz, 2H), 6.34 (s, 1H), 3.14-3.05 (m, 2H), 2.78-2.66 (m, 2H), 1.22 (s, 9H); MS (ESI) m/z: 457 (M+H⁺).

Example 103

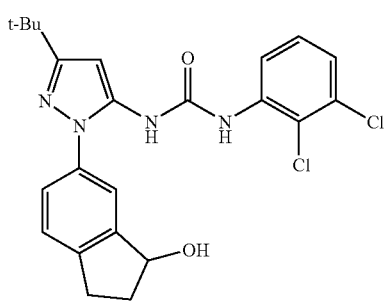

A solution of Example 102 (120 mg, 0.26 mmol) in MeOH (20 ml) was treated with NaBH₄ (19 mg, 0.5 mmol) and stirred at RT for 2 h. After removal of the solvent, the residue was purified by preparative HPLC to yield 1-[5-t-butyl-2-(3-hydroxy-indan-5-yl)-2 H-pyrazol-3-yl]-3-(2,3-dichlorophenyl)urea (67 mg, 56% yield). ¹H NMR (300 MHz, CD₃OD): δ 8.04 (m, 1H), 7.45-7.21 (m, 4H), 6.45 (s, 1H), 5.25 (t, J=6.3 Hz, 1H), 3.10 (m, 1H), 2.85 (m, 1H), 2.50 (m, 1H), 2.00 (m, 1H), 1.34 (s, 9H); MS (ESI) m/z: 459 (M+H⁺).

Example 104

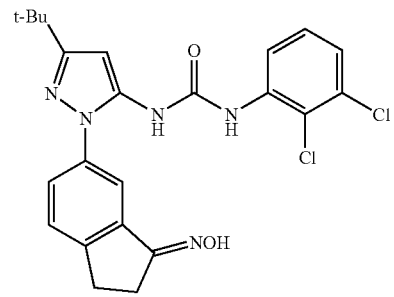

To a mixture of Example 102 (120 mg, 0.26 mmol) and K₂CO₃ (0.1 g, 0.7 mmol) in EtOH (20 mL) was added HONH₂.HCl (500 mg). The resulting mixture was heated at reflux for 3 h, then concentrated and the residue was purified by reverse phase chromatography to yield 1-[5-t-butyl-2-(3-hydroxyimino-indan-5-yl)-2H-pyrazol-3-yl]-3-(2,3-dichlorophenyl)urea (75 mg, 61% yield). ¹H NMR (300 MHz, CD₃OD): δ 8.04 (d, J=5.4 Hz, 1H), 7.73 (s, 1H), 7.52-7.43 (m, 2H), 7.22-7.20 (m, 2H), 6.48 (s, 1H), 3.20-3.12 (m, 2H), 2.97 (m, 2H), 1.33 (s, 9H); MS (ESI) m/z: 473 (M+H⁺).

Example 105

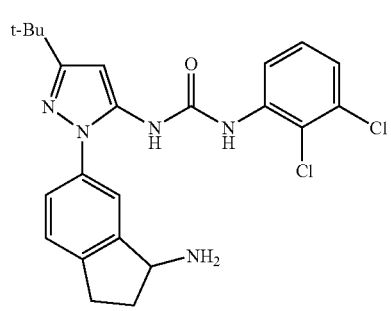

A mixture of Example 104 (45 mg, 0.09 mmol) and Raney® Ni (0.1 g) in EtOH (20 mL) was stirred under 30 psi of H₂ atmosphere for 3 h. After filtration and removal of the solvent, the residue was purified by reverse phase chromatography to give 1-[2-(3-amino-indan-5-yl)-5-t-butyl-2H-pyrazol-3-yl]-3-(2,3-dichlorophenyl)urea (20 mg, 48% yield). ¹H NMR (300 MHz, CD₃OD): δ 7.98 (t, J=5.4 Hz, 1H), 7.62 (s, 1H), 7.50 (s, 2H), 7.22 (d, J=4.5 Hz, 2H), 6.42 (s, 1H), 3.20 (m, 1H), 3.10-3.02 (m, 2H), 2.20-2.12 (m, 2H), 1.30 (s, 9H); MS (ESI) m/z: 458 (M+H⁺).

Example A29

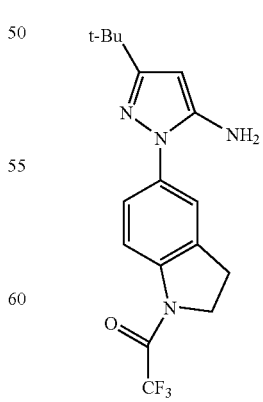

To a solution of 5-nitroindoline (5.00 g, 30.5 mmol) in CH₂Cl₂ (100 mL) at RT was added Et3N (4.25 mL, 3.08 g, 30.5 mmol) followed by the careful addition of TFAA (4.23 mL, 6.40 g, 30.5 mmol). The resulting solution was stirred at RT for 1 h, followed by the addition of more Et$_3$N (4.25 mL, 3.08 g, 30.5 mmol) and TFAA (4.23 mL, 6.40 g, 30.5 mmol). After 2 h of stirring at RT, H$_2$O (100 mL) was added and the mixture was extracted with CH$_2$Cl$_2$ (3×100 mL). The combined organics were dried (MgSO$_4$), filtered, and concentrated and dried under vacuum to give 8.9 g (crude yield>100%) of 2,2,2-trifluoro-1-(5-nitroindolin-1-yl)ethanone as a yellow-brown solid. $^1$H NMR (400 MHz, CDCl$_3$): δ 8.33 (d, J=8.8 Hz, 1H), 8.20 (dd, J=8.4, and 2.0 Hz, 1H), 8.14 (d, J=0.8 Hz, 1H), 4.42 (t, J=8.4 Hz, 2H), 3.38 (t, J=8.6 Hz, 2H); MS (ESI) m/z: 261.0 (M+H$^+$).

To a suspension of 2,2,2-trifluoro-1-(5-nitroindolin-1-yl)ethanone (7.92 g, 30.4 mmol) in MeOH (100 mL) was added 10% Pd/C (0.648 g, 0.609 mmol) and the slurry was stirred under H$_2$ (1 atm) overnight. The mixture was filtered through a pad of Celite® and the filtrate was concentrated and dried under vacuum to give 7.7 g (crude yield>100%) of 1-(5-aminoindolin-1-yl)-2,2,2-trifluoroethanone as a yellow-brown solid. $^1$HNMR (400 MHz, CDCl$_3$): δ 8.00 (d, J=8.8 Hz, 1H), 6.59 (s, 1H), 6.57 (d, J=8.4 Hz, 1H), 4.23 (t, J=8.0 Hz, 2H), 3.69 (brs, 2H), 3.16 (t, J=8.2 Hz, 2H); MS (ESI) m/z: 231.0 (M+H$^+$).

To an ice-cold solution of 1-(5-aminoindolin-1-yl)-2,2,2-trifluoroethanone (7.00 g, 30.4 mmol) in 6N HCl (50 mL) was dropwise added a solution of NaNO$_2$ (2.10 g, 30.4 mmol) in H$_2$O (5 mL). The resulting slurry was stirred at 0° C. for 30 min. A solution of SnCl$_2$.2H$_2$O (13.7 g, 60.8 mmol) in conc. HCl (60 mL) was added dropwise and after the addition was complete the resulting slurry was stirred at RT for 2 h. The mixture was filtered and the resulting solid was collected. The solid was redissolved in EtOH (200 mL), pivaloyl acetonitrile was added (4.57 g, 36.5 mmol) and the solution was heated at reflux temperature overnight. Water (100 mL) was added and the mixture was extracted with CH$_2$Cl$_2$ (3×100 mL), dried (MgSO$_4$), concentrated and purified via column chromatography to yield 1-(5-(5-amino-3-t-butyl-1H-pyrazol-1-yl)indolin-1-yl)-2,2,2-trifluoroethanone (492 mg, 4% yield). $^1$H NMR (400 MHz, CD$_3$OD): δ 8.39 (d, J=8.4 Hz, 1H), 7.55 (s, 1H), 7.48 (dd, J=8.8, and 2.0 Hz, 1H), 4.44 (t, J=8.2 Hz, 2H), 3.40 (t, J=8.6 Hz, 2H), 1.39 (s, 9H), pyrazolamine protons not visible; MS (ESI) m/z: 353.0 (M+H$^+$).

Example 106

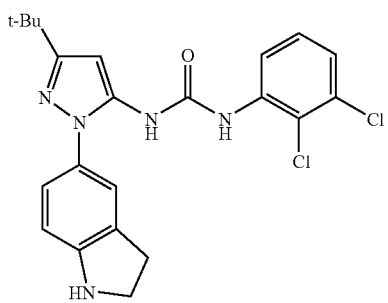

Using general method A, Example A29 (0.200 g, 0.514 mmol) and 2,3-dichlorophenyl isocyanate (0.145 g, 0.772 mmol) were combined and deprotected according to general method G to yield of 1-(3-t-butyl-1-(indolin-5-yl)-1H-pyrazol-5-yl)-3-(2,3-dichlorophenyl)urea (229 mg, 93% yield) as a white solid. $^1$H NMR (400 MHz, CD$_3$OD): δ 8.04 (t, J=4.8 Hz, 1H), 7.67 (s, 1H), 7.59 (dd, J=8.4, and 2.0 Hz, 1H), 7.51 (d, J=8.4 Hz, 1H), 7.26 (d, J=4.8 Hz, 1H), 7.26 (d, J=4.8 Hz, 1H), 6.67 (s, 1H), 3.91 (t, J=7.8 Hz, 2H), 3.39 (t, J=7.8 Hz, 2H), 1.39 (s, 9H), amine and urea protons not visible; MS (ESI) m/z: 444.0 (M+H$^+$).

Example 107

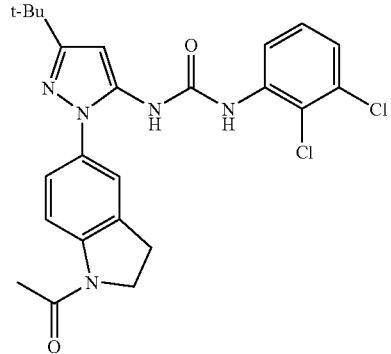

To a solution of Example 106 (0.100 g, 0.208 mmol) in CH$_2$Cl$_2$ (5 mL) was added pyridine (0.049 g, 0.624 mmol) and AcCl (0.033 g, 0.42 mmol) and the resulting solution was stirred at room temperature for 30 min. Water was added (20 mL) and the mixture was extracted with CH$_2$Cl$_2$ (3×20 mL), dried (MgSO$_4$), concentrated and purified via column chromatography to yield 1-(1-(1-acetylindolin-5-yl)-3-t-butyl-1H-pyrazol-5-yl)-3-(2,3-dichlorophenyl)urea (68 mg, 67% yield) as a white foam. $^1$H NMR (400 MHz, acetone-d$_6$): δ 8.53 (brs, 1H), 8.28 (dd, J=8.8, and 1.6 Hz, 1H), 8.20 (brs, 1H), 8.17 (d, J=8.4 Hz, 1H), 7.35 (brs, 1H), 7.32-7.28 (m, 2H), 7.23 (dd, J=8.0, and 1.6 Hz, 1H), 6.47 (s, 1H), 4.22 (t, J=8.4 Hz, 2H), 3.25 (t, J=8.6 Hz, 2H), 2.20 (s, 3H), 1.31 (s, 9H); MS (ESI) m/z: 486.2 (M+H$^+$).

Example 108

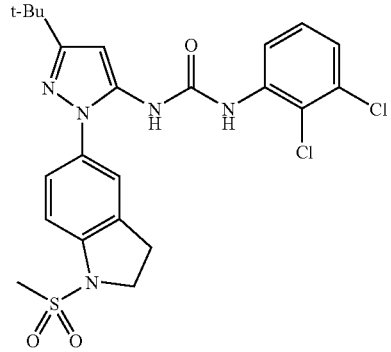

To a solution of Example 106 (0.077 g, 0.16 mmol) in CH$_2$Cl$_2$ (5 mL) was added pyridine (0.038 g, 0.48 mmol) and MsCl (0.037 g, 0.32 mmol) and the resulting pink solution was stirred at RT for 2 h. Water (20 mL) was added and the mixture was extracted with CH$_2$Cl$_2$ (3×20 mL), dried (MgSO$_4$), concentrated and purified via column chromatography to yield 1-(3-t-butyl-1-(1-(methylsulfonyl)indolin-5-yl)-1H-pyrazol-5-yl)-3-(2,3-dichlorophenyl)urea (61 mg, 73% yield) as a white solid. $^1$H-NMR (300 MHz, acetone-d$_6$): δ 8.52 (brs, 1H), 8.26 (dt, J=8.4, and 2.0 Hz, 1H), 8.16 (brs, 1H), 7.42 (brs, 1H), 7.40-7.29 (m, 3H), 7.24 (dd, J=8.4, and 1.6 Hz, 1H), 6.47 (s, 1H), 4.07 (t, J=8.6 Hz, 2H), 3.23 (t, J=8.6 Hz, 2H), 3.02 (s, 3H), 1.32 (s, 9H); MS (ESI) m/z: 522.0 (M+H$^+$).

Example 109

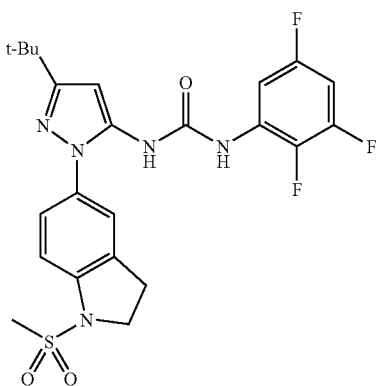

Using general method D, Example A29 (0.150 g, 0.28 mmol) and 2,3,5-trifluoroaniline (0.125 g, 0.853 mmol) were combined and subsequently deprotected according to general method G to afford 1-(3-t-butyl-1-(indolin-5-yl)-1H-pyrazol-5-yl)-3-(2,3,5-trifluorophenyl)urea, which was dissolved in $CH_2Cl_2$ (3 mL). Pyridine (0.200 mL, 0.196 g, 8.70 mmol) and MsCl (0.296 g, 9.09 mmol) were added sequentially at 0° C. The mixture was allowed to reach RT and stirred for 3 h. Water (20 mL) was added and the mixture was extracted with EtOAc (3×30 mL), dried ($MgSO_4$), concentrated and purified via column chromatography to yield of 1-(3-t-butyl-1-(1-(methylsulfonyl)indolin-5-yl)-1H-pyrazol-5-yl)-3-(2,3,5-trifluorophenyl)urea (25 mg, 17% yield) as a light brown solid. $^1$H-NMR (400 MHz, acetone-$d_6$): δ 8.62 (brs, 1H), 8.34 (brs, 1H), 8.01-7.96 (m, 1H), 7.42 (s, 1H), 7.39 (d, J=8.4 Hz, 1H), 7.35 (dd, J=8.4, 2.0 Hz, 1H), 6.88-6.81 (m, 1H), 6.47 (s, 1H), 4.07 (t, J=8.4 Hz, 2H), 3.23 (t, J=8.6 Hz, 2H), 3.03 (s, 3H), 1.32 (s, 9H); MS (ESI) m/z: 508.3 (M+H$^+$).

Example 110

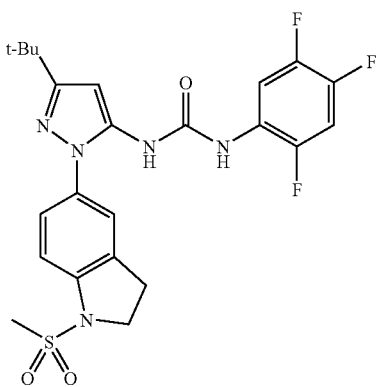

Using the same method as for Example 109, Example A29 (0.150 g, 0.28 mmol) and 2,4,5-trifluoroaniline (0.125 g, 0.853 mmol) were combined to afford 1-(3-t-butyl-1-(1-(methylsulfonyl)indolin-5-yl)-1H-pyrazol-5-yl)-3-(2,4,5-trifluorophenyl)urea (38 mg, 26% yield) as a light brown solid. $^1$H-NMR (400 MHz, acetone-$d_6$): δ 8.47 (brs, 1H), 8.34 (brs, 1H), 8.31-8.23 (m, 1H), 7.42 (s, 1H), 7.39 (d, J=8.4 Hz, 1H), 7.36-7.25 (m, 2H), 6.46 (s, 1H), 4.06 (t, J=8.8 Hz, 2H), 3.22 (t, J=8.4 Hz, 2H), 3.02 (s, 3H), 1.31 (s, 9H); MS (ESI) m/z: 508.3 (M+H$^+$).

Example 111

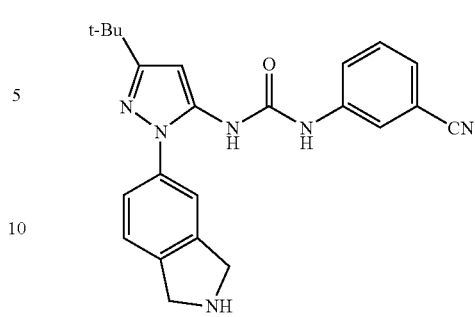

Using general method A, Example A29 (70 mg, 0.20 mmol) and 3-cyanophenyl isocyanate (30 mg, 0.20 mmol) were combined to yield 1-(3-t-butyl-1-(indolin-5-yl)-1H-pyrazol-5-yl)-3-(3-cyanophenyl)urea HCl salt (53 mg, 67% yield). $^1$H NMR (400 MHz, DMSO-$d_6$): δ 9.82 (s, 1H), 8.87 (s, 1H), 7.94 (t, J=2.0 Hz, 1H), 7.62 (dt, J=1.2, and 10.4 Hz, 1H), 7.56 (s, 1H), 7.43 (m, 2H), 6.39 (s, 1H), 3.73 (t, J=8.0 Hz, 2H), 3.23 (t, J=8.0 Hz, 2H), 1.28 (s, 9H); LC-MS (EI) m/z: 497.2 (M+H$^+$).

Example A30

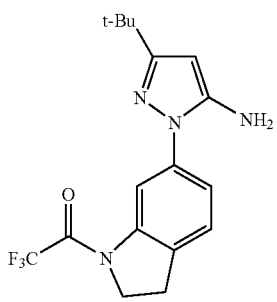

To a solution of 6-nitroindoline (5.00 g, 30.5 mmol) in $CH_2Cl_2$ (100 mL) was added $Et_3N$ (4.25 mL, 3.08 g, 30.5 mmol) and TFAA (4.23 mL, 6.40 g, 30.5 mmol) and the resulting solution stirred at RT for 1 h. More $Et_3N$ (4.25 mL, 3.08 g, 30.5 mmol) and TFAA (4.23 mL, 6.40 g, 30.5 mmol) were added and the solution was stirred at RT for another 2 h. Water (100 mL) was added and the mixture was extracted with $CH_2Cl_2$ (3×100 mL), dried ($MgSO_4$), and concentrated to yield 2,2,2-trifluoro-1-(6-nitroindolin-1-yl)ethanone (8.9 g, crude yield>100%) as a yellow-brown solid. $^1$H-NMR (300 MHz, $CDCl_3$): δ 9.01 (s, 1H), 8.05 (d, J=8.0 Hz, 1H), 7.40 (d, J=8.0 Hz, 1H), 4.42 (t, J=8.2 Hz, 2H), 3.38 (t, J=8.4 Hz, 2H); MS (ESI) m/z: 261.0 (M+H$^+$).

To a suspension of 2,2,2-trifluoro-1-(6-nitroindolin-1-yl)ethanone (7.92 g, 30.4 mmol) in MeOH (100 mL) was added 10% Pd/C (0.648 g, 0.609 mmol) and the slurry was stirred under $H_2$ (1 atm) overnight. The mixture was filtered through a pad of Celite and the filtrate was concentrated and dried under vacuum to yield 1-(6-aminoindolin-1-yl)-2,2,2-trifluoroethanone (7.7 g, crude yield>100%) as a yellow-brown solid. $^1$H-NMR (400 MHz, $CDCl_3$): δ 7.64 (d, J=2.0 Hz, 1H), 7.01 (d, J=8.0 Hz, 1H), 6.49 (dd, J=8.4, and 2.0 Hz, 1H), 4.24 (t, J=8.0 Hz, 2H), 3.85 (brs, 2H), 3.13 (t, J=8.2 Hz, 2H); MS (ESI) m/z: 231.0 (M+H$^+$).

To an ice-cold solution of 1-(6-aminoindolin-1-yl)-2,2,2-trifluoroethanone (7.00 g, 30.4 mmol) in 6N HCl (50 mL) was dropwise added a solution of $NaNO_2$ (2.10 g, 30.4 mmol) in $H_2O$ (5 mL). The resulting slurry was stirred at 0° C. for 30 min. A solution of SnCl$_2$.2H$_2$O (11.5 g, 60.8 mmol) in conc. HCl (60 mL) was added dropwise and after the addition was complete the resulting slurry was stirred at RT for 2 h. The mixture was filtered and the resulting solid was redissolved in EtOH (200 mL). Pivaloyl acetonitrile (4.57 g, 36.5 mmol) was added and the solution was heated at reflux overnight. Water (100 mL) was added and the mixture was extracted with CH$_2$Cl$_2$ (3×100 mL), dried (MgSO$_4$), concentrated and purified by recrystallization from ethyl acetate/hexanes to yield 1-(6-(5-amino-3-t-butyl-1 H-pyrazol-1-yl)indolin-1-yl)-2,2,2-trifluoroethanone (3.2 g, 30% yield) as a light-brown solid. $^1$H-NMR (400 MHz, acetone-d$_6$): δ 8.49 (d, J=2.0 Hz, 1H), 7.51 (dd, J=8.4, and 2.0 Hz, 1H), 4.41 (t, J=8.2 Hz, 2H), 3.32 (t, J=8.2 Hz, 2H), 1.32 (s, 9H), pyrazolamine protons not observed; MS (ESI) m/z: 353.2 (M+H$^+$).

Example A31

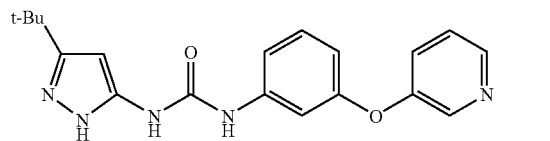

To a solution of 2,3-dichloroaniline (0.200 g, 1.23 mmol) in EtOAc (5 mL) was added NaOH (1M, 2 mL, 2 mmol) and Troc-Cl (0.262 g, 1.23 mmol) and the resulting mixture was stirred overnight. Water (50 mL) was added and the mixture was extracted with EtOAc (3×100 mL), dried (MgSO$_4$), concentrated and purified via column chromatography to yield 2,2,2-trichloroethyl-2,3-dichlorophenylcarbamate (408 mg, 98%) as a yellow foam. $^1$H NMR (400 MHz, CDCl$_3$): δ 8.11 (d, J=6.4 Hz, 1H), 7.43 (brs, 1H), 7.25-7.22 (m, 2H), 4.86 (s, 2H); MS (EI) m/z: 335.8 (M+H$^+$).

A solution of 2,2,2-trichloroethyl-2,3-dichlorophenylcarbamate (0.400 g, 1.19 mmol) and 3-amino-5-t-butylpyrazole (0.165 g, 1.19 mmol) in DMF (1 mL) was stirred at 80° C. overnight. Water (50 mL) was added and the mixture was extracted with EtOAc (3×100 mL), dried (MgSO$_4$), concentrated and purified via column chromatography to yield 1-(3-t-butyl-1H-pyrazol-5-yl)-3-(2,3-dichlorophenyl)urea (230 mg, 59% yield) as a pink foam. $^1$H NMR (400 MHz, CDCl$_3$): δ 8.26 (d, J=6.8 Hz, 1H), 7.20-7.14 (m, 2H), 5.85 (brs, 1H), 1.34 (s, 9H), amine and urea protons not visible; MS (EI) m/z: 327.0 (M+H$^+$).

Example A32

A mixture of Example A9 (0.100 g, 0.386 mmol), Troc-Cl (0.164 g, 0.772 mmol), 2N NaOH (2.00 mL, 4.00 mmol) and EtOAc (2 mL) was stirred at RT overnight. Water (30 mL) was added and the mixture was extracted with EtOAc (3×100 mL), dried (MgSO$_4$), concentrated and purified via column chromatography to yield 2,2,2-trichloroethyl-3-(pyridin-3-yloxy)phenylcarbamate (45 mg, 32% yield) as a yellow oil. $^1$H NMR (CDCl$_3$): δ 8.42 (s, 1H), 8.38 (d, J=4.4 Hz, 1H), 7.36-7.24 (m, 5H), 7.17 (d, J=7.6 Hz, 1H), 6.76 (dd, J=8.2, and 1.8 Hz, 1H), 4.80 (s, 2H); MS (EI) m/z: 361.0 (M+H$^+$).

A mixture of 2,2,2-trichloroethyl-3-(pyridin-3-yloxy)phenylcarbamate (0.040 g, 0.11 mmol), 5-amino-3-t-butylpyrazole (0.031 g, 0.22 mmol) and i-Pr$_2$NEt (0.029 g, 0.22 mmol) in DMF (2 mL) was stirred at 100° C. overnight. Water (20 mL) was added and the mixture was extracted with EtOAc (3×100 mL), dried (MgSO$_4$), concentrated and purified via column chromatography to yield 1-(3-t-butyl-1H-pyrazol-5-yl)-3-(3-(pyridin-3-yloxy)phenyl)urea (26 mg, 67% yield) of the desired product as a red-brown oil. $^1$H-NMR (400 MHz, CDCl$_3$): δ 10.1 (brs, 1H), 8.40 (s, 1H), 8.35 (d, J=3.6 Hz, 1H), 8.02 (s, 1H), 7.35-7.28 (m, 4H), 6.71 (dt, J=6.4, and 2.2 Hz, 1H), 5.67 (brs, 1H), 1.32 (s, 9H), urea protons not visible; MS (EI) m/z: 352.3 (M+H$^+$).

Example 112

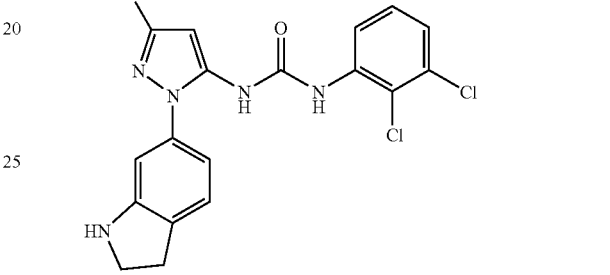

Using general method A, Example A30 (0.400 g, 1.14 mmol) and 2,3-dichlorophenyl isocyanate (0.426 g, 2.28 mmol) were combined and deprotected according to general method G to yield 1-(3-t-butyl-1-(indolin-6-yl)-1H-pyrazol-5-yl)-3-(2,3-dichlorophenyl)urea (230 mg, 42% yield) as an off-white solid. $^1$H-NMR (400 MHz, CD$_3$OD): δ 8.01 (dd, J=7.2, and 4.4 Hz, 1H), 7.64-7.58 (m, 3H), 7.25-7.23 (m, 2H), 6.51 (s, 1H), 3.91 (t, J=7.8 Hz, 2H), 3.38 (t, J=8.0 Hz, 2H), 1.37 (s, 9H); MS (ESI) m/z: 444.0 (M+H$^+$).

Example 113

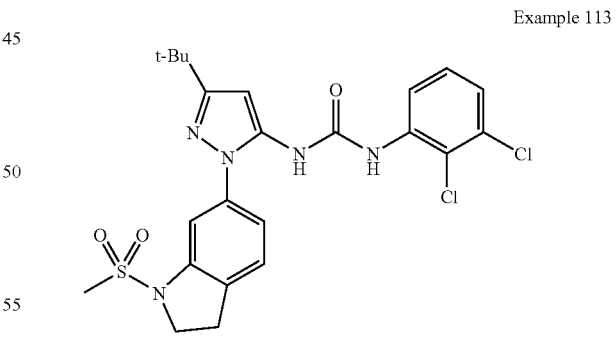

Using the same method as for Example 109, Example 112 (0.150 g, 0.312 mmol) was transformed to 1-(3-t-butyl-1-(1-(methylsulfonyl)indolin-6-yl)-1H-pyrazol-5-yl)-3-(2,3-dichlorophenyl)urea (100 mg, 61% yield) as a pink foam. $^1$H-NMR (400 MHz, acetone-d$_6$): δ 8.58 (brs, 1H), 8.27 (dt, J=8.4, 1.6 Hz, 1H), 8.17 (brs, 1H), 7.54 (d, J=2.0 Hz, 1H), 7.35 (d, J=7.6 Hz, 1H), 7.30 (t, J=8.0 Hz, 1H), 7.22-7.20 (m, 2H), 6.46 (s, 1H), 4.06 (t, J=8.4 Hz, 2H), 3.23 (t, J=8.6 Hz, 2H), 2.98 (s, 3H), 1.32 (s, 9H); MS (ESI) m/z: 522.0 (M+H$^+$).

Example 114

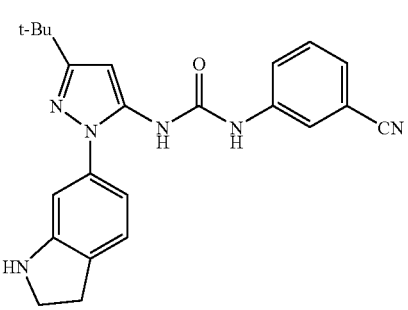

Using general method A, Example A30 (70 mg, 0.2 mmol) and 3-cyanophenylisocyanate (29 mg, 0.2 mmol) were combined and deprotected according to general method G to yield 1-(3-t-butyl-1-(indolin-6-yl)-1H-pyrazol-5-yl)-3-(3-cyanophenyl)urea HCl salt (67 mg, 77% yield). $^1$H-NMR (400 MHz, CD$_3$OD): δ 7.94 (t, J=1.6 Hz, 1H), 7.79 (s, 1H), 7.72 (m, 2H), 7.63 (m, 1H), 7.61 (m, 1H), 7.46 (t, J=7.6 Hz, 1H), 7.40 (t, J=1.2 Hz, 1H), 7.38 (t, J=1.6 Hz, 1H), 3.99 (t, J=7.6 Hz, 2H), 3.45 (t, J=7.6 Hz, 2H), 1.41 (s, 9H); LC-MS (EI) m/z: 497.2 (M+H$^+$).

Example 115

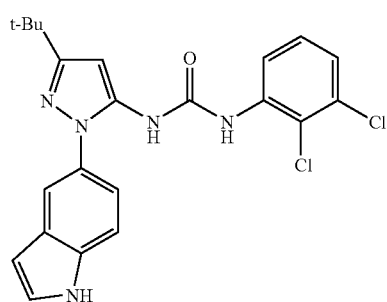

A mixture of Example A31 (63 mg, 0.19 mmol), 1-N-Boc-indole-5-boronic acid (75 mg, 0.28 mmol, commercially available from Anichem), Cu(OAc)$_2$ (53 mg, 0.28 mmol), pyridine (0.05 mL) and molecular sieves (activated, 4 A) in CH$_2$Cl$_2$ (12 mL) was stirred open to the air at RT for 3 days. The reaction mixture was filtered through a pad of Celite®, concentrated, and purified via column chromatography to yield 1-(3-t-butyl-1-(1H-indol-5-yl)-1H-pyrazol-5-yl)-3-(2,3-dichlorophenyl)urea (50 mg, 48% yield). LC-MS (EI) m/z: 542.3 (M+H$^+$). This material was dissolved in CH$_2$Cl$_2$ (1 mL) and TFA (0.5 mL) and stirred at RT overnight. Concentration and purification by column chromatography yielded 1-(3-t-butyl-1-(1H-indol-5-yl)-1H-pyrazol-5-yl)-3-(2,3-dichlorophenyl)urea (19 mg, 47% yield). $^1$H-NMR (400 MHz, DMSO-d$_6$): δ 9.11 (s, 1H), 8.82 (s, 1H), 8.08 (dd, J=2.4, and 9.6 Hz, 1H), 7.62 (d, J=2.0 Hz, 1H), 7.53 (d, J=8.8 Hz, 1H), 7.48 (t, J=2.8 Hz, 1H), 7.29 (m, 2H), 7.16 (dd, J=1.6, and 8.4 Hz, 1H), 6.55 (brs, 1H), 6.38 (s, 1H), 3.86 (s, 3H), 1.28 (s, 9H); LC-MS (EI) m/z: 442.0 (M+H$^+$).

Example 116

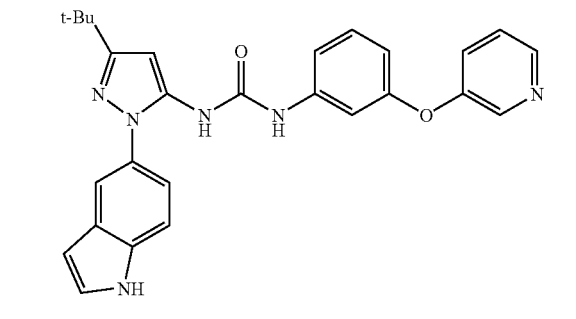

Using the same procedureas for Example 115, Example A32 (0.07 g, 0.2 mmol) and 1-N-Boc-indole-5-boronic acid (0.05 g, 0.2 mmol, commercially available from Anichem), were combined to yield 1-(3-t-butyl-1-(1H-indol-5-yl)-1H-pyrazol-5-yl)-3-(3-(pyridin-3-yloxy)phenyl)urea (7 mg, 7% yield). $^1$H NMR (400 MHz, DMSO-d$_6$): δ 9.18 (s, 1H), 8.42 (brs, 2H), 8.26 (s, 1H), 7.59 (d, J=2.0 Hz, 1H), 7.52 (d, J=8.4 Hz, 1H), 7.48 (t, J=2.8 Hz, 1H), 7.46 (s, 2H), 7.28 (t, J=8.4 Hz, 1H), 7.24 (t, J=1.6 Hz, 1H), 7.13 (dd, J=2.0, and 8.4 Hz, 1H), 7.05 (dd, J=0.8, and 8.4 Hz, 1H), 6.67 (dd, J=2.0, and 8.0 Hz, 1H), 6.53 (t, J=2.0 Hz, 1H), 6.33 (s, 1H), 1.27 (s, 9H); LC-MS (EI) m/z: 467.3 (M+H$^+$).

Example 117

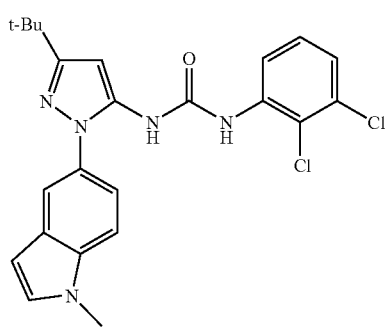

Using the same procedureas for Example 115, Example A31 (63 mg, 0.19 mmol) and 1-N-methylindole-5-boronic acid (51 mg, 0.28 mmol, commercially available from Anachem) were combined to yield 1-(3-t-butyl-1-(1-methyl-1H-indol-5-yl)-1H-pyrazol-5-yl)-3-(2,3-dichlorophenyl)urea as a white solid (54 mg, 61% yield). $^1$H NMR (400 MHz, DMSO-d$_6$): δ 9.10 (s, 1H), 8.80 (s, 1H), 8.08 (dd, J=2.8, and 7.6 Hz, 1H), 7.63 (d, J=2.0 Hz, 1H), 7.59 (d, J=8.8 Hz, 1H), 7.46 (d, J=2.8 Hz, 1H), 7.30 (m, 2H), 7.23 (dd, J=2.0, and 8.8 Hz, 1H), 6.54 (d, J=2.4 Hz, 1H), 6.38 (s, 1H), 3.86 (s, 3H), 1.26 (s, 9H); LC-MS (EI) m/z: 456.0 (M+H$^+$).

Example 118

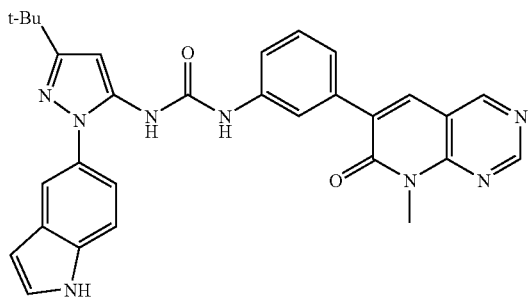

Commercially available N-Boc-5-indoleboronic acid (0.30 g, 1.1 mmol) was dissolved in CH₂Cl₂ (20 mL) and pyridine (1 mL) with molecular sieves (activated 4 A) and stirred overnight at RT. Commercially available ethyl 3-t-butyl-1 H-pyrazole-5-carboxylate, Cu(OAc)₂ and molecular sieves (4 A activated, powder) were added to the boronic acid solution and the whole stirred at RT open to the atmosphere for 2d. The reaction mixture was filtered through a pad of Celite®, concentrated and purified by column chromatography to yield ethyl 5-(3-t-butyl-5-(ethoxycarbonyl)-1H-pyrazol-1-yl)-1H-indole-1-carboxylate (0.18 g, 38% yield). LC-MS (EI) m/z: 412.3 (M+H⁺).

Using general method E, the material from the previous reaction was saponified to yield 1-(1-(t-butoxycarbonyl)-1H-indol-5-yl)-3-t-butyl-1H-pyrazole-5-carboxylic acid which was used directly in the next step.

To a solution of 1-(1-(t-butoxycarbonyl)-1H-indol-5-yl)-3-t-butyl-1H-pyrazole-5-carboxylic acid (0.09 g, 0.23 mmol) in toluene (2 mL) was added triethyl amine (0.026 mL, 0.26 mmol) and Example A11 (0.065 g, 0.26 mmol). The reaction mixture was stirred at RT and DPPA (71 mg, 0.26 mmol) was added. The reaction mixture was heated at 100° C. for 2 h, cooled, concentrated and the residue purified via column chromatography to yield t-butyl 5-(3-t-butyl-5-(3-(3-(8-methyl-7-oxo-7,8-dihydropyrido[2,3-d]pyrimidin-6-yl)phenyl)ureido)-1 H-pyrazol-1-yl)-1H-indole-1-carboxylate.

Using general method F; t-Butyl 5-(3-t-butyl-5-(3-(3-(8-methyl-7-oxo-7,8-dihydropyrido[2,3-d]pyrimidin-6-yl)phenyl)ureido)-1H-pyrazol-1-yl)-1H-indole-1-carboxylate was transformed to 1-(3-t-butyl-1-(1H-indol-5-yl)-1H-pyrazol-5-yl)-3-(3-(8-methyl-7-oxo-7,8-dihydropyrido[2,3-d]pyrimidin-6-yl)phenyl)urea as a pale yellow solid (17 mg, 13% yield). ¹H-NMR (DMSO-d₆): δ 9.20 (bs, 1H), 9.15 (s, 1H), 9.11 (s, 1H), 8.31 (s, 1H), 8.16 (s, 1H), 7.81 (t, J=2.0 Hz, 1H), 7.63 (d, J=2.0 Hz, 1H), 7.54 (d, J=8.4 Hz, 1H), 7.49 (t, J=2.8 Hz, 1H), 7.42 (m, 1H), 7.36 (t, J=8.0 Hz, 1H), 7.29 (dt, J=1.2, and 8.0 Hz, 1H), 7.17 (dd, J=2.4, and 8.8 Hz, 1H), 6.56 (m, 1H), 6.39 (s, 1H), 3.71 (s, 3H), 1.29 (s, 9H); LC-MS (EI) m/z: 594.2 (M+H⁺).

Example A33

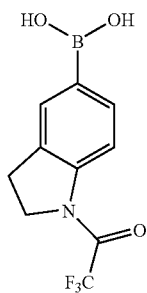

To a solution of 5-bromoindoline (1.00 g, 5.05 mmol) in CH₂Cl₂ (20 mL) was added Et₃N (0.7 mL, 0.51 g, 5.05 mmol). Trifluoroacetic anhydride (0.7 mL, 1.06 g, 5.05 mmol) was added dropwise into the reaction mixture and the resulting solution was stirred at RT for 4 h. Water (20 mL) was added and the mixture was extracted with CH₂Cl₂ (3×100 mL). The organic layer was dried (Na₂SO₄), concentrated and dried under vacuum to yield (1.42 g, 96% yield) as a yellow solid. ¹H NMR (400 MHz, CDCl₃): δ 8.11 (d, J=9.6 Hz, 1H), 7.41 (m, 2H), 4.32 (t, J=8.4 Hz, 2H), 3.28 (t, J=8.4 Hz, 2H); LC-MS (EI) m/z: 294.0 (M+H⁺), 296 (M+3H⁺).

To a solution of 1-(5-bromoindolin-1-yl)-2,2,2-trifluoroethanone (0.70 g, 2.4 mmol) in DMF (10 mL) were added sequentially KOAc (0.70 g, 7.1 mmol), pinacoldiboron (0.91 g, 3.6 mmol) and PdCl₂(dppf) (98 mg, 0.12 mmol). After flushing the reaction vessel with N₂, the reaction mixture was sealed and heated at 80° C. for 3 h. The reaction mixture was partitioned between H₂O and EtOAc. The combined organic extracts were washed with brine, dried (Na₂SO₄), concentrated and purified via column chromatography to yield 2,2,2-trifluoro-1-(5-(4,4,5,5-tetramethyl-1,3,2-dioxaborolan-2-yl)indolin-1-yl)ethanone (0.84 g, 100%) as a yellow solid. ¹H NMR (400 MHz, CDCl₃): δ 8.20 (d, J=7.6 Hz, 1H), 7.75 (d, J=7.6 Hz, 1H), 7.72 (s, 1H), 4.30 (t, J=8.4 Hz, 2H), 3.27 (t, J=8.4 Hz, 2H), 1.37 (s, 12H); LC-MS (EI) m/z: 342.3 (M+H⁺).

To a solution of 2,2,2-trifluoro-1-(5-(4,4,5,5-tetramethyl-1,3,2-dioxaborolan-2-yl)indolin-1-yl)ethanone (0.7 g, 2.1 mmol) in THF/H₂O (4/1, 15 mL) was added NaIO₄ (1.4 g, 6.4 mmol). The reaction mixture was stirred at RT for 30 min and then treated with 2N HCl (18 mL). After stirring at RT for 3 h, the reaction mixture was filtered and washed with THF. The filtrate was concentrated and the residue triturated with EtOAc (1 mL) to yield 1-(2,2,2-trifluoroacetyl)indolin-6-yl-boronic acid (0.45 g, 81% yield). ¹H NMR (400 MHz, DMSO-d₆): δ 8.04 (s, 2H), 8.01 (d, J=8.0 Hz, 1H), 7.75 (brs, 1H), 7.72 (d, J=8.4 Hz, 1H), 4.29 (t, J=8.0 Hz, 2H), 3.27 (t, J=8.0 Hz, 2H); LC-MS (EI) m/z: 260.0 (M+H⁺).

Example 119

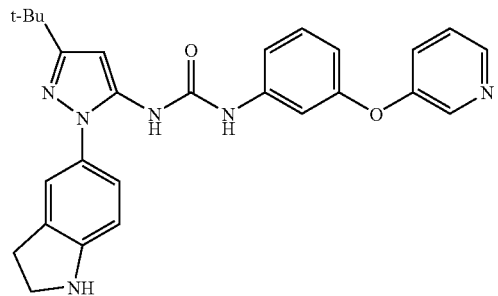

Using the same procedureas for Example 115, Example A33 and Example A32 were combined to yield 1-(3-t-butyl-1-(indolin-5-yl)-1H-pyrazol-5-yl)-3-(3-(pyridin-3-yloxy)phenyl)urea (20 mg, 11% yield) as the HCl salt. ¹H NMR (400 MHz, DMSO-d₆): ☐ 9.62 (s, 1H), 8.74 (s, 1H), 8.56 (brm, 2H), 7.70 (m, 2H), 7.53 (brs, 1H), 7.42 (brd, J=8.0 Hz, 1H), 7.34 (m, 2H), 7.13 (brd, J=7.6 Hz, 1H), 7.12 (brm, 1H), 6.72 (dd, J=6.8 Hz, 1H), 6.34 (s, 1H), 3.72 (brt, J=7.2 Hz, 2H), 3.22 (brt, J=7.2 Hz, 2H), 1.26 (s, 9H); LC-MS (EI) m/z: 469.2 (M+H⁺).

Example 120

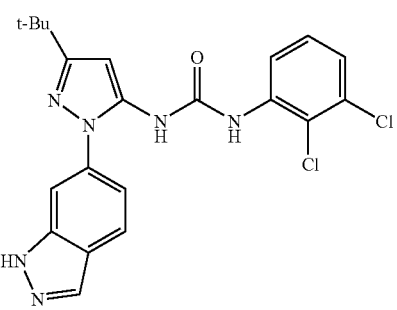

A mixture of 6-nitro-1H-indazole (25 g, 0.153 mmol, commercially available) and 10% Pd/C (2.0 g) in MeOH was stirred under $H_2$ (1 atm) overnight. After filtration, the filtrate was concentrated to yield 1H-indazol-6-ylamine (18.5 g, 94% yield) as a yellow solid. $^1$H NMR (300 MHz, DMSO-$d_6$): 12.20 (br s, 1H), 7.70 (s, 1H), 7.35 (d, J=5.4 Hz, 1H), 6.49-6.44 (m, 2H), 5.17 (brs, 2H). MS (ESI) m/z: 134 (M+H$^+$).

To a solution of 1H-indazol-6-ylamine (20 g, 153 mmol) in conc. HCl (50 mL) was added an aqueous solution (50 mL) of $NaNO_2$ (19 g, 158 mmol) at 0° C. and the resulting mixture was stirred for 1 h. A solution of $SnCl_2.2H_2O$ (90 g, 306 mmol) in conc. HCl (70 mL) pre-cooled to 0° C. was then added, and the mixture stirred for 2 h at RT. The precipitate was filtered and washed with $Et_2O$ to yield (1H-indazol-6-yl)-hydrazine hydrochloride as a yellow solid, which was used without further purification.

A mixture of (1H-indazol-6-yl)-hydrazine hydrochloride and 4,4-dimethyl-3-oxo-pentanenitrile (17 g, 1.05 eq) in EtOH (200 mL) was heated at reflux overnight. The reaction was concentrated and the residue purified by column chromatography to yield 3-t-butyl-1-(1H-indazol-6-yl)-1H-pyrazol-5-amine (21 g, 58% yield, for two steps). $^1$H NMR (300 MHz, DMSO-$d_6$): 8.21 (s, 1H), 7.96 (d, J=8.1 Hz, 1H), 7.81 (s, 1H), 7.25 (d, J=8.1 Hz, 1H), 5.71 (s, 1H), 1.31 (s, 9H); MS (ESI) m/z: 256 (M+H$^+$).

To a solution of 3-t-butyl-1-(1H-indazol-6-yl)-1H-pyrazol-5-amine (15 g, 49 mmol) dissolved in dioxane (100 mL) at RT was added 10% NaOH (50 mL) and the mixture stirred for 0.5 h. Boc anhydride (12 g, 1.2 eq) was then added to the mixture and the solution stirred for 3 h. The mixture was extracted with $CH_2Cl_2$ (3×100 mL). The combined organic extracts were concentrated and purified by column chromatography to yield 6-(5-amino-3-t-butyl-pyrazol-1-yl)-indazole-1-carboxylic acid t-butyl ester (13.1 g, 75% yield). $^1$H NMR (300 MHz, DMSO-$d_6$): δ 8.41 (s, 1H), 8.35 (s, 1H), 7.90 (d, J=8.1 Hz, 1H), 7.68 (d, J=8.1 Hz, 1H), 5.42 (s, 1H), 5.38 (brs, 2H), 1.65 (s, 9H), 1.22 (s, 9H); MS (ESI) m/z: 356 (M+H$^+$).

Using general method A, the material from the previous reaction (0.150 g, 0.422 mmol, 1.00) and 2,3-dichlorophenyl isocyanate (0.0557 ml, 0.422 mmol, 1.00 eq) were combined to yield of t-butyl 6-(3-t-butyl-5-(3-(2,3-dichlorophenyl)ureido)-1H-pyrazol-1-yl)-1H-indazole-1-carboxylate (0.130 g, 57% yield). $^1$H NMR (DMSO-$d_6$): δ 9.42 (s, 1H), 8.79 (s, 1H), 8.51-8.50 (m, 1H), 8.23-8.22 (m, 1H), 8.10-8.02 (m, 2H), 7.65-7.62 (m, 1H), 7.34-7.29 (m, 2H), 6.46 (s, 1H), 1.60 (s, 9H), 1.31 (s, 9H); MS (ESI) m/z: 543.0 (M+H$^+$), 545.0 (M+2+H$^+$).

A solution of yield of t-butyl 6-(3-t-butyl-5-(3-(2,3-dichlorophenyl)ureido)-1H-pyrazol-1-yl)-1H-indazole-1-carboxylate (0.13 g, 0.239 mmol, 1.00 eq) in satd. HCl/EtOH (5.00 ml) and stirred at 65° C. for 2 h until the reaction was clear and homogeneous. It was cooled to RT and evaporated. The syrupy residue was dissolved in MeCN/$H_2O$, frozen and lyophilized to yield 1-(3-t-butyl-1-(1H-indazol-6-yl)-1H-pyrazol-5-yl)-3-(2,3-dichlorophenyl)urea (97.1 mg, 85% yield) as the HCl salt. $^1$H NMR (DMSO-$d_6$): δ 9.32 (s, 1H), 8.81 (s, 1H), 8.17-8.16 (m, 1H), 8.13-8.12 (m, 1H), 8.10-8.07 (m, 1H), 7.92-7.82 (m, 1H), 7.65-7.59 (m, 1H), 7.24-7.25 (m, 2H), 6.44 (s, 1H), 1.30 (s, 9H); MS (ESI) m/z: 443.0 (M+H$^+$), 445.0 (M+2+H$^+$).

Example 121

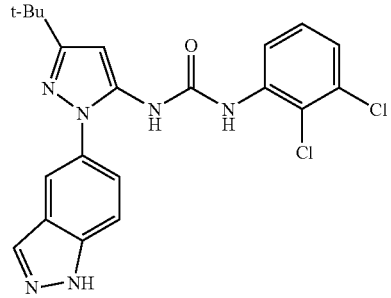

A mixture of 5-nitro-1H-indazole (25 g, 0.153 mmol, commercially available) and 10% Pd/C (2.0 g) in MeOH was stirred under $H_2$ (1 atm) overnight. After filtration, the filtrate was concentrated to yield 20 g (97%) of 1H-indazol-5-amine as a yellow solid. $^1$H NMR (300 MHz, DMSO-$d_6$): δ 12.50 (brs, 1H), 7.70 (s, 1H), 7.21 (d, J=8.7 Hz, 1H), 6.77 (d, J=8.7 Hz, 1H), 6.74 (s, 1H), 4.71 (brs, 1H), 3.15 (d, J=4.8 Hz, 2H); MS (ESI) m/z: 134 (M+H$^+$).

To a solution of 1H-indazol-5-ylamine (20 g, 153 mmol) in conc. HCl (50 mL) was added an aqueous solution (50 mL) of $NaNO_2$ (19 g, 158 mmol) at 0° C. and the resulting mixture was stirred for 1 h. A solution of $SnCl_2.2H_2O$ (90 g, 306 mmol) in conc. HCl (70 mL), pre-cooled to 0° C., was then added. The reaction solution was stirred for 2 h at RT. The precipitate was filtered and washed with ether to yield (1H-indazol-5-yl)-hydrazine hydrochloride as a yellow solid, which was used for the next reaction without further purification.

A mixture of (1H-indazol-5-yl)-hydrazine hydrochloride and 4,4-dimethyl-3-oxo-pentanenitrile (19 g, 1.05 eq) in EtOH (200 mL) was heated at reflux overnight. The reaction was concentrated and the residue purified by column chromatography to yield 3-t-butyl-1-(1H-indazol-5-yl)-1H-pyrazol-5-amine (23 g, 60% of two steps). $^1$H NMR (300 MHz, DMSO-$d_6$): 8.24 (s, 1H), 8.06 (s, 1H), 7.75 (d, J=9.0 Hz, 1H), 7.45 (dd, J=9.0 Hz, 1.8 Hz, 1H), 5.7 (s, 1H), 1.31 (s, 9H). MS (ESI) m/z: 256 (M+H$^+$).

To a solution of 3-t-butyl-1-(1H-indazol-5-yl)-1H-pyrazol-5-amine (14 g, 48 mmol) in dioxane (100 mL) was added 10% NaOH (50 mL) at RT and the mixture stirred for 0.5 h. Boc anhydride (12 g, 1.2 eq) was added to the mixture and the solution stirred for 3 h. The mixture was extracted with $CH_2Cl_2$ (3×100 mL). The combined organic extracts were concentrated and purified by column chromatography to yield t-butyl 5-(5-amino-3-t-butyl-1H-pyrazol-1-yl)-1H-indazole-1-carboxylate (7.8 g, 46%). $^1$H NMR (300 MHz, DMSO-$d_6$): 8.44 (s, 1H), 8.10 (d, J=9.0 Hz, 1H), 8.00 (s, 1H), 7.82 (d, J=9.0 Hz, 1H), 5.39 (s, 1H), 5.24 (br s, 2H), 1.65 (s, 9H), 1.21 (s, 9H). MS (ESI) m/z: 356 (M+H$^+$).

Using general method A, t-butyl 5-(5-amino-3-t-butyl-1H-pyrazol-1-yl)-1H-indazole-1-carboxylate (0.150 g, 0.422 mmol, 1.00 eq) and 2,3-dichlorophenyl isocyanate (0.0557 ml, 0.422 mmol, 1.00 eq). were combined to yield t-butyl 5-(3-t-butyl-5-(3-(2,3-dichlorophenyl)ureido)-1H-pyrazol-1-yl)-1H-indazole-1-carboxylate (115.5 mg, 50% yield). $^1$H NMR (DMSO-d$_6$): δ 9.25 (s, 1H), 8.73 (s, 1H), 8.53 (brs, 1H), 8.22-8.19 (m, 1H), 8.06-8.01 (m, 2H), 7.79-7.76 (m, 1H), 7.33-7.29 (m, 2H), 6.43 (s, 1H), 1.67 (s, 9H), 1.30 (s, 9H); MS (ESI) m/z: 543.0 (M+H$^+$), 545.0 (M+2+H$^+$).

t-Butyl 5-(3-t-butyl-5-(3-(2,3-dichlorophenyl)ureido)-1H-pyrazol-1-yl)-1H-indazole-1-carboxylate (0.1155 g, 0.213 mmol, 1.00 eq) was dissolved in satd. HCl/EtOH. The solution was heated at 80° C. for 1 h. After cooling to RT, the reaction was concentrated to dryness and treated with 80:20 MeCN/H$_2$O. The resulting suspension was thoroughly chilled. The solids were collected by filtration, rinsed with 80:20 MeCN/H$_2$O, MeCN and dried on the filter to yield 1-(3-t-butyl-1-(1H-indazol-5-yl)-1H-pyrazol-5-yl)-3-(2,3-dichlorophenyl)urea (55.5 mg, 54.4% yield) as the HCl salt. $^1$H NMR (DMSO-d$_6$): 9.18 (s, 1H), 8.76 (s, 1H), 8.19 (s, 1H), 8.08-8.06 (m, 1H), 7.89-7.88 (m, 1H), 7.70-7.67 (m, 1H), 7.47-7.44 (m, 1H), 7.33-7.28 (m, 2H), 6.40 (s, 1H), 1.29 (s, 9H); MS (ESI) m/z: 502.0 (M+H$^+$), 504.0 (M+2+H$^+$).

Example A34

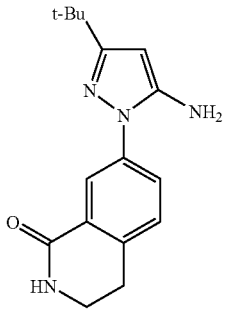

To a solution of phenethylamine (60.5 g, 0.5 mol) and Na$_2$CO$_3$ (63.6 g, 0.6 mol) in EtOAc/HO (800 mL, 4:1) was added ethyl chloroformate dropwise (65.1 g, 0.6 mol) at 0° C. during a period of 1 h. The mixture was warmed to RT and stirred for an additional 1 h. The organic phase was separated and the aqueous layer was extracted with EtOAc. The combined organic phases were washed with H$_2$O and brine, dried (Na$_2$SO$_4$), filtered and concentrated to a crude solid, which was purified by flash chromatography to afford ethyl phenethyl carbamate (90.2 g). $^1$H NMR (400 MHz, CDCl$_3$): δ 7.32-7.18 (m, 5H), 4.73 (brs, 1H), 4.14-4.08 (q, J=6.8 Hz, 2H), 3.44-3.43 (m, 2H), 2.83-2.79 (t, J=6.8 Hz, 2H), 1.26-1.21 (t, J=6.8 Hz, 3H).

A suspension of ethyl phenethyl carbamate (77.2 g, 40 mmol) in polyphosphoric acid (300 mL) was heated to 140-160° C. and stirred for 2.5 h. The reaction mixture was cooled to RT, carefully poured into ice-H$_2$O and stirred for 1 h. The aqueous solution was extracted with EtOAc (3×300 mL). The combined organic phases were washed with H$_2$O, 5% K$_2$CO$_3$ and brine, dried (Na$_2$SO$_4$), filtered and concentrated to a crude solid which was purified by flash chromatography to afford 3,4-dihydro-2H-isoquinolin-1-one (24 g). $^1$H NMR (400 MHz, DMSO-d$_6$): δ 7.91 (brs, 1H), 7.83 (d, J=7.5 Hz, 1H,), 7.43 (t, J=7.5 Hz, 1H), 7.33-7.25 (m, 2H), 3.37-3.32 (m, 2H), 2.87 (t, J=6.6 Hz, 2H).

To an ice-salt bath cooled mixture of conc. HNO$_3$ and conc. H$_2$SO$_4$ (200 mL, 1:1) was added 4-dihydro-2H-isoquinolin-1-one (15 g, 0.102 mol) dropwise over 15 min. After stirring for 2 h, the resulting mixture was poured into ice-H$_2$O and stirred for 30 min. The precipitate was filtered, washed with H$_2$O, and dried in air to afford 7-nitro-3,4-dihydro-2H-isoquinolin-1-one (13 g). $^1$H NMR (300 MHz, DMSO-d$_6$): δ 8.53 (d, J=2.4 Hz, 1H,), 8.31 (d, J=2.4 Hz, 1H), 8.29 (d, J=2.4 Hz, 1H), 7.62 (d, J=8.4 Hz, 1H), 3.44-3.39 (m, 2H), 3.04 (t, J=6.6 Hz, 2H).

A suspension of 7-nitro-3,4-dihydro-2H-isoquinolin-1-one (11.6 g, 60 mmol) and 10% Pd/C (1.2 g,) in MeOH was stirred overnight at RT under H$_2$ (40 psi). The mixture was filtered through Celite® and washed with MeOH. The filtrate was evaporated under vacuum to afford 8.2 g of 7-amino-3,4-dihydro-2H-isoquinolin-1-one, which was used without further purification.

To a suspension of 7-amino-3,4-dihydro-2H-isoquinolin-1-one (8.1 g, 50 mmol) in conc. HCl (100 mL) cooled in an ice-H$_2$O bath was added a solution of NaNO$_2$ (3.45 g, 50 mmol) in H$_2$O dropwise at such a rate that the reaction mixture never rose above 5° C. After stirring for 30 min, to the resulting mixture was added a solution of SnCl$_2$.2H$_2$O (22.5 g, 0.1 mol) in conc. HCl (150 mL) dropwise at 0° C. in an ice-H$_2$O bath. The resulting mixture was stirred for another 2 h at 0° C. The precipitate was collected by suction, washed with ether to afford 7-hydrazino-3,4-dihydro-2H-isoquinolin-1-one (8.3 g), which was used for the next reaction without further purification.

A mixture of 7-amino-3,4-dihydro-2H-isoquinolin-1-one (8.0 g, 37.6 mmol) and 4,4-dimethyl-3-oxo-pentanenitrile (5.64 g, 45 mmol) in EtOH (100 mL) and conc. HCl (10 mL) was heated at reflux overnight. After removal of the solvent, the residue was washed with ether to afford 7-(5-Amino-3-t-butyl-pyrazol-1-yl)-3,4-dihydro-2H-isoquinolin-1-one hydrochloride as a yellow solid (11.5 g, 96% yield), which was used without further purification.

Example 122

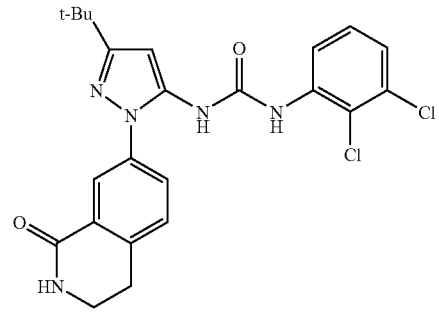

Using general method A, Example A34 (2.0 g, 6.2 mmol) and 1,2-dichloro-3-isocyanato-benzene (1.42 g, 7.5 mmol) were combined to afford 1.2 g 1-[3-t-butyl-1-(1-oxo-1,2,3,4-tetrahydroisoquinolin-7-yl)-1H-pyrazol-5-yl]-3-(2,3-dichlorophenyl)urea (1.2 g, 41% yield). $^1$H NMR (300 MHz, CDCl$_3$): δ 9.08 (brs, 1H), 8.34 (brs, 1H), 8.15 (brs, 1H), 8.02 (m, 1H), 7.60 (brs, 1H), 7.53 (d, J=8.1 Hz, 1H), 7.29 (d, J=8.7 Hz, 1H), 7.15-7.09 (m, 2H), 6.62 (s, 1H), 3.5 (brm, 2H), 3.94 (brm, 2H), 1.34 (s, 9H).

Example 123

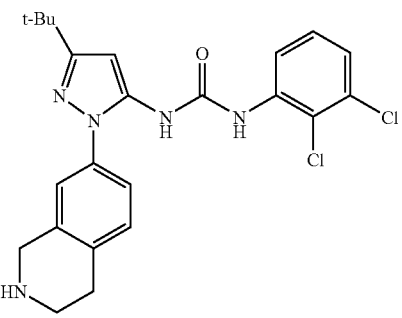

Using general method C, Example 122 (120 mg, 0.25 mmol) was reduced to yield 1-[3-t-butyl-1-(1,2,3,4-tetrahydroisoquinolin-7-yl)-1H-pyrazol-5-yl]-3-(2,3-dichloro-phenyl)urea (80 mg, 70% yield). $^1$H NMR (300 MHz, CD$_3$OD): δ 7.98 (t, J=4.8 Hz, 1H), 7.45-7.39 (m, 3H), 7.23 (d, J=5.1 Hz, 2H), 6.41 (s, 1H), 4.41 (s, 2H), 3.52 (t, J=6.3 Hz, 2H), 3.19 (t, J=6.3 Hz, 2H), 1.33 (s, 9H).

Example 124

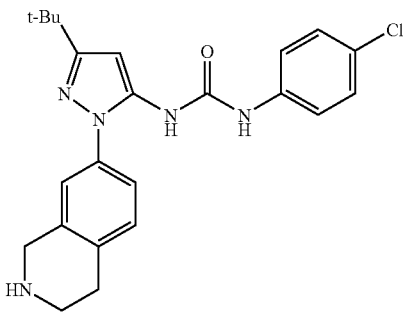

Using general method A, Example A34 (2.0 g, 6.2 mmol) and 1-chloro-4-isocyanatobenzene (1.15 g, 7.5 mmol) were combined to afford 1-[3-t-butyl-1-(1-oxo-1,2,3,4-tetrahydroisoquinolin-7-yl)-1H-pyrazol-5-yl]-3-(4-chlorophenyl)urea (1.5 g, 55% yield). $^1$H NMR (300 MHz, CDCl$_3$): δ 9.03 (s, 1H), 8.77 (s, 1H), 7.90 (s, 1H), 7.54 (d, J=7.5 Hz, 1H), 7.30 (d, J=9 Hz, 3H), 7.19 (d, J=9 Hz, 2H), 6.88 (brs, 1H), 6.74 (s, 1H), 3.45 (brs, 2H), 2.88 (t, J=6 Hz, 2H), 1.37 (s, 9H).

Using general method C, 1-[3-t-butyl-1-(1-oxo-1,2,3,4-tetrahydroisoquinolin-7-yl)-1 H-pyrazol-5-yl]-3-(4-chlorophenyl)urea (1.0 g, 2.3 mmol) was reduced to afford 1-[3-t-butyl-1-(1,2,3,4-tetrahydroisoquinolin-7-yl)-1H-pyrazol-5-yl]-3-(4-chloro-phenyl)urea (0.8 g, 82% yield). $^1$H NMR (300 MHz, DMSO-d$_6$): δ 9.13 (brs, 1H), 8.34 (brs, 1H), 7.41-7.12 (m, 7H), 6.31 (s, 1H), 3.88 (s, 2H), 2.95 (t, J=6.0 Hz, 2H), 2.70 (t, J=6.0 Hz, 2H), 1.24 (s, 9H).

Example 125

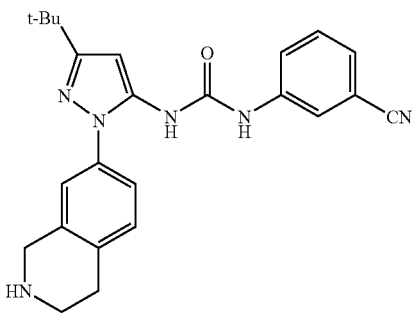

To a solution of Example A34 (20 g, 0.070 mol) in THF (400 mL) was added LAH (15 g, 0.395 mol) in portions at 0-5° C. The resulting mixture was heated at reflux overnight, followed by the addition of 10% NaOH solution. After stirring for 1 h at RT, Boc$_2$O (23 g, 0.106 mol) was added and the solution stirred overnight. After filtration, the filtrate was concentrated to afford the crude product, which was purified by reverse phase chromatography to give 7-(5-amino-3-t-butyl-pyrazol-1-yl)-3,4-dihydro-1H-isoquinoline-2-carboxylic acid t-butyl ester (12 g, 75% yield). $^1$H NMR (300 MHz, DMSO-d$_6$): 7.32 (s, 1H), 7.29 (d, J=2.7 Hz, 1H), 7.18 (d, J=8.4 Hz, 1H), 5.32 (s, 1H), 5.15 (s, 1H), 4.51 (s, 2H), 3.52 (t, J=5.6 Hz, 2H), 2.75 (t, J=5.6 Hz, 2H), 1.40 (s, 9H), 1.17 (s, 9H); MS (ESI) m/z: 371 (M+H$^+$).

Using general method D, 7-(5-amino-3-t-butyl-pyrazol-1-yl)-3,4-dihydro-1H-isoquinoline-2-carboxylic acid t-butyl ester (0.250 g, 0.675 mmol) and 3-aminobenzonitrile (0.0796 g, 0.674 mmol, 1.00 eq) were combined to yield 0.34 g (98%) of t-butyl 7-(3-t-butyl-5-(3-(3-cyanophenyl)ureido)-1H-pyrazol-1-yl)-3,4-dihydroisoquinoline-2(1H)-carboxylate as an oil. MS (ESI) m/z: 515.2 (M+H$^+$).

To t-butyl 7-(3-t-butyl-5-(3-(3-cyanophenyl)ureido)-1H-pyrazol-1-yl)-3,4-dihydroisoquinoline-2(1H)-carboxylate (0.34 g, 0.66 mmol) in EtOAc (5.0 ml) was added 3M HCl/EtOAc (1.1 mL, 3.3 mmol). The resulting mixture was stirred at 20-25° C. for 6.5 h. The suspension was diluted with Et$_2$O to fully precipitate the solids. These were collected by filtration, rinsed with Et$_2$O and dried to yield 1-(3-t-butyl-1-(1,2,3,4-tetrahydroisoquinolin-7-yl)-1H-pyrazol-5-yl)-3-(3-cyanophenyl)urea (0.1377 g, 46% yield) of as an off-white solid. $^1$H NMR (400 MHz, DMSO-d$_6$): 10.1 (s, 1H), 9.47 (brs, 2H), 8.97 (s, 1H), 7.94-7.93 (m, 1H), 7.63-7.60 (m, 1H), 7.49-7.33 (m, 5H), 6.37 (s, 1H), 4.36 (brs, 2H), 3.37 (brs, 2H), 3.06-3.03 (m, 2H), 1.28 (s, 9H); MS (ESI) m/z: 415.3 (M+H$^+$).

Example 126

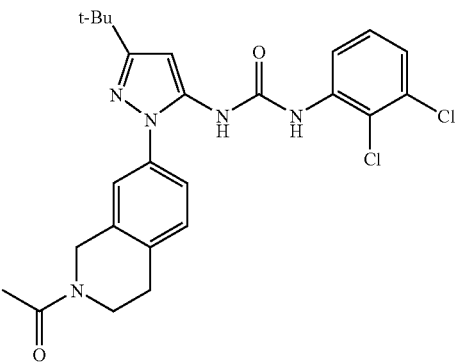

Using the same method as for Example 107, Example 123 (100 mg, 0.22 mmol) was converted to 1-[1-(2-acetyl-1,2,3,4-tetrahydroisoquinolin-7-yl)-3-t-butyl-1H-pyrazol-5-yl]-3-(2,3-dichlorophenyl)urea (55 mg, 50% yield). $^1$H NMR (300 MHz, DMSO-d$_6$): □ 9.16 (m, 1H), 8.74 (s, 1H), 8.00 (s, 1H), 7.20-7.36 (m, 5H), 6.33 (s, 1H), 4.66 (s, 2H), 4.61 (s, 2H), 2.76-2.86 (m, 2H), 2.04 (s, H), 1.22 (s, 9H); MS (ESI) m/z: 500 (M+H$^+$).

Example 127

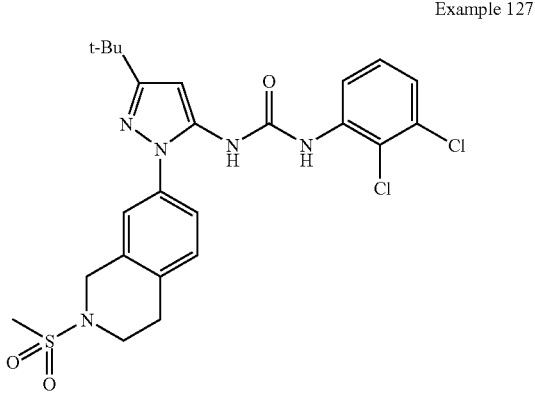

Using the same method as for Example 108, Example 123 (100 mg, 0.22 mmol) was converted to 1-{3-t-butyl-1-[2-(methanesulfonyl)-1,2,3,4-tetrahydroisoquinolin-7-yl]-1H-pyrazol-5-yl}-3-(2,3-dichlorophenyl)urea (45 mg, 38% yield). ¹H NMR (300 MHz, DMSO-d₆): 🗆09.18 (s, 1H), 8.75 (s, 1H), 8.03 (m, 1H), 7.26-7.33 (m, 5H), 6.35 (s, 1H), 4.40 (s, 2H), 3.42 (s, 2H), 2.94 (s, 2H), 2.93 (s, 3H), 1.23 (s, 9H); MS (ESI) m/z: 536 (M+H⁺).

A mixture of CDI (810 mg, 5.0 mmol) and methanesulfonamide (500 mg, 5.0 mmol) in DMF (10 mL) was stirred at 60° C. for 5 h. To 1 mL of the reaction mixture was added Example 123 (100 mg, 0.23 mmol). The resulting mixture was stirred overnight at RT. After Example 128 removal of the solvent, the residue was purified by reverse phase chromatography to afford N-(7-{3-t-butyl-5-[3-(4-chloro-phenyl)ureido]pyrazol-1-yl}-3,4-dihydro-1H-isoquinoline-2-carbonyl)methane-sulfonamide (55 mg, 44% yield). ¹H NMR (300 MHz, DMSO-d₆): δ 10.6 (s, 1H), 9.09 (s, 1H), 8.37 (s, 1H), 7.41-7.26 (m, 7H), 6.33 (s, 1H), 4.60 (s, 2H), 3.62 (brm, 2H), 3.24 (s, 3H), 2.88-2.85 (m, 2H), 1.24 (s, 9H).

Example 129

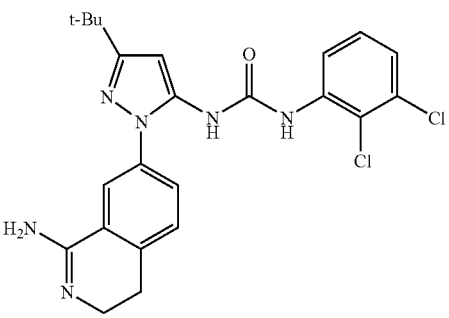

A suspension of Example A34 (1.00 g, 3.12 mmol), Et₃N (0.43 mL, 0.315 g, 3.12 mmol) and Lawesson's reagent (1.26 g, 3.12 mmol) in dioxane (30 mL) was heated at reflux. After 1 h, the mixture was cooled to RT. Water (50 mL) was added and the mixture was extracted with EtOAc (3×100 mL), dried (MgSO₄) and filtered. The filtrate was filtered through a pad of silica gel and the silica gel was thoroughly rinsed with MeOH. The solvents were evaporated under reduced pressure and the residue purified by column chromatography to yield of 7-(3-t-butyl-5-amino-1H-pyrazol-1-yl)-3,4-dihydroisoquinoline-1(2H)-thione as a yellow solid (310 mg, 33% yield). ¹H NMR (400 MHz, DMSO-d₆): δ 10.6 (brs, 1H), 8.49 (d, J=2.4 Hz, 1H), 7.66 (dd, J=8.0, and 2.4 Hz, 1H), 7.35 (d, J=8.4 Hz, 1H), 5.38 (s, 1H), 5.16 (brs, 2H), 3.42-3.38 (m, 2H), 2.93 (t, J=6.8 Hz, 2H), 2.21 (s, 9H); MS (ESI) m/z: 301.2 (M+H⁺).

A suspension of 7-(3-t-butyl-5-amino-1H-pyrazol-1-yl)-3,4-dihydroisoquinoline-1(2H)-thione (0.150 g, 0.499 mmol) in THF (3 mL) was added to a solution of 2,3-dichlorophenyl isocyanate (0.141 g, 0.749 mmol), pyridine (0.061 mL, 0.059 g, 0.749 mmol) and THF (3 mL). The flask which contained the starting material was again rinsed with THF (4 mL) and the solution was added to the reaction flask. The resulting yellow suspension was briefly heated with a heat gun, causing the reaction mixture to become clear. After 18 h, the solution was concentrated and the residue was purified by column chromatography to yield 1-[3-t-butyl-1-(1-thioxo-1,2,3,4-tetrahydroisoquinolin-7-yl)-1H-pyrazol-5-yl]-3-(2,3-dichlorophenyl)urea as a yellow solid (203 mg, 83% yield). ¹H NMR (400 MHz, acetone-d₆): δ 9.60 (brs, 1H), 8.66 (d, J=2.0 Hz, 1H), 8.61 (brs, 1H), 8.26 (dd, J=8.4, and 2.0 Hz, 1H), 8.17 (brs, 1H), 7.68 (dd, J=8.0, and 2.0 Hz, 1H), 7.40 (d, J=8.4 Hz, 1H), 7.30 (t, J=8.2 Hz, 1H), 7.23 (dd, J=7.6, and 1.2 Hz, 1H), 6.48 (s, 1H), 3.62-3.58 (m, 2H), 3.07 (t, J=6.6 Hz, 2H), 1.33 (s, 9H); MS (ESI) m/z: 488.0 (M+H⁺).

1-[3-t-Butyl-1-(1-thioxo-1,2,3,4-tetrahydroisoquinolin-7-yl)-1H-pyrazol-5-yl]-3-(2,3-dichlorophenyl)urea (0.170 g, 0.348 mmol) was dissolved in 0.5M NH₃/dioxane (30 mL). Mercuric chloride (0.142 g, 0.522 mmol) was added and the mixture was stirred at 80° C. After 18 h, H₂O (2 mL) was added. The mixture was stirred for 30 min and filtered through a pad of Celite®. The solvent was removed under vacuum and the residue was purified by reverse-phase chromatography to yield 1-[1-(1-amino-3,4-dihydroisoquinolin-7-yl)-3-t-butyl-1 H-pyrazol-5-yl]-3-(2,3-dichlorophenyl)urea (25 mg, 15% yield). ¹H NMR (400 MHz, CD₃OD): 🗆 8.14 (d, J=2.0 Hz, 1H), 7.99-7.96 (m, 1H), 7.84 (dd, J=8.0, and 2.0 Hz, 1H), 7.63 (d, J=8.0 Hz, 1H), 7.23-7.21 (m, 2H), 6.46 (s, 1H), 3.62 (t, J=6.8 Hz, 2H), 3.14 (t, J=6.8 Hz, 2H), 1.35 (s, 9H); MS (ESI) m/z: 471.3 (M+H⁺).

Example 130

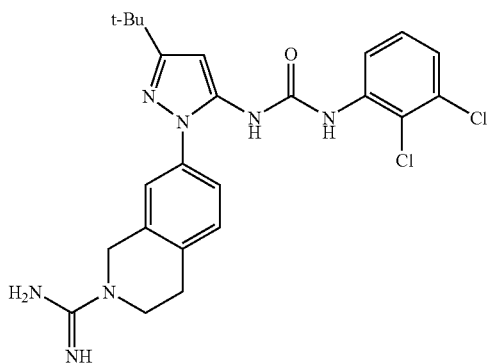

Example 123 (crude, 0.241 mmol) was suspended in DMF (1 mL). Triethylamine (0.1 mL, 0.073 g, 0.072 mmol), di-t-butoxycarbonylthiourea (67 mg, 0.241 mmol) and mercuric chloride (72 mg, 0.265 mmol) were added and the mixture was stirred for 20 min. The mixture was filtered through a pad of Celite® and concentrated to afford a crude solid which was purified by column chromatography to yield 1-[3-t-butyl-1-(N,N'-(t-butyloxycarbonyl)-2-amidino-1,2,3,4-tetrahydroisoquinolin-7-yl)-1H-pyrazol-5-yl]-3-(2,3-dichlorophenyl)-urea (76 mg, 45% yield). $^1$H NMR (400 MHz, CDCl$_3$): δ 10.1 (brs, 1H), 8.07 (dd, J=6.4, and 3.2 Hz, 1H), 8.03 (brs, 1H), 7.97 (brs, 1H), 7.22 (dd, J=8.4, and 1.6 Hz, 1H), 7.12-7.10 (m, 3H), 7.06 (d, J=8.0 Hz, 1H), 6.36 (s, 1H), 4.57 (brs, 2H), 3.63 (brs, 2H), 2.79 (brs, 2H), 1.48 (s, 18H), 1.30 (s, 9H); MS (ESI) m/z: 700.3 (M+H$^+$).

1-[3-t-Butyl-1-(N,N'-(t-butyloxycarbonyl)-2-amidino-1,2,3,4-tetrahydroisoquinolin-7-yl)-1H-pyrazol-5-yl]-3-(2,3-dichlorophenyl)-urea (0.076 g, 1.1 mmol) and TFA (0.7 mL, 8.7 mmol) were dissolved in CH$_2$Cl$_2$ (4 mL), stirred overnight, concentrated under reduced pressure and the resulting solid purified by reverse-phase chromatography to yield 1-[3-t-butyl-1-(2-carbamimidoyl-1,2,3,4-tetrahydroisoquinolin-7-yl)-1H-pyrazol-5-yl]-3-(2,3-dichlorophenyl)urea (51 mg, 77% yield). $^1$H NMR (400 MHz, CD$_3$OD): δ 8.02 (dd, 1H, J=6.4, 3.2 Hz), 7.44-7.43 (m, 2H), 7.37 (br s, 1H), 7.25 (d, 1H, J=2.8 Hz), 7.24 (s, 1H), 6.45 (s, 1H), 4.67 (s, 2H), 3.70 (t, 2H, J=6.0 Hz), 3.09 (t, 2H, J=5.8 Hz), 1.35 (s, 9H); MS (ESI) m/z: 500.3 (M+H$^+$).

Example A35

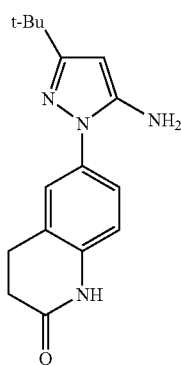

To a solution of hydrocarbostyril (9.00 g, 61.2 mmol) in conc. H$_2$SO$_4$ (180 mL) cooled to −10° C. was slowly added H$_2$O (45 mL), followed by HNO$_3$ (65%, 4.5 mL). The yellow solution was stirred at −10° C. for 10 min and then carefully quenched at −10° C. with H$_2$O (500 mL). The precipitated yellow solid was filtered off, washed with H$_2$O and dried in vacuo to yield 1,2-dihydro-6-nitroisoquinolin-3(4H)-one (10.3 g, 88% yield). $^1$H NMR (400 MHz, CDCl$_3$): δ 9.35 (brs, 1H), 8.12-8.09 (m, 2H), 6.95-6.92 (m, 1H), 3.10 (t, J=7.6 Hz, 2H), 2.73 (t, J=7.8 Hz, 2H); MS (ESI) m/z: 193.0 (M+H$^+$).

To a suspension of 1,2-dihydro-6-nitroisoquinolin-3(4H)-one (10.3 g, 53.6 mmol) in MeOH (150 mL) was added 10% Pd/C (1.14 g, 1.07 mmol) and the mixture was stirred overnight under H$_2$ (1 atm). After filtration, the filtrate was concentrated and the residue was suspended in acetone, filtered and precipitated with conc. HCl (10 mL). The resulting precipitate was collected, washed with H$_2$O and acetone and recrystallized from MeOH/H$_2$O to yield 6-amino-1,2-dihydroisoquinolin-3(4H)-one as a grey solid (6.7 g, 63% yield). $^1$H NMR (400 MHz, CD$_3$OD): δ 7.22 (d, J=2.0 Hz, 1H), 7.20 (dd, J=8.4, and 2.4 Hz, 1H), 6.98 (d, J=8.4 Hz, 1H), 3.01 (t, J=7.6 Hz, 2H), 2.59 (t, J=7.6 Hz, 2H); MS (ESI) m/z: 163.0 (M+H$^+$).

To a suspension of 6-amino-1,2-dihydroisoquinolin-3(4H)-one (4.00 g, 20.1 mmol) in 2M HCl (40 mL) at −10° C. was added solid NaNO$_2$ (1.39 g, 20.1 mmol) causing all solids to dissolve. The mixture was stirred at −10° C. for 30 min and then solid SnCl$_2$.2H$_2$O (9.09 g, 40.3 mmol) was added at −10° C. The mixture was allowed to warm to RT over a period of 30 min and then stirred for 2 h. Ethanol (160 mL) and pivaloylacetonitrile (2.52 g, 20.1 mmol) were added and the solution was heated at reflux overnight under Ar atm. The EtOH was removed under reduced pressure, H$_2$O (200 mL) was added, and the mixture was extracted with CH$_2$Cl$_2$ (3×200 mL), dried (MgSO$_4$), concentrated and purified via column chromatography to yield 6-(3-t-butyl-5-amino-1H-pyrazol-1-yl)-1,2-dihydroisoquinolin-3(4H)-one (1.98 g, 35% yield). $^1$H NMR (400 MHz, CDCl$_3$): δ 7.82 (brs, 1H), 7.40 (brs, 1H), 7.35 (dd, J=8.4, and 2.4 Hz, 1H), 6.80 (d, J=8.8 Hz, 1H), 5.52 (s, 1H), 3.67 (brs, 2H), 3.01 (t, J=7.8 Hz, 2H), 2.65 (t, J=7.4 Hz, 2H), 1.30 (s, 9H); MS (ESI) m/z: 285.2 (M+H$^+$).

Example 131

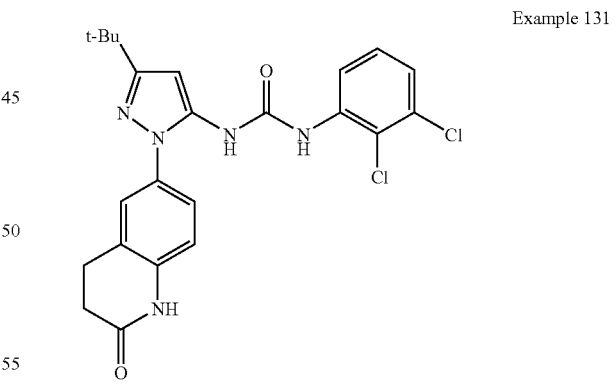

Using general method A, Example A35 and 2,3-dichlorophenyl isocyanate (0.145 g, 0.774 mmol) were combined to yield 1-[3-t-butyl-1-(2-oxo-1,2,3,4-tetrahydroquinolin-6-yl)-1H-pyrazol-5-yl]-3-(2,3-dichlorophenyl)urea (307 mg, 92% yield). $^1$H NMR (400 MHz, acetone-d$_6$): δ 9.26 (brs, 1H), 8.55 (brs, 1H), 8.28 (dd, J=8.4, and 1.6 Hz, 1H), 8.21 (brs, 1H), 7.36 (s, 1H), 7.32 (d, J=8.4 Hz, 1H), 7.31 (t, J=8.2 Hz, 1H), 7.24 (dd, J=8.4, and 1.6 Hz, 1H), 7.03 (d, J=8.4 Hz, 1H), 6.47 (s, 1H), 3.01 (t, J=7.4 Hz, 2H), 2.53 (t, J=7.6 Hz, 2H), 1.31 (s, 9H); MS (ESI) m/z: 472.2 (M+H$^+$).

Example 132

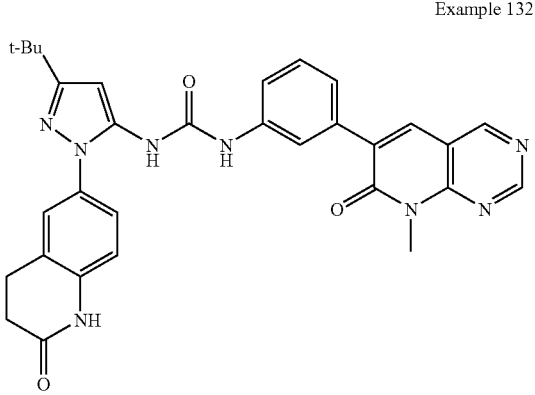

Using general method D, Example A35 (0.075 g, 0.16 mmol) and Example A11 (0.04 g, 0.16 mmol) were combined to yield 1-(3-t-butyl-1-(2-oxo-1,2,3,4-tetrahydroquinolin-6-yl)-1H-pyrazol-5-yl)-3-(3-(8-methyl-7-oxo-7,8-dihydropyrido[2,3-d]pyrimidin-6-yl)phenyl)urea (0.065 g, 63%) as a solid, $^1$H NMR (400 MHz, DMSO-$d_6$): δ 10.29 (s, 1H), 9.32 (s, 1H), 9.16 (s, 1H), 9.12 (s, 1H), 8.48 (s, 1H), 8.17 (s, 2H), 7.82 (s, 1H), 7.46-7.27 (m, 5H), 6.98 (d, J=8.4 Hz, 1H), 6.36 (s, 1H), 3.71 (s, 3H), 2.96 (t, J=7.2 Hz, 2H), 1.27 (s, 9H); MS (ESI) m/z: 563.3 (M+H$^+$).

Example A36

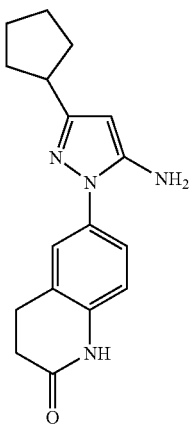

6-Hydrazinyl-3,4-dihydroquinolin-2(1H)-one (1.00 g, 4.68 mmol, available from Example A35) was dissolved in EtOH (10 mL) and 3-cyclopentyl-3-oxopropanenitrile (0.706 g, 5.15 mmol) was added. The reaction mixture was heated at 80° C. for 22 h. The reaction mixture was concentrated and the residue was suspended in EtOAc (30 mL) and treated slowly with satd. Na$_2$CO$_3$ (30 mL). The solution was extracted with EtOAc (3×), and the combined organics were washed H$_2$O and dried (Na$_2$SO$_4$), filtered, concentrated and dried to yield 6-(5-amino-3-cyclopentyl-1H-pyrazol-1-yl)-3,4-dihydroquinolin-2(1H)-one (1.2 g, 87% yield) which was used without further purification. LC-MS (EI) m/z: 297.2 (M+H$^+$).

Example 133

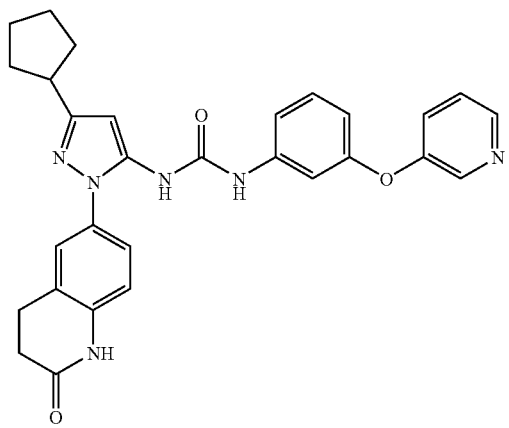

Using general method D, Example A36 (0.15 g, 0.32 mmol) and Example A9 (70 mg, 0.38 mmol) were combined to yield 1-(3-cyclopentyl-1-(2-oxo-1,2,3,4-tetrahydroquinolin-6-yl)-1H-pyrazol-5-yl)-3-(3-(pyridin-3-yloxy)phenyl)urea (60 mg, 28% yield, 2 steps) as an off-white solid HCl salt. $^1$H-NMR (DMSO-$d_6$): δ 10.3 (s, 1H), 9.41 (s, 1H), 8.56 (bs, 1H), 8.52 (s, 1H), 8.51 (bs, 1H), 7.71 (m, 2H), 7.33 (m, 2H), 7.25 (dd, J=2.4, and 8.8 Hz, 1H), 7.12 (dd, J=1.6, and 8.0 Hz, 1H), 6.95 (d, J=8.0 Hz, 1H), 6.73 (dd, J=2.0, and 8.0 Hz, 1H), 6.26 (s, 1H), 2.98 (m, 1H), 2.93 (t, J=7.6 Hz, 2H), 2.47 (t, J=7.6 Hz, 2H), 1.95 (m, 2H), 1.64 (m, 6H); LC-MS (EI) m/z: 509.2 (M+H$^+$).

Example 134

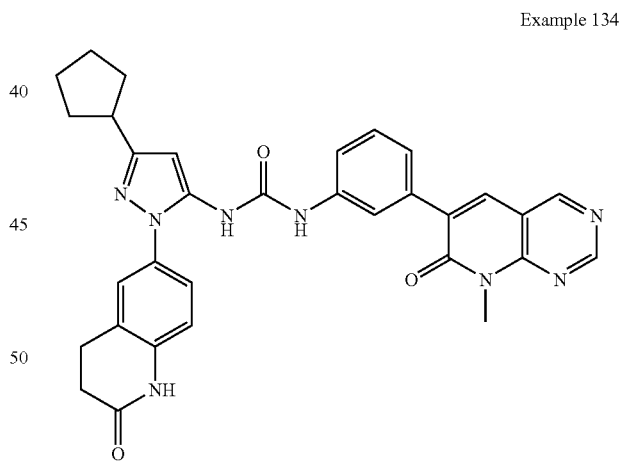

Using general method D, Example A36 and Example A11 were combined to yield 1-(3-cyclopentyl-1-(2-oxo-1,2,3,4-tetrahydroquinolin-6-yl)-1H-pyrazol-5-yl)-3-(3-(8-methyl-7-oxo-7,8-dihydropyrido[2,3-d]pyrimidin-6-yl)phenyl)urea (11 mg, 6% yield, 2 steps). $^1$H-NMR (DMSO-$d_6$): δ 10.3 (s, 1H), 9.18 (s, 1H), 9.15 (s, 1H), 9.12 (s, 1H), 8.38 (s, 1H), 8.17 (s, 1H), 7.82 (bt, 1H), 7.46 (m, 1H), 7.37 (t, J=8.0 Hz, 1H), 7.31 (m, 1H), 7.26 (m, 1H), 6.98 (d, J=8.4 Hz, 1H), 6.30 (s, 1H), 3.71 (s, 3H), 2.96 (m, 3H), 1.96 (m, 2H), 1.68 (m, 6H); LC-MS (EI) m/z: 575.2 (M+H$^+$).

Example 135

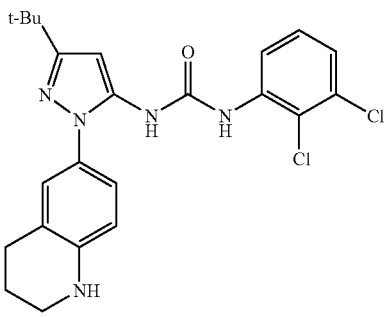

Using general method C, Example 131 was reduced to yield 1-[3-t-butyl-1-(1,2,3,4-tetrahydroquinolin-6-yl)-1H-pyrazol-5-yl]-3-(2,3-dichlorophenyl)urea hydrochloride (204 mg, 70% yield). ¹H NMR (400 MHz, CD₃OD): δ 8.11 (dd, J=6.0, and 4.0 Hz, 1H), 7.40-7.36 (m, 2H), 7.28 (d, J=2.0 Hz, 1H), 7.27 (s, 1H), 7.11 (d, J=8.0 Hz, 1H), 6.85 (s, 1H), 3.48 (t, J=5.8 Hz, 2H), 2.95 (t, J=6.2 Hz, 2H), 2.08 (quintet, J=5.8 Hz, 2H), 1.42 (s, 9H); MS (ESI) m/z: 458.3 (M+H⁺).

Example 136

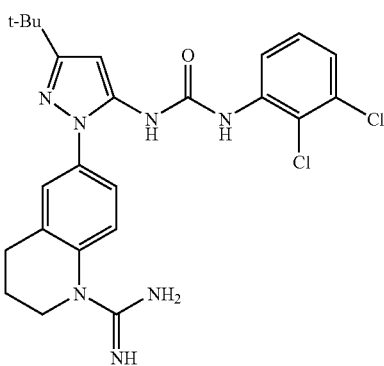

To a suspension of Example 135 (0.151 g, 0.305 mmol), Et₃N (0.124 g, 1.22 mmol) and di-t-butoxycarbonyl-thiourea (0.084 g, 0.305 mmol) in DMF (2 mL) at RT was added HgCl₂ (0.091 g, 0.336 mmol) and the resulting mixture was stirred overnight. Water (20 mL) was added and the mixture extracted with Et₂O (3×20 mL), dried (MgSO₄), concentrated, and purified via column chromatography to yield 1-(3-t-butyl-1-(N,N'-(t-butyloxycarbonyl)-1-amidino-1,2,3,4-tetrahydroquinolin-6-yl)-1H-pyrazol-5-yl)-3-(2,3-dichlorophenyl)urea as a colorless solid (92 mg, 43% yield). ¹H NMR (400 MHz, acetone-d₆): δ 9.64 (brs, 1H), 8.56 (brs, 1H), 8.27 (dd, J=8.0, and 1.6 Hz, 1H), 8.16 (brs, 1H), 7.37-7.33 (m, 3H), 7.30 (d, J=8.4 Hz, 1H), 7.24 (dd, J=8.0, and 1.2 Hz, 1H), 6.46 (s, 1H), 3.78 (t, J=6.4 Hz, 2H), 2.83 (t, J=6.8 Hz, 2H), 2.01 (quintet, J=6.4 Hz, 2H), 1.37 (brs, 18H), 1.32 (s, 9H); MS (ESI) m/z: 700.3 (M+H⁺).

A solution of 1-(3-t-butyl-1-(N,N'-(t-butyloxycarbonyl)-1-amidino-1,2,3,4-tetrahydroquinolin-6-yl)-1H-pyrazol-5-yl)-3-(2,3-dichlorophenyl)urea (0.088 g, 0.13 mmol) in 3 N HCl/EtOAc (10 mL) was stirred overnight at RT. The solvent was evaporated and the residue was redissolved in H₂O/MeCN 2:1 (5 mL) and lyophilized to yield 1-[3-t-butyl-1-(1-amidino-1,2,3,4-tetrahydroquinolin-6-yl]-1H-pyrazol-5-yl)-3-(2,3-dichlorophenyl)urea as the hydrochloride salt (65 mg, 96% yield). ¹H NMR (400 MHz, CD₃OD): δ 7.99 (t, J=4.8 Hz, 1H), 7.58 (d, J=8.4 Hz, 1H), 7.52-748 (m, 2H), 7.26-7.25 (m, 2H), 6.68 (s, 1H), 3.81 (t, J=6.4 Hz, 2H), 2.90 (t, J=6.6 Hz, 2H), 2.09 (quintet, J=6.4 Hz, 2H), 1.40 (s, 9H); MS (ESI) m/z: 501.2 (M+H⁺).

Example A37

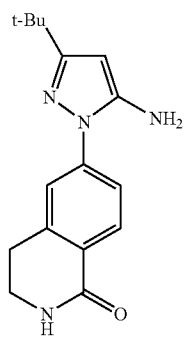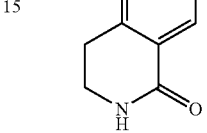

To an ice-cold solution of 2-(3-methoxyphenyl)-1-ethanamine (5.00 g, 33.1 mmol) and Et₃N (5.10 mL, 3.70 g, 36.6 mmol) in CH₂Cl₂ (100 mL) was added ethyl chloroformate (3.50 mL, 3.62 g, 33.4 mmol). The resulting solution was allowed to warm to RT and was stirred for 2 h. Water (100 mL) was added and the mixture was extracted with CH₂Cl₂ (3×50 mL), dried (MgSO₄) and concentrated to yield ethyl 3-methoxyphenethylcarbamate (7.32 g, 99% yield) as a pale yellow oil. ¹H NMR (400 MHz, CDCl₃): δ 7.22 (t, J=7.8 Hz, 1H), 6.78 (d, J=8.0 Hz, 1H), 6.77 (d, J=8.0 Hz; 1H), 6.74 (s, 1H), 4.65 (brs, 1H), 4.11 (q, J=7.2 Hz, 2H), 3.80 (s, 3H), 3.44 (q, J=6.4 Hz, 2H), 2.79 (t, J=7.0 Hz, 2H), 1.23 (t, J=7.0 Hz, 3H); MS (ESI) m/z: 224.2 (M+H⁺).

A mixture of ethyl 3-methoxyphenethylcarbamate (7.32 g, 32.8 mmol) and polyphosphoric acid (30 g) was heated at 120° C. for 2 h after which H₂O (100 mL) was added and the mixture was cooled to RT. The mixture was extracted with EtOAc (6×100 mL), dried (MgSO₄) and concentrated to yield crude 6-methoxy-3,4-dihydroisoquinolin-1(2H)-one (8.0 g, 138%) as a sticky gum. ¹H NMR (400 MHz, acetone-d₆): δ 7.88 (d, J=8.4 Hz. 1H), 7.04 (brS, 1H), 6.87 (dd, J=8.4, and 2.4 Hz, 1H), 6.82 (d, J=2.4 Hz, 1H), 3.84 (s, 3H), 3.49 (t, J=6.4 Hz, 2H), 2.94 (t, J=6.2 Hz, 2H); MS (ESI) m/z: 178.0 (M+H⁺).

A mixture of 6-methoxy-3,4-dihydroisoquinolin-1(2H)-one (6.40 g, 35.6 mmol) and pyridinium hydrochloride (41.1 g, 356 mmol) was heated at 200° C. for 3 h. Water was added (200 mL) and the mixture was extracted with CH₂Cl₂ (3×200 mL), dried (MgSO₄) and concentrated to yield 6-hydroxy-3,4-dihydroisoquinolin-1(2H)-one (1.60 g, 39%, 2 steps) as a yellow solid. ¹H NMR (400 Mhz, acetone-d₆): δ 8.91 (brs, 1H), 7.81 (d, J=8.4 Hz, 1H), 7.40 (brs, 1H), 6.77 (d, J=8.4 Hz, 1H), 6.70 (s, 1H), 3.47 (dt, J=6.8, and 3.2 Hz, 2H), 2.88 (t, J=6.6 Hz, 2H); MS (ESI) m/z: 164.0 (M+H⁺).

To a suspension of 6-hydroxy-3,4-dihydroisoquinolin-1(2H)-one (1.60 g, 9.81 mmol) and Et₃N (1.37 mL, 0.992 g, 9.81 mmol) in CH₂Cl₂ (100 mL) was added triflic chloride (1.65 g, 9.81 mmol). After 2 h of stirring, H₂O (100 mL) was added and the mixture was extracted with CH₂Cl₂ (3×100 mL), dried (MgSO₄), concentrated and purified via column chromatography to yield 1-oxo-1,2,3,4-tetrahydroisoquinolin-6-yl trifluoromethanesulfonate (1.70 mg, 59% yield) as a colorless solid. ¹H NMR (400 MHz, CDCl₃): δ8.19 (d, J=8.4 Hz, 1H), 7.27 (dd, J=8.4, and 2.4 Hz, 1H), 7.19 (d, J=2.4 Hz, 1H), 6.58 (brs, 1H), 3.64 (dt, J=6.8, and 2.4 Hz, 2H), 3.08 (t, J=6.6 Hz, 2H); MS (ESI) m/z: 296.0 (M+H⁺).

To a suspension of 1-oxo-1,2,3,4-tetrahydroisoquinolin-6-yl trifluoromethanesulfonate (1.70 g, 5.76 mmol), benzophenone hydrazone (1.36 g, 6.91 mmol), Cs₂CO₃ (2.81 g, 8.64 mmol) and DPPF (0.048 g, 0.086 mmol) in degassed PhMe (40 mL) was added Pd(OAc)₂ (0.013 g, 0.058 mmol) and the resulting mixture was stirred at RT for 30 min and then heated at 90° C. After 16 h, the mixture was cooled to RT, H₂O (50 mL) was added and the mixture was extracted with EtOAc (3×50 mL), dried (MgSO₄), concentrated and purified via column chromatography to yield 6-(2-(diphenylmethylene) hydrazinyl)-3,4-dihydroisoquinolin-1(2H)-one (980 mg, 50% yield). ¹H NMR (400 MHz, acetone-d₆): δ 8.69 (brs, 1H), 7.79 (d, J=9.2 Hz, 1H), 7.63-7.54 (m, 5H), 7.37-7.31 (m, 5H), 7.11-7.08 (m, 2H), 6.67 (brS, 1H), 3.47 (dt, J=7.2, and 3.2 Hz, 2H), 2.90 (t, J=6.6 Hz, 2H); MS (ESI) m/z: 342.0 (M+H⁺).

A solution of 6-(2-(diphenylmethylene)hydrazinyl)-3,4-dihydroisoquinolin-1(2H)-one (0.980 g, 2.87 mmol), pivaloylacetonitrile (0.539 g, 4.31 mmol) and p-TsOH (4.04 g, 28.8 mmol) in EtOH (20 mL) was heated at reflux overnight. The reaction was cooled and H₂O was added (20 mL). The mixture was extracted with CH₂Cl₂ (3×50 mL), dried (MgSO₄), concentrated and recrystallized to yield 6-(5-amino-3-t-butyl-1H-pyrazol-1-yl)-3,4-dihydroisoquinolin-1 (2H)-one (387 mg, 48% yield). Purification of the mother liquors via column chromatography yielded an additional 330 mg (40%) of 6-(5-amino-3-t-butyl-1H-pyrazol-1-yl)-3,4-dihydroisoquinolin-1(2H)-one. ¹H NMR (400 MHz, acetone-d₆): δ 7.99 (d, J=8.4 Hz, 1H), 7.65 (dd, J=8.4, and 2.0 Hz, 1H), 7.60 (s, 1H), 6.99 (brs, 1H), 5.53 (s, 1H), 4.92 (brs, 2H), 3.55 (dt, J=6.8, and 2.8 Hz, 2H), 3.02 (t, J=6.4 Hz, 2H), 1.25 (s, 9H); MS (ESI) m/z: 285.2 (M+H⁺).

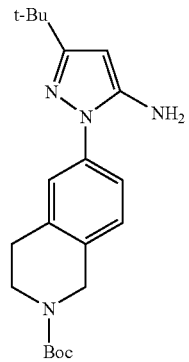

Example A38

Using general method C, Example A37 (0.200 g, 0.703 mmol) was reduced to 3-t-butyl-1-(1,2,3,4-tetrahydroisoquinolin-6-yl)-1H-pyrazol-5-amine which was used without further purification. MS (ESI) m/z: 446.3 (M+H⁺), 271.3 (M+2H⁺).

To a solution of 3-t-butyl-1-(1,2,3,4-tetrahydroisoquinolin-6-yl)-1H-pyrazol-5-amine in CH₂Cl₂ (20 mL) was added Boc anhydride (0.154 g, 0.703 mmol) and the solution was stirred at RT for 30 min. Evaporation and column chromatography yielded t-butyl 6-(5-amino-3-t-butyl-1H-pyrazol-1-yl)-3,4-dihydroisoquinoline-2(1H)-carboxylate (154 mg, 59% yield, 2 steps) as a yellow oil. ¹H NMR (400 MHz, acetone-d₆): δ 7.44-7.39 (m, 2H), 7.21 (d, J=7.6 Hz, 1H), 5.47 (s, 1H), 4.76 (brs, 2H), 4.56 (brs, 2H), 3.64 (t, J=5.8 Hz, 2H), 2.85 (t, J=6.0 Hz, 2H), 1.46 (s, 9H), 1.24 (s, 9H); MS (ESI) m/z: 371.2 (M+H⁺).

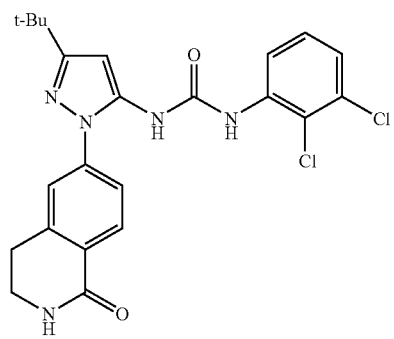

Example 137

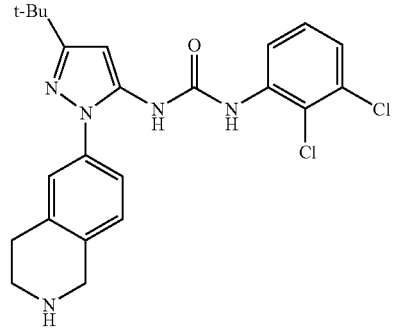

Example 138

Using general method A, Example A37 (0.070 g, 0.069 mmol) and 2,3-dichlorophenyl isocyanate (0.069 g, 0.37 mmol) were combined to yield 1-(3-t-butyl-1-(1-oxo-1,2,3,4-tetrahydroisoquinolin-6-yl)-1H-pyrazol-5-yl)-3-(2,3-dichloro-phenyl)urea (90 mg, 77% yield) as a pale yellow solid. ¹H NMR (400 Mhz, acetone-d₆): δ 9.01 (brs, 1H), 8.54 (brs, 1H), 8.30 (d, J=8.4 Hz, 1H), 7.93 (d, J=8.0 Hz, 1H), 7.55 (d, J=8.4 Hz, 1H), 7.50 (s, 1H), 7.33-7.29 (m, 2H), 7.23 (d, J=8.0 Hz, 1H), 6.55 (s, 1H), 3.55 (dt, J=−6.4, and 1.6 Hz, 2H), 3.05 (t, J=6.2 Hz, 2H), 1.33 (s, 9H); MS (ESI) m/z: 472.0 (M+H⁺).

Using general method A, Example A38 (0.150 g, 0.405 mmol) and 2,3-dichlorophenyl isocyanate (0.100 g, 0.532) were combined, and the product deprotected using general method F to yield 1-(3-t-butyl-1-(1,2,3,4-tetrahydroisoquinolin-6-yl)-1H-pyrazol-5-yl)-3-(2,3-dichlorophenyl)urea (125 mg, 88% yield). ¹H NMR (400 MHz, CD₃OD): δ 8.07-8.05 (m, 1H), 7.55-7.50 (m, 3H), 7.28-7.27 yield (m, 2H), 6.69 (brs, 1H), 4.50 (s, 2H), 3.58 (t, J=6.2 Hz, 2H), 3.27-3.23 (m, 2H), 1.41 (s, 9H); MS (ESI) m/z: 460.0 (M+H⁺).

Starting with Example A38, the following compounds were made using either general method A or D and deprotection using general method F. Yields are reported over two (general method A) or three (general method D) steps starting from Example A38.

| Example | Name | MS (EI) (M + H⁺) | ¹H NMR (400 MHz, CD₃OD) |
|---|---|---|---|
| Example 139 | 1-(3-t-butyl-1-(1,2,3,4-tetrahydro-isoquinolin-6-yl)-1H-pyrazol-5-yl)-3-(3-cyanophenyl)urea 19 mg, 24% yield | 415.3 | δ 7.90-7.89 (m, 1H), 7.61 (d, 1H, J = 8.4 Hz), 7.54 (s, 1H), 7.52 (d, J = 2.0 Hz, 1H), 7.46 (d, J = 8.0 Hz, 1H), 7.43 (d, J = 3.6 Hz, 1H), 7.38 (dt, J = 7.2, and 1.2 Hz, 1H), 7.00 (s, 1H), 4.47 (s, 2H), 3.56 (t, J = 6.2 Hz, 2H), 3.24 (t, J = 6.4 Hz, 2H), 1.40 (s, 9H), |
| Example 140 | 1-(3-t-butyl-1-(1,2,3,4-tetrahydro-isoquinolin-6-yl)-1H-pyrazol-5-yl)-3-(3-phenoxyphenyl)urea 54 mg, 84% yield | 482.3 | δ 7.54-7.52 (m, 2H), 7.47 (d, J = 8.8 Hz, 1H), 7.37-7.33 (m, 2H), 7.24 (t, J = 8.2 Hz, 1H), 7.19 (t, J = 2.0 Hz, 1H), 7.12 (t, J = 7.4 Hz, 1H), 7.06 (dd, J = 8.0, and 1.2 Hz, 1H), 7.00-6.97 (m, 2H), 6.67 (s, 1H), 6.65 (dd, J = 8.4, and 2.4 Hz, 1H), 4.47 (s, 2H), 3.56 (t, J = 6.4 Hz, 2H), 3.23 (t, J = 6.2 Hz, 2H), 1.39 (s, 9H) |
| Example 141 | 1-(3-t-butyl-1-(1,2,3,4-tetrahydro-isoquinolin-6-yl)-1H-pyrazol-5-yl)-3-(3-(pyridin-3-yloxy)phenyl)urea 38 mg, 36% yield | 483.3 | δ 8.68 (d, J = 2.8 Hz, 1H), 8.61 (d, J = 6.0 Hz, 1H), 8.24 (ddd, J = 8.8, 2.4, and 0.8 Hz, 1H), 8.07 (dd, J = 9.0, and 5.8 Hz, 1H), 7.60-7.59 (m, 2H), 7.56-7.54 (m, 2H), 7.44 (t, J = 8.2 Hz, 1H), 7.31 (dd, J = 8.4, and 1.2 Hz, 1H), 6.92 (dd, J = 8.0, and 1.6 Hz, 1H), 4.52 (s, 2H), 3.59 (t, J = 6.2 Hz, 2H), 3.28 (t, J = 6.4 Hz, 2H), 1.43 (s, 9H), pyrazolamine, urea and amine protons not visible |
| Example 142 | 1-(3-t-butyl-1-(1,2,3,4-tetrahydro-isoquinolin-6-yl)-1H-pyrazol-5-yl)-3-(4-methyl-3-(pyrimidin-2-ylamino)phenyl)-urea 53 mg, 84% yield | 497.2 | δ 8.59 (d, J = 4.8 Hz, 2H), 7.66 (d, J = 2.4 Hz, 1H), 7.51-7.44 (m, 3H), 7.35 (d, J = 8.4 Hz, 1H), 7.30 (dd, J = 8.0, and 2.0 Hz, 1H), 7.10 (t, J = 5.6 Hz, 1H), 6.60 (s, 1H), 4.47 (s, 2H), 3.56 (t, J = 6.4 Hz, 2H), 3.24 (t, J = 6.4 Hz, 2H), 2.25 (s, 3H), 1.37 (s, 9H) |

-continued

| Example | Name | MS (EI) (M + H⁺) | ¹H NMR (400 MHz, CD₃OD) |
|---|---|---|---|
| Example 143 | 1-(3-t-butyl-1-(1,2,3,4-tetrahydroisoquinolin-6-yl)-1H-pyrazol-5-yl)-3-(4-phenoxyphenyl)-urea 45 mg, 70% yield | 482.2 | δ 7.57-7.50 (m, 3H), 7.40 (d, J = 9.2 Hz, 2H), 7.33 (t, J = 8.8 Hz, 2H), 7.08 (t, J = 7.6 Hz, 1H), 6.95-6.93 (m, 4H), 6.76 (s, 1H), 4.50 (s, 2H), 3.58 (t, J = 6.4 Hz, 2H), 3.26 (t, J = 6.2 Hz, 2H), 1.41 (s, 9H) |
| Example 144 | 1-(3-t-butyl-1-(1,2,3,4-tetrahydroisoquinolin-6-yl)-1H-pyrazol-5-yl)-3-(2,3-difluorophenyl)-urea 110 mg, 47% yield | 426.2 | (DMSO-d₆): δ 9.37 (m, 1H), 9.24 (m, 1H), 9.11 (m, 1H), 7.88 (m, 1H), 7.42 (m, 2H), 7.36 (m, 2H), 7.12 (m, 1H), 7.04 (m, 1H), 6.38 (s, 1H), 4.32 (brt, 2H), 3.39 (brm, 2H), 3.08 (brt, 2H), 1.28 (s, 9H) |
| Example 145 | 1-(3-t-butyl-1-(1,2,3,4-tetrahydroisoquinolin-6-yl)-1H-pyrazol-5-yl)-3-(2,4-difluorophenyl)-urea 180 mg, 77% yield | 426.2 | (DMSO-d₆): δ 9.23 (brs, 2H), 8.93 (m, 1H), 8.89 (m, 1H), 8.00 (m, 1H), 7.2-7.5 (m, 4H), 7.01 (m, 1H), 6.36 (s, 1H), 4.32 (bt, 2H), 3.40 (m, 2H), 3.07 (t, J = 6.4 Hz, 2H), 1.27 (s, 9H) |
| Example 146 | 1-(3-t-butyl-1-(1,2,3,4-tetrahydroisoquinolin-6-yl)-1H-pyrazol-5-yl)-3-(2,4,5-trifluorophenyl)-urea 120 mg, 53% yield | 444.0 | (DMSO-d₆): δ 9.27 (brm, 1H), 9.19 (brs, 1H), 9.03 (brs, 1H), 8.13 (m, 1H), 7.63 (m, 1H), 7.38 (m, 3H), 6.38 (s, 1H), 4.36 (brm, 2H), 3.39 (brm, 2H), 3.07 (brt, J = 6.4 Hz, 2H), 1.25 (s, 9H) |

| Example | Name | MS (EI) (M + H+) | 1H NMR (400 MHz, CD3OD) |
|---|---|---|---|
| Example 147 | 1-(3-t-butyl-1-(1,2,3,4-tetrahydroiso-quinolin-6-yl)-1H-pyrazol-5-yl)-3-(2,3,4-trifluorophenyl)-urea 45 mg, 18% yield | 444.0 | (DMSO-d6): δ 9.32 (brm, 1H), 9.17 (s, 1H), 9.01 (s, 1H), 7.78 (m, 1H), 7.37 (m, 3H), 6.35 (s, 1H), 4.32 (brm, 2H), 3.39 (brm, 2H), 3.07 (brt, J = 6.4 Hz, 2H), 1.25 (s, 9H) |

Example 148

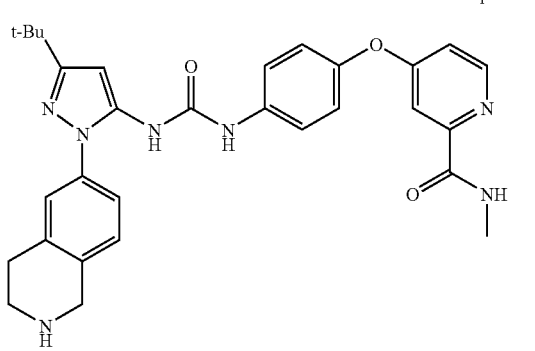

Using general method D, Example A38 (0.08 g, 0.15 mmol) and Example A12 (0.04 g, 0.16 mmol) were combined and the product deprotected using general method F to yield 1-(3-t-butyl-1-(1,2,3,4-tetrahydroisoquinolin-6-yl)-1H-pyrazol-5-yl)-3-(4-(2-(methylcarbamoyl)pyridin-4-yloxy)phenyl)urea (54 mg, 52% yield, 3 steps) as the HCl salt. 1H NMR (400 MHz, DMSO-d6): δ 9.78 (s, 1H), 9.55 (brs, 2H), 8.87 (brs, 2H), 8.52 (d, J=5.6 Hz, 1H), 7.55-7.43 (m, 5H), 7.39-7.34 (m, 2H), 7.16-7.14 (m, 2H), 6.35 (s, 1H), 4.30 (brs, 2H), 3.39-3.37 (m, 2H), 3.12-3.09 (m, 2H), 2.78 (d, J=5.6 Hz, 3H), 1.28 (s, 9H); MS (ESI) m/z: 540.3 (M+H+).

Example 149

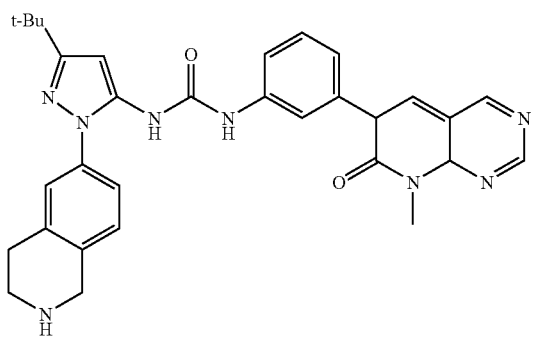

Using general method D, Example A38 (0.08 g, 0.15 mmol) and Example A11 (0.037 g, 0.15 mmol) were combined and the product deprotected using general method F to yield 1-(3-t-butyl-1-(1,2,3,4-tetrahydroisoquinolin-6-yl)-1H-pyrazol-5-yl)-3-(3-(8-methyl-7-oxo-7,8-dihydropyrido[2,3-d]pyrimidin-6-yl)phenyl)urea (32 mg, 29% yield, 3 steps) as the HCl salt. 1H NMR (400 MHz, DMSO-d6): δ 9.46 (s, 1H), 9.29 (brs, 2H), 9.16 (s, 1H), 9.11 (s, 1H), 8.65 (s, 1H), 8.15 (s, 1H), 7.82 (s, 1H), 7.46-7.44 (m, 2H), 7.38-7.34 (m, 2H), 7.29-7.23 (m, 2H), 7.18-7.16 (m, 1H), 6.36 (s, 1H), 4.31 (brs, 2H), 3.71 (s, 3H), 3.41-3.37 (m, 2H), 3.09 (t, J=6.0 Hz, 2H), 1.28 (s, 9H); MS (ESI) m/z: 549.3 (M+H+).

Example 150

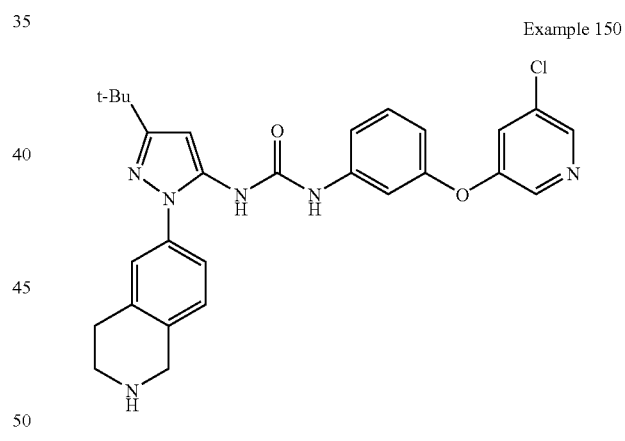

Using general method D, Example A38 (0.1 g, 0.22 mmol) and Example A13 (0.037 g, 0.15 mmol) were combined and the product deprotected using general method F to yield 1-(1-(3-(2-amino-2-oxoethyl)phenyl)-3-t-butyl-1H-pyrazol-5-yl)-3-(4-(2-(methylcarbamoyl)pyridin-4-yloxy)phenyl)urea 1-(3-t-butyl-1-(1,2,3,4-tetrahydroisoquinolin-6-yl)-1H-pyrazol-5-yl)-3-(3-(5-chloropyridin-3-yloxy)phenyl)urea (27 mg, 51%, 2 steps) as the HCl salt. 1H NMR (400 MHz, DMSO-d6): δ 9.77 (s, 1H), 9.49 (brs, 2H), 8.83 (s, 1H), 8.43 (d, J=1.6 Hz, 1H), 8.33 (d, J=2.0 Hz, 1H), 7.63-7.62 (m, 1H), 7.43-7.41 (m, 2H), 7.34-7.29 (m, 3H), 7.15-7.13 (m, 1H), 6.72 (dd, J=8.0 Hz, 2.0 Hz, 1H), 6.32 (s, 1H), 4.29 (brs, 2H), 3.38-3.35 (m, 2H), 3.08 (t, J=6.0 Hz, 2H), 1.26 (s, 9H); MS (ESI) m/z: 517.3 (M+H+).

Example A39

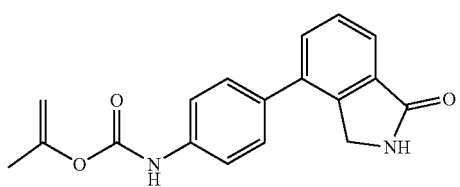

Using general method H, 4-(4-aminophenyl)isoindolin-1-one (150 mg, 0.67 mmol, made according to literature procedures) was transformed to yield prop-1-en-2-yl 4-(1-oxoisoindolin-4-yl)phenylcarbamate (176 mg, 85% yield). $^1$H NMR (400 MHz, DMSO-d$_6$): δ 10.1 (s, 1H), 8.67 (s, 1H), 7.65 (apparent td, J=7.6, 1.2 Hz, 2H), 7.61-7.55 (m, 5H), 4.77 (brt, J=1.0 Hz, 1H), 4.76 (s, 1H), 4.50 (s, 2H), 1.96 (s, 3H); MS (ESI) m/z: 309.0 (M+H$^+$).

Example A40

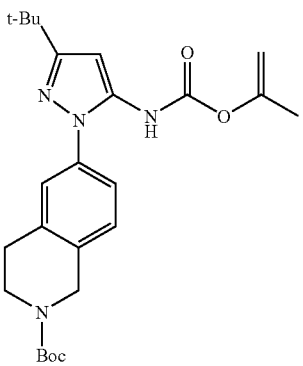

Using general method H, Example A39 (665 mg, 1.79 mmol) was transformed to yield t-butyl 6-(3-t-butyl-5-((prop-1-en-2-yloxy)carbonyl)-1H-pyrazol-1-yl)-3,4-dihydroisoquinoline-2(1H)-carboxylate (843 mg, 100% yield). $^1$H NMR (400 MHz, CDCl$_3$): δ 7.30-7.22 (m, 3H), 6.71 and 6.45 (brs, 1H total), 4.77 (brs, 1H), 4.74 (m, 1H), 4.63 (s, 2H), 3.68 (m, 2H), 2.91 (t, J=5.6 Hz, 2H), 1.98 (s, 3H), 1.52 (s, 9H), 1.36 (s, 9H); MS (ESI) m/z: 455.3 (M+H$^+$).

Example 151

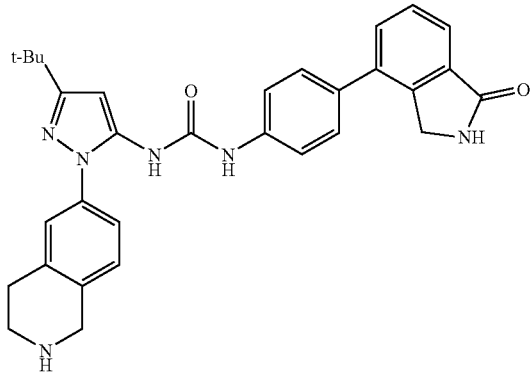

A solution of Example A39 (58.5 mg, 0.19 mmol), Example A38 (70 mg, 0.019 mmol) and N-methyl pyrrolidine (8.9 mg, 0.10 mmol) in THF (0.4 mL) was heated at 55° C. for 24 h. The crude reaction mixture was chromatographed on silica gel to provide t-butyl 6-(3-t-butyl-5-(3-(4-(1-oxoisoindolin-4-yl)phenyl)ureido)-1H-pyrazol-1-yl)-3,4-dihydroisoquinoline-2(1H)-carboxylate (76 mg). MS (ESI) m/z: 621.3 (M+H$^+$).

Using general method F, t-butyl 6-(3-t-butyl-5-(3-(4-(1-oxoisoindolin-4-yl)phenyl)ureido)-1H-pyrazol-1-yl)-3,4-dihydroiso-quinoline-2(1H)-carboxylate (74 mg, 0.12 mmol) was deprotected to yield 1-(3-t-butyl-1-(1,2,3,4-tetrahydroisoquinolin-6-yl)-1H-pyrazol-5-yl)-3-(4-(1-oxoisoindolin-4-yl)phenyl)urea hydrochloride (45 mg, 43% yield, 2 steps). $^1$H NMR (400 MHz, DMSO-d$_6$): δ 9.59 (s, 1H), 9.36 (brs, 2H), 8.75 (s, 1H), 8.67 (s, 1H), 7.64 (m, 2H), 7.59-7.51 (m, 5H), 7.45 (m, 2H), 7.36 (d, J=9.2 Hz, 1H), 6.37 (s, 1H), 4.50 (s, 2H), 4.31 (brs, 2H), 3.39 (m, 2H), 3.10 (t, J=6.1 Hz, 2H), 1.29 (s, 9H); MS (ESI) m/z: 519.2 (M+H$^+$).

Example 152

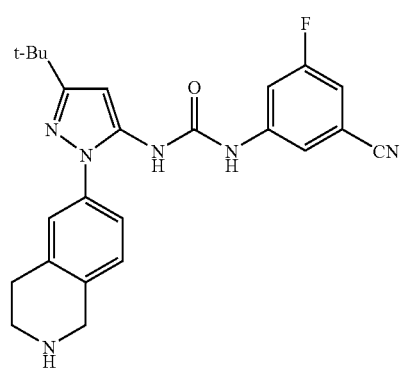

Using the same procedureas for Example 151, Example A40 (145 mg, 0.32 mmol) and 3-amino-5-fluorobenzonitrile (50 mg, 0.37 mmol) were combined to yield 1-(3-t-butyl-1-(1,2,3,4-tetrahydroisoquinolin-6-yl)-1H-pyrazol-5-yl)-3-(3-cyano-5-fluorophenyl)urea hydrochloride (55 mg, 38% yield, 2 steps). $^1$H NMR (400 MHz, DMSO-d$_6$): δ 10.2 (s, 1H), 9.36 (brs, H), 8.96 (s, 1H), 7.65 (dt, J=11.2, and 2.0 Hz, 1H), 7.62 (t, J=1.9 Hz, 1H), 7.44-7.40 (m, 3H), 7.34 (d, J=9.1 Hz, 1H), 6.37 (s, 1H), 4.30 (s, 2H), 3.39 (m, 2H), 3.09 (t, J=6.0 Hz, 2H), 1.28 (s, 9H); MS (ESI) m/z: 433.3 (M+H$^+$).

Example 153

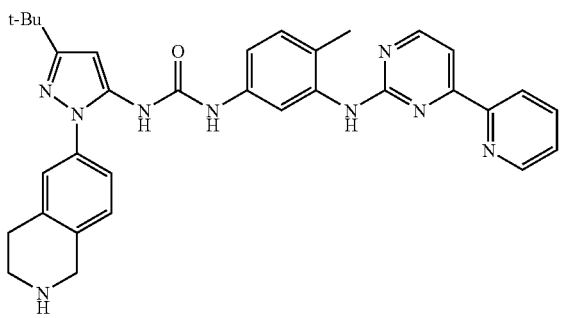

Using the same procedureas for Example 151, Example A40 (136 mg, 0.30 mmol) and 6-methyl-N1-(4-(pyridin-3- yl)pyrimidin-2-yl)ben-zene-1,3-diamine (80 mg, 0.29 mmol, made according to literature procedures) were combined to afford 1-(3-t-butyl-1-(1,2,3,4-tetrahydroisoquinolin-6-yl)-1H-pyrazol-5-yl)-3-(4-methyl-3-(4-(pyridin-3-yl)pyrimidin-2-ylamino)phenyl)urea dihydrochloride (109 mg, 56% yield). $^1$H NMR (400 MHz, DMSO-d$_6$): δ 9.56 (s, 1H), 9.50 (brs, 2H), 9.43 (d, J=1.7 Hz, 1H), 9.10 (s, 1H), 8.99 (brd, J=8.3 Hz, 1H), 8.92 (dd, J=5.4, 1.3 Hz, 1H), 8.83 (s, 1H), 8.60 (d, J=5.3 Hz, 1H), 7.94 (dd, J=8.0, 5.4 Hz, 1H), 7.98 (s, 1H), 7.57 (d, J=5.3 Hz, 1H), 7.46-7.42 (m, 2H), 7.34 (d, J=8.4 Hz, 1H), 7.14-7.08 (m, 2H), 6.35 (s, 1H), 4.29 (m, 2H), 3.37 (m, 2H), 3.09 (t, J=6.0 Hz, 2H), 2.18 (s, 3H), 1.28 (s, 9H); MS (ESI) m/z: 574.2 (M+H$^+$).

Example 154

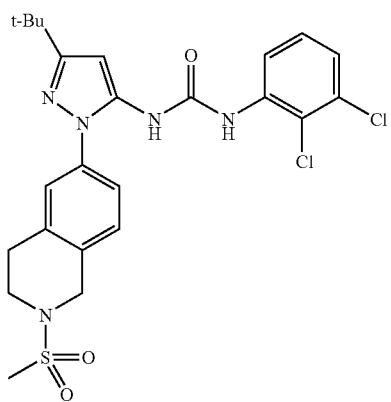

Using the same procedureas for Example 108, Example 138 (0.070 g, 0.14 mmol) and MsCl (0.032 g, 0.28 mmol) were combined to yield 1-(3-t-butyl-1-(2-(methylsulfonyl)-1,2,3,4-tetrahydroisoquinolin-6-yl)-1H-pyrazol-5-yl)-3-(2,3-dichlorophenyl)urea (57 mg, 75%) as a colorless solid. $^1$H NMR (400 Mhz, acetone-d$_6$): δ 8.56 (brs, 1H), 8.26 (dd, J=8.4, and 1.6 Hz, 1H), 8.17 (brs, 1H), 7.42-7.40 (m, 2H), 7.33-7.29 (m, 2H), 7.24 (dd, J=8.4, and 2.0 Hz, 1H), 6.48 (s, 1H), 4.49 (s, 2H), 3.56 (t, J=6.0 Hz, 2H), 3.03 (t, J=5.8 Hz, 2H), 2.93 (s, 3H), 1.32 (s, 9H); MS (ESI) m/z: 536.0 (M+H$^+$).

Example A41

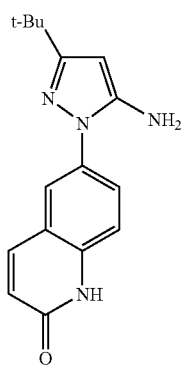

To a solution of hydrocarbostyril (7.8 g, 0.53 mol) in conc. H$_2$SO$_4$ (200 mL) was slowly added H$_2$O (50 mL) at −10° C. Conc. HNO$_3$ (70%, 4.0 mL) was added dropwise at −10° C. The yellow solution was stirred at −10° C. for 10 min and then carefully quenched with ice H$_2$O (500 mL). The precipitated yellow solid was filtered, washed with H$_2$O and dried under vacuum to obtain 6-nitro-3,4-dihydroquinolin-2(1H)-one (7.9 g, 78% yield). $^1$H NMR (400 Mhz, CDCl$_3$): δ 9.28 (s, 1H), 8.12 (m, 2H), 6.95 (d, J=9.2 Hz, 1H), 3.12 (t, J=7.2 Hz, 2H), 2.75 (d, J=7.2 Hz, 2H).

To a solution of 6-nitro-3,4-dihydroquinolin-2(1H)-one (0.46 g, 2.4 mmol) and NBS (0.53 g, 3.0 mmol) in CHCl$_3$ (20 mL) was added benzoyl peroxide (cat. amount) at RT. The mixture was refluxed at 80° C. for 3 h. More NBS (0.25 g) was added and the reaction mixture was refluxed at 80° C. for 1 h. The solvent was evaporated and the residue was dissolved in EtOH. The solid was filtered, washed with EtOH and dried under vacuum to obtain 6-nitroquinolin-2-ol as a pale yellow solid (0.36 g, 79% yield). $^1$H NMR (400 MHz, DMSO-d$_6$): δ 8.71 (d, J=−2.0 Hz, 1H), 8.34 (dd, J=2.8, and 9.2 Hz, 1H), 8.14 (d, J=9.6 Hz, 1H), 7.44 (d, J=9.2 Hz, 1H), 6.68 (dd, J=1.6, and 9.6 Hz, 1H). LC-MS (EI) m/z: 191.0 (M+H$^+$).

A mixture of 6-nitroquinolin-2-ol and PtO$_2$ (20 mg) in EtOH (30 mL) was stirred under H$_2$ (1 atm) for 20 h. More PtO$_2$ (10 mg) was added and was stirred under H$_2$ (1 atm) for 2 days. The solution was filtered and washed with MeOH and CHCl$_3$. The solvent was evaporated and the residue was dried under vacuum to obtain 6-aminoquinolin-2(1H)-one as a yellow solid (0.28 g, 92% yield). LC-MS (EI) m/z: 161.0 (M+H$^+$).

To a solution of 6-aminoquinolin-2(1H)-one in conc. HCl (1.5 mL) was added an aqueous solution (0.75 mL) of NaNO$_2$ dropwise at 0° C. The reaction mixture was stirred at 0° C. for 1 h, and then added a solution of SnCl$_2$.2H$_2$O in conc. HCl (0.75 mL) dropwise at 0° C. The reaction mixture was allowed to reach RT over a period of 30 min and then stirred for additional 2 h. The reaction mixture was diluted with EtOH. The mixture was filtered to remove some solids and then pivaloylacetonitrile was added into the solution. The reaction mixture was heated at 80° C. for 16 h. The reaction mixture was evaporated and the residue was suspended in ethyl acetate (30 mL) and treated slowly with satd. Na$_2$CO$_3$ (30 mL). The solution was extracted with EtOAc (3×). The combined organics were washed H$_2$O and dried (Na$_2$SO$_4$). Filtration, evaporation, and drying under vacuum provided crude 6-(5-amino-3-t-butyl-1H-pyrazol-1-yl)quinolin-2 (1H)-one which was used as is in the next reaction. LC-MS (EI) m/z: 283.0 (M+H$^+$).

Example 155

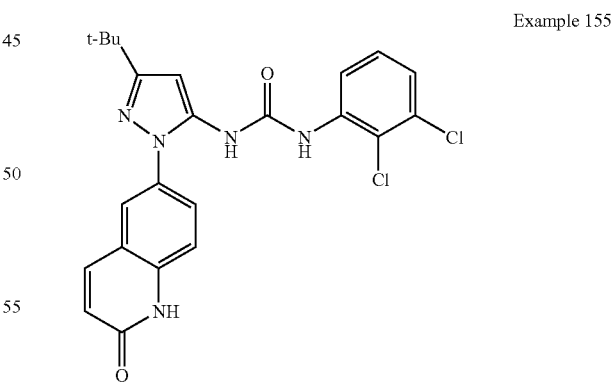

Using general method A, Example A41 (90 mg, 0.32 mmol) in THF (3 mL) and 2,3-dichlorophenyl isocyanate (72 mg, 0.38 mmol) were combined to yield 1-(3-t-butyl-1-(2-oxo-1,2-dihydroquinolin-6-yl)-1H-pyrazol-5-yl)-3-(2,3-dichlorophenyl)-urea as a yellow solid (52 mg, 35% yield). $^1$H NMR (400 MHz, DMSO-d$_6$): δ 9.22 (s, 1H), 8.74 (s, 1H), 8.07 (dd, J=3.2, and 6.4 Hz, 1H), 8.01 (d, J=10.0 Hz, 1H), 7.85 (d, J=2.4 Hz, 1H), 7.64 (dd, J=−2.4, and 8.4 Hz, 1H), 7.43 (d, J=8.8 Hz, 1H), 7.31 (d, J=3.24 Hz, 1H), 7.30 (s, 1H), 6.59 (dd, J=1.6, and 9.2 Hz, 1H), 6.41 (s, 1H), 1.28 (s, 9H); MS (EI) m/z: 470.0 (M+H⁺).

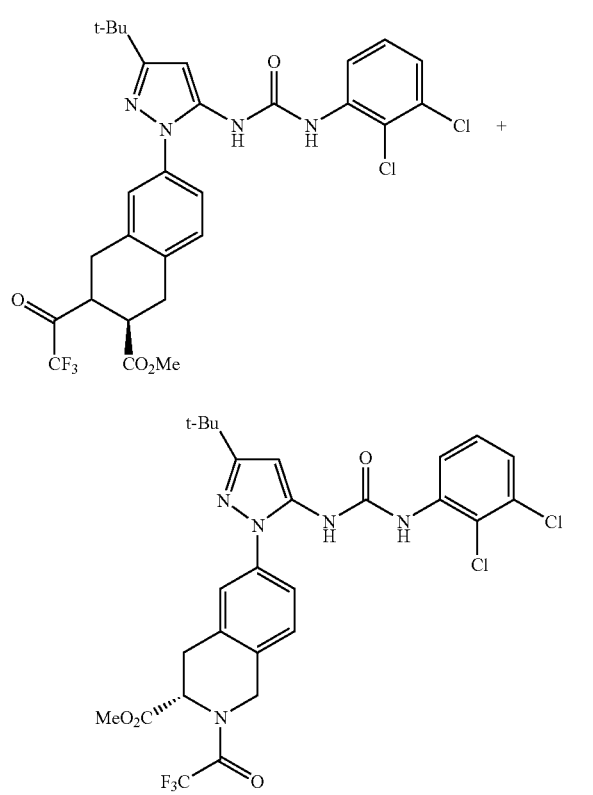

Example A42

To a solution of (S)-1,2,3,4-tetrahydroisoquinolone-3-carboxylic acid (5.00 g, 28.2 mmol) in conc. H₂SO₄ (20 mL) at RT was added dropwise a solution of KNO₃ (2.95 g, 29.2 mmol) in conc. H₂SO₄ (10 mL) without cooling. When the addition was complete, the mixture was stirred for 5 min and then carefully diluted with H₂O and neutralized with conc. NH₄OH (about 100 mL). The precipitate was filtered, washed with H₂O and acetone and dried in vacuo to give 6.60 g (crude yield>100%) of a mixture of nitrated compounds which was used as is in the next reaction. MS (EI) m/z: 223.0 (M+H⁺).

To a solution of the mixture from the previous reaction (4.40 g, 18.6 mmol) in CH₂Cl₂ (100 mL) was added TFAA (3.89 mL, 5.87 g, 27.9 mmol) and the resulting solution was stirred at RT for 30 min. Water (100 mL) was added and the mixture was extracted with CH₂Cl₂ (3×100 mL). The organic layer was dried (MgSO₄), concentrated, and dried to yield 6.2 g (100%) of (S)-methyl 7-nitro-2-(2,2,2-trifluoroacetyl)-1,2,3,4-tetrahydroisoquinoline-3-carboxylate and the 6-nitro isomer as a mixture. MS (EI) m/z: 333.0 (M+H⁺).

To a solution of the two regioisomers (6.20 g, 18.7 mmol) in MeOH (100 mL) was added 10% Pd/C (0.397 g, 0.161 mmol) and the mixture was stirred under H₂ (1 atm). The mixture was filtered through Celite® and concentrated to yield a yellow syrup of (S)-methyl 7-amino-2-(2,2,2-trifluoroacetyl)-1,2,3,4-tetrahydroisoquinoline-3-carboxylate and the 6-amino isomer as a mixture (6.1 g, crude yield>100%) which was used without further purification. MS (EI) m/z: 303.0 (M+H⁺).

To a solution of the mixture from the previous reaction (5.60 g, 16.5 mmol) in 2N HCl (30 mL) at 0° C. was added in portions solid NaNO₂ (1.14 g, 16.5 mmol) and the resulting solution was stirred for 45 min at 0° C. SnCl₂.2H₂O (7.46 g, 33.1 mmol) was then added and the mixture was allowed to reach RT and was stirred for 90 min. Ethanol (270 mL) and pivaloylacetonitrile (3.10 g, 24.8 mmol) were added and the resulting solution was heated at reflux overnight. Ethanol was removed under reduced pressure and 2N HCl (500 mL) was added to the residue. The mixture was extracted with CH₂Cl₂ (3×500 ml), the organic layer was dried (MgSO₄), concentrated, and purified via column chromatography to yield (3S)-methyl 7-(5-amino-3-t-butyl-1H-pyrazol-1-yl)-2-(2,2,2-trifluoroacetyl)-1,2,3,4-tetrahydroisoquinoline-3-carboxylate and (3S)-methyl 6-(5-amino-3-t-butyl-1H-pyrazol-1-yl)-2-(2,2,2-trifluoroacetyl)-1,2,3,4-tetrahydroisoquinoline-3-carboxylate as a mixture (3.10 mg, 44%) heavily contaminated with pivaloylacetonitrile (around 70 mol %). This material was used directly for the next step. MS (EI) m/z: 425.2 (M+H⁺).

Using general method A, the previous mixture (1.60 g, 3.77 mmol) and 2,3-dichlorophenyl isocyanate (4.50 g, 23.9 mmol) were combined and the mixture of two compounds separated by column chromatography to yield (3S)-methyl 7-(3-t-butyl-5-(3-(2,3-dichlorophenyl)ureido)-1H-pyrazol-1-yl)-2-(2,2,2-trifluoroacetyl)-1,2,3,4-tetrahydroiso-quinoline-3-carboxylate (275 mg, 12% yield), MS (EI) m/z: 612.1 (M+H⁺) and (3S)-methyl 6-(3-t-butyl-5-(3-(2,3-dichlorophenyl)ureido)-1H-pyrazol-1-yl)-2-(2,2,2-trifluoroacetyl)-1,2,3,4-tetrahydroisoquinoline-3-carboxylate (80 mg, 4% yield), MS (EI) m/z: 612.0 (M+H⁺).

Example 156

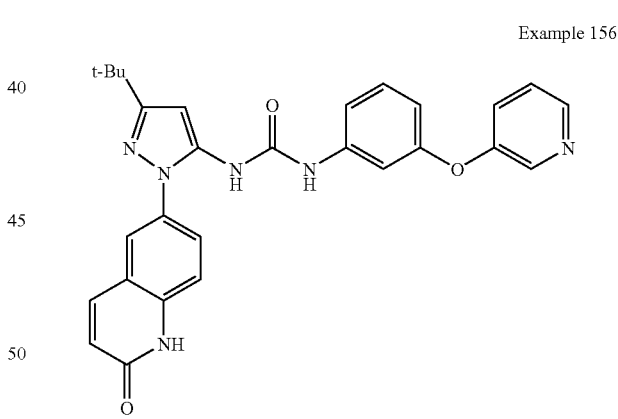

Using general method D, Example A41 (50 mg, 0.18 mmol) and Example A9 (34 mg, 0.18 mmol) were combined to yield 1-(3-t-butyl-1-(2-oxo-1,2-dihydroquinolin-6-yl)-1H-pyrazol-5-yl)-3-(3-(pyridin-3-yloxy)phenyl)urea as an off-white solid (34 mg, 45% yield). ¹H NMR (DMSO-d₆): δ 9.01 (s, 1H), 8.40 (s, 1H), 8.37 (m, 2H), 7.98 (d, J=9.6 Hz, 1H), 7.82 (d, J=2.4 Hz, 1H), 7.61 (dd, J=2.4, and 8.8 Hz, 1H), 7.43 (m, 3H), 7.29 (t, J=8.0 Hz, 1H), 7.24 (t, J=2.4 Hz, 1H), 7.08 (dd, J=1.6, and 8.4 Hz, 1H), 6.70 (dd, J=2.4, and 8.4 Hz, 1H), 6.58 (dd, J=2.0, and 10.0 Hz, 1H), 6.36 (s, 1H), 1.27 (s, 9H); LC-MS (EI) m/z: 495.2 (M+H⁺).

Example 157

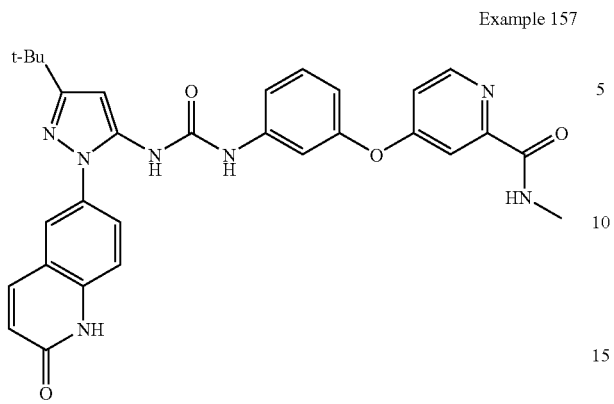

Example 159

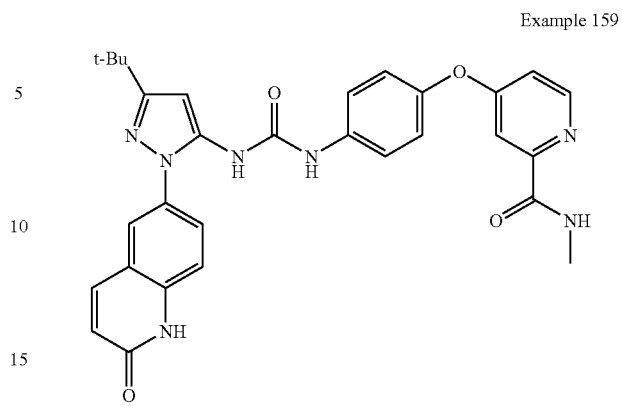

Using general method D, Example A41 (0.090 g, 0.20 mmol, 1.0 eq) and Example A12 (0.053 g, 0.22 mmol, 1.10 eq) and i-Pr$_2$NEt (0.044 ml, 0.25 mmol, 1.25 eq) were combined to yield 1-(3-t-butyl-1-(2-oxo-1,2-dihydroquinolin-6-yl)-1H-pyrazol-5-yl)-3-(3-(2-(methylcarbamoyl)pyridin-4-yloxy)phenyl)urea (11.2 mg. 10% yield, 2 steps. $^1$H NMR (acetone-d$_6$): 9.04 (s, 1H), 8.49-8.48 (m, 1H), 8.44 (s, 1H), 8.35 (brs, 1H), 7.96-7.94 (m, 1H), 7.87-7.86 (m, 1H), 7.76-7.73 (m, 1H), 7.65-7.64 (m, 1H), 7.59-7.58 (m, 1H), 7.47-7.39 (m, 2H), 7.31-7.29 (m, 1H), 7.31-7.29 (m, 1H), 7.14-7.12 (m, 1H), 6.85-6.82 (m, 1H), 6.55 (s, 1H), 6/52 (s, 1H), 2.94 (s, 3H), 1.33 (s, 9H); MS (ESI) m/z: 552.2 (M+H$^+$).

Using general method D, Example A41 (0.081 g, 0.19 mmol) and Example A12 (0.05 g, 0.21 mmol) were combined to afford 1-(3-t-butyl-1-(2-oxo-1,2-dihydroquinolin-6-yl)-1H-pyrazol-5-yl)-3-(4-(2-(methylcarbamoyl)pyridin-4-yloxy)phenyl)urea (0.04 g, 60%, 2 steps) as a white solid HCl salt. $^1$H NMR (400 MHz, DMSO-d$_6$): δ9.48 (s, 1H), 8.89 (s, 1H), 8.72 (s, 1H), 8.52 (d, J=5.6 Hz, 1H), 8.01 (d, J=9.6 Hz, 1H), 7.88 (s, 1H), 7.66 (dd, J=8.8 Hz, 2.0 Hz, 1H), 7.53 (d, J=8.8 Hz, 2H), 7.47-7.43 (m, 3H), 7.18-7.13 (m, 3H), 6.59 (d, J=9.6 Hz, 1H), 6.37 (s, 1H), 2.79 (d, J=4.8 Hz, 3H), 1.29 (s, 9H); MS (ESI) m/z: 552.2 (M+H$^+$).

Example 158

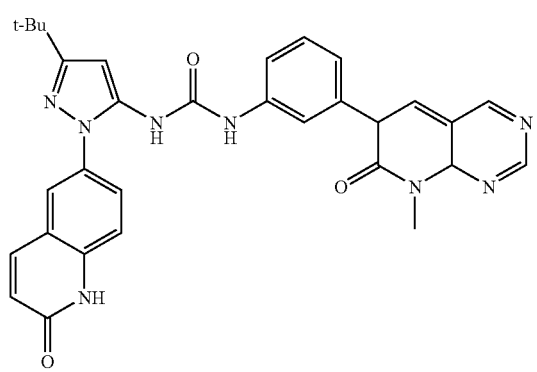

Example A43

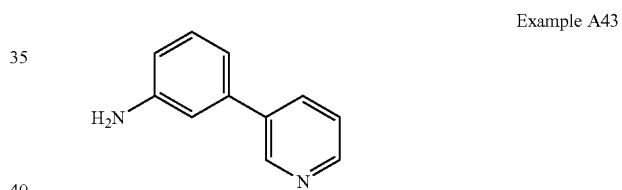

Using general method D, Example A41 (0.075 g, 0.16 mmol) and Example A11 (0.04 g, 0.16 mmol) were combined to afford 1-(3-t-butyl-1-(2-oxo-1,2-dihydroquinolin-6-yl)-1H-pyrazol-5-yl)-3-(3-(8-methyl-7-oxo-7,8-dihydropyrido[2,3-d]pyrimidin-6-yl)phenyl)urea (0.062 g, 60%) as the HCl salt. $^1$H NMR (400 MHz, DMSO-d$_6$): □ 9.37 (brs, 1H), 9.17 (s, 1H), 9.12 (s, 1H), 8.65 (brs, 1H), 8.16 (s, 1H), 8.01 (d, J=9.6 Hz, 1H), 7.87 (d, J=2.4 Hz, 1H), 7.81 (brs, 1H), 7.66 (dd, J=8.8 Hz, 2.0 Hz, 1H), 7.45-7.41 (m, 2H), 7.36 (t, J=8.0 Hz, 1H), 7.30-7.28 (m, 1H), 6.58 (d, J=9.6 Hz, 1H), 6.40 (s, 1H), 3.70 (s, 3H), 1.28 (s, 9H); MS (ESI) m/z: 561.3 (M+H$^+$).

To a degassed solution of 1-iodo-3-nitrobenzene (0.35 g, 1.4 mmol) in DME (5 mL) was added Pd(PPh$_3$)$_4$ (0.08 g, 10% mol). After stirring for 5 min, 3-pyridylboronic acid (0.2 g, 1.65 mmol) and 2M Na$_2$CO$_3$ (1 mL) solution were added. After refluxing for 16 h under an Ar atmosphere, the reaction mixture was poured into H$_2$O (15 mL) and extracted with EtOAc (2×30 mL). The combined organic extracts were washed with brine, dried (Na$_2$SO$_4$), concentrated and purified via column chromatography to yield 3-(3-nitrophenyl)pyridine (0.22 g, 78%) as a white solid. $^1$H NMR (CDCl$_3$): δ 8.94 (brs, 1H), 8.73 (brs, 1H), 8.48 (t, J=1.6 Hz, 1H), 8.32-8.29 (m, 1H), 7.98-7.93 (m, 2H), 7.72-7.68 (m, 1H), 7.48 (brs, 1H); Exact mass: 200.0, Found: 201.0 (M+1)$^+$.

To a solution of 3-(3-nitrophenyl)pyridine (0.22 g, 1.1 mmol) in EtOAc (10 mL) was added PtO$_2$ (0.025 g, 10% mol) and the mixture was stirred for 4 h under H$_2$ (1 atm). It was filtered through Celite® and the combined filtrates were concentrated to yield 3-(pyridin-3-yl)benzenamine (0.175 g, 94%) as a semi solid which was used without further purification. $^1$H NMR (DMSO-d$_6$): δ8.77 (d, J=2.0 Hz, 1H), 8.53 (dd, J=8.8 Hz, 1.6 Hz, 1H), 7.57-7.52 (m, 1H), 7.46-7.43 (m, 1H), 7.13 (t, J=8.0 Hz, 1H), 6.86-6.80 (m, 2H), 6.63-6.60 (m, 1H), 5.23 (s, 2H); Exact mass: 170.0, Found: 171.0 (M+1)$^+$.

Example A44

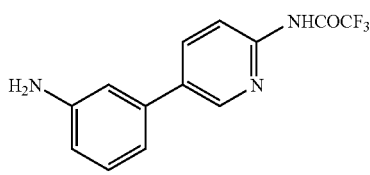

Using the same procedureas for Example A43, 5-iodo-2-aminopyridine (0.31 g, 1.4 mmol) and 3-nitrophenylboronic acid (0.28 g, 1.7 mmol) were combined to yield 5-(3-nitrophenyl)pyridin-2-amine (0.18 g, 60%) as a white solid. $^1$H NMR (DMSO-d$_6$): δ 8.37 (d, J=2.4 Hz, 1H), 8.34 (t, J=2.0 Hz, 1H), 8.11-8.04 (m, 2H), 7.83 (dd, J=8.0 Hz, 2.4 Hz, 1H), 7.68 (t, J=8.0 Hz, 1H), 6.55 (dd, J=8.4 Hz, 0.8 Hz, 1H), 6.26 (s, 2H); Exact mass: 215.0, Found: 216.0 (M+1)$^+$.

To a solution of 5-(3-nitrophenyl)pyridin-2-amine (0.17 g, 0.8 mmol) in CH$_2$Cl$_2$ (10 mL) was added pyridine (0.12 g, 1.6 mmol) and TFAA (0.2 g, 0.9 mmol). After stirring for 1 h at RT, 3M HCl (20 mL) was added to the reaction and the product was extracted with CH$_2$Cl$_2$ (2×20 mL). The combined organic extracts were washed with satd. NaHCO$_3$ solution (1×25 mL) and brine, then dried (Na$_2$SO$_4$) and concentrated to yield a solid. This solid was dissolved in EtOAc, and PtO$_2$ was added to this mixture which was stirred under H$_2$ (1 atm) for 4 h. The mixture was filtered through Celite®, and the combined filtrates were concentrated to yield N-(5-(3-aminophenyl)pyridin-2-yl)-2,2,2-trifluoroacetamide (0.21 g, 95%) as a solid which was used without further purification. $^1$H NMR (DMSO-d$_6$): δ 8.65 (d, J=2.4 Hz, 1H), 8.11-8.09 (m, 1H), 8.03-8.01 (m, 1H), 7.16 (t, J=8.0 Hz, 1H), 6.92-6.88 (m, 2H), 6.66-6.64 (m, 1H); Exact mass: 281.1, Found: 282.3 (M+1)$^+$.

Example 160

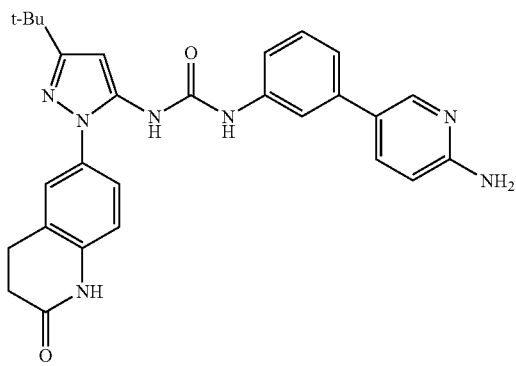

Using general procedure D3, Example A35 (0.09 g, 0.2 mmol) and Example A44 (0.05 g, 0.20 mmol) were combined and deprotected using general method G to yield 1-(3-(6-aminopyridin-3-yl)phenyl)-3-(3-t-butyl-1-(2-oxo-1,2,3,4-tetrahydroquinolin-6-yl)-1H-pyrazol-5-yl)urea (47 mg, 45% yield) as a solid. $^1$H NMR (400 MHz, DMSO-d$_6$): δ 10.27 (s, 1H), 9.40 (s, 1H), 8.58 (s, 1H), 8.23-8.21 (m, 2H), 8.11 (brs, 1H), 7.77 (s, 1H), 7.38-7.33 (m, 2H), 7.28-7.24 (m, 2H), 7.10 (d, J=0.8 Hz, 1H), 6.97 (d, J=0.8 Hz, 1H), 6.35 (s, 1H), 2.95 (t, J=6.4 Hz, 2H), 1.27 (s, 9H); MS (ESI) m/z: 496.3 (M+H$^+$).

Example 161

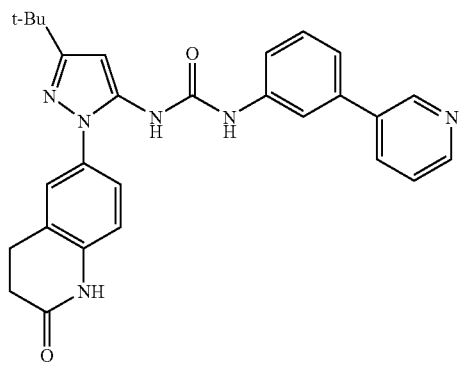

Using general method D, Example A35 (0.09 g, 0.2 mmol) and Example A43 (0.034 g, 0.2 mmol) were combined to yield 1-(3-t-butyl-1-(2-oxo-1,2,3,4-tetrahydroquinolin-6-yl)-1H-pyrazol-5-yl)-3-(3-(pyridin-3-yl)phenyl)urea (76 mg, 74%) as a white solid as the HCl salt. $^1$H NMR (400 MHz, DMSO-d$_6$): δ 10.27 (s, 1H), 9.70-9.67 (m, 1H), 9.16 (s, 1H), 8.89 (s, 1H), 8.77 (brs, 2H), 8.11-8.08 (m, 1H), 7.95 (s, 1H), 7.47 (s, 2H), 7.35 (s, 1H), 7.29 (d, J=8.4 Hz, 1H), 6.97 (d, J=8.4 Hz, 1H), 6.36 (s, 1H), 2.95 (t, J=7.6 Hz, 2H), 1.27 (s, 9H); MS (ESI) m/z: 481.2 (M+H$^+$).

Example A45

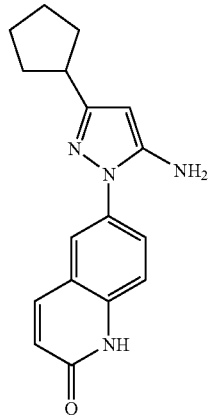

To a suspension of 6-aminoquinolin-2(1H)-one (0.72 g, 4.5 mmol, see Example A41) in conc. HCl (5 mL) was slowly added NaNO$_2$ (0.43 g, 6.3 mmol) solution in H$_2$O (5 mL) at 0° C. After stirring for 1 h, SnCl$_2$.2H$_2$O (2.0 g, 9.0 mmol), dissolved in conc. HCl (7 mL), was slowly added at such a rate that the temperature of the mixture did not rise above 5° C., After stirring for 2 h, the resultant solid was filtered, dried, and suspended in EtOH. To this were added 3-cyclopentyl-3-oxopropanenitrile (0.68 g, 4.9 mmol) and a few drops of HCl and the mixture was heated at 80° C. for 16 h. The solution was concentrated, dissolved in satd. NaHCO$_3$ solution and the product was extracted with EtOAc (2×30 mL). The combined organic extracts were washed with brine, dried (Na$_2$SO$_4$), concentrated and the resultant solid triturated with toluene (10 mL) and filtered to yield 6-(5-amino-3-cyclopentyl-1H-pyrazol-1-yl)quinolin-2(1H)-one (0.75 g, 57% yield) as a solid. $^1$H NMR (400 MHz, DMSO-d$_6$): δ 7.95 (d, J=10.0 Hz, 1H), 7.81 (d, J=2.4 Hz, 1H), 7.68 (dd, J=8.8 Hz, 2.0 Hz, 1H), 7.35 (d, J=8.8 Hz, 1H), 6.54 (d, J=8.8 Hz, 1H), 5.32 (s, 1H), 5.24 (brs, 2H), 2.92-2.84 (m, 1H), 1.94-1.86 (m, 2H), 1.73-1.57 (m, 6H); MS (ESI) m/z: 295.2 (M+H⁺).

Example 162

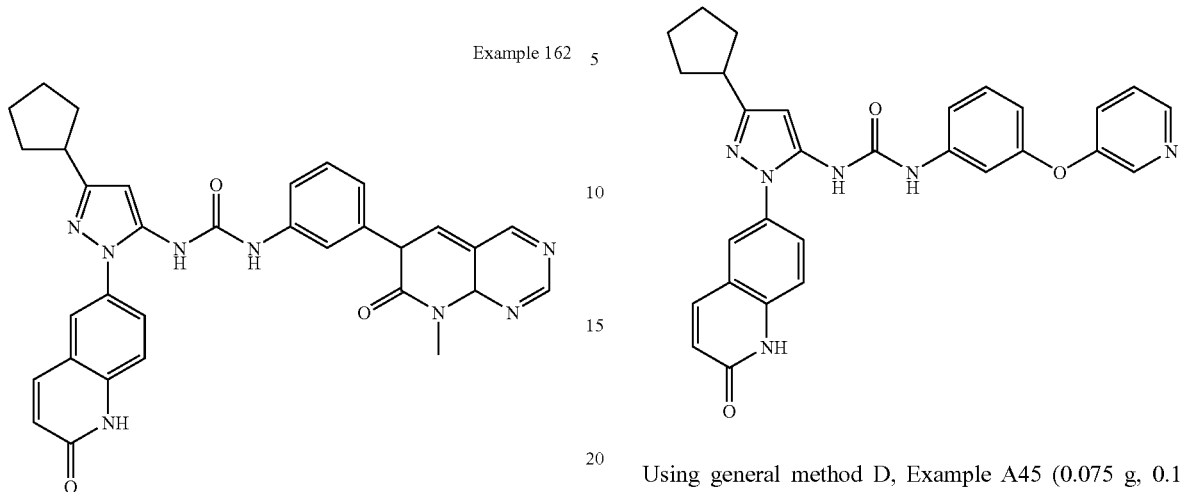

Using general method D, Example A45 (0.075 g, 0.16 mmol)) and Example A11 (0.04 g, 0.16 mmol) were combined to yield 1-(3-cyclopentyl-1-(2-oxo-1,2-dihydroquinolin-6-yl)-1H-pyrazol-5-yl)-3-(3-(8-methyl-7-oxo-7,8-dihydropyrido[2,3-d]pyrimidin-6-yl)phenyl)urea (0.075 g, 47% yield, 2 steps) as a solid HCl salt. ¹H NMR (400 MHz, DMSO-d₆): δ 9.71 (brs, 1H), 9.17 (s, 1H), 9.12 (s, 1H), 8.56 (brs, 1H), 8.15 (s, 1H), 8.11 (d, J=9.6 Hz, 1H), 7.90 (d, J=2.4 Hz, 1H), 7.79 (brs, 1H), 7.67 (dd, J=8.8 Hz, 2.0 Hz, 1H), 7.46-7.41 (m, 2H), 7.35 (t, J=8.0 Hz, 1H), 7.28-7.26 (m, 1H), 6.57 (d, J=9.6 Hz, 1H), 6.33 (s, 1H), 3.70 (s, 3H), 3.06-2.98 (m, 1H), 1.99-1.94 (m, 2H), 1.72-1.59 (m, 6H); MS (ESI) m/z: 573.3 (M+H⁺).

Example 163

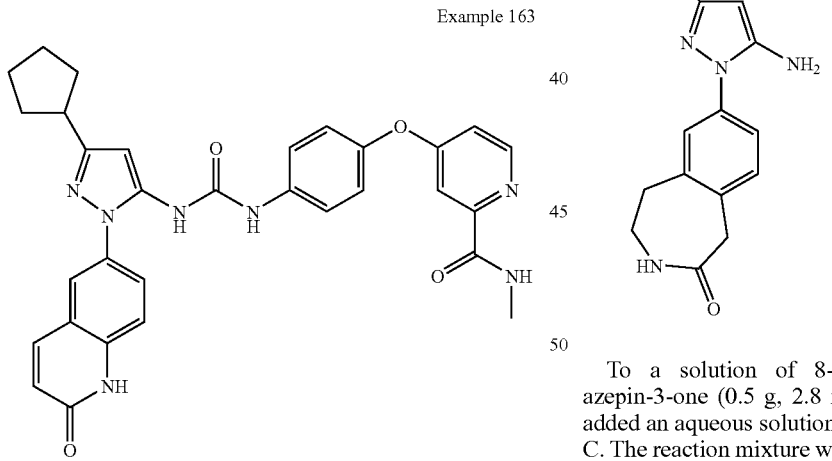

Using general method D, Example A45 (0.075 g, 0.16 mmol) and Example A12 (0.04 g, 0.16 mmol) were combined to yield 1-(3-cyclopentyl-1-(2-oxo-1,2-dihydroquinolin-6-yl)-1H-pyrazol-5-yl)-3-(4-(2-(methylcarbamoyl)pyridin-4-yloxy)phenyl)urea (0.038 g, 31% yield, 2 steps) as a solid HCl salt. ¹H NMR (400 MHz, DMSO-d₆): δ 9.59 (brs, 1H), 8.88 (brs, 1H), 8.81 (s, 1H), 8.51 (d, J=6.0 Hz, 1H), 8.01 (d, J=9.6 Hz, 1H), 7.89 (d, J=2.4 Hz, 1H), 7.67 (dd, J=8.8 Hz, 2.0 Hz, 1H), 7.54-7.42 (m, 4H), 7.17-7.13 (m, 3H), 7.58 (d, J=9.6 Hz, 1H), 6.33 (s, 1H), 3.06-2.98 (m, 1H), 2.78 (d, J=6.0 Hz, 3H), 1.99-1.94 (m, 2H), 1.72-1.59 (m, 6H); MS (ESI) m/z: 564.3 (M+H⁺).

Example 164

Using general method D, Example A45 (0.075 g, 0.16 mmol) and Example A9 (0.03 g, 0.16 mmol) were combined to yield 1-(3-cyclopentyl-1-(2-oxo-1,2-dihydroquinolin-6-yl)-1H-pyrazol-5-yl)-3-(3-(pyridin-3-yloxy)phenyl)urea (0.07 g, 52%, 2 steps) as a solid. ¹H NMR (400 MHz, DMSO-d₆): δ 9.63-9.61 (m, 1H), 8.80-8.79 (m, 1H), 8.65-8.64 (m, 1H), 8.57-8.56 (m, 1H), 7.98 (d, J=10.0 Hz, 1H), 7.93-7.90 (m, 1H), 7.86 (d, J=4.4 Hz, 1H), 7.83-7.79 (m, 1H), 7.64 (dd, J=8.8 Hz, 2.0 Hz, 1H), 7.42-7.38 (m, 2H), 7.34 (t, J=8.0 Hz, 1H), 7.15-7.13 (m, 1H), 6.76 (dd, J=8.0 Hz, 2.0 Hz, 1H), 6.57 (d, J=10.0 Hz, 1H), 6.29 (s, 1H), 3.04-2.97 (m, 1H), 1.98-1.93 (m, 2H), 1.72-1.60 (m, 6H); MS (ESI) m/z: 507.2 (M+H⁺).

Example A46

To a solution of 8-amino-1,2,4,5-tetrahydrobenzo[c]azepin-3-one (0.5 g, 2.8 mmol) in conc. HCl (3 mL) was added an aqueous solution (2 mL) of NaNO₂ dropwise at 0° C. The reaction mixture was stirred at 0° C. for 1 h, and then treated dropwise with a solution of SnCl₂.2H₂O in conc. HCl (2 mL) at 0° C. The reaction mixture was allowed to reach room temperature over a period of 30 min and then stirred for an additional 2 h at RT. This solution was concentrated and used directly for the next step.

The material from the previous reaction (0.65 g, 2.8 mmol) was dissolved in EtOH (10 mL) and some solid was filtered off. Pivaloylacetonitrile (0.36 g, 2.8 mmol) was added to the solution. The reaction mixture was heated at 80° C. overnight, then evaporated and the residue was suspended in EtOAc (30 mL) and treated slowly with satd. Na₂CO₃ (30 mL). The solution was extracted with EtOAc (3×), and the combined organics were washed with H₂O, dried (Na₂SO₄), filtered, concentrated and dried under vacuum to provide crude product in 65% yield. This was dissolved in toluene (10 mL) with molecular sieves (4 Å). The reaction mixture was refluxed overnight, concentrated and the residue dried under vacuum. This was used for the next reaction without further purification. MS (EI) m/z: 299.0 (M+H$^+$).

Example 165

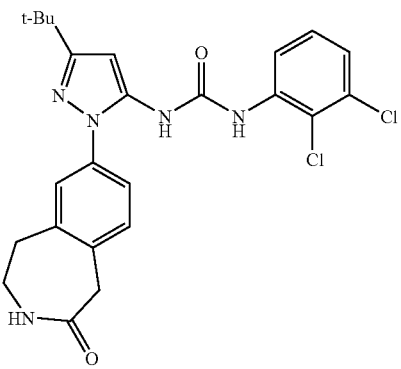

Using general method A, Example A46 (23 mg, 0.077 mmol) and 2,3-dichlorophenylisocyanate (17 mg, 0.092 mmol) were combined to yield 1-(3-t-butyl-1-(2-oxo-2,3,4,5-tetrahydro-1H-benzo[d]azepin-7-yl)-1H-pyrazol-5-yl)-3-(2,3-dichlorophenyl)urea (23 mg, 61% yield) as a pale yellow powder. $^1$H NMR (400 MHz, DMSO-d$_6$): δ 9.20 (s, 0.84H), 9.04 (s, 0.26H), 8.76 (s, 0.84H), 8.75 (s, 0.26H), 8.06 (m, 1H), 7.66 (t, J=5.6 Hz, 0.84H), 7.51 (t, J=5.6 Hz, 0.26H), 7.31 (m, 4H), 6.38 (s, 0.26H), 6.37 (s, 0.84H), 3.88 (s, 0.48H), 3.82 (s, 1.72H), 3.48 (dd, J=5.6, and 11.6 Hz, 1.72H), 3.41 (m, 0.48H), 3.07 (t, J=6.0 Hz, 2H), 1.27 (s, 7.56H), 1.26 (s, 2.16H); MS (EI) m/z: 487.0 (M+H$^+$).

Example A47

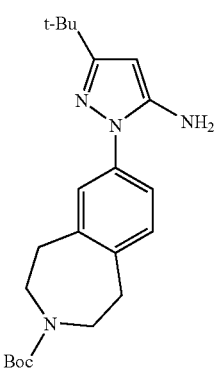

beta-Tetralone (34 mmol) was suspended in 300 mL of 85% H$_3$PO$_4$ and treated portion wise with NaN$_3$ (68 mmol) with vigorous stirring over a period of 1 h. During this time the reaction mixture was brought slowly to about 70° C. After stirring for a further 2 h at 70° C., no more N$_2$ evolution was observed. The reaction mixture was cooled to RT, then poured into cold H$_2$O (400 mL) and extracted with CHCl$_3$ (3×). The organic layer was dried (MgSO$_4$), concentrated and the residue was dissolved in EtOAc and the solid was filtered and washed with EtOAc to yield 4,5-dihydro-1H-benzo[d]azepin-2(3H)-one as a white solid (20% yield) along with a varying amount of the other region isomer 1,2,4,5-tetrahydrobenzo[c]azepin-3-one.

To a solution of regioisomers from the previous reaction (16.6 mmol) in CH$_2$Cl$_2$ were added Et$_3$N (16.6 mmol), di-t-butyl dicarbonate (33.1 mmol) and DMAP (16.6 mmol), and the mixture stirred at RT for 24 h. The reaction mixture was purified by column chromatography to yield Boc-protected 4,5-dihydro-1H-benzo[d]azepin-2(3H)-one as white solid in 20% yield. A solution of this material (2.7 mmol) in 3N HCl/EtOAc (4 mL) was stirred at 0° C. for 3 h. The solvent was neutralized by 20% NaOH. The solution was extracted with CHCl$_3$ (3×) and washed with H$_2$O. The organic layer was dried (MgSO$_4$), and concentrated to afford 4,5-dihydro-1H-benzo[d]azepin-2(3H)-one (0.64 g, 91% yield) as a white solid. LC-MS (EI) m/z: 162.2 (M+H$^+$).

A solution of 4,5-dihydro-1H-benzo[d]azepin-2(3H)-one (3.5 mmol) was in THF (25 mL) was stirred at 0° C. for 5 min. A solution of 1M BH$_3$.THF (4 mL) was added dropwise to the reaction mixtureat 0° C. over a period of 30 min. The ice bath was removed and the reaction stirred at RT for 30 min. The reaction mixture was heated at 60° C. overnight, then cooled to 0° C. and additional 1M BH$_3$.THF (2.5 mL) was added dropwise into the reaction mixtureat 0° C. over a period of 15 min. The ice bath was removed and it was stirred at RT for 30 min then heated at 60° C. for 7 h. The reaction mixture was cooled to RT, then further cooled with an ice-bath. The reaction was quenched by the addition of 2M HCl (15 mL). The mixture was heated for 30 min and then 20% NaOH (7.5 mL) was added with ice cooling. The solution was extracted with chloroform (3×) and the organic layer was washed with H$_2$O. The organic layer was dried (Na$_2$SO$_4$), concentrated and redissolved in 2 mL of EtOAc and acidified with 3M HCl/EtOAc. The solid was filtered and dried under vacuum to obtain 2,3,4,5-tetrahydro-1H-benzo[d]azepine as a shiny powder (0.36 g, 69% yield). LC-MS (EI) m/z: 148.2 (M+H$^+$).

A solution of 2,3,4,5-tetrahydro-1H-benzo[d]azepine dissolved in conc. H$_2$SO$_4$ (1.5 mL) was cooled to 0° C. and a mixture of concentrated H$_2$SO$_4$ (0.12 mL) and fuming HNO3 (0.06 mL) (also cooled to 0° C.) was added dropwise. After the addition was complete, the mixture was stirred for 15-30 min. The reaction mixture was poured onto 10 g of crushed ice, followed by the dropwise addition of 20% NaOH solution. The mixture was extracted with EtOAc (3×). The organic layer was washed with H$_2$O, dried (Na$_2$SO$_4$), concentrated and under vacuum to afford 7-nitro-2,3,4,5-tetrahydro-1H-benzo[d]azepine as a brown liquid (0.12 g, 46% yield). LC-MS (EI) m/z: 193.0 (M+H$^+$).

To a solution of 7-nitro-2,3,4,5-tetrahydro-1H-benzo[d]azepine (1.1 mmol) in CH$_2$Cl$_2$ (5 mL) was added TFAA (1.7 mmol) and the resulting solution was stirred at RT for 30 min. Water (10 mL) was added and the mixture was extracted with CH$_2$Cl$_2$ (3×10 mL), dried (MgSO$_4$), and concentrated under vacuum to yield 2,2,2-trifluoro-1-(7-nitro-1,2,4,5-tetrahydrobenzo[d]azepin-3-yl)ethanone as a yellow syrup (0.32 g, 96% yield). LC-MS (EI) m/z: 299.3 (M+H$^+$).

To a suspension of 2,2,2-trifluoro-1-(7-nitro-1,2,4,5-tetrahydrobenzo[d]azepin-3-yl)ethanone (1.1 mmol) in MeOH (5 mL) was added 10% Pd/C and the mixture was stirred at RT under H$_2$ (1 atm) for 24 h. After filtration, the filtrate was concentrated to afford 1-(7-amino-1,2,4,5-tetrahydrobenzo[d]azepin-3-yl)-2,2,2-trifluoroethanone (0.27 g, 95% yield). LC-MS (EI) m/z: 259.0 (M+H$^+$).

To a solution of 1-(7-amino-1,2,4,5-tetrahydrobenzo[d]azepin-3-yl)-2,2,2-trifluoroethanone (1.6 mmol) in conc. HCl (2 mL) was added an aqueous solution (1 mL) of NaNO$_2$ (2.4 mmol) dropwise at 0° C. The reaction mixture was stirred at 0° C. for 1 h, and was followed by the addition of a solution of SnCl$_2$.2H$_2$O (5.0 mmol) in conc. HCl (1 mL) dropwise at 0° C. The reaction mixture was allowed to reach RT over a period of 30 min and then stirred for additional 2 h. The solution was concentrated and redissolved in EtOH, and pivaloylacetonitrile (3.7 mmol) was added. The reaction mixture was heated at reflux for 16 h. The reaction mixture was evaporated and the residue suspended in EtOAc (30 mL) and treated slowly with satd. NaHCO$_3$ (30 mL). The biphasic mixture was stirred at RT for 2 h. The aqueous layer was treated with 6M NaOH to pH 8 and filtered to remove the tin salts. The filtrate was extracted with EtOAc (3×). The combined organics were washed with satd. NaHCO$_3$ (1×), brine (1×) and dried (Na$_2$SO$_4$). Filtration, evaporation and drying under vacuum provided crude product (0.21 g, 71% yield). LC-MS (EI) m/z: 285.2 (M+H$^+$).

This material (0.74 mmol) was dissolved in CH$_2$Cl$_2$ and Boc anhydride (0.74 mmol) was added. The resultant solution was stirred at RT for 30 min and evaporated to yield t-butyl 7-(5-amino-3-t-butyl-1H-pyrazol-1-yl)-1,2,4,5-tetrahydrobenzo[d]azepine-3-carboxylate (0.26 g, 98% yield). LC-MS (EI) m/z: 385.2 (M+H$^+$).

Example 166

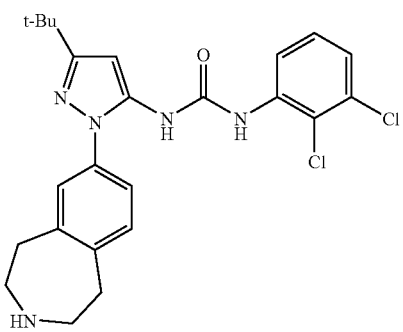

Using general method A, Example A47 (65 mg, 0.17 mmol) and 2,3-dichlorophenyl isocyanate (32 mg, 0.17 mmol) were combined and the product deprotected using general method F to yield 1-(3-t-butyl-1-(2,3,4,5-tetrahydro-1H-benzo[d]azepin-7-yl)-1 H-pyrazol-5-yl)-3-(2,3-dichlorophenyl)urea (50 mg, 58% yield). $^1$H NMR (400 MHz, DMSO-d$_6$): δ 9.28 (s, 1H), 8.89 (m, 1H), 8.81 (s, 1H), 8.03 (dd, J=4.0, and 5.6 Hz, 1H), 7.42 (brs, 1H), 7.31 (m, 4H), 6.37 (s, 1H), 3.20 (m, 4H), 3.14 (m, 4H), 1.26 (s, 9H); LC-MS (EI) m/z: 472.0 (M+H$^+$).

Example 167

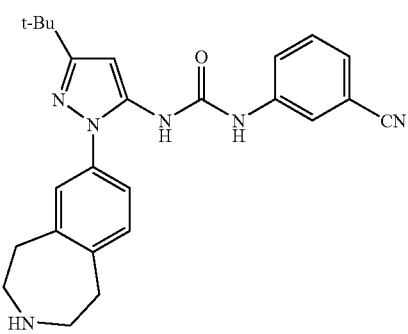

Using general method A, Example A47 (70 mg, 0.18 mmole) and 3-cyanophenylisocynate (26 mg, 0.18 mmol) were combined and the product deprotected using general method F to yield 1-(3-t-butyl-1-(2,3,4,5-tetrahydro-1H-benzo[d]azepin-7-yl)-1H-pyrazol-5-yl)-3-(3-cyanophenyl) urea HCl salt (24 mg, 29% yield). $^1$H NMR (DMSO-d$_6$): δ 9.78 (s, 1H), 9.04 (m, 1H), 8.73 (s, 1H), 7.93 (t, J=1.6 Hz, 1H), 7.61 (dt, J=1.2, and 9.2 Hz, 1H), 7.48 (t, J=7.6 Hz, 1H), 7.42 (m, 2H), 7.34 (s, 1H), 6.37 (s, 1H), 3.19 (m, 4H), 3.14 (m, 4H), 1.27 (s, 9H); LC-MS (EI) m/z: 429.2 (M+H$^+$).

Example A48

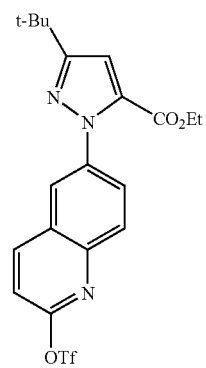

To a solution of commercially available 6-bromo-1,2,3,4-tetrahydro-2-quinolinone (5.0 g, 22 mmol) and NBS (4.9 g, 27 mmol) in CHCl$_3$ (80 mL) was added a catalytic portion of benzoyl peroxide at RT. The mixture was refluxed at 80° C. for 3 h, after which additional NBS (2.0 g) was added and the reaction refluxed overnight at 80° C. Additional NBS (0.9 g) was added into the reaction mixture which was refluxed at 80° C. for 5 h. The solid was filtered, washed with EtOH and dried to yield 6-bromoquinolin-2(1H)-one (4.35 g, 88% yield) as a pale yellow solid. $^1$H NMR (400 MHz, DMSO-d$_6$): δ 7.93 (d, J=2.8 Hz, 1H), 7.88 (d, J=9.6 Hz, 1H), 7.64 (dd, J=2.0, and 8.8 Hz, 1H), 7.25 (d, J=8.8 Hz, 1H), 6.55 (dd, J=2.0, and 9.6 Hz, 1H); LC-MS (EI) m/z: 224.0 (M+H$^+$).

6-Bromoquinolin-2(1H)-one (4.0 g, 18 mmol), 4-methoxybenzyl chloride (3.6 g, 23 mmol), and tetrabutylammonium bromide (1.2 g, 3.6 mmol) were dissolved in PhMe (200 mL) and then KOH (powder, 1.8 g, 32 mmol) was added into the reaction mixture. The reaction mixture was stirred at RT for 4 h, then poured into H$_2$O and extracted with EtOAc (3×50 mL). The organic layer was washed with H$_2$O, dried (Na$_2$SO$_4$), and concentrated. Trituration with hexane, followed by collection of the solids yielded 1-(4-methoxybenzyl)-6-bromoquinolin-2(1H)-one (5.4 g, 87% yield) as a yellow solid. $^1$H NMR (400 MHz, CDCl$_3$): δ 7.70 (d, J=2.4 Hz, 1H), 7.66 (d, J=9.6 Hz, 1H), 7.52 (dd, J=2.0, and 8.8 Hz, 1H), 7.19 (d, J=9.2 Hz, 1H), 7.16 (d, J=8.8 Hz, 2H), 6.85 (d, J=8.8 Hz, 2H), 6.83 (d, J=9.4 Hz, 1H), 5.48 (brs, 2H), 3.78 (s, 3H), 1.36 (s, 12H); LC-MS (EI) m/z: 344.0 (M+H$^+$).

Potassium acetate (54.3 g, 44 mmol), pinacol diboron (5.5 g, 22 mmol) and PdCl$_2$(dppf) (0.60 mg, 0.73 mmol) were added sequentially to a solution 1-(4-methoxybenzyl)-6-bromoquinolin-2(1H)-one (5.0 g, 15 mmol) in DMF (70 mL). After flushing with N$_2$, the reaction vessel was sealed and heated at 80° C. for 14 h and then partitioned between H$_2$O and EtOAc. The combined organic extracts were washed with brine, dried (MgSO$_4$) concentrated and purified via column chromatography to yield 1-(4-methoxybenzyl)-6-(4,4,5,5-tetramethyl-1,3,2-dioxaborolan-2-yl)quinolin-2(1H)-one (38 g, 67% yield) as a yellow solid. $^1$H NMR (400 MHz, CDCl$_3$): δ 8.04 (brs, 1H), 7.86 (dd, J=1.2, and 8.4 Hz, 1H), 7.76 (d, J=9.6 Hz, 1H), 7.32 (d, J=9.2 Hz, 1H), 7.17 (d, J=8.4 Hz, 2H), 6.83 (d, J=8.8 Hz, 2H), 6.80 (d, J=9.6 Hz, 1H), 5.52 (brs, 2H), 3.77 (s, 3H), 1.36 (s, 12H); LC-MS (EI) m/z: 392.3 (M+H$^+$).

Sodium periodate (5.9 g, 28 mmol) was added to a solution of 1-(4-methoxybenzyl)-6-(4,4,5,5-tetramethyl-1,3,2-dioxaborolan-2-yl)quinolin-2(1H)-one (3.6 g, 9.2 mmol) in THF/H$_2$O (4/1, 40 mL). The reaction mixture was stirred at RT for 30 min, after which 2N HCl (9.2 mL) was added and the solution was then stirred at RT for 3 h. The solution was extracted with EtOAc (3×50 mL) and the organic layer was dried (MgSO$_4$), and concentrated to yield crude 1-(4-methoxybenzyl)-2-oxo-1,2-dihydroquinolin-6-ylboronic acid (2.6 g, 90% yield) which was used without further purification. $^1$H NMR (400 MHz, DMSO-d$_6$): δ 8.10 (brs, 1H), 7.96 (d, J=9.2 Hz, 1H), 7.88 (dd, J=1.6, and 8.8 Hz, 1H), 7.39 (d, J=9.2 Hz, 1H), 7.16 (d, J=8.4 Hz, 2H), 6.86 (d, J=8.4 Hz, 2H), 6.69 (d, J=9.6 Hz, 1H), 5.45 (brs, 2H), 3.69 (s, 3H); LC-MS (EI) m/z: 310.0 (M+H$^+$).

1-(4-Methoxybenzyl)-2-oxo-1,2-dihydroquinolin-6-ylboronic acid (1.8 g, 5.8 mmol) was dissolved in CH$_2$Cl$_2$ (120 mL) and pyridine (10 mL) with molecular sieves (activated, 4 Å) and the solution was kept overnight at RT. Commercially available ethyl 3-t-butyl-1H-pyrazole-5-carboxylate (1.2 g, 5.8 mmol), Cu(OAc)$_2$ (1.1 g, 5.8 mmol) and molecular sieves (4 Å activated, powder) were added to the boronic acid solution and the reaction mixture was stirred open to the air at RT for 3 days. The reaction mixture was filtered through a pad of Celite®, and the filtrate was evaporated under reduced pressureand purified by silica gel column chromatography to yield ethyl 1-(1-(4-methoxybenzyl)-2-oxo-1,2-dihydroquinolin-6-yl)-3-t-butyl-1H-pyrazole-5-carboxylate (2.5 g, 94% yield). LC-MS (EI) m/z: 460.3 (M+H$^+$).

A solution of ethyl 1-(1-(4-methoxybenzyl)-2-oxo-1,2-dihydroquinolin-6-yl)-3-t-butyl-1 H-pyrazole-5-carboxylate (1.5 g, 3.3 mmol) in TFA (25 mL) was heated in a sealed tube at 100° C. for 7 h. The mixture was cooled, concentrated and purified by silica gel column chromatography to yield ethyl 3-t-butyl-1-(2-oxo-1,2-dihydroquinolin-6-yl)-1H-pyrazole-5-carboxylate (1.0 g, 90% yield). $^1$H NMR (400 MHz, CDCl$_3$): δ 7.95 (d, J=9.6 Hz, 1H), 7.77 (d, J=2.0 Hz, 1H), 7.66 (dd, J=2.4, and 8.4 Hz, 1H), 7.46 (d, J=8.8 Hz, 1H), 6.94 (s, 1H), 6.82 (d, J=9.2 Hz, 1H). LC-MS (EI) m/z: 340.3 (M+H$^+$).

To a stirred suspension of ethyl 3-t-butyl-1-(2-oxo-1,2-dihydroquinolin-6-yl)-1H-pyrazole-5-carboxylate (1.0 g, 2.95 mmol) and Et$_3$N (0.45 g, 4.45 mmol) in CH$_2$Cl$_2$ (30 ml) was added triflic anhydride (1.66 g, 5.9 mmol) at −78° C. and then maintained at this temperature for 30 min. The reaction was allowed to warm to RT over a period 1.5 h, then quenched by pouring onto ice. The organic layer was washed with 10% NaOH, extracted with CH$_2$Cl$_2$ (3×50 mL). washed with brine, dried (Na$_2$SO$_4$), concentrated and purified by column chromatography to yield ethyl 3-t-butyl-1-(2-(trifluoromethylsulfonyloxy)quinolin-6-yl)-1H-pyrazole-5-carboxylate (1.3 g, 94% yield). $^1$H NMR (400 MHz, CDCl$_3$): δ 8.40 (d, J=8.8 Hz, 1H), 8.12 (d, J=9.2 Hz, 1H), 8.04 (d, J=2.0 Hz, 1H), 7.90 (dd, J=2.4 and, 9.2 Hz, 1H), 7.31 (d, J=8.8 Hz, 1H), 6.99 (s, 1H), 4.28 (q, J=7.2 Hz, 2H), 1.41 (s, 9H), 1.30 (t, J=7.2 Hz, 3H); LC-MS (EI) m/z: 472.0 (M+H$^+$).

Example A49

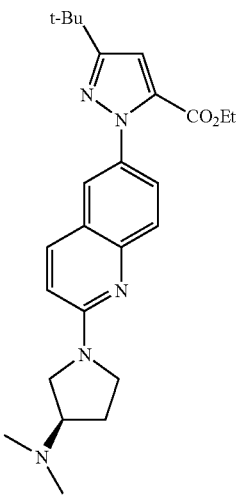

To a solution of Example A48 (0.10 g, 0.21 mmol) in DMSO (1 mL) was added (R)—N,N-dimethylpyrrolidin-3-amine (0.055 g, 0.47 mmol). The reaction mixture was heated at 40° C. for 1 h. Ethyl acetate was added and the resulting solution was washed with brine, dried (Na$_2$SO$_4$) and concentrated under reduced pressure to yield ethyl 3-t-butyl-1-(2-((R)-3-(dimethylamino)pyrrolidin-1-yl)quinolin-6-yl)-1H-pyrazole-5-carboxylate (88 mg, 95% yield). $^1$H NMR (400 MHz, CDCl$_3$): δ 7.89 (d, J=8.8 Hz, 1H), 7.75 (d, J=8.8 Hz, 1H), 7.69 (d, J=2.0 Hz, 1H), 7.56 (dd, J=2.0 and, 8.4 Hz, 1H), 6.92 (s, 1H), 6.76 (d, J=9.2 Hz, 1H), 4.21 (q, J=7.6 Hz, 2H), 4.03 (m, 1H), 3.88 (m. 1H), 3.60 (m, 1H), 3.49 (m, 1H), 2.98 (m, 1H), 2.63 (s, 6H), 2.33 (m, 1H), 2.04 (m, 1H), 1.40 (s, 9H), 1.21 (t, J=7.6 Hz, 3H); LC-MS (EI) m/z: 436.2 (M+H$^+$).

Example A50

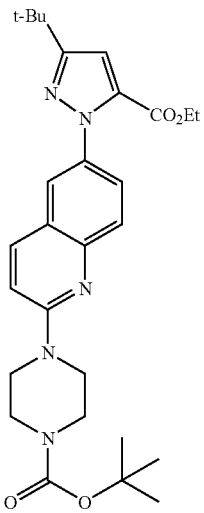

Using the same procedureas for Example A49, Example A48 (0.2 g, 0.42 mmol) and t-butyl piperazine-1-carboxylate (0.17 g, 0.93 mmol) were combined to yield t-butyl 4-(6-(5-amino-3-t-butyl-1H-pyrazol-1-yl)quinolin-2-yl)piperazine-1-carboxylate (210 mg, 98% yield). $^1$H NMR (400 MHz, CDCl$_3$): δ 7.94 (d, J=8.8 Hz, 1H), 7.74 (d, J=8.8 Hz, 1H), 7.71 (d, J=2.4 Hz, 1H), 7.58 (dd, J=2.4 and, 8.8 Hz, 1H), 7.01 (d, J=9.2 Hz, 1H), 6.92 (s, 1H), 4.22 (q, J=7.2 Hz, 2H), 3.77 (m, 4H), 3.61 (m. 4H), 2.64 (s, 6H), 1.52 (s, 9H), 2.33 (m, 1H), 1.40 (s, 9H), 1.22 (t, J=7.6 Hz, 3H); LC-MS (EI) m/z: 508.3 (M+H⁺).

Example A51

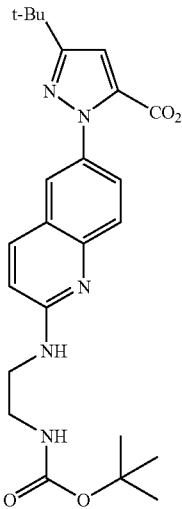

Using the same procedureas for Example A49, Example A48 (0.20 g, 0.42 mmol) and t-butyl 2-aminoethylcarbamate (0.15 g, 0.93 mmol) were combined to yield ethyl 1-(2-(2-(t-butoxycarbonyl)ethylamino)quinolin-6-yl)-3-t-butyl-1H-pyrazole-5-carboxylate (0.20 mg, 98% yield). ¹H NMR (400 MHz, CDCl₃): δ 7.85 (d, J=9.2 Hz, 1H), 7.75 (d, J=8.8 Hz, 1H), 7.70 (d, J=2.4 Hz, 1H), 7.59 (dd, J=2.4 and, 8.8 Hz, 1H), 6.93 (s, 1H), 6.73 (m, 1H), 5.57 (brs, 1H), 4.23 (q, J=7.2 Hz, 2H), 3.70 (brq, J=5.2 Hz, 2H), 3.45 (brq, J=5.2 Hz, 2H), 1.45 (s, 9H), 1.40 (s, 9H), 1.24 (t, J=7.2 Hz, 3H); LC-MS (EI) m/z: 482.2 (M+H⁺).

Example A52

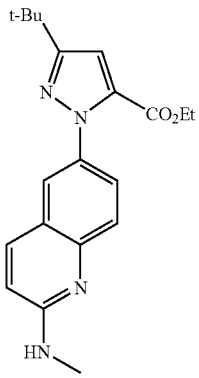

Using the same procedureas for Example A49, Example A48 (0.20 g, 0.42 mmol) and MeNH₂.HCl (0.043 g, 0.64 mmol) were combined to yield ethyl 3-t-butyl-1-(2-(dimethylamino)quinolin-6-yl)-1H-pyrazole-5-carboxylate (82 mg, 55% yield). ¹H NMR (400 MHz, CDCl₃): δ 7.90 (d, J=9.2 Hz, 1H), 7.68 (d, J=2.8 Hz, 1H), 7.53 (d, J=9.2 Hz, 1H), 7.46 (dd, J=2.0, and 8.8 Hz, 1H), 7.17 (q, J=4.8 Hz, 1H), 6.98 (s, 1H), 6.80 (d, J=8.8 Hz, 1H), 2.92 (d, J=4.8 Hz, 3H), 1.32 (s, 9H); LC-MS (EI) m/z: 353.2 (M+H⁺).

Example A53

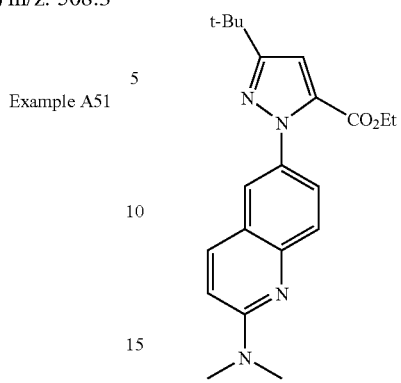

Using the same procedureas for Example A49, Example A48 (0.20 g, 0.42 mmol) and Me₂NH.HCl (0.026 g, 0.32 mmol) were combined to yield ethyl 3-t-butyl-1-(2-(dimethylamino)quinolin-6-yl)-1H-pyrazole-5-carboxylate (82 mg, 55% yield). ¹H NMR (400 MHz, CDCl₃): δ 8.04 (s, 1H), 7.88 (m, 1H), 7.73 (m, 1H), 7.68 (brs, 1H), 7.57 (m, 1H), 6.94 (d, J=8.8 Hz, 1H), 6.92 (s, 1H), 4.21 (q, J=7.2 Hz, 2H), 2.98 (s, 3H), 2.90 (s, 3H), 1.40 (s, 9H), 1.21 (t, J=7.2 Hz, 3H); LC-MS (EI) m/z: 367.3 (M+H⁺).

Example A54

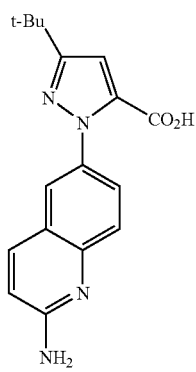

Using the same procedureas for Example A49, Example A48 (0.15 g, 0.42 mmol) and 4-methoxybenzylamine (0.13 g, 0.93 mmol) were combined to yield ethyl 1-(2-(4-methoxybenzylamino)quinolin-6-yl)-3-t-butyl-1H-pyrazole-5-carboxylate (150 mg, 77%). LC-MS (EI) m/z: 459.2 (M+H⁺). Using general method E, this material was saponified to yield 1-(2-(4-methoxybenzylamino)quinolin-6-yl)-3-t-butyl-1H-pyrazole-5-carboxylic acid in quantitative yield. A solution of this material in TFA (25 mL) was heated in sealed tube at 100° C. for 7 h. The mixture was cooled, concentrated and purified by silica gel column chromatography to yield 1-(2-aminoquinolin-6-yl)-3-t-butyl-1H-pyrazole-5-carboxylic acid (0.1 g, 99% yield). LC-MS (EI) m/z: 311.2 (M+H⁺).

Example 168

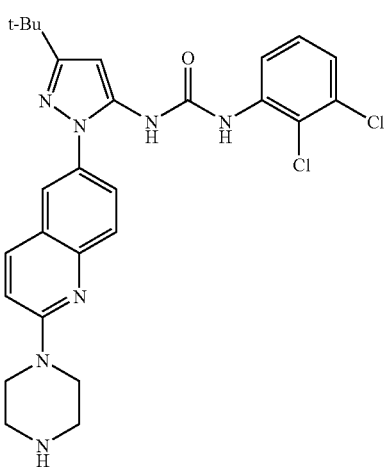

To a solution of Example A50 (0.21 g, 0.41 mmol) in a mix of EtOH:dioxane:H$_2$O (1:1:1) (1 mL) was added LiOH (40 mg, 1.7 mmol). The mixture was stirred overnight at RT then diluted with EtOAc (50 mL) and 5% citric acid (50 mL). The organic phase was separated, washed with brine (20 mL), dried (Na$_2$SO$_4$), concentrated and dried to yield 1-(2-(4-(t-butoxycarbonyl)piperazin-1-yl)quinolin-6-yl)-3-t-butyl-1H-pyrazole-5-carboxylic acid as a yellow solid in quantitative yield. LC-MS (EI) m/z: 480.2 (M+H$^+$).

To a solution of 1-(2-(4-(t-butoxycarbonyl)piperazin-1-yl)quinolin-6-yl)-3-t-butyl-1H-pyrazole-5-carboxylic acid (0.1 g, 0.21 mmol) in toluene (2 mL) was added Et$_3$N (0.032 mL, 0.23 mmol) and 2,3-dichloroaniline (84 mg, 0.52 mmol). The reaction mixture was stirred at RT and DPPA (63 mg, 0.23 mmol) was added. The reaction mixture was heated at 100° C. for 2 h, cooled, quenched with H$_2$O, and extracted with EtOAc (3×50 mL). The organic extracts were washed with brine, dried (Na$_2$SO$_4$), concentrated and purified by column chromatography to yield t-butyl 4-(6-(3-t-butyl-5-(3-(2,3-dichlorophenyl)ureido)-1H-pyrazol-1-yl)quinolin-2-yl)piperazine-1-carboxylate (0.11 g, 83% yield). $^1$H NMR (400 MHz, DMSO-d$_6$): δ 9.26 (s, 1H), 8.77 (s, 1H), 8.17 (d, J=9.6 Hz, 1H), 8.07 (dd, J=3.2, and 6.8 Hz, 1H), 7.87 (d, J=2.0 Hz, 1H), 7.68 (m, 2H), 7.31 (m, 3H), 6.42 (s, 1H), 3.74 (m, 4H), 3.47 (m, 4H), 1.44 (s, 9H), 1.30 (s, 9H); LC-MS (EI) m/z: 638.3 (M+H$^+$).

The material from the previous reaction (0.11 g, 0.17 mmol) was dissolved in EtOAc, 3M HCl/EtOAc (2 mL) was added and the solution was stirred at RT for 5 h. The solution was concentrated and the residue was dissolved in H$_2$O/CH$_3$CN (1:1, 4 mL) and lyophilized to obtain 1-(3-t-butyl-1-(2-(piperazin-1-yl)quinolin-6-yl)-1H-pyrazol-5-yl)-3-(2,3-dichlorophenyl)urea (65 mg, 66% yield) as a white solid HCl salt. $^1$H NMR (400 MHz, DMSO-d$_6$): δ 9.55 (brs, 1H), 9.37 (brs, 2H), 8.89 (s, 1H), 8.40 (brd, J=7.6 Hz, 1H), 8.07 (brs, 1H), 8.00 (m, 2H), 7.87 (m, 1H), 7.53 (brd, J=8.4 Hz, 1H), 7.29 (d, J=4.8 Hz, 2H), 6.42 (s, 1H), 4.10 (m, 4H), 3.29 (m, 4H), 1.30 (s, 9H); LC-MS (EI) m/z: 538.3 (M+H$^+$).

Example 169

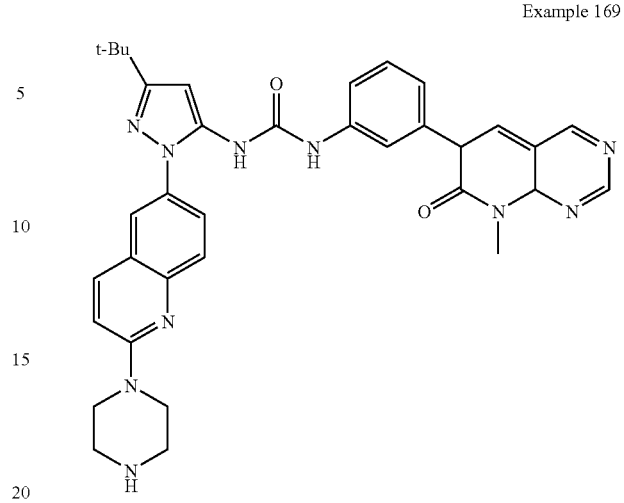

Using the same procedureas for Example 168 Example A50 (100 mg, 0.21 mmol), and Example A11 (58 mg, 0.23 mmol) were combined to yield 1-(3-t-butyl-1-(2-(piperazin-1-yl)quinolin-6-yl)-1H-pyrazol-5-yl)-3-(3-(8-methyl-7-oxo-7,8-dihydropyrido[2,3-d]pyrimidin-6-yl)phenyl)urea (69 mg, 42% yield, 3 steps) as the HCl salt. $^1$H NMR (400 MHz, DMSO-d$_6$): δ 9.30 (brm, 1H), 9.15 (s, 1H), 9.11 (s, 1H), 8.96 (brm, 2H), 8.60 (brm, 2H), 8.27 (brm, 1H), 8.15 (s, 1H), 7.97 (brm, 1H), 7.81 (brs, 1H), 7.78 (brm, 1H), 7.43 (m, 1H), 7.35 (brt, J=7.6 Hz, 1H), 7.28 (m, 1H), 6.41 (s, 1H), 4.01 (m, 4H), 3.97 (m, 4H), 3.71 (s, 3H), 3.26 (m, 4H), 1.30 (s, 9H); LC-MS (EI) m/z: 629.2 (M+H$^+$).

Example 170

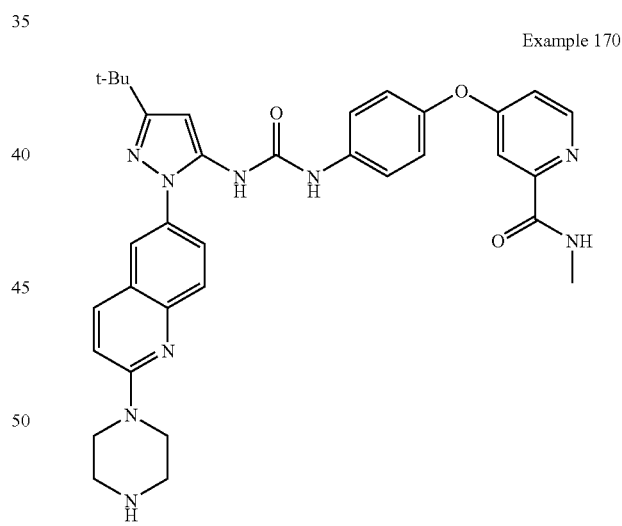

Using the same procedureas for Example 168, Example A50 (0.10 g, 0.21 mmol) and Example A12 (0.13 g, 0.52 mmol) were combined to yield 1-(3-t-butyl-1-(2-(piperazin-1-yl)quinolin-6-yl)-1H-pyrazol-5-yl)-3-(4-(2-(methylcarbamoyl)pyridin-4-yloxy)phenyl)urea (90 mg, 59% yield, 3 steps) as an off-white solid HCl salt. $^1$H NMR (400 MHz, DMSO-d$_6$): δ 9.33 (brs, 1H), 9.02 (brs, 2H), 8.78 (m, 2H), 8.63 (brs, 1H), 8.50 (d, J=5.6 Hz, 1H), 8.30 (m, 1H), 7.94 (m, 1H), 7.80 (m, 1H), 7.52 (m, 2H), 7.45 (m, 1H), 7.36 (d, J=2.4 Hz, 1H), 7.13 (m, 2H), 6.41 (s, 1H), 4.01 (m, 4H), 3.27 (m, 4H), 2.78 (d, J=4.8 Hz, 3H), 1.31 (s, 9H); LC-MS (EI) m/z: 620.2 (M+H$^+$).

Example 171

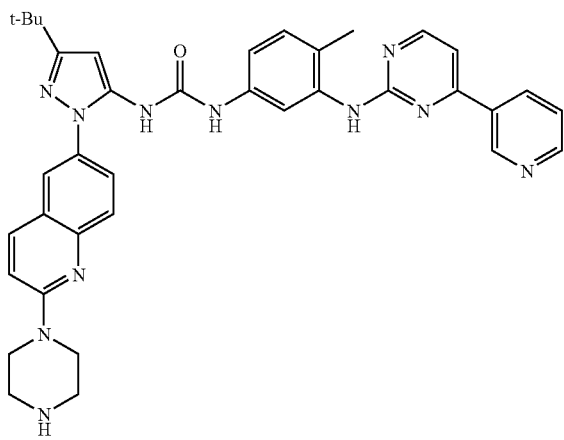

Using the same procedureas for Example 168, Example A50 (0.10 g, 0.21 mmol), and Example A7 (0.14 g, 0.52 mmol) were combined to yield 1-(3-t-butyl-1-(2-(piperazin-1-yl)quinolin-6-yl)-1H-pyrazol-5-yl)-3-(4-methyl-3-(4-(pyridin-3-yl)pyrimidin-2-ylamino)phenyl)urea (94 mg, 57% yield, 3 steps) as the HCl salt. $^1$H NMR (400 MHz, 400 MHz, DMSO-$d_6$): δ 9.36 (brm, 1H), 9.27 (brm, 1H), 8.99 (brs, 1H), 8.82 (brd, J=4.8 Hz, 1H), 8.78 (brm, 1H), 8.56 (d, J=5.2 Hz, 1H), 8.37 (brd, J=9.2 Hz, 1H), 8.04 (brs, 1H), 7.95 (brm, 1H), 7.83 (m, 1H), 7.76 (brm, 1H), 7.49 (m, 2H), 7.11 (d, J=8.8 Hz, 1H), 7.06 (dd, J=2.0, and 8.4 Hz, 2H), 6.41 (s, 1H), 4.14 (brm, 4H), 3.28 (brm, 4H), 3.15 (brd, J=4.8 Hz, 3H), 2.18 (s, 3H), 1.32 (s, 9H); LC-MS (EI) m/z: 654.3 (M+H$^+$).

Example 172

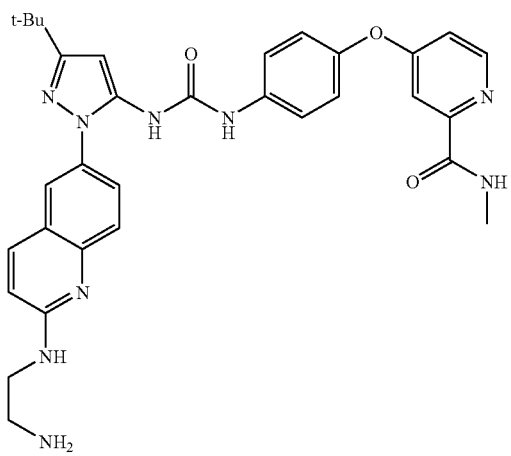

Using the same procedureas for Example 168, Example A51 (0.10 g, 0.21 mmol) and Example A12 (0.11 g, 0.44 mmol) were combined to yield 1-(1-(2-(2-aminoethylamino)quinolin-6-yl)-3-t-butyl-1H-pyrazol-5-yl)-3-(4-(2-(methylcarbamoyl)pyridin-4-yloxy)phenyl)urea (100 mg, 75% yield, 3 steps) as a pale yellow solid HCl salt. $^1$H NMR (400 MHz, DMSO-$d_6$): δ 9.51 (brs, 1H), 8.80 (brs, 1H), 8.78 (m, 1H), 8.50 (d, J=6.0 Hz, 1H), 8.39 (m, 1H), 8.15 (m, 3H), 7.98 (m, 1H), 7.52 (m, 2H), 7.36 (d, J=2.8 Hz, 1H), 7.21 (m, 1H), 7.14 (m, 3H), 6.42 (s, 1H), 3.92 (m, 2H), 3.18 (m, 2H), 2.78 (d, J=4.8 Hz, 3H), 1.31 (s, 9H); LC-MS (EI) m/z: 594.2 (M+H$^+$).

Example 173

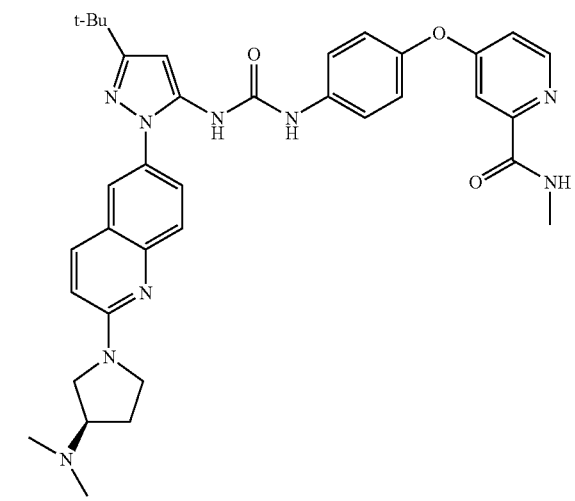

Using the same procedureas for Example 168, Example A49 (0.08 g, 0.21 mmol) and Example A12 (0.13 g, 0.52 mmol) were combined to yield 1-(3-t-butyl-1-(2-((R)-3-(dimethylamino)pyrrolidin-1-yl)quinolin-6-yl)-1H-pyrazol-5-yl)-3-(4-(2-(methylcarbamoyl)pyridin-4-yloxy)phenyl)urea (30 mg, 20% yield) as a yellow solid HCl salt. $^1$H NMR (400 MHz, CDCl$_3$): δ 9.38 (s, 1H), 8.77 (m, 2H), 7.35 (d, J=2.8 Hz, 1H), 7.14 (m, 3H), 6.41 (s, 1H), 4.15 (brs, 1H), 4.06 (brs, 1H), 3.95 (brs, 1H), 3.64 (brs, 1H), 2.87 (brt, J=5.6 Hz, 6H), 2.78 (d, J=4.8 Hz, 3H), 1.31 (s, 9H); LC-MS (EI) m/z: 648.2 (M+H$^+$).

Example 174

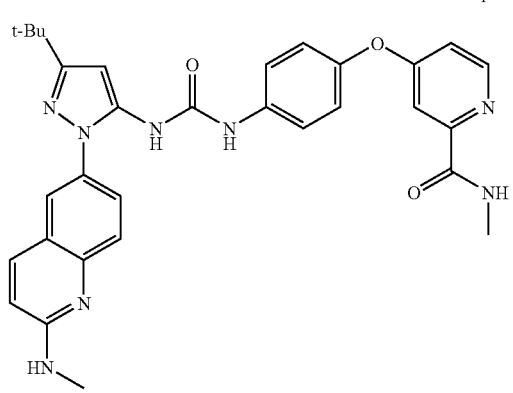

Using the same procedureas for Example 168, Example A52 (0.04 g, 0.11 mmol) and Example A12 (0.07 g, 0.27 mmol) were combined to yield 1-(3-t-butyl-1-(2-(methylamino)quinolin-6-yl)-1H-pyrazol-5-yl)-3-(4-(2-(methylcarbamoyl)pyridin-4-yloxy)phenyl)urea (53 mg, 74% yield) as the HCl salt. $^1$H NMR (400 MHz, DMSO-$d_6$): δ 9.87 (brm, 1H), 9.38 (brs, 1H), 8.78 (brm, 1H), 8.74 (s, 1H), 8.50 (d, J=5.6 Hz, 1H), 8.35 (brd, J=9.2 Hz, 1H), 8.13 (brs, 1H), 8.11 (brm, 1H), 7.97 (dd, J=2.0, and 9.2 Hz, 1H), 7.52 (d, J=8.8 Hz, 2H), 7.34 (d, J=2.8 Hz, 1H), 7.14 (m, 3H), 6.42 (s, 1H), 3.15 (brd, J=4.8 Hz, 3H), 2.78 (d, J=5.2 Hz, 3H), 1.31 (s, 9H); LC-MS (EI) m/z: 565.3 (M+H$^+$).

Example 175

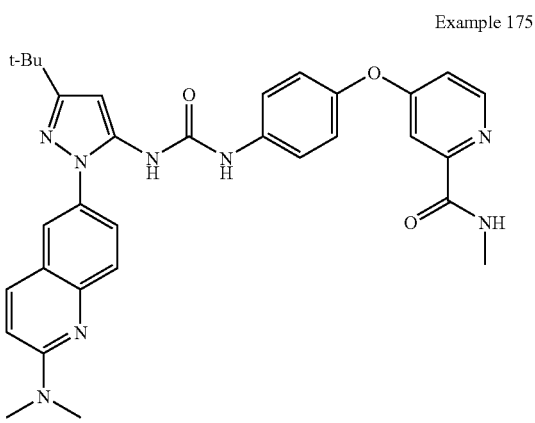

Example A55

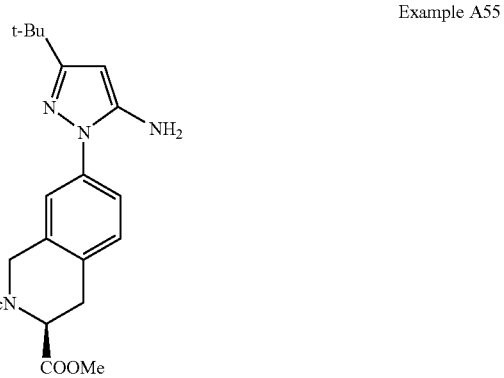

Using the same procedureas for Example 168, Example A53 (0.08, 0.21 mmol) and Example A12 (0.13 g, 0.52 mmol) were combined to yield 1-(3-t-butyl-1-(2-(dimethylamino)quinolin-6-yl)-1H-pyrazol-5-yl)-3-(4-(2-(methylcarbamoyl)pyridin-4-yloxy)phenyl)urea (61 mg, 51% yield) as a pale yellow solid HCl salt. $^1$H NMR (400 MHz, DMSO-d$_6$): δ 9.30 (brs, 1H), 8.78 (q, J=4.4 Hz, 1H), 8.69 (brs, 1H), 8.50 (d, J=5.6 Hz, 1H), 8.15 (m, 2H), 7.98 (m, 1H), 7.52 (m, 2H), 7.34 (d, J=2.4 Hz, 1H), 7.14 (m, 3H), 6.42 (s, 1H), 3.38 (brs, 6H), 2.78 (d, J=4.8 Hz, 3H), 1.31 (s, 9H); LC-MS (EI) m/z: 579.2 (M+H$^+$).

Example 176

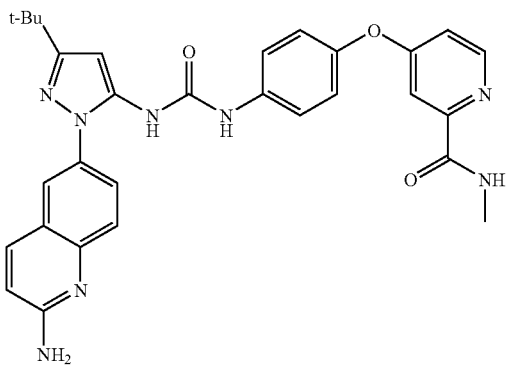

Using the same procedureas for Example 168, Example A54 (0.085 g, 0.27 mmol) and Example A12 (0.10 g, 0.41 mmol) were combined to yield 1-(1-(2-aminoquinolin-6-yl)-3-t-butyl-1H-pyrazol-5-yl)-3-(4-(2-(methylcarbamoyl)pyridin-4-yloxy)phenyl)urea (48 mg, 33% yield) as the HCl salt. $^1$H NMR (400 MHz, DMSO-d$_6$): δ 9.59 (brs, 1H), 9.20 (brs, 1H), 8.90 (brs, 1H), 8.79 (q, J=4.4 Hz, 1H), 8.50 (d, J=5.6 Hz, 1H), 8.48 (d, J=9.2 Hz, 1H), 8.17 (d, J=2.4 Hz, 1H), 7.97 (dd, J=2.0, and 8.8 Hz, 1H), 7.84 (d, J=8.8 Hz, 1H), 7.52 (m, 2H), 7.37 (m, 3H), 7.17 (m, 4H), 6.41 (s, 1H), 2.78 (d, J=4.4 Hz, 3H), 1.31 (s, 9H); LC-MS (EI) m/z: 551.2 (M+H$^+$).

To a solution of (S)-1,2,3,4-tetrahydroisoquinolone-3-carboxylic acid (5.00 g, 28.2 mmol) in conc. H$_2$SO$_4$ (20 mL) at RT was added dropwise a solution of KNO$_3$ (2.95 g, 29.2 mmol) in conc. H$_2$SO$_4$ (10 mL). The mixture was stirred for 5 min, then carefully diluted with H$_2$O and neutralized with conc. NH$_4$OH (100 mL). The precipitate was filtered, washed with HO and acetone and dried in vacuo to yield 6.60 g (crude yield>100%) of nitrated compounds. The crude mixture was used directly without further purification. MS (ESI) m/z: 223.0 (M+H$^+$).

To a suspension of the mixture from the previous reaction (6.60 g, 29.7 mmol) in MeOH (50 mL) was added dropwise conc. H$_2$SO$_4$ (5.0 mL, 9.2 g, 3.16 mmol). The mixture was heated at 60° C. for 5 h, neutralized and basified with 2N NaOH and extracted with EtOAc (3×100 mL). The combined organic layers were dried (MgSO$_4$), filtered and evaporated to yield 2.85 g (43%, 2 steps) of a mixtureas a yellow solid. MS (ESI) m/z: 237.0 (M+H$^+$).

To a stirring solution of the mixture from the previous reaction (2.80 g, 1.9 mmol) in CH$_2$Cl$_2$ was added Boc anhydride (3.10 g, 14.2 mmol) and the resulting mixture was stirred for 3 h. The mixture was concentrated and the residue was purified by column chromatography to yield 1.15 g (29%) of (S)-2-t-butyl-3-methyl-3,4-dihydro-7-nitroisoquinoline-2,3(1H)-dicarboxylate. MS (ESI) m/z: 359.2 (M+Na$^+$).

To a suspension of (S)-2-t-butyl-3-methyl-3,4-dihydro-7-nitroisoquinoline-2,3(1H)-dicarboxylate (1.15 g, 3.42 mmol) in MeOH (15 mL) was added 10% Pd/C (0.073 g, 0.068 mmol) and the mixture was stirred under H$_2$ (1 atm). After 18 h, the mixture was filtered through a pad of Celite®, acidified with conc. HCl (0.060 mL, 0.072 mmol) and concentrated to yield 970 mg (83%) of (S)-2-t-butyl-3-methyl-7-amino-3,4-dihydroisoquinoline-2,3(1H)-dicarboxylate as the hydrochloride salt. MS (ESI) m/z: 329.2 (M+Na$^+$).

To a solution of (S)-2-t-butyl-3-methyl-7-amino-3,4-dihydroisoquinoline-2,3-(1H)-dicarboxylate (0.960 g, 2.80 mmol) in 2M HCl (10 mL) was at −10° C. added solid NaNO$_2$ (0.190 g, 2.80 mmol) and the resulting solution was stirred for 45 min at a temperature below 0° C. Solid SnCl$_2$.2H$_2$O (1.26 g, 5.60 mmol) was added and the mixture was allowed to warm to RT and stirred for 2 h. Ethanol (80 mL) and pivaloylacetonitrile (0.350 g, 2.80 mmol) were added and the resulting solution was heated at reflux overnight. Ethanol was removed under reduced pressureand H$_2$O (100 mL) was added to the residue. The mixture was extracted with CH$_2$Cl$_2$ (3×100 ml), dried (MgSO$_4$), and concentrated. The residue was dissolved in MeOH (200 mL) and conc. H2SO$_4$ (15 mL) was added and the mixture was heated at reflux for 4 h. After cooling, the mixture was neutralized with 3N NaOH (approx.

150 mL) and MeOH was removed under reduced pressure. The mixture was extracted with CH$_2$Cl$_2$ (3×100 mL), dried (MgSO$_4$), and concentrated. The residue was dried in vacuo overnight and resuspended in CH$_2$Cl$_2$ (30 mL). A solution of Boc anhydride (0.611 g, 2.80 mmol) in CH$_2$Cl$_2$ (5 mL) was added dropwise at 0° C. and the resulting mixture was allowed to reach RT and stirred for 3 h. Water (100 mL) was added and the mixture was extracted with EtOAc (3×100 mL), dried (MgSO$_4$), concentrated and purified by column chromatography to yield 118 mg (10%) of (3S)-2-t-butyl 3-methyl-7-(3-t-butyl-5-amino-1H-pyrazol-1-yl)-3,4-dihydroisoquinoline-2,3(1H)-dicarboxylate as a yellow foam. MS (ESI) m/z: 429.2 (M+H$^+$).

Example 177

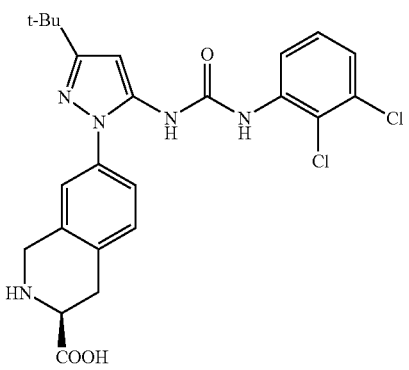

Using general method A, Example A55 (0.215 g, 0.501 mmol) and 2,3-dichlorophenyl isocyanate (0.104 g, 0.552 mmol) were combined, and the product deprotected using general methods F and E to yield (3S)-7-(3-t-butyl-5-(3-(2,3-dichlorophenyl)ureido)-1H-pyrazol-1-yl)-1,2,3,4-tetrahydroisoquinoline-3-carboxylic acid (128 mg, 60% yield) as a colorless solid. $^1$H-NMR (400 MHz, acetone-d$_6$): δ 8.60 (brs, 1H), 8.27 (d, J=8.4 Hz, 1H), 8.19 (brS, 1H), 7.40 (d, J=8.0 Hz, 1H), 7.38-7.34 (m, 2H), 7.31 (d, J=8.0 Hz, 1H), 7.24 (d, J=8.0 Hz, 1H), 6.49 (s, 1H), 4.12 (d, J=14.4 Hz, 1H), 3.89 (d, J=14.8 Hz, 1H), 3.63 (d, J=10.4 Hz, 1H), 3.17 (d, J=15.6 Hz, 1H), 2.90 (dd, J=16.0, and 10.8 Hz, 1H), 1.32 (s, 9H); MS (ESI) m/z: 502.0 (M+H$^+$).

Example 178

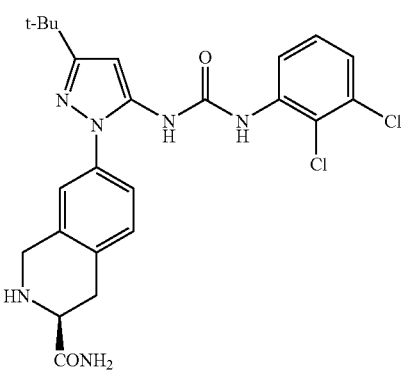

A solution of (3S)-2-t-butyl 3-methyl 7-(3-t-butyl-5-(3-(2,3-dichlorophenyl)ureido)-1H-pyrazol-1-yl)-3,4-dihydroisoquinoline-2,3 (1H)-dicarboxylate (from Example 177, 0.100 g, 0.163 mmol) in 7N NH$_3$/MeOH (3 mL) was stirred at RT overnight. The solvent was removed under reduced pressure- and the residue was dissolved in CH$_2$Cl$_2$ (2 mL). Boc anhydride (0.036 g, 0.163 mmol) was added and the solution was stirred at room temperature for 30 min. The solvent was evaporated and the residue was purified by column chromatography to yield (3S)-t-butyl 7-(3-t-butyl-5-(3-(2,3-dichlorophenyl)ureido)-1 H-pyrazol-1-yl)-3-carbamoyl-3,4-dihydroisoquinoline-2(1H)-carboxylate (85 mg, 87% yield) as a white solid. $^1$H-NMR (400 MHz, acetone-d$_6$): δ 8.66 (brs, 1H), 8.27 (dd, J=8.4, and 2.0 Hz, 1H), 8.21 (brs, 1H), 7.42-7.37 (m, 2H), 7.35-7.29 (m, 2H), 7.24 (dd, J=8.0, and 1.6 Hz, 1H), 6.88 (brs, 1H), 6.49 (s, 1H), 6.33 (brs, 1H), 4.97-4.45 (m, 3H), 3.36-3.09 (m, 2H), 1.47-1.45 (m, 9H), 1.32 (s, 9H); MS (ESI) m/z: 601.2 (M+H$^+$). (3S)-t-butyl 7-(3-t-butyl-5-(3-(2,3-dichlorophenyl)ureido)-1H-pyrazol-1-yl)-3-carbamoyl-3,4-dihydroisoquinoline-2(1H)-carboxylate (0.085 g, 0.14 mmol) was dissolved in 4N HCl in dioxane (5 mL) and the solution was stirred at RT for 30 min. The solvent was removed under reduced pressureand the residue was dissolved in H$_2$O/MeCN (1:1) and lyophilized to yield 1-(3-t-butyl-1-((3S)-3-carbamoyl-1,2,3,4-tetrahydroisoquinolin-7-yl)-1 H-pyrazol-5-yl)-3-(2,3-dichlorophenyl)urea (65 mg, 85% yield) as a white solid. $^1$H-NMR (CD$_3$OD) shows rotameric mixture. MS (ESI) m/z: 501.2 (M+H$^+$).

Example A56

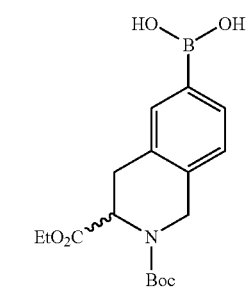

To a suspension of DL-m-tyrosine (5.00 g, 11.0 mmol) in 0.05 N HCl (50 mL) was added 37% aq. formaldehyde (5.00 mL, 5.2 g, 64.0 mmol) and the resulting slurry was heated at 90° C. for 1 h and then cooled to RT. The mixture was filtered and the resulting solid was washed with H$_2$O and acetone and dried in vacuo to yield 6-hydroxy-1,2,3,4-tetrahydroisoquinoline-3-carboxylic acid (3.31 g, 52% yield) as an off-white solid. MS (EI) m/z: 194.0 (M+H$^+$). $^1$H NMR (400 MHz, CD$_3$OD): δ 7.03 (d, J=8.0 Hz, 1H), 6.69 (dd, J=8.8, and 2.4 Hz, 1H), 7.00 (s, 1H), 4.28-4.19 (m, 2H), 3.80 (dd, J=11.6, and 5.2 Hz, 1H), 3.31-3.27 (m, 1H), 3.05 (dd, J=16.8, and 11.2 Hz, 1H), acid, hydroxy and amine protons not visible.

Acetyl chloride (30 mL, 33 g, 422 mmol) was added carefully to ice-cold anhydrous EtOH and the resulting solution was stirred at RT for 10 min. 6-Hydroxy-1,2,3,4-tetrahydroisoquinoline-3-carboxylic acid (3.30 g, 14 mmol) was added and the mixture was stirred at 50° C. for 5 h. The solvent was evaporated and the residue was dried under vacuum to yield ethyl 6-hydroxy-1,2,3,4-tetrahydroisoquinoline-3-carboxylate (4.35 g, crude yield>100%) as a yellow solid. MS expected 222.1 found 222.0. $^1$H NMR (400 MHz, CD$_3$OD): δ 7.06 (d, J=8.4 Hz, 1H), 6.74 (dd, J=8.0, and 2.4 Hz, 1H), 6.69 (d, J=2.4 Hz, 1H), 4.44-4.29 (m, 5H), 3.35 (dd, J=17.2, and 5.2 Hz, 1H), 3.15 (dd, J=17.2, and 11.6 Hz, 1H), 1.35 (t, J=7.2 Hz, 3H).

To a solution of the material from the previous reaction (3.70 g, 14.4 mmol) and Et$_3$N (6.00 mL, 4.36 g, 43.1 mmol) in CH$_2$Cl$_2$ (100 mL) was added Boc anhydride (3.76 g, 17.2 mmol) at RT and the resulting mixture was stirred for 1 h.

Water (100 mL) was added and the mixture was extracted with CH$_2$Cl$_2$ (3×100 mL), dried (MgSO$_4$), and concentrated under vacuum to yield 2-t-butyl 3-ethyl 6-hydroxy-3,4-dihydroisoquinoline-2,3(1H)-dicarboxylate (5.80 g, crude yield>100%) as a light brown foam. MS (EI) m/z: 344.3 (M+Na$^+$). $^1$H NMR (400 Mhz, CDCl$_3$) shows rotameric mixture.

To a solution of material from the previous reaction (4.61 g, 14.3 mmol) in CH$_2$Cl$_2$ (100 mL) at RT was added Et$_3$N (3.00 mL, 2.18 g, 21.5 mmol) and triflic chloride (2.29 mL, 3.63 g, 21.5 mmol) and the resulting solution was stirred at RT for 1 h. Water (100 mL) was added and the mixture was extracted with CH$_2$Cl$_2$ (3×100 mL), dried (MgSO$_4$), concentrated and purified by column chromatography to yield 2-t-butyl 3-ethyl 6-(trifluoromethylsulfonyloxy)-3,4-dihydroisoquinoline-2,3(1H)-dicarboxylate (6.30 g, 97% yield, 3 steps) as a white wax-like solid. MS (EI) m/z: 476.0 (M+Na$^+$). $^1$H NMR (400 MHz, CDCl$_3$) shows rotameric mixture.

To a degassed solution of the material from the previous reaction (3.270 g, 7.21 mmol), bis(pinacolato)diboron (2.75 g, 0.662 mmol), and KOAc (2.12 g, 21.6 mmol) in DMF (10 mL) was added PdCl$_2$(dppf)$_2$ (0.2945 g, 0.361 mmol) and the resulting mixture was stirred at 80° C. overnight. Water (100 mL) was added and the mixture was extracted with EtOAc (3×100 mL), dried (MgSO$_4$), concentrated and purified by column chromatography to yield 2-t-butyl 3-ethyl 6-(4,4,5,5-tetramethyl-1,3,2-dioxaborolan-2-yl)-3,4-dihydroisoquinoline-2,3(1H)-dicarboxylate (2.77 g, 89%) as a colorless oil. MS (EI) m/z: 454.2 (M+Na$^+$).

To a solution of the material from the previous reaction (0.105 g, 0.243 mmol) in THF/H2O (4:1) (2 mL) was added NaIO$_4$ (0.160 g, 0.730 mmol) and the thick mixture was stirred for 30 min. Hydrochloric acid (2N, 0.24 mL, 0.48 mmol) was added and the resulting solution was stirred at RT overnight. Water (30 mL) was added and the mixture was extracted with EtOAc (3×100 mL), dried (MgSO$_4$), concentrated and dried under vacuum to yield 2-(t-butoxycarbonyl)-3-(ethoxycarbonyl)-1,2,3,4-tetrahydroisoquinolin-6-ylboronic acid (66 mg, 78%) of the crude boronic acid as an orange-yellow solid. MS (EI) m/z: 372.3 (M+Na$^+$). This material was used without further purification.

Example 179

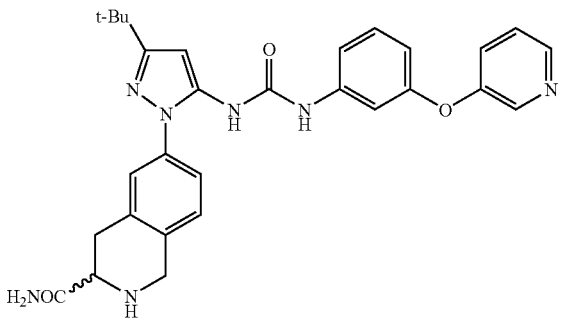

To a solution of Example A32 (0.025 g, 0.071 mmol), Example A56 (0.064 g, 0.180 mmol) and pyridine (0.011 g, 0.14 mmol) in CH$_2$Cl$_2$ (2 mL) was added Cu(OAc)$_2$ (0.019 g, 0.11 mmol) and the resulting green solution was stirred at RT open to air for 72 h, replacing evaporated solvent as needed. Water (20 mL) was added and the mixture was extracted with CH$_2$Cl$_2$ (3×20 mL), dried (MgSO$_4$), concentrated and purified by column chromatography to yield 2-t-butyl 3-ethyl 6-(3-t-butyl-5-(3-(3-(pyridin-3-yloxy)phenyl)ureido)-1H-pyrazol-1-yl)-3,4-dihydroisoquinoline-2,3(1H)-dicarboxylate (13 mg, 28% yield) as a yellow oil. MS (EI) m/z: 655.2 (M+H$^+$).

A solution of the material from the previous reaction (0.013 g, 0.020 mmol) in 2N HCl in EtOH (5 mL) was stirred overnight. The solvent was evaporated and the residue was dissolved in 7N NH$_3$/MeOH and the solution was stirred in a sealed vessel at 60° C. overnight. The solvent was evaporated and the residue was purified by reverse phase chromatography. Basic reextraction and acidification with HCl yielded 1-(3-t-butyl-1-(3-carbamoyl-1,2,3,4-tetrahydroisoquinolin-6-yl)-1H-pyrazol-5-yl)-3-(3-(pyridin-3-yloxy)phenyl)urea (7 mg, 59% yield) as an off-white solid. $^1$H NMR (400 MHz, CD$_3$OD): δ 8.66 (d, J=2.8 Hz, 1H), 8.59 (d, J=5.6 Hz, 1H), 8.21 (ddd, J=8.8, 2.4, and 1.2 Hz, 1H), 8.04 (dd, J=8.4, and 5.4 Hz, 1H), 7.58 (t, J=2.2 Hz, 1H), 7.52 (s, 1H), 7.50 (d, J=1.6 Hz, 1H), 7.45 (d, J=10.0 Hz, 1H), 7.41 (d, J=7.6 Hz, 1H), 7.19 (ddd, J=8.0, 1.8, and 0.8 Hz, 1H), 6.89 (ddd, J=8.0, 2.4, and 1.2 Hz, 1H), 6.50 (s, 1H), 4.54 (d, J=16.0 Hz, 1H), 4.49 (d, J=16.0 Hz, 1H), 4.29 (dd, J=12.0, and 5.0 Hz, 1H), 3.54 (dd, J=−17.2, and 4.8 Hz, 1H), 1.36 (s, 9H), one proton is buried under the MeOH peak; MS (EI) m/z: 526.2 (M+H$^+$).

Example 180

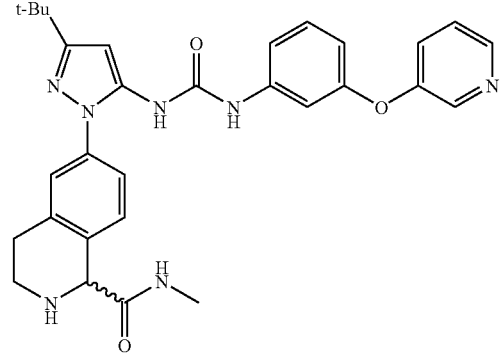

Using the same procedureas for Example 179, 2-t-butyl 3-ethyl 6-(3-t-butyl-5-(3-(3-(pyridin-3-yloxy)phenyl)ureido)-1H-pyrazol-1-yl)-3,4-dihydroisoquinoline-2,3(1H)-dicarboxylate (0.053 g, 0.081 mmol), available from Example 188) in 3N hydrochloric acid in MeOH (10.0 mL) was stirred at RT for 1 h. The solvent was evaporated and the residue was dissolved in 8N MeNH$_2$/MeOH (3 mL) and the solution was stirred in a sealed vessel at 50° C. overnight. The solvent was evaporated and the residue was purified by reverse phase chromatography and coevaporated with THF/4N HCl to yield 1-(3-t-butyl-1-(1-(methylcarbamoyl)-1,2,3,4-tetrahydroisoquinolin-6-yl)-1H-pyrazol-5-yl)-3-(3-(pyridin-3-yloxy)phenyl)urea (43 mg, 87% yield) as a yellow solid. $^1$H-NMR (MeOH-d$_4$): δ 8.66 (d, 1H, J=2.4 Hz), 8.59 (d, 1H, J=5.6 Hz), 8.22 (ddd, 1H, J=9.2, 2.4, 1.2 Hz), 8.05 (dd, 1H, J=8.0, 6.0 Hz), 7.60-7.54 (m, 4H), 7.42 (t, 1H, J=8.0 Hz), 7.20 (dd, 1H, J=7.6, 1.2 Hz), 6.90 (dd, 1H, J=8.4, 2.0 Hz), 6.53 (s, 1H), 5.23 (s, 1H), 3.80-3.74 (m, 1H), 3.56-3.49 (m, 1H), 3.26-3.14 (m, 2H), 2.88 (s, 3H). 1.36 (s, 9H). MS expected 540.3 found 540.3

Example 181

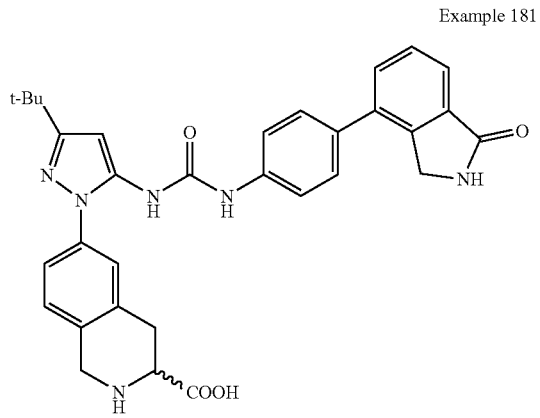

Example 182

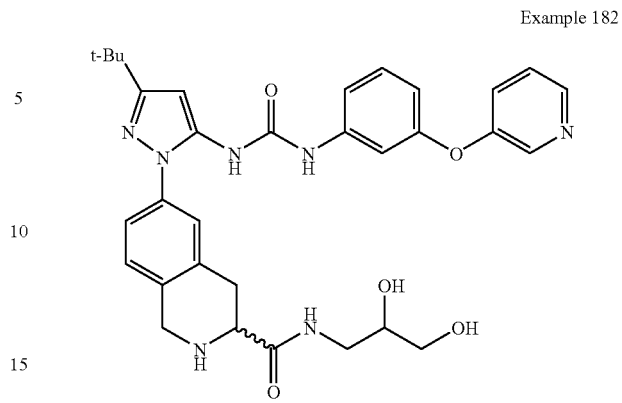

To a solution of 4-(4-aminophenyl)isoindolin-1-one (0.327 g, 1.46 mmol, made according to literature procedures) in EtOAc (5 mL) was added NaOH (2N, 2 mL, 4 mmol) and Troc-Cl (0.618 g, 2.92 mmol) and the resulting mixture was stirred at RT for 6 h. Water (20 mL) was added and the mixture was extracted with EtOAc (3×20 mL), dried (MgSO$_4$) and concentrated. The residue was dissolved in DMF (2 mL) to which was added 5-amino-3-t-butylpyrazole (0.831 g, 5.97 mmol, made according to literature procedures) and i-Pr$_2$NEt (0.406 g, 2.92 mmol) and the solution was stirred at 90° C. overnight. Water (100 mL) was added and the mixture was extracted with EtOAc (3×100 mL), dried (MgSO$_4$) and concentrated. Addition of CH$_2$Cl$_2$ to the residue resulted in precipitation of the product. The product was collected and dried to yield 1-(3-t-butyl-1H-pyrazol-5-yl)-3-(4-(1-oxoisoindolin-4-yl)phenyl)urea (270 mg, 48% yield) as a light brown powder. $^1$H-NMR (DMSO-d$_6$): δ 9.31 (s, br, 1H), 8.95 (s, br, 1H), 8.65 (s, br, 1H), 7.65-7.63 (m, 2H), 7.58-7.52 (m, 5H), 6.00 (s, br, 1H), 4.51 (s, 2H), 1.25 (s, 9H), one NH is not visible. MS expected 390.2 found 390.2.

To a solution of the material from the previous reaction (0.200 g, 0.514 mmol) and Example A54 (0.179 g, 0.514 mmol) in DMF (2 mL) was added pyridine (0.122 g, 1.54 mmol) and Cu(OAc)$_2$ (0.140 g, 0.770 mmol) and the resulting solution was stirred under a balloon of air at RT for 96 h. Water (20 mL) was added and the mixture was extracted with EtOAc (3×20 mL), dried (MgSO$_4$), concentrated and purified by column chromatography to yield 2-t-butyl 3-ethyl 6-(3-t-butyl-5-(3-(4-(1-oxoisoindolin-4-yl)phenyl)ureido)-1H-pyrazol-1-yl)-3,4-dihydroisoquinoline-2,3(1H)-dicarboxylate (50 mg, 14%) as a yellow powder. MS expected 693.3 found 693.2.

A solution of the material from the previous reaction (0.025 g, 0.036 mmol) in 3N HCl/MeOH was stirred at RT for 1 h. The solvent was evaporated and the residue was dried in vacuo. The residue was dissolved in THF (3 mL) and 2N NaOH (2 mL) was added. MeOH was added until the mixture became homogenous. After 1 h, the mixture was acidified with conc. HCl, concentrated and purified by reverse phase chromatography to yield 6-(3-t-butyl-5-(3-(4-(1-oxoisoindolin-4-yl)phenyl)ureido)-1H-pyrazol-1-yl)-1,2,3,4-tetrahydroisoquinoline-3-carboxylic acid (16 mg, 74%) as a white solid. $^1$H-NMR (MeOH-d$_4$): δ 7.79 (d, 1H, J=7.2 Hz), 7.66-7.48 (m, 9H), 6.63 (s, 1H), 4.62-4.47 (m, 5H), 3.61 (dd, 1H, J=17.6, 4.8 Hz), 3.38-3.31 (m, 1H), 1.40 (s, 9H). MS expected 565.3 found 565.3.

Using the same method as for Example 184, a solution of methyl 6-(3-t-butyl-5-(3-(3-(pyridin-3-yloxy)phenyl)ureido)-1H-pyrazol-1-yl)-1,2,3,4-tetrahydroisoquinoline-3-carboxylate (0.017 g, 0.026 mmol, available in Example 179) in 3N HCl in MeOH (2 mL) was stirred at RT overnight. The solvent was evaporated and the residue was dissolved in MeOH (0.5 mL). 3-Amino-1,2-dihydroxypropane (0.200 g, 2.20 mmol) was added and the solution was kept at RT overnight. The mixture was directly loaded on to a reverse phase column and purified to yield 1-(1-(3-((2,3-dihydroxypropyl)carbamoyl)-1,2,3,4-tetrahydroisoquinolin-6-yl)-3-t-butyl-1H-pyrazol-5-yl)-3-(3-(pyridin-3-yloxy)phenyl)urea (16 mg, 97% yield) as a yellow solid. $^1$H-NMR (MeOH-d$_4$): δ 8.66 (s, 1H), 8.60 (d, 1H, J=–5.6 Hz), 8.23-8.20 (m, 1H), 8.05 (dd, 1H, J=8.8, 5.6 Hz), 7.57 (t, 1H, J=2.0 Hz), 7.52-7.40 (m, 4H), 7.23 (d, 1H, J=8.4 Hz), 6.89 (dd, 1H, J=7.6, 1.6 Hz), 6.54 (s, 1H), 4.56 (d, 1H, J=16.8 Hz), 4.51 (d, 1H, J=16.8 Hz), 4.29 (dd, 1H, J=12.0, 4.4 Hz), 3.78-3.72 (m, 1H), 3.54-3.45 (m, 5H), 1.36 (s, 9H), one proton is buried under the MeOH peak, urea, amide, amine and hydroxy protons not visible. MS expected 600.3 found 600.2

Example 183

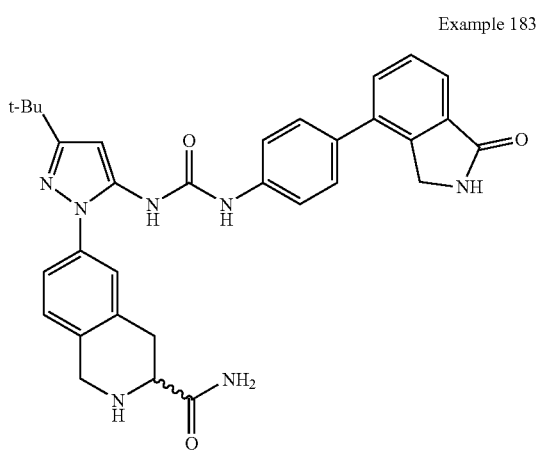

A solution of Example 181 (0.025 g, 0.036 mmol) was dissolved in 7N ammonia in MeOH (3 mL) and the solution was kept at RT overnight, then purified via reverse phase column chromatography to yield 1-(3-t-butyl-1-(3-carbamoyl-1,2,3,4-tetrahydroisoquinolin-6-yl)-1H-pyrazol-5-yl)-3-(4-(1-oxoisoindolin-4-yl)phenyl)urea (8 mg, 37%) as a white solid. $^1$H-NMR (MeOH-d$_4$): δ 7.78 (dd, 1H, J=7.4, 1.4 Hz), 7.65 (dd, 1H, J=8.0, 1.0 Hz), 7.61 (d, 1H, J=7.6 Hz), 7.58-7.45

(m, 7H), 6.51 (s, 1H), 4.55 (s, 2H), 4.54 (d, 2H, J=16.0 Hz), 4.49 (d, 2H, J=16.0 Hz), 4.28 (dd, 1H, J=11.6, 5.2 Hz), 3.53 (dd, 1H, J=17.2, 5.2 Hz), 1.38 (s, 9H), one proton is buried under the MeOH peak, urea, amine and amide protons not visible. MS expected 564.3 found 564.3

Example 184

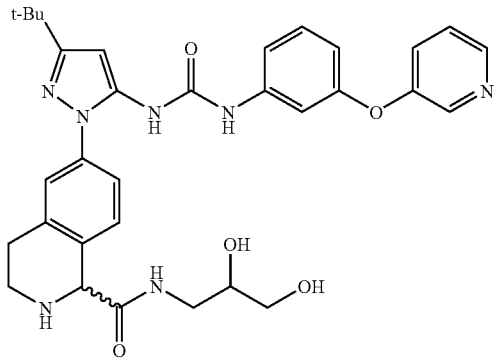

Using the same procedureas for Example 179, 2-t-butyl 3-ethyl 6-(3-t-butyl-5-(3-(3-(pyridin-3-yloxy)phenyl)ureido)-1H-pyrazol-1-yl)-3,4-dihydroisoquinoline-2,3(1H)-dicarboxylate (0.029 g, 0.044 mmol), available from experimental 184) in 3N hydrochloric acid in MeOH (10.0 mL) was stirred at RT for 1 h. The solvent was evaporated and the residue was dissolved in 3-amino-1,2-dihydroxypropane (0.200 g, 2.2 mmol) in MeOH (0.5 mL) and the solution was stirred at RT for 2 d. The solvent was evaporated and the residue was purified by reverse phase chromatography and coevaporated with THF/4N HCl to yield 1-(1-(1-((2,3-dihydroxypropyl)carbamoyl)-1,2,3,4-tetrahydroisoquinolin-6-yl)-3-t-butyl-1H-pyrazol-5-yl)-3-(3-(pyridin-3-yloxy)phenyl)urea (24 mg, 81% yield) as a pale yellow solid. $^1$H-NMR (MeOH-d$_4$): δ 8.68 (d, 1H, J=3.2 Hz), 8.60 (d, 1H, J=7.6 Hz), 8.23 (ddd, 1H, J=8.8, 2.6, 1.0 Hz), 8.06 (dd, 1H, J=8.4, 1.4 Hz), 7.70 (dd, 1H, J=−9.0, 1.8 Hz), 7.58-7.54 (m, 3H), 7.42 (t, 1H, J=8.0 Hz), 7.22 (dt, 1H, J=8.4, 1.0 Hz), 6.90 (dd, 1H, J=6.8, 1.6 Hz), 6.58 (d, 1H, J=1.2 Hz), 5.29 (s, 1H), 3.84-3.63 (m, 2H), 3.63-3.51 (m, 5H), 3.30-2.87 (m, 2H), 1.37 (s, 9H), urea, amine, hydroxy and amide protons not visible. MS expected 600.3 found 600.2.

Example 185

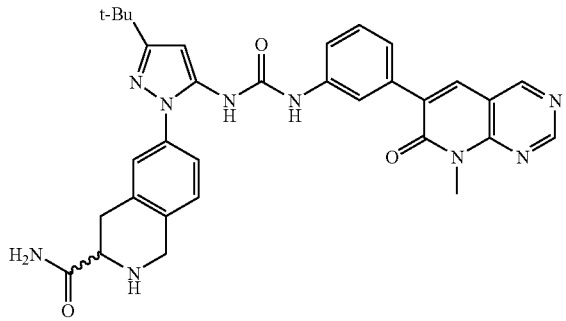

To a solution of benzyl 3-t-butyl-1H-pyrazole-5-carboxylate (0.100 g, 0.387 mmol, synthesized by trans-esterification of commercially available ethyl 3-t-butyl-1H-pyrazole-5-carboxylate), 2-(t-butoxycarbonyl)-3-(methoxycarbonyl)-1,2,3,4-tetrahydroisoquinolin-6-ylboronic acid (0.195 g, 0.581 mmol, made analogously to Example A56) and pyridine (0.092 g, 1.16 mmol) in methylene chloride (4 mL) was added copper(II)-acetate (0.105 g, 0.581 mmol) and the resulting mixture was stirred at Rt for 1d. The mixture was directly loaded on a silica gel column, chromatographed and concentrated to yield 2-t-butyl 3-methyl 6-(5-(benzyloxycarbonyl)-3-t-butyl-1H-pyrazol-1-yl)-3,4-dihydroisoquinoline-2,3 (1H)-dicarboxylate (171 mg, 81% yield) as a colorless foam. MS expected 548.3 found 548.3. To this material (0.136 g, 0.248 mmol) in EtOAc (5 mL) was added palladium on charcoal (10%, 0.013 g, 0.012 mmol) and the mixture was stirred under an atmosphere of H$_2$ overnight. The mixture was filtered and the filtrate was concentrated to yield 1-(2-(t-butoxycarbonyl)-3-(methoxycarbonyl)-1,2,3,4-tetrahydroisoquinolin-6-yl)-3-t-butyl-1H-pyrazole-5-carboxylic acid (114 mg, 100%) as a colorless foam. MS expected 458.2 found 458.3.

To a solution of the material from the previous reaction (0.070 g, 0.153 mmol) and Example A11 (0.062 g, 0.245 mmol) in toluene (2 mL) was added triethylamine (0.031 g, 0.306 mmol) and diphenylphosphonic azide (0.063 g, 0.229 mmol) and the resulting solution was stirred at 100° C. for 1 h. The mixture was directly loaded on a column and purified via column chromatography to yield 2-t-butyl 3-methyl 6-(3-t-butyl-5-(3-(3-(8-methyl-7-oxo-7,8-dihydropyrido[2,3-d]pyrimidin-6-yl)phenyl)ureido)-1H-pyrazol-1-yl)-3,4-dihydroisoquinoline-2,3(1H)-dicarboxylate (89 mg, 82%) as a yellow oil. MS expected 707.3 found 707.2

A solution of material from the previous reaction (0.088 g, 0.120 mmol) in 3N HCl in MeOH was stirred at RT for 1 h. The solvent was evaporated and the residue was dried in vacuo. The residue was dissolved in 7N ammonia in MeOH and the mixture was kept at RT overnight. The mixture purified via reverse phase column chromatography to yield 1-(3-t-butyl-1-(3-carbamoyl-1,2,3,4-tetrahydroisoquinolin-6-yl)-1H-pyrazol-5-yl)-3-(3-(8-methyl-7-oxo-7,8-dihydropyrido[2,3-d]pyrimidin-6-yl)phenyl)urea dihydrochloride (63 mg, 76%) as a yellow crystalline solid. $^1$H-NMR (MeOH-d$_4$): δ 9.27 (s, br, 2H), 8.17 (s, 1H), 7.89 (s, 1H), 7.60-7.49 (m, 4H), 7.42-7.38 (m, 2H), 6.71 (s, 1H), 4.58 (d, 1H, J=16.4 Hz), 4.53 (d, 1H, J=16.4 Hz), 4.33 (dd, 1H, J=11.6, 4.4 Hz), 3.89 (s, 3H), 3.57 (dd, 1H, J=17.6, 5.2 Hz), 1.40 (s, 9H), one proton is buried under the MeOH peak, urea, amide and amine protons not visible. MS expected 592.3 found 592.3.

Example 186

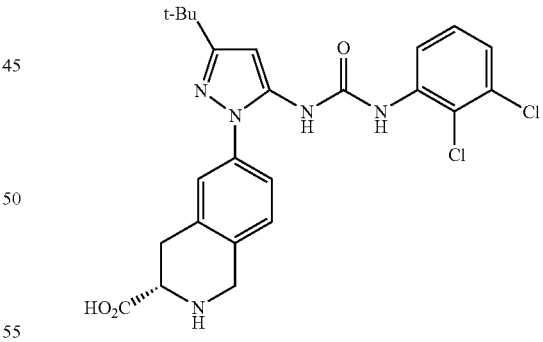

Using general method G, followed by general method E, (3S)-methyl 6-(3-t-butyl-5-(3-(2,3-dichlorophenyl)ureido)-1H-pyrazol-1-yl)-2-(2,2,2-trifluoroacetyl)-1,2,3,4-tetrahydro-isoquinoline-3-carboxylate from Example A42 (0.080 g, 0.13 mmol) was deprotected and lyophilized to yield (3S)-6-(3-t-butyl-5-(3-(2,3-dichlorophenyl)ureido)-1H-pyrazol-1-yl)-1,2,3,4-tetrahydroisoquinoline-3-carboxylic acid (42 mg, 60% yield) as an off-white solid. $^1$H NMR (400 MHz, CD$_3$OD): δ 7.98 (t, J=4.8 Hz, 1H), 7.49 (s, 1H), 7.48 (d, J=7.6 Hz, 1H), 7.42 (d, J=8.4 Hz, 1H), 7.24 (d, J=4.8 Hz, 1H), 7.24 (d, J=4.8 Hz, 1H), 6.42 (s, 1H), 4.55 (d, J=16.4 Hz, 1H), 4.48

(d. J=16.4 Hz, 1H), 4.41 (dd, J=10.8, and 4.8 Hz, 1H), 3.56 (dd, J=17.6, and 4.4 Hz, 1H), 1.35 (s, 9H), one aliphatic proton is buried under the MeOH peak; MS (EI) m/z: 504.0 (M+H+).

Example 187

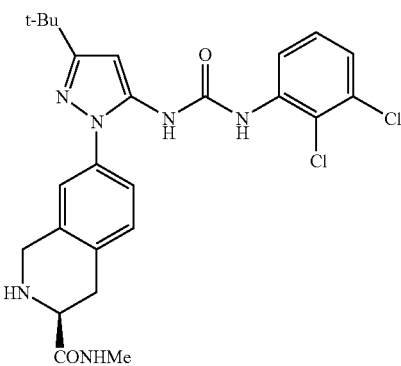

A solution of (3S)-methyl 7-(3-t-butyl-5-(3-(2,3-dichlorophenyl)ureido)-1H-pyrazol-1-yl)-2-(2,2,2-trifluoroacetyl)-1,2,3,4-tetrahydroiso-quinoline-3-carboxylate from Example A42 (0.153 g, 0.250 mmol), methylamine hydrochloride (1.000 g, 14.8 mmol) and triethylamine (2.05 mL, 1.49 g, 14.7 mmol) in MeOH (5 mL) was stirred at 60° C. for 24 h. H2O was added (50 mL) and the mixture was extracted with CH$_2$Cl$_2$ (3×50 mL), dried (MgSO$_4$) and concentrated. The residue was redissolved in CH$_2$Cl$_2$ (5 mL). Boc anhydride (0.055 g, 0.250 mmol) was added and the solution was stirred at RT for 30 min. The solvent was evaporated and the residue was purified by column chromatography to yield (3S)-t-butyl 7-(3-t-butyl-5-(3-(2,3-dichlorophenyl)ureido)-1H-pyrazol-1-yl)-3-(methyl-carbamoyl)-3,4-dihydroisoquinoline-2(1H)-carboxylate (52 mg, 34% yield) as a white solid. $^1$H NMR (400 MHz, acetone-d$_6$) shows rotameric mixture. MS (EI) m/z: 615.2 (M+H+).

Using general method F, the material from the previous reaction (0.050 g, 0.14 mmol) was deprotected and lyophilized to yield 1-(3-t-butyl-1-((3S)-3-(methylcarbamoyl)-1,2,3,4-tetrahydroisoquinolin-7-yl)-1H-pyrazol-5-yl)-3 (2,3-dichlorophenyl)urea (42 mg, 94% yield) as a white solid. $^1$H NMR (400 MHz, CD$_3$OD) shows rotameric mixture. MS (EI) m/z: 515.0 (M+H+).

Example 188

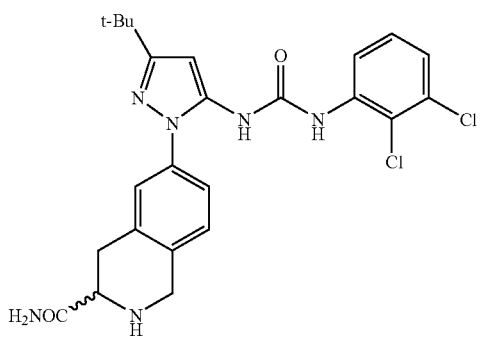

To a solution of Example A31 (0.066 g, 0.200 mmol), Example A56 (0.070 g, 0.200 mmol) and pyridine (0.032 g, 0.401 mmol) in CH$_2$Cl$_2$ (2 mL) was added copper(II)-acetate (0.055 g, 0.301 mmol) and the resulting green solution was stirred at RT open to air for 96 h, replacing evaporated solvent as needed. H2O was added (20 mL) and the mixture was extracted with CH$_2$Cl$_2$ (3×20 mL), EtOAc (3×100 mL), dried (MgSO$_4$), concentrated and purified via reverse phase column chromatography to yield 2-t-butyl 3-ethyl-6-(3-t-butyl-5-(3-(2,3-dichlorophenyl)ureido)-1H-pyrazol-1-yl)-3,4-dihydroisoquinol-ine-2,3(1H)-dicarboxylate (50 mg, 40%) as an off-white solid. MS (EI) m/z: 630.2 (M+H+).

A solution of the material from the previous reaction (0.040 g, 0.063 mmol) in 7N ammonia in MeOH (3 mL, 21 mmol) was heated at 70° C. for 8 h. The solvent was evaporated and the residue was purified by reverse phase chromatography to yield 1-(3-t-butyl-1-(3-carbamoyl-1,2,3,4-tetrahydroisoquinolin-6-yl)-1H-pyrazol-5-yl)-3-(2,3-dichlorophenyl)urea (17 mg, 50% yield) as an off-white solid. $^1$H NMR (400 Mhz, CD$_3$OD): δ 8.03 (t, J=4.8 Hz, 1H), 7.56-7.54 (m, 2H), 7.49 (d, J=8.8 Hz, 1H), 7.26-7.25 (m, 2H), 6.61 (s, 1H), 4.57 (d, J=16.8 Hz, 1H), 4.51 (d, J=16.4 Hz, 1H), 4.30 (dd, J=12.0, and 4.6 Hz, 1H), 3.54 (dd, J=17.6, and 4.8 Hz, 1H), 1.38 (s, 9H), one proton is buried under the MeOH peak, urea, amide and amine protons not visible; MS (EI) m/z: 501.2 (M+H+).

Example 189

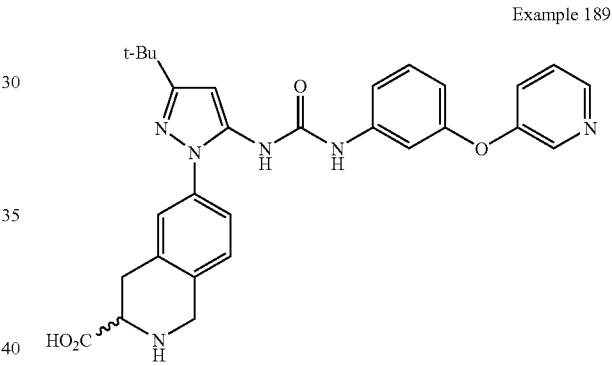

A solution of 2-t-butyl 3-ethyl 6-(3-t-butyl-5-(3-(3-(pyridin-3-yloxy)phenyl)ureido)-1H-pyrazol-1-yl)-3,4-dihydroisoquinoline-2,3(1H)-dicarboxylate (available from Example 179, 0.102 g, 0.160 mmol) in 3N HCl in MeOH (5 mL) was stirred for 1 h. The solvent was evaporated. The residue was dissolved in THF (2 mL). 2N NaOH was added (2 mL) and then MeOH until homogenous. The solution was stirred at RT for 1 h. The solvents were evaporated, the residue was purified by reverse phase chromatography followed by coevaporation with THF/HCl to yield 6-(3-t-butyl-5-(3-(3-(pyridin-3-yloxy)phenyl)ureido)-1H-pyrazol-1-yl)-1,2,3,4-tetrahydroisoquinoline-3-carboxylic acid (20 mg, 100%) as a white solid. $^1$H NMR (400 MHz, CD$_3$OD): δ 8.66 (d, J=2.8 Hz, 1H), 8.59 (d, J=5.2 Hz, 1H), 8.22 (ddd, J=9.2, 2.8, and 0.8 Hz, 1H), 8.05 (dd, J=8.8, 5.6 Hz, 1H), 7.58 (t, J=2.0 Hz, 1H), 7.54-7.46 (m, 3H), 7.42 (t, J=8.2 Hz, 1H), 7.21 (d, J=8.0 Hz, 1H), 6.89 (dd, J=8.4, and 2.4 Hz, 1H), 6.57 (s, 1H), 6.59 (d, J=16.0 Hz, 1H), 4.51 (d, J=16.0 Hz, 1H), 4.49 (dd, J=11.2, and 5.2 Hz, 1H), 3.60 (dd, J=18.0, and 4.8 Hz, 1H), 1.37 (s, 9H), acid, amine and urea protons not visible, one proton is buried under the MeOH peak; MS (EI) m/z: 527.2 (M+H+).

Example 190

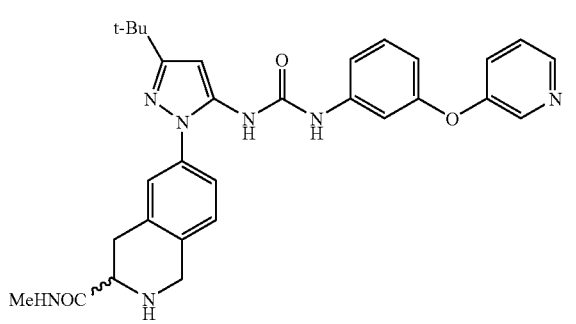

A solution of 2-t-butyl 3-ethyl 6-(3-t-butyl-5-(3-(3-(pyridin-3-yloxy)phenyl)ureido)-1H-pyrazol-1-yl)-3,4-dihydroisoquinoline-2,3(1H)-dicarboxylate (available from Example 179, 0.102 g, 0.160 mmol) in 3N HCl in MeOH (5 mL) was stirred for 1 h. The solvent was evaporated and the residue was redissolved in 8N methylamine in EtOH and stirred at RT overnight. The solvent was evaporated, the residue was purified by reverse phase chromatography and coevaporation with THF/HCl to yield 1-(3-t-butyl-1-(3-(methylcarbamoyl)-1,2,3,4-tetrahydroisoquinolin-6-yl)-1H-pyrazol-5-yl)-3-(3-(pyridin-3-yloxy)phenyl)urea (20 mg, 92% yield) as a white solid. $^1$H NMR (400 MHz, CD$_3$OD): δ 8.67 (d, J=2.8 Hz, 1H), 8.60 (d, J=-5.6 Hz, 1H), 8.23 (ddd, J=8.8, 2.8, and 1.0 Hz, 1H), 8.06 (dd, J=8.8, and 5.6 Hz, 1H), 7.58 (t, J=2.2 Hz, 1H), 7.54 (d, J=8.0 Hz, 1H), 7.50 (t, J=7.6 Hz, 2H), 7.43 (t, J=8.2 Hz, 1H), 7.26 (dd, J=8.0, and 1.6 Hz, 1H), 6.90 (ddd, J=8.4, 2.0, and 0.8 Hz, 1H), 6.64 (s, 1H), 4.56 (d, J=16.4 Hz, 1H), 4.52 (d, J=16.4 Hz, 1H), 4.28 (dd, J=11.6, and 4.8 Hz, 1H), 3.50 (dd, J=17.2, and 4.8 Hz, 1H), 2.86 (s, 3H), 1.38 (s, 9H), amide, urea and amine protons not visible, one proton is buried under the MeOH peak, methylamide protons split due to rotation barrier; MS (EI) m/z: 540.3 (M+H$^+$).

Example 191

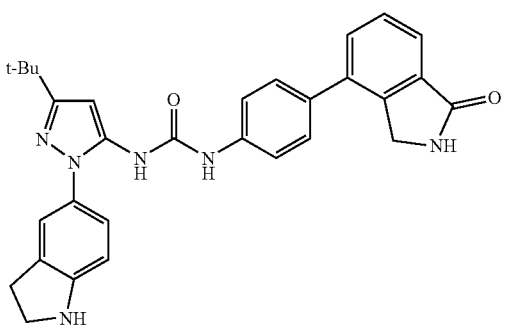

Using general method H, Example A29 (116 mg, 0.30 mmol) was transformed to prop-1-en-2-yl 3-t-butyl-1-(1-(2,2,2-trifluoroacetyl)indolin-5-yl)-1H-pyrazol-5-ylcarbamate (119 mg, 91% yield). MS (ESI) m/z: 437.3 (M+H$^+$). Using the same procedureas for Example 151, this material (117 mg, 0.27 mmol) and 4-(4-aminophenyl)isoindolin-1-one (61 mg, 0.27 mmol) were combined to yield 1-(3-t-butyl-1-(1-(2,2,2-trifluoroacetyl)indolin-5-yl)-1H-pyrazol-5-yl)-3-(4-(1-oxoisoindolin-4-yl)phenyl)urea (152 mg, 94% yield). MS (ESI) m/z: 603.3 (M+H$^+$). To this material (149 mg, 0.25 mmol) was added NH$_3$/MeOH (7.0 M, 3.0 mL, 21 mmol) and the resultant mixture was stirred at RT overnight. Ether (9 mL) was added, the reaction was filtered and the precipitate was washed with 3:1 Et$_2$O-MeOH (10 mL) and Et$_2$O (10 mL). The tan-colored solid was dried in vacuo to provide 1-(3-t-butyl-1-(indolin-5-yl)-1H-pyrazol-5-yl)-3-(4-(1-oxoisoindolin-4-yl)phenyl)urea (100 mg, 79% yield). $^1$H NMR (400 MHz, DMSO-d$_6$): δ 9.21 (s, 1H), 8.57 (s, 1H), 8.26 (s, 1H), 7.66-7.62 (m, 2H), 7.56 (m, 1H), 7.54-7.50 (m, 4H), 7.08 (brs, 1H), 6.97 (dd, J=8.2, and 2.1 Hz, 1H), 6.58 (d, J=8.2 Hz, 1H), 6.32 (s, 1H), 5.81 (s, 1H), 4.51 (s, 2H), 3.50 (td, J=8.5, and 1.5 Hz, 2H), 2.99 (t, J=8.5 Hz, 2H), 1.26 (s, 9H); MS (ESI) m/z: 507.2 (M+H$^+$).

Example 192

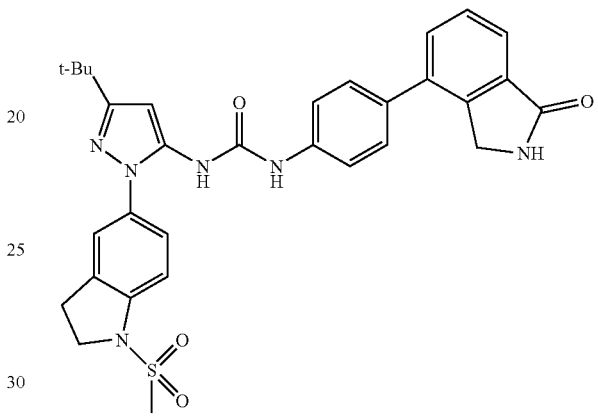

Using the same procedureas for Example 108, Example 191 (55 mg, 0.11 mmol) was transformed to yield 1-(3-t-butyl-1-(1-(methylsulfonyl)indolin-5-yl)-1H-pyrazol-5-yl)-3-(4-(1-oxoisoindolin-4-yl)phenyl)urea (5 mg, 8% yield) as an off-white solid. $^1$H NMR (400 MHz, DMSO-d$_6$): δ 9.15 (s, 1H), 8.57 (s, 1H), 8.44 (s, 1H), 7.66-7.62 (m, 2H), 7.56 (m, 1H), 7.54-7.52 (m, 4H), 7.43 (m, 1H), 7.36-7.32 (m, 2H), 6.38 (s, 1H), 4.50 (s, 2H), 4.02 (t, J=8.5, 2H), 3.20 (t, J=8.5 Hz, 2H), 3.07 (s, 3H), 1.286 (s, 9H); MS (ESI) m/z: 585.3 (M+H$^+$).

Example 193

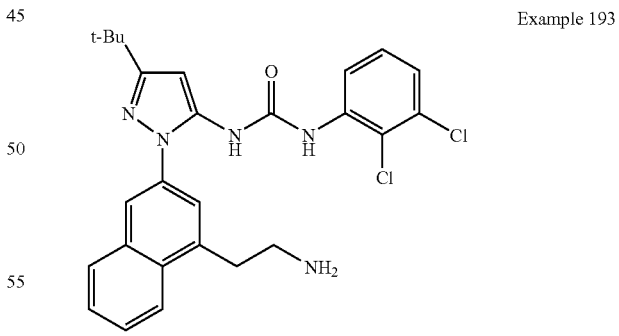

To a solution of Example A27 (500 mg, 1.5 mmol) in absolute THF was added powder LiAlH$_4$ (300 mg, 7.5 mmol) in portions at 0° C. under N$_2$ atmosphere. After stirring for 3 h, the reaction was quenched by addition of H$_2$O and 2N NaOH. The suspension was filtered and the filtrate was concentrated to the crude product, which was purified by reverse phase chromatography to yield 2-(3-(5-amino-3-t-butyl-1H-pyrazol-1-yl)naphthalen-1-yl)(400 mg, 86% yield) as a white solid. $^1$H NMR (300 MHz, DMSO-d$_6$): δ 8.02-8.05 (m, 1H), 7.90-7.93 (m, 1H), 7.86 (s, 1H), 7.61 (s, 1H), 7.50-7.47 (m, 2H), 5.38 (s, 1H), 5.27 (s, 2H), 4.73 (t, J=5.4 Hz, 1H), 3.69 (t, J=6.9 Hz, 2H), 3.20 (t, J=6.9 Hz, 2H), 1.20 (s, 9H); MS (ESI) m/z: 310 (M+H$^+$).

To a stirred solution of the material from the previous reaction (400 mg, 1.3 mmol) and DPPA (0.419 mL, 2 mmol) in dry THF (10 mL) at 0° C. was added DBU (0.293 mL, 2 mmol). The resulting mixture was allowed to warm to 25° C. and stirred under N$_2$ for 18 h. The mixture was concentrated and purified by column chromatography to yield 1-(4-(2-azidoethyl)naphthalen-2-yl)-3-t-butyl-1H-pyrazol-5-amine (150 mg, 30% yield). $^1$H NMR (300 MHz, DMSO-d$_6$): δ 8.75-8.78 (m, 1H), 7.90-7.95 (m, 1H), 7.92 (s, 1H), 7.69 (s, 1H), 7.55-7.50 (m, 2H), 5.39 (s, 1H), 5.30 (s, 2H), 3.68 (t, J=7.2 Hz, 2H), 3.35 (t, J=7.2 Hz, 2H), 1.21 (s, 1H); MS (ESI) m/z: 335 (M+H$^+$).

To a mixture of the material from the previous reaction (150 mg, 0.45 mmol) and Et$_3$N (0.186 mL, 1.3 mmol) in CH$_2$Cl$_2$ (10 mL) was added a solution of 1,2-dichloro-3-isocyanatobenzene (84 mg, 1.5 mmol) in CH$_2$Cl$_2$ dropwise at 0° C. under N$_2$ atmosphere. The mixture was allowed to come to room temperature and stirred overnight before being poured into ice cold 1.0N HCl. The mixture was extracted with CH$_2$Cl$_2$ (3×100 mL), and the combined organic layers were washed with brine, dried (Na$_2$SO$_4$), filtered and concentrated to give a dark oil, which was purified by column chromatography to yield 1-(1-(4-(2-azidoethyl)naphthalen-2-yl)-3-t-butyl-1H-pyrazol-5-yl)-3-(2,3-dichlorophenyl)urea (200 mg, 30% yield) as a white solid. $^1$H NMR (300 MHz, DMSO-d$_6$): δ 9.29 (s, 1H), 8.74 (s, 1H), 8.12-8.15 (m, 1H), 8.12-8.00 (m, 2H), 7.93-7.96 (m, 1H), 7.62-7.53 (m, 3H), 7.30-7.24 (m, 2H), 6.42 (s, 1H), 3.69 (t, J=7.2 Hz, 2H), 3.37 (t, J=7.2 Hz, 2H), 1.23 (s, 1H); MS (ESI) m/z: 522 (M+H$^+$).

To a solution of the material from the previous reaction (200 mg, 0.38 mmol) in absolute THF was added LiAlH$_4$ powder (77 mg, 1.9 mmol) in portions at 0° C. under N$_2$. After stirring for 3 h, the reaction was quenched by addition of H$_2$O and 2N NaOH. The suspension was filtered and the filtrate was concentrated to give the crude product, which was purified by reverse phase chromatography to yield 1-(1-(4-(2-aminoethyl)naphthalen-2-yl)-3-t-butyl-1H-pyrazol-5-yl)-3-(2,3-dichlorophenyl)urea (20 mg, 10% yield) as a white solid. $^1$H NMR (300 MHz, DMSO-d$_6$): δ 9.30 (s, 1H), 8.71 (s, 1H), 8.12 (d, J=7.8 Hz, 1H), 8.03-7.98 (m, 3H), 7.84 (s, 2H), 7.60-7.56 (m, 3H), 7.25-7.24 (m, 2H), 6.40 (s, 1H), 3.43-3.46 (m, 2H), 3.10-3.15 (m, 2H), 1.25 (s, 9H); MS (ESI) m/z: 496 (M+H$^+$).

mixture was diluted with H$_2$O (30 mL) and stirred overnight. The brown solid was collected by filtration and dried to yield 7-nitroquinazolin-4-ol (3.62 g, 86% yield). $^1$H NMR (300 MHz, DMSO-d$_6$): 8.38-8.33 (m, 2H), 8.27-8.23 (m, 2H).

A solution of 7-nitroquinazolin-4-ol (3.62 g, 18.9 mmol) with 10% Pd/C (0.25 g) in DMF (15 mL) was stirred under H$_2$ (1 atm) for 18 h, then partially concentrated at elevated temperature, filtered warm through Celite® to remove catalyst and then concentrated to a brown solid. The solid was triturated with EtOAc (50 mL), filtered, dried, redissolved in DMF (25 mL), treated with 10% Pd/C (0.25 g) and stirred overnight under an H$_2$ atmosphere. The mixture was filtered free of catalyst and the filtrate evaporated at reduced pressure to yield a brown solid which was triturated with EtOAc (50 mL) and filtered to yield 7-aminoquinazolin-4-ol (2.27 g, 74% yield). MS (ESI) m/e (M+H$^+$) 162.3.

To a stirred suspension of 7-aminoquinazolin-4-ol (2.00 g, 12.4 mmol) in conc. HCl (20.0 ml) at 0° C. was added dropwise NaNO$_2$ (0.98 g, 14.3 mmol, 1.15 eq) as a solution in H$_2$O (15.0 ml). The resulting mixture was stirred at 0° C. for 1 h, and then treated with a solution of SnCl$_2$.2H$_2$O (12.0 g, 53.4 mmol, 4.30 eq) in conc. HCl (15.0 ml). The reaction was stirred at 0° C. for 1 h and then at RT for 2 h. The reaction was diluted with EtOH (130 ml) and 4,4-dimethyl-3-oxopentanenitrile (2.02 g, 16.1 mmol, 1.30 eq) added, heated at reflux overnight, then cooled to RT and concentrated. The residue was diluted with EtOAc (100 mL), placed in an ice/H$_2$O bath and the stirred solution made basic (pH 8) with solid NaOH. The mixture was filtered through Celite®, washed with H$_2$O (50 mL) and then EtOAc (100 mL). The organic phase washed with brine, dried (Na$_2$SO$_4$) and concentrated to yield a tan solid, which was dried then stirred in ether (100 mL) and allowed to stand. The solid was collected by filtration and dried to yield 7-(5-amino-3-t-butyl-1H-pyrazol-1-yl)quinazolin-4(3H)-one (1.69 g, 48% yield). $^1$H NMR (300 MHz, DMSO-d$_6$): 8.17-8.11 (m, 2H), 7.90-7.83 (m, 2H), 5.47 (m, 3H), 1.23 (s, 9H). MS (ESI) m/e (M+H$^+$) 284.2.

Using general method A, 7-(5-amino-3-t-butyl-1H-pyrazol-1-yl)quinazolin-4(3H)-one (120 mg, 0.424 mmol) and 2,3-dichlorophenylisocyanate (79 mg, 0.487 mmol) were combined to yield 1-(3-t-butyl-1-(4-oxo-3,4-dihydroquinazolin-7-yl)-1H-pyrazol-5-yl)-3-(2,3-dichlorophenyl)urea (102 mg, 51% yield) as a white solid. $^1$H NMR (300 MHz, DMSO-d$_6$): 9.41 (s, 1H), 8.79 (s, 1H), 8.25-8.23 (s, 1H), 8.16 (s, 1H), 8.08-8.02 (m, 1H), 7.82-7.75 (m, 2H), 7.32-7.30 (m, 2H), 6.46 (s, 1H), 1.30 (s, 9H). MS (ESI) m/e (M+H$^+$) 471.0.

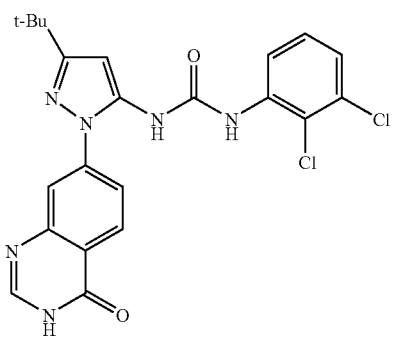

Example 194

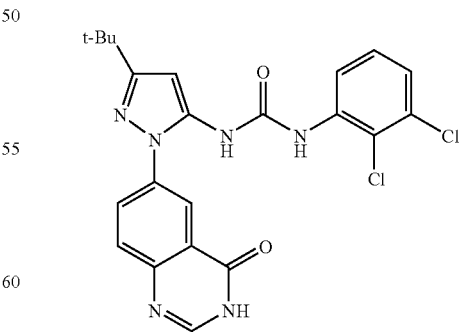

Example 195

A mixture of formamide (7.91 g, 176 mmol) and 4-nitroanthranilic acid (4.00 g, 22.0 mmol) was warmed to 160° C. and stirred for 7 h then cooled to RT and stirred overnight. The A mixture of formamide (14 g, 0.3 mol) and 2-amino-5-nitrobenzoic acid (9.1 g, 0.05 mol) was heated at 155° C. for 7 h, cooled to RT and stirred overnight. The mixture was diluted with H$_2$O (30 mL) and filtered. The resultant brown solid was dissolved in i-PrOH (300 mL), warmed to reflux, cooled to RT and filtered and dried to yield 6-nitroquinazolin-4(3H)-one, (5.85 g, 61% yield). MS (ESI) m/e (M+H⁺) 192.0

A mixture of 6-nitroquinazolin-4(3H)-one (4.15 g, 21.7 mmol) and 10% Pd/C (0.3 g) in MeOH (25 mL) and THF (50 mL) was stirred under H₂ (1 atm) at 40° C. for 18 h. The mixture was diluted with DMF (50 mL), stirred overnight under H₂, then placed under an Ar atmosphere. After the addition of Pd/C (0.4 g), the mixture was placed under an H₂ atmosphere and warmed to 50° C. and stirred for 4 h. The reaction mixture was filtered through Celite®, washed with warm DMF (75 mL) and the combined filtrates evaporated to yield 6-aminoquinazolin-4(3H)-one (3.10 g, 88% yield) as a yellow solid. MS (ESI) m/e (M+H⁺) 162.3

To a suspension of 6-aminoquinazolin-4(3H)-one (3.07 g, 19.0 mmol, 1.0 eq) in conc. HCl (30.0 ml) at 0° C. was added dropwise NaNO₂ (1.51 g, 21.9 mmol, 1.15 eq) as a solution in H₂O (20.0 ml). The resulting mixture was stirred at 0° C. for 1 h, and then treated with a solution of SnCl₂.2H₂O (18.5 g, 81.9 mmol, 4.30 eq) in conc. HCl (20.0 ml). The reaction was stirred at 0° C. for 1 h and then at RT for 2 h. The reaction was diluted with EtOH (200 ml), treated with 4,4-dimethyl-3-oxopentanenitrile (3.10 g, 24.8 mmol, 1.30 eq), heated at reflux overnight, then cooled to RT and concentrated. The residue was diluted with EtOAc (100 mL), then stirred in an ice/H2O bath and made basic (pH 8) with solid NaOH. The mixture was filtered through Celite®, washed with H₂O (50 mL) and then EtOAc (100 mL). The organic phase was washed with brine, dried (Na₂SO₄) and concentrated to yield a yellow solid, which was triturated from Et₂O (100 ml) to yield 6-(5-amino-3-t-butyl-1H-pyrazol-1-yl)quinazolin-4(3H)-one (1.2 g, 22% yield). MS (ESI) m/e (M+H⁺) 284.2

Using general method A, the material from the previous reaction (120 mg, 0.424 mmol) and 2,3-dichlorophenyl isocyanate (96 mg, 0.508 mmol) were combined to yield 1-(3-t-butyl-1-(4-oxo-3,4-dihydroquinazolin-6-yl)-1H-pyrazol-5-yl)-3-(2,3-dichlorophenyl)urea as a tan solid (107 mg, 53% yield). ¹H-NMR (DMSO-d₆): δ 1.30 (s, 9H), 6.42 (s, 1H), 7.27-7.32 (m, 2H), 7.80-7.83 (m, 1H), 7.98-8.03 (m, 2H), 8.15 (s, 1H), 8.20-8.21 (m, 1H), 8.72 (s, 1H), 9.40 (br s, 1H). MS (ESI) m/e (M+H⁺) 471.0

Example 196

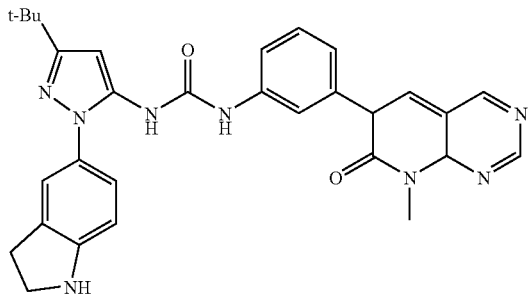

Using general method D, Example A29 (0.25 g, 0.47 mmol) in DMSO (2 mL) and Example A11 (0.13 g, 0.52 mmol) were combined to yield 1-(3-t-butyl-1-(1-(2,2,2-trifluoroacetyl)indolin-5-yl)-1H-pyrazol-5-yl)-3-(3-(8-methyl-7-oxo-6,7,8,8a-tetrahydropyrido[2,3-d]pyrimidin-6-yl)phenyl)urea, which was deprotected with 7N NH₃/MeOH (2 mL) at room temperature for 2 h. Water (10 mL) was added and the mixture was extracted with CH₂Cl₂ (3×20 mL). The organic extracts were dried (MgSO₄), concentrated and purified by column chromatography to yield 1-(3-t-butyl-1-(indolin-5-yl)-1H-pyrazol-5-yl)-3-(3-(8-methyl-7-oxo-7,8-dihydropyrido[2,3-d]pyrimidin-6-yl)phenyl)urea (0.20 g, 79% yield). ¹H NMR (400 MHz, DMSO-d₆): δ 9.22 (s, 1H), 9.16 (s, 1H), 9.11 (s, 1H), 8.23 (s, 1H), 8.17 (s, 1H), 7.83 (t, J=1.6 Hz, 1H), 7.44 (m, 1H), 7.37 (t, J=8.0 Hz, 1H), 7.30 (m, 1H), 7.08 (brs, 1H), 6.96 (dd, J=2.0, and 8.0 Hz, 1H), 6.58 (d, J=8.4 Hz, 1H), 6.32 (s, 1H), 5.81 (brs, 1H), 3.71 (s, 3H), 3.49 (brt, J=8.4 Hz, 2H), 2.98 (t, J=8.4 Hz, 2H), 1.25 (s, 9H); LC-MS (EI) m/z: 535.2 (M+H⁺). To a solution of this material (30 mg, 0.06 mmol) in EtOAc (1 mL) was added 3M HCl/EtOAc (21 □L). The solid was filtered and dried under vacuum to obtain 1-(3-t-butyl-1-(indolin-5-yl)-1H-pyrazol-5-yl)-3-(3-(8-methyl-7-oxo-7,8-dihydropyrido[2,3-d]pyrimidin-6-yl)phenyl)urea (31 mg, 97% yield) as the HCl salt. ¹H NMR (400 MHz, DMSO-d₆): δ 9.32 (brs, 1H), 9.16 (s, 1H), 9.12 (s, 1H), 8.47 (brs, 1H), 8.17 (s, 1H), 7.83 (t, J=1.6 Hz, 1H), 7.45 (m, 1H), 7.37 (brs, 1H), 7.36 (t, J=8.0 Hz, 1H), 7.29 (m, 1H), 7.28 (brs, 1H), 7.08 (brs, 1H), 6.37 (s, 1H), 3.71 (s, 3H), 3.65 (m, 2H), 3.14 (m, 2H), 1.27 (s, 9H); LC-MS (EI) m/z: 535.2 (M+H⁺).

Example 197

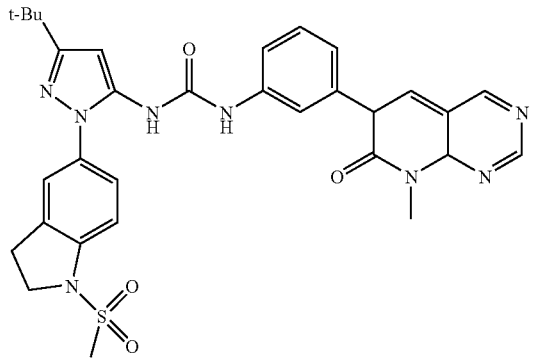

Using the same procedureas for Example 108, Example 196 (170 mg, 0.32 mmol) and methanesulfonyl chloride (73 mg, 0.64 mmol) were combined to yield 1-(3-t-butyl-1-(1-(methylsulfonyl)indolin-5-yl)-1H-pyrazol-5-yl)-3-(3-(8-methyl-7-oxo-7,8-dihydropyrido[2,3-d]pyrimidin-6-yl)phenyl)urea (60 mg, 31% yield) as a pale yellow solid. ¹H NMR (400 MHz, DMSO-d₆): δ 9.18 (brs, 1H), 9.16 (s, 1H), 9.12 (s, 1H), 8.41 (brs, 1H), 8.17 (s, 1H), 7.84 (t, J=2.0 Hz, 1H), 7.46 (m, 1H), 7.42 (d, J=1.2 Hz, 1H), 7.36 (m, 4H), 7.30 (dt, J=1.6, and 7.6 Hz, 1H), 6.38 (s, 1H), 4.02 (t, J=8.4 Hz, 2H), 3.71 (s, 3H), 3.20 (t, J=8.4 Hz, 2H), 1.27 (s, 9H); LC-MS (EI) m/z: 613.3 (M+H⁺).

Example 198

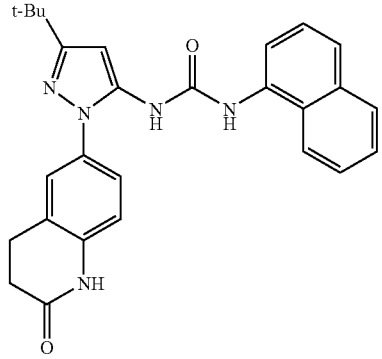

Using general method D, Example A35 (0.12 g, 0.4 mmol) and 1-Aminonaphthalene (0.034 g, 0.23 mmol) were combined to yield 1-(3-t-butyl-1-(2-oxo-1,2,3,4-tetrahydroquinolin-6-yl)-1H-pyrazol-5-yl)-3-(naphthalen-1-yl)urea (36 mg, 19% yield, 2 steps). ¹H NMR (400 MHz, DMSO-d₆): δ 10.3 (s, 1H), 9.04 (s, 1H), 8.76 (s, 1H), 8.00 (d, J=7.6 Hz, 1H), 7.92 (m, 2H), 7.65 (d, J=8.4 Hz, 1H), 7.54 (m, 2H), 7.46 (t, J=8.0 Hz, 1H), 7.35 (d, J=2.4 Hz, 1H), 7.32 (dd, J=2.4, and 8.0 Hz, 1H), 7.01 (d, J=8.4 Hz, 1H), 6.39 (s, 1H), 2.98 (t, J=6.8 Hz, 1H), 1.28 (s, 9H); MS (EI) m/z: 454.2 (M+H⁺).

Example 199

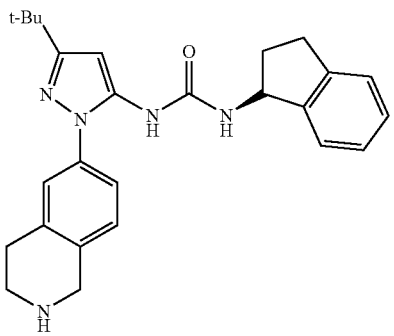

Using general method D, Example A38 (0.20 g, 0.54 mmol) and (S)-aminoindane (0.035 g, 0.26 mmol) were combined to yield 1-(3-t-butyl-1-(1,2,3,4-tetrahydroisoquinolin-6-yl)-1H-pyrazol-5-yl)-3-((S)-2,3-dihydro-1H-inden-1-yl) urea HCl salt (82 mg, 53% yield, 2 steps). ¹H NMR (400 MHz, DMSO-d₆): δ 9.51 (brs, 2H), 8.32 (m, 1H), 7.23 (m, 5H), 7.07 (m, 1H), 6.47 (brs, 1H), 6.23 (s, 1H), 5.09 (m, 1H), 4.30 (m, 2H), 3.37 (m, 2H), 3.07 (brt, J=4.8 Hz, 2H), 2.90 (m, 1H), 2.76 (m, 1H), 2.38 (m, 1H), 1.71 (m, 1H), 1.27 (s, 9H); MS (EI) m/z: 430.2 (M+H⁺).

Example 200

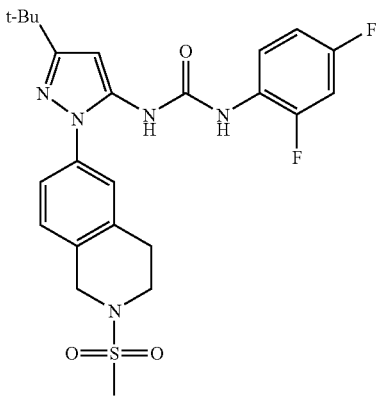

Using the same procedureas for Example 108, Example 145 (0.14 g, 0.3 mmol) was transformed 1-(3-t-butyl-1-(2-(methylsulfonyl)-1,2,3,4-tetrahydroisoquinolin-6-yl)-1H-pyrazol-5-yl)-3-(2,4-difluorophenyl)urea (60 mg, 40% yield). ¹H NMR (400 MHz, DMSO-d₆): δ 8.88 (brs, 1H), 8.77 (s, 1H), 8.04 (m, 1H), 7.31 (m, 4H), 7.02 (m, 1H), 6.38 (s, 1H), 4.43 (s, 2H), 3.46 (t, J=6.0 Hz, 2H), 3.00 (t, J=6.0 Hz, 2H), 2.98 (s, 3H), 1.25 (s, 9H); LC-MS (EI) m/z: 504.2 (M+H⁺).

Example 201

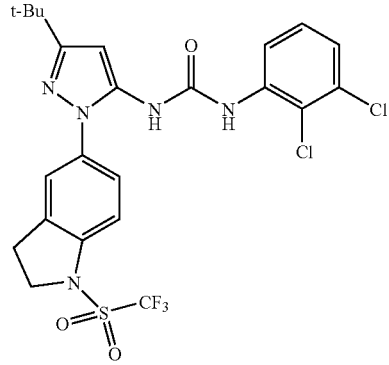

To a stirred suspension of Example 106 (20 mg, 0.045 mmol) and Bu Et₃N (6.8 mg, 0.068 mmol) in CH₂Cl₂ (2.0 ml) was added triflic anhydride (14 mg, 0.051 mmol) at −78° C. which was stirred for 30 min. The reaction was quenched with saturated NaHCO₃ and allowed to warm to RT. The mixture was diluted with EtOAc and the organic layer was washed with NH₄Cl, NaHCO₃, brine, and dried (MgSO₄), and concentrated under reduced pressure to obtain 1-(3-t-butyl-1-(1-(trifluoromethylsulfonyl)indolin-5-yl)-1H-pyrazol-5-yl)-3-(2,3-dichlorophenyl)urea as a pale yellow solid (20 mg, 100% yield). ¹H NMR (400 MHz, DMSO-d₆): δ 9.22 (s, 1H), 8.74 (brs, 1H), 8.04 (dd, J=4.4, and 5.6 Hz, 1H), 7.54 (brs, 1H), 7.43 (d, J=2.4 Hz, 1H), 7.42 (s, 1H), 7.32 (d, J=1.6 Hz, 1H), 6.39 (s, 1H), 4.30 (t, J=8.4 Hz, 2H), 3.33 (s, 2H), 3.32 (t, J=8.4 Hz, 2H), 1.27 (s, 9H); LC-MS (EI) m/z: 576.2 (M+H⁺).

Example 202

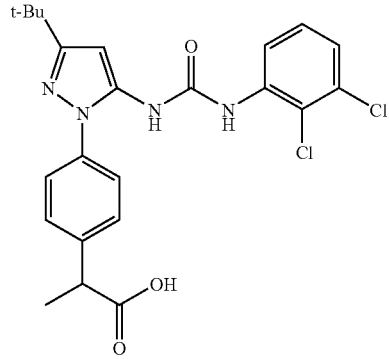

A solution of Example A57 (415 mg, 1.23 mmol) in THF (4 mL) of THF was cooled to −78° C. and treated with sodium bis(trimethylsilylamide) (11.0M in THF, 2.6 mL, 2.6 mmol). The reaction mixture was stirred for 30 min at −78° C. Methyl iodide (0.090 mL, 1.47 mmol) was added and the reaction mixture was allowed to slowly warm to 0° C. over 90 min. The reaction was partitioned between saturated aqueous NH₄Cl (10 mL) and EtOAc (30 mL). The organic layer was washed with H₂O (10 mL) and brine (10 mL). The combined aqueous washes were extracted with ether (10 mL). All organics were combined, dried (Na₂SO₄) and purified via column chromatography to yield ethyl 2-(4-(5-amino-3-t-butyl-1H-pyrazol-1-yl)phenyl)propanoate (99 mg, 26% yield). MS (ESI) m/z: 316.3 (M+H⁺).

Using general method A, the material from the previous step (97 mg, 0.31 mmol) and 2,3-dichlorophenyl isocyanate (0.061 mL, 0.46 mmol) were combined to yield ethyl 2-(4-

(3-t-butyl-5-(3-(2,3-dichlorophenyl)ureido)-1H-pyrazol-1-yl)phenyl)propanoate (89 mg, 57% yield) as a foam. MS (ESI) m/z: 503.3 (M+H$^+$).

Using general method E, the material from the previous step (84 mg, 0.17 mmol) was saponified to yield 2-(4-(3-t-butyl-5-(3-(2,3-dichlorophenyl)ureido)-1H-pyrazol-1-yl)phenyl)propanoic acid (67 mg, 84% yield). $^1$H NMR (400 MHz, DMSO-d$_6$): δ 12.42 (brs, 1H), 9.32 (s, 1H), 8.81 (s, 1H), 8.09 (m, 1H), 7.49-7.43 (m, 4H), 7.35-7.29 (m, 2H), 6.39 (s, 1H), 3.77 (q, J=7.2 Hz, 1H), 1.41 (d, J=7.2 Hz, 3H), 1.27 (s, 9H); MS (ESI) m/z: 475.2 (M+H$^+$).

Example 203

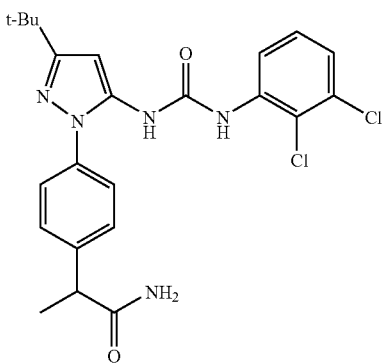

A solution of Example 202 (51 mg, 0.11 mmol) in DMF (1.5 mL) was treated with ammonia (0.5M in dioxane, 1.5 mL, 0.75 mmol). PyBOP (80 mg, 0.15 mmol) was added and the resultant solution was stirred overnight at RT. Water (10 mL) was added and the precipitate was filtered and further purified via column chromatography to yield 1-(1-(4-(1-amino-1-oxopropan-2-yl)phenyl)-3-t-butyl-1H-pyrazol-5-yl)-3-(2,3-dichlorophenyl)urea (42 mg, 83% yield). $^1$H NMR (400 MHz, DMSO-d$_6$): δ 9.31 (s, 1H), 8.82 (s, 1H), 8.10 (m, 1H), 7.50-7.43 (m, 5H), 7.35-7.29 (m, 2H), 6.88 (s, 1H), 6.39 (s, 1H), 3.66 (q, J=7.2 Hz, 1H), 1.36 (d, J=7.2 Hz, 3H), 1.27 (s, 9H); MS (ESI) m/z: 474.0 (M+H$^+$).

Example A57

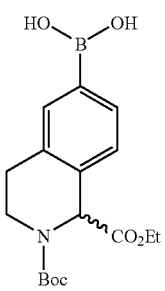

To a solution of 3-hydroxy phenethylamine hydrochloride (0.500 g, 2.88 mmol) in ethanol (10 mL) was added ethyl glyoxylate (50% in toluene, 1.18 g, 5.76 mmol) and the mixture was heated at 80° C. for 2 h. The solution was cooled to RT and triethylamine (0.874 g, 4.32 mmol) and Boc anhydride (0.943 g, 4.32 mmol) were added and the resulting solution was stirred at RT for 1 h. Evaporation of the solvent and column chromatography yielded 2-t-butyl 1-ethyl 6-hydroxy-3,4-dihydroisoquinoline-1,2(1H)-dicarboxylate (720 mg, 78% yield) as a colorless foam. $^1$H NMR (400 MHz, CDCl$_3$): δ 7.35 (t, J=8.0 Hz, 1H), 6.69 (d, J=8.4 Hz, 1H), 6.63 (s, 1H), 5.49 (s, 0.4H), 5.33 (s, 0.6H), 4.95 (brs, 0.6H), 4.93 (brs, 0.4H), 4.17-4.10 (m, 2H), 3.77-3.69 (m, 2H), 2.93-2.75 (m, 2H), 1.49 (s, 4H), 1.47 (s, 5H), 1.28-1.21 (m, 3H); MS (ESI) m/z: 344.3 (M+Na$^+$).

To a solution of the material from the previous step (0.770 g, 2.240 mmol) in CH$_2$Cl$_2$ (10 mL) was added triethylamine (0.401 mL, 0.291 g, 2.88 mmol) and triflic chloride (0.306 mL, 0.485 g, 2.88 mmol) and the resulting solution was stirred at RT for 3 h. Water was added (50 mL) and the mixture was extracted with CH$_2$Cl$_2$ (3×50 mL), dried (MgSO$_4$) and concentrated to yield 2-t-butyl 1-ethyl 6-(trifluoromethylsulfonyloxy)-3,4-dihydroisoquinoline-1,2(1H)-dicarboxylate (1.05 g, 97% yield) of the crude product as a colorless oil which was used without further purification. $^1$H NMR (400 MHz, CDCl$_3$): δ 7.61 (d, J=8.8 Hz, 0.4H), 7.60 (d, J=8.8 Hz, 0.6H), 7.13 (d, J=8.4 Hz, 1H), 5.62 (s, 0.4H), 5.44 (s, 0.6H), 4.18 (q, J=7.0 Hz, 2H), 3.96-3.83 (m, 1H), 3.73-3.64 (m, 1H), 3.15-3.09 (m, 1H), 2.96-2.89 (m, 2H), 1.53 (s, 4H), 1.47 (s, 5H), 1.29-1.23 (m, 3H); MS (ESI) m/z: 476.0 (M+Na$^+$).

To a degassed solution of the material from the previous step (1.05 g, 2.32 mmol), bis(pinacolato)diboron (0.882 g, 3.47 mmol), and potassium acetate (0.682 g, 6.95 mmol) in DMF (10 mL) was added PdCl$_2$(dppf) (0.095 g, 0.116 mmol) and the resulting mixture was stirred at 80° C. for 3 h. Water was added (100 mL) and the mixture was extracted with EtOAc (3×100 mL), dried (MgSO$_4$), concentrated and purified via column chromatography to yield 2-t-butyl 1-ethyl 6-(4,4,5,5-tetramethyl-1,3,2-dioxaborolan-2-yl)-3,4-dihydroisoquinoline-1,2(1H)-dicarboxylate (935 mg, 94% yield) as a colorless oil. $^1$H NMR (400 MHz, CDCl$_3$): δ 7.65 (d, 1H, J=7.6 Hz), 7.61 (s, 0.6H), 7.60 (s, 0.4H), 7.50 (t, J=8.8 Hz, 1H), 5.58 (s, 0.4H), 5.42 (s, 0.6H), 4.14 (q, J=7.2 Hz, 2H), 3.79-3.73 (m, 2H), 2.98-2.84 (m, 2H), 1.49 (s, 4H), 1.47 (s, 5H), 1.34 (s, 12H), 1.20 (t, J=7.6 Hz, 3H); MS (ESI) m/z: 454.2 (M+Na$^+$).

To a solution of the material from the previous step (0.900 g, 2.09 mmol) in acetone/water 4:1 was added sodium periodate (1.34 g, 6.26 mmol) and the resulting slurry was stirred at RT for 30 min. 2N HCl was added (2.09 mL, 4.17 mmol) and the resulting mixture was stirred at RT overnight. Water was added (100 mL) and the mixture was extracted with EtOAc (3×100 mL), dried (MgSO$_4$) and concentrated to yield 2-(t-butoxycarbonyl)-1-(ethoxycarbonyl)-1,2,3,4-tetrahydroisoquinolin-6-ylboronic acid (670 mg, 92% yield) as a brown solid which was used without further purification. MS (ESI) m/z: 372.3 (M+Na$^+$).

Example A58

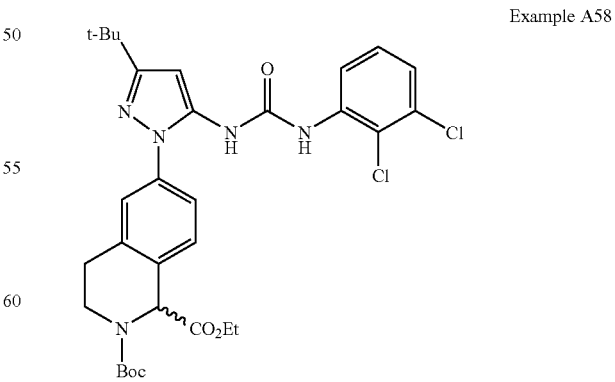

To a solution of Example A31 (0.075 g, 0.229 mmol), Example A57 (0.100 g, 0.286 mmol) and pyridine (0.054 g, 0.688 mmol) in CH$_2$Cl$_2$ (5 mL) was added copper(II)-acetate (0.062 g, 0.688 mmol) and the resulting green solution was stirred at RT until all starting material was consumed. Water was added (100 mL) and the mixture was extracted with CH₂Cl₂ (3×50 mL), dried (MgSO₄), concentrated and purified via column chromatography to yield 2-t-butyl 1-ethyl 6-(3-t-butyl-5-(3-(2,3-dichlorophenyl)ureido)-1H-pyrazol-1-yl)-3,4-dihydroisoquinoline-1,2 (1H)-dicarboxylate (85 mg, 59% yield) as a colorless foam. ¹H NMR (400 MHz, CDCl₃): δ 8.62 (brs, 1H), 8.25 (d, J=8.0 Hz, 1H), 8.19 (brs, 1H), 7.65 (d, J=8.4 Hz, 0.5H), 7.61 (d, J=8.4 Hz, 0.5H), 7.49-7.44 (m, 2H), 7.31 (t, J=8.2 Hz, 1H), 7.24 (dd, J=7.6, and 1.6 Hz, 1H), 6.49 (s, 1H), 5.58 (s, 0.5H), 5.51 (s, 0.5H), 4.21-4.14 (m, 2H), 3.88-3.78 (m, 1H), 3.75-3.63 (m, 1H), 2.99-2.90 (m, 2H), 1.48 (s, 4H), 1.46 (s, 5H), 1.32 (s, 9H), 1.26-1.21 (m, 3H); MS (ESI) m/z: 630.2 (M+H⁺).

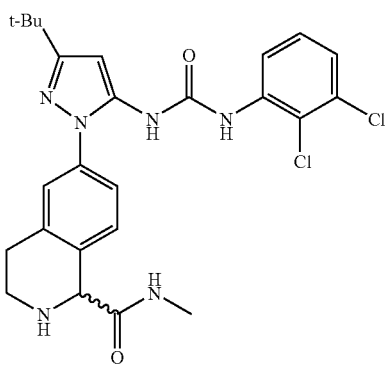

Example 204

A solution of Example A58 (0.080 g, 0.130 mmol) in 3N hydrochloric acid in methanol (10.0 mL) was stirred at RT for 1 h. The solvent was evaporated and the residue was dissolved in 8N methylamine in ethanol (3 mL) and the solution was stirred at 50° C. overnight. The solvent was evaporated and the residue was purified by reverse phase chromatography and coevaporated with THF/4N HCl to yield 1-(3-t-butyl-1-(1-(methylcarbamoyl)-1,2,3,4-tetrahydroisoquinolin-6-yl)-1H-pyrazol-5-yl)-3-(2,3-dichlorophenyl)urea (43 mg, 59% yield) of as a colorless solid. ¹H NMR (400 MHz, CD₃OD): δ 8.03 (t, J=5.0 Hz, 1), 7.64-7.58 (m, 3H), 7.28-7.27 (m, 2H), 6.60 (s, 1H), 5.23 (s, 1H), 3.88-3.81 (m, 1H), 3.56-3.50 (m, 1H), 3.30-3.15 (m, 2H), 2.90 (s, 3H), 1.39 (s, 9H); MS (ESI) m/z: 515.0 (M+H⁺).

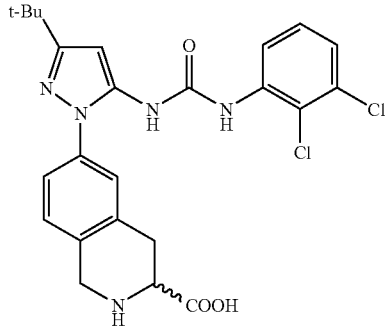

Example 205

Using general method E, Example A58 (0.280 g, 0.444 mmol) was saponified to yield 2-(t-butoxycarbonyl)-6-(3-t-butyl-5-(3-(2,3-dichlorophenyl)ureido)-1H-pyrazol-1-yl)-1,2,3,4-tetrahydroisoquinoline-3-carboxylic acid (234 mg, 88% yield) as an off-white foam. MS (ESI) m/z: 602.2 (M+H⁺). A solution of this material (0.065 g, 0.11 mmol) was stirred in 4N hydrogen chloride in dioxane (5 mL) for 1 h. Evaporation of the solvent and purification via reverse phase chromatography and co-evaporation with HCl/ethanol (2×100 mL) yielded (25 mg, 43% yield) of the desired product as its hydrochloride. ¹H NMR (400 MHz, CD₃OD): δ 8.05 (t, J=5.0 Hz, 1H), 7.59-7.56 (m, 2H), 7.52 (d, J=8.4 Hz, 1H), 7.27-7.26 (m, 2H), 6.69 (s, 1H), 4.62 (d, J=16.4 Hz, 1H), 4.54 (d, J=14.4 Hz, 1H), 4.50 (dd, J=11.2, and 4.8 Hz, 1H), 3.59-3.56 (m, 1H), 3.38-3.30 (m, 1H), 1.40 (s, 9H), urea, acid and amine protons not visible; MS (ESI) m/z: 502.0 (M+H⁺).

General Experimental for Examples 206-213

Example A3 and the appropriate aniline were combined as indicated.

| Example | Name | MS (EI) (M + H⁺) | ¹H NMR (400 MHz), (acetone-d₆) |
|---|---|---|---|
| Example 206 | 1-(3-t-butyl-1-(3-cyanophenyl)-1H-pyrazol-5-yl)-3-(3,4-difluorophenyl)urea 168 mg, 88%, yield General method D | 396.3 | δ 8.63 (brs, 1H), 8.04-8.02 (m, 1H), 8.03 (brs, 1H), 7.98 (dt, J = 7.6, and 1.8 Hz, 1H), 7.75 (dt, J = 7.6 and 1.4 Hz, 1H), 7.71 (t, J = 7.6 Hz, 1H), 7.68-7.63 (m, 1H), 7.23-7.17 (m, 1H), 7.13-7.09 (m, 1H), 6.44 (s, 1H), 1.32 (s, 9H) |

| Example | | Name | MS (EI) (M + H+) | 1H NMR (400 MHz), (acetone-d6) |
|---|---|---|---|---|
| 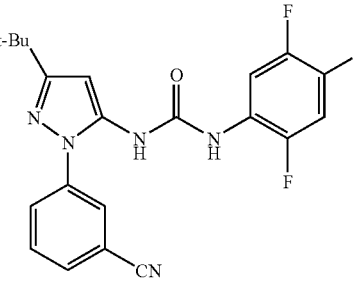 Example 207 | | 1-(3-t-butyl-1-(3-cyanophenyl)-1H-pyrazol-5-yl)-3-(2,4,5-trifluorophenyl)urea 138 mg, 69% yield General method D | 413.7 | δ 8.45 (brs, 1H), 8.38 (brs 1H), 8.25-8.18 (m, 1H), 8.04 (t, J = 1.8 Hz, 1H), 7.98 (dt, J = 8.0, and 1.8 Hz, 1H), 7.77 (dt, J = 8.8, and 1.4 Hz, 1H), 7.72 (t, J = 8.0 Hz, 1H), 7.34-7.27 (m, 1H), 6.49 (s, 1H), 1.32 (s, 9H) |
| 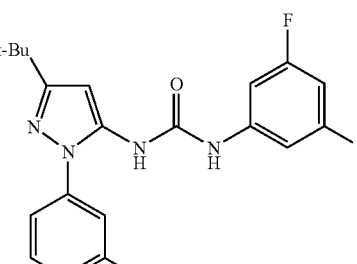 Example 208 | | 1-(3-t-butyl-1-(3-cyanophenyl)-1H-pyrazol-5-yl)-3-(3,5-difluorophenyl)urea 165 mg, 87% yield General method D | 396.3 | δ 8.82 (brs, 1H), 8.09 (brs, 1H), 8.03 (t, J = 7.2 Hz, 1H), 7.97 (dt, J = 7.6, and 1.6 Hz, 1H), 7.76 (dt, J = 7.6, and 1.6 Hz, 1H), 7.71 (t, J = 7.6 Hz, 1H), 7.19-7.13 (m, 2H), 6.62 (dt, J = 9.4, and 2.2 Hz, 1H), 6.45 (s, 1H), 1.32 (s, 9H) |
| 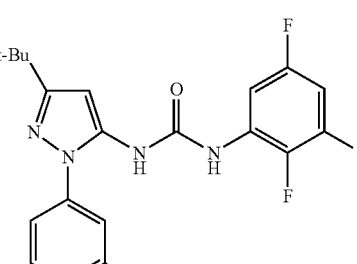 Example 209 | | 1-(3-t-butyl-1-(3-cyanophenyl)-1H-pyrazol-5-yl)-3-(2,3,5-trifluorophenyl)urea 66 mg, 51% yield General method D | 414.0 | δ 8.69 (brs, 1H), 8.48 (brs, 1H), 8.05 (t, J = 1.6 Hz, 1H), 7.99 (dt, J = 8.0, and 2.0 Hz, 1H), 7.96-7.90 (m, 1H), 7.77 (dt, J = 7.6, and 1.4 Hz, 1H), 7.72 (t, J = 7.6 Hz, 1H), 6.89-6.82 (m, 1H), 6.50 (s, 1H), 1.33 (s, 9H) |
| 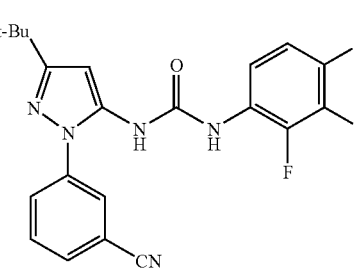 Example 210 | | 1-(3-t-butyl-1-(3-cyanophenyl)-1H-pyrazol-5-yl)-3-(2,3,4-trifluorophenyl)urea 141 mg, 71% yield General method D | 414.0 | δ 8.41 (brs, 1H), 8.34 (brs, 1H), J = 1.6 Hz, 1H), 7.98 (dt, J = 8.0, and 2.0 Hz, 1H), 7.97-7.87 (m, 1H), 7.77 (dt, J = 7.6, and 1.4 Hz, 1H), 7.72 (t, J = 7.2 Hz, 1H), 7.17-7.10 (m, 1H), 6.47 (s, 1H), 1.32 (s, 9H) |
| 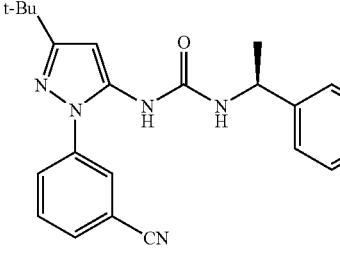 Example 211 | | 1-[3-t-butyl-1-(3-cyanophenyl)-1H-pyrazol-5-yl]-3-((S)-1-phenylethyl)urea 55 mg, 28% yield General method B | 388.1 | 1H NMR (300 MHz, DMSO-d6): δ 8.17 (s, 1H), 7.92 (s, 1H), 7.85-7.78 (m, 2H), 7.65 (m, 1H), 7.31-7.18 (m, 5H), 7.00 (d, J = 8.1 Hz, 1H), 6.24 (s, 1H), 4.69 (m, 1H), 1.31 (d, J = 6.9 Hz, 3H), 1.21 (s, 9H) |

-continued

| Example | Name | MS (EI) (M + H+) | 1H NMR (400 MHz), (acetone-d6) |
|---|---|---|---|
| 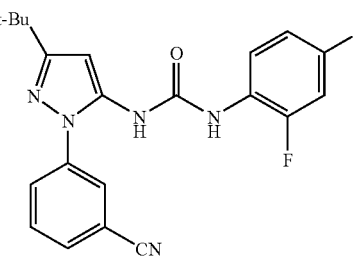<br>Example 212 | 1-(3-t-butyl-1-(3-cyanophenyl)-1H-pyrazol-5-yl)-3-(2,4-difluorophenyl)urea 165 mg, 87% yield General method D | 396.3 | δ 8.30 (brs, 1H), 8.25 (brs, 1H), 8.18-8.10 (m, 1H), 8.04 (t, J = 1.8 Hz, 1H), 7.99 (dt, J = 8.0, and 2.0 Hz, 1H), 7.76 (dt, J = 8.0, and 1.4 Hz, 1H), 7.72 (t, J = 7.6 Hz, 1H), 7.06 (ddd, J = 11.6, 8.8, and 2.8 Hz, 1H), 6.99-6.94 (m, 1H), 6.47 (s, 1H), 1.32 (s, 9H) |
| 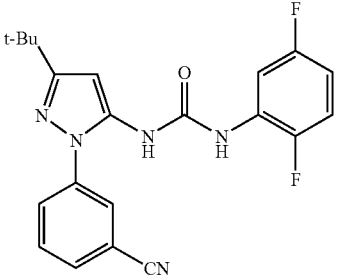<br>Example 213 | 1-(3-t-butyl-1-(3-cyanophenyl)-1H-pyrazol-5-yl)-3-(2,5-difluorophenyl)urea 91 mg, 48% yield General method D | 396.3 | δ 8.48 (brs, 1H), 8.44 (brs, 1H), 8.12-8.07 (m, 1H), 8.05 (t, J = 1.6 Hz, 1H), 7.99 (dt, J = 8.0, and 2.0 Hz, 1H), 7.77 (dt, J = 8.0, and 1.6 Hz, 1H), 7.72 (t, J = 8.0 Hz, 1H), 7.20-7.14 (m, 1H), 6.79-6.73 (m, 1H), 6.51 (s, 1H), 1.33 (s, 9H) |

Example 214

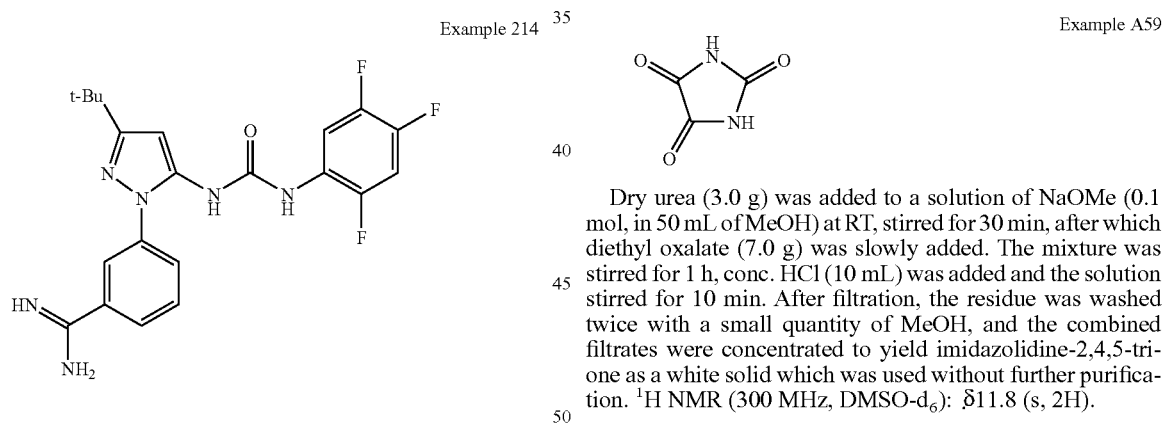

To a solution of Example 207 (0.092 g, 0.22 mmol) in dry ethanol (2 mL) was at −78° C. added acetyl chloride (1.1 g, 14 mmol) and the resulting solution was kept at RT overnight. The solvent was evaporated and to the residue was added 7N ammonia in methanol (2 mL) and the mixture was stirred at RT overnight. The solvent was evaporated and the residue was purified by reverse-phase chromatography, which was followed by an additional basic extraction and reacidification with HCl to yield 1-(3-t-butyl-1-(3-carbamimidoylphenyl)-1H-pyrazol-5-yl)-3-(2,4,5-trifluorophenyl)urea (45 mg, 43% yield) as a white solid. $^1$H NMR (400 MHz, CD$_3$OD): δ 8.05 (t, J=1.6 Hz, 1H), 8.02-7.92 (m, 3H), 7.83 (t, J=8.0 Hz, 1H), 7.23 (dt, J=10.8, and 7.2 Hz, 1H), 6.60 (s, 1H), 1.39 (s, 9H), amidine and urea protons not visible; MS (ESI) m/z: 431.0 (M+H+).

Example A59

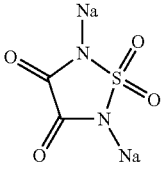

Dry urea (3.0 g) was added to a solution of NaOMe (0.1 mol, in 50 mL of MeOH) at RT, stirred for 30 min, after which diethyl oxalate (7.0 g) was slowly added. The mixture was stirred for 1 h, conc. HCl (10 mL) was added and the solution stirred for 10 min. After filtration, the residue was washed twice with a small quantity of MeOH, and the combined filtrates were concentrated to yield imidazolidine-2,4,5-trione as a white solid which was used without further purification. $^1$H NMR (300 MHz, DMSO-d$_6$): δ11.8 (s, 2H).

Example A60

To a solution of NaOMe (0.15 mol, in 60 mL of MeOH) was added 7.2 g of sulfamide at RT. The resulting mixture was stirred for 30 min, after which dimethyl oxalate (11.0 g) was added. The suspension was heated at reflux for 16 h, cooled, filtered, the precipitate washed with MeOH, and dried under vacuum to yield 1,2,5-thiadiazolidine-3,4-dione 1,1-dioxide as the disodium salt (12.2 g). $^{13}$C-NMR (300 MHz, D$_2$O): δ 173 (s, 2 C).

Example 215

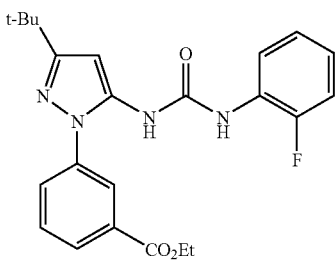

Using general method A, Example A1 (143 mg, 0.5 mmol) and 1-fluoro-2-isocyanato-benzene (67 mg, 0.5 mmol) were combined to afford ethyl 3-{3-t-butyl-5-[3-(2-fluorophenyl)ureido]-1H-pyrazol-1-yl}benzoate (40 mg, 19% yield).

Example 216

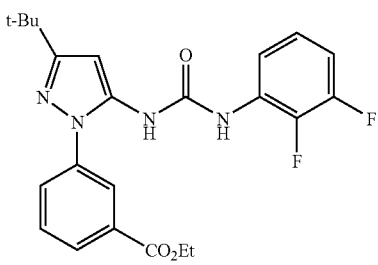

Using general method B, Example A1 (143 mg, 0.5 mmol) and 2,3-difluorophenylamine (67 mg, 0.5 mmol) were combined to afford ethyl 3-{3-t-butyl-5-[3-(2,3-difluorophenyl)ureido]-1H-pyrazol-1-yl}benzoate (50 mg, 23% yield).

Example 217

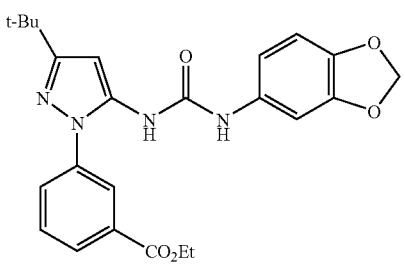

Using general method A, Example A1 (500 mg, 1.74 mmol) and 5-isocyanato-benzo[1,3]dioxole (290 mg, 1.8 mmol) were combined to afford ethyl 3-{5-[3-(benzo[d][1,3]dioxo-5-yl)ureido]-3-t-butyl-1H-pyrazol-1-yl}benzoate (320 mg, 41% yield). $^1$H NMR (300 MHz, DMSO-$d_6$): δ 8.73 (s, 1H), 8.34 (s, 1H), 8.03 (s, 1H), 7.92 (d, J=8.4 Hz, 1H), 7.78 (d, J=7.8 Hz, 1H), 7.63 (t, J=7.8 Hz, 1H), 7.09 (s, 1H), 6.76 (d, J=–8.1 Hz, 2H), 6.68 (d, J=8.4 Hz, 1H), 6.32 (s, 1H), 5.92 (s, 2H), 4.29 (q, J=6.9 Hz, 2H), 1.28 (s, 9H), 1.26 (t, J=6.9 Hz, 3H); MS (ESI) m/z: 451 (M+H$^+$).

Example 218

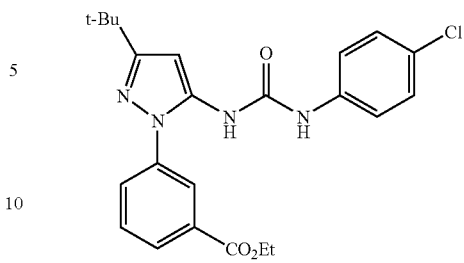

Using general method A, Example A1 (10.7 g, 70.0 mmol) and 4-nitrophenyl 4-chlorophenylcarbamate (10 g, 34.8 mmol) were combined to yield ethyl 3-{3-t-butyl-5-[3-(4-chlorophenyl)ureido]-1H-pyrazol-1-yl}benzoate (8.0 g, 52% yield). $^1$H NMR (DMSO-$d_6$): δ 9.11 (s, 1H), 8.47 (s, 1H), 8.06 (m, 1H), 7.93 (d, J=7.6 Hz, 1H), 7.81 (d, J=8.0 Hz, 1H), 7.65 (dd, J=8.0, 7.6 Hz, 1H), 7.43 (d, J=8.8 Hz, 2H), 7.30 (d, J=8.8 Hz, 2H), 6.34 (s, 1H), 4.30 (q, J=6.8 Hz, 2H), 1.27 (s, 9H), 1.25 (t, J=6.8 Hz, 3H); MS (ESI) m/z: 441 (M$^+$+H).

Example 219

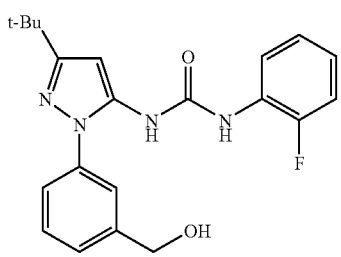

Using General method C, Example 215 (35 mg, 0.083 mmol) was reduced to afford 1-{3-t-butyl-1-[3-(hydroxymethyl)phenyl]-1H-pyrazol-5-yl}-3-(2-fluorophenyl)urea (20 mg, 63% yield). $^1$H-NMR (300 MHz, DMSO-$d_6$): δ 8.90 (br s, 1H), 8.81 (s, 1H), 8.08 (t, J=6.3 Hz, 1H), 7.48-6.98 (m, 7H), 6.36 (s, 1H), 5.30 (t, J=5.7 Hz, 1H), 4.55 (d, J=5.7 Hz, 1H), 1.22 (s, 9H); MS (ESI) m/z: 383 (M+H$^+$).

Example 220

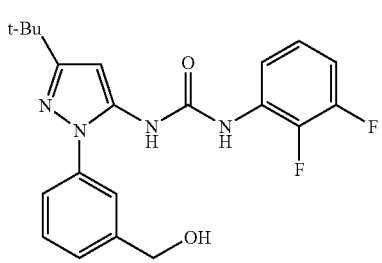

Using General method C, Example 216 (45 mg, 0.10 mmol) was reduced to afford 1-{3-t-butyl-1-[3-(hydroxymethyl)phenyl]-1H-pyrazol-5-yl}-3-(2,3-difluorophenyl)urea (30 mg, 75% yield). $^1$H-NMR (300 MHz, DMSO-$d_6$): δ 9.08 (s, 1H), 8.85 (s, 1H), 7.88 (t, J=7.5 Hz, 1H), 7.48-7.42 (m, 2H), 7.33 (d, J=7.5 Hz, 2H), 7.13-6.95 (m, 2H), 6.36 (s, 1H), 4.55 (s, 1H), 1.24 (s, 9H); MS (ESI) m/z: 401 (M+H$^+$).

Example 221

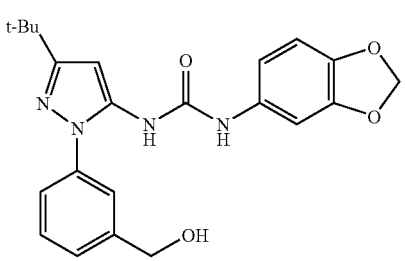

Using General method C, Example 217 (100 mg, 0.22 mmol) was reduced to afford 1-(benzo[d][1,3]dioxol-5-yl)-3-(3-t-butyl-1-(3-(hydroxymethyl)phenyl)-1H-pyrazol-5-yl) urea (50 mg, 56% yield). $^1$H NMR (300 MHz, CD$_3$OD): δ 7.52-7.47 (m, 4H), 7.02 (s, 1H), 6.65-6.69 (m, 2H), 6.41 (s, 1H), 5.89 (s, 2H), 4.69 (s, 2H), 1.33 (s, 9H); MS (ESI) m/z: 409 (M+H$^+$).

Example A61

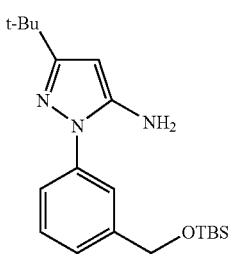

To a solution of CuI (1 mol %), 1,10-phenanthroline (10 mol %), Cs$_2$CO$_3$ (9.8 g, 30 mmol) and DMF (20 mL) was added t-butyl carbazate (3.4 g, 25 mmol), 3-iodobenzyl alcohol (5.0 g, 21 mmol). The reaction mixture was heated at 80° C. for 2 h. The reaction mixture was filtered through a pad of silica gel and the filtrate was evaporated under reduced pressure to obtain crude product, 1-Boc-1-(3-carbinol)phenylhydrazine as yellow oil. The product was used for the next reaction without further purification.

To a solution of 1-Boc-1-(3-carbinol)phenylhydrazine (2.0 g, 8.4 mmol) in absolute ethanol (30 mL) at RT was added conc. HCl (3.5 mL, 42 mmol). The reaction mixture was stirred at 60° C. for 30 min. Pivaloylacetonitrile (1.3 g, 10 mmol) was added into the reaction mixture, which was heated at 90° C. for 3 h. The solvent was evaporated under reduced pressureand the residue was dissolved in water and lyophilized to obtain the crude product [3-(5-amino-3-t-butyl-1H-pyrazol-1-yl)phenyl]methanol as the HCl salt. The product was used for the next step without further purification. $^1$H-NMR (DMSO-d$_6$): δ 7.4-7.6 (m, 4H), 5.62 (br s, 1H), 4.59 (s, 2H), 1.29 (s, 9H).

To a solution of [3-(5-amino-3-t-butyl-1H-pyrazol-1-yl)phenyl]methanol hydrochloride salt (2.0 g, 7.1 mmol) in DMF (20 mL) was added imidazole (2.7 g, 39 mmol) and TBSCl (2.1 g, 14 mmol), which was stirred at RT for 8 h. The reaction mixture was quenched with water and extracted with EtOAc (3×). Organic extracts were washed with NaHCO$_3$, H$_2$O and 10% LiCl solution. The combined organic extracts were washed with brine, dried (Na$_2$SO$_4$), filtered, concentrated and purified via column chromatography to yield 3-t-butyl-1-(3-[(t-butylmethylsilyloxy)methyl]phenyl}-1H-pyrazol-5-amine in 36% yield (for three steps): $^1$H-NMR (CDCl$_3$): δ 7.3-7.6 (m, 4H), 5.54 (s, 1H), 4.80 (s, 2H), 1.34 (s, 9H), 0.97 (s, 9H), 0.13 (s, 6H); MS (EI) m/z: 360 (M+H$^+$).

Example 222

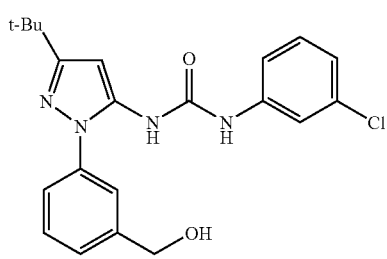

To a solution of Example A61 (100 mg, 0.18 mmol) in THF (2 mL) was added pyridine (45 mL, 0.56 mmol) and 3-chlorophenyl isocyanate (43 mg, 0.18 mmol). The reaction mixture was stirred at RT for 20 min, heated until all solids were dissolved, and stirred at RT for 4 h. The reaction mixture was concentrated under reduced pressure to yield 1-(3-t-butyl-1-{3-[(t-butyldimethylsilyloxy)methyl]phenyl}-1H-pyrazol-5-yl)-3-(3-chlorophenyl)urea (62 mg, 43% yield).

To a solution of 1-(3-t-butyl-1-{3-[(t-butyldimethylsilyloxy)methyl]phenyl}-1H-pyrazol-5-yl)-3-(3-chlorophenyl) urea (120 mg, 0.12 mmol) in THF (2 mL) was added TBAF (1.0 M, 0.13 mL, 0.13 mmol). The reaction mixture was stirred at RT for 2.5 h. The solvent was removed under reduced pressure. EtOAc was added into the residue followed by 1N—HCl (5 drops). The combined organic extracts were washed with brine, dried (Na$_2$SO$_4$), filtered, concentrated and purified via column chromatography to yield 1-(3-t-butyl-1-(3-hydroxymethyl)phenyl)-1H-pyrazol-5-yl)-3-(3-chlorophenyl)urea as a white powder (34 mg, 71% yield). $^1$H-NMR (CDCl$_3$): δ 8.11 (s, 1H), 7.34 (t, J=2.0 Hz, 1H), 7.05-7.25 (m, 7H), 6.99 (dt, J=1.3, and 7.8 Hz, 1H), 6.39 (s, 1H), 4.39 (s, 2H), 1.33 (s, 9H); MS (EI) m/z: 399 (M+H$^+$).

Example 223

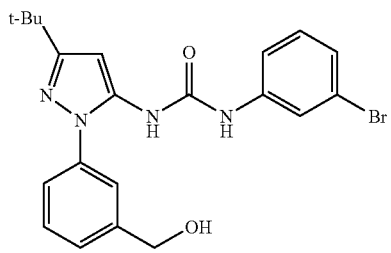

Using the same procedureas for Example 222, Example A61 (100 mg, 0.28 mmol) and 3-bromophenyl isocyanate (55 mg, 0.28 mmol) were combined to yield 1-{3-t-butyl-1-[3-(hydroxymethyl)phenyl]-1H-pyrazol-5-yl}-3-(3-bromophenyl)urea as a white powder (19 mg, 15% yield). $^1$H-NMR (CDCl$_3$): δ 8.17 (s, 1H), 7.47 (t, J=1.8 Hz, 1H), 7.34 (s, 1H), 7.00-7.25 (m, 7H), 6.39 (s, 1H), 4.37 (s, 2H), 1.32 (s, 9H); MS (EI) m/z: 443 and 445 (M$^+$ and M$^+$+2H$^+$).

Example 224

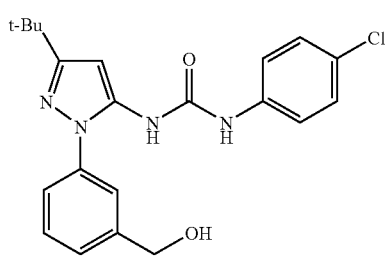

To a stirred solution of Example 218 (1.60 g, 3.63 mmol) in THF (200 mL) was added LiAlH$_4$ powder (413 mg, 10.9 mmol) at −10° C. under N$_2$. The mixture was stirred for 2 h and excess LiAlH₄ was quenched by adding ice. The solution was acidified to pH=7 with dilute HCl. Solvents were slowly removed and the solid was filtered and washed with EtOAc (200+100 mL). The filtrate was concentrated to yield 1-{3-t-butyl-1-[3-hydroxymethyl)phenyl]-1H-pyrazol-5-yl}-3-(4-chlorophenyl)urea (1.40 g, 97% yield). $^1$H NMR (DMSO-d₆): δ 9.11 (s, 1H), 8.47 (s, 1H), 7.47-7.27 (m, 8H), 6.35 (s, 1H), 5.30 (t, J=5.6 Hz, 1H), 4.55 (d, J=5.6 Hz, 2H), 1.26 (s, 9H); MS (ESI) m/z: 399 (M+H⁺).

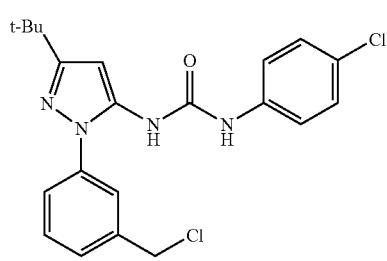

Example A62

A solution of Example 224 (800 mg, 2.0 mmol) and SOCl₂ (0.30 mL, 4 mmol) in CHCl₃ (30 mL) was refluxed gently for 3 h. The solvent was evaporated in vacuo and the residue was taken up to in CH₂Cl₂ (2×20 mL). After removal of the solvent, 1-{3-t-butyl-1-[3-(chloromethyl)phenyl]-1H-pyrazol-5-yl}-3-(4-chlorophenyl)urea (812 mg, 97% yield) was obtained as white powder. $^1$H NMR (DMSO-d₆): δ 9.57 (s, 1H), 8.75 (s, 1H), 7.63 (s, 1H), 7.50-7.26 (m, 7H), 6.35 (s, 1H), 4.83 (s, 2H), 1.27 (s, 9H); MS (ESI) m/z: 417

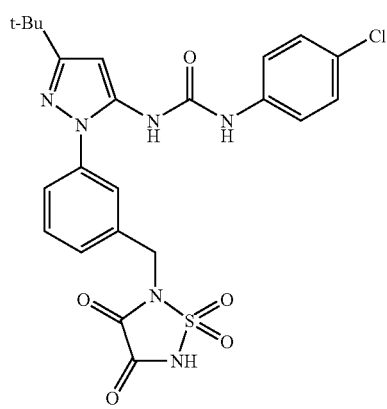

Example 225

To a mixture of Example A62 (100 mg, 0.24 mmol) in DMF (2 mL) was added Example A60 (91.0 mg, 0.48 mmol) at RT, which was stirred overnight at RT. The reaction solution was concentrated and the residue purified via column chromatography to yield 1-{5-t-butyl-2-[3-(1,1,3,4-tetraoxo-1λ⁶-[1,2,5]thiadiazolidin-2-ylmethyl)phenyl]-2H-pyrazol-3-yl}-3-(4-chlorophenyl)urea (40 mg, 31% yield). $^1$H-NMR (300 MHz, DMSO-d₆): δ 8.96 (s, 1H), 8.45 (s, 1H), 7.53 (s, 1H), 7.25-7.46 (m, 7H), 6.35 (s, 1H), 4.69 (s, 2H), 1.25 (s, 9H).

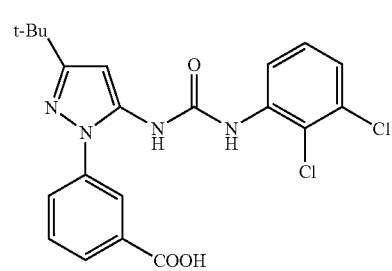

Example 226

Using General method E, Example A2 (80 mg, 0.17 mmol) was saponified to afford 3-{3-t-butyl-5-[3-(2,3-dichlorophenyl)ureido]-1H-pyrazol-1-yl}benzoic acid (60 mg, 79% yield). $^1$H-NMR (300 MHz, DMSO-d₆): δ 9.46 (br s, 1H), 8.82 (br s, 1H), 8.05 (br s, 1H), 7.98 (t, J=4.8 Hz, 1H), 7.92 (d, J=7.8 Hz, 1H), 7.80 (d, J=8.7 Hz, 1H), 7.63 (t, J=7.8 Hz, 1H), 7.27 (d, J=4.5 Hz, 2H), 6.37 (s, 1H), 1.26 (s, 9H)

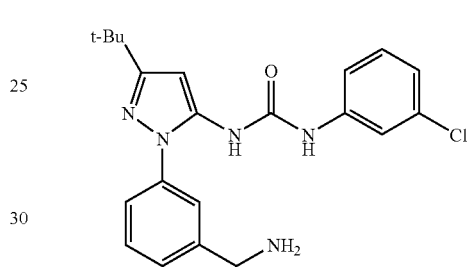

Example 227

Using the same procedureas for Example 41, Example 116 (0.11 g, 0.28 mmol) was reduced to afford 1-{1-[3-(aminomethyl)phenyl]-3-t-butyl-1H-pyrazol-5-yl}-3-(3-chloro-phenyl)urea as an off-white HCl salt (77.2 mg, 64% yield). $^1$H NMR (DMSO-d₆): δ 10.11 (s, 1H), 8.91 (s, 1H), 8.43 (br s, 3H), 7.72 (s, 1H), 7.68 (s, 1H), 7.56-7.55 (m, 2H), 7.48-7.46 (m, 1H), 7.31-7.25 (m, 2H), 7.02-6.99 (m, 1H), 6.42 (s, 1H), 4.16-4.12 (m, 2H), 1.30 (s, 9H); MS (ESI) m/z: 398.3 (M+H⁺), 400.2 (M+2+H⁺).

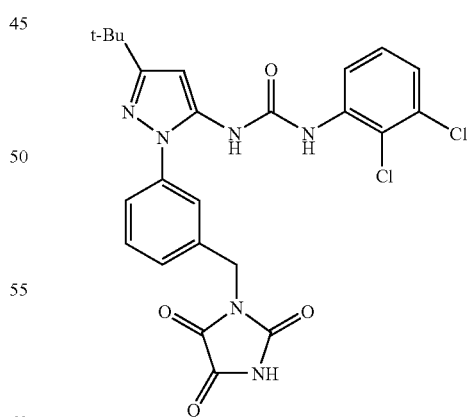

Example 228

To a solution of Example 1 (150 mg, 0.34 mmoL), Example A59 (43 mg, 3.7 mmol) and PPh₃ (98 mg, 3.7 mmoL) in anhydrous THF (1 mL) was slowly added a solution of DEAD (74 μL, 3.7 mmoL) in THF (1 mL). The reaction mixture was allowed to stir for 3 h and then quenched with H₂O, extracted with CH₂Cl₂ (3×25 mL), dried (MgSO₄), filtered, concentrated and purified by column chromatography to yield 1-(3-t-butyl-1-(3-((2,4,5-trioxoimidazolidin-1-yl)methyl)phenyl)-1H-pyrazol-5-yl)-3-(2,3-dichlorophenyl)urea (60 mg, 33.4%). ¹H NMR (300 MHz, DMSO-d₆): 12.05 (s, 1H), 9.24 (s, 1H), 8.70 (s, 1H), 8.04 (m, 1H), 7.35-7.46 (m, 4H), 7.25-7.27 (m, 2H), 6.37 (s, 1H), 4.68 (s, 2H), 1.28 (s, 9H); MS (ESI) m/z: 529 (M+H⁺)

Example 229

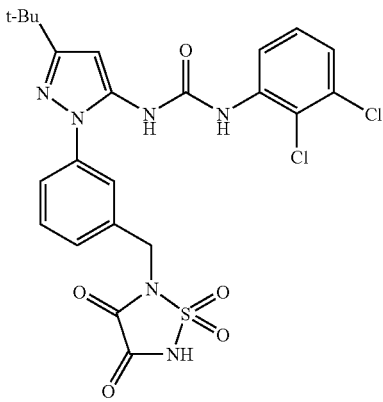

To a solution of Example 1 (300 mg, 0.7 mmol) in anhydrous DMF (6 mL) was added SOCl₂ (165 mg, 0.1 mL, 1.4 mmol) at 0°C. The solution was heated at reflux for 4 h and concentrated to yield 1-(3-t-butyl-1-(3-(chloromethyl)phenyl)-1H-pyrazol-5-yl)-3-(2,3-dichlorophenyl)urea (150 mg, 43% yield), which was used without further purification. MS (ESI) m/z: 451 (M+H⁺).

To a solution of the material from the previous reaction (150 mg, 0.33 mmol) in anhydrous DMF (10 mL) was added 1,2,5-thiadiazolidine-3,4-dione 1,1-dioxide disodium salt (136 mg, 0.70 mmol) and KI (17 mg, 0.1 mmol). The mixture was stirred at 40° C. overnight. After filtration, the solution was concentrated to give the crude product, which was purified by reverse phase chromatography to afford 1-{5-t-butyl-2-[3-(4-methylene-1,1,3-trioxo-[1,2,5]thiadiazolidin-2-ylmethyl)-phenyl]-2H-pyrazol-3-yl}-3-(2,3-dichlorophenyl)-urea (18 mg, 5%). ¹H NMR (DMSO-d₆): 9.28 (s, 1H), 8.73 (s, 1H), 8.04 (t, J=3.3 Hz, 1H), 7.52 (s, 1H), 7.45 (d, J=7.8 Hz, 1H), 7.35 (q, J=7.8 Hz, 2H), 7.27 (t, J=3.3 Hz, 2H), 6.36 (s, 1H), 4.70 (s, 2H), 4.65 (s, 1H), 1.24 (s, 9H). MS (ESI) m/z: 565 (M+H⁺).

Example 230

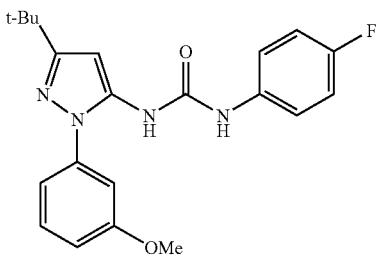

Using General method A, Example A4 (70 mg, 0.29 mmol) and 4-fluorophenylisocyanate (39 mg, 0.29 mmol) were combined to afford 1-(3-t-butyl-1-(3-methoxyphenyl)-1H-pyrazol-5-yl)-3-(4-fluorophenyl)urea as a white powder (38 mg, 35% Yield). ¹H NMR (300 MHz, CDCl₃): δ 7.59 (brs, 1H), 7.16 (t, J=8.4 Hz, 1H), 6.8-7.1 (m-, 8H), 6.77 (dd, J=1.8 and 8.7 Hz, 1H), 6.30 (s, 1H), 3.66 (s, 3H), 1.27 (s, 9H); MS (EI) m/z: 383 (M+H⁺).

Example 231

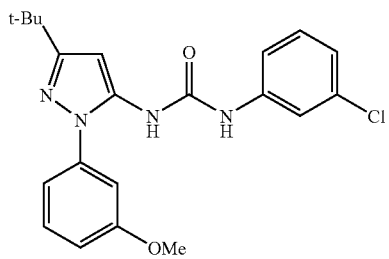

Using General method A, Example A4 (70 mg, 0.29 mmol) and 3-chlorophenylisocyanate (44 mg, 0.29 mmol) were combined to afford 1-(3-t-butyl-1-(3-methoxyphenyl)-1H-pyrazol-5-yl)-3-(3-chlorophenyl)urea (83 mg, 73% yield). ¹H NMR (300 MHz, CDCl₃): δ 8.30 (s, 1H), 7.38 (s, 1H), 7.20 (t, J=1.8 Hz, 1H), 7.07 (m, 2H), 6.95 (dt, J=1.2, and 7.8 Hz, 2H), 6.82 (t, J=2.1 Hz, 1H), 6.78 (s, 1H), 7.72 (dd, J=2.1, and 8.7 Hz, 1H), 6.28 (s, 1H), 3.56 (s, 3H), 1.21 (s, 9H); MS (EI) m/z: 399 (M+H⁺).

Example 232

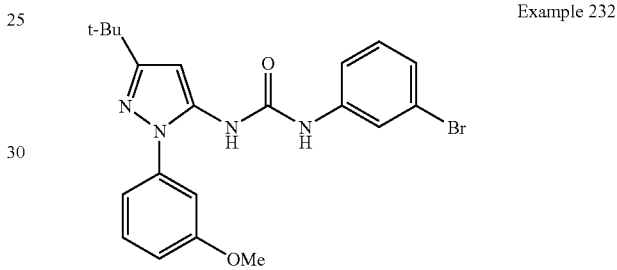

Using General method A, Example A4 (70 mg, 0.29 mmol) and 3-bromophenylisocyanate (57 mg, 0.29 mmol) were combined to afford 1-(3-t-butyl-1-(3-methoxyphenyl)-1H-pyrazol-5-yl)-3-(3-bromophenyl)urea as a white solid (107 mg, 85% yield). ¹H NMR (300 MHz, CDCl₃): δ 8.08 (brs, 1H), 7.38 (s, 1H), 7.23 (s, 1H). 7.0-7.2 (m, 4H), 7.8-7.9 (m, 2H), 6.75 (dd, J=2.4 and 8.4 Hz, 1H), 6.32 (s, 1H), 3.59 (s, 3H), 1.24 (s, 9H); MS (EI) m/z: 443 and 445 (M⁺ and M+2H⁺).

Example 233

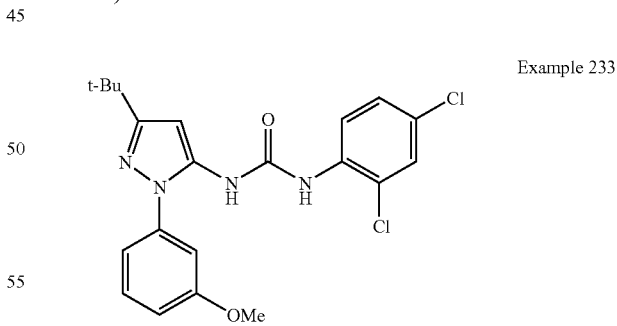

Using General method A, Example A4 (70 mg, 0.29 mmol) and 2,4-dichlorophenyl isocyanate (54 mg, 0.29 mmol) were combined to afford 1-(3-t-butyl-1-(3-methoxyphenyl)-1H-pyrazol-5-yl)-3-(2,4-dichlorophenyl)urea (76 mg, 61% yield). ¹H NMR (CDCl₃): δ 7.96 (d, J=9.0 Hz), 7.67 (s, 1H), 7.65 (s, 1H), 7.29 (d, J=2.4 Hz, 1H), 7.19 (t, J=7.8 Hz, 1H), 7.14 (dd, J=2.4, and 9.0 Hz, 1H), 6.9-7.0 (m, 2H), 6.78 (dd, J=2.4, and 8.7 Hz, 1H), 6.33 (s, 1H), 3.70 (s, 3H), 1.32 (s, 9H); MS (EI) m/z: 433 (M+H⁺).

Example 234

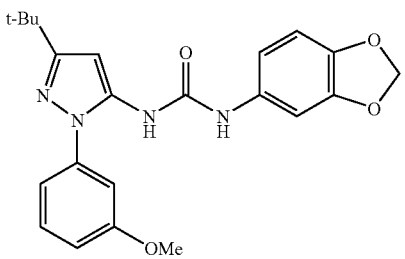

Using General method A, Example A4 (86 mg, 0.35 mmol) and 5-isocyanatobenzo[d][1,3]dioxole (69 mg, 0.43 mmol) were combined to afford 1-(benzo[d][1,3]dioxo-5-yl)-3-(3-t-butyl-1-(3-methoxyphenyl)-1H-pyrazol-5-yl)urea as a pale yellow solid (98 mg, 68% yield). $^1$H NMR (400 MHz, DMSO-d$_6$): δ 8.94 (s, 1H), 8.92 (brs, 1H), 8.31 (s, 1H), 7.42 (t, J=8.1 Hz, 1H), 7.0-7.2 (m, 3H), 6.98 (dd, J=1.8, and 8.4 Hz, 1H), 6.80 (d, J=8.4 Hz, 1H), 6.71 (dd, J=2.0, and 8.4 Hz, 1H), 6.35 (s, 1H), 5.96 (s, 2H), 3.80 (s, 3H), 1.28 (s, 9H); MS (EI) m/z: 409 (M+H$^+$).

Example 235

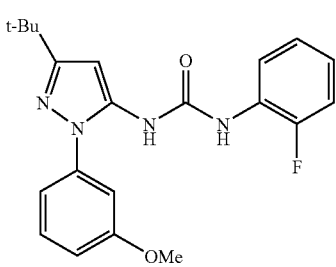

To a solution of Example A4 (123 mg, 0.5 mmol) and triethylamine (101 mg, 1.0 mmol) in anhydrous THF (5 mL) was added 1-fluoro-2-isocyanato-benzene (69 mg, 0.5 mmol) at 0° C. This resulted mixture was stirred at RT for 3 h, and extracted with EtOAc. The combined organic extracts were washed with brine, dried (Na$_2$SO$_4$), filtered, concentrated and purified by preparative TLC to afford 1-[3-t-butyl-1-(3-methoxy-phenyl)-1H-pyrazol-5-yl]-3-(2-fluorophenyl)urea. $^1$H-NMR (300 MHz, DMSO-d$_6$): δ 8.92 (s, 1H), 8.80 (s, 1H), 8.06 (t, J=7.5 Hz, 1H), 7.39 (t, J=7.5 Hz, 1H), 7.17-6.96 (m, 6H), 6.35 (s, 1H), 3.75 (s, 3H), 1.22 (s, 9H); MS (ESI) m/z: 383 (M+H$^+$).

Example 236

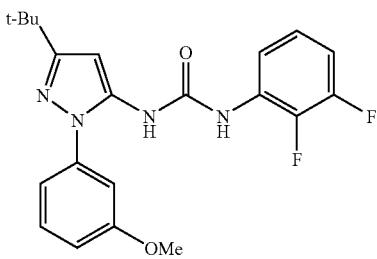

Using General method B, Example A4 (123 mg, 0.5 mmol) and 2,3-difluoro-phenylamine (65 mg, 0.5 mmol) were combined to afford 1-[3-t-butyl-1-(3-methoxy-phenyl)-1H-pyrazol-5-yl]-3-(2,3-difluorophenyl)urea. $^1$H NMR (300 MHz, DMSO-d$_6$): δ 9.11 (s, 1H), 8.84 (s, 1H), 7.87 (t, J=7.8 Hz, 1H), 7.40 (t, J=7.8 Hz, 1H), 7.09-6.94 (m, 5H), 6.36 (s, 1H), 3.76 (s, 3H), 1.23 (s, 9H); MS (ESI) m/z: 401 (M+H$^+$).

Example A63

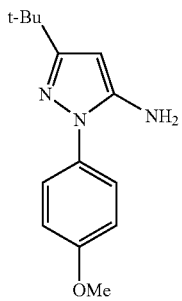

A mixture of (4-methoxy-phenyl)-hydrazine (17.4 g, 0.1 mol) and 4,4-dimethyl-3-oxo-pentanenitrile (13.8 g, 0.11 mol) in ethanol (500 mL) and conc. HCl (50 mL) was heated to reflux overnight. After removal of the solvent, the residue was purified by column chromatography to give 3-t-butyl-1-(4-methoxyphenyl)-1H-pyrazol-5-amine (20 g, 82% yield). $^1$H-NMR (300 MHz, DMSO-d$_6$): δ 7.38 (d, J=9.0 Hz, 2H), 6.97 (d, J=9.0 Hz, 2H), 5.32 (s, 1H), 4.99 (br s, 2H), 3.75 (s, 3H), 1.17 (s, 9H); MS (ESI) m/z: 246 (M+H$^+$).

Example 237

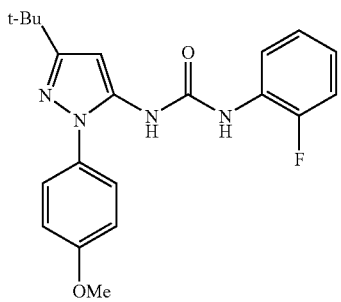

Using General method A, Example A63 (123 mg, 0.5 mmol) and 1-fluoro-2-isocyanato-benzene (69 mg, 0.5 mmol) were combined to afford 1-[3-t-butyl-1-(4-methoxyphenyl)-1H-pyrazol-5-yl]-3-(2-fluorophenyl)urea. $^1$H NMR (300 MHz, DMSO-d$_6$): δ 9.01 (s, 1H), 8.89 (s, 1H), 8.09 (t, J=7.8 Hz, 1H), 7.36 (d, J=8.7 Hz, 2H), 7.09-7.21 (m, 2H), 7.05 (d, J=8.7 Hz, 2H), 6.97 (t, J=8.7 Hz, 1H), 6.32 (s, 1H), 3.79 (s, 3H), 1.23 (s, 9H); MS (ESI) m/z: 383 (M+H$^+$).

Example 238

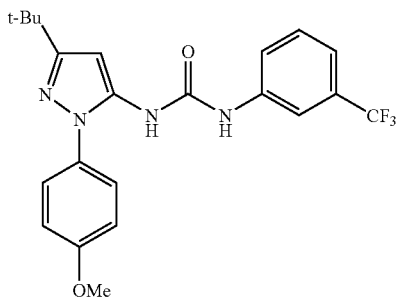

Using General method A, Example A63 (123 mg, 0.5 mmol) and 1-isocyanato-3-trifluoromethyl-benzene (93 mg, 0.5 mmol) were combined to afford 1-[3-t-butyl-1-(4-methoxyphenyl)-1H-pyrazol-5-yl]-3-(3-trifluoromethylphenyl)urea (65 mg, 30% yield). $^1$H NMR (300 MHz, DMSO-d$_6$): δ 9.38 (s, 1H), 8.40 (s, 1H), 7.94 (br s, 1H), 7.45 (d, J=4.8 Hz, 2H), 7.38 (d, J=9.0 Hz, 2H), 7.27 (m, 1H), 7.03 (d, J=9.0 Hz, 2H), 6.32 (s, 1H), 3.78 (s, 3H), 1.24 (s, 9H); MS (ESI) m/z: 433 (M+H$^+$).

Example 239

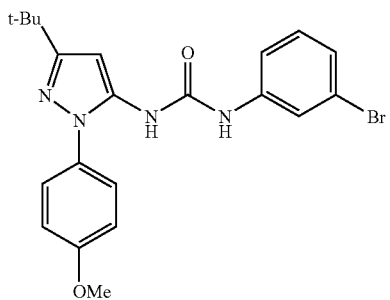

Using General method A, Example A63 (123 mg, 0.5 mmol) and 1-bromo-3-isocyanato-benzene (98 mg, 0.5 mmol) were combined to afford 1-(3-bromophenyl)-3-[3-t-butyl-1-(4-methoxyphenyl)-1 H-pyrazol-5-yl]urea (65 mg, 29% yield). $^1$H-NMR (300 MHz, DMSO-$d_6$): δ 9.18 (s, 1H), 8.34 (s, 1H), 7.80 (br s, 1H), 7.37 (d, J=9.0 Hz, 2H), 7.18 (d, J=5.1 Hz, 2H), 7.12 (m, 1H), 7.03 (d, J=9.0 Hz, 2H), 6.31 (s, 1H), 3.78 (s, 3H), 1.24 (s, 9H); MS (ESI) m/z: 443 (M+H$^+$).

Example 240

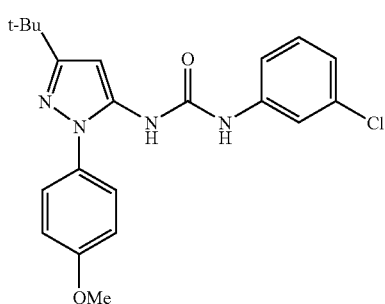

Using General method A, Example A63 (123 mg, 0.5 mmol) and 1-chloro-3-isocyanato-benzene (76 mg, 0.5 mmol) were combined to afford 1-[3-t-butyl-1-(4-methoxyphenyl)-1H-pyrazol-5-yl]-3-(3-chlorophenyl)urea (65 mg, 33% yield). $^1$H-NMR (300 MHz, DMSO-$d_6$): δ 9.17 (s, 1H), 8.34 (s, 1H), 7.65 (t, J=2.1 Hz, 1H), 7.37 (d, J=9.0 Hz, 2H), 7.22 (m, 1H), 7.15 (m, 1H), 6.31 (s, 1H), 3.78 (s, 3H), 1.24 (s, 9H); MS (ESI) m/z: 399 (M+H$^+$).

Example 241

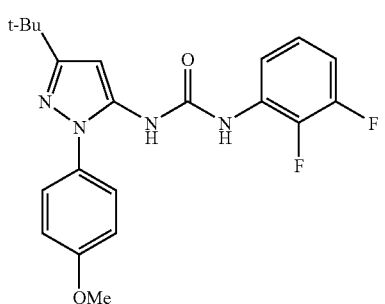

Using General method B, Example A63 (123 mg, 0.5 mmol) and 1-fluoro-2,3-difluorophenylamine (65 mg, 0.5 mmol) were combined to afford 1-[3-t-butyl-1-(4-methoxyphenyl)-1H-pyrazol-5-yl]-3-(2,3-difluorophenyl)urea (65 mg, 32% yield). $^1$H-NMR (300 MHz, DMSO-$d_6$): δ9.08 (s, 1H), 8.77 (s, 1H), 7.90 (t, J=7.2 Hz, 1H), 7.37 (d, J=9.0 Hz, 2H), 7.13-6.95 (m, 4H), 6.33 (s, 1H), 3.79 (s, 3H), 1.23 (s, 9H); MS (ESI) m/z: 401 (M+H$^+$).

Example A64

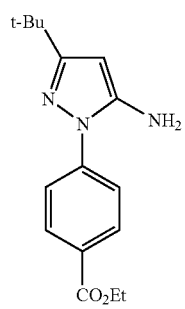

Ethyl 4-(3-t-butyl-5-amino-1H-pyrazol-1-yl)benzoate (3.67 mmol) was prepared from ethyl 4-hydrazinobenzoate and pivaloylacetonitrile by the procedure of Regan, et al., *J. Med. Chem.*, 45, 2994 (2002).

Example 242

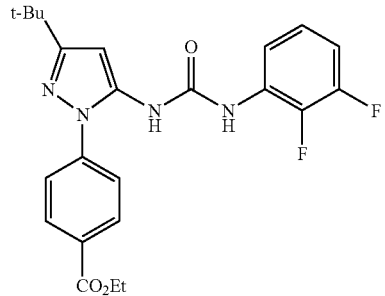

Using General method B, Example A64 (287 mg, 1.0 mmol), and 2,3-difluorophenylamine (134 mg, 1.0 mmol) were combined to afford ethyl 4-{3-t-butyl-5-[3-(2,3-difluorophenyl)ureido]-1H-pyrazol-1-yl}benzoate (250 mg, 57% yield).

Example 243

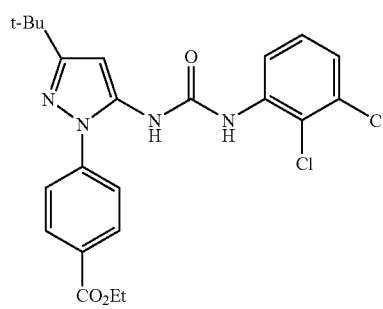

Using the same procedureas for Example A18, Example A64 (1 g, 3.09 mmol) and 1,2-dichloro-3-isocyanato-benzene (0.7 g, 3.71 mmol) were combined to afford ethyl 4-{3-t-butyl-5-[3-(2,3-dichlorophenyl)ureido]-1H-pyrazol-1-yl}benzoate (0.7 g, 48% yield). $^1$H-NMR (300 MHz, DMSO-$d_6$): δ 9.20 (br s, 1H), 8.77 (br s, 1H), 8.04 (m, 1H), 7.44 (br s, 4H), 7.29-7.26 (m, 2H), 6.36 (s, 1H), 4.31 (q, J=7.2 Hz, 2H), 1.27 (s, 9H), 1.26 (t, J=7.2 Hz, 3H).

Example 244

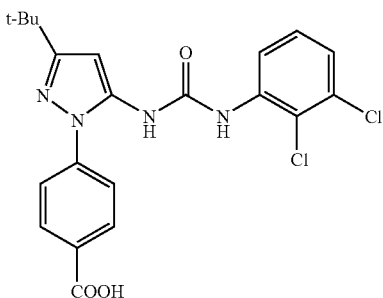

Using General method E, Example 243 (80 mg, 0.17 mmol) was saponified to afford 4-{3-t-butyl-5-[3-(2,3-dichlorophenyl)ureido]-1H-pyrazol-1-yl}benzoic acid (60 mg, 79% yield). $^1$H NMR (300 MHz, DMSO-$d_6$): δ 9.39 (br s, 1H), 8.78 (br s, 1H), 8.07-8.02 (m, 3H), 7.68 (d, J=8.4 Hz, 2H), 7.29 (d, J=7.8 Hz, 1H), 6.41 (s, 1H), 1.21 (s, 9H)

Example 245

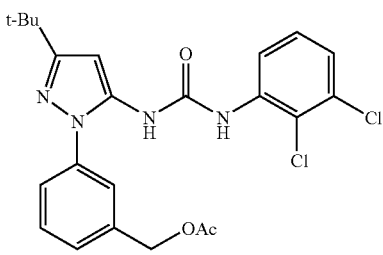

To a solution of Example 1 (100 mg, 0.23 mmol) and Et$_3$N (50 mg 0.5 mmol) in anhydrous CH$_2$Cl$_2$ (10 mL), was add acetyl chloride (22 mg, 0.28 mmol) at 0° C. The mixture was stirred at RT for 3 h and then poured into H$_2$O. The mixture was extracted with CH$_2$Cl$_2$ (3×50 mL). The combined organic layers were washed with brine, dried (Na$_2$SO$_4$), filtered, concentrated and purified via reverse phase chromatography to afford 3-(3-t-butyl-5-(3-(2,3-dichlorophenyl)ureido)-1H-pyrazol-1-yl)benzyl acetate (58 mg ◊53% yield). $^1$H NMR (DMSO-$d_6$): 9.25 (s, 1H), 8.73 (s, 1H), 8.00 (m, 1H), 7.48-7.41 (m, 3H), 7.36 (m, 1H), 7.26-7.22 (m, 2H), 6.33 (s, 1H), 5.09 (s, 2H), 1.98 (s, 3H), 1.22 (s, 9H). MS (ESI) m/z: 475 (M+H$^+$).

Example 246

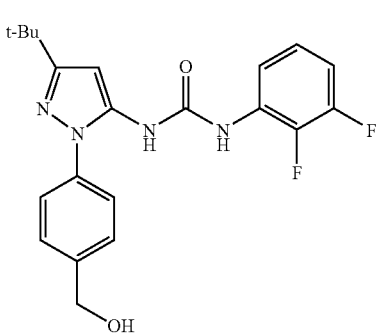

Using General method C, Example 242 (230 mg, 0.52 mmol) was reduced to afford 1-{3-t-butyl-1-[4-(hydroxymethyl)phenyl]-1H-pyrazol-5-yl}-3-(2,3-difluoro-phenyl)urea (160 mg, 80% yield). $^1$H NMR (300 MHz, DMSO-$d_6$): δ 9.14 (s, 1H), 8.95 (s, 1H), 7.84-6.82 (m, 7H), 6.25 (s, 1H), 5.27 (t, J=5.7 Hz, 1H), 4.42 (br s, 2H), 1.14 (s, 9H); MS (ESI) m/z: 401 (M+H$^+$).

Example 247

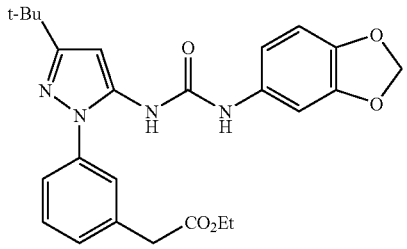

To a solution of Example A5 (1.0 g, 3.32 mmol) and triethylamine (606 mg, 6.0 mmol) in THF (50 mL) was added 5-isocyanato-benzo[1,3]dioxole (570 mg, 3.5 mmol) in THF (5.0 mL) at 0° C. The mixture was stirred at RT for 3 h, and then poured into water (100 mL). The mixture was extracted with CH$_2$Cl$_2$ (3×). The combined organic extracts were washed with brine, dried (Na$_2$SO$_4$), filtered, concentrated and purified via column chromatography to afford ethyl 2-(3-{5-[3-(benzo[d][1,3]dioxol-5-yl)ureido]-3-t-butyl-1H-pyrazol-1-yl}phenyl)-acetate (950 mg, 62% yield). $^1$H NMR (300 MHz, DMSO-$d_6$): δ 8.84 (s, 1H), 8.28 (s, 1H), 7.48-7.34 (m, 3H), 7.27 (d, J=8.4 Hz, 1H), 7.11 (s, 1H), 6.76 (d, J=7.8 Hz, 1H), 6.66 (d, J=7.8 Hz, 1H), 6.31 (s, 1H), 5.92 (s, 2H), 4.04 (q, J=7.2 Hz, 2H), 3.73 (s, 2H), 1.23 (s, 9H), 1.15 (t, J=7.8 Hz, 3H); MS (ESI) m/z: 465 (M+H$^+$).

Example 248

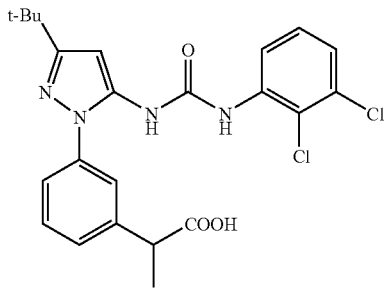

A suspension of Example A5 (575 mg, 1.70 mmol) in THF (10 mL) was cooled in a dry ice/acetone bath under Ar and treated with KHMDS (0.5 M in toluene, 6.0 mL, 3 mmol). The resultant red-brown-colored reaction mixture was stirred 15 min at −78° C. and was treated with methyl iodide (0.22 mL, 3.5 mmol) and stirred 30 min at −78° C., then allowed to warm to RT and quenched with saturated aqueous NH$_4$Cl (15 mL). The reaction mixture was partitioned between EtOAc (40 mL) and H$_2$O (15 mL). The organic layer was washed with H$_2$O, 5% Na$_2$S$_2$O$_3$, brine, dried (Na$_2$SO$_4$), filtered, concentrated and purified via column chromatography to yield 323 mg of a mixture of ethyl 2-(3-(5-amino-3-t-butyl-1H-pyrazol-1-yl)phenyl)propanoate and ethyl 2-(3-(5-amino-3-t-butyl-1H-pyrazol-1-yl)phenyl)-2-methylpropanoate (approx 2.5:1 ratio).

Using general method A, this mixture was combined with 2,3-dichlorophenyl isocyanate (0.15 mL, 1.14 mmol) to yield ethyl 2-(3-(3-t-butyl-5-(3-(2,3-dichlorophenyl)ureido)-1H-pyrazol-1-yl)phenyl)-2-methylpropanoate [MS (ESI) m/z: 517.0 (M+H⁺)] and ethyl 2-(3-(3-t-butyl-5-(3-(2,3-dichlorophenyl)ureido)-1H-pyrazol-1-yl)phenyl)propanoate (200 mg, MS (ESI) m/z: 503.0 (M+H⁺), which were separable by column chromatography. The latter compound was saponified using general method E to yield 2-(3-(3-t-butyl-5-(3-(2,3-dichlorophenyl)ureido)-1H-pyrazol-1-yl)phenyl)propanoic acid (61.5 mg, 72% yield) as a colorless crystalline solid. ¹H NMR (400 MHz, DMSO-d₆): δ 12.43 (s, 1H), 9.24 (s, 1H), 8.75 (s, 1H), 8.07 (m, 1H), 7.49 (t, J=8.0 Hz, 1H), 7.45-7.39 (m, 2H), 7.35-7.29 (m, 3H), 6.39 (s, 1H), 3.79 (q, J=7.2 Hz, 1H), 1.39 (d, J=7.2 Hz, 3H), 1.28 (s, 9H); MS (ESI) m/z: 475.0 (M+H⁺).

Example 249

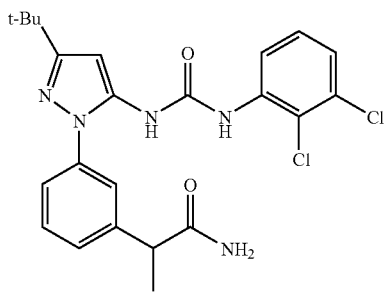

Using general method I, Example 248 (38 mg, 0.08 mmol) and NH₃ (0.5 M in dioxane, 0.48 mL, 0.24 mmol) were combined and the product crystallized from Et₂O to yield 1-(1-(3-(1-amino-1oxopropan-2-yl)phenyl)-3-t-butyl-1H-pyrazol-5-yl)-3-(2,3-dichlorophenyl)urea (13 mg, 34% yield). ¹H NMR (400 MHz, DMSO-d₆): δ 9.25 (s, 1H), 8.75 (s, 1H), 8.09 (m, 1H), 7.49-7.43 (m, 3H), 7.39-7.33 (m, 2H), 7.32-7.27 (m, 2H), 6.87 (br s, 1H), 6.39 (s, 1H), 3.66 (q, J=7.2 Hz, 1H), 1.34 (d, J=7.2 Hz, 3H), 1.28 (s, 9H); MS (ESI) m/z: 474.2 (M+H⁺).

Example 250

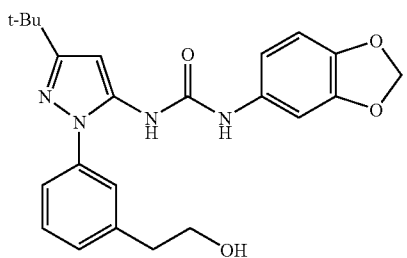

Using general method C, Example 247 (930 mg, 2.0 mmol) was reduced to afford 1-(benzo[d][1,3]dioxol-5-yl)-3-{3-t-butyl-1-[3-(2-hydroxyethyl)phenyl]-1H-pyrazol-5-yl}urea (800 mg, 95% yield). ¹H NMR (300 MHz, DMSO-d₆): δ 8.86 (s, 1H), 8.26 (s, 1H), 7.39-7.30 (m, 4H), 7.11 (s, 1H), 6.76 (d, J=8.1 Hz, 1H), 6.65 (d, J=7.8 Hz, 1H), 6.31 (s, 1H), 5.92 (s, 2H), 4.64 (t, J=5.4 Hz, 1H), 3.60 (q, J=6.9 Hz, 2H), 2.76 (t, J=7.2 Hz, 2H), 1.23 (s, 9H), 1.05 (t, J=7.2 Hz, 3H); MS (ESI) m/z: 423 (M+H⁺).

Example 251

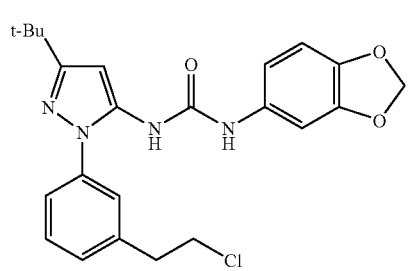

To a solution of Example 250 (750 mg, 1.78 mmol) in THF (50 mL) was added dropwise SOCl₂ (1.0 mL, 14 mmol) at 0° C. The mixture was heated to reflux for 3 h, then concentrated under reduced pressure to yield 1-(benzo[d][1,3]dioxol-5-yl)-3-{3-t-butyl-1-[3-(2-chloroethyl)phenyl]-1H-pyrazol-5-yl}urea (680 mg, 87% yield), which was used for the next reaction without further purification. MS (ESI) m/z: 441 (M+H⁺).

Example 252

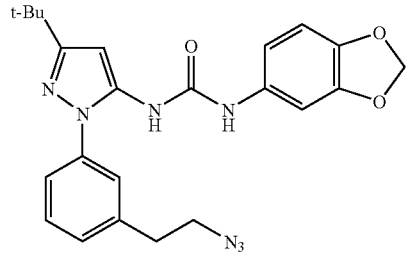

To a solution of Example 251 (680 mg, 1.5 mmol) in DMF (15 mL) was added NaN₃ powder (130 mg, 2.0 mmol), which was stirred at RT overnight. The mixture was poured into ice-water and extracted with EtOAc (3×). The combined organic extracts were washed with brine, dried (Na₂SO₄), filtered, concentrated and purified via column chromatography to afford 1-{1-[3-(2-azidoethyl)phenyl]-3-t-butyl-1H-pyrazol-5-yl}-3-(benzo[d][1,3]dioxol-5-yl)urea (450 mg, 67% yield). MS (ESI) m/z: 448 (M+H⁺).

Example 253

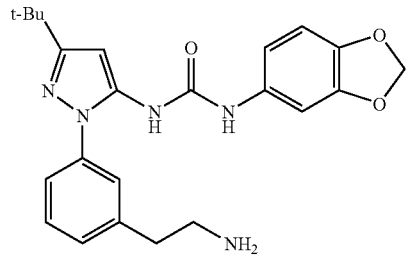

A mixture of Example 252 (200 mg, 0.45 mmol) and Pd/C (40 mg, 20%) in methanol (20 mL) was stirred at RT under 20 psi of H₂ for 3 h, and then filtered. The filtrate was concentrated and purified by preparative HPLC to afford the TFA salt. The mixture of TFA salt in MeCN/H₂O (50 mL) was basified to pH=10.0 with a aqueous solution of 1.0 N Na₂CO₃. After lyophilization, the residue was dissolved in THF and filtered. The filtrate was adjusted to pH=6.0 with 1.0 N HCl/MeOH (2.0 mL), then concentrated to yield 1-{1-[3-

(2-aminoethyl)phenyl]-3-t-butyl-1 H-pyrazol-5-yl}-3-(benzo[d][1,3]dioxol-5-yl)urea as the hydrochloride salt (80 mg, 40% yield). $^1$H NMR (300 MHz, DMSO-$d_6$): δ 9.37 (s, 1H), 8.65 (s, 1H), 7.92 (br s, 3H), 7.52-7.47 (m, 3H), 7.28 (d, J=7.8 Hz, 1H), 7.02 (s, 1H), 6.65-6.69 (m, 2H), 6.31 (s, 1H), 5.92 (s, 2H), 3.13-3.07 (m, 2H), 2.96-2.88 (m, 2H), 1.24 (s, 9H); MS (ESI) m/z: 422 (M+H$^+$).

Example 254

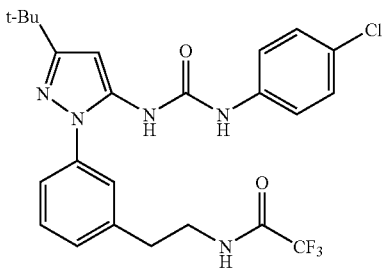

To a stirring solution of Example A17 (0.180 g, 0.51 mmol) in dry CH$_2$Cl$_2$ (5 ml) at RT was added 4-chlorophenyl isocyanate (82 mg, 0.53 mmol). The resulting mixture was stirred at RT overnight. More 4-chlorophenyl isocyanate was added (40 mg, 0.26 mmol) and stirring was continued. After 2 h, the reaction was concentrated to dryness and purified by flash chromatography to yield pure 1-(3-t-butyl-1-{3-[2-(2,2,2-trifluoroacetamido)ethyl]-phenyl}-1H-pyrazol-5-yl)-3-(4-chlorophenyl)urea as an orange foam (0.134 g, 52% yield). $^1$H NMR (CDCl$_3$): δ 8.14 (br s, 1H), 7.39-7.20 (m, 8H), 7.03 (br s, 1H), 6.57 (s, 1H), 3.77 (m, 2H), 2.88 (m, 2H), 1.35 (s, 9H); MS (ESI) m/z: 508.3 (M+H$^+$).

Example 255

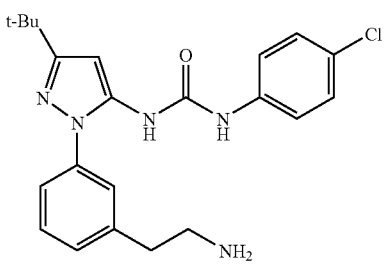

To a stirring solution of Example 254 (0.134 g, 0.264 mmol) in MeOH (10 ml) and H$_2$O (0.6 ml) at RT was added potassium carbonate (0.182 g, 1.32 mmol). The resulting suspension was stirred at 60-65° C. for 2 h, then cooled to RT and the volatiles evaporated. The residue was carefully dissolved in 1M HCl to pH 1-2 and extracted with Et$_2$O (2x). The aqueous was then basified (pH 13-14) with 3M NaOH and extracted with CH$_2$Cl$_2$ (4x). The combined CH$_2$Cl$_2$ extracts were washed with brine (1x), dried (Na$_2$SO$_4$), filtered, and concentrated to provided 1-{1-[3-(2-aminoethyl)phenyl]-3-t-butyl-1H-pyrazol-5-yl}-3-(4-chlorophenyl)urea as a foam (70.6 mg, 65% yield). $^1$H NMR (CDCl$_3$): δ 8.64 (br s, 1H), 7.33-7.00 (m, 8H), 6.39 (s, 1H), 2.65 (m, 4H), 1.31 (s, 9H); MS (ESI) m/z: 412.3 (M+H).

Example 256

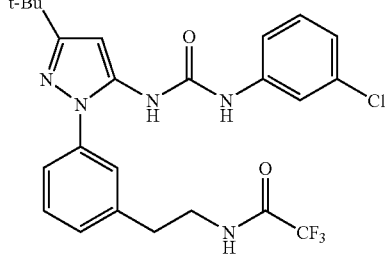

Using General method A, Example A15 (50 mg, 0.14 mmol) and 3-chlorophenyl isocyanate (0.034 ml, 0.28 mmol) were combined to afford 1-(3-t-butyl-1-{3-[2-(2,2,2-trifluoroacetamido)ethyl]phenyl}-1H-pyrazol-5-yl)-3-(3-chlorophenyl)urea (32.2 mg, 45% yield). $^1$H NMR (300 MHz, CDCl$_3$): δ 8.18 (s, 1H), 7.51-7.48 (m, 2H), 7.43 (s, 1H), 7.37-7.34 (m, 3H), 7.20-7.14 (m, 2H), 7.08-7.05 (m, 1H), 7.02-6.99 (m, 1H), 6.58 (s, 1H), 3.78 (q, J=6.4 Hz, 2H), 2.88 (t, J=6.4 Hz, 2H), 1.36 (s, 9H); MS (ESI) m/z: 508.3 (100, M+H$^+$), 510.2 (37, M+2H$^+$).

Example 257

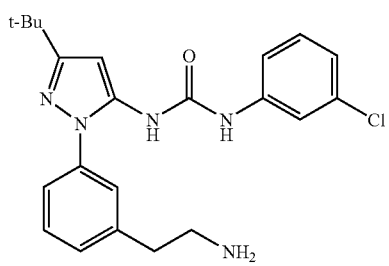

Using the same procedureas for Example 39, Example 122 (32.2 mg, 0.063 mmol) was deprotected to afford 1-{1-[3-(2-aminoethyl)phenyl]-3-t-butyl-1H-pyrazol-5-yl}-3-(3-chlorophenyl)urea (19.1 mg, 73% yield). $^1$H NMR (400 MHz, CDCl$_3$): δ 8.29 (brs, 1H), 7.46 (s, 1H), 7.43-7.29 (m, 1H), 7.23-7.19 (m, 2H), 7.16-7.10 (m, 3H), 7.01-6.97 (m, 2H), 6.41 (s, 1H), 2.94 (brs, 2H), 2.71 (brs, 2H), 1.34 (s, 9H); MS (ESI) m/z: 412.3 (100, M+H$^+$), 414.2 (36, M+2).

Example 258

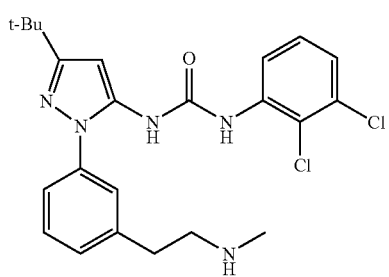

To a solution of 1-(3-t-butyl-1-(3-(2-(methylamino)-2-oxoethyl)phenyl)-1H-pyrazol-5-yl)-3-(2,3-dichlorophenyl)urea (0.071 g, 0.15 mmol) in THF (2 mL) was added a solution of 1M BH$_3$-THF (1 mL, 1 mmol) at 0° C. under Ar. After stirring the mixtureat 60° C. for 24 h, it was cooled to 0° C., and 3M HCl was added slowly. The mixture was heated to 60° C. for 30 min, cooled to 0° C., and basified with 20% NaOH solution. The product was extracted with CHCl$_3$ (3×25 mL).

The combined organic extracts were washed with H₂O (1×30 mL), brine, dried (Na₂SO₄) and concentrated. The resultant residue was dissolved in CH₂Cl₂ (2 mL) and 3M HCl/EtOAc solution (1 mL) was added and stirred for 10 min to yield (0.025 g, 36%) 1-(3-t-butyl-1-(3-(2-(methylamino)ethyl) phenyl)-1H-pyrazol-5-yl)-3-(2,3-dichlorophenyl)urea as a solid. ¹H NMR (300 MHz, DMSO-d₆): □ 9.52 (s, 1H), 8.92 (s, 1H), 8.70-8.66 (brs, 2H), 8.05 (dd, J=6.0 Hz, 4.0 Hz, 1H), 7.51-7.42 (m, 3H), 7.34-7.28 (m, 3H), 6.39 (s, 1H), 3.24-3.17 (m, 2H), 3.02-2.98 (m, 2H), 2.58-2.55 (m, 3H), 1.28 (s, 9H). MS (ESI) m/z: 460.2 (M+H⁺).

Example 259

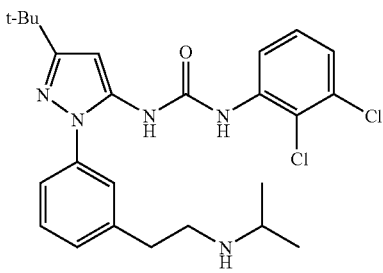

Using the same procedureas for Example 258, Example 441 (0.083 g, 0.16 mmol) was reacted with 1M BH₃-THF (1 mL, 1 mmol) to afford (0.071 g, 88%) 1-(3-t-butyl-1-(3-(2-(isopropylamino)ethyl)phenyl)-1H-pyrazol-5-yl)-3-(2,3-dichlorophenyl)urea as a solid. ¹H NMR (300 MHz, DMSO-d₆): □ 9.70 (s, 1H), 9.03 (s, 1H), 8.93 (brs, 1H), 8.02 (dd, J=6.0 Hz, 4.0 Hz, 1H), 7.51-7.42 (m, 3H), 7.33-7.28 (m, 3H), 6.38 (s, 1H), 3.03-3.17 (m, 3H), 3.07-3.02 (m, 2H), 1.28 (s, 9H), 1.23 (d, J=6.8 Hz, 6H); MS (ESI) m/z: 488.2 (M+H⁺)

Example 260

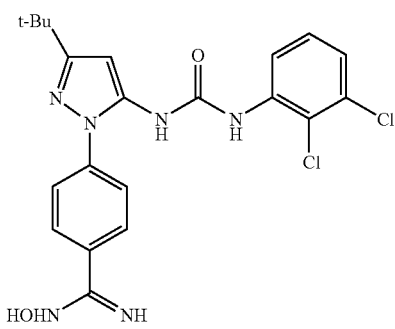

To a solution of Example A35 (100 mg, 0.23 mmol) in CH₃OH (3 mL) was added NH₂OH.HCl (61 mg, 0.58 mmol) and I-PR2NET (0.073 mL, 0.28 mmol), then the solution was stirred overnight at RT. After the solvent was removed, the residue was purified by prep-HPLC to give 4-{3-t-butyl-5-[3-(2,3-dichlorophenyl)ureido]pyrazol-1-yl}-N-hydroxybenza-midine (75 mg, 71% yield) as a white power. ¹H NMR (300 MHz, DMSO-d₆): δ 9.33 (s, 1H), 8.75 (s, 1H), 7.99 (m, 1H), 7.84-7.81 (d, J=9.0 Hz, 2H), 7.76-7.73 (d, J=9.0 Hz, 2H), 7.27-7.24 (d, J=6.9 Hz, 2H), 6.40 (s, 1H), 1.26 (s, 9H); MS (ESI) m/z: 461 (M+H⁺).

Example 261

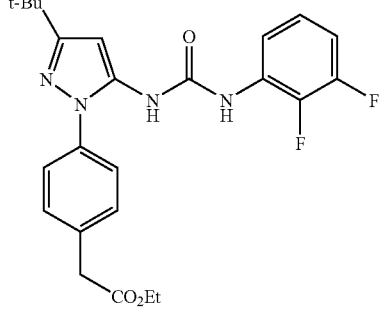

Using General method B, Example A18 (300 mg, 1 mmol) and 2,3-difluorophenylamine (129 mg, 1.0 mmol) were combined to afford ethyl 2-(4-(3-t-butyl-5-(3-(2,3-difluorophenyl)ureido)-1H-pyrazol-1-yl)phenyl)acetate (220 mg, 48% yield).

Example 262

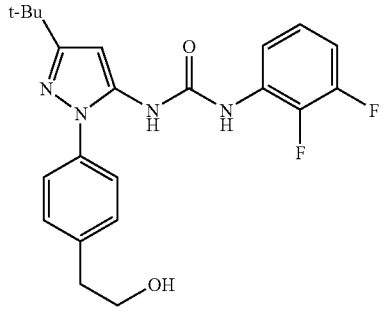

Using General method C, Example 261 (100 mg, 0.21 mmol) was transformed to 1-(3-t-butyl-1-(4-(2-hydroxyethyl)phenyl)-1H-pyrazol-5-yl)-3-(2,3-difluoro-phenyl)urea (55 mg, 63% yield). ¹H NMR (300 MHz, DMSO-d₆): δ 9.10 (br s, 1H), 8.85 (s, 1H), 7.89 (m, 1H), 7.36 (br s, 4H), 7.11-6.98 (m, 2H), 6.35 (s, 1H), 4.66 (t, J=5.1 Hz, 1H), 3.62 (q, J=6.9 Hz, 2H), 2.76 (t, J=7.2 Hz, 2H), 1.23 (s, 9H); MS (ESI) m/z: 415 (M+H⁺).

Example A65

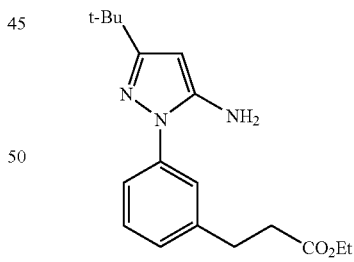

To a solution of 3-nitro-benzaldehyde (15.1 g, 0.1 mol) in CH₂Cl₂ (200 mL) was added dropwise (triphenyl-λ5-phosphanylidene)-acetic acid ethyl ester (34.8 g, 0.1 mol) in CH₂Cl₂ (100 mL) at 0° C. After the addition was complete, the resulting mixture was stirred for 1 h. After removal the solvent under reduced pressure, the residue was purified by column chromatography to afford 3-(3-nitrophenyl)acrylic acid ethyl ester (16.5 g, 74.6% yield). ¹H NMR (400 MHz, CDCl₃): δ 8.42 (s, 1H), 8.23 (dd, J=0.8, and 8.0 Hz, 1H), 7.82 (d, J=7.6 Hz, 1H), 7.72 (d, J=16.0 Hz, 1H), 7.58 (t, J=8.0 Hz, 1H), 6.56 (d, J=16.0 Hz, 1H), 4.29 (q, J=7.2 Hz, 2H), 1.36 (t, J=6.8 Hz, 3H).

A mixture of 3-(3-nitrophenyl)acrylic acid ethyl ester (16.5 g, 74.6 mmol) and Pd/C (1.65 g) in methanol (200 mL) was stirred under 40 psi of H₂ at RT for 2 h, then filtered through celite. After removal the solvent, 14 g of 3-(3-aminophenyl) propionic acid ethyl ester was obtained. ¹H NMR (400 MHz, CDCl₃): δ 7.11 (t, J=5.6 Hz, 1H), 6.67 (d, J=7.2 Hz, 1H), 6.63-6.61 (m, 2H), 4.13 (q, J=7.2 Hz, 2H), 2.87 (t, J=8.0 Hz, 2H), 2.59 (t, J=7.6 Hz, 2H), 1.34 (t, J=6.8 Hz, 3H); MS (ESI): m/z: 194 (M+H⁺).

To a solution of 3-(3-aminophenyl)propionic acid ethyl ester (14 g, 72.5 mmol) in conc. HCl (200 mL) was added aqueous (10 mL) of NaNO₂ (5 g, 72.5 mmol) at 0° C. and the resulting mixture was stirred for 1 h. A solution of SnCl₂.2H₂O (33 g, 145 mmol) in conc. HCl (150 mL) was then added at 0° C. The reaction solution was stirred for an additional 2 h at RT. The precipitate was filtered and washed with ethanol and ether to yield 3-(3-hydrazinophenyl)propionic acid ethyl ester as a white solid, which was used for the next reaction without further purification. MS (ESI): m/z: 209 (M+H⁺).

A mixture of 3-(3-hydrazinophenyl)propionic acid ethyl ester (13 g, 53.3 mmol) and 4,4-dimethyl-3-oxopentanenitrile (6.9 g, 55 mol) in ethanol (150 mL) was heated to reflux overnight. The reaction solution was evaporated under vacuum. The residue was purified by column chromatography to yield ethyl 3-(3-(3-t-butyl-5-amino-1H-pyrazol-1-yl) phenyl)propanoate (14.3 g, 85% yield) as a white solid. ¹H NMR (300 MHz, DMSO-d₆); δ 7.50-7.42 (m, 4H), 5.63 (s, 1H), 5.14 (s, 2H), 4.04 (q, J=6.9 Hz, 2H), 2.92 (t, J=7.5 Hz, 2H), 2.66 (t, J=7.5 Hz, 2H), 1.27 (s, 9H), 1.16 (t, J=7.5 Hz, 3H); MS (ESI) m/z: 316 (M+H⁺).

Example 263

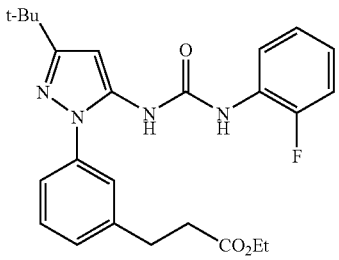

Using General method A, Example A65 (101 mg, 1.0 mmol) and 1-fluoro-2-isocyanato-benzene (137 mg, 1.0 mmol) were combined to afford 3-(3-{3-t-butyl-5-[3-(2-fluorophenyl)-ureido]-1H-pyrazol-1-yl}phenyl)propionic acid ethyl ester (240 mg, 53% yield), which was used with further purification.

Example 264

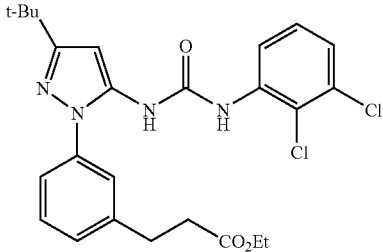

Using General method A, Example A65 (300 mg, 1.0 mmol) and 1,2-dichloro-3-isocyanato-benzene (187 mg, 1.0 mmol) were combined to afford 3-(3-{3-t-butyl-5-[3-(2,3-dichlorophenyl)ureido]-1H-pyrazol-1-yl}phenyl)propionic acid ethyl ester (210 mg, 42% yield), which was used without further purification ¹H NMR (DMSO-d₆): δ 9.20 (s, 1H), 8.76 (s, 1H), 8.05 (m, 1H), 7.47-7.26 (m, 6H), 6.38 (s, 1H), 4.04 (q, J=7.2 Hz, 2H), 2.93 (t, J=7.5 Hz, 2H), 2.65 (t, J=7.5 Hz, 2H), 1.28 (s, 9H), 1.15 (t, J=7.2 Hz, 3H); MS (ESI) m/z: 503 (M+H⁺).

Example 265

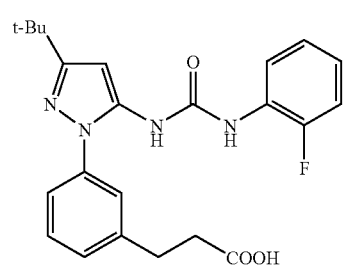

Using General method E, Example 263 (100 mg, 0.221 mmol) was saponified to afford 3-(3-{3-t-butyl-5-[3-(2-fluorophenyl)ureido]-1H-pyrazol-1-yl}-phenyl)propionic acid (80 mg, 85% yield). ¹H NMR (300 MHz, DMSO-d₆): δ 8.90 (br s, 1H), 8.81 (s, 1H), 7.08 (t, J=7.5 Hz, 1H), 7.42 (t, J=7.5 Hz, 1H), 7.35 (s, 1H), 7.28 (t, J=6.9 Hz, 1H), 7.28 (m, 1H), 7.07 (t, J=7.5 Hz, 1H), 6.98 (m, 1H), 6.37 (s, 1H), 2.87 (t, J=7.5 Hz, 2H), 2.55 (t, J=7.5 Hz, 2H), 1.24 (s, 9H); MS (ESI) m/z: 425 (M+H⁺).

Example A66

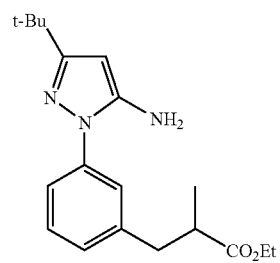

To a suspension of 2-(3-bromo-phenyl)-5-t-butyl-2H-pyrazol-3-ylamine (5.8 g, 20 mmol), Pd(OAc)₂ (450 mg, 2 mmol), PPh₃ (1.0 g, 4 mmol), and K₂CO₃ (5.5 g, 40 mmol) in DMF (50 mL) was added 2-methyl-acrylic acid ethyl ester (2.8 g, 25 mmol) at RT under N₂. The mixture was stirred at 80° C. overnight, concentrated under reduced pressure, and purified by column chromatography to afford (E)-3-[3-(5-amino-3-t-butyl-1H-pyrazol-1-yl)phenyl]-2-methylacrylic acid (3.2 g). MS (ESI) m/z: 328 (M+H⁺)

A mixture of (E)-3-(3-(3-t-butyl-5-amino-1H-pyrazol-1-yl)phenyl)-2-methylacrylic acid ethyl ester (3.0 g, 9.14 mmol) and Pd/C (0.3 g) in methanol (50 mL) was stirred at RT under 40 psi of H₂ for 2 h. The reaction mixture was filtered and the filtrate was concentrated to afford ethyl 3-[3-(5-amino-3-t-butyl-1H-pyrazol-1-yl)phenyl]-2-methylpropanoate (2.5 g, 83% yield). MS (ESI) m/z: 330 (M+H⁺).

Example 266

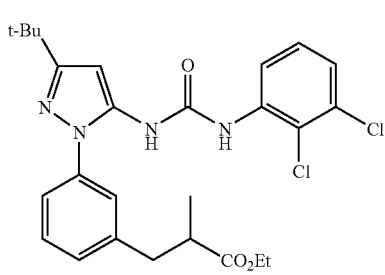

Using General method A, Example A66 (200 mg, 0.61 mmol) and 1,2-dichloro-3-isocyanatobenzene (187 mg, 1.0 mmol) were combined to yield 180 ethyl 3-(3-{3-t-butyl-5-[3-(2,3-dichlorophenyl)ureido]-1H-pyrazol-1-yl}phenyl)-2-methylpropanoate (180 mg, 57% yield). MS (ESI) m/z: 517 (M+H$^+$).

Example 267

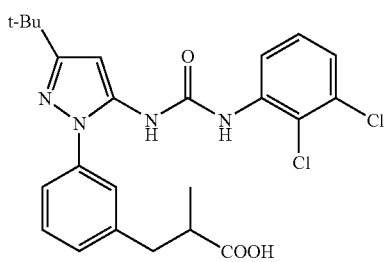

Using General method E, Example 266 (100 mg, 0.19 mmol) was saponified to afford 3-(3-{3-t-butyl-5-[3-(2,3-dichlorophenyl)ureido]-1H-pyrazol-1-yl}-phenyl)-2-methylpropanoic acid (60 mg, 65% yield). $^1$H-NMR (DMSO-d$_6$): δ 9.20 (s, 1H), 8.72 (s, 1H), 8.03 (m, 1H), 7.43-7.19 (m, 6H), 6.34 (s, 1H), 2.95 (m, 1H), 2.69-2.62 (m, 2H), 1.24 (s, 9H), 1.01 (d, J=6.3 Hz, 3H); MS (ESI) m/z: 489 (M+H$^+$).

Example A67

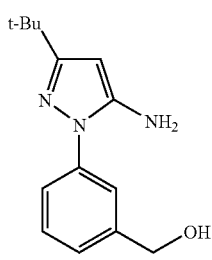

To a stirred solution of Example A1 (19.5 g, 68.0 mmol) in THF (200 mL) was added LiAlH$_4$ powder (5.30 g, 0.136 mol) at −10° C. under N$_2$. The mixture was stirred for 2 h at RT and excess LiAlH$_4$ was destroyed by slow addition of ice. The reaction mixture was acidified to pH=7 with diluted HCl, the solution concentrated under reduced pressure, and the residue was extracted with ethyl acetate. The combined organic extracts were concentrated to yield [3-(5-amino-3-t-butyl-pyrazol-1-yl)-phenyl]-methanol (16.35 g, 98%) as a white powder. $^1$H NMR (DMSO-d6): 9.19 (s, 1H), 9.04 (s, 1H), 8.80 (s, 1H), 8.26-7.35 (m, 1H), 6.41 (s, 1H), 4.60 (s, 2H), 1.28 (s, 9H); MS (ESI) m/z: 415 (M+H$^+$).

Example A68

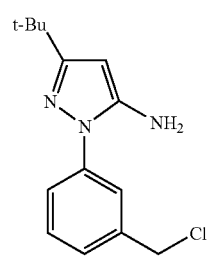

A solution of Example A67 (13.8 g, 56 mmol) and SOCl$_2$ (8.27 mL, 0.11 mol) in THF (200 mL) was refluxed for 3 h and concentrated under reduced pressure to yield 5-t-butyl-2-(3-chloromethyl-phenyl)-2H-pyrazol-3-ylamine (14.5 g, 98%) as a white powder which was used without further purification. $^1$H NMR (DMSO-d6), δ 7.62 (s, 1H), 7.53 (d, J=8.0 Hz, 1H), 7.43 (t, J=8.0 Hz, 1H), 7.31 (d, J=7.2 Hz, 1H), 5.38 (s, 1H), 5.23 (br s, 2H), 4.80 (s, 2H), 1.19 (s, 9H). MS (ESI) m/z: 264 (M+H$^+$).

Example A69

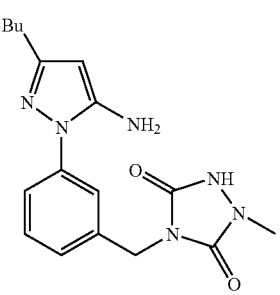

To a suspension of NaH (26 mg, 0.67 mmol) in DMSO (2 mL) was added powder 1-methyl-[1,2,4]triazolidine-3,5-dione (77 mg, 0.67 mmol) at RT under N$_2$ atmosphere. The resulting mixture was stirred for 30 min and then added to a solution of Example A68 (100 mg, 0.33 mmol) and Et$_3$N (1 mL) in DMSO (2 mL). After stirring for 3 h, the reaction mixture was quenched with methanol, concentrated and purified by column chromatography to afford 90 mg of 4-[3-(5-amino-3-t-butyl-pyrazol-1-yl)-benzyl]-1-methyl-[1,2,4]triazolidine-3,5-dione.

Example 268

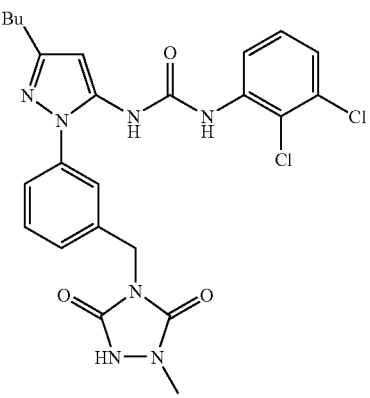

To a suspension of Example A69 (90 mg, 0.26 mmol) and triethylamine (0.5 mL) in fresh THF (10 mL) was added a solution of 1,2-dichloro-3-isocyanato-benzene (95 mg, 0.5 mmol) in THF (2 mL) dropwise through syringe at 0° C. under N₂ atmosphere. The mixture was allowed to rise to RT and stirred overnight. The reaction mixture was quenched with ice-cold aqueous HCl (1 mol/L) and extracted with EtOAc (3×50 mL). The combined organic layers were washed with brine, dried (Na₂SO₄), filtered, concentrated and purified column chromatography to afford 80 mg of 1-{5-t-butyl-2-[3-(1-methyl-3,5-dioxo-[1,2,4]triazolidin-4-ylmethyl)-phenyl]-2H-pyrazol-3-yl}-3-(2,3-dichloro-phenyl)-urea. ¹H-NMR (DMSO-d₆), δ11.30 (s, 1H), 9.27 (s, 1H), 8.70 (s, 1H), 8.04 (m, 1H), 7.50-7.46 (m, 3H), 7.28-7.26 (m, 3H), 6.37 (s, 1H), 4.74 (s, 2H), 2.96 (s, 3H), 1.25 (s, 9H).

Example A70

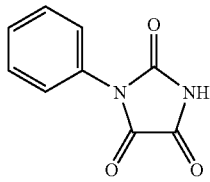

To a solution of aniline (2.51 g, 27 mmol) dissolved in glacial acetic acid (14 mL) and water (28 mL) was slowly added a solution of potassium cyanate (4.4 g, 54 mmol) dissolved in water (35 mL). The mixture stirred for 2 h at RT, filtered, washed with water and dried under reduced pressure to yield phenylurea as a white solid (1.85 g, 50% yield). ¹H NMR (DMSO-d₆): δ 8.47 (s, 1H), 7.38 (dd, J=8.4 Hz, 0.9 Hz, 2H), 7.2 (t, J=7.6 Hz, 2H), 6.88 (t, J=7.6 Hz, 1H), 5.81 (brs, 2H); MS (ESI) m/z: 137 (M+H⁺).

A suspension of Example A19 (0.4 g, 3 mmol) in ether (20 mL) was added oxalylchloride (0.8 g, 6 mmol) and refluxed for 3 h. Solvent was removed under reduced pressure and solid was dried to yield 1-phenylimidazolidine-2,4,5-trione (0.51 g, 89% yield), which was used without purification. ¹H NMR (300 MHz, DMSO-d₆): δ 7.53-7.38 (m, 5H); MS (ESI) m/z: 191 (M+H⁺).

Example 269

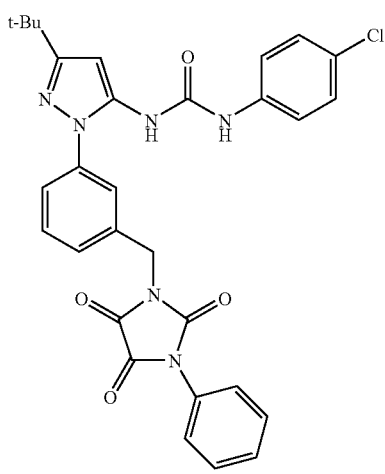

To a solution of triphenyl phosphine (0.23 g, 0.88 mmol) in THF (5 mL) at −20° C. were added di-t-butyl azadicarboxylate (DBAD) (0.2 g, 0.88 mmol), a solution of Example 224 (0.175 g, 0.44 mmol) in THF (5 mL) and Example A70 (0.1 g, 0.53 mmol). The resulting clear yellow solution was heated at 60° C. for 8 h, followed by the further addition of one equivalent of triphenyl phosphine and DBAD and additional heating at 60° C. overnight. One additional equivalent of triphenyl phosphine and DBAD were added and reaction mixture was heated at 60° C. for 3 h. The reaction mixture was concentrated and purified via column chromatography to yield 1-(3-t-butyl-1-(3-[(2,4,5-trioxo-3-phenylimidazolidin-1-yl)methyl]phenyl}-1H-pyrazol-5-yl)-3-(4-chlorophenyl)urea as a white solid (70 mg, 28% yield). ¹H NMR (400 MHz, DMSO-d₆): δ 9.02 (s, 1H), 8.45 (s, 1H), 7.53-7.28 (m, 12H), 6.39 (s, 1H), 4.87 (s, 2H), 1.28 (s, 9H); MS (ESI) m/z: 571 (M+H⁺).

Example 270

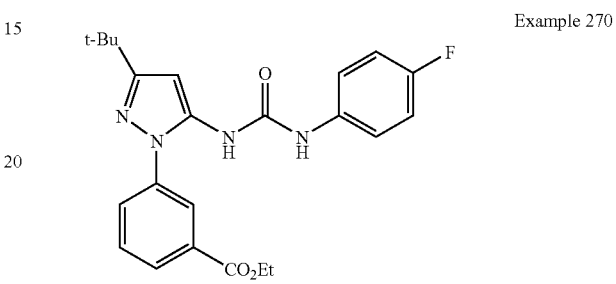

To a solution of Example A1 (0.57 g, 2 mmol) in THF were added pyridine (0.31 g, 4 mmol) 4-fluoro phenyl isocyanate (0.27 g, 2 mmol) and reaction mixture was stirred at RT for 20 h. Then solvent was removed under reduced pressure, and the residue was solidified by stirring with hexane to yield of ethyl 3-{3-t-butyl-5-[3-(4-fluorophenyl)ureido)-1H-pyrazol-1-yl}benzoate as a white solid (0.78 g, 92% yield) ¹H NMR (400 MHz, DMSO-d₆): □ 9.02 (s, 1H), 8.44 (s, 1H), 8.08 (t, J=1.6 Hz, 1H), 7.95 (d, J=8.0 Hz, 1H), 7.83 (dd, J=8 Hz, 1.6 Hz, 1H), 7.67 (t, J=8 Hz, 1H), 7.42-7.39 (m, 2H), 7.09 (t, J=8.8 Hz, 2H), 6.37 (s, 1H), 4.32 (q, J=7.2 Hz, 2H), 1.30-1.28 (m, 12H); MS (ESI) m/z: 425 (M+H⁺).

Example 271

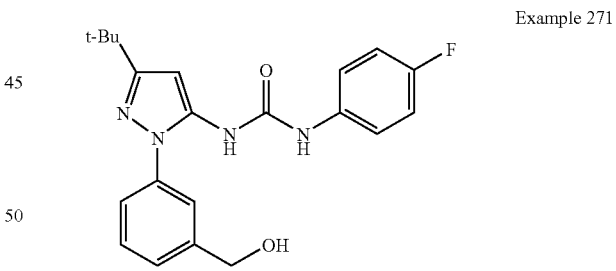

To a solution of Example 270 (0.78 g, 1.8 mmol) in THF (20 mL) was added LAH (5.5 mL of 1M solution in THF) at 0° C. The mixture was warmed to RT, stirred for 1 h, quenched with ice at 0° C. and concentrated under reduced pressure. The residue was acidified with 1M HCl and product was extracted with EtOAc (2×50 mL). The combined organic extracts were washed with brine, dried (Na₂SO₄) and concentrated under reduced pressure to yield 1-{3-t-butyl-1-[3-(hydroxymethyl)phenyl]-1H-pyrazol-5-yl}-3-(4-fluorophenyl) urea as a white solid (0.66 g, 94% yield) ¹H NMR (DMSO-d₆): δ9.20 (s, 1H), 8.48 (s, 1H), 7.48-7.36 (m, 6H), 7.10 (t, J=8.8 Hz, 2H), 6.37 (s, 1H), 4.58 (s, 2H), 1.28 (s, 9H); MS (ESI) m/z: 383 (M+H⁺).

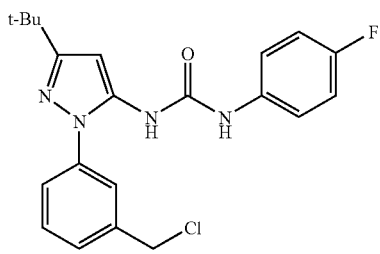

Example A71

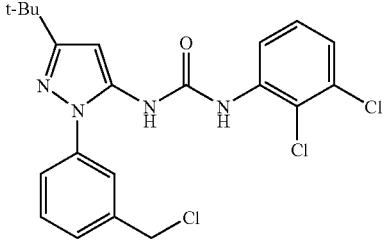

Example A72

To a solution of Example 271 (0.45 g, 1.2 mmol) in chloroform (20 mL) was added thionyl chloride (0.28 g, 2.4 mmol) and mixture was stirred for 2 h at 65° C. Water was added and organic layer separated. The aqueous layer was extracted with CH$_2$Cl$_2$ (1×50 mL) and the combined organic extracts were washed with brine, dried (Na$_2$SO$_4$) and concentrated under reduced pressure to yield 1-{3-t-butyl-1-[3-(chloromethyl)phenyl]-1H-pyrazol-5-yl}-3-(4-fluorophenyl)urea as a solid (0.43 g, 96% yield). $^1$H NMR (CDCl$_3$): δ7.52 (s, 1H), 7.39-7.34 (m, 3H), 7.23-7.19 (m, 2H), 6.97-6.95 (m, 3H), 6.41 (s, 1H), 4.57 (s, 2H), 1.36 (s, 9H); MS (ESI) m/z: 401 (M+H$^+$).

Using the same procedureas for Example A71, Example 1 (0.61 g, 1.4 mmol) was transformed to yield 1-(3-t-butyl-1-(3-(chloromethyl)phenyl)-1H-pyrazol-5-yl)-3-(2,3-dichlorophenyl)urea as a solid (0.6 g, 94% yield). $^1$H NMR (CDCl$_3$): δ8.12-8.09 (m, 1H), 7.65 (s, 1H), 7.58 (s, 1H), 7.47-7.36 (m, 3H), 7.19-7.17 (m, 2H), 6.95 (br s, 1H), 6.44 (s, 1H), 4.58 (s, 2H), 1.38 (s, 9H); MS (ESI) m/z: 451 (M+H$^+$).

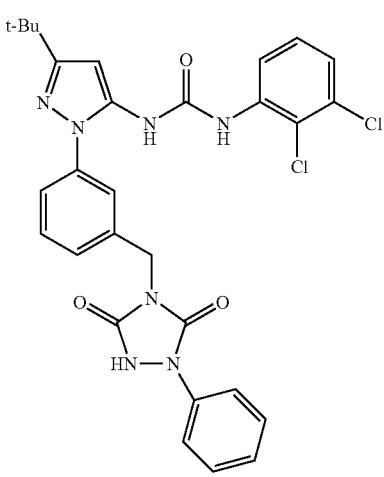

Example 273

Example 272

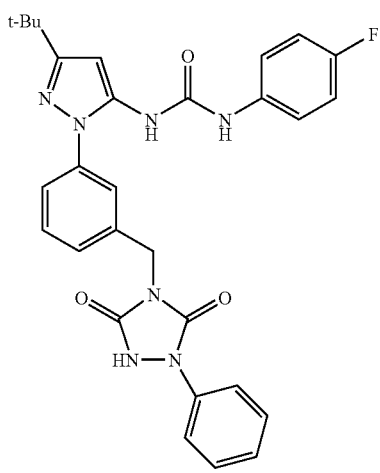

A solution of Example A70 (80 mg, 0.45 mmol), DMF (4 mL) and NaH (5 mg, 0.22 mmol) under Ar at 0° C. was stirred for 30 min. Example A71 (90 mg, 0.22 mmol) was added and the mixture was warmed to RT, stirred for 6 h, quenched with water (20 mL) and extracted with ethyl acetate (2×25 mL). The combined organic extracts were washed with water, brine, dried (Na$_2$SO$_4$), concentrated under reduced pressureand purified via column chromatography to yield 1-(3-t-butyl-1-{3-[(3,5-dioxo-1-phenyl-1,2,4-triazolidin-4-yl)methyl]phenyl}-1H-pyrazol-5-yl)-3-(4-fluorophenyl)urea as a white solid (65 mg, 53% yield) $^1$H NMR (DMSO-d$_6$): δ 8.96 (s, 1H), 8.44 (s, 1H), 7.49-7.33 (m, 9H), 7.24 (s, 1H), 7.12-7.08 (m, 3H), 6.35 (s, 1H), 4.64 (s, 2H), 1.28 (s, 9H); MS (ESI) m/z: 542 (M+H$^+$).

A solution of Example A70 (70 mg, 0.4 mmol), DMF (5 mL) and NaH (5 mg, 0.2 mmol) under Ar at 0° C. was stirred for 30 min, after which Example A72 (90 mg, 0.2 mmol) was added. The mixture was warmed to RT, stirred for 6 h, quench with water (20 mL) and extracted with EtOAc (2×). The combined organic extracts were washed with water, brine, dried Na$_2$SO$_4$), concentrated under reduced pressureand purified via column chromatography to yield 1-(3-t-butyl-1-{3-[(3,5-dioxo-1-phenyl-1,2,4-triazolidin-4-yl)methyl]phenyl}-1H-pyrazol-5-yl)-3-(2,3-dichlorophenyl)urea as a white solid (85 mg, 72% yield). $^1$H NMR (DMSO-d$_6$): δ 9.29 (s, 1H), 8.73 (s, 1H), 8.07 (dd, J=6.4 Hz, 3.2 Hz, 1H), 7.50-7.44 (m, 4H), 7.37-7.25 (m, 5H), 7.12-7.10 (m, 1H), 6.38 (s, 1H), 4.64 (s, 2H), 1.28 (m, 9H); MS (ESI) m/z: 592 (M+H$^+$).

General Experimental for Examples 274-277

A solution of Example A20 and the appropriate isocyanate (general method A) or the appropriate aniline (general method D) were combined to yield the indicated compound.

| Example | Name | MS (EI) (M + H⁺) | ¹H NMR (400 MHz), DMSO-d₆ |
|---|---|---|---|
| Example 274 | 1-[5-t-butyl-2-(3-pyridin-3-yl-phenyl)-2H-pyrazol-3-yl]-3-cyclohexyl-urea 95 mg, 37% general method A | 418 | 9.07 (s, 1H), 8.71 (d, J = 4.5 Hz, 1H), 8.43 (d, J = 7.8 Hz, 1H), 8.11 (s, 1H), 7.83 (s, 1H), 7.77-7.74 (m, 2H), 7.63 (t, J = 7.8 Hz, 1H), 7.54 (d, J = 7.8 Hz, 2H), 6.47 (s, J = 7.8 Hz, 1H), 6.26 (s, 1H), 3.31 (m, 1H), 1.71-1.52 (m, 5H), 1.22 (s, 9H), 1.18-0.97 (m, 5H) |
| Example 275 | 1-(3-t-butyl-1-(3-(pyridin-3-yl)phenyl)-1H-pyrazol-5-yl)-3-(2,4,5-trifluorophenyl)urea 49 mg, 14% yield, 2 steps general method D | 466.2 | 9.21 (brs, 2H), 9.16 (s, 1H), 8.80 (dd, J = 1.2, and 5.2 Hz, 1H), 8.65 (brd, J = 8.0 Hz, 1H), 8.13 (m, 1H), 7.98 (t, J = 2.0 Hz, 1H), 7.87 (m, 2H), 7.72 (t, J = 8.0 Hz, 1H), 7.66 (m, 1H), 7.60 (dd, J = 3.2, and 10.8, 1H), 6.45 (s, 1H), 1.30 (s, 9H) |
| Example 276 | 1-[5-t-butyl-2-(3-pyridin-3-yl-phenyl)-2H-pyrazol-3-yl]-3-(2,3-dichlorophenyl)urea 115 mg, 39% general method A | 480 | 9.35 (s, 1H), 9.01 (s, 1H), 8.79 (s, 1H), 8.64 (d, J = 4.5 Hz, 1H), 8.29 (d, J = 8.4 Hz, 1H), 7.98 (t, J = 4.5 Hz, 1H), 7.86 (s, 1H), 7.77 (d, J = 7.8 Hz, 1H), 7.67-7.57 (m, 3H) 7.26 (d, J = 5.1 Hz, 2H), 6.39 (s, 1H), 1.25 (s, 9H); MS (ESI) |
| Example 277 | 1-(3-t-butyl-1-(3-(pyridin-3-yl)phenyl)-1H-pyrazol-5-yl)-3-(3-(pyridin-3-yloxy)phenyl)urea 0.80 g, 40% | 505.2 | 9.80 (s, 1H), 9.33 (s, 1H), 8.96 (s, 1H), 8.85 (d, J = 5.2 Hz, 1H), 8.81 (d, J = 8.0 Hz, 1H), 8.54 (d, J = 1.6 Hz, 1H), 8.49 (d, J = 4.4 Hz, 1H), 8.00 (m, 2H), 7.86 (d, J = 6.8 Hz, 1H), 7.69 (m, 4H), 7.35 (s, 1H), 7.31 (d, J = 8.4, 1H), 7.13 (d, J = 8.0 Hz, 1H), 6.72 (bd, J = 7.6 Hz, 1H), 6.40 (s, 1H), 1.29 (s, 9H); LC-MS (EI |

Example 278

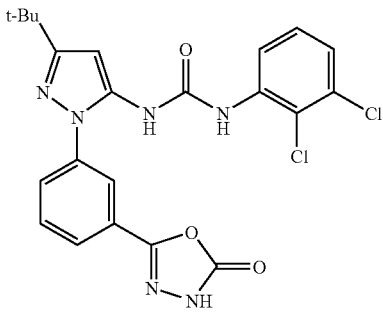

Using General method E, Example A1 (318 mg, 0.982 mmol) was saponified to yield (277 mg, >100% yield) 3-(5-amino-3-t-butyl-1 H-pyrazol-1-yl)benzoic acid as a foam.

Using general method J, this crude material (277 mg, 0.983 mmol) 1-NH and hydrazine hydrate (0.18 mL, 3.69 mmol) were combined to yield 3-(5-amino-3-t-butyl-1H-pyrazol-1-yl)benzohydrazide (100 mg, 37% yield). MS (ESI) m/z: 274.2 (M+H$^+$).

This material (30 mg, 0.11 mmol) in THF (2 mL) was treated with CDI (30 mg, 0.19 mmol) and the reaction mixture was stirred at RT. After 30 min, another portion of CDI (30 mg, 0.19 mmol) was added. After another 30 min, the reaction was quenched with satd. NaHCO$_3$ (5 mL) and extracted with EtOAc (2×15 mL). The organics were washed with 5% citric acid (2×10 mL), H$_2$O (10 mL), brine (10 mL), dried (Na$_2$SO$_4$), filtered and concentrated to yield 5-(3-(5-amino-3-t-butyl-1H-pyrazol-1-yl)phenyl)-1,3,4-oxadiazol-2(3H)-one (50 mg, >100% yield) as a film. MS (ESI) m/z: 300.3 (M+H$^+$).

Using General method A, this crude material (50 mg, 0.11 mmol theory) and 2,3-dichlorophenyl isocyanate (0.060 mL, 0.45 mmol) were combined to yield 1-(3-t-butyl-1-(3-(5-oxo-4,5-dihydro-1,3,4-oxadiazol-2-yl)phenyl)-1H-pyrazol-5-yl)-3-(2,3-dichlorophenyl)urea (40 mg, 74% yield over 2 steps). $^1$H NMR (400 MHz, DMSO-d$_6$): δ 12.69 (br s, 1H), 9.30 (s, 1H), 8.76 (s, 1H), 8.00 (m, 1H), 7.92 (t, J=1.7 Hz, 1H), 7.82-7.66 (m, 3H), 7.32-7.29 (m, 2H), 6.42 (s, 1H), 1.30 (s, 9H). MS (ESI) m/z: 487.3.0 (M+H$^+$).

Example 279

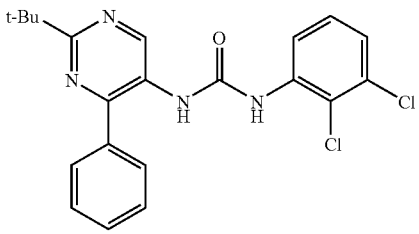

Pivalamidine hydrochloride (5.00 g, 37 mmol) dissolved in methanol (80 mL) was treated with NaOMe (2.0 g, 37 mmol) and stirred at RT for 15 min. To this was added dimethyl 2-(methoxymethylene)malonate (6.4 g, 37 mmol) and the solution stirred at RT overnight. The solution was heated at reflux for 1 h, then cooled to RT and concentrated. The oily mass was dissolved in H$_2$O (125 mL) and the pH adjusted to ~3 (wet litmus) with AcOH. The precipitated solids were collected by filtration, washed with H$_2$O (50 mL) and dried to yield methyl 2-t-butyl-4-hydroxypyrimidine-5-carboxylate (3.50 g, 45%). $^1$H NMR (400 MHz, DMSO-d$_6$): δ 1.29 (s, 9H), 2.97 (s, 3H), 8.47 (s, 1H).

To ice cold (0-5° C.) POCl$_3$ (35 mL) was added dropwise Et$_3$N (0.4 mL), followed by methyl 2-t-butyl-4-hydroxypyrimidine-5-carboxylate (3.45 g, 16.4 mmol). The mixture was then warmed to 40° C. and stirred under Ar for 1 h, then concentrated and diluted with CHCl$_3$ (100 mL) and poured carefully onto ice (~300 g) and stirred at RT until the ice all melted. The organic phase was separated, washed with NaHCO$_3$ (100 mL), H$_2$O (100 mL), dried (Na$_2$SO$_4$), concentrated and dried to yield methyl 2-t-butyl-4-chloropyrimidine-5-carboxylate (3.28 g, 87% yield). $^1$H NMR (400 MHz, DMSO-d$_6$): δ 1.35 (s, 9H), 3.90 (s, 3H), 9.14 (s, 1H).

In a mixture of satd. NaHCO$_3$:PhMe:EtOH (1:2:1) (12 mL) was dissolved the material from the previous reaction (3.25 g, 14.2 mmol), phenylboronic acid (3.5 g, 28.4 mmol) and Pd(PPh$_3$)$_4$ (328 mg). The mixture was stirred at 75° C., under Ar overnight, then diluted with EtOAc (60 mL) and H$_2$O (60 mL) and the mixture filtered through Celite® and the organic phase separated. The organic phase was washed with 5% citric acid (50 mL), brine (50 mL) dried (Na$_2$SO$_4$), concentrated to an oil and purified by column chromatography to yield methyl 2-t-butyl-4-phenylpyrimidine-5-carboxylate (1.26 g, 33% yield). $^1$H NMR (400 MHz, DMSO-d$_6$): δ 1.29 (s, 9H), 3.61 (s, 3H), 7.40-7.42 (m, 3H), 7.51-7.53 (m, 2H), 8.66 (s, 1H).

Using general method E, the material from the previous reaction (1.26 g, 4.70 mmol) was saponified to yield 2-t-butyl-4-phenylpyrimidine-5-carboxylic acid (1.10 g, 92% yield) as a white solid. $^1$H NMR (400 MHz, DMSO-d$_6$): δ 1.40 (s, 9H), 7.50-7.52 (m, 3H), 7.67-7.69 (m, 2H), 9.02 (s, 1H). 2-t-butyl-4-phenylpyrimidine-5-carboxylic acid (1.10 g, 4.29 mmol) was combined in t-BuOH (11 mL) with DPPA (1.18 g, 4.29 mmol) and Et$_3$N (0.434 g, 4.29 mmol). The mixture was heated at reflux, stirred overnight, then cooled to RT and diluted with EtOAc (75 mL) and H$_2$O (75 mL). The organic phase was separated, washed with brine, dried (Na$_2$SO$_4$) and concentrated. The resultant solid was treated with EtOAc (5 mL) and sonicated for 5 min then filtered free of solids and evaporated to a small volume and the solution purified by column chromatography to yield t-butyl 2-t-butyl-4-phenylpyrimidin-5-ylcarbamate (1.2 g, 85% yield) as a white foam. LC-MS (EI) m/z: 328.3 (M+H$^+$). This material (1.02 g, 3.0 mmol) was dissolved in CH$_2$Cl$_2$ (10 mL) and treated with 3N HCl/EtOAc (10 mL), stirred at RT and subsequently treated with additional 3N HCl/EtOAc (5 mL) and then concentrated to yield 2-t-butyl-4-phenylpyrimidin-5-amine hydrochloride as a yellow solid (0.724 g, 88%). LC-MS (EI) m/z: 228.2 (M+H$^+$). Using general method A, this material (120 mg, 0.455 mmol) and 1,2-dichloro-3-isocyanatobenzene (94 mg, 0.500 mmol) were combined to yield 1-(2-t-butyl-4-phenylpyrimidin-5-yl)-3-(2,3-dichlorophenyl)urea (45 mg, 24% yield). $^1$H NMR (400 MHz, DMSO-d6): δ 1.39 (s, 9H), 7.29-7.34 (m, 2H), 7.53-7.59 (m, 3H), 7.77-7.79 (m, 2H), 8.06-8.08 (m, 1H), 8.20 (s, 1H), 8.98-9.02 (m, 2H); LC-MS (EI) m/z: 417.0 (M+H$^+$).

Example 280

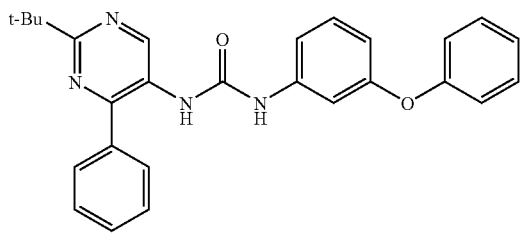

Using general method A, 2-t-butyl-4-phenylpyrimidin-5-amine hydrochloride (100 mg, 0.379 mmol, available from Example 279) and 1-(3-isocyanatophenoxy)benzene (88 mg, 0.417 mmol) were combined to yield 1-(2-t-butyl-4-phenylpyrimidin-5-yl)-3-(3-phenoxyphenyl)urea (42 mg, 25% yield). $^1$H NMR (DMSO-d6): δ 1.38 (s, 9H), 6.61-6.63 (m, 1H), 7.01-7.56 (m, 1H), 7.73-7.75 (m, 2H), 8.10 (s, 1H), 9.02 (s, 1H), 9.19 (s, 1H). LC-MS (EI) m/z: 439.3 (M+H$^+$).

Example 281

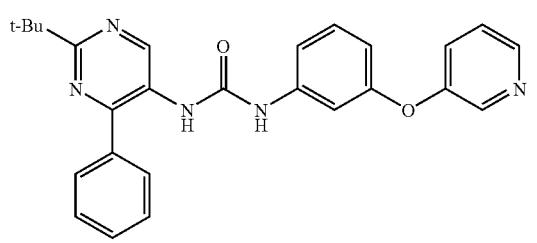

Using general method D, 2-t-butyl-4-phenylpyrimidin-5-amine hydrochloride (150 mg, 0.569 mmol, available from Example 279) and 3-(pyridin-3-yloxy)benzenamine (128 mg, 0.683 mmol) were combined to yield 1-(2-t-butyl-4-phenylpyrimidin-5-yl)-3-(3-(pyridin-3-yloxy)phenyl)urea (133 mg, 51% yield). $^1$H NMR (DMSO-d6) δ 1.38 (s, 9H), 6.73-6.76 (m, 1H), 6.89-7.05 (m, 1H), 7.14-7.16 (m, 1H), 7.32-7.38 (m, 2H), 7.51-7.56 (m, 3H), 7.74-7.79 (m, 4H), 8.38 (s, 1H), 8.53-8.62 (m, 2H), 9.00 (s, 1H), 9.56 (s, 1H). LC-MS (EI) m/z: 440.2 (M+H$^+$).

Example 282

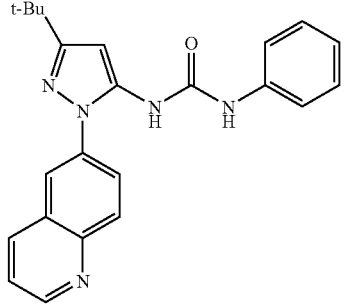

Using general method A, Example A21 (133 mg, 0.5 mmoL) and isocyanatobenzene (60 mg, 0.5 mmol) were combined to afford 1-[3-t-butyl-1-(quinolin-6-yl)-1H-pyrazol-5-yl]-3-phenylurea (90 mg, 47% yield). $^1$H NMR (300 MHz, DMSO-d$_6$): δ 8.99 (s, 1H), 8.97 (d, J=4.5 Hz, 1H), 8.58 (s, 1H), 8.56 (d, J=8.4 Hz, 1H), 8.19 (s, 1H), 8.16 (d, J=8.7 Hz, 1H), 7.99 (d, J=8.7 Hz, 1H), 7.67 (m, 1H), 7.35 (d, J=7.8 Hz, 2H), 7.21 (t, J=7.8 Hz, 2H), 6.92 (t, J=7.8 Hz, 1H), 6.42 (s, 1H), 1.28 (s, 9H).

General Experimental for Examples 283-285

A solution of Example A21 and the appropriate isocyanate or aniline was converted to the target compound using the general method indicated.

| Example | Name | MS (EI) (M + H$^+$) | $^1$H NMR (300 MHz/ 400 MHz, DMSO-d$_6$) |
|---|---|---|---|
| Example 283 | 1-(3-t-butyl-1-(quinolin-6-yl)-1H-pyrazol-5-yl)-3-(2,3-difluorophenyl)urea 38 mg, 14% yield General method D | 422.2 | 9.01 (s, 1H), 9.04 (s, 1H), 8.97 (dd, J = 1.6, and 4.0 Hz, 1H), 8.49 (d, J = 8.4 Hz, 1H), 8.18 (d, J = 9.2 Hz, 1H), 8.16 (s, 1H), 7.94 (dd, J = 2.4, and 9.2 Hz, 1H), 7.90 (d, J = 8.0 Hz, 1H), 7.63 (dd, J = 4.4, 8.8 Hz, 1H), 7.11 (m, 1H), 7.03 (m, 1H), 6.48 (s, 1H), 1.31 (s, 9H) |
| Example 284 | 1-(3-t-butyl-1-(quinolin-6-yl)-1H-pyrazol-5-yl)-3-(2,4-difluorophenyl)urea 35 mg, 11% yield General method D | 422.2 | 8.97 (dd, J = 1.6, and 4.0 Hz, 1H), 8.95 (s, 1H), 8.87 (d, J = 1.6 Hz, 1H), 8.49 (dd, J = 1.6, and 8.8 Hz, 1H), 8.17 (d, J = 11.6 Hz, 1H), 8.16 (s, 1H), 8.04 (m, 1H), 7.63 (dd, J = 4.0, and 8.4 Hz, 1H), 7.29 (m, 1H), 7.03 (m, 1H), 6.47 (s, 1H), 1.30 (s, 9H) |

| Example | Name | MS (EI) (M + H⁺) | $^1$H NMR (300 MHz/ 400 MHz, DMSO-$d_6$) |
|---|---|---|---|
| Example 285 | 1-(3-t-butyl-(quinolin-6-yl)-1H-pyrazol-5-yl)-3-(2,3,4-trifluorophenyl)urea 36 mg, 5% yield General method D | 440.2 | 9.04 (s, 1H), 8.99 (s, 1H), 8.97 (dd, J = 1.6, and 4.4 Hz, 1H), 8.48 (d, J = 8.4 Hz, 1H), 8.17 (d, J = 10.2 Hz, 1H), 8.16 (s, 1H), 7.94 (dd, J = 2.0, and 8.8 Hz, 1H), 7.83 (m, 1H), 7.63 (dd, J = 4.0, and 8.4 Hz, 1H), 7.26 (m, 1H), 6.47 (s, 1H), 1.31 (s, 9H) |

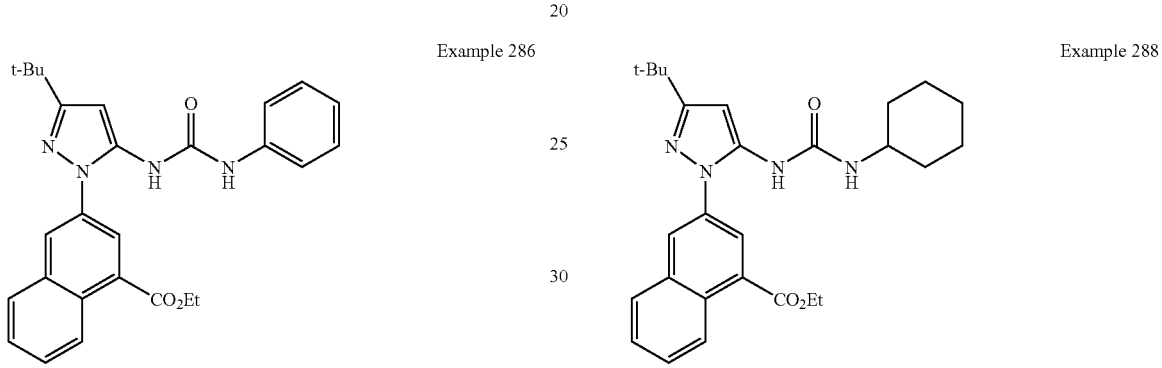

Example 286

Example 288

Using general method A, Example A23 (169 mg, 0.5 mmol) and isocyanatobenzene (60 mg, 0.5 mmol) were combined to afford ethyl 3-[3-t-butyl-5-(3-phenylureido)-1H-pyrazol-1-yl]-1-naphthoate (110 mg, 48% yield). $^1$H NMR (300 MHz, DMSO-$d_6$): δ 8.96 (s, 1H), 8.73 (d, J=8.1 Hz, 1H), 8.53 (s, 1H), 8.33 (s, 1H), 8.23 (s, 1H), 8.10 (d, J=8.1 Hz, 1H), 7.62-7.71 (m, 2H), 7.35 (d, J=7.5 Hz, 2H), 7.21 (t, J=7.5 Hz, 2H), 6.92 (t, J=7.2 Hz, 1H), 6.41 (s, 1H), 4.37 (q, J=7.2 Hz, 2H), 1.30 (t, J=7.2 Hz, 3H), 1.29 (s, 9H).

Using general method A, Example A23 (200 mg, 0.593 mmol) and 4-cyclohexylisocyanate (256 mg, 1.78 mmol) were combined to afford ethyl 3-(3-t-butyl-5-(3-cyclohexylureido)-1H-pyrazol-1-yl)-1-naphthoate (15 mg, 5.5% yield). $^1$H NMR (400 MHz, DMSO-$d_6$): δ 1.05-1.30 (m, 5H), 1.29 (s, 9H), 1.36-1.41 (m, 3H), 1.47-1.73 (m, 5H), 3.32-3.38 (m, 1H), 4.40-4.46 (m, 2H), 6.32 (s, 1H), 6.40-6.42 (m, 1H), 7.67-7.71 (m, 2H), 8.09-8.27 (m, 4H), 8.74-8.76 (m, 1H); LC-MS (EI) m/z: 462.7 (M+H⁺).

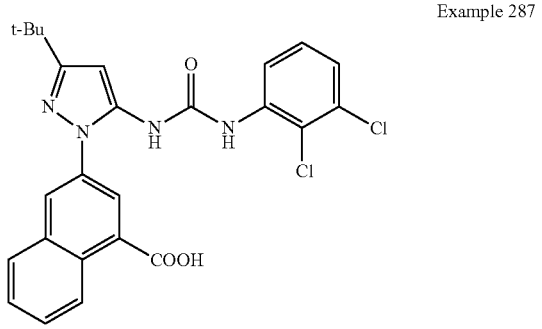

Example 287

Example 289

Using general method E, Example 58 (100 mg, 0.20 mmol) is saponified to afford 3-{3-t-butyl-5-(3-(2,3-dichlorophenyl)ureido]-1H-pyrazol-1-yl}-1-naphthoic acid (60 mg, 60% yield). $^1$H NMR (300 MHz, DMSO-$d_6$): δ 9.37 (s, 1H), 8.35 (d, J=8.7 Hz, 1H), 8.76 (s, 1H), 8.30 (m, 1H), 8.10 (m, 1H), 8.00 (t, J=4.8 Hz, 1H), 57.67 (m, 1H), 7.28 (d, J=4.8 Hz, 1H), 6.45 (s, 1H), 1.30 (s, 9H); MS (EI) m/z: 497.1 (M+H⁺).

Using general method D, Example A24 (120 mg, 0.234 mmol) and 2,4-difluoroaniline (30 mg, 0.234 mmol) were combined to yield ethyl 3-(3-t-butyl-5-(3-(2,4-difluorophenyl)ureido)-1H-pyrazol-1-yl)-1-naphthoate (89 mg, 77% yield). $^1$H NMR (400 MHz, DMSO-$d_6$): δ 1.25-1.31 (m, 3H), 1.29 (s, 9H), 4.39-4.47 (m, 2H), 6.45 (s, 1H), 7.02-7.03 (m, 1H), 7.28-7.29 (m, 1H), 7.68-7.73 (m, 2H), 7.99-8.01 (m, 1H), 8.13-8.15 (m, 1H), 8.24 (s, br, 1H), 8.36 (s, 1H), 8.76-8.78 (m, 1H), 8.84 (s, 1H), 8.91 (s, 1H); LC-MS (EI) m/z: 493.2 (M+H⁺).

Example 290

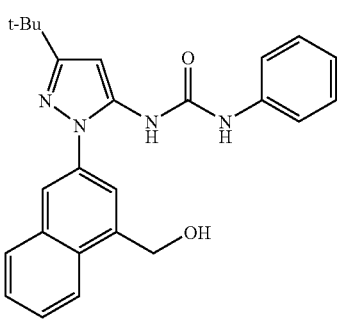

Using general method C, Example 286 (100 mg, 0.22 mmol) was reduced to afford 1-[3-t-butyl-1-(4-(hydroxymethyl)naphthalen-2-yl)-1H-pyrazol-5-yl]-3-phenylurea (50 mg, 55% yield). $^1$H NMR (300 MHz, DMSO-d$_6$): δ 8.99 (s, 1H), 8.49 (s, 1H), 8.06 (m, 1H), 8.01 (m, 1H), 7.92 (s, 1H), 7.69 (s, 1H), 7.54-7.60 (m, 2H), 7.35 (d, J=7.8 Hz, 2H), 7.21 (t, J=7.8 Hz, 2H), 6.92 (t, J=7.5 Hz, 1H), 6.41 (s, 1H), 5.01 (s, 2H), 1.28 (s, 9H).

Example 291

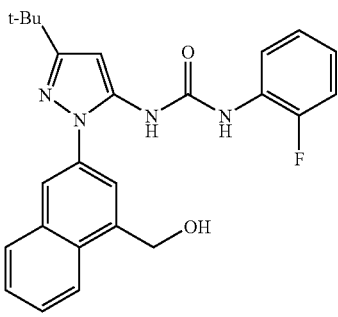

Using General method D, Example A24 (120 mg, 0.234 mmol) and 2-fluoroaniline (26 mg, 0.234 mmol) were combined to yield ethyl 3-(3-t-butyl-5-(3-(2-fluorophenyl)ureido)-1H-pyrazol-1-yl)-1-naphthoate (104 mg, 93% yield). Using General method C, ethyl 3-(3-t-butyl-5-(3-(2-fluorophenyl)ureido)-1H-pyrazol-1-yl)-1-naphthoate (104 mg, 0.22 mmol) was reduced to afford 1-(3-t-butyl-1-(4-(hydroxymethyl)naphthalen-2-yl)-1H-pyrazol-5-yl)-3-(2-fluorophenyl)urea (32 mg, 34% yield). $^1$H NMR (400 MHz, DMSO-d$_6$): δ 1.30 (s, 9H), 5.04 (s, 2H), 6.46 (s, 1H), 6.98-7.02 (m, 1H), 7.09-7.22 (m, 2H), 7.61 (s, br, 2H), 7.71 (s, 1H), 7.95 (s, 1H), 8.03-8.14 (m, 3H), 8.92-8.95 (m, 2H); LC-MS (EI) m/z: 433.2 (M+H$^+$).

Example 292

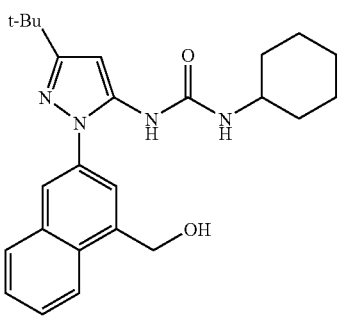

Using general method D, Example A24 (120 mg, 0.234 mmol) and cyclohexylamine (23 mg, 0.234 mmol) were combined to afford 65 mg (60%), ethyl 3-(3-t-butyl-5-(3-cyclohexylureido)-1H-pyrazol-1-yl)-1-naphthoate, used as is. Using general method C, this ester (65 mg, 0.14 mmol) was reduced to give 1-(3-t-butyl-1-(4-(hydroxymethyl)naphthalen-2-yl)-1H-pyrazol-5-yl)-3-cyclohexylurea (34 mg, 58% yield) as a foam, $^1$H NMR (400 MHz, DMSO-d$_6$): δ 1.07-1.98 (m, 10H), 1.29 (s, 9H), 3.34-3.39 (m, 1H), 5.02 (brs, 2H), 5.47 (s, br, 1H), 6.32 (brs, 1H), 6.46-6.47 (m, 1H), 7.60-7.68 (m, 3H), 7.86 (brs, 1H), 8.00-8.08 (m, 3H); LC-MS (EI) m/z: 421.2 (M+H$^+$).

Example 293

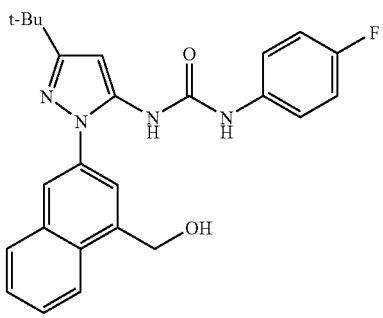

Using general method D, Example A24 (120 mg, 0.234 mmol) and 4-fluoroaniline (26 mg, 0.234 mmol) to afford 89 mg (80%), ethyl 3-(3-t-butyl-5-(3-(4-fluorophenyl)ureido)-1H-pyrazol-1-yl)-1-naphthoate. Using general method C, this ester (89 mg, 0.19 mmol) was reduced to give 1-(3-t-butyl-1-(4-(hydroxymethyl)naphthalen-2-yl)-1H-pyrazol-5-yl)-3-cyclohexylurea (59 mg, 73% yield). $^1$H NMR (400 MHz, DMSO-d$_6$); δ 1.31 (s, 9H), 5.04 (s, 2H), 6.43 (s, 1H), 7.06-7.11 (m, 2H), 7.38-7.41 (m, 2H), 7.57-7.62 (m, 2H), 7.73 (s, br, 1H), 7.98 (s, 1H), 8.02-8.10 (m, 2H), 8.62 (s, 1H), 9.24 (s, 1H). LC-MS (EI) m/z: 433.3 (M+H$^+$).

Example 294

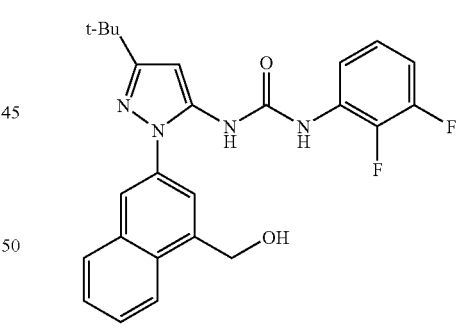

Using general method D, Example A24 (120 mg, 0.234 mmol) and 2,3-difluoroaniline (30 mg, 0.234 mmol) were combined to give 82 mg (71%), ethyl 3-(3-t-butyl-5-(3-(2,3-difluorophenyl)ureido)-1H-pyrazol-1-yl)-1-naphthoate. Using general method C, this ester (82 mg, 0.17 mmol) was reduced give 1-(3-t-butyl-1-(4-(hydroxymethyl)naphthalen-2-yl)-1H-pyrazol-5-yl)-3-cyclohexylurea (51 mg, 68% yield) an off white solid. $^1$H NMR (400 MHz, DMSO-d$_6$): δ 1.31 (s, 9H), 5.04-5.05 (m, 2H), 5.50 (m, 1H), 6.46 (s, 1H), 7.02-7.14 (m, 2H), 7.60-7.62 (m, 2H), 7.59-7.62 (m, 2H), 7.71 (s, 1H), 7.91-7.96 (m, 2H), 8.03-8.11 (m, 2H), 8.98 (s, 1H), 9.11 (s, 1H). LC-MS (EI) m/z: 451.2 (M+H$^+$).

Example A73

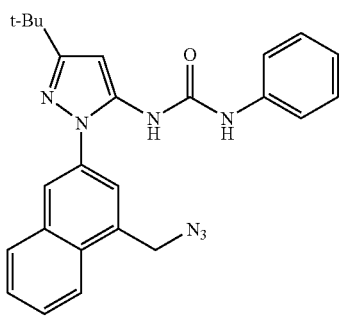

To a solution of Example A23 (400 mg, 1.25 mmol) and triethylamine (303 mg, 3.0 mmol) in THF (10.0 mL) was added isocyanato-benzene (250 mg, 1.5 mmol) in THF (2.0 mL) at 0° C. The mixture was stirred at RT overnight then poured into water (50 mL). The mixture was extracted with $CH_2Cl_2$ (3×100 mL). The combined organic extracts were washed with brine, dried ($Na_2SO_4$), filtered, concentrated and purified via column chromatography to afford 1-[1-(4-(azidomethyl)naphthalen-2-yl)-3-t-butyl-1H-pyrazol-5-yl]-3-phenylurea (320 mg, 58% yield). MS (ESI) m/z: 440 (M+H$^+$).

Example 295

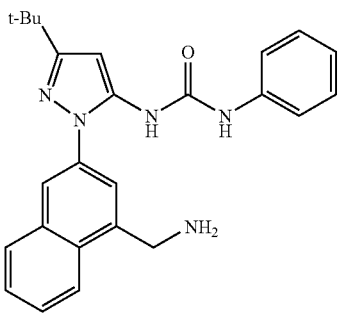

A mixture of Example A73 (300 mg, 0.68 mmol) and Pd/C (60 mg, 20%) in methanol (20 mL) was stirred at RT under 20 psi of $H_2$ for 3 h and then filtered. The filtrate was concentrated to yield the crude product, which was purified by preparative HPLC to afford the TFA salt. The mixture of TFA salt in MeCN/$H_2O$ (50 mL) was basified to pH=10 with 1N $Na_2CO_3$. After lyophilization, the residue was dissolved in THF and filtered. The filtrate was adjusted to pH=6 with 1N HCl/MeOH (2.0 mL) and then concentrated to 1-[1-(4-(aminomethyl)naphthalen-2-yl)-3-t-butyl-1H-pyrazol-5-yl]-3-phenylurea (180 mg, 64% yield). $^1$H NMR (300 MHz, DMSO-d$_6$): δ 9.81 (s, 1H), 8.96 (s, 1H), 8.58 (brs, 1H), 8.16 (s, 2H), 8.09 (d, J=5.1 Hz, 1H), 7.87 (s, 1H), 7.64 (s, 2H), 7.38 (d, J=5.7 Hz, 2H), 7.21 (t, J=−5.4 Hz, 2H), 6.91 (t, J=5.4 Hz, 1H), 6.44 (s, 1H), 4.61 (s, 2H), 1.29 (s, 9H); MS (ESI) m/z: 414 (M+H$^+$).

Example 296

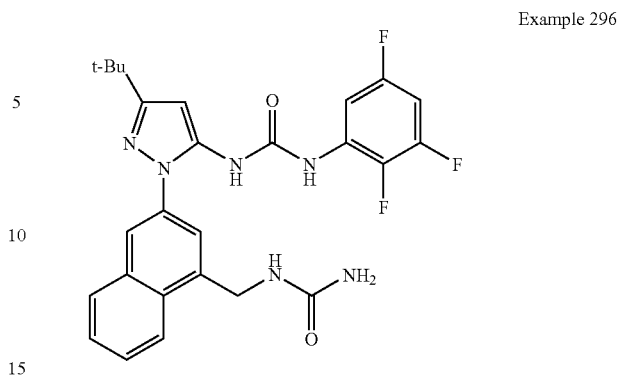

To a solution of Example 70 (0.12 g, 0.24 mmol) in water (5 mL) was added glacial acetic acid (43 mg, 0.71 mmol). Potassium cyanate (58 mg, 0.71 mmol) was added into the reaction mixture over a period of 30 min. The reaction mixture was stirred at room temperature overnight. The mixture was kept in refrigerator. The solid was filtered, washed with water and acetic acid (1:1) mixture. The solid was dissolved in $CH_3CN:H_2O$ (1:1 4 mL) and lyophilized to obtain the diurea solid (105 mg, 86% yield) as an off-white. $^1$H NMR (400 MHz, DMSO-d$_6$): δ 9.43 (s, 1H), 9.17 (brs, 1H), 8.20 (m, 1H), 8.05 (m, 1H), 7.97 (d, J=1.6 Hz, 1H), 7.87 (m, 1H), 7.61 (m, 1H), 7.10 (m, 1H), 6.61 (t, J=5.6 Hz, 1H), 6.48 (s, 1H), 4.73 (d, J=5.6 Hz, 2H), 1.31 (s, 9H); LC-MS (EI) m/z: 511.2 (M+H$^+$).

Example 297

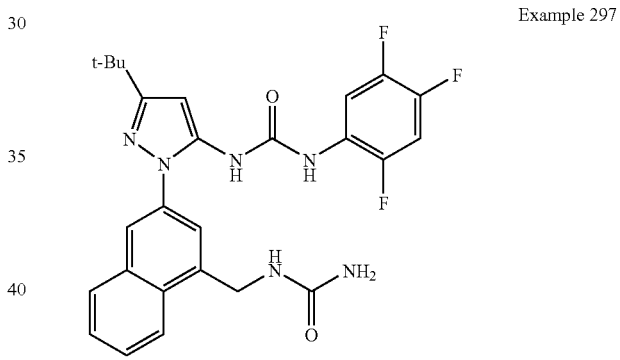

Using the same procedureas for Example 296, Example 71 (0.10 g, 0.21 mmol) and potassium cyanate (51 mg, 0.63 mmol) were combined to afford the diurea (78 mg, 73% yield) as an off-white solid. $^1$H NMR (400 MHz, DMSO-d$_6$): δ 9.12 (s, 1H), 8.98 (brs, 1H), 8.18 (m, 2H), 8.05 (m, 1H), 7.96 (d, J=1.6 Hz, 1H), 7.61 (m, 3H), 6.59 (t, J=5.6 Hz, 1H), 6.47 (s, 1H), 4.73 (d, J=5.6 Hz, 2H), 1.31 (s, 9H); LC-MS (EI) m/z: 511.2 (M+H$^+$).

Example 298

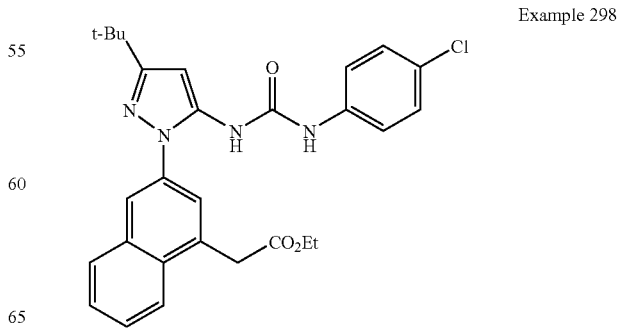

Using general method A, Example A27 (400 mg, 1.1 mmol) 1-chloro-4-isocyanatobenzene (260 mg, 1.7 mmol) were combined to afford (3-{3-t-butyl-5-[3-(4-chlorophenyl)ureido]pyrazol-1-yl}naphthalen-1-yl)acetic acid ethyl ester (154 mg, 30% yield) as a white solid. ¹H NMR (300 MHz, DMSO-d₆): δ 9.10 (s, 1H), 8.51 (s, 1H), 8.00-7.93 (m, 3H), 7.60-7.55 (m, 3H), 7.37 (d, J=9.0 Hz, 2H), 7.28 (d, J=9.0 Hz, 2H), 6.40 (s, 1H), 4.19 (s, 2H), 4.07 (q, J=7.2 Hz, 2H), 1.26 (s, 9H), 1.13 (t, J=7.2 Hz, 3H); MS (ESI) m/z: 505 (M+H⁺).

Example 299

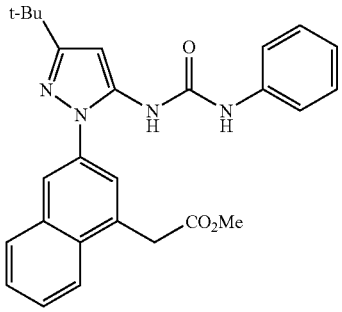

Using general method A, Example A27 (1 g, 2.8 mmol) and isocyanatobenzene (407 mg, 3.4 mmol) were combined to afford {3-[3-t-butyl-5-(3-phenylureido)pyrazol-1-yl]naphthalen-1-yl}acetic acid methyl ester (790 mg, 62% yield) as a white solid. ¹H NMR (300 MHz, DMSO-d₆): δ 8.97 (s, 1H), 8.49 (s, 1H), 8.02-7.94 (m, 3H), 7.62 (s, 1H), 7.60-7.56 (m, 2H), 7.35 (d, J=7.5 Hz, 2H), 7.22 (t, J=8.1 Hz, 2H), 6.95 (t, J=7.5 Hz, 1H), 6.41 (s, 1H), 4.23 (s, 2H), 3.57 (s, 3H), 1.27 (s, 9H); MS (ESI) m/z: 457 (M+H⁺).

Example 300

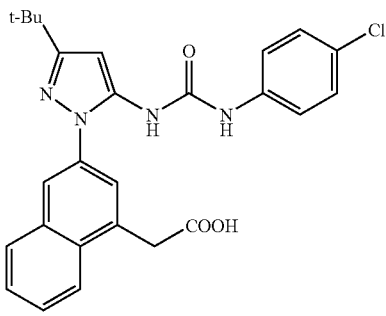

Using general method E, Example 298 (100 mg, 0.2 mmol) was saponified to afford (3-{3-t-butyl-5-[3-(4-chlorophenyl)ureido]pyrazol-1-yl}naphthalen-1-yl)acetic acid (85 mg, 90% yield) as a white solid. ¹H NMR (300 MHz, DMSO-d₆): δ 9.28 (s, 1H), 9.18 (s, 1H), 8.64 (s, 1H), 7.97 (brs, 2H), 7.60-7.54 (m, 2H), 7.45-7.36 (m, 3H), 7.29-7.23 (m, 3H), 6.39 (s, 1H), 4.10 (s, 2H), 1.27 (s, 9H); MS (ESI) m/z: 511 (M+H⁺).

Example 301

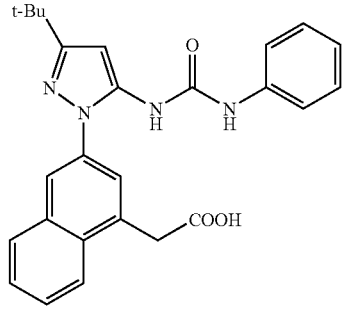

Using general method E, Example 299 (250 mg, 0.54 mmol) was saponified to afford {3-[3-t-butyl-5-(3-phenylureido)pyrazol-1-yl]naphthalen-1-yl}acetic acid (180 mg, 87% yield) as a white solid. ¹H NMR (300 MHz, DMSO-d₆): δ 8.00-7.94 (m, 3H), 7.58-7.56 (m, 3H), 7.33 (d, J=8.4 Hz, 2H), 7.21 (t, J=8.1 Hz, 2H), 6.91 (t, J=6.6 Hz, 1H), 6.40 (s, 1H), 4.10 (s, 2H), 1.26 (s, 9H); MS (ESI) m/z: 443 (M+H⁺).

Example 302

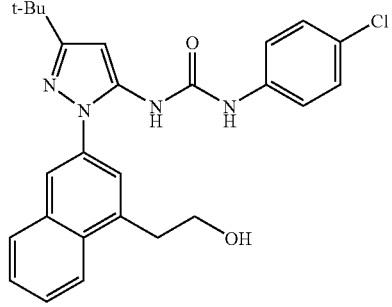

Using general method C, Example 298 (350 mg, 0.7 mmol) was reduced to afford 1-{5-t-butyl-2-[4-(2-hydroxyethyl)naphthalen-2-yl]-2H-pyrazol-3-yl}-3-(4-chlorophenyl)urea (268 mg, 83% yield) as a white solid. ¹H-NMR (300 MHz, DMSO-d₆): δ 9.17 (s, 1H), 8.53 (s, 1H), 8.12 (m, 1H), 7.96 (m, 1H), 7.89 (s, 1H), 7.55 (m, 2H), 7.51 (s, 1H), 7.31 (dd, J=9.0 Hz, 9.0 Hz, 4H), 6.39 (s, 1H), 3.71 (t, J=6.9 Hz, 2H), 3.23 (t, J=6.9 Hz, 2H), 1.27 (s, 1H); MS (ESI) m/z: 463 (M+H).

Example 303

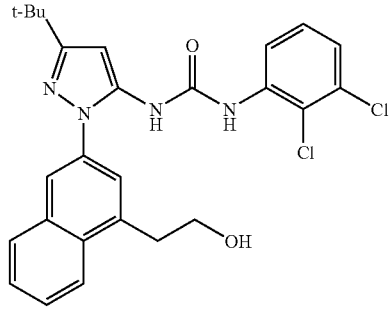

Using general method C, Example 76 (70 mg, 0.13 mmol) was reduced to afford 1-{5-t-butyl-2-[4-(2-hydroxyethyl)naphthalen-2-yl]-2H-pyrazol-3-yl}-3-(2,3-dichlorophenyl)urea (57 mg, 86% yield) as a white solid. ¹H NMR (300 MHz, DMSO-d$_6$): δ 9.29 (s, 1H), 8.77 (s, 1H), 8.12 (m, 1H), 8.13-7.95 (m, 2H), 7.90 (s, 1H), 7.56-7.52 (m, 3H), 7.28-7.26 (m, 2H), 6.41 (s, 1H), 3.73 (t, J=6.9 Hz, 2H), 3.24 (t, J=6.9 Hz, 2H), 1.27 (s, 9H); MS (ESI) m/z: 497 (M+H$^+$).

Example 304

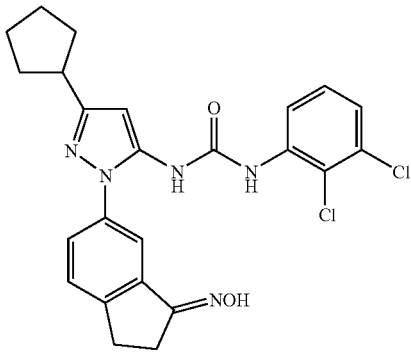

To a mixture of Example 102 (120 mg, 0.26 mmol) and K$_2$CO$_3$ (0.1 g, 0.7 mmol) in ethanol (20 mL) was added hydroxylamine hydrochloride (500 mg). The resulting mixture was heated to reflux for 3 h. After removal of the solvent, the residue was purified by preparative HPLC to give 1-[5-t-butyl-2-(3-hydroxyiminoindan-5-yl)-2H-pyrazol-3-yl]-3-(2,3-dichloro phenyl)urea (75 mg, 61% yield). $^1$H NMR (300 MHz, MeOD-d$_6$): δ 8.04 (d, J=5.4 Hz, 1H), 7.73 (s, 1H), 7.52-7.43 (m, 2H), 7.22-7.20 (m, 2H), 6.48 (s, 1H), 3.20-3.12 (m, 2H), 2.97 (m, 2H), 1.33 (s, 9H); MS (ESI) m/z: 473 (M+H$^+$).

Example 305

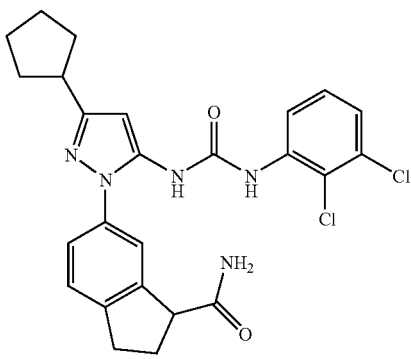

In a 1:1:1 mix of EtOH:H2O:dioxane (6 mL) was placed ethyl 6-(3-cyclopentyl-5-(3-(2,3-dichlorophenyl)ureido)-1H-pyrazol-1-yl)-2,3-dihydro-1H-indene-1-carboxylate (520 mg, 0.986 mmol) and lithium hydroxide (71 mg, 2.96 mmol). The solution warmed to 40 C and stirred, ON. LC shows complete reaction. The solution cooled to RT and diluted with 5% citric acid (20 mL) and Ethyl acetate (20 mL). The organic phase separated, washed with brine and dried over sodium sulfate. The solvents were evaporated at reduced pressure to give 6-(3-cyclopentyl-5-(3-(2,3-dichlorophenyl) ureido)-1H-pyrazol-1-yl)-2,3-dihydro-1H-indene-1-carboxylic acid as a foam, 474 mg (96%), used as is. In DMF (5 mL) was placed 6-(3-cyclopentyl-5-(3-(2,3-dichlorophenyl) ureido)-1H-pyrazol-1-yl)-2,3-dihydro-1H-indene-1-carboxylic acid (474 mg, 0.949 mmol), HOBt (196 mg, 1.09 mmol) and EDAC (218 mg, 1.42 mmol). The mixture was stirred at RT for 1 hr and then treated with a solution of 0.5N ammonia in dioxane (7.59 mL, 3.80 mmol). The mixture was stirred at RT, ON. LC shows complete reaction. The mixture was diluted with 5% citric acid (20 mL) and Ethyl acetate (20 mL). The organic phase separated, washed with saturated sodium bicarbonate (20 mL), brine (20 mL) and dried over sodium sulfate. The solvents evaporated at reduced pressure to give a foam, dried on high vacuum line at RT for 2 hrs. The foam was then purified by Biotage chromatography (S1-25 column, 65-95% Ethyl acetate/Hex). Fractions 10-19 were combined and evaporated at reduced pressure to give 1-(1-(3-carbamoyl-2,3-dihydro-1H-inden-5-yl)-3-cyclopentyl-1H-pyrazol-5-yl)-3-(2,3-dichlorophenyl)urea as a white solid. The solid was dried on the high vacuum line at 65 C in the abderhalden for 3 hrs, 210 mg (44%). 1H NMR (DMSO-d6) 1.59-1.73 (m, 6H), 1.95-1.99 (m, 2H), 2.23-2.33 (m, 2H), 2.88-3.06 (m, 3H), 3.90-4.04 (m, 1H), 6.31 (s, 1H), 6.98 (s, 1H), 7.26-7.42 (m, 5H), 7.63 (br s, 1H), 8.07-8.09 (m, 1H), 8.77 (s, 1H), 9.21 (s, 1H). LC-MS (EI) m/z: 500.0 (M+H$^+$).

Example 306

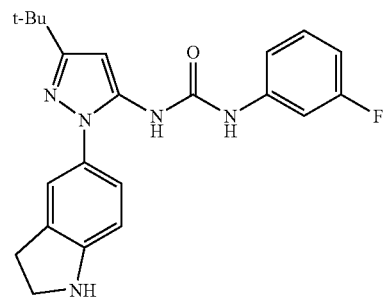

Using general method D, Example A78 (70 mg, 0.20 mmol,) and 1-fluoro-3-isocyanatobenzene (27 mg, 0.20 mmol) were combined to yield 1-(3-t-butyl-1-(indolin-5-yl)-1H-pyrazol-5-yl)-3-(3-fluorophenyl)urea HCl salt (47 mg, 60% yield). $^1$H NMR (400 MHz, DMSO-d$_6$): δ 9.53 (s, 1H), 8.66 (s, 1H), 7.49 (s, 1H), 7.43 (m, 1H), 7.37 (m, 1H), 7.27 (m, 2H), 7.06 (dd, J=1.2, and 8.0 Hz, 1H), 6.78 (dt, J=2.4, and 8.8 Hz, 1H), 6.37 (s, 1H), 3.70 (t, J=8.4 Hz, 2H), 3.20 (t, J=8.4 Hz, 2H), 1.28 (s, 9H); LC-MS (EI) m/z: 490.2 (M+H$^+$).

Example 307

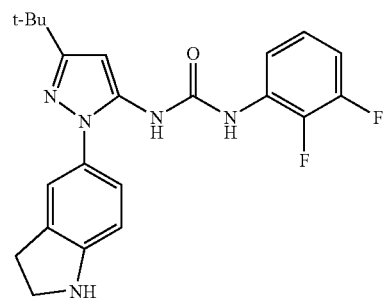

Using general method D, A78 (85 mg, 0.24 mmol,) and 2,3-difluorobenzenamine (90 mg, 0.68 mmol) were combined to yield 1-(3-t-butyl-1-(indolin-5-yl)-1H-pyrazol-5-yl)-3-(2,3-difluorophenyl)urea HCl salt (80 mg, 74% yield). $^1$H NMR (400 MHz, DMSO-d$_6$): δ 9.20 (s, 1H), 9.03 (brs, 1H), 7.90 (t, J=8.0 Hz, 1H), 7.48 (brs, 1H), 7.36 (m, 1H), 7.26 (m, 1H), 7.13 (m, 1H), 7.02 (m, 1H), 6.39 (d, J=1.6 Hz, 1H), 3.70 (t, J=6.4 Hz, 2H), 3.19 (t, J=8.0 Hz, 2H), 1.28 (s, 9H); LC-MS (EI) m/z: 412.3 (M+H$^+$).

Example 308

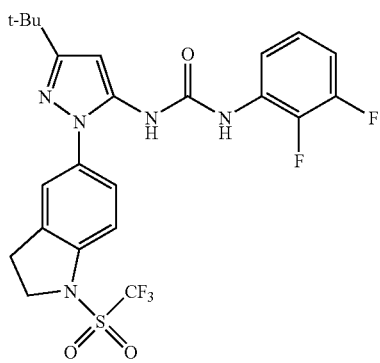

Using the same method as for Example 108, Example 307 (80 mg, 0.20 mmol,) and triflic anhydride (70 mg, 0.2 mmol) were combined to yield 1-(3-t-butyl-1-(1-(trifluoromethylsulfonyl)indolin-5-yl)-1H-pyrazol-5-yl)-3-(2,3-dichlorophenyl)urea (50 mg, 43% yield) as a pale yellow solid. $^1$H NMR (400 MHz, DMSO-$d_6$): δ 9.08 (brs, 1H), 8.89 (brs, 1H), 7.90 (dt, J=1.6, and 7.6 Hz, 1H), 7.53 (brs, 1H), 7.43 (d, J=2.0 Hz, 1H), 7.13 (m, 1H), 7.04 (m, 1H), 6.39 (s, 1H), 4.32 (t, J=8.8 Hz, 2H), 3.32 (s, 2H), 3.31 (t, J=8.4 Hz, 2H), 1.27 (s, 9H); LC-MS (EI) m/z: 544.2 (M+H$^+$).

General Experimental for Examples 309-314

A solution of Example A35 and the appropriate isocyanate (general method A) or the appropriate aniline (general method D) were combined to yield the indicated compound.

| Example | Name | MS (EI) (M + H$^+$) | $^1$H NMR (400 MHz, DMSO-$d_6$) |
|---|---|---|---|
| Example 309 | 1-[3-t-butyl-1-(1-oxo-1,2,3,4-tetrahydroisoquinolin-7-yl)-1H-pyrazol-5-yl]-3-(4-chlorophenyl)urea 1.5 g, 55% yield General method A | | 300 MHz, CDCl$_3$: δ 9.03 (s, 1H), 8.77 (s, 1H), 7.90 (s, 1H), 7.54 (d, J = 7.5 Hz, 1H), 7.30 (d, J = 9 Hz, 3H), 7.19 (d, J = 9 Hz, 2H), 6.88 (brs, 1H), 6.74 (s, 1H), 3.45 (brs, 2H), 2.88 (t, J = 6 Hz, 2H), 1.37 (s, 9H) |
| Example 310 | 1-(3-t-butyl-1-(1-oxo-1,2,3,4-tetrahydroisoquinolin-7-yl)-1H-pyrazol-5-yl)-3-cyclohexylurea 38 mg, 24% yield General method D | 410.2 | 1.05-1.30 (m, 5H), 1.27 (s, 9H), 1.48-1.52 (m, 1H), 1.58-1.63 (m, 2H), 1.70-1.75 (m, 2H), 2.94-2.97 (m, 2H), 3.32-3.41 (m, 3H), 6.25 (s, 1H), 6.39-6.41 (m, 1H), 7.42-7.44 (m, 1H), 7.53-7.56 (m, 1H), 7.87 (s, 1H), 8.03 (s, 1H), 8.10 (s, 1H). |
| Example 311 | 1-(3-t-butyl-1-(1-oxo-1,2,3,4-tetrahydroisoquinolin-7-yl)-1H-pyrazol-5-yl)-3-(2,4-difluorophenyl)urea 84 mg, 54% yield General method D | 440.2 | 1.28 (s, 9H), 2.90-2.92 (m, 2H), 3.39-3.42 (m, 2H), 6.37 (s, 1H), 7.02 (m, 1H), 7.28-7.29 (m, 1H), 7.46-7.48 (m, 1H), 7.61-7.64 (m, 1H), 7.92 (s, 1H), 8.01-8.02 (s, 1H), 8.11 (s, br, 1H), 8.90 (s, br, 1H), 8.94 (s, br, 1H). |

| Example | Name | MS (EI) (M + H+) | 1H NMR (400 MHz, DMSO-d6) |
|---|---|---|---|
| 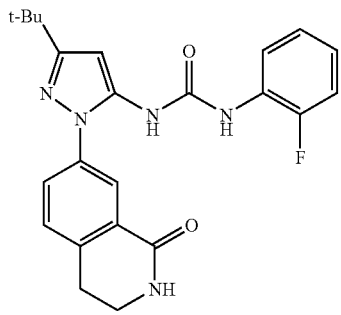

Example 312 | 1-(3-t-butyl-1-(1-oxo-1,2,3,4-tetrahydroiso-quinolin-7-yl)-1H-pyrazol-5-yl)-3-(2-fluorophenyl)urea
28 mg, 28% yield
General method D | 422.2 | 1.28 (s, 9H), 2.97-2.99 (m, 2H), 3.40-3.49 (m, 2H), 6.39 (s, 1H), 6.95-7.25 (m, 3H), 7.47-7.49 (m, 1H), 7.62 (m, 1H), 7.91 (s, 1H), 8.09-8.12 (m, 2H), 8.89 (s, 2H). |
| 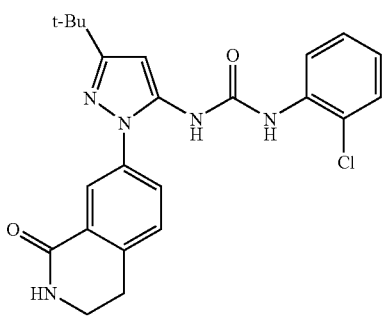

Example 313 | 1-(3-t-butyl-1-(1-oxo-1,2,3,4-tetrahydroiso-quinolin-7-yl)-1H-pyrazol-5-yl)-3-(2-chlorophenyl)urea
41 mg, 33% yield
General method D | 437.8 | 1.28 (s, 9H), 2.95-2.98 (m, 2H), 3.38-3.43 (m, 2H), 6.38 (s, 1H), 7.01-7.06 (m, 1H), 7.26-7.30 (m, 1H), 7.42-7.48 (m, 2H), 7.62-7.65 (m, 1H), 7.94 (s, br, 1H), 8.04-8.07 (s, 1H), 8.11 (s, br, 1H), 8.58 (s, 1H), 9.23 (s, br, 1H). |
| 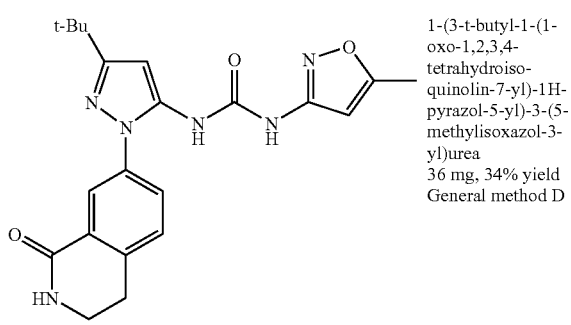

Example 314 | 1-(3-t-butyl-1-(1-oxo-1,2,3,4-tetrahydroiso-quinolin-7-yl)-1H-pyrazol-5-yl)-3-(5-methylisoxazol-3-yl)urea
36 mg, 34% yield
General method D | 409.2 | 1.28 (s, 9H), 2.33 (s, 3H), 2.94-2.98 (m, 2H), 3.39-3.42 (m, 2H), 6.37 (s, 1H), 6.46 (s, 1H), 7.44-7.46 (m, 1H), 7.60-7.63 (m, 1H), 7.90 (s, 1H), 8.11 (s, br, 1H), 8.75 (s, 1H), 9.84 (s, 1H). |

General Experimental for Examples 315-326

A solution of Example A35 and the appropriate isocyanate (general method A) or the appropriate aniline (general method D) were combined to yield the indicated compound.

| Example | Name | MS (EI) (M + H+) | 1H NMR (400 MHz, DMSO-d6) |
|---|---|---|---|
| 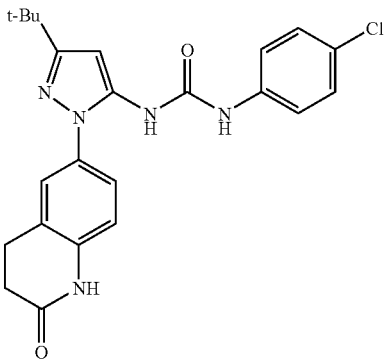 Example 315 | 1-(3-t-butyl-1-(2-oxo-1,2,3,4-tetrahydro-quinolin-6-yl)-1H-pyrazol-5-yl)-3-(4-chlorophenyl)urea 461 mg, 60% yield General method A | 438.3 | acetone-d6: δ 9.29 (brs 1H), 8.55 (brs, 1H), 7.87 (brs, 1H), 7.50 (dt, J = 8.8, and 2.4 Hz, 2H), 7.36 (brs, 1H), 7.32 (dd, J = 8.4, 2.4 Hz, 1H), 7.27 (dt, J = 8.4, 2.4 Hz, 2H), 7.03 (d, 1H, J = 8.0 Hz), 6.44 (s, 1H), 3.00 (t, J = 7.4 Hz, 2H), 2.53 (t, J = 7.4 Hz, 2H), 1.31 (s, 9H) |
| 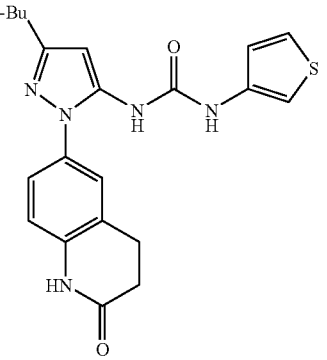 Example 316 | 1-(3-t-butyl-1-(2-oxo-1,2,3,4-tetrahydro-quinolin-6-yl)-1H-pyrazol-5-yl)-3-(thiophen-3-yl)urea 0.33 g, 22% yield General method A | 410.0 | 10.3 (s, 1H), 9.24 (s, 1H), 8.29 (s, 1H), 7.43 (dd, J = 3.2, and 5.2 Hz, 1H), 7.30 (m, 1H), 7.24 (m, 2H), 6.96 (m, 1H), 6.34 (s, 1H), 2.95 (t, J = 7.2 Hz, 2H), 1.26 (s, 9H) |
| 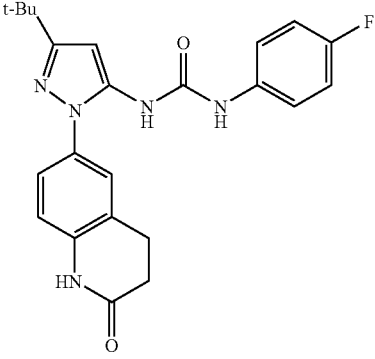 Example 317 | 1-(3-t-butyl-1-(2-tetrahydroquinolin-6-yl)-1H-pyrazol-5-yl)-3-(4-fluorophenyl)urea 72 mg, 49% yield General method A | 422.2 | 10.3 (s, 1H), 9.02 (s, 1H), 8.32 (s, 1H), 7.44 (m, 2H), 7.31 (brs, 1H), 7.26 (dd, J = 2.0, and 8.4 Hz, 1H), 7.12 (m, 2H), 6.97 (d, J = 8.4 Hz, 1H), 6.33 (s, 1H), 4.79 (m, 1H), 2.97 (t, J = 7.6 Hz, 2H), 1.26 (s, 9H) |

-continued

| Example | | Name | MS (EI) (M + H+) | 1H NMR (400 MHz, DMSO-d6) |
|---|---|---|---|---|
| 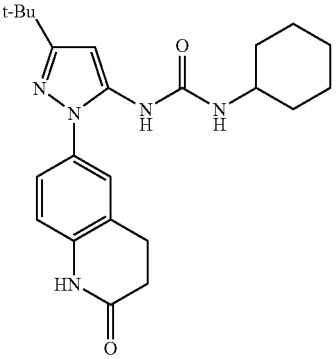
Example 318 | | 1-(3-t-butyl-1-(2-oxo-1,2,3,4-tetrahydroquinolin-6-yl)-1H-pyrazol-5-yl)-3-cyclohexylurea
52 mg, 39% yield
General method A | 410.2 | 10.3 (s, 1H), 7.91 (s, 1H), 7.24 (d, J = 2.0 Hz, 1H), 7.18 (dd, J = 2.4, and 8.0 Hz, 1H), 6.94 (d, J = 8.4 Hz, 1H), 6.47 (d, J = 8.0 Hz, 1H), 6.24 (s, 1H), 3.39 (m, 1H), 2.93 (t, J = 7.6 Hz, 2H), 2.47 (m, 2H), 1.75 (m, 2H), 1.62 (m, 2H), 1.51 (m, 1H), 1.28 (m, 2H), 1.23 (s, 9H), 1.12 (m, 3H) |
| 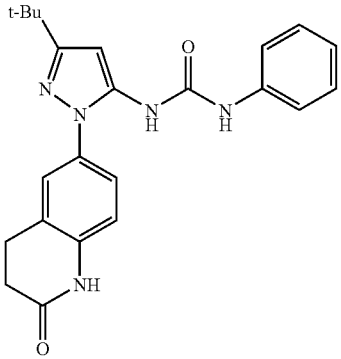
Example 319 | | 1-(3-t-butyl-1-(2-oxo-1,2,3,4-tetrahydro-quinolin-6-yl)-1H-pyrazol-5-yl)-3-phenylurea as a off-white powder
27 mg, 19% yield
General method A | 404.2 | 10.3 (s, 1H), 8.99 (s, 1H), 8.33 (s, 1H), 7.39 (dd, J = 0.8, and 8.4 Hz, 2H), 7.27 (m, 4H), 6.97 (d, J = 8.8 Hz, 2H), 6.35 (s, 1H), 4.79 (m, 1H), 2.96 (t, J = 7.6 Hz, 2H), 1.26 (s, 9H) |
| 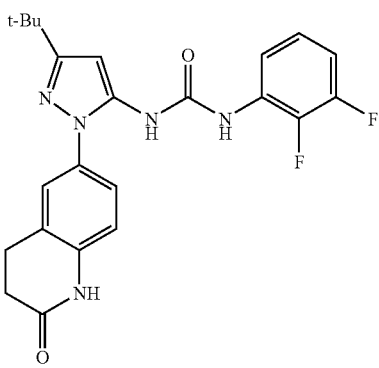
Example 320 | | 1-(3-t-butyl-1-(2-oxo-1,2,3,4-tetrahydro-quinolin-6-yl)-1H-pyrazol-5-yl)-3-(2,3-difluorophenyl)urea
0.035 g, 13% yield, 2 steps
General method D | 440.2 | 10.3 (s, 1H), 9.11 (brs, 1H), 8.85 (s, 1H), 7.94 (t, J = 6.8 Hz, 1H), 7.31 (d, J = 2.0 Hz, 1H), 7.25 (dd, J = 2.0, and 8.0 Hz, 1H), 7.13 (m, 1H), 7.03 (m, 1H), 6.98 (d, J = 8.4 Hz, 1H), 6.37 (s, 1H), 2.96 (t, J = 7.2 Hz, 2H), 1.26 (s, 9H) |

| Example | Name | MS (EI) (M + H+) | 1H NMR (400 MHz, DMSO-d6) |
|---|---|---|---|
| 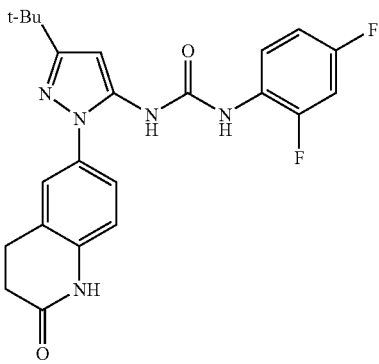 Example 321 | 1-(3-t-butyl-1-(2-oxo-1,2,3,4-tetrahydro-quinolin-6-yl)-1H-pyrazol-5-yl)-3-(2,4-difluorophenyl)urea 58 mg, 51% yield General method D | 440.2 | 1.26 (s, 9H), 2.45-2.52 (m, 2H), 2.93-2.97 (m, 2H), 6.35 (s, 1H), 6.96-7.03 (m, 2H), 7.23-7.32 (m, 3H), 8.03-8.07 (m, 1H), 8.76 (brs, 1H), 8.89 (brs, 1H), 10.28 (s, 1H) |
| 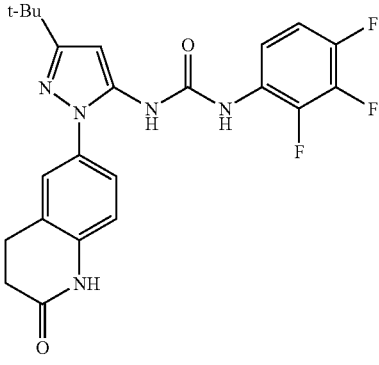 Example 322 | 1-(3-t-butyl-1-(2-oxo-1,2,3,4-tetrahydro-quinolin-6-yl)-1H-pyrazol-5-yl)-3-(2,3,4-trifluorophenyl)urea 16 mg, 16% yield General method D | 458.3 | 1.25 (s, 9H), 2.45-2.52 (m, 2H), 2.93-2.97 (m, 2H), 6.35 (s, 1H), 6.96-6.98 (m, 1H), 7.23-7.31 (m, 3H), 7.85-7.87 (m, 1H), 8.78 (s, 1H), 9.05 (s, 1H), 10.29 (s, 1H) |
| 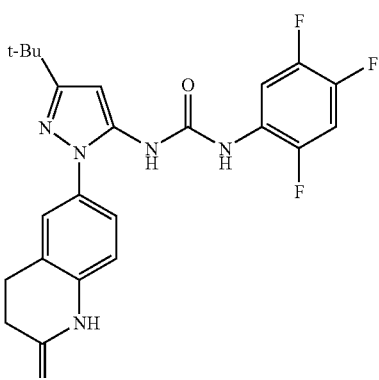 Example 323 | 1-(3-t-butyl-1-(2-oxo-1,2,3,4-tetrahydro-quinolin-6-yl)-1H-pyrazol-5-yl)-3-(2,4,5-trifluorophenyl)urea, 23 mg, 23% yield General method D | 458.3 | 1.26 (s, 9H), 2.47-2.56 (m, 2H), 2.93-2.97 (m, 2H), 6.37 (s, 1H), 6.97-6.99 (d, 1H), 7.23-7.31 (m, 2H), 7.60-7.64 (m, 1H), 8.16-8.19 (m, 1H), 8.84 (s, 1H), 9.10 (s, 1H), 10.29 (m, 1H) |

-continued

| Example | Name | MS (EI) (M + H+) | 1H NMR (400 MHz, DMSO-d6) |
|---|---|---|---|
| 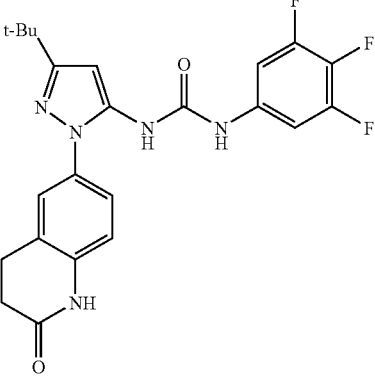<br>Example 324 | 1-(3-t-butyl-1-(2-oxo-1,2,3,4-tetrahydro-quinolin-6-yl)-1H-pyrazol-5-yl)-3-(3,4,5-trifluorophenyl)urea<br>28 mg, 28% yield<br>General method D | 458.3 | 1.26 (s, 9H), 2.46-2.52 (m, 2H), 2.92-2.96 (m, 2H), 6.34 (s, 1H), 6.94-6.96 (d, 1H), 7.23-7.34 (m, 4H), 8.51 (s, 1H), 9.30 (s, 1H), 10.27 (s, 1H) |
| 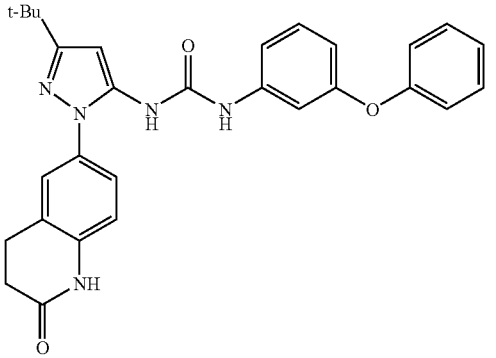<br>Example 325 | 1-(3-t-butyl-1-(2-oxo-1,2,3,4-tetrahydro-quinolin-6-yl)-1H-pyrazol-5-yl)-3-(3-phenoxyphenyl)urea.<br>50 mg, 42% yield<br>General method A | 496.3 | 1.24 (s, 9H), 2.46-2.50 (m, 2H), 2.92-2.95 (m, 2H), 6.31 (s, 1H), 6.61 (d, 1H), 6.95-7.41 (m, 11H), 8.29 (s, 1H), 9.09 (s, 1H), 10.27 (s, 1H) |
| 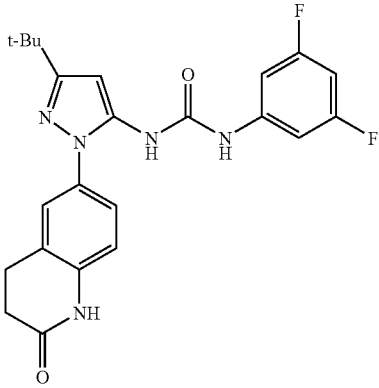<br>Example 326 | 1-(3-t-butyl-1-(2-oxo-1,2,3,4-tetrahydro-quinolin-6-yl)-1H-pyrazol-5-yl)-3-(3,5-difluorophenyl)urea<br>34 mg, 18% yield<br>General method A | 440.2 | 1.26 (s, 9H), 2.46-2.50 (m, 2H), 2.92-2.96 (m, 2H), 6.34 (s, 1H), 6.77-6.82 (m, 1H), 6.95-6.97 (m, 1H), 7.11-7.14 (m, 2H), 7.23-7.31 (m, 2H), 8.49 (s, 1H), 9.36 (s, 1H), 10.27 (s, 1H) |

Example 327

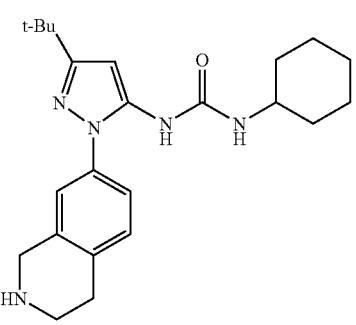

To a solution of amide compound (Example 310, 0.31 g, 0.8 mmol) in THF (10 mL) was added a solution of Lithium Aluminum Hydride (8 mL of 1M soln, 8 mmol) at RT and stirred for 16 h at 65° C. under Ar. The mixture was cooled to 0° C., to this were added 0.3 mL of water, 0.3 mL of 3M NaOH and 0.3 mL water sequentially. The resultant suspension was stirred at RT for 6 h, filtered over celite, celite was washed with EtOAC (3×5 mL). The combined filtrate was concentrated to afford residue, which was stirred with 1 mL of HCl in ethyl acetate for 30 min. The resultant solid was filtered and washed with ether, dried under vacuum to yield 1-(3-t-butyl-1-(1,2,3,4-tetrahydroisoquinolin-7-yl)-1H-pyrazol-5-yl)-3-cyclohexylurea (80 mg, 27% yield) as a solid. $^1$H NMR (400 MHz, DMSO-d$_6$): δ 9.57 (brs, 2H), 8.27 (s, 1H), 7.40-7.32 (m, 3H), 6.73 (brs, 1H), 6.25 (s, 1H), 4.35-4.31 (m, 2H), 3.39-3.37 (m, 3H), 3.04 (t, J=6.4 Hz, 2H), 1.74-1.51 (m, 6H), 1.25 (s, 9H), 1.19-1.07 (s, 4H). MS (ESI) m/z: 393.3 (M+H$^+$).

Example 328

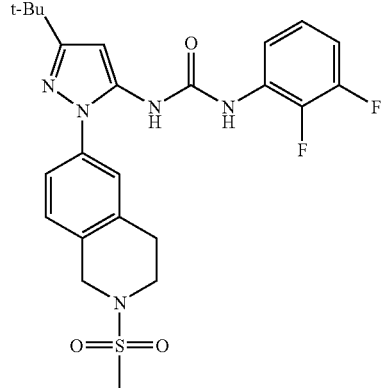

Using the same method as for Example 108, Example 144 (70 mg, 0.15 mmol) and methanesulfonyl chloride (34 mg, 0.30 mmol) were combined to yield 1-(3-t-butyl-1-(2-(methylsulfonyl)-1,2,3,4-tetrahydroisoquinolin-6-yl)-1H-pyrazol-5-yl)-3-(2,3-difluorophenyl)urea (60 mg, 80% yield). $^1$H NMR (400 MHz, DMSO-d$_6$): δ 9.11 (brs, 1H), 8.87 (s, 1H), 7.92 (m, 1H), 7.35 (m, 3H), 7.13 (m, 1H), 7.03 (m, 1H), 6.40 (s, 1H), 4.43 (s, 2H), 3.50 (t, J=6.0 Hz, 2H), 3.00 (t, J=6.0 Hz, 2H), 2.98 (s, 3H), 1.27 (s, 9H); LC-MS (EI) m/z: 504.2 (M+H$^+$).

General Experimental for Examples 329-333

A solution of Example A5 and the appropriate isocyanate (general method A) or the appropriate aniline (general method D) were combined to yield the indicated compound.

| Example | | Name | MS (EI) (M + H$^+$) | $^1$H NMR (400 MHz, DMSO-d$_6$) |
|---|---|---|---|---|
| Example 329 | | 1-(3-t-butyl-1-(2-oxo-1,2-dihydroquinolin-6-yl)-1H-pyrazol-5-yl)-3-(2,3-difluorophenyl)urea 39 mg, 41% yield General method A | 438.0 | 9.06 (s, 1H), 8.88 (s, 1H), 8.01 (d, J = 9.6 Hz, 1H), 7.93 (m, 1H), 7.84 (d, J = 2.4 Hz, 1H), 7.63 (dd, J = 2.0 Hz, 1H), 7.44 (d, J = 8.8 Hz, 1H), 7.13 (m, 1H), 7.03 (m, 1H), 6.60 (dd, J = 2.0, and 9.6 Hz, 1H), 6.41 (s, 1H), 1.28 (s, 9H) |

-continued

| Example | Name | MS (EI) (M + H⁺) | ¹H NMR (400 MHz, DMSO-d₆) |
|---|---|---|---|
| Example 330 | t-butyl-1-(2-oxo-1,2-dihydroquinolin-6-yl)-1H-pyrazol-5-yl)-3-(2,4,5-trifluorophenyl)urea as a pale yellow powder 35 mg, 39% yield General method D | 456.0 | 9.06 (s, 1H), 8.88 (s, 1H), 8.18 (m, 1H), 8.00 (d, J = 6.4 Hz, 1H), 7.84 (d, J = 2.4 Hz, 1H), 7.63 (m, 2H), 7.43 (d, J = 8.8 Hz, 1H), 6.59 (dd, J = 2.0, and 9.6 Hz, 1H), 6.42 (s, 1H), 1.28 (s, 9H) |
| Example 331 | 1-(3-t-butyl-1-(2-oxo-1,2-dihydroquinolin-6-yl)-1H-pyrazol-5-yl)-trifluorophenyl)urea as a pale yellow powder 15 mg, 17% yield General method D | 456.0 | 9.30 (s, 1H), 8.97 (s, 1H), 8.01 (d, J = 9.6 Hz, 1H), 7.87 (m, 1H), 7.84 (d, J = 2.4 Hz, 1H), 7.63 (dd, J = 2.4, and 8.4 Hz 1H), 7.12 (m, 1H), 6.59 (dd, J = 2.0, and 9.6 Hz, 1H), 6.43 (s, 1H), 1.28 (s, 9H) |
| Example 332 | 1-(3-t-butyl-1-(2-oxo-1,2-dihydroquinolin-6-yl)-1H-pyrazol-5-yl)-3-(2,4-difluorophenyl)urea as off-white solid 28 mg, 12% yield General method D | 438.0 | 8.84 (d, J = 2.0 Hz, 1H), 8.79 (s, 1H), 8.06 (m, 1H), 8.00 (d, J = 9.6 Hz, 1H), 7.83 (d, J = 2.0 Hz, 1H), 7.62 (dd, J = 2.0, and 8.8 Hz, 1H), 7.43 (d, J = 8.8 Hz, 1H), 7.29 (m, 1H), 7.04 (m, 1H), 6.59 (dd, J = 2.0, and 9.6 Hz, 1H), 6.40 (s, 1H), 1.28 (s, 9H) |

| Example | Name | MS (EI) (M + H⁺) | ¹H NMR (400 MHz, DMSO-d₆) |
|---|---|---|---|
| 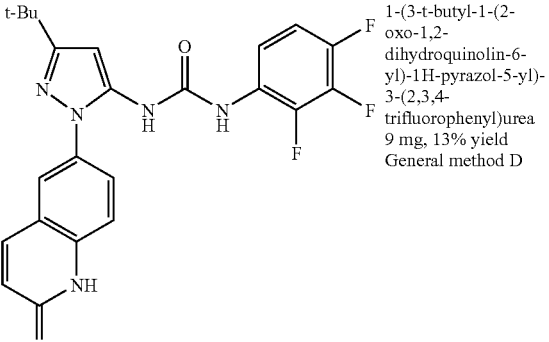<br>Example 333 | 1-(3-t-butyl-1-(2-oxo-1,2-dihydroquinolin-6-yl)-1H-pyrazol-5-yl)-3-(2,3,4-trifluorophenyl)urea 9 mg, 13% yield General method D | 456.0 | 9.05 (s, 1H), 8.83 (s, 1H), 8.06 (m, 1H), 8.00 (d, J = 9.6 Hz, 1H), 7.83 (d, J = 2.0 Hz, 1H), 7.63 (dd, J = 2.0, and 8.8 Hz, 1H), 7.43 (d, J = 8.8 Hz, 1H), 7.26 (m, 1H), 6.60 (dd, J = 2.0, and 9.6 Hz, 1H), 6.40 (s, 1H), 1.28 (s, 9H) |

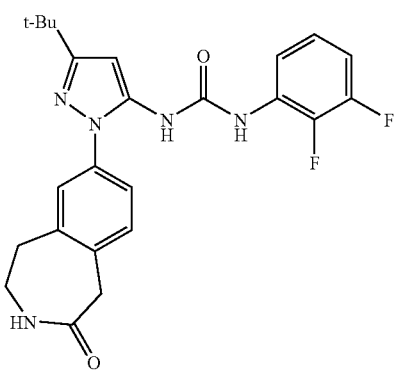

Example 334

Using general method D, Example A46 (0.55 mg, 1.8 mmol) and 2,3-difluoroaniline (27 mg, 0.21 mmol) were combined to yield 1-(3-t-butyl-1-(2-oxo-2,3,4,5-tetrahydro-1H-benzo[d]azepin-7-yl)-1 H-pyrazol-5-yl)-3-(2,3-difluorophenyl)urea as a pale yellow powder (15 mg, 2% yield). ¹H NMR (400 MHz, DMSO-d₆): δ 9.11 (s, 0.65H), 9.06 (s, 0.35H), 8.86 (s, 0.65H), 8.72 (s, 0.35H), 7.91 (m, 1H), 7.68 (t, J=5.6 Hz, 0.65H), 7.61 (t, J=5.6 Hz, 0.35H), 7.38-7.02 (m, 4H), 6.39 (s, 0.35H), 6.38 (s, 0.65H), 3.89 (s, 0.70H), 3.87 (s, 1.30H), 3.52 (dd, J=5.6, and 11.6 Hz, 1.30H), 3.41 (m, 0.70H), 3.07 (t, J=6.0 Hz, 2H), 1.26 (s, 5.85H), 1.24 (s, 3.15H); MS (EI) m/z: 454.0 (M+H⁺).

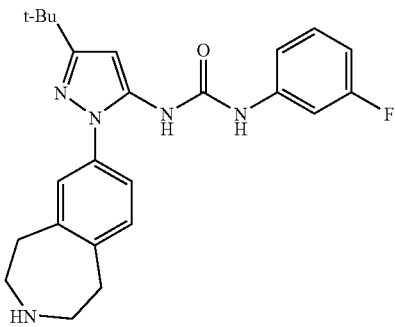

Example 335

Using general method A, Example A46 (70 mg, 0.18 mmol) and 3-fluorophenyl isocyanate (25 mg, 0.18 mmol) were combined to yield 1-(3-t-butyl-1-(2,3,4,5-tetrahydro-1H-benzo[d]azepin-7-yl)-1 H-pyrazol-5-yl)-3-(3-fluorophenyl)urea HCl salt. (0.21 g, 25% yield). ¹H NMR (400 MHz, DMSO-d₆): δ 9.59 (brs, 1H), 9.09 (m, 1H), 9.04 (m, 1H), 8.63 (s, 1H), 7.45 (t, J=2.0 Hz, 1H), 7.42 (m, 2H), 7.34 (m, 1H), 7.28 9 m, 1H), 7.06 (dd, J=1.6, and 8.0 Hz, 1H), 6.78 (dt, J=2.4, and 8.4 Hz, 1H), 6.36 (d, J=1.6 Hz, 1H), 3.20 (m, 4H), 3.15 (m, 4H), 1.27 (s, 9H); LC-MS (EI) m/z: 422.2 (M+H⁺).

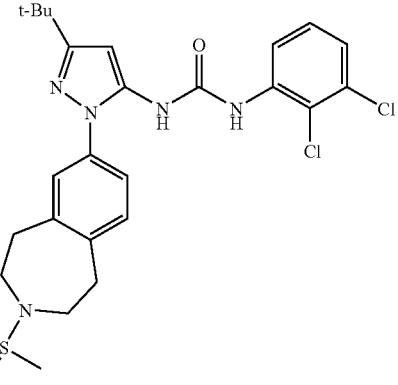

Example 336

Using the same method as for Example 108, Example 166 (70 mg, 0.14 mmol) and methanesulfonyl chloride (19 mg, 0.17 mmol) were combined to yield 1-(3-t-butyl-1-(3-(methylsulfonyl)-2,3,4,5-tetrahydro-1H-benzo[d]azepin-7-yl)-1 H-pyrazol-5-yl)-3-(2,3-dichlorophenyl)urea as a white off solid (22 mg, 29% yield). ¹H NMR (400 MHz, CDCl₃): δ 8.17 (dd, J=2.0, and 7.2 Hz, 1H), 7.70 (s, 1H), 7.24 (m, 5H), 6.55 (bs, 1H), 6.46 (s, 1H), 3.47 (m, 4H), 3.07 (m, 4H), 2.82 (s, 3H), 1.40 (s, 9H); LC-MS (EI) m/z: 550.0 (M+H⁺).

Example A74

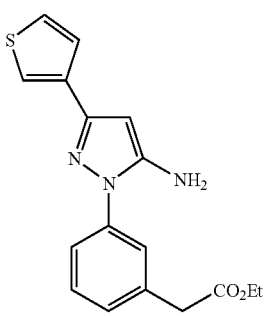

3-Aminophenylacetic acid (2.00 g, 13 mmol, 1.0 eq) was dissolved with sonication in 1M HCl (40 ml, 40 mmol, 3.00 eq) and cooled thoroughly in an ice/salt bath until the internal temperature was −5-0° C. A solution of NaNO$_2$ (0.98 g, 14 mmol, 1.07 eq) in H$_2$O (3 ml) was added slowly such that the internal temperature did not exceed 0° C. After 15 min the reaction was treated with a solution of SnCl$_2$.2H$_2$O (15 g, 66 mmol, 5.00 eq) in conc. HCl (15 ml). The reaction was stirred for 2 h with warming to +15° C. The yellow solution was filtered through a cotton plug (to remove particulates and a little dark sludge) into a solution of 3-oxo-3-(thiophen-3-yl) propanenitrile (2.4 g, 16 mmol, 1.2 eq) in EtOH (60 ml). The reaction was heated in a 75° C. oil bath overnight. The reaction was complete, consisting of a roughly 2:1 mixture of desired ester and the corresponding acid. The reaction was cooled to RT and then concentrated to remove most of the EtOH. The aqueous residue was chilled in an ice bath and treated with 6M NaOH (ca. 55 ml) to pH 8. EtOAc (100 ml) was added and the mixture shaken to dissolve product. The suspension was vacuum filtered through paper to remove tin salts and the cake washed with EtOAc (50 ml). The layers of the clear filtrate were separated and the organic washed with brine (2×) and dried (MgSO$_4$). Filtration and evaporation gave 4.6 g of a dark oil. This was dissolved in EtOH (55 ml), treated with satd. HCl/EtOH (5-6 ml) and heated at 75° C. overnight. When the esterification was complete, the reaction was cooled to RT and concentrated to remove EtOH. The residue was treated with satd. NaHCO$_3$ and extracted with EtOAc (2×). The combined organics were washed with satd. NaHCO$_3$ (1×), brine (1×) and dried (MgSO$_4$). Filtration and evaporation gave 4.2 g of crude product as an oil. This was purified by flash chromatography, eluting with 13-50% EtOAc/hexanes. Fractions containing product were pooled and concentrated to yield ethyl 2-(3-(5-amino-3-(thiophen-3-yl)-1H-pyrazol-1-yl)phenyl)acetate (2.4 g, 55% yield). $^1$H NMR (300 MHz, DMSO-d$_6$): 7.73-7.72 (m, 1H), 7.56-7.53 (m, 3H), 7.46-7.42 (m, 2H), 7.24-7.22 (m, 1H), 5.82 (s, 1H), 5.43 (brs, 2H), 4.11 (q, 2H, J=7.2 Hz), 3.76 (s, 2H), 1.21 (t, 3H, J=7.2 Hz); MS (ESI) m/z: 328.0 (M+H$^+$).

Example 337

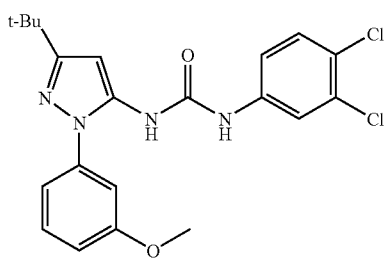

Using general method A, Example A4 (70 mg, 0.29 mmol) and 3,4-dichlorophenyl isocyanate (54 mg, 0.29 mmol) were combined to afford 1-(3-t-butyl-1-(3-methoxyphenyl)-1H-pyrazol-5-yl)-3-(3,4-dichlorophenyl)urea (38 mg, 31% yield). $^1$H NMR (300 MHz, CDCl$_3$): δ 8.13 (s, 1H), 7.35 (d, J=2.4 Hz, 1H), 7.24 (dd, J=0.6, and 3.3 Hz, 1H), 7.19 (s, 1H), 7.12 (t, J=8.1 Hz, 1H), 6.96 (dd, J=2.4, and 8.7 Hz, 1H), 6.7-6.9 (m, 3H), 6.37 (s, 1H), 3.62 (s, 3H), 1.24 (s, 9H); MS (EI) m/z: 433 (M+H$^+$).

Example 338

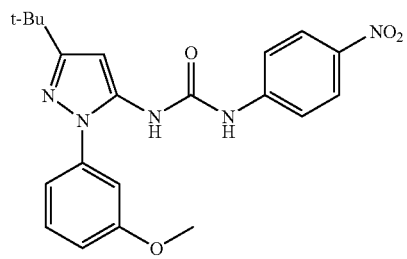

Using general method A, Example A4 (70 mg, 0.29 mmol) and 4-nitrophenylisocyanate (47 mg, 0.29 mmol) were combined to afford 1-(3-t-butyl-1-(3-methoxyphenyl)-1H-pyrazol-5-yl)-3-(4-nitrophenyl)urea (62 mg, 53% yield). $^1$H NMR (300 MHz, CDCl$_3$): δ8.54 (s, 1H), 8.08 (AB quartet, J=9.0 Hz, 2H), 7.45 (AB quartet, J=9.0 Hz, 2H), 7.38 (s, 1H), 7.11 (t, J=8.1 Hz, 1H), 6.7-6.9 (m, 3H), 6.45 (s, 1H), 3.61 (s, 3H), 1.26 (s, 9H); MS (EI) m/z: 410 (M+H$^+$).

Example 339

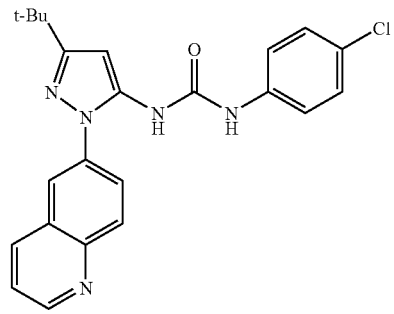

Using general method A, Example A21 (133 mg, 0.5 mmoL) and 1-chloro-4-isocyanatobenzene (90 mg, 0.6 mmoL) were combined to afford 1-[3-t-butyl-1-(quinolin-6-yl)-1H-pyrazol-5-yl]-3-(4-chlorophenyl)urea (100 mg, 48% yield). $^1$H NMR (300 MHz, DMSO-d$_6$): δ 9.12 (s, 1H), 8.91 (d, J=3.9 Hz, 1H), 8.60 (s, 1H), 8.43 (d, J=8.4 Hz, 1H), 8.12 (d, J=8.7 Hz, 1H), 8.10 (s, 1H), 7.93 (d, J=8.7 Hz, 1H), 7.57 (m, 1H), 7.38 (d, J=8.7 Hz, 2H), 7.25 (d, J=8.7 Hz, 2H), 6.41 (s, 1H), 1.28 (s, 9H).

Example 340

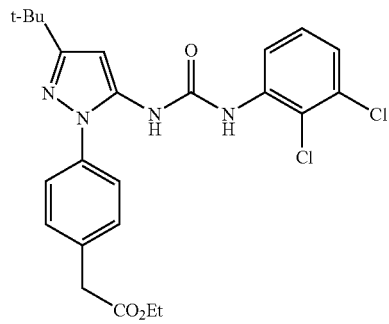

Using general method A, Example A18 (5 g, 14.8 mmol) and 1,2-dichloro-3-isocyanatobenzene (2.8 g, 15.0 mmol) were combined to afford 2-(4-{3-t-butyl-5-[3-(2,3-dichlorophenyl)ureido]-1H-pyrazol-1-yl}phenyl)acetic acid (2.1 g, 29% yield). $^1$H NMR (DMSO-d$_6$): δ 9.24 (s, 1H), 8.77 (s, 1H), 8.05 (m, 1H), 7.47-7.38 (m, 4H), 7.30-7.28 (m, 2H), 6.36 (s, 1H), 4.08 (q, J=7.2 Hz, 2H), 2.72 (s, 2H), 1.25 (s, 9H), 1.18 (t, J=7.2 Hz, 3H); MS (ESI) m/z: 489 (M+H$^+$).

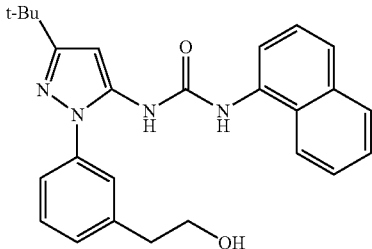

Example 341

Using general method A, Example A34 (5 g, 14.8 mmol) and 1-isocyanatonaphthalene (2.5 g, 15.0 mmol) were combined to afford ethyl 2-(3-{3-t-butyl-5-[3-(naphthalen-1-yl)ureido]-1H-pyrazol-1-yl}phenyl)acetate (1.5 g, 22% yield). MS (ESI) m/z: 471 (M+H$^+$).

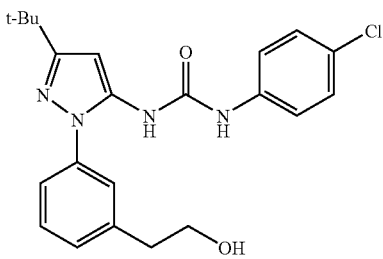

Example 342

Using general method C, the previous compound (80 mg, 0.17 mmol) was reduced to afford 1-{3-t-butyl-1-[3-(2-hydroxyethyl)phenyl]-1H-pyrazol-5-yl}-3-(naphthalen-1-yl)urea (50 mg, 69% yield). $^1$H NMR (300 MHz, DMSO-d$_6$): δ 9.00 (s, 1H), 8.75 (s, 1H), 8.00-7.87 (m, 3H), 7.65-7.21 (m, 8H), 6.38 (s, 1H), 4.68 (m, 1H), 3.65 (t, J=7.2 Hz, 2H), 2.79 (t, J=6.9 Hz, 2H), 1.26 (s, 9H); MS (ESI) m/z: 429 (M+H$^+$).

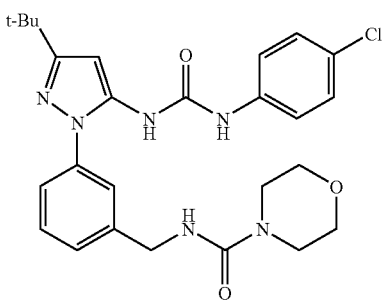

Example 343

Using general method A, Example A5 (5 g, 14.8 mmol) and 1-chloro-4-isocyanato-benzene (2.2 g, 15.0 mmol) were combined to afford ethyl 2-(3-{3-t-butyl-5-[3-(4-chlorophenyl)ureido]-1H-pyrazol-1-yl}phenyl)acetate (2.7 g, 40% yield). $^1$H NMR (DMSO-d$_6$): δ 9.10 (s, 1H), 8.39 (s, 1H), 7.46-7.37 (m, 5H), 7.28-7.25 (m, 3H), 6.34 (s, 1H), 4.04 (q, J=7.2 Hz, 2H), 3.72 (s, 2H), 1.25 (s, 9H), 1.14 (t, J=7.2 Hz, 3H); MS (ESI) m/z: 455 (M+H$^+$).

Using general method C, the previous compound (100 mg, 0.22 mmol) was reduced to afford 1-{3-t-butyl-1-[3-(2-hydroxyethyl)phenyl]-1H-pyrazol-5-yl}-3-(4-chlorophenyl)urea (65 mg, 72% yield). $^1$H NMR (DMSO-d$_6$): δ 9.11 (s, 1H), 8.36 (s, 1H), 7.41-7.21 (m, 8H), 6.33 (s, 1H), 3.61 (q, J=7.2 Hz, 2H), 2.76 (t, J=6.9 Hz, 2H), 1.24 (s, 9H); MS (ESI) m/z: 413 (M+H$^+$).

Using general method C, Example 114 (87 mg, 0.22 mmol) was reduced to afford 1-{1-[3-(aminomethyl)phenyl]-3-t-butyl-1H-pyrazol-5-yl}-3-(4-chloro-phenyl)urea as the HCl salt (78 mg, 82% yield). $^1$H NMR (DMSO-d$_6$): δ 9.96 (s, 1H), 8.85 (s, 1H), 8.42 (br s, 3H), 7.72 (s, 1H), 7.56-7.55 (m, 2H), 7.48-7.45 (m, 3H), 7.32-7.30 (m, 2H), 6.41 (s, 1H), 4.16-4.12 (m, 2H), 1.29 (s, 9H); MS (ESI) m/z: 398.3 (M+H$^+$), 400.2 (M+2+H$^+$).

The previous compound (100.0 mg, 0.25 mmol) and CDI (45 mg, 0.28 mmol) were combined in DMF (2 mL) and stirred at RT for 2 h. Morpholine (0.028 mL) was added and the mixture was stirred overnight at RT. The mixture was concentrated and the residue was purified silica gel column chromatography to yield 1-(3-t-butyl-1-{3-[(morpholine-4-carboxamido)methyl]phenyl}-1H-pyrazol-5-yl)-3-(4-chlorophenyl)urea (25 mg, 20% yield). $^1$H-NMR (300 MHz, DMSO-d$_6$): δ 9.18 (s, 1H), 8.40 (s, 1H), 7.25-7.45 (m, 8H), 7.15 (t, J=6.0 Hz, 1H), 6.35 (s, 1H), 4.29 (d, J=5.4 Hz, 2H), 3.49 (t, J=4.8 Hz, 4H), 3.25 (t, J=4.8 Hz, 4H), 1.25 (s, 9H).

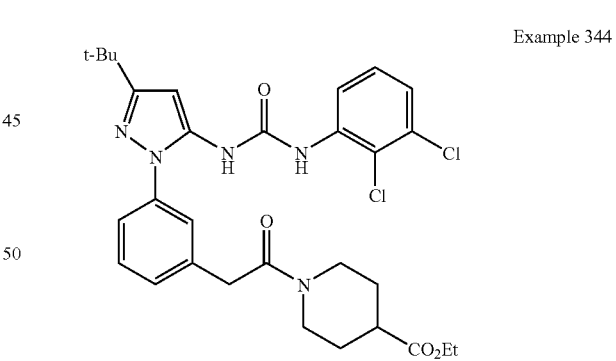

Example 344

Using general method I, Example 373 (200 mg, 0.46 mmol) and piperidine-4-carboxylic acid ethyl ester (102 mg, 0.65 mmol) were combined to afford ethyl 1-[2-(3-{3-t-butyl-5-[3-(2,3-dichlorophenyl)ureido]-1H-pyrazol-1-yl}phenyl)acetyl]piperidine-4-carboxylate (125 mg, 45% yield). $^1$H NMR (300 MHz, DMSO-d$_6$): δ 9.21 (br s, 1H), 8.74 (br s, 1H), 8.03 (m, 1H), 7.42-7.24 (m, 6H), 6.35 (s, 1H), 4.15 (m, 1H), 4.01 (q, J=7.2 Hz, 2H), 3.88 (m, 1H), 3.76 (q, J=5.4 Hz, 2H), 3.04 (m, 1H), 2.71 (m, 1H), 2.50 (m, 1H), 1.78-1.70 (m, 2H), 1.47-1.30 (m, 2H), 1.24 (s, 9H), 1.12 (t, J=7.2 Hz, 3H); MS (ESI) m/z: 600 (M+H$^+$).

Example 345

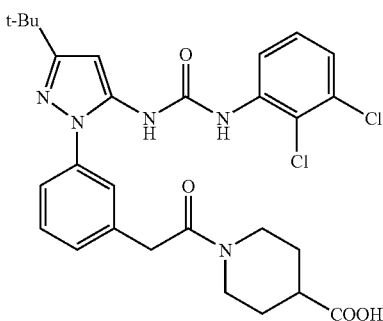

Using general method E, Example 344 (75 mg, 0.13 mmol) was saponified to afford acid 1-[2-(3-{3-t-butyl-5-[3-(2,3-dichlorophenyl)ureido]-1H-pyrazol-1-yl}phenyl)acetyl]piperidine-4-carboxylic acid (50 mg, 67% yield). $^1$H NMR (300 MHz, DMSO-$d_6$): δ 9.22 (s, 1H), 8.75 (s, 1H), 8.03 (m, 1H), 7.42-7.20 (m, 6H), 6.35 (s, 1H), 4.17 (m, 1H), 3.86 (m, 1H), 3.76 (s, 2H), 3.56 (m, 1H), 2.69 (m, 1H), 2.60 (m, 1H), 1.77-1.63 (m, 2H), 1.44-1.25 (m, 2H), 1.24 (s, 9H); MS (ESI) m/z: 572 (M+H$^+$).

Example 346

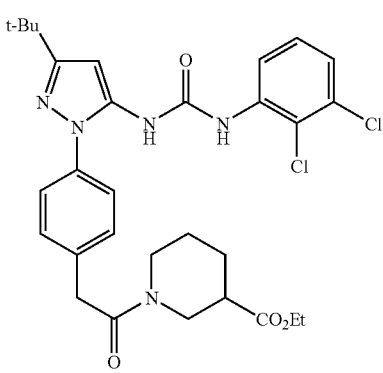

Using general method I, Example 383 (200 mg, 0.43 mmol) and piperidine-3-carboxylic acid ethyl ester (102 mg, 0.65 mmol) were combined to afford ethyl 1-[2-(4-{3-t-butyl-5-[3-(2,3-dichlorophenyl)ureido]-1H-pyrazol-1-yl}phenyl)acetyl]piperidine-3-carboxylate (120 mg, 47% yield). $^1$H NMR (300 MHz, CDCl$_3$): δ 8.60 (s, 1H), 8.50 (s, 1H), 8.12 (m, 1H), 7.37 (d, J=7.8 Hz, 2H), 7.25-7.15 (m, 4H), 6.59 (s, 1H), 4.35 (m, 1H), 4.18-4.12 (m, 2H), 3.88-3.52 (m, 5H), 2.41 (m, 1H), 2.05-1.88 (m, 2H), 1.78-1.62 (m, 2H), 1.34 (s, 9H), 1.25 (t, J=7.2 Hz, 3H); MS (ESI) m/z: 600 (M+H$^+$).

Example 347

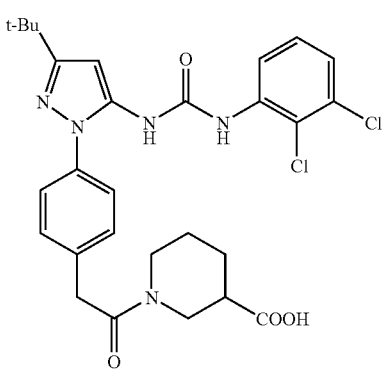

Using general method E, Example 346 (70 mg, 0.12 mmol) was saponified to afford 1-[2-(4-{3-t-butyl-5-[3-(2,3-dichlorophenyl)ureido]-1H-pyrazol-1-yl}-phenyl)acetyl]piperidine-3-carboxylic acid (50 mg, 73% yield). $^1$H NMR (300 MHz, DMSO-$d_6$): δ 9.26 (s, 1H), 8.77 (s, 1H), 8.02 (m, 1H), 7.41 (d, J=8.4 Hz, 2H), 7.34-7.25 (m, 4H), 6.30 (s, 1H), 4.36 (m, 1H), 3.84 (m, 1H), 3.79-3.74 (m, 2H), 3.40 (m, 1H), 3.00 (m, 1H), 2.55 (m, 1H), 1.88-1.85 (m, 2H), 1.67-1.48 (m, 2H), 1.23 (s, 9H); MS (ESI) m/z: 572 (M+H$^+$).

Example 348

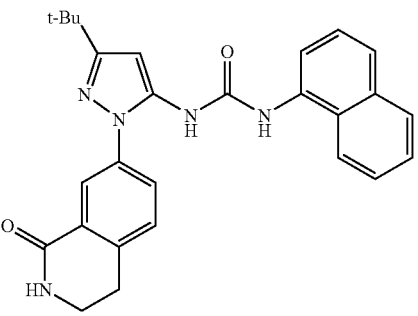

Using general method A, Example A34 (2.0 g, 6.2 mmol) and 1-isocyanatonaphthalene (1.27 g, 7.5 mmol) were combined to afford 1-[3-t-butyl-1-(1-oxo-1,2,3,4-tetrahydroisoquinolin-7-yl)-1 H-pyrazol-5-yl]-3-(naphthalen-1-yl)urea. $^1$H NMR (300 MHz, CDCl$_3$): δ 8.59 (brs, 1H), 8.32 (brs, 1H), 8.02 (brs, 1H), 7.85-7.04 (m, 10H), 6.62 (s, 1H), 3.42 (m, 2H), 2.83 (m, 2H), 1.34 (s, 9H)

Example 349

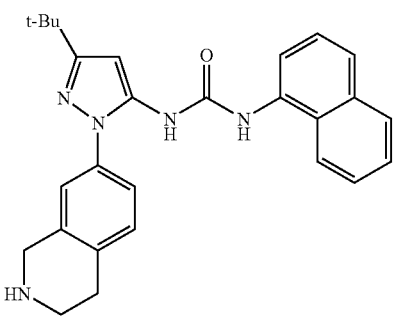

Using general method C, Example 348 (1.5 g, 3.3 mmol) was reduced to afford 1-[3-t-butyl-1-(1,2,3,4-tetrahydroisoquinolin-7-1H-pyrazol-5-yl]-3-(naphthalen-1-yl)urea (1.0 g, 69% yield). $^1$H NMR (400 MHz, CDCl$_3$): δ 7.86-6.92 (m, 10H), 6.44 (s, 1H), 3.03 (t, J=6 Hz, 2H), 2.70 (t, J=6 Hz, 2H), 1.33 (s, 9H).

General Experimental for Examples

The specified intermediates and the appropriate isocyanate (general method A) or the appropriate aniline (general method D) were combined to yield the pyrazole urea ester which was saponified using General method E to yield the indicated compound.

| Example | | Name | MS (EI) (M + H⁺) | ¹H NMR (400 MHz, DMSO-d₆) |
|---|---|---|---|---|
| 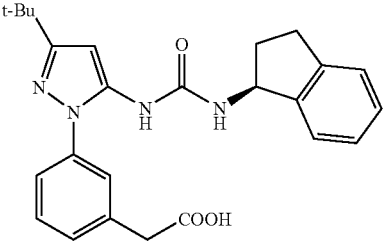 Example 350 | | 2-(3-(3-t-butyl-5-(3-((S)-2,3-dihydro-1H-inden-1-yl)ureido)-1H-pyrazol-1-yl)phenyl)acetic acid From Example A5 0.42 g, 60% yield, 3 steps General method D | 433.2 | δ 8.09 (s, 1H), 7.46-7.18 (m, 8H), 6.91 (d, J = 8.0 Hz, 1H), 6.33 (s, 1H), 5.09 (q, J = 7.6 Hz, 1H), 3.65 (s, 2H), 2.92-2.74 (m, 2H), 2.43-2.36 (m, 1H), 1.76-1.67 (m, 1H), 1.27 (s, 9H). |
| 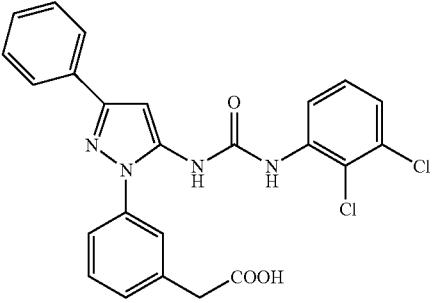 Example 351 | | 2-(3-(5-(3-(2,3-dichlorophenyl)-ureido)-3-phenyl-1H-pyrazol-1-yl)phenyl)acetic acid From Example 500 1.4 g, 64% yield, 2 steps General method A | 481.0 | 9.42 (s, 1H), 8.88 (s, 1H), 8.09 (dd, J = 6.8 Hz, 3.2 Hz, 1H), 7.86-7.83 (m, 2H), 7.60-7.57 (m, 2H), 7.50-7.32 (m, 7H), 6.95 (s, 1H), 3.69 (s, 2H). |
| 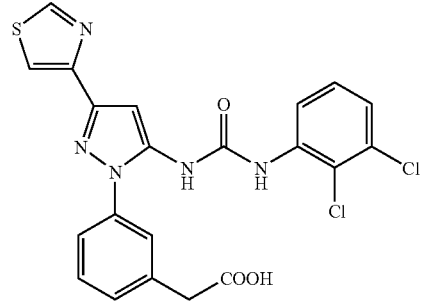 Example 352 | | 2-(3-(5-(3-(2,3-dichlorophenyl)-ureido)-3-(thiazol-4-yl)-1H-pyrazol-1-yl)phenyl)acetic acid From Example 503 0.6 g, 55%, 2 steps General method A | 488.0 | 9.41 (s, 1H), 9.18 (d, J = 2.4 Hz, 8.67 (s, 1H), 8.08 (dd, J = 6.8 Hz, 2.8 Hz, 1H), 8.01 (d, J = 2.4 Hz, 1H), 7.54-7.51 (m, 3H), 7.41-7.32 (m, 3H) 6.92 (s, 1H), 3.72 (s, 2H). |
| 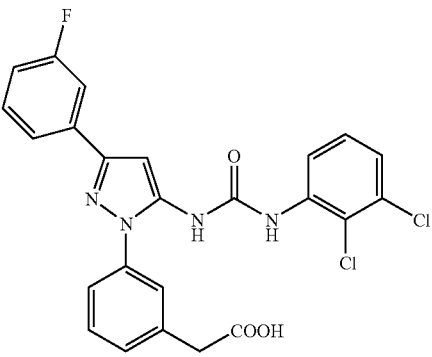 Example 353 | | 2-(3-(5-(3-(2,3-dichlorophenyl)-ureido)-3-(3-fluorophenyl)-1H-pyrazol-1-yl)phenyl)acetic acid From Example 504 0.3 g, 68% yield, 2 steps General method A | 499.0 | 9.40 (s, 1H), 8.85 (s, 1H), 8.07 (dd, J = 6.4 Hz, 3.6 Hz, 1H), 7.70 (d, J = 8.0 Hz, 1H), 7.65-7.63 (m, 1H), 7.56-7.45 (m, 4H), 7.40-7.31 (m, 3H), 7.18 (td, J = 8.8 Hz, 2.4 Hz, 1H), 7.01 (s, 1H), |

| Example | Name | MS (EI) (M + H⁺) | ¹H NMR (400 MHz, DMSO-d₆) |
|---|---|---|---|
| Example 354 | 2-(3-(5-(3-(2,3-dichlorophenyl)-ureido)-3-(2-fluorophenyl)-1H-pyrazol-1-yl)phenyl)acetic acid<br>From Example 505<br>0.17 g, 39% yield,<br>2 steps<br>General method A | 499.0 | 9.44 (s, 1H), 8.88 (s, 1H), 8.08 (dd, J = 6.4 Hz, 3.6 Hz, 1H), 7.99 (td, J = 7.6 Hz, 1.6 Hz, 1H), 7.56-7.52 (m, 3H), 7.42-7.31 (m, 5H), 7.29-7.26 (m, 1H), 6.91 (d, J = 4.0 Hz, 1H), 3.71 (s, 2H) |
| Example 355 | 2-(3-(3-t-butyl-5-(3-(2,3-difluorophenyl)-ureido)-1H-pyrazol-1-yl)phenyl)acetic acid<br>From Example A5<br>0.28 g, 44% yield,<br>3 steps<br>General method D | 429.0 | δ 9.13 (s, 1H), 8.92 (s, 1H), 7.94-7.90 (m, 1H), 7.50-7.32 (m, 4H), 7.16-7.00 (m, 2H), 6.40 (s, 1H), 3.69 (s, 2H), 1.28 (s, 9H) |
| Example 356 | 2-(3-(3-t-butyl-5-(3-(2,3,4-trifluorophenyl)-ureido)-1H-pyrazol-1-yl)phenyl)acetic acid<br>From Example A5<br>0.65 g, 95% yield,<br>3 steps<br>General method D | 447.2 | δ 9.12 (s, 1H), 8.92 (s, 1H), 7.88-7.81 (m 1H), 7.49-7.40 (m, 3H), 7.33-7.25 (m, 2H), 6.38 (s, 1H), 3.68 (s, 2H), 1.27 (s, 9H). |
| Example 357 | ethyl 2-(3-(3-t-butyl-5-(3-((S)-1,2,3,4-tetrahydro-naphthalen-1-yl)ureido)-1H-pyrazol-1-yl)phenyl)acetate<br>From Example A5<br>0.55 g, 67% yield,<br>3 steps<br>General method D | 447.3 | 8.02 (s, 1H), 7.45-7.41 (m, 1H), 7.37-7.33 (m, 2H), 7.30-7.28 (m, 1H), 7.20-7.13 (m, 3H), 7.09-7.06 (m, 1H), 6.94-6.92 (m, 1H), 6.33 (s, 1H), 4.81-4.76 (m, 1H), 3.65 (s, 2H), 2.78-2.64 (m, 1H), 1.89-1.84 (m, 1H), 1.78-1.68 (m, 3H), 1.27 (s, 9H) |
| Example 358 | 2-(3-(5-(3-(2,3-dichloro-phenyl)ureido)-3-(4-fluorophenyl)-1H-pyrazol-1-yl)phenyl)acetic acid<br>0.15 g, 79% yield,<br>2 steps<br>General method A | 501.0 | 9.39 (s, 1H), 8.86 (s, 1H), 8.09-8.06 (m, 1H), 7.91-7.87 (m, 2H), 7.55-7.51 (m, 2H), 7.40-7.37 (m, 1H), 7.34-7.24 (m, 4H), 6.95 (s, 1H), 3.72 (s, 2H) |

-continued

| Example | | Name | MS (EI) (M + H+) | 1H NMR (400 MHz, DMSO-d$_6$) |
|---|---|---|---|---|
| 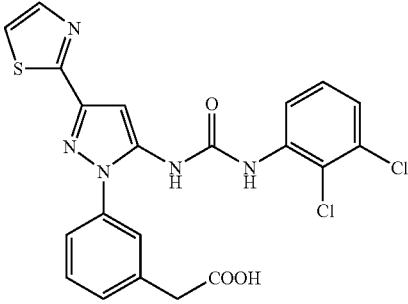

Example 359 | | 2-(3-(5-(3-(2,3-dichlorophenyl)ureido)-3-(thiazol-2-yl)-1H-pyrazol-1-yl)phenyl)acetic acid
55 mg, 11% yield, 2 steps
General method A | 490.0 | 9.49 (s, 1H), 8.91 (s, 1H), 8.09-8.06 (m, 1H), 7.92-7.91 (m, 1H), 7.75-7.74 (m, 1H), 7.59-7.51 (m 3H), 7.45-7.43 (m, 1H), 7.37-7.32 (m, 2H), 6.99 (s, 1H), 3.74 (s, 2H) |
| 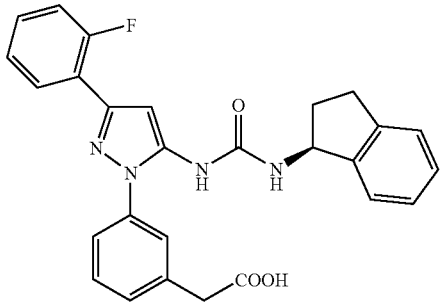

Example 360 | | 2-(3-(5-(3-((S)-2,3-dihydro-1H-inden-1-yl)ureido)-3-(2-fluorophenyl)-1H-pyrazol-1-yl)phenyl)acetic acid
From Example 505
0.184 g, 67% yield, 3 steps
General method D | 471.3 | 9.27 (brs, 1H), 8.10-7.99 (m, 2H), 7.52 (brs, 1H), 7.40-7.12 (m, 10 H), 6.87-6.85 (m, 1H), 5.15-5.09 (m, 1H), 3.25 (s, 2H), 2.95-2.88 (m, 1H), 2.81-2.72 (m, 1H), 2.43-2.32 (m, 1H), 1.80-1.71 (m, 1H) |
| 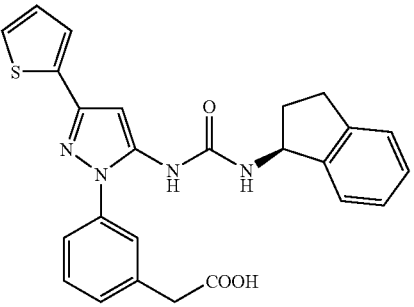

Example 361 | | 2-(3-(5-(3-((S)-2,3-dihydro-1H-inden-1-yl)ureido)-3-(thiophen-2-yl)-1H-pyrazol-1-yl)phenyl)acetic acid.
From Example 506
0.1091 g 8% yield, 3 steps
General method D | 459.0 | 8.27 (s, 1H), 7.50-7.41 (m, 5H), 7.37-7.36 (m, 1H), 7.25-7.18 (m, 4H), 7.13-7.10 (m, 1H), 7.02-7.00 (m, 1H), 6.81 (s, 1H), 5.13 (q, 1H, J = 7.6 Hz), 3.70 (s, 2H), 2.94-2.87 (m, 1H), 2.83-2.75 (m, 1H), 2.45-2.38 (m, 1H), 1.79-1.69 (m, 1H) |
| 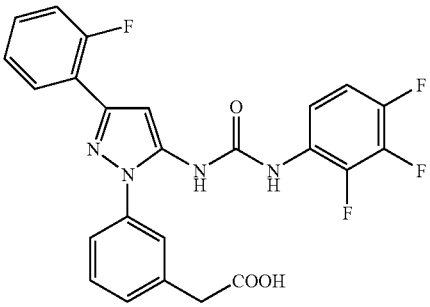

Example 362 | | 2-(3-(3-(2-fluorophenyl)-5-(3-(2,3,4-trifluorophenyl)-ureido)-1H-pyrazol-1-yl)phenyl)acetic acid
From Example 505
0.40 g, 62% yield, 3 steps
General method D | 485.0 | 9.14 (s, 1H), 9.02 (s, 1H), 7.99 (dt, J = 2.0, and 8.0 Hz, 1H), 7.86 (m, 1H), 7.20-7.60 (m, 8H), 6.91 (d, J = 4.4 Hz, 1H), 3.73 (s, 2H) |

-continued

| Example | Name | MS (EI) (M + H+) | 1H NMR (400 MHz, DMSO-d6) |
|---|---|---|---|
| Example 363 | 2-(3-(3-(2-Fluorophenyl)-5-(3-(naphthalen-1-yl)ureido)-1H-pyrazol-1-yl)phenyl)acetic acid<br>From Example 505<br>0.30 g, 86% yield,<br>2 steps<br>General method A | 485.0 | 9.14 (s, 1H), 9.02 (s, 1H), 7.99 (dt, J = 2.0, and 8.0 Hz, 1H), 7.86 (m, 1H), 7.20-7.60 (m, 8H), 6.91 (d, J = 4.4 Hz, 1H), 3.73 (s, 2H) |
| Example 364 | 2-(3-(5-(3-(naphthalen-1-yl)ureido)-3-(thiophen-2-yl)-1H-pyrazol-1-yl)phenyl)acetic acid<br>From Example 506<br>0.35 g, 15% yield,<br>3 steps<br>General method D | 469.0 | 10.7 (brs, 1H), 10.5 (brs, 1H), 8.70 (d, J = 6.8 Hz, 1H), 8.03 (d, J = 7.2 Hz, 1H), 7.86 (dd, J = 2.4, and 9.6 Hz, 1H), 7.68 (s, 1H), 7.58 (d, J = 8.4 Hz, 1H), 7.45 (m, 5H), 7.38 (t, J = 7.6 Hz, 1H), 7.30 (d, J = 7.6 Hz, 1H), 7.20 (d, J = 7.2 Hz, 1H), 7.12 (dd, J = 3.6, and 5.2 Hz, 1H), 6.90 (s, 1H), 3.40 (s, 2H) |
| Example 365 | 2-(3-(3-(thiophen-2-yl)-5-(3-(2,3,4-trifluorophenyl)-ureido)-1H-pyrazol-1-yl)phenyl)acetic acid<br>From Example 506<br>0.36 g, 14% yield,<br>3 steps<br>General method D | 473.0 | 7.58 (brs, 1H), 7.54 (m, 1H), 7.45 (dd, J = 0.8, and 5.2 Hz, 1H), 7.43 (dd, J = 1.2, and 3.6 Hz, 1H), 7.31 (q, J = 7.6 Hz, 1H), 7.26 (m, 1H), 7.14 (m, 2H), 7.08 (dd, J = 3.2, and 4.8 Hz, 1H), 6.71 (s, 1H) |
| Example 366 | 2-(3-(5-(3-(2,3-dichlorophenyl)-ureido)-3-(thiophen-2-yl)-1H-pyrazol-1-yl)phenyl)acetic acid<br>From Example 506<br>73.8 mg, 96% yield,<br>3 steps<br>General method D | 489.0 | (CDCl3): 9.21 (s, 1H), 8.54 (s, 1H), 8.10-8.08 (m, 1H), 7.47 (s, 1H), 7.36-7.35 (m, 2H), 7.25-7.23 (m 2H), 7.13-7.01 (m, 3H), 6.94-6.92 (m, 1H), 6.74 (s, 1H), 3.55 (s, 2H). |

| Example | Name | MS (EI) (M + H⁺) | ¹H NMR (400 MHz, DMSO-d$_6$) |
|---|---|---|---|
| 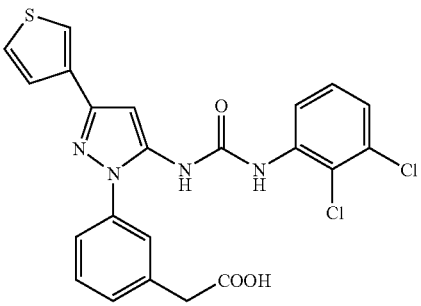<br>Example 367 | 2-(3-(5-(3-(2,3-dichlorophenyl)-ureido)-3-(thiophen-3-yl)-1H-pyrazol-1-yl)phenyl)acetic acid<br>From Example A74<br>0.25 g, 94% yield,<br>2 steps<br>General method A | 487.0 | 9.41 (s, 1H), 8.87 (s, 1H), 8.08 (dd, J = 6.8 Hz, 3.2 Hz, 1H), 7.88-7.87 (m, 1H), 7.61 (dd, J = 5.2 Hz, 2.8 Hz, 1H), 7.53-7.49 (m, 4H), 7.38-7.31 (m, 3H), 6.86 (s, 1H), 3.71 (s, 2H). |
| 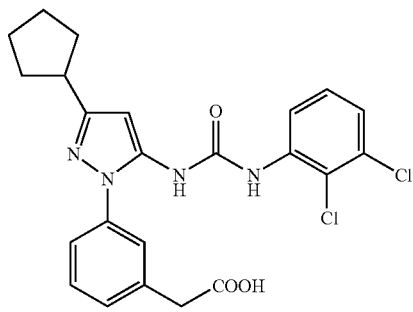<br>Example 368 | 2-(3-(3-cyclopentyl-5-(3-(2,3-dichlorophenyl)-ureido)-1H-pyrazol-1-yl)phenyl)acetic acid<br>From Example A14<br>0.214 g, 61%, yield,<br>2 steps<br>General method A | 475.0 | 9.24 (s, 1H), 8.77 (s, 1H), 8.09-8.04 (m, 1H), 7.49-7.39 (m, 3H), 7.34-7.29 (m, 3H), 6.33 (s, 1H), 3.68 (s, 2H), 3.06-2.98 (m, 1H), 2.02-1.93 (m, 2H), 1.76-1.59 (m, 6H); |
| 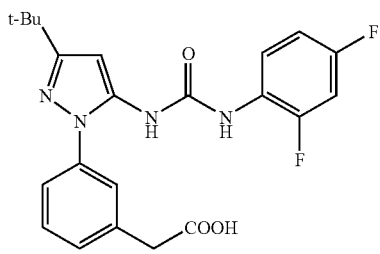<br>Example 369 | 2-(3-(3-t-butyl-5-(3-(2,4-difluorophenyl)-ureido)-1H-pyrazol-1-yl)phenyl)acetic acid<br>From Example A5<br>0.46 g, 66% yield,<br>3 steps<br>General method D | 429.0 | δ 8.91 (s, 1H), 8.84 (s, 1H), 8.07-8.01 (m, 1H), 7.47 (t, J = 8.0 Hz, 1H), 7.42-7.27 (m, 4H), 7.06-7.00 (m, 1H), 6.38 (s, 1H), 3.69 (s, 2H), 1.27 (s, 9H); |
| 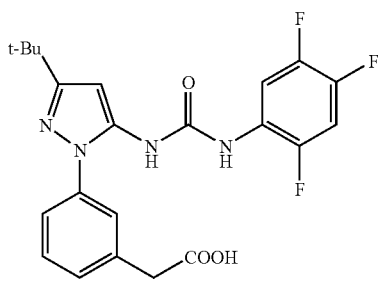<br>Example 370 | 2-(3-(3-t-butyl-5-(3-(2,4,5-trifluorophenyl)-ureido)-1H-pyrazol-1-yl)phenyl)acetic acid<br>From Example A5<br>0.47 g, 54% yield,<br>3 steps<br>General method D | 447.2 | δ 9.12 (s, 1H), 8.91 (s, 1H), 8.20-8.13 (m, 1H), 7.66-7.58 (m, 1H), 7.48 (t, J = 8.0 Hz, 1H), 7.42-7.38 (m, 2H), 7.33 (d, J = 8.0 Hz, 1H), 6.40 (s, 1H), 3.69 (s, 2H), 1.27 (s, 9H). |

| Example | | Name | MS (EI) (M + H⁺) | ¹H NMR (400 MHz, DMSO-$d_6$) |
|---|---|---|---|---|
| 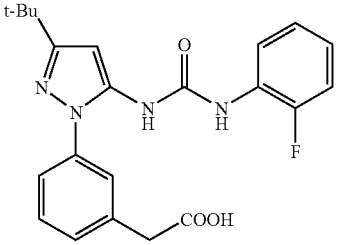 Example 371 | | 2-(3-(3-t-butyl-5-(3-(2-fluorophenyl)-ureido)-1H-pyrazol-1-yl)phenyl)acetic acid<br>From Example A5<br>0.38 g, 70% yield, 2 steps)<br>General method A | 410.7 | δ 8.93 (d, J = 2.0 Hz, 1H), 8.87 (s, 1H), 8.12 (dt, J = 2.0, and 8.4 Hz, 1H), 7.48 (t, J = 8.0 Hz, 1H), 7.39 (m, 2H), 7.33 (d, J = 7.6 Hz, 1H), 7.22 (m, 1H), 7.13 (t, J = 7.6 Hz, 1H), 7.01 (m, 1H), 6.40 (s, 1H), 3.69 (s, 2H), 1.28 (s, 9H). |
| 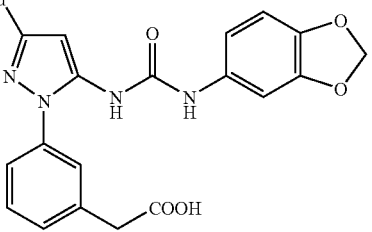 Example 372 | | 2-(3-{5-[3-(benzo[1,3]dioxol-5-yl)ureido]-3-t-butyl-1H-pyrazol-1-yl}phenyl)acetic acid<br>From Example A5<br>450 mg, 94% yield, 2 steps<br>General method A | 437 | 7.52-7.35 (m, 4H), 7.01 (s, 1H), 6.70-6.61 (m, 2H), 6.40 (s, 1H), 5.89 (s, 2H), 3.72 (s, 2H), 1.32 (s, 9H) |
| 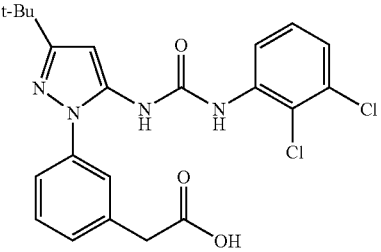 Example 373 | | 2-(3-{3-t-butyl-5-[3-(2,3-dichlorophenyl)-ureido]-1H-pyrazol-1-yl}phenyl)acetic acid<br>From Example A5<br>1.7 g, 84% yield, 2 steps<br>General method A | 461 | 9.26 (s, 1H), 8.76 (s, 1H), 8.03 (m, 1H), 7.48-7.35 (m, 3H), 7.27-7.25 (m, 3H), 6.36 (s, 1H), 3.64 (s, 2H), 1.24 (s, 9H) |
| 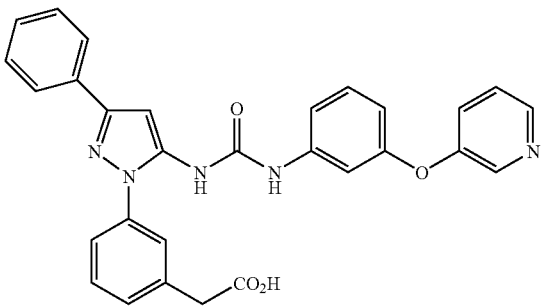 Example 374 | | 2-(3-(3-phenyl-5-(3-(3-(pyridin-3-yloxy)phenyl)-ureido)-1H-pyrazol-1-yl)phenyl)acetic acid<br>From Example 500<br>General method D | 506.0 | δ 8.38-8.35 (m, 2H), 7.84 (s, 1H), 7.82 (s, 1H), 7.59 (s, 1H), 7.43-7.26 (m, 12H), 7.17-7.15 (m, 1H), 6.83 (s, 1H), 6.64-6.62 (m, 1H), 3.56 (s, 2H). |

General Experimental for Examples

The specified intermediates and the appropriate isocyanate (general method A) or the appropriate aniline (general method D) were combined to yield the pyrazole urea ester which was saponified using General method E to yield the indicated compound.

| Example | Name | MS (EI) (M + H+) | 1H NMR (400 MHz, DMSO-d6) |
|---|---|---|---|
| Example 375 | 2-(4-(5-(3-(2,3-dichlorophenyl)-ureido)-3-phenyl-1H-pyrazol-1-yl)phenyl)acetic acid<br>61 mg, 61% yield,<br>2 steps<br>General method A | 481.0 | 9.42 (s, 1H), 8.88 (s, 1H), 8.09 (dd, J = 6.8 Hz, 3.2 Hz, 1H), 7.85-7.83 (m, 2H), 7.59-7.57 (m, 2H), 7.50-7.32 (m, 7H), 6.95 (s, 1H), 3.69 (s, 2H) |
| Example 376 | 2-(4-(3-t-butyl-5-(3-(2,4-difluorophenyl)-ureido)-1H-pyrazol-1-yl)phenyl)acetic acid<br>From Example A18<br>0.55 g, 64% yield,<br>3 steps<br>General method D | 429.0 | 9.15 (s, 1H), 8.93 (s, 1H), 7.94 (t, J = 8.0 Hz, 1H), 7.46 (d, J = 8.4 Hz, 2H), 7.43 (d, J = 8.4 Hz, 2H), 7.18-7.0 (m, 3H), 6.40 (s, 1H), 3.66 (s, 2H), 1.27 (s, 9H) |
| Example 377 | 2-(4-(3-t-butyl-5-(3-(2,3,4-trifluorophenyl)-ureido)-1H-pyrazol-1-yl)phenyl)acetic acid<br>From Example A18<br>0.15 g, 53% yield,<br>3 steps<br>General method D | 447.2 | 9.11 (s, 1H), 8.91 (s, 1H), 7.87-7.81 (m, 1H), 7.46 (d, J = 8.4 Hz, 2H), 7.42 (d, J = 8.4 Hz, 2H), 7.29-7.22 (m, 1H), 6.38 (s, 1H), 3.75 (s, 2H), 1.27 (s, 9H) |
| Example 378 | 2-(4-(5-(3-(2,3-dichlorophenyl)ureido)-3-(thiophen-2-yl)-1H-pyrazol-1-yl)phenyl)acetic acid<br>From Example 511<br>0.18 g, 47% yield,<br>2 steps<br>General method A | 487.0 | 9.45 (s, 1H), 8.90 (s, 1H), 8.09 (dd, J = 6.8 Hz, 3.2 Hz, 1H), 7.55-7.47 (m, 5H), 7.34-7.31 (m, 3H), 7.11 (dd, J = 4.8 Hz, 3.6 Hz, 1H), 6.86 (s, 1H), 3.69 (s, 2H) |

-continued

| Example | Name | MS (EI) (M + H+) | 1H NMR (400 MHz, DMSO-d6) |
|---|---|---|---|
| 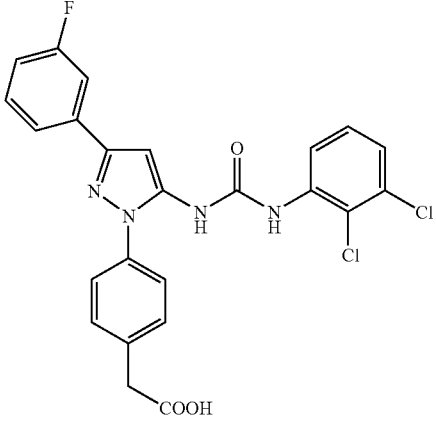
Example 379 | 2-(4-(5-(3-(2,3-dichlorophenyl)ureido)-3-(3-fluorophenyl)-1H-yl)phenyl)acetic acid pyrazol-1-
0.15 g, 55% yield, 2 steps
General method A | 499.0 | 9.45 (s, 1H), 8.89 (s, 1H), 8.09 (dd, J = 6.8 Hz, 3.2 Hz, 1H), 7.69 (d, J = 8.0 Hz, 1H), 7.64-7.62 (m, 1H), 7.58 (d, J = 8.0 Hz, 2H), 7.49-7.45 (m, 3H), 7.34-7.31 (m, 2H), 7.17 (td, J = 8.8 Hz, 2.4 Hz, 1H), 7.01 (s, 1H), 3.70 (s, 2H) |
| 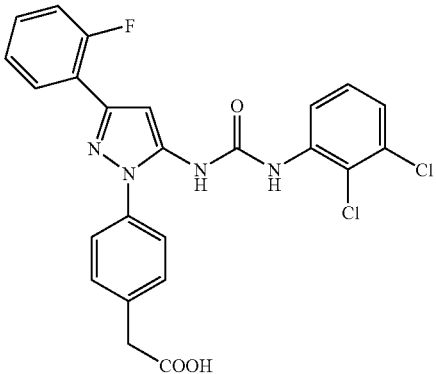
Example 380 | 2-(4-(5-(3-(2,3-dichlorophenyl)ureido)-3-(2-fluorophenyl)-1H-pyrazol-1-yl)phenyl)acetic acid
0.19 g, 55% yield, 2 steps
General method A | 499.0 | 9.47 (s, 1H), 8.90 (s, 1H), 8.12 (dd, J = 6.4 Hz, 3.2 Hz, 1H), 7.99 (td, J = 7.6 Hz, 2.4 Hz, 1H), 7.59 (d, J = 8.4 Hz, 2H), 7.49 (d, J = 8.4 Hz, 2H), 7.44-7.31 (m, 4H), 7.29-7.26 1H), 6.91 (d, J = 4.0 Hz, 1H), 3.71 (s, 2H) |
| 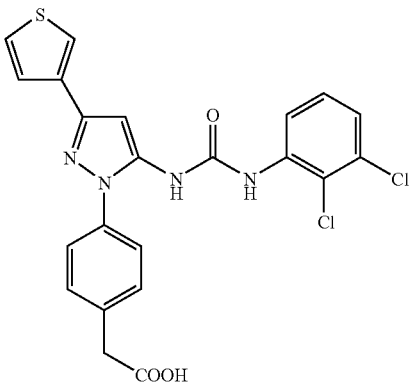
Example 381 | 2-(4-(5-(3-(2,3-dichlorophenyl)ureido)-3-(thiophen-3-yl)-1H-pyrazol-1-yl)phenyl)acetic acid
0.20 g, 50% yield, 2 steps
General method A | 487.0 | 9.40 (s, 1H), 8.86 (s, 1H), 8.09 (dd, J = 6.8 Hz, 3.2 Hz, 1H), 7.87 (dd, J = 3.2 Hz, 1.2 Hz, 1H), 7.61 (dd, J = 5.2 Hz, 2.8 Hz, 1H), 7.56 (d, J = 8.4 Hz, 2H), 7.51 (dd, J = 5.2 Hz, 1.2 Hz, 1H), 7.48 (d, J = 8.4 Hz, 2H), 7.34-7.32 (m, 2H), 6.86 (s, 1H), 3.80 (s, 2H) |

-continued

| Example | Name | MS (EI) (M + H+) | ¹H NMR (400 MHz, DMSO-d₆) |
|---|---|---|---|
| Example 382 | 2-(4-(3-t-butyl-5-(3-(2,3-difluorophenyl)ureido)-1H-pyrazol-1-yl)phenyl)acetic acid<br>From Example A18<br>0.231 g, 48% yield,<br>3 steps<br>General method D | 429.2 | (Acetone-d₆): δ 8.51 (s, 1H), 8.45 (s, 1H), 8.13-8.09 (m, 1H), 7.56-7.53 (m, 2H), 7.47-7.45 (m, 2H), 7.18-7.11 (m, 1H), 6.99-6.92 (s, 1H), 6.52 (s, 1H), 3.74 (m, 2H), 1.33 (s, 9H) |
| Example 383 | 2-(4-{5-t-butyl-3-[3-(2,3-dichlorophenyl)ureido]-2H-pyrazol-1-yl}phenyl)acetic acid<br>From Example A18<br>1.5 g, 80% yield,<br>2 steps<br>General method A | 461 | 9.70 (s, 1H), 9.00 (s, 1H), 7.98 (m, 1H), 7.46 (d, J = 8.4 Hz, 2H), 7.35 (d, J = 8.4 Hz, 2H), 7.25-7.24 (m, 2H), 6.30 (s, 1H), 3.61 (s, 2H), 1.23 (s, 9H) |
| Example 384 | 2-(4-(5-(3-(2,3-dichlorophenyl)ureido)-3-(thiazol-4-yl)-1H-pyrazol-1-yl)phenyl)acetic acid<br>From Example 47<br>0.15 g, 31% yield,<br>2 steps<br>General method A | 488.0 | 9.54 (s, 1H), 9.18 (d, J = 1.6 1H), 8.94 (s, 1H), 8.08 (dd, J = 7.2 Hz, 2.8 Hz, 1H), 7.99 (d, J = 2.0 Hz, 1H), 7.58 (d, J = 8.4 Hz, 2H), 7.48 (d, J = 8.4 Hz, 2H), 7.36-7.30 (m, 2H), 6.91 (s, 1H), 3.70 (s, 2H) |
| Example 385 | (S)-2-(4-(3-t-butyl-5-(3-(2,3-dihydro-1H-inden-1-yl)ureido)-1H-pyrazol-1-yl)phenyl)acetic acid<br>From Example A18<br>0.08 g, 22% yield,<br>3 steps<br>General method D | 433.2 | 8.10 (s, 1H), 7.43-7.37 (m, 4H), 7.24-7.19 (m, 4H), 6.93 (d, J = 7.6 Hz, 1H), 6.33 (s, 1H), 5.09 (q, J = 7.6 Hz, 1H), 3.64 (s, 2H), 2.92-2.74 (m, 2H), 2.43-2.37 (m, 1H), 1.76-1.67 (m, 1H), 1.27 (s, 9H) |

-continued

| Example | Name | MS (EI) (M + H⁺) | ¹H NMR (400 MHz, DMSO-d₆) |
|---|---|---|---|
| Example 386 | 2-(4-(3-t-butyl-5-(3-fluorophenyl)ureido)-1H-pyrazol-1-yl)phenyl)acetic acid From Example A18 0.28 g, 62% yield, 2 steps General method A | 411.2 | 8.96 (s, 1H), 8.88 (s, 1H), 8.12 (td, J = 8.0 Hz, 1.6 Hz, 1H), 7.47-7.41 (m, 4H), 7.24-7.19 (m, 1H), 7.12 (t, J = 8.0 Hz, 1H), 7.03-6.98 (m, 1H), 6.39 (s, 1H), 3,66 (s, 2H), 1.27 (s, 9H) |
| Example 387 | (S)-2-(4-(3-t-butyl-5-(3-(1,2,3,4-tetrahydronaphthalen-1-yl)ureido)-1H-pyrazol-1-yl)phenyl)acetic acid From Example A18 0.49 g, 72% yield, 3 steps General method D | 447.3 | 8.05 (s, 1H), 7.42-7.37 (m, 4H), 7.21-7.14 (m, 3H), 7.09-7.06 (m, 1H), 6.97-6.95 (m, 1H), 6.34 (s, 1H), 4.81-4.76 (m, 1H), 3.64 (s, 2H), 2.78-2.64 (m, 2H), 1.90-1.84 (m, 1H), 1.79-1.68 (m, 3H), 1.27 (s, 9H) |
| Example 388 | 2-(4-(3-(2-fluorophenyl)-5-(3-(2,3,4-trifluorophenyl)ureido)-1H-pyrazol-1-yl)phenyl)acetic acid 0.20 g, 53% yield, 2 steps General method A | 485.2 | 9.17 (s, 1H), 9.05 (s, 1H), 8.01-7.96 (m, 1H), 7.90-7.84 (m, 1H), 7.59-7.56 (m, 2H), 7.51-7.49 (m, 2H), 7.44-7.38 (m, 1H), 7.34-7.24 (m, 3H), 6.92-6.91 (m, 1H), 3.71 (s, 2H) |
| Example 389 | 2-(4-(5-(3-((S)-2,3-dihydro-1H-inden-1-yl)ureido)-3-(thiophen-2-yl)-1H-pyrazol-1-yl)phenyl)acetic acid 51.6 mg, 83% yield, 3 steps General method D | 459.0 | 8.28 (s, 1H), 7.50-7.43 (m, 6H), 7.25-7.18 (m, 4H), 7.12-7.10 (m, 1H), 7.05-7.03 (m, 1H), 6.80 (s, 1H), 5.16-5.10 (m, 1H), 3.67 (s, 2H), 2.94-2.87 (m, 1H), 2.83-2.73 (m, 1H), 2.45-2.37 (m, 1H), 1.79-1.69 (m, 1H) |

-continued

| Example | Name | MS (EI) (M + H+) | 1H NMR (400 MHz, DMSO-d6) |
|---|---|---|---|
| 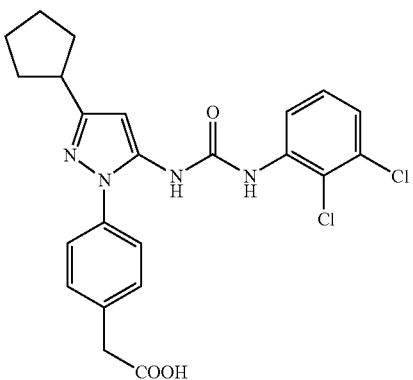
Example 390 | 2-(4-(3-cyclopentyl-5-(3-(2,3-dichlorophenyl)ureido)-1H-pyrazol-1-yl)phenyl)acetic acid 0.1113 g, 72%, 2 steps General method A | 473 | 9.29 (s, 1H), 8.81 (s, 1H), 8.11-8.06 (m, 1H), 7.48-7.41 (m, 4H), 7.34-7.29 (m, 2H), 6.33 (s, 1H), 3.66 (s, 2H), 3.05-2.97 (m, 1H), 2.01-1.95 (m, 2H), 1.73-1.59 (m, 6H); |

General Experimental for Examples

The specified example and the appropriate amine were coupled using the method indicated to produce the target amide. Alternatively, the specified example and the appropriate isocyanate were coupled to yield the target amide.

| Example | Name | MS (EI) (M + H+) | 1H NMR (400 MHz, DMSO-d6) |
|---|---|---|---|
| 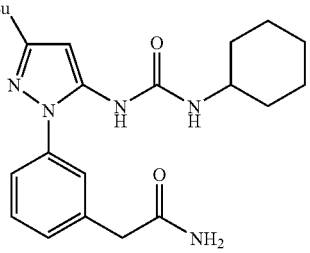
Example 391 | 1-{1-[3-(2-amino-2-oxoethyl)phenyl]-3-t-butyl-1H-pyrazol-5-yl}-3-cyclohexylurea From Example A8 60 mg, 30% yield General method A | 397 | 8.11 (s, 1H), 7.48 (br s, 1H), 7.41-7.13 (m, 4 H), 6.88 (br s, 1H), 6.42 (d, J = 7.2 Hz, 1H), 6.23 (s, 1H), 3.41 (s, 2H), 3.35 (m, 1H), 1.77-1.37 (m, 4H), 1.21 (s, 9H), 1.22-1.10 (m, 6H) |
| 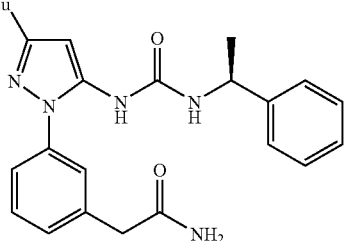
Example 392 | 1-{1-[3-(2-amino-2-oxoethyl)phenyl]-3-t-butyl-1H-pyrazol-5-yl}-3-((S)-1-phenylethyl)urea From Example A8 85 mg, 41% yield General method A | | 8.09 (s, 1H), 7.49 (br s, 1H), 7.36 (t, J = 7.5 Hz, 1H), 7.19-7.29 (m, 8H), 7.00 (d, J = 7.8 Hz, 1H), 6.90 (br s, 1H), 6.22 (s, 1H), |

-continued

| Example | Name | MS (EI) (M + H+) | 1H NMR (400 MHz, DMSO-d6) |
|---|---|---|---|
| 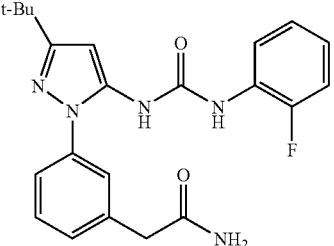<br>Example 393 | 1-{1-[3-(2-amino-2-oxoethyl)phenyl]-3-t-butyl-1H-pyrazol-5-yl}-3-(2-fluorophenyl)urea<br>From Example A8<br>55 mg, 27% yield<br>General method A | | 8.90 (br s, 1H), 8.85 (br s, 1H), 8.05 (br s, 1H), 7.50-7.20 (m, 5H), 7.20-7.00 (m, 2H), 7.00-6.80 (m, 2H), 6.34 (s, 1H), 3.41 (s, 2H), 1.22 (s, 9H) |
| 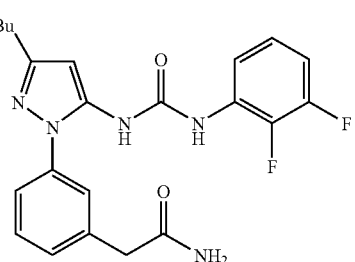<br>Example 394 | 1-{1-[3-(2-amino-2-oxoethyl)phenyl]-3-t-butyl-1H-pyrazol-5-yl}-3-(2,3-difluorophenyl)urea<br>From Example A8<br>60 mg, 28% yield<br>General method A | 428 | 7.86 (m, 1H), 7.55-7.37 (m, 4H), 7.08 (m, 1H), 6.89 (m, 1H), 6.46 (s, 1H), 3.63 (s, 2H), 1.32 (s, 9H) |
| 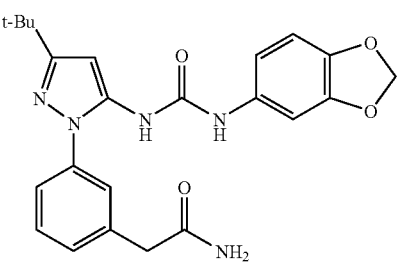<br>Example 395 | 1-{1-[3-(2-amino-2-oxoethyl)phenyl]-3-t-butyl-1H-pyrazol-5-yl}-3-(benzo[d][1,3]dioxol-5-yl)urea<br>From Example 372<br>70 mg, 80% yield<br>General method K | 436 | 8.85 (s, 1H), 8.31 (s, 1H), 7.51-7.26 (m, 5 H), 7.11 (s, 1H), 6.90 (br s, 1H), 6.76 (d, J = 8.4 Hz, 1H), 6.65 (d, J = 7.8 Hz, 1H), 6.32 (s, 1H), 5.92 (s, 2H), 3.42 (s, 2H), 1.23 (s, 9H) |
| 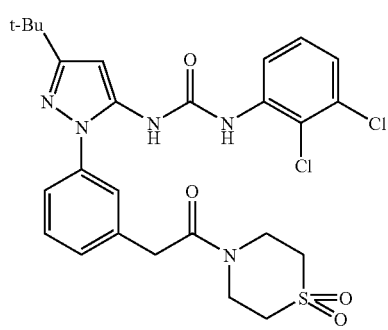<br>Example 396 | 1-(3-t-butyl-1-{3-[2-(1,1-dioxo-1λ6-thiomorpholin-4-yl)-2-oxoethyl]phenyl}-1H-pyrazol-5-yl)-3-(2,3-dichlorophenyl)urea<br>From Example 373<br>54 mg, 42% yield<br>General method I | 578 | 9.22 (s, 1H), 8.75 (s, 1H), 8.05 (m, 1H), 7.46-7.21 (m, 6H), 6.35 (s, 1H), 3.87 (s, 2H), 3.85-3.79 (m, 4H), 3.20-3.12 (m, 2H), 3.09-3.04 (m, 2H), 1.24 (s, 9H) |

-continued

| Example | Name | MS (EI) (M + H+) | 1H NMR (400 MHz, DMSO-d6) |
|---|---|---|---|
| 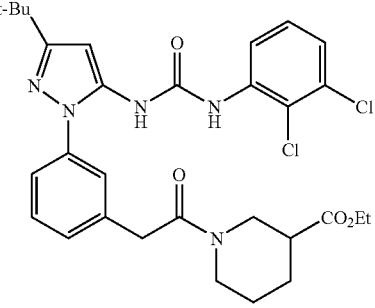<br>Example 397 | ethyl 1-[2-(3-{3-t-butyl-5-[3-(2,3-dichlorophenyl)ureido]-1H-pyrazol-1-yl}phenyl)acetyl]piperidine-3-carboxylate<br>From Example 373<br>130 mg, 47% yield<br>General method I | 600 | 9.22 (s, 1H), 8.74 (s, 1H), 8.02 (m, 1H), 7.46-7.21 (m, 6H), 6.34 (s, 1H), 4.30 (m, 1H), 4.01 (q, J = 7.2 Hz, 2H), 3.90-3.70 (m, 3H), 3.34 (m, 1H), 2.95 (m, 1H), 2.72 (m, 1H), 1.90-1.75 (m, 2H), 1.70-1.40 (m, 2H), 1.24 (s, 9H), 1.11 (t, J = 7.2 Hz, 3H) |
| 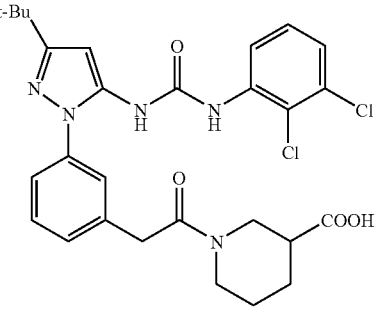<br>Example 398 | 1-[2-(3-{3-t-butyl-5-[3-(2,3-dichlorophenyl)-ureido]-1H-pyrazol-1-yl}-phenyl)acetyl]piperidine-3-carboxylic acid<br>From Example 373<br>55 mg, 69% yield<br>General method E | 572 | 9.21 (s, 1H), 8.74 (s, 1H), 8.02 (m, 1H), 7.42-7.21 (m, 6H), 6.34 (s 1H), 4.38 (m, 1H), 3.88-3.74 (m, 3H), 3.32 (m, 1H), 2.97 (m, 1H), 2.68 (m, 1H), 1.90-1.75 (m, 2H), 1.70-1.40 (m, 2H), 1.24 (s, 9H) |
| 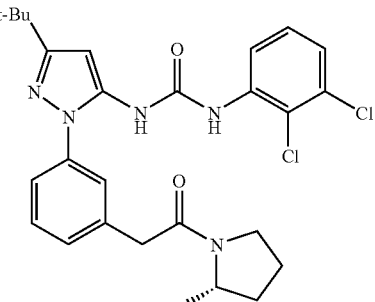<br>Example 399 | (2R)-methyl 1-[2-(3-{3-t-butyl-5-[3-(2,3-dichlorophenyl)ureido]-1H-pyrazol-1-yl}phenyl)-acetyl]pyrrolidine-2-carboxylate<br>From Example 373<br>160 mg, 64% yield<br>General method I | 572 | 9.25 (s, 1H), 8.76 (s, 1H), 8.04 (m, 1H), 7.46-7.09 (m, 6H), 6.35 (s, 1H), 4.25 (m, 1H), 3.62-3.58 (m, 2H), 3.57- 3.55 (m, 2H), 3.51 (s, 3H), 1.90-1.66 (m, 4H), 1.24 (s, 9H) |
| 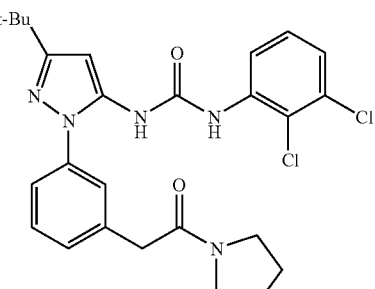<br>Example 400 | (2R)-1-[2-(3-{3-t-butyl-5-[3-(2,3-dichlorophenyl)ureido]-1H-pyrazol-1-yl}phenyl)acetyl]pyrrolidine-2-carboxylic acid<br>From Example 373<br>68 mg, 55% yield<br>General method E | 558 | 9.25 (s, 1H), 8.77 (s, 1H), 8.04 (m, 1H), 7.46-7.21 (m, 6H), (s, 1H), 4.18 (m, 1H), 3.73 (s, 2H), 3.60-3.57 (m, 2H), 1.88-1.73 (m, 4H), 1.24 (s, 9H) |

-continued

| Example | Name | MS (EI) (M + H+) | 1H NMR (400 MHz, DMSO-d6) |
|---|---|---|---|
| 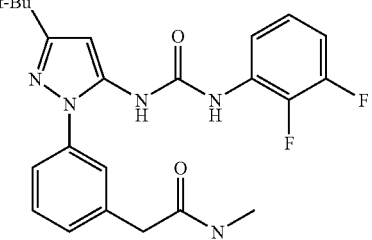<br>Example 401 | 1-(3-t-butyl-1-(3-(2-(methylamino)-2-oxoethyl)phenyl)-1H-pyrazol-5-yl)-3-(2,3-difluorophenyl)urea<br>Example 355<br>0.09 g, 89% yield<br>General method I | 442.2 | 8.58 (s, 1H), 8.52 (s, 1H), 8.12-8.08 (m, 1H), 7.65 (d, J = 0.8 Hz, 1H), 7.46-7.44 (m, 2H), 7.35-7.30 (m, 2H), 7.18-7.12 (m, 1H), 6.99-6.92 (m, 1H), 6.54 (s, 1H), 3.60 (s, 2H), 2.72 (d, J = 4.4 Hz, 3H), 1.34 (s, 9H) |
| 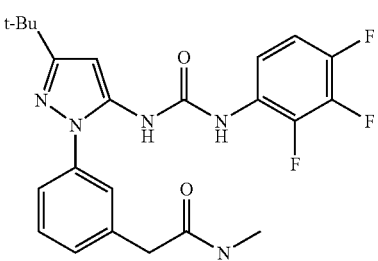<br>Example 402 | 1-(3-t-butyl-1-(3-(2-(methylamino)-2-oxoethyl)phenyl)-1H-pyrazol-5-yl)-3-(2,3,4-trifluorophenyl)urea<br>Example 356<br>0.045 g, 44% yield<br>General method I | 460.2 | 9.05 (s, 1H), 8.85 (s, 1H), 8.03-8.01 (m, 1H), 7.89-7.83 (m, 1H), 7.46 (t, J = 8.0 Hz, 1H), 7.41-7.25 (m, 5H), 6.38 (s, 1H), 3.47 (s, 2H), 3.16 (d, J = 5.2 Hz, 3H), 1.27 (s, 9H) |
| 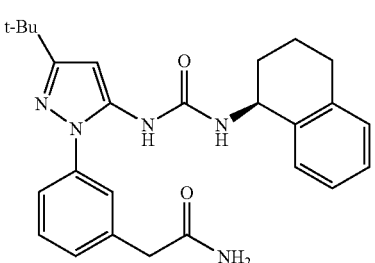<br>Example 403 | 1-(1-(3-(2-amino-2-oxoethyl)phenyl)-3-t-butyl-1H-pyrazol-5-yl)-3-((S)-1,2,3,4-tetrahydronaphthalen-1-yl)urea<br>Example 357<br>0.254 g, 51% yield<br>General method J | 446.3 | 8.03 (s, 1H), 7.50 (brs, 1H), 7.43-7.37 (m, 2H), 7.32-7.28 (m, 2H), 7.21-7.13 (m, 3H), 7.09-7.06 (m, 1H), 6.93-6.91 (m, 2H), 6.34 (s, 1H), 4.81-4.76 (m, 1H), 3.44 (s, 2H), 2.79-2.64 (m, 2H), 1.90-1.67 (m, 4H), 1.27 (s, 9H) |
| 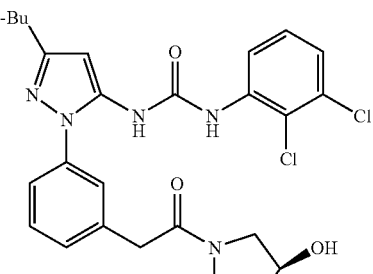<br>Example 404 | 1-(3-t-butyl-1-(3-(2-((S)-3-hydroxypyrrolidin-oxoethyl)phenyl)-1H-pyrazol-5-yl)-3-(2,3-dichlorophenyl)urea<br>Example 373<br>37.7 mg, 63% yield<br>General method K | 532.2 | 9.27 9s, 1H), 8.79 (s, 1H), 8.10-8.07 (m, 1H), 7.48-7.37 (m, 3H), 7.34-7.28 (m 3H), 6.39 (s, 1H), 5.02 and 4.92 (d, 1H, J = 3.6 Hz), 4.29-4.27 and 4.22-4.21 (m, 1H), 3.72-3.69 (m, 2H), 3.62-3.56 and 3.39-3.30 (m, 3H), 1.93-1.69 (m, 2H), 1.28 (s, 9H) |

-continued

| Example | Name | MS (EI) (M + H⁺) | ¹H NMR (400 MHz, DMSO-d₆) |
|---|---|---|---|
| 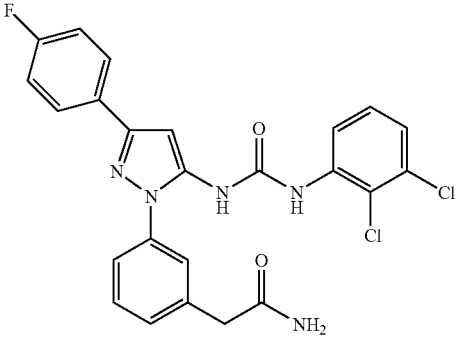<br>Example 405 | 1-(1-(3-(2-amino-2-oxoethyl)phenyl)-3-(4-fluorophenyl)-1H-pyrazol-5-yl)-3-(2,3-dichlorophenyl)urea<br>Example 358<br>45.4 mg 46% yield<br>General method K | 498.0 | 9.40 (s, 1H), 8.85 (s, 1H), 8.10-8.08 (m, 1H), 7.91-7.87 (m, 2H), 7.55-7.47 (m, 4H), 7.39-7.24 (m, 5H), 6.95 (s, 2H), 3.50 (s, 2H) |
| 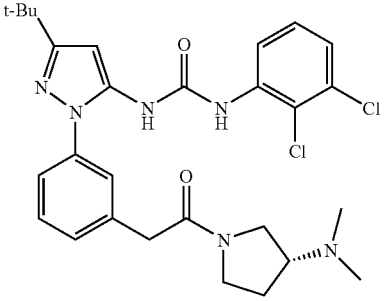<br>Example 406 | 1-(3-t-butyl-1-(3-(2-((R)-3-(dimethylamino)pyrrolidin-1-yl)-2-oxoethyl)phenyl)-1H-pyrazol-5-yl)-3-(2,3-dichlorophenyl)urea<br>Example 373<br>0.053 g, 29% yield<br>General method K | 557.3 | 9.41 and 9.39 (s, 1H), 8.88 and 8.87 (s, 1H), 8.08-8.05 (m, 1H), 7.50-7.39 (m, 4H), 7.34-7.27 (m, 4H), 6.38 (s, 1H), 3.02-3.75 (m, 4H), 3.59-3.48 (m, 2H), 2.81-2.75 (m, 6H), 2.33-2.07 (m, 2H), 1.28 (s, 9H) |
| 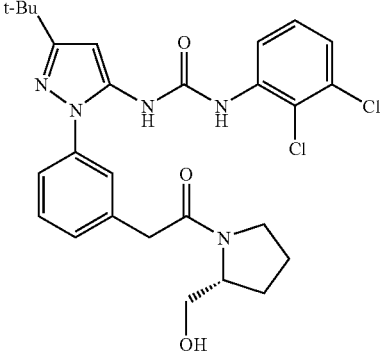<br>Example 407 | 1-(3-t-butyl-1-(3-(2-((R)-2-(hydroxymethyl)pyrrolidin-1-yl)-2-oxoethyl)phenyl)-1H-pyrazol-5-yl)-3-(2,3-dichlorophenyl)urea<br>Example 373<br>34 mg, 21% yield<br>General method K | 544.2 | 9.26 (s, 1H), 8.79 (s, 1H), 8.10-8.07 (m, 1H), 7.48-7.44 (m 1H), 7.39-7.37 (m 2H), 7.36-7.27 (m, 3H), 6.38 (s, 1H), 5.01-4.98 and 4.75-4.72 (m 2H), 4.05-3.92 (m 2H), 3.72-3.70 (m, 2H), 3.51-3.41 (m 3H), 3.32-3.23 (m, 2H), 1.91-1.74 (m, 4H), 1.28 (s, 9H) |
| 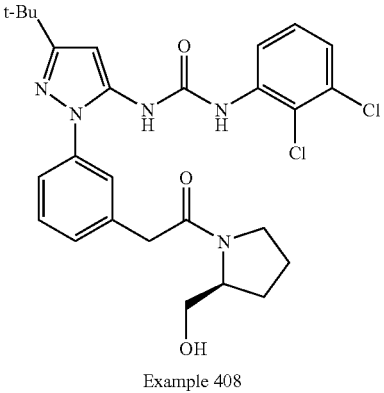<br>Example 408 | 1-(3-t-butyl-1-(3-(2-((S)-2-(hydroxymethyl)pyrrolidin-1-yl)-2-oxoethyl)phenyl)-1H-pyrazol-5-yl)-3-(2,3-dichlorophenyl)urea<br>Example 373<br>32.7 mg, 20% yield<br>General method K | 544.2 | 9.26 (s, 1H), 8.79 (s, 1H), 8.10-8.07 (m, 1H), 7.49-7.44 (m, 1H), 7.39-7.37 (m, 2H), 7.34-7.27 (, 3H), 6.39 (s, 1H), 5.00- 4.98 and 4.74-4.71 (m 2H), 4.05-4.04 and 3.96-3.90 (m, 2H), 3.72 (brs, 2H), 3.54-3.41 and 3.31-3.28 (m, 3H), 1.92-1.74 (m, 4H), 1.28 (s, 9H) |

-continued

| Example | Name | MS (EI) (M + H⁺) | ¹H NMR (400 MHz, DMSO-d₆) |
|---|---|---|---|
| 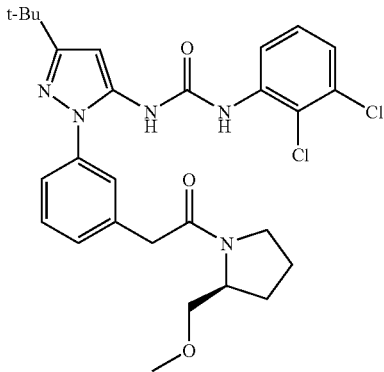<br>Example 409 | 1-(3-t-butyl-1-(3-(2-((S)-2-(methoxymethyl)pyrrolidin-1-yl)-2-oxoethyl)phenyl)-1H-pyrazol-5-yl)-3-(2,3-dichlorophenyl)urea<br>Example 373<br>22.6 mg, 14% yield<br>General method K | 558.3 | 9.26 (s, 1H), 8.78 (s, 1H), 8.10-8.06 (m, 1H), 7.49-7.44 (m, 1H), 7.39-7.37 (m, 2H), 7.34-7.25 (m, 3H), 6.38 (s, 1H), 4.25-4.21 and 4.05-4.01 (m, 1H), 3.86-3.76 and 3.75-3.67 (m, 2H), 3.52-3.46 and 3.42-3.38 (m, 2H), 3.36-3.28 and 3.26-3.19 (m, 2H), 3.27 and 3.19 (s, 3H), 1.91-1.76 (m, 4H), 1.28 (s, 9H) |
| 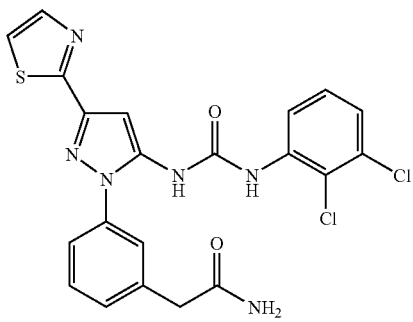<br>Example 410 | 1-(1-(3-(2-amino-2-oxoethyl)phenyl)-3-(thiazol-2-yl)-1H-pyrazol-5-yl)-3-(2,3-dichlorophenyl)urea<br>Example 359<br>7.0 mg, 27% yield<br>General method J | 487.0 | 9.51 (s, 1H), 8.90 (s, 1H), 8.10-8.08 (m, 1H), 7.92-7.91 (m, 1H), 7.75-7.74 (m, 1H), 7.57-7.42 (m, 5H), 7.37-7.32 (m, 2H), 6.99 (s, 1H), 6.96 (brs, 1H), 3.62 (s, 2H) |
| 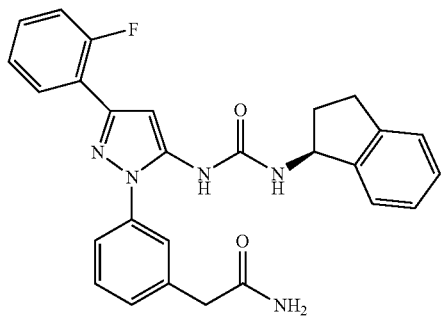<br>Example 411 | 1-(1-(3-(2-amino-2-oxoethyl)phenyl)-3-(2-fluorophenyl)-1H-pyrazol-5-yl)-3-((S)-2,3-dihydro-1H-inden-1-yl)urea<br>Example 360<br>56.4 mg, 24% yield<br>General method J | 470.2 | 8.29 (s, 1H), 8.01-7.97 (m, 1H), 7.53-7.19 (m, 11H), 7.03-7.01 (m, 1H), 6.95 (brs, 1H), 6.87-6.86 (m, 1H), 5.16-5.10 (m, 1H), 3.48 (s, 2H), 2.94-2.75 (m, 2H), 2.46-2.38 (m, 1H), 1.79-1.70 (m, 1H) |
| 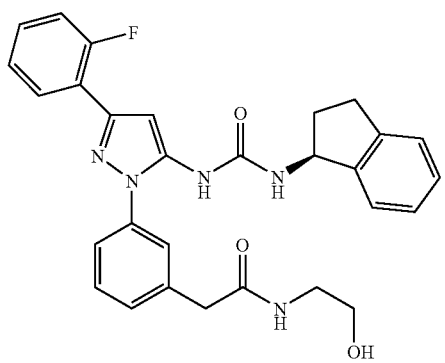<br>Example 412 | 1-((S)-2,3-dihydro-1H-inden-1-yl)-3-(3-(2-fluorophenyl)-1-(3-(2-(2-hydroxyethylamino)-2-oxoethyl)phenyl)-1H-pyrazol-5-yl)urea<br>Example 360<br>87.9 mg, 67% yield<br>General method K | 514.2 | 8.30 (s, 1H), 8.15-8.12 (m, 1H), 8.01-7.96 (m, 1H), 7.51-7.17 (m, 11H), 7.03-7.01 (m, 1H), 6.88-6.86 (m, 1H), 5.16-5.10 (m, 1H), 3.53 (m, 2H), 3.43-3.39 (m, 2H), 3.13-3.09 (m, 2H), 2.94-2.87 (m, 1H), 2.83-2.75 (m, 1H), 2.46-2.38 (m, 1H), 1.79-1.69 (m, 1H) |

| Example | Name | MS (EI) (M + H⁺) | ¹H NMR (400 MHz, DMSO-d₆) |
|---|---|---|---|
| Example 413 | 1-((S)-2,3-dihydro-1H-inden-1-yl)-3-(1-(3-(2-(2,3-dihydroxypropylamino)-2-oxoethyl)phenyl)-3-(2-fluorophenyl)-1H-pyrazol-5-yl)urea Example 360 108.7 mg, 78% yield General method K | 544.2 | 8.29 (s, 1H), 8.12-8/09 (m, 1H), 8.01-7.97 (m, 1H), 7.52-7.19 (m, 10 H), 7.03-7.01 (m, 1H), 6.88-6.87 (m, 1H), 5.16-5.10 (m, 1H), 4.76 (d, 1H, J = 5.2 Hz), 4.52 (t, 1H, J = 5.6 Hz), 3.55 (s, 2H), 3.52-3.45 (m, 1H), 3.30-3.19 (m, 3H), 2.99-2.87 (m, 2H), 2.83-2.74 (m, 1H), 2.46-2.38 (m, 1H), 1.79-1.70(m, 1H) |
| Example 414 | 1-(2,3-dichlorophenyl)-3-(1-(3-(2-((S)-3-hydroxypyrrolidin-1-yl)-2-oxoethyl)phenyl)-3-(thiophen-2-yl)-1H-pyrazol-5-yl)urea Example 366 128.5 mg, 75% yield General method K | 556.0 | 9.42 (s, 1H), 8.87 (s, 1H), 8.11-8.09 (m, 1H), 7.54-7.45 (m, 5H), 7.38-7.32 (m, 3H), 7.13-7.11 (m, 1H), 6.87 (s, 1H), 5.03 and 4.92 (d, 1H, J = 3.6 Hz), 4.31-4.29 and 4.23-4.22 (m, 1H), 3.76 and 3.72 (s, 2H), 3.64-3.59 (m, 1H), 3.45-3.36 (m, 1H), 3.35-3.25 (m, 1H), 1.97-1.70 (m, 2H) |
| Example 415 | 1-(1-(3-(2-amino-2-oxoethyl)phenyl)-3-(thiophen-2-yl)-1H-pyrazol-5-yl)-3-((S)-2,3-dihydro-1H-inden-1-yl)urea Example 361 27.2 mg, 38% yield General method J | 458.0 | 8.26 (s, 1H), 7.53 (brs, 1H), 7.50-7.45 (m, 4H), 7.41-7.35 (m, 2H), 7.26-7.18 (m, 4H), 7.12-7.10 (m, 1H), 7.02-6.99 (m, 1H), 6.94 (brs, 1H), 6.81 (s, 1H), 5.13 (q, 1H, J = 7.6 Hz), 3.48 (s, 2H), 2.94-2.87 (m, 1H), 2.83-2.73 (m, 1H), 2.47-2.38 (m, 1H), 1.79-1.69 (m, 1H) |
| Example 416 | 1-((S)-2,3-dihydro-1H-inden-1-yl)-3-(1-(3-(2-(2-hydroxyethylamino)-2-oxoethyl)phenyl)-3-(thiophen-2-yl)-1H-pyrazol-5-yl)urea Example 361 13.3 mg, 17% yield General method J | 502.2 | 8.26 (s, 1H), 8.15-8.11 (m, 1H), 7.49-7.45 (m, 4H), 7.40-7.34 (m, 2H), 7.26-7.18 (m, 4H), 7.12-7.10 (m, 1H), 7.02-6.99 (m, 1H), 6.81 (s, 1H), 5.15-5.10 (m, 1H), 3.52 (s, 2H), 3.41-3.37 (m, 2H), 3.14-3.09 (m, 2H), 2.95-2.74 (m, 2H), 2.45-2.38 (m, 1H), 1.79-1.71 (m, 1H) |

-continued

| Example | Name | MS (EI) (M + H+) | 1H NMR (400 MHz, DMSO-d6) |
|---|---|---|---|
| Example 417 | 1-((S)-2,3-dihydro-1H-inden-1-yl)-3-(1-(3-(2-(2,3-dihydroxypropylamino)-2-oxoethyl)phenyl)-3-(thiophen-2-yl)-1H-pyrazol-5-yl)urea Example 361 24.5 mg, 30% yield General method K | 532.3 | 8.28 (s, 1H), 8.12-8.09 (m, 1H), 7.50-7.45 (m, 4H), 7.40-7.36 (m, 2H), 7.25-7.18 (m, 4H), 7.12-7.10 (m, 1H), 7.02-7.00 (m, 1H), 6.81 (s, 1H), 5.16-5.10 (m, 1H), 4.75 (brs, 1H), 4.52 (brs, 1H), 3.55 (s, 2H), 3.51-3.45 (m, 1H), 3.28-3.19 (m, 3H), 2.99-2.87 (m, 2H), 2.83-2.75 (m, 1H), 2.46-2.38 (m, 1H), 1.79-1.69 (m, 1H) |
| Example 418 | 1-(3-cyclopentyl-1-(3-(2-(2,3-dihydroxypropylamino)-2-oxoethyl)phenyl)-1H-pyrazol-5-yl)-3-(2,3-dichlorophenyl)urea Example 368 24.5 mg, 30% yield General method K | 546.0 | 9.27 (s, 1H), 8.78 (s, 1H), 8.11-8.06 (m, 2H), 7.47-7.43 (m, 2H), 7.37-7.29 (m, 3H), 6.33 (s, 1H), 3.53 (s, 2H), 3.51-3.44 (m, 1H), 3.30-3.18 (m, 3H), 3.03-2.92 (m, 2H), 1.99-1.95 (m, 2H), 1.74-1.59 (m, 6H) |
| Example 419 | 1-(3-cyclopentyl-1-(3-(2-((S)-3-(dimethylamino)pyrrolidin-1-yl)-2-oxoethyl)phenyl)-1H-pyrazol-5-yl)-3-(2,3-dichlorophenyl)urea Example 368 68.0 mg, 46% yield General method K | 569.3 | 9.54 (s, 1H), 8.95 (s, 1H), 8.05-8.02 (m, 1H), 7.48-7.20 (m, 5H), 7.20-7.02 (m, 1H), 6.32 (s, 1H), 4.09-3.67 (m, 5H), 3.62-3.49 (m, 2H), 3.06-2.97 (m, 1H), 2.74-2.72 (m, 6H), 2.32-2.11 (m, 2H), 2.02-1.92 (m, 2H), 1.74-1.57 (m, 6H) |
| Example 420 | 1-(2,3-dichlorophenyl)-3-(1-(3-(2-((S)-3-(dimethylamino)pyrrolidin-1-yl)-2-oxoethyl)phenyl)-3-(thiophen-2-yl)-1H-pyrazol-5-yl)urea Example 366 133.7 mg, 56% yield General method K | 583.0 | 10.74 (brs, 1H), 9.52 (s, 1H), 8.94 (s, 1H), 8.09-8.06 (m, 1H), 7.55-7.47 (m, 5H), 7.39-7.31 (m, 3H), 7.13-7.11 (m, 1H), 6.87 (s, 1H), 4.07-4.02 and 3.93-3.73 (m, 5H), 3.61-3.45 and 3.30-3.22 (m, 2H), 2.80-2.76 (m, 6H), 2.37-2.04 (m, 2H) |

-continued

| Example | Name | MS (EI) (M + H⁺) | ¹H NMR (400 MHz, DMSO-d₆) |
|---|---|---|---|
| 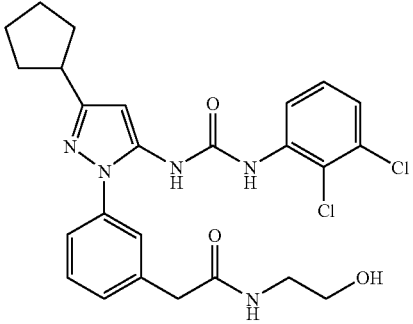  Example 421 | 1-(3-cyclopentyl-1-(3-(2-(2-hydroxyethylamino)-2-oxoethyl)phenyl)-1H-pyrazol-5-yl)-3-(2,3-dichlorophenyl)urea Example 368 41.0 mg, 34% yield General method K | 516.0 | 9.27 (s, 1H), 8.78 (s, 1H), 8.13-8.07 (m, 2H), 7.47-7.43 (m, 2H), 7.38-7.35 (m, 1H), 7.34-7.29 (m, 3H), 6.33 (s, 1H), 4.39-4.37 (m, 1H), 3.50 (s, 2H), 3.41-3.38 (m, 2H), 3.12-3.08 (m, 2H), 3.05-2.97 (m, 1H), 1.99-1.95 (m, 2H), 1.74-1.59 (m, 6H) |
| 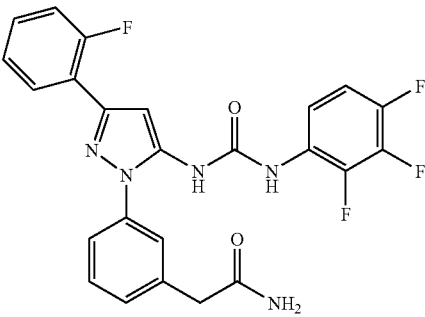  Example 422 | 1-(1-(3-(2-Amino-2-oxoethyl)phenyl)-3-(2-fluorophenyl)-1H-pyrazol-5-yl)-3-(2,3,4-trifluorophemyl)urea Example 362 100 mg, 84% yield General method I | 484.2 | 9.13 (s, 1H), 9.03 (s, 1H), 7.99 (dt, J = 2.0, and 8.0 Hz, 1H), 7.87 (m, 1H), 7.20-7.60 (m, 8H), 6.95 (brs, 1H), 6.91 (d, J = 4.4 Hz, 1H), 3.51 (s, 2H) |
| 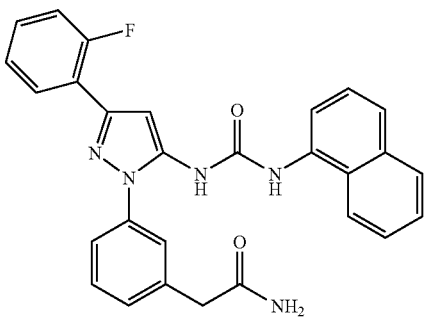  Example 423 | 1-(1-(3-(2-amino-2-oxoethyl)phenyl)-3-(2-fluorophenyl)-1H-pyrazol-5-yl)-3-(naphthalen-1-yl)urea Example 363 70 mg, 70% yield General method I | 480.2 | 9.13 (s, 1H), 9.02 (s, 1H), 7.9-8.1 (m, 4H), 7.2-7.7 (m, 12H), 6.96 (brs, 1H), 6.95 (d, J = 4.4 Hz, 1H), 3.53 (s, 2H) |
| 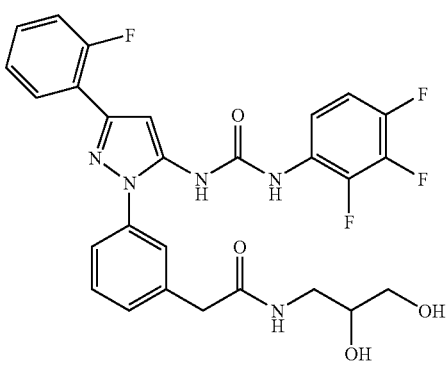  Example 424 | 1-(1-(3-(2-(2,3-Dihydroxypropylamino)-2-oxoethyl)phenyl)-3-(2-fluorophenyl)-1H-pyrazol-5-yl)-3-(2,3,4-trifluorophenyl)urea Example 362 95 mg, 83% yield General method J | 558.3 | 9.14 (s, 1H), 9.04 (s, 1H), 8.12 (t, J = 6.8 Hz, 1H), 7.99 (dt, J = 2.0, and 8.0 Hz, 1H), 7.88 (m, 1H), 7.55 (s, 1H), 7.52 (d, J = 7.2 Hz, 1H), 7.2-7.5 (m, 6H), 6.91 (d, J = 4.0 Hz, 1H), 4.76 (d, J = 4.4 Hz, 1H), 4.52 (t, J = 5.6 Hz, 1H), 3.58 (s, 2H), 3.49 (m, 1H), 3.2-3.4 (m, 4H), 2.97 (m, 1H) |

-continued

| Example | Name | MS (EI) (M + H⁺) | $^1$H NMR (400 MHz, DMSO-d$_6$) |
|---|---|---|---|
| Example 425 | 1-(1-(3-(2-(2,3-dihydroxypropylamino)-2-oxoethyl)phenyl)-3-(2-fluorophenyl)-1H-pyrazol-5-yl)-3-(naphthalen-1-yl)urea<br>Example 363<br>49 mg, 50% yield<br>General method J | 554.2 | 9.14 (s, 1H), 9.03 (s, 1H), 7.9-8.2 (m, 5H), 7.2-7.7 (m, 12H), 6.95 (d, J = 4.0 Hz, 1H), 4.77 (d, J = 5.2 Hz, 1H), 4.52 (t, J = 6.0 Hz, 1H), 3.60 (s, 2H), 3.49 (m, 1H), 3.2-3.4 (m, 4H), 2.98 (m, 1H) |
| Example 426 | 1-(3-(2-fluorophenyl)-1-(3-(2-(2-hydroxyethylamino)-2-oxoethyl)phenyl)-1H-pyrazol-5-yl)-3-(naphthalen-1-yl)urea<br>Example 363<br>50 mg, 57% yield<br>General method J | 524.3 | 9.13 (s, 1H), 9.02 (s, 1H), 8.16 (t, J = 5.2 Hz, 1H), 7.9-8.1 (m, 4H), 7.3-7.7 (m, 11H), 6.95 (d, J = 4.4 Hz, 1H), 4.69 (t, J = 4.8Hz, 1H), 3.57 (s, 2H), 3.40 (q, J = 6.0 Hz, 2H), 3.14 (s, J = 6.0 Hz, 2H) |
| Example 427 | 1-(1-(3-(2-amino-2-oxoethyl)phenyl)-3-(thiophen-2-yl)-1H-pyrazol-5-yl)-3-(naphthalen-1-yl)urea<br>Example 364<br>66 mg, 83% yield<br>General method I | 468.0 | 9.12 (s, 1H), 9.01 (s, 1H), 8.02 (d, J = 8.0 Hz, 1H), 7.95 (d, J = 7.6 Hz, 1H), 7.93 (dd, J = 2.0, and 9.2 Hz, 1H), 7.67 (d, J = 8.0 Hz, 1H), 7.45-7.60 (m, 8H), 7.41 (d, J = 7.2 Hz, 1H), 7.12 (dd, J = 3.6, and 4.8 Hz, 1H), 6.96 (s, 1H), 6.90 (s, 1H), 3.53 (s, 2H) |
| Example 428 | 1-(1-(3-(2-(2-hydroxyethylamino)-2-oxoethyl)phenyl)-3-(thiophen-2-yl)-1H-pyrazol-5-yl)-3-(naphthalen-1-yl)urea<br>Example 364<br>51 mg, 58% yield<br>General method J | 512.3 | 9.12 (s, 1H), 9.00 (s, 1H), 8.17 (brt, J = 5.6 Hz, 1H), 8.02 (brd, J = 8.0 Hz, 1H), 7.96 (d, J = 6.8 Hz, 1H), 7.92 (dd, J = 2.0, and 7.2 Hz, 1H), 7.67 (d, J = 8.0 Hz, 1H), 7.45-7.60 (m, 8H), 7.41 (d, J = 7.6 Hz, 1H), 7.12 (dd, J = 4.0, and 5.2 Hz, 1H), 6.90 (s, 1H), 4.69 (t, J = 5.2 Hz, 1H), 3.57 (s, 2H), 3.40 (q, J = 6.4 Hz, 2H), 3.12 (q, J = 6.0 Hz, 2H) |

| Example | Name | MS (EI) (M + H⁺) | ¹H NMR (400 MHz, DMSO-d₆) |
|---|---|---|---|
| Example 429 | 1-(1-(3-(2-(2,3-dihydroxypropylamino)-2-oxoethyl)phenyl)-3-(thiophen-2-yl)-1H-pyrazol-5-yl)-3-(naphthalen-1-yl)urea<br>Example 364<br>60 mg, 65% yield<br>General method J | 542.3 | 9.13 (s, 1H), 9.00 (s, 1H), 8.13 (brt, J = 5.6 Hz, 1H), 8.02 (brd, J = 8.0 Hz, 1H), 7.96 (d, J = 6.8 Hz, 1H), 7.93 (dd, J = 2.0, and 7.2 Hz, 1H), 7.67 (d, J = 8.0 Hz, 1H), 7.45-7.60 (m, 8H), 7.42 (d, J = 7.6 Hz, 1H), 7.12 (dd, J = 4.0, and 5.2 Hz, 1H), 6.90 (s, 1H), 4.77 (d, J = 4.8 Hz, 1H), 4.52 (t, J = 5.2 Hz, 1H), 3.59 (s, 2H), 3.48 (m, 1H), 3.26 (m, 2H), 2.98 (m, 1H) |
| Example 430 | 1-(1-(3-(2-(1,3-dihydroxypropan-2-ylamino)-2-oxoethyl)phenyl)-3-(thiophen-2-yl)-1H-pyrazol-5-yl)-3-(naphthalen-1-yl)urea<br>Example 364<br>67 mg, 72% yield<br>General method J | 542.3 | 9.13 (s, 1H), 9.00 (s, 1H), 8.02 (d, J = 8.0 Hz, 1H), 7.93 (m, 2H), 7.67 (d, J = 8.0 Hz, 1H), 7.45-7.60 (m, 8H), 7.41 (d, J = 7.2 Hz, 1H), 7.12 (dd, J = 3.6, and 5.2 Hz, 1H), 6.90 (s, 1H), 4.64 (t, J = 5.6 Hz, 2H), 3.71 (m, 1H), 3.60 (s, 2H), 3.42 (t, J = 5.6 Hz, 2H) |
| Example 431 | 1-(1-(3-(2-amino-2-oxoethyl)phenyl)-3-(thiophen-3-yl)-1H-pyrazol-5-yl)-3-(2,3,4-trifluorophenyl)urea<br>Example 365<br>0.06 g, 75% yield<br>General method I | 472.0 | 9.10 (brs, 1H), 8.97 (s, 1H), 7.87 (m, 2H), 7.60 (dd, J = 2.8, and 4.8 Hz, 1H), 7.51 (m, 4H), 7.44 (m, 1H), 7.38 (m, 1H), 7.28 (m, 1H), 6.95 (brs, 1H), 6.86 (s, 1H), 3.50 (s, 2H) |
| Example 432 | 1-(1-(3-(2-amino-2-oxoethyl)phenyl)-3-t-butyl-1H-pyrazol-5-yl)-3-(2,4-difluorophenyl)urea<br>From Example 369<br>0.105 g, 84% yield<br>General method I | 428.3 | 8.88 (s, 1H), 8.80 (s, 1H), 8.09-8.03 (m, 1H), 7.52 (brs, 1H), 7.46 (t, J = 8.0 Hz, 1H), 7.41-7.27 (m, 4H), 7.06-7.01 (m, 1H), 6.93 (brs, 1H), 6.38 (s, 1H), 3.47 (s, 2H), 1.27 (s, 9H); |

-continued

| Example | Name | MS (EI) (M + H+) | 1H NMR (400 MHz, DMSO-d6) |
|---|---|---|---|
| Example 433 | 1-(1-(3-(2-amino-2-oxoethyl)phenyl)-3-t-butyl-1H-pyrazol-5-yl)-3-(3-phenoxyphenyl)urea<br>From Example A8<br>0.05 g, 50% yield<br>General method D | 484.2 | 1H NMR (DMSO-d6): δ 9.10 (s, 1H), 8.37 (s, 1H), 7.44 (brs, 1H), 7.42-7.01 (m, 12H), 6.93 (brs, 1H), 6.63-6.61 (m, 1H), 6.34 (s, 1H), 3.45 (s, 2H), 1.28 (s, 9H). |
| Example 434 | 1-(1-(3-(2-amino-2-oxoethyl)phenyl)-3-t-butyl-1H-pyrazol-5-yl)-3-(2,4,5-trifluorophenyl)urea<br>From Example A8<br>0.048 g, 18% yield<br>General method D | 446.2 | 1H NMR (DMSO-d6): δ 9.10 (s, 1H), 8.89 (s, 1H), 8.21-8.14 (m, 1H), 7.65-7.58 (m, 1H), 7.52 (brs, 1H), 7.46 (t, J = 8.0 Hz, 1H), 7.41-7.31 (m, 3H), 6.40 (s, 1H), 3.46 (s, 2H), 1.28 (s, 9H). |
| Example 435 | 1-(1-(3-(2-amino-2-oxoethyl)phenyl)-3-t-butyl-1H-pyrazol-5-yl)-3-(2,3,4-trifluorophenyl)urea<br>From Example 356<br>0.045 g, 46% yield<br>General method I | 446.2 | 1H NMR (DMSO-d6): δ 9.06 (s, 1H), 8.85 (s, 1H), 7.88-7.82 (m, 1H), 7.53 (brs, 1H), 7.46 (t, J = 8.0 Hz, 1H), 7.42-7.25 (m, 4H), 6.94 (brs, 1H), 6.38 (s, 1H), 3.46 (s, 2H), 1.27 (s, 9H) |
| Example 436 | 1-(1-(3-(2-amino-2-oxoethyl)phenyl)-3-t-butyl-1H-pyrazol-5-yl)-3-(3,4-difluorophenyl)urea<br>From Example A8<br>0.045 g, 47%<br>General method D | 428.2 | 1H NMR (DMSO-d6): δ 9.40 (s, 1H), 8.58 (s, 1H), 7.65-7.59 (m, 1H), 7.54 (brs, 1H), 7.46-7.28 (m, 5H), 7.07-7.04 (m, 1H), 6.94 (brs, 1H), 6.37 (s, 1H), 3.46 (s, 2H), 1.28 (s, 9H); Exact mass: 427.2 found: (M + 1)+. |
| Example 437 | 1-(1-(3-(2-amino-2-oxoethyl)phenyl)-3-t-butyl-1H-pyrazol-5-yl)-3-(3-(pyrazin-2-yl)phenyl)urea<br>From Example A8<br>0.08 g, 68%<br>General method D | 470.2 | 1H NMR (DMSO-d6): δ 9.22 (s, 1H), 9.18 (d, J = 1.2 Hz, 1H), 8.72 (dd, J = 2.8 Hz, 1.2 Hz, 1H), 8.62 (d, J = 2.8 Hz, 1H), 8.27 (t, J = 1.6 Hz, 1H), 7.75-7.72 (m, 1H), 7.53-7.31 (m, 7H), 6.94 (s, 1H), 6.41 (s, 1H). |

| Example | Name | MS (EI) (M + H+) | 1H NMR (400 MHz, DMSO-d6) |
|---|---|---|---|
| Example 438 | 1-(1-(3-(2-amino-2-oxoethyl)phenyl)-3-t-butyl-1H-pyrazol-5-yl)-3-(3-(pyridin-3-yl)phenyl)urea From Example A8 0.08 g, 38% General method D | 469.2 | 1H NMR (DMSO-d6): δ 9.15 (s, 1H), 8.83 (s, 1H), 8.58 (s, 1H), 8.48 (s, 1H), 8.02 (d, J = 7.6 Hz, 1H), 7.79 (s, 1H), 7.52-7.31 (m, 9H), 6.93 (s, 1H), 6.40 (s, 1H), 3.47 (s, 2H), 1.28 (s, 9H). |
| Example 439 | 1-(1-(3-(2-amino-2-oxoethyl)phenyl)-3-t-butyl-1H-pyrazol-5-yl)-3-(3-(6-aminopyridin-3-yl)phenyl)urea From Example A8 35 mg, 29% General method D | 484.2 | 1H NMR (DMSO-d6): δ 9.46 (s, 1H), 8.70 (s, 1H), 8.23-8.16 (m, 3H), 7.77 (s, 1H), 7.57 (s, 1H), 7.46-7.23 (m, 7H), 7.12-7.09 (m, 1H), 6.94 (s, 1H), 6.38 (s, 1H), 3.47 (s, 1H), 1.28 (s, 9H). |
| Example 440 | 1-(3-t-butyl-1-(3-(2-(2,3-dihydroxypropylamino)-2-oxoethyl)phenyl)-1H-pyrazol-5-yl)-3-(2,3-dichlorophenyl)urea From Example 373 69 mg, 46% yield General method J | 536.0 | δ 1.27 (s, 9H), 2.95-2.96 (m, 1H), 3.19-3.48 (m, 4H), 3.53 (s, 2H), 4.40-4.80 (br. M, 2H), 6.39 (s, 1H), 7.30-7.45 (m, 6H), 8.07-8.10 (m, 2H), 8.78 (s, 1H), 9.26 (s, 1H). |
| Example 441 | 1-(3-t-butyl-1-(3-(2-(isopropylamino)-2-oxoethyl)phenyl)-1H-pyrazol-5-yl)-3-(2,3-dichlorophenyl)urea From Example 373 (90 mg, 59% yield) General method I | 502.0 | δ 9.27 (s, 1H), 8.79 (s, 1H), 8.09 (dd, J = 3.2, and 6.4 Hz, 1H), 8.01 (d, J = 7.6 Hz, 1H), 7.2-7.5 (m, 5H), 6.39 (s, 1H), 3.78 (m, 1H), 3.45 (s, 2H), 1.28 (s, 9H), 1.04 (d, J = 6.8 Hz, 6H) |

-continued

| Example | Name | MS (EI) (M + H+) | 1H NMR (400 MHz, DMSO-d6) |
|---|---|---|---|
| 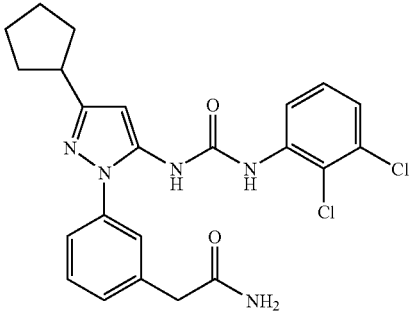  Example 442 | 1-(1-(3-(2-amino-2-oxoethyl)phenyl)-3-cyclopentyl-1H-pyrazol-5-yl)-3-(2,3-dichlorophenyl)urea From Example 368 56.0 mg 41% General method J | 472.2 | 9.27 (s, 1H), 8.78 (s, 1H), 8.10-8.05 (m, 1H), 7.52 (brs, 1H), 7.49-7.44 (m, 2H), 7.38-7.28 (m, 4H), 6.93 (brs, 1H), 6.33 (s, 1H), 3.46 (s, 2H), 3.05-2.98 (m, 1H), 2.01- 1.93 (m, 2H), 1.74-1.60 (m, 6H) |
| 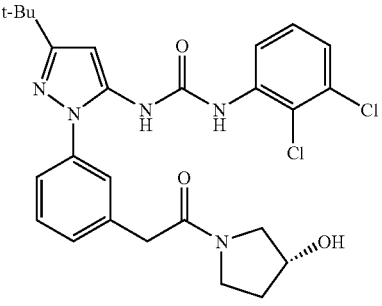  Example 443 | 1-(3-t-butyl-1-(3-(2-((R)-3-hydroxypyrrolidin-1-yl)-2-oxoethyl)phenyl)-1H-pyrazol-5-yl)-3-(2,3-dichlorophenyl)urea 51.8 mg, 87% yield General method K | 530.2 | 9.26 (s, 1H), 8.78 (s, 1H), 8.10-8.07 (m, 1H), 7.48-7.37 (m, 3H), 7.32-7.28 (m 3H), 6.39 (s, 1H), 5.02 and 4.91 (d, 1H, J = 3.6 Hz), 4.29-4.27 and 4.22-4.21 (m, 1H), 3.72-3.69 (m, 2H), 3.62-3.56 and 3.39-3.27 (m, 3H), 1.93-1.69 (m, 2H), 1.28 (s, 9H) |
| 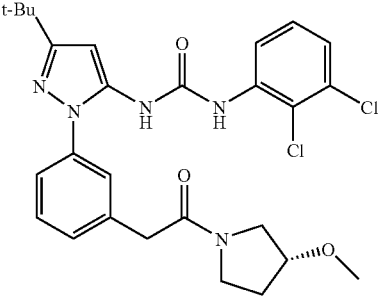  Example 444 | 1-(3-t-butyl-1-(3-(2-((R)-3-methoxypyrrolidin-1-yl)-2-oxoethyl)phenyl)-1H-pyrazol-5-yl)-3-(2,3-dichlorophenyl)urea 67 mg, 63% yield General method K | 544.2 | 9.27 and 9.26 (s, 1H), 8.79 (s, 1H), 8.10-8.07 (m, 1H), 7.48-7.45 (m, 1H), 7.41-7.37 (m, 2H), 7.34-7.28 (m, 3H), 6.39 (s, 1H), 3.96-3.94 and 3.91-3.88 (m, 1H), 3.73 and 3.72 (s, 2H), 3.66-3.56 and 3.53-3.39 (m, 3H), 3.33-3.21 (m, 1H), 3.20 and 3.19 (s, 3H), 1.97-1.79 (m, 2H), 1.28 (s, 9H) |
| 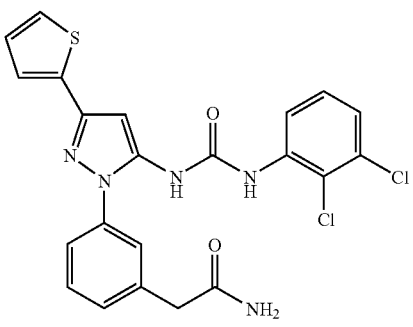  Example 445 | 1-(1-(3-(2-amino-2-oxoethyl)phenyl)-3-(thiophen-2-yl)-1H-pyrazol-5-yl)-3-(2,3-dichlorophenyl)urea: From Example 366 0.052 g, 69% yield General method I | 486.0 | 9.42 (s, 1H), 8.86 (s, 1H), 8.10 (dd, J = 6.8 Hz, 3.2 Hz, 1H), 7.54-7.447 (m, 6H), 7.39-7.32 (m, 3H), 7.12 (dd, J = 4.8 Hz, 3.2 Hz, 1H), 6.95 (brs, 1H), 6.87 (s, 1H), 3.72 (s, 2H) |

| Example | Name | MS (EI) (M + H⁺) | ¹H NMR (400 MHz, DMSO-d₆) |
|---|---|---|---|
| Example 446 | (S)-1-(1-(4-(2-amino-2-oxoethyl)phenyl)-3-t-butyl-1H-pyrazol-5-yl)-3-(2,3-dihydro-1H-inden-1-yl)urea<br>0.04 g, 49% yield<br>General method I | 432.2 | 8.09 (s, 1H), 7.52 (s, 1H), 7.41-7.36 (m, 4H), 7.24-7.19 (m, 4H), 6.95-6.92 (m, 2H), 6.32 (s, 1H), 5.09 (q, J = 7.6 Hz, 1H), 3.43 (s, 2H), 2.92-2.74 (m, 2H), 2.44-2.36 (m, 1H), 1.76-1.66 (m, 1H), 1.27 (s, 9H) |
| Example 447 | 1-(1-(3-(2-amino-2-oxoethyl)phenyl)-3-phenyl-1H-pyrazol-5-yl)-3-(2,3-dichlorophenyl)urea<br>From Example 351<br>61 mg, 61% yield<br>General method J | 480.0 | 9.42 (s, 1H), 8.88 (s, 1H), 8.09 (dd, J = 6.8 Hz, 2.8 Hz, 1H), 7.83 (d, J = 8 Hz, 2H), 7.58-7.55 (m, 3H), 7.49-7.32 (m, 7H), 6.94 (brs, 2H), 3.48 (s, 2H) |
| Example 448 | 1-(1-(3-(2-amino-2-oxoethyl)phenyl)-3-(thiazol-4-yl)-1H-pyrazol-5-yl)-3-(2,3-dichlorophenyl)urea<br>From Example 352<br>87 mg, 61% yield<br>General method J | 487.0 | 9.42 (s, 1H), 9.18 (d, J = 2.0 Hz, 1H), 8.86 (s, 1H), 8.09 (dd, J = 7.4 Hz, 2.8 Hz, 1H), 8.01 (d, J = 2.4 Hz, 1H), 7.54-7.48 (m, 4H), 7.40-7.32 (m, 3H) 6.95 (brs, 1H), 6.92 (s, 1H), 3.50 (s, 2H) |
| Example 449 | 1-(1-(3-(2-amino-2-oxoethyl)phenyl)-3-t-butyl-1H-pyrazol-5-yl)-3-(thiazol-2-yl)urea<br>From Example 512<br>0.017 g, 21% yield<br>General method I | 399.2 | 10.83 (s, 1H), 8.92 (s, 1H), 7.52 (brs, 1H), 7.46 (t, J = 8.0 Hz, 1H), 7.42-7.32 (m, 4H), 7.13 (d, J = 3.2 Hz, 1H), 6.93 (brs, 1H), 6.44 (s, 1H), 3.47 (s, 214), 1.28 (s, 9H) |

-continued

| Example | Name | MS (EI) (M + H+) | 1H NMR (400 MHz, DMSO-d6) |
|---|---|---|---|
| 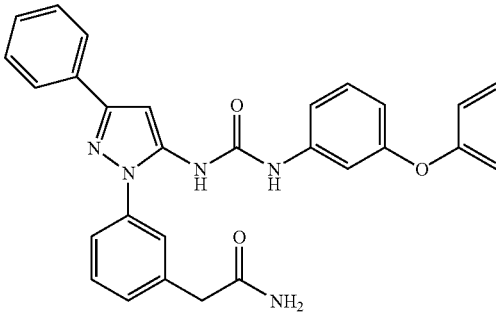 Example 450 | 1-(1-(3-(2-amino-2-oxoethyl)phenyl)-3-phenyl-1H-pyrazol-5-yl)-3-(3-(pyridin-3-yloxy)phenyl)urea 37 mg, 67% yield General method I | 505.2 | 9.21 (s, 1H), 8.57 (s, 1H), 8.40-8.37 (m, 2H), 7.85-7.83 (m, 2H), 7.54-7.27 (m, 12H), 7.14-7.11 (m, 1H), 6.95 (brs, 1H), 6.91 (s, 1H), 6.69 (dd, J = 8.0 Hz, 2.4 Hz, 1H), 3.49 (s, 2H) |
| 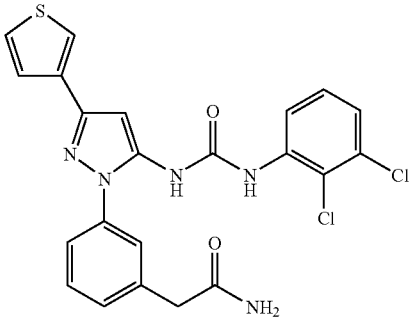 Example 451 | 1-(1-(3-(2-amino-2-oxoethyl)phenyl)-3-(thiophen-3-yl)-1H-pyrazol-5-yl)-3-(2,3-dichlorophenyl)urea From Example 367 61 mg, 77% yield General method I | 486.0 | 9.38 (s, 1H), 8.84 (s, 1H), 8.10 (dd, J = 6.8 Hz, 2.8 Hz, 1H), 7.88-7.87 (m, 1H), 7.62-7.60 (m, 1H), 7.52-7.44 (m, 5H), 7.38-7.32 (m, 3H), 6.94 (brs, 1H), 6.86 (s, 1H), 3.49 (s, 2H |
| 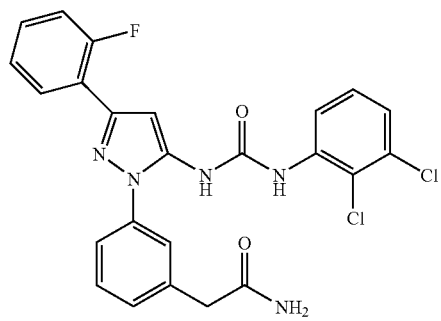 Example 452 | 1-(1-(3-(2-amino-2-oxoethyl)phenyl)-3-(2-fluorophenyl)-1H-pyrazol-5-yl)-3-(2,3-dichlorophenyl)urea From Example 354 42 mg, 58% yield General method I | 498.0 | 9.44 (s, 1H), 8.88 (s, 1H), 8.09 (dd, J = 6.4 Hz, 3.6 Hz, 1H), 7.99 (td, J = 7.6 Hz, 1.2 Hz, 1H), 7.56-7.48 (m, 4H), 7.41-7.31 (m, 5H), 7.28 (t, J = 7.6 Hz, 1H), 6.96 (brs, 1H), 6.92 (d, J = 4.0 Hz, 1H), 3.50 (s, 2H) |
| 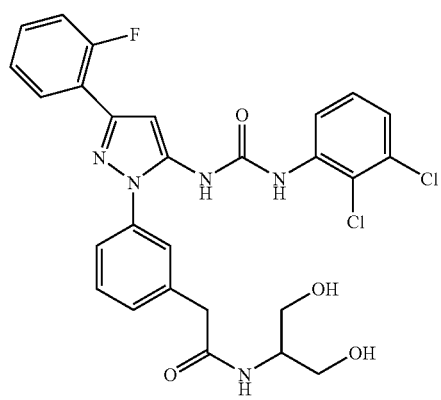 Example 453 | 1-(2,3-dichlorophenyl)-3-(1-(3-(2-(1,3-dihydroxypropan-2-ylamino)-2-oxoethyl)phenyl)-3-(2-fluorophenyl)-1H-pyrazol-5-yl)urea From Example 354 68 mg, 60% yield General method I | 572.0 | 9.45 (s, 1H), 8.89 (s, 1H), 8.10 (dd, J = 6.4 Hz, 3.6 Hz, 1H), 8.00 (td, J = 7.6 Hz, 2.0 Hz, 1H), 7.90 (d, J = 8.4 Hz, 1H), 7.56-7.47 (m, 3H), 7.42-7.26 (m, 6H), 6.92 (d, J = 4.0 Hz, 1H), 3.72-3.68 (m, 1H), 3.57 (s, 2H), 3.43-3.40 (m, 4H) |

| Example | Name | MS (EI) (M + H+) | 1H NMR (400 MHz, DMSO-d6) |
|---|---|---|---|
| 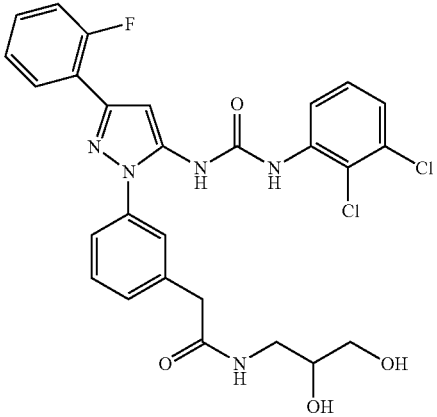<br>Example 454 | 1-(2,3-dichlorophenyl)-3-(1-(3-(2-(2,3-dihydroxypropylamino)-2-oxoethyl)phenyl)-3-(2-fluorophenyl)-1H-pyrazol-5-yl)urea<br>From Example 354<br>26 mg, 23% yield<br>General method I | 572.0 | 9.45 (s, 1H), 8.88 (s, 1H), 8.14-8.09 (m, 2H), 7.99 (td, J = 8.0 Hz, 1.6 Hz, 1H), 7.57-7.48 (m, 3H), 7.41-7.26 (m, 6H), 6.92 (d, J = 4.0 Hz, 1H), 4.76 (d, J = 4.4 Hz, 1H), 4.52 (t, J = 6.0 Hz, 1H), 3.57 (s, 2H), 3.50-3.46 (m, 1H), 3.30-3.19 (m, 3H), 2.99-2.93 (m, 1H) |
| 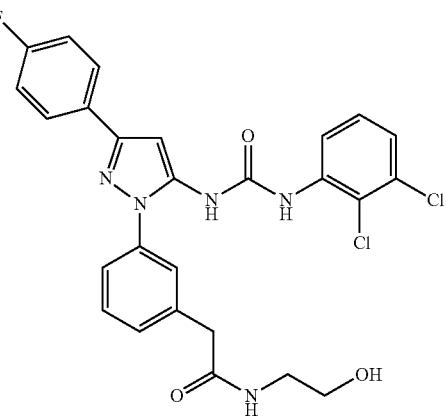<br>Example 455 | 1-(2,3-dichlorophenyl)-3-(3-(4-fluorophenyl)-1-(3-(2-(2-hydroxyethylamino)-2-oxoethyl)phenyl)-1H-pyrazol-5-yl)urea<br>55% yield<br>General method I | 542.0 | 9.44 (s, 1H), 8.87 (s, 1H), 8.15 (t, J = 5.2 Hz, 1H), 8.09 (dd, J = 6.8 Hz, 3.6 Hz, 1H), 7.90-7.87 (m, 2H), 7.55 (brs, 1H), 7.51-7.46 (m, 2H), 7.38-7.31 (m, 3H), 7.26 (t, J = 8.8 Hz, 2H), 6.94 (s, 1H), 3.54 (s, 2H), 3.39 (t, J = 6.0 Hz, 2H), 3.11 (q, J = 6.0 Hz, 2H) |
| 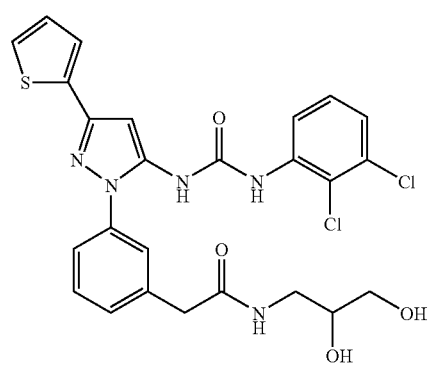<br>Example 456 | 1-(2,3-dichlorophenyl)-3-(1-(3-(2-(2,3-dihydroxypropylamino)-2-oxoethyl)phenyl)-3-(thiophen-2-yl)-1H-pyrazol-5-yl)urea<br>From Example 366<br>59 mg, 68% yield<br>General method I | 560.0 | 9.44 (s, 1H), 8.88 (s, 1H), 8.14-8.08 (m, 2H), 7.53-7.43 (m, 4H), 7.40-7.31 (m, 3H), 7.13-7.10 (m, 1H), 6.87 (s, 1H), 3.57 (s, 2H), 3.50-3.46 (m, 1H), 3.28-3.20 (m, 3H), 2.99-2.94 (m, 1H); |

-continued

| Example | Name | MS (EI) (M + H+) | 1H NMR (400 MHz, DMSO-d6) |
|---|---|---|---|
| 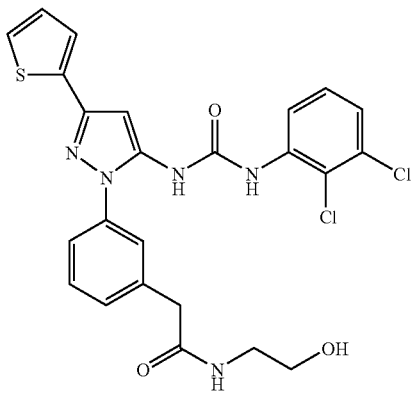<br>Example 457 | 1-(2,3-dichlorophenyl)-3-(1-(3-(2-(2-hydroxyethylamino)-2-oxoethyl)phenyl)-3-(thiophen-2-yl)-1H-pyrazol-5-yl)urea<br>From Example 366<br>68 mg, 83% yield<br>General method I | 530.0 | .42 (s, 1H), 8.87 (s, 1H), 8.14 (t, J = 5.6 Hz, 1H), 8.10 (dd, J = 6.8 Hz, 2.8 Hz, 1H), 7.53-7.43 (m, 4H), 7.39-7.31 (m, 3H), 7.13-7.10 (m, 1H), 6.87 (s, 1H), 4.66 (brs, 1H), 3.54 (s, 2H), 3.41-3.38 (m, 2H), 3.11 (q, J = 6.0 Hz, 2H) |
| 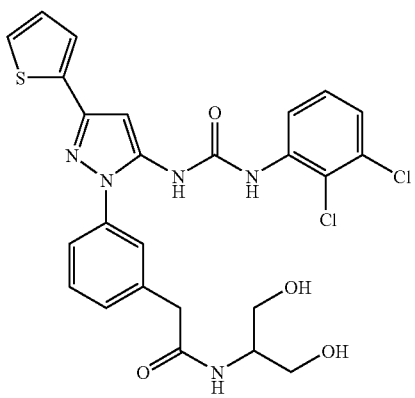<br>Example 458 | 1-(2,3-dichlorophenyl)-3-(1-(3-(2-(1,3-dihydroxypropan-2-ylamino)-2-oxoethyl)phenyl)-3-(thiophen-2-yl)-1H-pyrazol-5-yl)urea<br>From Example 366<br>55 mg, 64% yield<br>General method I | 560.2 | 9.43 (s, 1H), 8.88 (s, 1H), 8.10 (dd, J = 6.8 Hz, 3.2 Hz, 1H), 7.90 (d, J = 3.6 Hz, 1H), 7.53-7.38 (m, 6H), 7.34-7.31 (m, 2H), 7.13-7.10 (m, 1H), 6.87 (s, 1H), 4.63 (t, J = 5.6 Hz, 2H), 3.73-3.68 (m, 1H), 3.57 (s, 2H), 3.42 (t, J = 5.6 Hz, 4H) |
| 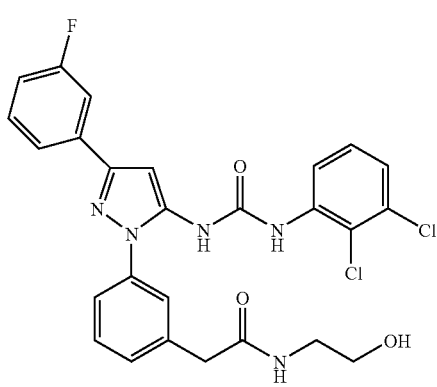<br>Example 459 | 1-(2,3-dichlorophenyl)-3-(3-(3-fluorophenyl)-1-(3-(2-(2-hydroxyethylamino)-2-oxoethyl)phenyl)-1H-pyrazol-5-yl)urea<br>From Example 353<br>65 mg, 74% yield<br>General method I | 542.0 | 9.43 (s, 1H), 8.86 (s, 1H), 8.14 (t, J = 5.2 Hz, 1H), 8.09 (dd, J = 6.8 Hz, 2.8 Hz, 1H), 7.70 (d, J = 7.6 Hz, 1H), 7.65-7.62 (m, 1H), 7.55 (brs, 1H), 7.51-7.45 (m, 3H), 7.39-7.31 (m, 3H), 7.18 (dt, J = 8.8 Hz, 3.2 Hz, 1H), 7.01 (s, 1H), 4.68 (t, J = 5.2 Hz, 2H), 3.54 (s, 2H), 3.42-3.37 (m, 2H), 3.11 (q, J = 6.0 Hz, 2H) |

-continued

| Example | Name | MS (EI) (M + H⁺) | ¹H NMR (400 MHz, DMSO-d$_6$) |
|---|---|---|---|
| 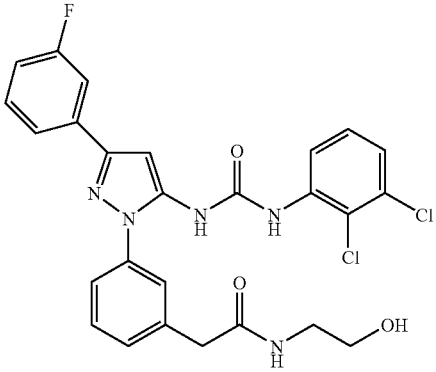 Example 460 | 1-(1-(3-(2-amino-2-oxoethyl)phenyl)-3-(3-fluorophenyl)-1H-pyrazol-5-yl)-3-(2,3-dichlorophenyl)urea From Example 353 67 mg, 90% yield General method I | 498.0 | 9.410 (s, 1H), 8.85 (s, 1H), 8.09 (dd, J = 6.8 Hz, 3.6 Hz, 1H), 7.70 (d, J = 8.0 Hz, 1H), 7.65-7.62 (m, 1H), 7.55-7.45 (m, 5H), 7.40-7.31 (m, 3H), 7.18 (td, J = 8.8 Hz, 2.8 Hz, 1H), 7.01 (s, 1H), 6.95 (brs, 1H), 3.50 (s, 2H |
| 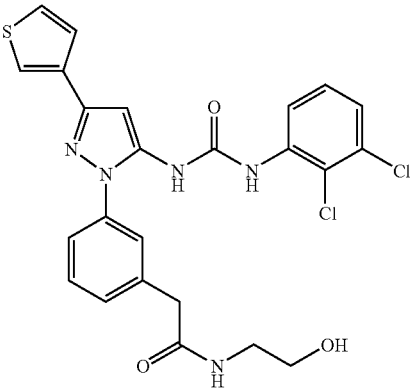 Example 461 | 1-(2,3-dichlorophenyl)-3-(1-(3-(2-(2-hydroxyethylamino)-2-oxoethyl)phenyl)-3-(thiophen-3-yl)-1H-pyrazol-5-yl)urea From Example 367 37 mg, 43% yield General method I | 530.0 | 9.38 (s, 1H), 8.84 (s, 1H), 8.15-8.09 (m, 2H), 7.87 (dd, J = 3.2 Hz, 1.2 Hz, 1H), 7.61 (dd, J = 5.2 Hz, 3.2 Hz, 1H), 7.52-7.44 (m, 4H), 7.38-7.32 (m, 3H), 6.86 (s, 1H), 4.67 (t, J = 5.6 Hz, 1H), 3.53 (s, 2H), 3.42-3.37 (m, 2H), 3.11 (q, J = 5.6 Hz, 2H) |
| 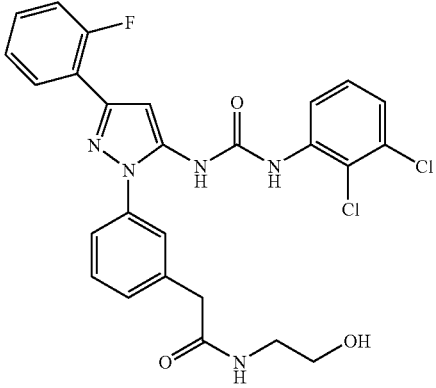 Example 462 | 1-(2,3-dichlorophenyl)-3-(3-(2-fluorophenyl)-1-(3-(2-(2-hydroxyethylamino)-2-oxoethyl)phenyl)-1H-pyrazol-5-yl)urea From Example 354 75 mg, 70% yield General method I | 542.0 | 9.47 (s, 1H), 8.89 (s, 1H), 8.15 (t, J = 5.2 Hz, 1H), 8.10 (dd, J = 6.4 Hz, 3.2 Hz, 1H), 7.99 (td, J = 8.0 Hz, 1.6 Hz, 1H), 7.56-7.48 (m, 3H), 7.42-7.26 (m, 6H), 6.91 (d, J = 4.0 Hz, 1H), 3.55 (s, 2H), 3.39 (t, J = 6.0 Hz, 2H), 3.13-3.09 (m, 2H |

-continued

| Example | Name | MS (EI) (M + H⁺) | ¹H NMR (400 MHz, DMSO-d₆) |
|---|---|---|---|
| 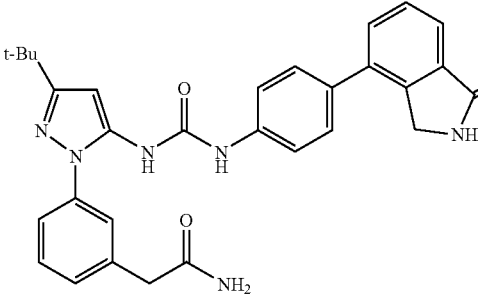

Example 463 | 1-(1-(3-(2-amino-2-oxoethyl)phenyl)-3-t-butyl-1H-pyrazol-5-yl)-3-(4-(1-oxoisoindolin-4-yl)phenyl)urea
From Example A8
0.053 g, 36%
General method D | 523.2 | 9.15 (s, 1H), 8.66 (s, 1H), 8.41 (s, 1H), 7.66-7.31 (m, 12H), 6.94 (s, 1H), 6.40 (s, 1H), 4.50 (s, 2H), 3.47 (s, 2H), 1.29 (s, 9H) |
| 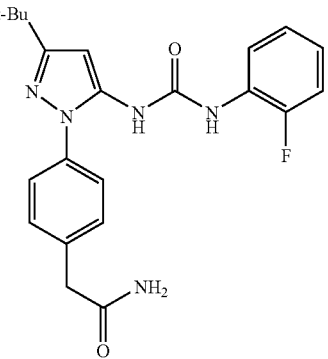

Example 464 | 1-(1-(4-(2-amino-2-oxoethyl)phenyl)-3-t-butyl-1H-pyrazol-5-yl)-3-(2-fluorophenyl)urea
From Example 386
56 mg, 69% yield
General method I | 410.2 | (Acetone-d₆): δ 8.42 (s, 1H), 8.36 (s, 1H), 8.31 (td, J = 8.4 Hz, 1.6 Hz, 1H), 7.51-7.48 (m, 3H), 7.45-7.43 (m, 2H), 7.17-7.11 (m, 2H), 7.05-7.00 (m, 1H), 6.52 (s, 1H), 3.58 (s, 2H), 1.33 (s, 9H) |
| 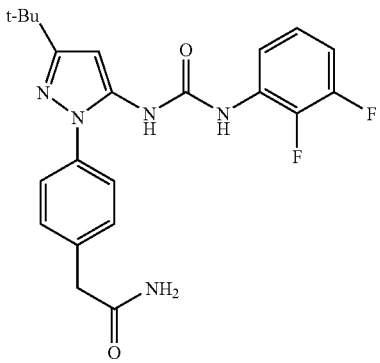

Example 465 | 1-(1-(4-(2-amino-2-oxoethyl)phenyl)-3-t-butyl-1H-pyrazol-5-yl)-3-(2,3-difluorophenyl)urea
From Example 382
0.04 g, 49% yield
General method I | 428.2 | 9.14 (s, 1H), 8.92 (s, 1H), 7.94 (dd, J = 8.0 Hz, 6.8 Hz, 1H), 7.55 (brs, 1H), 7.45-7.41 (m, 4H), 7.16-7.10 (m, 1H), 7.06-7.00 (m, 1H), 6.93 (brs, 1H), 6.39 (s, 1H), 3.45 (s, 2H), 1.27 (s, 9H) |
| 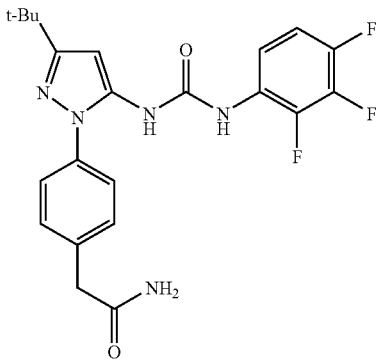

Example 466 | 1-(1-(4-(2-amino-2-oxoethyl)phenyl)-3-t-butyl-1H-pyrazol-5-yl)-3-(2,3,4-trifluorophenyl)urea
From Example 377
0.075 g, 84% yield
General method I | 446.2 | 9.08 (s, 1H), 8.85 (s, 1H), 7.88-7.83 (m, 1H), 7.54 (brs, 1H), 7.45-7.40 (m, 4H), 7.29-7.22 (m, 1H), 6.93 (brs, 1H), 6.38 (s, 1H), 3.44 (s, 2H), 1.27 (s, 9H) |

-continued

| Example | Name | MS (EI) (M + H+) | 1H NMR (400 MHz, DMSO-d6) |
|---|---|---|---|
| 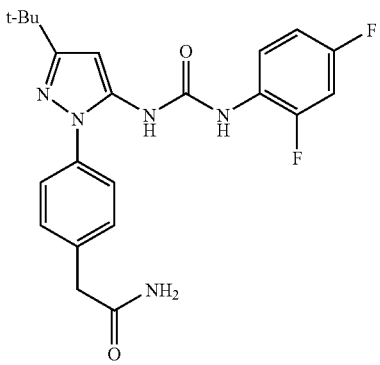<br>Example 467 | 1-(1-(4-(2-amino-2-oxoethyl)phenyl)-3-t-butyl-1H-pyrazol-5-yl)-3-(2,4-difluorophenyl)urea<br>From Example 376<br>0.125 g, 80% yield<br>General method I | 428.2 | 8.92 (s, 1H), 8.82 (s, 1H), 8.09-8.03 (m, 1H), 7.55 (brs, 1H), 7.45-7.40 (m, 4H), 7.32-7.27 (m, 1H), 7.06-7.01 (m, 1H), 6.94 (brs, 1H), 6.37 (s, 1H), 3.44 (s, 2H), 1.27 (s, 9H) |
| 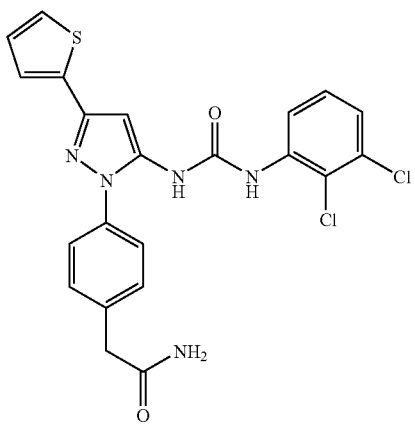<br>Example 468 | 1-(1-(4-(2-amino-2-oxoethyl)phenyl)-3-(thiophen-2-yl)-1H-pyrazol-5-yl)-3-(2,3-dichlorophenyl)urea<br>From Example 378<br>41 mg, 55% yield<br>General method I | 486.0 | 9.44 (s, 1H), 8.90 (s, 1H), 8.10 (dd, J = 6.8 Hz, 2.8 Hz, 1H), 7.57 (brs, 1H), 7.53-7.46 (m, 6H), 7.34-7.31 (m, 2H), 7.11 (dd, J = 5.2 Hz, 3.2 Hz, 1H), 6.95 (brs, 1H), 6.86 (s, 1H), 3.48 (s, 2H) |
| 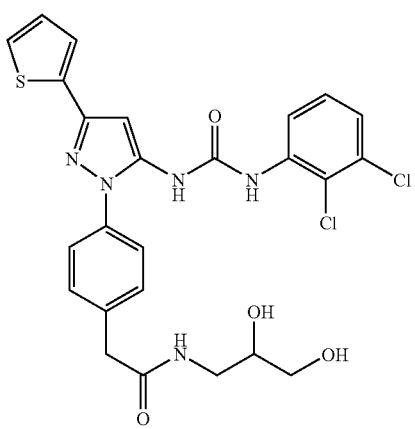<br>Example 469 | 1-(2,3-dichlorophenyl)-3-(1-(4-(2-(2,3-dihydroxypropylamino)-2-oxoethyl)phenyl)-3-(thiophen-2-yl)-1H-pyrazol-5-yl)urea<br>From Example 378<br>81 mg, 79% yield<br>General method I | 560.0 | 9.50 (s, 1H), 8.93 (s, 1H), 8.17 (t, J = 5.6 Hz, 1H), 8.10 (dd, J = 6.8 Hz, 3.6 Hz, 1H), 7.53-7.46 (m, 6H), 7.36-7.30 (m, 2H), 7.12-7.10 (m, 1H), 6.85 (s, 1H), 3.55 (s, 2H), 3.53-3.47 (m, 1H), 3.31-3.21 (m, 3H), 3.02-2.95 (m, 1H) |

-continued

| Example | Name | MS (EI) (M + H⁺) | ¹H NMR (400 MHz, DMSO-d₆) |
|---|---|---|---|
| 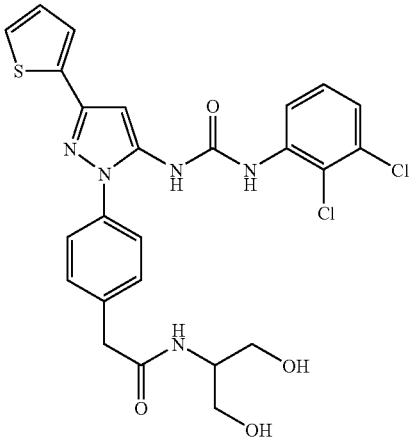 Example 470 | 1-(2,3-dichlorophenyl)-3-(1-(4-(2-(1,3-dihydroxypropan-2-ylamino)-2-oxoethyl)phenyl)-3-(thiophen-2-yl)-1H-pyrazol-5-yl)urea From Example 378 57 mg, 56% yield General method I | 560.2 | 9.47 (s, 1H), 8.91 (s, 1H), 8.10 (dd, J = 6.8 Hz, 2.8 Hz, 1H), 7.92 (d, J = 8.4 Hz, 1H), 7.53-7.46 (m, 6H), 7.34-7.31 (m, 2H), 7.12-7.10 (m, 1H), 6.85 (s, 1H), 3.74-3.69 (m, 1H), 3.55 (s, 2H), 3.43 (d, J = 5.2 Hz, 4H) |
| 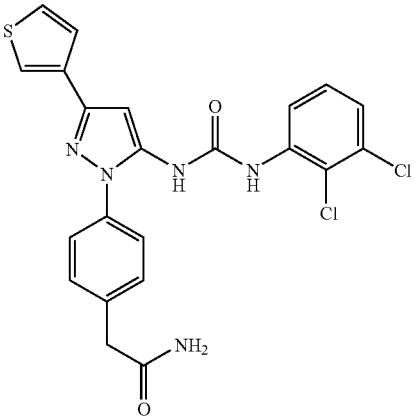 Example 471 | 1-(1-(4-(2-amino-2-oxoethyl)phenyl)-3-(thiophen-3-yl)-1H-pyrazol-5-yl)-3-(2,3-dichlorophenyl)urea From Example 381 53 mg, 71% yield General method I | 486.0 | 9.41 (s, 1H), 8.88 (s, 1H), 8.10 (dd, J = 7.2 Hz, 3.2 Hz, 1H), 7.86 (dd, J = 2.8 Hz, 1.2 Hz, 1H), 7.61-7.59 (m, 1H), 7.57 (brs, 1H), 7.54-7.50 (m, 3H), 7.47 (d, J = 8.4 Hz, 2H), 7.33-7.32 (m, 2H), 6.95 (brs, 1H), 6.85 (s, 1H), 3.47 (s, 2H) |
| 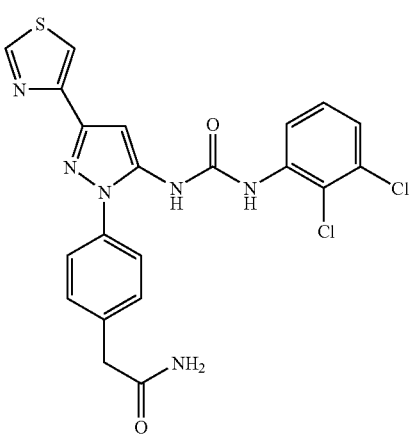 Example 472 | 1-(1-(4-(2-amino-2-oxoethyl)phenyl)-3-(thiazol-4-yl)-1H-pyrazol-5-yl)-3-(2,3-dichlorophenyl)urea 20 mg, 27% yield General method I | 487.0 | 9.46 (s, 1H), 9.18 (d, J = 2.0 Hz, 1H), 8.90 (s, 1H), 8.10 (dd, J = 7.2 Hz, 2.4 Hz, 1H), 8.01 (d, J = 2.4 Hz, 1H), 7.58 (s, 1H), 7.55 (d, J = 8.4 Hz, 2H), 7.48 (d, J = 8.4 Hz, 2H), 7.34-7.31 (m, 2H) 6.96 (brs, 1H), 6.92 (s, 1H), 3.50 (s, 2H) |

-continued

| Example | Name | MS (EI) (M + H⁺) | ¹H NMR (400 MHz, DMSO-d₆) |
|---|---|---|---|
| 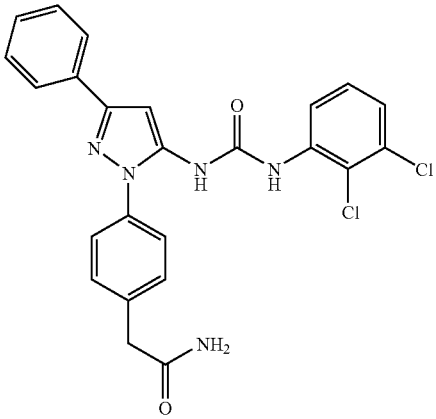<br>Example 473 | 1-(1-(4-(2-amino-2-oxoethyl)phenyl)-3-phenyl-1H-pyrazol-5-yl)-3-(2,3-dichlorophenyl)urea<br>From Example 375<br>General method J | 480.0 | 9.42 (s, 1H), 8.88 (s, 1H), 8.11 (dd, J = 6.8 Hz, 2.8 Hz, 1H), 7.83 (d, J = 8 Hz, 2H), 7.57-7.55 (m, 3H), 7.49-7.32 (m, 7H), 6.94 (brs, 2H), 3.48 (s, 2H). |
| 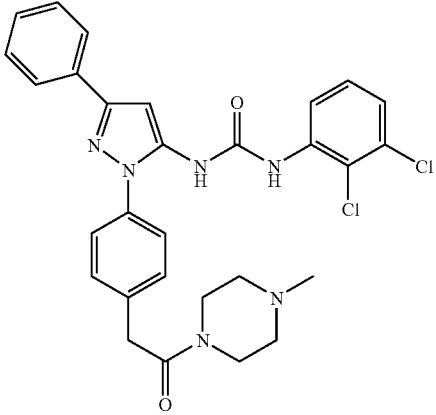<br>Example 474 | 1-(2,3-dichlorophenyl)-3-(1-(4-(2-(4-methylpiperazin-1-yl)-2-oxoethyl)phenyl)-3-phenyl-1H-pyrazol-5-yl)urea<br>From Example 375<br>36 mg, 38% yield<br>General method I | 563.2 | 10.16 (brs, 1H), 9.46 (s, 1H), 8.89 (s, 1H), 8.09 (dd, J = 6.4 Hz, 3.2 Hz, 1H), 7.84 (d, J = 7.2 Hz, 2H), 7.59 (d, J = 8.4 Hz, 2H), 7.45-7.31 (m, 7H), 6.95 (s, 1H), 4.49-4.46 (m, 1H), 4.27-4.23 (m, 1H), 3.89-3.84 (m, 2H), 3.46-3.43 (m, 3H), 3.04-2.95 (m, 3H), 2.81 (d, J = 4.4 Hz, 3H). |
| 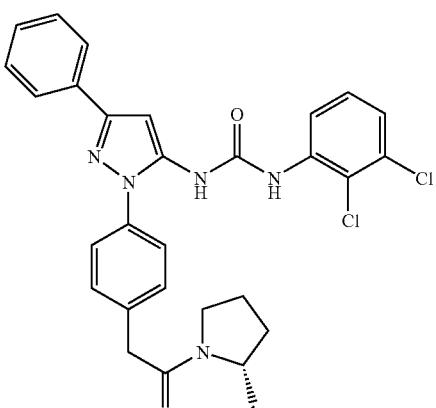<br>Example 475 | (R)-1-(2,3-dichlorophenyl)-3-(1-(4-(2-(2-(hydroxymethyl)pyrrolidin-1-yl)-2-oxoethyl)phenyl)-3-phenyl-1H-pyrazol-5-yl)urea<br>From Example 375<br>45 mg, 48% yield<br>General method I | 564.1 | 9.42 (s, 1H), 8.87 (s, 1H), 8.09 (dd, J = 7.2 Hz, 2.8 Hz, 1H), 7.85-7.83 (m, 2H), 7.57-7.54 (m, 2H), 7.45-7.32 (m, 7H), 6.95 (s, 1H), 4.04-3.73 (m, 3H), 3.54-3.46 (m, 2H), 3.30-3.26 (m, 1H), 1.94-1.81 (m, 4H); |

| Example | Name | MS (EI) (M + H+) | 1H NMR (400 MHz, DMSO-d6) |
|---|---|---|---|
| 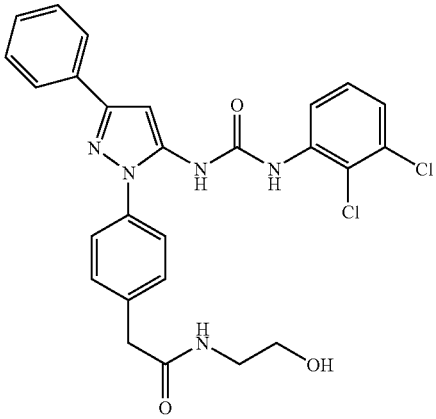Example 476 | 1-(2,3-dichlorophenyl)-3-(1-(4-(2-(2-hydroxyethylamino)-2-oxoethyl)phenyl)-3-phenyl-1H-pyrazol-5-yl)urea From Example 375 72 mg, 65% yield General method I | 524.0 | 9.43 (s, 1H), 8.89 (s, 1H), 8.18 (t, J = 5.6 Hz, 1H), 8.10 (dd, J = 6.8 Hz, 2.8 Hz, 1H), 7.85-7.83 (m, 2H), 7.56-7.31 (m, 9H), 6.94 (s, 1H), 4.71 (t, J = 5.6 Hz, 1H), 3.52 (s, 2H), 3.45-3.40 (m, 2H), 3.16-3.12 (m, 2H) |
| 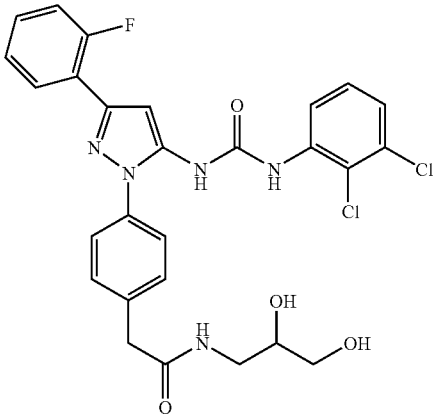Example 477 | 1-(2,3-dichlorophenyl)-3-(1-(4-(2-(2,3-dihydroxypropylamino)-2-oxoethyl)phenyl)-3-(2-fluorophenyl)-1H-pyrazol-5-yl)urea From Example 380 68 mg, 73% yield General method I | 572.0 | 9.53 (s, 1H), 8.94 (s, 1H), 8.18 (t, J = 5.6 Hz, 1H), 8.10 (dd, J = 6.8 Hz, 3.2 Hz, 1H), 7.98 (td, J = 8.0 Hz, 1.6 Hz, 1H), 7.57 (d, J = 8.4 Hz, 2H), 7.49 (d, J = 8.4 Hz, 2H), 7.42-7.25 (m, 5H), 6.91 (d, J = 4.0 Hz, 1H), 3.56 (s, 2H), 3.52-3.49 (m, 1H), 3.34-3.21 (m, 3H), 3.02-2.96 (m, 1H) |
| 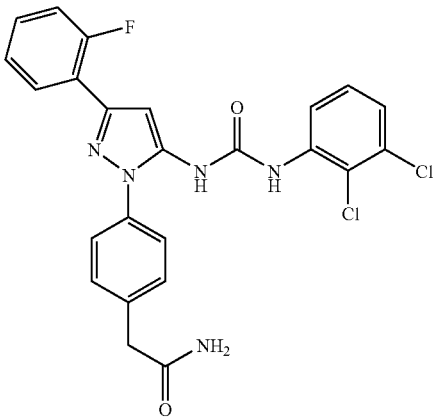Example 478 | 1-(1-(4-(2-amino-2-oxoethyl)phenyl)-3-(2-fluorophenyl)-1H-pyrazol-5-yl)-3-(2,3-dichlorophenyl)urea From Example 380 59 mg, 82% yield General method I | 498.0 | 9.48 (s, 1H), 8.91 (s, 1H), 8.10 (dd, J = 6.8 Hz, 2.8 Hz, 1H), 7.99 (td, J = 8.0 Hz, 2.4 Hz, 1H), 7.57 (d, J = 8.4 Hz, 3H), 7.49 (d, J = 8.4 Hz, 2H), 7.43-7.27 (m, 5H), 6.96 (brs, 1H), 6.92 (d, J = 4.0 Hz, 1H), 3.50 (s, 2H) |

-continued

| Example | Name | MS (EI) (M + H+) | 1H NMR (400 MHz, DMSO-d6) |
|---|---|---|---|
| 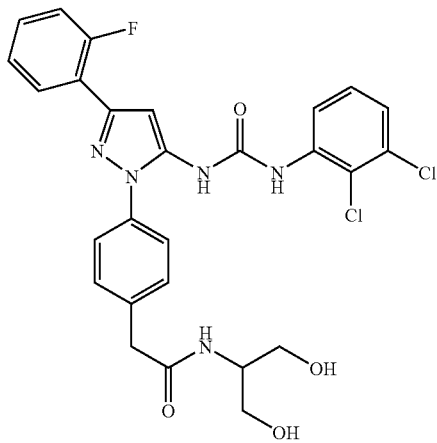 Example 479 | 1-(2,3-dichlorophenyl)-3-(1-(4-(2-(1,3-dihydroxypropan-2-ylamino)-2-oxoethyl)phenyl)-3-(2-fluorophenyl)-1H-pyrazol-5-yl)urea From Example 380 64 mg, 69% yield General method I | 572.0 | 9.49 (s, 1H), 8.92 (s, 1H), 8.11 (dd, J = 6.8 Hz, 2.8 Hz, 1H), 7.98 (td, J = 8.0 Hz, 1.6 Hz, 1H), 7.94 (d, J = 8.0 Hz, 1H), 7.57 (d, J = 8.4 Hz, 2H), 7.49 (d, J = 8.4 Hz, 2H), 7.42-7.25 (m, 5H), 6.91 (d, J = 4.0 Hz, 1H), 3.74-3.71 (m, 1H), 3.56 (s, 2H), 3.43 (d, J = 5.6 Hz, 4H) |
| 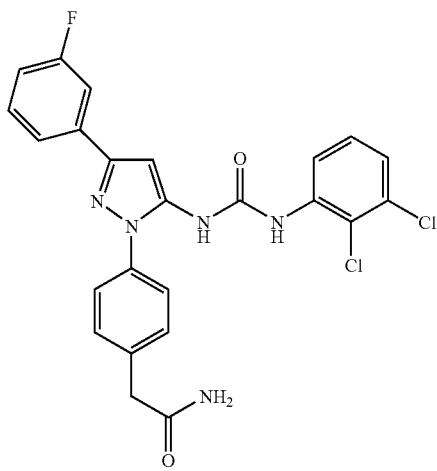 Example 480 | 1-(1-(4-(2-amino-2-oxoethyl)phenyl)-3-(3-fluorophenyl)-1H-pyrazol-5-yl)-3-(2,3-dichlorophenyl)urea: From Example 379 48 mg, 64% yield General method I | 498.0 | 9.47 (s, 1H), 8.90 (s, 1H), 8.09 (dd, J = 7.2 Hz, 2.8 Hz, 1H), 7.69 (d, J = 8.0 Hz, 1H), 7.64-7.61 (m, 1H), 7.56 (d, J = 8.0 Hz, 3H), 7.50-7.45 (m, 3H), 7.34-7.31 (m, 2H), 7.17 (td, J = 8.8 Hz, 2.4 Hz, 1H), 7.00 (s, 1H), 6.95 (brs, 1H), 3.48 (s, 2H) |
| 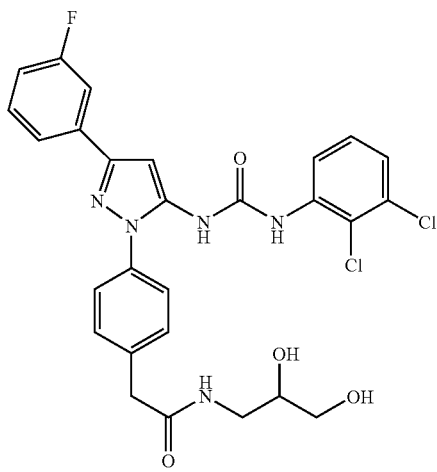 Example 481 | 1-(2,3-dichlorophenyl)-3-(1-(4-(2-(2,3-dihydroxypropylamino)-2-oxoethyl)phenyl)-3-(3-fluorophenyl)-1H-pyrazol-5-yl)urea From Example 379 25 mg, 27% yield General method I | 572.0 | 9.43 (s, 1H), 8.88 (s, 1H), 8.14 (t, J = 5.2 Hz, 1H), 8.10 (dd, J = 7.2 Hz, 3.2 Hz, 1H), 7.69 (d, J = 8.0 Hz, 1H), 7.63-7.61 (m, 1H), 7.56 (d, J = 8.0 Hz, 2H), 7.50-7.45 (m, 3H), 7.36-7.31 (m, 2H), 7.20-7.14 (m, 1H), 7.00 (s, 1H), 4.79 (d, J = 4.8 Hz, 1H), 4.54 (t, J = 5.6 Hz, 1H), 3.55 (s, 2H), 3.53-3.48 (m, 1H), 3.30-3.22 (m, 3H), 3.02-2.96 (m, 1H) |

-continued

| Example | Name | MS (EI) (M + H+) | 1H NMR (400 MHz, DMSO-d6) |
|---|---|---|---|
| 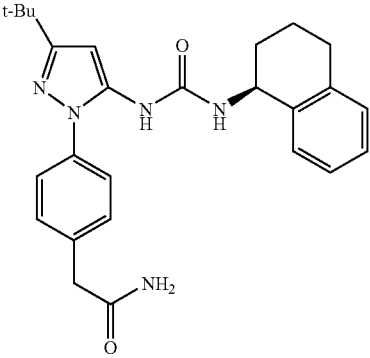 Example 482 | (S)-1-(1-(4-(2-amino-2-oxoethyl)phenyl)-3-t-butyl-1H-pyrazol-5-yl)-3-(1,2,3,4-tetrahydronaphthalen-1-yl)urea<br>From Example 387<br>0.329 g, 72% yield<br>General method K | 446.3 | 8.03 (s, 1H), 7.52 (brs, 1H), 7.41-7.37 (m, 4H), 7.21-7.13 (m 3H), 7.09-7.06 (m, 1H), 6.96-6.95 (m, 1H), 6.92 (brs, 1H), 6.33 (s, 1H), 4.81-4.76 (m 1H), 3.42 (s, 2H), 2.78-3.64 (m, 2H), 1.90-1.84 (m, 1H), 1.79-1.66 (m, 3H), 1.26 (s, 9H) |
| 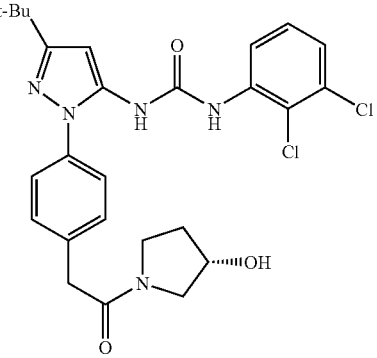 Example 483 | (S)-1-(3-t-butyl-1-(4-(2-(3-hydroxypyrrolidin-1-yl)-2-oxoethyl)phenyl)-1H-pyrazol-5-yl)-3-(2,3-dichlorophenyl)urea<br>From Example 383<br>0.329 g, 72% yield<br>General method K | 530.2 | 9.30 (s, 1H), 8.82 (s, 1H), 8.10-8.08 (m, 1H), 7.46-7.44 (m, 2H), 7.41-7.39 (m, 2H), 7.34-7.29 (m, 2H), 6.39 (s, 1H), 4.335-4.31 and 4.27-4.24 (m, 1HY), 3.71 na d 3.67 (s, 2H), 3.64-3.56 and 3.46-3.26 (m, 4H), 1.99-1.71 (m, 2H), 1.27 (s, 9H) |
| 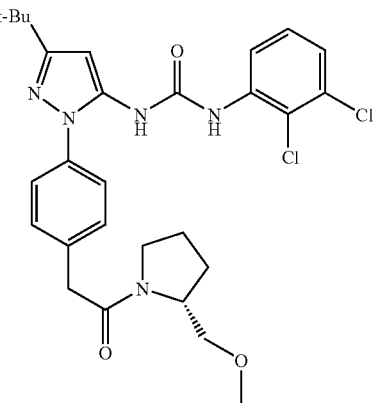 Example 484 | (R)-1-(3-t-butyl-1-(4-(2-(2-(methoxymethyl)pyrrolidin-1-yl)-2-oxoethyl)phenyl)-1H-pyrazol-5-yl)-3-(2,3-dichlorophenyl)urea<br>From Example 383<br>115 mg 96% yield<br>General method K | 558.3 | 9.28 (s, 1H), 8.81 (s, 1H), 8.10-8.07 (m, 1H), 7.46-7.44 (m, 2H), 7.39-7.36 (m, 2H), 7.34-7.29 (m, 2H), 6.39 (s, 1H), 4.27-4.22 and 4.09- 4.06 (m, 1H), 3.85-3.74 and 3.72-3.66 (m, 2H), 3.54-3.31 (m, 3H), 3.30 and 3.23 (s, 3H), 3.29-3.24 (m, 1H), 1.97-1.80 (m, 4H), 1.28 (s, 9H) |

-continued

| Example | Name | MS (EI) (M + H⁺) | $^1$H NMR (400 MHz, DMSO-d$_6$) |
|---|---|---|---|
| 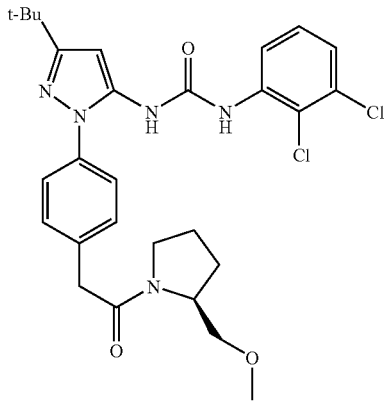
Example 485 | (S)-1-(3-t-butyl-1-(4-(2-(2-(methoxymethyl) pyrrolidin-1-yl)-2-oxoethyl)phenyl)-1H-pyrazol-5-yl)-3-(2,3-dichlorophenyl)urea.
From Example 383
104 mg, 87% yield
General method K | 558.3 | 9.28 (s, 1H), 8.81 (s, 1H), 8.10-8.07 (m, 1H), 7.46-7.44 (m, 2H), 7.39-7.36 (m, 2H), 7.34-7.29 (m, 2H), 6.39 (s, 1H), 4.27-4.22 and 4.10-4.04 (m, 1H), 3.85-3.75 and 3.74-3.66 (m, 2H), 3.54-3.31 (m, 3H), 3.30 and 3.23 (s, 3H), 3.29-3.24 (m, 1H), 1.97-1.80 (m, 4H), 1.28 (s, 9H) |
| 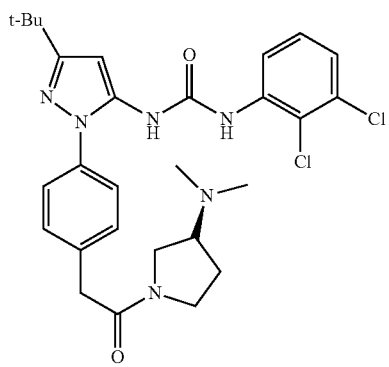
Example 486 | (S)-1-(3-t-butyl-1-(4-(2-(3-(dimethylamino) pyrrolidin-1-yl)-2-oxoethyl)phenyl)-1H-pyrazol-5-yl)-3-(2,3-dichlorophenyl)urea
From Example 383
44 mg, 59% yield
General method K | 557.3 | 9.42 and 9.40 (s, 1H), 8.88 and 8.87 (s, 1H), 8.10-8.05 (m, 1H), 7.48-7.46 (m, 2H), 7.42-7.36 (m, 2H), 7.34-7.28 (m 2H), 6.38 (s, 1H), 4.07-3.24 (m, 7H), 2.80-2.76 (m, 6H), 2.40-2.08 (m, 2H), 1.28 (s, 9H) |
| 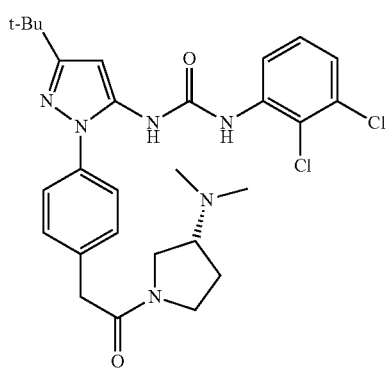
Example 487 | (R)-1-(3-t-butyl-1-(4-(2-(3-(dimethylamino) pyrrolidin-1-yl)-2-oxoethyl)phenyl)-1H-pyrazol-5-yl)-3-(2,3-dichlorophenyl)urea
From Example 383
105 mg, 86% yield
General method K | 557.3 | 9.41 (brs, 1H), 8.88 (brs, 1H), 8.10-8.05 (m, 1H), 7.48-7.46 (m, 2H), 7.42-7.37 (m, 2H), 7.34-7.29 (m, 2H), 6.38 (s, 1H), 4.07-3.71 (m, 5H), 3.64-3.24 (m, 2H), 2.80-2.76 (m, 6H), 2.41-2.09 (m, 2H), 1.28 (s, 9H) |

-continued

| Example | Name | MS (EI) (M + H+) | 1H NMR (400 MHz, DMSO-d$_6$) |
|---|---|---|---|
| 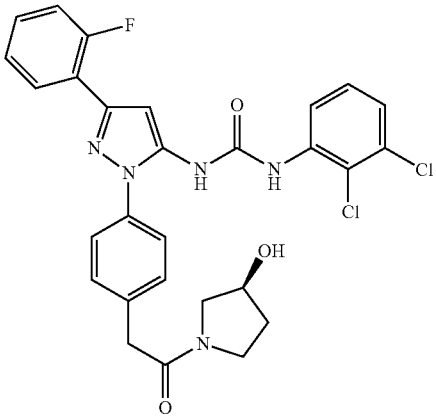  Example 488 | 1-(2,3-dichlorophenyl)-3-(3-(2-fluorophenyl)-1-(4-(2-((S)-3-hydroxypyrrolidin-1-yl)-2-oxoethyl)phenyl)-1H-pyrazol-5-yl)urea From Example 380 33.9 mg, 30% yield General method K | 568.2 | 9.47 (s, 1H), 8.91 (s, 1H), 8.12-8.09 (m, 1H), 8.01-7.97 (m, 1H), 7.58-7.57 (m, 2H), 7.48-7.46 (m, 2H), 7.44-7.39 (m, 1H), 7.36-7.25 (m, 4H), 6.92 and 6.91 (s, 1H), 4.36-4.32 and 4.28-4.25 (m, 1H), 3.75 and 3.72 (s, 2H), 3.66-3.62 (m, 1H), 3.48-3.31 (m 2H), 2.01-1.72 (m, 2H) |
| 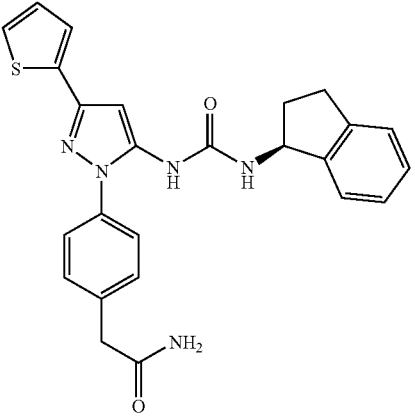  Example 489 | 1-(1-(4-(2-amino-2-oxoethyl)phenyl)-3-(thiophen-2-yl)-1H-pyrazol-5-yl)-3-((S)-2,3-dihydro-1H-inden-1-yl)urea From Example 389 31.0 mg, 18% yield General method J | 458.0 | 8.27 (s, 1H), 7.55 (brs, 1H), 7.49-7.43 (m, 6H), 7.26-7.19 (m, $H), 7.12-7.10 (m, 1H), 7.05-7.03 (m, 1H), 6.94 (s, 1H), 6.80 (s, 1H), 5.16-5.10 (m, 1H), 3.46 (s, 2H), 2.94-2.87 (m, 1H), 2.83-2.75 (m, 1H), 2.46-2.38 (m, 1H), 1.78-1.69 (m, 1H) |
| 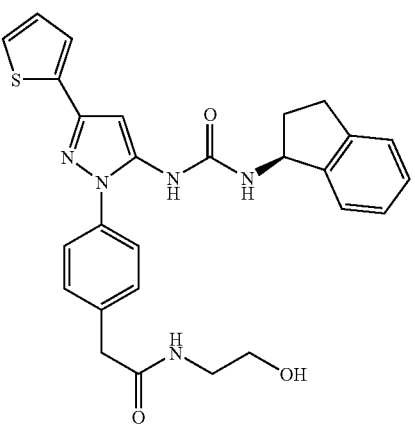  Example 490 | 1-((S)-2,3-dihydro-1H-inden-1-yl)-3-(1-(4-(2-(2-hydroxyethylamino)-2-oxoethyl)phenyl)-3-(thiophen-2-yl)-1H-pyrazol-5-yl)urea From Example 389 55.6 mg, 29% yield General method J | 502.2 | 8.27 (s, 1H), 8.17-8.14 (m, 1H), 7.49-7.42 (m, 6H), 7.26-7.19 (m, 4H), 7.12-7.10 (m, 1H), 7.05-7.03 (m, 1H), 6.80 (s, 1H), 5.16-5.10 (m, 1H), 3.51 (s, 2H), 3.42 (t, 2H, J = 6.0 Hz), 3.13 (q, 2H, J = 5.60 Hz), 2.94-2.87 (m, 1H), 2.83-2.75 (m, 1H), 2.45-2.38 (m, 1H), 1.78-1.69 (m, 1H) |

-continued

| Example | Name | MS (EI) (M + H+) | 1H NMR (400 MHz, DMSO-d6) |
|---|---|---|---|
| 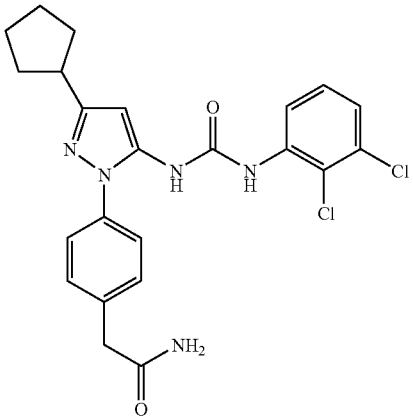 Example 491 | 1-(1-(4-(2-amino-2-oxoethyl)phenyl)-3-cyclopentyl-1H-pyrazol-5-yl)-3-(2,3-dichlorophenyl)urea From Example 390 39 mg, 48% yield General method K | 472.2 | 9.29 (s, 1H), 8.82 (s, 1H), 8.10-8.08 (m, 1H), 7.55 (brs, 1H), 7.46-7.41 (m, 4H), 7.34-7.29 (m, 2H), 6.93 (brs, 1H), 6.33 (s, 1H), 3.44 (s, 2H), 3.04-2.97 (m, 1H), 2.01-1.93 (m, 2H), 1.73-1.58 (m, 6H) |
| 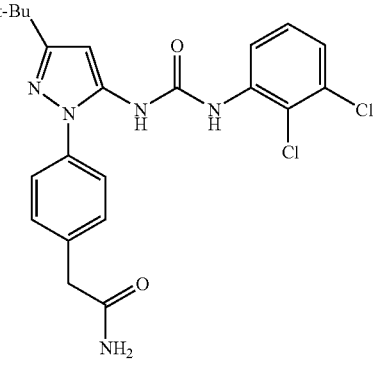 Example 492 | 1-(1-(4-(2-amino-2-oxoethyl)phenyl)-3-t-butyl-1H-pyrazol-5-yl)-3-(2,3-dichlorophenyl)urea | 459.1 | |
| 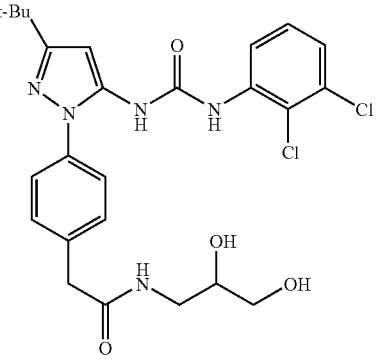 Example 493 | 1-(3-t-butyl-1-(4-(2-(2,3-dihydroxypropylamino)-2-oxoethyl)phenyl)-1H-pyrazol-5-yl)-3-(2,3-dichlorophenyl)urea From Example 383 119 mg, 72% yield General method J | 536.0 | δ 1.27 (s, 9H), 2.95-3.00 (m, 1H), 3.20-3.49 (m, 4H), 3.51 (s, 2H), 4.5-4.8 (br. s, 2H), 6.38 (s, 1H), 7.29-7.34 (m, 2H), 7.40-7.45 (m, 4I-I), 8.08-8.12 (m, 2H), 8.82 (s, 1H), 9.28 (s, 1H). |

-continued

| Example | | Name | MS (EI) (M + H+) | 1H NMR (400 MHz, DMSO-d6) |
|---|---|---|---|---|
| 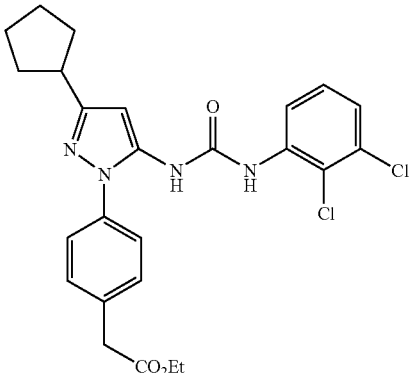  Example 494 | | ethyl 2-(4-(3-cyclopentyl-5-(3-(2,3-dichlorophenyl)ureido)-1H-pyrazol-1-yl)phenyl)acetate | 959.3 | |
| 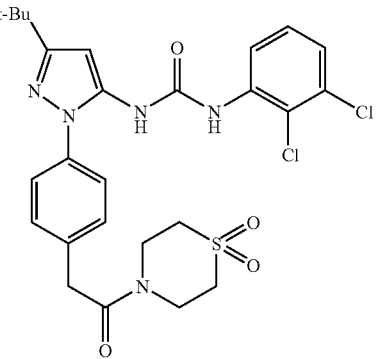  Example 495 | | 1-(3-t-butyl-1-{4-[2-(1,1-dioxo-1□6-thiomorpholin-4-yl)-2-oxoethyl]phenyl-1H-pyrazol-5-yl)-3-(2,3-dichlorophenyl)urea From Example 383 45 mg, 35% yield General method I | 578 | 9.26 (s, 1H), 8.78 (s, 1H), 8.03 (m, 1H), 7.42 (d, J = 7.8 Hz, 2H), 7.34 (d, J = 8.4 Hz, 2H), 7.27-7.26 (m, 2H), 6.34 (s, 1H), 3.90-3.88 (m, 4H), 3.84 (s, 2H), 3.34-3.15 (m, 2H), 3.15-3.02 (m, 2H), 1.23 (s, 9H) |
| 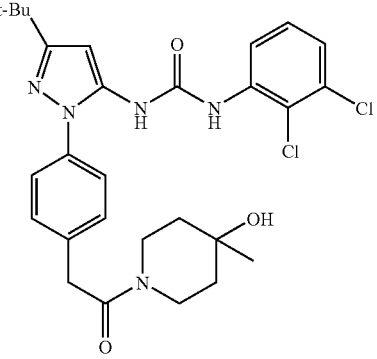  Example 496 | | 1-(3-t-butyl-1-{4-[2-(4-hydroxy-4-methylpiperidin-1-yl)-2-oxoethyl]phenyl}-1H-pyrazol-5-yl)-3-(2,3-dichlorophenyl)urea From Example 383 50 mg, 41% yield General method I | 558 | 9.22 (s, 1H), 8.75 (s, 1H), 8.03 (m, 1H), 7.40 (d, J = 7.8 Hz, 2H), 7.32 (d, J = 8.4 Hz, 2H), 7.26-7.22 (m, 3H), 6.34 (s, 1H), 3.93-3.89 (m, 2H), 3.17-2.97 (m, 4H), 1.43-1.31 (m, 4H), 1.23 (s, 9H), 1.06 (s, 3H) |

| Example | Name | MS (EI) (M + H+) | 1H NMR (400 MHz, DMSO-d6) |
|---|---|---|---|
| 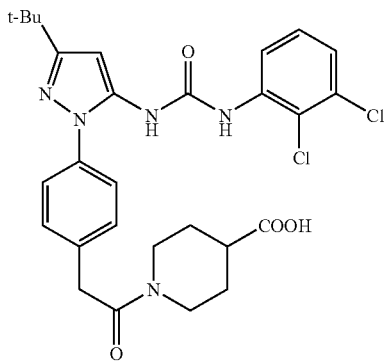

Example 497 | ethyl 1-[2-(4-{3-t-butyl-5-[3-(2,3-dichlorophenyl)ureido]-1H-pyrazol-1-ylphenyl)-acetyl]-piperidine-4-carboxylate<br>From Example 383<br>140 mg, 53% yield<br>General method I | 600 | 8.49 (s, 1H), 8.14-8.11 (m, 2H), 7.37 (d, J = 8.4 Hz, 2H), 7.20 (d, J = 8.1 Hz, 2H), 7.15 (d, J = 5.1 Hz, 1H), 6.56 (s, 1H), 4.33 (m, 1H), 4.14 (q, J = 7.2 Hz, 2H), 3.87 (m, 1H), 3.68 (br s, 2H), 3.15 (m, 1H), 2.86 (m, 1H), 2.54 (m, 1H), 1.93-1.87 (m, 2H), 1.63-1.48 (m, 2H), 1.33 (s, 9H), 1.25 (t, J = 7.2 Hz, 3H) |
| Example 498 | 1-[2-(4-{3-t-butyl-5-[3-(2,3-dichlorophenyl)ureido]-1H-pyrazol-1-yl}-phenyl)acetyl]piperidine-4-carboxylic acid<br>From Example 497<br>55 mg, 74% yield<br>General method E | 572 | 9.35 (s, 1H), 8.83 (s, 1H), 8.02 (m, 1H), 7.42 (d, J = 8.4 Hz, 2H), 7.32 (d, J = 8.4 Hz, 2H), 7.27-7.25 (m, 2H), 6.32 (s, 1H), 4.19 (m, 1H), 3.88 (m, 1H), 3.74 (d, J = 5.1 Hz, 2H), 3.33 (m, 1H), 3.08 (m, 1H), 2.52 (m, 1H), 1.78-1.74 (m, 2H), 1.38-1.31 (m, 2H), 1.23 (s, 9H) |

Example A75

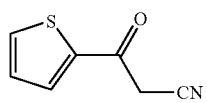

To a flask charged with THF (250 ml) was added dropwise n-butyl lithium (18.4 mL, 46 mmol) at −78° C. under a $N_2$ atmosphere. After addition the resulting solution warmed to −50° C. and dry MeCN (1.86 g, 45 mmol) was added slowly. After 1 h, the reaction was cooled to −78° C. and was treated with thiophene-2-carboxylic acid ethyl ester (6.93 g, 44.5 mmol). After stirring for 1 h the resulting mixture was warmed to RT and stirred for 1 h. Water was added dropwise at 0° C. to quench the reaction and the solution was extracted with ethyl acetate (3×200 mL). The organic layers were combined, washed with brine, dried ($Na_2SO_4$) and the solvent was evaporated under reduced pressure to give a solid residue, which was re-crystallized from $CH_2Cl_2$. After the solid was collected by filtration, they were redissolved in ethyl acetate (100 mL), and acidified with dilute hydrochloride (2N). The aqueous layer was extracted with ethyl acetate (3×200 mL) and the combined organic layers were washed with brine, dried ($Na_2SO_4$), filtered and concentrated to yield 3-oxo-3-thiophen-2-yl-propionitrile (4.7 g, yield=70%) as a yellow solid, which was used directly in the next step without purification.

Example A76

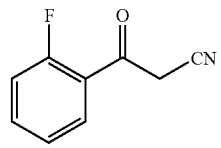

To a flask charged with KOtBu (4 g, 36 mmol) and ether (100 mL, dry) was added dropwise a mixture of 2-fluorobenzonitrile (2.1 g, 17.5 mmol) and MeCN (0.738 g, 18 mmol) at 0° C. After addition the mixture was stirred at RT. for 2 days. Water was added and the reaction and extracted with ether (3×100 mL). The organic layers were combined, washed with brine and dried ($Na_2SO_4$). The solvent was evaporated under reduced pressure to afford a yellow oil, which was dissolved in $CH_2Cl_2$ and the solution was acidified with 3M HCl. After stirring the solution at RT for 2 hours, the solution was extracted with dichloromethane (3×200 mL). The organic layers were combined, washed with brine and dried ($Na_2SO_4$). After filtration, the filtrate was concentrated in vacuo to give 3-(2-fluoro-phenyl)-3-oxo-propionitrile (2 g, 70% yield) as a yellow solid.

1H NMR (300 MHz, DMSO-d6): 7.99-7.92 (m, 1H), 7.70-7.58 (m, 1H), 7.35-7.14 (m, 2H), 4.09 (m, 2H).

General Experimental for Examples

Using General method M, the following Examples were prepared from the appropriate aniline and 3-oxo-3-substituted-propanenitrile (General method L)

| Example | Name | MS (EI) (M + H⁺) | ¹H NMR (400 MHz, DMSO-d₆) |
|---|---|---|---|
| 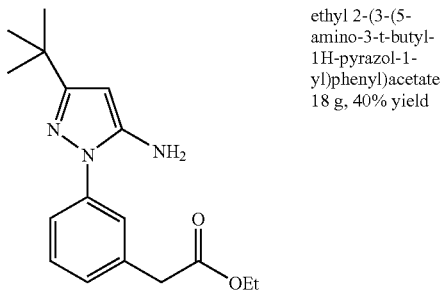 Example 499 | ethyl 2-(3-(5-amino-3-t-butyl-1H-pyrazol-1-yl)phenyl)acetate 18 g, 40% yield | 303.3 | δ 7.6-7.4 (m, 4H), 6.61 (s, 1H), 4.09-5.05 (m, 2H), 3.76 (s, 2H), 1.26 (s, 9H), 1.19-1.15 (m, 3H) |
| 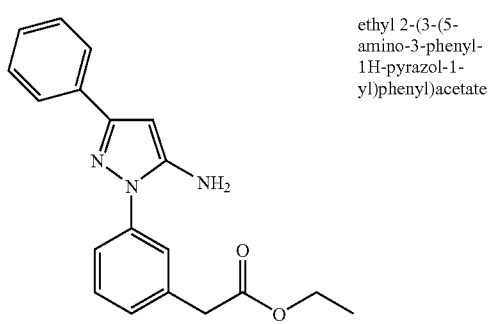 Example 500 | ethyl 2-(3-(5-amino-3-phenyl-1H-pyrazol-1-yl)phenyl)acetate | 322.2 | δ 7.74-7.20 (m, 9H), 5.89 (s, 1H), 5.42 (s, 2H), 4.10-4.05 (m, 2H), 3.73 (s, 2H), 1.19-1.13 (m, 3H) |
| 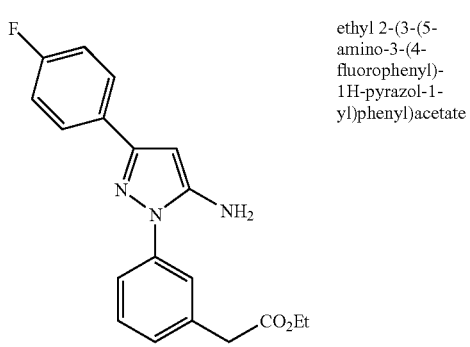 Example 501 | ethyl 2-(3-(5-amino-3-(4-fluorophenyl)-1H-pyrazol-1-yl)phenyl)acetate | 340.1 | |
| 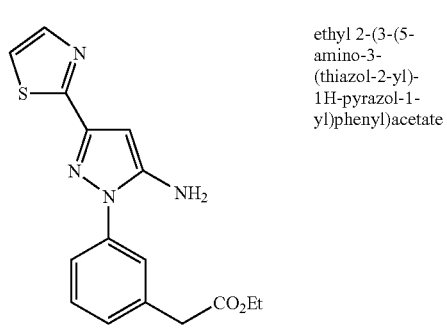 Example 502 | ethyl 2-(3-(5-amino-3-(thiazol-2-yl)-1H-pyrazol-1-yl)phenyl)acetate | 329.1 | |

-continued
| Example | Name | MS (EI) (M + H⁺) | ¹H NMR (400 MHz, DMSO-d₆) |
|---|---|---|---|
| 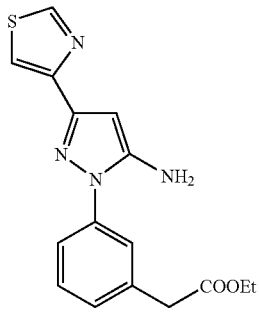 Example 503 | ethyl 2-(3-(5-amino-3-(thiazol-4-yl)-1H-pyrazol-1-yl)phenyl)acetate | 329.4 | δ 9.11-9.1 (m, 1H), 7.88-7.87 (m, 1H), 7.52-7.22 (m, 4H), 5.93 (s, 1H), 5.61 (brs, 2H), 4.1-4.03 (m, 2H), 3.73 (s, 2H), 1.18-1.14 (m, 3H) |
| 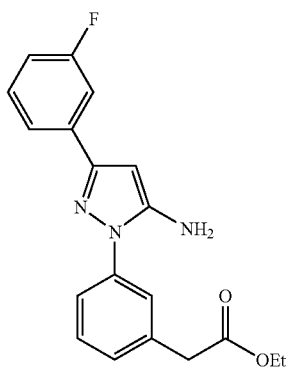 Example 504 | ethyl 2-(3-(5-amino-3-(3-fluorophenyl)-1H-pyrazol-1-yl)phenyl)acetate | 340.4 | |
| 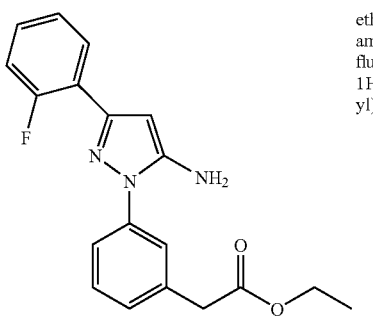 Example 505 | ethyl 2-(3-(5-amino-3-(2-fluorophenyl)-1H-pyrazol-1-yl)phenyl)acetate | 340.3 | |
| 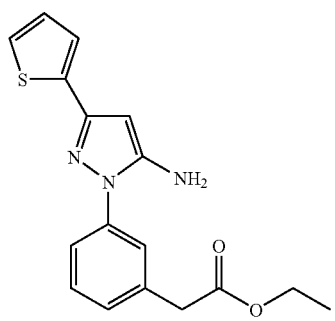 Example 506 | ethyl 2-(3-(5-amino-3-(thiophen-2-yl)-1H-pyrazol-1-yl)phenyl)acetate | 328.2 | |

| Example | Name | MS (EI) (M + H+) | 1H NMR (400 MHz, DMSO-d6) |
|---|---|---|---|
| Example 507 | ethyl 2-(3-(5-amino-3-(thiophen-3-yl)-1H-pyrazol-1-yl)phenyl)acetate | 328.4 | |
| Example 508 | ethyl 2-(3-(5-amino-3-cyclopentyl-1H-pyrazol-1-yl)phenyl)acetate | 314.6 | δ 7.6-7.4 (m, 4H), 5.72 (s, 1H), 4.1-4.03 (m, 2H), 3.76 (s, 2H), 3.07-3.0 (m, 1H), 2.00-1.98 (m, 2H), 1.7-1.58 (m, 6H), 1.04-0.98 (m, 3H) |
| Example 509 | ethyl 2-(3-(5-amino-3-phenyl-1H-pyrazol-1-yl)phenyl)acetate | 321.4 | |
| Example 510 | ethyl 2-(4-(5-amino-3-(thiophen-3-yl)-1H-pyrazol-1-yl)phenyl)acetate 34% yield | 328.0 | 7.92 (brs, 1H), 7.63-7.59 (m, 3H), 7.51-7.50 (m, 1H), 7.44 (d, J = 8.0 Hz, 2H) 5.97 (s, 1H), 4.10 (q, J = 6.8 Hz, 2H); 3.76 (s, 2H), 1.20 (t, J = 6.8 Hz, 3H); (M + 1)+. |

| Example | Name | MS (EI) (M + H$^+$) | $^1$H NMR (400 MHz, DMSO-d$_6$) |
|---|---|---|---|
| Example 511 | ethyl 2-(4-(5-amino-3-(thiophen-2-yl)-1H-pyrazol-1-yl)phenyl)acetate (55%) | 328.0 | ☐ 7.57 (d, J = 8.4 Hz, 2H), 7.46 (dd, J = 4.8 Hz, 1.6 Hz, 1H), 7.41-7.36 (m, 3H), 7.09-7.07 (m, 1H), 5.85 (s, 1H), 4.10 (q, J = 7.2 Hz, 2H); 3.73 (s, 2H), 1.20 (t, J = 7.2 Hz, 3H) |

Example 512

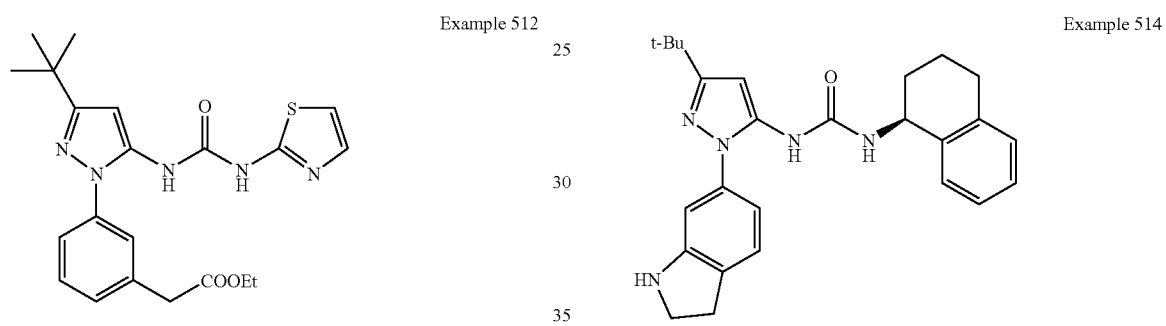

Using general method D, Example 499 (0.22 g, 0.47 mmol) and 2-amino thiazole (0.071 g, 0.7 mmol) were combined to afford ethyl 2-(3-(3-t-butyl-5-(3-(thiazol-2-yl)ureido)-1H-pyrazol-1-yl)phenyl)acetate (0.13, 64%) as a solid. $^1$H NMR (400 MHz, Acetone-d$_6$): ☐ 10.05 (s, 1H), 7.56 (s, 1H), 7.53-7.44 (m, 2H), 7.38-7.36 (m, 1H), 7.28 (d, J=3.6 Hz, 1H), 7.06 (d, J=3.6 Hz, 1H), 6.54 (s, 1H), 4.12 (q, J=7.2 Hz, 2H), 3.75 (s, 2H), 1.34 (s, 9H), 1.21 (t, J=7.2 Hz, 3H); MS (ESI) m/z: 428.0 (M+H$^+$).

Example 513

Using general method E, ethyl 2-(3-(3-t-butyl-5-(3-(thiazol-2-yl)ureido)-1H-pyrazol-1-yl)phenyl)acetate (0.12 g, 0.28 mmol) was saponified to afford 2-(3-(3-t-butyl-5-(3-(thiazol-2-yl)ureido)-1 H-pyrazol-1-yl)phenyl)acetic acid/Example 512 (0.1 g, 93%) as a solid. $^1$H NMR (400 MHz, DMSO-d$_6$): ☐08.92 (s, 1H), 7.48 (t, J=8.0 Hz, 1H), 7.42-7.39 (m, 2H), 7.34-7.32 (m, 2H), 7.12 (d, J=3.6 Hz, 1H), 6.44 (s, 1H), 3.68 (s, 2H), 1.28 (s, 9H); MS (ESI) m/z: 400.2 (M+H$^+$).

Example 514

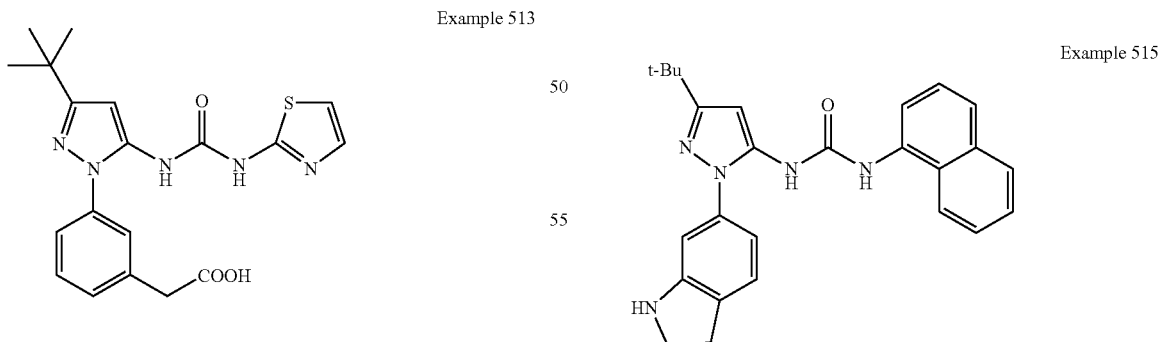

Using general method D, Example A30 (53 mg, 0.15 mmol) and (S)-1,2,3,4-tetrahydronaphthalen-1-amine (68 mg, 0.46 mmol) were combined, and the product deprotected using general method G to yield 1-(3-t-butyl-1-(indolin-6-yl)-1H-pyrazol-5-yl)-3-((S)-1,2,3,4-tetrahydronaphthalen-1-yl)urea (30 mg, 49% yield) as the HCl salt. $^1$H NMR (400 MHz, CD$_3$OD): δ 7.52 (m, 1H), 7.13 (m, 2H), 3.89 (t, J=7.6 Hz, 2H), 3.37 (t, J=7.6 Hz, 2H), 2.78 (m, 2H), 1.99 (m, 1H), 1.82 (m, 3H), 1.41 (s, 914); LC-MS (EI) m/z: 526.2 (M+H$^+$).

Example 515

Using general method A, Example A30 (70 mg, 0.20 mmol) and 1-naphthalylisocyanate (34 mg, 0.20 mmol) were combined and the resultant product deprotected using general method G to yield 1-(3-t-butyl-1-(indolin-6-yl)-1H-pyrazol-5-yl)-3-(naphthalen-1-yl)urea as the HCl salt (71 mg, 84% yield). $^1$H NMR (400 MHz, DMSO-d$_6$): δ 9.32 (s, 1H), 9.24

(s, 1H), 8.17 (d, J=7.2 Hz, 1H), 7.92 (m, 2H), 7.63 (d, J=8.4 Hz, 1H), 7.51 (m, 5H), 6.41 (s, 1H), 3.72 (t, J=8.4 Hz, 2H), 3.19 (t, J=8.4 Hz, 2H), 1.30 (s, 9H); LC-MS (EI) m/z: 426.2 (M+H⁺).

Example 516

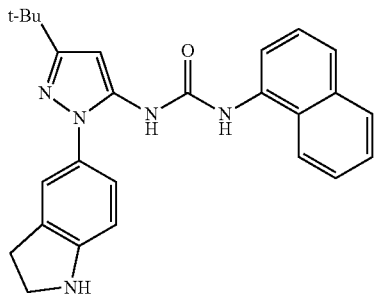

Using general method A, Example A29 ((70 mg, 0.20 mmol) and 1-naphthalylisocyanate (34 mg, 0.20 mmol) were combined and the resultant product deprotected using general method G to yield 1-(3-t-butyl-1-(indolin-5-yl)-1H-pyrazol-5-yl)-3-(naphthalen-1-yl)urea (33 mg, 39% yield) as the HCl salt. ¹H NMR (400 MHz, DMSO-d₆): δ 9.26 (s, 1H), 9.11 (s, 1H), 8.12 (d, J=8.0 Hz, 1H), 7.92 (d, J=8.0 Hz, 1H), 7.64 (d, J=8.0 Hz, 1H), 7.55 (m, 2H), 7.46 (t, J=7.6 Hz, 1H), 7.32 (m, 1H), 6.41 (s, 1H), 3.72 (t, J=8.0 Hz, 2H), 3.22 (t, J=8.0 Hz, 2H), 1.30 (s, 9H); LC-MS (EI) m/z: 426.2 (M+H⁺).

Example 517

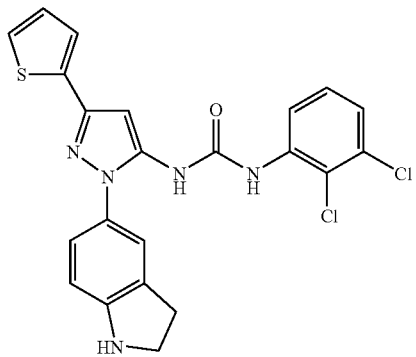

Using general method D, 2,3-dichloroaniline (0.31 g, 0.91 mmol) and 5-amino-3-(2-thienyl)pyrazole (0.15 g, 0.91 mmol, available commercially) were combined to yield 1-(2,3-dichlorophenyl)-3-(3-(thiophen-2-yl)-1H-pyrazol-5-yl)urea (0.31 g, 96% yield). LC-MS (EI) m/z: 353.0 (M+H⁺).

Using the same procedureas for Example 115, Example A33 (37 mg, 0.14 mmol) and the material from the previous reaction (50 mg, 0.14 mmol) were coupled and the resultant product deprotected using general method G to yield 1-(2,3-dichlorophenyl)-3-(1-(indolin-5-yl)-3-(thiophen-2-yl)-1H-pyrazol-5-yl)urea HCl salt (10 mg, 15% yield). ¹H NMR (400 MHz, DMSO-d₆): δ 9.32 (bs, 1H), 8.92 (s, 1H), 8.08 (dd, J=3.2, and 6.4 Hz, 1H), 7.48 (dd, J=0.8, and 4.8 Hz, 1H), 7.44 (dd, J=0.8, and 3.2 Hz, 1H), 7.33 (m, 2H), 7.18 (m, 1H), 7.10 (dd, J=3.6, and 4.8 Hz, 1H), 6.89 (m, 1H), 6.79 (s, 1H), 3.09 (t, J=8.0 Hz, 2H); LC-MS (EI) m/z: 470.0 (M+H⁺).

Example 518

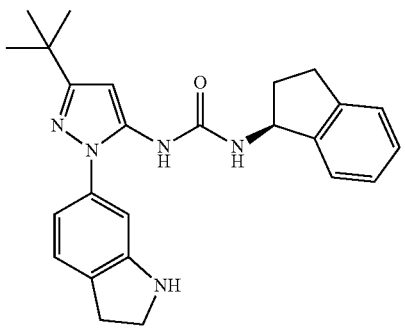

Using general method D, Example A30 was combined with (S)-1-aminoindan (0.200 g, 1.50 mmol) and the resulting product deprotected using general method G to yield 173 mg (90%) of 1-1H (3-t-butyl-1-(indolin-6-yl)-1H-pyrazol-5-yl)-3-((S)-2,3-dihydro-1H-inden-1-yl)urea hydrochloride as a white solid. ¹H-NMR (methanol-d₄): δ 7.59 (d, 1H, J=−7.6 Hz), 7.53 (s, 1H), 7.52 (d, 1H, J=8.0 Hz), 7.23-7.16 (m, 4H), 6.48 (s, 1H), 5.17 (t, 1H, J=7.6 Hz), 3.90 (t, 2H, J=7.8 Hz), 3.37 (t, 2H, J=8.0 Hz), 2.96 (ddd, 1H, J=16.0, 8.8, 4.0 Hz), 2.83 (ddd, 1H, J=16.4, 8.0, 8.0 Hz), 2.53-2.46 (m, 1H), 1.82-1.75 (m, 1H), 1.37 (s, 9H). LC-MS (EI) m/z: 416.2 (M+H+).

Example 519

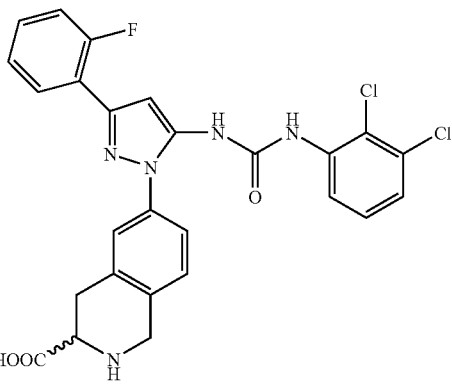

A solution of -(2-fluorophenyl)-3-oxopropanenitrile (1.02 g, 6.25 mmol; general method L) and hydrazine hydrate (0.313 g, 6.25 mmol) in EtOH (10 mL) was heated at 70° C. for 2 h. The solvent was evaporated and the residue was purified by column chromatography to give 3-(2-fluorophenyl)-1H-pyrazol-5-amine as a yellow wax-like solid (400 mg, 36% yield). ¹H-NMR (CDCl₃): δ 7.64 (dt, 1H, J=7.8, 1.6 Hz), 7.35-7.29 (m, 1H), 7.23-7.13 (m, 2H), 6.06 (s, 1H), 5.28 (s, br, 3H). LC-MS (EI) m/z: 178.2 (M+H⁺).

A solution of 2,2,2-trichloroethyl 2,3-dichlorophenylcarbamate (0.286 g, 0.847 mmol; general method D), 3-(2-fluorophenyl)-1H-pyrazol-5-amine (0.150 g, 0.847 mmol) and I-PR2NET (0.219 g, 1.69 mmol) in DMF (1 mL) was stirred at 90° C. overnight. Water was added (30 mL) and the mixture was extracted with EtOAc (3×30 mL), dried (MgSO₄), filtered and concentrated to yield crude 1-(2,3-dichlorophenyl)-3-(3-(2-fluorophenyl)-1H-pyrazol-5-yl)urea as an off-white solid (285 mg, 92% yield). ¹H-NMR (DMSO-d₆): δ 9.86 (s, 1H), 8.25 (d, 1H, J=7.2 Hz), 7.81 (t, 1H, J=7.2 Hz), 7.45-7.27 (m, 5H), 6.65 (s, br, 1H). 5.67 (s, 1H), one urea proton not visible. LC-MS (EI) m/z: 365.0 367.0 (M+H⁺).

A mixture of 1-(2,3-dichlorophenyl)-3-(3-(2-fluorophenyl)-1H-pyrazol-5-yl)urea (0.100 g, 0.274 mmol), Example A56 (0.191 g, 0.548 mmol), pyridine (0.065 g, 0.82 mmol), Cu(OAc)$_2$ (0.075 g, 0.411 mmol) and CH$_2$Cl$_2$ (5 mL) was stirred open to air, occasionally replacing evaporated solvent for 2d. Water was added (50 mL) and the mixture was extracted with CH$_2$Cl$_2$ (3×50 mL). The combined organic extracts were dried (MgSO$_4$), concentrated, and purified by column chromatography to yield 2-t-butyl 3-ethyl 6-(5-(3-(2,3-dichlorophenyl)ureido)-3-(2-fluorophenyl)-1H-pyrazol-1-yl)-3,4-dihydroisoquinoline-2,3(1H)-dicarboxylate as a yellow foam (139 mg, 76% yield). LC-MS (EI) m/z: 668.2 670.3 (M+H$^+$).

To a solution of 2-t-butyl 3-ethyl 6-(5-(3-(2,3-dichlorophenyl)ureido)-3-(2-fluorophenyl)-1H-pyrazol-1-yl)-3,4-dihydroisoquinoline-2,3(1H)-dicarboxylate (0.050 g, 0.075 mmol) in THF (2 mL) was added 6N HCl (2 mL) and the solution was stirred at 50° C. overnight. The organic solvent was evaporated and the precipitate was collected to yield 6-(5-(3-(2,3-dichlorophenyl)ureido)-3-(2-fluorophenyl)-1H-pyrazol-1-yl)-1,2,3,4-tetrahydroisoquinoline-3-carboxylic acid hydrochloride as a white solid (15 mg, 35% yield). $^1$H-NMR (acetone-d$_6$): δ 8.01-7.96 (m, 2H), 7.62-7.60 (m, 2H), 7.47 (d, 1H, J=8.0 Hz), 7.42-7.37 (m, 1H), 7.27-7.19 (m, 4H), 6.92 (d, 1H, J=3.6 Hz), 4.59 (d, 1H, J=16.0 Hz), 4.50 (d, 1H, J=16.0 Hz), 4.48 (dd, 1H, J=11.4, 5.0 Hz), 3.61 (dd, 1H, J=18.0, 5.2 Hz), urea, acid and amine protons not visible, one proton is buried under the methanol peak. LC-MS (EI) m/z: 540.0 542.0 (M+H$^+$).

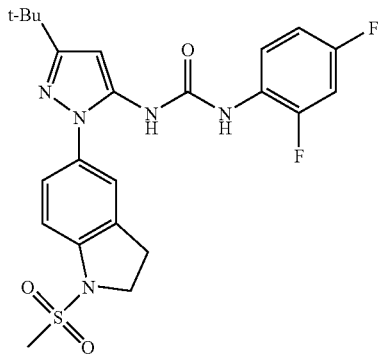

Example 520

Using general method D, Example A29 (0.15 g, 0.28 mmol) was combined with 2,4-difluoroaniline (0.11 g, 0.85 mmol) to yield 1-(3-t-butyl-1-(1-(2,2,2-trifluoroacetyl)indolin-5-yl)-1H-pyrazol-5-yl)-3-(2,4-difluorophenyl)urea. Using general method G, this product was deprotected and the resulting product transformed as in Example 109 to yield 1-(3-t-butyl-1-(1-(methylsulfonyl)indolin-5-yl)-1H-pyrazol-5-yl)-3-(2,4-difluorophenyl)urea (32 mg, 23%). $^1$H-NMR (acetone-d$_6$): δ 8.23-8.16 (m, 3H), 7.42 (s, br, 1H), 7.39 (d, 1H, J=8.4 Hz), 7.35 (dd, 1H, J=8.4, 2.0 Hz), 7.05 (ddd, 1H, J=11.6, 8.4, 2.8 Hz), 6.45 (s, 1H), 4.06 (t, 2H, J=8.4 Hz), 3.22 (t, 2H, J=8.4 Hz), 3.02 (s, 3H), 1.31 (s, 9H).

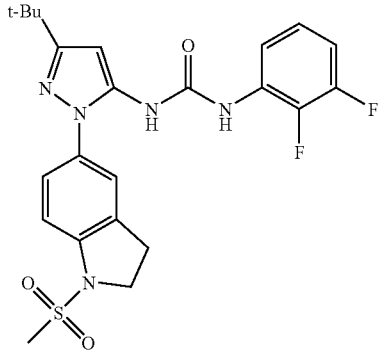

Example 521

Using the same approach as described for Example 520, Example A29 and 2,3-difluoroaniline were combined, deprotected and transformed to yield 1-(3-t-butyl-1-(1-(methylsulfonyl)indolin-5-yl)-1H-pyrazol-5-yl)-3-(2,3-difluorophenyl)urea (30 mg, 22%). $^1$H-NMR (acetone-d$_6$): δ 8.41 (s, br 1H), 8.27 (s, br, 1H), 8.06 (t, 1H, J=7.8 Hz), 7.42 (s, 1H), 7.40 (d, 1H, J=7.2 Hz), 7.35 (dd, 1H, J=–8.8, 2.0 Hz), 7.16-7.09 (m, 1H), 6.97-6.90 (m, 1H), 6.47 (s, 1H), 4.07 (t, 2H, J=8.4 Hz), 3.23 (t, 2H, J=8.8 Hz), 3.02 (s, 3H), 1.31 (s, 9H).

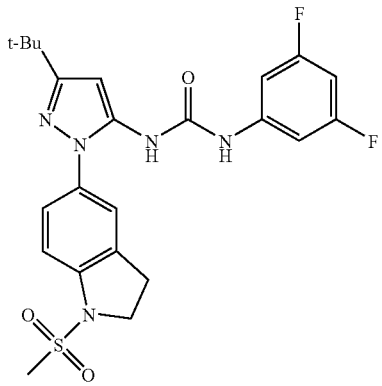

Example 522

Using the same approach as described for Example 520, Example A29 and 3,5-difluoroaniline were combined, deprotected and transformed to yield 1-(3-t-butyl-1-(1-(methylsulfonyl)indolin-5-yl)-1H-pyrazol-5-yl)-3-(3,5-difluorophenyl)urea (35 mg, 25%). $^1$H-NMR (acetone-d$_6$): δ 7.46 (s, 1H), 7.42 (d, 1H, J=8.8 Hz), 7.39 (d, 1H, J=8.4 Hz), 7.25-7.20 (m, 2H), 6.63-6.57 (m, 1H), 4.06 (t, 2H, J=8.6 Hz), 3.24 (t, 2H, J=8.6 Hz), 3.03 (s, 3H), 1.36 (s, 9H), urea and pyrazole protons not visible.

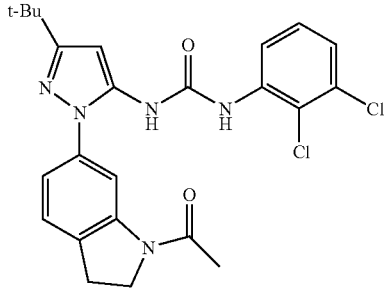

Example 523

Using general method A, Example A30 (0.40 g, 1.14 mmol) was combined with 2,3-dichlorophenyl isocyanate (0.21 g 1.14 mmol) and the resulting product deprotected according to general method G to yield 1-(3-t-butyl-1-(indolin-6-yl)-1H-pyrazol-5-yl)-3-(2,3-dichlorophenyl)urea (0.23 g, 42%). This product was transformed 1-(1-(1-acetylindolin-6-yl)-3-t-butyl-1H-pyrazol-5-yl)-3-(2,3-dichlorophenyl) urea (103 mg, 70%). $^1$H-NMR (acetone-$d_6$): δ 8.61 (s, br, 1H), 8.30 (s, 1H), 8.27 (dd, 1H, J=8.0, 1.2 Hz), 8.21 (s, br, 1H), 7.30 (d, 1H, J=8.4 Hz), 7.29 (s, 1H), 7.28 (d, 1H, J=8.0 Hz), 7.22 (dd, 1H, J=8.0, 1.2 Hz), 7.12 (d, 1H, J=8.0, 2.0 Hz), 6.47 (s, 1H), 4.22 (t, 2H, J=8.8 Hz), 3.25 (t, 1H, J=8.6 Hz), 2.16 (s, 3H), 1.31 (s, 9H).

Example 524

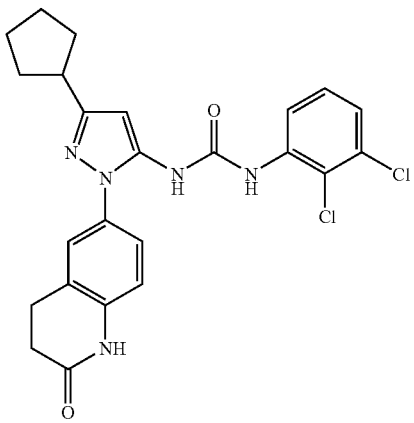

Using general method A, Example A34 (0.20 g, 0.675 mmol) and 2,3-dichlorophenyl isocyanate (0.127 g, 0.675 mmol) were combined to yield 1-(3-cyclopentyl-1-(2-oxo-1,2,3,4-tetrahydroquinolin-6-yl)-1H-pyrazol-5-yl)-3-(2,3-dichlorophenyl)urea (195 mg, 60% yield) as an off-white solid. $^1$H NMR (400 MHz, DMSO-$d_6$): δ 10.3 (s, 1H), 9.18 (s, 1H), 8.77 (s, 1H), 8.06 (dd, J=3.6, and 6.8 Hz, 1H), 7.32 (m, 3H), 7.26 (dd, J=2.8, and 8.4 Hz, 1H), 6.97 (d, J=8.4 Hz, 2H), 6.30 (s, 1H), 3.00 (m, 1H), 2.95 (t, J=8.0 Hz, 2H), 2.48 (t, J=8.0 Hz, 2H), 1.94 (m, 2H), 1.67 (m, 6H); LC-MS (EI) m/z: 484.0 (M+H$^+$).

Example 525

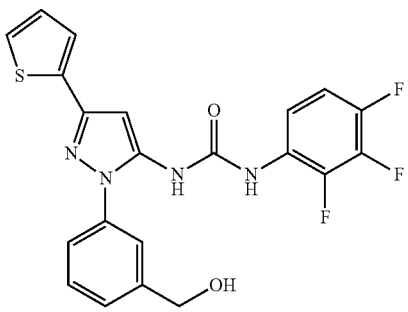

To a solution of 1-(3-((t-butyldimethylsilyloxy)methyl) phenyl)-3-(thiophen-2-yl)-1H-pyrazol-5-amine (available from ethyl 3-(5-amino-3-(thiophen-2-yl)-1H-pyrazol-1-yl) benzoate using general method C followed by protection with TBSCl) (0.5 g, 1.3 mmol) in THF (3 mL) was added pyridine (0.10 g, 1.3 mmol) and 1,2,3-trifluoro-4-isocyanatobenzene (0.27 g, 1.6 mmol). The reaction mixture was stirred at room temperature for 22 hours. Water was added and the solid was filtered, washed with H$_2$O and dried under vacuum to obtain the crude product. To a solution of the crude product in THF was added TBAF (1.6 mL, 1.0 M). The reaction mixture was stirred at room temperature for 3 hours. The solvent was removed under reduced pressure. Ethyl acetate was added into the residue and then 1N—HCl (5 drops) was added. The organic layer was washed with water, dried (Na$_2$SO$_4$) and evaporated under reduced pressure to obtain the crude product. The crude was dissolved in methanol and the solid filtered and dried under vacuum to yield 1-(1-(3-(hydroxymethyl) phenyl)-3-(thiophen-2-yl)-1H-pyrazol-5-yl)-3-(2,3,4-trifluorophenyl)urea (0.42 g, 73% yield). $^1$H NMR (400 MHz, DMSO-$d_6$): δ 9.13 (brs, 1H), 8.99 (s, 1H), 7.85 (m, 1H), 7.4-7.6 (m, 6H), 7.28 (m, 1H), 7.11 (dd, J=3.6, and 4.8 Hz, 1H), 6.86 (s, 1H), 5.39 (t, J=6.0 Hz, 1H), 4.62 (d, J=6.0 Hz, 2H); MS (EI) m/z: 445.0 (M+H$^+$).

Example 526

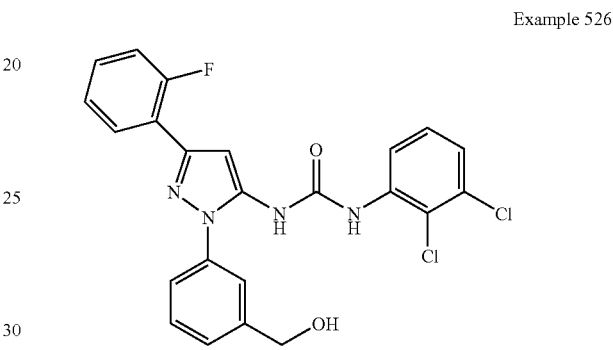

Using general method A, 1-(3-((t-butyldimethylsilyloxy) methyl)phenyl)-3-(2-fluorophenyl)-1H-pyrazol-5-amine (available from ethyl 3-(5-amino-3-(2-fluorophenyl)-1H-pyrazol-1-yl)benzoate using general method C, followed by protection with TBSCl) (0.4 g, 1.0 mmol) was combined with 2,3-dichlorophenyl isocyanate (0.32 g, 1.2 mmol) to yield 1-(2,3-dichlorophenyl)-3-(3-(2-fluorophenyl)-1-(3-(hydroxymethyl)phenyl)-1H-pyrazol-5-yl)urea (0.28 g, 59% yield). $^1$H NMR (400 MHz, DMSO-$d_6$): δ 9.05 (s, 1H), 8.87 (s, 1H), 8.08 (m, 1H), 7.99 (dt, J=2.0, and 8.0 Hz, 1H), 7.58 (m, 1H), 7.55 (d, J=7.6 Hz, 1H), 7.50 (brd, J=7.6 Hz, 1H), 7.45 (brd, J=7.2 Hz, 1H), 7.41 (m, 1H), 7.32 (m, 3H), 6.91 (d, J=4.4 Hz, 1H), 5.39 (t, J=6.0 Hz, 1H), 4.62 (d, J=6.0 Hz, 2H); MS (EI) m/z: 471.0 (M+H$^+$).

Example 527

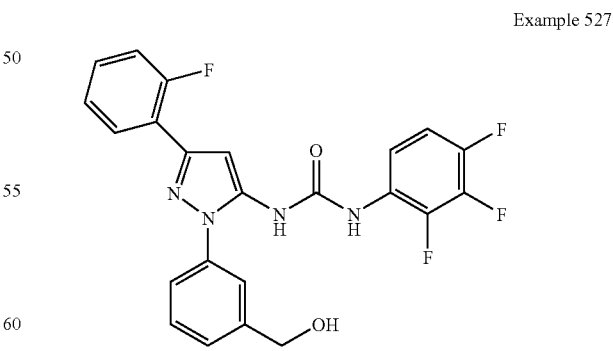

Using general method A, 1-(3-((t-butyldimethylsilyloxy) methyl)phenyl)-3-(2-fluorophenyl)-1H-pyrazol-5-amine (available from ethyl 3-(5-amino-3-(2-fluorophenyl)-1H-pyrazol-1-yl)benzoate using general method followed by protection with TBSCl) (0.4 g, 1.0 mmol) was combined with 2,3,4-trifluorophenyl isocyanate (0.32 g, 1.2 mmol) to yield 1-(2,3,4-trifluorophenyl)-3-(3-(2-fluorophenyl)-1-(3-(hydroxymethyl)phenyl)-1H-pyrazol-5-yl)urea (330 mg, 72% yield). $^1$H NMR (400 MHz, DMSO-d$_6$): δ 9.14 (brs, 1H), 9.01 (s, 1H), 7.98 (dt, J=1.6, and 8.0 Hz, 1H), 7.86 (m, 1H), 7.2-7.6 (m, 8H), 6.96 (d, J=4.0 Hz, 1H), 5.39 (t, J=6.0 Hz, 1H), 4.62 (d, J=6.0 Hz, 2H); MS (EI) m/z: 457.0 (M+H$^+$).

Example 528

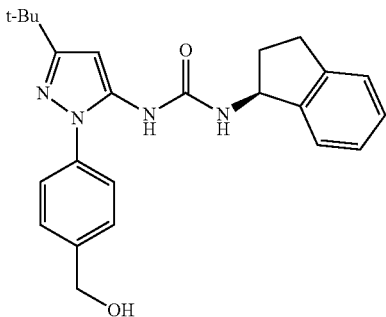

Using general method D, ethyl 4-(5-amino-3-t-butyl-1H-pyrazol-1-yl)benzoate (0.48 g, 0.87 mmol, available from Example 19) and (S)-(+)-aminoindane (0.11 ml, 0.87 mmol, 1.0 eq) were combined to yield (S)-ethyl 4-(3-t-butyl-5-(3-(2,3-dihydro-1H-inden-1-yl)ureido)-1H-pyrazol-1-yl)benzoate (0.243 g, 62% yield) as an off-white solid. $^1$H NMR (CDCl$_3$): δ8.11-8.08 (m, 2H), 7.66-7.64 (m, 2H), 7.23-7.22 (m, 2H), 7.19-7.15 (m, 1H), 7.09-7.07 (m, 1H), 6.35 (s, 1H), 5.37-5.31 (m, 1H), 4.401-4.34 (m, 2H), 2.96-2.79 (m, 2H), 2.60-2.52 (m, 1H), 1.73-1.63 (m, 1H), 1.45-1.39 (m, 3H), 1.34 (s, 9H); MS (ESI) m/z: 447.3 (M+H$^+$).

This material was reduced using general method C to yield (S)-1-(3-t-butyl-1-(4-(hydroxymethyl)phenyl)-1H-pyrazol-5-yl)-3-(2,3-dihydro-1H-inden-1-yl)urea (29.4 mg, 13% yield) as a white solid. $^1$H NMR (DMSO-d$_6$): δ 8.07 (s, 1H), 7.43 (m, 4H), 7.24-7.19 (m, 4H), 6.95-6.93 (m, 1H), 6.33 (s, 1H), 5.12-5.06 (m, 2H), 4.56 (s, 2H), 2.93-2.86 (m, 1H), 2.82-2.74 (m, 1H), 2.43-2.36 (m, 1H), 1.76-1.67 (m, 1H), 1.27 (s, 9H); MS (ESI) m/z: 405.2 (M+H$^+$).

Example 529

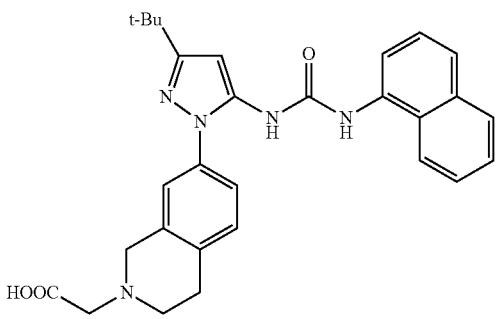

To a stirring solution of Example 349 (0.060 g, 0.14 mmol) and Et$_3$N (0.023 ml, 0.16 mmol) in THF (1.4 ml) was added t-butyl bromoacetate (0.021 ml, 0.14 mmol). The resulting mixture was stirred at RT overnight. The completed reaction was diluted with EtOAc and washed with H$_2$O (1×), 5% citric acid (1×), satd. NaHCO$_3$ (1×), brine (1×), dried (Na$_2$SO$_4$), filtered, concentrated and purified via column chromatography to yield t-butyl 2-(7-(3-t-butyl-5-(3-(naphthalen-1-yl)ureido)-1H-pyrazol-1-yl)-3,4-dihydroisoquinolin-2(1H)-yl)acetate (23.8 mg, 31% yield). $^1$H NMR (CDCl$_3$): δ 7.89-7.82 (m, 2H), 7.73-7.72 (m, 1H), 7.68-7.66 (m, 1H), 7.46-7.38 (m, 2H), 7.34-7.31 (m, 1H), 7.08-7.03 (m, 2H), 6.97-6.95 (m, 1H), 6.43 (s, 1H), 3.72 (brs, 2H), 3.31 (brs, 2H), 2.86 (brs, 2H), 2.78-2.77 (m, 2H), 1.50 (s, 9H), 1.33 (s, 9H); MS (ESI) m/z: 554.2 (M+H$^+$).

This material (0.0238 g, 0.0430 mmol) was dissolved in 100% formic acid (2 ml) and stirred at RT overnight. The completed reaction was concentrated to dryness. The residue was dissolved in 1M HCl and extracted with EtOAc (2×). The combined organics were washed with 1M HCl (1×). The combined aqueous were diluted with iPrOH and concentrated (3×) until a foam resulted. This was dissolved in MeCN/H$_2$O frozen and lyophilized to yield 2-(7-(3-t-butyl-5-(3-(naphthalen-1-yl)ureido)-1H-pyrazol-1-yl)-3,4-dihydroisoquinolin-2(1H)-yl)acetic acid (17.5 mg, 76% yield) as an off-white solid as the HCl salt. $^1$H NMR (DMSO-d$_6$): δ 9.51 (s, 1H), 9.44 (s, 1H), 8.27 (s, 1H), 7.95-7.90 (m, 2H), 7.63-7.61 (m, 1H), 7.56-7.51 (m, 4H), 7.46-7.38 (m, 2H), 7.23-7.10 (m, 1H), 6.38 (s, 1H), 4.59 (brs, 2H), 4.26 (brs, 2H), 3.47 (brs, 2H), 3.18 (brs, 2H), 1.29 (s, 9H); MS (ESI) m/z: 498.2 (M+H$^+$).

Example 530

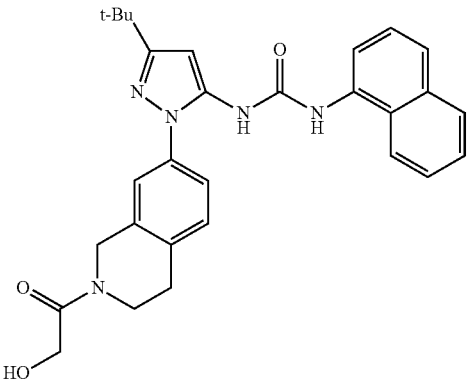

To a stirring solution of Example 349 (0.060 g, 0.14 mmol), glycolic acid (0.011 g, 0.15 mmol) and DCC (0.034 g, 0.16 mmol) in MeCN (1.5 ml) was added DMAP (0.0050 g, 0.041 mmol). The resulting mixture was stirred at RT for 30 min and then heated at 80-85° C. overnight. The completed reaction was cooled to RT and then cooled in ice to precipitate the DCU. The suspension was filtered and the filtrate concentrated and purified by reverse phase chromatography to yield of 1-(3-t-butyl-1-(2-(2-hydroxyacetyl)-1,2,3,4-tetrahydroisoquinolin-7-yl)-1H-pyrazol-5-yl)-3-(naphthalen-1-yl)urea (36.0 mg, 53% yield) as an off-white solid. $^1$H NMR (DMSO-d$_6$; mixture of rotamers): δ 9.05 (s, 1H), 8.83 and 8.79 (s, 1H), 8.03-8.01 (m, 1H), 7.96-7.91 (m, 2H), 7.66-7.64 (m, 1H), 7.59-7.52 (m, 2H), 7.49-7.36 (m, 4H), 6.42 (s, 1H), 4.73 and 4.66 (s, 2H), 4.21 and 4.19 (s, 2H), 3.76-3.73 and 3.63-3.61 (m, 2H), 2.95-2.92 and 2.87-2.86 (m, 1H), 1.29 (s, 9H); MS (ESI) m/z: 498.2 (M+H$^+$).

Example 531

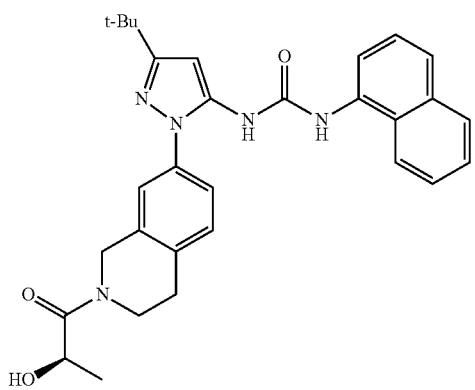

Using general method K, Example 349 (0.300 g, 0.683 mmol) and D-lactic acid, sodium salt (0.0841 g, 0.751 mmol) were combined to yield 1-(3-t-butyl-1-(2-((R)-2-hydroxypropanoyl)-1,2,3,4-tetrahydroisoquinolin-7-yl)-1H-pyrazol-5-yl)-3-(naphthalen-1-yl)urea (65.4 mg, 19% yield). $^1$H NMR (DMSO-$d_6$; rotamers): δ 9.04 (s, 1H), 8.83 and 8.78 (s, 1H), 8.03-7.99 (m, 1H), 7.97-7.91 (m, 2H), 7.66-7.64 (m, 1H), 7.58-7.35 (m, 6H), 6.42 (s, 1H), 4.89-4.67 (m, 2H), 4.57-4.52 (m, 1H), 3.84-3.78 and 3.70-3.65 (m, 2H), 2.94-2.91 and 2.88-2.85 (m, 2H), 1.29 (s, 9H), 1.25-1.23 and 1.21-1.19 (m, 3H); MS (ESI) m/z: 512.3 (M+H$^+$).

Example 532

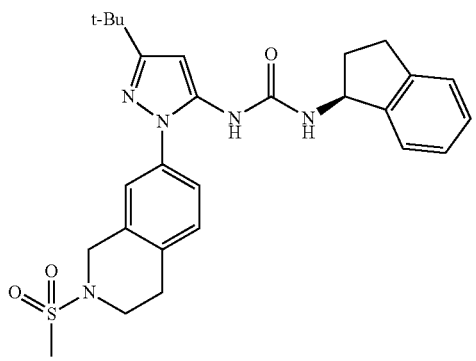

Using general method D, Example A34 (0.280 g, 0.609 mmol) and (S)-(+)-aminoindane (0.0781 ml, 0.609 mmol, 1.00 eq) were combined to yield 1-(3-t-butyl-1-(1-oxo-1,2,3,4-tetrahydroisoquinolin-7-yl)-1H-pyrazol-5-yl)-3-((S)-2,3-dihydro-1H-inden-1-yl)urea (151.0 mg, 56% yield) of as an off-white solid. $^1$H NMR (CDCl$_3$): δ 8.08-8.02 (m, 2H), 7.64-7.61 (m, 1H), 7.28-7.27 (m, 1H), 7.23-7.10 (m, 4H), 6/69 (brs, 1H), 6.39 (s, 1H), 5.82 (brs, 1H), 5.36-5.30 (m, 1H), 3.45-3.42 (m, 2H), 2.93-2.76 (m, 4H), 2.59-2.51 (m, 1H), 1.75-1.66 (m 1H), 1.33 (s, 9H); MS (ESI) m/z: 444.2 (M+H$^+$).

This material was reduced using general method C to yield 1-(3-t-butyl-1-(1,2,3,4-tetrahydroisoquinolin-7-yl)-1H-pyrazol-5-yl)-3-((S)-2,3-dihydro-1H-inden-1-yl)urea (0.103 g, 81% yield) as an off-white solid as the HCl salt. $^1$H NMR (DMSO-$d_6$): δ 9.54 (brs, 2H), 8.36 (s, 1H), 7.41-7.32 (m, 4H), 7.25-7.14 (m, 3H), 6.32 (s, 1H), 6.06 (s, 1H), 5.12-5.06 (m, 1H), 4.32 (brs, 2H), 3.38 (brs, 2H), 3.06-3.02 (m, 2H), 2.93-2.86 (m, 1H), 2.82-2.74 (m, 1H), 2.44-2.33 (m, 1H), 1.77-1.57 (m, 1H), 1.27 (s, 9H); MS (ESI) m/z: 430.2 (M+H$^+$).

The material from the previous reaction (0.0775 g, 0.166 mmol) and methanesulfonyl chloride (0.0386 ml, 0.499 mmol) were combined to yield 1-(3-t-butyl-1-(2-(methylsulfonyl)-1,2,3,4-tetrahydroisoquinolin-7-yl)-1H-pyrazol-5-yl)-3-((S)-2,3-dihydro-1H-inden-1-yl)urea (18.5 mg, 22% yield). $^1$H NMR (CDCl$_3$): δ 7.31-7.28 (m, 2H), 7.22-7.11 (m, 5H), 6.69 (brs, 1H), 6.32 (s, 1H), 5.45 (brs, 1H), 5.29-5.23 (m, 1H), 4.42 (brs, 2H), 3.54-3.46 (m, 2H), 2.96-2.77 (m, 3H), 2.81 (s, 3H), 2.56-2.48 (m, 1H), 1.74-1.64 (m, 1H), 1.33 (s, 9H); MS (ESI) m/z: 508.3 (M+H$^+$).

Example 533

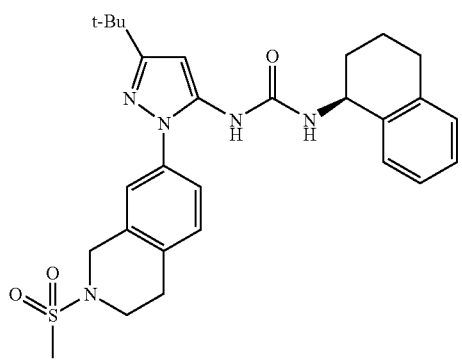

Using general method D, Example A34 0.280 g, 0.609 mmol) and (S)-1,2,3,4-tetrahydro-naphthalen-1-amine were combined and the resultant lactam (440 mg, 88.4% yield, MS (ESI) m/z: 458.3 (M+H$^+$) was reduced using general method C to yield 1-(3-t-butyl-1-(1,2,3,4-tetrahydroisoquinolin-7-yl)-1H-pyrazol-5-yl)-3-((S)-1,2,3,4-tetrahydronaphthalen-1-yl)urea (83.6 mg, 20% yield, MS (ESI) m/z: 444.2 (M+H$^+$)). This material (0.160 g, 0.361 mmol) and methanesulfonyl chloride (0.0558 ml, 0.721 mmol) were combined to yield pure 1-(3-t-butyl-1-(2-(methylsulfonyl)-1,2,3,4-tetrahydroisoquinolin-7-yl)-1H-pyrazol-5-yl)-3-((S)-1,2,3,4-tetrahydro-naphthalen-1-yl)urea (62.3 mg, 33% yield) as a white solid. $^1$H NMR (CDCl$_3$): δ 7.34-7.32 (m, 1H), 7.25-7.22 (m, 2H), 7.19-7.07 (m, 4H), 6.29 (s, 1H), 6.24 (brs, 1H), 5.18-5.15 (m, 1H), 5.04-4.99 (m, 1H), 4.49-4.42 (m, 2H), 3.58-3.50 (m, 2H), 2.99-2.96 (m, 2H), 2.83 (s, 3H), 2.77-2.74 (m, 2H), 2.04-1.99 (m, 1H), 1.83-1.71 (m, 3H), 1.33 (s, 9H); MS (ESI) m/z: 522.2 (M+H$^+$).

Example 534

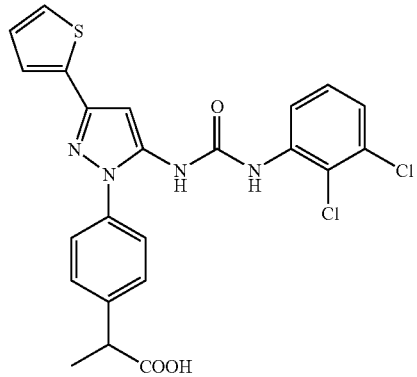

To a solution of ethyl 2-(4-(5-amino-3-(thiophen-2-yl)-1H-pyrazol-1-yl)phenyl)acetate (0.244 g, 0.745 mmol) in THF (7.5 ml), thoroughly cooled to −78° C., was added KHMDS in PhMe (1.79 ml, 0.894 mmol, 0.500 M). The resulting very dark mixture was stirred at −78° C. for 1 h and then treated with MeI (0.056 ml, 0.894 mmol). The reaction was stirred with gradual warming to RT overnight. The completed reaction was quenched by addition of 3M HCl, diluted with EtOAc and the layers separated. The aqueous was extracted with EtOAc (2×) and the combined organics were washed with satd. NaHCO$_3$ (1×), brine (1×), dried (MgSO$_4$), filtered, and concentrated to yield ethyl 2-(4-(5-amino-3-(thiophen-2-yl)-1H-pyrazol-1-yl)phenyl)propanoate (0.25 g) of crude which was used without further purification in the next reaction. MS (ESI) m/z: 342.3 (M+H$^+$).

Using general method A, this material was combined with 2,3-dichlorophenyl isocyanate (0.0967 ml, 0.732 mmol) and the resultant ester saponified using general method E to yield 2-(4-(5-(3-(2,3-dichlorophenyl)ureido)-3-(thiophen-2-yl)-1H-pyrazol-1-yl)phenyl)propanoic acid (68.9 mg, 35% yield). $^1$H NMR (DMSO-d$_6$:acid): δ 9.47 (s, 1H), 8.89 (s, 1H), 8.12-8.09 (m, 1H), 7.58-7.47 (m, 6H), 7.34-7.31 (m, 2H), 7.13-7.01 (m, 1H), 6.87 (s, 1H), 3.81 (q, 1H, J=6.8 Hz), 1.43 (d, 3H, J=6.8 Hz); MS (ESI) m/z: 501.0 (M+H), 503.0 (M+2+H$^+$).

Example 535

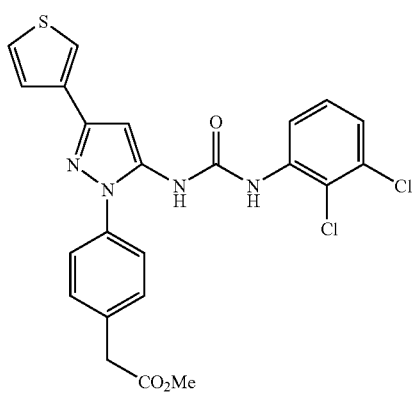

To a solution of 2-(4-(5-(3-(2,3-dichlorophenyl)ureido)-3-(thiophen-3-yl)-1H-pyrazol-1-yl)phenyl)acetic acid (0.073 g, 0.15 mmol) in DMF (1 ml) were added PyBop (0.18 mmol) and MeOH (0.1 g, 0.45 mmol) and stirred for 4 h at RT. The reaction mixture was poured into cold H$_2$O and the product was extracted with EtOAc (3×20 ml). The combined organic extracts were washed with 3M HCl, brine, dried (Na$_2$SO$_4$) and concentrated to yield a crude product. To the crude product was added CH$_2$Cl$_2$ (2 ml) and stirred for 10 min and the resultant solid was filtered and dried to afford pure methyl 2-(4-(5-(3-(2,3-dichlorophenyl)ureido)-3-(thiophen-3-yl)-1H-pyrazol-1-yl)phenyl)acetate. $^1$H NMR (400 MHz, DMSO-d$_6$): δ 9.40 (s, 1H), 8.87 (s, 1H), 8.10 (dd, J=6.8 Hz, 2.4 Hz, 1H), 7.87-7.86 (m, 1H), 7.60 (dd, J=4.8 Hz, 2.8 Hz, 1H), 7.57 (d, J=8.0 Hz, 2H), 7.52-7.49 (m, 1H), 7.48 (d, J=8.0 Hz, 2H), 7.34-7.32 (m, 2H), 6.85 (s, 1H), 3.80 (s, 2H), 3.65 (s, 3H); MS (ESI) m/z: 501.0 (M+H$^+$).

Example 536

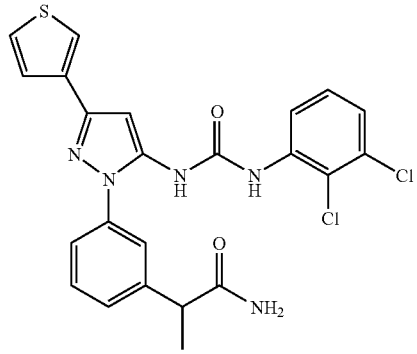

Using the same general approach as for Example 524, ethyl 2-(3-(5-amino-3-(thiophen-3-yl)-1H-pyrazol-1-yl)phenyl) acetate (0.2258 g, 0.450 mmol, 1.00 eq) was transformed to ethyl 2-(3-(5-amino-3-(thiophen-3-yl)-1H-pyrazol-1-yl)phenyl)propanoate. This, in turn, was combined with 2,3-dichlorophenyl isocyanate, according to general method A, to afford 2-(3-(5-(3-(2,3-dichlorophenyl)ureido)-3-(thiophen-3-yl)-1H-pyrazol-1-yl)phenyl)propanoic acid. Using general method J, this product was combined with 0.5M NH$_3$ in dioxane (4.50 ml, 2.25 mmol, 5.00 eq). to afford 0.1731 g (77%) of pure 1-(1-(3-(1-amino-1-oxopropan-2-yl)phenyl)-3-(thiophen-3-yl)-1H-pyrazol-5-yl)-3-(2,3-dichlorophenyl) urea. $^1$H NMR (DMSO-d$_6$): δ 9.38 (s, 1H), 8.82 (s, 1H), 8.12-8.09 (m, 1H), 7.88-7.87 (m, 1H), 7.62-7.60 (m, 1H), 7.57-7.42 (m, 6H), 7.36-7.31 (m, 2H), 6.89 (brs, 1H), 6.86 (s, 1H), 3.69 (q, 1H, J=7.2 Hz), 1.36 (d, 3H, J=7.2 Hz); MS (ESI) m/z: 500.0 (M+H$^+$), 502.0 (M+2+H$^+$).

Example 537

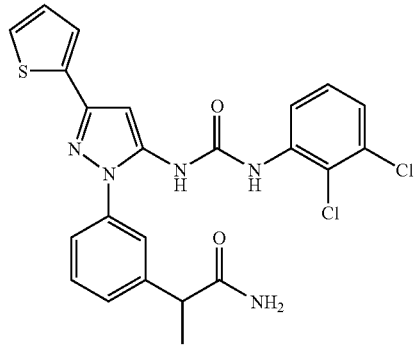

Using the same general approach as for Example 524, ethyl 2-(3-(5-amino-3-(thiophen-2-yl)-1H-pyrazol-1-yl)phenyl) acetate (0.202 g, 0.403 mmol, 1.00 eq) was transformed to ethyl 2-(3-(5-amino-3-(thiophen-2-yl)-1H-pyrazol-1-yl) phenyl)propanoate. This, in turn, was combined with 2,3-dichlorophenyl isocyanate, according to general method A, to afford 2-(3-(5-(3-(2,3-dichlorophenyl)ureido)-3-(thiophen-2-yl)-1H-pyrazol-1-yl)phenyl)propanoic acid. Using general method J, this product was combined with 0.5M NH$_3$ in dioxane (4.03 ml, 2.01 mmol, 5.00 eq) to afford 0.145 g (72%) of 1-(1-(3-(1-amino-1-oxopropan-2-yl)phenyl)-3-(thiophen-2-yl)-1H-pyrazol-5-yl)-3-(2,3-dichlorophenyl) urea.

$^1$H NMR (DMSO-d$_6$): δ 9.42 (s, 1H), 8.84 (s, 1H), 8.12 (m, 1H), 7.55-7.43 (m, 7H), 7.36-7.31 (m, 2H), 7.13-7.11 (m,

1H), 6.89 (brs, 1H), 6.87 (s, 1H), 3.69 (q, 1H, J=7.2 Hz), 1.36 (d, 3H, J=7.2 Hz); MS (ESI) m/z: 500.0 (M+H⁺), 502.0 (M+2+H⁺).

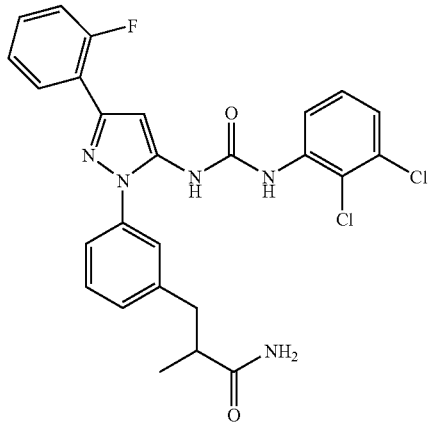

Example 538

3-(2-Fluorophenyl)-1-(3-iodophenyl)-1H-pyrazol-5-amine (0.500 g, 1.32 mmol, 1.00 eq), methacrylamide (0.281 g, 3.30 mmol, 2.50 eq), Pd(OAc)₂ (0.0118 g, 0.0527 mmol, 0.04 eq), Ph₃P (0.0346 g, 0.132 mmol, 0.10 eq) and Et₃N (0.919 ml, 6.59 (mmol, 5.00 eq) were combined in DMF (3 ml) and heated at 80° C. overnight. The reaction was cooled to RT, diluted with H₂O and extracted with EtOAc (2×). The combined organics were washed with 5% citric acid (2×), brine (1×) and dried (MgSO₄). Filtration and evaporation gave crude product which was purified by flash chromatography to afford 0.4192 g (95%) of pure (E)-3-(3-(5-amino-3-(2-fluorophenyl)-1H-pyrazol-1-yl)phenyl)-2-methylacrylamide. MS (ESI) m/z: 337.2 (M+H⁺).

(E)-3-(3-(5-amino-3-(2-fluorophenyl)-1H-pyrazol-1-yl) phenyl)-2-methylacrylamide (0.4192 g, 1.25 mmol, 1.00 eq) was hydrogenated (3.5 atm) over 10% Pd/C (0.0838 g, 0.0394 mmol, 0.0316 eq) in MeOH (5 ml) at RT for 36 h. Filtration through Celite® and evaporation yielded 0.245 g (58%) of crude 3-(3-(5-amino-3-(2-fluorophenyl)-1H-pyrazol-1-yl) phenyl)-2-methylpropanamide which was used as is in the next reaction. MS (ESI) m/z: 339.2 (M+H⁺).

Using general method A, 3-(3-(5-amino-3-(2-fluorophenyl)-1H-pyrazol-1-yl)phenyl)-2-methylpropanamide (0.1225 g, 0.362 mmol, 1.00 eq) was combined with 2,3-dichlorophenyl isocyanate (0.102 g, 0.543 mmol, 1.50 eq) to yield 34.2 mg (18%) of pure 1-(1-(3-(3-amino-2-methyl-3-oxopropyl)phenyl)-3-(2-fluorophenyl)-1H-pyrazol-5-yl)-3-(2,3-dichlorophenyl)urea. ¹H NMR (DMSO-d₆): δ 9.40 (s, 1H), 8.89 (s, 1H), 8.11-8.08 (s, 1H), 8.02-7.98 (m, 1H), 7.53-7.39 (m, 4H), 7.36-7.26 (m, 6H), 6.92-6.91 (m, 1H), 6.76 (brs, 1H), 3.00-2.93 (m, 1H), 2.65-2.57 (m, 2H), 1.03-1.02 (m, 3H); MS (ESI) m/z: 526.0 (M+H), 528.0 (M+2+H⁺).

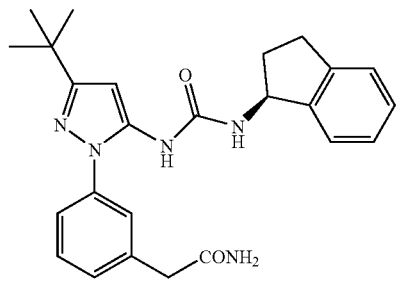

Example 539

Using general method J, Example 350 (81 mg, 0.2 mmol) and 0.5 NH₃ in dioxane (1 mL) were combined to afford 1-(1-(3-(2-amino-2-oxoethyl)phenyl)-3-t-butyl-1H-pyrazol-5-yl)-3-((S)-2,3-dihydro-1H-inden-1-yl)urea (25 mg, 31%) as white solid. ¹H NMR (400 MHz, DMSO-d₆): □ 8.08 (s, 1H), 7.50 (s, 1H), 7.44-7.19 (m, 8H), 6.91-6.89 (m, 2H), 6.33 (s, 1H), 5.09 (q, J=7.6 Hz, 1H), 3.44 (s, 2H), 2.92-2.73 (m, 2H), 2.44-2.36 (m, 1H), 1.76-1.66 (m, 1H), 1.27 (s, 9H); MS (ESI) m/z: 432.2 (M+H⁺).

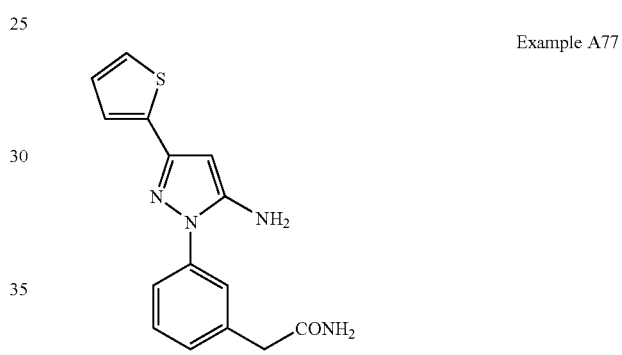

Example A77

Example 506 (0.32 g, 1 mmol) was dissolved in 7N NH₃/MeOH (10 mL) and the mixture was stirred for 24 h at 50° C. Then solvent was removed under vacuum and the residue was purified by column chromatography to afford 2-(3-(5-amino-3-(thiophen-2-yl)-1H-pyrazol-1-yl)phenyl)acetamide (0.2 g, 67%) as a solid. ¹H NMR (400 MHz, DMSO-d₆): δ7.51-7.42 (m, 5H), 7.34 (dd, J=3.2 Hz, 1.2 Hz, 1H), 7.24-7.22 (m, 1H), 7.08-7.06 (m, 1H), 6.93 (brs, 1H), 5.82 (s, 1H), 5.47 (s, 2H), 3.46 (s, 2H); MS (ESI) m/z: 299.0 (M+H⁺).

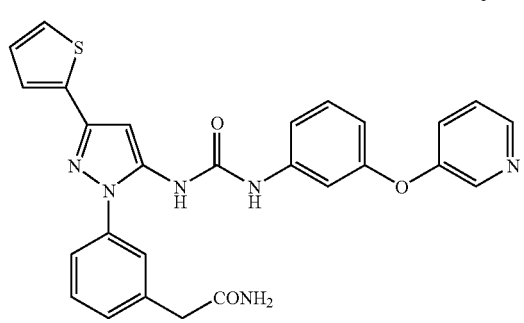

Example 540

To a solution of phosgene (0.3 mL of 20% w/v solution in toluene) in MeCN (1 mL) was added a mixture of 3-(pyridin-3-yloxy)benzenamine (0.046 g, 0.25 mmol) and Et₃N (0.066 g, 0.66 mmol) in MeCN (1 mL) at 0° C. under Ar over a period of 10 min. After stirring for 30 min at RT, to the mixture was added a solution that contained 2-(3-(5-amino-3-(thiophen-2-yl)-1H-pyrazol-1-yl)phenyl)acetamide (0.05 g, 0.16 mmol) and Et₃N (0.06 g, 0.66 mmol) and stirred for 16 h at RT. The solvents were removed to afford a residue which was purified by column chromatography to afford material that upon treatment with 3M HCl/EtOAc yielded 1-(1-(3-(2-amino-2-oxoethyl)phenyl)-3-(thiophen-2-yl)-1H-pyrazol-5-yl)-3-(3-(pyridin-3-yloxy)phenyl)urea (12 mg, 14%) urea as white solid. ¹H NMR (400 MHz, DMSO-d₆): δ 9.50 (s, 1H), 8.76 (s, 1H), 8.57 (s, 1H), 8.51 (d, J=4.8 Hz, 1H), 7.57-7.68 (m, 2H), 7.57 (s, 1H), 7.51-7.32 (m, 8H), 7.16-7.09 (m, 2H), 6.95 (s, 1H), 6.82 (s, 1H), 6.75 (dd, J=8.0 Hz, 2.4 Hz, 1H), 3.49 (s, 2H); MS (ESI) m/z: 511.0 (M+H⁺).

Example 541

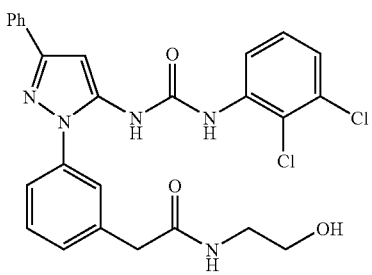

Using general method J, Example 351 (81 mg, 0.17 mmol) ethanolamine (13 mg, 0.22 mmol) were combined to afford 1-(2,3-dichlorophenyl)-3-(1-(3-(2-(2-hydroxyethylamino)-2-oxoethyl)phenyl)-3-phenyl-1H-pyrazol-5-yl)urea (55 mg, 62%) as a white solid. ¹H NMR (400 MHz, DMSO-d₆): δ 9.41 (s, 1H), 8.86 (s, 1H), 8.15 (t, J=5.6 Hz, 1H), 8.09 (dd, J=6.8 Hz, 2.8 Hz, 1H), 7.86-7.84 (m, 2H), 7.56-7.31 (m, 9H), 6.95 (s, 1H), 3.54 (s, 2H), 3.39 (t, J=6 Hz, 2H), 3.13-3.09 (m, 2H); MS (ESI) m/z: 524.0 (M+H⁺).

Example 542

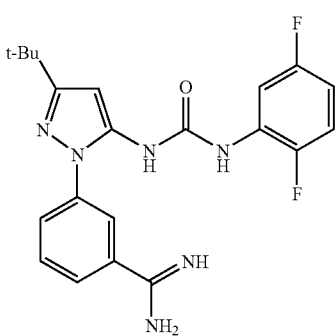

To a solution of Example 213 (0.054 g, 0.137 mmol) in dry ethanol (2 mL) was at −78° C. added acetyl chloride (1.1 g, 14 mmol) and the resulting solution was kept at room temperature overnight. The solvent was evaporated and to the residue was added 7N ammonia in methanol (2 mL) and the mixture was stirred at room temperature overnight. The solvent was evaporated and the residue was purified by reverse-phase chromatography (CV 12 mL, 20% acetonitrile in water to 50% acetonitrile in water, both solvents with 0.1% TFA, 20 CV). Basic extraction and reacidification with HCl gave 21 mg (34%) of 1-(3-t-butyl-1-(3-carbamimidoylphenyl)-1H-pyrazol-5-yl)-3-(2,5-difluorophenyl)urea as a white solid.

¹H-NMR (methanol-d₄): δ 8.09 (t, 1H, J=1.8 Hz), 8.02-7.98 (m, 2H), 7.94-7.89 (m, 1H), 7.87 (t, 1H, J=8.2 Hz), 7.15-7.09 (m, 1H), 6.79-6.71 (m, 1H), 1.41 (s, 9H), amidine, urea and pyrazolamine protons not visible. LC-MS (EI) m/z: 413.0 (M+H⁺).

Example A78

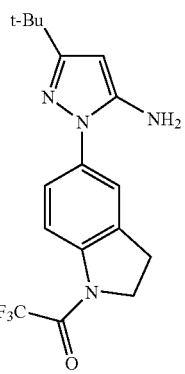

Using the same method as Example A28, 5-nitroindoline (5.0 g, 152 mmol) was converted to 1-[5-(2-amino-4-t-butylpyrrol-1-yl)-2,3-dihydroindol-1-yl]-2,2,2-trifluoroethanone (9.2 g, 40% yield, 3 steps) as a light-brown solid. ¹H NMR (300 MHz, DMSO-d₆): δ 8.13-8.16 (m, 1H), 7.57 (s, 1H), 7.44-7.47 (m, 1H), 5.61 (t, J=7.8 Hz, 2H), 4.34 (t, J=7.8 Hz, 2H), 3.28 (s, 1H), 1.26 (s, 1H). MS (ESI) m/z: 353.2 (M+H⁺).

Example A79

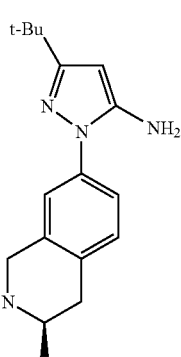

To a solution of (S)-1,2,3,4-Tetrahydroisoquinolone-3-carboxylic acid (5.00 g, 28.2 mmol) in sulfuric acid (20 mL) was at 0° C. dropwise added a solution of potassium nitrate (2.95 g, 29.2 mmol) in sulfuric acid (10 mL). When the addition was complete, the mixture was stirred for 5 min and the carefully diluted with water and neutralized with ammonium hydroxide (about 100 mL). The precipitate was filtered, washed with water and dried in vacuo to give (S)-7-nitro-1,2,3,4-tetrahydroisoquinoline-3-carboxylic acid (4.70 g, 75% yield) as a yellow solid. Acetyl chloride (20.0 mL, 22.1 g, 281 mmol) was added carefully to methanol (50 mL) at −20° C. The solution was allowed to reach room temperature and stirred for 10 min. (S)-7-nitro-1,2,3,4-tetrahydroisoquinoline-3-carboxylic acid (4.70 g, 21.2 mmol) was then added and the resulting suspension was stirred at 50° C. for 5 h. The solvent was evaporated and the residue was dried in vacuo to give (S)-methyl 7-nitro-1,2,3,4-tetrahydroisoquinoline-3-carboxylate hydrochloride (5.77 g, 100% yield) as a crude form. (S)-methyl 7-nitro-1,2,3,4-tetrahydroisoquinoline-3-carboxylate hydrochloride (4.77 g, 17.5 mmol) was suspended in methylene chloride (50 mL). Triethylamine (2.93 mL, 2.12 g, 2.10 mmol) was added and then carefully trifluoroacetyl anhydride (2.92 mL, 4.41 g, 21.0 mmol). the mixture was stirred for 10 min. Water was added (100 mL) and the mixture was extracted with methylene chloride (3×100 mL), dried over magnesium sulfate and concentrated. Column chromatography (CV 120 mL, 10% ethyl acetate hexanes to 30% ethyl acetate in hexanes, 20 (CV) gave the desired product, (S)-methyl 7-nitro-2-(2,2,2-trifluoroacetyl)-1,2,3,4-tetrahydroisoquinoline-3-carboxylate (2.70 g, 47% yield), and 1.28 g of coeluting byproduct mixture. $R_f$(ethyl acetate) 0.89. To a solution of (S)-methyl 7-nitro-2-(2,2,2-trifluoroacetyl)-1,2,3,4-tetrahydroisoquinoline-3-carboxylate (2.70 g, 8.13 mmol) in methanol (50 mL) was added palladium on charcoal (10%, 0.432 g, 0.406 mmol) and the resulting suspension was stirred in an atmosphere of hydrogen overnight. The mixture was filtered, charged with conc. HCl (1 mL) and concentrated to give (S)-methyl 7-amino-2-(2,2,2-trifluoroacetyl)-1,2,3,4-tetrahydroisoquinoline-3-carboxylate hydrochloride (2.60 g, 95% yield) as a grey solid. $R_f$ (ethyl acetate)=0.82. Using general method M, (S)-methyl 7-amino-2-(2,2,2-trifluoroacetyl)-1,2,3,4-tetrahydroisoquinoline-3-carboxylate hydrochloride (2.60 g, 7.68 mmol) and pivaloylacetonitrile (0.961 g, 7.68 mmol) were combined to yield (3S)-methyl 7-(5-amino-3-t-butyl-1H-pyrazol-1-yl)-2-(2,2,2-trifluoroacetyl)-1,2,3,4-tetrahydroisoquinoline-3-carboxylate which was used without purification.

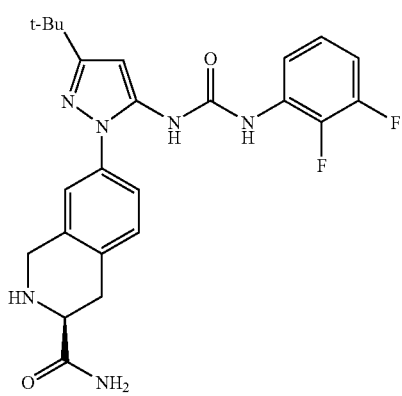

Example 544

Using General method D, a solution of Example A79 (0.615 g, 7.68 mmol) and 2,3-difluoroaniline (0.032 g, 0.250 mmol) were combined to yield the crude product which was deprotected by ammonia in methanol (7N, 1 mL, 7 mmol) to afford the amination and de-trifluoroacetylation product, 1-(3-t-butyl-1-((3S)-3-carbamoyl-1,2,3,4-tetrahydroisoquinolin-7-yl)-1H-pyrazol-5-yl)-3-(2,3-difluorophenyl)urea (20 mg, 24%, 2 steps) as an off-white solid. $^1$H NMR (400 MHz, CD$_3$OD): δ 7.80 (t, 1H, J=7.6 Hz), 7.56-7.51 (m, 3H), 7.11-7.06 (m, 1H), 6.98-6.91 (m, 1H), 6.58 (s, 1H), 4.56 (d, J=15.2 Hz, 1H), 4.50 (d, J=15.2 Hz, 1H), 4.30 (dd, J=11.2, and 5.0 Hz, 1H), 3.54 (dd, J=17.2, 4.8 Hz, 1H), 1.28 (s, 9H); LC-MS (EI) m/z: 469.0 (M+H$^+$).

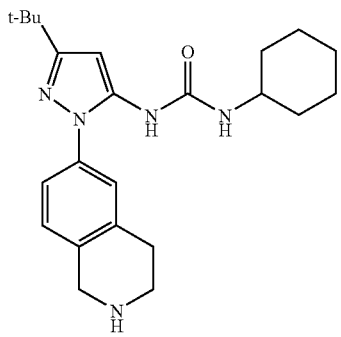

Example 543

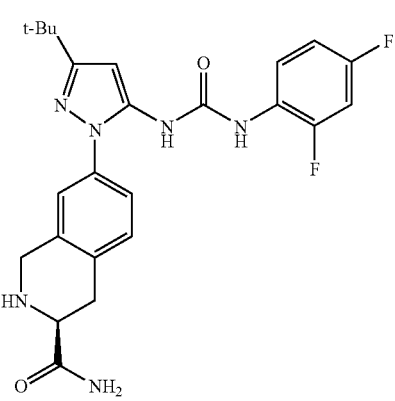

Example 545

Using General method D, Example A36 (0.500 g, 1.35 mmol) and cyclohexylamine (0.031 g, 0.242 mmol) to yield t-butyl 6-(3-t-butyl-5-(3-cyclohexylureido)-1H-pyrazol-1-yl)-3,4-dihydroisoquinoline-2(1H)-carboxylate (83 mg, 83% yield) as a white powder, which was deprotected using general method F to afford 1-(3-t-butyl-1-(1,2,3,4-tetrahydroisoquinolin-6-yl)-1H-pyrazol-5-yl)-3-cyclohexylurea (59 mg, 85% yield) as a colorless solid. $^1$H NMR (400 MHz, CD$_3$OD): δ 7.51-7.46 (m, 3H), 6.62 (s, 1H), 4.48 (s, 2H), 3.57 (t, J=6.2 Hz, 2H), 3.55-3.50 (m, 1H), 3.23 (t, J=6.0 Hz, 2H), 1.86-1.82 (m, 2H), 1.73-1.69 (m, 2H), 1.61-1.58 (m, 1H), 1.39 (s, 9H), 1.38-1.20 (m, 2H), 1.26-1.16 (m, 3H); LC-MS (EI) m/z: 396.3 (M+H$^+$).

Using the same method as for Example 544, Example A79 (0.615 g, 7.68 mmol) and 2,4-difluoroaniline (0.032 g, 0.250 mmol) were combined to afford 1-(3-t-butyl-1-((3S)-3-carbamoyl-1,2,3,4-tetrahydroisoquinolin-7-yl)-1H-pyrazol-5-yl)-3-(2,4-difluorophenyl)urea (19 mg, 23% yield, 2 steps) as a green/white solid. $^1$H NMR (400 MHz, CD$_3$OD): δ 7.93-7.87 (m, 1H), 7.56-7.51 (m, 3H), 7.04-6.99 (m, 1H), 6.95-6.89 (m, 1H), 6.54 (s, 1H), 4.55 (d, J=16.4 Hz, 1H), 4.50 (d, J=15.6 Hz, 1H), 4.20 (dd, J=11.6, and 5.2 Hz, 1H), 3.53 (dd, J=17.2, and 4.8 Hz, 1H), 1.37 (s, 9H); LC-MS (EI) m/z: 469.2 (M+H$^+$).

Example 546

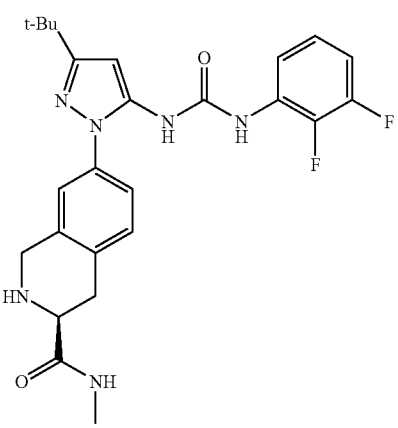

Using the same method as for Example 544, Example A79 (0.615 g, 7.68 mmol) and 2,3-difluoroaniline (0.032 g, 0.250 mmol) were combined to yield the crude product which was treated with methylamine in ethanol (8N, 1 mL, 8 mmol) to afford the methylamminated and deprotected product, 1-(3-t-butyl-1-((3S)-3-(methylcarbamoyl)-1,2,3,4-tetrahydroisoquinolin-7-yl)-1H-pyrazol-5-yl)-3-(2,3-difluorophenyl)urea (13 mg, 15% yield, 2 steps) as an off-white solid. $^1$H NMR (400 MHz, CD$_3$OD): δ 7.79 (dt, J=8.0, and 1.6 Hz, 1H), 7.56-7.49 (m, 3H), 7.12-7.05 (m, 1H), 6.98-6.91 (m, 1H), 6.57 (s, 1H), 4.55 (d, J=15.6 Hz, 1H), 4.50 (d, J=16.0 Hz, 1H), 4.25 (dd, J=11.6, and 5.2 Hz, 1H), 3.46 (dd, J=19.6, and 5.2 Hz, 1H), 2.86 (s, 3H), 1.37 (s, 9H); LC-MS (EI) m/z: 483.3 (M+H$^+$).

Example 547

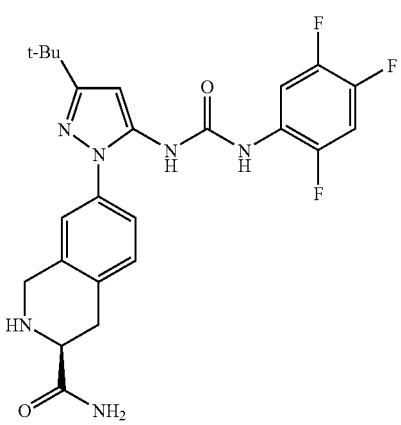

Using the same method as for Example 544, Example A79 (0.615 g, 7.68 mmol) and 2,4,5-trifluoroaniline (0.050 g, 0.334 mmol) were combined to afford 1-(3-t-butyl-1-((3S)-3-carbamoyl-1,2,3,4-tetrahydroisoquinolin-7-yl)-1H-pyrazol-5-yl)-3-(2,4,5-trifluorophenyl)urea (12 mg, 14% yield, 2 steps) as an off-white solid. $^1$H NMR (400 MHz, CD$_3$OD): δ 8.06-7.98 (m, 1H), 7.54-7.48 (m, 3H), 7.26-7.19 (m, 1H), 6.51 (s, 1H), 4.54 (d, J=16.0 Hz, 1H), 4.28 (dd, J=12.0, and 5.2 Hz, 1H), 4.49 (d, J=16.4 Hz, 1H), 3.61-3.47 (m, 2H), 1.35 (s, 9H); LC-MS (EI) m/z: 487.3 (M+H$^+$).

Example A80

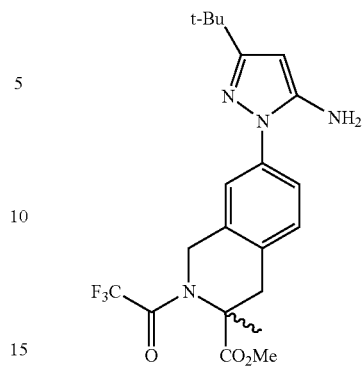

To a suspension of alpha-methyl-DL-phenylalanine (2.00 g, 11.2 mmol) in conc. HCl (30 mL) was added formaldehyde (37%, 4.0 mL, 4.36 g, 4.81 mmol) and the resulting suspension was stirred at 60° C. for 48 h. The precipitated solid was collected and dried in vacuo to give 1.02 g (40%) of 3-methyl-1,2,3,4-tetrahydroisoquinoline-3-carboxylic acid hydrochloride. $^1$H NMR (400 MHz, CD$_3$OD): δ 7.33-7.24 (m, 4H), 4.53 (d, J=16.8 Hz, 1H), 4.42 (d, J=16.0 Hz, 1H), 3.43 (d, J=17.6 Hz, 1H), 3.18 (d, J=17.2 Hz, 1H), 1.67 (s, 3H); LC-MS (EI) m/z: 192.0 (M+H$^+$). Using the same method as for VP-2851, 3-methyl-1,2,3,4-tetrahydroisoquinoline-3-carboxylic acid hydrochloride (1.01 g, 4.436 mmol) was converted to yield methyl 7-amino-3-methyl-2-(2,2,2-trifluoroacetyl)-1,2,3,4-tetrahydroisoquinoline-3-carboxylate hydrochloride (600 mg, 38% yield, 2 steps) as a grey solid. $^1$H NMR (400 MHz, CD$_3$OD): δ 7.48 (d, J=7.6 Hz, 1H), 7.38 (s, 1H), 7.37 (dd, J=8.0, 2.4 Hz, 1H), 4.83 (d, J=15.2 Hz, 1H), 4.78 (d, J=15.2 Hz, 1H), 3.63 (s, 3H), 3.27 (d, J=14.8 Hz, 1H), 3.15 (d, J=14.4 Hz, 1H), 1.51 (s, 3H); LC-MS (EI) m/z: 317.0 (M+H$^+$). Using general method M, methyl 7-amino-3-methyl-2-(2,2,2-trifluoroacetyl)-1,2,3,4-tetrahydroisoquinoline-3-carboxylate hydrochloride (0.600 g, 1.70 mmol) and pivaloylacetonitrile (0.21 g, 1.7 mmol) were combined to afford methyl 7-(5-amino-3-t-butyl-1H-pyrazol-1-yl)-3-methyl-2-(2,2,2-trifluoroacetyl)-1,2,3,4-tetrahydroisoquinoline-3-carboxylate (240 mg, 30% yield) as a yellow foam. LC-MS (EI) m/z: 439.0 (M+H$^+$).

Example 548

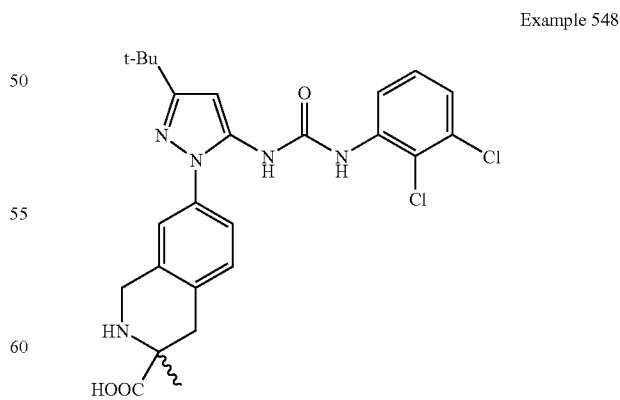

Using general method A, Example A80 (0.070 g, 0.160 mmol) and 2,3-dichlorophenyl isocyanate (0.060 g, 0.319 mmol) were combined to yield methyl 7-(3-t-butyl-5-(3-(2,3-dichlorophenyl)ureido)-1H-pyrazol-1-yl)-3-methyl-2-(2, 2,2-trifluoroacetyl)-1,2,3,4-tetrahydroisoquinoline-3-carboxylate. LC-MS (EI) m/z: 626.0 (M+H⁺).

Using general method G, methyl 7-(3-t-butyl-5-(3-(2,3-dichloro-phenyl)ureido)-1H-pyrazol-1-yl)-3-methyl-2-(2,2,2-trifluoroacetyl)-1,2,3,4-tetrahydroisoquinoline-3-carboxylate (0.100 g, 0.160 mmol) was deprotected to yield 7-(3-t-butyl-5-(3-(2,3-dichlorophenyl)ureido)-1H-pyrazol-1-yl)-3-methyl-1,2,3,4-tetrahydroisoquinoline-3-carboxylic acid (60 mg, 68% yield) as a yellow solid. $^1$H NMR (400 MHz, CD$_3$OD): δ 8.08-8.05 (t, J=5.0 Hz, 1H), 7.62-7.55 (m, 3H), 7.28-7.25 (m, 2H), 6.76 (s, 1H), 4.68 (d, J=16.8 Hz, 1H), 4.57 (d, J=16.8 Hz, 1H), 3.58 (d, J=17.6 Hz, 1H), 3.35 (d, J=18.0 Hz, 1H), 1.68 (s, 3H), 1.40 (s, 9H); LC-MS (EI) m/z: 516.0 518.0 (M+H⁺).

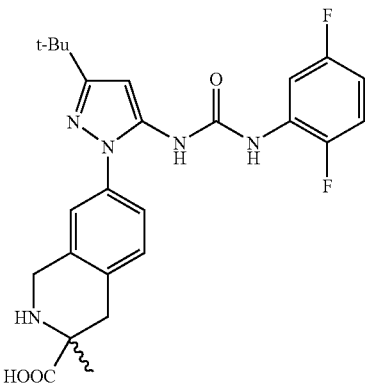

Example 549

Using general method D, Example A80 and 2,4,5-trifluoroaniline (0.041 g, 0.28 mmol) were combined to yield methyl 7-(3-t-butyl-5-(3-(2,5-difluorophenyl)ureido)-1H-pyrazol-1-yl)-1-methyl-2-(2,2,2-trifluoroacetyl)-1,2,3,4-tetrahydroisoquinoline-3-carboxylate which was deprotected using the general method G to afford 7-(3-t-butyl-5-(3-(2,4,5-trifluorophenyl)ureido)-1H-pyrazol-1-yl)-3-methyl-1,2,3,4-tetrahydroisoquinoline-3-carboxylic acid hydrochloride (30 mg, 40% yield, 2 steps) as a yellow solid. $^1$H NMR (400 MHz, CD$_3$OD): δ 8.11-8.04 (m, 1H), 7.60-7.54 (m, 3H), 7.27-7.20 (m, 1H), 6.68 (s, 1H), 4.66 (d, J=16.8 Hz, 1H), 4.55 (d, J=16.8 Hz, 1H), 3.56 (d, J=17.6 Hz, 1H), 1.74 (s, 3H), 1.39 (s, 9H); LC-MS (EI) m/z: 502.2 (M+H⁺).

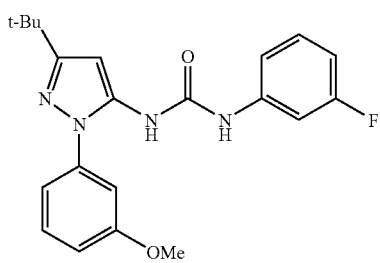

Example 550

Using the general method A, Example C (60 mg, 0.21 mmol) and 3-fluorophenyl isocyanate (29 mg, 0.21 mmol) were combined to afford 1-(3-t-butyl-1-(3-methoxyphenyl)-1H-pyrazol-5-yl)-3-(3-fluorophenyl)urea (49 mg, 60% yield). $^1$H NMR (300 MHz, CDCl$_3$): δ 7.2-7.3 (m, 3H), 7.17 (brs, 1H), 6.95-7.05 (m, 2H), 6.93 (dd, J=1.6, and 8.2 Hz, 1H), 6.87 (dd, J=1.8, and 7.6 Hz, 1H), 6.79 (dt, J=1.9, and 8.8 Hz, 1H), 6.64 (s, 1H), 6.39 (s, 1H), 3.77 (s, 3H), 1.35 (s, 9H); MS (EI) m/z: 383 (M+H⁺).

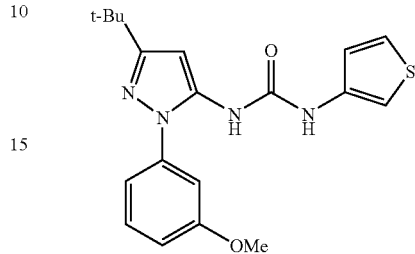

Example 551

Using general method A, Example C (70 mg, 0.29 mmol) and 3-thienyl isocyanate (36 mg, 0.29 mmol) were combined to afford 1-(3-t-butyl-1-(3-methoxyphenyl)-1H-pyrazol-5-yl)-3-(thiophen-3-yl)urea (45 mg, 43% yield). $^1$H NMR (300 MHz, CDCl$_3$): δ 7.05-7.3 (m, 4H), 6.8-7.0 (m, 4H), 6.76 (s, 1H), 6.40 (s, 1H), 3.76 (s, 3H), 1.35 (s, 9H); MS (EI) m/z: 371 (M+H⁺).

Example A81

To a solution of m-aminobenzoic acid ethyl ester (200 g, 1.21 mmol) in conc. HCl (200 mL) was added an aqueous solution (250 mL) of NaNO$_2$ (102 g, 1.46 mmol) at 0° C. and the reaction mixture was stirred for 1 h. A solution of SnCl$_2$.2H$_2$O (662 g, 2.92 mmol) in conc. HCl (2 L) was then added at 0° C. The reaction solution was stirred for 2 h at RT. The precipitate was filtered and washed with ethanol and ether to yield ethyl 3-hydrazinobenzoate, which was used for the next reaction without further purification.

To a mixture of 3-hydrazinobenzoic acid ethyl ester (4.5 g, 25.0 mmol) and commercially available 3-oxo-3-phenylpropionitrile (5.5 g, 37.5 mmol) in ethanol (50 mL) was added conc. HCl (5 mL). The resulting mixture was heated to reflux for 3 h. After removal of the solvent, the residue was washed with Et$_2$O to afford ethyl 3-(5-amino-3-phenyl-1H-pyrazol-1-yl)benzoate (7 g, 2% yield, 2 steps) which was used in the next reaction without further purification.

Example A82

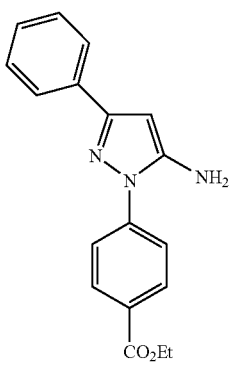

Using the same procedureas Example A81, 4-aminobenzoic acid ethyl ester (200 g, 1.21 mmol) and commercially available, 3-oxo-3-phenylpropanenitrile were combined to ethyl 4-(5-amino-3-phenyl-1H-pyrazol-1-yl)benzoate (7.4 g, 2% yield, 2 steps) which was used in the next reaction without further purification.

Example A83

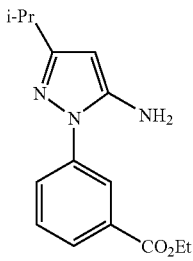

To a suspension of NaH (60%, 6.0 g, 0.15 mol) in THF (100 mL) was added dropwise isobutyric acid ethyl ester (11.6 g, 0.1 mol) and anhydrous acetonitrile (50 g, 0.12 mol) in THF (100 mL) at 80° C. The resulting mixture was refluxed overnight, then cooled to RT. After removal of the volatiles in vacuo, the residue was diluted in EtOAc and aqueous 10% HCL. The combined organic extracts were dried ($Na_2SO_4$), filtered, concentrated to yield 4-methyl-3-oxopentanenitrile (8.5 g), which was used for the next step reaction without further purification.

To a mixture of ethyl 3-hydrazinobenzoate (from Example A81, 3 g, 16.6 mmol) and 4-methyl-3-oxopentanenitrile (2.7 g, 24.9 mmol) in ethanol (50 mL) was added conc. HCl (5 mL). The resulting mixture was heated to reflux for 3 h. After removal of the solvent, the residue was washed with $Et_2O$ to afford ethyl 3-(5-amino-3-isopropyl-1H-pyrazol-1-yl)benzoate (4 g), which was used in the next reaction without further purification.

Example A84

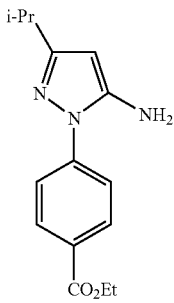

Using the same method as Example A83, 4-hydrazinobenzoic acid ethyl ester (from Example A82, 3 g, 16.6 mmol) and 4-methyl-3-oxopentanenitrile (from Example A83, 2.7 g, 27.9 mmol) were combined to afford ethyl 4-(5-amino-3-isopropyl-1H-pyrazol-1-yl)benzoate (4 g, 88% yield), which was used to the next reaction without further purification.

Example 552

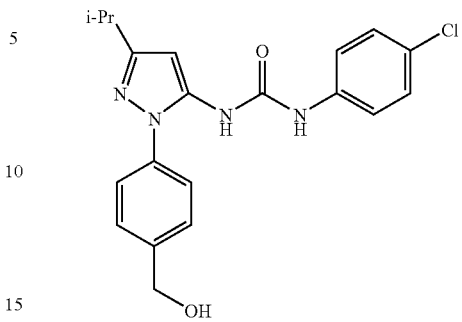

Using the same procedureas for Example 1, A84 (1.37 g, 5.0 mmol) and 1-chloro-4-isocyanatobenzene (0.9 g, 60 mol) were combined to afford ethyl 4-{5-[3-(4-chlorophenyl)ureido]-3-isopropyl-1H-pyrazol-1-yl}benzoate (1.3 g, 61% yield).

Using the same procedureas for Example 2, ethyl 4-{5-[3-(4-chlorophenyl)ureido]-3-isopropyl-1H-pyrazol-1-yl}benzoate (100 mg, 0.23 mmol) was reduced to afford 1-(4-chlorophenyl)-3-{1-[4-(hydroxymethyl)phenyl]-3-isopropyl-1H-pyrazol-5-yl}urea (80 mg, 91% yield). $^1$H NMR (400 MHz, DMSO-$d_6$): δ 9.15 (brs, 1H), 8.70 (brs, 1H), 7.46-7.36 (m, 6H), 7.26 (d, J=8.8 Hz, 2H), 6.25 (s, 1H), 5.28 (t, J=6.0 Hz, 1H), 4.52 (d, J=5.2 Hz, 2H), 2.85 (m, 1H), 1.20 (d, J=6.8 Hz, 6H).

Example A85

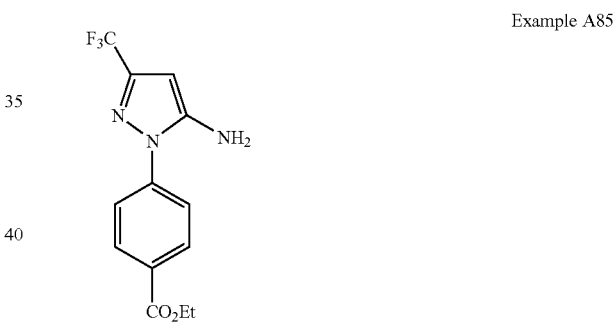

Using the same method as Example QQ, 4-hydrazinobenzoic acid ethyl ester (From Example A82, 3.0 g, 16.6 mmol) and commercially available 1N NH 4,4,4-trifluoro-3-oxobutyronitrile (3.4 g, 24.9 mmol) were combined to afford ethyl 4-[5-amino-3-(trifluoromethyl)-1H-pyrazol-1-yl]benzoate (4.5 g, 91% yield), which was used to the next reaction without further purification.

Example 553

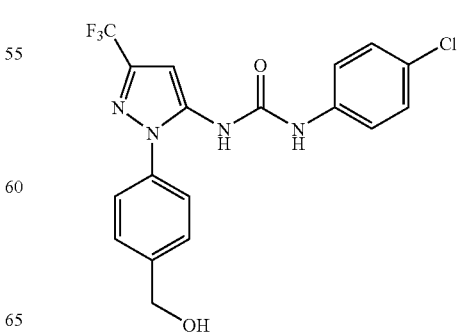

Using the same procedureas for Example 1, Example A85 (1.45 g, 5.0 mmol) and 1-chloro-4-isocyanatobenzene (0.9 g, 6.0 mol) were combined to afford ethyl 4-{5-[3-(4-chlorophenyl)ureido]-3-(trifluoromethyl)-1H-pyrazol-1-yl}benzoate (0.85 g, 38% yield). Using the same procedureas for Example 2, ethyl 4-{5-[3-(4-chlorophenyl)ureido]-3-(trifluoromethyl)-1H-pyrazol-1-yl}benzoate (100 mg, 0.22 mmol) was reduced to afford 1-(4-chlorophenyl)-3-{3-(trifluoromethyl)-1-[4-(hydroxymethyl)phenyl]-1H-pyrazol-5-yl}urea (80 mg, 89% yield). $^1$H NMR (400 MHz, DMSO-d$_6$): δ 9.65 (s, 1H), 9.09 (s, 1H), 7.54 (d, J=8.4 Hz, 2H), 7.48 (d, J=8.4 Hz, 2H), 7.41 (d, J=8.8 Hz, 2H), 7.28 (d, J=8.8 Hz, 2H), 6.81 (s, 1H), 5.36 (t, J=6.0 Hz, 1H), 4.56 (d, J=5.6 Hz, 2H).

Example 554

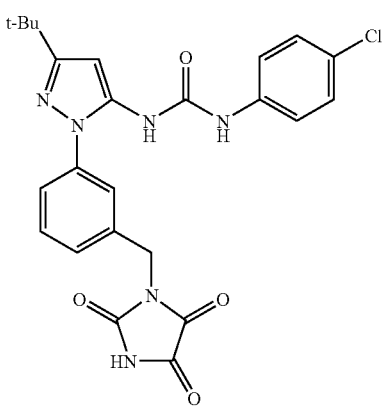

Using the same procedureas for Example 325, Example A62 (100 mg, 0.24 mmol), and Example A59 (29.0 mg, 0.24 mmol) were combined to afforded 1-{3-t-butyl-2-{3-[(2,4,5-trioxoimidazolidin-1-yl)methyl]phenyl}-1H-pyrazol-3-yl}-3-(4-chlorophenyl)urea (55 mg, 46% yield). $^1$H NMR (300 MHz, DMSO-d$_6$): δ 12.10 (s, 1H), 9.00 (s, 1H), 8.45 (s, 1H), 7.50-7.35 (m, 6H), 7.28 (d, J=8.7 Hz, 2H), 6.37 (s, 1H), 4.70 (s, 2H), 1.27 (s, 9H).

Example 555

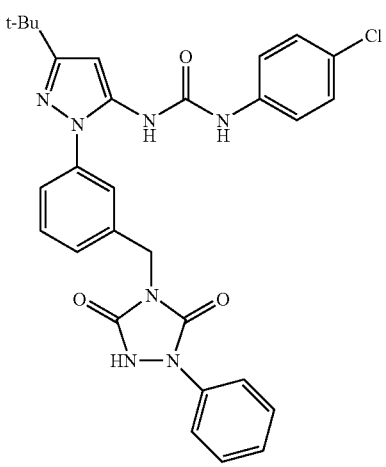

A mixture of 1-phenylurazole (70 mg, 0.4 mmol), DMF (5 mL) and NaH (5 mg, 0.2 mmol) under Ar at 0° C. was stirred for 30 min. Example A62 (83 mg, 0.2 mmol) was added at 0° C., reaction mixture was warmed to RT, stirred for 8 h, quenched with water (25 mL), and extracted with EtOAc (2×25 mL). The combined organic extracts were washed with water and brine, dried (Na$_2$SO$_4$), concentrated under reduced pressureand purified by column chromatography to yield 1-(3-t-butyl-1-{3-[(3,5-dioxo-1-phenyl-1,2,4-triazolidin-4-yl)methyl]phenyl}-1H-pyrazol-5-yl)-3-(4-chlorophenyl) urea as a white solid (85 mg, 77% yield). $^1$H NMR (400 MHz, DMSO-d$_6$): □ 9.06 (s, 1H), 8.49 (s, 1H), 7.48-7.29 (m, 12H), 7.24 (s, 1H), 7.1-7.08 (m, 1H), 6.36 (s, 1H), 4.64 (s, 2H), 1.28 (s, 9H); MS (ESI) m/z: 558 (M+H$^+$).

Example A86

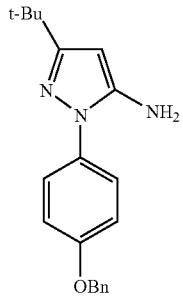

To a mixture of 4-nitrophenol (10.0 g, 71.9 mmol), K$_2$CO$_3$ (19.9 g, 143.9 mmol) and KI (2.6 g, 15.8 mmol) in acetonitrile was added chloromethylbenzene (10.0 g, 79.1 mmol) at RT. The resultant mixture was heated to reflux for 3 h. After removal of the solvent, the residue was dissolved in EtOAc. The combined organic extracts were washed with brine, dried (Na$_2$SO$_4$), filtered and concentrated to afford 4-benzyloxynitrobenzene (14.9 g, 90% yield). $^1$H NMR (400 MHz, CDCl$_3$): δ 8.20 (d, J=8.0 Hz, 2H), 7.43-7.37 (m, 5H), 7.03 (d, J=8.0 Hz, 2H), 5.17 (s, 2H).

A mixture of 4-benzyloxynitrobenzene (13.0 g, 56.5 mmol) and Raney-Ni (15.0 g) in EtOH (50 mL) was stirred at RT under 30 psi of H$_2$. The mixture was stirred at RT overnight, then filtered. The filtrate was concentrated to 4-benzyloxyphenylamine (10.5 g, 93% yield) as a brown solid. $^1$H NMR (400 MHz, CDCl$_3$): δ 7.43 (d, J=7.2 Hz, 2H), 7.38 (t, J=7.2 Hz, 1H), 7.32 (d, J=7.2 Hz, 2H), 6.83 (d, J=8.8 Hz, 2H), 6.65 (d, J=8.8 Hz, 2H), 5.00 (s, 2H), 2.94 (brs, 2H); MS (ESI) m/z: 200 (M+H$^+$).

Using the same method as Example OO, 4-benzyloxyphenylamine (10.0 g, 50.2 mmol) was converted to (4-benzyloxyphenyl)hydrazine hydrochloride (9.6 g, 76% yield) which was treated with commercially available 4,4-dimethyl-3-oxopentanenitrile (5.0 g, 40 mmol) to afford 3-t-butyl-1-(4-(benzyloxy)phenyl)-1H-pyrazol-5-amine (8.2 g, 85% yield). $^1$H NMR (400 MHz, DMSO-d$_6$): δ 10.2 (brs, 3H), 7.49-7.45 (m, 4H), 7.39 (t, J=7.2 Hz, 1H), 7.34-7.29 (m, 2H), 7.19 (d, J=8.8 Hz, 2H), 5.62 (s, 1H), 5.19 (s, 2H), 1.26 (s, 9H); MS (ESI) m/z: 322 (M+H$^+$).

Example 557

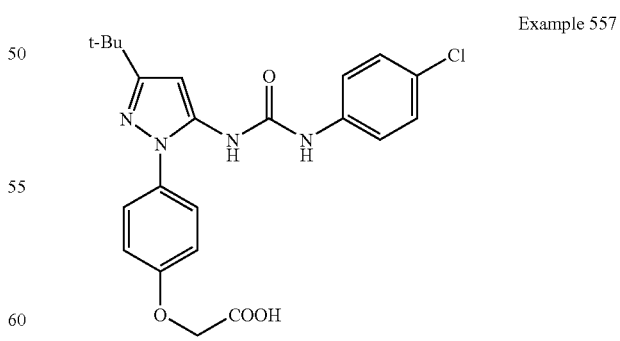

Using general method A, Example A86 (350 mg, 1.5 mmol) and 1-chloro-4-isocyanatobenzene (230 mg, 1.5 mmol) were combined to afford 1-(3-t-butyl-1-(4-hydroxyphenyl)-1H-pyrazol-5-yl)-3-(4-chlorophenyl)urea (120 mg, 20% yield). $^1$H NMR (300 MHz, DMSO-d$_6$): δ 9.82 (brs, 1H), 9.12 (s, 1H), 8.25 (s, 1H), 7.41 (d, J=9.0 Hz, 2H), 7.28 (d, J=9.0 Hz, 2H), 7.24 (d, J=8.7 Hz, 2H), 6.86 (d, J=8.7 Hz, 2H), 6.30 (s, 1H), 1.24 (s, 9H); MS (ESI) m/z: 385 (M+H⁺).

The material from the previous reaction, 1-(3-t-butyl-1-(4-hydroxyphenyl)-1H-pyrazol-5-yl)-3-(4-chlorophenyl)urea (120 mg, 0.31 mmol) and chloroacetic acid ethyl ester (76.5 mg, 0.62 mmol) were combined to afford 1-(3-t-butyl-1-(4-(carbomethoxymethyl)oxyphenyl)-1H-pyrazol-5-yl)-3-(4-chlorophenyl-1-yl)urea (110 mg, 75% yield) as a white solid. ¹H NMR (300 MHz, DMSO-d₆): δ 9.09 (s, 1H), 8.31 (s, 1H), 7.40 (d, J=5.4 Hz, 2H), 7.34 (d, J=5.4 Hz, 2H), 7.27 (d, J=9.0 Hz, 2H), 7.04 (d, J=9.0 Hz, 2H), 6.30 (s, 1H), 4.81 (s, 2H), 4.16 (q, J=7.2 Hz, 2H), 1.24 (s, H), 1.20 (t, J=7.2 Hz, 3H); MS (ESI) m/z: 471 (M+H⁺).

Using the material from the previous reaction, 1-(3-t-butyl-1-(4-(carbomethoxymethyl)oxyphenyl)-1H-pyrazol-5-yl)-3-(4-chlorophenyl-1-yl)urea (60 mg, 0.13 mmol) was saponified to afford 1-(3-t-butyl-1-(4-(carboxymethyl)oxyphenyl)-1H-pyrazol-5-yl)-3-(4-chlorophenyl-1-yl)urea (40 mg, 71% yield) as a white solid. ¹H NMR (300 MHz, DMSO-d₆): δ 9.14 (s, 1H), 8.35 (s, 1H), 7.40 (d, J=6.9 Hz, 2H), 7.37 (d, J=6.9 Hz, 2H), 7.27 (d, J=9.0 Hz, 2H), 7.02 (d, J=9.0 Hz, 2H), 6.30 (s, 1H), 4.71 (s, 2H), 1.23 (s, 9H); MS (ESI) m/z: 443 (M+H⁺).

Example 558

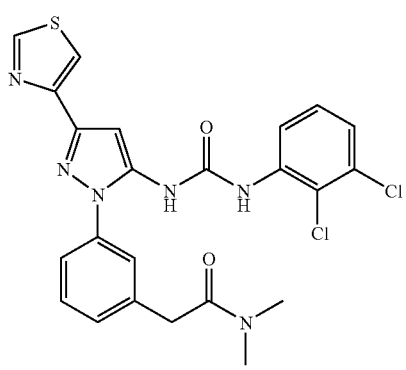

Using general method I, Example 352 (88 mg, 0.18 mmol) N,N-dimethylamine hydrochloride (0.044 g, 0.54 mmol) were combined to yield 1-(2,3-dichlorophenyl)-3-(1-(3-(2-(dimethylamino)-2-oxoethyl)phenyl)-3-(thiazol-4-yl)-1H-pyrazol-5-yl)urea (46 mg, 51% yield) as a pale yellow colored solid. ¹H NMR (300 MHz, DMSO-d₆): δ 9.50 (s, 1H), 9.19 (s, 1H), 8.90 (s, 1H), 8.10 (dd, J=7.2 Hz, and 2.8 Hz, 1H), 8.06-8.01 (m, 2H), 7.54-7.47 (m, 3H), 7.39-7.31 (m, 3H), 6.91 (s, 1H), 3.51 (s, 2H), 2.56 (d, J=4.4 Hz, 3H); MS (ESI) m/z: 501.1 (M+H⁺).

Example 559

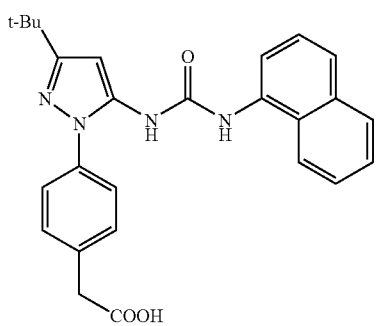

Using General method A, Example A17 (5 g, 0.014 mol) and 1-isocyanatonaphthalene (2.53 g, 0.015 mol) were combined to afford {4-[3-t-butyl-5-(3-naphthalen-1-ylureido)pyrazol-1-yl]phenyl}acetic acid ethyl ester (0.6 g, 25% yield) as a white solid. MS (ESI) m/z: 471 (M+H⁺). This compound was saponified using General method E to yield {4-[3-t-butyl-5-(3-naphthalen-1-ylureido)pyrazol-1-yl]phenyl}acetic acid (0.4 g, 99% yield) as a white solid. ¹H NMR (300 MHz, DMSO-d₆): δ 9.05 (s, 1H), 8.84 (s, 1H), 8.00-7.40 (m, 1H), 6.38 (s, 1H), 3.64 (s, 1H), 1.25 (s, 9H); MS (ESI) m/z: 443 (M+H⁺).

Example 560

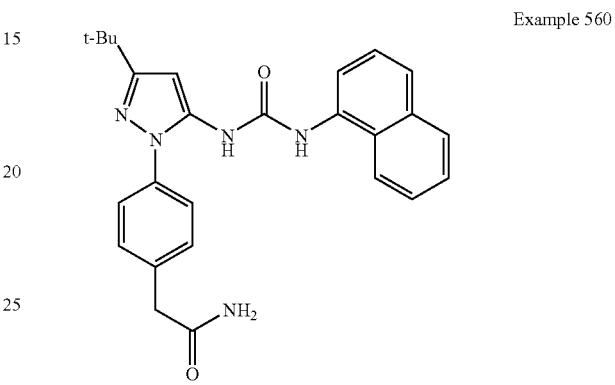

To a solution of {4-[3-t-butyl-5-(3-naphthalen-1-yl-ureido)pyrazol-1-yl]phenyl}acetic acid ethyl ester (150 mg, 0.32 mmol, intermediate in Example 559) in MeOH (2 mL) was added NH₃/MeOH (10 mL) at RT. The mixture was stirred at that temperature overnight. After removal of the solvent, the crude product was purified by preparative HPLC to afford 2-{4-[3-t-butyl-5-(3-naphthalen-1-ylureido)pyrazol-1-yl]phenyl}acetamide (48 mg, 31% yield). ¹H NMR (300 MHz, CD₃OD): δ 7.87 (m, 2H), 7.76 (d, J=5.4 Hz, 1H), 7.68 (d, J=6.0 Hz, 1H), 7.53-7.42 (m, 7H), 6.57 (s, 1H), 3.64 (s, 2H), 1.36 (s, 9H); MS (ESI) m/z: 442 (M+H⁺).

Example 561

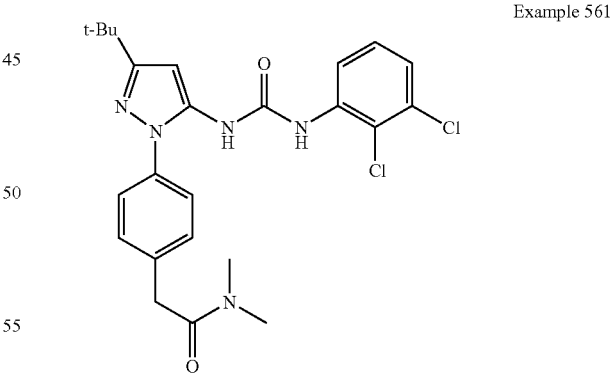

Using General method I, Example 385 (150 mg, 0.33 mmol) and Me₂NH HCl (80 mg, 0.398 mmol) were combined to afford 2-(4-{3-t-butyl-5-[3-(2,3-dichlorophenyl)ureido]pyrazol-1-yl}phenyl)N,N-dimethylacetamide (135 mg, 85% yield). ¹H NMR (300 MHz, DMSO-d₆): δ 9.29 (s, 1H), 8.81 (s, 1H), 8.06 (q, J=3.3 Hz 1H), 7.43 (d, J=8.1 Hz, 2H), 7.35 (d, J=8.4 Hz, 2H), 7.29 (t, J=3.0 Hz, 2H), 6.37 (s, 1H), 3.74 (s, 2H), 3.03 (s, 3H), 2.83 (s, 3H), 1.25 (s, 9H); MS (ESI) m/z: 488 (M+H⁺).

Example 562

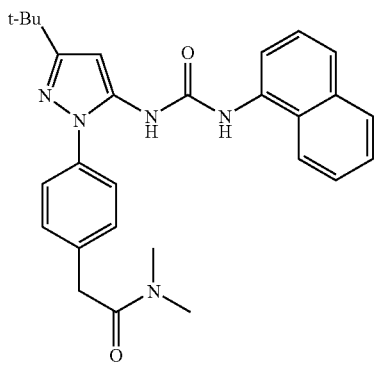

Using General method I, Example 559 (250 mg, 0.56 mmol) and salt (50 mg, 1.1 mmol) were combined to afford 2-{4-[3-t-butyl-5-(3-naphthalen-1-yl-ureido)pyrazol-1-yl]phenyl}-N,N-dimethylacetamide (46 mg, 17% yield). $^1$H NMR (300 MHz, DMSO-$d_6$): δ 9.06 (s, 1H), 8.83 (s, 1H), 7.97 (d, J=7.5 Hz, 1H), 7.90-7.87 (m, 2H), 7.61 (d, J=8.1 Hz, 1H), 7.53-7.35 (m, 7H), 6.37 (s, 1H), 3.74 (s, 2H), 3.00 (s, 3H), 2.81 (s, 3H), 1.24 (s, 9H); MS (ESI) m/z: 470 (M+H$^+$).

Example A87

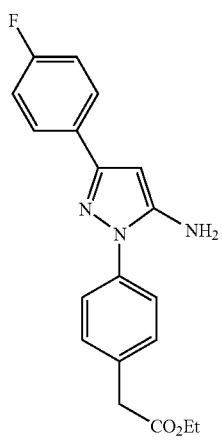

To an ice-cold bath solution of 4-fluorobenzoic acid (100 g, 0.714 mmol) in ethanol was dropwise added SOCl$_2$ (140 mL, 2.14 mol). After 30 min the ice bath was removed and the solution was heated to reflux overnight. The reaction was monitored with TLC and LC-MS until completion. After evaporation of the solvent, the mixture was diluted with the aqueous solution of K$_2$CO$_3$ and EtOAc. The organic phase was collected and dried over sodium sulfate and concentrated to the product of ethyl 4-fluorobenzoate (119 g, 99% yield). $^1$H-NMR (300 MHz, DMSO-$d_6$): δ 8.06 (d, J=6.0 Hz, 2H), 7.10 (d, J=9.0 Hz, 2H), 4.36 (q, J=10.8 Hz, 2H), 1.39 (t, J=7.5 Hz, 3H).

Using general method L, ethyl 4-fluorobenzoate (119 g, 0.71 mol) and MeCN (75 mL) were combined to afford 3-(4-fluorophenyl)-3-oxopropionitrile (100 g, 86% yield). $^1$H NMR (300 MHz, CDCl$_3$): δ 7.98-7.94 (m, 2H), 7.22 (d, J=6.6 Hz, 2H), 4.07 (s, 2H).

Using general method M, (4-hydrazinophenyl)acetic acid ethyl ester (36 g, 0.217 mol) and 3-(4-fluorophenyl)-3-oxopropionitrile (38 g, 0.26 mol) were combined to yield {4-[5-amino-3-(4-fluorophenyl)pyrazol-1-yl]phenyl}acetic acid ethyl ester (50 g, 68% yield). $^1$H NMR (300 MHz, CDCl$_3$): δ 7.80 (s, 2H), 7.40 (m, 4H), 7.00 (m, 2H), 6.29 (s, 1H), 4.07 (q, J=3.9 Hz, 2H), 3.53 (s, 2H), 1.23 (t, J=3.9 Hz, 3H); MS (ESI) m/z: 340 (M+H$^+$).

Example 563

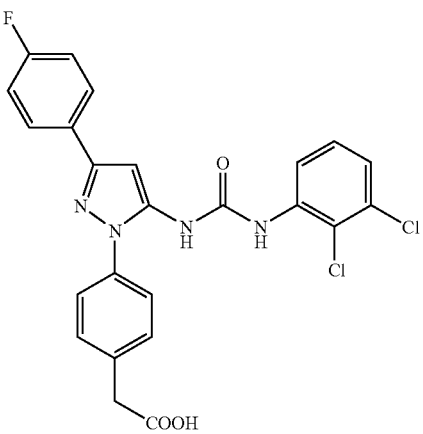

Using General method A, Example A87 (8 g, 0.024 mol) 1,2-dichloro-3-isocyanatobenzene (3.7 mL, 0.028 mol) were combined to afford {4-[5-[3-(2,3-dichlorophenyl)ureido]-3-(4-fluorophenyl)pyrazol-1-yl]phenyl}acetic acid ethyl ester (5 g, 40% yield). MS (ESI) m/z: 527 (M+H$^+$). Using General method E, {4-[5-[3-(2,3-dichlorophenyl)ureido]-3-(4-fluorophenyl)pyrazol-1-yl]phenyl}acetic acid ethyl ester (5 g, 9.5 mmol) was saponified to yield of {4-[5-[3-(2,3-dichlorophenyl)ureido]-3-(4-fluorophenyl)pyrazol-1-yl]phenyl}acetic acid (2.6 g, 55% yield). $^1$H NMR (300 MHz, DMSO-$d_6$): δ 9.34 (s, 1H), 8.84 (s, 1H), 8.09-8.02 (m, 1H), 7.87-7.82 (m, 2H), 7.54 (d, J=4.2 Hz, 2H), 7.42 (d, J=4.2 Hz, 2H), 7.33-7.29 (m, 1H), 7.22 (t, J=9.0 Hz, 2H), 6.82 (s, 1H), 3.66 (s, 2H); MS (ESI) m/z: 499 (M+H$^+$).

Example 564

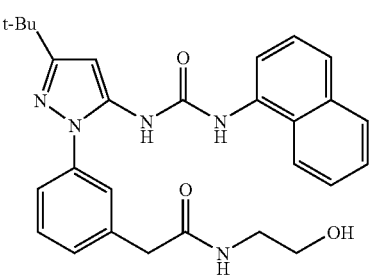

To a solution of 2-(3-(3-t-butyl-5-(3-(naphthalen-1-yl)ureido)-1H-pyrazol-1-yl)phenyl)acetic acid (200 mg, 0.43 mmol) in THF (10 mL) was added 2-amino-ethanol (260 mg, 4.3 mmol) and Et$_3$N (0.5 mL), then this mixture was heated to 40° C. and stirred overnight. After removal of the solvent, this mixture was extracted with EtOAc and washed with 1N HCl aqueous solution and the organic layer was dried over Na$_2$SO$_4$. After removal of the solvent, a crude product was obtained, which was purified by preparative HPLC to afford 2-{3-[3-t-butyl-5-(3-naphthalen-1-yl-ureido)pyrazol-1-yl]phenyl}-N-(2-hydroxy-ethyl)acetamide (104 mg, 50% yield). $^1$H NMR (300 MHz, DMSO-d$_6$): δ 9.01 (s, 1H), 8.81 (s, 1H), 8.12 (m, 1H), 7.98 (d, J=9.3 Hz, 1H), 7.92-7.87 (m, 2H), 7.61 (d, J=8.1 Hz, 1H), 7.53-7.49 (m, 2H), 7.47-7.38 (m, 4H), 7.29 (d, J=7.5 Hz, 1H), 6.39 (s, 1H), 3.49 (s, 2H), 3.35 (t, J=6.0 Hz, 2H), 3.07 (q, J=6.0 Hz, 2H), 1.25 (s, 9H); MS (ESI) m/z: 487 (M+H$^+$).

Example 565

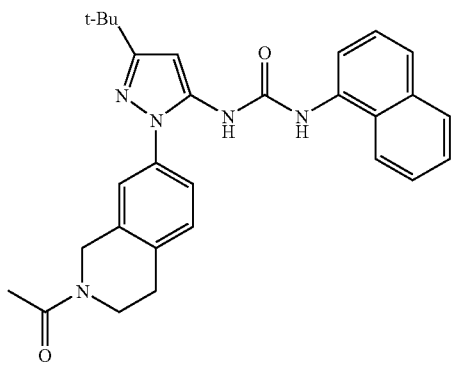

Example 349 (100 mg, 0.456 mmol) was acetylated to afford 1-[2-(2-acetyl-1,2,3,4-tetrahydroisoquinolin-7-yl)-5-t-butyl-2H-pyrazol-3-yl]-3-(3-fluorophenyl)urea (60 mg, 90% yield) as a white solid. $^1$H NMR (300 MHz, CD$_3$OD): δ 7.85 (m, 2H), 7.70 (m, 2H), 7.44-7.51 (m, 3H), 7.40 (s, 3H), 6.53 (d, J=11.1 Hz, 1H), 4.77 (d, J=5.4 Hz, 2H), 3.71 (q, J=8.4 Hz, 2H), 3.01 (m, J=19.2 Hz, 2H), 2.19 (d, J=7.7 Hz, 3H), 1.35 (s, 9H); MS (ESI) m/z: 482 (M+H$^+$).

Example 566

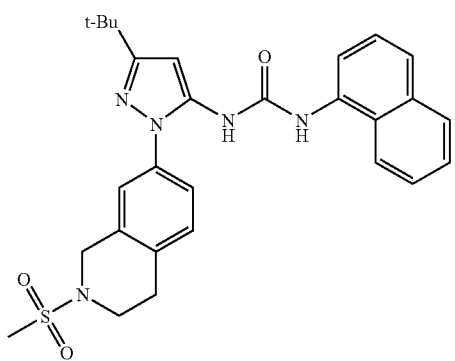

Example 349 (100 mg, 0.456 mmol) and methanesulfonyl chloride (63 mg, 0.274 mmol) were combined to afford 1-[5-t-butyl-2-(2-methanesulfonyl-1,2,3,4-tetrahydroisoquinolin-7-yl)-2 H-pyrazol-3-yl]-3-(3-fluorophenyl)urea (60 mg, 87% yield) as 0%, a white solid. $^1$H NMR (300 MHz, DMSO-d$_6$): δ 9.11 (s, 1H), 8.89 (s, 1H), 8.03 (m, 1H), 7.89-7.87 (m, 2H), 7.61 (m, 1H), 7.52-7.49 (m, 2H), 7.44 (m, 1H), 7.39-7.34 (m, 3H), 6.36 (s, 1H), 4.43 (s, 2H), 3.43 (m, J=11.4, 2H), 2.93 (m, 5H), 1.24 (s, 9H); MS (ESI) m/z: 518 (M+H$^+$).

Example 567

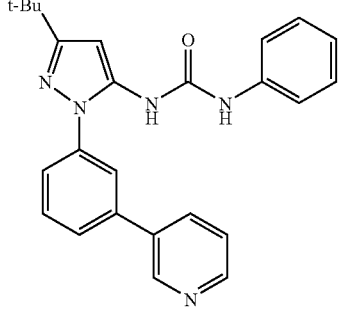

Using general method A, Example A20 (200 mg, 0.61 mmol) and isocyanatobenzene (73 mg, 0.61 mmol) were combined to afford 1-[5-t-butyl-2-(3-pyridin-3-ylphenyl)-2H-pyrazol-3-yl]-3-phenylurea (185 mg, 74% yield). $^1$H NMR (300 MHz, DMSO-d$_6$): δ 9.08 (s, 1H), 8.98 (s, 1H), 8.60 (d, J=5.4 Hz, 1H), 8.51 (s, 1H), 8.23 (d, J=6.6 Hz, 1H), 7.84 (s, 1H), 7.75 (d, J=6.9 Hz, 1H), 7.66-7.56 (m, 3H) 7.34 (d, J=8.1 Hz, 2H), 7.20 (t, J=7.8 Hz, 2H), 6.91 (t, J=6.9 Hz, 1H), 6.37 (s, 1H), 1.25 (s, 9H); MS (ESI) m/z: 412 (M+H$^+$).

Example 568

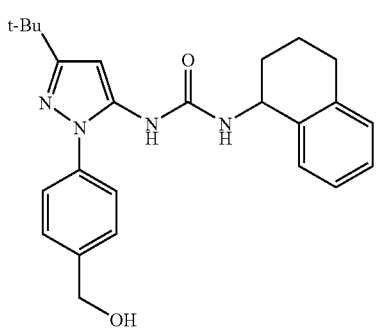

Using general method B, Example A18 (287 mg, 1.0 mmol), and 1,2,3,4-tetrahydro-naphthalen-1-ylamine (147 mg, 1.0 mmol) were combined to afford ethyl 4-(3-t-butyl-5-(3-(1,2,3,4-tetrahydronaphthalen-4-yl)ureido)-1H-pyrazol-1-yl)benzoate (245 mg, 59% yield).

Using general method E, ethyl 4-(3-t-butyl-5-(3-(1,2,3,4-tetrahydronaphthalen-4-yl)ureido)-1H-pyrazol-1-yl)benzoate (230 mg, 0.50 mmol) was reduced to afford 1-(3-t-butyl-1-(4-(hydroxymethyl)phenyl)-1H-pyrazol-5-yl)-3-(1,2,3,4-tetrahydronaphthalen-4-yl)urea (170 mg, 81% yield). $^1$H NMR (300 MHz, DMSO-d$_6$): □ 7.97 (s, 1H), 7.38 (s, 4H), 7.14-7.04 (m, 4H), 6.92 (d, J=8.4 Hz, 1H), 6.29 (s, 1H), 5.27 (t, J=5.7 Hz, 1H), 4.74 (m, 1H), 4.52 (d, J=5.7 Hz, 2H), 2.70-2.62 (m, 2H), 1.85-1.63 (m, 4H), 1.23 (s, 9H). MS (ESI) m/z: 419 (M+H$^+$)

Example 569

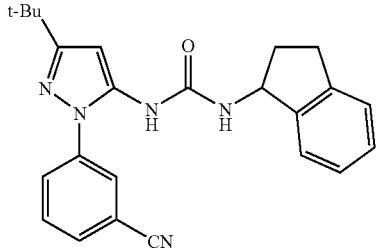

Using general method B, Example A3 (120 mg, 0.5 mmol), and indan-1-ylamine (133 mg, 1.0 mmol) were combined to afford 1-[3-t-butyl-1-(3-cyanophenyl)-1H-pyrazol-5-yl]-3-(2,3-dihydro-1 H-indan-1-yl)urea (52 mg, 26% yield). $^1$H NMR (300 MHz, DMSO-d$_6$): δ 8.17 (s, 1H), 7.94 (s, 1H), 7.83 (t, J=8.4 Hz, 2H), 7.67 (t, J=8.4 Hz, 1H), 7.19-7.08 (m, 4H), 6.92 (d, J=8.4 Hz, 1H), 6.31 (s, 1H), 5.04 (m, 1H), 2.86-2.73 (m. 2H), 2.34 (m, 1H), 1.70 (m, 1H), 1.24 (s, 9H); MS (ESI) m/z: 400 (M+H$^+$).

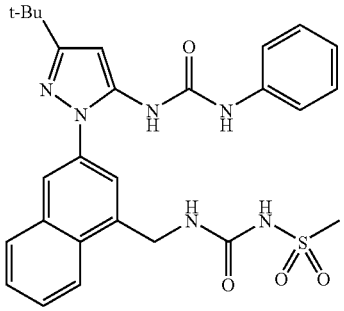

Example 570

A solution of Example 295 (130 mg, 0.32 mmoL), DMF (2 mL) and CDI (65 mg, 0.38 mmoL) was stirred at RT for 40 mins then was treated with a solution of CH$_3$SO$_2$NH$_2$ (36 mg, 0.38 mmoL) and NaH (16 mg, 0.4 mmoL) in DMF (2 mL). The reaction mixture was stirred overnight, then quenched with water and extracted with EtOAc (3×20 mL). The combined organic extracts were washed with brine, dried (Na$_2$SO$_4$), filtered, concentrated and purified via preparative TLC to yield 1-{3-t-butyl-1-[1-(methanesulfonylureidoamidomethyl)-naphthalen-3-yl]-1H-pyrazol-5-yl}-3-(phenyl) urea (50 mg, 29% yield). $^1$H NMR (300 MHz, DMSO-d$_6$): □ 9.21 (br s, 1H), 8.60 (br s, 1H), 8.15 (br s, 1H), 8.00 (m, 1H), 7.99 (s, 1H), 7.55-7.58 (m, 3H), 7.35 (d, J=7.8 Hz, 2H), 7.19 (t, J=7.8 Hz, 2H), 6.90 (t, J=7.8 Hz, 1H), 6.39 (s, 1H), 4.69 (s, 2H), 2.91 (s, 3H), 1.28 (s, 9H); MS (ESI) m/z: 535 (M+H$^+$)

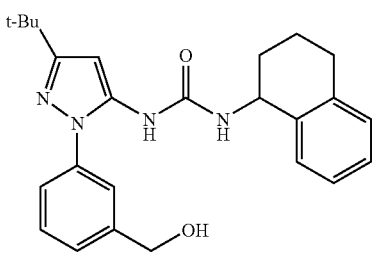

Example 571

Using general method D, Example A1 (143 mg, 0.5 mmol) and 1,2,3,4-tetrahydro-naphthalen-1-ylamine (67 mg, 0.5 mmol) were combined to afford ethyl 3-{3-t-butyl-5-[3-(1,2,3,4-tetrahydronaphthalen-1-yl)ureido]-1H-pyrazol-1-yl}benzoate (60 mg, 26% yield).

Using general method C, the previous compound (55 mg, 0.12 mmol) was reduced to afford 1-{3-t-butyl-1-[3-(hydroxymethyl)phenyl]-1H-pyrazol-5-yl}-3-(1,2,3,4-tetrahydronaphthalen-1-yl)urea (40 mg, 80% yield). $^1$H-NMR (300 MHz, DMSO-d$_6$): □ 7.97 (s, 1H), 7.44-7.38 (m, 2H), 7.30-7.28 (m, 2H), 7.17-7.02 (m, 4H), 6.90 (d, J=8.4 Hz, 1H), 6.30 (s, 1H), 4.74 (m, 1H), 4.52 (s, 2H), 2.71-2.64 (m, 2H), 1.70-1.65 (m, 4H), 1.24 (s, 9H); MS (ESI) m/z: 419 (M+H$^+$).

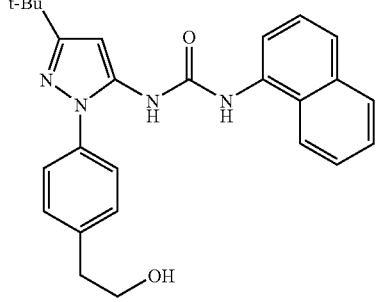

Example 572

Using general method A, Example A17 (5 g, 14.8 mmol) and 1-isocyanatonaphthalene (2.5 g, 15.0 mmol) were combined to afford ethyl 2-(4-{3-t-butyl-5-[3-(naphthalen-1-yl)ureido]-1H-pyrazol-1-yl}phenyl)acetate (1.7 g, 24% yield). MS (ESI) m/z: 471 (M+H$^+$).

Using general method C, the previous compound (80 mg, 0.17 mmol) was reduced to afford 1-{3-t-butyl-1-[4-(2-hydroxyethyl)phenyl]-1H-pyrazol-5-yl}-3-(naphthalen-1-yl) urea (50 mg, 69% yield). $^1$H NMR (DMSO-d$_6$): δ 9.05 (s, 1H), 8.79 (s, 1H), 8.00 (d, J=7.2 Hz, 1H), 7.93-7.89 (m, 2H), 7.63 (d, J=8.1 Hz, 1H), 7.55-7.51 (m, 2H), 7.47-7.37 (m, 5H), 6.39 (s, 1H), 4.68 (t, J=5.1 Hz, 1H), 3.65 (q, J=7.2 Hz, 2H), 2.79 (t, J=6.9 Hz, 2H), 1.26 (s, 9H). MS (ESI) m/z: 429 (M+H$^+$).

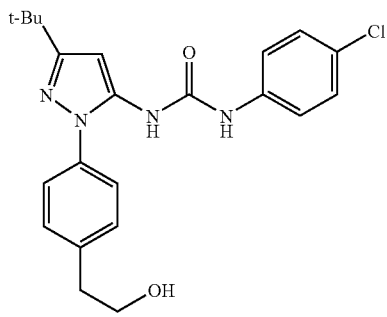

Example 573

Using general method A, Example A17 (5 g, 14.8 mmol) and 1-chloro-4-isocyanato-benzene (2.2 g, 15.0 mmol) were combined to afford ethyl 2-(4-{3-t-butyl-5-[3-(4-chlorophenyl)ureido]-1H-pyrazol-1-yl}phenyl)acetate (2.7 g, 40% yield). $^1$H NMR (DMSO-d$_6$): δ 9.12 (s, 1H), 8.42 (s, 1H), 7.46-7.37 (m, 6H), 7.28 (d, J=8.1 Hz, 2H), 6.34 (s, 1H), 4.08 (q, J=7.2 Hz, 2H), 2.79 (t, J=7.2 Hz, 2H), 3.72 (s, 2H), 1.25 (s, 9H), 1.18 (t, J=7.2 Hz, 3H); MS (ESI) m/z: 455 (M+H$^+$).

Using general method C, the previous compound (100 mg, 0.22 mmol) was reduced to afford 1-{3-t-butyl-1-[4-(2-hydroxyethyl)phenyl]-1H-pyrazol-5-yl}-3-(4-chlorophenyl) urea (65 mg, 72% yield). $^1$H NMR (DMSO-d$_6$): δ 9.57 (s, 1H), 8.92 (s, 1H), 7.45-7.39 (m, 4H), 7.34-7.25 (m, 4H), 6.30 (s, 1H), 4.65 (t, J=5.1 Hz, 1H), 3.62 (q, J=7.2 Hz, 2H), 2.70 (t, J=6.9 Hz, 2H), 1.25 (s, 9H). MS (ESI) m/z: 413 (M+H$^+$).

Example A88

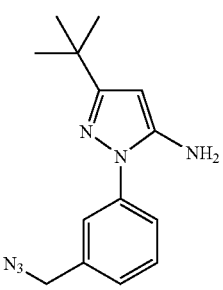

Using general method C, Example A1 (20.0 g, 69.6 mmol) was reduced to afford [3-(5-amino-3-t-butyl-1H-pyrazol-1-yl)phenyl]methanol (15.2 g, 89%). ¹H NMR (DMSO-d₆): 7.49 (s, 1H), 7.37 (m, 2H), 7.19 (d, J=7.2 Hz, 1H), 5.35 (s, 1H), 5.25 (t, J=5.6 Hz, 1H), 5.14 (s, 2H), 4.53 (d, J=5.6 Hz, 2H), 1.19 (s, 9H); MS (ESI) m/z: 246.19 (M+H⁺).

The crude material from the previous reaction (5.0 g, 20.4 mmol) was dissolved in dry THF (50 mL) and SOCl₂ (4.85 g, 40.8 mmol), stirred for 2 h at RT, concentrated in vacuo to yield 3-t-butyl-1-(3-chloromethylphenyl)-1H-pyrazol-5-amine (5.4 g), which was added to NaN₃ (3.93 g, 60.5 mmol) in DMF (50 mL). The reaction mixture was heated at 30° C. for 2 h, poured into H₂O (50 mL), and extracted with CH₂Cl₂. The organic layers were combined, dried (MgSO₄), filtered and concentrated in vacuo to yield crude 3-t-butyl-1-[3-(azidomethyl)phenyl]-1H-pyrazol-5-amine (1.50 g, 5.55 mmol).

Example 574

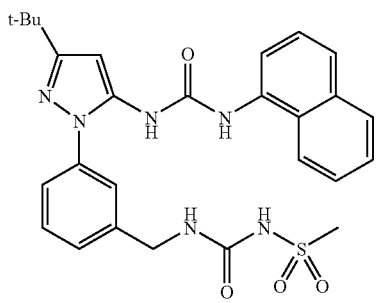

Using general method A, Example A88 and 1-isocyano naphthalene (1.13 g, 6.66 mmol) were combined to yield 1-[2-(3-azidomethyl-phenyl)-5-t-butyl-2H-pyrazol-3-yl]-3-naphthalen-1-yl-urea (2.4 g, 98%) as a white solid.

The crude material from the previous reaction and 10% Pd/C (0.4 g) in THF (30 mL) was reduced under H₂ (1 atm) at RT for 2 h. The catalyst was removed by filtration and the filtrate concentrated in vacuo to yield 1-(3-t-butyl-1-(3-(aminomethyl)phenyl)-1H-pyrazol-5-yl)-3-(naphthalen-1-yl) urea (2.2 g, 96%) as a yellow solid. ¹H NMR (DMSO-d₆): 9.02 (s, 1H), 7.91 (d, J=7.2 Hz, 1H), 7.89 (d, J=7.6 Hz, 2H), 7.67-7.33 (m, 9H), 6.40 (s, 1H), 3.81 (s, 2H), 1.27 (s, 9H); MS (ESI) m/z: 414 (M+H⁺).

The material from the previous reaction, 1-(3-t-butyl-1-(3-(aminomethyl)phenyl)-1H-pyrazol-5-yl)-3-(naphthalen-1-yl)urea (100 mg, 0.24 mmol) and methanesulfonamide (500 mg, 5.0 mmol) were combined to yield N-{7-[3-t-butyl-5-(3-naphthalen-1-yl-ureido)-pyrazol-1-yl]-3-benzylamine-2-carbonyl}methanesulfonamide (45 mg, 35% yield). ¹H-NMR (300 MHz, DMSO-d₆): δ 10.35 (s, 1H), 9.15 (s, 1H), 8.88 (s, 1H), 8.00 (d, J=8.1 Hz, 1H), 7.85-7.91 (m, 2H), 7.61 (d, J=6.0 Hz, 2H), 7.40-7.53 (m, 6H), 7.27 (d, J=6.9 Hz, 1H), 7.15 (t, J=6.9 Hz, 1H), 6.39 (s, 1H), 4.33 (d, J=5.4 Hz, 2H), 3.18 (s, 3H), 1.27 (s, 9H).

Example 575

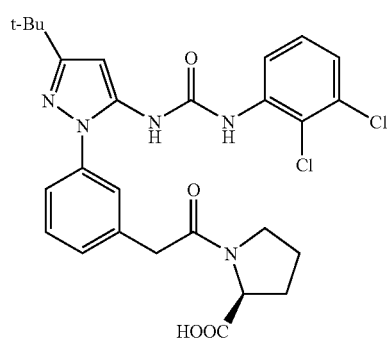

Using general method J, Example 373 (200 mg, 0.44 mmol) and (S)-pyrrolidine-2-carboxylic acid methyl ester hydrochloride (100 mg, 0.60 mmol) were combined to afford (2S)-methyl-1-[2-(3-{3-t-butyl-5-[3-(2,3-dichlorophenyl)-ureido]-1H-pyrazol-1-yl}phenyl)acetyl]pyrrolidine-2-carboxylate (165 mg, 66% yield). ¹H-NMR (300 MHz, DMSO-d₆): 19.23 (s, 1H), 8.75 (s, 1H), 8.04 (m, 1H), 7.46-7.23 (m, 6H), 6.35 (s, 1H), 4.25 (m, 1H), 3.74 (s, 2H), 3.57-3.55 (m, 2H), 3.54 (s, 3H), 1.85-1.74 (m, 4H), 1.23 (s, 9H); MS (ESI) m/z: 572 (M+H⁺).

Using general method E, (2S)-methyl-1-[2-(3-{3-t-butyl-5-[3-(2,3-dichlorophenyl)-ureido]-1H-pyrazol-1-yl}phenyl) acetyl]pyrrolidine-2-carboxylate (100 mg, 0.22 mmol) was saponified to afford (2S)-1-[2-(3-{3-t-butyl-5-[3-(2,3-dichlorophenyl)ureido]-1H-pyrazol-1-yl}phenyl)acetyl]pyrrolidine-2-carboxylic acid (68 mg, 55% yield). ¹H-NMR (300 MHz, DMSO-d₆): δ 9.28 (s, 1H), 8.78 (s, 1H), 8.04 (m, 1H), 7.46-7.25 (m, 6H), 6.34 (s, 1H), 4.17 (m, 1H), 3.73 (s, 2H), 3.35-3.50 (m, 2H), 1.73-2.05 (m, 4H), 1.27 (s, 9H); MS (ESI) m/z: 558 (M+H⁺).

Example 576

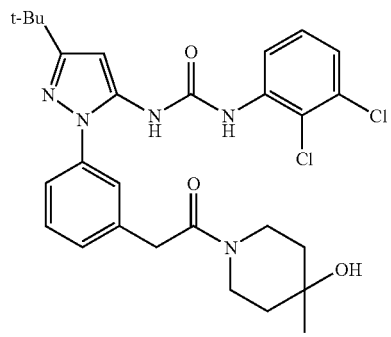

Example 373 (100 mg, 0.23 mmol) and 4-methyl-piperidin-4-ol (35 mg, 0.3 mmol) were combined to afford 1-(3-t-butyl-1-{3-[2-(4-hydroxy-4-methylpiperidin-1-yl)-2-oxoethyl]phenyl}-1H-pyrazol-5-yl)-3-(2,3-dichlorophenyl)urea (50 mg, 39% yield). ¹H NMR (300 MHz, DMSO-d$_6$): δ 9.20 (s, 1H), 8.74 (s, 1H), 8.02 (m, 1H), 7.45-7.20 (m, 6H), 6.35 (s, 1H), 3.90 (m, 1H), 3.75 (s, 2H), 3.57 (m, 1H), 3.31 (m, 1H), 2.95 (m, 1H), 1.41-1.25 (m, 4H), 1.24 (s, 9H), 1.04 (s, 3H); MS (ESI) m/z: 558 (M+H⁺).

yl)urea (400 mg, 63% yield). ¹H NMR (300 MHz, DMSO-d$_6$): δ 9.55 (s, 1H), 9.33 (s, 1H), 9.05 (m, 2H), 8.22 (d, J=7.8 Hz, 1H), 7.69 (d, J=8.1 Hz, 1H), 7.43-7.28 (m, 3H), 6.38 (s, 1H), 4.30 (m, 2H), 3.34 (m, 2H), 3.00 (t, J=6.9 Hz, 2H), 1.25 (s, 9H); MS (ESI) m/z: 447 (M+H⁺).

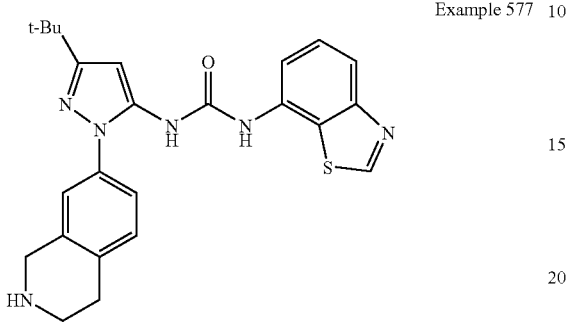

Example 577

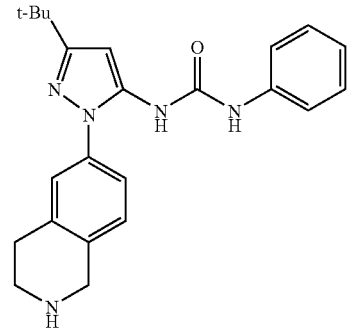

Example 578

Using general method B, Example A34 (1.0 g, 3.5 mmol) benzo[d]thiazol-6-amine (1.0 g, 7.0 mmol) were combined to yield 1-(benzo[d]thiazol-6-yl)-3-(3-butyl-1-(1-oxo-1,2,3,4-tetrahydroisoquinolin-7-yl)-1H-pyrazol-5-yl)urea (650 mg, 41% yield) as a white solid. ¹H NMR (300 MHz, DMSO-d$_6$): δ 9.22 (s, 1H), 9.17 (s, 1H), 8.52 (s, 1H), 8.28 (s, 1H), 8.06 (s, 1H), 7.93-7.90 (m, 2H), 7.60 (m, 1H), 7.44-7.40 (m, 2H), 6.35 (s, 1H), 3.37 (t, J=6.6 Hz, 2H), 2.93 (t, J=6.6 Hz, 2H), 1.25 (s, 9H); MS (ESI): m/z: 461 (M+H⁺). Using general method C, 1-(benzo[d]thiazol-6-yl)-3-(3-butyl-1-(1-oxo-1,2,3,4-tetrahydroisoquinolin-7-yl)-1H-pyrazol-5-yl)urea (650 mg, 1.4 mmol) was reduced to afford 1-(benzo[d]thiazol-6-yl)-3-(3-butyl-1-(1,2,3,4-tetrahydroisoquinolin-7-yl)-1H-pyrazol-5-

Using general method A, Example A36 (0.15 g, 0.40 mmol) and phenylisocyanate (53 mg, 0.45 mmol) were combined to afford t-butyl 6-(3-t-butyl-5-(3-phenylureido)-1H-pyrazol-1-yl)-3,4-dihydroisoquinoline-2(1H)-carboxylate which was deprotected using general method F to yield 1-(3-t-butyl-1-(1,2,3,4-tetrahydroisoquinolin-6-yl)-1H-pyrazol-5-yl)-3-phenylurea HCl salt as white solid (0.14 g, 80% yield). ¹H NMR (400 MHz, DMSO-d$_6$): δ 9.37 (m, 2H), 8.68 (brs, 1H), 7.3-7.5 (m, 4H), 7.25 (m, 2H), 6.95 (t, J=7.2 Hz, 1H), 6.35 (s, 1H), 4.30 (m, 2H), 3.38 (m, 2H), 3.08 (t, J=6.0 Hz, 2H), 1.28 (s, 9H); MS (ESI) m/z: 390.2 (M+H⁺).

Using the general procedures outlined herein, the following examples were prepared.

| Example | Name | MS (EI) (M + H⁺) | ¹H NMR (400 MHz, DMSO-d$_6$) |
|---|---|---|---|
|  | ethyl 2-(4-(5-amino-3-(4-chlorophenyl)-1H-pyrazol-1-yl)phenyl)acetate | 356.1 |  |

-continued

| Example | Name | MS (EI) (M + H⁺) | ¹H NMR (400 MHz, DMSO-d₆) |
|---------|------|------------------|---------------------------|
| | ethyl 2-(4-(5-amino-3-(3-fluorophenyl)-1H-pyrazol-1-yl)phenyl)acetate | 340.1 | |
| | ethyl 2-(4-(5-amino-3-(2-fluorophenyl)-1H-pyrazol-1-yl)phenyl)acetate | 340.1 | |
| | ethyl 2-(4-(5-amino-3-(thiazol-4-yl)-1H-pyrazol-1-yl)phenyl)acetate | 329 | |

-continued

| Example | Name | MS (EI) (M + H⁺) | ¹H NMR (400 MHz, DMSO-d₆) |
|---|---|---|---|
| | ethyl 2-(4-(5-amino-3-cyclopentyl-1H-pyrazol-1-yl)phenyl)acetate | 314.2 | |
| | 2-(3-(3-phenyl-5-(3-(3-(pyridin-3-yloxy)phenyl)ureido)-1H-pyrazol-1-yl)phenyl)acetic acid 0.055 g, 87% yield | 506.0 | δ 8.38-8.35 (m, 2H), 7.84 (s, 1H), 7.82 (s, 1H), 7.59 (s, 1H), 7.43-7.26 (m, 12H), 7.17-7.15 (m, 1H), 6.83 (s, 1H), 6.64-6.62 (m, 1H), 3.56 (s, 2H) |
| | (S)-2-(4-(3-phenyl-5-(3-(1,2,3,4-tetrahydronaphthalen-1-yl)ureido)-1H-pyrazol-1-yl)phenyl)acetic acid | 467.2 | |
| | (S)-2-(4-(3-phenyl-5-(3-(1,2,3,4-tetrahydronaphthalen-1-yl)ureido)-1H-pyrazol-1-yl)phenyl)acetic acid | 467.2 | |

Abl Kinase Assay

Assay A1

The activity of Abl kinase was determined by following the production of ADP from the kinase reaction through coupling with the pyruvate kinase/lactate dehydrogenase system (e.g., Schindler, et al. Science (2000) 289, 1938-1942). In this assay, the oxidation of NADH (thus the decrease at $A_{340\ nm}$) was continuously monitored spectrophotometrically. The reaction mixture (100 μl) contained Abl kinase (1.9 nM, nominal concentration), peptide substrate (EAIYAAP-FAKKK, 0.2 mM), pyruvate kinase (3.5 units), lactate dehydrogenase (5.5 units), phosphoenolpyruvate (1 mM), and NADH (0.28 mM) in 60 mM Tris buffer containing 0.13% octyl-glucoside, 13 mM $MgCl_2$ and 3.5% DMSO at pH 7.5. The reaction was initiated by adding ATP (0.2 mM, final concentration). The absorption at 340 nm was continuously monitored for 3 h at 30° C. on a Polarstar Optima plate reader (BMG). The reaction rate was calculated using the 1 h to 2 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package.

Assay A2

Abl kinase assay A2 is the same as for assay A1 except that (1) a nominal concentration of 1.1 nM of enzyme was employed (2) the reaction was pre-incubated at 30° C. for 2 h prior to initiation with ATP (3) 0.5 mM ATP (final concentration) was used to initiate the reaction.

```
Abl protein sequence used for screening:
SPNYDKWEMERTDITMKHKLGGGQYGEVYEGVWKKYSLTVAVKTLKEDTM

EVEEFLKEAAVMKEIKHPNLVQLLGVCTREPPFYIITEFMTYGNLLDYLR

ECNRQEVNAVVLLYMATQISSAMEYLEKKNFIHRDLAARNCLVGENHLVK

VADFGLSRLMTGDTYTAHAGAKFPIKWTAPESLAYNKFSIKSDVWAFGVL

LWEIATYGMSPYPGIDLSQVYELLEKDYRMERPEGCPEKVYELMRACWQW

NPSDRPSFAEIHQAFETMFQESSISDEVEKELGK
```

KDR Kinase Assay

Assay K1

The activity of KDR kinase was determined by following the production of ADP from the kinase reaction through coupling with the pyruvate kinase/lactate dehydrogenase system (e.g., Schindler, et al. Science (2000) 289, 1938-1942). In this assay, the oxidation of NADH (thus the decrease at $A_{340\ nm}$) was continuously monitored spectrophotometrically. The reaction mixture (100 μl) contained KDR (1.5 nM to 7.1 nM, nominal concentration), polyE4Y (1 mg/ml), pyruvate kinase (3.5 units), lactate dehydrogenase (5.5 units), phosphoenolpyruvate (1 mM), and NADH (0.28 mM) in 60 mM Tris buffer containing 0.13% octyl-glucoside, 13 mM $MgCl_2$, 6.8 mM DTT, and 3.5% DMSO at pH 7.5. The reaction was initiated by adding ATP (0.2 mM, final concentration). The absorption at 340 nm was continuously monitored for 3 h at 30° C. on a Polarstar Optima plate reader (BMG). The reaction rate was calculated using the 1 h to 2 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package.

Assay K2

KDR kinase assay K2 is the same as for assay K1 except that (1) a nominal concentration of 2.1 nM of enzyme was employed (2) the reaction was pre-incubated at 30° C. for 2 h prior to initiation with ATP (3) 1.0 mM ATP (final concentration) was used to initiate the reaction.

```
KDR protein sequence used for screening:
DPDELPLDEHCERLPYDASKWEFPRDRLKLGKPLGRGAFGQVIEADAFGI

DKTATCRTVAVKMLKEGATHSEHRALMSELKILIHIGHHLNVVNLLGACT

KPGGPLMVIVEFCKFGNLSTYLRSKRNEFVPYKVAPEDLYKDFLTLEHLI

CYSFQVAKGMEFLASRKCIHRDLAARNILLSEKNVVKICDFGLARDIYKD

PDYVRKGDARLPLKWMAPETIFDRVYTIQSDVWSFGVLLWEIFSLGASPY

PGVKIDEEFCRRLKEGTRMRAPDYTTPEMYQTMLDCWHGEPSQRPTFSEL

VEHLGNLLQANAQQD
```

B-Raf(V599E) Kinase Assay

Assay B1

The activity of B-Raf(V599E) kinase was determined by following the formation of ADP from the reaction through coupling with the pyruvate kinase/lactate dehydrogenase system (e.g., Schindler, et al. Science (2000) 289, 1938-1942). In this assay, the oxidation of NADH (thus the decrease at $A_{340\ nm}$) was continuously monitored spectrophotometrically. The reaction mixture (100 μl) contained B-Raf(V599E) kinase (0.34 nM nominal concentration, construct 1), unphosphorylated, full-length MEK1 (42 nM), $MgCl_2$ (13 mM), pyruvate kinase (3.5 units), lactate dehydrogenase (5.5 units), phosphoenolpyruvate (1 mM), and NADH (0.28 mM), in 60 mM Tris buffer, containing 0.13% octyl-glucoside and 3.5% DMSO concentration at pH 7.5. The test compounds were incubated with the reaction mixture at 30° C. for 2 h. The reaction was initiated by adding ATP (0.2 mM, final concentration). The absorption at 340 nm was continuously monitored for 3 h at 30° C. on a Polarstar Optima plate reader (BMG). The reaction rate was calculated using the 1.5 h to 2.5 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package.

Assay B2

Same as assay B1 except that (1) construct 2 was employed at a nominal concentration of 2 nM (2) the reaction was pre-incubated at 30° C. for 1 h prior to initiation with ATP (3) a reading time frame of 0.5 h to 1.5 h.

```
B-Raf(V599E) construct 1 protein sequence used for
screening:
KSPGQRERKSSSSSEDRNRMKTLGRRDSSDDWEIPDGQITVGQRIGSGSF

GTVYKGKWHGDVAVKMLNVTAPTPQQLQAFKNEVGVLRKTRHVNILLFMG

YSTKPQLAIVTQWCEGSSLYHHLHIIETKFEMIKLIDIARQTAQGMDYLH

AKSIIHRDLKSNNIFLHEDLTVKIGDFGLATEKSRWSGSHQFEQLSGSIL
```

-continued
WMAPEVIRMQDKNPYSFQSDVYAFGIVLYELMTGQLPYSNINNRDQIIFM

VGRGYLSPDLSKVRSNCPKAMKRLMAECLKKKRDERPLFPQILASIELLA

RSLPKIHRSASEPSLNRAGFQTEDFSLYACASPKTPIQAGGYGAFPVH

B-Raf(V599E) construct 2 protein sequence used for screening:
EDRNRMKTLGRRDSSDDWEIPDGQITVGQRIGSGSFGTVYKGKWHGDVAV

KMLNVTAPTPQQLQAFKNEVGVLRKTRHVNILLFMGYSTKPQLAIVTQWC

EGSSLYHHLHIIETKFEMIKLIDIARQTAQGMDYLHAKSIIHRDLKSNNI

FLHEDLTVKIGDFGLATEKSRWSGSHQFEQLSGSILWMAPEVIRMQDKNP

YSFQSDVYAFGIVLYELMTGQLPYSNINNRDQIIFMVGRGYLSPDLSKVR

SNCPKAMKRLMAECLKKKR DERPLFPQILASIELLARSLPKIHR

MEK1 protein sequence used for screening:
MELKDDDFEKISELGAGNGGVVFKVSHKPSGLVMARKLIHLEIKPAIRNQ

IIRELQVLHECNSPYIVGFYGAFYSDGEISICMEHMDGGSLDQVLKKAGR

IPEQILGKVSIAVIKGLTYLREKHKIMHRDVKPSNILVNSRGEIKLCDFG

VSGQLIDSMANSFVGTRSYMSPERLQGTHYSVQSDIWSMGLSLVEMAVGR

YPIPPPDAKELELMFGCQVEGDAAETPPRPRTPGRPLSSYGMDSRPPMAI

FELLDYIVNEPPPKLPSGVFSLEFQDFVNKCLIKNPAERADLKQLMVHAF

IKRSDAEEVDFAGWLCSTIGLNQPSTPTHAAGV

P-38 Alpha Kinase Assay

Assay P1

The activity of phosphorylated p-38-alpha kinase was determined by following the formation of ADP from the kinase reaction through coupling with the pyruvate kinase/lactate dehydrogenase system (e.g., Schindler, et al. Science (2000) 289, 1938-1942). In this assay, the oxidation of NADH (thus the decrease at $A_{340\ nm}$) was continuously measured spectrophotometrically. The reaction mixture (100 µl) contained phosphorylated p-38 alpha kinase (7.1-9 nM nominal concentration), peptide substrate (IPTSPITTTYFFFKKK-OH, 0.2 mM), MgCl$_2$ (13 mM), pyruvate kinase (3.5 units), lactate dehydrogenase (5.5 units), phosphoenolpyruvate (1 mM), and NADH (0.28 mM) in 60 mM Tris buffer at pH 7.5, containing 130 uM n-Dodecyl-B-D-maltopyranoside and 3.5% DMSO concentration. The test compounds were incubated with the reaction mixture at 30° C. for 2 h before the addition of ATP (0.3 mM final concentration). The absorption at 340 nm was monitored continuously for up to 3 h at 30° C. on Polarstar Optima plate reader (BMG). The reaction rate was calculated using the time frame from 1.5 h to 2.5 h. Percent inhibition was obtained by comparison of reaction rate with that of a control (i.e. with no test compound). IC$_{50}$ values were calculated from a series of percent inhibition values determined at a range of inhibitor concentrations using software routines as implemented in the GraphPad Prism software package.

Assay P2

Same as assay P1 except that (1) the reaction was not pre-incubated.

P38-alpha protein sequence used for screening:
MSQERPTFYRQELNKTIWEVPERYQNLSPVGSGAYGSVCAAFDTKTGLRV

AVKKLSRPFQSIIHAKRTYRELRLLKHMKHENVIGLLDVFTPARSLEEFN

-continued
DVYLVTHLMGADLNNIVKCQKLTDDHVQFLIYQILRGLKYIHSADIIHRD

LKPSNLAVNEDCELKILDFGLARHTDDEMTGYVATRWYRAPEIMLNWMHY

NQTVDIWSVGCIMAELLTGRTLFPGTDHINQLQQIMRLTGTPPAYLINRM

PSHEARNYIQSLTQMPKMNFANVFIGANPLAVDLLEKMLVLDSDKRITAA

QALAHAYFAQYHDPDDEPVADPYDQSFESRDLLIDEWKSLTYDEVISFVP

PPLDQEEMES

| Abl Kinase Assay Data | | |
|---|---|---|
| Example | Abl Data | Method |
| 1 | 0.31 | A1 |
| 2 | 2.0 | A1 |
| 3 | 8.4 | A1 |
| 4 | 2.9 | A1 |
| 5 | 2.0 | A1 |
| 6 | 3.0 | A1 |
| 7 | 5.2 | A1 |
| 8 | 81% @ 10 µM | A1 |
| 9 | 0.18 | A1 |
| 10 | 4.3 | A1 |
| 11 | 5.1 | A1 |
| 12 | 0.39 | A1 |
| 13 | 2.0 | A1 |
| 14 | 2.4 | A1 |
| 15 | 0.39 | A1 |
| 16 | 5.9 | A1 |
| 17 | 0.37 | A1 |
| 18 | 0.83 | A1 |
| 19 | 0.62 | A1 |
| 20 | 1.6 | A1 |
| 21 | 0.0018 | A2 |
| 22 | 0.0022 | A2 |
| 23 | 3.8 | A1 |
| 24 | 0.83 | A1 |
| 25 | 0.67 | A1 |
| 26 | 0.021 | A2 |
| 27 | 0.063 | A1 |
| 28 | 0.023 | A2 |
| 29 | 0.0066 | A2 |
| 30 | 0.11 | A2 |
| 31 | 0.077 | A2 |
| 32 | 0.29 | A2 |
| 33 | 0.25 | A2 |
| 34 | 1.6 | A1 |
| 35 | 1.2 | A1 |
| 36 | 0.72 | A1 |
| 37 | 1.4 | A1 |
| 38 | 1.4 | A2 |
| 39 | 0.35 | A1 |
| 40 | 0.57 | A1 |
| 41 | 3.7 | A1 |
| 42 | 1.5 | A1 |
| 43 | 0.68 | A1 |
| 44 | 0.44 | A1 |
| 45 | 0.78 | A1 |
| 46 | 2.5 | A1 |
| 48 | 4.2 | A1 |
| 50 | 0.38 | A1 |
| 51 | 0.052 | A2 |
| 52 | 0.14 | A1 |
| 53 | 0.36 | A1 |
| 54 | 0.12 | A1 |
| 55 | 0.0035 | A2 |
| 56 | 4.8 | A1 |
| 58 | 4.7 | A1 |
| 59 | 0.079 | A1 |
| 60 | 0.063 | A1 |
| 61 | 0.81 | A1 |
| 62 | 0.11 | A1 |
| 63 | 0.30 | A1 |

Abl Kinase Assay Data

| Example | Abl Data | Method |
|---|---|---|
| 64 | 0.063 | A1 |
| 65 | 0.11 | A2 |
| 66 | 0.071 | A1 |
| 67 | 0.001 | A2 |
| 68 | 0.53 | A1 |
| 69 | 0.14 | A1 |
| 70 | 0.050 | A1 |
| 71 | 0.090 | A1 |
| 72 | 0.002 | A2 |
| 73 | 0.19 | A2 |
| 74 | 2.1 | A1 |
| 75 | 0.063 | A1 |
| 76 | 31% @ 10 μM | A1 |
| 77 | 0.26 | A1 |
| 78 | 0.072 | A1 |
| 79 | 0.18 | A1 |
| 80 | 0.079 | A1 |
| 81 | 0.12 | A2 |
| 82 | 0.36 | A1 |
| 83 | 0.087 | A1 |
| 84 | 0.39 | A1 |
| 85 | 0.033 | A1 |
| 86 | 0.001 | A2 |
| 87 | 0.073 | A1 |
| 94 | 0.13 | A2 |
| 95 | 0.056 | A2 |
| 96 | 0.10 | A1 |
| 97 | 0.0015 | A2 |
| 98 | 0.034 | A1 |
| 99 | 0.038 | A1 |
| 100 | 0.15 | A1 |
| 101 | 0.36 | A1 |
| 102 | 0.11 | A1 |
| 103 | 0.24 | A1 |
| 105 | 0.24 | A1 |
| 106 | 0.68 | A1 |
| 107 | 0.18 | A1 |
| 108 | 0.25 | A1 |
| 109 | 0.14 | A1 |
| 110 | 0.36 | A1 |
| 111 | 0.62 | A1 |
| 112 | 0.48 | A1 |
| 113 | 0.19 | A1 |
| 114 | 0.64 | A1 |
| 115 | 0.17 | A1 |
| 116 | 0.0066 | A2 |
| 117 | 0.23 | A1 |
| 118 | 0.011 | A2 |
| 119 | 0.012 | A2 |
| 120 | 5.1 | A2 |
| 121 | 1.0 | A2 |
| 122 | 2.8 | A1 |
| 123 | 0.29 | A2 |
| 124 | 1.4 | A1 |
| 125 | 0.18 | A1 |
| 126 | 0.44 | A1 |
| 127 | 0.22 | A1 |
| 128 | 7.5 | A1 |
| 129 | 0.27 | A1 |
| 130 | 0.23 | A1 |
| 131 | 0.28 | A1 |
| 132 | 0.013 | A2 |
| 133 | 0.048 | A2 |
| 134 | 0.052 | A2 |
| 135 | 0.84 | A1 |
| 136 | 0.10 | A1 |
| 137 | 0.15 | A1 |
| 138 | 0.10 | A2 |
| 139 | 0.14 | A2 |
| 140 | 0.12 | A1 |
| 141 | 0.0015 | A2 |
| 142 | 0.17 | A1 |
| 143 | 0.25 | A1 |
| 144 | 0.2 | A1 |
| 145 | 0.41 | A1 |
| 146 | 0.19 | A2 |
| 147 | 0.14 | A1 |
| 148 | 0.0012 | A2 |
| 149 | 0.0012 | A2 |
| 150 | 0.0013 | A2 |
| 151 | 0.008 | A2 |
| 152 | 0.57 | A2 |
| 153 | 0.0012 | A2 |
| 154 | 0.27 | A1 |
| 155 | 0.26 | A1 |
| 156 | 0.005 | A2 |
| 157 | 0.031 | A2 |
| 158 | 0.018 | A2 |
| 159 | 0.0023 | A2 |
| 160 | 14.9 | A2 |
| 161 | 3% @ 1 μM | A2 |
| 162 | 0.080 | A2 |
| 163 | 0.0063 | A2 |
| 164 | 0.033 | A2 |
| 165 | 0.20 | A1 |
| 166 | 0.23 | A1 |
| 167 | 0.31 | A1 |
| 168 | 1.1 | A2 |
| 169 | 0.021 | A2 |
| 170 | 0.0018 | A2 |
| 171 | 0.0040 | A2 |
| 172 | 0.0019 | A2 |
| 173 | 0.0042 | A2 |
| 174 | 0.0018 | A2 |
| 175 | 0.0015 | A2 |
| 176 | 0.0028 | A2 |
| 177 | 1.8 | A1 |
| 178 | 0.23 | A1 |
| 179 | 0.003 | A2 |
| 180 | 0.009 | A2 |
| 181 | 0.0066 | A2 |
| 182 | 0.0034 | A2 |
| 183 | 0.020 | A2 |
| 184 | 0.010 | A2 |
| 185 | 0.0027 | A2 |
| 186 | 0.060 | A1 |
| 187 | 0.56 | A1 |
| 188 | 0.11 | A1 |
| 189 | 0.003 | A2 |
| 190 | 0.004 | A2 |
| 191 | 0.021 | A2 |
| 192 | 0.027 | A2 |
| 193 | 0.081 | A1 |
| 194 | 0.54 | A2 |
| 195 | 0.91 | A2 |
| 196 | 0.031 | A2 |
| 197 | 0.012 | A2 |
| 276 | 2.3 | A1 |
| 277 | 0.029 | A2 |
| 373 | 3.5 | A1 |

KDR Kinase Assay Data

| Example | KDR Data | Method |
|---|---|---|
| 1 | 0.13 | K1 |
| 2 | 0.46 | K1 |
| 3 | 0.72 | K2 |
| 4 | 0.31 | K2 |
| 5 | 0.85 | K2 |
| 7 | 0.87 | K2 |
| 8 | 96% @ 10 μM | K2 |
| 9 | 0.047 | K1 |
| 12 | 0.28 | K2 |
| 13 | 0.36 | K1 |
| 15 | 0.081 | K1 |
| 16 | 3.4 | K2 |

KDR Kinase Assay Data

| Example | KDR Data | Method |
|---|---|---|
| 18 | 0.24 | K2 |
| 19 | 0.71 | K1 |
| 20 | 0.13 | K1 |
| 23 | 1.0 | K2 |
| 24 | 0.38 | K1 |
| 33 | 0.014 | K2 |
| 34 | 1.0 | K1 |
| 39 | 0.24 | K1 |
| 40 | 0.47 | K1 |
| 42 | 0.36 | K1 |
| 43 | 0.36 | K1 |
| 44 | 2.4 | K1 |
| 45 | 0.36 | K1 |
| 46 | 0.17 | K1 |
| 48 | 0.73 | K1 |
| 49 | 0.086 | K2 |
| 50 | 0.052 | K1 |
| 52 | 0.063 | K2 |
| 53 | 0.49 | K2 |
| 54 | 0.24 | K2 |
| 55 | 0.0040 | K2 |
| 56 | 3.1 | K2 |
| 60 | 0.062 | K1 |
| 61 | 1.5 | K1 |
| 68 | 1.4 | K1 |
| 69 | 0.40 | K1 |
| 72 | 0.0085 | K2 |
| 74 | 2.5 | K2 |
| 75 | 0.14 | K1 |
| 106 | 0.12 | K1 |
| 108 | 0.013 | K2 |
| 109 | 0.038 | K1 |
| 110 | 0.14 | K2 |
| 112 | 0.21 | K1 |
| 115 | 0.81 | K2 |
| 116 | 0.0050 | K2 |
| 117 | 0.058 | K2 |
| 119 | 0.018 | K1 |
| 122 | 1.4 | K1 |
| 123 | 0.19 | K1 |
| 126 | 0.21 | K1 |
| 127 | 0.22 | K1 |
| 129 | 0.50 | K1 |
| 130 | 0.32 | K1 |
| 131 | 0.077 | K1 |
| 135 | 0.27 | K1 |
| 136 | 0.029 | K1 |
| 137 | 1.0 | K1 |
| 138 | 0.30 | K1 |
| 140 | 2.3 | K1 |
| 141 | 0.0085 | K2 |
| 143 | 0.94 | K1 |
| 151 | 0.0035 | K2 |
| 154 | 0.092 | K1 |
| 156 | 0.0032 | K2 |
| 165 | 0.21 | K1 |
| 166 | 0.21 | K1 |
| 177 | 0.23 | K1 |
| 178 | 0.18 | K1 |
| 179 | 0.0064 | K2 |
| 180 | 0.0078 | K2 |
| 186 | 0.90 | K1 |
| 187 | 0.15 | K1 |
| 188 | 0.15 | K2 |
| 189 | 0.023 | K1 |
| 190 | 0.0081 | K2 |
| 198 | 1.3 | K2 |
| 199 | 34.4 | K2 |
| 200 | 2.7 | K2 |
| 201 | 0.13 | K1 |
| 202 | 0.23 | K1 |
| 203 | 0.16 | K1 |
| 204 | 0.099 | K1 |
| 205 | 0.28 | K1 |
| 206 | 0.48 | K2 |
| 207 | 0.34 | K1 |
| 208 | 0.47 | K2 |
| 209 | 0.26 | K2 |
| 210 | 0.11 | K2 |
| 212 | 0.40 | K1 |
| 213 | 0.21 | K2 |
| 214 | 0.84 | K1 |
| 220 | 0.95 | K1 |
| 225 | 9.6 | K2 |
| 227 | 9.3 | K1 |
| 232 | 2.6 | K2 |
| 233 | 0.41 | K2 |
| 235 | 3.5 | K2 |
| 236 | 3.5 | K2 |
| 237 | 4.9 | K2 |
| 240 | 3.7 | K2 |
| 241 | 0.57 | K1 |
| 249 | 0.59 | K2 |
| 257 | 6.6 | K1 |
| 262 | 2.7 | K2 |
| 264 | 0.14 | K1 |
| 265 | 9.8 | K2 |
| 267 | 0.55 | K1 |
| 268 | 2.6 | K2 |
| 273 | 1.7 | K1 |
| 277 | 0.010 | K2 |
| 282 | 2.4 | K1 |
| 283 | 0.44 | K2 |
| 285 | 0.38 | K1 |
| 296 | 0.20 | K1 |
| 297 | 0.27 | K1 |
| 307 | 0.72 | K1 |
| 316 | 12.9 | K1 |
| 318 | 10.1 | K1 |
| 319 | 4.3 | K1 |
| 330 | 0.39 | K2 |
| 333 | 0.23 | K2 |
| 334 | 3.4 | K2 |
| 336 | 0.17 | K1 |
| 337 | 2.0 | K2 |
| 338 | 5.0 | K2 |
| 339 | 1.2 | K2 |
| 340 | 0.72 | K2 |
| 341 | 5.5 | K2 |
| 342 | 5.7 | K2 |
| 343 | 18.0 | K2 |
| 344 | 2.7 | K2 |
| 345 | 2.9 | K2 |
| 346 | 1.7 | K2 |
| 347 | 1.1 | K1 |
| 348 | 16.5 | K2 |
| 349 | 4.1 | K2 |
| 382 | 10.3 | K2 |
| 383 | 0.28 | K1 |
| 394 | 2.7 | K2 |
| 396 | 3.1 | K2 |
| 397 | 3.4 | K2 |
| 398 | 2.7 | K2 |
| 400 | 3.7 | K2 |
| 495 | 1.5 | K1 |
| 496 | 0.47 | K1 |
| 497 | 1.2 | K2 |
| 498 | 1.7 | K2 |

BRaf Kinase Assay Data

| Example | B-Raf Data | Method |
|---|---|---|
| 1 | 0.0046 | B1 |
| 2 | 0.019 | B1 |
| 3 | 2.49 | B2 |
| 5 | 0.087 | B1 |

BRaf Kinase Assay Data

| Example | B-Raf Data | Method |
|---|---|---|
| 6 | 0.180 | B1 |
| 7 | 0.0082 | B1 |
| 9 | 0.0046 | B1 |
| 13 | 0.0052 | B1 |
| 14 | 0.070 | B1 |
| 15 | 0.0033 | B1 |
| 17 | 0.089 | B1 |
| 18 | 0.458 | B1 |
| 19 | 0.0048 | B1 |
| 20 | 0.0085 | B1 |
| 21 | 0.022 | B1 |
| 22 | 0.075 | B2 |
| 23 | 0.0048 | B1 |
| 24 | 0.0023 | B1 |
| 25 | 0.0035 | B1 |
| 26 | 0.010 | B1 |
| 27 | 0.043 | B1 |
| 28 | 0.0080 | B1 |
| 29 | 0.020 | B1 |
| 31 | 0.036 | B2 |
| 34 | 0.0038 | B1 |
| 35 | 0.011 | B1 |
| 37 | 0.0057 | B1 |
| 39 | 0.0071 | B1 |
| 40 | 0.0087 | B1 |
| 41 | 0.089 | B1 |
| 42 | 0.010 | B1 |
| 43 | 0.0043 | B1 |
| 44 | 0.0040 | B1 |
| 45 | 0.0062 | B1 |
| 46 | 0.0033 | B1 |
| 48 | 0.0059 | B1 |
| 49 | 0.0038 | B1 |
| 50 | 0.168 | B2 |
| 51 | 0.029 | B2 |
| 52 | 0.0018 | B1 |
| 53 | 0.0045 | B1 |
| 54 | 0.0048 | B1 |
| 55 | 0.0054 | B1 |
| 59 | 0.0087 | B1 |
| 60 | 0.0026 | B1 |
| 61 | 0.018 | B1 |
| 62 | 0.0032 | B1 |
| 63 | 0.0040 | B1 |
| 64 | 0.0033 | B1 |
| 65 | 0.0030 | B1 |
| 66 | 0.0085 | B1 |
| 67 | 0.0048 | B1 |
| 68 | 0.024 | B1 |
| 69 | 0.0042 | B1 |
| 70 | 0.0050 | B1 |
| 71 | 0.0041 | B1 |
| 72 | 0.0044 | B1 |
| 73 | 0.045 | B1 |
| 74 | 0.934 | B2 |
| 75 | 0.0042 | B1 |
| 76 | 0.011 | B1 |
| 77 | 0.0039 | B1 |
| 78 | 0.0035 | B1 |
| 80 | 0.0045 | B1 |
| 81 | 0.0041 | B1 |
| 82 | 0.0059 | B1 |
| 83 | 0.0085 | B1 |
| 84 | 0.011 | B1 |
| 85 | 0.219 | B2 |
| 86 | 0.179 | B2 |
| 88 | 0.012 | B1 |
| 89 | 0.0055 | B1 |
| 90 | 0.0039 | B1 |
| 91 | 0.020 | B1 |
| 92 | 0.0082 | B1 |
| 93 | 0.060 | B1 |
| 94 | 0.0048 | B1 |
| 95 | 0.0029 | B1 |
| 96 | 0.378 | B2 |
| 97 | 0.0072 | B1 |
| 100 | 0.0069 | B1 |
| 101 | 0.0071 | B1 |
| 102 | 0.0025 | B1 |
| 103 | 0.0045 | B1 |
| 105 | 0.012 | B1 |
| 106 | 0.0036 | B1 |
| 107 | 0.0021 | B1 |
| 108 | 0.0015 | B1 |
| 109 | 0.0027 | B1 |
| 110 | 0.0034 | B1 |
| 111 | 0.097 | B1 |
| 112 | 0.0029 | B1 |
| 113 | 0.0033 | B1 |
| 114 | 0.115 | B1 |
| 115 | 0.979 | B2 |
| 116 | 0.0059 | B1 |
| 117 | 0.0032 | B1 |
| 118 | 0.023 | B2 |
| 119 | 0.0091 | B1 |
| 120 | 0.214 | B2 |
| 121 | 0.105 | B2 |
| 122 | 0.011 | B1 |
| 123 | 0.0049 | B1 |
| 124 | 0.173 | B1 |
| 126 | 0.0065 | B1 |
| 127 | 0.0034 | B1 |
| 128 | 0.067 | B1 |
| 129 | 0.0042 | B1 |
| 131 | 0.0019 | B1 |
| 132 | 0.0048 | B1 |
| 134 | 0.041 | B2 |
| 135 | 0.0045 | B1 |
| 136 | 0.0049 | B1 |
| 137 | 0.0025 | B1 |
| 138 | 0.0032 | B1 |
| 140 | 0.0046 | B1 |
| 141 | 0.0075 | B1 |
| 142 | 0.035 | B1 |
| 143 | 0.014 | B1 |
| 144 | 0.0096 | B1 |
| 145 | 0.013 | B1 |
| 146 | 0.0088 | B1 |
| 147 | 0.010 | B1 |
| 148 | 0.031 | B1 |
| 149 | 0.0093 | B1 |
| 150 | 0.0047 | B1 |
| 153 | 0.027 | B1 |
| 154 | 0.0029 | B1 |
| 155 | 0.0014 | B1 |
| 156 | 0.0041 | B1 |
| 157 | 0.040 | B2 |
| 158 | 0.0084 | B1 |
| 159 | 0.014 | B1 |
| 162 | 0.0067 | B1 |
| 163 | 0.018 | B1 |
| 165 | 0.0024 | B1 |
| 166 | 0.0057 | B1 |
| 168 | 0.030 | B1 |
| 169 | 0.194 | B2 |
| 170 | 0.040 | B1 |
| 172 | 0.029 | B1 |
| 173 | 0.063 | B1 |
| 174 | 0.245 | B2 |
| 175 | 0.030 | B1 |
| 176 | 0.044 | B2 |
| 177 | 0.0063 | B1 |
| 178 | 0.0020 | B1 |
| 179 | 0.017 | B1 |
| 180 | 0.011 | B1 |
| 185 | 0.0069 | B1 |
| 186 | 0.0092 | B1 |
| 187 | 0.0030 | B1 |
| 188 | 0.0058 | B1 |
| 189 | 0.918 | B2 |
| 193 | 0.0026 | B1 |
| 195 | 0.298 | B2 |

BRaf Kinase Assay Data

| Example | B-Raf Data | Method |
| --- | --- | --- |
| 196 | 0.029 | B2 |
| 197 | 0.027 | B2 |
| 211 | 0.785 | B1 |
| 212 | 0.026 | B1 |
| 213 | 0.012 | B1 |
| 219 | 0.055 | B1 |
| 220 | 0.033 | B1 |
| 221 | 0.088 | B1 |
| 222 | 0.047 | B1 |
| 223 | 0.054 | B1 |
| 225 | 0.170 | B1 |
| 226 | 0.020 | B1 |
| 227 | 0.061 | B1 |
| 228 | 0.0038 | B1 |
| 229 | 0.014 | B1 |
| 230 | 0.052 | B1 |
| 231 | 0.027 | B1 |
| 232 | 0.038 | B1 |
| 233 | 0.028 | B1 |
| 234 | 0.032 | B1 |
| 235 | 1.04 | B2 |
| 236 | 2.05 | B2 |
| 237 | 0.059 | B1 |
| 238 | 0.065 | B1 |
| 240 | 0.050 | B1 |
| 241 | 0.024 | B1 |
| 243 | 0.041 | B1 |
| 244 | 0.038 | B1 |
| 245 | 0.0053 | B1 |
| 246 | 0.039 | B1 |
| 247 | 0.070 | B1 |
| 248 | 0.0081 | B1 |
| 249 | 0.0045 | B1 |
| 253 | 0.075 | B1 |
| 255 | 0.086 | B1 |
| 257 | 0.062 | B1 |
| 258 | 0.0034 | B1 |
| 259 | 0.0083 | B1 |
| 260 | 0.0040 | B1 |
| 262 | 0.034 | B1 |
| 264 | 0.0073 | B1 |
| 265 | 0.014 | B1 |
| 267 | 0.0079 | B1 |
| 268 | 0.011 | B1 |
| 269 | 0.279 | B1 |
| 272 | 0.061 | B1 |
| 273 | 0.0087 | B1 |
| 274 | 0.134 | B1 |
| 275 | 0.832 | B2 |
| 276 | 0.0049 | B1 |
| 277 | 0.011 | B1 |
| 278 | 0.153 | B2 |
| 279 | 0.697 | B1 |
| 280 | 0.275 | B1 |
| 281 | 0.369 | B1 |
| 282 | 0.041 | B1 |
| 283 | 0.0064 | B1 |
| 284 | 0.0085 | B1 |
| 285 | 0.0051 | B1 |
| 287 | 0.041 | B1 |
| 288 | 0.056 | B1 |
| 289 | 0.028 | B1 |
| 290 | 0.012 | B1 |
| 291 | 0.0053 | B1 |
| 292 | 0.022 | B1 |
| 293 | 0.0070 | B1 |
| 294 | 0.0033 | B1 |
| 295 | 0.052 | B1 |
| 296 | 0.0030 | B1 |
| 297 | 0.0032 | B1 |
| 298 | 0.083 | B1 |
| 299 | 0.020 | B1 |
| 300 | 0.0092 | B1 |
| 301 | 0.010 | B1 |
| 302 | 0.013 | B1 |
| 303 | 0.0043 | B1 |
| 304 | 0.0036 | B1 |
| 305 | 0.788 | B2 |
| 306 | 0.036 | B1 |
| 307 | 0.010 | B1 |
| 308 | 0.047 | B1 |
| 309 | 0.249 | B1 |
| 310 | 0.098 | B1 |
| 311 | 0.032 | B1 |
| 312 | 0.035 | B1 |
| 313 | 0.046 | B1 |
| 314 | 0.266 | B1 |
| 315 | 0.186 | B1 |
| 316 | 0.066 | B1 |
| 317 | 0.036 | B1 |
| 318 | 0.029 | B1 |
| 319 | 0.032 | B1 |
| 320 | 0.0046 | B1 |
| 321 | 0.0072 | B1 |
| 322 | 0.0041 | B1 |
| 323 | 0.0034 | B1 |
| 324 | 0.017 | B1 |
| 325 | 0.0045 | B1 |
| 326 | 0.017 | B1 |
| 327 | 0.330 | B1 |
| 328 | 0.025 | B1 |
| 329 | 0.0042 | B1 |
| 330 | 0.0032 | B1 |
| 331 | 0.0034 | B1 |
| 332 | 0.0044 | B1 |
| 333 | 0.0034 | B1 |
| 334 | 0.011 | B1 |
| 335 | 0.104 | B1 |
| 336 | 0.0020 | B1 |
| 356 | 0.014 | B1 |
| 366 | 0.157 | B1 |
| 367 | 3.69 | B2 |
| 368 | 0.0062 | B1 |
| 369 | 0.015 | B1 |
| 370 | 0.0080 | B1 |
| 371 | 0.010 | B1 |
| 372 | 0.027 | B1 |
| 373 | 0.0032 | B1 |
| 382 | 0.077 | B1 |
| 383 | 0.0081 | B1 |
| 390 | 0.037 | B1 |
| 391 | 0.037 | B1 |
| 392 | 0.221 | B1 |
| 393 | 0.020 | B1 |
| 394 | 0.0088 | B1 |
| 395 | 0.050 | B1 |
| 396 | 0.032 | B1 |
| 397 | 0.057 | B1 |
| 398 | 0.012 | B1 |
| 400 | 0.019 | B1 |
| 432 | 0.010 | B1 |
| 433 | 0.0051 | B1 |
| 434 | 0.0067 | B1 |
| 435 | 0.0073 | B1 |
| 436 | 0.018 | B1 |
| 437 | 0.279 | B1 |
| 438 | 0.035 | B1 |
| 439 | 0.020 | B1 |
| 440 | 0.0041 | B1 |
| 441 | 0.0064 | B1 |
| 442 | 0.016 | B1 |
| 443 | 0.0090 | B1 |
| 444 | 0.020 | B1 |
| 445 | 0.838 | B1 |
| 491 | 0.032 | B1 |
| 492 | 0.0064 | B1 |
| 493 | 0.011 | B1 |
| 494 | 0.161 | B1 |
| 495 | 0.055 | B1 |
| 496 | 0.026 | B1 |

BRaf Kinase Assay Data

| Example | B-Raf Data | Method |
|---|---|---|
| 497 | 0.047 | B1 |
| 498 | 0.052 | B1 |

P38 Kinase Assay Data

| Example | P-38 Data | method |
|---|---|---|
| 1 | 0.011 | P1 |
| 2 | 0.024 | P1 |
| 3 | 0.11 | P1 |
| 4 | 0.042 | P1 |
| 5 | 0.038 | P2 |
| 7 | 0.10 | P1 |
| 8 | 0.025 | P2 |
| 9 | 0.013 | P1 |
| 13 | 0.045 | P1 |
| 16 | 1.3 | P1 |
| 19 | 0.007 | P1 |
| 20 | 0.060 | P1 |
| 21 | 0.015 | P1 |
| 22 | 0.025 | P1 |
| 23 | 0.021 | P1 |
| 24 | 0.011 | P1 |
| 27 | 0.082 | P1 |
| 28 | 0.012 | P1 |
| 29 | 0.009 | P1 |
| 31 | 0.011 | P1 |
| 33 | 0.30 | P1 |
| 34 | 0.022 | P1 |
| 39 | 0.037 | P2 |
| 40 | 0.10 | P1 |
| 43 | 0.013 | P1 |
| 44 | 0.070 | P1 |
| 45 | 0.005 | P1 |
| 46 | 0.006 | P1 |
| 48 | 0.014 | P1 |
| 50 | 0.029 | P1 |
| 52 | 0.023 | P1 |
| 55 | 0.13 | P1 |
| 60 | 0.018 | P1 |
| 67 | 0.035 | P1 |
| 69 | 0.11 | P1 |
| 75 | 0.006 | P1 |
| 86 | 0.024 | P1 |
| 91 | 0.350 | P1 |
| 94 | 0.068 | P1 |
| 96 | 0.048 | P1 |
| 97 | 0.025 | P1 |
| 100 | 0.005 | P1 |
| 101 | 0.15 | P1 |
| 106 | 0.012 | P1 |
| 108 | 0.009 | P1 |
| 112 | 0.012 | P1 |
| 115 | 0.49 | P1 |
| 117 | 0.059 | P1 |
| 119 | 0.060 | P1 |
| 120 | 0.031 | P1 |
| 121 | 0.040 | P1 |
| 122 | 0.13 | P1 |
| 123 | 0.052 | P1 |
| 126 | 0.010 | P1 |
| 127 | 0.013 | P1 |
| 129 | 0.13 | P1 |
| 131 | 0.033 | P1 |
| 132 | 0.059 | P1 |
| 135 | 0.044 | P1 |
| 136 | 0.13 | P1 |
| 137 | 0.055 | P1 |
| 138 | 0.14 | P1 |
| 141 | 0.73 | P1 |
| 154 | 0.012 | P1 |
| 155 | 0.11 | P1 |
| 159 | 0.072 | P1 |
| 165 | 0.007 | P1 |
| 166 | 0.061 | P1 |
| 175 | 0.16 | P1 |
| 177 | 0.043 | P1 |
| 178 | 0.046 | P1 |
| 179 | 0.096 | P1 |
| 180 | 0.065 | P1 |
| 185 | 0.023 | P1 |
| 186 | 0.050 | P1 |
| 188 | 0.017 | P1 |
| 190 | 0.078 | P1 |
| 195 | 0.046 | P1 |
| 196 | 0.013 | P1 |
| 197 | 0.028 | P1 |
| 198 | 0.059 | P1 |
| 201 | 0.15 | P1 |
| 202 | 0.012 | P1 |
| 203 | 0.017 | P1 |
| 204 | 0.009 | P1 |
| 205 | 0.029 | P1 |
| 210 | 0.024 | P1 |
| 212 | 0.046 | P1 |
| 213 | 0.067 | P1 |
| 220 | 0.042 | P1 |
| 224 | 0.038 | P1 |
| 225 | 0.27 | P1 |
| 227 | 0.11 | P2 |
| 230 | 0.30 | P2 |
| 232 | 0.35 | P2 |
| 233 | 0.050 | P1 |
| 235 | 0.12 | P1 |
| 236 | 0.25 | P1 |
| 237 | 0.58 | P1 |
| 240 | 0.47 | P1 |
| 241 | 0.22 | P1 |
| 248 | 0.027 | P1 |
| 249 | 0.011 | P1 |
| 255 | 0.51 | P2 |
| 257 | 0.40 | P2 |
| 264 | 0.082 | P1 |
| 265 | 0.19 | P1 |
| 267 | 0.012 | P1 |
| 268 | 0.024 | P1 |
| 273 | 0.034 | P1 |
| 277 | 0.18 | P1 |
| 279 | 1.050 | P1 |
| 281 | 5.8 | P1 |
| 301 | 0.16 | P1 |
| 305 | 0.019 | P1 |
| 336 | 0.011 | P1 |
| 337 | 0.068 | P2 |
| 338 | 0.52 | P2 |
| 340 | 0.011 | P1 |
| 341 | 0.027 | P1 |
| 343 | 0.52 | P2 |
| 345 | 0.019 | P1 |
| 347 | 0.006 | P1 |
| 349 | 0.030 | P1 |
| 353 | 0.011 | P1 |
| 354 | 0.007 | P1 |
| 356 | 0.072 | P1 |
| 359 | 0.070 | P1 |
| 360 | 0.020 | P1 |
| 361 | 0.030 | P1 |
| 362 | 0.038 | P1 |
| 363 | 0.013 | P1 |
| 364 | 0.013 | P1 |
| 365 | 0.070 | P1 |
| 367 | 0.007 | P1 |
| 368 | 0.004 | P1 |
| 377 | 0.008 | P1 |
| 379 | 0.013 | P1 |
| 380 | 0.009 | P1 |
| 381 | 0.006 | P1 |

P38 Kinase Assay Data

| Example | P-38 Data | method |
|---|---|---|
| 382 | 0.049 | P1 |
| 383 | 0.007 | P1 |
| 388 | 0.091 | P1 |
| 389 | 0.013 | P1 |
| 390 | 0.005 | P1 |
| 394 | 0.038 | P1 |
| 396 | 0.031 | P1 |
| 398 | 0.026 | P1 |
| 400 | 0.046 | P1 |
| 401 | 0.063 | P1 |
| 402 | 0.026 | P1 |
| 406 | 0.011 | P1 |
| 407 | 0.045 | P1 |
| 408 | 0.046 | P1 |
| 409 | 0.15 | P1 |
| 410 | 0.088 | P1 |
| 411 | 0.037 | P1 |
| 412 | 0.041 | P1 |
| 413 | 0.028 | P1 |
| 414 | 0.025 | P1 |
| 415 | 0.017 | P1 |
| 416 | 0.032 | P1 |
| 417 | 0.029 | P1 |
| 418 | 0.006 | P1 |
| 419 | 0.038 | P1 |
| 420 | 0.042 | P1 |
| 421 | 0.007 | P1 |
| 422 | 0.098 | P1 |
| 423 | 0.021 | P1 |
| 424 | 0.047 | P1 |
| 425 | 0.029 | P1 |
| 426 | 0.038 | P1 |
| 427 | 0.014 | P1 |
| 428 | 0.012 | P1 |
| 429 | 0.014 | P1 |
| 430 | 0.031 | P1 |
| 434 | 0.068 | P1 |
| 435 | 0.013 | P1 |
| 438 | 0.18 | P1 |
| 439 | 0.33 | P1 |
| 440 | 0.007 | P1 |
| 442 | 0.005 | P1 |
| 444 | 0.063 | P1 |
| 445 | 0.008 | P1 |
| 450 | 0.076 | P1 |
| 451 | 0.006 | P1 |
| 452 | 0.013 | P1 |
| 453 | 0.030 | P1 |
| 454 | 0.005 | P1 |
| 455 | 0.082 | P1 |
| 456 | 0.008 | P1 |
| 457 | 0.008 | P1 |
| 458 | 0.008 | P1 |
| 459 | 0.018 | P1 |
| 460 | 0.022 | P1 |
| 461 | 0.007 | P1 |
| 462 | 0.015 | P1 |
| 463 | 0.120 | P1 |
| 466 | 0.022 | P1 |
| 468 | 0.009 | P1 |
| 469 | 0.010 | P1 |
| 470 | 0.013 | P1 |
| 471 | 0.009 | P1 |
| 477 | 0.016 | P1 |
| 478 | 0.038 | P1 |
| 479 | 0.030 | P1 |
| 480 | 0.073 | P1 |
| 481 | 0.033 | P1 |
| 483 | 0.006 | P1 |
| 484 | 0.013 | P1 |
| 485 | 0.012 | P1 |
| 486 | 0.007 | P1 |
| 487 | 0.007 | P1 |
| 488 | 0.037 | P1 |
| 489 | 0.035 | P1 |
| 490 | 0.053 | P1 |
| 491 | 0.011 | P1 |
| 493 | 0.004 | P1 |
| 495 | 0.008 | P1 |
| 496 | 0.005 | P1 |
| 498 | 0.009 | P1 |

We claim:
1. A compound of the formula
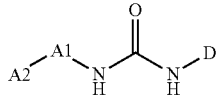
I
wherein A2 is a bicyclic fused heteroaryl selected from the group consisting of
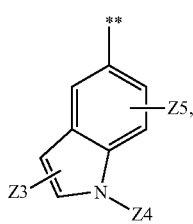
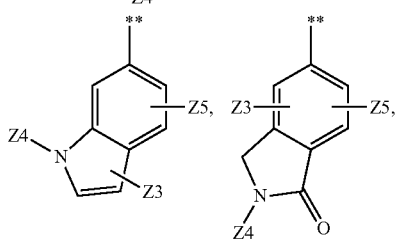
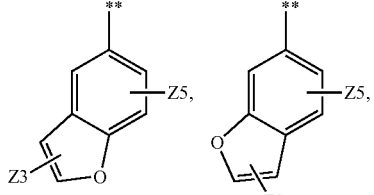
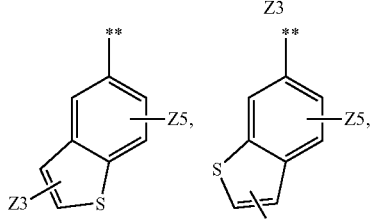
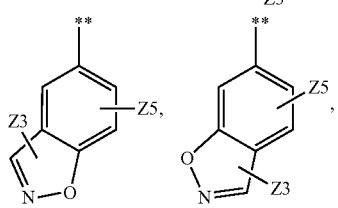
-continued
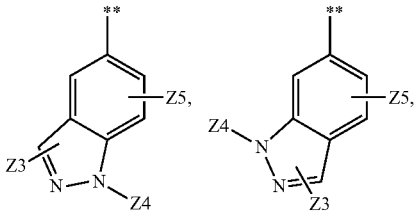
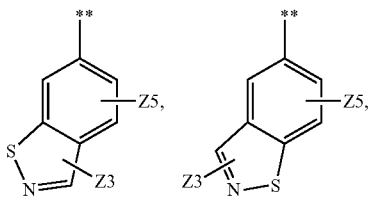
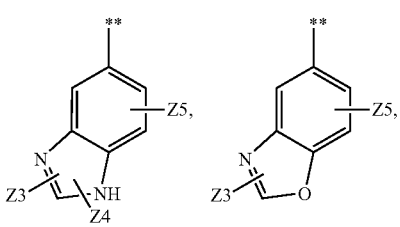
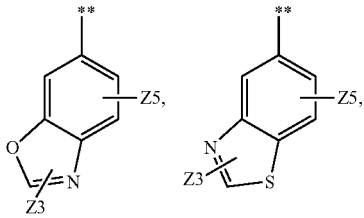
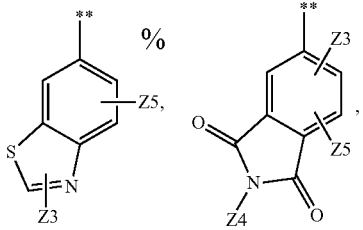
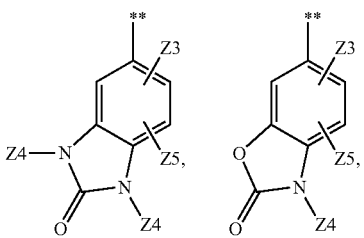

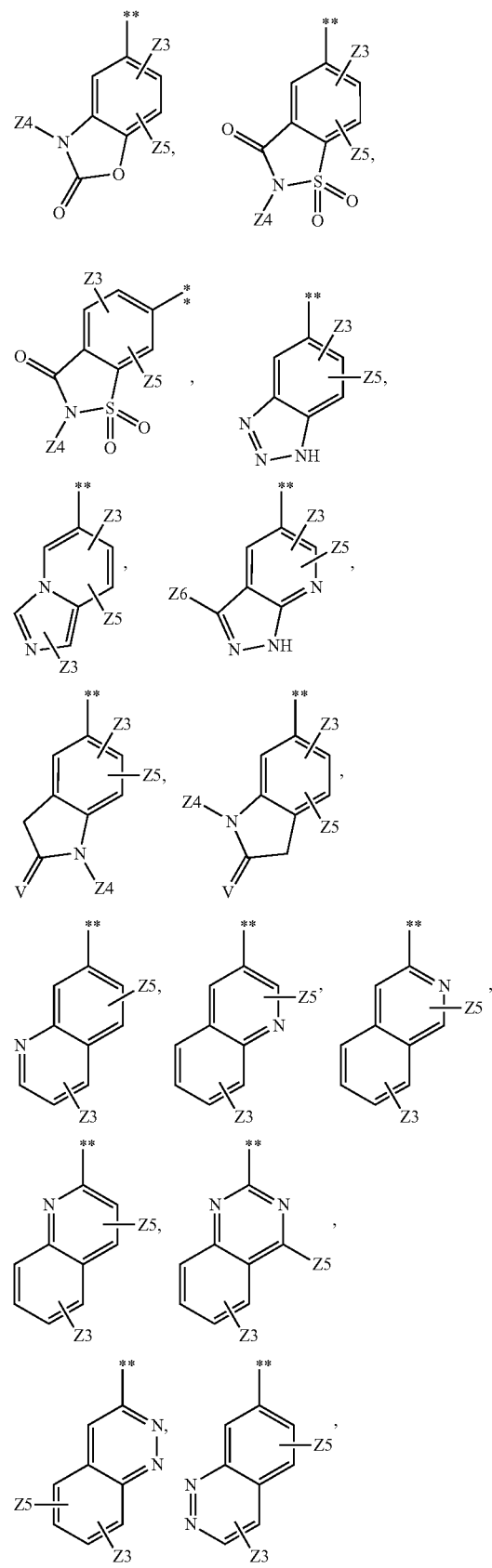
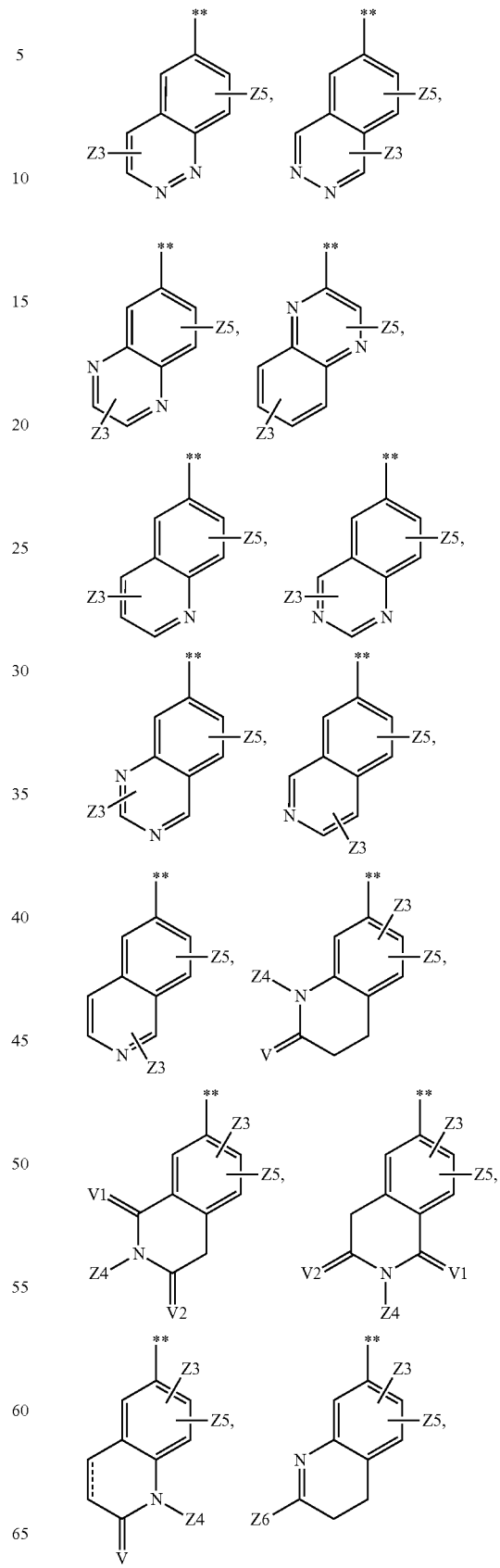

-continued

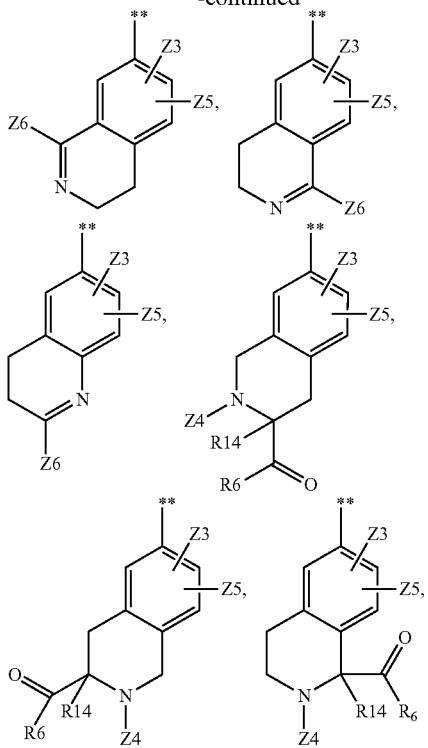

and wherein the symbol (**) is the point of attachment to the A1 ring of formula I;

and wherein ---- indicates either a saturated or an unsaturated bond;

wherein each Z3 and Z5 may be independently attached to either of the rings making up the foregoing bicyclic structures;

A1 is R2-substituted monocyclic 5-membered ring heteroaryl;

D is a moiety of the formula

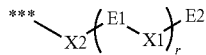

wherein E1 is phenyl;
wherein the symbol (***) is the point of attachment to the Y group of formula I;
X1 is selected from the group consisting of O, S, NR3, —C(=O)—, —O—(CH$_2$)$_n$—, —S—(CH$_2$)$_n$—, —NR3-(CH$_2$)$_n$—, —O—(CH$_2$)$_q$—O—, —O—(CH$_2$)$_q$—NR3-, —N(R3)-(CH$_2$)$_q$—N(R3)-, —(CH$_2$)$_n$—N(R4)-C(=O)—, —(CH$_2$)$_n$—N(R4)-C(=O)—(CH$_2$)$_n$—, —(CH$_2$)$_n$—CO—N(R4)-, —(CH$_2$)$_p$—, C2-C5alkenyl, C2-C5alkynyl, C3-C6cycloalkyl, and a direct bond wherein the E1 ring and the E2 ring are directly linked by a covalent bond;
and wherein the carbon atoms of —(CH$_2$)$_n$—, —(CH$_2$)$_q$—, (CH$_2$)$_p$, C2-C5alkenyl, and C2-C5alkynyl moieties of X1 may be further substituted by one or more C1-C6alkyl;
X2 is a direct bond wherein E1 is directly linked to the Y group of formula I;
and wherein the E2 ring is Z5- and/or Z6-substituted pyridinyl, pyrimidinyl;

each Z2 is independently and individually selected from the group consisting of hydroxyl, hydroxyC1-C6alkyl, cyano, (R3)$_2$N—, (R4)$_2$N—, (R4)$_2$NC1-C6alkyl, (R4)$_2$NC2-C6alkylN(R4)-(CH$_2$)$_n$, (R4)$_2$NC2-C6alkylO—(CH$_2$)$_n$, (R3)$_2$N—C(=O)—, (R4)$_2$N—C(=O)—, (R4)$_2$ N—CO—C1-C6alkyl, carboxyl, carboxyC1-C6alkyl, C1-C6alkoxycarbonyl, C1-C6 alkoxycarbonylC1-C6alkyl, (R3)$_2$NSO$_2$, (R4)$_2$NSO$_2$, —SO$_2$R5-, —(CH$_2$)$_n$N(R4)C(O)R8, =O, =NOH, =N(OR6), heteroarylC1-C6alkyl, heterocyclylC1-C6alkyl, heteroaryloxyC1-C6alkyl, heterocyclyloxyC1-C6alkyl, arylaminoC1-C6alkyl, heteroarylaminoC1-C6alkyl, heterocyclylaminoC1-C6alkyl, and moieties of the formulae

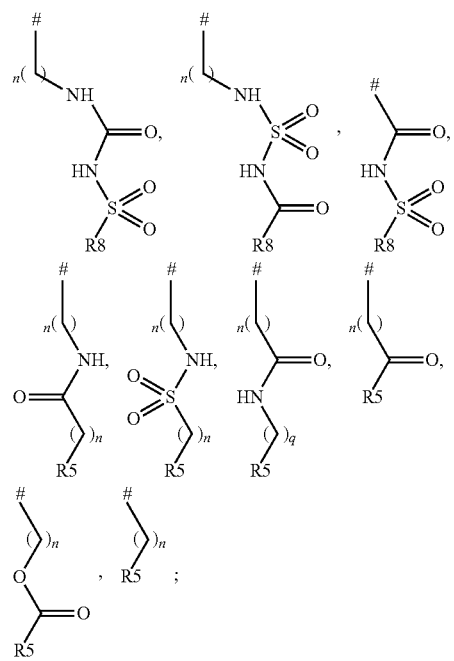

wherein the symbol (#) indicates the point of attachment of the Z2 moiety to the A2 ring of formula I; in the event that Z2 contains an alkyl or alkylene moiety, such moieties may be further substituted with one or more C1-C6alkyls;

each Z3 is independently and individually selected from the group consisting of H, C1-C6alkyl, hydroxyl, hydroxyC1-C6alkyl, cyano, C1-C6alkoxy, C1-C6alkoxyC1-C6alkyl, halogen, CF$_3$, (R3)$_2$N—, (R4)$_2$N—, (R4)$_2$NC1-C6alkyl, (R4)$_2$NC2-C6alkylN (R4)-CH$_2$)$_n$, (R4)$_2$NC2-C6alkylO—(CH$_2$)$_n$, —R8C (=O)—, (R4)$_2$N—CO—C1-C6alkyl, carboxyl, carboxyC1-C6alkyl, C1-C6alkoxycarbonyl, C1-C6alkoxycarbonylC1-C6alkyl, (R3)$_2$NSO$_2$, —SO$_2$R3, SOR3, (R4)$_2$NSO$_2$, —SO$_2$R4, —SOR4, —(CH$_2$)$_n$N(R4)C(O)R8, —C=(NOH)R6, —C=(NOR3)R6, heteroaryl, heterocyclyl, heteroarylC1-C6alkyl, heterocyclylC1-C6alkyl, heteroaryloxy, heterocyclyloxy, heteroaryloxyC1-C6alkyl, heterocyclyloxyC1-C6alkyl, arylamino, heteroarylamino, heterocyclylamino, arylaminoC1-C6alkyl, heteroarylaminoC1-C6alkyl, heterocyclylaminoC1-C6alkyl, and moieties of the formulae

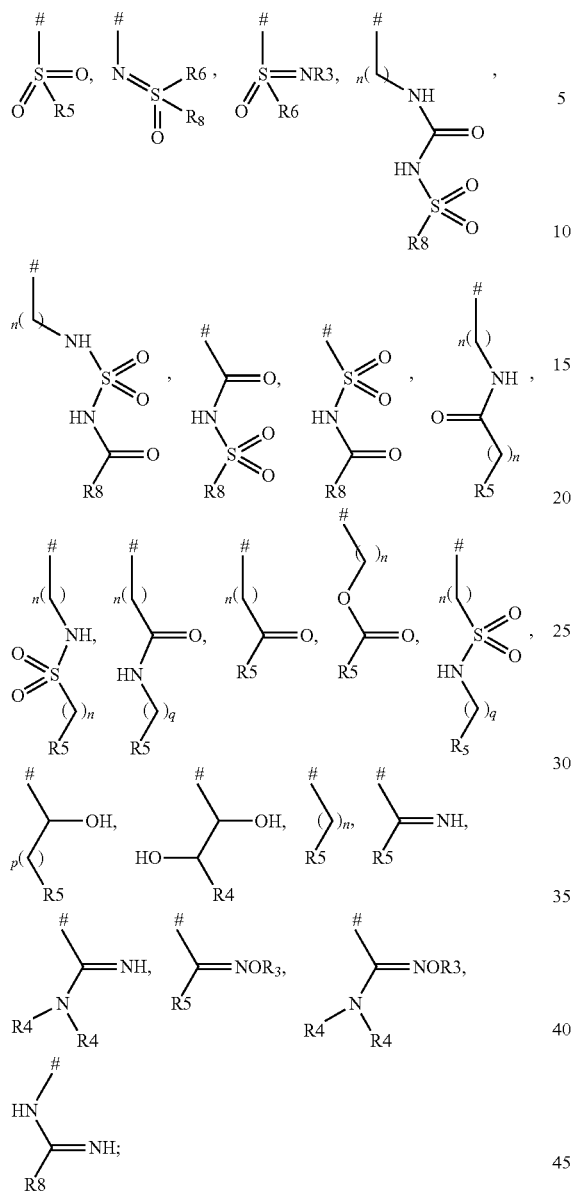

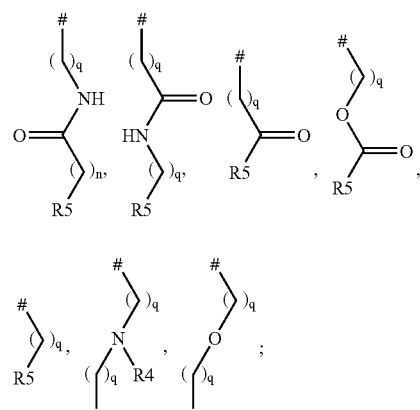

wherein the symbol (#) indicates the point of attachment of the Z4 moiety to the A2 ring for formula I;

in the event that Z4 contains an alkyl or alkylene moiety, such moieties may be further substituted with one or more C1-C6alkyls;

each Z5 is independently and individually selected from the group consisting of H, C1-C6alkyl, branched C3-C7alkyl, halogen, fluoroalkyl, cyano, hydroxyl, alkoxy, oxo, aminocarbonyl, carbonylamino, aminosulfonyl, sulfonylamino, —N(R3)$_2$, —O—(CH$_2$)$_q$—N(R4)$_2$, —N(R3)-(CH$_2$)$_q$—N(R4)$_2$, —R5, —O—(CH$_2$)$_q$—O-Alkyl, —O—(CH$_2$)$_q$—N(R4)$_2$, —N(R3)-(CH$_2$)$_q$—O-Alkyl, —N(R3)-(CH$_2$)$_q$—N(R4)$_2$, —O—(CH$_2$)$_q$—R5, and —N(R3)-(CH$_2$)$_q$—R5;

each Z6 is independently and individually selected from the group consisting of H, C1-C6alkyl, branched C3-C7alkyl, hydroxyl, C1-C6alkoxy, heteroaryl, heterocyclyl, heteroaryloxy, heterocyclyloxy, arylamino, heteroarylamino, and heterocyclylamino, (R3)$_2$N—, —N(R3)COR8, (R4)$_2$N—, —R5, —N(R4)COR8, —N(R3)SO$_2$R6-, —CON(R3)$_2$, —CON(R4)$_2$, —COR5, and —SO$_2$NHR4;

each R2 is selected from the group consisting of monocyclic heteroaryl, C1-C6alkyl, branched C3-C7alkyl, R19 substituted C3-C8-carbocyclyl wherein R19 is H or C1-C6alkyl, C1-C6-fluoroalkyl wherein the alkyl group is partially or fully fluorinated, phenyl wherein the phenyl group is optionally substituted by one or more fluorine substituents and chlorine;

each R3 is independently and individually selected from the group consisting of H, C1-C6alkyl, branched C3-C7alkyl, C3-C7-carbocyclyl, and phenyl;

each R4 is selected from the group consisting of H, C1-C6alkyl, hydroxyC1-C6alkyl, dihydroxyC1-C6alkyl, C1-C6alkoxyC1-C6alkyl, branched C3-C7alkyl, branched hydroxyC1-C6 alkyl, branched C1-C6alkoxyC1-C6alkyl, branched dihydroxyC1-C6alkyl, carbocyclyl, hydroxyl substituted carbocyclyl, alkoxy substituted carbocyclyl, dihydroxy substituted carbocyclyl, phenyl, heteroaryl, heterocyclyl, phenylC1-C6alkyl, heteroarylC1-C6alkyl, and heterocyclylC1-C6alkyl;

each R5 is independently and individually selected from the group consisting of wherein the symbol (#) indicates the point of attachment of the Z3 moiety to the A2 ring of formula I;

in the event that Z3 contains an alkyl or alkylene moiety, such moieties may be further substituted with one or more C1-C6alkyls;

each Z4 is a substituent attached to a ring nitrogen and is independently and individually selected from the group consisting of H, C1-C6alkyl, hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C2-C6alkyl, carboxyC2-C6alkyl, C1-C6alkoxycarbonylC2-C6alkyl, —C2-C6alkylN(R4)C(O)R8, R8-C(=NR3)-, —SO$_2$R8, —COR8, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

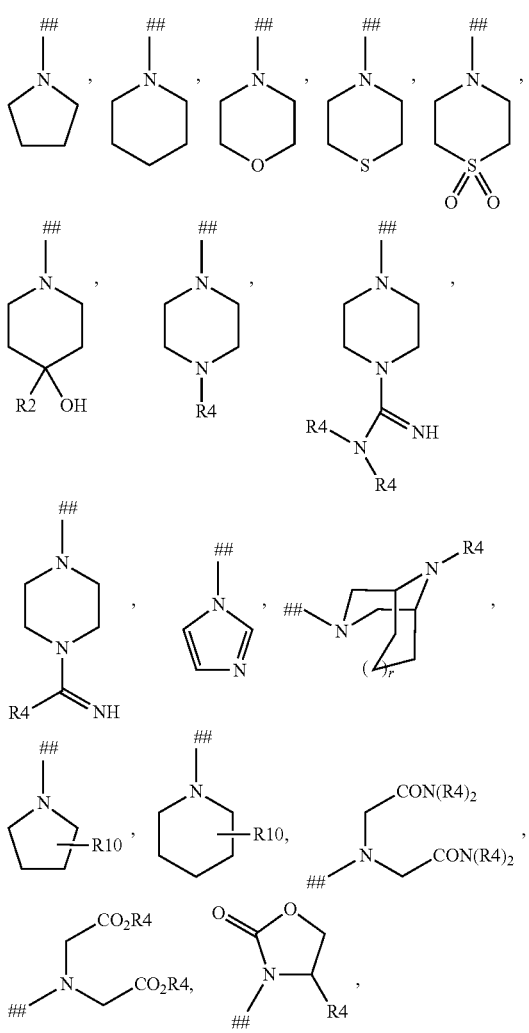

and wherein the symbol (##) is the point of attachment to respective R8, R10, Z2, or Z3 moieties containing a R5 moiety;

each R6 is independently and individually selected from the group consisting of C1-C6alkyl, branched C3-C7alkyl, carbocyclyl, phenyl, heteroaryl, and heterocyclyl;

each R8 is independently and individually selected from the group consisting of C1-C6alkyl, branched C3-C7alkyl, fluoroalkyl wherein the alkyl moiety is partially or fully fluorinated, carbocyclyl, phenyl, phenyC1-C6lalkyl, heteroaryl, heteroarylC1-C6alkyl, heterocyclyl, heterocyclylC1-C6alkyl, OH, C1-C6alkoxy, N(R3)$_2$, N(R4)$_2$, and R5;

each R10 is independently and individually selected from the group consisting of CO$_2$H, CO$_2$C1-C6alkyl, CO—N (R4)$_2$, OH, C1-C6alkoxy, and —N(R4)$_2$;

each R13 is independently and individually selected from the group consisting of H, C1-C6alkyl, branched C3-C7alkyl, carbocyclyl, hydroxyC2-C7alkyl, C1-C6alkoxyC2-C7alkyl, (R4)$_2$N—CO, (R4)$_2$N—CO—C1-C6alkyl, carboxyC1-C6alkyl, C1-C6alkoxycarbonyl, C1-C6alkoxycarbonylC1-C6alkyl, (R4)$_2$N—C2-C6alkyl, (R4)$_2$N—C2-C6alkylN(R4)-(CH$_2$)$_q$, R5-C2-C6alkylN(R4)-(CH$_2$)$_q$, (R4)$_2$N—C2-C6alkylO-(CH$_2$)$_q$, R5-C2-C6alkyl-O—(CH$_2$)$_q$, —(CH$_2$)$_q$N(R4)C(O)R8, aryl, arylC1-C6alkyl, heteroaryl, heteroarylC1-C6alkyl, heterocyclyl, heterocyclylC1-C6alkyl, aryloxyC2-C6alkyl, heteroaryloxyC2-C6alkyl, heterocyclyloxyC2-C6alkyl, arylaminoC2-C6alkyl, heteroarylaminoC2-C6alkyl, and heterocyclylaminoC2-C6alkyl;

V, V1, and V2 are each independently O or represent two hydrogens connected to the methylene carbon to which the V, V1, or V2 is attached;

wherein two R3 or R4 moieties are independently and individually taken from the group consisting of C1-C6alkyl and branched C3-C6alkyl, hydroxyalkyl, and alkoxyalkyl and are attached to the same nitrogen atom, said moieties may cyclize to form a C3-C7 heterocyclyl ring;

n is 0-4; p is 1-4; q is 2-6; r is 1; and v is 1 or 2;

or a tautomer, diastereomer, geometric isomer, enantiomer, hydrate, or salt of any of the foregoing.

2. The compound of claim 1 wherein A2 is selected from the group consisting of

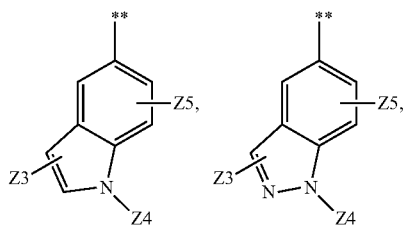

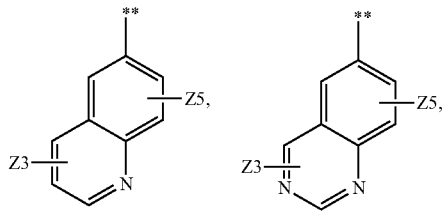

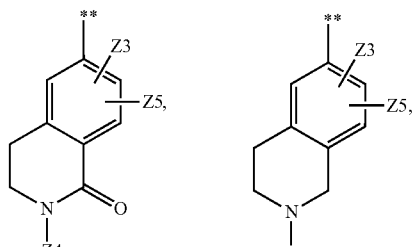

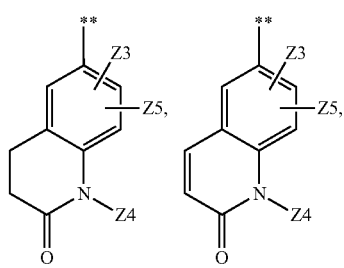

-continued

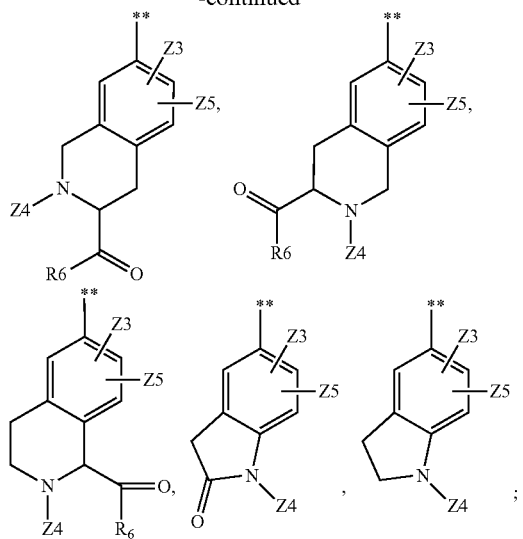

and wherein the symbol (**) is the point of attachment to the A1 ring of formula I;

wherein each Z3 and Z5 is independently attached to either aryl or heteroaryl ring of the A2 bicyclic ring.

3. The compound of claim 1, wherein A1 is selected from the group consisting of

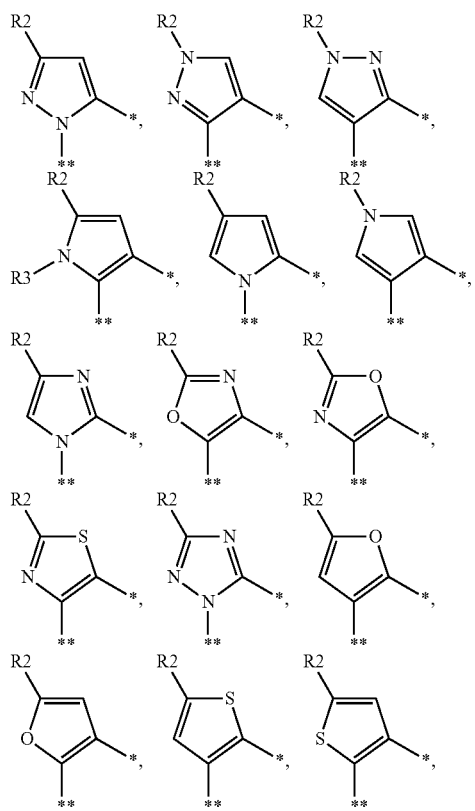

wherein the symbol (*) denotes the attachment to the W moiety of formula I and the symbol (**) denotes the attachment to the A2 moiety of formula I.

4. A compound of the formula

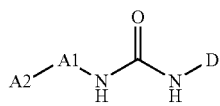

wherein A2 is selected from the group consisting of

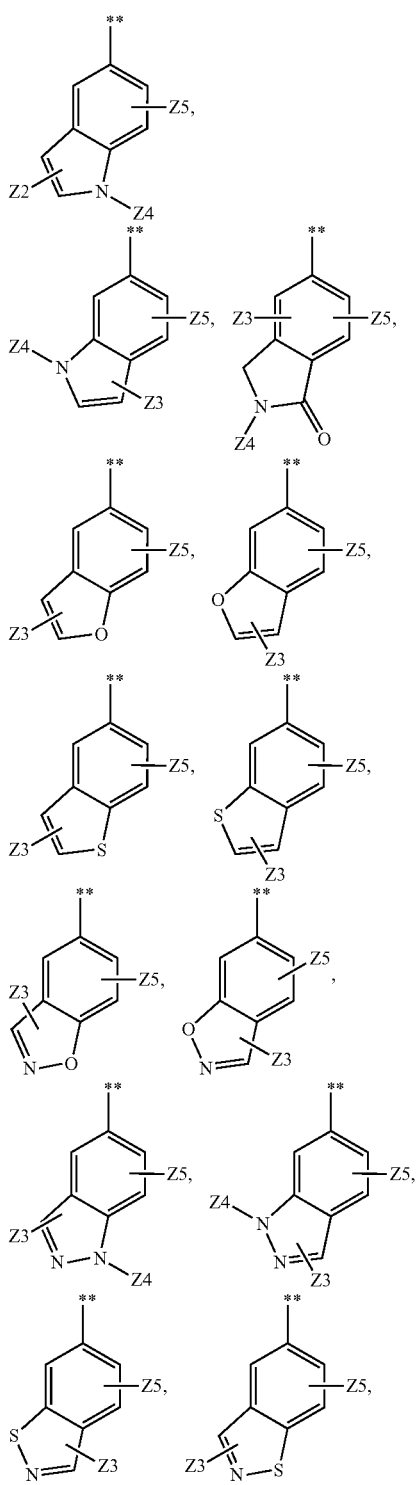

747
-continued
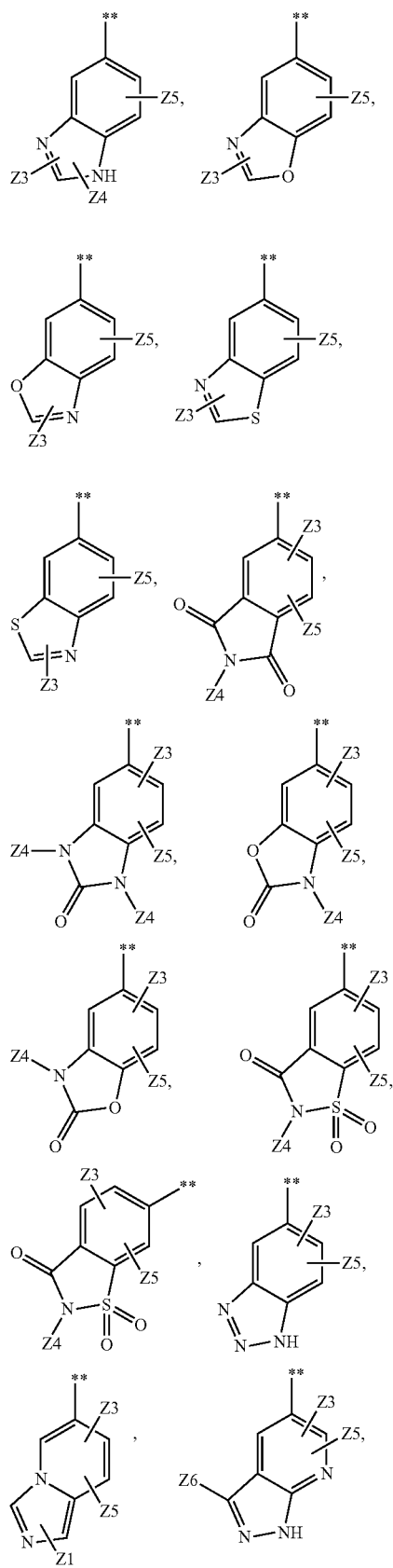
748
-continued
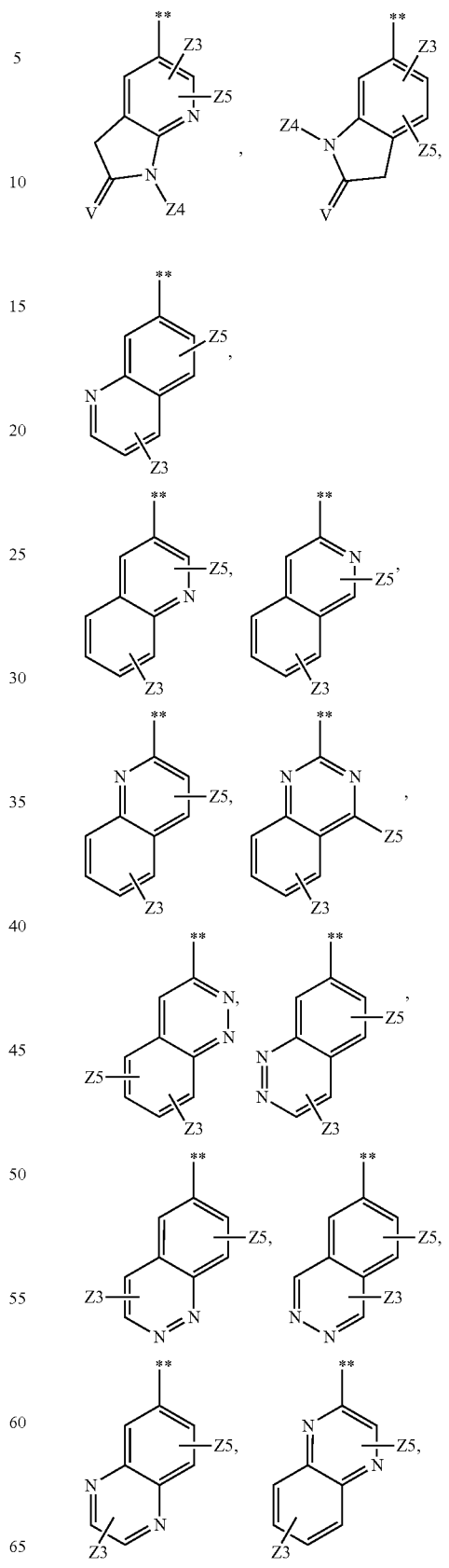

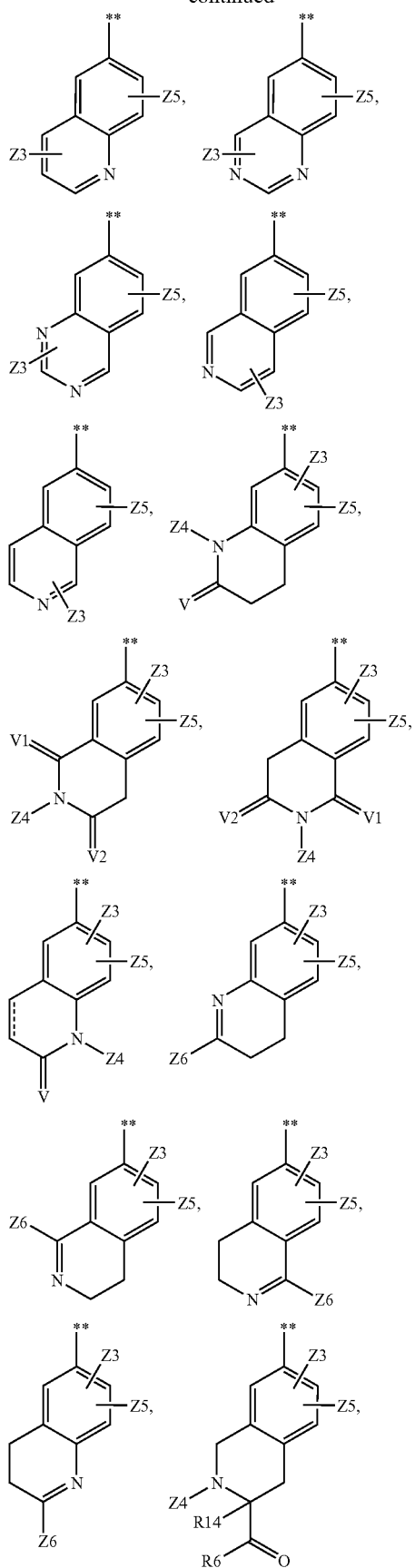

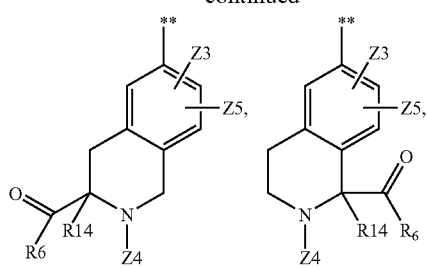

wherein each Z3 and Z5 is independently attached to either aryl or heteroaryl ring of the A2 bicyclic ring;

wherein the symbol (**) denotes the attachment to the A1 moiety of formula I;

A1 is selected from the group consisting of

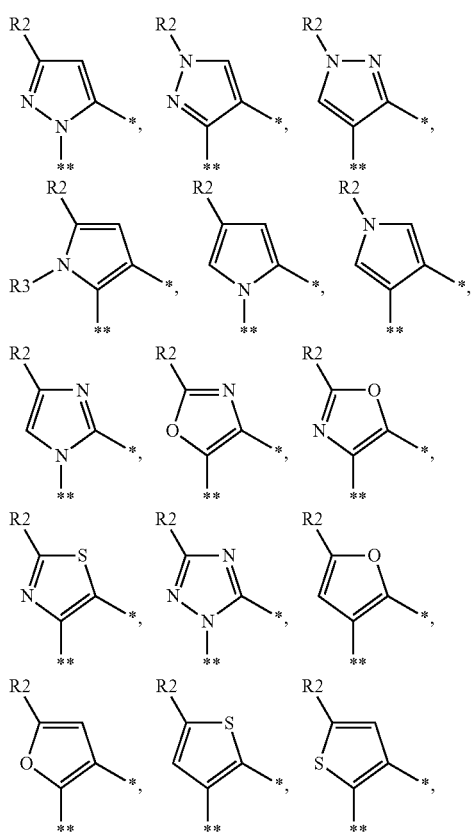

wherein the symbol (*) denotes the attachment to the NH moiety of formula I and the symbol (**) denotes the attachment to the A2 moiety of formula I;

D is selected from the group consisting of

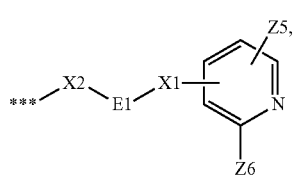

751

-continued

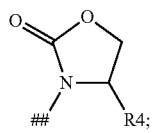

wherein E1 is phenyl;

X1 is selected from the group consisting of O;

X2 is a direct bond wherein E1 is directly linked to the Y group of formula I;

each R2 is selected from the group consisting of monocyclic heteroaryl, C1-C6alkyl, branched C3-C7alkyl, R19 substituted C3-C8-carbocyclyl wherein R19 is H or C1-C6alkyl, C1-C6-fluoroalkyl wherein the alkyl group is partially or fully fluorinated, phenyl wherein the phenyl group is optionally substituted by one or more fluorine substituents and chlorine;

each R3 is independently and individually selected from the group consisting of H, C1-C6alkyl, branched C3-C7 alkyl, C3-C7-carbocyclyl, and phenyl;

each R4 is selected from the group consisting of H, C1-C6alkyl, hydroxyC1-C6 alkyl, dihydroxyC1-C6alkyl, C1-C6alkoxyC1-C6alkyl, branched C3-C7alkyl, branched hydroxyC1-C6 alkyl, branched C1-C6alkoxyC1-C6alkyl, branched dihydroxyC1-C6alkyl, carbocyclyl, hydroxyl substituted carbocyclyl, alkoxy substituted carbocyclyl, dihydroxy substituted carbocyclyl, phenyl, heteroaryl, heterocyclyl, phenylC1-C6alkyl, heteroarylC1-C6alkyl, and heterocylylC1-C6alkyl;

each R5 is independently and individually selected from the group consisting of

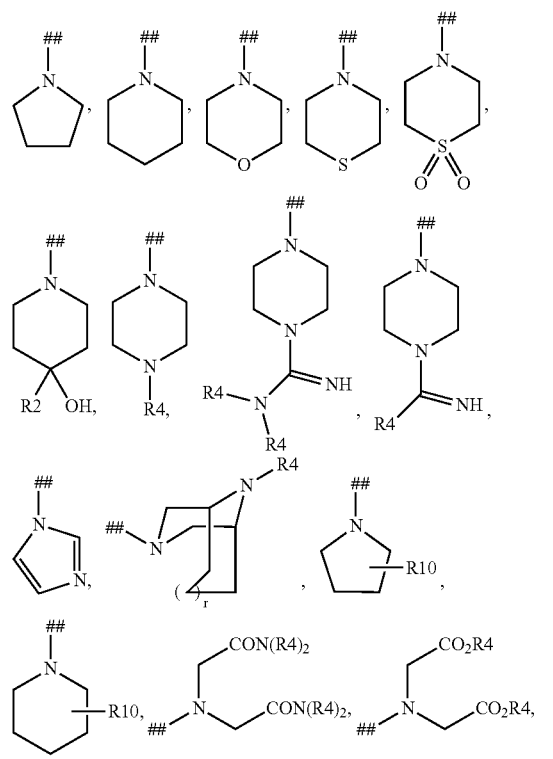

752

-continued and wherein the symbol (##) is the point of attachment to respective R8, R10, R13, Z2, Z3, Z4, Z5, or A2 ring moieties containing a R5 moiety;

wherein each R6 is independently and individually selected from the group consisting of C1-C6alkyl, branched C3-C7alkyl, carbocyclyl, phenyl, heteroaryl, and heterocyclyl;

each R8 is independently and individually selected from the group consisting of C1-C6alkyl, branched C3-C7alkyl, fluoroalkyl wherein the alkyl moiety is partially or fully fluorinated, carbocyclyl, phenyl, phenylC1-C6lalkyl, heteroaryl or heteroarylC1-C6alkyl, heterocyclyl, heterocyclylC1-C6alkyl, OH, C1-C6alkoxy, N(R3)$_2$, N(R4)$_2$, and R5;

each R10 is independently and individually selected from the group consisting of CO$_2$H, CO$_2$C1-C6alkyl, CO—N(R4)$_2$, OH, C1-C6alkoxy, and —N(R4)$_2$;

each R13 is independently and individually selected from the group consisting of H, C1-C6alkyl, branched C3-C7alkyl, carbocyclyl, hydroxyC2-C7alkyl, C1-C6alkoxyC2-C7alkyl, (R4)$_2$N—CO, (R4)$_2$N—CO—C1-C6alkyl, carboxyC1-C6alkyl, C1-C6alkoxycarbonyl, C1-C6alkoxycarbonylC1-C6alkyl, (R4)$_2$N—C2-C6alkyl, (R4)$_2$N—C2-C6alkylN(R4)-(CH$_2$)$_q$, R5-C2-C6alkylN(R4)-(CH$_2$)$_q$, (R4)$_2$N—C2-C6alkylO-(CH$_2$)$_q$, R5-C2-C6alkyl-O—(CH$_2$)$_q$, —(CH$_2$)$_q$N(R4)C(O)R8, aryl, arylC1-C6alkyl, heteroaryl, heteroarylC1-C6alkyl, heterocyclyl, heterocyclylC1-C6alkyl, aryloxyC2-C6alkyl, heteroaryloxyC2-C6alkyl, heterocyclyloxyC2-C6alkyl, arylaminoC2-C6alkyl, heteroarylaminoC2-C6alkyl, and heterocyclylaminoC2-C6alkyl;

V, V1, and V2 are each independently or represent two hydrogens connected to the methylene carbon to which the V, V1, or V2 is attached;

each Z2 is independently and individually selected from the group consisting of hydroxyl, hydroxyC1-C6alkyl, cyano, (R3)$_2$N—, (R4)$_2$N—, (R4)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—C(=O)—, (R4)$_2$N—C(=O)—, (R4)$_2$ N—CO—C1-C6alkyl, carboxyl, carboxyC1-C6alkyl, C1-C6alkoxycarbonyl, C1-C6 alkoxycarbonylC1-C6alkyl, (R3)$_2$NSO$_2$, (R4)$_2$NSO$_2$, —SO$_2$R5-, —(CH$_2$)$_n$ N(R4)C(O)R8, =O, =NOH, =N(OR6), heteroarylC1-C6alkyl, heterocyclylC1-C6alkyl, heteroaryloxyC1-C6alkyl, heterocyclyloxyC1-C6alkyl, arylaminoC1-C6alkyl, heteroarylaminoC1-C6alkyl, heterocyclylaminoC1-C6alkyl, and moieties of the formulae

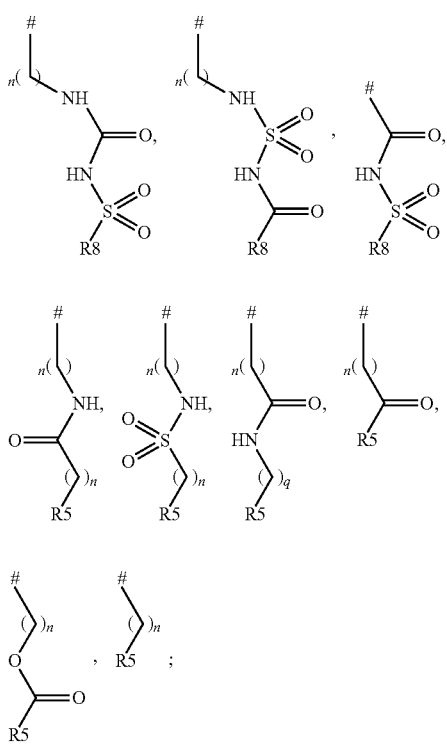

wherein the symbol (#) indicates the point of attachment of the Z2 moiety to the A2 ring of formula I; in the event that Z2 contains an alkyl or alkylene moiety, such moieties may be further substituted with one or more C1-C6alkyls;

each Z3 is independently and individually selected from the group consisting of H, C1-C6alkyl, hydroxyl, hydroxyC1-C6alkyl, cyano, C1-C6alkoxy, C1-C6alkoxyC1-C6alkyl, halogen, $CF_3$, $(R3)_2N-$, $(R4)_2N-$, $(R4)_2NC1\text{-}C6alkyl$, $(R4)_2NC2\text{-}C6alkylN(R4)\text{-}CH_2)_n$, $(R4)_2NC2\text{-}C6alkylO-(CH_2)_n$, R8CO—, $(R4)_2N-CO-C1\text{-}C6alkyl$, carboxyl, carboxyC1-C6alkyl, C1-C6alkoxycarbonyl, C1-C6alkoxycarbonylC1-C6alkyl, $(R3)_2NSO_2$, $-SO_2R3$, SOR3, $(R4)_2NSO_2$, $-SO_2R4$, $-SOR4$, $-(CH_2)_nN(R4)C(O)R8$, $-C=(NOH)R6$, $-C=(NOR3)R6$, heteroaryl, heterocyclyl, heteroarylC1-C6alkyl, heterocyclylC1-C6alkyl, heteroaryloxy, heterocyclyloxy, heteroaryloxyC1-C6alkyl, heterocyclyloxyC1-C6alkyl, arylamino, heteroarylamino, heterocyclylamino, arylaminoC1-C6alkyl, heteroarylaminoC1-C6alkyl, heterocyclylaminoC1-C6alkyl, and moieties of the formulae

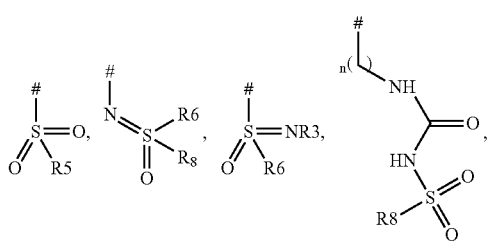

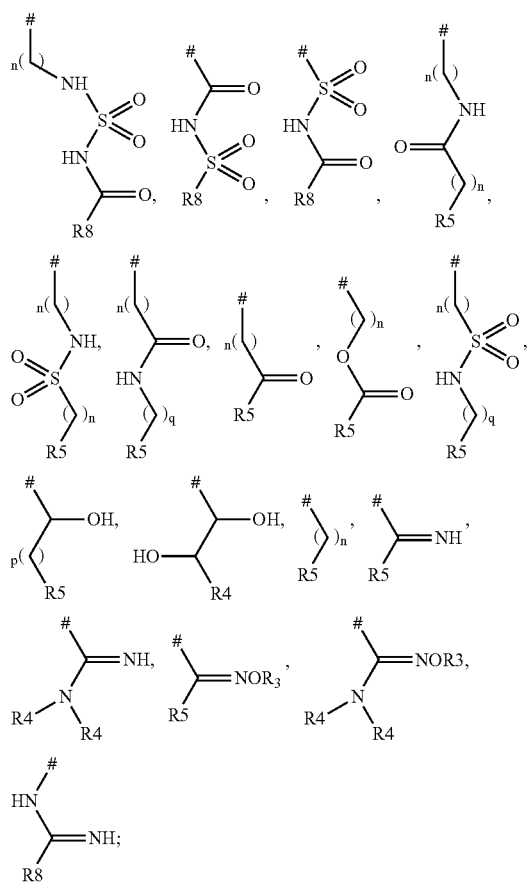

wherein the symbol (#) indicates the point of attachment of the Z3 moiety to the A2 ring of formula I;

in the event that Z3 contains an alkyl or alkylene moiety, such moieties may be further substituted with one or more C1-C6alkyls;

each Z4 is a substituent attached to a ring nitrogen and is independently and individually selected from the group consisting of H, C1-C6alkyl, hydroxyC2-C6alkyl, C1-C6alkoxyC2-C6alkyl, $(R4)_2N-C2\text{-}C6alkyl$, $(R4)_2N-C2\text{-}C6alkylN(R4)\text{-}C2\text{-}C6alkyl$, $(R4)_2N-C2\text{-}C6alkyl\text{-}O-C2\text{-}C6alkyl$, $(R4)_2N-CO-C2\text{-}C6alkyl$, carboxyC2-C6alkyl, C1-C6alkoxycarbonylC2-C6alkyl, $-C2\text{-}C6alkylN(R4)C(O)R8$, $R8\text{-}C(=NR3)-$, $-SO_2R8$, $-COR8$, heteroaryl, heteroarylC1-C6alkyl, heterocyclyl, heterocyclylC1-C6alkyl, heteroaryloxyC2-C6alkyl, heterocyclyloxyC2-C6alkyl, arylaminoC2-C6alkyl, heteroarylaminoC2-C6alkyl, heterocyclylaminoC2-C6alkyl, and moieties of the formulae

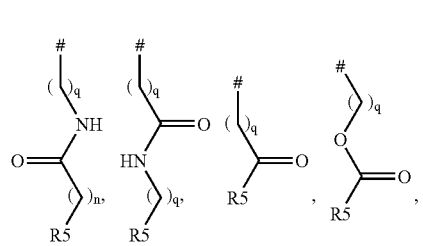

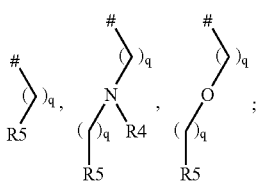

wherein the symbol (#) indicates the point of attachment of the Z4 moiety to the A2 ring for formula I;

in the event that Z4 contains an alkyl or alkylene moiety, such moieties may be further substituted with one or more C1-C6alkyls;

Z5 is independently and individually selected from the group consisting of H, C1-C6alkyl, branched C3-C7alkyl, halogen, fluoroalkyl, cyano, hydroxyl, alkoxy, oxo, aminocarbonyl, carbonylamino, aminosulfonyl, sulfonylamino, —N(R3)$_2$, —O—(CH$_2$)$_q$—N(R4)$_2$, —N(R3)-(CH$_2$)$_q$—N(R4)$_2$, —R5, —O—(CH$_2$)$_q$—O-Alkyl, —O—(CH$_2$)$_q$—N(R4)$_2$, —N(R3)-(CH$_2$)$_q$—O-Alkyl, —N(R3)-(CH$_2$)$_q$—N(R4)$_2$, —O—(CH$_2$)$_q$—R5, and —N(R3)-(CH$_2$)$_q$—R5;

each Z6 is independently and individually selected from the group consisting of H, C1-C6alkyl, branched C3-C7alkyl, hydroxyl, C1-C6alkoxy, heteroaryl, heterocyclyl, heteroaryloxy, heterocyclyloxy, arylamino, heteroarylamino, and heterocyclylamino, (R3)$_2$N—, —N(R3)COR8, (R4)$_2$N—, —R5, —N(R4)COR8, —N(R3)SO$_2$R6-, —CON(R3)$_2$, —CON(R4)$_2$, —COR5, and —SO$_2$NHR4;

wherein two R3 or R4 moieties are independently and individually taken from the group consisting of C1-C6alkyl and branched C3-C6alkyl, hydroxyalkyl, and alkoxyalkyl and are attached to the same nitrogen atom, said moieties may cyclize to form a C3-C7 heterocyclyl ring;

n is 0-4; p is 1-4; q is 2-6; and v is 1 or 2;

or a tautomer, diastereomer, geometric isomer, enantiomer, hydrate, or salt of any of the foregoing.

5. The compound of claim 4 having the formula If

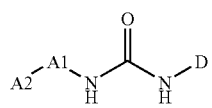

wherein A2 is selected from the group consisting of

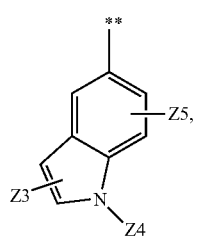

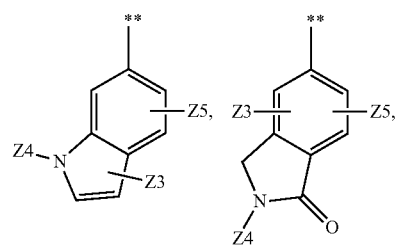

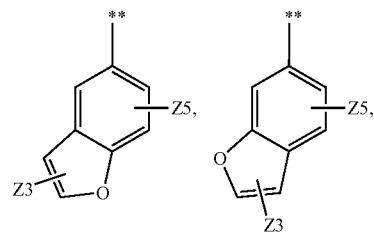

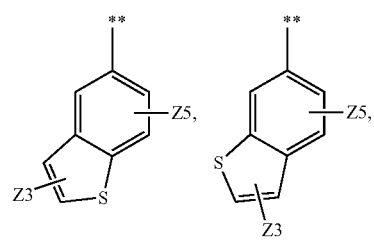

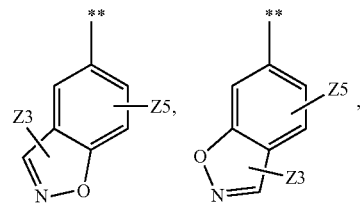

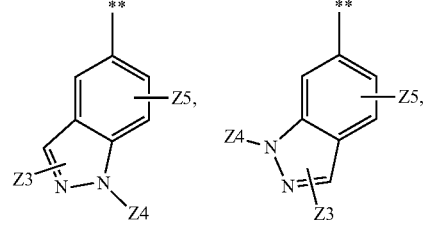

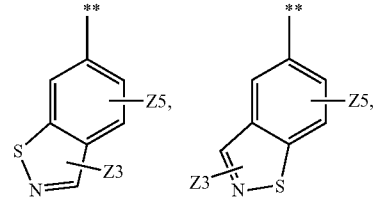

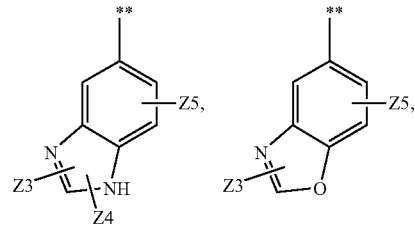

-continued

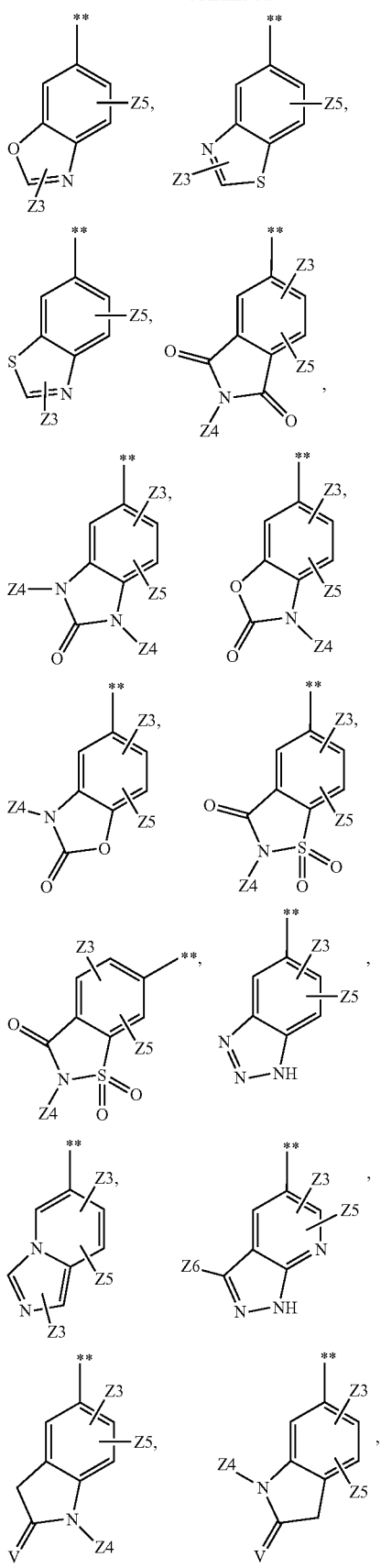

wherein the symbol (**) denotes the attachment to the A1 moiety of formula If;

wherein each Z3 and Z5 is independently attached to either aryl or heteroaryl ring of the A2 bicyclic ring;

wherein A1 is selected from the group consisting of

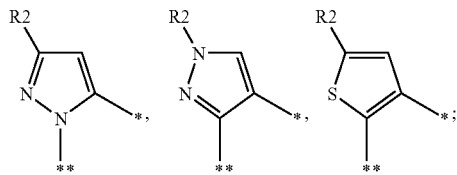

wherein the symbol (*) denotes the attachment to the NH moiety of formula If and the symbol (**) denotes the attachment to the A2 moiety of formula If;

wherein D is

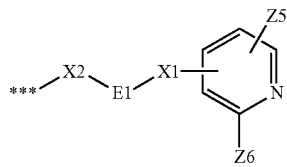

wherein the symbol (***) denotes the attachment to the NH moiety of formula If;

wherein E1 is phenyl;

wherein X1 is selected from the group consisting of O;

wherein X2 is a direct bond.

6. Compounds of claim 4 having the formula If

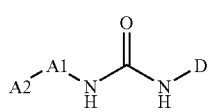

If wherein A2 is selected from the group consisting of

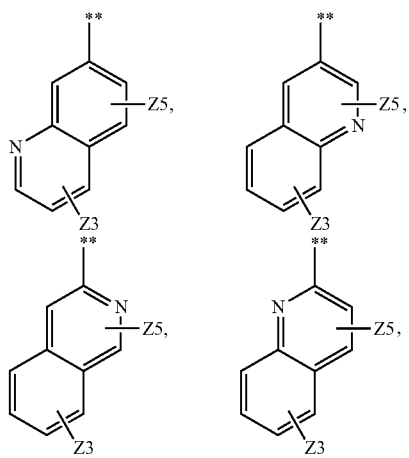

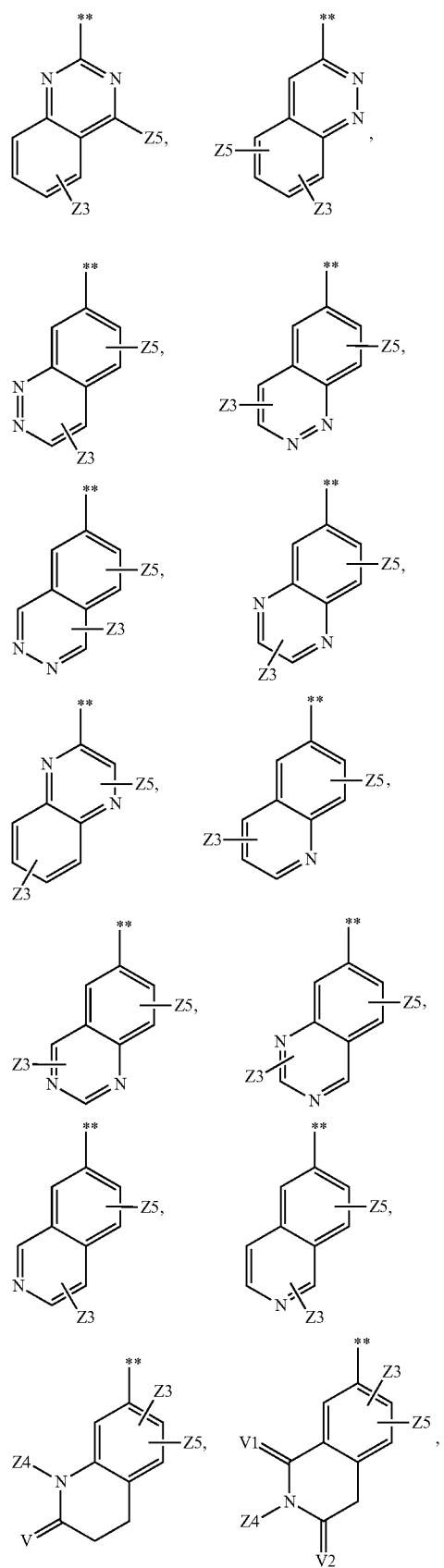
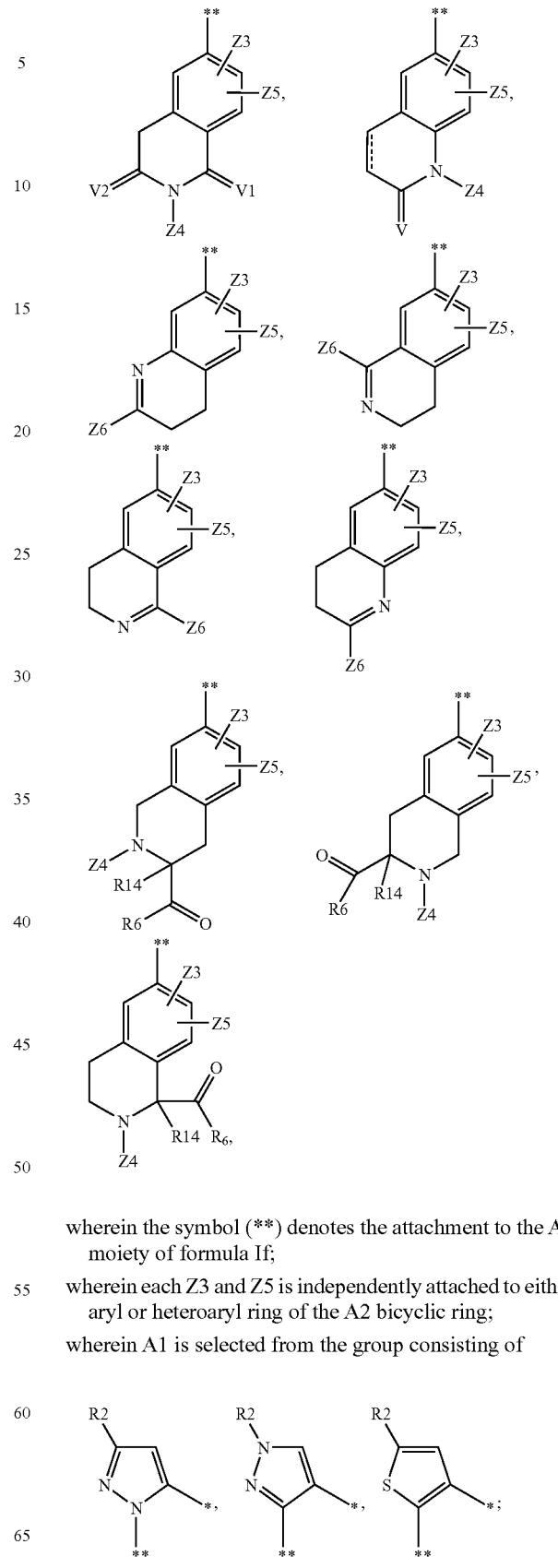
wherein the symbol (**) denotes the attachment to the A1 moiety of formula If;
wherein each Z3 and Z5 is independently attached to either aryl or heteroaryl ring of the A2 bicyclic ring;
wherein A1 is selected from the group consisting of
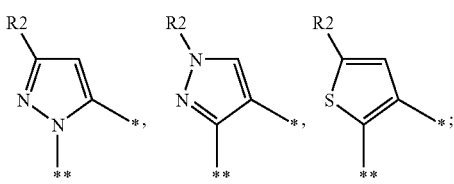

wherein the symbol (*) denotes the attachment to the NH moiety of formula If and the symbol (**) denotes the attachment to the A2 moiety of formula If;
wherein D is

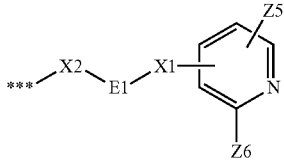

wherein the symbol (***) denotes the attachment to the NH moiety of formula If;
wherein E1 is phenyl;
wherein X1 is selected from the group consisting of O; and
wherein X2 is a direct bond.

7. A compound selected from
1-(3-tert-butyl-1-(quinolin-6-yl)-1H-pyrazol-5-yl)-3-(3-(pyridin-3-yloxy)phenyl)urea,
1-(3-tert-butyl-1-(1H-indol-5-yl)-1H-pyrazol-5-yl)-3-(3-(pyridin-3-yloxy)phenyl)urea,
1-(3-tert-butyl-1-(indolin-5-yl)-1H-pyrazol-5-yl)-3-(3-(pyridin-3-yloxy)phenyl)urea,
1-(3-tert-butyl-1-(1,2,3,4-tetrahydroisoquinolin-6-yl)-1H-pyrazol-5-yl)-3-(3-(pyridin-3-yloxy)phenyl)urea,
1-(3-tert-butyl-1-(1,2,3,4-tetrahydroisoquinolin-6-yl)-1H-pyrazol-5-yl)-3-(4-(2-(methylcarbamoyl)pyridin-4-yloxy)phenyl)urea,
1-(3-tert-butyl-1-(1,2,3,4-tetrahydroisoquinolin-6-yl)-1H-pyrazol-5-yl)-3-(3-(5-chloropyridin-3-yloxy)phenyl)urea,
1-(3-tert-butyl-1-(2-oxo-1,2-dihydroquinolin-6-yl)-1H-pyrazol-5-yl)-3-(3-(pyridin-3-yloxy)phenyl)urea,
1-(3-tert-butyl-1-(2-oxo-1,2-dihydroquinolin-6-yl)-1H-pyrazol-5-yl)-3-(3-(2-(methylcarbamoyl)pyridin-4-yloxy)phenyl)urea,
1-(3-tert-butyl-1-(2-oxo-1,2-dihydroquinolin-6-yl)-1H-pyrazol-5-yl)-3-(4-(2-(methylcarbamoyl)pyridin-4-yloxy)phenyl)urea,
1-(3-cyclopentyl-1-(2-oxo-1,2-dihydroquinolin-6-yl)-1H-pyrazol-5-yl)-3-(4-(2-(methylcarbamoyl)pyridin-4-yloxy)phenyl)urea,
1-(3-cyclopentyl-1-(2-oxo-1,2-dihydroquinolin-6-yl)-1H-pyrazol-5-yl)-3-(3-(pyridin-3-yloxy)phenyl)urea,
1-(3-tert-butyl-1-(2-(piperazin-1-yl)quinolin-6-yl)-1H-pyrazol-5-yl)-3-(4-(2-(methylcarbamoyl)pyridin-4-yloxy)phenyl)urea,
1-(1-(2-(2-aminoethylamino)quinolin-6-yl)-3-tert-butyl-1H-pyrazol-5-yl)-3-(4-(2-(methylcarbamoyl)pyridin-4-yloxy)phenyl)urea,
1-(3-tert-butyl-1-(2-((R)-3-(dimethylamino)pyrrolidin-1-yl)quinolin-6-yl)-1H-pyrazol-5-yl)-3-(4-(2-(methylcarbamoyl)pyridin-4-yloxy)phenyl)urea,
1-(3-tert-butyl-1-(2-(methylamino)quinolin-6-yl)-1H-pyrazol-5-yl)-3-(4-(2-(methylcarbamoyl)pyridin-4-yloxy)phenyl)urea,
1-(3-tert-butyl-1-(2-(dimethylamino)quinolin-6-yl)-1H-pyrazol-5-yl)-3-(4-(2-(methylcarbamoyl)pyridin-4-yloxy)phenyl)urea,
1-(1-(2-aminoquinolin-6-yl)-3-tert-butyl-1H-pyrazol-5-yl)-3-(4-(2-(methylcarbamoyl)pyridin-4-yloxy)phenyl)urea,
1-(3-tert-butyl-1-(3-carbamoyl-1,2,3,4-tetrahydroisoquinolin-6-yl)-1H-pyrazol-5-yl)-3-(3-(pyridin-3-yloxy)phenyl)urea,
1-(3-tert-butyl-1-(1-(methylcarbamoyl)-1,2,3,4-tetrahydroisoquinolin-6-yl)-1H-pyrazol-5-yl)-3-(3-(pyridin-3-yloxy)phenyl)urea,
1-(1-(3-((2,3-dihydroxypropyl)carbamoyl)-1,2,3,4-tetrahydroisoquinolin-6-yl)-3-tert-butyl-1H-pyrazol-5-yl)-3-(3-(pyridin-3-yloxy)phenyl)urea,
6-(3-tert-butyl-5-(3-(3-(pyridin-3-yloxy)phenyl)ureido)-1H-pyrazol-1-yl)-1,2,3,4-tetrahydroisoquinoline-3-carboxylic acid,
1-(3-tert-butyl-1-(3-(methylcarbamoyl)-1,2,3,4-tetrahydroisoquinolin-6-yl)-1H-pyrazol-5-yl)-3-(3-(pyridin-3-yloxy)phenyl)urea, and
1-(1-(1-((2,3-dihydroxypropyl)carbamoyl)-1,2,3,4-tetrahydroisoquinolin-6-yl)-3-t-butyl-1H-pyrazol-5-yl)-3-(3-(pyridin-3-yloxy)phenyl)urea.

8. A pharmaceutical composition comprising a compound of claim 1, 4, or 7, together with a pharmaceutically acceptable carrier, said carried including an additive selected from the group including adjuvants, excipients, diluents, and stabilizers.

* * * * *